(12) United States Patent
Allen et al.

(10) Patent No.: US 9,550,762 B2
(45) Date of Patent: Jan. 24, 2017

(54) CYCLOPROPYL FUSED THIAZIN-2-AMINE COMPOUNDS AS BETA-SECRETASE INHIBITORS AND METHODS OF USE

(71) Applicant: AMGEN INC., Thousand Oaks, CA (US)

(72) Inventors: Jennifer R. Allen, Newbury Park, CA (US); Albert Amegadzie, Moorpark, CA (US); Matthew P. Bourbeau, Woodland Hills, CA (US); James A. Brown, Moorpark, CA (US); Jian J. Chen, Camarillo, CA (US); Yuan Cheng, Newbury Park, CA (US); Michael J. Frohn, Thousand Oaks, CA (US); Angel Guzman-Perez, Belmont, MA (US); Paul E. Harrington, Camarillo, CA (US); Longbin Liu, Thousand Oaks, CA (US); Qingyian Liu, Camarillo, CA (US); Jonathan D. Low, Reseda, CA (US); Vu Van Ma, Oak Park, CA (US); James Manning, Pleasant Hill, CA (US); Ana Elena Minatti, Santa Monica, CA (US); Thomas T. Nguyen, Newbury Park, CA (US); Nobuko Nishimura, West Hills, CA (US); Mark H. Norman, Thousand Oaks, CA (US); Liping H. Pettus, Thousand Oaks, CA (US); Alexander J. Pickrell, Westlake Village, CA (US); Wenyuan Qian, Thousand Oaks, CA (US); Shannon Rumfelt, Camarillo, CA (US); Robert M. Rzasa, Thousand Oaks, CA (US); Aaron C. Siegmund, Ventura, CA (US); Markian M. Stec, Thousand Oaks, CA (US); Ryan D. White, Somerville, MA (US); Qiufen Xue, Thousand Oaks, CA (US)

(73) Assignee: Amgen, Inc., Thousand Oaks, CA (US)

(*) Notice: Subject to any disclaimer, the term of this patent is extended or adjusted under 35 U.S.C. 154(b) by 0 days.

(21) Appl. No.: 14/819,256

(22) Filed: Aug. 5, 2015

(65) Prior Publication Data
US 2016/0046618 A1 Feb. 18, 2016

Related U.S. Application Data

(60) Provisional application No. 62/035,269, filed on Aug. 8, 2014.

(51) Int. Cl.
C07D 417/12 (2006.01)
C07D 417/14 (2006.01)
(Continued)

(52) U.S. Cl.
CPC ........... *C07D 417/12* (2013.01); *C07D 279/08* (2013.01); *C07D 417/04* (2013.01); *C07D 417/14* (2013.01); *C07D 471/04* (2013.01); *C07D 513/10* (2013.01)

(58) Field of Classification Search
USPC ................. 544/65; 514/219.18, 224.2, 224.5
See application file for complete search history.

(56) References Cited

U.S. PATENT DOCUMENTS

| | | |
|---|---|---|
| 5,441,870 A | 8/1995 | Seubert et al. |
| 5,712,130 A | 1/1998 | Hajko et al. |
| (Continued) | | |

FOREIGN PATENT DOCUMENTS

| | | |
|---|---|---|
| AR | 86653 A1 | 1/2014 |
| EP | 2500344 A1 | 9/2012 |
| (Continued) | | |

OTHER PUBLICATIONS

U.S. Appl. No. 14/932,787, filed Nov. 4, 2012, Amgen Inc.
(Continued)

*Primary Examiner* — Kahsay Habte
(74) *Attorney, Agent, or Firm* — Bernard P. Friedrichsen; Markus Bergauer

(57) ABSTRACT

The present invention provides a new class of compounds useful for the modulation of beta-secretase enzyme (BACE) activity. The compounds have a general Formula I:

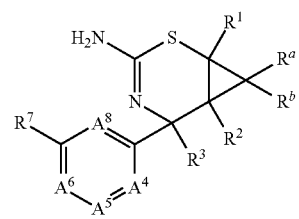

wherein variables $A^4$, $A^5$, $A^6$, $A^8$, and each of $R^a$, $R^b$, $R^1$, $R^2$, $R^3$ and $R^7$ of Formula I, independently, are defined herein. The invention also provides pharmaceutical compositions comprising the compounds, and uses of the compounds and compositions for treatment of disorders and/or conditions related to A-beta plaque formation and deposition, resulting from the biological activity of BACE. Such BACE mediated disorders include, for example, Alzheimer's Disease, cognitive deficits, cognitive impairments, schizophrenia and other central nervous system conditions. The invention further provides compounds of Formulas II and III, and sub-formula embodiments thereof, intermediates and methods for preparing compounds of the invention.

95 Claims, No Drawings

(51) Int. Cl.
  *C07D 471/04*     (2006.01)
  *C07D 513/10*     (2006.01)
  *C07D 417/04*     (2006.01)
  *C07D 279/08*     (2006.01)

(56) References Cited

U.S. PATENT DOCUMENTS

| | | |
|---|---|---|
| 5,942,400 A | 8/1999 | Anderson et al. |
| 8,168,630 B2 | 5/2012 | Tamura et al. |
| 8,173,642 B2 | 5/2012 | Kobayashi et al. |
| 8,637,504 B2 | 1/2014 | Hori et al. |
| 8,653,067 B2 | 2/2014 | Kobayashi et al. |
| 9,085,576 B2 | 7/2015 | Minatti et al. |
| 9,133,129 B2 | 9/2015 | Yamashita et al. |
| 9,296,734 B2 | 3/2016 | Minatti et al. |
| 2006/0111370 A1 | 5/2006 | Zhu et al. |
| 2009/0082560 A1 | 3/2009 | Kobayashi et al. |
| 2009/0209755 A1 | 8/2009 | Suzuki et al. |
| 2010/0075957 A1 | 3/2010 | Tamura et al. |
| 2010/0160290 A1 | 6/2010 | Kobayashi et al. |
| 2011/0152253 A1 | 6/2011 | Motoki et al. |
| 2011/0294149 A1 | 12/2011 | Gurney et al. |
| 2012/0202803 A1 | 8/2012 | Hilpert et al. |
| 2012/0238557 A1 | 9/2012 | Masui et al. |
| 2012/0245154 A1 | 9/2012 | Anan et al. |
| 2012/0245157 A1 | 9/2012 | Masui et al. |
| 2012/0258962 A1 | 10/2012 | Hilpert et al. |
| 2012/0302549 A1 | 11/2012 | Narquizian et al. |
| 2013/0072478 A1 | 3/2013 | Hilpert et al. |
| 2014/0051691 A1 | 2/2014 | Masui et al. |
| 2014/0235626 A1 | 8/2014 | Tada et al. |
| 2014/0249104 A1 | 9/2014 | Minatti et al. |
| 2015/0252011 A1 | 9/2015 | Minatti et al. |
| 2016/0046618 A1 | 2/2016 | Allen et al. |

FOREIGN PATENT DOCUMENTS

| | | | |
|---|---|---|---|
| EP | 2 514 747 A1 | 10/2012 | |
| EP | 2511268 A1 | 10/2012 | |
| EP | 1 942 105 B1 | 4/2014 | |
| EP | 2703401 A1 | 5/2014 | |
| JP | 2012/250933 A | 12/2012 | |
| WO | 00/17369 A2 | 3/2000 | |
| WO | 2005/058311 A1 | 6/2005 | |
| WO | 2006/065277 A2 | 6/2006 | |
| WO | 2007/049532 A1 | 5/2007 | |
| WO | 2008/103351 A2 | 8/2008 | |
| WO | 2008/133273 A1 | 11/2008 | |
| WO | 2009/134617 A1 | 11/2009 | |
| WO | 2009/151098 A1 | 12/2009 | |
| WO | 2010/013302 A1 | 2/2010 | |
| WO | 2010/013794 A1 | 2/2010 | |
| WO | 2010/128058 A1 | 11/2010 | |
| WO | 2011/005738 A1 | 1/2011 | |
| WO | 2011/009898 A1 | 1/2011 | |
| WO | 2011/020806 A1 | 2/2011 | |
| WO | 2011/029803 A1 | 3/2011 | |
| WO | 2011/044181 A1 | 4/2011 | |
| WO | 2011/058763 A1 | 5/2011 | |
| WO | 2011/069934 A1 | 6/2011 | |
| WO | 2011/070029 A1 | 6/2011 | |
| WO | 2011/070781 A1 | 6/2011 | |
| WO | 2011/071057 A1 | 6/2011 | |
| WO | 2011/071109 A1 | 6/2011 | |
| WO | 2011/071135 A1 | 6/2011 | |
| WO | 2012/095463 A1 | 7/2012 | |
| WO | 2012/095521 A1 | 7/2012 | |
| WO | 2012/39425 A1 | 10/2012 | |
| WO | 2012/138734 A1 | 10/2012 | |
| WO | 2012/139993 A1 | 10/2012 | |
| WO | 2012/147762 A1 | 11/2012 | |
| WO | 2012/147763 A1 | 11/2012 | |
| WO | 2012/156284 A1 | 11/2012 | |
| WO | 2012/162330 A1 | 11/2012 | |
| WO | 2012/162334 A1 | 11/2012 | |
| WO | 2012/168164 A1 | 12/2012 | |
| WO | 2012/168175 A1 | 12/2012 | |
| WO | 2013/004676 A1 | 1/2013 | |
| WO | 2013/027188 A1 | 2/2013 | |
| WO | 2013/028670 A1 | 2/2013 | |
| WO | 2013/030713 A1 | 3/2013 | |
| WO | 2013/054291 A1 | 4/2013 | |
| WO | 2013/061962 A1 | 5/2013 | |
| WO | 2013/110622 A1 | 8/2013 | |
| WO | 2013/142613 A1 | 9/2013 | |
| WO | 2013/164730 A1 | 11/2013 | |
| WO | 2013/182638 A1 | 12/2013 | |
| WO | 2014/001228 A1 | 1/2014 | |
| WO | 2014/013076 A1 | 1/2014 | |
| WO | 2014/045162 A1 | 3/2014 | |
| WO | 2014/059185 A1 | 4/2014 | |
| WO | 2014/062549 A1 | 4/2014 | |
| WO | 2014/062553 A1 | 4/2014 | |
| WO | 2014/065434 A1 | 5/2014 | |
| WO | 2014/066132 A1 | 5/2014 | |
| WO | 2014/093190 A1 | 6/2014 | |
| WO | 2014/097038 A1 | 6/2014 | |
| WO | 2014/098831 A1 | 6/2014 | |
| WO | 2014/099788 A9 | 6/2014 | |
| WO | 2014/099794 A1 | 6/2014 | |
| WO | 2014/114532 A1 | 7/2014 | |
| WO | 2014/138484 A1 | 9/2014 | |
| WO | 2014/166906 A1 | 10/2014 | |
| WO | 2014/173917 A1 | 10/2014 | |
| WO | 2015/156421 A1 | 10/2015 | |
| WO | 2016/001266 A1 | 1/2016 | |
| WO | 2016/022724 A1 | 2/2016 | |

OTHER PUBLICATIONS

Vassar, R. and Yan, R., "Targeting the β secretase BACE1 for Alzheimer's disease therapy," *Lancet Neurology* 13:319-329 (2014).

Joachim, C. L. and Selkoe, D. J., "The Seminal Role of β-Amyloid in the Pathogenesis of Alzheimer Disease," *Alzheimer Disease and Associated Disorders* 6(1):7-34 (1992).

Selkoe, D. J., "The Molecular Pathology of Alzheimer's Disease," *Neuron* 6:487-498 (1991).

Seubert, P. et al., "Isolation and quantification of soluble Alzheimer's β-peptide from biological fluids," *Nature* 359:325-327 (1992).

Citron, M., "β-Secretase inhibition for the treatment of Alzheimer's disease—promise and challenge," *TRENDS in Pharmacological Sciences* 25(2):92-97 (2004).

Shankar, G. M. et al., "Amyloid-β protein dimers isolated directly from Alzheimer's brains impair synaptic plasticity and memory," *Nature Medicine* 14(8):837-842 (2008).

Sinha, S. et al., "Purification and cloning of amyloid precursor protein β-secretase from human brain," *Nature* 402:537-540 (1999).

Sabbagh, M. N. et al., "β-Amyloid and Treatment Opportunities for Alzheimer's Disease," *Alzheimer's Disease Review* 3:1-19 (1997).

Cole, S.L. and Vassar, R., "The Alzheimer's disease β-secretase enzyme, BACE1," *Molecular Neurodegeneration* 2(22):1-25 (2007).

Luo, Y et al., "Mice deficient in BACE1, the Alzheimer's β-secretase, have normal phenotype and abolished β-amyloid generation," *Nature Neuroscience* 4:231-232 (2001).

Henley, D. B. et al., "Development of semagacestat (LY450139), a functional γ-secretase inhibitor, for the treatment of Alzheimer's disease," *Expert Opin. Pharmacother*. 10(10):1657-1664 (2009).

Siemers, E. R. et al., "Safety, Tolerability, and Effects on Plasma and Cerebrospinal Fluid Amyloid-β After Inhibition of γ-Secretase," *Clin. Neuropharmacol*. 30(6):317-325 (2007).

Siemers, E. R. et al., "Effects of a γ-secretase inhibitor in a randomized study of patients with Alzheimer's disease," *Neurology* 66:602-604 (2006).

Shacka, J. J. and Roth, K. A., "Cathepsin D Deficiency and NCL/Batten Disease: There's More to Death than Apoptosis," *Autophagy*, 3(5):474-476 (2007).

(56) References Cited

OTHER PUBLICATIONS

Follo, C. et al., "Knock-Down of Cathepsin D Affects the Retinal Pigment Epithelium, Impairs Swim-Bladder Ontogenesis and Causes Premature Death in Zebrafish," *PLoS One* 6(7):e21908, pp. 1-13 (2011).

Karran, E. et al. "The amyloid cascade hypothesis for Alzheimer's disease: an appraisal for the development of therapeutics," *Nature Reviews Drug Discovery* 10:698-712 (2011).

Office Action mailed May 22, 2015 for U.S. Appl. No. 14/691,715, filed Apr. 21, 2015, pp. 1-5.

International Preliminary Report on Patentability and Written Opinion for International Patent Application No. PCT/US2014/021412, issued Sep. 8, 2015, pp. 1-7.

International Search Report for International Patent Application No. PCT/US2014/021412, mailed May 13, 2014, pp. 1-3.

Koike, M. et al., "Involvement of two different cell death pathways in retinal atrophy of cathepsin D-deficient mice," *Molecular and Cellular Neuroscience* 22:146-161 (2003).

Alzforum Networking for a Cure, "Barcelona: Out of Left Field—Hit to the Eye Kills BACE Inhibitor," pp. 1-7 (Mar. 31, 2011); access online: www.alzforum.org/news/conference-coverage/barcelona-out-left-field-hit-eye-kills-bace-inhibitor (last accessed Dec. 16, 2015).

Hilpert, H. et al., "β-Secretase (BACE1) Inhibitors with High in Vivo Efficacy Suitable for Clinical Evaluation in Alzheimer's Disease," *J. Med. Chem.* 56(10):3980-3995 (2013).

Gulnik, S. V. et al. "Design of sensitive fluorogenic substrates for human cathespin D," *FEBS Letters* 413:379-384 (1997).

Yasuda, Y. et al., "Characterization of New Fluorogenic Substrates for the Rapid and Sensitive Assay of Cathepsin E and Cathepsin D," *J. Biochem.* 125(6):1137-1143 (1999).

Hsiao, K. et al., "Correlative Memory Deficits, Aβ Elevation, and Amyloid Plaques in Transgenic Mice," *Science* 274:99-102 (1996).

Dovey, H. F. et al., "Functional gamma-secretasae inhibitors reduce beta-amyloid peptide levels in brain," *Journal of Neurochemistry* 76:173-181 (2001).

Best, J. D. et al., "Quantitative Measurement of Changes in Amyloid -β(40) in the Rat Brain and Cerebrospinal Fluid Following Treatment with the γ-Secretase Inhibitor LY-411575 [$N^2$-[(2S)-2-(3,5-Difluorophenyl)-2-hydroxyethanoyl]-$N^1$-[(7S)-5-methyl-6-oxo-6,7-dihydro-5H-dibenzo[b,d]azepin-7-yl]L-alaninamide]," *Journal of Pharmacology and Experimental Therapeutics* 313(2):902-908 (2005).

De Meyer, G. et al., "Diagnosis-Independent Alzheimer Disease Biomarker Signature in Cognitively Normal Elderly People," *Arch. Neurol.* 67(8):949-956 (2010).

Tanzi, R. E. and Bertram, L., "Twenty Years of the Alzheimer's Disease Amyloid Hypothesis: A Genetic Perspective," *Cell* 120(4): 545-555 (2005).

Walsh, D. M. and Selkoe, D. J., "Deciphering the Molecular Basis of Memory Failure in Alzheimer's Disease," *Neuron* 44(1):181-193 (2004).

Palop, J. J. and Mucke, L., "Amyloid-β-induced neuronal in Alzheimer's disease: from synapses toward neural networks," *Nature Neuroscience* 13(7):812-818 (2010).

Selkoe, D. J., "Soluble oligomers of the amyloid β-protein impair synaptic plasticity and behavior," *Behavioural Brain Research* 192:106-113 (2008).

Games, D. et al., "Alzheimer-type neuropathology in transgenic mice overexpressing V717F β-amyloid precursor protein," *Nature* 373:523-527 (1995).

Götz, J. et al., "Transgenic animal models of Alzheimer's disease and related disorders: histopahtology, behavior and therapy," *Molecular Psychiatry* 9:664-683 (2004).

Hsia, A. Y. et al., "Plaque-independent disruption of neural circuits in Alzheimer's disease mouse models," *Proc. Natl. Acad. Sci. USA* 96:3228-3233 (1999).

Harris, J. A. et al, "Transsynaptic Progression of Amyloid-β-Induced Neuronal Dysfunction within the Entorhinal-Hippocampal Network," *Neuron* 68:428-441 (2010).

Vassar, R. et al, "The β-Secretase Enzyme BACE in Health and Alzheimer's Disease: Regulation, Cell Biology, Function, and Therapeutic Potential," *Journal of Neuroscience* 29(41):12787-12794 (2009).

May, P. C. et al., "Robust Central Reduction of Amyloid-β in Humans with an Orally Available, Non-Peptidic β-Secretase Inhibitor," *Journal of Neuroscience* 31(46):16507-16516 (2011).

International Preliminary Report on Patentability and Written Opinion for International Patent Application No. PCT/US2014/019100, issued Sep. 1, 2015, pp. 1-8.

International Search Report for International Patent Application No. PCT/US2014/019100, mailed Aug. 5, 2014, pp. 1-6.

"1,9-Dioxa-3-azaspiro[5.5]undec-2-en-2-amine, 4-[2-fluoro-5-[(3-methoxy-2-pyridinyl)amino]phenyl]-4-methyl-, (4S)" CAS No. 1457976-71-4, Chemical Abstracts Service, Columbus, Ohio, USA, p. 1.

Notice of Allowance mailed Oct. 15, 2015 for U.S. Appl. No. 14/192,710, filed Feb. 27, 2014, pp. 1-7.

Written Opinion of the International Searching Authority mailed Nov. 13, 2015 for International Patent Application No. PCT/US2015/043868, pp. 1-6.

International Search Report mailed Nov. 13, 2015 for International Patent Application No. PCT/US2015/043868, pp. 1-4.

CYCLOPROPYL FUSED THIAZIN-2-AMINE COMPOUNDS AS BETA-SECRETASE INHIBITORS AND METHODS OF USE

RELATED APPLICATIONS

This application claims the benefit of and priority to U.S. Provisional Patent Application No. 62/035,269, filed on Aug. 8, 2014, which specification is hereby incorporated herein by reference in its entirety and for all purposes as if specifically set forth herein.

FIELD OF THE INVENTION

The invention relates generally to pharmaceutically active compounds, pharmaceutical compositions and methods of use thereof, to treat beta-secretase mediated diseases and conditions, including, without limitation, Alzheimer's disease, plaque formation and associated central nervous system (CNS) disorders.

BACKGROUND OF THE INVENTION

Alzheimer's disease (AD) affects greater than 12 million aging people worldwide, and importantly, the number affected continues to grow. AD accounts for the majority of dementias clinically diagnosed after the age of 60. AD is generally characterized by the progressive decline of memory, reasoning, judgement and orientation. As the disease progresses, motor, sensory, and vocal abilities are affected until there is global impairment of multiple cognitive functions. The loss of cognitive function occurs gradually, typically leading to a diminished cognition of self, family and friends. Patients with severe cognitive impairment and/or diagnosed as end-stage AD are generally bedridden, incontinent, and dependent on custodial care. The AD patient eventually dies in about nine to ten years, on average, after initial diagnosis. Due to the incapacitating, generally humiliating and ultimately fatal effects of AD, there is a need to treat AD effectively upon diagnosis.

AD is characterized by two major physiological changes in the brain. The first change, beta amyloid plaque formation, supports the "amyloid cascade hypothesis" which conveys the thought that AD is caused by the formation of characteristic beta amyloid peptide (A-beta), or A-beta fragments thereof, deposits in the brain (commonly referred to as beta amyloid "plaques" or "plaque deposits") and in cerebral blood vessels (beta amyloid angiopathy). A wealth of evidence suggests that beta-amyloid and accompanying amyloid plaque formation is central to the pathophysiology of AD and is likely to play an early role in this intractable neurodegenerative disorder. Vassar & Yan, *Lancet Neurology*, 13:319-329 (2014). The second change in AD is the formation of intraneuronal tangles, consisting of an aggregate form of the protein tau. Besides being found in patients with AD, intraneuronal tangles are also found in other dementia-inducing disorders. Joachim et al., *Alz. Dis. Assoc. Dis.*, 6:7-34 (1992).

Several lines of evidence indicate that progressive cerebral deposition of A-beta plays a seminal role in the pathogenesis of AD and can precede cognitive symptoms by years or even decades. Selkoe, *Neuron*, 6:487 (1991). Release of A-beta from neuronal cells grown in culture and the presence of A-beta in cerebrospinal fluid (CSF) of both normal individuals and AD patients has been demonstrated. Seubert et al., *Nature*, 359:325-327 (1992). Autopsies of AD patients have revealed large numbers of lesions comprising these 2 factors in areas of the human brain believed to be important for memory and cognition.

Smaller numbers of these lesions in a more restricted anatomical distribution are found in the brains of most aged humans who do not have clinical AD. Amyloid containing plaques and vascular amyloid angiopathy were also found in the brains of individuals with Down's Syndrome, Hereditary Cerebral Hemorrhage with Amyloidosis of the Dutch-type (HCHWA-D), and other neurodegenerative disorders.

It has been hypothesized that A-beta formation is a causative precursor or factor in the development of AD. More specifically, deposition of A-beta in areas of the brain responsible for cognitive factors is believed to be a major factor in the development of AD. Beta amyloid plaques are primarily composed of amyloid beta peptide (A-beta peptide). A-beta peptide is derived from the proteolytic cleavage of a large transmembrane amyloid precursor protein (APP), and is a peptide comprised of about 39-42 amino acid residues. A-beta 42 (42 amino acids long) is thought to be the major component of these plaque deposits in the brains of Alzheimer's Disease patients. Citron, *Trends in Pharmacological Sciences*, 25(2):92-97 (2004).

Similar plaques appear in some variants of Lewy body dementia and in inclusion body myositis, a muscle disease. Aβ also forms aggregates coating cerebral blood vessels in cerebral amyloid angiopathy. These plaques are composed of a tangle of regularly ordered fibrillar aggregates called amyloid fibers, a protein fold shared by other peptides such as prions associated with protein misfolding diseases. Research on laboratory rats suggest that the dimeric, soluble form of the peptide is a causative agent in the development of Alzheimer's and is the smallest synaptotoxic species of soluble amyloid beta oligomer. Shankar, G. M., *Nature Medicine* (Jun. 22, 2008) online doi 10:1038 nm 1782.

Several aspartyl proteases, including beta-secretase and gamma-secretase, are thought to be involved in the processing or cleavage of APP, resulting in the formation of A-beta peptide. Beta secretase (BACE, also commonly referred to as memapsin) is thought to first cleave APP to generate two fragments: (1) a first N-terminus fragment (beta APP) and (2) a second C-99 fragment, which is subsequently cleaved by gamma secretase to generate the A-beta peptide. APP has also been found to be cleaved by alpha-secretase to produce alpha-sAPP, a secreted form of APP that does not result in beta-amyloid plaque formation. This alternate pathway precludes the formation of A-beta peptide. A description of the proteolytic processing fragments of APP is found, for example, in U.S. Pat. Nos. 5,441,870, 5,712,130 and 5,942,400.

BACE is an aspartyl protease enzyme comprising 501 amino acids and responsible for processing APP at the beta-secretase specific cleavage site. BACE is present in two forms, BACE 1 and BACE 2, designated as such depending upon the specific cleavage site of APP. Beta secretase is described in Sinha et al., *Nature*, 402:537-554 (1999) (p 510) and PCT application WO 2000/17369. It has been proposed that A-beta peptide accumulates as a result of APP processing by BACE. Moreover, in vivo processing of APP at the beta secretase cleavage site is thought to be a rate-limiting step in A-beta production. Sabbagh, M. et al., *Alz. Dis. Rev.* 3:1-19 (1997). Thus, inhibition of the BACE enzyme activity is desirable for the treatment of AD.

Studies have shown that the inhibition of BACE may be linked to the treatment of AD. The BACE enzyme is essential for the generation of beta-amyloid or A-beta. BACE knockout mice do not produce beta-amyloid and are free from Alzheimer's associated pathologies including neuronal loss and certain memory deficits. Cole, S. L., Vasser, R., *Molecular Degeneration* 2:22, 2007. When crossed with transgenic mice that over express APP, the progeny of BACE deficient mice show reduced amounts of A-beta in brain extracts as compares with control animals (Luo et al., *Nature Neuroscience*, 4:231-232 (2001)). The fact that BACE initiates the formation of beta-amyloid, and the observation that BACE levels are elevated in this disease provide direct and compelling reasons to develop therapies directed at BACE inhibition thus reducing beta-amyloid and its associated toxicities. To this end, inhibition of beta secretase activity and a corresponding reduction of A-beta in the brain should provide a therapeutic method for treating AD and other beta amyloid or plaque related disorders.

Consequently, the approach of regulating or reducing the formation of A-beta peptide formation and deposition as a potential treatment for AD has received tremendous attention, support and commitment from both researchers and investors alike. A small molecule gamma-secretase inhibitor, LY450139 ("Semagacestat"), an A-beta lowering agent, advanced to phase III clinical trials for the treatment of Alzheimer's Disease. The pharmacokinetics of semagacestat in plasma, as well as the plasma and cerebral spinal fluid (CSF) A-Beta peptide levels as pharmacodynamic responses to semagacestat administration were evaluated in healthy human subjects in single and multiple doses, and pharmacokinetic and pharmacodynamic changes were also assessed in mild to moderate AD patients in two (2) clinical trials (*Expert Opin. Pharmacother.* (2009), 10 (10); *Clin. Neuropharmacol.* 2007; 30 (pgs 317-325); and *Neurology*, 2006, 66 (pgs 602-624)).

Additional approaches have been taken in attempts to treat AD and plaque-related disorders. One such approach to reduce the formation of plaque deposits in the brain involves the inhibition of and, therefore, the reduction of BACE activity. Vassar & Yan, *Lancet Neurology*, 13:319-329 (2014). For example, each of the following patent publications: WO14/098831, WO14/099794, WO14/099788, WO14/097038, WO14/093190, WO14/066132, WO14/65434, WO14/062553, WO14/062549, WO14/013076, WO13/182638, WO13/164730, WO13/030713, WO13/028670, WO13/004676, WO2012162334, WO12/162330, WO12/147762, WO2013139425, WO2012138734, US20120245157, US20120245154, US20120238557, US2009082560, US2010160290, US2010075957, WO2009151098, WO2011029803, WO2014045162, WO201105738, WO2009134617, WO201013794, WO201013302, US20110152253, US2009209755, EP 2703401 (equivalent of WO2012146762) and EP01942105 describe inhibitors of BACE, useful for treating AD and other beta-secretase mediated disorders. For Example, US20120245154 describes "Substituted Aminothiazine Derivative" as BACE inhibitors for the treatment of neurological disorders of the general formula:

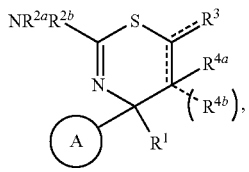

while EP2703401 describes "Pyridine Derivative and BACE1 Inhibitor Containing Same" and discloses compounds of the general formula:

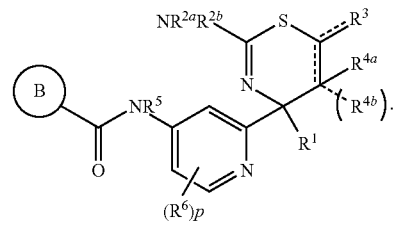

The lysosomal aspartic protease Cathepsin D (CatD) is ubiquitously expressed in eukaryotic organisms. CatD activity is essential to accomplish the acid-dependent extensive or partial proteolysis of protein substrates within endosomal and lysosomal compartments therein delivered via endocytosis, phagocytosis or autophagocytosis. CatD may also act at physiological pH on small-size substrates in the cytosol and in the extracellular milieu. Mouse and fruit fly CatD knock-out models have highlighted the multi-pathophysiological roles of CatD in tissue homeostasis and organ development.

Inhibition of protein Cathepsin D has been implicated in undesirable side effects. For instance, the inhibition of Cathepsin D is believed to be linked to adverse retinal development and retinal atrophy. Particularly, in mice it was found that cathepsin D is essential for the metabolic maintenance of retinal photoreceptor cells and that its deficiency induces apoptosis of the cells, while the loss of INL neurons is mediated by nitric oxide release from microglial cells. However, in the very same mice, it was also found that no atrophic change was detected in the retina of mice deficient in cathepsin B or L. *Mol. Cell. Neurosci,* 2003, Feb. 22 (2):146-161. Further, Animal models of cathepsin D (CatD) deficiency are characterized by a progressive and relentless neurodegenerative phenotype similar to that observed in Neuronal Ceroid Lipofuscinoses (NCL), a group of pediatric neurodegenerative diseases known collectively as Batten Disease. It has been shown that the targeted deletion of the pro-apoptotic molecule Bax prevents apoptotic markers but not neuronal cell death and neurodegeneration induced by CatD deficiency, which suggests that alterations in the macroautophagy-lysosomal degradation pathway can mediate neuronal cell death in NCL/Batten Disease in the absence of apoptosis. *Autophagy,* 2007, September-October; 3(5):474-476. Finally, an adverse effect of the inhibition of Cat D is evident from the data presented in *PLoS One,* 2011; 6(7):e21908, published Jul. 1, 2011. The authors of the PLoS One paper found that knock-down of cathepsin D affects the retinal pigment epithelium, impairs swim-bladder ontogenesis and causes premature death in zebrafish. The main phenotypic alterations produced by CatD knock-down in zebrafish were: 1. abnormal development of the eye and of retinal pigment epithelium; 2. absence of the swim-bladder; 3. skin hyper-pigmentation; 4. reduced growth and premature death. Rescue experiments confirmed the involvement of CatD in the developmental processes leading to these phenotypic alterations.

Moreover, such toxicity findings which, in view of the literature, may have played a role in the termination of a human Bace-mediated Alzheimer's Disease clinical trial. Eli Lilly terminated a phase I clinical trial of LY 2811376 after rat toxicology studies showed that a higher compound dose given for three months damaged the pigment epithelium of the rat's eye. The retinal layer had inclusions and extensive damage. The Ph I dosing trial was terminated and people brought in for eye assessments did not show any abnormalities (Alzheimer's Research Forum News, Mar. 31, 2011 reporting on Martin Citron's presentation at the AD/PD Conference March 2011 in Barcelona, Spain)

Hence, it is desirable to provide compounds which modulate the activity of and are reasonably selective for BACE, while not suffering from undesirable side effects possibly due to intervention with or the reduction and/or direct or indirect inhibition of the expression and/or function of other proteins or biological pathways.

BRIEF DESCRIPTION OF THE INVENTION

The present invention provides a new class of compounds useful for the modulation of beta secretase activity, and as treatment of AD. Particularly, the compounds of the invention are useful for the regulation or reduction of the formation of A-beta peptide and, consequently, the regulation and/or reduction of formation of beta amyloid plaque both on the brain, as well as in the CNS. To this end, the compounds are useful for the treatment of AD and other beta secretase and/or plaque-related and/or mediated disorders. For example, the compounds are useful for the prophylaxis and/or treatment, acute and/or chronic, of AD and other diseases or conditions involving the deposition or accumulation of beta amyloid peptide, and formation of plaque, on the brain.

The compounds provided by the invention, including stereoisomers, tautomers, hydrates, solvates and pharmaceutically acceptable salts thereof, are generally defined by Formula I

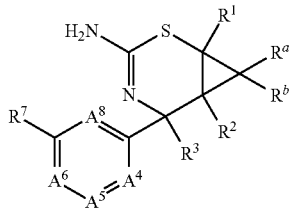

wherein each of $A^4$, $A^5$, $A^6$, $A^8$, $R^a$, $R^b$, $R^1$, $R^2$, $R^3$ and $R^7$ of Formula I are defined below. The invention also provides procedures for making compounds of Formula I, and sub-Formulas thereof, as well as intermediates useful in such procedures.

The invention further provides pharmaceutical compositions comprising compounds of the invention, and uses of these compositions in the treatment of beta secretase mediated diseases. For example, and in one embodiment, the invention provides a pharmaceutical composition comprising an effective dosage amount of a compound of Formula I in association with at least one pharmaceutically acceptable excipient.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In embodiment 1 of the invention, there are provided compounds, including stereoisomers, tautomers, hydrates, solvates and pharmaceutically acceptable salts thereof, which are generally defined by Formula I:

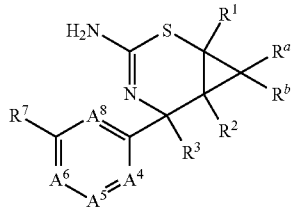

or a stereoisomer, tautomer, hydrate, solvate or pharmaceutically acceptable salt thereof, wherein
$A^4$ is $CR^4$ or N;
$A^5$ is $CR^5$ or N;
$A^6$ is $CR^6$ or N;
$A^8$ is $CR^8$ or N, provided that no more than two of $A^4$, $A^5$, $A^6$ and $A^8$ is N;
each of $R^a$ and $R^b$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;
each of $R^1$ and $R^2$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl, —$C(O)NH_2$, —$CH=CHC(O)NHC_{1-6}$-alkyl, —$CH=CHC(O)_2H$, —$CH=CHCH_2OH$, $C_{1-6}$-alkyl-$C(O)NHC_{1-6}$-alkyl, $C(O)C_{1-6}$-alkyl or —$C(O)C_{1-6}$-alkenyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl, $C(O)C_{1-6}$-alkyl, —$C(O)C_{1-6}$-alkenyl, —$CH=CHC(O)NHC_{1-6}$-alkyl and $C_{1-6}$-alkyl-$C(O)NHC_{1-6}$-alkyl, are optionally substituted with 1-4 substituents of F, CN, oxo or OH;
$R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;
each of $R^4$, $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;
$R^7$ is —NH—$R^9$ or —NH—C(=O)—$R^9$;
$R^9$ is a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the ring is optionally substituted, independently, with 1-5 substituents of $R^{10}$;
each $R^{10}$, independently, is H, halo, haloalkyl, CN, OH, $NO_2$, $NH_2$, $SF_5$, acetyl, —$C(O)NHCH_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazopyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$dialkylamino, $C_{1-3}$thioalkoxyl, oxazolyl, isoxazolyl, thiazolyl, isothiazolyl, thiadiazolyl, thienyl, furyl, pyrrolyl, tetrahydropyranyl, tetrahydropyrrolyl or oxetan-3yl; and the subscript o is selected from 0, 1, or 2.

In an alternative embodiment 1 of the invention, there are provided compounds, including stereoisomers, tautomers, hydrates, solvates and pharmaceutically acceptable salts thereof, which are generally defined by Formula I:

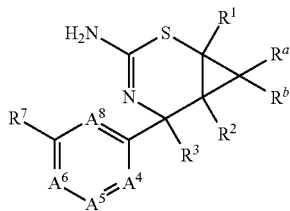

wherein $A^4$ is $CR^4$ or N;

$A^5$ is $CR^5$ or N;

$A^6$ is $CR^6$ or N;

$A^8$ is $CR^8$ or N, provided that no more than two of $A^4$, $A^5$, $A^6$ and $A^8$ is N;

each of $R^a$ and $R^b$, independently, is H, F, Cl, $C_{2-4}$alkenyl, $C_{2-4}$alkynyl, CN, —$CH_2OC_{1-6}$-alkyl, —$OC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;

$R^1$ and either $R^a$ or $R^b$ may optionally join to form a 5-membered saturated ring that includes one S heteroatom;

$R^1$ is H, F, Cl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$C_{1-6}$-alkylNH$_2$, —$C_{1-6}$-alkylNHC$_{1-6}$-alkyl, —$C_{1-6}$-alkylNHC(O)OC$_{1-6}$-alkyl, —$C_{1-6}$-alkylNHC(O)NHC$_{1-6}$-alkyl, —$C_{1-6}$-alkylNHC(O)C$_{1-6}$-alkyl, —$C(O)NH_2$, —CH=CHC(O)NH$_2$, —CH=CHC(O)NHC$_{1-6}$-alkyl, —CH=CHC(O)N($C_{1-6}$-alkyl)$_2$, —CH=CHC(O)NHC$_{1-6}$-alkyl-OC$_{1-6}$-alkyl, —CH=CHC(O)-heterocyclyl, —CH=C(CH$_3$)C(O)-heterocyclyl, —CH=CHC(O)$_2$H, —CH=CHC(O)OC$_{1-6}$-alkyl, —CH=CHCH$_2$OH, $C_{1-6}$-alkyl-C(O)NHC$_{1-6}$-alkyl, $C_{1-6}$-alkyl-C(O)N($C_{1-6}$-alkyl)$_2$, —C(O)C$_{1-6}$-alkyl, —C(O)C$_{1-6}$-alkenyl, —C(O)OH, —C(O)OC$_1$-C$_6$alkyl, —C(O)NHC$_{1-6}$-alkyl, —C(O)N($C_{1-6}$-alkyl)$_2$, —C(O)NHC$_{3-6}$-cycloalkyl, —C(O)NHOC$_{1-6}$-alkyl, —C(O)N($C_{1-6}$-alkyl)OC$_{1-6}$-alkyl, —C(O)-heterocyclyl, —CH$_2$-heteroaryl, or heteroaryl, wherein the heterocyclyl groups of the —CH=CHC(O)-heterocyclyl, —CH=C(CH$_3$)C(O)-heterocyclyl, and —C(O)-heterocyclyl groups are fully or partially unsaturated 3-, 4-, 5-, 6- or 7-membered monocyclic rings that include 1 heteroatom selected from N, O, or S if the ring is a 3-membered ring, that include 1 or 2 heteroatoms independently selected from N, O, or S if the ring is a 4- or 5-membered ring, and include 1, 2, or 3 heteroatoms independently selected from N, O, or S if the ring is a 6- or 7-membered ring, wherein the heteroaryl groups of the —CH$_2$-heteroaryl and heteroaryl groups is a 5- or 6-membered ring that includes 1, 2, 3, or 4 heteroatoms selected from N, O, or S, wherein each of the $C_{1-6}$-alkyl, $C_{2-4}$alkenyl, $C_{2-4}$alkynyl, and $C_{3-6}$cycloalkyl portion of $C_{1-6}$-alkyl, $C_{2-4}$alkenyl, $C_{2-4}$alkynyl, —CH$_2$OC$_{1-6}$-alkyl, —OC$_{1-6}$-alkyl, —S(O)$_o$C$_{1-6}$-alkyl, —NHC$_{1-6}$-alkyl, C(O)C$_{1-6}$-alkyl, —C(O)C$_{1-6}$-alkenyl, —C(O)NHC$_{1-6}$-alkyl, —C(O)N(C$_{1-6}$-alkyl)$_2$, —C(O)NHC$_{3-6}$cycloalkyl, —CH=CHC(O)NHC$_{1-6}$-alkyl and $C_{1-6}$-alkyl-C(O)NHC$_{1-6}$-alkyl groups are optionally substituted with 1-4 substituents of F, CN, methyl, oxo, or OH, and further wherein each of the heterocyclyl groups of the —CH=CHC(O)-heterocyclyl, —CH=C(CH$_3$)C(O)-heterocyclyl, and —C(O)heterocyclyl groups is optionally substituted with 1-4 substituents independently selected from F, methyl, OH, or OCH$_3$, and further wherein each of the heteroaryl groups of the —CH$_2$-heteroaryl and heteroaryl groups is optionally substituted with 1-3 substituents independently selected from halo, methyl, or OH;

$R^2$ is H, F, Cl, $C_{1-6}$-alkyl, $C_{2-4}$alkenyl, $C_{2-4}$alkynyl, CN, —CH$_2$OC$_{1-6}$-alkyl, —OC$_{1-6}$-alkyl, —S(O)$_o$C$_{1-6}$-alkyl, —NHC$_{1-6}$-alkyl, —C(O)NH$_2$, —CH=CHC(O)NHC$_{1-6}$-alkyl, —CH=CHC(O)$_2$H, —CH=CHCH$_2$OH, $C_{1-6}$-alkyl-C(O)NHC$_{1-6}$-alkyl, —C(O)C$_{1-6}$-alkyl or —C(O)C$_{1-6}$-alkenyl, wherein each of the $C_{1-6}$-alkyl, $C_{2-4}$alkenyl, $C_{2-4}$alkynyl, and $C_{1-6}$-alkyl portion of —CH$_2$OC$_{1-6}$-alkyl, —OC$_{1-6}$-alkyl, —S(O)$_o$C$_{1-6}$-alkyl, —NHC$_{1-6}$-alkyl, C(O)C$_{1-6}$-alkyl, —C(O)C$_{1-6}$-alkenyl, —CH=CHC(O)NHC$_{1-6}$-alkyl and $C_{1-6}$-alkyl-C(O)NHC$_{1-6}$-alkyl, are optionally substituted with 1-4 substituents of F, CN, oxo or OH;

$R^3$ is $C_{1-4}$alkyl, CH$_2$OC$_{1-4}$alkyl, CH$_2$OH, $C_{1-4}$haloalkyl or cyclopropyl, wherein each of the $C_{1-4}$alkyl, CH$_2$OC$_{1-4}$alkyl, $C_{1-4}$haloalkyl and cyclopropyl is optionally substituted with 1-4 F atoms;

each of $R^4$, $R^5$, $R^6$ and $R^8$, independently, is H, halo, haloalkyl, haloalkoxyl, $C_{1-4}$-alkyl, CN, OH, OC$_{1-4}$-alkyl, S(O)$_o$C$_{1-4}$-alkyl, NHC$_{1-4}$-alkyl, C(O)C$_{1-4}$-alkyl, C(O) OC$_{1-4}$-alkyl, or CH$_2$OH;

$R^7$ is —NH—$R^9$ or —NH—C(=O)—$R^9$;

$R^9$ is a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the ring is optionally substituted, independently, with 1-5 substituents of $R^{10}$;

each $R^{10}$, independently, is H, halo, haloalkyl, CN, OH, $NO_2$, $NH_2$, $SF_5$, acetyl, —C(O)NHC$_{1-6}$-alkyl, —OCH$_2$C(O) NHC$_{1-6}$-alkyl, —OCH$_2$C(O)N(C$_{1-6}$-alkyl)$_2$, —OCH$_2$CH$_2$-pyrollidinonyl, oxo, cyclopropylmethoxy, 2-propynyloxy, 2-butynyloxy, 3-butynyloxy, 3-pentynyloxy, 2-pentyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, —OC$_2$-C$_6$alkenyl, $C_{1-6}$thioalkoxyl, —OCH$_2$C$_{3-6}$cycloalkyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl, dioxolyl, —O-heterocyclyl, or —OCH$_2$-heteroaryl, wherein the heterocyclyl of the —O-heterocyclyl group is a 3-, 4-, 5-, 6- or 7-membered monocyclic saturated ring that includes 1 heteroatom selected from N, O, or S if the heterocyclyl ring is a 3-membered ring, that includes 1 or 2 heteroatoms independently selected from N, O, or S if the heterocyclyl ring is a 4- or 5-membered ring, and includes 1, 2, or 3 heteroatoms independently selected from N, O, or S if the heterocyclyl ring is a 6- or 7-membered ring wherein the heteroaryl group of the —OCH$_2$-heteroaryl group is a 5- or 6-membered ring that includes 1, 2, 3, or 4 heteroatoms selected from N, O, or S, and further wherein each of the cyclopropylmethoxy, 2-propynyloxy, 2-butynyloxy, 2-pentyloxy, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, —OCH$_2$C$_{3-6}$cycloalkyl, morpholinyl, pyrazolyl, isoxazolyl, dihydropyranyl, pyrrolidinyl, oxetan-3-yl, dioxolyl, or —OCH$_2$-heteroaryl is optionally substituted independently with 1-5 substituents of F, Cl, Br, CN, NO$_2$, NH$_2$, OH, oxo, CF$_3$, CHF$_2$, CH$_2$F, methyl, methoxy, ethyl, ethoxy, CH$_2$CF$_3$, CH$_2$CHF$_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, phenyl, C$_{1-3}$alkylamino-, C$_{1-3}$dialkylamino, C$_{1-3}$thioalkoxyl, oxazolyl, isoxazolyl, thiazolyl, isothiazolyl, thiadiazolyl, thienyl, furyl, pyrrolyl, tetrahydropyranyl, tetrahydropyrrolyl, oxetan-2-yl, or oxetan-3yl; and the subscript o is selected from 0, 1, or 2.

In some embodiments of the alternative embodiment 1, the invention provides compounds according to alternative embodiment 1, or a stereoisomer or pharmaceutically acceptable salt thereof wherein R$^1$ is a —CH$_2$-heteroaryl or a heteroaryl and the heteroaryl groups of the —CH$_2$-heteroaryl and heteroaryl is selected from triazolyl, oxazolyl, or isoxazolyl optionally substituted with 1 or 2 methyl groups. In some such embodiments, R$^{10}$ is a —OCH$_2$-heteroaryl and the heteroaryl group of the —OCH$_2$-heteroaryl is selected from an oxadiazolyl, thiadiazolyl, oxazolyl, thiazolyl, pyridinyl, or pyrimidinyl optionally substituted independently with 1 or 2 F, Cl, Br, or methyl groups.

In some embodiments of the alternative embodiment 1, the invention provides compounds according to alternative embodiment 1, or a stereoisomer or pharmaceutically acceptable salt thereof wherein, R$^{10}$ is a —OCH$_2$-heteroaryl and the heteroaryl group of the —OCH$_2$-heteroaryl is selected from an oxadiazolyl, thiadiazolyl, oxazolyl, isoxazolyl, thiazolyl, pyridinyl, or pyrimidinyl optionally substituted independently with 1 or 2 F, Cl, Br, or methyl groups.

In embodiment 2, the invention provides compounds according to embodiment 1, or a stereoisomer or pharmaceutically acceptable salt thereof, wherein each of R$^1$ and R$^2$, independently, is H, F, CH$_3$, CH$_2$OCH$_3$, CH$_2$F, CHF$_2$, CF$_3$, —C(O)NH$_2$, —CH=CHC(O)NHC$_{1-6}$alkyl, —CH=CHC(O)$_2$H, —CH=CHCH$_2$OH or C$_{1-6}$-alkyl-C(O)NHC$_{1-6}$-alkyl.

In embodiment 3, the invention provides compounds according to any one of embodiments 1 and 2, or a stereoisomer or pharmaceutically acceptable salt thereof, wherein each of R$^a$ and R$^b$, independently, is H, F, CH$_3$, CH$_2$F, CHF$_2$ or CF$_3$.

In embodiment 4, the invention provides compounds according to any one of embodiments 1, 2 and 3, or a stereoisomer or pharmaceutically acceptable salt thereof, wherein each of R$^1$ and R$^2$, independently, is H, F, CH$_2$OCH$_3$, or CF$_3$.

In embodiment 5, the invention provides compounds according to any one of embodiments 1-4, or a stereoisomer or pharmaceutically acceptable salt thereof, wherein each of R$^a$ and R$^b$, independently, is H or F.

In embodiment 6, the invention provides compounds according to any one of embodiments 1-5, or a stereoisomer or pharmaceutically acceptable salt thereof, wherein each of H, F, CH$_2$OCH$_3$, or CF$_3$; and each of R$^a$ and R$^b$, independently, is H or F.

In embodiment 6a, the invention provides compounds according to any one of embodiments 1-5, or a stereoisomer or pharmaceutically acceptable salt thereof, wherein each of H or CH$_2$OCH$_3$; and each of R$^a$ and R$^b$, independently, is H.

In embodiment 7, the invention provides compounds according to any one of embodiments 1-6, or a stereoisomer or pharmaceutically acceptable salt thereof, wherein each of R$^1$, R$^2$, R$^a$ and R$^b$, independently, is H.

In embodiment 8, the invention provides compounds according to any one of embodiments 1-7, or a stereoisomer or pharmaceutically acceptable salt thereof, wherein R$^3$ is CH$_3$, CF$_3$, CH$_2$F or CHF$_2$.

In embodiment 9, the invention provides compounds according to any one of embodiments 1-8, or a stereoisomer or pharmaceutically acceptable salt thereof, wherein R$^7$ is —NH—C(=O)—R$^9$;

or R$^7$ is

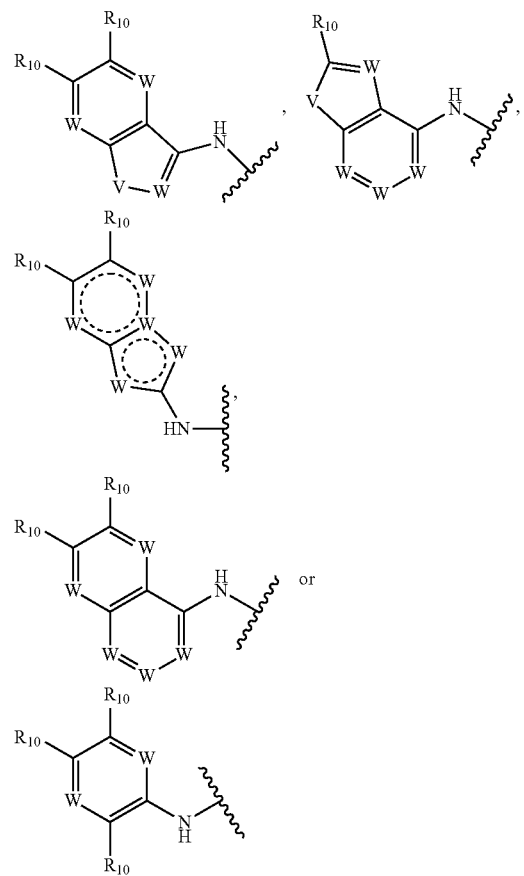

wherein V is NR$^{10}$, O or S; and
each W, independently, is CH, CF, CCl, CCH$_3$ or N.

In embodiment 10, the invention provides compounds according to any one of embodiments 1 and 9, or a stereoisomer or pharmaceutically acceptable salt thereof, wherein
A$^4$ is CR$^4$ or N;
A$^5$ is CR$^5$ or N;
A$^6$ is CR$^6$ or N;
A$^8$ is CR$^8$ or N, provided that no more than one of A$^4$, A$^5$, A$^6$ and A$^8$ is N;
each of R$^a$ and R$^b$, independently, is H, F, Cl, CF$_3$, OCF$_3$, methyl, ethyl, CN, OH, OCH$_3$, SCH$_3$, NHCH$_3$, C(O)CH$_3$ or CH$_2$OCHF$_2$;

each of $R^1$ and $R^2$, independently, is H, F, Cl, CF$_3$, OCF$_3$, methyl, ethyl, CN, OH, OCH$_3$, SCH$_3$, NHCH$_3$, C(O)CH$_3$, CH$_2$OCH$_3$ or CH$_2$OCHF$_2$;

$R^3$ is C$_{1-4}$alkyl, C$_{1-4}$haloalkyl, CH$_2$OH, CH$_2$OCHF$_2$ or cyclopropyl; and each of $R^4$, $R^5$, $R^6$ and $R^8$, independently, is H, F, Cl, CF$_2$H, CH$_2$F, CF$_3$, OCF$_3$, methyl, ethyl, CN, OH, OCH$_3$, SCH$_3$, NHCH$_3$ or C(O)CH$_3$.

In embodiment 11, the invention provides compounds according to any one of embodiments 1-9, or a stereoisomer or pharmaceutically acceptable salt thereof, wherein each of $R^1$ and $R^2$, independently, is H, F, CH$_2$OCH$_3$ or CF$_3$;

each of $R^a$ and $R^b$, independently, is H or F;

$R^3$ is CH$_3$, CF$_3$, CH$_2$F or CHF$_2$; and $R^7$ is —NH—C(=O)—$R^9$ or

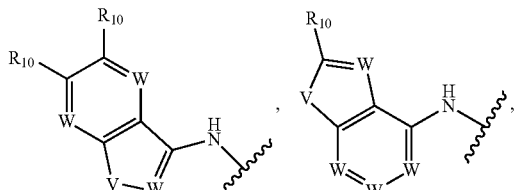

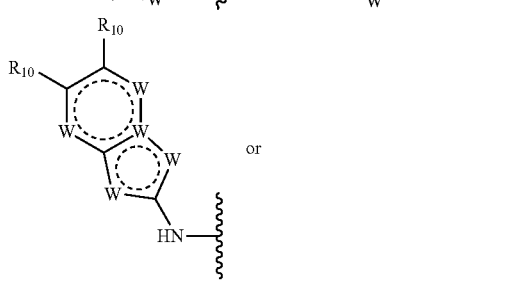

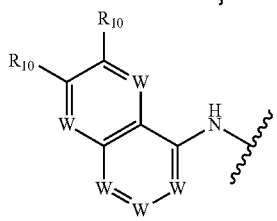

wherein V is NR$^{10}$, O or S; and each W, independently, is CH, CF, CCl, CCH$_3$ or N.

In embodiment 12, the invention provides compounds according to any one of embodiments 1-11, or a stereoisomer or pharmaceutically acceptable salt thereof, wherein $R^7$ is —NH—C(=O)—$R^9$.

In embodiment 13, the invention provides compounds according to any one of embodiments 1-11, or a stereoisomer or pharmaceutically acceptable salt thereof, wherein $R^7$ is

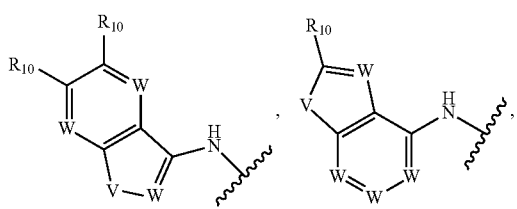

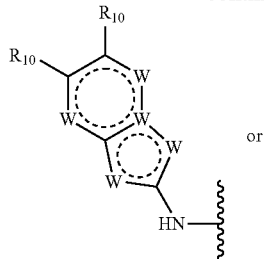

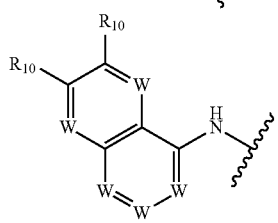

wherein V is NR$^{10}$, O or S; and each W, independently, is CH, CF, CCl, CCH$_3$ or N.

In embodiment 14, the invention provides compounds according to any one of embodiments 1-13, or a stereoisomer or pharmaceutically acceptable salt thereof, wherein $A^4$ is CR$^4$;

$A^5$ is CR$^5$ or N;

$A^6$ is CR$^6$; and $A^8$ is CR$^8$ or N, provided only one of $A^5$ and $A^8$ is N, and wherein each of $R^4$, $R^5$, $R^6$ and $R^8$, independently, is H, F, Cl, CF$_3$, CF$_2$H, CH$_2$F or CH$_3$.

In embodiment 15, the invention provides compounds, including stereoisomers, tautomers, hydrates, solvates and pharmaceutically acceptable salts thereof, which are generally defined by Formula I:

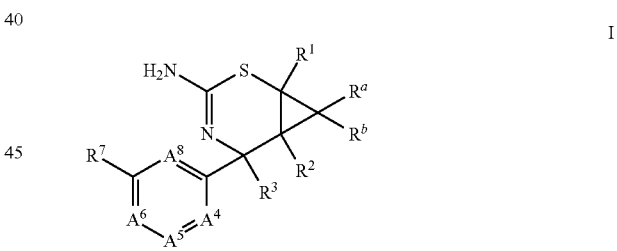

or a stereoisomer, tautomer, hydrate, solvate or pharmaceutically acceptable salt thereof, wherein $A^4$ is CH, CF or CCl;

$A^5$ is CH, CF, CCl, CCH$_3$ or N;

$A^6$ is CH or CF;

$A^8$ is CH, CF or N, provided that no more than one of $A^5$ and $A^8$ is N;

each of $R^1$ and $R^2$, independently, is H, F, CH$_3$, CH$_2$OCH$_3$, CH$_2$F, CHF$_2$ or CF$_3$;

each of $R^a$ and $R^b$, independently, is H, F, CH$_3$, CH$_2$F, CHF$_2$ or CF$_3$;

$R^3$ is C$_{1-4}$alkyl, CH$_2$OC$_{1-4}$alkyl, CH$_2$OH, C$_{1-4}$haloalkyl or cyclopropyl, wherein each of the C$_{1-4}$alkyl, CH$_2$OC$_{1-4}$alkyl, C$_{1-4}$haloalkyl and cyclopropyl is optionally substituted with 1-4 F atoms;

R⁷ is —NH—R⁹ or —NH—C(=O)—R⁹;
or R⁷ is

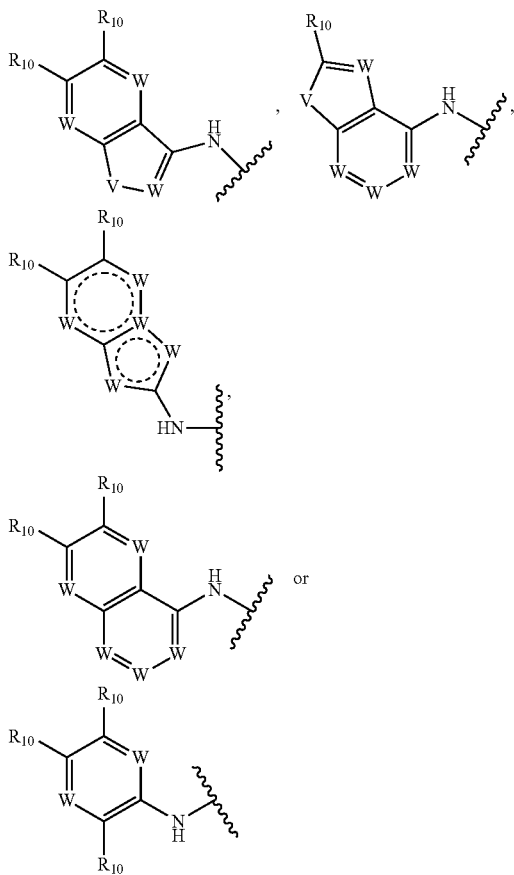

wherein V is NR¹⁰, O or S; and
each W, independently, is CH, CF, CCl, CCH₃ or N;
R⁹ is a ring selected from phenyl, pyridyl, pyrimidyl, pyrazinyl, pyridazinyl, pyrazolyl, pyrazolo[3,4-c]pyridinyl, oxazolyl, isoxazolyl, thiazolyl, isothiazolyl or thienyl, wherein the ring is optionally substituted with 1-5 substituents of R¹⁰; and each R¹⁰, independently, is H, halo, haloalkyl, CN, OH, NO₂, NH₂, SF₅, acetyl, —C(O)NHCH₃, oxo, cyclopropylmethoxy, 2-propynyloxy, 2-butynyloxy, C₁₋₆alkyl, C₂₋₆alkenyl, C₂₋₆alkynyl, C₃₋₆cycloalkyl, C₁₋₆alkylamino-, C₁₋₆dialkylamino-, C₁₋₆alkoxyl, C₁₋₆thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazopyridinyl or dioxolyl, wherein each of the cyclopropylmethoxy, 2-propynyloxy, 2-butynyloxy, C₁₋₆alkyl, C₂₋₆alkenyl, C₂₋₆alkynyl, C₃₋₆cycloalkyl, C₁₋₆alkylamino-, C₁₋₆dialkylamino-, C₁₋₆alkoxyl, C₁₋₆thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO₂, NH₂, OH, oxo, CF₃, CHF₂, CH₂F, methyl, methoxy, ethyl, ethoxy, CH₂CF₃, CH₂CHF₂, propyl, propoxy, isopropyl, isopropoxy, cyclopropyl, butyl, butoxyl, cyclobutyl, isobutoxy, tert-butoxyl, isobutyl, sec-butyl, tert-butyl, cyclopentyl, cyclohexyl, C₁₋₃alkylamino-, C₁₋₃dialkylamino, C₁₋₃thioalkoxyl, oxazolyl, isoxazolyl, thiazolyl, isothiazolyl, thiadiazolyl, thienyl, furyl, pyrrolyl, tetrahydropyranyl, tetrahydropyrrolyl or oxetan-3yl.

In embodiment 16, the invention provides compounds, including stereoisomers, tautomers, hydrates, solvates and pharmaceutically acceptable salts thereof, which are generally defined by Formula II:

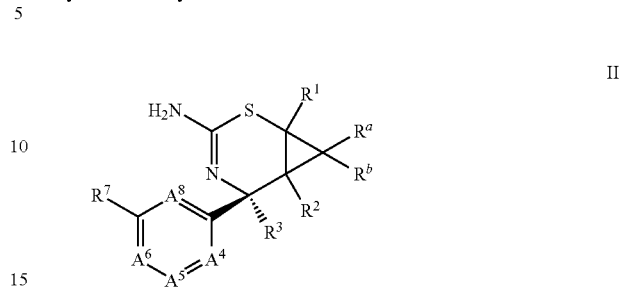

II wherein

A⁴ is CR⁴ or N;

A⁵ is CR⁵ or N;

A⁶ is CR⁶ or N;

A⁸ is CR⁸ or N, provided that no more than two of A⁴, A⁵, A⁶ and A⁸ is N;

each of $R^a$ and $R^b$, independently, is H, F, Cl, C₁₋₆-alkyl, C₂₋₄alkenyl, C₂₋₄alkynyl, CN, —CH₂OC₁₋₆-alkyl, —OC₁₋₆-alkyl, —S(O)ₒC₁₋₆-alkyl, —NHC₁₋₆-alkyl or —C(O)C₁₋₆-alkyl, wherein each of the C₁₋₆-alkyl, C₂₋₄alkenyl, C₂₋₄alkynyl, and C₁₋₆-alkyl portion of —CH₂OC₁₋₆-alkyl, —OC₁₋₆-alkyl, —S(O)ₒC₁₋₆-alkyl, —NHC₁₋₆-alkyl and —C(O)C₁₋₆-alkyl are optionally substituted with 1-4 substituents of F, oxo or OH;

each of R¹ and R², independently, is H, F, Cl, C₁₋₆-alkyl, C₂₋₄alkenyl, C₂₋₄alkynyl, CN, —CH₂OC₁₋₆-alkyl, —OC₁₋₆-alkyl, —S(O)ₒC₁₋₆-alkyl, —NHC₁₋₆-alkyl, —C(O)NH₂, —CH=CHC(O)NHC₁₋₆-alkyl, —CH=CHC(O)₂H, —CH=CHCH₂OH, C₁₋₆-alkyl-C(O)NHC₁₋₆-alkyl, —C(O)C₁₋₆-alkyl or —C(O)C₁₋₆-alkenyl, wherein each of the C₁₋₆-alkyl, C₂₋₄alkenyl, C₂₋₄alkynyl, and C₁₋₆-alkyl portion of —CH₂OC₁₋₆-alkyl, —OC₁₋₆-alkyl, —S(O)ₒC₁₋₆-alkyl, —NHC₁₋₆-alkyl, C(O)C₁₋₆-alkyl, —C(O)C₁₋₆-alkenyl, —CH=CHC(O)NHC₁₋₆-alkyl and C₁₋₆-alkyl-C(O)NHC₁₋₆-alkyl, are optionally substituted with 1-4 substituents of F, CN, oxo or OH;

R³ is C₁₋₄alkyl, CH₂OC₁₋₄alkyl, CH₂OH, C₁₋₄haloalkyl or cyclopropyl, wherein each of the C₁₋₄alkyl, CH₂OC₁₋₄alkyl, C₁₋₄haloalkyl and cyclopropyl is optionally substituted with 1-4 F atoms;

each of R⁴, R⁵, R⁶ and R⁸, independently, is H, halo, haloalkyl, haloalkoxyl, C₁₋₄-alkyl, CN, OH, OC₁₋₄-alkyl, S(O)ₒC₁₋₄-alkyl, NHC₁₋₄-alkyl or C(O)C₁₋₄-alkyl;

R⁷ is —NH—C(=O)—R⁹;
or R⁷ is

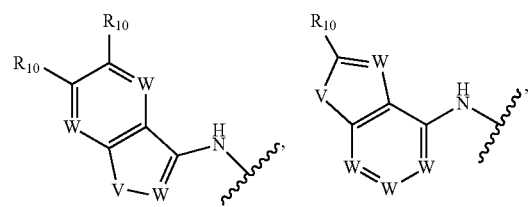

-continued

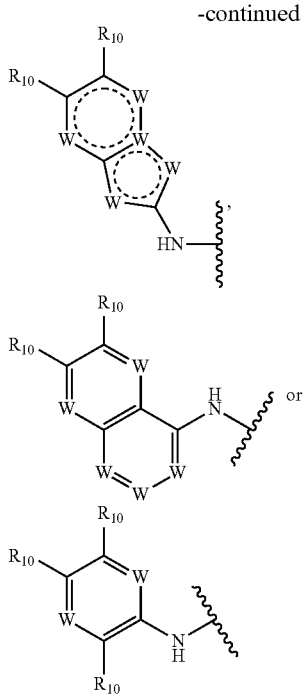

wherein V is NR$^{10}$, O or S; and
each W, independently, is CH, CF, CCl, CCH$_3$ or N;
R$^9$ is a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein ring is optionally substituted, independently, with 1-5 substituents of R$^{10}$;
each R$^{10}$, independently, is H, halo, haloalkyl, CN, OH, NO$_2$, NH$_2$, SF$_5$, acetyl, —C(O)NHCH$_3$, oxo, cyclopropylmethoxy, 2-propynyloxy, 2-butynyloxy, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazopyridinyl or dioxolyl, wherein each of the cyclopropylmethoxy, 2-propynyloxy, 2-butynyloxy, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO$_2$, NH$_2$, OH, oxo, CF$_3$, CHF$_2$, CH$_2$F, methyl, methoxy, ethyl, ethoxy, CH$_2$CF$_3$, CH$_2$CHF$_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, C$_{1-3}$alkylamino-, C$_{1-3}$dialkylamino, C$_{1-3}$thioalkoxyl, oxazolyl, isoxazolyl, thiazolyl, isothiazolyl, thiadiazolyl, thienyl, furyl, pyrrolyl, tetrahydropyranyl, tetrahydropyrrolyl or oxetan-3yl; and
the subscript o is selected from 0, 1, or 2.

In embodiment 17, the invention provides compounds according any one of embodiments 1 and 16, or a stereoisomer, tautomer or pharmaceutically acceptable salt thereof, wherein
A$^4$ is CR$^4$ or N;
A$^5$ is CR$^5$ or N;
A$^6$ is CR$^6$ or N;
A$^8$ is CR$^8$ or N, provided no more than one of A$^4$, A$^5$, A$^6$ and A$^8$ is N;
each of R$^a$ and R$^b$, independently, is H, F, CH$_3$, CH$_2$F, CHF$_2$ or CF$_3$;
each of R$^1$ and R$^2$, independently, is H, F, CH$_3$, CH$_2$OCH$_3$, CH$_2$F, CHF$_2$ or CF$_3$;
R$^3$ is C$_{1-4}$alkyl, C$_{1-4}$haloalkyl, CH$_2$OH, CH$_2$OCHF$_2$ or cyclopropyl; and
each of R$^4$, R$^5$, R$^6$ and R$^8$, independently, is H, F, Cl, CF$_2$H, CH$_2$F, CF$_3$, OCF$_3$, methyl, ethyl, CN, OH, OCH$_3$, SCH$_3$, NHCH$_3$ or C(O)CH$_3$.

In embodiment 18, the invention provides compounds according to any one of embodiments 1-6, 7 and 16-17, or a stereoisomer or pharmaceutically acceptable salt thereof, wherein
A$^4$ is CR$^4$;
A$^5$ is CR$^5$;
A$^6$ is CR$^6$; and
A$^8$ is CR$^8$; wherein each of R$^4$, R$^5$, R$^6$ and R$^8$, independently, is H, F, Cl, CF$_3$, CF$_2$H, CH$_2$F or CH$_3$;
R$^3$ is CH$_3$, CF$_3$, CH$_2$F or CHF$_2$; and
R$^7$ is —NH—C(=O)—R$^9$ or wherein V is NR$^{10}$, O or S; and
each W, independently, is CH, CF, CCl or N.

In embodiment 19, the invention provides compounds according to any one of embodiments 16-17, or a stereoisomer or pharmaceutically acceptable salt thereof, wherein R$^7$ is —NH—C(=O)—R$^9$.

In embodiment 20, the invention provides compounds according to any one of embodiments 16-18, or a stereoisomer or pharmaceutically acceptable salt thereof, wherein R$^7$ is

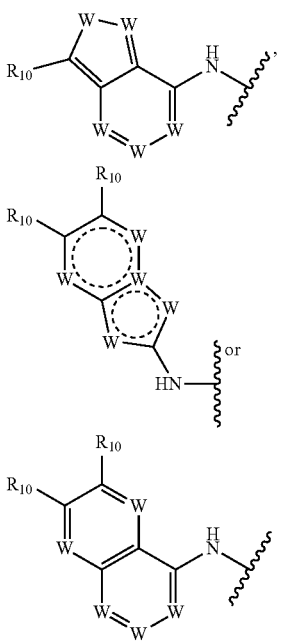

wherein V is NR[10], O or S; and
each W, independently, is CH, CF, CCl, CCH$_3$ or N.

In embodiment 21, the invention provides compounds according to any one of embodiments 16-20, or a stereoisomer or pharmaceutically acceptable salt thereof, wherein each of H, F, CH$_2$OCH$_3$ or CF$_3$; and each of R$^a$ and R$^b$, independently, is H or F.

In embodiment 22, the invention provides compounds according to any one of embodiments 1-12, or a stereoisomer or pharmaceutically acceptable salt thereof, having a Formula I-A

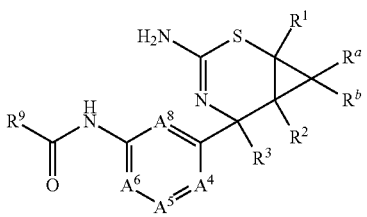

wherein
A$^4$ is CR$^4$ or N;
A$^5$ is CR$^5$ or N;
A$^6$ is CR$^6$ or N;
A$^8$ is CR$^8$ or N, provided that no more than one of A$^4$, A$^5$, A$^6$ and A$^8$ is N;
each of R$^a$ and R$^b$, independently, is H, F, Cl, C$_{1-6}$-alkyl, C$_{2-4}$alkenyl, C$_{2-4}$alkynyl, CN, —CH$_2$OC$_{1-6}$-alkyl, —OC$_{1-6}$-alkyl, —S(O)$_o$C$_{1-6}$-alkyl, —NHC$_{1-6}$-alkyl or —C(O)C$_{1-6}$-alkyl, wherein each of the C$_{1-6}$-alkyl, C$_{2-4}$alkenyl, C$_{2-4}$alkynyl, and C$_{1-6}$-alkyl portion of —CH$_2$OC$_{1-6}$-alkyl, —OC$_{1-6}$-alkyl, —S(O)$_o$C$_{1-6}$-alkyl, —NHC$_{1-6}$-alkyl and —C(O)C$_{1-6}$-alkyl are optionally substituted with 1-4 substituents of F, oxo or OH;
each of R$^1$ and R$^2$, independently, is H, F, Cl, C$_{1-6}$-alkyl, C$_{2-4}$alkenyl, C$_{2-4}$alkynyl, CN, —CH$_2$OC$_{1-6}$-alkyl, —OC$_{1-6}$-alkyl, —S(O)$_o$C$_{1-6}$-alkyl, —NHC$_{1-6}$-alkyl, —C(O)NH$_2$, —CH=CHC(O)NHC$_{1-6}$-alkyl, —CH=CHC(O)$_2$H, —CH=CHCH$_2$OH, C$_{1-6}$-alkyl-C(O)NHC$_{1-6}$-alkyl, —C(O)C$_{1-6}$-alkyl or —C(O)C$_{1-6}$-alkenyl, wherein each of the C$_{1-6}$-alkyl, C$_{2-4}$alkenyl, C$_{2-4}$alkynyl, and C$_{1-6}$-alkyl portion of —CH$_2$OC$_{1-6}$-alkyl, —OC$_{1-6}$-alkyl, —S(O)$_o$C$_{1-6}$-alkyl, —NHC$_{1-6}$-alkyl, C(O)C$_{1-6}$-alkyl, —C(O)C$_{1-6}$-alkenyl, —CH=CHC(O)NHC$_{1-6}$-alkyl and C$_{1-6}$-alkyl-C(O) NHC$_{1-6}$-alkyl, are optionally substituted with 1-4 substituents of F, CN, oxo or OH;
R$^3$ is C$_{1-4}$alkyl, CH$_2$OC$_{1-4}$alkyl, CH$_2$OH, C$_{1-4}$haloalkyl or cyclopropyl, wherein each of the C$_{1-4}$alkyl, CH$_2$OC$_{1-4}$alkyl, C$_{1-4}$haloalkyl and cyclopropyl is optionally substituted with 1-4 F atoms;
each of R$^4$, R$^5$, R$^6$ and R$^8$, independently, is H, F, Cl or CH$_3$;
R$^9$ is a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the ring is optionally substituted, independently, with 1-5 substituents of R$^{10}$;
each R$^{10}$, independently, is H, halo, haloalkyl, CN, OH, NO$_2$, NH$_2$, SF$_5$, acetyl, —C(O)NHCH$_3$, oxo, cyclopropylmethoxy, 2-propynyloxy, 2-butynyloxy, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazopyridinyl or dioxolyl, wherein each of the cyclopropylmethoxy, 2-propynyloxy, 2-butynyloxy, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO$_2$, NH$_2$, OH, oxo, CF$_3$, CHF$_2$, CH$_2$F, methyl, methoxy, ethyl, ethoxy, CH$_2$CF$_3$, CH$_2$CHF$_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, C$_{1-3}$alkylamino-, C$_{1-3}$dialkylamino, C$_{1-3}$thioalkoxyl, oxazolyl, isoxazolyl, thiazolyl, isothiazolyl, thiadiazolyl, thienyl, furyl, pyrrolyl, tetrahydropyranyl, tetrahydropyrrolyl or oxetan-3yl; and
the subscript o is selected from 0, 1, or 2.

In embodiment 23, the invention provides compounds according to any one of embodiments 1-3, 8-20 and 22, or a stereoisomer, tautomer or pharmaceutically acceptable salt thereof, wherein
A$^4$ is CR$^4$;
A$^5$ is CR$^5$;
A$^6$ is CR$^6$;
A$^8$ is CR$^8$; wherein each of R$^4$, R$^5$, R$^6$ and R$^8$, independently, is H, F, Cl, CF$_2$H, CH$_2$F, CF$_3$, OCF$_3$, methyl, ethyl, CN, OH, OCH$_3$, SCH$_3$, NHCH$_3$ or C(O)CH$_3$;
each of R$^a$ and R$^b$, independently, is H, F, CH$_3$, CH$_2$F, CHF$_2$ or CF$_3$;
each of R$^1$ and R$^2$, independently, is H, F, CH$_3$, CH$_2$OCH$_3$, CH$_2$F, CHF$_2$ or CF$_3$;
R$^3$ is CH$_3$, C$_2$H$_5$, CF$_2$H or CH$_2$F;
R$^9$ is a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the ring is optionally substituted, independently, with 1-5 substituents of R$^{10}$; and each $R^{10}$, independently, is H, halo, haloalkyl, CN, OH, $NO_2$, $NH_2$, $SF_5$, acetyl, —C(O)$NHCH_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazopyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl, oxazolyl, isoxazolyl, thiazolyl, isothiazolyl, thiadiazolyl, thienyl, furyl, pyrrolyl, tetrahydropyranyl, tetrahydropyrrolyl or oxetan-3yl.

In embodiment 24, the invention provides compounds according to any one of embodiments 1-19 and 22-23, or a stereoisomer or pharmaceutically acceptable salt thereof, wherein $A^4$ is $CR^4$ or N;
$A^5$ is $CR^5$ or N;
$A^6$ is $CR^6$ or N;
$A^8$ is $CR^8$ or N, wherein each of $R^4$, $R^5$, $R^6$ and $R^8$, independently, is H, F, Cl or $CH_3$, provided no more than one of $A^4$, $A^5$, $A^6$ and $A^8$ is N;
each of $R^1$, $R^2$, $R^a$ and $R^b$, independently, is H; and
$R^3$ is $CF_3$, $CH_3$, $CF_2H$ or $CH_2F$.

In embodiment 25, the invention provides compounds according to any one of embodiments 1-12, 16-19 and 22-24, or a stereoisomer or pharmaceutically acceptable salt thereof, having a Formula II-A

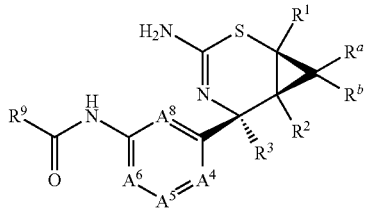

II-A wherein
$A^4$ is $CR^4$, wherein $R^4$ is H, F or Cl;
$A^5$ is $CR^5$ or N, wherein $R^5$ is H, F, Cl or $CH_3$;
$A^6$ is CH;
$A^8$ is $CR^8$ or N, wherein $R^8$ is H or F,
provided that no more than one of $A^5$ and $A^8$ is N;
each of $R^1$ and $R^2$, independently, is H, F, $CH_2OCH_3$ or $CF_3$;
each of $R^a$ and $R^b$, independently, is H or F;
$R^3$ is $CH_3$, $CF_3$, $CH_2F$ or $CHF_2$;
$R^9$ is a fully unsaturated 5- or 6-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the ring is optionally substituted, independently, with 1-5 substituents of $R^{10}$; and each $R^{10}$, independently, is H, halo, haloalkyl, CN, OH, $NO_2$, $NH_2$, $SF_5$, acetyl, —C(O)$NHCH_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazopyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl, oxazolyl, isoxazolyl, thiazolyl, isothiazolyl, thiadiazolyl, thienyl, furyl, pyrrolyl, tetrahydropyranyl, tetrahydropyrrolyl or oxetan-3yl.

In embodiment 26, the invention provides compounds according to embodiment 25, or a stereoisomer or pharmaceutically acceptable salt thereof, wherein each of $R^a$, $R^b$, $R^1$ and $R^2$, independently, is H.

In embodiment 27, the invention provides compounds according ng any one of embodiments 25 and 26, or a stereoisomer or pharmaceutically acceptable salt thereof, wherein $R^3$ is $CH_3$, $CH_2F$ or $CHF_2$.

In embodiment 28, the invention provides compounds according to any one of embodiments 25-27, or a stereoisomer or pharmaceutically acceptable salt thereof, wherein $R^3$ is $CH_2F$ or $CHF_2$.

In embodiment 29, the invention provides compounds according to any one of embodiments 25-28, or a stereoisomer or pharmaceutically acceptable salt thereof, wherein $R^3$ is $CH_2F$.

In embodiment 30, the invention provides compounds according to any one of embodiments 25-28, or a stereoisomer or pharmaceutically acceptable salt thereof, wherein $R^3$ is $CHF_2$.

In embodiment 31, the invention provides compounds according to any one of embodiments 25-30, or a stereoisomer or pharmaceutically acceptable salt thereof, wherein $A^4$ is CF or CCl;
$A^5$ is CH, CF, $CH_3$ or N;
$A^6$ is CH; and
$A^8$ is CH.

In embodiment 32, the invention provides compounds according to any one of embodiments 25-31, or a stereoisomer or pharmaceutically acceptable salt thereof, wherein $A^4$ is CF; $A^5$ is CH, CF or N;
$A^6$ is CH; and
$A^8$ is CH.

In embodiment 33, the invention provides compounds according to any one of embodiments 25-31, or a stereoisomer or pharmaceutically acceptable salt thereof, wherein $A^4$ is CCl;
$A^5$ is CH or CF;
$A^6$ is CH; and
$A^8$ is CH.

In embodiment 34, the invention provides compounds according to any one of embodiments 25-33, or a stereoisomer or pharmaceutically acceptable salt thereof, wherein $R^9$ is a ring selected from phenyl, pyridyl, pyrimidyl, pyrazinyl, pyridazinyl, pyrazolyl, pyrazolo[3,4-c]pyridinyl, oxazolyl, isoxazolyl, thiazolyl, isothiazolyl or thienyl, wherein the ring is optionally substituted with 1-5 substituents of $R^{10}$; and each $R^{10}$, independently, is H, halo, haloalkyl, CN, OH, $NO_2$, $NH_2$, $SF_5$, acetyl, —C(O)NHCH$_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl, oxazolyl, isoxazolyl, thiazolyl, isothiazolyl, thiadiazolyl, thienyl, furyl, pyrrolyl, tetrahydropyranyl, tetrahydropyrrolyl or oxetan-3yl.

In embodiment 35, the invention provides compounds according to any one of embodiments 25-33, or a stereoisomer or pharmaceutically acceptable salt thereof, wherein $R^9$ is a ring selected from pyridyl, pyrimidyl, pyrazinyl, pyridazinyl, pyrazolyl, pyrazolo[3,4-c]pyridinyl, oxazolyl, isoxazolyl, thiazolyl, isothiazolyl or thienyl, wherein the ring is optionally substituted with 1-5 substituents of $R^{10}$.

In embodiment 36, the invention provides compounds according to any one of embodiments 25-35 or a stereoisomer or pharmaceutically acceptable salt thereof, wherein $R^9$ is

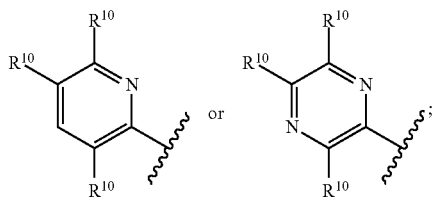

and each $R^{10}$, independently, is H, F, Cl, Br, $CF_3$, $CHF_2$, $CH_2F$, CN, OH, —C(O)NHCH$_3$, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkoxyl or $C_{1-6}$thioalkoxyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkoxyl and $C_{1-6}$thioalkoxyl is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl, oxazolyl or thiazolyl.

In embodiment 37, the invention provides compounds according to any one of embodiments 25-36, or a stereoisomer or pharmaceutically acceptable salt thereof, wherein $R^3$ is $CHF_2$; and $R^9$ is

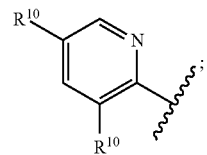

and each $R^{10}$, independently, is H, F, Cl, Br, $CH_3$, $CHF_2$, $CH_2F$, CN, 2-propynyloxy, 2-butynyloxy or $C_{1-2}$alkoxyl, wherein the $C_{1-2}$alkoxyl is optionally substituted independently with 1-5 substituents of F, Cl, methyl, methoxy, ethyl, ethoxy, oxazolyl or thiazolyl.

In embodiment 38, the invention provides compounds according to any one of embodiments 25-36, or a stereoisomer or pharmaceutically acceptable salt thereof, wherein $R^3$ is $CH_2F$; and $R^9$ is

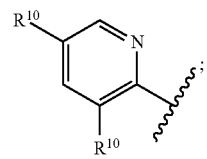

and each $R^{10}$, independently, is H, F, Cl, Br, $CH_3$, $CHF_2$, $CH_2F$, CN, 2-propynyloxy, 2-butynyloxy or $C_{1-2}$alkoxyl, wherein the $C_{1-2}$alkoxyl is optionally substituted independently with 1-5 substituents of F, Cl, methyl, methoxy, ethyl, ethoxy, oxazolyl or thiazolyl.

In embodiment 39, the invention provides compounds according to any one of embodiments 25-36, or a stereoisomer or pharmaceutically acceptable salt thereof, wherein $R^3$ is $CHF_2$; and $R^9$ is

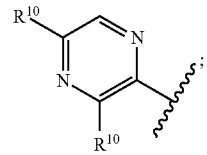

and each $R^{10}$, independently, is H, F, Cl, Br, $CH_3$, $CHF_2$, $CH_2F$, CN, 2-propynyloxy, 2-butynyloxy or $C_{1-2}$alkoxyl, wherein the $C_{1-2}$alkoxyl is optionally substituted independently with 1-5 substituents of F, Cl, methyl, methoxy, ethyl, ethoxy, oxazolyl or thiazolyl.

In embodiment 40, the invention provides compounds according to any one of embodiments 25-36, or a stereoisomer or pharmaceutically acceptable salt thereof, wherein $R^3$ is $CH_2F$; and $R^9$ is

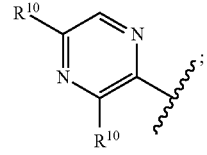

and each $R^{10}$, independently, is H, F, Cl, Br, $CH_3$, $CHF_2$, $CH_2F$, CN, 2-propynyloxy, 2-butynyloxy or $C_{1-2}$alkoxyl, wherein the $C_{1-2}$alkoxyl is optionally substituted independently with 1-5 substituents of F, Cl, methyl, methoxy, ethyl, ethoxy, oxazolyl or thiazolyl.

In embodiment 41, the invention provides compounds according to any one of embodiments 1-11, 13-18 and 20-21, or a stereoisomer, tautomer, hydrate, solvate or pharmaceutically acceptable salt thereof, having a Formula II-B:

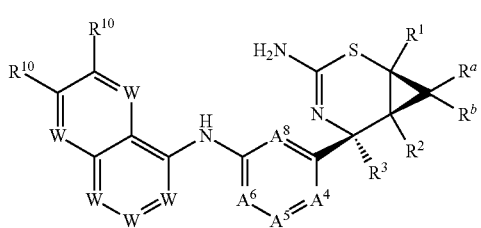

wherein $A^4$ is $CR^4$, wherein $R^4$ is H, F or Cl;
$A^5$ is $CR^5$ or N, wherein $R^5$ is H, F, Cl or $CH_3$;
$A^6$ is CH;
$A^8$ is $CR^8$ or N, wherein $R^8$ is H or F,
provided that no more than one of $A^5$ and $A^8$ is N;

each of $R^1$ and $R^2$, independently, is H, F, $CH_2OCH_3$ or $CF_3$;

each of $R^a$ and $R^b$, independently, is H or F;

$R^3$ is $CH_3$, $CF_3$, $CH_2F$ or $CHF_2$;

$R^9$ is a fully unsaturated 5- or 6-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the ring is optionally substituted, independently, with 1-5 substituents of $R^{10}$; and each $R^{10}$, independently, is H, halo, haloalkyl, CN, OH, $NO_2$, $NH_2$, $SF_5$, acetyl, $—C(O)NHCH_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazopyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl, oxazolyl, isoxazolyl, thiazolyl, isothiazolyl, thiadiazolyl, thienyl, furyl, pyrrolyl, tetrahydropyranyl, tetrahydropyrrolyl or oxetan-3yl; and each W, independently, is CH, CF, CCl, $CCH_3$ or N.

In embodiment 42, the invention provides compounds according to embodiment 40, or a stereoisomer or pharmaceutically acceptable salt thereof, wherein each of $R^a$, $R^b$, $R^1$ and $R^2$, independently, is H.

In embodiment 43, the invention provides compounds according to any one of embodiments 41 and 42, or a stereoisomer or pharmaceutically acceptable salt thereof, wherein $R^3$ is $CH_3$, $CH_2F$ or $CHF_2$.

In embodiment 44, the invention provides compounds according to any one of embodiments 41-43, or a stereoisomer or pharmaceutically acceptable salt thereof, wherein $R^3$ is $CH_2F$ or $CHF_2$.

In embodiment 45, the invention provides compounds according to any one of embodiments 41-44, or a stereoisomer or pharmaceutically acceptable salt thereof, wherein $R^3$ is $CH_2F$.

In embodiment 46, the invention provides compounds according to any one of embodiments 41-44, or a stereoisomer or pharmaceutically acceptable salt thereof, wherein $R^3$ is $CHF_2$.

In embodiment 47, the invention provides compounds according to any one of embodiments 41-46, or a stereoisomer or pharmaceutically acceptable salt thereof, wherein
$A^4$ is CF or CCl;
$A^5$ is CH, CF, $CH_3$ or N;
$A^6$ is CH; and
$A^8$ is CH.

In embodiment 48, the invention provides compounds according to any one of embodiments 41-47, or a stereoisomer or pharmaceutically acceptable salt thereof, wherein
$A^4$ is CF;
$A^5$ is CH, CF or N;
$A^6$ is CH; and
$A^8$ is CH.

In embodiment 49, the invention provides compounds according to any one of embodiments 41-47, or a stereoisomer or pharmaceutically acceptable salt thereof, wherein
$A^4$ is CCl;
$A^5$ is CH or CF;
$A^6$ is CH; and
$A^8$ is CH.

In embodiment 50, the invention provides compounds according to any one of embodiments 41-49 or a stereoisomer or pharmaceutically acceptable salt thereof, wherein

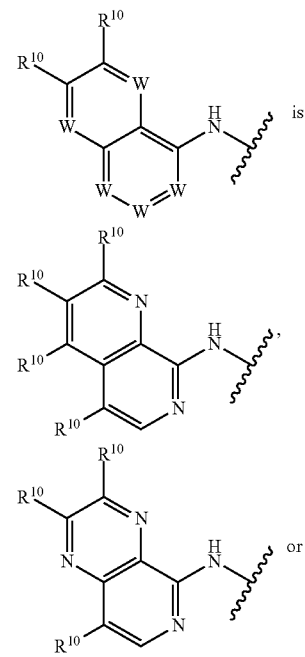

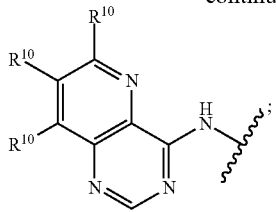

and each $R^{10}$, independently, is H, F, Cl, Br, $CH_3$, $CHF_2$, $CH_2F$, CN, 2-propynyloxy; 2-butynyloxy or $C_{1-2}$alkoxyl, wherein the $C_{1-2}$alkoxyl is optionally substituted independently with 1-5 substituents of F, Cl, methyl, methoxy, ethyl, ethoxy, oxazolyl or thiazolyl.

In embodiment 51, the invention provides compounds, including stereoisomers, tautomers, hydrates, solvates and pharmaceutically acceptable salts thereof, which are generally defined by Formula III:

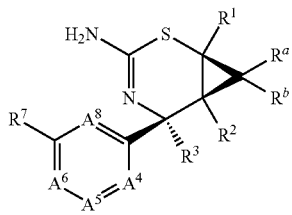

III wherein $A^4$ is $CR^4$;

$A^5$ is $CR^5$ or N;

$A^6$ is $CR^6$;

$A^8$ is $CR^8$ or N, provided that no more than two of $A^5$ and $A^8$ is N;

each of $R^a$ and $R^b$, independently, is H, F, $CH_3$, $CH_2F$, $CHF_2$ or $CF_3$;

each of $R^1$ and $R^2$, independently, is H, F, $CH_3$, $CH_2OCH_3$, $CH_2F$, $CHF_2$ or $CF_3$;

$R^3$ is $CH_3$, $CF_3$, $CH_2F$ or $CHF_2$;

$R^4$ is F or Cl;

$R^5$ is H, F, Cl or $CH_3$;

each of $R^6$ and $R^8$, independently, is H or F;

$R^7$ is —NH—C(=O)—$R^9$, or $R^7$ is

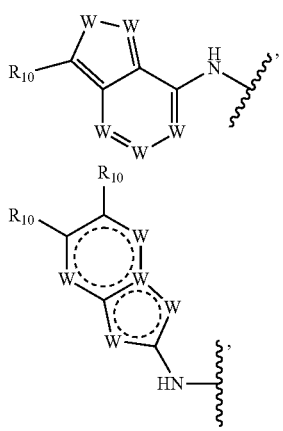

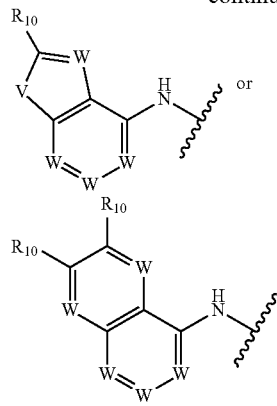

wherein V is $NR^{10}$, O or S; and each W, independently, is CH, CF, CCl, $CCH_3$ or N;

$R^9$ is a ring selected from phenyl, pyridyl, pyrimidyl, pyrazinyl, pyridazinyl, pyrazolyl, pyrazolo[3,4-c]pyridinyl, oxazolyl, isoxazolyl, thiazolyl, isothiazolyl or thienyl, wherein the ring is optionally substituted with 1-5 substituents of $R^{10}$; and each $R^{10}$, independently, is H, halo, haloalkyl, CN, OH, $NO_2$, $NH_2$, $SF_5$, acetyl, —C(O)NHCH$_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl, oxazolyl, isoxazolyl, thiazolyl, isothiazolyl, thiadiazolyl, thienyl, furyl, pyrrolyl, tetrahydropyranyl, tetrahydropyrrolyl or oxetan-3yl.

In embodiment 52, the invention provides compounds including stereoisomers, tautomers, hydrates, solvates and pharmaceutically acceptable salts thereof, according to embodiment 51, which are generally defined by Formula III-A:

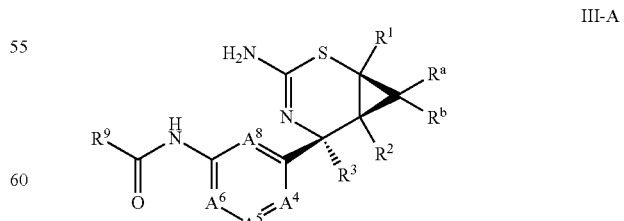

III-A wherein $A^4$ is $CR^4$, wherein $R^4$ is H, F or Cl;

$A^5$ is $CR^5$ or N, wherein $R^5$ is H, F, Cl or $CH_3$;

$A^6$ is CH;

$A^8$ is $CR^8$ or N, wherein $R^8$ is H or F, provided that no more than one of $A^5$ and $A^8$ is N;

each of $R^a$ and $R^b$, independently, is H or F;

each of $R^1$ and $R^2$, independently, is H, $CH_2OCH_3$ or F;

$R^3$ is $CH_3$, $CH_2F$ or $CHF_2$;

$R^9$ is a ring selected from phenyl, pyridyl, pyrimidyl, pyrazinyl, pyrazolyl, pyrazolo[3,4-c]pyridinyl, oxazolyl, isoxazolyl, thiazolyl, isothiazolyl or thienyl, wherein the ring is optionally substituted with 1-5 substituents of $R^{10}$; and each $R^{10}$, independently, is H, halo, haloalkyl, CN, OH, $NO_2$, $NH_2$, $SF_5$, acetyl, —C(O)$NHCH_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazopyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl, oxazolyl, isoxazolyl, thiazolyl, isothiazolyl, thiadiazolyl, thienyl, furyl, pyrrolyl, tetrahydropyranyl, tetrahydropyrrolyl or oxetan-3yl.

In embodiment 53, the invention provides compounds according to any one of embodiments 51-52 or a stereoisomer or pharmaceutically acceptable salt thereof, wherein $R^9$ is

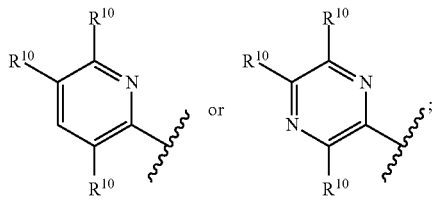

and each $R^{10}$, independently, is H, F, Cl, Br, $CF_3$, $CHF_2$, $CH_2F$, CN, OH, —C(O)$NHCH_3$, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkoxyl or $C_{1-6}$thioalkoxyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkoxyl and $C_{1-6}$thioalkoxyl is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl, oxazolyl or thiazolyl.

In embodiment 54, the invention provides compounds according to any one of embodiments 51-53, or a stereoisomer or pharmaceutically acceptable salt thereof, wherein $R^3$ is $CHF_2$; and $R^9$ is

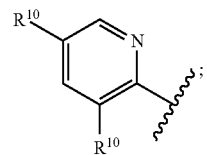

and each $R^{10}$, independently, is H, F, Cl, Br, $CH_3$, $CHF_2$, $CH_2F$, CN, 2-propynyloxy, 2-butynyloxy or $C_{1-2}$alkoxyl, wherein the $C_{1-2}$alkoxyl is optionally substituted independently with 1-5 substituents of F, Cl, methyl, methoxy, ethyl, ethoxy, oxazolyl or thiazolyl.

In embodiment 55, the invention provides compounds according to any one of embodiments 51-53, or a stereoisomer or pharmaceutically acceptable salt thereof, wherein $R^3$ is $CH_2F$; and $R^9$ is

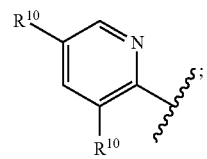

and each $R^{10}$, independently, is H, F, Cl, Br, $CH_3$, $CHF_2$, $CH_2F$, CN, 2-propynyloxy, 2-butynyloxy or $C_{1-2}$alkoxyl, wherein the $C_{1-2}$alkoxyl is optionally substituted independently with 1-5 substituents of F, Cl, methyl, methoxy, ethyl, ethoxy, oxazolyl or thiazolyl.

In embodiment 56, the invention provides compounds according to any one of embodiments 51-53 or a stereoisomer or pharmaceutically acceptable salt thereof, wherein $R^3$ is $CHF_2$; and $R^9$ is

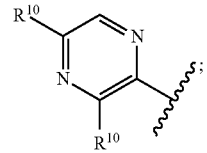

and each $R^{10}$, independently, is H, F, Cl, Br, $CH_3$, $CHF_2$, $CH_2F$, CN, 2-propynyloxy, 2-butynyloxy or $C_{1-2}$alkoxyl, wherein the $C_{1-2}$alkoxyl is optionally substituted independently with 1-5 substituents of F, Cl, methyl, methoxy, ethyl, ethoxy, oxazolyl or thiazolyl.

In embodiment 57, the invention provides compounds according to any one of embodiments 51-53, or a stereoisomer or pharmaceutically acceptable salt thereof, wherein $R^3$ is $CH_2F$; and $R^9$ is

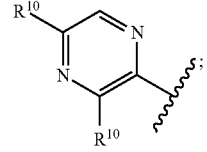

and
each $R^{10}$, independently, is H, F, Cl, Br, $CH_3$, $CHF_2$, $CH_2F$, CN, 2-propynyloxy, 2-butynyloxy or $C_{1-2}$alkoxyl, wherein the $C_{1-2}$alkoxyl is optionally substituted independently with 1-5 substituents of F, Cl, methyl, methoxy, ethyl, ethoxy, oxazolyl or thiazolyl.

In embodiment 58, the invention provides compounds, including stereoisomers, tautomers, hydrates, solvates and pharmaceutically acceptable salts thereof, which are generally defined by Formula III-B:

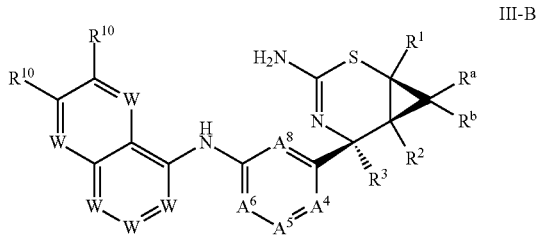

III-B wherein
$A^4$ is $CR^4$, wherein $R^4$ is H, F or Cl;
$A^5$ is $CR^5$ or N, wherein $R^5$ is H, F, Cl or $CH_3$;
$A^6$ is CH;
$A^8$ is $CR^8$ or N, wherein $R^8$ is H or F, provided that no more than one of $A^5$ and $A^8$ is N;
each of $R^a$ and $R^b$, independently, is H or F;
each of $R^1$ and $R^2$, independently, is H, $CH_2OCH_3$ or F;
$R^3$ is $CH_3$, $CH_2F$ or $CHF_2$;

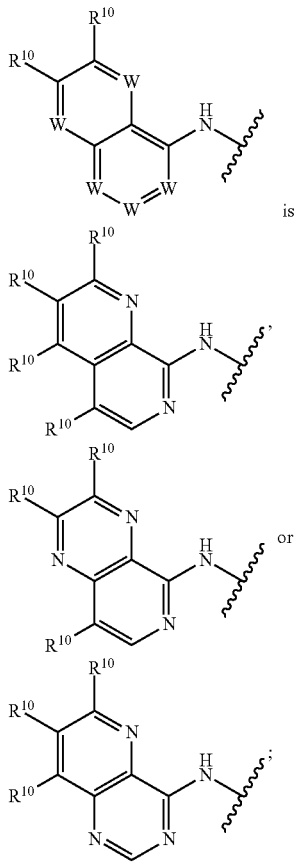

is and
each $R^{10}$, independently, is H, F, Cl, Br, $CH_3$, $CHF_2$, $CH_2F$, CN, 2-propynyloxy; 2-butynyloxy or $C_{1-2}$alkoxyl, wherein the $C_{1-2}$alkoxyl is optionally substituted independently with 1-5 substituents of F, Cl, methyl, methoxy, ethyl, ethoxy, oxazolyl or thiazolyl.

In embodiment 59, the invention provides compounds of formula III-A-1, or a pharmaceutically acceptable salt or tautomer thereof,

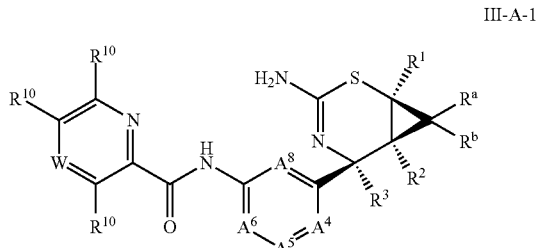

III-A-1 wherein, $A^4$ is CF;
$A^5$ is CH, CF, CCl, $CCH_3$ or N;
$A^6$ is CH;
$A^8$ is CH or N, provided that no more than one of $A^5$ and $A^8$ is N;
each of $R^a$ and $R^b$, independently, is H;
each of $R^1$ and $R^2$, independently, is H, $CH_2OCH_3$ or F;
$R^3$ is $CH_3$, $CH_2F$ or $CHF_2$;
W is $CR^{10}$ or N; and
each $R^{10}$, independently, is H, halo, haloalkyl, CN, OH, $NO_2$, $NH_2$, $SF_5$, acetyl, —C(O)$NHCH_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazopyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl, oxazolyl, isoxazolyl, thiazolyl, isothiazolyl, thiadiazolyl, thienyl, furyl, pyrrolyl, tetrahydropyranyl, tetrahydropyrrolyl or oxetan-3yl.

In embodiment 60, the invention provides compounds of formula III-A-2, or a pharmaceutically acceptable salt or tautomer thereof,

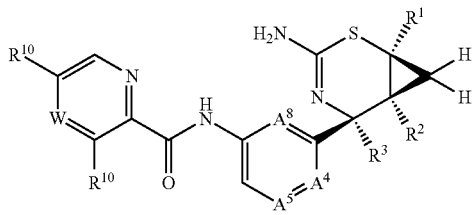

III-A-2 wherein
A⁴ is CF or CCl;
A⁵ is CH, CF, CCl, CCH₃ or N;
A⁸ is CH or N, provided no more than one of A⁵ and A⁸ is N;
R¹ is H, CH₂OCH₃ or F;
R³ is CH₃, CH₂F or CHF₂;
W is CH or N; and
each R¹⁰, independently, is H, F, Cl, Br, CH₃, CHF₂, CH₂F, CN, 2-propynyloxy, 2-butynyloxy or C$_{1-2}$alkoxyl, wherein the C$_{1-2}$alkoxyl is optionally substituted independently with 1-5 substituents of F, Cl, methyl, methoxy, ethyl, ethoxy, oxazolyl or thiazolyl.

In embodiment 61, the invention provides compounds according to any one of embodiments 59-60, or a stereoisomer or pharmaceutically acceptable salt thereof, wherein R³ is CHF₂.

In embodiment 62, the invention provides compounds according to any one of embodiments 59-60, or a stereoisomer or pharmaceutically acceptable salt thereof, wherein R³ is CH₂F.

In embodiment 63, the invention provides compounds according to any one of embodiments 59-62, or a stereoisomer or pharmaceutically acceptable salt thereof, wherein W is CH.

In embodiment 64, the invention provides compounds according to any one of embodiments 59-62, or a stereoisomer or pharmaceutically acceptable salt thereof, wherein W is N.

In embodiment 65, the invention provides compounds according to any one of embodiments 59-64, or a stereoisomer or pharmaceutically acceptable salt thereof, wherein each R¹⁰, independently, is H, F, Cl, Br, CH₃, CHF₂, CH₂F, CN, 2-propynyloxy, 2-butynyloxy or C$_{1-2}$alkoxyl, wherein the C$_{1-2}$alkoxyl is optionally substituted independently with 1-5 substituents of F, oxazolyl or thiazolyl.

In embodiment 66, the invention provides compounds according to any one of embodiments 59-65, or a stereoisomer or pharmaceutically acceptable salt thereof, wherein each R¹⁰, independently, is H, F, Cl, Br, CH₃, CHF₂, CH₂F, CN, 2-propynyloxy, 2-butynyloxy, —OCHF₂ or —OCH₃.

In embodiment 67, the invention provides compounds according to any one of embodiments 59-66, or a stereoisomer or pharmaceutically acceptable salt thereof, wherein A⁸ is CH.

In embodiment 68, the invention provides compounds according to any one of embodiments 59-67, or a stereoisomer or pharmaceutically acceptable salt thereof, wherein A⁵ is CH, CF, CCl or CCH₃.

In embodiment 68, the invention provides compounds according to any one of embodiments 59-67, or a stereoisomer or pharmaceutically acceptable salt thereof, wherein A⁵ is CH, CF or CCH₃.

In embodiment 68, the invention provides compounds according to any one of embodiments 59-67, or a stereoisomer or pharmaceutically acceptable salt thereof, wherein A⁵ is CH or N.

In embodiment 69, the invention provides compounds of formula III-A-3, or a pharmaceutically acceptable salt or tautomer thereof,

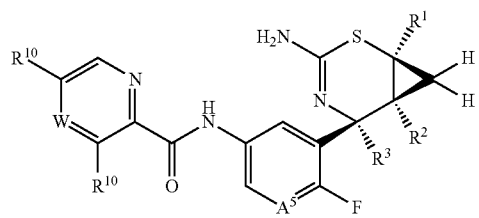

III-A-3 wherein
A⁵ is CH, CF, CCl, CCH₃ or N;
R³ is CH₃, CH₂F or CHF₂;
W is CH or N; and
each R¹⁰, independently, is H, F, Cl, Br, CH₃, CHF₂, CH₂F, CN, 2-propynyloxy; 2-butynyloxy or C$_{1-2}$alkoxyl, wherein the C$_{1-2}$alkoxyl is optionally substituted independently with 1-5 substituents of F, Cl, methyl, methoxy, ethyl, ethoxy, oxazolyl or thiazolyl.

In embodiment 70, the invention provides compounds according to any one of embodiment 69, or a stereoisomer or pharmaceutically acceptable salt thereof, wherein R³ is CHF₂.

In embodiment 71, the invention provides compounds according to any one of embodiment 69, or a stereoisomer or pharmaceutically acceptable salt thereof, wherein R³ is CH₂F.

In embodiment 72, the invention provides compounds according to any one of embodiments 69-71, or a stereoisomer or pharmaceutically acceptable salt thereof, wherein W is CH.

In embodiment 73, the invention provides compounds according to any one of embodiments 69-71, or a stereoisomer or pharmaceutically acceptable salt thereof, wherein W is N.

In embodiment 74, the invention provides compounds according to any one of embodiments 69-74, or a stereoisomer or pharmaceutically acceptable salt thereof, wherein each R¹⁰, independently, is H, F, Cl, Br, CH₃, CHF₂, CH₂F, CN, 2-propynyloxy, 2-butynyloxy or C$_{1-2}$alkoxyl, wherein the C$_{1-2}$alkoxyl is optionally substituted independently with 1-5 substituents of F, oxazolyl or thiazolyl.

In embodiment 75, the invention provides compounds according to any one of embodiments 69-75, or a stereoisomer or pharmaceutically acceptable salt thereof, wherein each R¹⁰, independently, is H, F, Cl, Br, CH₃, CHF₂, CH₂F, CN, 2-propynyloxy, 2-butynyloxy, —OCHF₂ or —OCH₃.

In embodiment 77, the invention provides compounds according to any one of embodiments 69-76, or a stereoisomer or pharmaceutically acceptable salt thereof, wherein A⁵ is CH, CF, CCH₃ or N.

In embodiment 78, the invention provides compounds according to any one of embodiments 69-77, or a stereoisomer or pharmaceutically acceptable salt thereof, wherein A⁵ is CH, CF or N.

In embodiment 79, the invention provides compounds according to any one of embodiments 69-78, or a stereoisomer or pharmaceutically acceptable salt thereof, wherein $A^5$ is CH or N.

In embodiment 80, the invention provides compounds according to any one of embodiments 69-79, or a stereoisomer or pharmaceutically acceptable salt thereof, wherein $A^5$ is CH.

In embodiment 81, the invention provides compounds according to any one of embodiments 69-79, or a stereoisomer or pharmaceutically acceptable salt thereof, wherein $A^5$ is N.

In embodiment 82, the invention provides compounds of formula III-B-1, or a pharmaceutically acceptable salt or tautomer thereof,

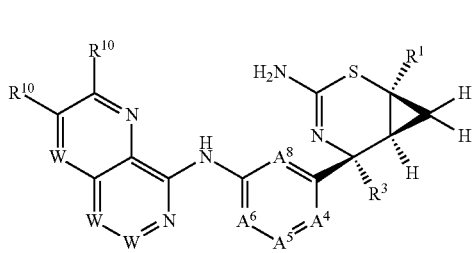

III-B-1 wherein $A^4$ is CF;

$A^5$ is CH, CF, CCl, CCH$_3$ or N;

$A^6$ is CH;

$A^8$ is CH or N, provided that no more than one of $A^5$ and $A^8$ is N;

$R^1$ is H, CH$_2$OCH$_3$ or F;

$R^3$ is CH$_3$, CH$_2$F or CHF$_2$;

each W, independently, is CR$^{10}$ or N, provided no more than 2 W's are N; and each R$^{10}$, independently, is H, halo, haloalkyl, CN, OH, NO$_2$, NH$_2$, SF$_5$, acetyl, —C(O)NHCH$_3$, oxo, cyclopropylmethoxy, 2-propynyloxy, 2-butynyloxy, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazopyridinyl or dioxolyl, wherein each of the cyclopropylmethoxy, 2-propynyloxy, 2-butynyloxy, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO$_2$, NH$_2$, OH, oxo, CF$_3$, CHF$_2$, CH$_2$F, methyl, methoxy, ethyl, ethoxy, CH$_2$CF$_3$, CH$_2$CHF$_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, C$_{1-3}$alkylamino-, C$_{1-3}$dialkylamino, C$_{1-3}$thioalkoxyl, oxazolyl, isoxazolyl, thiazolyl, isothiazolyl, thiadiazolyl, thienyl, furyl, pyrrolyl, tetrahydropyranyl, tetrahydropyrrolyl or oxetan-3yl.

In embodiment 83, the invention provides compounds of formula III-B-2, or a pharmaceutically acceptable salt or tautomer thereof,

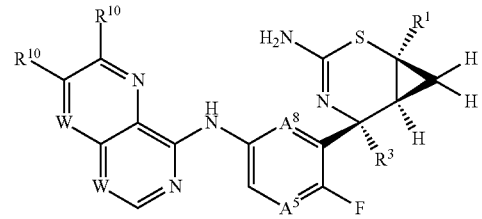

III-B-2 wherein $A^5$ is CH, CF, CCl, CCH$_3$ or N;

$A^8$ is CH or N, provided no more than one of $A^5$ and $A^8$ is N;

$R^3$ is CH$_3$, CH$_2$F or CHF$_2$;

each W, independently, is CR$^{10}$ or N, provided no more than 1 W is N; and each R$^{10}$, independently, is H, F, Cl, Br, CH$_3$, CHF$_2$, CH$_2$F, CN, 2-propynyloxy, 2-butynyloxy or C$_{1-2}$alkoxyl, wherein the C$_{1-2}$alkoxyl is optionally substituted independently with 1-5 substituents of F, Cl, methyl, methoxy, ethyl, ethoxy, oxazolyl or thiazolyl.

Similarly, the invention provides compounds of subformulas III-C, III-D, III-E and III-F, respectively, as described below,

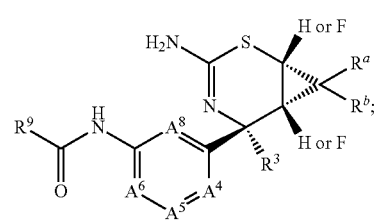

III-C

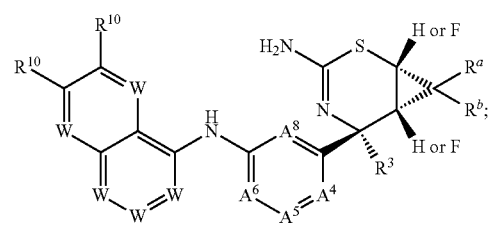

III-D

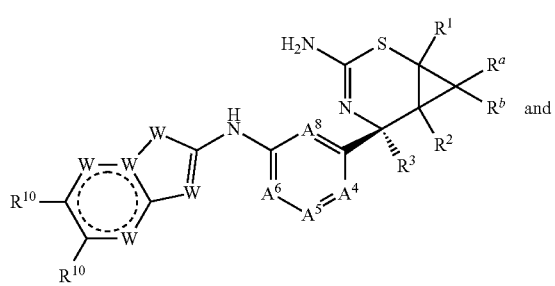

III-E and

-continued

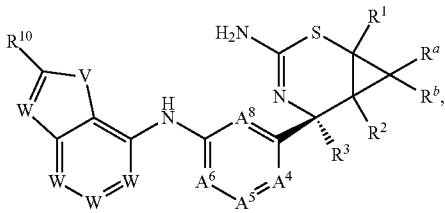

III-F in conjunction with any of the above or below embodiments, including those described in embodiments A, A-1 to A-4, B, B-1 to B-10, C, C-1 to C-10, D, D-1 to D-6, E, E-1 to E-5, F, F-1 to F-4, G, G-1 to G-4, H, H-1 to H-4, I, I-1 to I-9, J, J-1 to J-8, K, K-1 to K-2, L, M, N-1 to N-2, O-1 to O-2, P-1 to P-2, Q and Q-1 to Q-2 described herein.

The present invention contemplates that the various different embodiments of Formulas I, II and III, and sub-Formulas I-A, I-B, I-C and III-A through III-F thereof, described herein, may comprise the following embodiments with respect to individual variables of $A^4, A^5, A^6, A^8, R^1, R^2, R^3, R^7$, V and W, where applicable, as described below. Hence, these embodiments with respect to individual variables $A^4, A^5, A^6, A^8, R^1, R^2, R^3, R^7$, V and W where applicable, may be applied "in conjunction with any of the other {above and below} embodiments" to create various embodiments of general Formulas I, II and III, and each sub-formula thereof, which are not literally or identically described herein. More specifically, the term "in conjunction with any of the above or below embodiments" includes embodiments A, A-1 to A-4, B, B-1 to B10, C, C-1 to C-10, D, D-1 to D-6, E, E-1 to E-5, F, F-1 to F-4, G, G-1 to G-4, H, H-1 to H-4, I, I-1 to I-9, J, J-1 to J-8, K, K-1 to K-2, L, M, N-1 to N-2, O-1 to O-2, P-1 to P-2, Q and Q-1 to Q-2 described herein, as it applies to general Formulas I, II and III, and sub-formulas I-A, I-B and I-C and III-A through III-F, also described herein.

In another embodiment A, the invention includes compounds wherein each of $R^a$ and $R^b$, independently, is H, F, Cl, $C_{1-6}$ alkyl, $C_{2-4}$alkenyl, $C_{2-4}$alkynyl, CN, —$CH_2OC_{1-6}$-alkyl, —$OC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH, in conjunction with any of the above or below embodiments.

In another embodiment A-1, the invention includes compounds wherein each of $R^a$ and $R^b$, independently, is H, F, Cl, $CF_3$, $OCF_3$, methyl, ethyl, CN, OH, $OCH_3$, $SCH_3$, $NHCH_3$, $C(O)CH_3$ or $CH_2OCHF_2$, in conjunction with any of the above or below embodiments.

In another embodiment A-2, the invention includes compounds wherein each of $R^a$ and $R^b$, independently, is H, F, $CF_3$, $CH_3$, $CF_2H$ or $CH_2F$, in conjunction with any of the above or below embodiments.

In another embodiment A-3, the invention includes compounds wherein $R^1$ is H or F, in conjunction with any of the above or below embodiments.

In another embodiment A-4, the invention includes compounds wherein $R^1$ is H, in conjunction with any of the above or below embodiments.

In another embodiment B, the invention includes compounds wherein $R^1$ is each of $R^1$ and $R^2$, independently, is H, F, Cl, $C_{1-6}$-alkyl, $C_{2-4}$alkenyl, $C_{2-4}$alkynyl, CN, —$CH_2OC_{1-6}$-alkyl, —$C(O)NH_2$, —$CH=CHC(O)NHC_{1-6}$-alkyl, —$CH=CHC(O)_2H$, —$CH=CHCH_2OH$, $C_{1-6}$-alkyl-$C(O)NHC_{1-6}$-alkyl, —$C(O)C_{1-6}$-alkyl or —$C(O)C_{1-6}$-alkenyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$ alkyl, $NHC_{1-6}$-alkyl, $C(O)C_{1-6}$-alkyl, —$C(O)C_{1-6}$-alkenyl, —$CH=CHC(O)NHC_{1-6}$-alkyl and $C_{1-6}$-alkyl-$C(O)NHC_{1-6}$-alkyl, are optionally substituted with 1-4 substituents of F, CN, oxo or OH, in conjunction with any of the above or below embodiments.

In another embodiment B-1, the invention includes compounds wherein $R^1$ is H, F, $C_{2-4}$alkenyl, $C_{2-4}$alkynyl, CN, —$OC_{1-3}$-alkyl and —$C(O)OC_{1-6}$-alkyl, wherein each of the $C_{1-6}$-alkyl, $C_{2-4}$alkenyl, $C_{2-4}$alkynyl and $C_{1-3}$-alkyl portion of —$CH_2OC_{1-3}$-alkyl, —$C(O)OC_{1-6}$-alkyl and —$OC_{1-3}$-alkyl are optionally substituted with 1-4 substituents of F and OH, in conjunction with any of the above or below embodiments.

In another embodiment B-2, the invention includes compounds wherein $R^1$ is H, F, $CH_3$, $CH_2OCH_3$, $CH_2F$, $CHF_2$, $CF_3$, —$C(O)NH_2$, —$CH=CHC(O)NHC_{1-6}$alkyl, —$CH=CHC(O)_2H$, —$CH=CHCH_2OH$ or $C_{1-6}$-alkyl-$C(O)NHC_{1-6}$-alkyl, in conjunction with any of the above or below embodiments.

In another embodiment B-3, the invention includes compounds wherein $R^1$ is H, F, $CH_3$, $C_2H_5$, $CF_2H$, $CH_2F$, or $CH_2OCH_3$, $CH_2OCF_2H$, $CH_2OCF_2H$ or $CH_2OCF_3$, in conjunction with any of the above or below embodiments.

In another embodiment B-4, the invention includes compounds wherein $R^1$ is H, F, Cl, $CF_3$, $CH_3$, $CF_2H$ or $CH_2F$, in conjunction with any of the above or below embodiments.

In another embodiment B-5, the invention includes compounds wherein $R^1$ is H, F, $CF_3$, $CH_3$, $CF_2H$ or $CH_2F$, in conjunction with any of the above or below embodiments.

In another embodiment B-6, the invention includes compounds wherein $R^1$ is H, F, $CH_2OCH_3$ or $CH_2OH$, in conjunction with any of the above or below embodiments.

In another embodiment B-7, the invention includes compounds wherein $R^1$ is H or F, in conjunction with any of the above or below embodiments.

In another embodiment B-8, the invention includes compounds wherein $R^1$ is H, in conjunction with any of the above or below embodiments.

In another embodiment B-9, the invention includes compounds wherein $R^1$ is F, in conjunction with any of the above or below embodiments.

In another embodiment B-10, the invention includes compounds wherein $R^1$ is H, $CH_2OCH_3$ or $CH_2OH$, in conjunction with any of the above or below embodiments.

In another embodiment C, the invention includes compounds wherein $R^2$ is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH, in conjunction with any of the above or below embodiments.

In another embodiment C-1, the invention includes compounds wherein $R^2$ is H, F, Cl, $C_{2-4}$alkenyl, $C_{2-4}$alkynyl, CN, —$CH_2OC_{1-3}$-alkyl, —$OC_{1-3}$-alkyl, wherein each of the $C_{2-4}$alkenyl, $C_{2-4}$alkynyl and $C_{1-3}$-alkyl portion of —$CH_2OC_{1-3}$-alkyl and —$OC_{1-3}$-alkyl are optionally substituted with 1-4 substituents of F, in conjunction with any of the above or below embodiments.

In another embodiment C-2, the invention includes compounds wherein $R^2$ is H, F, Cl, $CF_3$, $OCF_3$, methyl, ethyl, CN, OH, $OCH_3$, $SCH_3$, $NHCH_3$, $C(O)CH_3$ or $CH_2OCHF_2$, in conjunction with any of the above or below embodiments.

In another embodiment C-3, the invention includes compounds wherein $R^2$ is H, F, $CH_3$, $C_2H_5$, $CF_2H$, $CH_2F$, $CH_2OCH_2F$, $CH_2OCF_2H$ or $CH_2OCF_3$, in conjunction with any of the above or below embodiments.

In another embodiment C-4, the invention includes compounds wherein $R^2$ is H, F, Cl, $CF_3$, $CH_3$, $CF_2H$ or $CH_2F$, in conjunction with any of the above or below embodiments.

In another embodiment C-5, the invention includes compounds wherein $R^2$ is H, F, $CF_3$, $CH_3$, $CF_2H$ or $CH_2F$, in conjunction with any of the above or below embodiments.

In another embodiment C-6, the invention includes compounds wherein $R^2$ is H, F or $CF_3$, in conjunction with any of the above or below embodiments.

In another embodiment C-7, the invention includes compounds wherein $R^2$ is H or F, in conjunction with any of the above or below embodiments.

In another embodiment C-8, the invention includes compounds wherein $R^2$ is H, in conjunction with any of the above or below embodiments.

In another embodiment C-9, the invention includes compounds wherein $R^2$ is F, in conjunction with any of the above or below embodiments.

In another embodiment C-10, the invention includes compounds wherein $R^2$ is $CF_3$, in conjunction with any of the above or below embodiments.

In another embodiment D, the invention includes compounds wherein $R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms, in conjunction with any of the above or below embodiments.

In another embodiment D-1, the invention includes compounds wherein $R^3$ is $C_{1-4}$alkyl, $C_{1-4}$haloalkyl, $CH_2OH$, $CH_2OCHF_2$ or cyclopropyl, wherein each of the $C_{1-4}$alkyl, $C_{1-4}$haloalkyl and cyclopropyl is optionally substituted with 1-4 F atoms, in conjunction with any of the above or below embodiments.

In another embodiment D-2, the invention includes compounds wherein $R^3$ is $C_{1-4}$alkyl, $CH_2OH$, $CH_2OCH_2F$, $CH_2OCF_2H$, or cyclopropyl, wherein each of the $C_{1-4}$alkyl and cyclopropyl is optionally substituted with 1-2 F atoms, in conjunction with any of the above or below embodiments.

In another embodiment D-3, the invention includes compounds wherein $R^3$ is $CH_3$, $CF_3$, $CF_2H$ or $CH_2F$, in conjunction with any of the above or below embodiments.

In another embodiment D-4, the invention includes compounds wherein $R^3$ is $CH_3$, $CF_2H$ or $CH_2F$, in conjunction with any of the above or below embodiments.

In another embodiment D-5, the invention includes compounds wherein $R^3$ is $CH_3$ or $CH_2F$, in conjunction with any of the above or below embodiments.

In another embodiment D-6, the invention includes compounds wherein $R^3$ is $CH_2F$, in conjunction with any of the above or below embodiments.

In another embodiment E, the invention includes compounds wherein $A^4$ is $CR^4$ wherein $R^4$ is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl, in conjunction with any of the above or below embodiments.

In another embodiment E-1, the invention includes compounds wherein $A^4$ is $CR^4$ wherein $R^4$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment E-2, the invention includes compounds wherein $A^4$ is $CR^4$ wherein $R^4$ is H, F, $CF_3$, $CF_2H$, $CH_2F$ or $CH_3$, in conjunction with any of the above or below embodiments.

In another embodiment E-3, the invention includes compounds wherein $A^4$ is $CR^4$ wherein $R^4$ is H or F, in conjunction with any of the above or below embodiments.

In another embodiment E-4, the invention includes compounds wherein $A^4$ is $CR^4$ wherein $R^4$ is F, in conjunction with any of the above or below embodiments.

In another embodiment E-5, the invention includes compounds wherein $A^4$ is N, in conjunction with any of the above or below embodiments.

In another embodiment F, the invention includes compounds wherein $A^5$ is $CR^5$ and $R^5$ is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl, in conjunction with any of the above or below embodiments.

In another embodiment F-1, the invention includes compounds wherein $A^5$ is $CR^5$ wherein $R^5$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment F-2, the invention includes compounds wherein $A^5$ is $CR^5$ and $R^5$ is H, F, Cl, $CF_3$, $CF_2H$, $CH_2F$, $CH_3$ or N in conjunction with any of the above or below embodiments.

In another embodiment F-3, the invention includes compounds wherein $A^5$ is $CR^5$ and $R^5$ is H, F, Cl or $CH_3$, in conjunction with any of the above or below embodiments.

In another embodiment F-4, the invention includes compounds wherein $A^5$ is N, in conjunction with any of the above or below embodiments.

In another embodiment G, the invention includes compounds wherein $A^6$ is $CR^6$ wherein $R^6$ is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl, in conjunction with any of the above or below embodiments.

In another embodiment G-1, the invention includes compounds wherein $A^6$ is $CR^6$ wherein $R^6$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment G-2, the invention includes compounds wherein $A^6$ is $CR^6$ wherein $R^6$ is H, F, $CF_3$, $CF_2H$, $CH_2F$ or $CH_3$, in conjunction with any of the above or below embodiments.

In another embodiment G-3, the invention includes compounds wherein $A^6$ is $CR^6$ wherein $R^6$ is H or F, in conjunction with any of the above or below embodiments.

In another embodiment G-4, the invention includes compounds wherein $A^6$ is N, in conjunction with any of the above or below embodiments.

In another embodiment H, the invention includes compounds wherein $A^8$ is $CR^8$ wherein $R^8$ is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl, in conjunction with any of the above or below embodiments.

In another embodiment H-1, the invention includes compounds wherein $A^8$ is $CR^8$ wherein $R^8$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment H-2, the invention includes compounds wherein $A^8$ is $CR^8$ wherein $R^8$ is H, F, $CF_3$, $CF_2H$, $CH_2F$ or $CH_3$, in conjunction with any of the above or below embodiments.

In another embodiment H-3, the invention includes compounds wherein $A^8$ is $CR^8$ wherein $R^8$ is H or F, in conjunction with any of the above or below embodiments.

In another embodiment H-4, the invention includes compounds wherein $A^8$ is N, in conjunction with any of the above or below embodiments.

In another embodiment I, the invention includes compounds wherein no more than two of $A^4$, $A^5$, $A^6$ and $A^8$ is N, in conjunction with any of the above or below embodiments.

In another embodiment I-1, the invention includes compounds wherein no more than one of $A^4$, $A^5$, $A^6$ and $A^8$ is N, in conjunction with any of the above or below embodiments.

In another embodiment I-2, the invention includes compounds wherein $A^4$ is $CR^4$, $A^5$ is $CR^5$ or N, $A^6$ is $CR^6$ and $A^8$ is $CR^8$, in conjunction with any of the above or below embodiments.

In another embodiment, the invention includes compounds wherein $A^4$ is $CR^4$ or N, $A^5$ is $CR^5$, $A^6$ is $CR^6$ and $A^8$ is $CR^8$, in conjunction with any of the above or below embodiments.

In another embodiment I-3, the invention includes compounds wherein $A^4$ is N, $A^5$ is $CR^5$, $A^6$ is $CR^6$ and $A^8$ is $CR^8$, in conjunction with any of the above or below embodiments.

In another embodiment I-4, the invention includes compounds wherein $A^4$ is $CR^4$, $A^5$ is N, $A^6$ is $CR^6$, and $A^8$ is $CR^8$, in conjunction with any of the above or below embodiments.

In another embodiment I-5, the invention includes compounds wherein $A^4$ is $CR^4$, $A^5$ is $CR^5$, $A^6$ is N, and $A^8$ is $CR^8$, in conjunction with any of the above or below embodiments.

In another embodiment I-6, the invention includes compounds wherein $A^4$ is $CR^5$, $A^5$ is $CR^5$, $A^6$ is $CR^6$, and $A^8$ is N, in conjunction with any of the above or below embodiments.

In another embodiment I-7, the invention includes compounds of Formulas I, II or III, wherein
$A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N;
each of $R^a$ and $R^b$, independently, is H, F, Cl, $CF_3$, $OCF_3$, methyl, ethyl, CN, OH, $OCH_3$, $SCH_3$, $NHCH_3$, $C(O)CH_3$ or $CH_2OCHF_2$;
each of $R^1$ and $R^2$, independently, is H, F, Cl, $CF_3$, $OCF_3$, methyl, ethyl, CN, OH, $OCH_3$, $SCH_3$, $NHCH_3$, $C(O)CH_3$, $C(O)OC_{1-3}$alkyl, $CH_2OCH_3$ or $CH_2OCHF_2$;
$R^3$ is $C_{1-4}$alkyl, $C_{1-4}$haloalkyl, $CH_2OH$, $CH_2OCHF_2$ or cyclopropyl; and
each of $R^4$, $R^5$, $R^6$ and $R^8$, independently, is H, F, Cl, $CF_2H$, $CH_2F$, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment I-8, the invention includes compounds of Formulas I, II or III, wherein
$A^4$ is $CR^4$;
$A^5$ is $CR^5$;
$A^6$ is $CR^6$; and
$A^8$ is $CR^8$; wherein each of $R^4$, $R^5$, $R^6$ and $R^8$, independently, is H, F, $CF_3$, $CF_2H$, $CH_2F$ or $CH_3$, in conjunction with any of the above or below embodiments.

In another embodiment I-9, the invention includes compounds of Formulas I, II or III, wherein $A^4$ is CH, CF or N, $A^5$ is CH, CF or N, $A^6$ is CH, CF or N, $A^8$ is CH, CF or N, one of $A^4$, $A^5$, $A^6$ and $A^8$ is N, in conjunction with any of the above or below embodiments.

In another embodiment J, the invention includes compounds of Formulas I, II or III, wherein $R^7$ is —NH—$R^9$ or —NH—C(=O)—$R^9$; or $R^7$ is

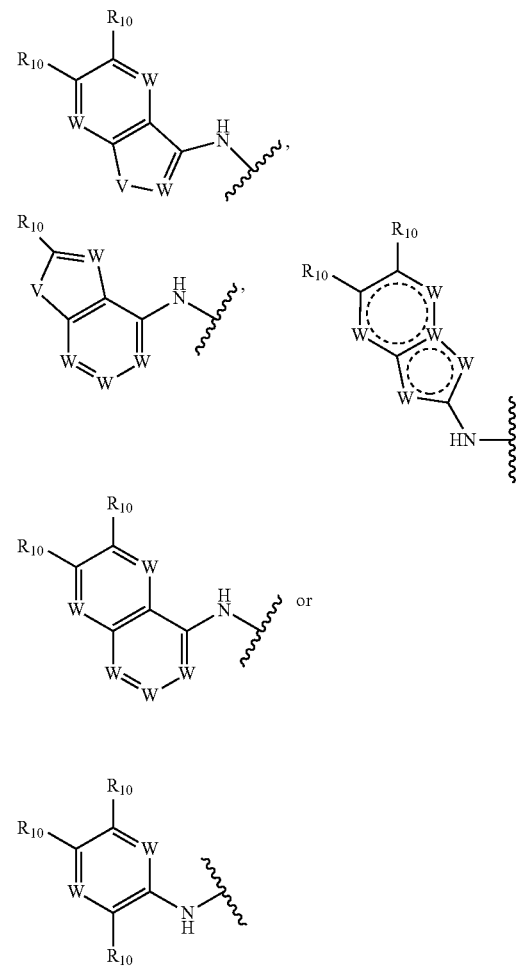

wherein V is $NR^{10}$, O or S;
each W, independently, is CH, CF, CCl, $CCH_3$ or N; and
each $R^{10}$ is as defined herein, in conjunction with any of the above or below embodiments.

In another embodiment J-1, the invention includes compounds of Formulas I, II or III, wherein $R^7$ is —NH—$R^9$, —NH—C(=O)—$R^9$ or

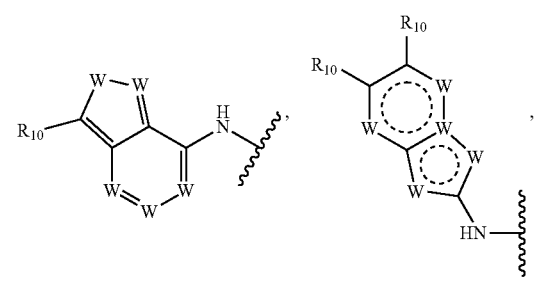

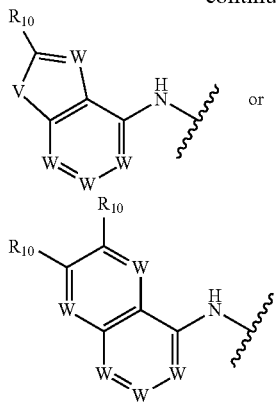

or

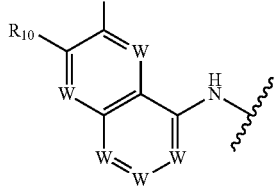

wherein V is NR$^{10}$, O or S; and
each W, independently, is CH, CF, CCl, CCH$_3$ or N; and
each R$^{10}$ is as defined herein, in conjunction with any of the above or below embodiments.

In another embodiment J-2, the invention includes compounds of Formulas I, II or III, wherein R$^7$ is —NH—C(=O)—R$^9$ or

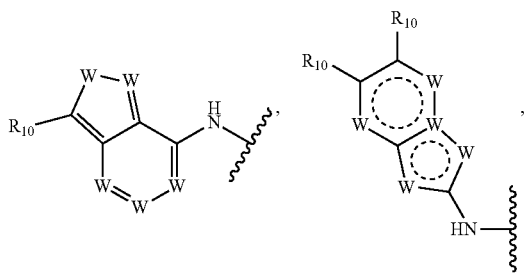

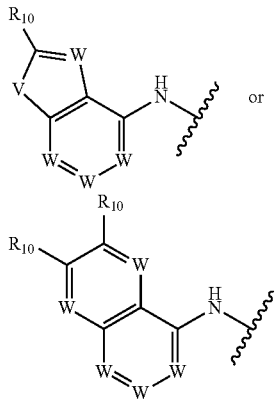

or wherein V is NR$^{10}$, O or S; and
each W, independently, is CH, CF, CCl or N; and
each R$^{10}$ is as defined herein, in conjunction with any of the above or below embodiments.

In another embodiment J-3, the invention includes compounds of Formulas I, II or III, wherein R$^7$ is —NH—C(=O)—R$^9$, in conjunction with any of the above or below embodiments.

In another embodiment J-4, the invention includes compounds of Formulas I, II or III, wherein R$^7$ is —NH—R$^9$, in conjunction with any of the above or below embodiments.

In another embodiment J-5, the invention includes compounds wherein R$^7$ is

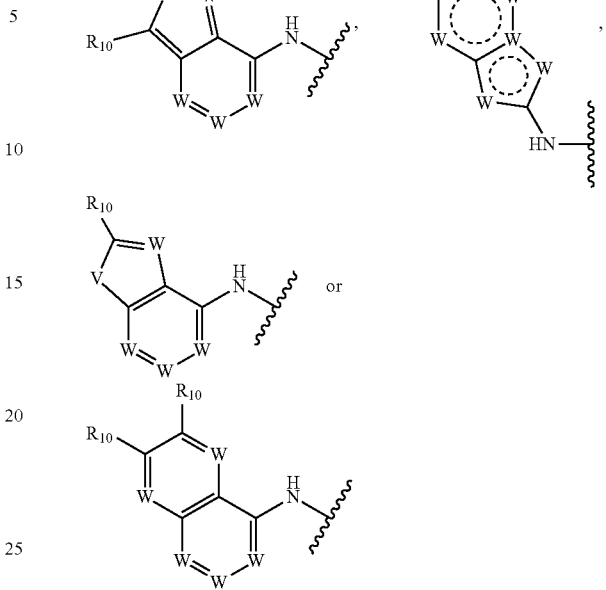

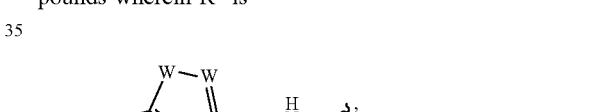

wherein V is NR$^{10}$, O or S; and
each W, independently, is CH, CF, CCl, CCH$_3$ or N, in conjunction with any of
the above or below embodiments.

In another embodiment J-6, the invention includes compounds wherein R$^7$ is

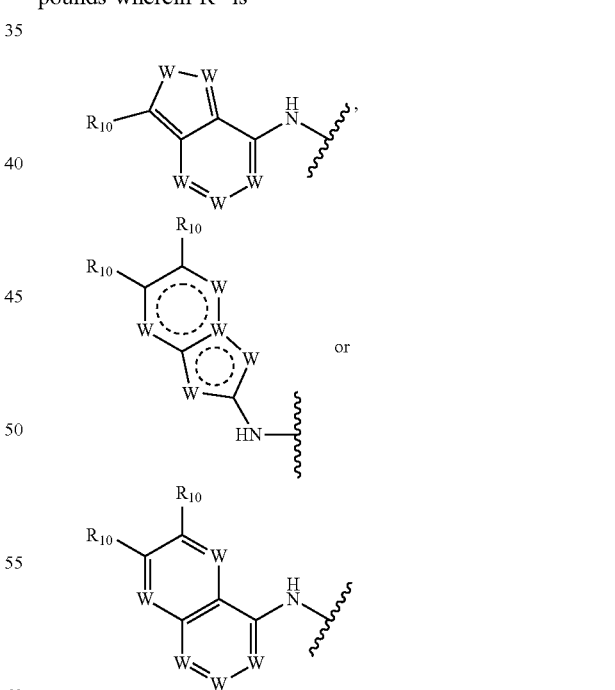

wherein V is NR$^{10}$, O or S; and
each W, independently, is CH, CF, CCl, CCH$_3$ or N, in conjunction with any of the above or below embodiments.

In another embodiment J-7, the invention includes compounds wherein R$^7$ is —NH—R$^9$, in conjunction with any of the above or below embodiments.

In another embodiment J-8, the invention includes compounds wherein R$^7$ is —NH—R$^9$ or —NH—C(=O)—R$^9$, wherein R$^9$ is a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the ring is optionally substituted, independently, with 1-5 substituents of R$^{10}$, in conjunction with any of the above or below embodiments.

In another embodiment K, the invention includes compounds wherein each R$^9$, independently, is a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the C$_{1-6}$-alkyl, C$_{2-4}$alkenyl, C$_{2-4}$alkynyl and ring are optionally substituted, independently, with 1-5 substituents of R$^{10}$, in conjunction with any of the above or below embodiments.

In another embodiment K-1, the invention includes compounds wherein each R$^9$ is a ring selected from phenyl, pyridyl, pyrimidyl, pyrazinyl, pyridazinyl, pyrazolyl, pyrazolo[3,4-c]pyridinyl, oxazolyl, isoxazolyl, thiazolyl, isothiazolyl or thienyl, wherein the ring is optionally substituted with 1-5 substituents of R$^{10}$, in conjunction with any of the above or below embodiments.

In another embodiment K-2, the invention includes compounds of Formulas I, II, and III, and any sub-formula thereof as described herein, wherein R$^9$ is a ring selected from the group consisting of phenyl, pyridyl, pyrimidyl, pyrazinyl, pyridazinyl, pyrazolyl, isoxazolyl, thiazolyl, thienyl, furanyl and pyrrolyl, wherein the ring is optionally substituted, independently, with 1-3 substituents of R$^{10}$, wherein each R$^{10}$, independently, is F, Cl, CN, NO$_2$, NH$_2$, OH, CF$_3$, CHF$_2$, CH$_2$F, CH$_3$, —OCH$_3$, C$_2$H$_5$, —OC$_2$H$_5$, —CH$_2$CF$_3$, —CH$_2$CHF$_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopropylmethoxy, 2-butynyloxy or oxetan-3yl, in conjunction with any of the above or below embodiments.

In another embodiment L, the present invention provides compounds, and solvates, tautomers, hydrates, stereoisomers and pharmaceutically acceptable salts thereof, as defined by Formulas I, I-A, I-B, I-C or II, wherein
A$^4$ is CR$^4$ or N;
A$^5$ is CR$^5$ or N;
A$^6$ is CR$^6$ or N;
A$^8$ is CR$^8$ or N, provided no more than one of A$^4$, A$^5$, A$^6$ and A$^8$ is N;
each of R$^a$ and R$^b$, independently, is H, F, CH$_3$, CH$_2$F, CHF$_2$ or CF$_3$;
each of R$^1$ and R$^2$, independently, is H, F, CH$_3$, CH$_2$OCH$_3$, CH$_2$F, CHF$_2$ or CF$_3$;
R$^3$ is C$_{1-4}$alkyl, C$_{1-4}$haloalkyl, CH$_2$OH, CH$_2$OCHF$_2$ or cyclopropyl; and
each of R$^4$, R$^5$, R$^6$ and R$^8$, independently, is H, F, Cl, CF$_2$H, CH$_2$F, CF$_3$, OCF$_3$, methyl, ethyl, CN, OH, OCH$_3$, SCH$_3$, NHCH$_3$ or C(O)CH$_3$, in conjunction with any of the above or below embodiments.

In another embodiment M, the present invention provides compounds, and solvates, tautomers, hydrates, stereoisomers and pharmaceutically acceptable salts thereof, as defined by Formulas I and II, wherein
R$^7$ is —NH—R$^9$, —NH—C(=O)—R$^9$ or

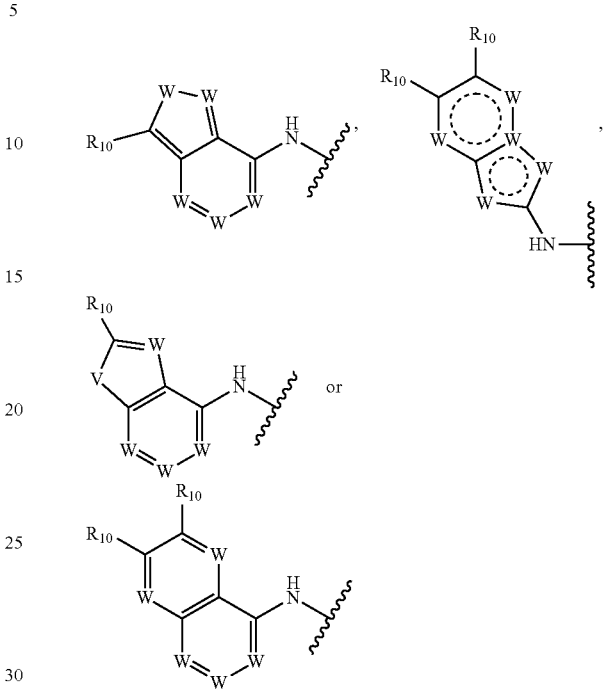

wherein V is NR$^{10}$, O or S; and
each W, independently, is CH, CF, CCl, CCH$_3$ or N, in conjunction with any of the above or below embodiments.

In another embodiment N-1, the invention includes compounds of Formula I-A wherein A$^4$ is CR$^4$;
A$^5$ is CR$^5$ or N;
A$^6$ is CR$^6$;
A$^8$ is CR$^8$; wherein each of R$^4$, R$^5$, R$^6$ and R$^8$, independently, is H, F, Cl, CF$_3$, OCF$_3$, methyl, ethyl, CN, OH, OCH$_3$, SCH$_3$, NHCH$_3$ or C(O)CH$_3$;
each of R$^a$ and R$^b$, independently, is H, F, CH$_3$, CH$_2$F, CHF$_2$ or CF$_3$;
R$^1$ is H, F, CH$_3$, CH$_2$OCH$_3$, CH$_2$F, CHF$_2$ or CF$_3$;
R$^2$ is H, F, CH$_3$, CH$_2$F, CHF$_2$ or CF$_3$;
R$^3$ is CH$_3$, C$_2$H$_5$, CF$_2$H or CH$_2$F;
R$^9$ is acetyl, C$_{1-6}$-alkyl, C$_{2-4}$alkenyl, C$_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the C$_{1-6}$-alkyl, C$_{2-4}$alkenyl, C$_{2-4}$alkynyl and ring are optionally substituted, independently, with 1-5 substituents of R$^{10}$; and
each R$^{10}$, independently, is H, halo, haloalkyl, CN, OH, NO$_2$, NH$_2$, SF$_5$, acetyl, —C(O)NHCH$_3$, oxo, cyclopropylmethoxy, 2-propynyloxy, 2-butynyloxy, C$_{1-6}$alkyl, C$_{2-6}$alkenyl, C$_{2-6}$alkynyl, C$_{3-6}$cycloalkyl, C$_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-propynyloxy, 2-butynyloxy, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl, oxazolyl, isoxazolyl, thiazolyl, isothiazolyl, thiadiazolyl, thienyl, furyl, pyrrolyl, tetrahydropyranyl, tetrahydropyrrolyl or oxetan-3yl.

In another embodiment N-2, the invention includes compounds of Formula I-A
wherein $A^4$ is $CR^4$;
$A^5$ is $CR^5$;
$A^6$ is $CR^6$;
$A^8$ is $CR^8$; wherein each of $R^4$, $R^5$, $R^6$ and $R^8$, independently, is H, F, $CF_3$, $OCF_3$, methyl, ethyl, CN or $OCH_3$;
each of $R^a$ and $R^b$, independently, is H or F;
$R^1$ is H, F, $CH_2OCH_3$ or $CF_3$;
$R^2$ is H, F or $CF_3$;
$R^3$ is $CF_3$, $CH_3$, $CF_2H$ or $CH_2F$;
$R^9$ is a ring selected from phenyl, pyridyl, pyrimidyl, pyrazinyl, pyridazinyl, pyrazolyl, isoxazolyl, thiazolyl, furanyl, thienyl and pyrrolyl, wherein the ring is optionally substituted, independently, with 1-3 substituents of $R^{10}$; and
each $R^{10}$, independently, is H, halo, haloalkyl, CN, OH, $NO_2$, $NH_2$, $SF_5$, acetyl, —C(O)$NHCH_3$, oxo, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazopyridinyl or dioxolyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl, oxazolyl, isoxazolyl, thiazolyl, isothiazolyl, thiadiazolyl, thienyl, furyl, pyrrolyl, tetrahydropyranyl, tetrahydropyrrolyl or oxetan-3yl.

In another embodiment O-1, the invention includes compounds of Formula I-B
wherein $A^4$ is $CR^4$;
$A^5$ is $CR^5$;
$A^6$ is $CR^6$;
$A^8$ is $CR^8$; wherein each of $R^4$, $R^5$, $R^6$ and $R^8$, independently, is H, F, Cl, $CF_3$, $OCF_3$, methyl, ethyl, CN, OH, $OCH_3$, $SCH_3$, $NHCH_3$ or C(O)$CH_3$;
each of $R^a$ and $R^b$, independently, is H, F, $CH_3$, $CH_2F$, $CHF_2$ or $CF_3$;
each of $R^1$ and $R^2$, independently, is H, F, $CH_3$, $CH_2F$, $CHF_2$ or $CF_3$; and
$R^3$ is $CH_3$, $C_2H_5$, $CF_2H$ or $CH_2F$, in conjunction with any of the above or below embodiments with respect to Formula I-B.

In another embodiment O-2, the invention includes compounds of Formula I-B wherein $A^4$ is $CR^4$ or N;
$A^5$ is $CR^5$ or N;
$A^6$ is $CR^6$ or N;
$A^8$ is $CR^8$ or N, wherein each of $R^4$, $R^5$, $R^6$ and $R^8$, independently, is H or F and provided no more than one of $A^4$, $A^5$, $A^6$ and $A^8$ is N;
each of $R^1$ and $R^2$, independently, is H, F or $CF_3$;
each of $R^a$ and $R^b$, independently, is H or F; and
$R^3$ is $CF_3$, $CH_3$, $CF_2H$ or $CH_2F$, in conjunction with any of the above or below embodiments with respect to Formula I-B.

In another embodiment P-1, the invention includes compounds of Formula I-C wherein $A^4$ is $CR^4$;
$A^5$ is $CR^5$;
$A^6$ is $CR^6$;
$A^8$ is $CR^8$; wherein each of $R^4$, $R^5$, $R^6$ and $R^8$, independently, is H, F, Cl, $CF_3$, $OCF_3$, methyl, ethyl, CN, OH, $OCH_3$, $SCH_3$, $NHCH_3$ or C(O)$CH_3$;
each of $R^a$ and $R^b$, independently, is H, F, $CH_3$, $CH_2F$, $CHF_2$ or $CF_3$;
each of $R^1$ and $R^2$, independently, is H, F, $CH_3$, $CH_2F$, $CHF_2$ or $CF_3$; and
$R^3$ is $CH_3$, $C_2H_5$, $CF_2H$ or $CH_2F$, in conjunction with any of the above or below embodiments with respect to Formula I-C.

In another embodiment P-2, the invention includes compounds of Formula I-C wherein $A^4$ is $CR^4$ or N;
$A^5$ is $CR^5$ or N;
$A^6$ is $CR^6$ or N;
$A^8$ is $CR^8$ or N, wherein each of $R^4$, $R^5$, $R^6$ and $R^8$, independently, is H or F and provided no more than one of $A^4$, $A^5$, $A^6$ and $A^8$ is N;
each of $R^1$ and $R^2$, independently, is H, F or $CF_3$;
each of $R^a$ and $R^b$, independently, is H or F; and
$R^3$ is $CF_3$, $CH_3$, $CF_2H$ or $CH_2F$, in conjunction with any of the above or below embodiments with respect to Formula I-C.

In another embodiment, the invention provides one or more of the compounds, or a pharmaceutically acceptable salt thereof, of Formulas I, II and III, and sub-formulas thereof, as taught and described herein.

In another embodiment, the invention provides the compound of Formula I, II or III, or a stereoisomer or pharmaceutically acceptable salt thereof, selected from N-(3-((1S,5S,6S)-3-amino-5-(fluoromethyl)-2-thia-4-azabicyclo[4.1.0]hept-3-en-5-yl)-4-fluorophenyl)-5-chloro-2-pyridinecarboxamide;

N-(3-((1S,5S,6S)-3-amino-5-(fluoromethyl)-2-thia-4-azabicyclo[4.1.0]hept-3-en-5-yl)-4-fluorophenyl)-5-cyano-2-pyridinecarboxamide;

N-(3-((1S,5S,6S)-3-amino-5-(fluoromethyl)-2-thia-4-azabicyclo[4.1.0]hept-3-en-5-yl)-4-fluorophenyl)-5-cyano-3-methyl-2-pyridinecarboxamide;

N-(3-((1S,5S,6S)-3-amino-5-(fluoromethyl)-2-thia-4-azabicyclo[4.1.0]hept-3-en-5-yl)-4-fluorophenyl)-5-methoxy-2-pyrazinecarboxamide; and N-(3-((1S,5S,6S)-3-amino-5-(fluoromethyl)-2-thia-4-azabicyclo[4.1.0]hept-3-en-5-yl)-4,5-difluorophenyl)-5-chloro-2-pyridinecarboxamide;

N-(3-((1S,5S,6S)-3-amino-5-methyl-2-thia-4-azabicyclo[4.1.0]hept-3-en-5-yl)-4,5-difluorophenyl)-5-chloro-2-pyridinecarboxamide;

N-(3-((1S,5S,6S)-3-amino-5-(fluoromethyl)-2-thia-4-azabicyclo[4.1.0]hept-3-en-5-yl)-4,5-difluorophenyl)-5-cyano-2-pyridinecarboxamide;

N-(3-((1S,5S,6S)-3-amino-1-(fluoromethyl)-5-methyl-2-thia-4-azabicyclo[4.1.0]hept-3-en-5-yl)-4,5-difluorophenyl)-5-chloro-2-pyridinecarboxamide;

N-(3-((1S,5S,6S)-3-amino-5-(fluoromethyl)-2-thia-4-azabicyclo[4.1.0]hept-3-en-5-yl)-4,5-difluorophenyl)-5-cyano-3-methyl-2-pyridinecarboxamide;

N-(3-((1S,5S,6S)-3-amino-5-(fluoromethyl)-2-thia-4-azabicyclo[4.1.0]hept-3-en-5-yl)-4,5-difluorophenyl)-5-(2-propyn-1-yloxy)-2-pyrazinecarboxamide;

8-((3-((1S,5S,6S)-3-amino-5-methyl-2-thia-4-azabicyclo[4.1.0]hept-3-en-5-yl)-4,5-difluorophenyl)amino)-1,7-naphthyridine-3-carbonitrile;

N-(3-((1S,5S,6S)-3-amino-5-methyl-2-thia-4-azabicyclo[4.1.0]hept-3-en-5-yl)-4,5-difluorophenyl)-5-(2-propyn-1-yloxy)-2-pyrazinecarboxamide;

8-((3-((1S,5S,6S)-3-amino-5-(fluoromethyl)-2-thia-4-azabicyclo[4.1.0]hept-3-en-5-yl)-4,5-difluorophenyl)amino)-1,7-naphthyridine-3-carbonitrile;

4-((3-((1S,5S,6S)-3-amino-5-(fluoromethyl)-2-thia-4-azabicyclo[4.1.0]hept-3-en-5-yl)-4,5-difluorophenyl)amino)pyrido[3,2-d]pyrimidine-7-carbonitrile;

8-((3-((1S,5S,6S)-3-amino-1-(methoxymethyl)-5-methyl-2-thia-4-azabicyclo[4.1.0]hept-3-en-5-yl)-4,5-difluorophenyl)amino)-1,7-naphthyridine-3-carbonitrile;

N-(3-((1S,5S,6S)-3-amino-1-(methoxymethyl)-5-methyl-2-thia-4-azabicyclo[4.1.0]hept-3-en-5-yl)-4,5-difluorophenyl)-7-chloropyrido[3,2-d]pyrimidin-4-amine;

4-((3-((1S,5S,6S)-3-amino-5-methyl-2-thia-4-azabicyclo[4.1.0]hept-3-en-5-yl)-4,5-difluorophenyl)amino)pyrido[3,2-d]pyrimidine-7-carbonitrile;

8-((3-((1S,5S,6S)-3-amino-5-(fluoromethyl)-2-thia-4-azabicyclo[4.1.0]hept-3-en-5-yl)-4-fluorophenyl)amino)-1,7-naphthyridine-3-carbonitrile;

N-(3-((1S,5S,6S)-3-amino-5-(fluoromethyl)-2-thia-4-azabicyclo[4.1.0]hept-3-en-5-yl)-4-fluorophenyl)-7-chloropyrido[3,2-d]pyrimidin-4-amine;

4-((3-((1S,5S,6S)-3-amino-1-(methoxymethyl)-5-methyl-2-thia-4-azabicyclo[4.1.0]hept-3-en-5-yl)-4,5-difluorophenyl)amino)pyrido[3,2-d]pyrimidine-7-carbonitrile;

((1S,5S,6S)-3-amino-5-((7-chloropyrido[3,2-d]pyrimidin-4-yl)amino)-2-fluorophenyl)-5-(fluoromethyl)-2-thia-4-azabicyclo[4.1.0]hept-3-en-1-yl)methanol;

4-((3-((1S,5S,6S)-3-amino-5-(fluoromethyl)-2-thia-4-azabicyclo[4.1.0]hept-3-en-5-yl)-4-fluorophenyl)amino)pyrido[3,2-d]pyrimidine-7-carbonitrile;

((1S,5S,6S)-3-amino-5-(fluoromethyl)-5-(2-fluoro-5-((3-(2-propyn-1-yloxy)-1,7-naphthyridin-8-yl)amino)phenyl)-2-thia-4-azabicyclo[4.1.0]hept-3-en-1-yl)methanol;

8-((3-((1S,5S,6S)-3-amino-1-(hydroxymethyl)-5-methyl-2-thia-4-azabicyclo[4.1.0]hept-3-en-5-yl)-4,5-difluorophenyl)amino)-1,7-naphthyridine-3-carbonitrile;

N-(3-((1S,5S,6S)-3-amino-5-(fluoromethyl)-2-thia-4-azabicyclo[4.1.0]hept-3-en-5-yl)-4-fluorophenyl)-2-(1,3-oxazol-2-ylmethoxy)pyrido[3,4-b]pyrazin-5-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(2-propyn-1-yloxy)-2-pyrazinecarboxamide;

((1S,5S,6S)-3-amino-5-(2,3-difluoro-5-((2-(2-propyn-1-yloxy)pyrido[3,4-b]pyrazin-5-yl)amino)phenyl)-5-methyl-2-thia-4-azabicyclo[4.1.0]hept-3-en-1-yl)methanol;

N-(3-((1S,5S,6S)-3-amino-5-(fluoromethyl)-2-thia-4-azabicyclo[4.1.0]hept-3-en-5-yl)-4,5-difluorophenyl)-3-methyl-5-(2-propyn-1-yloxy)-2-pyrazinecarboxamide; or 4-((3-((1S,5S,6S)-3-amino-1-(difluoromethyl)-5-methyl-2-thia-4-azabicyclo[4.1.0]hept-3-en-5-yl)-4,5-difluorophenyl)amino)pyrido[3,2-d]pyrimidine-7-carbonitrile.

In another embodiment, the invention provides the compound of Formula I or a tautomer, stereoisomer, or pharmaceutically acceptable salt thereof selected from N-(5-((1S,5S,6S)-3-amino-1-(fluoromethyl)-5-methyl-2-thia-4-azabicyclo[4.1.0]hept-3-en-5-yl)-6-fluoro-3-pyridinyl)-2-(2-propyn-1-yloxy)pyrido[3,4-b]pyrazin-5-amine;

N-(5-((1S,5S,6S)-3-amino-1-(fluoromethyl)-5-methyl-2-thia-4-azabicyclo[4.1.0]hept-3-en-5-yl)-6-fluoro-3-pyridinyl)-2-(1,3-oxazol-2-ylmethoxy)pyrido[3,4-b]pyrazin-5-amine;

N-(5-((1S,5S,6S)-3-amino-1-(fluoromethyl)-5-methyl-2-thia-4-azabicyclo[4.1.0]hept-3-en-5-yl)-6-fluoro-3-pyridinyl)-3-methyl-5-(2-propyn-1-yloxy)-2-pyrazinecarboxamide;

8-((5-((1S,5S,6S)-3-amino-1-(fluoromethyl)-5-methyl-2-thia-4-azabicyclo[4.1.0]hept-3-en-5-yl)-6-fluoro-3-pyridinyl)amino)-1,7-naphthyridine-3-carbonitrile;

N-(5-((1S,5S,6S)-3-amino-1-(fluoromethyl)-5-methyl-2-thia-4-azabicyclo[4.1.0]hept-3-en-5-yl)-6-fluoro-3-pyridinyl)-7-(1,3-oxazol-2-ylmethoxy)pyrido[3,2-d]pyrimidin-4-amine;

N-(5-((1S,5S,6S)-3-amino-1-(fluoromethyl)-5-methyl-2-thia-4-azabicyclo[4.1.0]hept-3-en-5-yl)-6-fluoro-3-pyridinyl)-5-(2-propyn-1-yloxy)-2-pyrazinecarboxamide;

N-(5-((1S,5S,6S)-3-amino-1-(fluoromethyl)-5-methyl-2-thia-4-azabicyclo[4.1.0]hept-3-en-5-yl)-6-fluoro-3-pyridinyl)-5-(1,3-oxazol-2-ylmethoxy)-2-pyrazinecarboxamide;

((1R,5S,6S)-3-amino-5-(2-fluoro-5-((7-(1,3-oxazol-2-ylmethoxy)pyrido[3,2-d]pyrimidin-4-yl)amino)-3-pyridinyl)-5-methyl-2-thia-4-azabicyclo[4.1.0]hept-3-en-1-yl)acetonitrile;

N-(5-((1S,5S,6S)-3-amino-1-(fluoromethyl)-5-methyl-2-thia-4-azabicyclo[4.1.0]hept-3-en-5-yl)-6-fluoro-3-pyridinyl)-5-(2,2,3,3-tetrafluoropropoxy)-2-pyridinecarboxamide;

N-(5-((1S,5S,6S)-3-amino-1-(fluoromethyl)-5-methyl-2-thia-4-azabicyclo[4.1.0]hept-3-en-5-yl)-6-fluoro-3-pyridinyl)-5-(2,2,3,3-tetrafluoropropoxy)-2-pyrazinecarboxamide;

N-(5-((1S,5S,6S)-3-amino-1-(fluoromethyl)-5-methyl-2-thia-4-azabicyclo[4.1.0]hept-3-en-5-yl)-6-methoxy-3-pyridinyl)-2-(2-propyn-1-yloxy)pyrido[3,4-b]pyrazin-5-amine;

N-(5-((1S,5S,6S)-3-amino-1-(fluoromethyl)-5-methyl-2-thia-4-azabicyclo[4.1.0]hept-3-en-5-yl)-6-methoxy-3-pyridinyl)-5-(2-propyn-1-yloxy)-2-pyrazinecarboxamide;

N-(5-((1S,5S,6S)-3-amino-1-(fluoromethyl)-5-methyl-2-thia-4-azabicyclo[4.1.0]hept-3-en-5-yl)-6-fluoro-3-pyridinyl)-2-((~2~H_5_)-2-butyn-1-yloxy)pyrido[3,4-b]pyrazin-5-amine;

N-(3-((1S,5S,6S)-3-amino-1-(fluoromethyl)-5-methyl-2-thia-4-azabicyclo[4.1.0]hept-3-en-5-yl)-4,5-difluorophenyl)-3-methyl-5-(2,2,2-trifluoroethoxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-3-methyl-5-(2,2,2-trifluoroethoxy)-2-pyrazinecarboxamide;

N-(3-((1S,5S,6S)-3-amino-1-(fluoromethyl)-5-methyl-2-thia-4-azabicyclo[4.1.0]hept-3-en-5-yl)-4,5-difluorophenyl)-3-methyl-5-(((1S)-1-methyl-2-propyn-1-yl)oxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-3-methyl-5-(((1S)-1-methyl-2-propyn-1-yl)oxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-(2,2,2-trifluoroethoxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-3-methyl-5-(((1S)-1-methyl-2-propyn-1-yl)oxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-3-methyl-5-(2,2,2-trifluoroethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-3-methyl-5-(((1S)-1-methyl-2-propyn-1-yl)oxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-(((1S)-1-methyl-2-propyn-1-yl)oxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-3-methyl-5-(2,2,2-trifluoroethoxy)-2-pyrazinecarboxamide;

N-(5-((1S,5S,6S)-3-amino-1-(fluoromethyl)-5-methyl-2-thia-4-azabicyclo[4.1.0]hept-3-en-5-yl)-6-methoxy-3-pyridinyl)-5-chloro-2-pyridinecarboxamide;

N-(5-((1S,5S,6S)-3-amino-1-(fluoromethyl)-5-methyl-2-thia-4-azabicyclo[4.1.0]hept-3-en-5-yl)-6-methoxy-3-pyridinyl)-7-(2-propyn-1-yloxy)pyrido[3,2-d]pyrimidin-4-amine;

N-(5-((1S,5S,6S)-3-amino-1-(fluoromethyl)-5-methyl-2-thia-4-azabicyclo[4.1.0]hept-3-en-5-yl)-6-methoxy-3-pyridinyl)-2-(1,3-oxazol-2-ylmethoxy)pyrido[3,4-b]pyrazin-5-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-2-(2-propyn-1-yloxy)pyrido[3,4-b]pyrazin-5-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-2-(1,3-oxazol-4-ylmethoxy)pyrido[3,4-b]pyrazin-5-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-3-methoxy-1,7-naphthyridin-8-amine;

N-(3-((1R,5S,6S)-3-amino-5-methyl-1-(methylsulfonyl)-2-thia-4-azabicyclo[4.1.0]hept-3-en-5-yl)-4,5-difluorophenyl)-2-(2-propyn-1-yloxy)pyrido[3,4-b]pyrazin-5-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-2-(1,3-oxazol-2-ylmethoxy)pyrido[3,4-b]pyrazin-5-amine;

N-(3-((1S,5S,6S)-3-amino-5-methyl-1-(1-pyrrolidinylcarbonyl)-2-thia-4-azabicyclo[4.1.0]hept-3-en-5-yl)-4-fluorophenyl)-2-(2-propyn-1-yloxy)pyrido[3,4-b]pyrazin-5-amine;

N-(3-((1S,5S,6S)-3-amino-5-methyl-1-(1-pyrrolidinylcarbonyl)-2-thia-4-azabicyclo[4.1.0]hept-3-en-5-yl)-4-fluorophenyl)-5-(2-propyn-1-yloxy)-2-pyrazinecarboxamide;

N-(3-((1S,5S,6S)-3-amino-5-methyl-1-(1-pyrrolidinylcarbonyl)-2-thia-4-azabicyclo[4.1.0]hept-3-en-5-yl)-4-fluorophenyl)-5-(2,2,2-trifluoroethoxy)-2-pyrazinecarboxamide;

N-(3-((1S,5S,6S)-3-amino-1,5-bis(fluoromethyl)-2-thia-4-azabicyclo[4.1.0]hept-3-en-5-yl)-4-fluorophenyl)-2-(2-methoxyethoxy)pyrido[3,4-b]pyrazin-5-amine;

N-(3-((1S,5S,6S)-3-amino-5-methyl-2-thia-4-azabicyclo[4.1.0]hept-3-en-5-yl)-4,5-difluorophenyl)-7-fluoropyrido[3,2-d]pyrimidin-4-amine;

N-(5-((1S,5S,6S)-3-amino-5-methyl-2-thia-4-azabicyclo[4.1.0]hept-3-en-5-yl)-6-fluoro-3-pyridinyl)-5-chloro-2-pyridinecarboxamide;

5-((5-((1S,5S,6S)-3-amino-5-methyl-2-thia-4-azabicyclo[4.1.0]hept-3-en-5-yl)-6-fluoro-3-pyridinyl)amino)pyrido[3,4-b]pyrazin-2(1H)-one;

N-(5-((1S,5S,6S)-3-amino-5-methyl-2-thia-4-azabicyclo[4.1.0]hept-3-en-5-yl)-6-fluoro-3-pyridinyl)-2-(2-propyn-1-yloxy)pyrido[3,4-b]pyrazin-5-amine;

N-(5-((1S,5S,6S)-3-amino-5-methyl-2-thia-4-azabicyclo[4.1.0]hept-3-en-5-yl)-6-fluoro-3-pyridinyl)-2-(1,3-oxazol-2-ylmethoxy)pyrido[3,4-b]pyrazin-5-amine;

8-((5-((1S,5S,6S)-3-amino-5-methyl-2-thia-4-azabicyclo[4.1.0]hept-3-en-5-yl)-6-fluoro-3-pyridinyl)amino)-1,7-naphthyridine-3-carbonitrile;

N-(3-((1S,5S,6S)-3-amino-1-(difluoromethyl)-5-methyl-2-thia-4-azabicyclo[4.1.0]hept-3-en-5-yl)-4-fluorophenyl)-3-methyl-5-(1,3-oxazol-2-ylmethoxy)-2-pyridinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-3-methyl-5-(1,3-oxazol-2-ylmethoxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-3-methyl-5-(1,3-oxazol-2-ylmethoxy)-2-pyridinecarboxamide;

N-(3-((1S,5S,6S)-3-amino-1-(fluoromethyl)-5-methyl-2-thia-4-azabicyclo[4.1.0]hept-3-en-5-yl)-4,5-difluorophenyl)-3-methyl-5-(1,3-oxazol-2-ylmethoxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-(1,3-oxazol-2-ylmethoxy)-2-pyridinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-3-methyl-5-(((1S)-1-methyl-2-propyn-1-yl)oxy)-2-pyridinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-3-methyl-5-(((1S)-1-methyl-2-propyn-1-yl)oxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-3-methyl-5-(((1S)-1-methyl-2-propyn-1-yl)oxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-(((1S)-1-methyl-2-propyn-1-yl)oxy)-2-pyridinecarboxamide;

N-(3-((1S,5S,6S)-3-amino-1-(fluoromethyl)-5-methyl-2-thia-4-azabicyclo[4.1.0]hept-3-en-5-yl)-4-fluorophenyl)-3-methyl-5-(((1S)-1-methyl-2-propyn-1-yl)oxy)-2-pyridinecarboxamide;

N-(3-((1S,5S,6S)-3-amino-1-(fluoromethyl)-5-methyl-2-thia-4-azabicyclo[4.1.0]hept-3-en-5-yl)-4-fluorophenyl)-3-methyl-5-(1,3-oxazol-2-ylmethoxy)-2-pyridinecarboxamide;

N-(5-((1S,5S,6S)-3-amino-1-(difluoromethyl)-5-methyl-2-thia-4-azabicyclo[4.1.0]hept-3-en-5-yl)-6-fluoro-3-pyridinyl)-2-(2-propyn-1-yloxy)pyrido[3,4-b]pyrazin-5-amine;

N-(5-((1S,5S,6S)-3-amino-1-(difluoromethyl)-5-methyl-2-thia-4-azabicyclo[4.1.0]hept-3-en-5-yl)-6-fluoro-3-pyridinyl)-2-(1,3-oxazol-2-ylmethoxy)pyrido[3,4-b]pyrazin-5-amine;

N-(5-((1S,5S,6S)-3-amino-1-(difluoromethyl)-5-methyl-2-thia-4-azabicyclo[4.1.0]hept-3-en-5-yl)-6-fluoro-3-pyridinyl)-5-chloro-2-pyridinecarboxamide;

8-((5-((1S,5S,6S)-3-amino-1-(difluoromethyl)-5-methyl-2-thia-4-azabicyclo[4.1.0]hept-3-en-5-yl)-6-fluoro-3-pyridinyl)amino)-N-(1-methylethyl)-1,7-naphthyridine-3-carboxamide;

8-((5-((1S,5S,6S)-3-amino-1-(difluoromethyl)-5-methyl-2-thia-4-azabicyclo[4.1.0]hept-3-en-5-yl)-6-fluoro-3-pyridinyl)amino)-1,7-naphthyridine-3-carbonitrile;

4-((5-((1S,5S,6S)-3-amino-1-(difluoromethyl)-5-methyl-2-thia-4-azabicyclo[4.1.0]hept-3-en-5-yl)-6-fluoro-3-pyridinyl)amino)pyrido[3,2-d]pyrimidine-7-carbonitrile;

(1R)-1-((1S,5S,6S)-3-amino-5-(2-fluoro-5-((2-(2-propyn-1-yloxy)pyrido[3,4-b]pyrazin-5-yl)amino)-3-pyridinyl)-5-methyl-2-thia-4-azabicyclo[4.1.0]hept-3-en-1-yl)-2,2,2-trifluoroethanol;

(1S)-1-((1S,5S,6S)-3-amino-5-(2-fluoro-5-((2-(2-propyn-1-yloxy)pyrido[3,4-b]pyrazin-5-yl)amino)-3-pyridinyl)-5-methyl-2-thia-4-azabicyclo[4.1.0]hept-3-en-1-yl)-2,2,2-trifluoroethanol;

((1S,5S,6R)-3-amino-7,7-difluoro-5-(2-fluoro-5-((2-(2-propyn-1-yloxy)pyrido[3,4-b]pyrazin-5-yl)amino)-3-pyridinyl)-5-methyl-2-thia-4-azabicyclo[4.1.0]hept-3-en-1-yl)methanol;

((1S,5S,6S)-3-amino-5-(2-fluoro-5-((2-(2-propyn-1-yloxy)pyrido[3,4-b]pyrazin-5-yl)amino)-3-pyridinyl)-5-methyl-2-thia-4-azabicyclo[4.1.0]hept-3-en-1-yl)methanol;

((1S,5S,6R)-3-amino-7,7-difluoro-5-(2-fluoro-5-((2-(1,3-oxazol-2-ylmethoxy)pyrido[3,4-b]pyrazin-5-yl)amino)-3-pyridinyl)-5-methyl-2-thia-4-azabicyclo[4.1.0]hept-3-en-1-yl)methanol;

((1S,5S,6R)-3-amino-7,7-difluoro-5-(2-fluoro-5-((7-(1,3-oxazol-2-ylmethoxy)pyrido[3,2-d]pyrimidin-4-yl)amino)-3-pyridinyl)-5-methyl-2-thia-4-azabicyclo[4.1.0]hept-3-en-1-yl)methanol;

(1R)-1-((1S,5S,6S)-3-amino-5-(2-fluoro-5-((7-(2-propyn-1-yloxy)pyrido[3,2-d]pyrimidin-4-yl)amino)-3-pyridinyl)-5-methyl-2-thia-4-azabicyclo[4.1.0]hept-3-en-1-yl)-2,2,2-trifluoroethanol;

(1S)-1-((1S,5S,6S)-3-amino-5-(2-fluoro-5-((7-(2-propyn-1-yloxy)pyrido[3,2-d]pyrimidin-4-yl)amino)-3-pyridinyl)-5-methyl-2-thia-4-azabicyclo[4.1.0]hept-3-en-1-yl)-2,2,2-trifluoroethanol;

(1R)-1-((1S,5S,6S)-3-amino-5-(2-fluoro-5-((7-(1,3-oxazol-2-ylmethoxy)pyrido[3,2-d]pyrimidin-4-yl)amino)-3-pyridinyl)-5-methyl-2-thia-4-azabicyclo[4.1.0]hept-3-en-1-yl)-2,2,2-trifluoroethanol;

(1S)-1-((1S,5S,6S)-3-amino-5-(2-fluoro-5-((7-(1,3-oxazol-2-ylmethoxy)pyrido[3,2-d]pyrimidin-4-yl)amino)-3-pyridinyl)-5-methyl-2-thia-4-azabicyclo[4.1.0]hept-3-en-1-yl)-2,2,2-trifluoroethanol;

((1S,5S,6R)-3-amino-7,7-difluoro-5-(2-fluoro-5-((3-(1,3-oxazol-2-ylmethoxy)-1,7-naphthyridin-8-yl)amino)-3-pyridinyl)-5-methyl-2-thia-4-azabicyclo[4.1.0]hept-3-en-1-yl)methanol;

((1S,5S,6S)-3-amino-5-(2-fluoro-5-((7-(2-propyn-1-yloxy)pyrido[3,2-d]pyrimidin-4-yl)amino)-3-pyridinyl)-5-methyl-2-thia-4-azabicyclo[4.1.0]hept-3-en-1-yl)methanol;

(1R)-1-((1S,5S,6S)-3-amino-5-(2-fluoro-5-((2-(2-propyn-1-yloxy)pyrido[3,4-b]pyrazin-5-yl)amino)phenyl)-5-methyl-2-thia-4-azabicyclo[4.1.0]hept-3-en-1-yl)-2,2,2-trifluoroethanol;

(1S)-1-((1S,5S,6S)-3-amino-5-(2-fluoro-5-((2-(2-propyn-1-yloxy)pyrido[3,4-b]pyrazin-5-yl)amino)phenyl)-5-methyl-2-thia-4-azabicyclo[4.1.0]hept-3-en-1-yl)-2,2,2-trifluoroethanol;

N-(3-((1S,5S,6S)-3-amino-5-methyl-1-((1R)-2,2,2-trifluoro-1-hydroxyethyl)-2-thia-4-azabicyclo[4.1.0]hept-3-en-5-yl)-4-fluorophenyl)-5-(2-propyn-1-yloxy)-2-pyrazinecarboxamide;

N-(3-((1S,5S,6S)-3-amino-5-methyl-1-((1S)-2,2,2-trifluoro-1-hydroxyethyl)-2-thia-4-azabicyclo[4.1.0]hept-3-en-5-yl)-4-fluorophenyl)-5-(2-propyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-(2,2,2-trifluoroethoxy)-2-pyridinecarboxamide;

N-(5-((1S,5S,6S)-3-amino-5-methyl-1-((1R)-2,2,2-trifluoro-1-methoxyethyl)-2-thia-4-azabicyclo[4.1.0]hept-3-en-5-yl)-6-fluoro-3-pyridinyl)-2-(2-propyn-1-yloxy)pyrido[3,4-b]pyrazin-5-amine;

N-(5-((1S,5S,6S)-3-amino-5-methyl-1-((1S)-2,2,2-trifluoro-1-methoxyethyl)-2-thia-4-azabicyclo[4.1.0]hept-3-en-5-yl)-6-fluoro-3-pyridinyl)-2-(2-propyn-1-yloxy)pyrido[3,4-b]pyrazin-5-amine;

N-(3-((1S,5S,6S)-3-amino-1-(fluoromethyl)-5-methyl-2-thia-4-azabicyclo[4.1.0]hept-3-en-5-yl)-4,5-difluorophenyl)-3-methyl-5-(2,2,2-trifluoroethoxy)-2-pyridinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-3-methyl-5-(2,2,2-trifluoroethoxy)-2-pyridinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-3-methyl-5-(2,2,2-trifluoroethoxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-3-methyl-5-(2,2,2-trifluoroethoxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-(2-propyn-1-yloxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-3-methyl-5-(2-propyn-1-yloxy)-2-pyridinecarboxamide;

N-(3-((1S,5S,6S)-3-amino-1-(fluoromethyl)-5-methyl-2-thia-4-azabicyclo[4.1.0]hept-3-en-5-yl)-4,5-difluorophenyl)-3-methyl-5-(2-propyn-1-yloxy)-2-pyridinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-3-methyl-5-(2-propyn-1-yloxy)-2-pyridinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-3-methyl-5-(2-propyn-1-yloxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-((1S)-1-(1,3-oxazol-2-yl)ethoxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-((1R)-1-(1,3-oxazol-2-yl)ethoxy)-2-pyridinecarboxamide;

N-(3-((1S,5S,6S)-3-amino-1-(fluoromethyl)-5-methyl-2-thia-4-azabicyclo[4.1.0]hept-3-en-5-yl)-4-fluorophenyl)-3-methyl-5-(2,2,2-trifluoroethoxy)-2-pyridinecarboxamide;

N-(3-((1S,5S,6S)-3-amino-1-(fluoromethyl)-5-methyl-2-thia-4-azabicyclo[4.1.0]hept-3-en-5-yl)-4-fluorophenyl)-3-methyl-5-(2-propyn-1-yloxy)-2-pyridinecarboxamide;

N-(3-((1S,5S,6S)-3-amino-1-(fluoromethyl)-5-methyl-2-thia-4-azabicyclo[4.1.0]hept-3-en-5-yl)-4,5-difluorophenyl)-3-chloro-5-(2-propyn-1-yloxy)-2-pyridinecarboxamide;

N-(3-((1S,5S,6S)-3-amino-1-(fluoromethyl)-5-methyl-2-thia-4-azabicyclo[4.1.0]hept-3-en-5-yl)-4,5-difluorophenyl)-5-(2,2,2-trifluoroethoxy)-2-pyridinecarboxamide;

N-(3-((1S,5S,6S)-3-amino-1-(fluoromethyl)-5-methyl-2-thia-4-azabicyclo[4.1.0]hept-3-en-5-yl)-4,5-difluorophenyl)-3-chloro-5-(2,2,2-trifluoroethoxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(2,2,2-trifluoroethoxy)-2-pyridinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-5-(2,2,2-trifluoroethoxy)-2-pyridinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-5-(2,2,2-trifluoroethoxy)-2-pyridinecarboxamide;

N-(3-((1S,5S,6S)-3-amino-1-(fluoromethyl)-5-methyl-2-thia-4-azabicyclo[4.1.0]hept-3-en-5-yl)-4-fluorophenyl)-5-(2,2,2-trifluoroethoxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(2,2,2-trifluoroethoxy)-2-pyridinecarboxamide;

N-(3-((1S,5S,6S)-3-amino-5-methyl-1-(1-pyrrolidinylcarbonyl)-2-thia-4-azabicyclo[4.1.0]hept-3-en-5-yl)-4,5-difluorophenyl)-5-(2,2,2-trifluoroethoxy)-2-pyridinecarboxamide;

(1S,5S,6S)-3-amino-5-(2,3-difluoro-5-(((5-(2,2,2-trifluoroethoxy)-2-pyridinyl)carbonyl)amino)phenyl)-N,5-dimethyl-2-thia-4-azabicyclo[4.1.0]hept-3-ene-1-carboxamide;

(1S,5S,6S)-3-amino-5-(2,3-difluoro-5-(((5-(2,2,2-trifluoroethoxy)-2-pyrazinyl)carbonyl)amino)phenyl)-N,5-dimethyl-2-thia-4-azabicyclo[4.1.0]hept-3-ene-1-carboxamide;

(1S,5S,6S)-3-amino-5-(2,3-difluoro-5-(((3-methyl-5-(2,2,2-trifluoroethoxy)-2-pyridinyl)carbonyl)amino)phenyl)-N,5-dimethyl-2-thia-4-azabicyclo[4.1.0]hept-3-ene-1-carboxamide;

4-((3-((1S,5S,6R)-3-amino-7,7-difluoro-1-(hydroxymethyl)-5-methyl-2-thia-4-azabicyclo[4.1.0]hept-3-en-5-yl)-4-fluorophenyl)amino)pyrido[3,2-d]pyrimidine-7-carbonitrile;

N-(3-((1S,5S,6R)-3-amino-7,7-difluoro-1-(hydroxymethyl)-5-methyl-2-thia-4-azabicyclo[4.1.0]hept-3-en-5-yl)-4-fluorophenyl)-5-chloro-2-pyridinecarboxamide;

((1S,5S,6R)-3-amino-7,7-difluoro-5-(2-fluoro-5-((2-(1,3-oxazol-2-ylmethoxy)pyrido[3,4-b]pyrazin-5-yl)amino)phenyl)-5-methyl-2-thia-4-azabicyclo[4.1.0]hept-3-en-1-yl)methanol;

((1S,5S,6R)-3-amino-7,7-difluoro-5-(2-fluoro-5-((2-(1,3-oxazol-4-ylmethoxy)pyrido[3,4-b]pyrazin-5-yl)amino)phenyl)-5-methyl-2-thia-4-azabicyclo[4.1.0]hept-3-en-1-yl)methanol;

((1S,5S,6R)-3-amino-7,7-difluoro-5-(2-fluoro-5-((2-(2-propyn-1-yloxy)pyrido[3,4-b]pyrazin-5-yl)amino)phenyl)-5-methyl-2-thia-4-azabicyclo[4.1.0]hept-3-en-1-yl)methanol;

N-(3-((1S,5S,6R)-3-amino-7,7-difluoro-1-(hydroxymethyl)-5-methyl-2-thia-4-azabicyclo[4.1.0]hept-3-en-5-yl)-4-fluorophenyl)-5-(2,2,3,3-tetrafluoropropoxy)-2-pyrazinecarboxamide;

4-((3-((1S,5S,6R)-3-amino-7,7-difluoro-1-(methoxymethyl)-5-methyl-2-thia-4-azabicyclo[4.1.0]hept-3-en-5-yl)-4-fluorophenyl)amino)pyrido[3,2-d]pyrimidine-7-carbonitrile;

N-(3-((1S,5S,6R)-3-amino-7,7-difluoro-1-(methoxymethyl)-5-methyl-2-thia-4-azabicyclo[4.1.0]hept-3-en-5-yl)-4-fluorophenyl)-5-chloro-2-pyridinecarboxamide;

N-(3-((1S,5S,6R)-3-amino-7,7-difluoro-1-(1-hydroxy-1-methylethyl)-5-methyl-2-thia-4-azabicyclo[4.1.0]hept-3-en-5-yl)-4-fluorophenyl)-5-chloro-2-pyridinecarboxamide;

2-((1S,5S,6R)-3-amino-7,7-difluoro-5-(2-fluoro-5-((2-(2-propyn-1-yloxy)pyrido[3,4-b]pyrazin-5-yl)amino)phenyl)-5-methyl-2-thia-4-azabicyclo[4.1.0]hept-3-en-1-yl)-2-propanol;

(1R)-1-((1S,5S,6R)-3-amino-7,7-difluoro-5-(2-fluoro-5-((2-(2-propyn-1-yloxy)pyrido[3,4-b]pyrazin-5-yl)amino)phenyl)-5-methyl-2-thia-4-azabicyclo[4.1.0]hept-3-en-1-yl)ethanol;

(1S)-1-((1S,5S,6R)-3-amino-7,7-difluoro-5-(2-fluoro-5-((2-(2-propyn-1-yloxy)pyrido[3,4-b]pyrazin-5-yl)amino)phenyl)-5-methyl-2-thia-4-azabicyclo[4.1.0]hept-3-en-1-yl)ethanol;

N-(3-((1S,5S,6S)-3-amino-1-(ethoxymethyl)-5-(fluoromethyl)-2-thia-4-azabicyclo[4.1.0]hept-3-en-5-yl)-4-fluorophenyl)-5-cyano-3-methyl-2-pyridinecarboxamide;

N-(3-((1S,5S,6S)-3-amino-5-(fluoromethyl)-1-(methoxymethyl)-2-thia-4-azabicyclo[4.1.0]hept-3-en-5-yl)-4-fluorophenyl)-5-cyano-3-methyl-2-pyridinecarboxamide;

8-((3-((1S,5S,6S)-3-amino-5-(fluoromethyl)-1-(methoxymethyl)-2-thia-4-azabicyclo[4.1.0]hept-3-en-5-yl)-4-fluorophenyl)amino)-1,7-naphthyridine-3-carbonitrile;

N-(3-((1R,5S,6S)-3-amino-1-(cyanomethyl)-5-(fluoromethyl)-2-thia-4-azabicyclo[4.1.0]hept-3-en-5-yl)-4-fluorophenyl)-5-chloro-2-pyridinecarboxamide;

8-((3-((1R,5S,6S)-3-amino-1-(cyanomethyl)-5-(fluoromethyl)-2-thia-4-azabicyclo[4.1.0]hept-3-en-5-yl)-4-fluorophenyl)amino)-1,7-naphthyridine-3-carbonitrile;

((1R,5S,6S)-3-amino-5-(fluoromethyl)-5-(2-fluoro-5-((2-(2-propyn-1-yloxy)pyrido[3,4-b]pyrazin-5-yl)amino)phenyl)-2-thia-4-azabicyclo[4.1.0]hept-3-en-1-yl)acetonitrile;

((1R,5S,6S)-3-amino-5-(fluoromethyl)-5-(2-fluoro-5-((2-(1,3-oxazol-2-ylmethoxy)pyrido[3,4-b]pyrazin-5-yl)amino)phenyl)-2-thia-4-azabicyclo[4.1.0]hept-3-en-1-yl)acetonitrile;

N-(3-((1S,5S,6S)-3-amino-5-(fluoromethyl)-1-(1H-1,2,3-triazol-1-ylmethyl)-2-thia-4-azabicyclo[4.1.0]hept-3-en-5-yl)-4-fluorophenyl)-5-chloro-2-pyridinecarboxamide;

N-(3-((1S,5S,6S)-3-amino-1-(2-cyanoethyl)-5-(fluoromethyl)-2-thia-4-azabicyclo[4.1.0]hept-3-en-5-yl)-4-fluorophenyl)-5-chloro-2-pyridinecarboxamide;

N-(3-((1S,5S,6S)-3-amino-5-(fluoromethyl)-1-((4-methyl-1H-1,2,3-triazol-1-yl)methyl)-2-thia-4-azabicyclo[4.1.0]

hept-3-en-5-yl)-4-fluorophenyl)-2-(2-propyn-1-yloxy) pyrido[3,4-b]pyrazin-5-amine;

N-(3-((1S,5S,6S)-3-amino-5-(fluoromethyl)-1-((5-methyl-1H-1,2,3-triazol-1-yl)methyl)-2-thia-4-azabicyclo[4.1.0] hept-3-en-5-yl)-4-fluorophenyl)-5-chloro-2-pyridinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-(1,3-oxazol-5-ylmethoxy)-1,7-naphthyridin-8-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-3-(1,3-oxazol-2-ylmethoxy)-1,7-naphthyridin-8-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-3-(1,3-oxazol-4-ylmethoxy)-1,7-naphthyridin-8-amine;

((8-((3-((1S,5S,6S)-3-amino-1-(methoxymethyl)-5-methyl-2-thia-4-azabicyclo[4.1.0]hept-3-en-5-yl)-4,5-difluorophenyl)amino)-1,7-naphthyridin-3-yl)oxy)acetonitrile;

N-(3-((1S,5S,6S)-3-amino-1-(methoxymethyl)-5-methyl-2-thia-4-azabicyclo[4.1.0]hept-3-en-5-yl)-4,5-difluorophenyl)-3-(1,2,4-oxadiazol-3-ylmethoxy)-1,7-naphthyridin-8-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-3-(2,2,3,3-tetrafluoropropoxy)-1,7-naphthyridin-8-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(2,2,3,3-tetrafluoropropoxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-(2-propyn-1-yloxy)-1,7-naphthyridin-8-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(2,2,3,3-tetrafluoropropoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-((5-chloro-1,3-thiazol-2-yl)methoxy)-1,7-naphthyridin-8-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-3-((4-bromo-1,3-thiazol-2-yl)methoxy)-1,7-naphthyridin-8-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-3-(1,3-thiazol-2-ylmethoxy)-1,7-naphthyridin-8-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(3,3,3-trifluoropropoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(2,2-difluoropropoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(3-fluoropropoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-((4,4,4-trifluoro-2-butyn-1-yl)oxy)-1,7-naphthyridin-8-amine;

N-(3-((1R,5S,6S)-3-amino-5-methyl-1-(methylsulfonyl)-2-thia-4-azabicyclo[4.1.0]hept-3-en-5-yl)-4,5-difluorophenyl)-5-chloro-2-pyridinecarboxamide;

N-(3-((1R,5S,6S)-3-amino-5-methyl-1-(methylsulfonyl)-2-thia-4-azabicyclo[4.1.0]hept-3-en-5-yl)-4,5-difluorophenyl)-5-(2-propyn-1-yloxy)-2-pyridinecarboxamide;

N-(3-((1R,5S,6S)-3-amino-5-methyl-1-(methylsulfonyl)-2-thia-4-azabicyclo[4.1.0]hept-3-en-5-yl)-4,5-difluorophenyl)-5-(2-propyn-1-yloxy)-2-pyrazinecarboxamide;

N-(3-((1R,5S,6S)-3-amino-5-methyl-1-(methylsulfonyl)-2-thia-4-azabicyclo[4.1.0]hept-3-en-5-yl)-4,5-difluorophenyl)-5-(1,3-oxazol-2-ylmethoxy)-2-pyridinecarboxamide;

N-(3-((1R,5S,6S)-3-amino-5-methyl-1-(methylsulfonyl)-2-thia-4-azabicyclo[4.1.0]hept-3-en-5-yl)-4,5-difluorophenyl)-5-(1,3-oxazol-2-ylmethoxy)-2-pyrazinecarboxamide;

N-(3-((1R,5S,6S)-3-amino-5-methyl-1-(methylsulfonyl)-2-thia-4-azabicyclo[4.1.0]hept-3-en-5-yl)-4,5-difluorophenyl)-2-(1,3-oxazol-2-ylmethoxy)pyrido[3,4-b]pyrazin-5-amine;

N-(3-((1R,5S,6R)-3-amino-7,7-difluoro-5-methyl-2-thia-4-azabicyclo[4.1.0]hept-3-en-5-yl)-4,5-difluorophenyl)-5-chloro-2-pyridinecarboxamide;

N-(3-((1S,5S,6R)-3-amino-7,7-difluoro-1-(hydroxymethyl)-5-methyl-2-thia-4-azabicyclo[4.1.0]hept-3-en-5-yl)-4-fluorophenyl)-5-(2-propyn-1-yloxy)-2-pyrazinecarboxamide;

((1S,5S,6R)-3-amino-7,7-difluoro-5-(2-fluoro-5-((7-(1,3-oxazol-2-ylmethoxy)pyrido[3,2-d]pyrimidin-4-yl)amino)phenyl)-5-methyl-2-thia-4-azabicyclo[4.1.0]hept-3-en-1-yl)methanol;

N-(3-((1S,5S,6R)-3-amino-7,7-difluoro-1-(hydroxymethyl)-5-methyl-2-thia-4-azabicyclo[4.1.0]hept-3-en-5-yl)-4-fluorophenyl)-5-(2,2,3,3-tetrafluoropropoxy)-2-pyridinecarboxamide;

N-(3-((4S,4aR,7aS)-2-amino-4-(fluoromethyl)-4,4a,4b,5-tetrahydrothieno[3',4':2,3]cyclopropa[1,2-e][1,3]thiazin-4-yl)-4-fluorophenyl)-5-chloro-2-pyridinecarboxamide;

N-(3-((4S,4aS,7aR)-2-amino-4-(fluoromethyl)-4,4a,4b,5-tetrahydrothieno[3',4':2,3]cyclopropa[1,2-e][1,3]thiazin-4-yl)-4-fluorophenyl)-5-chloro-2-pyridinecarboxamide;

N-(3-((4S,4aS,7aR)-2-amino-4-(fluoromethyl)-4,4a,4b,5-tetrahydrothieno[3',4':2,3]cyclopropa[1,2-e][1,3]thiazin-4-yl)-4-fluorophenyl)-5-chloro-2-pyridinecarboxamide;

N-(3-((1S,5S,6S)-3-amino-5-(fluoromethyl)-2-thia-4-azabicyclo[4.1.0]hept-3-en-5-yl)-4-fluorophenyl)-3-chloropyrido[2,3-d]pyridazin-8-amine;

ethyl(2E)-3-((1R,5S,6S)-3-amino-5-(5-(((5-chloro-2-pyridinyl)carbonyl)amino)-2-fluorophenyl)-5-(fluoromethyl)-2-thia-4-azabicyclo[4.1.0]hept-3-en-1-yl)-2-propenoate;

N-(3-((1R,5S,6S)-3-amino-5-(fluoromethyl)-1-((1E)-3-hydroxy-1-propen-1-yl)-2-thia-4-azabicyclo[4.1.0]hept-3-en-5-yl)-4-fluorophenyl)-5-chloro-2-pyridinecarboxamide;

(2E)-3-((1R,5S,6S)-3-amino-5-(5-(((5-chloro-2-pyridinyl)carbonyl)amino)-2-fluorophenyl)-5-(fluoromethyl)-2-thia-4-azabicyclo[4.1.0]hept-3-en-1-yl)-2-propenoic acid;

N-(3-((1S,5S,6S)-3-amino-5-(fluoromethyl)-1-(3-hydroxypropyl)-2-thia-4-azabicyclo[4.1.0]hept-3-en-5-yl)-4-fluorophenyl)-5-chloro-2-pyridinecarboxamide;

N-(3-((1R,5S,6S)-3-amino-1-((1E)-3-amino-3-oxo-1-propen-1-yl)-5-(fluoromethyl)-2-thia-4-azabicyclo[4.1.0]hept-3-en-5-yl)-4-fluorophenyl)-5-chloro-2-pyridinecarboxamide;

N-(3-((1R,5S,6S)-3-amino-5-(fluoromethyl)-1-((1E)-3-(methylamino)-3-oxo-1-propen-1-yl)-2-thia-4-azabicyclo[4.1.0]hept-3-en-5-yl)-4-fluorophenyl)-5-chloro-2-pyridinecarboxamide;

N-(3-((1R,5S,6S)-3-amino-1-((1E)-3-(dimethylamino)-3-oxo-1-propen-1-yl)-5-(fluoromethyl)-2-thia-4-azabicyclo[4.1.0]hept-3-en-5-yl)-4-fluorophenyl)-5-chloro-2-pyridinecarboxamide;

N-(3-((1S,5S,6S)-3-amino-5-(fluoromethyl)-2-thia-4-azabicyclo[4.1.0]hept-3-en-5-yl)-4-fluorophenyl)-2-(2-propyn-1-yloxy)pyrido[3,4-b]pyrazin-5-amine;

N-(3-((1S,5S,6S)-3-amino-5-(fluoromethyl)-2-thia-4-azabicyclo[4.1.0]hept-3-en-5-yl)-4-fluorophenyl)-7-(1,3-oxazol-2-ylmethoxy)pyrido[3,2-d]pyrimidin-4-amine;

N-(3-((1R,5S,6S)-3-amino-5-(fluoromethyl)-1-((1E)-3-(4-morpholinyl)-3-oxo-1-propen-1-yl)-2-thia-4-azabicyclo[4.1.0]hept-3-en-5-yl)-4-fluorophenyl)-5-chloro-2-pyridinecarboxamide;

N-(3-((1S,5S,6S)-3-amino-1-(3-(dimethylamino)-3-oxopropyl)-5-(fluoromethyl)-2-thia-4-azabicyclo[4.1.0]hept-3-en-5-yl)-4-fluorophenyl)-5-chloro-2-pyridinecarboxamide;

N-(3-((1R,5S,6S)-3-amino-5-(fluoromethyl)-1-((1E)-3-(3-methoxy-1-azetidinyl)-3-oxo-1-propen-1-yl)-2-thia-4-azabicyclo[4.1.0]hept-3-en-5-yl)-4-fluorophenyl)-5-chloro-2-pyridinecarboxamide;

N-(3-((1R,5S,6S)-3-amino-5-(fluoromethyl)-1-((1E)-3-((2-methoxyethyl)amino)-3-oxo-1-propen-1-yl)-2-thia-4-azabicyclo[4.1.0]hept-3-en-5-yl)-4-fluorophenyl)-5-chloro-2-pyridinecarboxamide;

(2E)-3-((1R,5S,6S)-3-amino-5-(fluoromethyl)-5-(2-fluoro-5-((2-(2-propyn-1-yloxy)pyrido[3,4-b]pyrazin-5-yl)amino)phenyl)-2-thia-4-azabicyclo[4.1.0]hept-3-en-1-yl)-N,N-dimethyl-2-propenamide;

(2E)-3-((1R,5S,6S)-3-amino-5-(fluoromethyl)-5-(2-fluoro-5-((2-(1,3-oxazol-2-ylmethoxy)pyrido[3,4-b]pyrazin-5-yl)amino)phenyl)-2-thia-4-azabicyclo[4.1.0]hept-3-en-1-yl)-N,N-dimethyl-2-propenamide;

(2E)-3-((1R,5S,6S)-3-amino-5-(fluoromethyl)-5-(2-fluoro-5-((3-(1,3-oxazol-2-ylmethoxy)-1,7-naphthyridin-8-yl)amino)phenyl)-2-thia-4-azabicyclo[4.1.0]hept-3-en-1-yl)-N,N-dimethyl-2-propenamide;

(2E)-3-((1R,5S,6S)-3-amino-5-(5-((3-(2-butyn-1-yloxy)-1,7-naphthyridin-8-yl)amino)-2-fluorophenyl)-5-(fluoromethyl)-2-thia-4-azabicyclo[4.1.0]hept-3-en-1-yl)-N,N-dimethyl-2-propenamide;

N-(3-((1R,5S,6S)-3-amino-1-((1E)-3-(3,3-difluoro-1-azetidinyl)-3-oxo-1-propen-1-yl)-5-(fluoromethyl)-2-thia-4-azabicyclo[4.1.0]hept-3-en-5-yl)-4-fluorophenyl)-5-chloro-2-pyridinecarboxamide;

N-(3-((1R,5S,6S)-3-amino-1-((1E)-3-(3,3-difluoro-1-azetidinyl)-3-oxo-1-propen-1-yl)-5-(fluoromethyl)-2-thia-4-azabicyclo[4.1.0]hept-3-en-5-yl)-4-fluorophenyl)-2-(2-propyn-1-yloxy)pyrido[3,4-b]pyrazin-5-amine;

N-(3-((1R,5S,6S)-3-amino-1-((1E)-3-(dimethylamino)-3-oxo-1-propen-1-yl)-5-(fluoromethyl)-2-thia-4-azabicyclo[4.1.0]hept-3-en-5-yl)-4-fluorophenyl)-5-(2-propyn-1-yloxy)-2-pyrazinecarboxamide;

(2E)-3-((1R,5S,6S)-3-amino-5-(fluoromethyl)-5-(2-fluoro-5-((7-(1,3-oxazol-2-ylmethoxy)pyrido[3,2-d]pyrimidin-4-yl)amino)phenyl)-2-thia-4-azabicyclo[4.1.0]hept-3-en-1-yl)-N,N-dimethyl-2-propenamide;

(2E)-3-((1R,5S,6S)-3-amino-5-(fluoromethyl)-5-(2-fluoro-5-((7-(2-propyn-1-yloxy)pyrido[3,2-d]pyrimidin-4-yl)amino)phenyl)-2-thia-4-azabicyclo[4.1.0]hept-3-en-1-yl)-N,N-dimethyl-2-propenamide;

N-(3-((1R,5S,6S)-3-amino-5-(fluoromethyl)-1-((1Z)-2-methyl-3-(4-morpholinyl)-3-oxo-1-propen-1-yl)-2-thia-4-azabicyclo[4.1.0]hept-3-en-5-yl)-4-fluorophenyl)-5-chloro-2-pyridinecarboxamide;

N-(3-((1R,5S,6S)-3-amino-5-(fluoromethyl)-1-((1E)-2-methyl-3-(4-morpholinyl)-3-oxo-1-propen-1-yl)-2-thia-4-azabicyclo[4.1.0]hept-3-en-5-yl)-4-fluorophenyl)-5-chloro-2-pyridinecarboxamide;

(1S,5S,6S)-3-amino-5-(fluoromethyl)-5-(2-fluoro-5-((2-(2-propyn-1-yloxy)pyrido[3,4-b]pyrazin-5-yl)amino)phenyl)-N,N-dimethyl-2-thia-4-azabicyclo[4.1.0]hept-3-ene-1-carboxamide;

N-(3-((1S,5S,6S)-3-amino-5-(fluoromethyl)-1-(1,3-oxazol-5-yl)-2-thia-4-azabicyclo[4.1.0]hept-3-en-5-yl)-4-fluorophenyl)-5-(2-propyn-1-yloxy)-2-pyrazinecarboxamide;

N-(3-((1S,5S,6S)-3-amino-5-(fluoromethyl)-1-(1,3-oxazol-5-yl)-2-thia-4-azabicyclo[4.1.0]hept-3-en-5-yl)-4-fluorophenyl)-2-(2-propyn-1-yloxy)pyrido[3,4-b]pyrazin-5-amine;

N-(3-((1S,5S,6S)-3-amino-5-(fluoromethyl)-1-(1,3-oxazol-5-yl)-2-thia-4-azabicyclo[4.1.0]hept-3-en-5-yl)-4-fluorophenyl)-7-(2-propyn-1-yloxy)pyrido[3,2-d]pyrimidin-4-amine;

N-(3-((1S,5S,6S)-3-amino-5-(fluoromethyl)-1-(1,3-oxazol-5-yl)-2-thia-4-azabicyclo[4.1.0]hept-3-en-5-yl)-4-fluorophenyl)-5-(1,3-oxazol-2-ylmethoxy)-2-pyrazinecarboxamide;

N-(3-((1S,5S,6S)-3-amino-5-(fluoromethyl)-1-(4-methyl-1,3-oxazol-5-yl)-2-thia-4-azabicyclo[4.1.0]hept-3-en-5-yl)-4-fluorophenyl)-5-(2-propyn-1-yloxy)-2-pyrazinecarboxamide;

N-(3-((1S,5S,6S)-3-amino-5-(fluoromethyl)-1-(1,3-oxazol-5-yl)-2-thia-4-azabicyclo[4.1.0]hept-3-en-5-yl)-4-fluorophenyl)-5-chloro-2-pyridinecarboxamide;

N-(3-((1S,5S,6S)-3-amino-5-(fluoromethyl)-1-(3-isoxazolyl)-2-thia-4-azabicyclo[4.1.0]hept-3-en-5-yl)-4-fluorophenyl)-5-chloro-2-pyridinecarboxamide;

N-(3-((1S,5S,6S)-3-amino-5-(fluoromethyl)-1-(4-methyl-1,3-oxazol-5-yl)-2-thia-4-azabicyclo[4.1.0]hept-3-en-5-yl)-4-fluorophenyl)-5-chloro-2-pyridinecarboxamide;

N-(3-((1S,5S,6S)-3-amino-5-(fluoromethyl)-1-(4-methyl-1,3-oxazol-5-yl)-2-thia-4-azabicyclo[4.1.0]hept-3-en-5-yl)-4-fluorophenyl)-7-(2-propyn-1-yloxy)pyrido[3,2-d]pyrimidin-4-amine;

N-(3-((1S,5S,6S)-3-amino-5-(fluoromethyl)-1-(4-methyl-1,3-oxazol-5-yl)-2-thia-4-azabicyclo[4.1.0]hept-3-en-5-yl)-4-fluorophenyl)-5-(2-propyn-1-yloxy)-2-pyridinecarboxamide;

(1S,5S,6S)-3-amino-5-(5-(((5-chloro-2-pyridinyl)carbonyl)amino)-2-fluorophenyl)-5-(fluoromethyl)-N,N-dimethyl-2-thia-4-azabicyclo[4.1.0]hept-3-ene-1-carboxamide;

(1S,5S,6S)-3-amino-N-cyclopropyl-5-(2-fluoro-5-((7-(2-propyn-1-yloxy)pyrido[3,2-d]pyrimidin-4-yl)amino)phenyl)-5-methyl-2-thia-4-azabicyclo[4.1.0]hept-3-ene-1-carboxamide;

(1S,5S,6S)-3-amino-5-(5-(((5-chloro-2-pyridinyl)carbonyl)amino)-2-fluorophenyl)-N-cyclopropyl-5-methyl-2-thia-4-azabicyclo[4.1.0]hept-3-ene-1-carboxamide;

N-(3-((1S,5S,6S)-3-amino-5-(fluoromethyl)-1-(3-isoxazolyl)-2-thia-4-azabicyclo[4.1.0]hept-3-en-5-yl)-4-fluorophenyl)-5-(2-propyn-1-yloxy)-2-pyridinecarboxamide;

(1S,5S,6S)-3-amino-N-cyclopropyl-5-(2-fluoro-5-((2-(2-propyn-1-yloxy)pyrido[3,4-b]pyrazin-5-yl)amino)phenyl)-5-methyl-2-thia-4-azabicyclo[4.1.0]hept-3-ene-1-carboxamide;

(1S,5S,6S)-3-amino-N-cyclopropyl-5-(2-fluoro-5-(((5-(2-propyn-1-yloxy)-2-pyrazinyl)carbonyl)amino)phenyl)-5-methyl-2-thia-4-azabicyclo[4.1.0]hept-3-ene-1-carboxamide;

(1S,5S,6S)-3-amino-N-cyclopropyl-5-(2-fluoro-5-((2-(1,3-oxazol-2-ylmethoxy)pyrido[3,4-b]pyrazin-5-yl)amino)phenyl)-5-methyl-2-thia-4-azabicyclo[4.1.0]hept-3-ene-1-carboxamide;

(1S,5S,6S)-3-amino-N-tert-butyl-5-(5-(((5-chloro-2-pyridinyl)carbonyl)amino)-2-fluorophenyl)-5-methyl-2-thia-4-azabicyclo[4.1.0]hept-3-ene-1-carboxamide;

(1S,5S,6S)-3-amino-N-tert-butyl-5-(2-fluoro-5-(((5-(2-propyn-1-yloxy)-2-pyrazinyl)carbonyl)amino)phenyl)-5-methyl-2-thia-4-azabicyclo[4.1.0]hept-3-ene-1-carboxamide;

(1S,5S,6S)-3-amino-N-cyclopropyl-5-(2-fluoro-5-(((5-(1,3-oxazol-2-ylmethoxy)-2-pyrazinyl)carbonyl)amino)phenyl)-5-methyl-2-thia-4-azabicyclo[4.1.0]hept-3-ene-1-carboxamide;

(1S,5S,6S)-3-amino-N-cyclopropyl-5-(2-fluoro-5-(((5-(2,2,2-trifluoroethoxy)-2-pyrazinyl)carbonyl)amino)phenyl)-5-methyl-2-thia-4-azabicyclo[4.1.0]hept-3-ene-1-carboxamide;

4-((3-((1S,5S,6S)-3-amino-1-(fluoromethyl)-5-methyl-2-thia-4-azabicyclo[4.1.0]hept-3-en-5-yl)-4,5-difluorophenyl)amino)pyrido[3,2-d]pyrimidine-7-carbonitrile;

N-(3-((1S,5S,6S)-3-amino-1-(fluoromethyl)-5-methyl-2-thia-4-azabicyclo[4.1.0]hept-3-en-5-yl)-4,5-difluorophenyl)-2-(1,3-oxazol-2-ylmethoxy)pyrido[3,4-b]pyrazin-5-amine;

N-(3-((1S,5S,6S)-3-amino-1-(fluoromethyl)-5-methyl-2-thia-4-azabicyclo[4.1.0]hept-3-en-5-yl)-4,5-difluorophenyl)-3-methyl-5-(1,3-oxazol-2-ylmethoxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-5-chloro-2-pyridinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-2-(2-propyn-1-yloxy)pyrido[3,4-b]pyrazin-5-amine;

N-(3-((1S,5S,6S)-3-amino-1-(fluoromethyl)-5-methyl-2-thia-4-azabicyclo[4.1.0]hept-3-en-5-yl)-4,5-difluorophenyl)-2-(2-propyn-1-yloxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-5-(2-propyn-1-yloxy)-2-pyrazinecarboxamide;

N-(3-((1S,5S,6S)-3-amino-1-(fluoromethyl)-5-methyl-2-thia-4-azabicyclo[4.1.0]hept-3-en-5-yl)-4,5-difluorophenyl)-7-(1,3-oxazol-2-ylmethoxy)pyrido[3,2-d]pyrimidin-4-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-7-(1,3-oxazol-2-ylmethoxy)pyrido[3,2-d]pyrimidin-4-amine;

N-(3-((1S,5S,6S)-3-amino-1-(fluoromethyl)-5-methyl-2-thia-4-azabicyclo[4.1.0]hept-3-en-5-yl)-4,5-difluorophenyl)-5-(2-propyn-1-yloxy)-2-pyrazinecarboxamide;

N-(3-((1S,5S,6S)-3-amino-1-(fluoromethyl)-5-methyl-2-thia-4-azabicyclo[4.1.0]hept-3-en-5-yl)-4,5-difluorophenyl)-5-(1,3-oxazol-2-ylmethoxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-7-(1,3-oxazol-2-ylmethoxy)pyrido[3,2-d]pyrimidin-4-amine;

N-(3-((1S,5S,6S)-3-amino-1-(fluoromethyl)-5-methyl-2-thia-4-azabicyclo[4.1.0]hept-3-en-5-yl)-4,5-difluorophenyl)-7-(2-propyn-1-yloxy)pyrido[3,2-d]pyrimidin-4-amine;

N-(3-((1S,5S,6S)-3-amino-1-(fluoromethyl)-5-methyl-2-thia-4-azabicyclo[4.1.0]hept-3-en-5-yl)-4,5-difluorophenyl)-5-(2,2,2-trifluoroethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(2,2,2-trifluoroethoxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-2-(2-propyn-1-yloxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4-fluorophenyl)-2-(1,3-oxazol-2-ylmethoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4-fluorophenyl)-5-chloro-2-pyridinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-7-(2-propyn-1-yloxy)pyrido[3,2-d]pyrimidin-4-amine;

N-(3-((1S,5S,6S)-3-amino-1-(difluoromethyl)-5-methyl-2-thia-4-azabicyclo[4.1.0]hept-3-en-5-yl)-4-fluorophenyl)-5-(2-propyn-1-yloxy)-2-pyrazinecarboxamide;

N-(3-((1S,5S,6S)-3-amino-1-(fluoromethyl)-5-methyl-2-thia-4-azabicyclo[4.1.0]hept-3-en-5-yl)-4-fluorophenyl)-5-chloro-2-pyridinecarboxamide;

N-(3-((1S,5S,6S)-3-amino-1-(fluoromethyl)-5-methyl-2-thia-4-azabicyclo[4.1.0]hept-3-en-5-yl)-4-fluorophenyl)-5-(2-propyn-1-yloxy)-2-pyrazinecarboxamide;

N-(3-((1S,5S,6S)-3-amino-1-(fluoromethyl)-5-methyl-2-thia-4-azabicyclo[4.1.0]hept-3-en-5-yl)-4-fluorophenyl)-2-(2-propyn-1-yloxy)pyrido[3,4-b]pyrazin-5-amine;

N-(3-((1S,5S,6S)-3-amino-1-(fluoromethyl)-5-methyl-2-thia-4-azabicyclo[4.1.0]hept-3-en-5-yl)-4-fluorophenyl)-7-(2-propyn-1-yloxy)pyrido[3,2-d]pyrimidin-4-amine;

N-(3-((1S,5S,6S)-3-amino-1-(fluoromethyl)-5-methyl-2-thia-4-azabicyclo[4.1.0]hept-3-en-5-yl)-4-fluorophenyl)-2-(1,3-oxazol-2-ylmethoxy)pyrido[3,4-b]pyrazin-5-amine;

N-(3-((1S,5S,6S)-3-amino-1-(fluoromethyl)-5-methyl-2-thia-4-azabicyclo[4.1.0]hept-3-en-5-yl)-4-fluorophenyl)-5-(2,2,2-trifluoroethoxy)-2-pyrazinecarboxamide;

N-(3-((1S,5S,6S)-3-amino-1-(fluoromethyl)-5-methyl-2-thia-4-azabicyclo[4.1.0]hept-3-en-5-yl)-4-fluorophenyl)-2-(((1S)-1-methyl-2-propyn-1-yl)oxy)pyrido[3,4-b]pyrazin-5-amine;

N-(3-((1S,5S,6S)-3-amino-1-(fluoromethyl)-5-methyl-2-thia-4-azabicyclo[4.1.0]hept-3-en-5-yl)-4-fluorophenyl)-2-((5-methyl-1,2,4-oxadiazol-3-yl)methoxy)pyrido[3,4-b]pyrazin-5-amine;

N-(3-((1S,5S,6S)-3-amino-1-(fluoromethyl)-5-methyl-2-thia-4-azabicyclo[4.1.0]hept-3-en-5-yl)-4-fluorophenyl)-3-methyl-5-(2-propyn-1-yloxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-3-methyl-5-(2-propyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-3-methyl-5-(2-propyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-chloro-2-pyridinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(2-propyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-3-methyl-5-(1,3-oxazol-2-ylmethoxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-3-methyl-5-(1,3-oxazol-2-ylmethoxy)-2-pyrazinecarboxamide;

N-(3-((1S,5S,6S)-3-amino-1-(fluoromethyl)-5-methyl-2-thia-4-azabicyclo[4.1.0]hept-3-en-5-yl)-4-fluorophenyl)-3-methyl-5-(1,3-oxazol-2-ylmethoxy)-2-pyrazinecarboxamide;

N-(3-((1S,5S,6S)-3-amino-1-(fluoromethyl)-5-methyl-2-thia-4-azabicyclo[4.1.0]hept-3-en-5-yl)-4,5-difluorophenyl)-5-(1,1-dideuterium-prop-2-yn-1-yloxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-5-(1,1-dideuterium-prop-2-yn-1-yloxy)-2-pyrazinecarboxamide;

N-(3-((1S,5S,6S)-3-amino-1-(methoxy)-5-methyl-2-thia-4-azabicyclo[4.1.0]hept-3-en-5-yl)-4,5-difluorophenyl)-5-(1,1-dideuterium-prop-2-yn-1-yloxy)pyrazine-2-carboxamide;

N-(3-((1S,5S,6S)-3-amino-5-(fluoromethyl)-2-thia-4-azabicyclo[4.1.0]hept-3-en-5-yl)-4,5-difluorophenyl)-2-(2-propyn-1-yloxy)pyrido[3,4-b]pyrazin-5-amine;

N-(3-((1S,5S,6S)-3-amino-5-(fluoromethyl)-2-thia-4-azabicyclo[4.1.0]hept-3-en-5-yl)-4,5-difluorophenyl)-2-(1,3-oxazol-2-ylmethoxy)pyrido[3,4-b]pyrazin-5-amine;

N-(3-((1S,5S,6S)-3-amino-5-(fluoromethyl)-2-thia-4-azabicyclo[4.1.0]hept-3-en-5-yl)-4,5-difluorophenyl)-2-(1,3-oxazol-4-ylmethoxy)pyrido[3,4-b]pyrazin-5-amine;

N-(5-((1S,5S,6S)-3-amino-1-(methoxymethyl)-5-methyl-2-thia-4-azabicyclo[4.1.0]hept-3-en-5-yl)-6-fluoro-3-pyridinyl)-7-chloropyrido[3,2-d]pyrimidin-4-amine;

N-(5-((1S,5S,6S)-3-amino-1-(methoxymethyl)-5-methyl-2-thia-4-azabicyclo[4.1.0]hept-3-en-5-yl)-6-fluoro-3-pyridinyl)-3-methyl-5-(2-propyn-1-yloxy)-2-pyrazinecarboxamide;

4-((5-((1S,5S,6S)-3-amino-1-(methoxymethyl)-5-methyl-2-thia-4-azabicyclo[4.1.0]hept-3-en-5-yl)-6-fluoro-3-pyridinyl)amino)pyrido[3,2-d]pyrimidine-7-carbonitrile;

8-((5-((1S,5S,6S)-3-amino-1-(methoxymethyl)-5-methyl-2-thia-4-azabicyclo[4.1.0]hept-3-en-5-yl)-6-fluoro-3-pyridinyl)amino)-1,7-naphthyridine-3-carbonitrile;

N-(5-((1S,5S,6S)-3-amino-1-(methoxymethyl)-5-methyl-2-thia-4-azabicyclo[4.1.0]hept-3-en-5-yl)-6-fluoro-3-pyridinyl)-2-(2-propyn-1-yloxy)pyrido[3,4-b]pyrazin-5-amine;

N-(5-((1S,5S,6S)-3-amino-1-(methoxymethyl)-5-methyl-2-thia-4-azabicyclo[4.1.0]hept-3-en-5-yl)-6-fluoro-3-pyridinyl)-2-(1,3-oxazol-2-ylmethoxy)pyrido[3,4-b]pyrazin-5-amine;

N-(5-((1S,5S,6S)-3-amino-5-methyl-1-(((~2~H_3_)methyloxy)methyl)-2-thia-4-azabicyclo[4.1.0]hept-3-en-5-yl)-6-fluoro-3-pyridinyl)-3-methyl-5-(2-propyn-1-yloxy)-2-pyrazinecarboxamide;

N-(5-((1S,5S,6S)-3-amino-5-methyl-1-(((~2~H_3_)methyloxy)methyl)-2-thia-4-azabicyclo[4.1.0]hept-3-en-5-yl)-6-fluoro-3-pyridinyl)-5-(2-propyn-1-yloxy)-2-pyrazinecarboxamide;

N-(5-((1S,5S,6S)-3-amino-5-methyl-1-(((~2~H_3_)methyloxy)methyl)-2-thia-4-azabicyclo[4.1.0]hept-3-en-5-yl)-6-fluoro-3-pyridinyl)-7-chloropyrido[3,2-d]pyrimidin-4-amine;

N-(5-((1S,5S,6S)-3-amino-5-methyl-1-(((~2~H_3_)methyloxy)methyl)-2-thia-4-azabicyclo[4.1.0]hept-3-en-5-yl)-6-fluoro-3-pyridinyl)-2-(2-propyn-1-yloxy)pyrido[3,4-b]pyrazin-5-amine;

N-(5-((1S,5S,6S)-3-amino-5-methyl-1-(((~2~H_3_)methyloxy)methyl)-2-thia-4-azabicyclo[4.1.0]hept-3-en-5-yl)-6-fluoro-3-pyridinyl)-2-((1,1-~2~H_2_)-2-propyn-1-yloxy)pyrido[3,4-b]pyrazin-5-amine;

methyl(1S,5S,6S)-3-amino-5-(5-(((5-chloro-2-pyridinyl)carbonyl)amino)-2-fluoro-3-(methoxycarbonyl)phenyl)-5-methyl-2-thia-4-azabicyclo[4.1.0]hept-3-ene-1-carboxylate;

methyl(1S,5S,6S)-3-amino-5-(2-fluoro-3-(methoxycarbonyl)-5-((2-(2-propyn-1-yloxy)pyrido[3,4-b]pyrazin-5-yl)amino)phenyl)-5-methyl-2-thia-4-azabicyclo[4.1.0]hept-3-ene-1-carboxylate;

methyl 3-((1S,5S,6S)-3-amino-1-(hydroxymethyl)-5-methyl-2-thia-4-azabicyclo[4.1.0]hept-3-en-5-yl)-2-fluoro-5-((2-(2-propyn-1-yloxy)pyrido[3,4-b]pyrazin-5-yl)amino)benzoate;

N-(3-((1S,5S,6S)-3-amino-1-(hydroxymethyl)-5-methyl-2-thia-4-azabicyclo[4.1.0]hept-3-en-5-yl)-4-fluoro-5-(hydroxymethyl)phenyl)-5-chloro-2-pyridinecarboxamide;

N-(5-((1S,5S,6S)-3-amino-1-(methoxymethyl)-5-methyl-2-thia-4-azabicyclo[4.1.0]hept-3-en-5-yl)-6-fluoro-3-pyridinyl)-5-(2-propyn-1-yloxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-3-methyl-5-(1,3-oxazol-2-ylmethoxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-3-methyl-5-(2-propyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-(2-propyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-(1,3-oxazol-2-ylmethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-((1S)-1-(1,3-oxazol-2-yl)ethoxy)-2-pyrazinecarboxamide;

N-(3-((1S,5S,6S)-3-amino-1,5-bis(fluoromethyl)-2-thia-4-azabicyclo[4.1.0]hept-3-en-5-yl)-4-fluorophenyl)-2-(2-butyn-1-yloxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-(1,3-oxazol-2-ylmethoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-(1,3-oxazol-4-ylmethoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-(2-butyn-1-yloxy)pyrido[3,4-b]pyrazin-5-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-2-(2-butyn-1-yloxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-((2-methyl-1,3-oxazol-4-yl)methoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-(3-fluoropropoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-(2,2-difluoropropoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-((3-fluoro-2-pyridinyl)methoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-((4-methyl-2-pyrimidinyl)methoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-(1,3-thiazol-4-ylmethoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-(1-methylethoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-((5-methyl-1,3,4-oxadiazol-2-yl)methoxy)pyrido[3,4-b]pyrazin-5-amine;

2-((5-((3-((1S,5S,6S)-3-amino-1-(difluoromethyl)-5-methyl-2-thia-4-azabicyclo[4.1.0]hept-3-en-5-yl)-4,5-difluorophenyl)amino)pyrido[3,4-b]pyrazin-2-yl)oxy)-N,N-dimethylacetamide;

N-(3-((1S,5S,6S)-3-amino-1,5-bis(fluoromethyl)-2-thia-4-azabicyclo[4.1.0]hept-3-en-5-yl)-4-fluorophenyl)-2-(((1S)-1-methyl-2-propyn-1-yl)oxy)pyrido[3,4-b]pyrazin-5-amine;

N-(3-((1S,5S,6S)-3-amino-1,5-bis(fluoromethyl)-2-thia-4-azabicyclo[4.1.0]hept-3-en-5-yl)-4-fluorophenyl)-2-((3-methyl-1,2,4-oxadiazol-5-yl)methoxy)pyrido[3,4-b]pyrazin-5-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-2-(2-pyrimidinylmethoxy)pyrido[3,4-b]pyrazin-5-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-2-((3-methyl-1,2,4-oxadiazol-5-yl)methoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-((5-methyl-1,2,4-oxadiazol-3-yl)methoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-(2-pyrimidinylmethoxy)pyrido[3,4-b]pyrazin-5-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-2-((5-methyl-1,2,4-oxadiazol-3-yl)methoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-((2,5-dimethyl-1,3-oxazol-4-yl)methoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-((3-methyl-1,2,4-oxadiazol-5-yl)methoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-((5-methyl-1,3-oxazol-2-yl)methoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-((5-methyl-1,3,4-thiadiazol-2-yl)methoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-(((1S)-1-methyl-2-propyn-1-yl)oxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-(((1R)-1-(1,3-oxazol-2-yl)ethoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-(((1S)-1-(1,3-oxazol-2-yl)ethoxy)pyrido[3,4-b]pyrazin-5-amine;

1-(2-((5-((3-((1S,5S,6S)-3-amino-1-(difluoromethyl)-5-methyl-2-thia-4-azabicyclo[4.1.0]hept-3-en-5-yl)-4,5-difluorophenyl)amino)pyrido[3,4-b]pyrazin-2-yl)oxy)ethyl)-2-pyrrolidinone;

N-(3-((1S,5S,6S)-3-amino-1-(difluoromethyl)-5-methyl-2-thia-4-azabicyclo[4.1.0]hept-3-en-5-yl)-4,5-difluorophenyl)-2-(((1S)-2-methoxy-1-methylethoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-methoxypyrido[3,4-b]pyrazin-5-amine;

5-((3-((1S,5S,6S)-3-amino-1-(difluoromethyl)-5-methyl-2-thia-4-azabicyclo[4.1.0]hept-3-en-5-yl)-4,5-difluorophenyl)amino)pyrido[3,4-b]pyrazin-2(1H)-one;

N-(3-((1S,5S,6S)-3-amino-5-methyl-2-thia-4-azabicyclo[4.1.0]hept-3-en-5-yl)-4,5-difluorophenyl)-7-methoxypyrido[3,2-d]pyrimidin-4-amine;

methyl(1S,5S,6S)-3-amino-5-(5-(((5-chloro-2-pyridinyl)carbonyl)amino)-2,3-difluorophenyl)-5-methyl-2-thia-4-azabicyclo[4.1.0]hept-3-ene-1-carboxylate;

(1S,5S,6S)-3-amino-5-(5-(((5-chloro-2-pyridinyl)carbonyl)amino)-2,3-difluorophenyl)-5-methyl-2-thia-4-azabicyclo[4.1.0]hept-3-ene-1-carboxylic acid;

N-(3-((1S,5S,6S)-3-amino-5-methyl-2-thia-4-azabicyclo[4.1.0]hept-3-en-5-yl)-4,5-difluorophenyl)-2-methoxypyrido[3,4-b]pyrazin-5-amine;

(1S,5S,6S)-3-amino-5-(5-((7-chloropyrido[3,2-d]pyrimidin-4-yl)amino)-2,3-difluorophenyl)-N-methoxy-N,5-dimethyl-2-thia-4-azabicyclo[4.1.0]hept-3-ene-1-carboxamide;

1-((1S,5S,6S)-3-amino-5-(5-((7-chloropyrido[3,2-d]pyrimidin-4-yl)amino)-2,3-difluorophenyl)-5-methyl-2-thia-4-azabicyclo[4.1.0]hept-3-en-1-yl)ethanone;

N-(3-((1S,5S,6S)-3-amino-1-(methoxymethyl)-5-methyl-2-thia-4-azabicyclo[4.1.0]hept-3-en-5-yl)-4,5-difluorophenyl)-3-(2-butyn-1-yloxy)-1,7-naphthyridin-8-amine;

4-((3-((1S,5S,6S)-1-acetyl-3-amino-5-methyl-2-thia-4-azabicyclo[4.1.0]hept-3-en-5-yl)-4,5-difluorophenyl)amino)pyrido[3,2-d]pyrimidine-7-carbonitrile;

(1S,5S,6S)-3-amino-5-(5-(((5-chloro-2-pyridinyl)carbonyl)amino)-2,3-difluorophenyl)-5-methyl-2-thia-4-azabicyclo[4.1.0]hept-3-ene-1-carboxamide;

N-(3-((1S,5S,6S)-1-acetyl-3-amino-5-methyl-2-thia-4-azabicyclo[4.1.0]hept-3-en-5-yl)-4,5-difluorophenyl)-5-chloro-2-pyridinecarboxamide;

4-((3-((1S,5S,6S)-3-amino-1-(1-hydroxyethyl)-5-methyl-2-thia-4-azabicyclo[4.1.0]hept-3-en-5-yl)-4,5-difluorophenyl)amino)pyrido[3,2-d]pyrimidine-7-carbonitrile;

4-((3-((1R,2S,6S)-4-amino-6-((R)-1-hydroxyethyl)-2-methyl-3-azabicyclo[4.1.0]hept-3-en-2-yl)-4,5-difluorophenyl)amino)pyrido[3,2-d]pyrimidine-7-carbonitrile;

4-((3-((1S,5S,6S)-3-amino-1-(1-hydroxy-1-methylethyl)-5-methyl-2-thia-4-azabicyclo[4.1.0]hept-3-en-5-yl)-4,5-difluorophenyl)amino)pyrido[3,2-d]pyrimidine-7-carbonitrile;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(1,3-oxazol-2-ylmethoxy)-2-pyrazinecarboxamide;

(1S,5S,6S)-3-amino-5-(2,3-difluoro-5-((2-(2-propyn-1-yloxy)pyrido[3,4-b]pyrazin-5-yl)amino)phenyl)-5-methyl-2-thia-4-azabicyclo[4.1.0]hept-3-ene-1-carboxamide;

(1S,5S,6S)-3-amino-5-(2,3-difluoro-5-((2-(2-propyn-1-yloxy)pyrido[3,4-b]pyrazin-5-yl)amino)phenyl)-N,N,5-trimethyl-2-thia-4-azabicyclo[4.1.0]hept-3-ene-1-carboxamide;

(1S,5S,6S)-3-amino-5-(2,3-difluoro-5-(((5-(2-propyn-1-yloxy)-2-pyrazinyl)carbonyl)amino)phenyl)-N,N,5-trimethyl-2-thia-4-azabicyclo[4.1.0]hept-3-ene-1-carboxamide;

(1S,5S,6S)-3-amino-5-(2,3-difluoro-5-(((5-(2-propyn-1-yloxy)-2-pyrazinyl)carbonyl)amino)phenyl)-N,5-dimethyl-2-thia-4-azabicyclo[4.1.0]hept-3-ene-1-carboxamide;

(1S,5S,6S)-3-amino-5-(2,3-difluoro-5-((2-(2-propyn-1-yloxy)pyrido[3,4-b]pyrazin-5-yl)amino)phenyl)-N,5-dimethyl-2-thia-4-azabicyclo[4.1.0]hept-3-ene-1-carboxamide;

(1S,5S,6S)-3-amino-5-(2,3-difluoro-5-((2-(2-propyn-1-yloxy)pyrido[3,4-b]pyrazin-5-yl)amino)phenyl)-5-methyl-2-thia-4-azabicyclo[4.1.0]hept-3-ene-1-carbonitrile;

(1S,5S,6S)-3-amino-5-(2,3-difluoro-5-((7-(2-propyn-1-yloxy)pyrido[3,2-d]pyrimidin-4-yl)amino)phenyl)-5-methyl-2-thia-4-azabicyclo[4.1.0]hept-3-ene-1-carboxamide;

(1S,5S,6S)-3-amino-5-(2,3-difluoro-5-((7-(1,3-oxazol-2-ylmethoxy)pyrido[3,2-d]pyrimidin-4-yl)amino)phenyl)-5-methyl-2-thia-4-azabicyclo[4.1.0]hept-3-ene-1-carboxamide;

(1S,5S,6S)-3-amino-5-(2,3-difluoro-5-(((5-(2-propyn-1-yloxy)-2-pyrazinyl)carbonyl)amino)phenyl)-5-methyl-2-thia-4-azabicyclo[4.1.0]hept-3-ene-1-carboxamide;

(1S,5S,6S)-3-amino-5-(5-((2-(2-butyn-1-yloxy)pyrido[3,4-b]pyrazin-5-yl)amino)-2,3-difluorophenyl)-5-methyl-2-thia-4-azabicyclo[4.1.0]hept-3-ene-1-carboxamide;

(1S,5S,6S)-3-amino-5-(2,3-difluoro-5-((7-(2-propyn-1-yloxy)pyrido[3,2-d]pyrimidin-4-yl)amino)phenyl)-5-methyl-2-thia-4-azabicyclo[4.1.0]hept-3-ene-1-carbonitrile;

(1S,5S,6S)-3-amino-5-(2,3-difluoro-5-(((5-(2,2,3,3-tetrafluoropropoxy)-2-pyrazinyl)carbonyl)amino)phenyl)-N,N,5-trimethyl-2-thia-4-azabicyclo[4.1.0]hept-3-ene-1-carboxamide;

(1S,5S,6S)-3-amino-5-(2,3-difluoro-5-((7-(1,3-oxazol-2-ylmethoxy)pyrido[3,2-d]pyrimidin-4-yl)amino)phenyl)-N,N,5-trimethyl-2-thia-4-azabicyclo[4.1.0]hept-3-ene-1-carboxamide;

N-(3-((1S,5S,6S)-3-amino-1-cyano-5-methyl-2-thia-4-azabicyclo[4.1.0]hept-3-en-5-yl)-4,5-difluorophenyl)-5-(2-propyn-1-yloxy)-2-pyrazinecarboxamide;

(1S,5S,6S)-3-amino-5-(2,3-difluoro-5-((2-(((1S)-1-methyl-2-propyn-1-yl)oxy)pyrido[3,4-b]pyrazin-5-yl)amino)phenyl)-N,N,5-trimethyl-2-thia-4-azabicyclo[4.1.0]hept-3-ene-1-carboxamide;

(1S,5S,6S)-3-amino-5-(2,3-difluoro-5-(((5-(2,2,2-trifluoroethoxy)-2-pyrazinyl)carbonyl)amino)phenyl)-N,N,5-trimethyl-2-thia-4-azabicyclo[4.1.0]hept-3-ene-1-carboxamide;

N-(3-((1S,5S,6S)-3-amino-1-cyano-5-methyl-2-thia-4-azabicyclo[4.1.0]hept-3-en-5-yl)-4-fluorophenyl)-5-(2-propyn-1-yloxy)-2-pyrazinecarboxamide;

(1S,5S,6S)-3-amino-5-(2-fluoro-5-((7-(2-propyn-1-yloxy)pyrido[3,2-d]pyrimidin-4-yl)amino)phenyl)-5-methyl-2-thia-4-azabicyclo[4.1.0]hept-3-ene-1-carbonitrile;

N-(3-((1S,5S,6S)-3-amino-1-cyano-5-methyl-2-thia-4-azabicyclo[4.1.0]hept-3-en-5-yl)-4-fluorophenyl)-5-chloro-2-pyridinecarboxamide;

(1S,5S,6S)-3-amino-5-(5-(((5-chloro-2-pyridinyl)carbonyl)amino)-2,3-difluorophenyl)-N,N,5-trimethyl-2-thia-4-azabicyclo[4.1.0]hept-3-ene-1-carboxamide;

(1S,5S,6S)-3-amino-5-(2,3-difluoro-5-((2-(((1S)-1-methyl-2-propyn-1-yl)oxy)pyrido[3,4-b]pyrazin-5-yl)amino)phenyl)-5-methyl-2-thia-4-azabicyclo[4.1.0]hept-3-ene-1-carbonitrile;

N-(3-((1S,5S,6S)-3-amino-1-cyano-5-methyl-2-thia-4-azabicyclo[4.1.0]hept-3-en-5-yl)-4,5-difluorophenyl)-5-chloro-2-pyridinecarboxamide;

N-(3-((1S,5S,6S)-3-amino-5-methyl-1-(1-pyrrolidinylcarbonyl)-2-thia-4-azabicyclo[4.1.0]hept-3-en-5-yl)-4,5-difluorophenyl)-7-(2-propyn-1-yloxy)pyrido[3,2-d]pyrimidin-4-amine;

N-(3-((1S,5S,6S)-3-amino-5-methyl-1-(1-pyrrolidinylcarbonyl)-2-thia-4-azabicyclo[4.1.0]hept-3-en-5-yl)-4,5-difluorophenyl)-5-(2-propyn-1-yloxy)-2-pyrazinecarboxamide;

N-(3-((1S,5S,6S)-3-amino-5-methyl-1-(1-pyrrolidinylcarbonyl)-2-thia-4-azabicyclo[4.1.0]hept-3-en-5-yl)-4,5-difluorophenyl)-5-chloro-2-pyridinecarboxamide;

N-(3-((1S,5S,6S)-3-amino-5-methyl-1-(1-pyrrolidinylcarbonyl)-2-thia-4-azabicyclo[4.1.0]hept-3-en-5-yl)-4,5-difluorophenyl)-7-(1,3-oxazol-2-ylmethoxy)pyrido[3,2-d]pyrimidin-4-amine;

N-(3-((1S,5S,6S)-3-amino-5-methyl-1-(1-pyrrolidinylcarbonyl)-2-thia-4-azabicyclo[4.1.0]hept-3-en-5-yl)-4,5-difluorophenyl)-2-(((1S)-1-methyl-2-propyn-1-yl)oxy)pyrido[3,4-b]pyrazin-5-amine;

N-(3-((1S,5S,6S)-3-amino-5-methyl-1-(1-pyrrolidinylcarbonyl)-2-thia-4-azabicyclo[4.1.0]hept-3-en-5-yl)-4,5-difluorophenyl)-2-((1S)-1-(1,3-oxazol-2-yl)ethoxy)pyrido[3,4-b]pyrazin-5-amine;

(1S,5S,6S)-3-amino-5-(2,3-difluoro-5-((2-((1S)-1-(1,3-oxazol-2-yl)ethoxy)pyrido[3,4-b]pyrazin-5-yl)amino)phenyl)-5-methyl-2-thia-4-azabicyclo[4.1.0]hept-3-ene-1-carbonitrile;

N-(3-((1S,5S,6S)-3-amino-1-cyano-5-methyl-2-thia-4-azabicyclo[4.1.0]hept-3-en-5-yl)-4,5-difluorophenyl)-5-(2,2,2-trifluoroethoxy)-2-pyrazinecarboxamide;

N-(3-((1S,5S,6S)-3-amino-5-(fluoromethyl)-2-thia-4-azabicyclo[4.1.0]hept-3-en-5-yl)-4-fluorophenyl)-7-(2-propyn-1-yloxy)pyrido[3,2-d]pyrimidin-4-amine;

N-(3-((1S,5S,6S)-3-amino-5-(fluoromethyl)-1-(methoxymethyl)-2-thia-4-azabicyclo[4.1.0]hept-3-en-5-yl)-4-fluorophenyl)-7-(2-propyn-1-yloxy)pyrido[3,2-d]pyrimidin-4-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-7-(2-propyn-1-yloxy)pyrido[3,2-d]pyrimidin-4-amine;

N-(5-((1S,5S,6S)-3-amino-1-(fluoromethyl)-5-methyl-2-thia-4-azabicyclo[4.1.0]hept-3-en-5-yl)-6-fluoro-3-pyridinyl)-7-(2-propyn-1-yloxy)pyrido[3,2-d]pyrimidin-4-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-7-(2-propyn-1-yloxy)pyrido[3,2-d]pyrimidin-4-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-7-(2-methoxyethoxy)pyrido[3,2-d]pyrimidin-4-amine;

N-(3-((1S,5S,6S)-3-amino-5-(fluoromethyl)-1-(methoxymethyl)-2-thia-4-azabicyclo[4.1.0]hept-3-en-5-yl)-4-fluorophenyl)-7-(2-methoxyethoxy)pyrido[3,2-d]pyrimidin-4-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-7-((2,5-dimethyl-1,3-oxazol-4-yl)methoxy)pyrido[3,2-d]pyrimidin-4-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-5-fluoro-3-(1,3-oxazol-2-ylmethoxy)-1,7-naphthyridin-8-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-5-fluoro-3-(1,3-oxazol-2-ylmethoxy)-1,7-naphthyridin-8-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-5-fluoro-3-(2-propyn-1-yloxy)-1,7-naphthyridin-8-amine;

(2E)-3-((1R,5S,6S)-3-amino-5-(fluoromethyl)-5-(2-fluoro-5-((2-(2-pentyn-1-yloxy)pyrido[3,4-b]pyrazin-5-yl)amino)phenyl)-2-thia-4-azabicyclo[4.1.0]hept-3-en-1-yl)-N,N-dimethyl-2-propenamide;

N-(3-((1S,5S,6S)-3-amino-5-(fluoromethyl)-1-((2,2,2-trifluoroethoxy)methyl)-2-thia-4-azabicyclo[4.1.0]hept-3-en-5-yl)-4-fluorophenyl)-5-(2-propyn-1-yloxy)-2-pyrazinecarboxamide;

N-(3-((1S,5S,6S)-3-amino-5-(fluoromethyl)-1-((2,2,2-trifluoroethoxy)methyl)-2-thia-4-azabicyclo[4.1.0]hept-3-en-5-yl)-4-fluorophenyl)-5-chloro-2-pyridinecarboxamide;

N-(3-((1S,5S,6S)-3-amino-5-(fluoromethyl)-1-((1-methylethoxy)methyl)-2-thia-4-azabicyclo[4.1.0]hept-3-en-5-yl)-4-fluorophenyl)-5-(2-propyn-1-yloxy)-2-pyrazinecarboxamide;

N-(3-((1S,5S,6S)-3-amino-5-(fluoromethyl)-1-(1H-1,2,3-triazol-4-yl)-2-thia-4-azabicyclo[4.1.0]hept-3-en-5-yl)-4-fluorophenyl)-5-chloro-2-pyridinecarboxamide;

N-(3-((1S,5S,6S)-3-amino-5-(fluoromethyl)-1-(1H-1,2,3-triazol-4-yl)-2-thia-4-azabicyclo[4.1.0]hept-3-en-5-yl)-4-fluorophenyl)-2-(1,3-oxazol-2-ylmethoxy)pyrido[3,4-b]pyrazin-5-amine;

N-(3-((1S,5S,6S)-3-amino-5-(fluoromethyl)-1-(1-propyn-1-yl)-2-thia-4-azabicyclo[4.1.0]hept-3-en-5-yl)-4-fluorophenyl)-2-(1,3-oxazol-2-ylmethoxy)pyrido[3,4-b]pyrazin-5-amine;

N-(3-((1S,5S,6S)-3-amino-5-(fluoromethyl)-1-(1H-1,2,3-triazol-4-yl)-2-thia-4-azabicyclo[4.1.0]hept-3-en-5-yl)-4-fluorophenyl)-5-(2-propyn-1-yloxy)-2-pyrazinecarboxamide;

N-(3-((1S,5S,6S)-3-amino-5-(fluoromethyl)-1-(1H-1,2,3-triazol-4-yl)-2-thia-4-azabicyclo[4.1.0]hept-3-en-5-yl)-4-fluorophenyl)-2-(2-propyn-1-yloxy)pyrido[3,4-b]pyrazin-5-amine;

N-(3-((1S,5S,6S)-3-amino-5-(fluoromethyl)-2-thia-4-azabicyclo[4.1.0]hept-3-en-5-yl)-4,5-difluorophenyl)-5-chloropicolinamide;

4-((3-((1R,5S,6S)-3-amino-7,7-difluoro-1-(hydroxymethyl)-5-methyl-2-thia-4-azabicyclo[4.1.0]hept-3-en-5-yl)-4-fluorophenyl)amino)pyrido[3,2-d]pyrimidine-7-carbonitrile; or N-(3-((4S,4aR,7aS)-2-amino-4-(fluoromethyl)-4a,4b,5,7-tetrahydro-4H-thieno[3',4':2,3]cyclopropa[1,2-e][1,3]thiazin-4-yl)-4-fluorophenyl)-5-chloropicolinamide.

In yet another embodiment, the invention provides the compound of Formula I or a tautomer, stereoisomer, or pharmaceutically acceptable salt thereof selected from (1S,5S,6S)-3-amino-5-(2,3-difluoro-5-(((5-(2,2,3,3-tetrafluoropropoxy)-2-pyrazinyl)carbonyl)amino)phenyl)-N,5-dimethyl-2-thia-4-azabicyclo[4.1.0]hept-3-ene-1-carboxamide;

N-(5-((1S,5S,6S)-3-amino-1-cyano-5-methyl-2-thia-4-azabicyclo[4.1.0]hept-3-en-5-yl)-6-methoxy-3-pyridinyl)-5-(2-propyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(((1S)-1-methyl-2-propyn-1-yl)oxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-5-(((1S)-1-methyl-2-propyn-1-yl)oxy)-2-pyrazinecarboxamide;

(1S,5S,6S)-3-amino-5-(2,3-difluoro-5-(((5-(((1S)-1-methyl-2-propyn-1-yl)oxy)-2-pyrazinyl)carbonyl)amino)phenyl)-N,5-dimethyl-2-thia-4-azabicyclo[4.1.0]hept-3-ene-1-carboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-((1R)-2,2,2-trifluoro-1-methylethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-((1S)-2,2,2-trifluoro-1-methylethoxy)-2-pyrazinecarboxamide;

N-(3-((1S,5S,6S)-3-amino-5-methyl-1-((trideuteriummethyloxy)methyl)-2-thia-4-azabicyclo[4.1.0]hept-3-en-5-yl)-4,5-difluorophenyl)-5-(2-propyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-((1S)-2-methoxy-1-methylethoxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-5-((1S)-2-methoxy-1-methylethoxy)-2-pyrazinecarboxamide;

(1S,5S,6S)-3-amino-5-(2-fluoro-5-(((5-(2,2,2-trifluoroethoxy)-2-pyrazinyl)carbonyl)amino)phenyl)-5-methyl-N-(2,2,2-trifluoroethyl)-2-thia-4-azabicyclo[4.1.0]hept-3-ene-1-carboxamide;

(1S,5S,6S)-3-amino-5-(2-fluoro-5-(((5-(2,2,2-trifluoroethoxy)-2-pyrazinyl)carbonyl)amino)phenyl)-N,5-dimethyl-2-thia-4-azabicyclo[4.1.0]hept-3-ene-1-carboxamide;

(1S,5S,6S)-3-amino-N-((1S)-1,2-dimethylpropyl)-5-(2-fluoro-5-(((5-(2,2,2-trifluoroethoxy)-2-pyrazinyl)carbonyl)amino)phenyl)-5-methyl-2-thia-4-azabicyclo[4.1.0]hept-3-ene-1-carboxamide;

methyl(1S,5S,6S)-3-amino-5-(2,3-difluoro-5-(((5-(2-propyn-1-yloxy)-2-pyrazinyl)carbonyl)amino)phenyl)-5-methyl-2-thia-4-azabicyclo[4.1.0]hept-3-ene-1-carboxylate;

(1S,5S,6S)-3-amino-5-(2-fluoro-5-(((5-(2,2,2-trifluoroethoxy)-2-pyrazinyl)carbonyl)amino)phenyl)-5-methyl-N-(1-methylethyl)-2-thia-4-azabicyclo[4.1.0]hept-3-ene-1-carboxamide;

(1S,5S,6S)-3-amino-N-ethyl-5-(2-fluoro-5-(((5-(2,2,2-trifluoroethoxy)-2-pyrazinyl)carbonyl)amino)phenyl)-5-methyl-2-thia-4-azabicyclo[4.1.0]hept-3-ene-1-carboxamide;

(1S,5S,6S)-3-amino-5-(2-fluoro-5-(((5-(((1S)-1-methyl-2-propyn-1-yl)oxy)-2-pyrazinyl)carbonyl)amino)phenyl)-N,5-dimethyl-2-thia-4-azabicyclo[4.1.0]hept-3-ene-1-carboxamide;

(1S,5S,6S)-3-amino-5-(2-fluoro-5-((2-(2-propyn-1-yloxy)pyrido[3,4-b]pyrazin-5-yl)amino)phenyl)-N,5-dimethyl-2-thia-4-azabicyclo[4.1.0]hept-3-ene-1-carboxamide;

tert-butyl((((1S,5S,6S)-3-amino-5-(2,3-difluoro-5-(((5-(2-propyn-1-yloxy)-2-pyrazinyl)carbonyl)amino)phenyl)-5-methyl-2-thia-4-azabicyclo[4.1.0]hept-3-en-1-yl)methyl)carbamate;

N-(3-((1S,5S,6S)-3-amino-1-(aminomethyl)-5-methyl-2-thia-4-azabicyclo[4.1.0]hept-3-en-5-yl)-4,5-difluorophenyl)-5-(2-propyn-1-yloxy)-2-pyrazinecarboxamide;

(1S,5S,6S)-3-amino-N-((1R)-2,2-difluorocyclopropyl)-5-(2-fluoro-5-(((5-(2,2,2-trifluoroethoxy)-2-pyrazinyl)carbonyl)amino)phenyl)-5-methyl-2-thia-4-azabicyclo[4.1.0]hept-3-ene-1-carboxamide;

(1S,5S,6S)-3-amino-N-((1S)-2,2-difluorocyclopropyl)-5-(2-fluoro-5-(((5-(2,2,2-trifluoroethoxy)-2-pyrazinyl)carbonyl)amino)phenyl)-5-methyl-2-thia-4-azabicyclo[4.1.0]hept-3-ene-1-carboxamide;

(1S,5S,6S)-3-amino-N-(2-fluoro-1,1-dimethylethyl)-5-(2-fluoro-5-(((5-(2,2,2-trifluoroethoxy)-2-pyrazinyl)carbonyl)amino)phenyl)-5-methyl-2-thia-4-azabicyclo[4.1.0]hept-3-ene-1-carboxamide;

(1S,5S,6S)-3-amino-5-(2-fluoro-5-(((5-(2,2,2-trifluoroethoxy)-2-pyrazinyl)carbonyl)amino)phenyl)-N-methoxy-N,5-dimethyl-2-thia-4-azabicyclo[4.1.0]hept-3-ene-1-carboxamide;

(1S,5S,6S)-3-amino-5-(5-(((5-chloro-2-pyridinyl)carbonyl)amino)-2-fluorophenyl)-N,5-dimethyl-2-thia-4-azabicyclo[4.1.0]hept-3-ene-1-carboxamide;

(1S,5S,6S)-3-amino-N-tert-butyl-5-(5-(((5-cyano-2-pyridinyl)carbonyl)amino)-2-fluorophenyl)-5-methyl-2-thia-4-azabicyclo[4.1.0]hept-3-ene-1-carboxamide;

(1S,5S,6S)-3-amino-5-(2-fluoro-5-(((5-(2-propyn-1-yloxy)-2-pyrazinyl)carbonyl)amino)phenyl)-N,5-dimethyl-2-thia-4-azabicyclo[4.1.0]hept-3-ene-1-carboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(((1R)-1-methyl-2-propyn-1-yl)oxy)-2-pyrazinecarboxamide;

N-(5-((1S,5S,6S)-3-amino-1-(difluoromethyl)-5-methyl-2-thia-4-azabicyclo[4.1.0]hept-3-en-5-yl)-6-methoxy-3-pyridinyl)-5-(2-propyn-1-yloxy)-2-pyrazinecarboxamide;

N-(5-((1S,5S,6S)-3-amino-1-(difluoromethyl)-5-methyl-2-thia-4-azabicyclo[4.1.0]hept-3-en-5-yl)-6-methoxy-3-pyridinyl)-5-chloro-2-pyridinecarboxamide;

N-(3-((1S,5S,6S)-3-amino-1-(((3R)-3-fluoro-1-pyrrolidinyl)carbonyl)-5-methyl-2-thia-4-azabicyclo[4.1.0]hept-3-en-5-yl)-4-fluorophenyl)-5-(2,2,2-trifluoroethoxy)-2-pyrazinecarboxamide;

N-(3-((1S,5S,6S)-3-amino-1-(((3S)-3-fluoro-1-pyrrolidinyl)carbonyl)-5-methyl-2-thia-4-azabicyclo[4.1.0]hept-3-en-5-yl)-4-fluorophenyl)-5-(2,2,2-trifluoroethoxy)-2-pyrazinecarboxamide;

(1S,5S,6S)-3-amino-N-cyclopropyl-5-(2-fluoro-5-(((5-(((1S)-1-methyl-2-propyn-1-yl)oxy)-2-pyrazinyl)carbonyl)amino)phenyl)-5-methyl-2-thia-4-azabicyclo[4.1.0]hept-3-ene-1-carboxamide;

(1S,5S,6S)-3-amino-N-tert-butyl-5-(2-fluoro-5-(((5-(((1S)-1-methyl-2-propyn-1-yl)oxy)-2-pyrazinyl)carbonyl)amino)phenyl)-5-methyl-2-thia-4-azabicyclo[4.1.0]hept-3-ene-1-carboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-((1S)-2,2,2-trifluoro-1-methylethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-((1R)-2,2,2-trifluoro-1-methylethoxy)-2-pyrazinecarboxamide;

(1S,5S,6S)-3-amino-N-((1R)-1,2-dimethylpropyl)-5-(2-fluoro-5-(((5-(2,2,2-trifluoroethoxy)-2-pyrazinyl)carbonyl)amino)phenyl)-5-methyl-2-thia-4-azabicyclo[4.1.0]hept-3-ene-1-carboxamide;

N-(3-((1S,5S,6S)-3-amino-5-methyl-1-(4-morpholinylcarbonyl)-2-thia-4-azabicyclo[4.1.0]hept-3-en-5-yl)-4-fluorophenyl)-5-(2,2,2-trifluoroethoxy)-2-pyrazinecarboxamide;

(1S,5S,6S)-3-amino-N-(2,2-difluoroethyl)-5-(2-fluoro-5-(((5-(2,2,2-trifluoroethoxy)-2-pyrazinyl)carbonyl)amino)phenyl)-5-methyl-2-thia-4-azabicyclo[4.1.0]hept-3-ene-1-carboxamide;

(1S,5S,6S)-3-amino-5-(2-fluoro-5-(((5-(2,2,2-trifluoroethoxy)-2-pyrazinyl)carbonyl)amino)phenyl)-N,N,5-trimethyl-2-thia-4-azabicyclo[4.1.0]hept-3-ene-1-carboxamide;

(1S,5S,6S)-3-amino-N-cyclopropyl-5-(2-fluoro-5-(((5-((1S)-2-methoxy-1-methylethoxy)-2-pyrazinyl)carbonyl)amino)phenyl)-5-methyl-2-thia-4-azabicyclo[4.1.0]hept-3-ene-1-carboxamide;

(1S,5S,6S)-3-amino-N-tert-butyl-5-(2-fluoro-5-(((5-(2,2,2-trifluoroethoxy)-2-pyrazinyl)carbonyl)amino)phenyl)-5-methyl-2-thia-4-azabicyclo[4.1.0]hept-3-ene-1-carboxamide;

(1S,5S,6S)-3-amino-N-tert-butyl-5-(2-fluoro-5-(((5-((1S)-2-methoxy-1-methylethoxy)-2-pyrazinyl)carbonyl)amino)phenyl)-5-methyl-2-thia-4-azabicyclo[4.1.0]hept-3-ene-1-carboxamide;

N-(3-((1S,5S,6S)-3-amino-5-methyl-1-(4-morpholinylcarbonyl)-2-thia-4-azabicyclo[4.1.0]hept-3-en-5-yl)-4,5-difluorophenyl)-5-(2-propyn-1-yloxy)-2-pyrazinecarboxamide;

N-(3-((1S,5S,6S)-3-amino-5-methyl-1-(4-morpholinylcarbonyl)-2-thia-4-azabicyclo[4.1.0]hept-3-en-5-yl)-4-fluorophenyl)-5-(2-propyn-1-yloxy)-2-pyrazinecarboxamide;

(1S,5S,6S)-3-amino-N-(2-fluoro-1,1-dimethylethyl)-5-(2-fluoro-5-(((5-(2-propyn-1-yloxy)-2-pyrazinyl)carbonyl)amino)phenyl)-5-methyl-2-thia-4-azabicyclo[4.1.0]hept-3-ene-1-carboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-chloro-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-((3-methyl-1,2,4-oxadiazol-5-yl)methoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(((1S)-1-methyl-2-propyn-1-yl)oxy)-2-pyrazinecarboxamide;

N-(3-((1S,5S,6S)-3-amino-1-cyano-5-methyl-2-thia-4-azabicyclo[4.1.0]hept-3-en-5-yl)-4,5-difluorophenyl)-5-((1S)-2-methoxy-1-methylethoxy)-2-pyrazinecarboxamide;

N-(3-((1S,5S,6S)-3-amino-1-cyano-5-methyl-2-thia-4-azabicyclo[4.1.0]hept-3-en-5-yl)-4,5-difluorophenyl)-5-(((1S)-1-methyl-2-propyn-1-yl)oxy)-2-pyrazinecarboxamide;

N-(3-((1S,5S,6S)-3-amino-1-cyano-5-methyl-2-thia-4-azabicyclo[4.1.0]hept-3-en-5-yl)-4,5-difluorophenyl)-5-(2,2,2-trifluoroethoxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-((5-methyl-1,2,4-oxadiazol-3-yl)methoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-((3-methyl-1,2,4-oxadiazol-5-yl)methoxy)-2-pyrazinecarboxamide;

N-(3-((1S,5S,6S)-3-amino-1-cyano-5-methyl-2-thia-4-azabicyclo[4.1.0]hept-3-en-5-yl)-4,5-difluorophenyl)-3-methyl-5-(2,2,2-trifluoroethoxy)-2-pyridinecarboxamide;

N-(3-((1S,5S,6S)-3-amino-1-cyano-5-methyl-2-thia-4-azabicyclo[4.1.0]hept-3-en-5-yl)-4,5-difluorophenyl)-3-methyl-5-(2-propyn-1-yloxy)-2-pyridinecarboxamide;

(1S,5S,6S)-3-amino-N-ethyl-5-(2-fluoro-5-(((5-(2-propyn-1-yloxy)-2-pyrazinyl)carbonyl)amino)phenyl)-5-methyl-2-thia-4-azabicyclo[4.1.0]hept-3-ene-1-carboxamide;

(1S,5S,6S)-3-amino-5-(5-(((5-cyano-2-pyridinyl)carbonyl)amino)-2-fluorophenyl)-N-(2-fluoro-1,1-dimethylethyl)-5-methyl-2-thia-4-azabicyclo[4.1.0]hept-3-ene-1-carboxamide;

(1S,5S,6S)-3-amino-N-(2-fluoro-1,1-dimethylethyl)-5-(2-fluoro-5-(((5-(((1S)-1-methyl-2-propyn-1-yl)oxy)-2-pyrazinyl)carbonyl)amino)phenyl)-5-methyl-2-thia-4-azabicyclo[4.1.0]hept-3-ene-1-carboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(cyclobutylmethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(cyclopropylmethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(3-oxetanylmethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(((2R)-2-methoxypropyl)oxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(((2S)-2-methoxypropyl)oxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-((1S)-2-methoxy-1-methylethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(2,2-difluoroethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-((3,3-difluorocyclobutyl)methoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-oxo-4,5-dihydro-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(2-methylpropoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-((2R)-2-oxetanylmethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-((2S)-2-oxetanylmethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-((2-methyl-2-propen-1-yl)oxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-((3-methyl-5-isoxazolyl)methoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-((5-methyl-3-isoxazolyl)methoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(benzyloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(1,3-thiazol-2-ylmethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(((1R)-2,2-difluorocyclopropyl)methoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-((1S)-2,2-difluorocyclopropyl)methoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(2-propen-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-((5-methyl-1,3,4-oxadiazol-2-yl)methoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-ethoxy-2-pyrazinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-5-((3-methyl-1,2,4-oxadiazol-5-yl)methoxy)-2-pyrazinecarboxamide;

(1S,5S,6S)-3-amino-N-(2-fluoroethyl)-5-(2-fluoro-5-(((5-(2,2,2-trifluoroethoxy)-2-pyrazinyl)carbonyl)amino)phenyl)-5-methyl-2-thia-4-azabicyclo[4.1.0]hept-3-ene-1-carboxamide;

(1S,5S,6S)-3-amino-5-(2-fluoro-5-(((5-(2,2,2-trifluoroethoxy)-2-pyrazinyl)carbonyl)amino)phenyl)-5-methyl-N-(1-methylcyclopropyl)-2-thia-4-azabicyclo[4.1.0]hept-3-ene-1-carboxamide;

N-(3-((1S,5S,6S)-1-((acetylamino)methyl)-3-amino-5-methyl-2-thia-4-azabicyclo[4.1.0]hept-3-en-5-yl)-4,5-difluorophenyl)-5-(2-propyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluoro-5-methylphenyl)-5-(2-propyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluoro-5-methylphenyl)-5-((3-methyl-1,2,4-oxadiazol-5-yl)methoxy)-2-pyrazinecarboxamide;

(1S,5S,6S)-3-amino-N-((1R)-2,2-difluoro-1-methylethyl)-5-(2-fluoro-5-(((5-(2,2,2-trifluoroethoxy)-2-pyrazinyl)carbonyl)amino)phenyl)-5-methyl-2-thia-4-azabicyclo[4.1.0]hept-3-ene-1-carboxamide;

(1S,5S,6S)-3-amino-N-((1S)-2,2-difluoro-1-methylethyl)-5-(2-fluoro-5-(((5-(2,2,2-trifluoroethoxy)-2-pyrazinyl)carbonyl)amino)phenyl)-5-methyl-2-thia-4-azabicyclo[4.1.0]hept-3-ene-1-carboxamide;

N-(3-((1S,5S,6S)-3-amino-1-(ethoxymethyl)-5-methyl-2-thia-4-azabicyclo[4.1.0]hept-3-en-5-yl)-4,5-difluorophenyl)-5-(2-propyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(3-pentyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(3-butyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-((1-methylcyclopropyl)methoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-((3-methyl-3-oxetanyl)methoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(((1R)-1-methyl-2-propen-1-yl)oxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(((1S)-1-methyl-2-propen-1-yl)oxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(2-fluoroethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(cyclopropylmethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(cyclobutylmethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(3-oxetanylmethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(2-methylpropoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(2,2-difluoroethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-((2R)-2-oxetanylmethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-((2S)-2-oxetanylmethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(3-pentyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(3-butyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-((1-methylcyclopropyl)methoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-((3-methyl-3-oxetanyl)methoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(((1R)-1-methyl-2-propen-1-yl)oxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(((1S)-1-methyl-2-propen-1-yl)oxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(2-fluoroethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluoro-5-methylphenyl)-5-(2,2,2-trifluoroethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluoro-5-methylphenyl)-5-chloro-2-pyridinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(oxetan-3-yloxy)pyrazine-2-carboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(oxetan-3-yloxy)pyrazine-2-carboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(neopentyloxy)pyrazine-2-carboxamide;

N-(3-((1S,5S,6S)-1-acetyl-3-amino-5-methyl-2-thia-4-azabicyclo[4.1.0]hept-3-en-5-yl)-4,5-difluorophenyl)-5-(prop-2-yn-1-yloxy)pyrazine-2-carboxamide;

N-(3-((1S,5S,6S)-3-amino-1-(methoxymethyl)-5-methyl-2-thia-4-azabicyclo[4.1.0]hept-3-en-5-yl)-4-fluoro-5-methylphenyl)-5-(oxazol-2-ylmethoxy)pyrazine-2-carboxamide;

N-(3-((1S,5S,6S)-3-amino-1-(difluoromethyl)-5-methyl-2-thia-4-azabicyclo[4.1.0]hept-3-en-5-yl)-4-fluoro-5-methylphenyl)-5-(prop-2-yn-1-yloxy)pyrazine-2-carboxamide;

N-(3-((1S,5S,6S)-3-amino-1-(difluoromethyl)-5-methyl-2-thia-4-azabicyclo[4.1.0]hept-3-en-5-yl)-4-fluoro-5-methylphenyl)-5-(2,2,2-trifluoroethoxy)pyrazine-2-carboxamide;

N-(3-((1S,5S,6S)-3-amino-1-(difluoromethyl)-5-methyl-2-thia-4-azabicyclo[4.1.0]hept-3-en-5-yl)-4-fluoro-5-methylphenyl)-5-(oxazol-2-ylmethoxy)pyrazine-2-carboxamide; or N-(3-((1S,5S,6S)-3-amino-1-(difluoromethyl)-5-methyl-2-thia-4-azabicyclo[4.1.0]hept-3-en-5-yl)-4-fluoro-5-methylphenyl)-5-((3-methyl-1,2,4-oxadiazol-5-yl)methoxy)pyrazine-2-carboxamide.

Additional generic and specific compounds representative of the invention include:

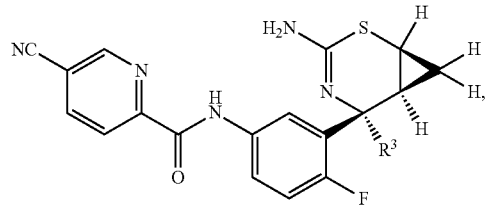

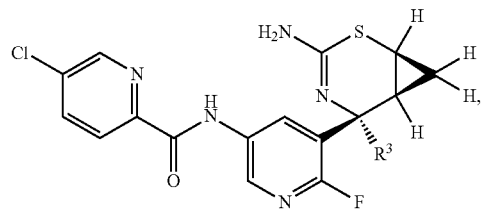

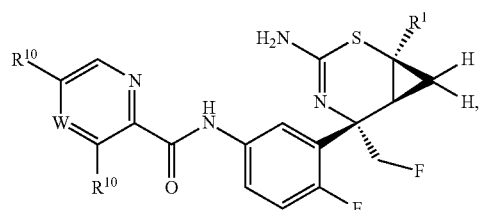

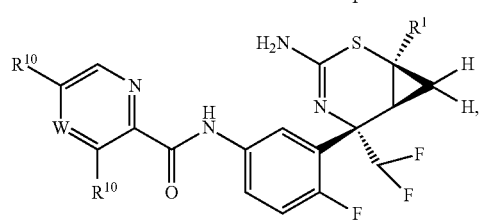

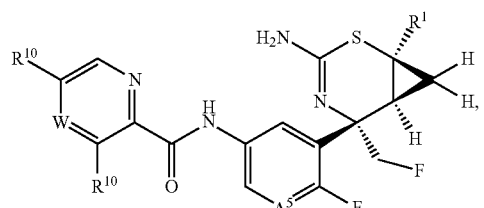

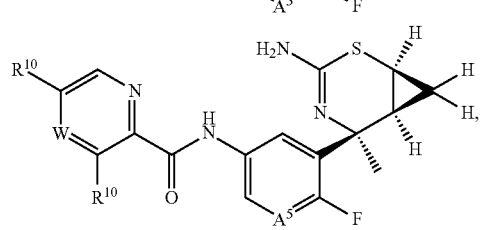

-continued

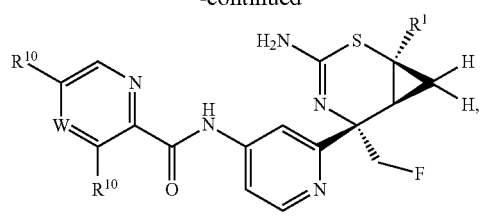

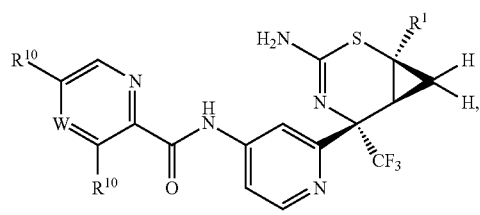

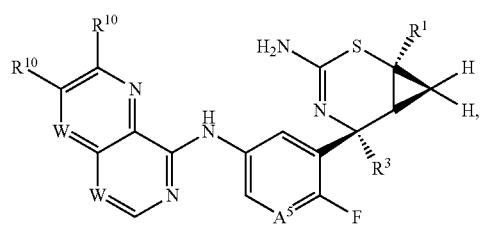

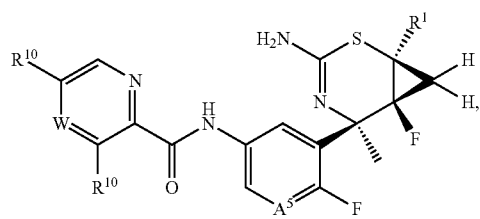

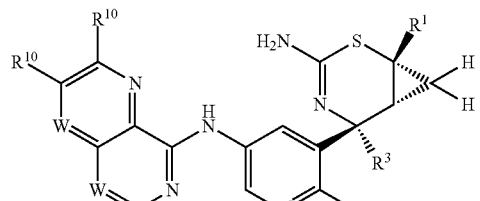

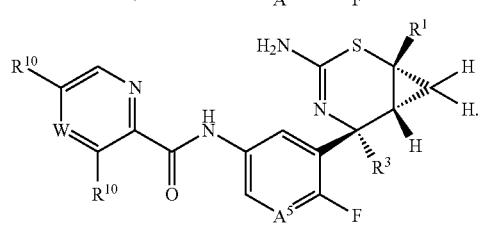

In an additional embodiment, the invention provides a compound, or a pharmaceutically acceptable salt or tautomer thereof, selected from:

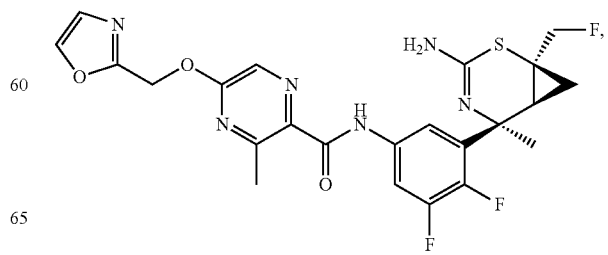

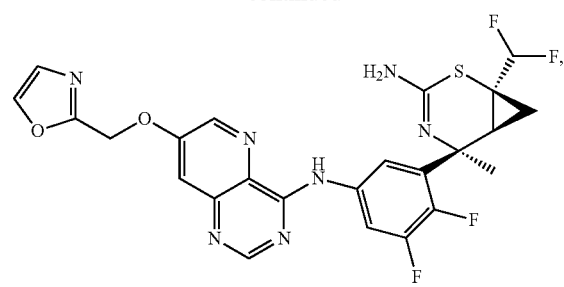
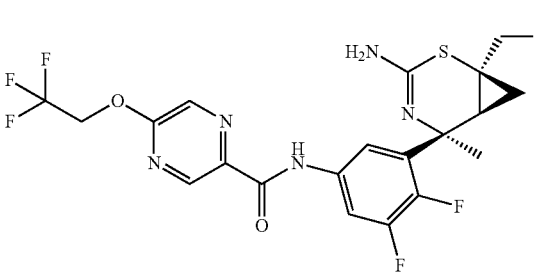
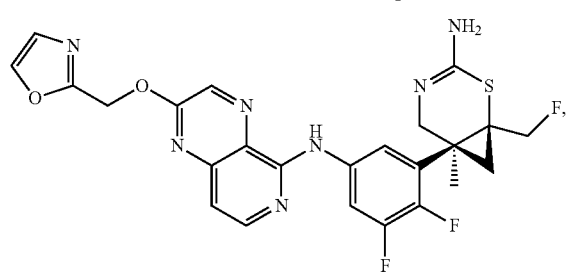
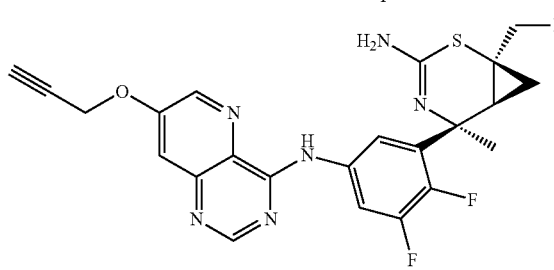
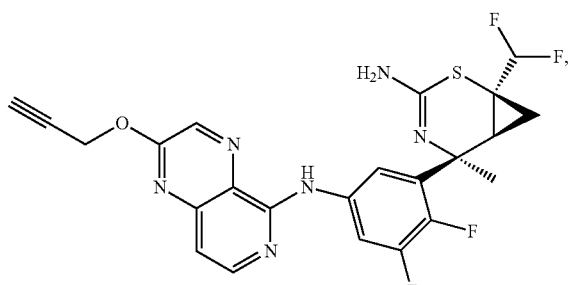
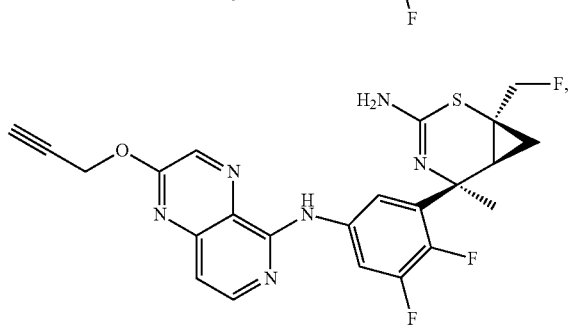
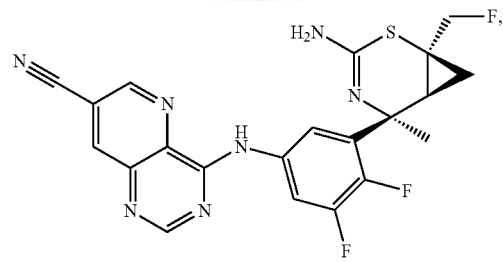
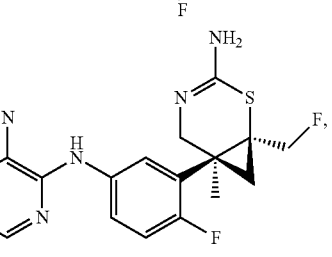
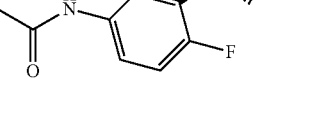
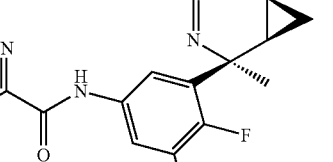
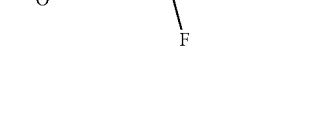
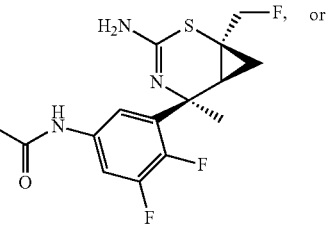

-continued

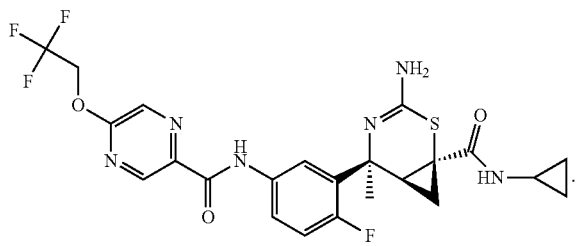

Thus, in one embodiment, the invention provides the compound

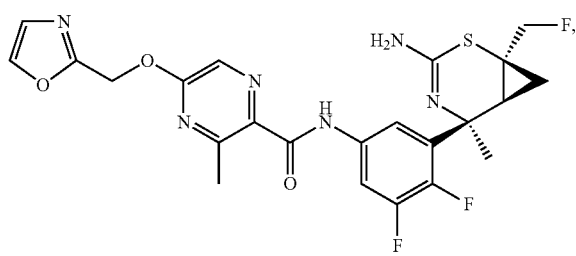 [SMILES: Cc1nc(OCc2ncco2)cnc1C(=O)Nc1cc(F)c(F)c([C@@]2(C)N=C(N)S[C@@]3(CF)C[C@H]32)c1]

or a pharmaceutically acceptable salt or tautomer thereof.

Thus, in one embodiment, the invention provides the compound

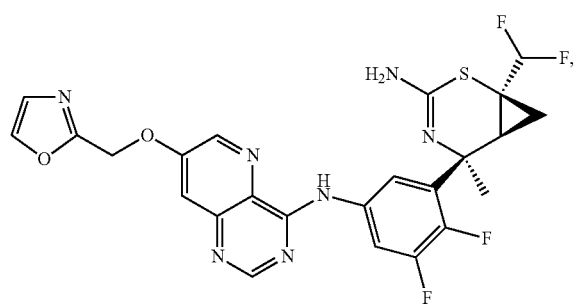 [SMILES: C[C@]1(c2cc(Nc3ncnc4cc(OCc5ncco5)cnc34)cc(F)c2F)N=C(N)S[C@@]2(C(F)F)C[C@@H]12]

or a pharmaceutically acceptable salt or tautomer thereof.

Thus, in one embodiment, the invention provides the compound

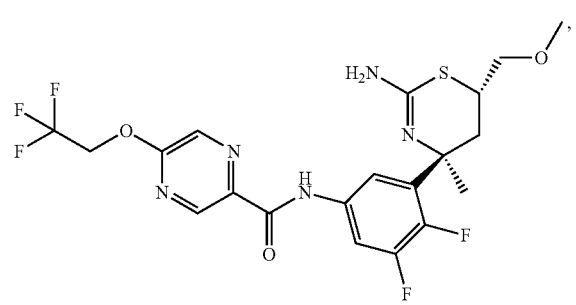 [SMILES: COC[C@@H]1C[C@@](C)(c2cc(NC(=O)c3cnc(OCC(F)(F)F)cn3)cc(F)c2F)N=C(N)S1]

or a pharmaceutically acceptable salt or tautomer thereof.

Thus, in one embodiment, the invention provides the compound

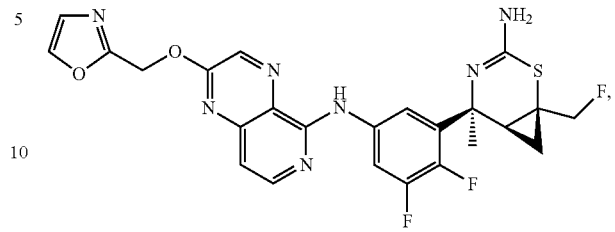

or a pharmaceutically acceptable salt or tautomer thereof.

Thus, in one embodiment, the invention provides the compound

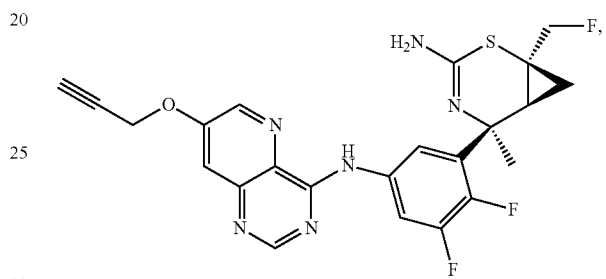

or a pharmaceutically acceptable salt or tautomer thereof.

Thus, in one embodiment, the invention provides the compound

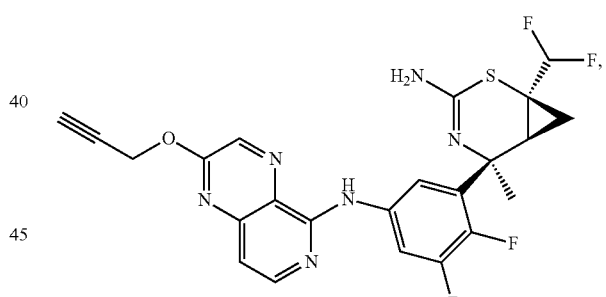

or a pharmaceutically acceptable salt or tautomer thereof.

Thus, in one embodiment, the invention provides the compound

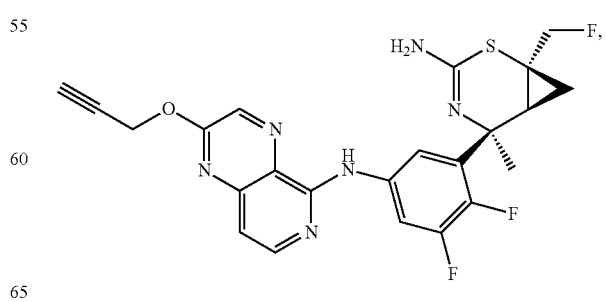

or a pharmaceutically acceptable salt or tautomer thereof.

Thus, in one embodiment, the invention provides the compound

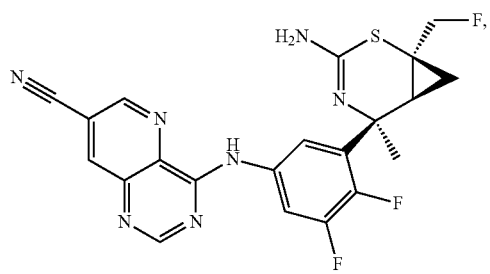 [SMILES: C[C@]1(c2cc(Nc3ncnc4cc(C#N)cnc34)cc(F)c2F)N=C(N)S[C@@]2(CF)C[C@H]21]

or a pharmaceutically acceptable salt or tautomer thereof.

Thus, in one embodiment, the invention provides the compound

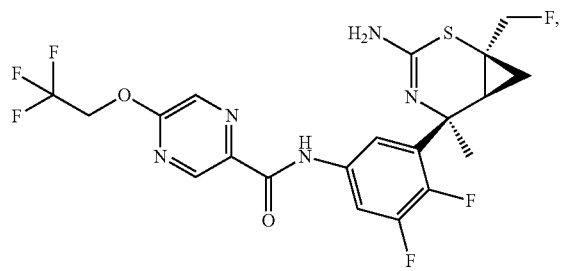 [SMILES: C[C@]1(c2cc(NC(=O)c3cnc(OCC(F)(F)F)cn3)cc(F)c2F)N=C(N)S[C@@]2(CF)C[C@H]21]

or a pharmaceutically acceptable salt or tautomer thereof.

Thus, in one embodiment, the invention provides the compound

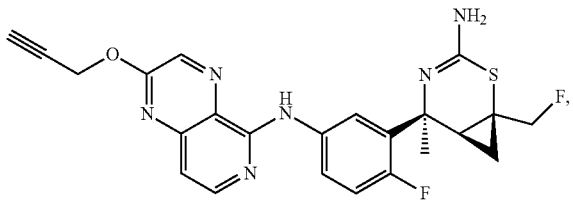 [SMILES: C#CCOc1cnc2c(Nc3ccc(F)c([C@@]4(C)N=C(N)S[C@@]5(CF)C[C@H]54)c3)nccc2n1]

or a pharmaceutically acceptable salt or tautomer thereof.

Thus, in one embodiment, the invention provides the compound

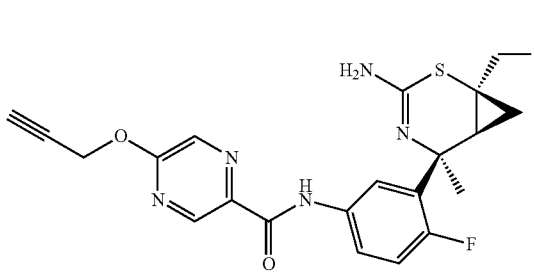

or a pharmaceutically acceptable salt or tautomer thereof.

Thus, in one embodiment, the invention provides the compound

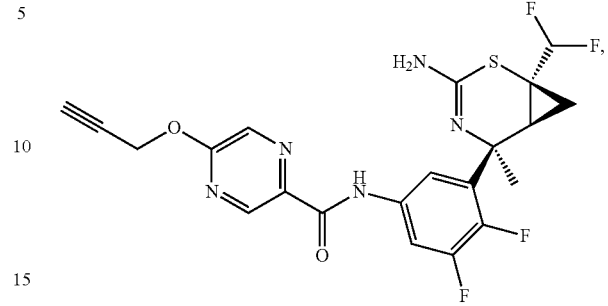

or a pharmaceutically acceptable salt or tautomer thereof.

Thus, in one embodiment, the invention provides the compound

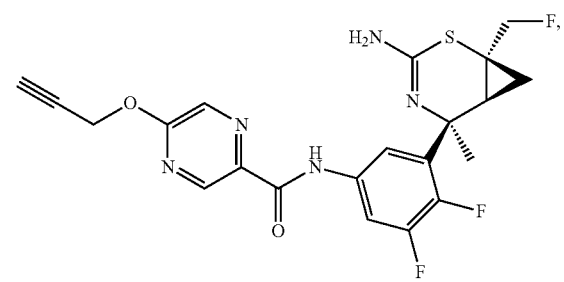 [SMILES: C#CCOc1cnc(C(=O)Nc2cc(F)c(F)c([C@@]3(C)N=C(N)S[C@@]4(CF)C[C@H]43)c2)cn1]

or a pharmaceutically acceptable salt or tautomer thereof.

Thus, in one embodiment, the invention provides the compound

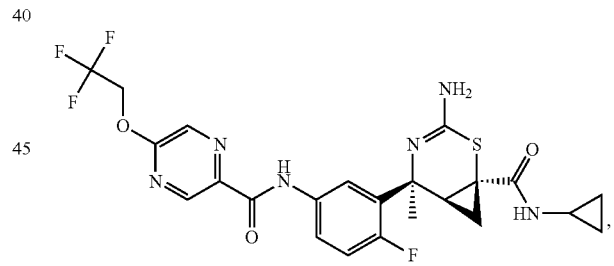

or a pharmaceutically acceptable salt or tautomer thereof.

In an additional embodiment, the invention provides a compound, or a pharmaceutically acceptable salt or tautomer thereof, selected from:

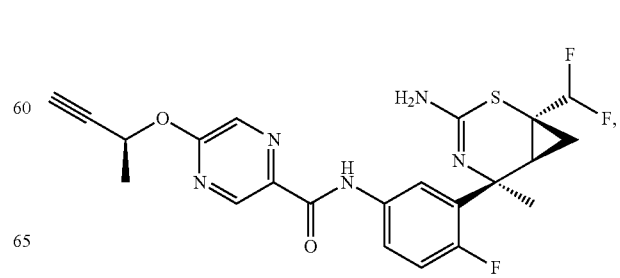

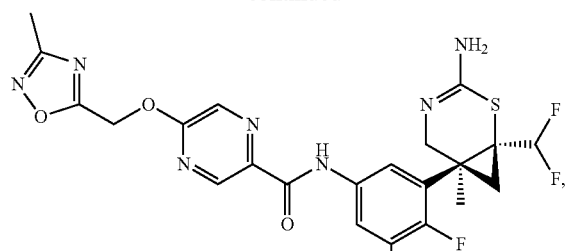
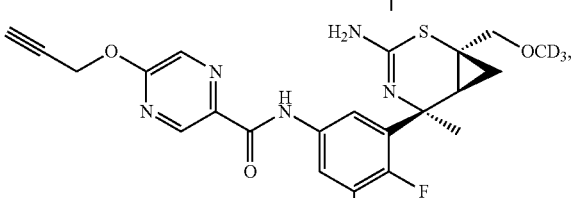
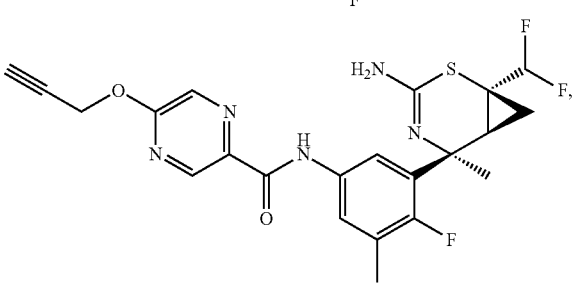
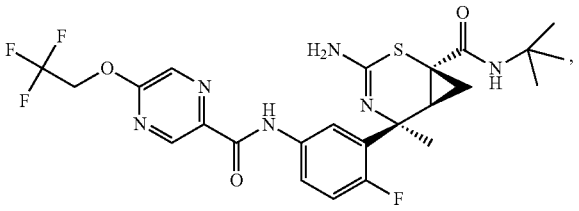
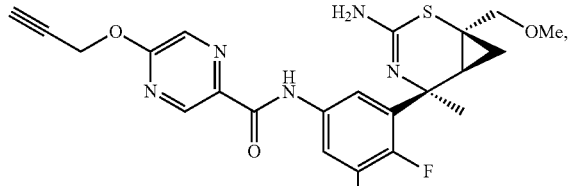
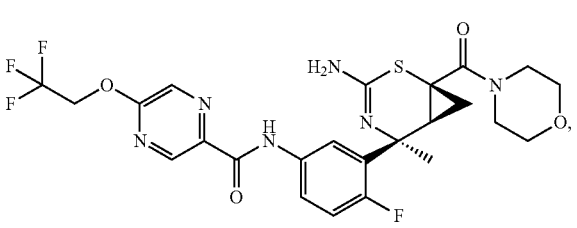
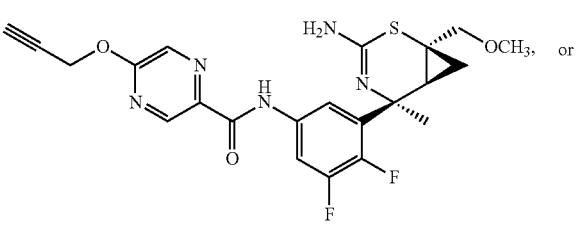

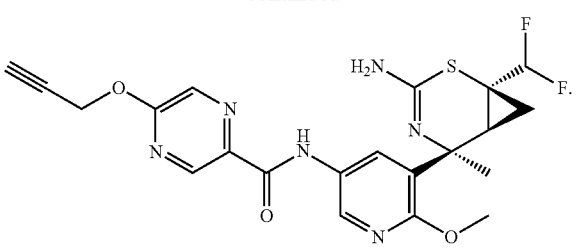

Thus, in one embodiment, the invention provides the compound

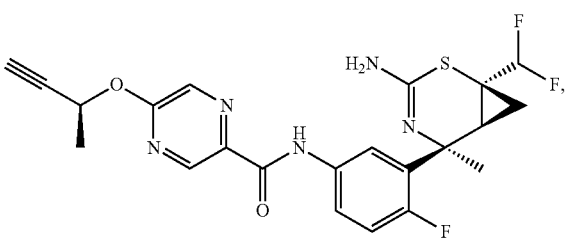 [SMILES: C#C[C@H](C)Oc1cnc(C(=O)Nc2ccc(F)c([C@@]3(C)N=C(N)S[C@@]4(C(F)F)C[C@@H]34)c2)cn1]

or a pharmaceutically acceptable salt or tautomer thereof.

Thus, in one embodiment, the invention provides the compound

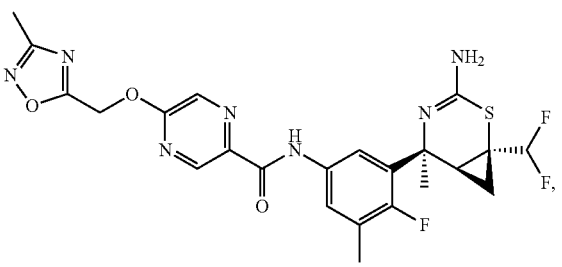 [SMILES: Cc1noc(COc2cnc(C(=O)Nc3cc(C)c(F)c([C@@]4(C)N=C(N)S[C@@]5(C(F)F)C[C@@H]45)c3)cn2)n1]

or a pharmaceutically acceptable salt or tautomer thereof.

Thus, in one embodiment, the invention provides the compound

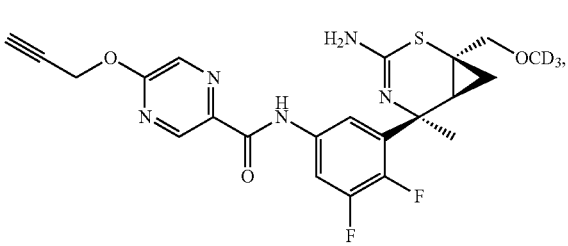

or a pharmaceutically acceptable salt or tautomer thereof.

Thus, in one embodiment, the invention provides the compound

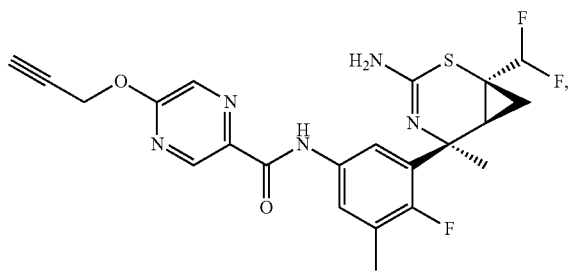 [SMILES: C#CCOc1cnc(C(=O)Nc2cc(C)c(F)c([C@@]3(C)N=C(N)S[C@@]4(C(F)F)C[C@@H]34)c2)cn1]

or a pharmaceutically acceptable salt or tautomer thereof.

Thus, in one embodiment, the invention provides the compound

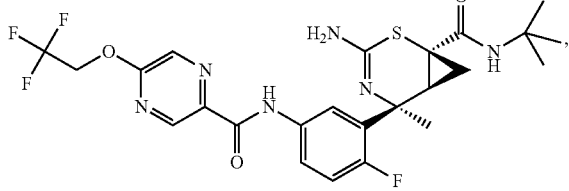

or a pharmaceutically acceptable salt or tautomer thereof.

Thus, in one embodiment, the invention provides the compound

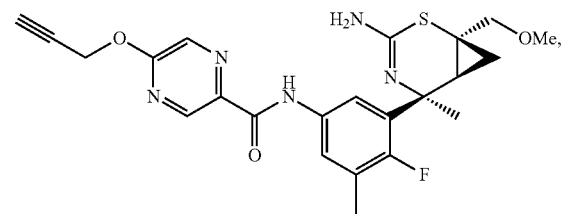 [SMILES: C#CCOc1cnc(C(=O)Nc2cc(C)c(F)c([C@@]3(C)N=C(N)S[C@@]4(COC)C[C@H]43)c2)cn1]

or a pharmaceutically acceptable salt or tautomer thereof.

Thus, in one embodiment, the invention provides the compound

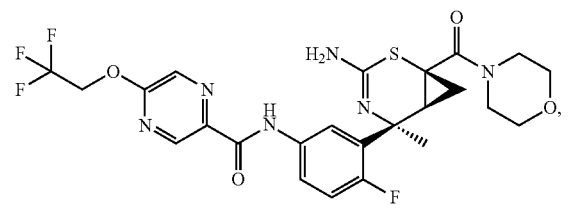 [SMILES: C[C@]1(c2cc(NC(=O)c3cnc(OCC(F)(F)F)cn3)ccc2F)N=C(N)S[C@@]2(C(=O)N3CCOCC3)C[C@H]21]

or a pharmaceutically acceptable salt or tautomer thereof.

Thus, in one embodiment, the invention provides the compound

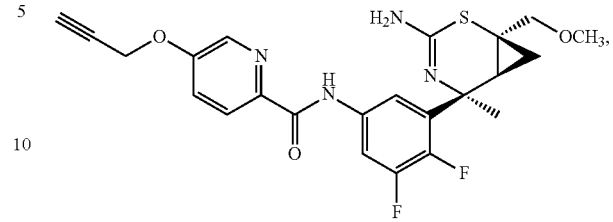

or a pharmaceutically acceptable salt or tautomer thereof.

Thus, in one embodiment, the invention provides the compound

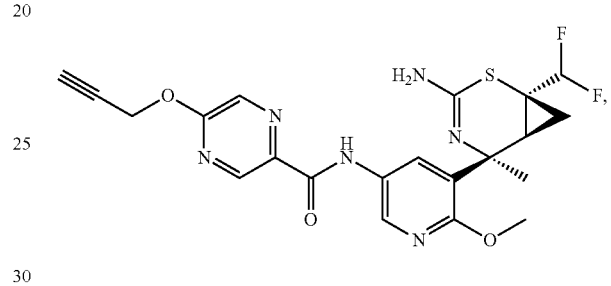

or a pharmaceutically acceptable salt or tautomer thereof.

In embodiment 84, the invention provides a compound, or a pharmaceutically acceptable salt or tautomer thereof, selected from:

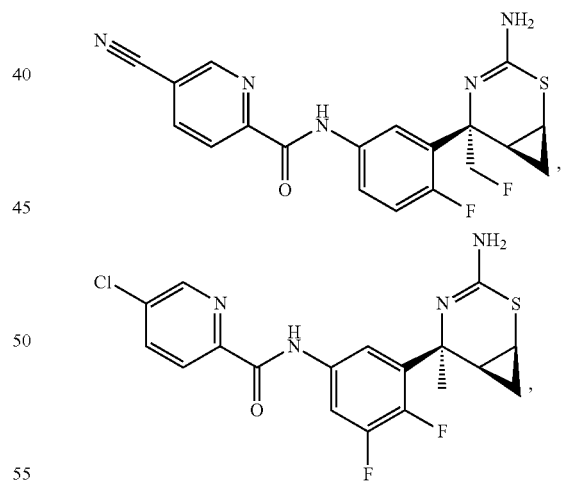

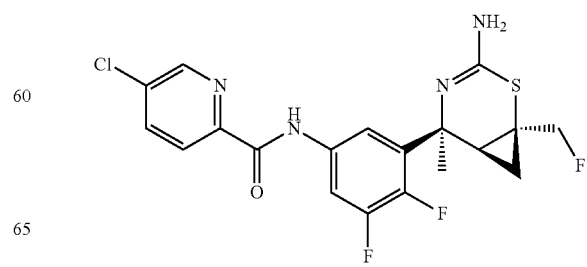

-continued
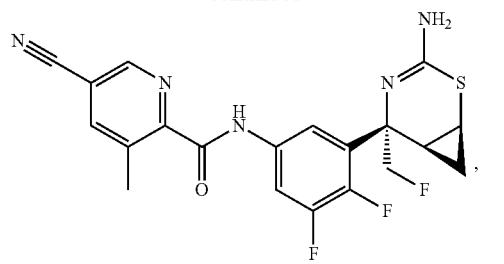,
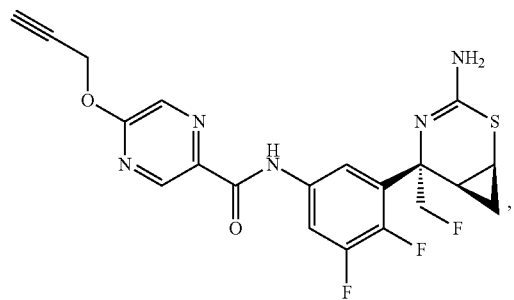,
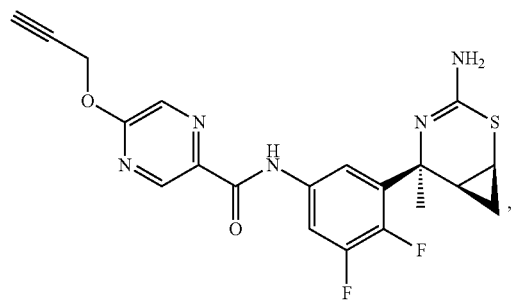,
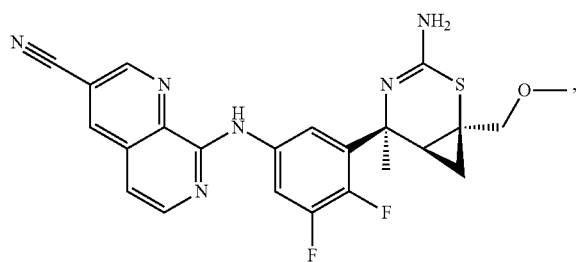,
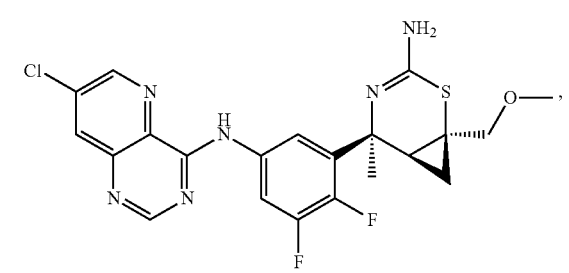,
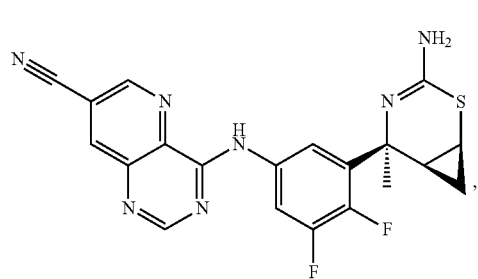,
-continued
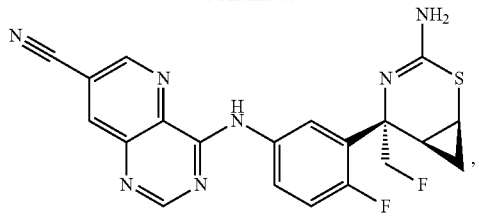,
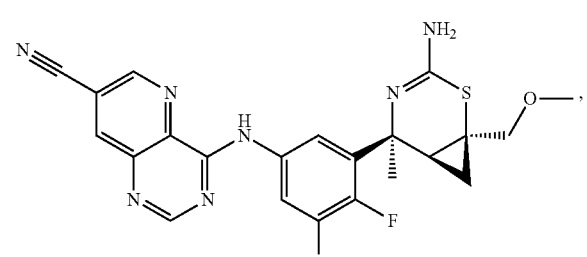,
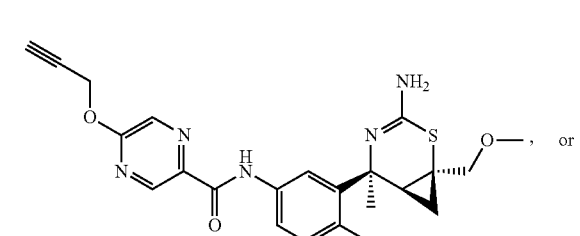, or
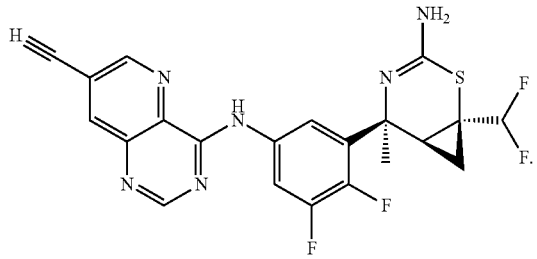.
In embodiment 85, the invention provides each individual compound according to embodiments 82-84, or a pharmaceutically acceptable salt or tautomer thereof.
For instance, in embodiment 86, the invention provides the compound
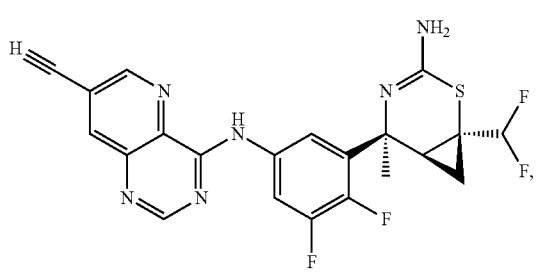
or a pharmaceutically acceptable salt or tautomer thereof.

In embodiment 87, the invention provides the compound

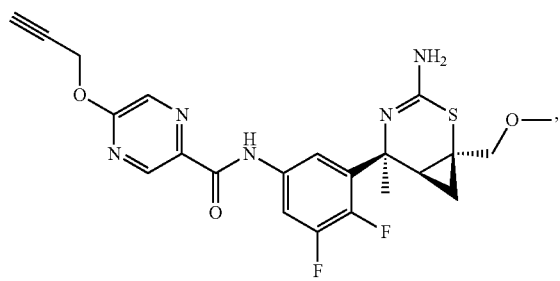 [SMILES: C#CCOc1cnc(C(=O)Nc2cc(F)c(F)c([C@@]3(C)N=C(N)S[C@@]4(COC)C[C@H]43)c2)cn1]

or a pharmaceutically acceptable salt or tautomer thereof.

In embodiment 88, the invention provides the compound

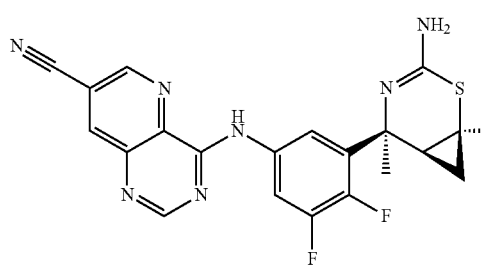

or a pharmaceutically acceptable salt or tautomer thereof.

In embodiment 89, the invention provides the compound

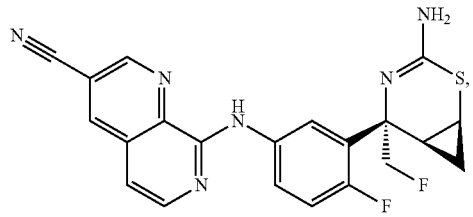

or a pharmaceutically acceptable salt or tautomer thereof.

In embodiment 90, the invention provides the compound

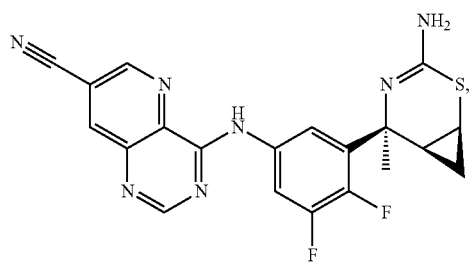 [SMILES: C[C@]1(c2cc(Nc3ncnc4cc(C#N)cnc34)cc(F)c2F)N=C(N)S[C@H]2C[C@H]21]

or a pharmaceutically acceptable salt or tautomer thereof.

In embodiment 91, the invention provides the compound

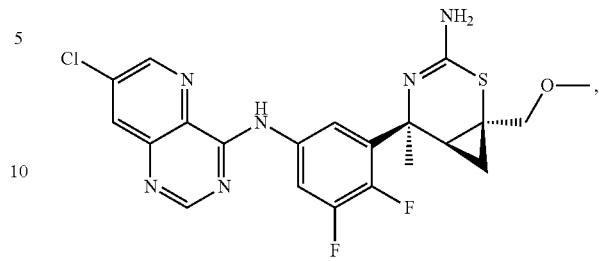

or a pharmaceutically acceptable salt or tautomer thereof.

In embodiment 92, the invention provides the compound

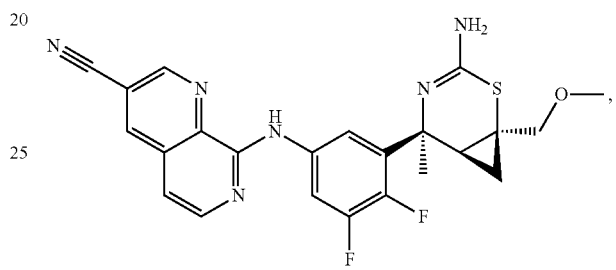

or a pharmaceutically acceptable salt or tautomer thereof.

In embodiment 93, the invention provides the compound

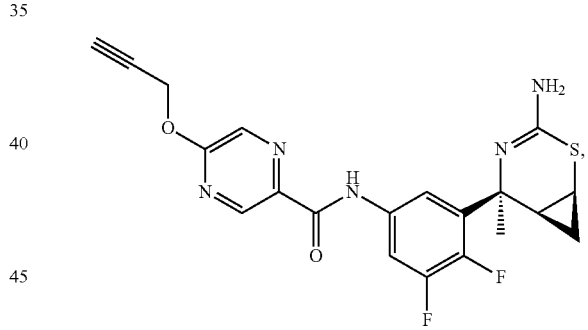

or a pharmaceutically acceptable salt or tautomer thereof.

In embodiment 94, the invention provides the compound

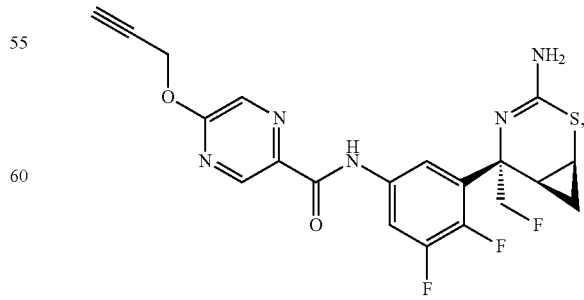

or a pharmaceutically acceptable salt or tautomer thereof.

In embodiment 95, the invention provides the compound

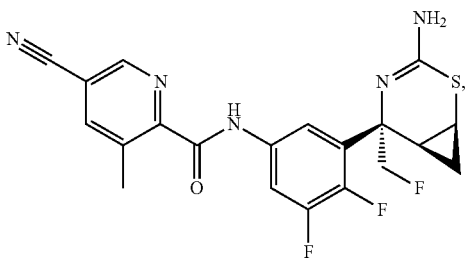 [SMILES: Cc1cc(C#N)cnc1C(=O)Nc1cc(F)c(F)c([C@@]2(CF)N=C(N)S[C@H]3C[C@H]32)c1]

or a pharmaceutically acceptable salt or tautomer thereof.
In embodiment 96, the invention provides the compound

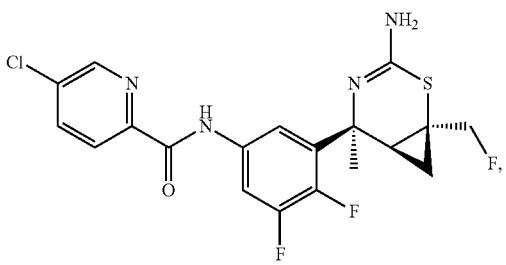 [SMILES: C[C@]1(c2cc(NC(=O)c3ccc(Cl)cn3)cc(F)c2F)N=C(N)S[C@@]2(CF)C[C@H]21]

or a pharmaceutically acceptable salt or tautomer thereof.
In embodiment 97, the invention provides the compound

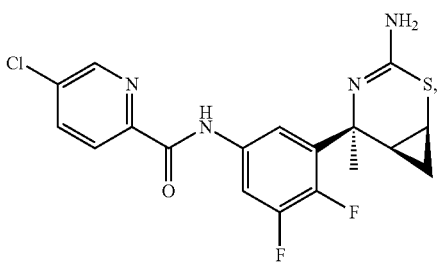 [SMILES: C[C@]1(c2cc(NC(=O)c3ccc(Cl)cn3)cc(F)c2F)N=C(N)S[C@H]2C[C@H]21]

or a pharmaceutically acceptable salt or tautomer thereof.
In embodiment 98, the invention provides the compound

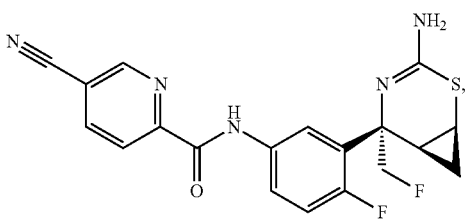 [SMILES: N#Cc1ccc(C(=O)Nc2ccc(F)c([C@@]3(CF)N=C(N)S[C@H]4C[C@H]43)c2)nc1]

or a pharmaceutically acceptable salt or tautomer thereof.

In the structures depicted hereinabove, an "—N" in the 1,3-oxazine head group is intended to be an —NH$_2$ (an amine groups); the "—N" in the amide linker is intended to be an —NH and lines ending without an atom are understood by persons of ordinary skill in the art to be a —CH$_3$ group.

All of the possible embodiments described herein for various of the R groups of the compounds of Formula I may be applied, as appropriate, to compounds of Formulas II and III, and any sub-formulas thereof.

In another embodiment, the invention provides each of the Examplary compounds, and stereoisomers, tautomers, solvates, pharmaceutically acceptable salts, derivatives or prodrugs thereof, and related intermediates, described herein.

In another embodiment, the invention provides the exemplified compounds described herein, and pharmaceutically acceptable salt forms of each thereof.

DEFINITIONS

The following definitions should assist in understanding the metes and bounds of the invention.

The term "comprising" is meant to be open ended, i.e., all encompassing and non-limiting. It may be used herein synonymously with "having." Comprising is intended to include each and every indicated or recited component or element(s) while not excluding any other components or elements.

The compounds of the invention may contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabeled compounds are useful as therapeutic or prophylactic agents, research reagents, e.g., assay reagents, and diagnostic agents, e.g., in vivo imaging agents. All isotopic variations of the compounds of the invention, whether radioactive or not, are intended to be encompassed within the scope of the invention. For example, if a variable is said to be H, this means that variable may also be deuterium (D) or tritium (T). However, in certain deuterated compounds, if a structure is drawn showing D groups, then this site is enriched with respect to D.

The term "C$_{\alpha-\beta}$alkyl", when used either alone or within other terms such as "haloalkyl" and "alkylamino", embraces linear or branched radicals having α to β number of carbon atoms (such as C$_1$-C$_{10}$; C$_1$-C$_6$; or C$_1$-C$_4$). Unless otherwise specified, one or more carbon atoms of the "alkyl" radical may be substituted, such as with a cycloalkyl moiety. Examples of "alkyl" radicals include methyl, cyclopropylmethyl, cyclobutylmethyl, cyclopentylmethyl, ethyl, cyclopropylethyl, cyclobutylethyl, cyclopentylethyl, n-propyl, isopropyl, n-butyl, cyclopropylbutyl, isobutyl, sec-butyl, tert-butyl, pentyl, isoamyl, hexyl and the like.

The term "C$_{\alpha-\beta}$alkenyl", when used alone or in combination, embraces linear or branched radicals having at least one carbon-carbon double bond in a moiety having a number of carbon atoms in the range from α and β. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "C$_{\alpha-\beta}$alkynyl", when used alone or in combination, denotes linear or branched radicals having at least one carbon-carbon triple bond in a moiety having a number of carbon atoms in the range from α and β. Examples of alkynyl radicals include "lower alkynyl" radicals having two to about six carbon atoms and, for example, lower alkynyl radicals having two to about four carbon atoms. Examples of such radicals include, without limitation, ethynyl, propynyl (propargyl), butynyl, and the like.

The term "$C_{\alpha-\beta}$-alkyl", "$C_{\alpha-\beta}$-alkenyl" and "$C_{\alpha-\beta}$-alkynyl", when used with other terms such as "wherein 1, 2 or 3 carbon atoms of said $C_{\alpha-\beta}$-alkyl, $C_{\alpha-\beta}$-alkenyl or $C_{2\alpha-\beta}$-alkynyl is optionally replaced with a heteroatom selected from O, S, S(O), S(O)$_2$ and N" embraces linear or branched radicals wherein one or more of the carbon atoms may be replaced with a heteroatom. Examples of such "alkyl" radicals include —O-methyl, —O— ethyl, —CH$_2$—O—CH$_3$, —CH$_2$CH$_2$—O—CH$_3$, —NH—CH$_2$, —CH$_2$CH$_2$—N(CH$_3$)—CH$_3$, —S—(CH$_2$)$_3$CH$_2$, —CH$_2$CH$_2$—S—CH$_3$ and the like. Accordingly, such radicals also include radicals encompassed by —OR$^7$ where R$^7$ may be defined as a $C_{\alpha-\beta}$-alkyl. Examples of such "alkenyl" radicals include —NH—CH$_2$CH═CH$_2$, —S—CH$_2$CH$_2$CH═CHCH$_3$ and the like. Similar examples exist for such "alkynyl" radicals, as appreciated by those skilled in the art.

The term "$C_{\alpha-\beta}$alkoxyl" or "—OC$_{\alpha-\beta}$alkyl" when used alone or in combination, embraces linear or branched oxygen-containing alkyl radicals each having α to β number of carbon atoms (such as $C_1$-$C_{10}$). The terms "alkoxy" and "alkoxyl", when used alone or in combination, embraces linear or branched oxygen-containing radicals each having alkyl and substituted alkyl portions of one or more carbon atoms. Examples of such radicals include methoxy, ethoxy, propoxy, butoxy, tert-butoxy and neopentoxy. Alkoxy radicals may be further substituted with one or more halo atoms, such as fluoro, chloro or bromo, to provide "haloalkoxy" radicals or with other substitution. Examples of such radicals include fluoromethoxy, chloromethoxy, trifluoromethoxy, trifluoroethoxy, fluoroethoxy and fluoropropoxy.

The term "aryl", when used alone or in combination, means a carbocyclic aromatic moiety containing one, two or even three rings wherein such rings may be attached together in a fused manner. Every ring of an "aryl" multi-ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be substituted, such as with 1 to 5 substituents including lower alkyl, hydroxyl, halo, haloalkyl, nitro, cyano, alkoxy and lower alkylamino, and the like. Phenyl substituted with —O—CH$_2$—O— or —O—CH$_2$—CH$_2$—O— forms an aryl benzodioxolyl substituent.

The term "$C_{\alpha-\beta}$-cycloalkyl", also referred to herein as "carbocyclic", when used alone or in combination, denotes a partially or fully saturated ring radical having a number of carbon atoms in the range from α and β. The "cycloalkyl" may contain one ("monocyclic"), two ("bicyclic") or even three ("tricyclic") rings wherein such rings may be attached together in a fused manner and each formed from carbon atoms. Examples of saturated carbocyclic radicals include saturated 3 to 6-membered monocyclic groups such as cyclopropane, cyclobutane, cyclopentane and cyclohexane. Cycloalkyls may be substituted as described herein.

The terms "ring" and "ring system" refer to a ring comprising the delineated number of atoms, the atoms being carbon or, where indicated, a heteroatom such as nitrogen, oxygen or sulfur. Where the number of atoms is not delineated, such as a "monocyclic ring system" or a "bicyclic ring system", the numbers of atoms are 3-8 for a monocyclic and 6-12 for a bicyclic ring. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The terms "partially or fully saturated or unsaturated" and "saturated or partially or fully unsaturated" with respect to each individual ring, refer to the ring either as fully aromatic (fully unsaturated), partially aromatic (or partially saturated) or fully saturated (containing no double or triple bonds therein). If not specified as such, then it is contemplated that each ring (monocyclic) in a ring system (if bicyclic or tricyclic) may either be fully aromatic, partially aromatic or fully saturated, and optionally substituted with up to 5 substituents. This includes carbocyclics, heterocyclics, aryl and heteroaryl rings.

The term "halo", when used alone or in combination, means halogens such as fluorine, chlorine, bromine or iodine atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, aza-quinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The terms "heterocycle" or "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and fully saturated heterocyclyls include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted" refers to a single ring of 3-, 4-, 5-, 6-, 7- or 8-atom membered or a 6-, 7-, 8-, 9-, 10-, 11 or 12-atom membered bicyclic ring system comprising the delineated number of atoms, the atoms being carbon or, where indicated, a heteroatom such as nitrogen (N), oxygen (O) or sulfur (S). Where the number of atoms is not delineated, such as a "monocyclic ring system" or a "bicyclic ring system", the numbers of atoms are 3-8 for a monocyclic and 6-12 for a bicyclic ring. The ring or ring system may contain substitutents thereon, attached at any atom that allows a stable compound to be formed. A bicyclic ring is intended to include fused ring systems as well as spiro-fused rings. This phrase encompasses carbocyclics, heterocyclics, aryl and heteroaryl rings.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N, N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The term "carbonyl", whether used alone or with other terms, such as "aminocarbonyl", denotes —(C=O)—. "Carbonyl" is also used herein synonymously with the term "oxo".

The term "alkylthio" or "thioalkoxy" embraces radicals containing a linear or branched alkyl radical, of one to ten carbon atoms, attached to a divalent sulfur atom. An example of "alkylthio" or "thioalkoxy" is methylthio, ($CH_3S$—).

The term "Formula I" includes any sub formulas, such as Formulas II and III. Similar with Formulas II and III, in that they include sub-formulas where described.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed.

Various compounds of the invention contain one or more chiral centers, and can exist as racemic mixtures of enantiomers, mixtures of diastereomers or enantiomerically or optically pure compounds. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al. (1997) Tetrahedron 33:2725; Eliel, E. L., Stereochemistry of Carbon Compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, Ind., 1972).

The present invention also includes tautomeric forms of compounds of the invention. For example, the invention comprises compounds of formula I as well as their tautomers, as shown:

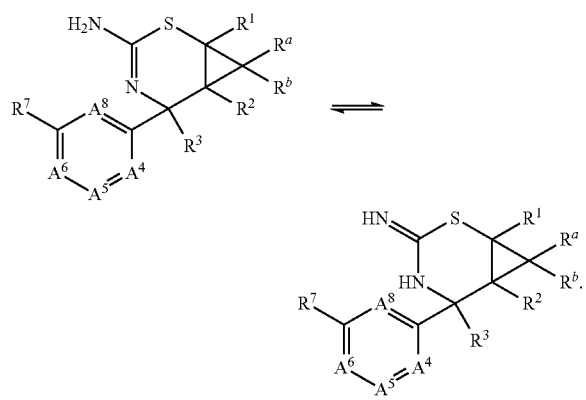

Similarly, tautomers of compounds of Formulas II and III, and of compounds of sub-formulas of compounds of Formulas I, II and III, are also included in the invention.

The term "pharmaceutically-acceptable" when used with reference to a compound of Formulas I-III is intended to refer to a form of the compound that is safe for administration. For example, a salt form, a solvate, a hydrate, a prodrug or derivative form of a compound of Formulas I-III, which has been approved for mammalian use, via oral ingestion or other routes of administration, by a governing body or regulatory agency, such as the Food and Drug Administration (FDA) of the United States, is pharmaceutically acceptable.

Included in the compounds of Formulas I-III are the pharmaceutically acceptable salt forms of the free-base compounds. The term "pharmaceutically-acceptable salts" embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I-III may be prepared from an inorganic acid or from an organic acid. Examples of such inorganic acids are hydrochloric, hydrobromic, hydroiodic, hydrofluoric, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I-III include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, TEA, disopropylethylamine and trimethylamine. All of these salts may be prepared by conventional means from the corresponding compound of the invention by reacting, for example, the appropriate acid or base with the compound of Formulas I-III.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Additional examples of such salts can be found in Berge et al., J. Pharm. Sci., 66:1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "pharmaceutically-acceptable derivative" as used herein, denotes a derivative which is pharmaceutically acceptable.

The compound(s) of Formulas I-III may be used to treat a subject by administering the compound(s) as a pharmaceutical composition. To this end, the compound(s) can be combined with one or more excipients, including without limitation, carriers, diluents or adjuvants to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies. Accordingly, this term is not limited to a single dose, but may comprise multiple dosages required to bring about a therapeutic or prophylactic response in the subject. For example, "effective dosage amount" is not limited to a single capsule or tablet, but may include more than one capsule or tablet, which is the dose prescribed by a qualified physician or medical care giver to the subject.

The term "leaving group" (also denoted as "LG") generally refers to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

General Synthetic Procedures

The present invention further comprises procedures for the preparation of compounds of Formulas I-III. The compounds of Formulas I-III can be synthesized according to the procedures described in the following Schemes 1, 2, 3a, 3b, 4 and 5, wherein the substituents are as defined for Formulas I-III above, except where further noted. The synthetic methods described below are merely exemplary, and the compounds of the invention may also be synthesized by alternate routes utilizing alternative synthetic strategies, as appreciated by persons of ordinary skill in the art.

The following list of abbreviations used throughout the specification represent the following and should assist in understanding the invention:
CAN—acetonitrile
Aq., aq.—aqueous
Ar—argon (gas)
Boc—tert-butoxycarbonyl
BOP—benzotriazol-1-yl-oxy Hexafluorophosphate
BuLi—Butyllithium
$Cs_2CO_3$—cesium carbonate
$CHCl_3$—chloroform
$CH_2Cl_2$, DCM—dichloromethane, methylene chloride
Cu(1)I—copper(1) iodide
COMU (1-cyano-2-ethoxy-2-oxoethylidenaminooxy)dimethylaminomorpholinocarbenium hexafluorophosphate
DCC—dicyclohexylcarbodiimide
DEA—diethylamine
DIC—1,3-diisopropylcarbodiimide
DIEA, DIPEA—diisopropylethylamine
DME—dimethoxyethane
DMF—dimethylformamide
DMAP—4-dimethylaminopyridine
DMSO—dimethylsulfoxide
EDC, EDCI—1-(3-dimethylaminopropyl)-3-ethylcarbodiimide $Et_2O$ diethyl ether
EtOAc—ethyl acetate
EtOH—ethanol
g, gm—gram
h, hr—hour
$H_2$—hydrogen (gas)
$H_2O$—water
HATU—O-(7-azabenzotriazol-1-yl)-N,N,N',N'-tetramethyluroniumhexafluorophosphate
HBr—hydrobromic acid
HCl—hydrochloric acid
HMDS—hexamethyldisilazane or bis(trimethylsilyl)amine
HOBt—1-hydroxybenzotriazole hydrate
HOAc—acetic acid
HPLC—high pressure liquid chromatography
IPA, iPrOH—isopropyl alcohol
$K_2CO_3$—potassium carbonate
KI—potassium iodide
LDA—Lithium diisopropylamide
LG—leaving group
LiHMDS—lithium bis(trimethylsilyl)amide
LiOH—lithium hydroxide
$MgSO_4$—magnesium sulfate
MS—mass spectrum
MeOH—methanol
$N_2$—nitrogen (gas)
$NaCNBH_3$—sodium cyanoborohydride
$Na_2CO_3$—sodium carbonate
$NaHCO_3$—sodium bicarbonate
NaH—sodium hydride
NaI—sodium iodide
$NaBH_4$—sodium borohydride
NaOH—sodium hydroxide
$Na_2SO_4$—sodium sulfate
$NH_4Cl$—ammonium chloride
$NH_4OH$—ammonium hydroxide
$P(t-Bu)_3$—tri(tert-butyl)phosphine
$Ph_3P$ or $PPh_3$—triphenylphosphine
Pd/C—palladium on carbon
$Pd(PPh_3)_4$—palladium(0)triphenylphosphine tetrakis
$Pd(dppf)Cl_2$—palladium(1,1-bisdiphenylphosphinoferrocene) II chloride
$Pd(PhCN)_2Cl_2$—palladium di-cyanophenyl dichloride
$Pd(OAc)_2$—palladium acetate
$Pd_2(dba)_3$—tris(dibenzylideneacetone)dipalladium
PyBop—benzotriazol-1-yl-oxy-tripyrrolidino-phosphonium hexafluorophosphate
RT, rt—room temperature
RBF, rbf—round bottom flask
SEM [2-(trimethylsilyl)ethoxy]methyl acetal
SFC—Supercritical fluid chromatography
T3P propylphosphonic anhydride
TBAF Tetrabutylammonium flouride
TBTU—O-benzotriazol-1-yl-N,N,N,N'-tetramethyluronium tetrafluoroborate
TEA, $Et_3N$—triethylamine
TFA—trifluoroacetic acid
THF—tetrahydrofuran
TLC, tlc—thin layer chromatography
TMSCl—trimethylsilyl chloride or chlorotrimethylsilane
UV—ultraviolet light General Synthetic Schemes and Examples The general synthetic schemes, starting materials, synthetic intermediates and compounds (examples) representative of the invention, ie., compounds of Formulas I-III, should assist in a better understanding and appreciation of the scope of the present invention and of the various methods which may be used to synthesize compounds of Formulas I-III. It should be appreciated that the general methods above and specific examples below are illustrative only, for the purpose of assistance and of understanding the present invention, and should not be construed as limiting the scope of the present invention in any manner.

Chromatography:

Unless otherwise indicated, crude product-containing residues were purified by passing the crude material or concentrate through either a Biotage or Isco brand silica gel column (pre-packed or individually packed with $SiO_2$) and eluting the product off the column with a solvent gradient as indicated. For example a description of (330 g $SiO_2$, 0-40% EtOAc/Hexane) means the product was obtained by elution from the column packed with 330 gms of silica, with a solvent gradient of 0% to 40% EtOAc in Hexanes.

Preparative HPLC Method:

Where so indicated, the compounds described herein were purified via reverse phase HPLC using one of the following instruments: Shimadzu, Varian, Gilson; utilizing one of the following two HPLC columns: (a) a Phenomenex Luna or (b) a Gemini column (5 micron or 10 micron, C18, 150×50 mm)

A typical run through the instrument included: eluting at 45 ml/min with a linear gradient of 10% (v/v) to 100% ACN (0.1% v/v TFA) in water (0.1% TFA) over 10 minutes; conditions can be varied to achieve optimal separations.

Proton NMR Spectra:

Unless otherwise indicated, all $^1$H NMR spectra were run on a Bruker series 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method (commonly referred to as an ESI MS) utilizing a PE SCIEX API 150EX MS instrument or an Agilent 1100 series LC/MSD system. Compounds having an isotopic atom, such as bromine and the like, are generally reported according to the detected isotopic pattern, as appreciated by those skilled in the art.

The compounds disclosed and described herein have been named using either (1) the naming convention provided with Chem-Draw Ultra 11.0 software, available in Chem Office, or (2) by the ISIS database software (Advanced Chemistry Design Labs or ACD software).

General Synthetic Scheme 1

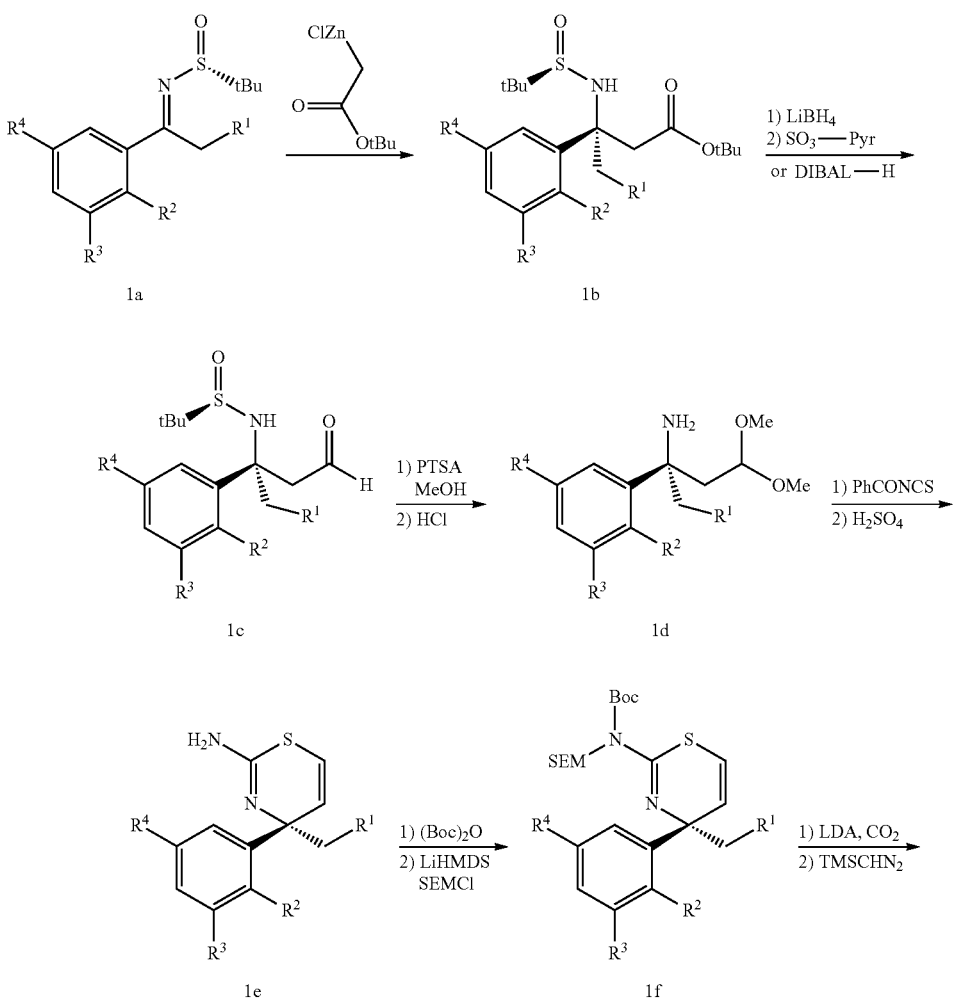

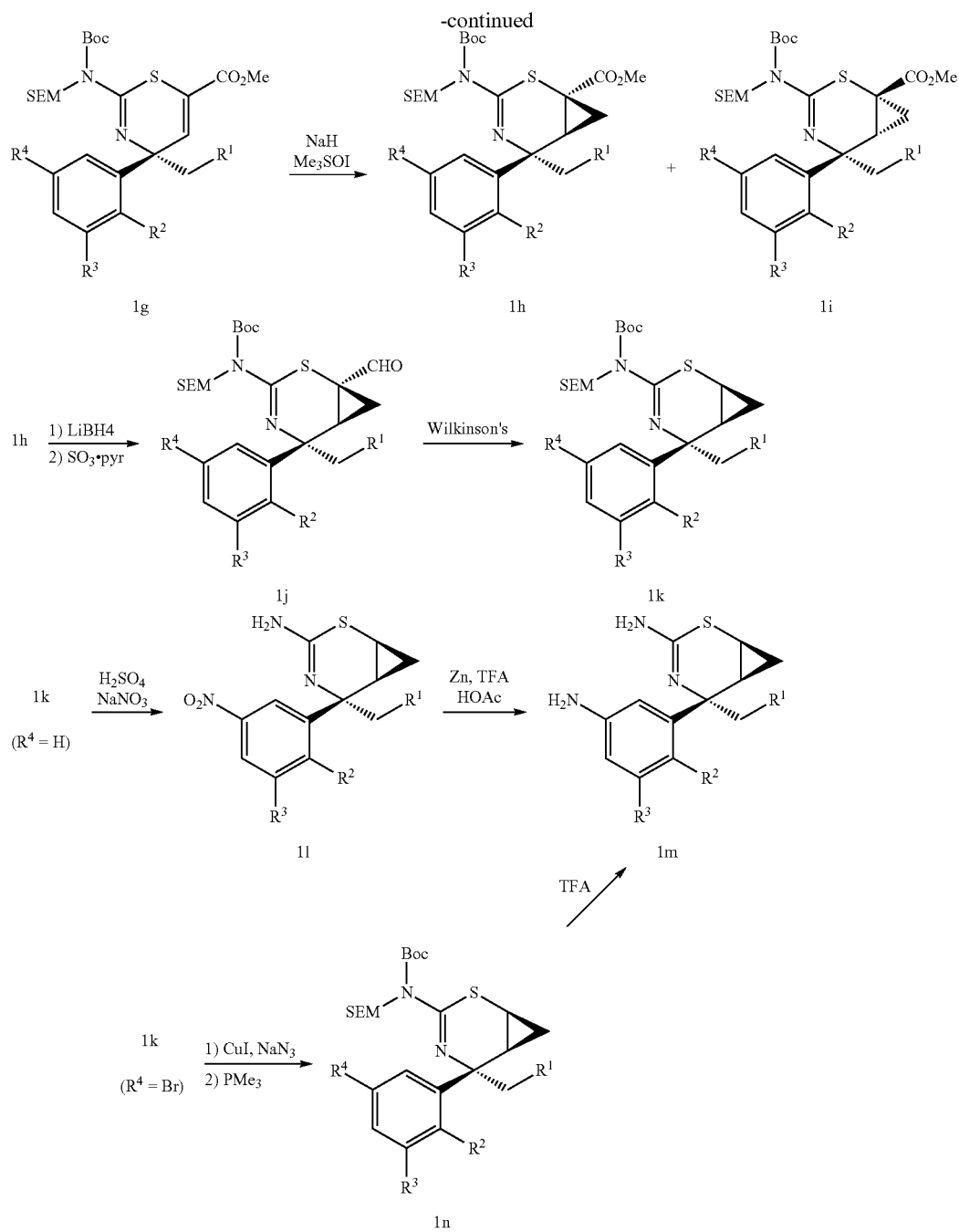

General Synthetic Scheme 1 describes an exemplary method for preparing the key intermediate, aniline 1m. Beginning with Compound 1a, ketimine was converted to the corresponding sulfinamide using (2-(tert-butoxy)-2-oxoethyl)zinc (II) chloride under suitable conditions. The ester of Compound 1b was transformed to aldehyde by either a two-step procedure (treatment with LiBH$_4$ followed by SO$_3$-Pyridine) or reduction using DIBAL-H, to afford intermediate 1c. The chiral auxiliary in 1c was removed with PTSA/MeOH and the aldehyde converted to dimethyl acetal using HCl/MeOH to give 1d. The treatment of 1d with PhCONCS followed by heating in conc. sulfuric acid afforded thiazine 1e. The amino group in 1e was protected with Boc and SEM to give 1f, which was converted to ester 1g via a three-step procedure (lithiation, carboxylic acid formation and esterification). Cyclopropanation of 1g gave a mixture 2 diastereomers, 1h (major product) and 1i (minor product), which could be separated via silica gel chromatography in most cases. Ester 1h was converted to aldehyde 1j (via treatment with LiBH$_4$ followed by SO$_3$-Pyridine), which was treated with chlorotris(triphenylphosphine)rhodium(I) (Wilkinson's) to afford intermediate 1k.

Aniline 1m was derived from 1k (R$^4$=H) via nitration followed by nitro group reduction. In other cases, aniline 1m was obtained from 1k (R$^4$=Br) by a three-step procedure: conversion of bromide to azide, azide reduction with trimethylphosphine followed by removal of protecting groups with TFA.

General Synthetic Scheme 2
General Synthetic Scheme 2 describes exemplary methods for preparing cPr-thiazine that bears a substituent at the C-1 position. Saponification of 1h gave an acid which could be derivatized to cyano (2a) or amide (2b). Reduction of 1h gave alcohol 2c which could be derivatized to $CH_2F$ (2d) or $CHF_2$ (2e) or $CH_2O$-Alkyl (2f).
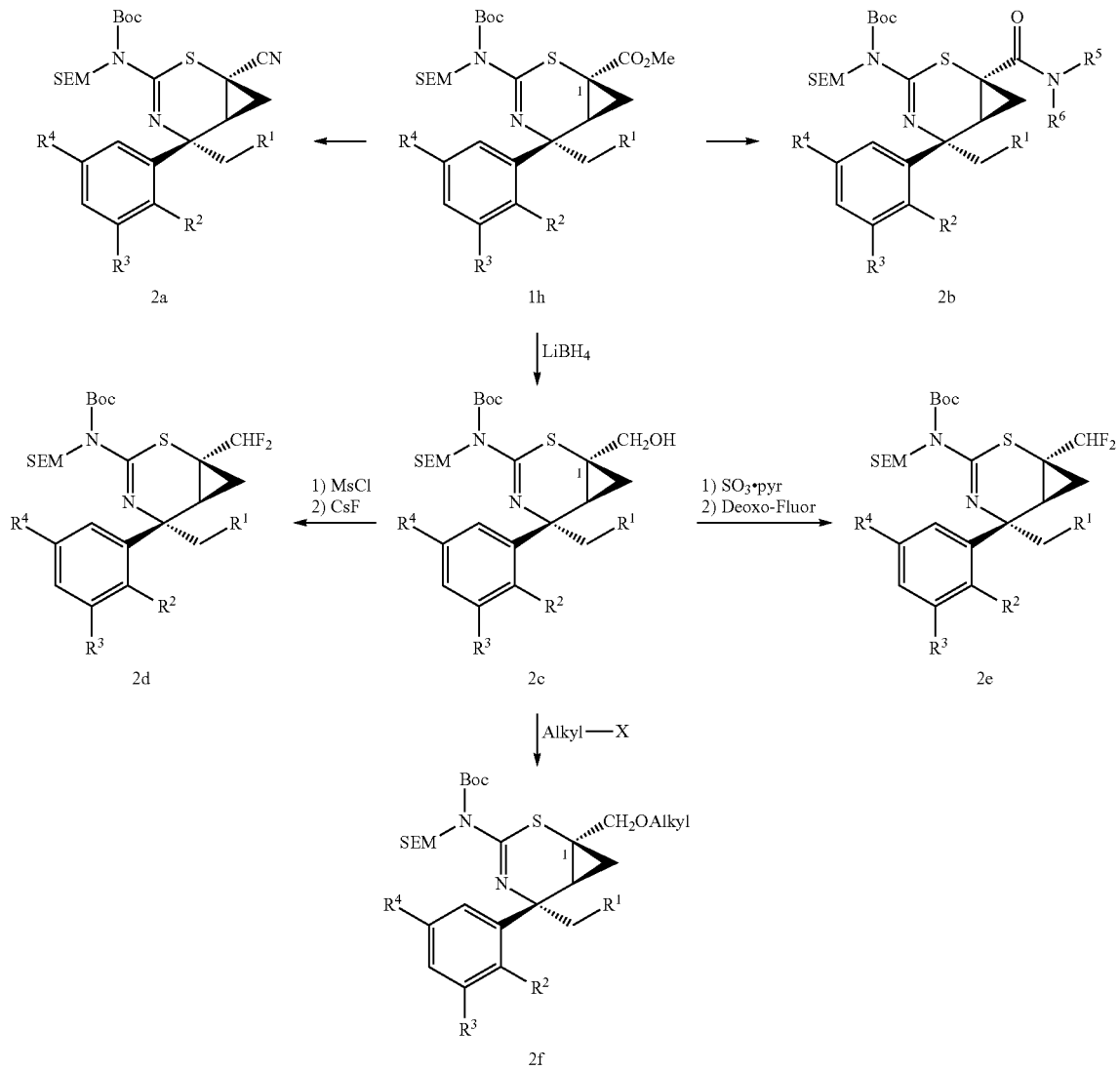
General Synthetic Scheme 3
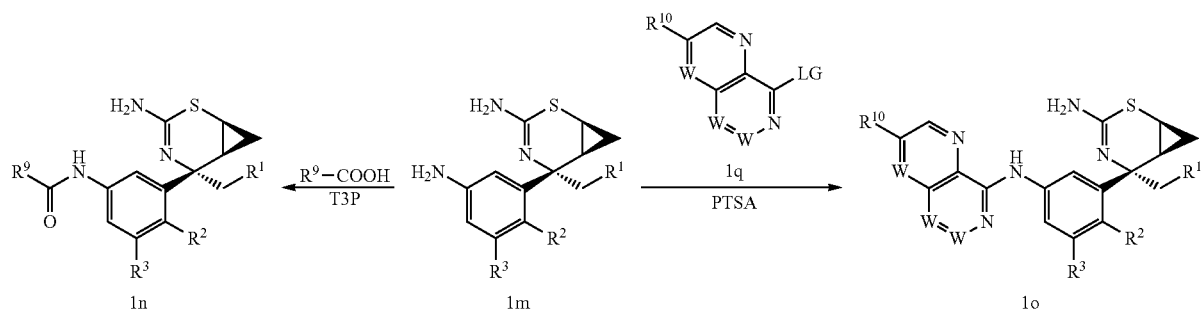

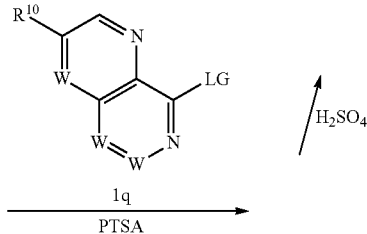
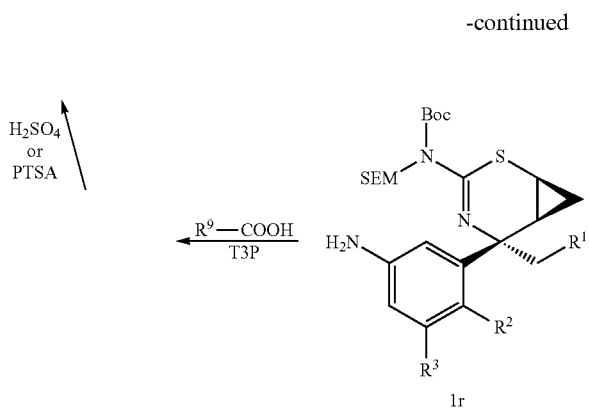

General Synthetic Scheme 3 describes exemplary methods for preparing the biological testing Compounds 1n and 1o. Aniline 1m was coupled with a carboxylic acid in the presence of propylphosphonic anhydride (T3P) to afford amide 1n. Displacement of the leaving group in 1q with aniline 1m in the presence of PTSA gave Compound 1o. If aniline 1r was used instead of aniline 1m, an acid (such as $H_2SO_4$ or PTSA) could be used to remove the protecting groups (Boc and SEM) on the war head N-atom.

Syntheses of Intermediates (R,Z)—N-(1-(2,3-Difluorophenyl)-2-fluoroethylidene)-2-methylpropane-2-sulfinamide (201A)

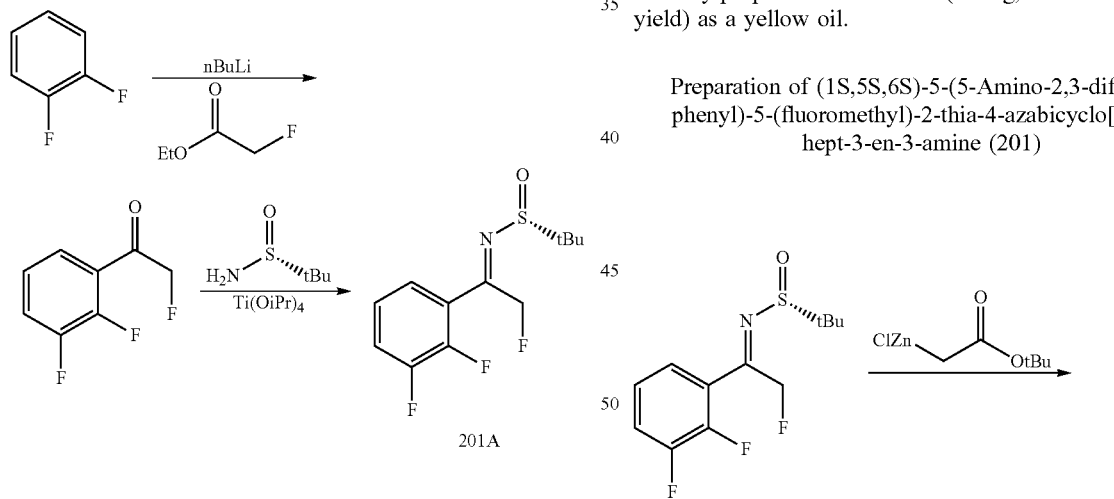

Preparation of 1-(2,3-difluorophenyl)-2-fluoroethanone. [Note: 3×10 g reactions were run separately. After quenched with saturated $NH_4Cl$, the reaction mixture were combined and then purified.] To a solution of 1,2-difluorobenzene (8.81 mL, 89 mmol) in THF (175 mL) at −78° C. was added dropwise n-BuLi (1.60 M in hexane, 61.50 mL, 98 mmol). After 2 h, ethyl fluoroacetate (8.64 mL, 89 mmol) was added dropwise. The reaction was stirred for 1 h at −78° C. and quenched with saturated $NH_4Cl$ and then warmed to RT. The three batches were combined and extracted with EtOAc. The organic extracts were washed with brine, dried over $Na_2SO_4$ and filtered. The filtrate was concentrated and purified by silica gel column (0-30% EtOAc/hexane) to afford 18.90 g of the desired product.

Preparation of Compound 201A. To a solution of 1-(2,3-difluorophenyl)-2-fluoroethanone (18.9 g, 109.0 mmol) in THF (400 mL) was added (R)-(+)-2-methyl-2-propanesulfinamide (26.3 g, 217.0 mmol) followed by tetraisopropoxytitanium (93.0 g, 326.0 mmol). The reaction was heated to reflux for 2 h. LCMS indicated complete consumption of the starting ketone. The mixture was allowed to cool to room temperature and then treated with brine (400 mL). The resulted suspension was stirred for 15 min and filtered through Celite® filter aid. The filter cake was washed with EtOAc. The filtrate was extracted with EtOAc (2×). The organic extracts were washed with brine, dried over $Na_2SO_4$ and filtered. The filtrate was concentrated and purified by silica gel column (0-20% EtOAc/hexanes) to afford (R,E)-N-(1-(2,3-difluorophenyl)-2-fluoroethylidene)-2-methylpropane-2-sulfinamide (12.3 g, 44.4 mmol, 40.9% yield) as a yellow oil.

Preparation of (1S,5S,6S)-5-(5-Amino-2,3-difluorophenyl)-5-(fluoromethyl)-2-thia-4-azabicyclo[4.1.0]hept-3-en-3-amine (201)

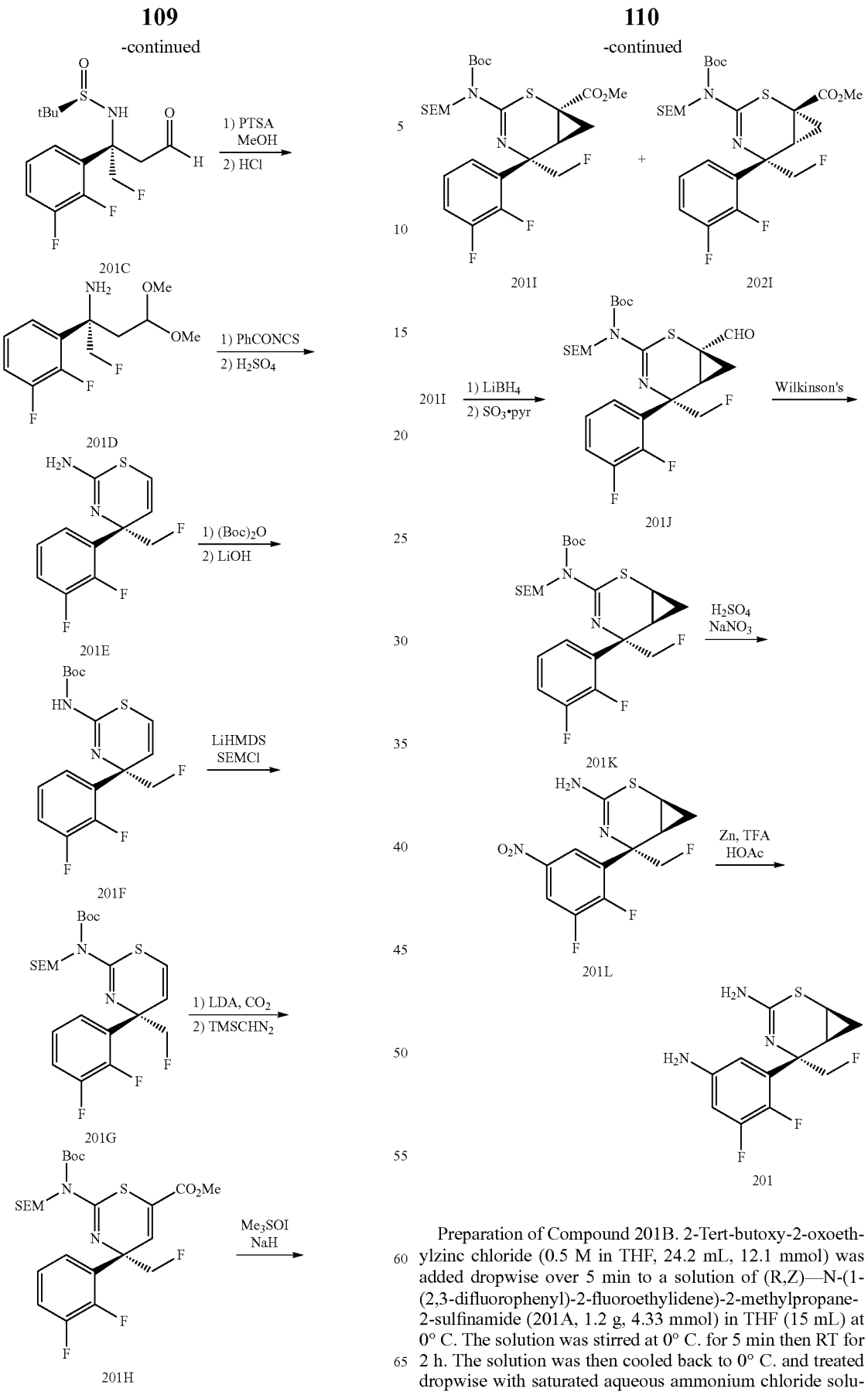

Preparation of Compound 201B. 2-Tert-butoxy-2-oxoethylzinc chloride (0.5 M in THF, 24.2 mL, 12.1 mmol) was added dropwise over 5 min to a solution of (R,Z)—N-(1-(2,3-difluorophenyl)-2-fluoroethylidene)-2-methylpropane-2-sulfinamide (201A, 1.2 g, 4.33 mmol) in THF (15 mL) at 0° C. The solution was stirred at 0° C. for 5 min then RT for 2 h. The solution was then cooled back to 0° C. and treated dropwise with saturated aqueous ammonium chloride solution (7.5 mL), which resulted in a suspension. The suspension was filtered through Celite® filter aid and the filter cake was washed with EtOAc. The filtrate was concentrated in vacuo and the crude product was adsorbed onto a plug of silica gel and purified by silica gel chromatography, eluting with 0-50% EtOAc/hexanes gradient, to provide (S)-tert-butyl 3-(2,3-difluorophenyl)-3-((R)-1,1-dimethylethylsulfinamido)-4-fluorobutanoate (201B, 1.55 g, 3.94 mmol, 91% yield) as an oil. LC/MS (ESI⁻) m/z=394.2 (M+H)⁺. $^1$H NMR (400 MHz, CHLOROFORM-d) δ 7.24-7.31 (m, 1H) 7.08-7.21 (m, 2H) 5.37 (s, 1H) 5.17 (dd, J=47.14, 10.37 Hz, 1H) 4.86 (dd, J=46.56, 10.17 Hz, 1H) 3.20 (dd, J=16.24, 2.15 Hz, 1H) 3.01 (d, J=15.85 Hz, 1H) 1.37-1.41 (m, 9H) 1.25 (s, 9H).

Preparation of Compound 201C. Lithium borohydride (2.0 M solution in THF, 90.0 mL, 180.0 mmol) was added slowly over ~6 min to a stirred solution of (S)-tert-butyl 3-(2,3-difluorophenyl)-3-((R)-1,1-dimethylethylsulfinamido)-4-fluorobutanoate (201B, 35.4 g, 90.0 mmol) in THF (500 mL) in a 500 mL RBF equipped with a thermometer. Anhydrous MeOH (29.2 mL, 720 mmol) was then added over ~4 min via addition funnel. The internal temperature of the reaction rose to 41° C. and bubbling occurred. The reaction mixture was stirred for another 0.5 h, then cooled to 0° C. and quenched with saturated aqueous ammonium chloride solution. The mixture was extracted two times with EtOAc and the combined organic layers were washed with saturated aqueous sodium chloride solution, dried over anhydrous magnesium sulfate, filtered, and concentrated in vacuo to provide (R)—N—((S)-2-(2,3-difluorophenyl)-1-fluoro-4-hydroxybutan-2-yl)-2-methylpropane-2-sulfinamide (201C, 27.8 g, 86 mmol, 96% crude yield) as a white solid that was used without further purification. LC/MS (ESI⁻) m/z=324.0 (M+H)⁺.

N,N-Diisopropylethylamine (16.1 mL, 93 mmol) was added to a stirred solution of (R)—N—((S)-2-(2,3-difluorophenyl)-1-fluoro-4-hydroxybutan-2-yl)-2-methylpropane-2-sulfinamide (10.00 g, 30.9 mmol, crude from reaction above) in DCM (100 mL) and dimethyl sulfoxide (50.0 mL) at −10° C. Sulfur trioxide pyridine complex (7.38 g, 46.4 mmol) was added in 4 portions over 8 min. The reaction mixture was stirred at −10° C. for another 8 min before being warmed to 0° C. and stirred for 3 h. Additional sulfur trioxide pyridine complex (0.74 g, 4.64 mmol) was added, and the reaction mixture was stirred at 0° C. for another 1 h. Additional sulfur trioxide pyridine complex (1.48 g, 9.28 mmol) was added, and the reaction mixture was stirred at 0° C. for another 1 h. Additional sulfur trioxide pyridine complex (2.96 g, 18.6 mmol) was added, and the reaction mixture was stirred at 0° C. for another 1 h. The reaction mixture was diluted with water and extracted with EtOAc. The organic layer was separated, washed with saturated aqueous ammonium chloride, washed with saturated aqueous sodium chloride solution, dried over anhydrous magnesium sulfate, filtered, and concentrated in vacuo. The resulting material was azeotroped with toluene to remove residual pyridine to give (R)—N—((S)-2-(2,3-difluorophenyl)-1-fluoro-4-oxobutan-2-yl)-2-methylpropane-2-sulfinamide as an oil (201C, 11.9 g, 37.0 mmol). LC/MS (ESI⁻) m/z=322.1 (M+H)⁺.

Preparation of Compound 201D. p-Toluenesulfonic acid monohydrate (0.35 g, 1.85 mmol) was added to a stirred solution of the crude (R)—N—((S)-2-(2,3-difluorophenyl)-1-fluoro-4-oxobutan-2-yl)-2-methylpropane-2-sulfinamide (201C, 11.9 g, 37.0) in MeOH (150 mL). The reaction mixture was heated to reflux for 3 h, then cooled to RT. HCl (4.0 M solution in 1,4-dioxane, 9.25 mL, 37.0 mmol) was added. The reaction mixture was stirred RT for 50 min, was partially concentrated in vacuo, and then was quenched with saturated aqueous sodium bicarbonate solution. The mixture was extracted with EtOAc (2×), the combined organic extracts were washed with saturated aqueous sodium chloride solution, dried over anhydrous magnesium sulfate, filtered, and concentrated in vacuo. The resulting oil was purified via silica gel chromatography, eluting with 0-50% EtOAc/heptane gradient, to provide (S)-2-(2,3-difluorophenyl)-1-fluoro-4,4-dimethoxybutan-2-amine (201D, 6.25 g, 23.7 mmol, 64.1% yield for 2 steps) as a brown oil. LC/MS (ESI⁻) m/z=264.0 (M+H)⁺. $^1$H NMR (400 MHz, CHLOROFORM-d) δ 7.36-7.44 (m, 1H) 7.07-7.19 (m, 2H) 4.68 (dd, J=13.11, 8.80 Hz, 1H) 4.56 (ddd, J=13.11, 8.80, 4.11 Hz, 1H) 4.20 (dd, J=7.04, 4.30 Hz, 1H) 3.21 (d, J=4.89 Hz, 6H) 2.25-2.38 (m, 1H) 1.93-2.22 (m, 3H).

Preparation of Compound 201E. To a 1000 mL 3-neck RBF equipped with an internal temperature probe was added (S)-2-(2,3-difluorophenyl)-1-fluoro-4,4-dimethoxybutan-2-amine (201D, 24.7 g, 94.0 mmol) and DCM (300 mL). The mixture was cooled to 0° C. and benzoyl isothiocyanate (13.9 mL, 103 mmol) was added. After stirring at 0° C. for 15 min, the mixture was allowed to warm to RT and stirred for 2 h. The reaction was then concentrated in vacuo to give a brown oil. Sulfuric acid (150 mL) was added in 2 portions and then the mixture was stirred at 60° C. for 6 h. The solution was cooled in an ice bath and then poured into ice (2×2 L Erlenmeyer flasks, each with 700 mL ice in it) and these mixtures were carefully neutralized with aqueous sodium hydroxide solution (10 N) while keeping the mixtures near RT. The resulting solution was extracted with EtOAc, (3×250 mL for each 2 L Erlenmeyer flask) and the combined extracts were washed with water, saturated aqueous sodium chloride solution, dried over anhydrous sodium sulfate, and then adsorbed onto silica gel. Purification by silica gel chromatography, eluting with 5-55% EtOAc/heptane gradient provided (S)-4-(2,3-difluorophenyl)-4-(fluoromethyl)-4H-1,3-thiazin-2-amine (201E, 19.8 g, 76.0 mmol, 82% yield) as a tan solid. LC/MS (ESI⁻) m/z=259.0 (M+H)⁺. $^1$H NMR (400 MHz, DMSO-d₆) δ 7.29-7.39 (m, 1H) 7.14-7.25 (m, 2H) 6.60-6.73 (m, 3H) 6.27 (dd, J=9.59, 5.48 Hz, 1H) 4.35-4.78 (m, 2H).

Preparation of Compound 201F. To a 2000 mL, 3-neck, RBF equipped with an internal temperature probe was added (S)-4-(2,3-difluorophenyl)-4-(fluoromethyl)-4H-1,3-thiazin-2-amine (201E, 19.7 g, 76 mmol) and THF (300 mL). di-tert-Butyl dicarbonate (21.6 g, 99 mmol) was then added in portions, then the mixture was heated at 50° C. for 15 h. Additional di-tert-butyl dicarbonate (3.2 g) was added, and the material was stirred for 2 h at 50° C. The mixture was allowed to cool to RT and then was concentrated in vacuo. Purification by silica gel chromatography, eluting with 0-40% EtOAc/hexane gradient, provided (S)-tert-butyl(4-(2,3-difluorophenyl)-4-(fluoromethyl)-4H-1,3-thiazin-2-yl)carbamate (201F, 26.5 g, 73.8 mmol, 97% yield LC/MS (ESI⁻) m/z=359.3 (M+H)⁺. $^1$H NMR (400 MHz, DMSO-d₆) δ 10.46 (br. s., 1H) 7.18-7.42 (m, 3H) 6.69 (d, J=9.78 Hz, 1H) 6.18 (dd, J=9.00, 4.11 Hz, 1H) 4.47-4.83 (m, 2H) 1.44 (s, 9H).

Preparation of Compound 201G. To a 1000 mL RBF equipped with an internal temperature probe was added (S)-tert-butyl(4-(2,3-difluorophenyl)-4-(fluoromethyl)-4H-1,3-thiazin-2-yl)carbamate (201F, 26.4 g, 73.7 mmol) and THF (220 mL). The mixture was cooled to −10° C. and lithium bis(trimethylsilyl)amide (1.0 M solution in THF, 81.0 mL, 81.0 mmol) was added over 5 min, keeping the internal temperature below −9° C. After the addition was complete, the solution was stirred at −10° C. for 20 min and then 2-(trimethylsilyl)ethoxymethyl chloride (14.3 mL, 81.0 mmol) in 20 mL THF was added slowly, keeping the temperature below −9° C. The solution was stirred for 5 min at −10° C. and then the cooling bath was removed and the solution was allowed to warm to RT. After 2 h, the solution was quenched with saturated aqueous ammonium chloride solution and the resulting mixture was extracted with EtOAc. The organic extracts were washed with saturated aqueous sodium chloride solution, dried over anhydrous sodium sulfate, and adsorbed onto silica. Purification by silica gel chromatography, eluting with 0 to 20% EtOAc/heptane gradient, provided (S)-tert-butyl(4-(2,3-difluorophenyl)-4-(fluoromethyl)-4H-1,3-thiazin-2-yl)((2-(trimethylsilyl)ethoxy)methyl)carbamate (201G, 32.4 g, 66.3 mmol, 90% yield) as a colorless oil. LC/MS (ESI$^-$) m/z=510.9 (M+Na)$^+$. $^1$H NMR (400 MHz, DMSO-$d_6$) δ 7.41 (dd, J=9.88, 2.25 Hz, 1H) 7.16-7.25 (m, 2H) 6.83 (d, J=9.39 Hz, 1H) 6.18 (dd, J=9.39, 4.11 Hz, 1H) 5.19 (s, 2H) 4.59-4.90 (m, 2H) 3.57 (t, J=8.02 Hz, 2H) 1.46 (s, 9H) 0.78-0.90 (m, 2H) −0.04 (s, 9H).

Preparation of Compound 201H. Lithium diisopropylamide (2.0 M solution in THF/heptane/ethylbenzene) (2.58 mL, 5.16 mmol) was added dropwise to a −78° C. solution of (S)-tert-butyl(4-(2,3-difluorophenyl)-4-(fluoromethyl)-4H-1,3-thiazin-2-yl)((2-(trimethylsilyl)ethoxy)methyl)carbamate (201G, 1.94 g, 3.97 mmol) in THF (18 mL). The mixture was stirred for 45 min before $CO_2$ gas was bubbled through the reaction at −78° C. After 3 min, the cold bath was removed, the addition of $CO_2$ was stopped, and the mixture was warmed to RT. The reaction was then quenched with saturated aqueous ammonium chloride solution, and the product was extracted into EtOAc (3×). The combined extracts were washed with aqueous HCl solution (1 M, 2×), saturated aqueous sodium chloride solution (1×), dried over anhydrous magnesium sulfate, filtered, and concentrated in vacuo to give a yellow oil.

The oil was dissolved in (9:1) THF/MeOH (20 mL) and the mixture was cooled to 0° C. (Trimethylsilyl)diazomethane (2.0 M in hexanes, 3.97 mL, 7.94 mmol) was added dropwise. This mixture was stirred for 30 min, at which time HOAc (0.92 mL, 32.9 mmol) was added dropwise. The mixture was stirred at that temperature until the solution became colorless. EtOAc and water were added, the layers were separated, and the aqueous layer was extracted with EtOAc (1×). The combined extracts were washed with saturated aqueous sodium bicarbonate solution, dried over anhydrous magnesium sulfate, filtered, and concentrated in vacuo to give a yellow oil. The oil was purified by silica gel chromatography, eluting with 0 to 50% EtOAc/heptane gradient, to give (S)-methyl 2-((tert-butoxycarbonyl)((2-(trimethylsilyl)ethoxy)methyl)amino)-4-(2,3-difluorophenyl)-4-(fluoromethyl)-4H-1,3-thiazine-6-carboxylate (201H, 1.63 g, 3.0 mmol, 75% yield) as a colorless oil. LC/MS (ESI$^-$) m/z=547.2 (M+H)$^+$. $^1$H NMR (400 MHz, CHLOROFORM-d) δ 7.17-7.17 (m, 1H) 6.98-7.25 (m, 3H) 5.29-5.36 (m, 2H) 4.90 (dd, J=46.95, 8.61 Hz, 1H) 4.68 (dd, J=47.14, 9.00 Hz, 1H) 3.84 (s, 3H) 3.65 (t, J=8.22 Hz, 2H) 1.54 (s, 9H) 0.89-0.96 (m, 2H) −0.01 (s, 9H).

Preparation of Compound 201I and Compound 202I

Preparation of Corey-Chaykovsky Reagent: Potassium tert-butoxide (3.42 g, 30.5 mmol) was added to a stirred suspension of trimethylsulfoxonium iodide (7.32 g, 33.3 mmol) in DMSO (27 mL) under an argon atmosphere at RT. The mixture was stirred for 1 h before being used as described below.

The ylide solution (13.5 mL, 15.3 mmol) was added to a stirred solution of (S)-methyl 2-((tert-butoxycarbonyl)((2-(trimethylsilyl)ethoxy)methyl)amino)-4-(2,3-difluorophenyl)-4-(fluoromethyl)-4H-1,3-thiazine-6-carboxylate (201H, 7.58 g, 13.87 mmol) in dimethyl sulfoxide (27 mL) under an argon atmosphere. The reaction mixture was stirred at RT for 1.5 h. An additional 2.0 mL of the ylide solution was added, and the reaction mixture was stirred for another 2.5 h. The reaction mixture was then quenched with saturated aqueous ammonium chloride solution and then extracted with EtOAc. The organic extracts were washed with water, saturated aqueous sodium chloride, dried over anhydrous magnesium sulfate, filtered, and concentrated in vacuo to give an oil. The oil was purified via silica gel chromatography, eluting with 0 to 20% EtOAc/heptane gradient to provide (1S,5S,6S)-methyl 3-((tert-butoxycarbonyl)((2-(trimethylsilyl) ethoxy)methyl)amino)-5-(2,3-difluorophenyl)-5-(fluoromethyl)-2-thia-4-azabicyclo[4.1.0]hept-3-ene-1-carboxylate (201I, 5.60 g, 10.0 mmol, 72% yield) and (1R,5S,6R)-methyl 3-((tert-butoxycarbonyl)((2-(trimethylsilyl)ethoxy)methyl)amino)-5-(2,3-difluorophenyl)-5-(fluoromethyl)-2-thia-4-azabicyclo[4.1.0]hept-3-ene-1-carboxylate (202I, 0.95 g, 1.70 mmol, 12% yield).

201I: LC/MS (ESI$^-$) m/z=561.2 (M+H)$^+$. $^1$H NMR (400 MHz, CHLOROFORM-d) δ 7.46 (t, J=7.14 Hz, 1H) 7.08-7.20 (m, 2H) 5.31 (d, J=10.37 Hz, 1H) 5.08 (d, J=10.56 Hz, 1H) 4.72-5.02 (m, 2H) 3.81 (s, 3H) 3.65 (t, J=8.22 Hz, 2H) 2.68 (t, J=8.80 Hz, 1H) 1.62 (dd, J=9.98, 5.28 Hz, 1H) 1.51-1.56 (m, 9H) 1.14 (dd, J=7.24, 5.48 Hz, 1H) 0.87-0.99 (m, 2H) 0.01 (s, 9H).

202I: LC/MS (ESI$^-$) m/z=561.2 (M+H)$^+$. $^1$H NMR (400 MHz, CHLOROFORM-d) δ 7.02-7.18 (m, 3H) 5.24 (d, J=10.37 Hz, 1H) 5.07 (d, J=10.37 Hz, 1H) 4.92 (dd, J=46.95, 8.61 Hz, 1H) 4.71 (dd, J=46.95, 8.80 Hz, 1H) 3.80 (s, 3H) 3.58 (dd, J=9.00, 7.43 Hz, 2H) 2.85 (dd, J=9.88, 7.34 Hz, 1H) 1.73 (dd, J=9.78, 5.48 Hz, 1H) 1.59-1.64 (m, 1H) 1.51 (s, 9H) 0.89 (dd, J=9.10, 7.34 Hz, 2H) −0.01-0.02 (m, 9H).

Preparation of Compound 201J. Lithium borohydride (2.0 M solution in THF, 9.9 mL, 19.8 mmol) was added slowly over ~3 min to a stirred solution of (1S,5S,6S)-methyl 3-((tert-butoxycarbonyl)((2-(trimethylsilyl)ethoxy)methyl) amino)-5-(2,3-difluorophenyl)-5-(fluoromethyl)-2-thia-4-azabicyclo[4.1.0]hept-3-ene-1-carboxylate (201I, 5.54 g, 9.9 mmol) in THF (60 mL) at RT under a nitrogen atmosphere. Anhydrous MeOH (3.20 mL, 79 mmol) was then added over ~1 min. The reaction mixture was stirred for 30 min, cooled to 0° C., and then saturated aqueous sodium chloride. The mixture was extracted with EtOAc (2×), then the combined extracts were washed with aqueous HCl solution (1 N), washed with saturated aqueous sodium bicarbonate solution, saturated aqueous sodium chloride solution, dried over anhydrous magnesium sulfate, filtered, and concentrated in vacuo to provide tert-butyl((1S,5S,6S)-5-(2,3-difluorophenyl)-5-(fluoromethyl)-1-(hydroxymethyl)-2-thia-4-azabicyclo[4.1.0]hept-3-en-3-yl)((2-(trimethylsilyl)ethoxy)methyl)carbamate (5.93 g) as a colorless oil.

TEA (5.50 mL, 39.5 mmol) was added slowly via syringe to a stirred solution of tert-butyl((1S,5S,6S)-5-(2,3-difluorophenyl)-5-(fluoromethyl)-1-(hydroxymethyl)-2-thia-4-azabicyclo[4.1.0]hept-3-en-3-yl)((2-(trimethylsilyl)ethoxy)methyl)carbamate (5.93 g, obtained from above reaction) in DCM (20 mL) and dimethyl sulfoxide (20 mL). Sulfur trioxide pyridine complex (3.15 g, 19.8 mmol) was added, and the reaction mixture was stirred at RT for 1 h. The reaction mixture was diluted with water and extracted with EtOAc. The organic extracts were combined and then washed with saturated aqueous ammonium chloride solution, water, saturated sodium chloride solution, then dried over anhydrous magnesium sulfate, filtered, and concentrated in vacuo to give an oil. The resulting crude product was purified via silica gel chromatography, eluting with 0 to 30% EtOAc/heptane gradient to provide tert-butyl((1S,5S,6S)-5-(2,3-difluorophenyl)-5-(fluoromethyl)-1-formyl-2-thia-4-azabicyclo[4.1.0]hept-3-en-3-yl)((2-(trimethylsilyl)ethoxy)methyl)carbamate (201J, 4.88 g, 9.2 mmol, 93% yield for 2 steps) LC/MS (ESI$^-$) m/z=531.2 (M+H)$^+$. $^1$H NMR (400 MHz, CHLOROFORM-d) δ 9.16 (s, 1H) 7.40-7.45 (m, 1H) 7.08-7.21 (m, 2H) 5.34 (d, J=10.37 Hz, 1H) 5.14 (d, J=10.56 Hz, 1H) 4.92 (dd, J=46.75, 8.61 Hz, 1H) 4.72 (dd, J=46.75, 8.61 Hz, 1H) 3.66 (t, J=8.31 Hz, 2H) 2.57 (t, J=8.71 Hz, 1H) 1.81 (dd, J=9.98, 5.67 Hz, 1H) 1.52-1.57 (m, 9H) 1.27 (dd, J=7.43, 5.67 Hz, 1H) 0.83-1.05 (m, 2H) −0.01-0.03 (m, 9H).

Preparation of Compound 201K. Chlorotris(triphenylphosphine)rhodium(I) (4.26 g, 4.61 mmol) was added to a stirred solution of tert-butyl((1S,5S,6S)-5-(2,3-difluorophenyl)-5-(fluoromethyl)-1-formyl-2-thia-4-azabicyclo[4.1.0]hept-3-en-3-yl)((2-(trimethylsilyl)ethoxy)methyl)carbamate (201J, 1.63 g, 3.07 mmol) in 1,2-dichloroethane (20 mL). The reaction mixture was heated to 80° C. and stirred for 6 h. The reaction mixture was concentrated in vacuo and the resulting reddish-brown sludge was triturated in heptane and then filtered through Celite® filter aid. The filter cake was washed multiple times with 9:1 EtOAc/heptane, then with DCM. The filtrate was concentrated in vacuo, slurried in DCM, and filtered. The yellow solid that was collected was discarded, and the filtrate was again concentrated in vacuo to give a brown oil. Heptane was added, the resulting suspension was filtered, and the collected solid was discarded. The filtrate was concentrated to give crude product, which was purified via silica gel chromatography, eluting with 0 to 20% EtOAc/heptane gradient to give tert-butyl ((1S,5S,6S)-5-(2,3-difluorophenyl)-5-(fluoromethyl)-2-thia-4-azabicyclo[4.1.0]hept-3-en-3-yl)((2-(trimethylsilyl)ethoxy)methyl)carbamate (201K, 1.54 g, 1.99 mmol, 65% yield) as a colorless oil. LC/MS (ESI$^-$) m/z=503.1 (M+H)$^+$. $^1$H NMR (400 MHz, CHLOROFORM-d) δ 7.43 (t, J=7.24 Hz, 1H) 7.06-7.17 (m, 2H) 5.30 (d, J=10.56 Hz, 1H) 5.07 (d, J=10.56 Hz, 1H) 4.73-5.02 (m, 2H) 3.62-3.69 (m, 2H) 2.24-2.31 (m, 1H) 2.00-2.07 (m, 1H) 1.53 (s, 9H) 1.05 (ddd, J=9.15, 7.48, 5.87 Hz, 1H) 0.94 (dd, J=9.10, 7.53 Hz, 2H) 0.65 (q, J=5.87 Hz, 1H) −0.02-0.03 (m, 9H).

Preparation of Compound 201L. At RT, concentrated sulfuric acid (5 mL, 94 mmol) was added to tert-butyl((1S,5S,6S)-5-(2,3-difluorophenyl)-5-(fluoromethyl)-2-thia-4-azabicyclo[4.1.0]hept-3-en-3-yl)((2-(trimethylsilyl)ethoxy)methyl)carbamate (201K, 1.00 g, 1.99 mmol). The mixture was stirred at RT for 15 min, then cooled to 0° C. Sodium nitrate (0.24 g, 2.79 mmol) was added. The reaction mixture was warmed to RT and stirred for 1 h. The reaction mixture was poured into ice and diluted with DCM. K$_3$PO$_4$ (20 g) was added in portions over 15 min, and the mixture was then brought to pH 7-8 with aqueous NaOH solution (10 N). The resulting biphasic mixture was separated, and the aqueous layer was extracted DCM (2×). The combined organic extracts were dried over anhydrous magnesium sulfate, filtered, and concentrated in vacuo to give an oil. This oil was purified via silica gel chromatography, eluting with 0 to 50% EtOAc/heptane gradient to provide (1S,5S,6S)-5-(2,3-difluoro-5-nitrophenyl)-5-(fluoromethyl)-2-thia-4-azabicyclo[4.1.0]hept-3-en-3-amine (201L, 0.54 g, 1.67 mmol, 85% yield) as a light yellow solid. LC/MS (ESI$^-$) m/z=318.0 (M+H)$^+$. $^1$H NMR (400 MHz, CHLOROFORM-d) δ 8.51-8.56 (m, 1H) 8.05 (ddd, J=9.05, 6.41, 2.93 Hz, 1H) 4.73 (d, J=4.11 Hz, 4H) 2.25-2.36 (m, 1H) 1.92-2.06 (m, 1H) 1.07-1.18 (m, 1H) 0.66 (q, J=5.74 Hz, 1H).

Preparation of Compound 201. Zinc (nanopowder, 1.73 g, 26.5 mmol) was added to a stirred mixture of (1S,5S,6S)-5-(2,3-difluoro-5-nitrophenyl)-5-(fluoromethyl)-2-thia-4-azabicyclo[4.1.0]hept-3-en-3-amine (201L, 1.68 g, 5.29 mmol) in HOAc (12 mL) and trifluroacetic acid (6 mL). The reaction mixture was stirred at RT for 45 min, then filtered through Celite® filter aid. The filtrate was diluted with EtOAc and treated with saturate sodium bicarbonate solution, and then the mixture was taken to pH~7 w/aqueous sodium NaOH (10 N). The organic layer was separated, and the aqueous layer was extracted once more with EtOAc. The combined organic extracts were washed with saturated sodium chloride solution, dried over anhydrous magnesium sulfate, filtered, and concentrated in vacuo. The resulting crude product was purified via silica gel chromatography, eluting with 0 to 10% MeOH/DCM gradient. The collected product was then dissolved in EtOAc and then washed two times with saturated sodium carbonate solution. The resulting organic solution was then washed with saturated sodium chloride solution, dried over anhydrous magnesium sulfate, filtered, and concentrated in vacuo to provide (1S,5S,6S)-5-(5-amino-2,3-difluorophenyl)-5-(fluoromethyl)-2-thia-4-azabicyclo[4.1.0]hept-3-en-3-amine (201, 1.29 g, 4.49 mmol, 85% yield) as a yellow solid. LC/MS (ESI$^-$) m/z=288.0 (M+H)$^+$. $^1$H NMR (400 MHz, CHLOROFORM-d) δ ppm 6.66 (dt, J=4.84, 2.57 Hz, 1H) 6.38-6.45 (m, 1H) 4.78 (s, 4H) 3.61 (br. s., 2H) 2.26-2.34 (m, 1H) 1.78-1.89 (m, 1H) 1.05-1.14 (m, 1H) 0.53 (d, J=5.87 Hz, 1H).

(1R,5S,6R)-5-(5-Amino-2,3-difluorophenyl)-5-(fluoromethyl)-2-thia-4-azabicyclo[4.1.0]hept-3-en-3-amine (202)

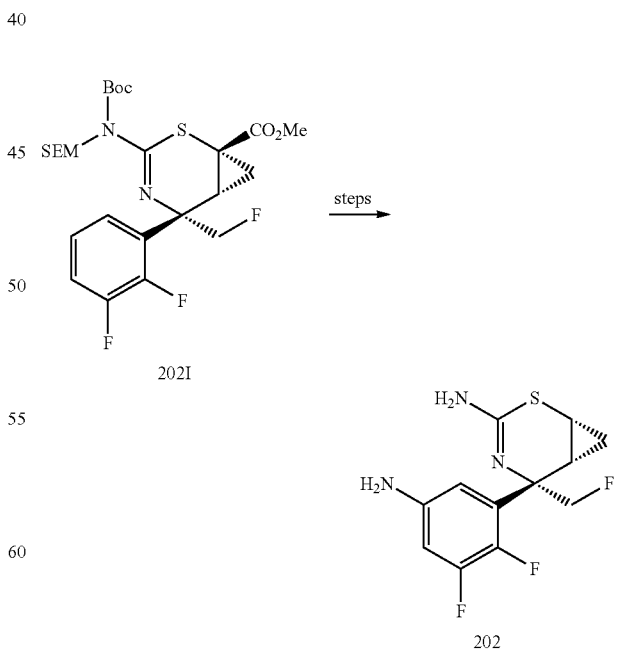

This compound was prepared from 202I using the chemical procedures similar to that described for intermediate 201.

LC/MS (ESI⁻) m/z=288.0 (M+H)⁺. ¹H NMR (400 MHz, CHLOROFORM-d) δ ppm 6.38-6.49 (m, 2H) 4.68-4.76 (m, 1H) 4.50-4.66 (m, 1H) 3.65 (br. s., 2H) 2.05-2.18 (m, 1H) 1.94-2.05 (m, 1H) 1.02-1.11 (m, 2H).

(R,E)-N-(1-(2,3-Difluorophenyl)ethylidene)-2-methylpropane-2-sulfinamide (203A)

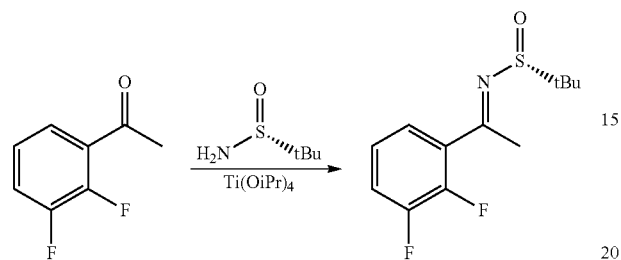

To a solution of 2,3-difluoroacetophenone (25.0 g, 160 mmol) in THF (500 mL) was added (R)-(+)-2-methyl-2-propanesulfinamide (38.8 g, 320 mmol) followed by tetraisopropoxytitanium (142 mL, 480 mmol). The reaction was heated to reflux for 3 d. The mixture was allowed to cool to RT and then treated with brine (550 mL). The resulted suspension was stirred for 15 min and filtered through a pad of Celite® filter aid. The filter cake was washed with EtOAc. The filtrate was extracted with EtOAc (2×). The organic extracts were washed with brine, dried over Na₂SO₄ and filtered. The filtrate was concentrated and purified by silica gel column (10-35% EtOAc/hexanes) to afford (R,E)-N-(1-(2,3-difluorophenyl)ethylidene)-2-methylpropane-2-sulfinamide (203A, 35.6 g, 137 mmol, 86% yield) as yellow oil. MS m/z=260.1 [M+H]⁺.

(1S,5S,6S)-5-(5-Amino-2,3-difluorophenyl)-5-methyl-2-thia-4-azabicyclo[4.1.0]hept-3-en-3-amine (203)

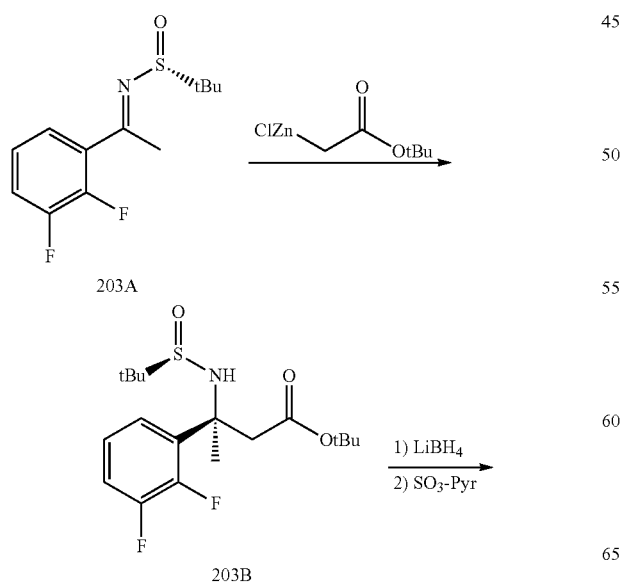

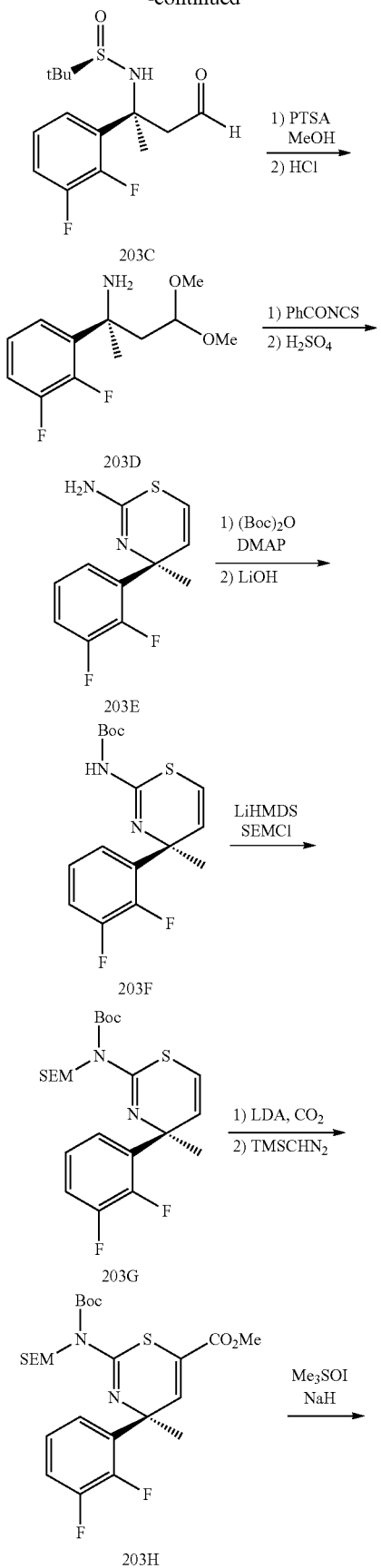

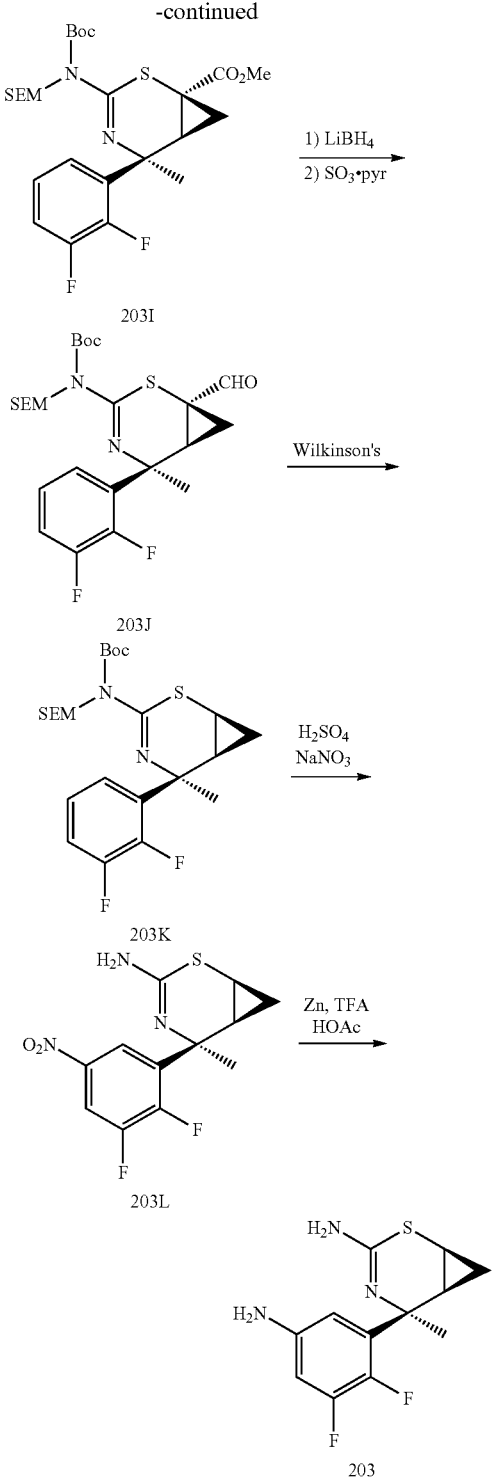

Preparation of Compound 203B. To a 3000 mL 3-neck RBF equipped with an addition funnel and internal temperature probe was added (R,E)-N-(1-(2,3-difluorophenyl)ethylidene)-2-methylpropane-2-sulfinamide (203A, 30 g, 116 mmol) and THF (450 mL). The mixture was cooled to 0° C. and 2-tert-butoxy-2-oxoethylzinc chloride (0.5 M in Et$_2$O, 463 mL, 231 mmol) was added dropwise over 2 h keeping the internal temperature under 2° C. The reaction mixture stayed homogeneous. After the addition was completed, the ice bath was allowed to melt (about 2-3 h) and warm to RT overnight. The reaction mixture was cooled with an ice bath and carefully quenched with the slow addition sat. NH$_4$Cl (200 mL). It was extracted with EtOAc (3×250 mL). The combined extracts were washed with brine (50 mL), dried (Na$_2$SO$_4$) and concentrated onto silica. Purification by silica gel chromatography (5-35% EtOAc/hexanes) afforded (S)-tert-butyl 3-(2,3-difluorophenyl)-3-((R)-1,1-dimethylethylsulfinamido)butanoate (203B, 30.2 g, 80 mmol, 69.5% yield) as a colorless oil. LC/MS (ESI⁻) m/z=376.1 (M+H)⁺.

Preparation of Compound 203C. To a solution of (S)-tert-butyl 3-(2,3-difluorophenyl)-3-((R)-1,1-dimethylethylsulfinamido)butanoate (203B, 11.6 g, 31.0 mmol) in 150 mL, of THF in a 500 mL 3-neck RBF equipped with an internal temperature probe at RT was added lithium borohydride (2.0 M solution in THF, 31.0 mL, 62.0 mmol) over 5 min. Anhydrous MeOH (10.0 mL, 248 mmol) was then added to the mixture slowly over 5 min. The internal temperature of the reaction rose to 37° C., and gentle bubbling ensued. The mixture was stirred for 60 min. The reaction was chilled to 0° C. and slowly quenched with 80 mL of aq. NH$_4$Cl. The mixture was then extracted with 3×150 mL of EtOAc. The combined organic extracts were dried over MgSO$_4$, filtered, and concentrated in vacuo to give (R)—N—((S)-2-(2,3-difluorophenyl)-4-hydroxybutan-2-yl)-2-methylpropane-2-sulfinamide (9.7 g) as an off-white amorphous solid which was used without further purification. LC/MS (ESI⁻) m/z=306.2 (M+H)⁺. N,N-diisopropylethylamine (21.6 mL, 124 mmol) was added dropwise via a syringe to a solution of (R)—N—((S)-2-(2,3-difluorophenyl)-4-hydroxybutan-2-yl)-2-methylpropane-2-sulfinamide (9.7 g crude from above reaction) in DCM (60 mL) and DMSO (30 mL) in 1000 mL RBF at −10° C. Pyridine sulfur trioxide (7.9 g, 49.6 mmol) was added in three portions over 1 min. The mixture was stirred for 5 min, and then the cooling bath was replaced with an ice bath. The mixture was stirred for 5 h at ~0° C. It was treated with water (50 mL) and extracted with 3×200 mL of DCM. The combined organic extracts were washed with saturated aqueous NH$_4$Cl (50 mL) followed by brine (25 mL), and dried over sodium sulfate. The solution was filtered and concentrated in vacuo to give the crude material. It was adsorbed onto a plug of silica gel and chromatographed through a Redi-Sep pre-packed silica gel column (220 g), eluting with a gradient of 1-5% MeOH in DCM, to provide (R)—N—((S)-2-(2,3-difluorophenyl)-4-oxobutan-2-yl)-2-methylpropane-2-sulfinamide (203C, 9.6 g, 31.6 mmol, 102% yield) as an amorphous solid. LC/MS (ESI⁻) m/z=304.1 (M+H)⁺.

Preparation of Compound 203D. To a 1000 mL RBF equipped with a reflux condenser was added (R)—N—((S)-2-(2,3-difluorophenyl)-4-oxobutan-2-yl)-2-methylpropane-2-sulfinamide (203C, 9.40 g, 31 mmol), MeOH (80 mL) and p-toluenesulfonic acid monohydrate (0.295 g, 1.550 mmol). The reaction mixture was stirred at 65° C. for 18 h. It was cooled to RT and treated with HCl (4.0 M solution in 1,4-dioxane, 8.14 mL, 32.6 mmol) dropwise. After the reaction mixture was stirred at RT for 3 h, it was concentrated in-vacuo, then diluted with 300 mL of chloroform and treated with 50 mL of sat. aq. NaHCO$_3$. The layers were separated and the aqueous layer was extracted with chloroform (2×100 mL). The combined organic extracts were washed with 10 mL of brine, dried over magnesium sulfate, filtered and concentrated in-vacuo to give light yellow oil. It was purified by silica gel chromatography (2×110 g Thomson column using a gradient of 1-8% MeOH in CH$_2$Cl$_2$) to provide (S)-2-(2,3-difluorophenyl)-4,4-dimethoxybutan-2-amine (203D, 6.05 g, 24.67 mmol, 80% yield) as a yellow oil. LC/MS (ESI⁻) m/z=246.2 (M+H)⁺. ¹H NMR (400 MHz, CHLOROFORM-d) δ 7.30 (m, 1H), 7.07 (m, 2H), 4.10 (m, 1H), 3.21 (s, 3H), 3.18 (s, 3H), 2.25-2.44 (m, 1H), 2.08 (m, 1H), 1.93 (br., 2H), 1.54 (s, 3H). $^{19}$F NMR (376 MHz, CHLOROFORM-d) δ −137.63 (d, J=20.16 Hz, 1F), −139.03 (d, J=19.51 Hz, 1F).

Preparation of Compound 203E. To a stirring solution of (S)-2-(2,3-difluorophenyl)-4,4-dimethoxybutan-2-amine (203D, 6.08 g, 24.79 mmol) in $CH_2Cl_2$ (50 mL) at 0° C. under nitrogen was added a solution of benzoyl isothiocyanate (4.45 g, 27.3 mmol) in $CH_2Cl_2$ (12 mL) dropwise. It was stirred at 0° C. for 20 min, and then treated with MeOH (1 mL). The solvents were removed under reduced pressure to afford a tan syrup. To the tan syrup at 0° C. was added neat sulfuric acid (29.1 ml, 545 mmol). The warmed solution was stirred for 20 min then heated to 50° C. for 22 h. The reaction was cooled to RT then poured onto 200 g of ice. To the slurry was added $CH_2Cl_2$ (200 mL), the biphasic solutions were chilled to 0° C. with external wet ice bath, then basified to pH=14 with very slow addition of 10 M NaOH. The organic layer was separated and the aqueous was extracted with 9:1 $CHCl_3$/IPA (2×50 mL). The combined organics were dried over $MgSO_4$, filtered, and concentrated under reduced pressure. The residue was purified by silica gel chromatography (160 g) using a gradient of 20-75% EtOAc in hexanes to afford (S)-4-(2,3-difluorophenyl)-4-methyl-4H-1,3-thiazin-2-amine (203E, 3.24 g, 13.48 mmol, 54% yield) as a brown amorphous solid. LC/MS (ESI$^-$) m/z=241.1 (M+H)$^+$. $^1$H NMR (400 MHz, CHLOROFORM-d) δ 7.19 (t, J=7.24 Hz, 1H), 6.98-7.09 (m, 2H), 6.26-6.32 (m, 2H), 5.00-4.00 (br., 2H), 1.74 (s, 3H). $^{19}$F NMR (377 MHz, CHLOROFORM-d) δ −138.00 (d, J=20.27 Hz, 1F), −138.75 (d, J=20.27 Hz, 1F).

Preparation of Compound 203F. A solution of (S)-4-(2,3-difluorophenyl)-4-methyl-4H-1,3-thiazin-2-amine (203E, 3.06 g, 12.74 mmol) and 4-(dimethylamino)pyridine (0.039 g, 0.318 mmol) in THF (50 mL) at RT was treated with di-tert-butyl dicarbonate (6.11 g, 28.0 mmol) in THF (10 mL) slowly via a syringe. The solution was heated to 50° C. in an oil bath for 1 h. The LCMS suggested full conversion to the di-Boc. The reaction mixture was cooled to 12° C. and treated with water (10 mL), lithium hydroxide monohydrate (1.603 g, 38.2 mmol), and MeOH (10 mL). The reaction was heated to 50° C. for 30 min. The LCMS suggested 100% conversion to the mono-Boc. The reaction was then partitioned between EtOAc (150 mL) and water (20 mL). Some white solid precipitated from the mixture. It was filtered through a fritted funnel. The solid was discarded (LCMS indicated no desired product). The filtrate was transferred to a separatory funnel. The aqueous was discarded. The organic layer was washed with 5 mL of brine, dried over sodium sulfate and concentrated. The residue was purified on a silica gel column (15-45% EtOAc in hexanes) to give (S)-tert-butyl(4-(2,3-difluorophenyl)-4-methyl-4H-1,3-thiazin-2-yl)carbamate (203F, 4.28 g, 12.57 mmol, 99% yield) as a viscous brown oil. LC/MS (ESI$^-$) m/z=341.1 (M+H)$^+$. $^1$H NMR (400 MHz, CHLOROFORM-d) δ 10.5 (br., 1H), 7.01-7.16 (m, 3H), 6.14-6.29 (m, 2H), 1.79 (br., 3H), 1.52 (s, 9H).

Preparation of Compound 203G. To a stirring solution of (S)-tert-butyl(4-(2,3-difluorophenyl)-4-methyl-4H-1,3-thiazin-2-yl)carbamate (203F, 4.20 g, 12.34 mmol) in THF (50 mL) at −12° C. (wet ice/acetone) under nitrogen was added lithium bis(trimethylsilyl)amide (1.0 M solution in THF, 16.04 mL, 16.04 mmol) at a rate not to exceed an internal temp of −5° C. After 15 min at −7° C., to the reaction mixture was added a solution of 2-(trimethylsilyl)ethoxymethyl chloride (2.84 mL, 16.04 mmol) in THF (10 mL) at a rate that did not exceed an internal temp of −2° C. After 15 min the cooling bath was removed and the reaction mixture became a clear solution. The reaction was run for 18 h at RT. The reaction was quenched with sat $NH_4Cl$ (20 mL) and extracted with EtOAc (2×100 mL). The organic solution was washed with brine (10 mL), dried over $MgSO_4$, concentrated under reduced pressure. The residue was purified by silica gel chromatography (5% EtOAc/Hextanes) to afford (S)-tert-butyl(4-(2,3-difluorophenyl)-4-methyl-4H-1,3-thiazin-2-yl)((2-(trimethylsilyl)ethoxy)methyl)carbamate (203G, 5.3 g, 11.26 mmol, 91% yield) as viscous yellow oil. LC/MS (ESI$^-$) m/z=471.1 (M+H)$^+$. $^1$H NMR (400 MHz, CHLOROFORM-d) δ 7.23 (m, 1H), 7.08 (m, 2H), 6.33 (d, J=9.19 Hz, 1H), 6.08 (dd, J=3.42, 9.29 Hz, 1H), 5.32 (d, J=10.37 Hz, 1H), 5.23 (d, J=10.56 Hz, 1H), 3.67 (m, 2H), 1.73 (s, 3H), 1.54 (s, 9H), 0.94 (m, 2H), 0.00 (s, 9H). $^{19}$F NMR (377 MHz, CHLOROFORM-d) δ −138.14 (d, J=20.27 Hz, 1F), −138.73 (d, J=20.27 Hz, 1F).

Preparation of Compound 203H. To a stirring solution of (S)-tert-butyl(4-(2,3-difluorophenyl)-4-methyl-4H-1,3-thiazin-2-yl)((2-(trimethylsilyl)ethoxy)methyl) carbamate (203G, 10.6 g, 22.5 mmol) in THF (100 mL) at −70° C. was added lithium diisopropylamide (2.0 M in heptane/THF/ethylbenzene, 13.51 mL, 27.0 mmol) at a rate that did not exceed −68° C. The dark solution was stirred for 20 min at −72° C. The reaction was then exposed to a gentle stream of carbon dioxide from a lecture bottle in the head space of the stirring solution (not submerged). The internal temp slowly climbed to −60° C. After 7 min the carbon dioxide stream was removed and internal temp was −65° C. The reaction was then slowly quenched with sat. $NH_4Cl$ (10 mL). Once the suspension reached 5° C., 1 M $KH_2PO_4$ (100 mL) was added. After the bubbling subsided, the reaction was partitioned between EtOAc (400 mL) and 1 M $KH_2PO_4$ (100 mL). The organic layer was separated, washed with brine (2×100 mL), dried over $MgSO_4$, filtered and concentrated under reduced pressure to afford the acid as colorless oil. The oil was dissolved in THF (100 mL) and MeOH (10 mL), chilled to 16° C. under nitrogen and (trimethylsilyl)diazomethane (2 M in hexanes, 28.2 mL, 56.3 mmol) added at a rate not to exceed 22° C. The reaction was stirred for 30 min then quenched with glacial HOAc (10 mL) with reaction at 6° C. The quench is exothermic with temp surging to 19° C. and gas evolution evident. The reaction was then partitioned between 1:1 EtOAc/heptane (500 mL) and 1 M $KH_2PO_4$ (100 mL). The organic layer was further washed with both 5% $NaHCO_3$ (100 mL) and brine (50 mL). The organic layer was dried over $MgSO_4$, filtered and concentrated under reduced pressure. The residue was purified by silica gel chromatography (330 g) eluting with a gradient of 0-10% EtOAc/heptane to afford (S)-methyl 2-((tert-butoxycarbonyl)((2-(trimethylsilyl)ethoxy)methyl)amino)-4-(2,3-difluorophenyl)-4-methyl-4H-1,3-thiazine-6-carboxylate (203H, 10.9 g, 20.62 mmol, 92% yield) as a colorless oil. LC/MS (ESI$^-$) m/z=529.1 (M+H)$^+$. $^1$H NMR (400 MHz, CHLOROFORM-d) δ ppm 7.27-7.33 (m, 1H), 7.01-7.13 (m, 3H), 5.30 (dd, J=10.37, 6.06 Hz, 1H), 5.18-5.23 (m, 1H), 3.82 (s, 3H), 3.62-3.68 (m, 2H), 1.76 (s, 3H), 1.52-1.55 (m, 9H), 0.86-0.95 (m, 2H), −0.01 (m, 9H).

Preparation of Compound 203I. Corey-Chaykovsky Reagent [0.2 M in DMSO] was prepared in this fashion: To a stirring solution of trimethylsulfoxonium iodide (8.39 g, 38.1 mmol) in dimethyl sulfoxide (200 mL) at 20° C. was added potassium tert-butoxide (4.28 g, 38.1 mmol) in one portion. The internal temperature increased to 22° C. The solution was stirred for 1 h.

To a stirring solution of (S)-methyl 2-((tert-butoxycarbonyl)((2-(trimethylsilyl)ethoxy)methyl)amino)-4-(2,3-difluorophenyl)-4-methyl-4H-1,3-thiazine-6-carboxylate (203H, 15.5 g, 29.3 mmol) in THF (200 mL) at 20° C. under nitrogen was added freshly prepared Corey-Chaykovsky Reagent [0.2 M in DMSO] dropwise via addition funnel over a 10 min period. The reaction remained in the 21-23° C. temperature range. After stirring at RT for 30 min, the reaction mixture was quenched with sat. NH$_4$Cl (50 mL) dropwise and diluted with water (400 mL). The reaction mixture was extracted with 3:1 heptane/EtOAc (600 mL). The aqueous was further extracted with 1:1 heptane/EtOAc (10 mL). The organics were washed with water (200 mL) then brine (50 mL), dried over MgSO$_4$, and concentrated under reduced pressure. The residue was purified by silica gel chromatography (330 g) loading material on with heptane and eluting products with 0-10% EtOAc/heptane gradient to afford (1S,5S,6S)-methyl 3-((tert-butoxycarbonyl)((2-(trimethylsilyl)ethoxy)methyl)amino)-5-(2,3-difluorophenyl)-5-methyl-2-thia-4-azabicyclo[4.1.0]hept-3-ene-1-carboxylate (203I, 12.7 g, 23.40 mmol, 80% yield) as colorless oil. LC/MS (ESI$^-$) m/z=543.1 (M+H)$^+$. $^1$H NMR (400 MHz, CHLOROFORM-d) δ ppm 7.37 (t, J=6.75 Hz, 1H) 7.01-7.12 (m, 2H) 5.26 (d, J=10.56 Hz, 1H) 5.01 (d, J=10.56 Hz, 1H) 3.78 (s, 3H) 3.59-3.69 (m, 2H) 2.61 (dd, J=8.71, 7.92 Hz, 1H) 1.76 (s, 3H) 1.50-1.55 (m, 9H) 1.46-1.50 (m, 1H) 1.21 (dd, J=7.43, 5.28 Hz, 1H) 0.90-0.96 (m, 2H) −0.03-0.00 (m, 9H).

Preparation of Compound 203J. At RT, a solution of (1S,5S,6S)-methyl 3-((tert-butoxycarbonyl)((2-(trimethylsilyl)ethoxy)methyl)amino)-5-(2,3-difluorophenyl)-5-methyl-2-thia-4-azabicyclo[4.1.0]hept-3-ene-1-carboxylate (203I, 4.1 g, 7.55 mmol) in 60 mL of THF was treated with lithium borohydride (2 M solution in THF) (7.55 mL, 15.11 mmol) followed by MeOH (2.45 mL, 60.4 mmol). The mixture was stirred for 1 h at RT then cooled with an ice bath, and quenched with the dropwise addition of 10 mL of aq. NH$_4$Cl. The resulting biphasic mixture was extracted with (3×50 mL) of EtOAc. The organic extracts were washed sequentially with 10 mL of ice cold 1 N HCl, 5 mL of 1 N NaOH and 5 mL of brine, and dried over MgSO$_4$. It was filtered and concentrated under reduced pressure to provide tert-butyl((1S,5S,6S)-5-(2,3-difluorophenyl)-1-(hydroxymethyl)-5-methyl-2-thia-4-azabicyclo[4.1.0]hept-3-en-3-yl)((2-(trimethylsilyl)ethoxy)methyl)carbamate (3.68 g, 7.15 mmol, 95% yield) as a clear viscous oil which was used without further purification. LC/MS (ESI$^-$) m/z=515.2 (M+H)$^+$. At RT. the above obtained crude tert-butyl((1S,5S,6S)-5-(2,3-difluorophenyl)-1-(hydroxymethyl)-5-methyl-2-thia-4-azabicyclo[4.1.0]hept-3-en-3-yl)((2-(trimethylsilyl)ethoxy)methyl)carbamate (3.36 g, 6.53 mmol) was taken up in 25 mL of DCM and 8.3 mL of DMSO. The solution was treated with Hunig's base (4.54 mL, 26.1 mmol) followed by pyridine-sulfur trioxide complex (2.078 g, 13.06 mmol). After 15 h, the mixture was diluted with 100 mL of DCM and washed with (2×15 mL) of sat. NH$_4$Cl followed by 10 mL of brine, then dried over MgSO$_4$. Filtration and concentration under reduced pressure afforded a yellow oil which was purified on a silica gel column (10-35% EtOAc in Hexanes) to provide tert-butyl((1S,5S,6S)-5-(2,3-difluorophenyl)-1-formyl-5-methyl-2-thia-4-azabicyclo[4.1.0]hept-3-en-3-yl)((2-(trimethylsilyl)ethoxy)methyl)carbamate (203J, 2.79 g, 5.44 mmol, 83% yield) as a yellow oil. LC/MS (ESI$^-$) m/z=513.2 (M+H)$^+$. $^1$H NMR (400 MHz, DMSO-d$_6$) δ 8.91 (br., 1H), 7.45 (m, 2H), 7.27 (m, 1H), 5.19 (d, J=10.56 Hz, 1H), 5.00 (d, J=10.76 Hz, 1H), 3.58-3.65 (m, 2H), 2.82 (m, 1H), 1.87 (dd, J=5.87, 9.78 Hz, 1H), 1.71 (s, 3H), 1.50 (s, 9H), 1.25-1.40 (m, 2H), 0.90 (m, 1H), 0.02 (s, 9H). $^{19}$F NMR (376 MHz, DMSO-d$_6$) δ −139.15 (d, J=21.40 Hz, 1F), −139.46 (d, J=21.46 Hz, 1F).

Preparation of Compound 203K. To a stirring solution of tert-butyl((1S,5S,6S)-5-(2,3-difluorophenyl)-1-formyl-5-methyl-2-thia-4-azabicyclo[4.1.0]hept-3-en-3-yl)((2-(trimethylsilyl)ethoxy)methyl)carbamate (203J, 2.0 g, 3.90 mmol) in 1,2-dichloroethane (23.05 mL) at 20° C. under nitrogen was added chlorotris(triphenylphosphine)rhodium (i) (Wilkinson's reagent, 5.41 g, 5.85 mmol) then heated to vigorous reflux under nitrogen. After 3 h the LCMS suggested 80% conversion. To the reaction mixture was added more Wilkinson's reagent (2.5 g) and returned to reflux for 1 h. It was cooled to RT and the solvents were removed under reduced pressure. The residue was triturated in 6:1 heptane/EtOAc (75 mL) by stirring for 20 h. The solid was further triturated in 6:1 heptane/EtOAc (2×50 mL) with the aid of sonication each time capturing the solid through a bed of Celite® filter aid. The resulting filtrate was concentrated under reduced pressure. The resulting oil/solid was further triturated in 6:1 heptane/EtOAc (2×50 mL) with the aid of sonication each time capturing the solid through a bed of Celite® filter aid. The resulting filtrate was concentrated under reduced pressure, loaded onto silica with heptane, then purified by silica gel chromatography (80 g) eluting with a gradient of 0-10% EtOAc/heptane to afford tert-butyl ((1S,5S,6S)-5-(2,3-difluorophenyl)-1-formyl-5-methyl-2-thia-4-azabicyclo[4.1.0]hept-3-en-3-yl)((2-(trimethylsilyl)ethoxy)methyl)carbamate (203K, 2.0 g, 3.90 mmol) as colorless oil. LC/MS (ESI$^-$) m/z=485.1 (M+H)$^+$. $^1$H NMR (400 MHz, CHLOROFORM-d) δ ppm 7.32-7.40 (m, 1H), 6.99-7.10 (m, 2H), 5.26 (d, J=10.56 Hz, 1H), 5.01 (d, J=10.37 Hz, 1H), 3.60-3.70 (m, 2H), 2.19 (td, J=8.36, 4.99 Hz, 1H), 1.94-2.05 (m, 1H), 1.78 (s, 3H), 1.51 (s, 9H), 0.90-0.98 (m, 2H), 0.83-0.90 (m, 1H), 0.70 (q, J=5.74 Hz, 1H), 0.00 (s, 9H).

Preparation of Compound 203L. At 0° C., to tert-butyl ((1S,5S,6S)-5-(2,3-difluorophenyl)-5-methyl-2-thia-4-azabicyclo[4.1.0]hept-3-en-3-yl)((2-(trimethylsilyl)ethoxy) methyl) carbamate (203K, 1.29 g, 2.66 mmol) was added H$_2$SO$_4$ (6.38 mL, 120 mmol). After 15 min, the ice bath was removed and syrup stirred for 30 min at 20° C. The reaction was cooled to 0° C. and sodium nitrate (0.317 g, 3.73 mmol) was added. The reaction was stirred for 30 min at 0° C. The ice bath was removed and reaction stirred at 20° C. for 15 min. The mixture was added to ice (100 g) via a pipet. The acidic solution was cooled with an ice bath and deluted with CH$_2$Cl$_2$ (50 mL). To the rapidly stirred mixture was added potassium phosphate tribasic (16.95 g, 80 mmol) over 20 min, and the mixture was then brought to pH~8 with 1 M NaOH. The organic layer was separated, and the aqueous layer was extracted with DCM (2×50 mL). The combined organic layers were dried over MgSO$_4$, filtered, concentrated under reduced pressure. The residue was purified via silica gel flash column chromatography eluting with a gradient of 0-25% EtOAc in heptane to afford (1S,5S,6S)-5-(2,3-difluoro-5-nitrophenyl)-5-methyl-2-thia-4-azabicyclo [4.1.0]hept-3-en-3-amine (203L, 0.45 g, 1.504 mmol, 56.5% yield) as tan oil. LC/MS (ESI$^-$) m/z=300.0 (M+H)$^+$. $^1$H NMR (400 MHz, CHLOROFORM-d) δ 8.44-8.50 (m, 1H), 7.98 (ddd, J=2.93, 6.31, 9.15 Hz, 1H), 4.04-4.95 (m, 2H), 2.24 (dt, J=5.28, 8.31 Hz, 1H), 1.84-1.99 (m, 1H), 1.77 (s, 3H), 0.85-0.97 (m, 1H), 0.64 (q, J=5.74 Hz, 1H).

Preparation of Compound 203. To a stirring solution of (1S,5S,6S)-5-(2,3-difluoro-5-nitrophenyl)-5-methyl-2-thia-4-azabicyclo[4.1.0]hept-3-en-3-amine (203L, 0.46 g, 1.54 mmol) in glacial HOAc (5 mL) and TFA (5 mL) at 20° C.

was added zinc (nanopowder, 0.6 g, 9.22 mmol) in small portions. After 90 min, the reaction was concentrated under reduced pressure to a thick oil/suspension. The residue was partitioned between 9:1 CHCl₃/IPA (50 mL) and 10% NH₄OH (50 mL). The separated aqueous layer was further extracted with 9:1 CHCl₃/IPA (20 mL). The combined organics were washed with sat. NaCl (20 mL), dried over MgSO₄, concentrated under reduced pressure. The remaining solid was purified by silica gel chromatography (12 g) eluting with a gradient of 1-6% of 2 M NH₃ in MeOH in DCM to afford (1S,5S,6S)-5-(5-amino-2,3-difluorophenyl)-5-methyl-2-thia-4-azabicyclo[4.1.0]hept-3-en-3-amine (203) (0.33 g, 1.22 mmol, 80% yield) as tan foam. LC/MS (ESI⁻) m/z=270.0 (M+H)⁺. ¹H NMR (400 MHz, CHLOROFORM-d) δ ppm 6.69 (dt, J=4.99, 2.59 Hz, 1H), 6.32-6.40 (m, 1H), 3.81-4.58 (br., 2H), 3.58 (br. s., 2H), 2.18 (td, J=8.22, 5.09 Hz, 1H), 1.80-1.91 (m, 1H), 1.70-1.75 (m, 3H), 0.88-0.97 (m, 1H), 0.59 (q, J=5.67 Hz, 1H).

(R,Z)—N-(1-(5-Bromo-2-fluorophenyl)-2-fluoroethylidene)-2-methylpropane-2-sulfinamide (204A)

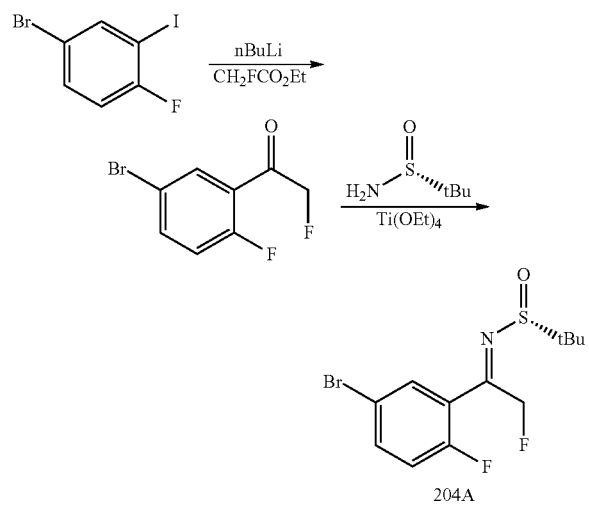

Preparation of 1-(5-bromo-2-fluorophenyl)-2-fluoroethanone. A solution of 4-bromo-1-fluoro-2-iodobenzene (5.0 g, 116 mmol, Aldrich) in THF (60 mL) under nitrogen atmosphere was cooled to −78° C. A solution of n-BuLi (2.5 M in hexanes; 7.31 mL, 18.28 mmol, Aldrich) was added dropwise and the reaction was stirred at −78° C. for 1 h. Ethyl monofluoroacetate (2.1 g, 19.94 mmol, Aldrich) was added drop wise and the reaction was stirred at −78° C. for 1 h. The reaction was quenched with aqueous saturated ammonium chloride solution and allowed to warm to RT. The reaction was diluted with water and EtOAc. The organic layer was separated, washed with brine, dried over magnesium sulfate, and concentrated under reduced pressure. The material was purified via silica gel flash chromatography using a gradient of 0-20% EtOAc in Hexanes to afford the title compound as an off white solid (2.45 g, 10.42 mmol, 63% yield). MS m/z=234.9 M⁺.

Preparation of (R)—N-(1-(5-bromo-2-fluorophenyl)-2-fluoroethylidene)-2-methylpropane-2-sulfinamide (204A). To a solution of 1-(5-bromo-2-fluorophenyl)-2-fluoroethanone (14 g, 59.6 mmol) and (R)-2-methylpropane-2-sulfinamide (14.44 g, 119 mmol, AK Scientific) in THF (120 ml) was added tetraethoxytitanium (27.2 g, 119 mmol, Aldrich). The reaction was stirred at RT for 16 h. The reaction mixture was poured slowly into vigorously stirring water (700 mL) and the resulting suspension was stirred for 20 min. EtOAc (400 mL) was added and the suspension was stirred for an additional 20 min. The suspension was filtered through Celite® filter aid and the filter cake was washed with additional EtOAc. The organic layer was separated, washed with brine, dried over magnesium sulfate and concentrated under reduced pressure. The material was purified via silica gel flash chromatography using a gradient of 0-25% EtOAc in Hexanes to afford the title compound as a yellow oil (204A, 15.35 g, 45.4 mmol, 76% yield). MS m/z=338.0 M⁺.

(1S,5S,6S)-5-(5-Amino-2-fluorophenyl)-5-(fluoromethyl)-2-thia-4-azabicyclo[4.1.0]hept-3-en-3-amine (204)

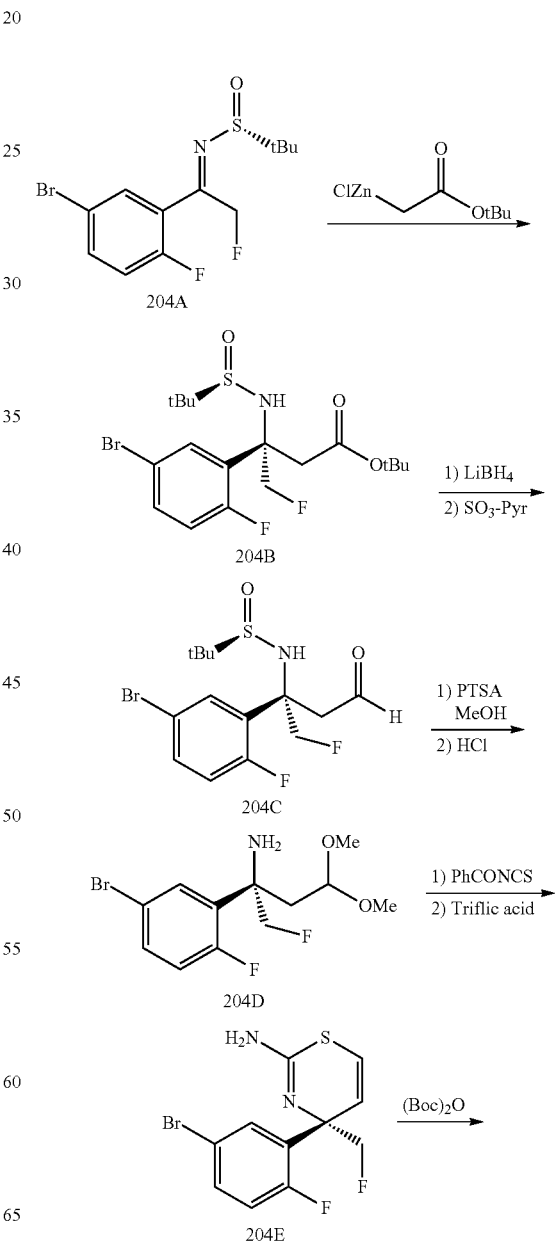

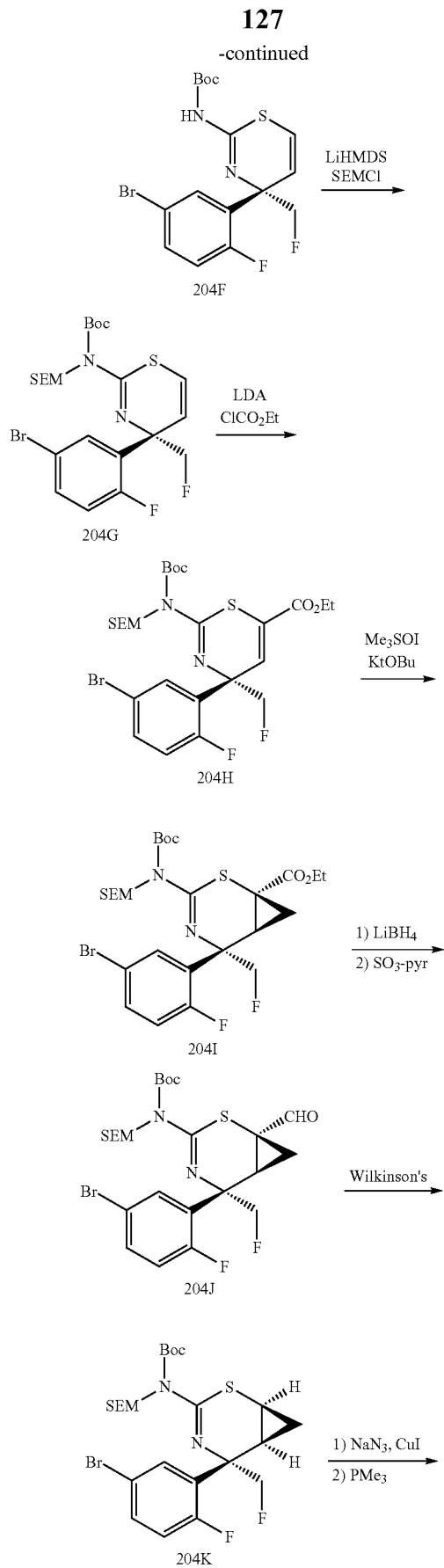

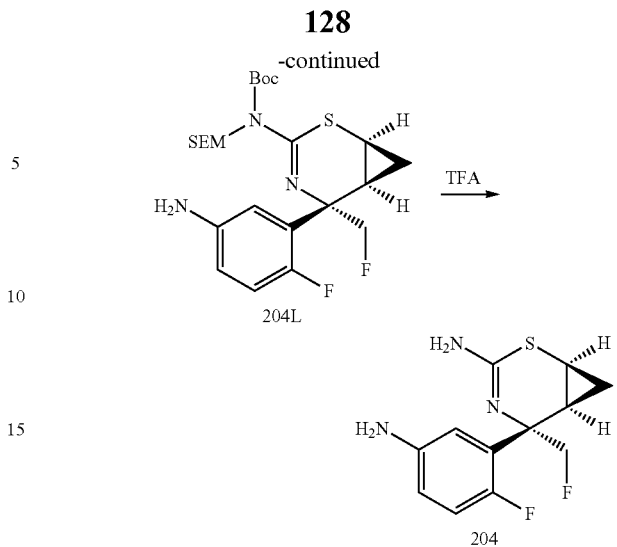

Preparation of Compound 204B. To a 2000 mL 3-neck RBF equipped with an addition funnel and internal temperature probe was added (R,Z)—N-(1-(5-bromo-2-fluorophenyl)-2-fluoroethylidene)-2-methylpropane-2-sulfinamide (204A, 21.35 g, 63.1 mmol) and THF (200 mL). The mixture was cooled to 0° C. and 2-tert-butoxy-2-oxoethylzinc chloride (0.5 M in Et$_2$O, 253 mL, 126 mmol) was added dropwise over 75 min keeping the internal temperature under 5° C. After the addition was completed, the ice bath was removed and the reaction mixture was stirred at RT for 80 min. The reaction mixture was carefully quenched with the slow addition of half-sat. NH$_4$Cl (100 mL) followed by water (200 mL). The layers were separated and the aqueous phase was extracted with EtOAc (200 mL). The combined organic extracts were washed with brine (300 mL), dried (Na$_2$SO$_4$) and concentrated. Purification by silica gel chromatography (5-50% EtOAc/hexanes) afforded (S)-tert-butyl 3-(5-bromo-2-fluorophenyl)-3-((R)-1,1-dimethylethylsulfinamido)-4-fluorobutanoate (204B, 22.33 g, 49.1 mmol, 78% yield) as a pale-yellow oil, which solidified upon standing. LC/MS (ESI$^-$) m/z=475.8 (M+Na)$^+$.

Preparation of Compound 204C. To a solution of (S)-tert-butyl 3-(5-bromo-2-fluorophenyl)-3-((R)-1,1-dimethylethylsulfinamido)-4-fluorobutanoate (204B, 22.3 g, 49.1 mmol) in THF (250 mL) in a 1000 mL 3-neck round-bottomed flask equipped with an internal temperature probe at RT was added lithium borohydride (2.0 M solution in THF, 50.0 mL, 100 mmol) over 45 min. Anhydrous MeOH (16.0 mL, 395 mmol) was then added to the mixture slowly over 55 min keeping the internal temperature under 35° C. The mixture was stirred for 30 min. The reaction was slowly quenched with 100 mL of sat. aq. NH$_4$Cl. The mixture was stirred at RT for 15 min then partitioned between water (100 mL) and EtOAc (100 mL). The aqueous phase was extracted with EtOAc (100 mL). The combined organic extracts were washed with brine (300 mL), dried over Na$_2$SO$_4$, filtered, and concentrated in vacuo. Purification by silica gel chromatography (30-80% EtOAc/hexanes) afforded ((R)—N—((S)-2-(5-bromo-2-fluorophenyl)-1-fluoro-4-hydroxybutan-2-yl)-2-methylpropane-2-sulfinamide (15.34 g, 39.9 mmol, 81%) as a white foam. LC/MS (ESI$^-$) m/z=383.8 (M+H)$^+$. This material was dissolved in DCM (140 mL) and DMSO (70 mL) in a 1000 mL 3-neck RBF equipped with an internal temperature probe. The mixture was cooled in an ice/acetone bath to −10° C. N,N-diisopropylethylamine (21 mL, 121 mmol) was added dropwise via a syringe followed by portion-wise addition of pyridine sulfur trioxide (9.51 g, 59.7 mmol) keeping the internal temperature below −5° C. The mixture was stirred for 5 min, and then the cooling bath was replaced with an ice bath. The mixture was stirred for 1 h at ~0° C. The mixture was poured into water (500 mL) and EtOAc (300 mL) was added. The layers were separated and the aqueous phase was extracted with EtOAc (3×150 mL). The combined organic extracts were washed with saturated aqueous ammonium chloride (2×500 mL), water (500 mL) and brine (500 mL). The organic was dried over $Na_2SO_4$, filtered and concentrated in vacuo to give the crude material. Purification by silica gel chromatography (20-80% EtOAc/hexanes) afforded (R)—N—((S)-2-(5-bromo-2-fluorophenyl)-1-fluoro-4-oxobutan-2-yl)-2-methylpropane-2-sulfinamide (204C, 11.36 g, 29.7 mmol, 74.6% yield) as a clear paste. LC/MS (ESI$^-$) m/z=381.8 (M+H)$^+$. $^1$H NMR (300 MHz, CHLOROFORM-d) δ 9.76 (s, 1H), 7.65 (d, J=7.02 Hz, 1H), 7.39-7.53 (m, 1H), 6.96 (dd, J=8.92, 11.98 Hz, 1H), 4.70-5.18 (m, 3H), 3.31-3.55 (m, 2H), 1.23-1.29 (m, 9H). $^{19}$F NMR (282 MHz, CHLOROFORM-d) δ −111.72 (s, 1F), −217.48 (s, 1F).

Preparation of Compound 204D. The mixture of (R)—N—((S)-2-(5-bromo-2-fluorophenyl)-1-fluoro-4-oxobutan-2-yl)-2-methylpropane-2-sulfinamide (2.44 g, 6.38 mmol) and 4-methylbenzene sulfonic acid hydrate (0.085 g, 0.447 mmol) in MeOH (50 mL) was heated at 80° C. in 2 h. After 2 h, the reaction was cooled to RT. To this mixture, stirred in an ice bath, was added HCl (1.6 mL of 4 M in dioxane solution, 6.38 mmol). After the addition, the mixture was stirred at RT overnight. The mixture was concentrated to dryness, saturated aqueous $Na_2CO_3$ was added, extracted with EtOAc (3×). The extracts were dried over $MgSO_4$, concentrated to give (S)-2-(5-bromo-2-fluorophenyl)-1-fluoro-4,4-dimethoxybutan-2-amine (204D, 2.06 g, 100%) which was used in the next step without further purification. LC/MS (ESI$^-$) m/z=324.0 (M+H)$^+$.

Preparation of Compound 204E. To a stirred solution of (S)-2-(5-bromo-2-fluorophenyl)-1-fluoro-4,4-dimethoxybutan-2-amine (204D, 25.4 g, 78 mmol) in DCM (150 mL) at 0° C. was added a solution of benzoyl isothiocyanate (14.07 g, 86 mmol) in DCM (100 mL). After the addition, the ice bath was removed and stirred at RT in 2 h. The mixture was concentrated to dryness to give a brown oil which was treated with triflic acid (5.65 mL, 63.6 mmol). The mixture was heated to 50° C. for 3 h, then 70° C. for 2 h. The reaction mixture was cooled, poured onto ice in a beaker, basified with 10 N NaOH until pH=9. It was extracted with DCM (3×). The extracts were dried over $Na_2SO_4$, concentrated and purified by silica gel chromatography (0-50% EtOAc/Hexanes) to give (S)-4-(5-bromo-2-fluorophenyl)-4-(fluoromethyl)-4H-1,3-thiazin-2-amine (204E, 1.59 g, 78%). $^1$H NMR (CHLOROFORM-d) δ: 7.58 (dd, J=6.8, 2.5 Hz, 1H), 7.37 (ddd, J=8.6, 4.3, 2.6 Hz, 1H), 6.92 (dd, J=11.2, 8.7 Hz, 1H), 6.47 (d, J=9.6 Hz, 1H), 6.32 (dd, J=9.6, 5.3 Hz, 1H), 4.90 (br. s., 2H), 4.81 (d, J=8.0 Hz, 0.5H), 4.70 (d, J=8.0 Hz, 0.5H), 4.63 (d, J=8.6 Hz, 0.5H), 4.52 (d, J=8.6 Hz, 0.5H). LC/MS (ESI$^-$) m/z=319.0 (M+H)$^+$.

Preparation of Compound 204F. A mixture of (S)-4-(5-bromo-2-fluorophenyl)-4-(fluoromethyl)-4H-1,3-thiazin-2-amine (204E, 4.81 g, 15.07 mmol) and di-tert-butyl dicarbonate (6.58 g, 30.1 mmol) was heated neat at 50° C. for 24 h. The reaction mixture was cooled to RT and purified by silica gel chromatography (0-20% EtOAc/Hexanes) to give (S)-tert-butyl(4-(5-bromo-2-fluorophenyl)-4-(fluoromethyl)-4H-1,3-thiazin-2-yl)carbamate (204F, 6.32 g, 100%). LC/MS (ESI$^-$) m/z=362.9.0 (M+H)$^+$.

Preparation of Compound 204G. To a stirred solution of (S)-tert-butyl(4-(5-bromo-2-fluorophenyl)-4-(fluoromethyl)-4H-1,3-thiazin-2-yl)carbamate (204F, 4 g, 9.54 mmol) in THF (20 mL) at −10° C. was added a solution of lithium bis(trimethylsilyl)amide (11.45 mL of 1 M solution in THF, 11.45 mmol) dropwise. The mixture was stirred at this temperature for 1 h, then a solution of 2-(trimethylsilyl)ethoxymethyl chloride (1.88 mL, 9.54 mmol) in THF (10 mL) was added. The reaction mixture was gradually warmed to RT and stirred for 16 h. It was treated with saturated aqueous $NH_4Cl$ and extracted with hexanes. The combined extracts were dried over $Na_2SO_4$, concentrated, then purified by silica gel chromatography (0-20% EtOAc/Hexanes) to give (S)-tert-butyl(4-(5-bromo-2-fluorophenyl)-4-(fluoromethyl)-4H-1,3-thiazin-2-yl)((2-(trimethylsilyl)ethoxy)methyl) carbamate (204G, 4.77 g, 91%). $^1$H NMR (DMSO-$d_6$) δ: 7.54-7.72 (m, 2H), 7.28 (dd, J=11.6, 8.5 Hz, 1H), 6.85 (d, J=9.4 Hz, 1H), 6.17 (dd, J=9.6, 4.3 Hz, 1H), 5.16-5.31 (m, 2H), 4.56-4.96 (m, 2H), 3.63 (dd, J=8.6, 7.4 Hz, 2H), 1.50 (s, 9H), 0.69-1.03 (m, 2H), 0.03 (s, 9H). LC/MS (ESI$^-$) m/z=573.0 (M+Na)$^+$.

Preparation of Compound 204H. To a stirred solution of (S)-tert-butyl(4-(5-bromo-2-fluorophenyl)-4-(fluoromethyl)-4H-1,3-thiazin-2-yl)((2-(trimethylsilyl)ethoxy)methyl)carbamate (3.27 g, 5.71 mmol) in THF (30 mL) at −78° C. was added LDA (3.71 mL of 1 M in THF solution, 7.43 mmol) dropwise. After the addition, the mixture was stirred at −78° C. for 45 min, and then ethyl chloroformate (6.58 mL, 68.6 mmol) was added in single portion. It was stirred at −78° C. for 10 min then quenched with saturated $NH_4Cl$, and extracted with EtOAc (3×). The organic extracts were dried over $Na_2SO_4$, concentrated and purified by silica gel chromatography (0-20% EtOAc/Hexanes to give (S)-ethyl 4-(5-bromo-2-fluorophenyl)-2-((tert-butoxycarbonyl)((2-(trimethylsilyl)ethoxy)methyl)amino)-4-(fluoromethyl)-4H-1,3-thiazine-6-carboxylate (204H, 1.75 g, 49.3%). 1H NMR (CHLOROFORM-d) δ: 7.57-7.69 (m, 1H), 7.65 (dd, J=6.8, 2.3 Hz, 1H), 7.19 (d, J=4.3 Hz, 1H), 6.97 (dd, J=11.0, 8.8 Hz, 1H), 5.35-5.44 (m, 1H), 5.24-5.33 (m, 1H), 4.78-4.99 (m, 1H), 4.55-4.75 (m, 1H), 4.30 (q, J=7.1 Hz, 2H), 3.63-3.73 (m, 2H), 1.52-1.60 (m, 9H), 1.34 (t, J=7.0 Hz, 3H), 0.87-1.04 (m, 2H), 0.03 (s, 9H). LC/MS (ESI$^-$) m/z=643.1 (M+Na)$^+$.

Preparation of Compound 204I. To a stirred suspension of trimethylsulfoxonium iodide (13.60 g, 61.8 mmol) in DMSO (30 mL) was added potassium tert-butoxide (6.35 g, 56.6 mmol) in single portion. After the addition, the mixture was stirred for 1 h. The resulting mixture was added to a stirred solution of (S)-ethyl 4-(5-bromo-2-fluorophenyl)-2-((tert-butoxycarbonyl)((2-(trimethylsilyl)ethoxy)methyl)amino)-4-(fluoromethyl)-4H-1,3-thiazine-6-carboxylate (204H, 16 g, 25.7 mmol) in DMSO (70 mL). The reaction mixture was stirred at RT for 1 h, the treated with saturated aqueous $NH_4Cl$, and extracted with EtOAc (3×). The extracts were dried over $Na_2SO_4$, concentrated and purified by silica gel chromatography (0-20% EtOAc/Hexanes) to give (1S,5S,6S)-ethyl 5-(5-bromo-2-fluorophenyl)-3-((tert-butoxycarbonyl)((2-(trimethylsilyl)ethoxy)methyl)amino)-5-(f (1S,5S,6S)-ethyl 5-(5-bromo-2-fluorophenyl)-3-((tert-butoxycarbonyl)((2-(trimethylsilyl)ethoxy)methyl)amino)-5-(fluoromethyl)-2-thia-4-azabicyclo[4.1.0]hept-3-ene-1-carboxylateluoromethyl)-2-thia-4-azabicyclo[4.1.0]hept-3-ene-1-carboxylate (204I, 3.94 g, 24%). $^1$H NMR (CHLOROFORM-d) δ: 7.84 (dd, J=6.8, 2.5 Hz, 1H), 7.41 (ddd, J=8.6, 4.3, 2.6 Hz, 1H), 6.98 (dd, J=11.5, 8.6 Hz, 1H), 5.29 (d, J=10.4 Hz, 1H), 5.04 (d, J=10.4 Hz, 1H), 4.59-4.99 (m, 2H), 4.24 (q, J=7.2 Hz, 2H), 3.67 (td, J=8.4, 1.5 Hz, 2H), 2.63 (ddd, J=9.9, 7.7, 1.8 Hz, 1H), 1.56 (d, J=4.9 Hz, 1H), 1.54 (s, 9H), 1.31 (t, J=7.1 Hz, 3H), 1.07 (dd, J=7.5, 5.2 Hz, 1H), 0.97 (dd, J=9.2, 7.4 Hz, 2H), −0.01-0.02 (s, 9H). LC/MS (ESI⁻) m/z=657.2 (M+Na)⁺.

Preparation of Compound 204J. To a stirred solution of (1S,5S,6S)-ethyl 5-(5-bromo-2-fluorophenyl)-3-((tert-butoxycarbonyl)((2-(trimethylsilyl)ethoxy)methyl)amino)-5-(fluoromethyl)-2-thia-4-azabicyclo[4.1.0]hept-3-ene-1-carboxylate (204I, 3.94 g, 6.20 mmol) in THF (40 mL) at RT was added lithium borohydride (6.20 mL of 1 M in THF solution, 12.40 mmol) dropwise. After the addition, MeOH (2.0 mL, 49.6 mmol) was added dropwise, and mixture stirred for 2 h. It was cooled in an ice bath and quenched with saturated aqueous NH₄Cl, extracted with EtOAc (3×). The extracts were dried over Na₂SO₄, concentrated to give tert-butyl((1S,5S,6S)-5-(5-bromo-2-fluorophenyl)-5-(fluoromethyl)-1-(hydroxymethyl)-2-thia-4-azabicyclo[4.1.0]hept-3-en-3-yl)((2-(trimethylsilyl)ethoxy)methyl)carbamate as a colorless oil (3.64 g, 99%). ¹H NMR (CHLOROFORM-d) δ: 7.77 (dd, J=6.8, 2.5 Hz, 1H), 7.39 (ddd, J=8.7, 4.2, 2.6 Hz, 1H), 6.96 (dd, J=11.6, 8.7 Hz, 1H), 5.32 (d, J=10.6 Hz, 1H), 5.07 (d, J=10.6 Hz, 1H), 4.62-5.00 (m, 2H), 3.84 (dd, J=11.9, 4.3 Hz, 1H), 3.67 (dd, J=8.8, 7.8 Hz, 2H), 3.50-3.56 (m, 1H), 2.04 (t, J=6.0 Hz, 1H), 1.91 (ddd, J=9.5, 6.9, 2.2 Hz, 1H), 1.52 (s, 9H), 0.93-1.06 (m, 3H), 0.73 (t, J=6.3 Hz, 1H), −0.02-0.04 (s, 9H). LC/MS (ESI⁻) m/z=617.2 (M+Na)⁺.

TEA (3.41 mL, 24.46 mmol) was added dropwise via syringe to a solution tert-butyl((1S,5S,6S)-5-(5-bromo-2-fluorophenyl)-5-(fluoromethyl)-1-(hydroxymethyl)-2-thia-4-azabicyclo[4.1.0]hept-3-en-3-yl)((2-(trimethylsilyl)ethoxy)methyl)carbamate (3.62 g, 6.12 mmol) in DCM (20 mL) and DMSO (20 mL) in 100 mL RBF. Pyridine sulfur trioxide (4.33 g, 12.23 mmol) was added and the mixture was stirred for 2 h. Water was added and the mixture was extracted with DCM (3×). The combined organic extracts were washed with saturated aqueous ammonium chloride, water, saturated aqueous sodium chloride, and dried over sodium sulfate. The solution was filtered and concentrated in vacuo to give tert-butyl((1S,5S,6S)-5-(5-bromo-2-fluorophenyl)-5-(fluoromethyl)-1-formyl-2-thia-4-azabicyclo[4.1.0]hept-3-en-3-yl)((2-(trimethylsilyl)ethoxy)methyl)carbamate (204J, 3.62 g, 100%). ¹H NMR (CHLOROFORM-d) δ: 9.15 (s, 1H), 7.83 (dd, J=6.8, 2.5 Hz, 1H), 7.44 (ddd, J=8.7, 4.3, 2.5 Hz, 1H), 7.00 (dd, J=11.5, 8.8 Hz, 1H), 5.33 (d, J=10.4 Hz, 1H), 5.11 (d, J=10.4 Hz, 1H), 4.59-4.97 (m, 2H), 3.67 (dd, J=9.0, 7.6 Hz, 2H), 2.40-2.59 (m, 1H), 1.77 (dd, J=10.0, 5.7 Hz, 1H), 1.50-1.58 (s, 9H), 1.16-1.34 (m, 1H), 0.98 (dd, J=9.2, 7.4 Hz, 2H), −0.03-0.04 (s, 9H). LC/MS (ESI⁻) m/z=615.0 (M+Na)⁺.

Preparation of Compound 204K. A mixture of tert-butyl ((1S,5S,6S)-5-(5-bromo-2-fluorophenyl)-5-(fluoromethyl)-1-formyl-2-thia-4-azabicyclo[4.1.0]hept-3-en-3-yl)((2-(trimethylsilyl)ethoxy)methyl)carbamate (3.22 g, 5.44 mmol) and chlorotris(triphenylphosphine) rhodium(i) (3.53 g, 3.81 mmol) in DCE (20 mL) was heated at 85° C. for 4 h. The mixture was cooled, concentrated to dryness, triturated in 40% EtOAc/Hexanes. The orange solid was filtered off, washed with 40% EtOAc/Hexanes. The filtrate was concentrated and purified by silica gel chromatography (0-20% EtOAc/Hexanes) to give tert-butyl((1S,5S,6S)-5-(5-bromo-2-fluorophenyl)-5-(fluoromethyl)-2-thia-4-azabicyclo[4.1.0]hept-3-en-3-yl)((2-(trimethylsilyl)ethoxy)methyl)carbamate (204K, 1.75 g, 57%). ¹H NMR (CHLOROFORM-d) δ: 7.81 (dd, J=7.0, 2.5 Hz, 1H), 7.39 (ddd, J=8.6, 4.2, 2.6 Hz, 1H), 6.96 (dd, J=11.6, 8.7 Hz, 1H), 5.29 (d, J=10.4 Hz, 1H), 5.04 (d, J=10.4 Hz, 1H), 4.69-4.98 (m, 2H), 3.62-3.70 (m, 2H), 2.25 (ddd, J=8.9, 7.7, 5.3 Hz, 1H), 2.00 (tdd, J=9.2, 6.6, 2.7 Hz, 1H), 1.52 (s, 9H), 0.94-1.05 (m, 2H), 0.88 (t, J=6.8 Hz, 1H), 0.60 (q, J=5.9 Hz, 1H), 0.00 (s, 9H). LC/MS (ESI⁻) m/z=585.0 (M+Na)⁺.

Preparation of Compound 204L. A mixture of tert-butyl ((1S,5S,6S)-5-(5-bromo-2-fluorophenyl)-5-(fluoromethyl)-2-thia-4-azabicyclo[4.1.0]hept-3-en-3-yl)((2-(trimethylsilyl)ethoxy)methyl)carbamate (3.31 g, 5.87 mmol), sodium (R)-2-((S)-1,2-dihydroxyethyl)-4-hydroxy-5-oxo-2,5-dihydrofuran-3-olate (0.291 g, 1.468 mmol), copper(I) iodide (0.280 g, 1.468 mmol), sodium azide (1.145 g, 17.62 mmol), and (1R,2R)—N1,N2-dimethylcyclohexane-1,2-diamine (0.232 mL, 1.468 mmol) in EtOH/H₂O (5:1, 60 mL) was heated at 85° C. for 2 h. The reaction mixture was cooled, diluted with EtOAc, washed with 10:1 saturated NH₄Cl/NH₄OH, brine, dried over Na₂SO₄, and concentrated to give an oil.

A solution of the oil in 9:1 of THF/H₂O (50 mL) was added trimethylphosphine (6.46 mL of 1 M in THF, 6.46 mmol). After stirring for 30 min, it was diluted with EtOAc, washed with H₂O, dried over Na₂SO₄, and concentrated to give tert-butyl((1S,5S,6S)-5-(5-amino-2-fluorophenyl)-5-(fluoromethyl)-2-thia-4-azabicyclo[4.1.0]hept-3-en-3-yl)((2-(trimethylsilyl)ethoxy)methyl)carbamate (204L, 2.85 g, 97%) as light brown oil. ¹H NMR (CHLOROFORM-d) δ: 6.96 (dd, J=6.5, 2.9 Hz, 1H), 6.85 (dd, J=11.9, 8.6 Hz, 1H), 6.55 (dt, J=8.5, 3.4 Hz, 1H), 5.29 (d, J=10.6 Hz, 1H), 5.05 (d, J=10.6 Hz, 1H), 4.85-5.02 (m, 1H), 4.66-4.84 (m, 1H), 3.62-3.69 (m, 2H), 2.20-2.29 (m, 1H), 1.99 (tdd, J=9.2, 6.7, 2.3 Hz, 1H), 1.51 (s, 9H), 0.97-1.04 (m, 1H), 0.90-0.97 (m, 2H), 0.58 (q, J=5.7 Hz, 1H), −0.02-0.02 (s, 9H). LC/MS (ESI⁻) m/z=500.1 (M+H)⁺.

Preparation of Compound 204. To a stirred solution of tert-butyl((1S,5S,6S)-5-(5-amino-2-fluorophenyl)-5-(fluoromethyl)-2-thia-4-azabicyclo[4.1.0]hept-3-en-3-yl)((2-(trimethylsilyl)ethoxy)methyl)carbamate (204L, 2.85 g, 5.70 mmol) in DCM (20 mL) was added TFA (4.39 mL, 57.0 mmol). The mixture was stirred at RT for 5 h then concentrated to dryness. The residue was treated with H₂O and basified with saturated aqueous NaHCO₃. The solid was collected, washed with H₂O, dried and purified by silica gel chromatography (0-40% acetone/DCM) to give (1S,5S,6S)-5-(5-amino-2-fluorophenyl)-5-(fluoromethyl)-2-thia-4-azabicyclo[4.1.0]hept-3-en-3-amine (204, 1.2 g, 78%). LC/MS (ESI⁻) m/z=270.1 (M+H)⁺. ¹H NMR (300 MHz, CHLOROFORM-d) δ 6.78-7.03 (m, 2H), 6.55 (td, J=3.45, 8.44 Hz, 1H), 4.01-5.31 (m, 4H), 3.08-3.97 (m, 2H), 2.29 (ddd, J=5.04, 7.53, 8.92 Hz, 1H), 1.87 (ddt, J=1.75, 6.87, 9.06 Hz, 1H), 1.08 (ddd, J=5.85, 7.38, 9.28 Hz, 1H), 0.50 (q, J=5.70 Hz, 1H).

(1S,5S,6S)-Methyl 3-amino-5-(5-amino-2,3-difluorophenyl)-5-(fluoromethyl)-2-thia-4-azabicyclo[4.1.0]hept-3-ene-1-carboxylate (205)

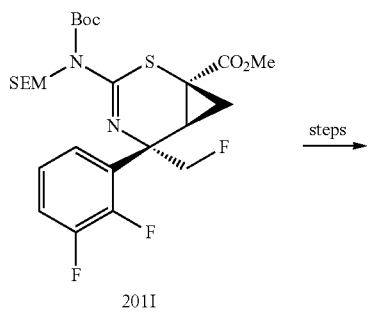

2011

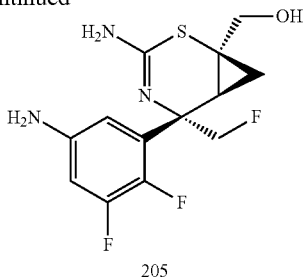

The title Compound was prepared from 201I using the chemical procedures similar to that described for intermediate 206 (see below). LC/MS (ESI⁻) m/z=318.0 (M+H)⁺. $^1$H NMR (400 MHz, DMSO-$d_6$) δ ppm 6.59-6.65 (m, 1H) 6.39 (ddd, J=12.57, 6.41, 2.74 Hz, 1H) 6.16 (s, 2H) 5.15 (s, 2H) 5.03 (t, J=5.97 Hz, 1H) 4.52-4.71 (m, 2H) 3.52 (dd, J=11.64, 6.16 Hz, 1H) 3.39 (dd, J=11.74, 5.67 Hz, 1H) 1.51-1.60 (m, 1H) 0.98 (dd, J=9.39, 5.09 Hz, 1H) 0.44 (t, J=5.67 Hz, 1H).

((1S,5S,6S)-3-Amino-5-(5-amino-2,3-difluorophenyl)-5-methyl-2-thia-4-azabicyclo[4.1.0]hept-3-en-1-yl)methanol (206)

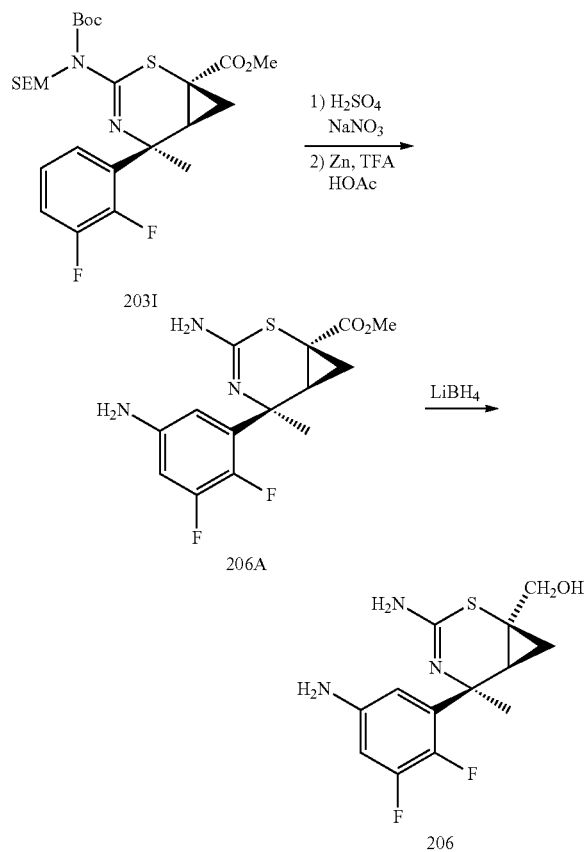

Preparation of Compound 206A. At RT, (1S,5S,6S)-methyl 3-((tert-butoxycarbonyl)((2-(trimethylsilyl)ethoxy)methyl)amino)-5-(2,3-difluorophenyl)-5-methyl-2-thia-4-azabicyclo[4.1.0]hept-3-ene-1-carboxylate (203I, 2.00 g, 3.69 mmol) was treated with 4 mL of sulfuric acid and stirred for 10 min, then chilled to 0° C. Sodium nitrate (0.41 g, 4.79 mmol) was added to the mixture. The mixture was stirred for 1 h. Additional sodium nitrate (0.41 g, 4.79 mmol) was added, and the mixture was warmed to RT. After 1 h, additional 3 mL of sulfuric acid was added (to try and solubilzed the starting material). The reaction was cooled to 0° C. to suppress an exotherm. After 30 min, the reaction mixture was poured into ~100 mL of wet ice. 50 mL of DCM was added. Potassium phosphate tribasic (29.70 g, 140 mmol) was added to the mixture over ~20 min. Aq 10 N NaOH was then added until the pH reached ~8. The mixture was extracted three times with 100 mL of 9:1 chloroform: IPA. The combined organic extracts were dried over $MgSO_4$. Filtration and concentration under reduced pressure afforded (1S,5S,6S)-methyl 3-amino-5-(2,3-difluoro-5-nitrophenyl)-5-methyl-2-thia-4-azabicyclo[4.1.0]hept-3-ene-1-carboxylate (LC/MS (ESI⁻) m/z=358.1 (M+H)⁺) as a sticky brown solid. The solid was taken up in 4 mL of HOAc and 2 mL of TFA. Zinc (nanopowder, 1.20 g, 18.43 mmol) was added to the mixture. The mixture was stirred for 30 min, and then concentrated under reduced pressure. The residue was taken up in 50 mL of 9:1 chloroform:IPA and basified to pH~8.0 with 1.0 N aq NaOH. ~10 mL of $NH_4OH$ was then added. The mixture was partitioned and the aqueous portion was extracted three times with 100 mL of 9:1 chloroform:IPA. The combined organic extracts were dried over $MgSO_4$. Filtration and concentration under reduced pressure, followed by flash chromatography on silica gel (40 g Grace column, eluted with 40-90% EtOAc in DCM) afforded (1S,5S,6S)-methyl 3-amino-5-(2,3-difluoro-5-nitrophenyl)-5-methyl-2-thia-4-azabicyclo[4.1.0]hept-3-ene-1-carboxylate (206A, 0.63 g, 52% yield) as a yellow solid. m/z (ESI, +ve ion) 328.1 (M+1)⁺. $^1$H NMR (400 MHz, CHLOROFORM-d) δ 6.74 (d, J=5.35 Hz, 1H), 6.39 (m, 1H), 3.78 (s, 3H), 3.59 (br. s., 2H), 2.52 (m, 1H), 1.69 (s, 3H), 1.56 (br., 2H), 1.54 (m, 1H), 1.11 (dd, J=5.18, 7.53 Hz, 1H).

Preparation of Compound 206. At RT, (1S,5S,6S)-methyl 3-amino-5-(5-amino-2,3-difluorophenyl)-5-methyl-2-thia-4-azabicyclo[4.1.0]hept-3-ene-1-carboxylate (206A, 0.63 g, 1.92 mmol) was taken up in 10 mL of THF and treated with lithium borohydride (2.0 M solution in THF, 4.81 ml, 9.62 mmol) followed by MeOH (1.56 mL, 38.5 mmol). The mixture was stirred for 15 h. The reaction was cooled to 0° C. and quenched by dropwise addition of 30 mL of sat aq $NH_4Cl$. The mixture was extracted twice with 20 mL of EtOAc and the combined organic extracts were washed with 20 mL of brine and dried over $MgSO_4$. Filtration and concentration under reduced pressure afforded ((1S,5S,6S)-3-amino-5-(5-amino-2,3-difluorophenyl)-5-methyl-2-thia-4-azabicyclo[4.1.0]hept-3-en-1-yl)methanol (206, 0.54 g, 1.80 mmol, 94% yield) as an off-white amorphous solid. m/z (ESI, +ve ion) 300.0 (M+1)⁺. $^1$H NMR (400 MHz, DMSO-$d_6$) δ 6.68 (br., 1H), 6.33 (m, 1H), 5.85 (br., 2H), 5.09 (br., 2H), 5.00 (t, J=5.87 Hz, 1H), 3.52 (dd, J=6.36, 11.64 Hz, 1H), 3.41 (dd, J=5.58, 11.64 Hz, 1H), 1.58 (m, 1H), 1.53 (s, 3H), 0.79 (m, 1H), 0.46 (t, J=5.58 Hz, 1H). $^{19}$F NMR (376 MHz, DMSO-$d_6$) δ −140.52 (d, J=23.35 Hz, 1F), −155.98 (d, J=23.35 Hz, 1F).

((1S,5S,6S)-3-Amino-5-(5-amino-2-fluorophenyl)-5-(fluoromethyl)-2-thia-4-azabicyclo[4.1.0]hept-3-en-1-yl)methanol (207)

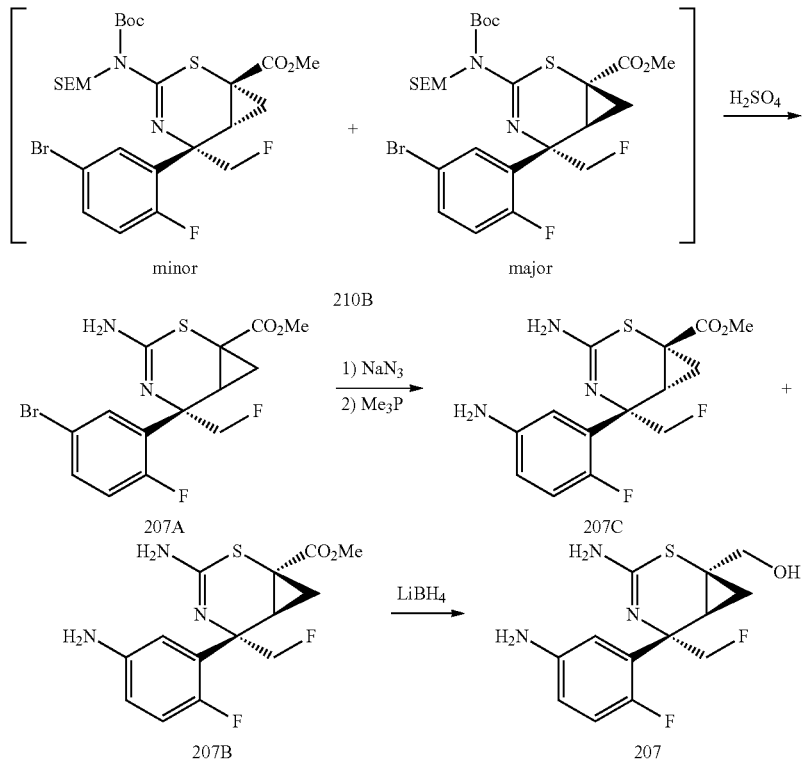

Preparation of Compound 207A. At RT, the mixture of diastereomers 210B (3.92 g, 6.31 mmol) was treated with conc. sulfuric acid (25 mL, 0.47 mol), and stirred at RT for 10 min. The sticky mixture was added to ice (200 mL) and EtOAc (50 mL). The pH was adjusted to 9 with 10 M NaOH. The aqueous phase was extracted with EtOAc (3×) and the combined organic extracts were washed with brine (1×), dried over MgSO$_4$, filtered, and concentrated to give (5S)-methyl 3-amino-5-(5-bromo-2-fluorophenyl)-5-(fluoromethyl)-2-thia-4-azabicyclo[4.1.0]hept-3-ene-1-carboxylate (207A) as an off white foam that was used in the next step without further purification. LC/MS (ESI) m/z=391.0 (M+H)$^+$.

Preparation of Compound 207B and Compound 207C. To a mixture of copper(I) iodide (0.241 g, 1.27 mmol), sodium azide (1.24 g, 19.1 mmol), and (5S)-methyl 3-amino-5-(5-bromo-2-fluorophenyl)-5-(fluoromethyl)-2-thia-4-azabicyclo[4.1.0]hept-3-ene-1-carboxylate (207A, material prepared as described above) at room temperature was added EtOH (9 mL) and water (4.5 mL). The reaction mixture was degassed by bubbling nitrogen through the solution for 5 min and N,N''-dimethylcyclohexane-1,2-diamine (0.200 mL, 1.27 mmol) was added. The reaction mixture was heated to 70° C. for 1.5 h and cooled to room temperature. The mixture was poured into 10:1 saturated NH$_4$Cl/ammonium hydroxide, and diluted with EtOAc. The aqueous phase was extracted with EtOAc (3×) and the combined organic extracts were washed with brine (1×), dried over MgSO$_4$, filtered, concentrated to give a dark yellow oil. The oil was dissolved in THF (20 mL) and water (7 mL) and trimethylphosphine (1.0 M solution in THF, 6.3 mL, 6.3 mmol) was added. The reaction mixture was stirred at RT for 15 min, transferred to a separatory funnel, and diluted with water and EtOAc. The aqueous phase was extracted with EtOAc (3×) and the combined organic extracts were washed with brine (1×), dried over MgSO$_4$, filtered, and concentrated to give a yellow foam. Purification by flash column chromatography on silica gel (80 g, eluted with 50% to 100% EtOAc in heptane gradient) gave (1S,5S,6S)-methyl 3-amino-5-(5-amino-2-fluorophenyl)-5-(fluoromethyl)-2-thia-4-azabicyclo[4.1.0]hept-3-ene-1-carboxylate (207B, 1.62 g) as a white foam. LC/MS (ESI) m/z=328.1 (M+H)$^+$. $^1$H NMR (400 MHz, CHLOROFORM-d) δ ppm 6.92 (d, J=6.40 Hz, 1H), 6.86 (dd, J=11.64, 8.51 Hz, 1H), 6.56 (dt, J=8.51, 3.47 Hz, 1H), 4.93 (dd, J=8.61, 1.17 Hz, 1H), 4.82 (dd, J=8.61, 1.37 Hz, 1H), 4.72 (d, J=9.39 Hz, 1H), 4.66 (s br, 2H), 4.61 (d, J=8.61 Hz, 1H), 3.77 (s, 3H), 3.56 (s br, 2H), 2.50-2.57 (m, 1H), 1.69 (dd, J=9.98, 5.09 Hz, 1H), 1.02 (dd, J=7.24, 5.09 Hz, 1H). In addition, (1R,5S,6R)-methyl 3-amino-5-(5-amino-2-fluorophenyl)-5-(fluoromethyl)-2-thia-4-azabicyclo[4.1.0]hept-3-ene-1-carboxylate (207C, 0.280 g) was isolated as a yellow foam. LC/MS (ESI) m/z=328.1 (M+H)$^+$. $^1$H NMR (400 MHz, CHLOROFORM-d) δ ppm 6.81-6.88 (m, 1H), 6.53-6.59 (m, 2H), 4.66 (s br, 2H), 4.53-4.83 (m, 2H), 3.74 (s, 3H), 3.52 (s br, 2H), 2.79 (dd, J=9.78, 7.43 Hz, 1H), 1.71 (dd, J=9.49, 5.38 Hz, 1H), 1.42-1.60 (m, 1H).

Preparation of Compound 207. To a solution of (1S,5S,6S)-methyl 3-amino-5-(5-amino-2-fluorophenyl)-5-(fluoromethyl)-2-thia-4-azabicyclo[4.1.0]hept-3-ene-1-carboxylate (207B, 1.24 g, 3.79 mmol) in THF (15 mL) at RT was added lithium borohydride (2.0 M solution in THF, 5.70 mL, 11.4 mmol) and MeOH (1.20 mL, 29.6 mmol). The reaction mixture was stirred at room temperature for 4 h and quenched slowly with saturated NH₄Cl. After bubbling ceased, the mixture was transferred to a separatory funnel and diluted with water, EtOAc, and saturated NH₄Cl. The aqueous phase was extracted with EtOAc (4×) and the combined organic extracts were washed with brine (1×), dried over MgSO₄, filtered, concentrated. Purification by flash column chromatography on silica gel (40 g, eluted with 40% to 100% EtOAc [10% MeOH (2 M NH₃)] in heptane gradient) gave ((1S,5S,6S)-3-amino-5-(5-amino-2-fluorophenyl)-5-(fluoromethyl)-2-thia-4-azabicyclo[4.1.0]hept-3-en-1-yl)methanol (207, 1.06 g, 3.54 mmol, 93% yield) as a white solid. LC/MS (ESI) m/z=300.0 (M+H)⁺. ¹H NMR (400 MHz, DMSO-d6) δ ppm 6.84 (dd, J=6.85, 2.93 Hz, 1H), 6.79 (dd, J=12.32, 8.61 Hz, 1H), 6.43 (dt, J=8.22, 3.52 Hz, 1H), 6.12 (s, 2H), 5.02 (t, J=5.97 Hz, 1H), 4.84 (s, 2H), 4.66-4.74 (m, 1H), 4.54-4.61 (m, 1H), 3.53 (dd, J=11.54, 6.26 Hz, 1H), 3.39 (dd, J=11.54, 5.48 Hz, 1H), 1.54-1.60 (m, 1H), 0.95 (dd, J=9.49, 4.99 Hz, 1H), 0.41 (t, J=5.77 Hz, 1H).

(1S,5S,6S)-Methyl 3-amino-5-(5-amino-2,3-difluorophenyl)-5-(fluoromethyl)-2-thia-4-azabicyclo[4.1.0]hept-3-ene-1-carboxylate (208)

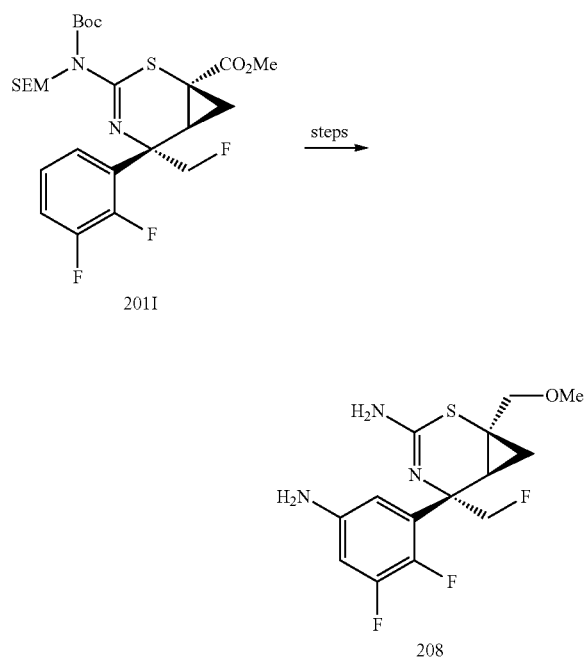 [SMILES: COC(=O)[C@]12C[C@H]1[C@@](CF)(c1cccc(F)c1F)N=C(N(COCC[Si](C)(C)C)C(=O)OC(C)(C)C)S2 ; COC[C@]12C[C@H]1[C@@](CF)(c1cc(N)cc(F)c1F)N=C(N)S2]

The title compound was prepared from 201I using the chemical procedures described for intermediate 209 (see below), except LHMDS was used in the place of NaHMDS. LC/MS (ESI⁻) m/z=332.0 (M+H)⁺. ¹H NMR (400 MHz, Chloroform-d) δ ppm (ddd, J=5.18, 2.93, 1.86 Hz, 1H) 6.38-6.45 (m, 1H) 4.56-4.91 (m, 3H) 3.60-3.65 (m, 1H) 3.39 (s, 3H) 3.31-3.37 (m, 1H) 1.69-1.75 (m, 1H) 1.10 (dd, J=9.59, 5.67 Hz, 1H) 0.74 (t, J=6.16 Hz, 1H).

(1S,5S,6S)-5-(5-Amino-2,3-difluorophenyl)-1-(methoxymethyl)-5-methyl-2-thia-4-azabicyclo[4.1.0]hept-3-en-3-amine (209)

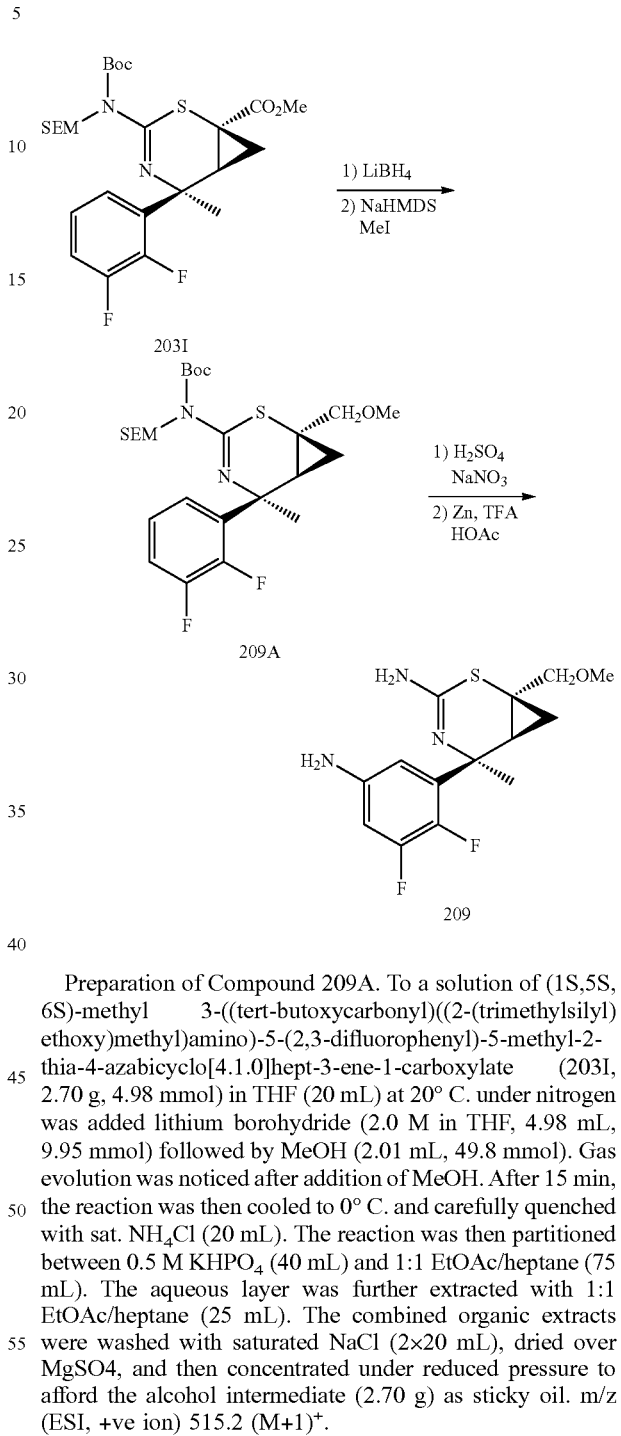

Preparation of Compound 209A. To a solution of (1S,5S,6S)-methyl 3-((tert-butoxycarbonyl)((2-(trimethylsilyl)ethoxy)methyl)amino)-5-(2,3-difluorophenyl)-5-methyl-2-thia-4-azabicyclo[4.1.0]hept-3-ene-1-carboxylate (203I, 2.70 g, 4.98 mmol) in THF (20 mL) at 20° C. under nitrogen was added lithium borohydride (2.0 M in THF, 4.98 mL, 9.95 mmol) followed by MeOH (2.01 mL, 49.8 mmol). Gas evolution was noticed after addition of MeOH. After 15 min, the reaction was then cooled to 0° C. and carefully quenched with sat. NH₄Cl (20 mL). The reaction was then partitioned between 0.5 M KHPO₄ (40 mL) and 1:1 EtOAc/heptane (75 mL). The aqueous layer was further extracted with 1:1 EtOAc/heptane (25 mL). The combined organic extracts were washed with saturated NaCl (2×20 mL), dried over MgSO4, and then concentrated under reduced pressure to afford the alcohol intermediate (2.70 g) as sticky oil. m/z (ESI, +ve ion) 515.2 (M+1)⁺.

To a solution of crude alcohol intermediate (2.70 g) in THF (6 mL) at 0° C. under nitrogen was added sodium bis(trimethylsilyl)amide (1.0 M in THF, 6.47 mL, 6.47 mmol) at a rate that did not exceed 5° C. The solution was stirred for 5 min at 0° C. then iodomethane (0.433 mL, 6.97 mmol) added at a rate that did not exceed 7° C. The cooling bath was removed and reaction stirred for 2 h at 20° C. The LCMS suggested 95% conversion. The reaction was quenched with sat. NH₄Cl (10 mL) and then partitioned between 0.5 M KHPO₄ (20 mL) with 1 M HCl (20 mL) and 1:1 EtOAc/heptane (75 mL). The aqueous portion was further extracted with 1:1 EtOAc/heptane (25 mL). The combined organic extracts were washed with sat. NaCl (2×20 mL), dried over MgSO₄, and concentrated under reduced pressure. The residue was purified by silica gel chromatography (120 g) eluting with a gradient of 0-15% EtOAc/heptane to afford tert-butyl((1S,5S,6S)-5-(2,3-difluorophenyl)-1-(methoxymethyl)-5-methyl-2-thia-4-azabicyclo[4.1.0]hept-3-en-3-yl)((2-(trimethylsilyl)ethoxy)methyl)carbamate (209A, 2.00 g, 3.78 mmol, 76% yield) as colorless oil. m/z (ESI, +ve ion) 529.3 (M+1)⁺.

Preparation of Compound 209. At RT, to tert-butyl((1S,5S,6S)-5-(2,3-difluorophenyl)-1-(methoxymethyl)-5-methyl-2-thia-4-azabicyclo[4.1.0]hept-3-en-3-yl)((2-(trimethylsilyl)ethoxy)methyl)carbamate (209A, 2.0 g, 3.78 mmol) in a 250 mL round bottom flask equipped with a magnetic stir bar and nitrogen line (no solvent) at 0° C. was added chilled (0° C.) neat sulfuric acid (15 mL). The internal temperature reached to 5° C., gas evolution was evident, and a red color developed. After 15 min, the reaction was cooled with an ice bath and treated with sodium nitrate (0.35 g, 4.16 mmol) in one portion. After 10 min, the reaction was poured onto wet ice (100 mL) contained in a 500 mL Erylmeyer flask. That flask was then jacketed with a wet ice cooling bath. To the mixture was added CH₂Cl₂ (50 mL) followed by dropwise addition of NaOH (4 M, 150 mL) at a rate that did not exceed an internal temp of 5° C. until pH 14 was achieved. To the flask was added 9:1 CHCl₃/IPA (50 mL). The mixture was transferred to a separatory funnel and the layers were separated. The aqueous portion was further extracted with CHCl₃/IPA (2×50 mL). The combined organic extracts were dried over MgSO₄, and concentrated under reduced pressure. The residue was purified by silica gel chromatography (120 g) eluting with a 0-1.5% of 2 M NH₃ in MeOH in CH₂Cl₂ to afford (1S,5S,6S)-5-(2,3-difluoro-5-nitrophenyl)-1-(methoxymethyl)-5-methyl-2-thia-4-azabicyclo[4.1.0]hept-3-en-3-amine (0.63 g, 1.83 mmol, 48% yield) as amber oil. m/z (ESI, +ve ion) 344.0 (M+1)⁺.

To a stirring solution of (1S,5S,6S)-5-(2,3-difluoro-5-nitrophenyl)-1-(methoxymethyl)-5-methyl-2-thia-4-azabicyclo[4.1.0]hept-3-en-3-amine (0.63 g, 1.83 mmol) in glacial HOAc (5 mL) and TFA (5 mL) at 20° C. was added nanopowder zinc (0.67 g, 10.29 mmol). After 90 min the reaction was concentrated under reduced pressure to a thick oil/suspension. The residue was partitioned between 9:1 CHCl₃/IPA (50 mL) and 10% NH₄OH (50 mL). The separated aqueous layer was further washed with 9:1 CHCl₃/IPA (20 mL). The combined organic solution was washed with sat. NaCl (20 mL), dried over MgSO₄, and concentrated under reduced pressure. The residue was purified by silica gel chromatography eluting with a gradient of 1-6% of 2 M NH₃ in MeOH in DCM to afford (1S,5S,6S)-5-(5-amino-2,3-difluorophenyl)-1-(methoxymethyl)-5-methyl-2-thia-4-azabicyclo[4.1.0]hept-3-en-3-amine (209, 0.53 g, 1.69 mmol, 92% yield) as tan foam. m/z (ESI, +ve ion) 314.1 (M+1)⁺. ¹H NMR (400 MHz, DMSO-d₆) δ 6.67 (br., 1H), 6.36 (m, 1H), 5.92 (br., 2H), 5.12 (br. s., 2H), 3.55 (d, J=10.95 Hz, 1H), 3.36 (d, J=10.95 Hz, 1H), 3.32 (s, 3H), 1.61 (br., 1H), 1.56 (s, 3H), 0.87 (br., 1H), 0.57 (br., 1H).

(1S,5S,6S)-5-(5-Amino-2-fluorophenyl)-5-(fluoromethyl)-1-(methoxymethyl)-2-thia-4-azabicyclo[4.1.0]hept-3-en-3-amine (210)

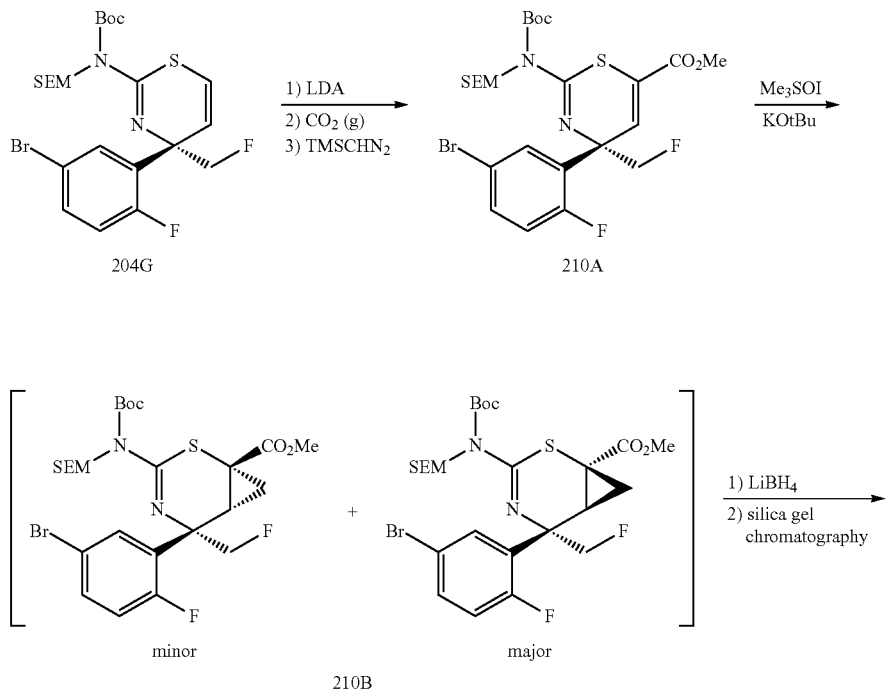

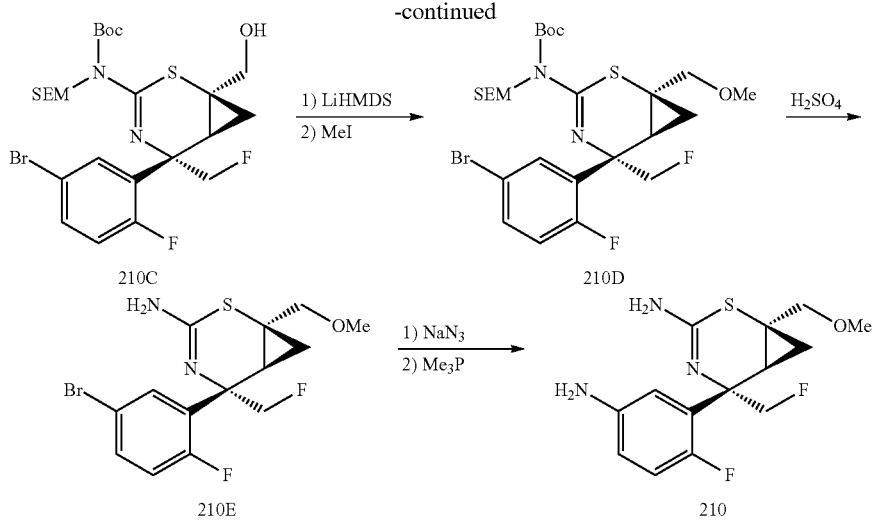

Preparation of Compound 210A. To a solution of (S)-tert-butyl(4-(5-bromo-2-fluorophenyl)-4-(fluoromethyl)-4H-1,3-thiazin-2-yl)((2-(trimethylsilyl)ethoxy)methyl)carbamate (204G, 40.2 g, 73.2 mmol) in THF (270 mL) under $N_2$ at −78° C. was added lithium diisopropylamide (2 M solution in THF/heptane/ethylbenzene, 36.6 mL, 73.2 mmol) dropwise at the rate where internal temperature did not exceed −50° C. After addition, the mixture was then stirred at the same temperature for 45 min. $CO_2$ (gas) was bubbled into the mixture at the rate where internal temperature did not exceed −50° C. for 30 min. The mixture was warmed to RT and was quenched with saturated ammonium chloride. It was diluted with EtOAc and $H_2O$. The organic layer was separated, washed with HCl (1 N) followed by brine, dried over $MgSO_4$, and concentrated. The residue was dissolved in THF (220 mL) and MeOH (24.44 mL) and cooled with an ice bath. (Trimethylsilyl)diazomethane (2.0 M solutions in hexanes, 43.9 mL, 88 mmol) was added dropwise to the mixture. It was stirred at 0° C. for 20 min and quenched with HOAc (5 mL). The mixture was washed with saturated $NaHCO_3$, brine, dried over $MgSO_4$, and concentrated. The residue was purified by silica gel flash column chromatography using ISCO instrument (0%-15% EtOAc/heptane) to give (S)-methyl 4-(5-bromo-2-fluorophenyl)-2-((tert-butoxycarbonyl)((2-(trimethylsilyl)ethoxy)methyl)amino)-4-(fluoromethyl)-4H-1,3-thiazine-6-carboxylate (210A, 31.2 g, 51.4 mmol, 70% yield) as a white solid. LC/MS (ESI⁻) m/z=607.1, 609.0, 629.0, 631.1. ¹H NMR (CHLOROFORM-d) δ: 7.65 (dd, J=6.8, 2.5 Hz, 1H), 7.42 (ddd, J=8.6, 4.3, 2.5 Hz, 1H), 7.22 (d, J=4.5 Hz, 1H), 6.96 (dd, J=11.2, 8.6 Hz, 1H), 5.27-5.43 (m, 2H), 4.55-4.96 (m, 2H), 3.84 (s, 3H), 3.63-3.72 (m, 2H), 1.56 (s, 9H), 0.95-1.02 (m, 2H), 0.00 (s, 9H).

Preparation of Compound 210B. To a solution of trimethylsulfoxonium iodide (8.74 g, 39.7 mmol) in dimethyl sulfoxide (39 mL) at 0° C. under $N_2$ was added potassium tert-butoxide (4.19 g, 37.3 mmol) in two portions. The reaction mixture (A) was stirred at RT for 1 h. 20 mL of reaction mixture (A) was added to a solution of (S)-methyl 4-(5-bromo-2-fluorophenyl)-2-((tert-butoxycarbonyl)((2-(trimethylsilyl)ethoxy)methyl)amino)-4-(fluoromethyl)-4H-1,3-thiazine-6-carboxylate (210A, 12.06 g, 19.85 mmol) in DMSO (50 mL) dropwise. After addition, the mixture was then stirred RT for 1 h. LCMS showed some starting material. It was treated with additional 2 mL of the mixture A and stirred at RT for overnight. LCMS showed some starting material. It was treated with 4 mL of the mixture A and stirred at RT for 4.5 h. LCMS showed no starting material. The reaction mixture was quenched with saturated $NH_4Cl$ and extracted with EtOAc (2×). The organic solution was washed with brine, dried over $MgSO_4$, and concentrated to give 13.16 g of thick oil, 210B, as a mixture of (1R,5S,6R)-methyl 5-(5-bromo-2-fluorophenyl)-3-((tert-butoxycarbonyl)((2-(trimethylsilyl)ethoxy)methyl)amino)-5-(fluoromethyl)-2-thia-4-azabicyclo[4.1.0]hept-3-ene-1-carboxylate (minor product) and (1S,5S,6S)-methyl-5-(5-bromo-2-fluorophenyl)-3-((tert-butoxycarbonyl)((2-(trimethylsilyl)ethoxy)methyl)amino)-5-(fluoromethyl)-2-thia-4-azabicyclo[4.1.0]hept-3-ene-1-carboxylate (major product). LC/MS (ESI⁻) m/z=621.0, 623.2

Preparation of Compound 210C. To a solution of 210B (6.1 g, 9.81 mmol) in THF (50 mL) at 0° C. under $N_2$ was added lithium borohydride (2 M solution in THF, 9.81 mL, 19.63 mmol) dropwise followed by MeOH (3.18 mL, 79 mmol). The mixture was stirred at 0° C. for 1 h and 45 min. It was quenched with saturated ammonium chloride, washed with HCl (1 N), then saturated $NaHCO_3$, brine, dried over $MgSO_4$, and concentrated. The residue was purified by silica gel flash column chromatography using ISCO instrument (0%-80% EtOAc/heptane) to give tert-butyl((1S,5S,6S)-5-(5-bromo-2-fluorophenyl)-5-(fluoromethyl)-1-(hydroxymethyl)-2-thia-4-azabicyclo[4.1.0]hept-3-en-3-yl)((2-(trimethylsilyl)ethoxy)methyl)carbamate (210C, 4.6 g, 7.75 mmol, 79% yield) as a light yellow oil. LC/MS (ESI⁻) m/z=593.2, 595.1. ¹H NMR (CHLOROFORM-d) δ: 7.77 (dd, J=6.8, 2.5 Hz, 1H), 7.40 (ddd, J=8.5, 4.3, 2.5 Hz, 1H), 6.96 (dd, J=11.5, 8.6 Hz, 1H), 5.28-5.31 (m, 1H), 5.07 (d, J=10.6 Hz, 1H), 4.82-4.99 (m, 1H), 4.61-4.79 (m, 1H), 3.49-3.87 (m, 4H), 1.88-1.95 (m, 1H), 1.52 (s, 9H), 0.94-1.07 (m, 3H), 0.73 (t, J=6.4 Hz, 1H), 0.00 (s, 9H)

Preparation of Compound 210D. To a solution of tert-butyl((1S,5S,6S)-5-(5-bromo-2-fluorophenyl)-5-(fluoromethyl)-1-(hydroxymethyl)-2-thia-4-azabicyclo[4.1.0]hept-3-en-3-yl)((2-(trimethylsilyl)ethoxy)methyl)carbamate (210C, 3.2 g, 5.39 mmol) in THF (20 mL) under $N_2$ at 0° C. was added lithium bis(trimethylsilyl)amide (1.0 M solution in THF, 8.09 mL, 8.09 mmol) dropwise. After addition, the mixture was stirred at 0° C. for 30 min and iodomethane (0.502 mL, 8.09 mmol) was added dropwise. It was stirred at 0° C. for 20 min followed by RT overnight. The mixture was quenched with saturated NH₄Cl and diluted with H₂O. It was extracted with EtOAc (2×). The combined organic extracts were washed with brine, dried over MgSO₄, and concentrated. The residue was purified by silica gel flash column chromatography using ISCO instrument (10%-60% EtOAc/heptane) to give tert-butyl((1S,5S,6S)-5-(5-bromo-2-fluorophenyl)-5-(fluoromethyl)-1-(methoxymethyl)-2-thia-4-azabicyclo[4.1.0]hept-3-en-3-yl)((2-(trimethylsilyl)ethoxy)methyl)carbamate (210D, 3.17 g, 5.22 mmol, 97% yield) as a light yellow oil. LC/MS (ESI⁻) m/z=607.1, 609.0. ¹H NMR (CHLOROFORM-d) δ: 7.83 (dd, J=6.9, 2.4 Hz, 1H), 7.36-7.42 (m, 1H), 6.96 (dd, J=11.6, 8.7 Hz, 1H), 5.01-5.32 (m, 2H), 4.64-4.96 (m, 2H), 3.63-3.69 (m, 2H), 3.39 (s, 3H), 1.87 (t, J=7.1 Hz, 1H), 1.52 (s, 9H), 0.94-1.06 (m, 3H), 0.77 (t, J=6.2 Hz, 1H), 0.00 (s, 9H).

Preparation of Compound 210E. To a RBF containing tert-butyl((1S,5S,6S)-5-(5-bromo-2-fluorophenyl)-5-(fluoromethyl)-1-(methoxymethyl)-2-thia-4-azabicyclo[4.1.0]hept-3-en-3-yl)((2-(trimethylsilyl)ethoxy)methyl)carbamate (210D, 3.17 g, 5.22 mmol) at 0° C. was added conc. sulfuric acid (13.90 mL, 261 mmol) dropwise. After the addition, the mixture was stirred at 0° C. for 30 min. It was adjusted to pH=10-14 by 5 N NaOH. The mixture was extracted with EtOAc (2×). The combined organic extracts were washed with brine, dried over MgSO₄, and concentrated. The residue was purified by silica gel flash column chromatography using ISCO instrument (0%-10% MeOH/DCM) to give (1S,5S,6S)-5-(5-bromo-2-fluorophenyl)-5-(fluoromethyl)-1-(methoxymethyl)-2-thia-4-azabicyclo[4.1.0]hept-3-en-3-amine (210E, 1.73 g, 4.59 mmol, 88% yield) as a yellow solid. LC/MS (ESI⁻) m/z=377.0, 379.0. ¹H NMR (CHLOROFORM-d) δ: 7.78 (dd, J=7.0, 2.5 Hz, 1H), 7.38 (ddd, J=8.6, 4.2, 2.7 Hz, 1H), 6.94 (dd, J=11.5, 8.6 Hz, 1H), 5.30 (s, 1H), 4.52-4.92 (m, 3H), 3.62 (d, J=10.6 Hz, 1H), 3.39 (s, 3H), 3.35 (d, J=10.6 Hz, 1H), 1.77 (t, J=8.2 Hz, 1H), 1.08 (dd, J=9.6, 5.9 Hz, 1H), 0.74 (t, J=6.3 Hz, 1H)

Preparation of Compound 210. To a solution of (1S,5S,6S)-5-(5-bromo-2-fluorophenyl)-5-(fluoromethyl)-1-(methoxymethyl)-2-thia-4-azabicyclo[4.1.0]hept-3-en-3-amine (210E, 1.73 g, 4.59 mmol) in EtOH (3.0 mL), IPA (3.0 mL), and water (1.50 mL) was added sodium azide (0.894 g, 13.76 mmol), copper(i) iodide (0.218 g, 1.146 mmol), sodium L-ascorbate (0.227 g, 1.146 mmol), and trans-N,N'-dimethylcyclohexane-1,2-diamine (0.181 mL, 1.146 mmol). Then, N₂ was bubbled into the mixture for 5 min. The mixture was stirred at 70° C. under N₂ for 3 h. It was quenched with saturated NH₄Cl/NH₄OH (10:1), extracted with EtOAc (2×). The combined organic extracts were dried over MgSO₄ and concentrated. The residue was dissolved in THF/H₂O (9:1, 20 mL) and trimethylphosphine (1.0M solution in THF) (4.59 mL, 4.59 mmol) was added. After the mixture was stirred at RT for 30 min, it was quenched with saturated NaHCO₃, and extracted with EtOAc. The organic solution was washed with brine, dried over MgSO₄ and concentrated. The residue was purified by silica gel flash column chromatography using ISCO instrument (0%-20% MeOH/DCM) to give (1S,5S,6S)-5-(5-amino-2-fluorophenyl)-5-(fluoromethyl)-1-(methoxymethyl)-2-thia-4-azabicyclo[4.1.0]hept-3-en-3-amine (210, 1.07 g, 3.41 mmol, 74.5% yield) as a yellow solid. LC/MS (ESI⁻) m/z=314.1. ¹H NMR (CHLOROFORM-d) δ: 6.89 (d, J=4.1 Hz, 1H), 6.84 (dd, J=11.6, 8.7 Hz, 1H), 6.54 (d, J=8.4 Hz, 1H), 4.58-4.93 (m, 2H), 3.63 (d, J=10.6 Hz, 1H), 3.38 (s, 3H), 3.33 (d, J=10.4 Hz, 1H), 1.75 (t, J=8.1 Hz, 1H), 1.04-1.11 (m, 1H), 0.72 (t, J=6.3 Hz, 1H).

(1S,5S,6S)-5-(5-Amino-2,3-difluorophenyl)-1-(difluoromethyl)-5-methyl-2-thia-4-azabicyclo[4.1.0]hept-3-en-3-amine (211)

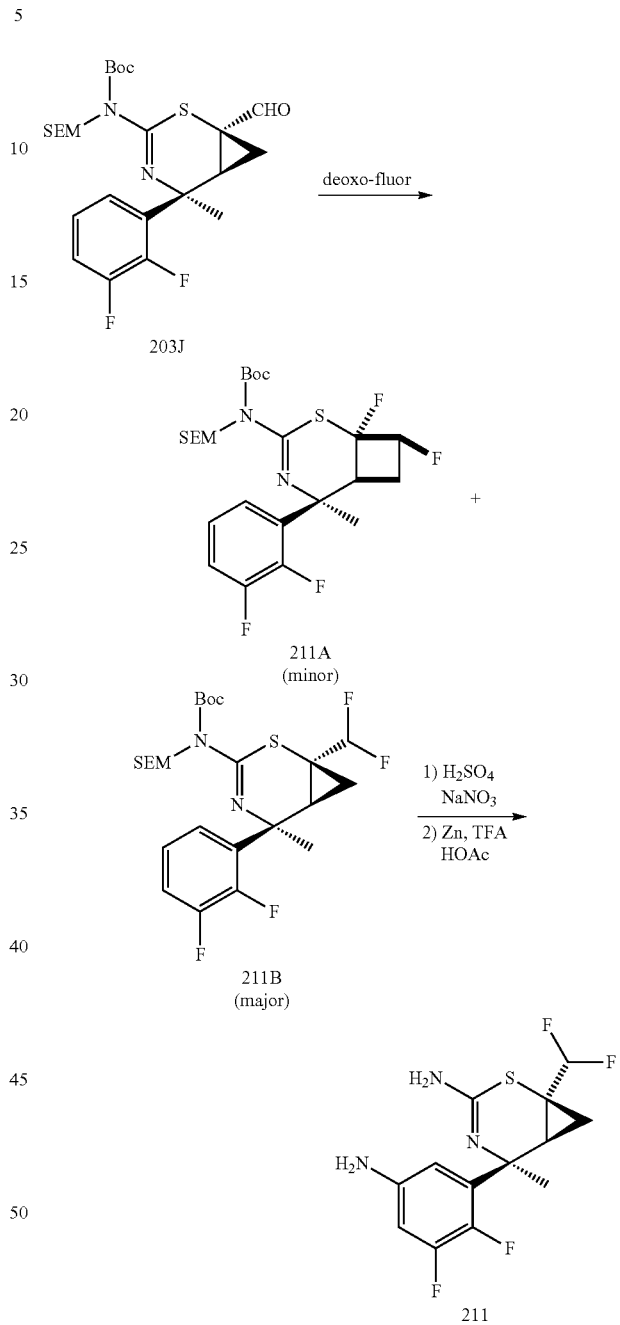

Preparation of Compound 211B. At −10° C. (ice/salt), to a stirred solution of tert-butyl((1S,5S,6S)-5-(2,3-difluorophenyl)-1-formyl-5-methyl-2-thia-4-azabicyclo[4.1.0]hept-3-en-3-yl)((2-(trimethylsilyl)ethoxy)methyl)carbamate (203J, 380 mg, 0.74 mmol) in 5 mL of DCM was added deoxo-fluor (0.48 mL, 2.59 mmol). It was stirred at 0° C. for 1 h then RT for 2 h. It was diluted with 30 mL of DCM, washed with 20 mL of sat NaHCO₃ followed by 5 mL of brine. The organic solution was dried over sodium sulfate and concentrated. The residue was purified on a silica gel column (5-10% EtOAc in hexanes) to give:

1) 1st eluent, tert-butyl((1R,5S,6S,8S)-5-(2,3-difluorophenyl)-1,8-difluoro-5-methyl-2-thia-4-azabicyclo[4.2.0]oct-3-en-3-yl)((2-(trimethylsilyl)ethoxy)methyl) carbamate (211A, 95 mg, 24% yield) as brown thick oil. m/z (ESI, +ve ion) 535.1 (M+1)+. 1H NMR (400 MHz, CHLOROFORM-d) δ 7.43 (t, J=7.40 Hz, 1H), 7.10 (m, 2H), 5.30 (d, J=10.76 Hz, 1H), 5.07-5.16 (m, 0.5H), 5.03 (d, J=8.61 Hz, 1H), 5.00 (m, 0.5H), 3.69 (m, 2H), 2.97 (m, 1H), 1.76 (m., 1H), 1.67 (s, 3H), 1.52 (s, 9H), 1.20 (m, 1H), 0.94 (m, 2H), 0.02 (s, 9H). 19F NMR (376 MHz, CHLOROFORM-d) δ −112.71 (s, 1F), −138.50 (d, J=19.94 Hz, 1F), −139.76 (d, J=19.94 Hz, 1F), −173.68 (s, 1F).

2) 2nd eluent, tert-butyl((1S,5S,6S)-1-(difluoromethyl)-5-(2,3-difluorophenyl)-5-methyl-2-thia-4-azabicyclo[4.1.0]hept-3-en-3-yl)((2-(trimethylsilyl)ethoxy)methyl) carbamate (211B, 249 mg, 0.46 mmol, 62% yield) as brown sticky oil. m/z (ESI, +ve ion) 535.1 (M+1)+. 1H NMR (400 MHz, CHLOROFORM-d) δ 7.34 (m, 1H), 7.07 (m, 2H), 5.55-5.88 (m, 1H), 5.29 (d, J=10.37 Hz, 1H), 5.05 (d, J=10.56 Hz, 1H), 3.65 (m, 2H), 2.11 (dd, J=7.73, 9.29 Hz, 1H), 1.78 (s, 3H), 1.52 (s, 9H), 1.23 (m, 1H), 0.95 (m, 3H), 0.00 (s, 9H). 19F NMR (376 MHz, CHLOROFORM-d) δ −118.00 (d, 1J=280 Hz, 1F), −120.01 (d, 1J=280 Hz, 1F), −138.73 (d, 2J=19.94 Hz, 1F), −139.18 (d, 2J=19.94 Hz, 1F).

Preparation of Compound 211. At RT, sulfuric acid (1 mL, 18.76 mmol) was added to tert-butyl((1S,5S,6S)-1-(difluoromethyl)-5-(2,3-difluorophenyl)-5-methyl-2-thia-4-azabicyclo[4.1.0]hept-3-en-3-yl)((2-(trimethylsilyl)ethoxy)methyl)carbamate (211B, 120 mg, 0.22 mmol). It was stirred at RT for 10 min. It was cooled with an ice bath and treated with sodium nitrate (24.80 mg, 0.29 mmol). Ice bath was removed. The mixture was stirred at RT for 2 h. It was cooled with an ice bath, treated with ice cube followed by 15 mL of DCM then potassium phosphate tribasic monohydrate (4.60 g, 20 mmol) in small portions. 2 mL of 2 N NaOH was added and pH was about 10. It was extracted with 2×20 mL of (9:1=CHCl3:iPrOH). The organic extracts were washed with 5 mL of brine and concentrated. The resulting brown residue containing (1S,5S,6S)-5-(2,3-difluoro-5-nitrophenyl)-1-(difluoromethyl)-5-methyl-2-thia-4-azabicyclo[4.1.0]hept-3-en-3-amine was dissolved in 0.8 mL of glacial HOAc and 0.4 mL of TFA and treated with zinc (nanopowder, 88 mg, 1.34 mmol) at RT. It was stirred at RT for 3 h then concentrated under reduced pressure to remove TFA. The residue was basified with 2 N NaOH until pH was about 10. The mixture was extracted with 2×20 mL of (9:1=CHCl3:iPrOH). The organic extracts were washed with 5 mL of brine and concentrated. The residue was purified on a silica gel column (5% MeOH in DCM followed by 5% 2 M NH3 in MeOH in DCM) to provide (1S,5S,6S)-5-(5-amino-2,3-difluorophenyl)-1-(difluoromethyl)-5-methyl-2-thia-4-azabicyclo[4.1.0]hept-3-en-3-amine (211, 47 mg, 0.15 mmol, 65% yield) as a brown amorphous solid. m/z (ESI, +ve ion) 320.0 (M+1)+. 1H NMR (400 MHz, DMSO-d6) δ 6.52 (br., 1H), 6.38 (m, 2H), 6.23 (br., 1H), 5.77-6.04 (m, 1H), 5.14 (br., 2H), 1.84 (m, 1H), 1.59 (s, 3H), 1.30 (m, 1H), 0.67 (m, 1H). 19F NMR (376 MHz, CHLOROFORM-d) δ −118.06 (d, 1J=273 Hz, 1F), −115.47 (d, 1J=273 Hz, 1F), −140.28 (d, 2J=22.54 Hz, 1F), −155.35 (d, 2J=22.64 Hz, 1F).

(1S,5S,6S)-Ethyl 3-amino-5-(5-amino-2,3-difluorophenyl)-5-methyl-2-thia-4-azabicyclo[4.1.0]hept-3-ene-1-carboxylate (212)

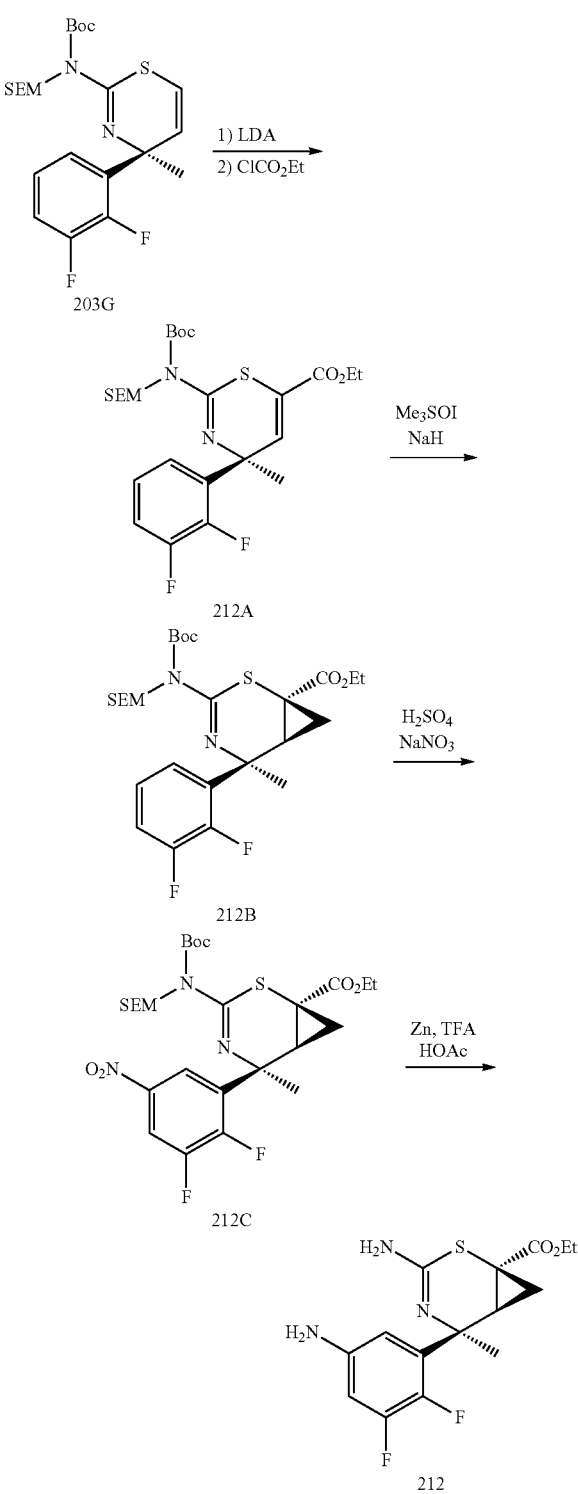

Preparation of Compound 212A. In a 500 mL RBF, a solution of (S)-tert-butyl(4-(2,3-difluorophenyl)-4-methyl-4H-1,3-thiazin-2-yl)((2-(trimethylsilyl)ethoxy)methyl)carbamate (3.05 g, 6.48 mmol) in 30 mL of THF at −78° C. was treated with lithium diisopropylamide (2 M solution in heptane/THF/ethylbenzene) (4.21 mL, 8.42 mmol) dropwise. The resulting mixture was stirred at −78° C. for 45 min and treated with ethyl chloroformate (1.852 mL, 19.44 mmol) via a syringe in one shot. The mixture was stirred for 30 min at −78° C., then quenched with 50 mL of aq. NH$_4$Cl and warmed to RT. It was extracted with (2×100 mL) of EtOAc. The organic layers were combined, washed with 15 mL of brine, dried over sodium sulfate and concentrated. The residue was purified via flash chromatography on silica gel (80 g Grace column, eluted with 5-15% EtOAc in hexanes) to give (S)-ethyl 2-((tert-butoxycarbonyl)((2-(trimethylsilyl)ethoxy)methyl)amino)-4-(2,3-difluorophenyl)-4-methyl-4H-1,3-thiazine-6-carboxylate (212A, 2.5 g, 4.61 mmol, 71% yield) as a colorless viscous oil. m/z (ESI, +ve ion) 543.0 (M+1)$^+$. $^1$H NMR (400 MHz, CHLOROFORM-d) δ 7.32 (m, 1H), 7.03-7.16 (m, 3H), 5.32 (d, J=10.37 Hz, 1H), 5.22 (d, J=10.37 Hz, 1H), 4.30 (m, 2H), 3.67 (m, 2H), 1.76 (s, 3H), 1.55 (s, 9H), 1.35 (t, J=7.14 Hz, 3H), 0.94 (m, 2H), 0.00 (s, 9H). $^{19}$F NMR (377 MHz, CHLOROFORM-d) δ −137.70 (d, J=20.27 Hz, 1F), −138.25 (d, J=20.27 Hz, 1F).

Preparation of Compound 212B. Preparation of Corey Chykovsky Reagent (0.25 M in DMSO): sodium hydride (60% wt.) (400 mg, 10 mmol) was added to a solution of trimethylsulfoxonium iodide (2.22 g, 10 mmol) in DMSO (40 mL) under argon. The mixture was stirred for 30 min before aliquots were used for cyclopropanation.

At RT, to a solution of (S)-ethyl 2-((tert-butoxycarbonyl)((2-(trimethylsilyl) ethoxy)methyl)amino)-4-(2,3-difluorophenyl)-4-methyl-4H-1,3-thiazine-6-carboxylate (212A, 2.5 g, 4.61 mmol) in 15 mL of THF was added freshly prepared Corey Chykovsky Reagent (0.25 M in DMSO) (27.6 mL, 6.91 mmol). The mixture was stirred at RT for 45 min. It was cooled with an ice bath and quenched with 50 mL of aq NH$_4$Cl, and extracted with (2×75 mL) EtOAc. The organic extracts were washed with 15 mL of brine, dried over MgSO$_4$ and concentrated under reduced pressure. The residue was purified via flash chromatography on silica gel (40 g Grace column, elute with 1-15% EtOAc in hexanes) to provide (1S,5S,6S)-ethyl 3-((tert-butoxycarbonyl)((2-(trimethylsilyl)ethoxy)methyl)amino)-5-(2,3-difluorophenyl)-5-methyl-2-thia-4-azabicyclo[4.1.0]hept-3-ene-1-carboxylate (212B, 2.11 g, 3.79 mmol, 82% yield) as a thick oil. m/z (ESI, +ve ion) 557.3 (M+1)$^+$.

Preparation of Compound 212C. At RT, sulphuric acid (5 mL, 94 mmol) was added to (1S,5S,6S)-ethyl 3-((tert-butoxycarbonyl)((2-(trimethylsilyl)ethoxy)methyl)amino)-5-(2,3-difluorophenyl)-5-methyl-2-thia-4-azabicyclo[4.1.0]hept-3-ene-1-carboxylate (2.03 g, 3.65 mmol). It was stirred at RT for 10 min then cooled with an ice bath and treated with sodium nitrate (0.40 g, 4.74 mmol). Ice bath was removed. The mixture was stirred at RT for 45 min. It was cooled with an ice bath, treated with ice cube followed by 15 mL of DCM then potassium phosphate tribasic monohydrate (23.03 g, 100 mmol) in small portions. The mixture had a pH of about 8; 5 mL of 1 N NaOH was added and pH was about 10. It was extracted with (2×50 mL) (9:1=CHCl$_3$:iPrOH). The organic extracts were concentrated and the residue was purified on a 40 g silica gel column (25-55% EtOAc in hexanes) to give (1S,5S,6S)-ethyl 3-amino-5-(2,3-difluoro-5-nitrophenyl)-5-methyl-2-thia-4-azabicyclo[4.1.0]hept-3-ene-1-carboxylate (212C, 1.21 g, 3.26 mmol, 89% yield) as a brown amorphous solid. m/z (ESI, +ve ion) 372.0 (M+1)$^+$. $^1$H NMR (400 MHz, DMSO-d$_6$) δ 8.51-8.56 (m, 1H), 8.37 (dt, J=3.13, 6.36 Hz, 1H), 6.46 (s, 2H), 4.19 (q, J=7.11 Hz, 2H), 2.41 (t, J=8.51 Hz, 1H), 1.63 (s, 3H), 1.42 (dd, J=5.28, 9.59 Hz, 1H), 1.27 (m, 3H), 1.04 (m, 1H).

Preparation of Compound 212. Zinc (0.819 g, 12.52 mmol) was added to a stirred mixture of (1S,5S,6S)-ethyl 3-amino-5-(2,3-difluoro-5-nitrophenyl)-5-methyl-2-thia-4-azabicyclo[4.1.0]hept-3-ene-1-carboxylate (0.93 g, 2.50 mmol) in HOAc (4 mL) and TFA (2 mL) at 0° C. The reaction mixture was stirred at RT for 45 min then concentrated under reduced pressure (to remove the TFA). The residue was partitioned between 150 mL of EtOAc and 20 mL of 5 N NaOH. The organic solution was washed with 5 mL of brine and concentrated. The resulting crude product was purified via silica gel flash column chromatography eluting with 2-5% MeOH in DCM to give (1S,5S,6S)-ethyl 3-amino-5-(5-amino-2,3-difluorophenyl)-5-methyl-2-thia-4-azabicyclo[4.1.0]hept-3-ene-1-carboxylate (212) (480 mg, 1.406 mmol, 56% yield) as a tan solid. m/z (ESI, +ve ion) 342.0 (M+1)$^+$. $^1$H NMR (400 MHz, DMSO-d$_6$) δ 6.71 (d, J=5.73 Hz, 1H), 6.37 (m, 1H), 6.10 (s, 2H), 5.16 (s, 2H), 4.17 (q, J=7.11 Hz, 2H), 2.29 (m, 1H), 1.55 (s, 3H), 1.42 (dd, J=4.89, 9.78 Hz, 1H), 1.21 (t, J=7.14 Hz, 3H), 0.95 (dd, J=5.09, 7.24 Hz, 1H). $^{19}$F NMR (376 MHz, DMSO-d$_6$) δ −140.14 (d, J=20.20 Hz, 1F), −156.28 (d, J=20.20 Hz, 1F).

(1R,5S,6S)-5-(5-Amino-2-fluorophenyl)-7,7-difluoro-5-methyl-2-thia-4-azabicyclo[4.1.0]hept-3-en-3-amine (213)

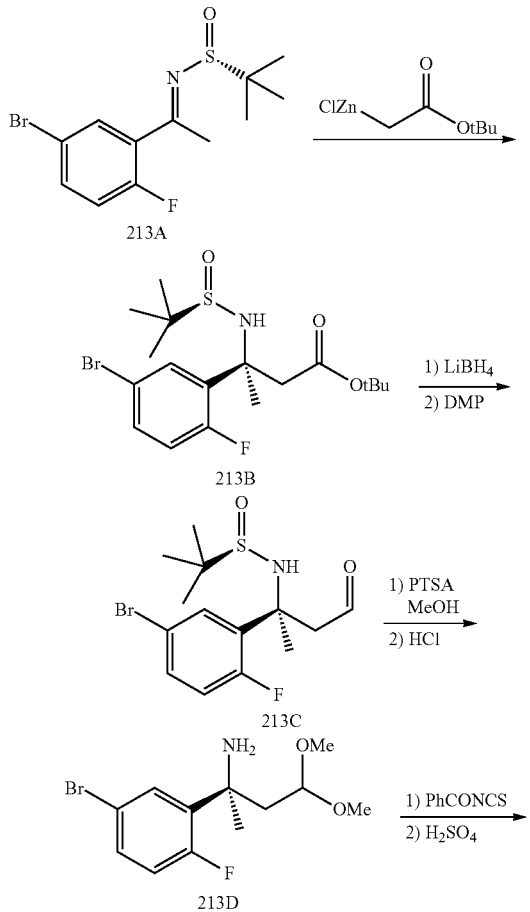

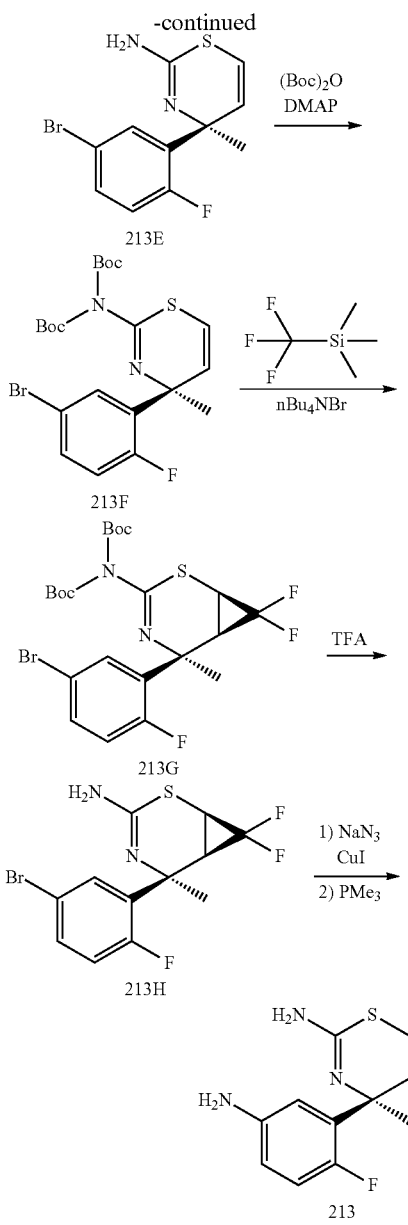

Preparation of (S)-tert-butyl 3-(5-bromo-2-fluorophenyl)-3-((R)-1,1-dimethylethylsulfinamido)butanoate (213B). To a 3-L 3-neck RBF was added (R,E)-N-(1-(5-bromo-2-fluorophenyl)ethylidene)-2-methylpropane-2-sulfinamide (213A, 51 g, 159 mmol) and THF (400 mL). The flask was equipped with a temperature probe, and an overhead stirrer. The solution was cooled in a dry ice/acetone bath to an internal temperature of −50.9° C. (2-(tert-butoxy)-2-oxoethyl)zinc (II) chloride (0.5 M in ether, 796 mL, 398 mmol, Rieke Metals) was added slowly to the stirring solution over 45 min via cannula. After 20 min, the dry ice/acetone bath was removed and the reaction warmed to ambient temperature and stirred for 16 h. The flask was placed in an ice/water bath and cooled to 5° C. before slowly adding saturated ammonium chloride (aq.) solution (300 mL) and water (300 mL). The reaction was extracted with EtOAc (2×300 mL). The combined organic layers were washed sequentially with a 9:1 saturated ammonium chloride to saturated ammonium hydroxide solution (2×) and brine before drying over magnesium sulfate and concentrating under reduced pressure to afford crude (S)-tert-butyl 3-(5-bromo-2-fluorophenyl)-3-((R)-1,1-dimethylethylsulfinamido)butanoate (74.44 g, 171 mmol, 213b, 107% yield) as a yellow oil which solidified upon sitting. The material was used in the next step without further purification assuming theoretical yield. MS m/z=436.0 M+.

Preparation of (R)—N—((S)-2-(5-bromo-2-fluorophenyl)-4-oxobutan-2-yl)-2-methylpropane-2-sulfinamide (213C). A 3-neck 3-L RBF was charged with a solution of (S)-tert-butyl 3-(5-bromo-2-fluorophenyl)-3-((R)-1,1-dimethylethylsulfinamido)butanoate (64.9 g, 149 mmol, 213b) in THF (400 mL). The flask was equipped with an overhead stirrer, a 250 mL addition funnel, and a temperature probe. The addition funnel was charged with LiBH$_4$ (2.0 M in THF, 186 mL, 372 mmol, Sigma Aldrich) via cannula. The LiBH$_4$ was added to the stirring solution at room temperature. The addition funnel was removed and replaced with a 125 mL addition funnel which was subsequently charged with MeOH (30.1 mL, 744 mmol). The MeOH was added dropwise to the stirring solution at RT via addition funnel. Evolution of gas observed and the internal temperature of the reaction rose to 47.5° C. over the course of the reaction and then began to subside. Upon reaching an internal temperature of 26° C., a 250 mL addition funnel was attached to the reaction flask and charged with an additional portion of LiBH$_4$ (186 mL of 2.0M in THF, 372 mmol, Sigma Aldrich) via cannula. The LiBH$_4$ was added to the reaction. The addition funnel was removed and replaced with a 125 mL addition funnel which was then with MeOH (30.1 mL, 744 mmol). The MeOH was added dropwise to the stirring solution. Evolution of gas was observed and the internal temperature increased to 35° C. and then subsided. After 20 min, the flask was placed in an ice/water bath and carefully quenched with saturated ammonium chloride (aq.) solution. The reaction was diluted with water and EtOAc and stirred for 16 h. The solids were filtered off and washed with EtOAc. The filtrate and washes were combined and transferred to a separatory funnel. The organic layer was separated, washed with brine, dried over magnesium sulfate and concentrated under reduced pressure to afford (R)—N—((S)-2-(5-bromo-2-fluorophenyl)-4-hydroxybutan-2-yl)-2-methylpropane-2-sulfinamide (50.93 g) as a white solid. MS m/z=366.0 M+. This material was used as crude.

(R)—N—((S)-2-(5-bromo-2-fluorophenyl)-4-hydroxybutan-2-yl)-2-methylpropane-2-sulfinamide (5.5 g, 15.02 mmol) was taken up in DCM (400 mL). Dess-martinperiodinane (DMP) (6.37 g, 15.02 mmol, Sigma Aldrich) was added. After 30 min, the reaction was quenched with 50 mL of aq. Na$_2$S$_2$O$_3$ and 50 mL of aq. NaHCO$_3$. The mixture was stirred for 10 min before partitioning. The aqueous portion was extracted with DCM (100 mL) and the combined organic layers were dried over MgSO$_4$. Filtration and concentration under reduced pressure, followed by silica gel flash chromatography on silica gel using a gradient of 10-60% EtOAc in hexanes afforded (R)—N—((S)-2-(5-bromo-2-fluorophenyl)-4-oxobutan-2-yl)-2-methylpropane-2-sulfinamide (213C, 3.3 g, 9.06 mmol, 60% yield) as a clear oil. MS m/z=364.0 M+.

Preparation of (S)-2-(5-bromo-2-fluorophenyl)-4,4-dimethoxybutan-2-amine (213D). (R)—N—((S)-2-(5-bromo-2-fluorophenyl)-4-oxobutan-2-yl)-2-methylpropane-2-sulfinamide (3.3 g, 9.06 mmol, 213c) was taken up in MeOH (50 mL). p-toluenesulfonic acid monohydrate (0.086 g, 0.453 mmol, Sigma Aldrich) was added, and the mixture was heated to 75° C. After 30 min, the mixture was cooled to RT and HCl (4.0 M in 1,4-dioxane, 3.40 mL, 13.59 mmol, Sigma Aldrich) was added. After 1 h, the solvent was removed under reduced pressure. The residue was partitioned between a solution of 9:1 chloroform:IPA (50 mL) and saturated aqueous NaHCO$_3$ (50 mL). The aqueous portion was extracted with 9:1 chloroform:IPA (50 mL). The combined organic extracts were dried over MgSO$_4$. Filtration and concentration under reduced pressure afforded (S)-2-(5-bromo-2-fluorophenyl)-4,4-dimethoxybutan-2-amine (213d, 2.7 g, 8.82 mmol, 97% yield) as a yellow oil. The product was carried on without additional purification. MS m/z=306.1 M$^+$.

Preparation of (R)-4-(5-bromo-2-fluorophenyl)-4-methyl-4H-thiopyran-2-amine (213E). To a solution of (S)-2-(5-bromo-2-fluorophenyl)-4,4-dimethoxybutan-2-amine (25.03 g, 82 mmol, 213d) in DCM (164 mL) was added benzoyl isothiocyanate (11.00 mL, 82 mmol, Sigma Aldrich) at RT. The reaction was stirred for 30 min then concentrated under reduced pressure. The residue was taken up in sulfuric acid (96 mL, 1799 mmol) and the reaction was heated to 50° C. for 16 h. The reaction was cooled to room temperature then carefully poured into an Erlenmeyer flask containing wet ice. The flask was placed in a water bath and the reaction was carefully basified to pH=14 by the slow addition of 10 N NaOH. The solution was extracted with DCM (3×). The combined organic layers were washed with brine, dried over magnesium sulfate and concentrated under reduced pressure. The crude residue was purified via silica gel flash chromatography using a gradient of 0-5% 2 M ammonia in MeOH in DCM) to afford (R)-4-(5-bromo-2-fluorophenyl)-4-methyl-4H-thiopyran-2-amine (213E, 12.5 g, 41.6 mmol, 51% yield) as a brown oil. MS m/z=301.0 M$^+$.

Preparation of N,N-Bis Boc protected (S)-4-(5-bromo-2-fluorophenyl)-4-methyl-4H-1,3-thiazin-2-amine (213F). To a solution of di-tert-butyl dicarbonate (0.91 g, 4.16 mmol, Sigma Aldrich) in THF (4.6 mL) at room temperature was added a solution of (S)-4-(5-bromo-2-fluorophenyl)-4-methyl-4H-1,3-thiazin-2-amine (213E, 0.57 g, 1.89 mmol) and 4-(dimethylamino)-pyridine (5.78 mg, 0.05 mmol, Sigma Aldrich) in THF (4.6 mL) dropwise via syringe. The reaction was stirred for one h. The reaction was diluted with water and EtOAc. The organic layer was separated, washed with brine, dried over magnesium sulfate and concentrated under reduced pressure. The crude residue was purified via silica gel flash chromatography using a gradient of 0-20% EtOAc in Hexanes to afford N,N-Bis Boc protected (S)-4-(5-bromo-2-fluorophenyl)-4-methyl-4H-1,3-thiazin-2-amine (213F, 0.80 g, 1.59 mmol, 84% yield). MS m/z=501.0 M$^+$.

Preparation of N,N-Bis Boc protected (1R,5S,6R)-5-(5-bromo-2-fluorophenyl)-7,7-difluoro-5-methyl-2-thia-4-azabicyclo[4.1.0]hept-3-en-3-amine (213G). A sealable vial was charged with N,N-Bis Boc protected (S)-4-(5-bromo-2-fluorophenyl)-4-methyl-4H-1,3-thiazin-2-amine (1.04 g, 2.07 mmol, 213F). THF was added to fully dissolve the starting material. The reaction was then concentrated to near dryness. Tetrabutylammonium bromide (0.07 g, 0.21 mmol, Sigma Aldrich) was added followed by (bromodifluoromethyl)trimethylsilane (2.11 g, 10.38 mmol, Synquest Laboratories). The vial was sealed and heated to 65° C. in an oil bath overnight. The reaction was diluted with water and EtOAc. The organic layer was separated, washed with brine, dried over magnesium sulfate and concentrated under reduced pressure. The crude residue was purified via silica gel flash chromatography using a gradient of 0-30% EtOAc in Hexanes to afford N,N-Bis Boc protected (1R,5S,6R)-5-(5-bromo-2-fluorophenyl)-7,7-difluoro-5-methyl-2-thia-4-azabicyclo[4.1.0]hept-3-en-3-amine (213G, 0.103 g, 0.188 mmol, 9% yield) as a pale yellow solid. MS m/z=551.0 M$^+$.

Preparation of (1R,5S,6R)-5-(5-bromo-2-fluorophenyl)-7,7-difluoro-5-methyl-2-thia-4-azabicyclo[4.1.0]hept-3-en-3-amine (213H). To a solution of N,N-Bis Boc protected (1R,5S,6R)-5-(5-bromo-2-fluorophenyl)-7,7-difluoro-5-methyl-2-thia-4-azabicyclo[4.1.0]hept-3-en-3-amine (0.103 g, 0.187 mmol, 213g) in DCM (1.87 mL) was added TFA (0.475 mL, 6.16 mmol, Sigma Aldrich). The reaction was stirred at room temperature for 3 h. The reaction was concentrated under reduced pressure. The crude residue was taken up in EtOAc and washed with saturated sodium bicarbonate (aq.) solution and brine. The organic layer was dried over magnesium sulfate and concentrated under reduced pressure to afford (1R,5S,6R)-5-(5-bromo-2-fluorophenyl)-7,7-difluoro-5-methyl-2-thia-4-azabicyclo[4.1.0]hept-3-en-3-amine (213H, 69 mg, 0.195 mmol, 105% yield) as a yellow oil. It was used without further purification assuming theoretical yield. MS m/z=350.9 M$^+$.

Preparation of (1R,5S,6R)-5-(5-azido-2-fluorophenyl)-7,7-difluoro-5-methyl-2-thia-4-azabicyclo[4.1.0]hept-3-en-3-amine (213). A sealable glass vial was charged with (1R,5S,6R)-5-(5-bromo-2-fluorophenyl)-7,7-difluoro-5-methyl-2-thia-4-azabicyclo[4.1.0]hept-3-en-3-amine (0.48 g, 1.37 mmol, 213H), (+)-sodium L-ascorbate (0.054 g, 0.275 mmol, Sigma Aldrich), copper(I) iodide (79 mg, 0.413 mmol, Sigma Aldrich), and sodium azide (0.268 g, 4.13 mmol, Sigma Aldrich). The vial was sealed and evacuated/backfilled with Nitrogen (3×). EtOH (4.8 mL) was added followed by water (2.0 mL) and (1R,2R)-(−)-N,N"-dimethylcyclohexane-1,2-diamine (0.043 mL, 0.27 mmol, Sigma Aldrich). The vial was stirred in a pre-heated 75° C. oil bath for 5.5 h. The reaction was cooled to room temperature. Additional sodium azide (0.268 g, 4.13 mmol), copper(I) iodide (79 mg, 0.413 mmol) and (1R,2R)-(−)-N,N"-dimethylcyclohexane-1,2-diamine (0.043 mL, 0.275 mmol) were added. The reaction was flushed with nitrogen and then stirred in a pre-heated 85° C. oil bath for an additional 1.5 h. The reaction was cooled to RT and poured into a separatory funnel containing a solution of 9:1 aqueous saturated ammonium chloride to aqueous saturated ammonium hydroxide. EtOAc was added and the organic phase was separated and washed sequentially with 9:1 saturated aqueous ammonium chloride to saturated aqueous ammonium hydroxide solution and brine. The organic layer was dried over magnesium sulfate and concentrated under reduced pressure. The crude residue was taken up in THF (5.2 ml) and water (1.7 mL). Trimethylphosphine (1.0 M in THF, 1.376 mL, 1.376 mmol, Sigma Aldrich) was added at RT. The reaction was stirred for 5 min. The reaction was diluted with water and EtOAc. The organic layer was separated, washed with brine, dried over magnesium sulfate and concentrated under reduced pressure. The crude residue was purified via silica gel flash chromatography using a gradient of 0-10% 2 M ammonia in MeOH in DCM to afford (1R,5S,6R)-5-(5-amino-2-fluorophenyl)-7,7-difluoro-5-methyl-2-thia-4-azabicyclo[4.1.0]hept-3-en-3-amine (213) (0.25 g, 0.86 mmol, 63% yield). $^1$H NMR (300 MHz, CDCl$_3$) δ=7.04 (dd, J=2.9, 6.7 Hz, 1H), 6.87 (dd, J=8.5, 12.0 Hz, 1H), 6.54 (ddd, J=3.0, 3.8, 8.6 Hz, 1H), 2.89 (dd, J=8.3, 13.2 Hz, 1H), 2.74-2.60 (m, 1H), 1.69 (d, J=1.0 Hz, 3H) MS m/z=288.0 M$^+$.

153
tert-Butyl((1S,5S,6S)-5-(5-amino-2-fluoropyridin-3-yl)-1-(fluoromethyl)-5-methyl-2-thia-4-azabicyclo[4.1.0]hept-3-en-3-yl)((2-(trimethylsilyl)ethoxy)methyl) carbamate (214)
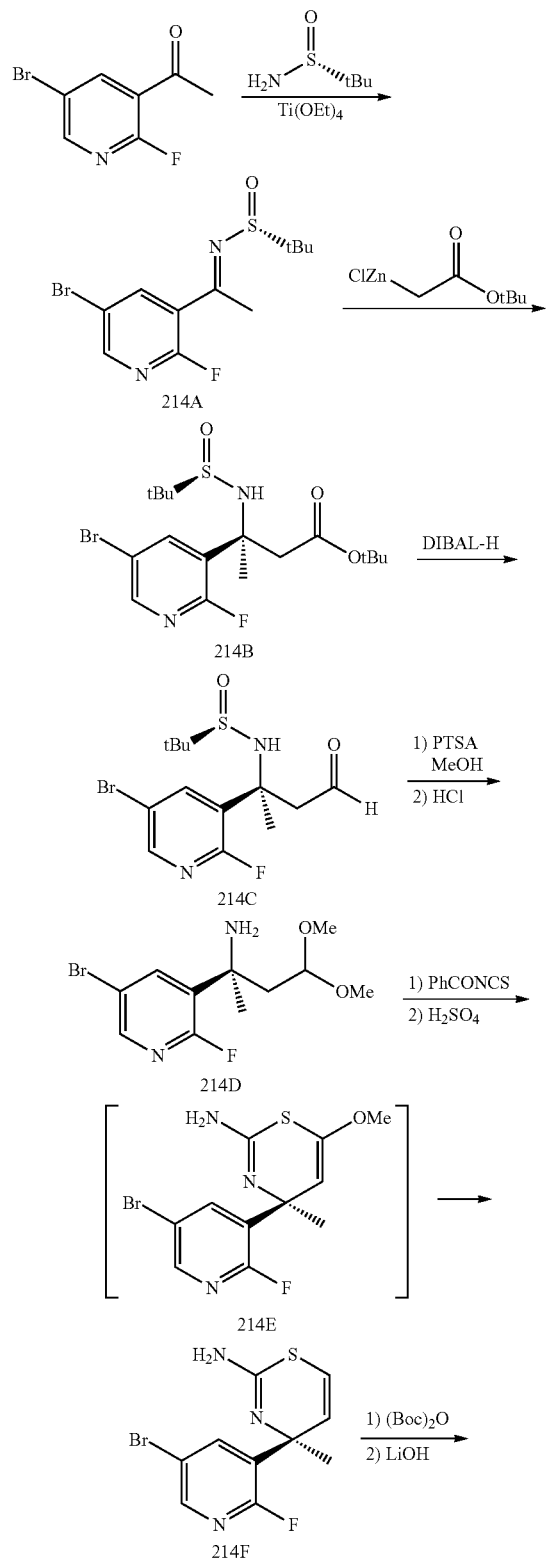
154
-continued
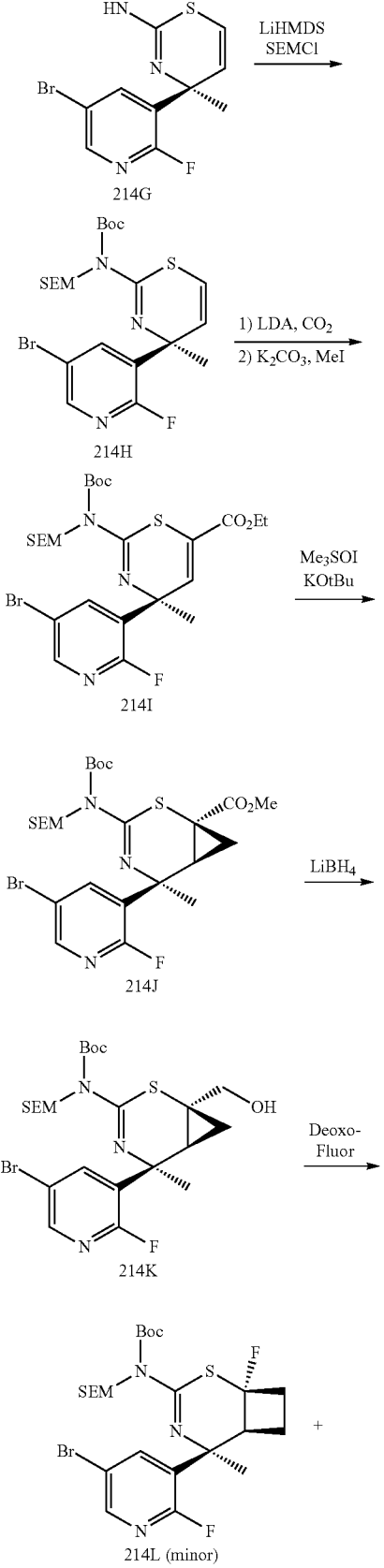

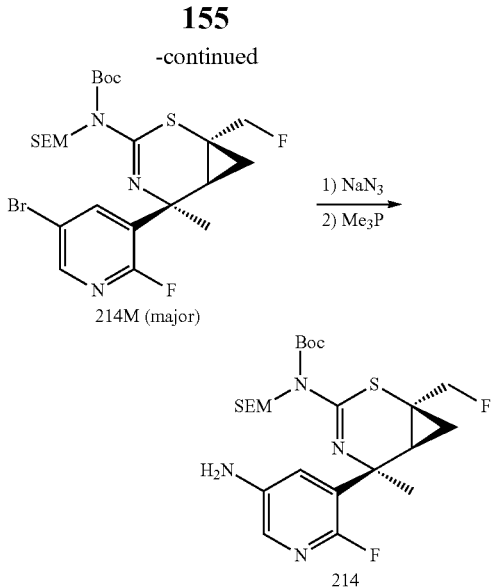

214M (major)

214

Preparation of (R,Z)—N-(1-(5-bromo-2-fluoropyridin-3-yl)ethylidene)-2-methylpropane-2-sulfinamide (214A). A mixture of 1-(5-bromo-2-fluoropyridin-3-yl)ethanone (prepared according to procedures described in WO2009016460; 11.0 g, 50.5 mmol), (R)-2-methylpropane-2-sulfinamide (AK Scientific, 12.2 g, 101.0 mmol) and titanium(IV) ethoxide (Aldrich, 26.1 mL, 126.0 mmol) in THF (100 mL) was heated to reflux for 2 h. The mixture was cooled to room temperature, and brine (200 mL) was added. The suspension was vigorously stirred for 10 min. The suspension was filtered through a pad of silica gel and the organic phase was separated. The aqueous phase was extracted with EtOAc. The combined organic layers were washed with brine, dried over $Na_2SO_4$ and concentrated under reduced pressure. The residue was purified by silica gel chromatography (gradient 0-20% EtOAc/hexanes) to afford (R,Z)—N-(1-(5-bromo-2-fluoropyridin-3-yl)ethylidene)-2-methylpropane-2-sulfinamide (214A) as a bright yellow oil (16 g, 49.8 mmol, 99% yield). MS m/z=320.8 [M+H]$^+$.

Preparation of (S)-tert-butyl 3-(5-bromo-2-fluoropyridin-3-yl)-3-((R)-1,1-dimethylethylsulfinamido)butanoate (214B). To a solution of (R,Z)—N-(1-(5-bromo-2-fluoropyridin-3-yl)ethylidene)-2-methylpropane-2-sulfinamide (214A, 41 g, 127 mmol) in THF (400 mL) in a 2 L flask at 0° C. was cannulated slowly (2-(tert-butoxy)-2-oxoethyl)zinc(II) chloride (0.5 M in Et$_2$O, 611 mL, 305 mmol) within 1 h. The reaction mixture was stirred at RT overnight, and then quenched with 200 mL of saturated NH$_4$Cl solution. The layers were separated. The aqueous layer was extracted again with 200 mL of EtOAc. The combined organic layers were then dried (Na$_2$SO$_4$) and concentrated to give an orange oil that was purified by flash column (DCM to DCM/ethyl acetate=10:1 to 5:1 to 3:1) to give (S)-tert-butyl 3-(5-bromo-2-fluoropyridin-3-yl)-3-((R)-1,1-dimethylethylsulfinamido)butanoate (214B, 43 g, 98 mmol, 77% yield). LC/MS (ESI$^+$) m/z=458.9 (M+Na). $^1$H NMR (300 MHz, CHLOROFORM-d) δ 8.17 (dd, J=1.61, 2.34 Hz, 1H), 8.03 (dd, J=2.48, 8.77 Hz, 1H), 5.44 (s, 1H), 3.18-3.29 (m, 1H), 2.98-3.11 (m, 1H), 1.82 (s, 3H), 1.33 (s, 9H), 1.30 (s, 9H).

Preparation of (R)—N—((S)-2-(5-bromo-2-fluoropyridin-3-yl)-4-oxobutan-2-yl)-2-methylpropane-2-sulfinamide (214C). A solution of (S)-tert-butyl 3-(5-bromo-2-fluoropyridin-3-yl)-3-((R)-1,1-dimethylethylsulfinamido)butanoate (214B, 42 g, 96 mmol) in 200 mL of anhydrous DCM in a 2 L round-bottom flask at −78° C. was treated with diisobutylaluminum hydride (1.0 M in hexanes) (211 mL, 211 mmol) via a syringe dropwise along the inner wall of the flask within 1.5 h. The stirring was continued for 1 h. The reaction was quenched at −78° C. by slow addition of 25 mL of MeOH along the inner wall of the flask. The reaction mixture was then taken out of the dry ice-acetone bath, and treated with 300 mL of 1 M tartaric acid solution. The mixture was stirred at RT for 1 h. A clear two phase separation was achieved and the organic phase was isolated. The aqueous was extracted with DCM (3×). The combined organic phase was evaporated to dryness. The residue was purified via silica gel chromatography (20-50% EtOAc in DCM) to Gi®(R)—N—((S)-2-(5-bromo-2-fluoropyridin-3-yl)-4-oxobutan-2-yl)-2-methylpropane-2-sulfinamide (214C, 31 g, 85 mmol, 88% yield) as a yellow gum. LC/MS (ESI$^+$) m/z=365.0 (M+H). $^1$H NMR (300 MHz, CHLOROFORM-d) δ 9.70 (s, 1H), 8.16 (dd, J=1.68, 2.41 Hz, 1H), 8.04 (dd, J=2.41, 8.84 Hz, 1H), 4.89 (s, 1H), 3.59-3.73 (m, 1H), 3.35-3.48 (m, 1H), 1.77 (s, 3H), 1.29 (s, 9H).

Preparation of (S)-2-(5-bromo-2-fluoropyridin-3-yl)-4,4-dimethoxybutan-2-amine (214D). To a 1000 mL RBF equipped with a reflux condenser was added (R)—N—((S)-2-(5-bromo-2-fluoropyridin-3-yl)-4-oxobutan-2-yl)-2-methylpropane-2-sulfinamide (28.5 g, 78.0 mmol), MeOH (200 mL) and p-toluenesulfonic acid monohydrate (0.7 g, 3.9 mmol). The solution was stirred at 65° C. overnight. It was cooled to RT and treated with hydrogen chloride (4.0 M solution in 1,4-dioxane, 21.5 mL, 86.0 mmol) dropwise. After stirring at RT for 3 h, the mixture was concentrated in vacuo. The residue was diluted with 300 mL of chloroform and treated with 50 mL of sat. aq. NaHCO$_3$. The layers were separated and the aqueous layer was extracted with EtOAc (50 mL). The chloroform extracts were washed with 10 mL of brine. The EtOAc extracts were washed with 10 mL of brine. The combined organic extracts were dried over magnesium sulfate, filtered and concentrated in vacuo to give a light yellow oil. It was purified by silica gel chromatography (50-100% EtOAc in DCM) to give (S)-2-(5-bromo-2-fluoropyridin-3-yl)-4,4-dimethoxybutan-2-amine (214D, 20.6 g, 67.2 mmol, 86% yield) as a gum. LC/MS (ESI$^+$) m/z=307.0 (M+H). $^1$H NMR (300 MHz, CHLOROFORM-d) δ 8.26 (dd, J=2.48, 8.77 Hz, 1H), 8.12-8.19 (m, 1H), 4.10-4.19 (m, 1H), 3.23 (d, J=2.05 Hz, 6H), 2.24-2.45 (m, 1H), 1.79-2.14 (m, 1H), 1.75 (br. s., 2H), 1.54 (s, 3H).

Preparation of (S)-4-(5-bromo-2-fluoropyridin-3-yl)-4-methyl-4H-1,3-thiazin-2-amine (214F). To a solution of (S)-2-(5-bromo-2-fluoropyridin-3-yl)-4,4-dimethoxybutan-2-amine (214D, 20.5 g, 66.7 mmol) in DCM (100 mL) at 0° C. under nitrogen was added a solution of benzoyl isothiocyanate (9.4 mL, 70.1 mmol) in DCM (30 mL) dropwise. The reaction was kept below 5° C. during the course of addition. After stirring at 0° C. for 20 min, the reaction mixture was treated with MeOH (1 mL). The solvents were removed under reduced pressure to afford a tan syrup. To the tan syrup at 0° C. was added neat sulfuric acid (53.4 mL, 1001 mmol). The mixture was stirred at RT for 20 min then heated at 60° C. for 5 h, then 80° C. for 2 h, then 65° C. overnight. LCMS indicated the ratio of 214E and 214F to be about 1:1. The mixture was heated at 85° C. for 3 h. The reaction was cooled to 20° C. then poured onto 200 g of ice. DCM (200 mL) was added to the slurry mixture. The resulting biphasic solution was chilled to 0° C. with external wet ice bath, then basified to pH=8 with very slow addition of 10 N NaOH solution. The organic layer was separated and the aqueous portion was extracted with DCM (3×) and EtOAc (1x). The combined organic extracts were dried over $Na_2SO_4$, filtered, and then concentrated under reduced pressure. The residue was purified by flash column (10-100% EtOAc in DCM) to give two compounds. The first eluent was (S)-4-(5-bromo-2-fluoropyridin-3-yl)-4-methyl-4H-1,3-thiazin-2-amine (214F, 12.0 g, 39.7 mmol, 59% yield) as a yellow solid. LC/MS (ESI$^+$) m/z=302.0 (M+H). $^1$H NMR (CHLOROFORM-d) δ: 8.12 (dd, J=2.5, 1.6 Hz, 1H), 8.02 (dd, J=8.6, 2.5 Hz, 1H), 6.30-6.39 (m, 1H), 6.17-6.27 (m, 1H), 1.66 (d, J=1.0 Hz, 3H). The second eluent was (4S)-4-(5-bromo-2-fluoropyridin-3-yl)-6-methoxy-4-methyl-5,6-dihydro-4H-1,3-thiazin-2-amine (214E, 6.0 g, 17.9 mmol).

A mixture of (4S)-4-(5-bromo-2-fluoropyridin-3-yl)-6-methoxy-4-methyl-5,6-dihydro-4H-1,3-thiazin-2-amine (214E, 6.0 g, 17.9 mmol) in 18 mL of $H_2SO_4$ was heated at 80° C. overnight. The reaction mixture was cooled to 20° C. then poured onto 200 g of ice. To the slurry was added DCM (200 mL), the resulting biphasic solution was chilled to 0° C. with external wet ice bath, then basified to pH=8 with very slow addition of 10 N NaOH solution. The organic layer was separated and the aqueous portion was extracted with DCM (3x) and EtOAc (1x). The combined organic extracts were dried over $Na_2SO_4$, filtered, and concentrated under reduced pressure. The residue was purified by flash column (10-30% EtOAc in DCM) to give (S)-4-(5-bromo-2-fluoropyridin-3-yl)-4-methyl-4H-1,3-thiazin-2-amine (214F, 4 g) as a yellow solid.

Preparation of (S)-tert-butyl(4-(5-bromo-2-fluoropyridin-3-yl)-4-methyl-4H-1,3-thiazin-2-yl)carbamate (214G). Using a procedure similar to that described for Intermediate 203F, (S)-4-(5-bromo-2-fluoropyridin-3-yl)-4-methyl-4H-1,3-thiazin-2-amine (214F, 1.74 g, 5.76 mmol), 4-(dimethylamino)pyridine (0.04 g, 0.29 mmol), Boc anhydride (3.30 mL, 14.40 mmol) and lithium hydroxide monohydrate (1.21, 28.80 mmol) were combined to afford the title compound (2.17 g, 5.39 mmol, 94% yield). LC/MS (ESI$^+$) m/z=403.0 (M+H). $^1$H NMR (300 MHz, CHLOROFORM-d) δ 8.14-8.20 (m, 1H), 8.00 (br. s., 1H), 6.30 (d, J=9.79 Hz, 1H), 6.14 (d, J=6.87 Hz, 1H), 1.69 (s, 3H), 1.54 (s, 9H).

Preparation of (S)-tert-butyl(4-(5-bromo-2-fluoropyridin-3-yl)-4-methyl-4H-1,3-thiazin-2-yl)((2-(trimethylsilyl)ethoxy)methyl)carbamate (214H). Using a similar procedure described for 203G, (S)-tert-butyl(4-(5-bromo-2-fluoropyridin-3-yl)-4-methyl-4H-1,3-thiazin-2-yl)carbamate (214G, 1.18 g, 2.93 mmol), lithium bis(trimethylsilyl)amide (3.8 mL of 1.0 M solution in THF, 3.8 mmol) and 2-(chloromethoxy)ethyltrimethylsilane (0.7 mL, 3.8 mmol) were combined to afford the title compound (214H, 1.5 g, 2.8 mmol, 95% yield). LC/MS (ESI$^+$) m/z=532.0/534.0 (M+H). $^1$H NMR (300 MHz, CHLOROFORM-d) δ 8.14-8.22 (m, 2H), 6.36 (d, J=9.50 Hz, 1H), 6.05-6.11 (m, 1H), 5.37 (d, J=10.38 Hz, 1H), 5.21 (d, J=10.38 Hz, 1H), 3.69 (dd, J=7.67, 8.84 Hz, 2H), 1.69 (d, J=1.17 Hz, 3H), 1.56 (s, 9H), 0.91-1.06 (m, 2H), 0.00 (s, 9H).

Preparation of (S)-methyl 4-(5-bromo-2-fluoropyridin-3-yl)-2-((tert-butoxycarbonyl)((2-(trimethylsilyl)ethoxy)methyl)amino)-4-methyl-4H-1,3-thiazine-6-carboxylate (214I). LDA (2.0 M heptane/THF/ethylbenzene) (0.92 mL, 1.83 mmol) was added dropwise to a solution of (S)-tert-butyl(4-(5-bromo-2-fluoropyridin-3-yl)-4-methyl-4H-1,3-thiazin-2-yl)((2-(trimethylsilyl)ethoxy)methyl)carbamate (214H, 0.75 g, 1.41 mmol) in THF (10 mL) at −78° C. The mixture was stirred for 25 min before $CO_2$ gas was bubbled through the reaction mixture at −78° C. After 3 min, the cold bath was removed, the addition of $CO_2$ was stopped, and the reaction mixture was quenched with saturated $NH_4Cl$ solution. The resulting solution was warmed to RT and extracted with EtOAc (2x). The aqueous layer was acidified to pH 4 with 1 N HCl solution and extracted again with EtOAc. The combined extracts were dried over $MgSO_4$, filtered, and concentrated in vacuo to give a yellow oil.

The oil was taken up in DMF (2.0 mL) and potassium carbonate (0.19 g, 1.41 mmol) and methyl iodide (0.09 mL, 1.41 mmol) were added. The mixture was stirred at RT for 2 h, diluted with water and extracted with EtOAc (2x). The combined organic extracts were dried over $MgSO_4$, filtered, and concentrated in vacuo. The residue was purified on an ISCO column using 0-15% EtOAc in hexanes to afford (S)-methyl 4-(5-bromo-2-fluoropyridin-3-yl)-2-((tert-butoxycarbonyl)((2-(trimethylsilyl)ethoxy)methyl)amino)-4-methyl-4H-1,3-thiazine-6-carboxylate (214I, 0.40 g, 0.68 mmol, 48.1% yield). LC/MS (ESI$^+$) m/z=590.0/592.0 (M+H). $^1$H NMR (300 MHz, CHLOROFORM-d) δ 8.16-8.23 (m, 2H), 7.11 (d, J=3.07 Hz, 1H), 5.38 (d, J=10.38 Hz, 1H), 5.20 (d, J=10.38 Hz, 1H), 3.84 (s, 3H), 3.62-3.73 (m, 2H), 1.72 (d, J=1.02 Hz, 3H), 1.50-1.58 (m, 9H), 0.98 (dd, J=7.45, 8.92 Hz, 2H), −0.02 (s, 9H).

Preparation of (1S,5S,6S)-methyl 5-(5-bromo-2-fluoropyridin-3-yl)-3-((tert-butoxycarbonyl)((2-(trimethylsilyl)ethoxy)methyl)amino)-5-methyl-2-thia-4-azabicyclo[4.1.0]hept-3-ene-1-carboxylate (214J). Using a similar procedure described for 210B, trimethylsulfoxonium iodide (0.30 g, 1.36 mmol), potassium tert-butoxide (0.15 g, 1.35 mmol), and (S)-methyl 4-(5-bromo-2-fluoropyridin-3-yl)-2-((tert-butoxycarbonyl)((2-(trimethylsilyl)ethoxy)methyl)amino)-4-methyl-4H-1,3-thiazine-6-carboxylate (214I, 0.40 g, 0.68 mmol) were combined to afford (1S,5S,6S)-methyl 5-(5-bromo-2-fluoropyridin-3-yl)-3-((tert-butoxycarbonyl)((2-(trimethylsilyl)ethoxy)methyl)amino)-5-methyl-2-thia-4-azabicyclo[4.1.0]hept-3-ene-1-carboxylate (214J, 0.27 g, 0.45 mmol, 65.9% yield). LCMS m/z=604.0/606.0 [M+H]$^+$. $^1$H NMR (300 MHz, CHLOROFORM-d) δ 8.17-8.27 (m, 2H), 5.30 (d, J=10.52 Hz, 1H), 5.03 (d, J=10.52 Hz, 1H), 3.82 (s, 3H), 3.62-3.74 (m, 2H), 2.68 (ddd, J=1.53, 7.71, 9.61 Hz, 1H), 1.75 (d, J=1.17 Hz, 3H), 1.51-1.57 (m, 9H), 1.24-1.36 (m, 1H), 1.16 (dd, J=5.26, 7.60 Hz, 1H), 0.85-1.07 (m, 2H), −0.06 (s, 9H). $^{19}$F NMR (282 MHz, CHLOROFORM-d) δ −67.27 (s, 1F).

Preparation of tert-butyl((1S,5S,6S)-5-(5-bromo-2-fluoropyridin-3-yl)-1-(hydroxymethyl)-5-methyl-2-thia-4-azabicyclo[4.1.0]hept-3-en-3-yl)((2-(trimethylsilyl)ethoxy)methyl)carbamate (214K). Using a similar procedure described for 210C, (1S,5S,6S)-methyl 5-(5-bromo-2-fluoropyridin-3-yl)-3-((tert-butoxycarbonyl)((2-(trimethylsilyl)ethoxy)methyl)amino)-5-methyl-2-thia-4-azabicyclo[4.1.0]hept-3-ene-1-carboxylate (214J, 0.46 g, 0.76 mmol) and lithium borohydride (2.0 M solution in THF, 0.76 mL, 1.52 mmol) and MeOH (0.12 mL, 3.04 mmol) were combined to afford the title compound (214K, 0.42 g, 0.73 mmol, 96% yield). LC/MS (ESI+) m/z=576.0/578.0 (M+H).

Preparation of tert-butyl((5S)-5-(5-bromo-2-fluoropyridin-3-yl)-1-(fluoromethyl)-5-methyl-2-thia-4-azabicyclo[4.1.0]hept-3-en-3-yl)((2-(trimethylsilyl)ethoxy)methyl)carbamate (214M). To a solution of tert-butyl((5S)-5-(5-bromo-2-fluoropyridin-3-yl)-1-(hydroxymethyl)-5-methyl-2-thia-4-azabicyclo[4.1.0]hept-3-en-3-yl)((2-(trimethylsilyl)ethoxy)methyl)carbamate (0.46 g, 0.80 mmol) in hexanes (10.0 mL) at −78° C. was added Deoxo-Fluor (0.22 mL, 1.20 mmol) dropwise. The reaction mixture was warmed to RT for 30 min and quenched with saturated $NaHCO_3$ solution. It was extracted with EtOAc (2x). The organic extracts were concentrated under reduced pressure and the residue purified by silica gel chromatography eluting products with 0-20% EtOAc/heptane gradient to afford:

1st eluent, tert-butyl((5S)-5-(5-bromo-2-fluoropyridin-3-yl)-1-fluoro-5-methyl-2-thia-4-azabicyclo[4.2.0]oct-3-en-3-yl)((2-(trimethylsilyl)ethoxy)methyl)carbamate (214L, 0.13 g, 0.22 mmol, 28.2% yield). LC/MS (ESI+) m/z=578.0/580.0 (M+H). $^{19}$F NMR (282 MHz, CHLOROFORM-d) δ −67.71 (s, 1F), −102.44 (s, 1F).

2nd eluent, tert-butyl((5S)-5-(5-bromo-2-fluoropyridin-3-yl)-1-(fluoromethyl)-5-methyl-2-thia-4-azabicyclo[4.1.0]hept-3-en-3-yl)((2-(trimethylsilyl)ethoxy)methyl)carbamate (214M, 0.17 g, 0.30 mmol, 37.0% yield). LC/MS (ESI+) m/z=578.0/580.0 (M+H). $^{19}$F NMR (282 MHz, CHLOROFORM-d) δ −67.71 (s, 1F), −213.42 (s, 1F).

Preparation of tert-butyl((1S,5S,6S)-5-(5-amino-2-fluoropyridin-3-yl)-1-(fluoromethyl)-5-methyl-2-thia-4-azabicyclo[4.1.0]hept-3-en-3-yl)((2-(trimethylsilyl)ethoxy)methyl)carbamate (214). Using a similar procedure described for 210, tert-butyl((5S)-5-(5-bromo-2-fluoropyridin-3-yl)-1-(fluoromethyl)-5-methyl-2-thia-4-azabicyclo[4.1.0]hept-3-en-3-yl)((2-(trimethylsilyl)ethoxy)methyl)carbamate (214M, 0.16 g, 0.28 mmol), sodium azide (0.05 g, 0.83 mmol), copper(I) iodide (13 mg, 0.07 mmol), sodium L-ascorbate (14 mg, 0.07 mmol), trans-N,N'-dimethyl-1,2-cyclohexanediamine (10.9 μL, 0.07 mmol) and trimethylphosphine (1 M solution in THF, 0.41 mL, 0.41 mmol) were combined to afford tert-butyl((5S)-5-(5-amino-2-fluoropyridin-3-yl)-1-(fluoromethyl)-5-methyl-2-thia-4-azabicyclo[4.1.0]hept-3-en-3-yl)((2-(trimethylsilyl)ethoxy)methyl)carbamate (214, 72 mg, 0.14 mmol, 51% yield). LC/MS (ESI−) m/z=515.2 (M+H)+.

(1S,5S,6S)-5-(5-Amino-2-methoxypyridin-3-yl)-1-(fluoromethyl)-5-methyl-2-thia-4-azabicyclo[4.1.0]hept-3-en-3-amine (215)

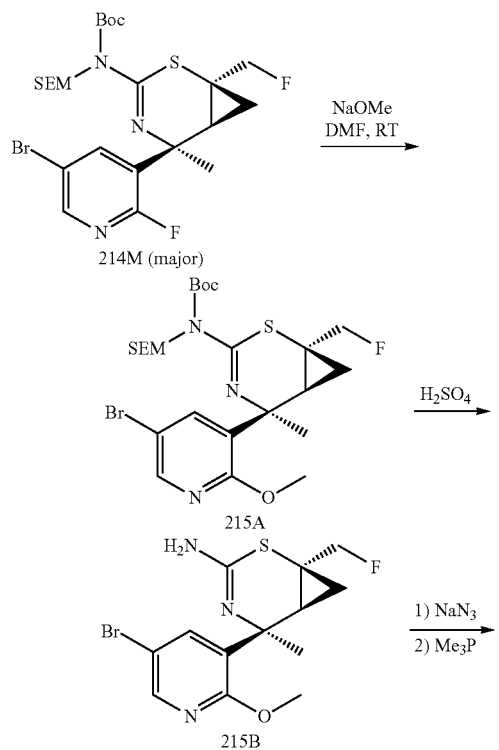

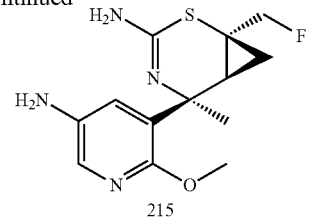

Preparation of Compound 215A. To a solution of tert-butyl((1S,5S,6S)-5-(5-bromo-2-fluoropyridin-3-yl)-1-(fluoromethyl)-5-methyl-2-thia-4-azabicyclo[4.1.0]hept-3-en-3-yl)((2-(trimethylsilyl)ethoxy)methyl)carbamate (214M, 2.53 g, 4.37 mmol) in DMF (10 mL) was added sodium methoxide (2.36 g, 43.7 mmol) at RT. The suspension was stirred at RT for 6 h, diluted with water and extracted with EtOAc (2×). The organic extracts were concentrated under reduced pressure and the residue was purified on a silica gel column (0-20% EtOAc/hexanes) to give tert-butyl((1S,5S,6S)-5-(5-bromo-2-methoxypyridin-3-yl)-1-(fluoromethyl)-5-methyl-2-thia-4-azabicyclo[4.1.0]hept-3-en-3-yl)((2-(trimethylsilyl)ethoxy)methyl)carbamate (2.00 g, 3.39 mmol, 77% yield). LC/MS (ESI+) m/z=590.2/592.1 (M+H).

Preparation of Compound 215B. To a round bottom flask containing tert-butyl((1S,5S,6S)-5-(5-bromo-2-methoxypyridin-3-yl)-1-(fluoromethyl)-5-methyl-2-thia-4-azabicyclo[4.1.0]hept-3-en-3-yl)((2-(trimethylsilyl)ethoxy)methyl)carbamate (215A, 2.0 g, 3.4 mmol) at 0° C. was added concentrated sulfuric acid (4 mL, 72.0 mmol) dropwise. After the addition, the mixture was stirred at RT for 30 min and the pH of the reaction mixture was adjusted to pH=10-14 by the addition of 5 N NaOH solution. The mixture was extracted with EtOAc (2×). The combined organic extracts were washed with brine, dried over MgSO$_4$, and concentrated to give (1S,5S,6S)-5-(5-bromo-2-methoxypyridin-3-yl)-1-(fluoromethyl)-5-methyl-2-thia-4-azabicyclo[4.1.0]hept-3-en-3-amine (1.2 g, 3.33 mmol, 98% yield). LC/MS (ESI+) m/z=360.2/362.0 (M+H).

Preparation of Compound 215. A mixture of (1S,5S,6S)-5-(5-bromo-2-methoxypyridin-3-yl)-1-(fluoromethyl)-5-methyl-2-thia-4-azabicyclo[4.1.0]hept-3-en-3-amine (215B, 1.2 g, 3.33 mmol), sodium azide (1.08 g, 16.66 mmol), copper(i) iodide (63 mg, 0.33 mmol), (+)-sodium L-ascorbate (0.13 g, 0.67 mmol), and trans-N,N'-dimethylcyclohexane-1,2-diamine (0.10 mL, 0.67 mmol) in EtOH/H$_2$O (4:1, 20 mL) was heated in a closed capped vial at 85° C. for 2 h. The reaction mixture was cooled, diluted with water and extracted with EtOAc (2×). The organic extracts were dried over Na$_2$SO$_4$ and concentrated.

The residue obtained was dissolved in a (8:2) mixture of THF/H$_2$O (10 mL) and trimethylphosphine (1 M solution in THF) (6.66 mL, 6.66 mmol) was added. After stirring at RT for 1 h, the reaction was quenched with saturated NaHCO$_3$, and extracted with EtOAc. The organic solution was concentrated and the residue was purified by silica gel flash column chromatography (0-15% MeOH/DCM) to give (1S,5S,6S)-5-(5-amino-2-methoxypyridin-3-yl)-1-(fluoromethyl)-5-methyl-2-thia-4-azabicyclo[4.1.0]hept-3-en-3-amine (0.25 g, 0.84 mmol, 25% yield). LC/MS (ESI+) m/z=297.2 (M+H). $^1$H NMR (400 MHz, CHLOROFORM-d) δ: 7.54 (d, J=2.93 Hz, 1H), 7.40 (d, J=2.93 Hz, 1H), 4.46-4.62 (m, 1H), 4.34-4.46 (m, 1H), 4.11-4.34 (m, 2H), 3.93 (s, 3H), 3.70-3.00 (br., 2H), 2.13 (ddd, J=0.98, 6.94, 9.68 Hz, 1H), 1.69 (s, 3H), 0.92 (dd, J=5.87, 9.59 Hz, 1H), 0.71 (dt, J=4.30, 6.16 Hz, 1H). $^{19}$F NMR (377 MHz, CHLOROFORM-d) δ −212.20.

(1S,5S,6S)-5-(5-Amino-2,3-difluorophenyl)-1-(fluoromethyl)-5-methyl-2-thia-4-azabicyclo[4.1.0]hept-3-en-3-amine (216)

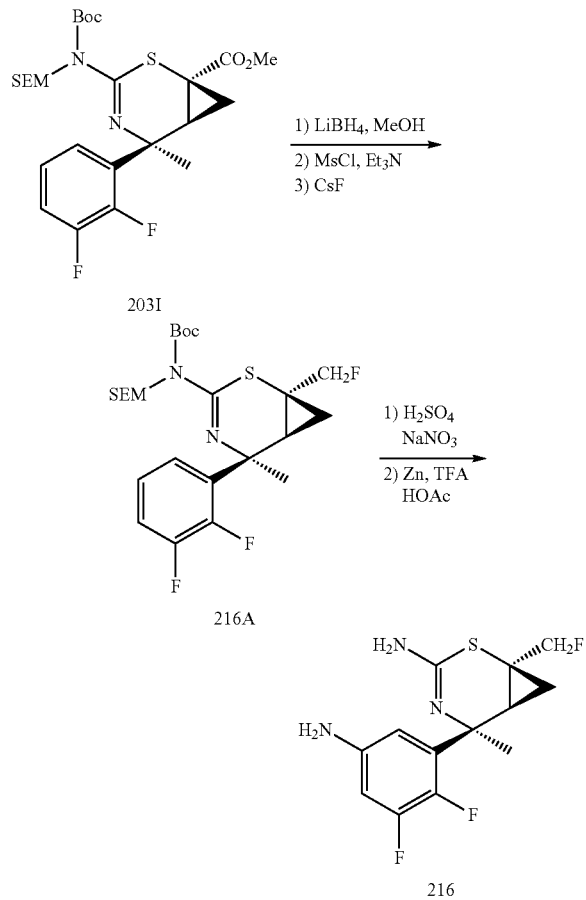

Preparation of tert-butyl((1S,5S,6S)-5-(2,3-difluorophenyl)-1-(fluoromethyl)-5-methyl-2-thia-4-azabicyclo[4.1.0]hept-3-en-3-yl)((2-(trimethylsilyl)ethoxy)methyl)carbamate (216A). At RT, to a solution of (1S,5S,6S)-methyl 3-((tert-butoxycarbonyl)((2-(trimethylsilyl)ethoxy)methyl)amino)-5-(2,3-difluorophenyl)-5-methyl-2-thia-4-azabicyclo[4.1.0]hept-3-ene-1-carboxylate (203I, 34.6 g, 63.8 mmol) in 300 mL of THF was added lithium borohydride (2.0 M solution in THF, 63.8 mL, 128 mmol) dropwise via an addition funnel. MeOH (20.66 mL, 510 mmol) was the added slowly to the mixture over 20 min. The mixture was stirred at RT for 2 h, during which time it warmed slightly (estimated ~40° C.). The mixture was then chilled to 0° C. and quenched by dropwise addition of 250 mL of aq. NH$_4$Cl. The reaction mixture was then extracted with 500 mL of EtOAc and the organic extracts were washed with 250 mL of brine and dried over MgSO$_4$. Filtration and concentration under reduced pressure afforded tert-butyl((1S,5S,6S)-5-(2,3-difluorophenyl)-1-(hydroxymethyl)-5-methyl-2-thia-4-azabicyclo[4.1.0]hept-3-en-3-yl)((2-(trimethylsilyl)ethoxy)methyl)carbamate (30.7 g, 59.6 mmol, 94% yield) as a viscous yellow oil. MS (ESI, positive ion) m/z: 515.3 (M+1). The crude material was used in the next step without further purification.

At 0° C., tert-butyl((1S,5S,6S)-5-(2,3-difluorophenyl)-1-(hydroxymethyl)-5-methyl-2-thia-4-azabicyclo[4.1.0]hept-3-en-3-yl)((2-(trimethylsilyl)ethoxy)methyl)carbamate (4.9 g, 9.52 mmol) in 50 mL of DCM was treated with TEA (1.72 mL, 12.38 mmol) followed by methanesulfonyl chloride (0.85 mL, 10.95 mmol). The mixture was stirred for 30 min, then quenched with 30 mL of aq. NaHCO$_3$ and 30 mL of water. The layers were separated and the aqueous portion was extracted with 25 mL of DCM. The combined organic extracts were dried over MgSO$_4$. Filtration and concentration under reduced pressure afforded an oil that was taken up in 20 mL of tBuOH. Cesium fluoride (4.34 g, 28.6 mmol) was added, and the mixture as heated at 75° C. for 10 h. The mixture was cooled to RT and partitioned between 100 mL of EtOAc and 100 mL of water. The organic portion was washed with 50 mL of brine and dried over MgSO$_4$. Filtration and concentration under reduced pressure, followed by flash chromatography on silica gel (5-25% EtOAc in heptanes) afforded tert-butyl((1S,5S,6S)-5-(2,3-difluorophenyl)-1-(fluoromethyl)-5-methyl-2-thia-4-azabicyclo[4.1.0]hept-3-en-3-yl)((2-(trimethylsilyl)ethoxy)methyl)carbamate (216A) (4.34 g, 8.40 mmol, 88% yield) as a clear oil. MS (ESI, positive ion) m/z: 517.3 (M+1). $^{19}$F NMR (376 MHz, DMSO-d$_6$) δ −139.35 (d, J=20.80 Hz, 1F), −139.82 (d, J=20.81 Hz, 1F), −212.18 (s, 1F).

Preparation of (1S,5S,6S)-5-(5-amino-2,3-difluorophenyl)-1-(fluoromethyl)-5-methyl-2-thia-4-azabicyclo[4.1.0]hept-3-en-3-amine (216). At 0° C., tert-butyl((1S,5S,6S)-5-(2,3-difluorophenyl)-1-(fluoromethyl)-5-methyl-2-thia-4-azabicyclo[4.1.0]hept-3-en-3-yl)((2-(trimethylsilyl)ethoxy)methyl)carbamate (4.3 g, 8.32 mmol) was treated with sulfuric acid (15.97 mL, 300 mmol) dropwise. The mixture was stirred for 5 min, then warmed to RT and stirred for 15 min. The mixture was chilled to 0° C. Sodium nitrate (0.70 g, 8.32 mmol) was added. The mixture was warmed to RT and stirred for 40 min. The mixture was then chilled to 0° C., and sodium nitrate (0.70 g, 8.32 mmol) was added. The mixture was warmed to RT. After 40 min, the mixture was chilled to 0° C. 200 mL of wet ice was added to the flask. Potassium phosphate tribasic monohydrate (72.8 g, 316 mmol) was then added slowly over 15 min. 10 N aq. NaOH was then added until the mixture had reached a pH~9.0. The mixture was diluted with 100 mL of water and 200 mL of chloroform:IPA (9:1), stirred for 5 min, then filtered to remove all solid material. The filtrate was transferred to a separatory funnel and the layers were separated. The aqueous portion was extracted with 100 mL of DCM. The combined organic extracts were then dried over MgSO$_4$. Filtration and concentration under reduced pressure, followed by flash chromatography on silica gel (5-50% EtOAc/heptanes) afforded (1S,5S,6S)-5-(2,3-difluoro-5-nitrophenyl)-1-(fluoromethyl)-5-methyl-2-thia-4-azabicyclo[4.1.0]hept-3-en-3-amine (1.44 g, 4.35 mmol, 52% yield) as a sticky yellow solid. MS (ESI, positive ion) m/z: 332.1 (M+1).

(1S,5S,6S)-5-(2,3-difluoro-5-nitrophenyl)-1-(fluoromethyl)-5-methyl-2-thia-4-azabicyclo[4.1.0]hept-3-en-3-amine (1.44 g, 4.35 mmol) was taken up in HOAc (6 mL, 104 mmol) and TFA (3 mL, 40.4 mmol). The mixture was cooled to 0° C., and zinc (nanopowder, 0.85 g, 13.04 mmol) was added in four portions over 20 min. The mixture was warmed to RT and stirred for 1 h. The solvents were removed under reduced pressure and the residue was partitioned between 75 mL of 9:1 aq. NH$_4$Cl:NH$_4$OH and 75 mL of DCM. The aqueous portion was extracted with 50 mL of DCM and the combined organic extracts were dried over MgSO$_4$. Filtration and concentration under reduced pressure, followed by flash chromatography on silica gel (1-5% MeOH/DCM) afforded (1S,5S,6S)-5-(5-amino-2,3-difluorophenyl)-1-(fluoromethyl)-5-methyl-2-thia-4-azabicyclo[4.1.0]hept-3-en-3-amine (0.85 g, 2.82 mmol, 65% yield) as a yellow solid. $^1$H NMR (400 MHz, DMSO-$d_6$) δ 6.67 (m, 1H), 6.36 (m, 1H), 6.04 (br., 2H), 5.13 (br., 2H), 4.53 (m, 1H), 4.41 (m, 1H), 1.74 (m, 1H), 1.56 (s, 3H) 1.01 (m, 1H), 0.63 (m, 1H). $^{19}$F NMR (377 MHz, DMSO-$d_6$) δ −140.38 (d, J=23.41 Hz, 1F), −155.86 (d, J=23.41 Hz, 1F), −211.45 (s, 1F). MS (ESI, positive ion) m/z: 302.0 (M+1).

(1S,5S,6S)-5-(5-amino-2-fluorophenyl)-1-(methoxymethyl)-5-methyl-2-thia-4-azabicyclo[4.1.0]hept-3-en-3-amine (217)

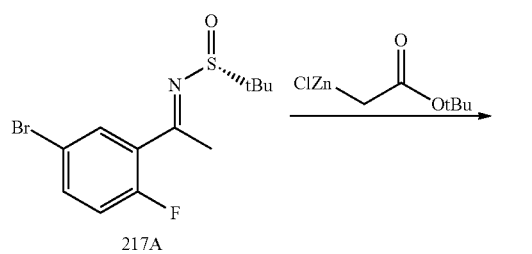

217A

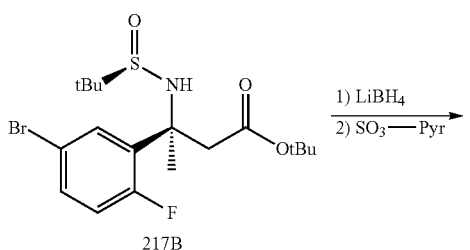

217B

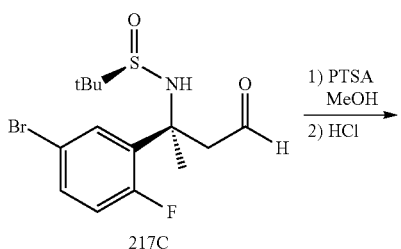

217C

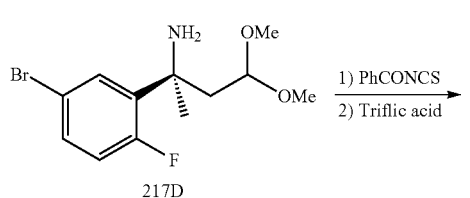

217D

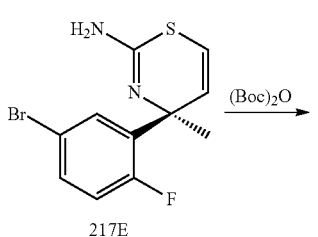

217E

-continued

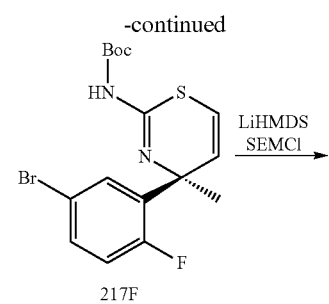

217F

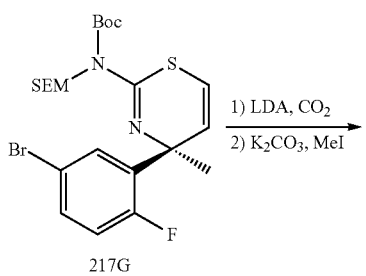

217G

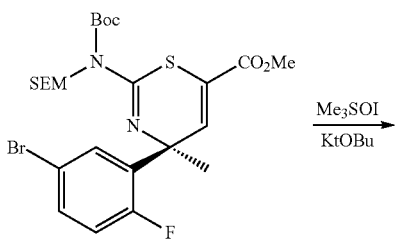

217H

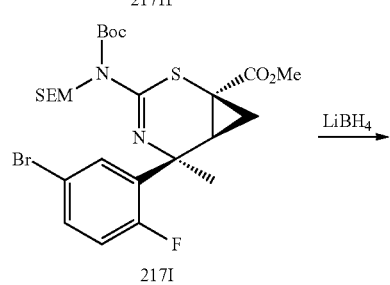

217I

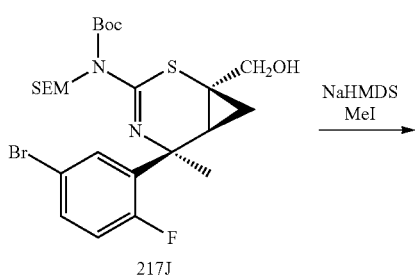

217J

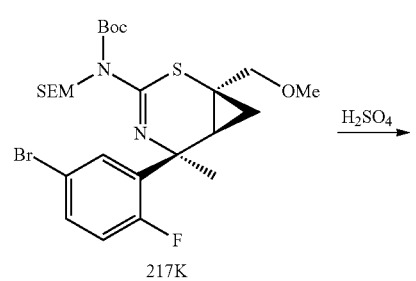

217K

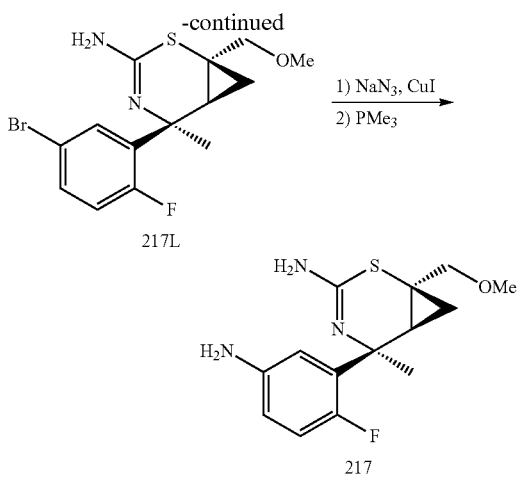

Preparation of (S)-tert-butyl(4-(5-bromo-2-fluorophenyl)-4-methyl-4H-1,3-thiazin-2-yl)((2-(trimethylsilyl)ethoxy)methyl)carbamate (217G). This intermediate was prepared in 9 steps from Compound 217A in a fashion similar to that described for intermediate 204G. $^1$H NMR (400 MHz, DMSO-d$_6$) δ 7.68 (dd, J=2.74, 7.04 Hz, 1H), 7.57 (ddd, J=2.74, 4.25, 8.66 Hz, 1H), 7.26 (dd, J=8.61, 11.54 Hz, 1H), 6.66 (d, J=9.39 Hz, 1H), 6.09 (dd, J=3.52, 9.39 Hz, 1H), 5.24 (d, J=10.56 Hz, 1H), 5.12 (d, J=10.76 Hz, 1H), 3.64 (m, 2H), 1.63 (s, 3H), 1.51 (s, 9H), 0.92 (m, 2H), −0.06 (s, 9H). $^{19}$F NMR (377 MHz, DMSO-d$_6$) δ −113.44 (s, 1F). MS (ESI, positive ion) m/z: 531/535 (M+1).

Preparation of (S)-methyl 4-(5-bromo-2-fluorophenyl)-2-((tert-butoxycarbonyl)((2-(trimethylsilyl)ethoxy)methyl)amino)-4-methyl-4H-1,3-thiazine-6-carboxylate (217H). To a stirring solution of (S)-tert-butyl(4-(5-bromo-2-fluorophenyl)-4-methyl-4H-1,3-thiazin-2-yl)((2-(trimethylsilyl)ethoxy)methyl)carbamate (217G) (15.0 g, 28.2 mmol) in THF (100 mL) at −78° C. was added lithium diisopropylamide (14.1 mL of 2 M in THF, 28.2 mmol) at a rate that the reaction temperature did not exceed −65° C. The light orange solution was stirred for 20 min at −78° C. The reaction was then exposed to carbon dioxide (g), first as a stream above the level of the solvent for 2 min, followed by the gas bubbled through the solvent for 2 min. The reaction was then slowly quenched with sat. NH$_4$Cl (25 mL). Once the suspension reached RT, both EtOAc (200 mL) and water (25 mL) were added. The organic layer was separated and the aqueous layer was extracted with EtOAc (1×). The combined extracts were then dried over MgSO$_4$ and concentrated under reduced pressure to afford the crude (S)-4-(5-bromo-2-fluorophenyl)-2-((tert-butoxycarbonyl)((2-(trimethylsilyl)ethoxy)methyl)amino)-4-methyl-4H-1,3-thiazine-6-carboxylic acid as a thick oil. MS (ESI, positive ion) m/z: 575/577 (M+1).

The resulting thick oil was dissolved in DMF (100 mL) and treated with potassium carbonate (7.8 g, 56.4 mmol) followed by iodomethane (3.5 mL, 56.4 mmol) at RT. The mixture was then stirred for 3 d at RT. The reaction mixture was diluted with 100 mL of EtOAc, and then water (50 mL) was added. The resulting biphasic mixture was separated and the aqueous layer was extracted with EtOAc (1×). The combined organic extracts were washed with water (2×), dried (MgSO$_4$), filtered, and concentrated in vacuo to give an oil. The crude material was loaded on a silica gel column and eluted with a gradient of 0-10% EtOAc in hexanes to afford (S)-methyl 4-(5-bromo-2-fluorophenyl)-2-((tert-butoxycarbonyl)((2-(trimethylsilyl)ethoxy)methyl)amino)-4-methyl-4H-1,3-thiazine-6-carboxylate (14.9 g, 46% yield) as a yellow viscous oil. $^1$H NMR (CHLOROFORM-d) δ: 7.73 (dd, J=7.0, 2.5 Hz, 1H), 7.39 (ddd, J=8.7, 4.3, 2.5 Hz, 1H), 7.11 (d, J=3.1 Hz, 1H), 6.97 (dd, J=11.3, 8.6 Hz, 1H), 5.34 (d, J=10.4 Hz, 1H), 5.21 (d, J=10.4 Hz, 1H), 3.83 (s, 3H), 3.58-3.73 (m, 2H), 1.71 (s, 3H), 1.56 (s, 9H), 0.87-1.08 (m, 2H), 0.00 (s, 9H). MS (ESI, positive ion) m/z: 589/591 (M+1).

Preparation of (1S,5S,6S)-methyl 5-(5-bromo-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylate (217I). Corey-Chaykovsky Reagent [~0.25 M in DMSO]: To a stirring solution of trimethylsulfoxonium iodide (12.46 g, 56.60 mmol) in DMSO (200 mL) at RT was added potassium tert-butoxide (6.35 g, 56.60 mmol) in one portion. The solution was stirred for 1 h and then used in the reaction outlined below.

To a stirring solution of (S)-methyl 4-(5-bromo-2-fluorophenyl)-2-((tert-butoxycarbonyl)((2-(trimethylsilyl)ethoxy)methyl)amino)-4-methyl-4H-1,3-thiazine-6-carboxylate (217H, 26.7 g, 45.3 mmol) in THF (200 mL) at RT was added freshly prepared Corey-Chaykovsky Reagent (56.60 mmol) via a syringe dropwise. The reaction mixture was stirred at RT for 1 h, then quenched with sat. NH$_4$Cl (300 mL) dropwise (exothermic!). It was extracted with of EtOAc (2×300 mL). The combined organic extracts were washed with water (2×30 mL) followed by brine (30 mL), dried over MgSO$_4$, and concentrated under reduced pressure. The resulting oil was purified by silica gel chromatography (0-20% EtOAc in hexanes) to give Compound 217I (24.05 g, 88% yield) as a light yellow oil. $^1$H NMR (300 MHz, CHLOROFORM-d) δ 7.77 (dd, J=2.63, 7.02 Hz, 1H), 7.35 (ddd, J=2.63, 4.24, 8.62 Hz, 1H), 6.95 (dd, J=8.62, 11.55 Hz, 1H), 5.25 (d, J=10.52 Hz, 1H), 5.00 (d, J=10.52 Hz, 1H), 3.78 (s, 3H), 3.61-3.72 (m, 2H), 2.63 (ddd, J=1.39, 7.86, 9.61 Hz, 1H), 1.72 (d, J=1.17 Hz, 3H), 1.51 (s, 9H), 1.46 (dd, J=5.19, 9.87 Hz, 1H), 1.17 (dd, J=5.33, 7.53 Hz, 1H), 0.88-1.03 (m, 2H), 0.00 (s, 9H). MS (ESI, positive ion) m/z: 603/605 (M+1).

Preparation of tert-butyl((1S,5S,6S)-5-(5-bromo-2-fluorophenyl)-1-(methoxymethyl)-5-methyl-2-thia-4-azabicyclo[4.1.0]hept-3-en-3-yl)((2-(trimethylsilyl)ethoxy)methyl)carbamate (217K). At RT, to a solution of (1S,5S,6S)-methyl 5-(5-bromo-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylate (217I, 8.7 g, 14.41 mmol) in 70 mL of THF was added lithium borohydride (2 M solution in THF, 14.41 mL, 28.8 mmol) slowly. MeOH (4.66 mL, 115 mmol) was then added to the mixture. The mixture began to bubble and the temperature rose to −40° C. over 15 min. After the mixture was stirred for 1 h, it was cooled to 0° C. and quenched with 70 mL of sat. aq. NH$_4$Cl. The mixture was extracted with 2×200 mL of EtOAc. The organic extracts were washed with 50 mL of brine and dried over MgSO$_4$. Filtration and concentration under reduced pressure afforded tert-butyl((1S,5S,6S)-5-(5-bromo-2-fluorophenyl)-1-(hydroxymethyl)-5-methyl-2-thia-4-azabicyclo[4.1.0]hept-3-en-3-yl)((2-(trimethylsilyl)ethoxy)methyl)carbamate (217J) as a light yellow oil. It was azeotroped with 2×5 mL of toluene. MS (ESI, positive ion) m/z: 575/577 (M+1).

At 0° C., to the crude alcohol (217J) in 50 mL of THF was added sodium bis(trimethylsilyl)amide (16.58 mL of 1 M in THF solution, 16.58 mmol) dropwise. The resulting mixture was stirred at 0° C. for 15 min, then treated with iodomethane (1.12 mL, 18.02 mmol). The mixture was stirred at 0° C.

for 1 h then RT for 15 h. It was diluted with DCM (400 mL) and washed with sat. NH$_4$Cl (50 mL) followed by brine (50 mL), dried over MgSO$_4$, filtered and concentrated. The crude material was purified by silica gel chromatography (5-15% EtOAc in hexanes) to give tert-butyl((1S,5S,6S)-5-(5-bromo-2-fluorophenyl)-1-(methoxymethyl)-5-methyl-2-thia-4-azabicyclo[4.1.0]hept-3-en-3-yl)((2-(trimethylsilyl)ethoxy)methyl)carbamate (217K) (6.61 g, 11.21 mmol, 78% yield). $^{19}$F NMR (376 MHz, DMSO-d$_6$) δ –114.48 (s, 1F). MS (ESI, positive ion) m/z: 589/591 (M+H)$^+$.

Preparation of Compound 217L. At RT, tert-butyl((1S,5S,6S)-5-(5-bromo-2-fluorophenyl)-1-(methoxymethyl)-5-methyl-2-thia-4-azabicyclo[4.1.0]hept-3-en-3-yl)((2-(trimethylsilyl)ethoxy)methyl)carbamate (6.60 g, 11.19 mmol) was treated with sulfuric acid (5.97 mL, 112 mmol). The brown reaction mixture was stirred at RT for 10 min, then cooled with an ice bath and treated with 100 g of ice. Potassium phosphate tribasic monohydrate (27.6 g, 120 mmol) was added in small portions. The pH was then adjusted to 9 with 5 M NaOH. The mixture was extracted with EtOAc (3×200 mL) and the combined organic extracts were washed with brine (2×20 mL), dried over MgSO$_4$, filtered, and concentrated. Purification by flash column chromatography on silica gel column (25-65% EtOAc in DCM) gave (1S,5S,6S)-5-(5-bromo-2-fluorophenyl)-1-(methoxymethyl)-5-methyl-2-thia-4-azabicyclo[4.1.0]hept-3-en-3-amine (3.31 g, 9.21 mmol, 82% yield) as a pale yellow amorphous solid. $^{19}$F NMR (376 MHz, DMSO-d$_6$) δ –113.99 (s, 1F). $^1$H NMR (400 MHz, DMSO-d$_6$) δ 7.90 (dd, J=2.74, 7.24 Hz, 1H), 7.49 (m, 1H), 7.13 (m, 1H), 6.12 (br., 2H), 3.55 (d, J=10.95 Hz, 1H), 3.34 (d, J=11.15 Hz, 1H), 3.28 (s, 3H), 1.70 (m, 1H), 1.55 (s, 3H), 0.82 (m, 1H), 0.53 (m, 1H). MS (ESI, positive ion) m/z: 359/361 (M+1).

Preparation of (1S,5S,6S)-5-(5-amino-2-fluorophenyl)-1-(methoxymethyl)-5-methyl-2-thia-4-azabicyclo[4.1.0]hept-3-en-3-amine (217). To a mixture of copper (I) iodide (0.41 g, 2.16 mmol), sodium azide (1.97 g, 30.3 mmol), (+)-sodium L-ascorbate (0.09 g, 0.45 mmol), and (1S,5S,6S)-5-(5-bromo-2-fluorophenyl)-1-(methoxymethyl)-5-methyl-2-thia-4-azabicyclo[4.1.0]hept-3-en-3-amine (217L, 3.11 g, 8.66 mmol) at RT was added EtOH (20 mL) and water (10 mL). The reaction mixture was degassed by bubbling nitrogen through the solution for 5 min and (1R,2R)-(–)-N,N"-dimethylcyclohexane-1,2-diamine (0.31 g, 2.16 mmol) was added. The reaction mixture was heated to 70° C. for 1.5 h. The mixture was cooled to RT, poured into 30 mL of 10/1 mixed solution of saturated NH$_4$Cl/ammonium hydroxide, and extracted with EtOAc (2×150 mL). The combined organic extracts were washed with brine (15 mL), dried over MgSO$_4$, filtered, and concentrated to give a green sticky oil which contained (1S,5S,6S)-5-(5-azido-2-fluorophenyl)-1-(methoxymethyl)-5-methyl-2-thia-4-azabicyclo[4.1.0]hept-3-en-3-amine. MS (ESI, positive ion) m/z: 322.0 (M+1). The green sticky oil was dissolved in THF (15 mL) and water (5 mL) and trimethylphosphine (1.0 M solution in THF, 8.66 mL, 8.66 mmol) was added. The reaction mixture was stirred at RT for 15 min, and then quenched by the addition of water (20 mL) and EtOAc (100 mL). The layers were separated. The aqueous phase was extracted with EtOAc (2×50 mL). The combined organic extracts were washed with brine (15 mL), dried over MgSO$_4$, filtered, and concentrated. Purification by flash column chromatography on silica gel (5-85% EtOAc in DCM followed by 5% MeOH in EtOAc) gave (1S,5S,6S)-5-(5-amino-2-fluorophenyl)-1-(methoxymethyl)-5-methyl-2-thia-4-azabicyclo[4.1.0]hept-3-en-3-amine (217) (1.96 g, 6.64 mmol, 77% yield) as a light yellow solid. MS (ESI, positive ion) m/z: 322.0 (M+1). $^1$H NMR (400 MHz, DMSO-d$_6$) δ 6.92 (dd, J=2.93, 7.24 Hz, 1H), 6.76 (dd, J=8.51, 12.42 Hz, 1H), 6.38 (td, J=3.45, 8.36 Hz, 1H), 5.87 (br., 2H), 4.79 (br., 2H), 3.55 (d, J=10.76 Hz, 1H), 3.38 (d, J=10.79 Hz, 1H), 3.35 (s, 3H), 1.63 (m, 1H), 1.54 (s, 3H), 0.81 (m, 1H), 0.54 (m, 1H). $^{19}$F NMR (377 MHz, DMSO-d$_6$) δ –128.23 (s, 1F).

(1S,5S,6S)-5-(5-Amino-2-fluorophenyl)-1-(difluoromethyl)-5-methyl-2-thia-4-azabicyclo[4.1.0]hept-3-en-3-amine (218)

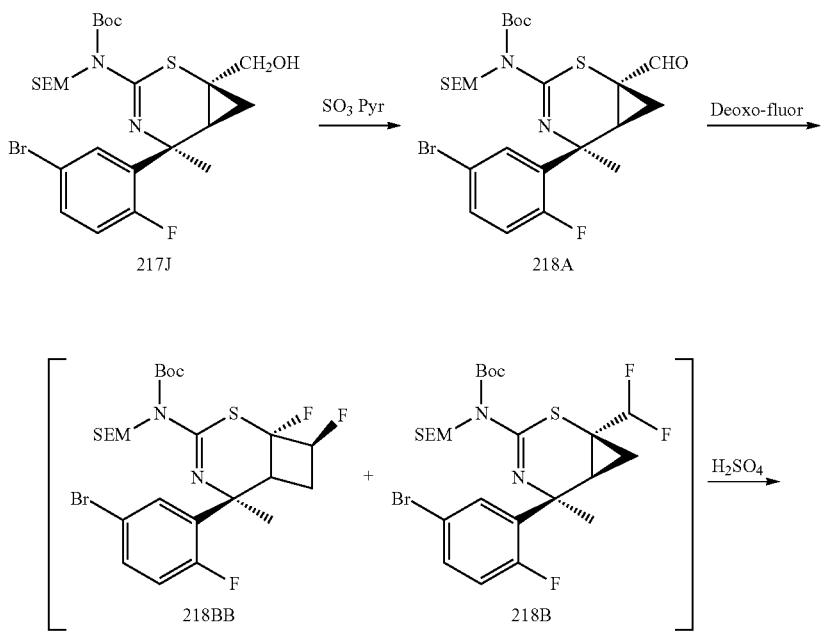

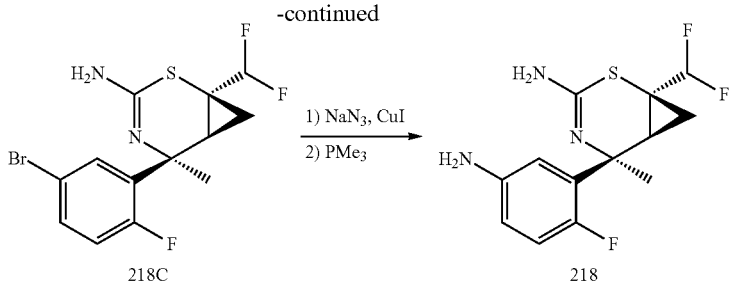

Preparation of tert-butyl((1S,5S,6S)-5-(5-bromo-2-fluorophenyl)-1-formyl-5-methyl-2-thia-4-azabicyclo[4.1.0]hept-3-en-3-yl)((2-(trimethylsilyl)ethoxy)methyl)carbamate (218A). At RT, to tert-butyl((1S,5S,6S)-5-(5-bromo-2-fluorophenyl)-1-(hydroxymethyl)-5-methyl-2-thia-4-azabicyclo[4.1.0]hept-3-en-3-yl)((2-(trimethylsilyl)ethoxy)methyl)carbamate (217J) (13.25 g, 23.03 mmol) in 45 mL of DCM and 15 mL of DMSO was added diisopropylethylamine (16.02 mL, 92 mmol) followed by pyridine sulfur trioxide (7.33 g, 46.1 mmol). The reaction mixture was stirred at RT for 18 h. It was diluted with DCM (400 mL) and washed with sat. NH$_4$Cl (50 mL) followed by brine (50 mL), dried over MgSO$_4$, filtered and concentrated. The crude material was purified by silica gel chromatography (5-15% EtOAc in hexanes) to give tert-butyl((1S,5S,6S)-5-(5-bromo-2-fluorophenyl)-1-formyl-5-methyl-2-thia-4-azabicyclo[4.1.0]hept-3-en-3-yl)((2-(trimethylsilyl)ethoxy)methyl)carbamate (218A, 10.68 g, 18.62 mmol, 81% yield) as a colorless viscous oil. MS (ESI, positive ion) m/z: 573/575 (M+1). $^{19}$F NMR (377 MHz, DMSO-d$_6$) δ −114.00 (s, 1F).

Preparation of (1S,5S,6S)-5-(5-bromo-2-fluorophenyl)-1-(difluoromethyl)-5-methyl-2-thia-4-azabicyclo[4.1.0]hept-3-en-3-amine (218C). At −10° C. (ice/salt bath), to a stirring solution of tert-butyl((1S,5S,6S)-5-(5-bromo-2-fluorophenyl)-1-formyl-5-methyl-2-thia-4-azabicyclo[4.1.0]hept-3-en-3-yl)((2-(trimethylsilyl)ethoxy)methyl)carbamate (218A, 10.67 g, 18.60 mmol) in 160 mL of hexanes was added Deoxo-Fluor (11.98 mL, 65.1 mmol). The reaction mixture was stirred at 0° C. for 1 h then RT overnight. The reaction mixture was diluted with EtOAc (400 mL), cooled with an ice bath and quenched with sat. NaHCO$_3$ (100 mL) slowly over a period of 30 min. The organic layer was separated, washed with brine (20 mL), dried over sodium sulfate, filtered and concentrated. The crude material was purified by column chromatography with 5-10% EtOAc in hexanes to give a mixture of two compounds (10.49 g) as a sticky oil, 218BB:218B, in about 1:6 ratio. Both products had the mass of MS (ESI, positive ion) m/z: 595/597 (M+1). The major product, tert-butyl((1S,5S,6S)-5-(5-bromo-2-fluorophenyl)-1-(difluoromethyl)-5-methyl-2-thia-4-azabicyclo[4.1.0]hept-3-en-3-yl)((2-(trimethylsilyl)ethoxy)methyl)carbamate (218B) had $^{19}$F NMR (376 MHz, DMSO-d$_6$) δ −114.34 (s, 1F), −115.62 (d, $^1$J=275.70 Hz, 1F), −118.55 (d, $^1$J=275.70 Hz, 1F).

To the above mixture of 218BB:218B (in about 1:6 ratio, 10.49 g) at RT was added sulfuric acid (9.91 mL, 186 mmol). The reaction mixture was stirred at RT for 10 min. It was poured onto 100 g of ice.

The brown mixture was cooled with an ice bath and treated with potassium phosphate tribasic monohydrate (43.8 g, 190 mmol) in small portions (pH was about 7). The pH was adjusted to 9 with 5 M NaOH. The aqueous phase was extracted with EtOAc (3×200 mL) and the combined organic extracts were washed with brine (2×20 mL), dried over MgSO$_4$, filtered, and concentrated. Purification by flash column chromatography on silica gel column (25-65% EtOAc in DCM) gave (1S,5S,6S)-5-(5-bromo-2-fluorophenyl)-1-(difluoromethyl)-5-methyl-2-thia-4-azabicyclo[4.1.0]hept-3-en-3-amine (218C, 3.69 g, 10.10 mmol, 54% yield) as a pale yellow foam. MS (ESI, positive ion) m/z: 365/367 (M+1).

Preparation of (1S,5S,6S)-5-(5-amino-2-fluorophenyl)-1-(difluoromethyl)-5-methyl-2-thia-4-azabicyclo[4.1.0]hept-3-en-3-amine (218). To a mixture of copper (I) iodide (0.48 g, 2.52 mmol), sodium azide (2.29 g, 35.3 mmol), (+)-sodium L-ascorbate (0.09 g, 0.45 mmol), and (1S,5S,6S)-5-(5-bromo-2-fluorophenyl)-1-(difluoromethyl)-5-methyl-2-thia-4-azabicyclo[4.1.0]hept-3-en-3-amine (218C, 3.68 g, 10.08 mmol) at RT was added EtOH (25 mL) and water (12.5 mL). The reaction mixture was degassed by bubbling nitrogen through the solution for 5 min and (1R,2R)-(−)-N,N"-dimethylcyclohexane-1,2-diamine (0.36 g, 2.52 mmol) was added. The reaction mixture was heated to 70° C. for 1.5 h. LCMS indicated the presence of 218C. Additional copper (I) iodide (0.24 g, 0.22 mmol) and (1R,2R)-(−)-N,N"-dimethylcyclohexane-1,2-diamine (0.18 g, 1.26 mmol) were added. Heating was resumed at 70° C. for 0.5 h. The mixture was cooled to RT, poured into 40 mL of 10:1 saturated NH$_4$Cl/ammonium hydroxide, and extracted with EtOAc (2×150 mL). The combined organic extracts were washed with brine (15 mL), dried over MgSO$_4$, filtered, and concentrated to give a brown sticky oil which contained (1S,5S,6S)-5-(5-azido-2-fluorophenyl)-1-(difluoromethyl)-5-methyl-2-thia-4-azabicyclo[4.1.0]hept-3-en-3-amine. MS (ESI, positive ion) m/z: 328.0 (M+1). The brown sticky oil was dissolved in THF (15 mL) and water (5 mL) and trimethylphosphine (1.0 M solution in THF) (10.08 mL, 10.08 mmol) was added. The reaction mixture was stirred at RT for 15 min, and diluted with water (20 mL) and EtOAc (100 mL). The layers were separated. The aqueous phase was extracted with EtOAc (2×50 mL). The combined organic extracts were washed with brine (15 mL), dried over MgSO$_4$, filtered, and concentrated. Purification by flash column chromatography on silica gel column (5-85% EtOAc in DCM) gave: 1) The 1st eluent was the recovered (1S,5S,6S)-5-(5-bromo-2-fluorophenyl)-1-(difluoromethyl)-5-methyl-2-thia-4-azabicyclo[4.1.0]hept-3-en-3-amine (218C, 240 mg). MS (ESI, positive ion) m/z: 365/367 (M+1). 2) The 2nd eluent was (1S,5S,6S)-5-(5-amino-2-fluorophenyl)-1-(difluoromethyl)-5-methyl-2-thia-4-azabicyclo[4.1.0]hept-3-en-3-amine (218) (1.77 g, 5.87 mmol, 58% yield) as a light yellow solid. $^1$H NMR (400 MHz, DMSO-d$_6$) δ 6.75 (m, 2H), 6.36 (m, 1H), 6.17 (br., 2H), 5.76-6.04 (m, 1H), 4.80 (br., 2H), 1.81 (m, 1H), 1.57 (s, 3H), 1.25 (m, 1H), 0.63 (m, 1H). $^{19}$F NMR (376 MHz, DMSO-d$_6$) δ −114.65 (d, $^1$J=274.10 Hz, 1F), −118.13 (d, $^1$J=274.10 Hz, 1F), −127.65 (s, 1F). MS (ESI, positive ion) m/z: 302.1 (M+1).

(1S,5S,6S)-5-(5-Amino-2-fluorophenyl)-1-(fluoromethyl)-5-methyl-2-thia-4-azabicyclo[4.1.0]hept-3-en-3-amine (219)

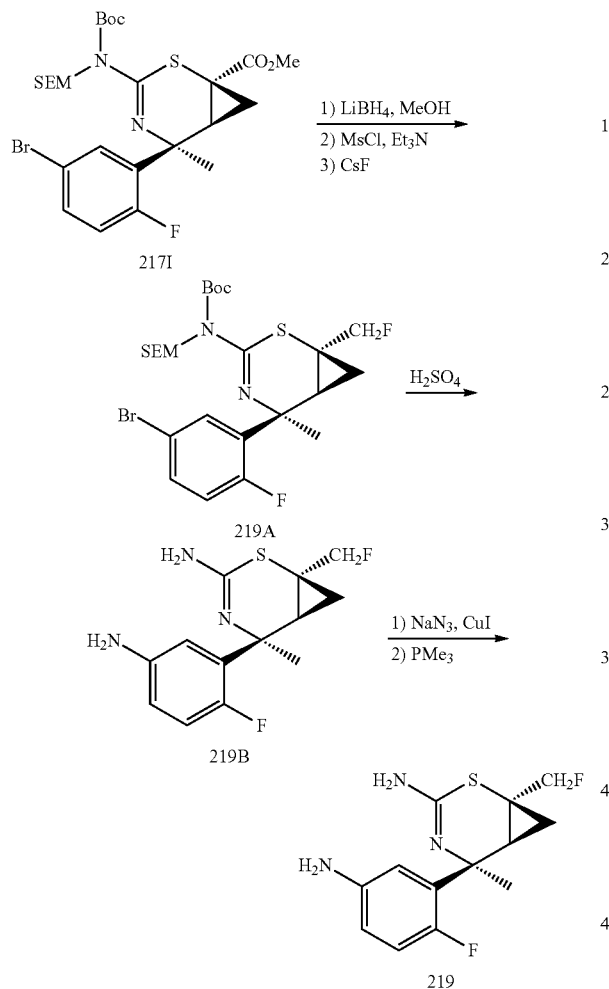

Preparation of tert-butyl((1S,5S,6S)-5-(5-bromo-2-fluorophenyl)-1-(fluoromethyl)-5-methyl-2-thia-4-azabicyclo[4.1.0]hept-3-en-3-yl)((2-(trimethylsilyl)ethoxy)methyl)carbamate (219A). This compound (3.40 g, 5.89 mmol, 70% yield) as a light yellow sticky oil was prepared from 217I (5.07 g, 8.40 mmol) according to the procedures similar to those described for intermediate 216A. MS (ESI, positive ion) m/z: 577/579 (M+1). $^{19}$F NMR (376 MHz, DMSO-d$_6$) δ −114.36 (s, 1F), −212.20 (s, 1F)

Preparation of (1S,5S,6S)-5-(5-amino-2-fluorophenyl)-1-(fluoromethyl)-5-methyl-2-thia-4-azabicyclo[4.1.0]hept-3-en-3-amine (219B). This compound (1.69 g, 4.87 mmol, 85% yield) as a pale yellow foam was prepared from tert-butyl((1S,5S,6S)-5-(5-bromo-2-fluorophenyl)-1-(fluoromethyl)-5-methyl-2-thia-4-azabicyclo[4.1.0]hept-3-en-3-yl)((2-(trimethylsilyl)ethoxy)methyl)carbamate (219A, 3.30 g, 5.71 mmol) according to the procedures similar to those described for intermediate 217L. $^{19}$F NMR (376 MHz, DMSO-d$_6$) δ −113.80 (s, 1F), −211.59 (s, 1F). $^1$H NMR (400 MHz, DMSO-d$_6$) δ 7.89 (dd, J=2.74, 7.24 Hz, 1H), 7.46 (m, 1H), 7.17 (dd, J=8.61, 11.93 Hz, 1H), 6.23 (br., 2H), 4.34-4.65 (m, 2H), 1.86 (m, 1H), 1.59 (s, 3H), 0.89 (m, 1H), 0.60 (m, 1H). MS (ESI, positive ion) m/z: 347/349 (M+1).

Preparation of (1S,5S,6S)-5-(5-amino-2-fluorophenyl)-1-(fluoromethyl)-5-methyl-2-thia-4-azabicyclo[4.1.0]hept-3-en-3-amine (219). This compound (1.08 g, 3.81 mmol, 79% yield) as a brown amorphous solid was prepared from (1S,5S,6S)-5-(5-bromo-2-fluorophenyl)-1-(fluoromethyl)-5-methyl-2-thia-4-azabicyclo[4.1.0]hept-3-en-3-amine (219B, 1.68 g, 4.84 mmol) according to the procedures similar to those described for intermediate 217. $^{19}$F NMR (376 MHz, DMSO-d$_6$) δ −128.09 (s, 1F), −211.32 (s, 1F). $^1$H NMR (400 MHz, DMSO-d$_6$) δ 6.88 (dd, J=2.74, 7.04 Hz, 1H), 6.76 (dd, J=8.51, 12.42 Hz, 1H), 6.39 (td, J=3.42, 8.41 Hz, 1H), 5.98 (br., 2H), 4.79 (br., 2H), 4.32-4.57 (m, 2H), 1.78 (m, 1H), 1.54 (s, 3H), 0.95 (m, 1H), 0.59 (q, J=5.15 Hz, 1H). MS (ESI, positive ion) m/z: 284.0 (M+1).

(1R,5S,6S)-5-(5-Amino-2,3-difluorophenyl)-5-methyl-1-(methylsulfonyl)-2-thia-4-azabicyclo[4.1.0]hept-3-en-3-amine (220)

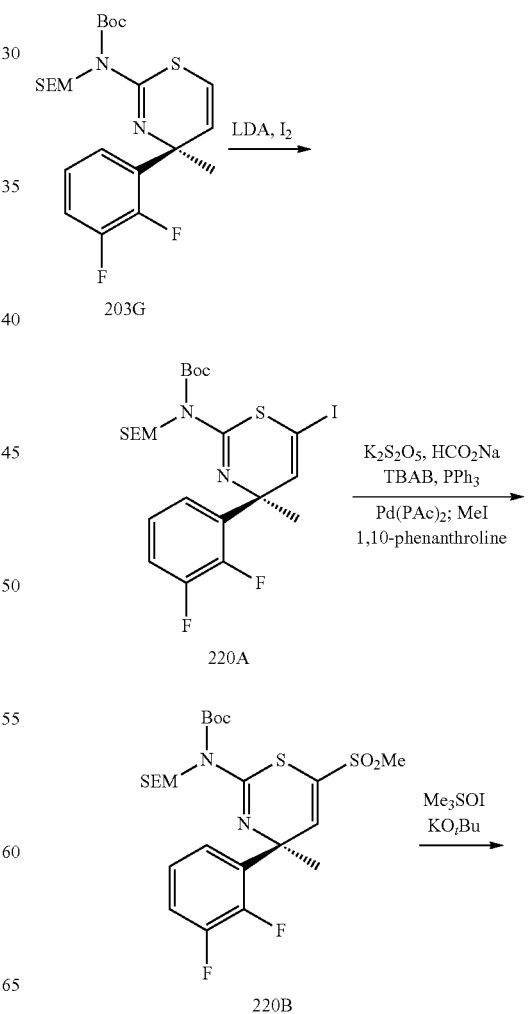

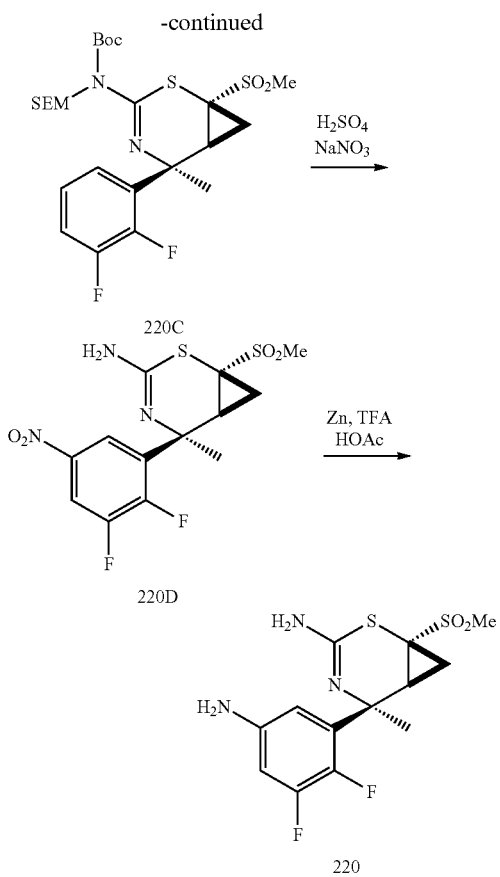

Preparation of (S)-tert-butyl(4-(2,3-difluorophenyl)-6-iodo-4-methyl-4H-1,3-thiazin-2-yl)((2-(trimethylsilyl)ethoxy)methyl)carbamate (220A). A solution of lithium diisopropylamide (2.0 M in THF/heptane/ethylbenzene) (4.2 mL, 8.4 mmol) was added dropwise to a stirring solution of (5)-tert-butyl(4-(2,3-difluorophenyl)-4-methyl-4H-1,3-thiazin-2-yl)((2-(trimethylsilyl)ethoxy)methyl)carbamate (203G, 3.3 g, 7.0 mmol) in THF (70 mL) under a nitrogen atmosphere at −78° C. The solution was stirred at −78° C. for 15 min and then a solution of iodine (2.1 g, 8.4 mmol) in THF (15 mL) was added dropwise. The dark red mixture was stirred at −78° C. for another 10 min and the reaction was quenched with saturated aqueous Na₂S₂O₃ solution (40 mL). The mixture was allowed to warm to RT and then diluted with water (40 mL) and extracted with EtOAc (2×75 mL). The combined organic extracts were washed with brine (40 mL), dried over Na₂SO₄, filtered and concentrated in vacuo. The residue was purified by silica gel chromatography eluting with a gradient of 2.5-10% EtOAc/heptane to give (S)-tert-butyl(4-(2,3-difluorophenyl)-6-iodo-4-methyl-4H-1,3-thiazin-2-yl)((2-(trimethylsilyl)ethoxy)methyl)carbamate as a yellow oil (220A, 4.2 g, 100%). LC/MS (ESI⁺) m/z=597.0 (M+H). ¹H NMR (400 MHz, chloroform-d) δ 7.24-7.30 (m, 1H), 6.98-7.15 (m, 2H), 6.68 (d, J=3.13 Hz, 1H), 5.30-5.37 (m, 1H), 5.20-5.27 (m, 1H), 3.65 (t, J=8.31 Hz, 2H), 1.72 (s, 3H), 1.55 (s, 9H), 0.91-0.96 (m, 2H), 0.00 (s, 9H).

Preparation of (S)-tert-butyl(4-(2,3-difluorophenyl)-4-methyl-6-(methylsulfonyl)-4H-1,3-thiazin-2-yl)((2-(trimethylsilyl)ethoxy)methyl)carbamate (220B). (S)-tert-Butyl (4-(2,3-difluorophenyl)-6-iodo-4-methyl-4H-1,3-thiazin-2-yl)((2-(trimethylsilyl)ethoxy)methyl)carbamate (220A, 4.2 g, 7.0 mmol), potassium metabisulfite (3.13 g, 14.1 mmol), tetrabutylammonium bromide (2.50 g, 7.74 mmol), sodium formate (1.05 g, 15.5 mmol), palladium(ii) acetate (0.079 g, 0.35 mmol), triphenylphosphine (0.277 g, 1.06 mmol), 1,10-phenanthroline (0.190 g, 1.06 mmol) and DMSO (20 mL) were combined under a nitrogen atmosphere. The mixture was degassed by bubbling nitrogen through it for 10 min. The mixture was then heated at 70° C. for 1 h. The mixture was allowed to cool to RT and then methyl iodide (0.66 mL, 10.6 mmol) was added. The mixture was stirred at RT for 1 h. The reaction was then diluted with water (40 mL) and extracted with EtOAc (3×30 mL). The combined organic extracts were washed with brine (40 mL), dried over Na₂SO₄, filtered and concentrated in vacuo. The residue was purified by silica gel chromatography eluting with a gradient of 0-35% EtOAc/heptane to give (S)-tert-butyl(4-(2,3-difluorophenyl)-4-methyl-6-(methylsulfonyl)-4H-1,3-thiazin-2-yl)((2-(trimethylsilyl)ethoxy)methyl)carbamate as a yellow oil (220B, 1.8 g, 47%). LC/MS (ESI⁺) m/z=549.0 (M+H). ¹H NMR (400 MHz, chloroform-d) δ 7.29-7.32 (m, 1H), 7.04-7.18 (m, 3H), 5.32-5.37 (m, 1H), 5.22-5.28 (m, 1H), 3.65 (t, J=8.22 Hz, 2H), 3.03 (s, 3H), 1.79 (s, 3H), 1.57 (s, 9H), 0.91-0.95 (m, 2H), −0.01 (s, 9H).

Preparation of tert-butyl((1R,5S,6S)-5-(2,3-difluorophenyl)-5-methyl-1-(methylsulfonyl)-2-thia-4-azabicyclo[4.1.0]hept-3-en-3-yl)((2-(trimethylsilyl)ethoxy)methyl)carbamate (220C). Potassium tert-butoxide (0.41 g, 3.6 mmol) was added to a solution of trimethylsulfoxonium iodide (0.81 g, 3.6 mmol) in DMSO (10 mL) at RT. The solution was stirred at RT for 1 h and then added dropwise over 5 min by addition funnel to a solution of (S)-tert-butyl (4-(2,3-difluorophenyl)-4-methyl-6-(methylsulfonyl)-4H-1,3-thiazin-2-yl)((2-(trimethylsilyl)ethoxy)methyl)carbamate (220B, 1.80 g, 3.28 mmol) in THF (10 mL). The solution was stirred at RT for 1 h. The reaction was quenched with saturated aqueous NH₄Cl (20 mL) and diluted with water (20 mL). The mixture was extracted with 3:1 heptane:EtOAc (2×50 mL) and the combined organic extracts were washed with water (30 mL), brine (30 mL), dried over MgSO₄, filtered and concentrated in vacuo. The residue was purified by silica gel chromatography eluting with a gradient of 3-30% EtOAc/heptane to give tert-butyl((1R,5S,6S)-5-(2,3-difluorophenyl)-5-methyl-1-(methylsulfonyl)-2-thia-4-azabicyclo[4.1.0]hept-3-en-3-yl)((2-(trimethylsilyl)ethoxy)methyl)carbamate as a yellow oil (220C, 1.55 g, 84%). LC/MS (ESI⁺) m/z=563.2 (M+H). ¹H NMR (400 MHz, chloroform-d) δ 7.30 (s, 1H), 7.01-7.19 (m, 2H), 5.37 (d, J=10.37 Hz, 1H), 5.13 (d, J=10.37 Hz, 1H), 3.66 (dt, J=2.54, 8.22 Hz, 2H), 3.12 (s, 3H), 2.55 (dd, J=7.92, 10.07 Hz, 1H), 1.93 (dd, J=6.16, 10.47 Hz, 1H), 1.84 (s, 3H), 1.55 (s, 9H), 1.15 (t, J=6.85 Hz, 1H), 0.91-0.98 (m, 2H), 0.02 (s, 9H).

Preparation of (1R,5S,6S)-5-(2,3-difluoro-5-nitrophenyl)-5-methyl-1-(methylsulfonyl)-2-thia-4-azabicyclo[4.1.0]hept-3-en-3-amine (220D). This compound (900 mg, 89% yield) as a yellow solid was prepared from intermediate 220C (1.5 g, 2.67 mmol) using the procedures similar to those described for intermediate 203L. LC/MS (ESI⁺) m/z=378.0 (M+H). ¹H NMR (400 MHz, chloroform-d) δ 8.26 (ddd, J=1.96, 2.84, 5.77 Hz, 1H), 8.04 (ddd, J=2.74, 6.36, 9.10 Hz, 1H), 4.78 (br. s., 2H), 3.06 (s, 3H), 2.47 (ddd, J=0.98, 7.73, 10.27 Hz, 1H), 2.04 (dd, J=6.26, 10.37 Hz, 1H), 1.83 (d, J=1.37 Hz, 3H), 1.03-1.09 (m, 1H).

Preparation of (1R,5S,6S)-5-(5-amino-2,3-difluorophenyl)-5-methyl-1-(methylsulfonyl)-2-thia-4-azabicyclo[4.1.0]hept-3-en-3-amine (220). This compound (420 mg, 51% yield) as a yellow crystalline solid was prepared from intermediate 220D (900 mg, 2.39 mmol) using the procedures similar to those described for intermediate 203. LC/MS (ESI+) m/z=348.1 (M+H). ¹H NMR (400 MHz, chloroform-d) δ 6.39 (ddd, J=2.74, 6.16, 11.25 Hz, 1H), 6.27-6.34 (m, 1H), 3.61 (br. s., 2H), 3.01 (s, 3H), 2.34 (dd, J=7.63, 10.37 Hz, 1H), 2.14 (dd, J=6.16, 10.27 Hz, 1H), 1.82 (d, J=0.98 Hz, 3H), 1.01-1.09 (m, 1H).

(1S,5S,6S)-3-Amino-5-(5-amino-2-fluorophenyl)-N-cyclopropyl-5-methyl-2-thia-4-azabicyclo[4.1.0]hept-3-ene-1-carboxamide (221) and tert-butyl((1S,5S,6S)-5-(5-amino-2-fluorophenyl)-1-(cyclopropylcarbamoyl)-5-methyl-2-thia-4-azabicyclo[4.1.0]hept-3-en-3-yl)((2-(trimethylsilyl)ethoxy)methyl)carbamate (221D)

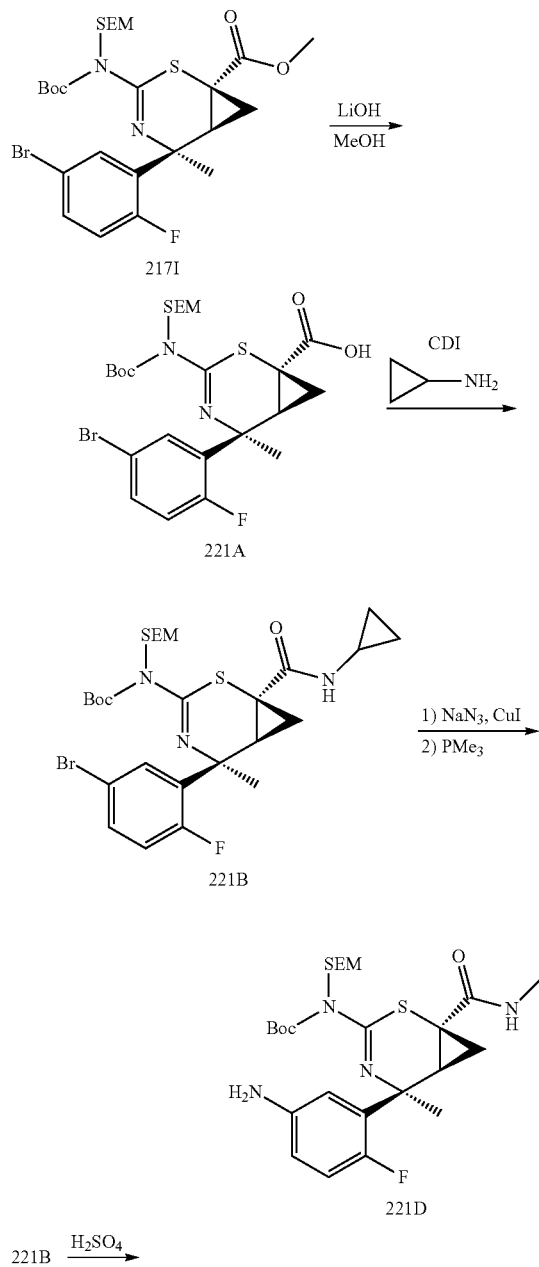

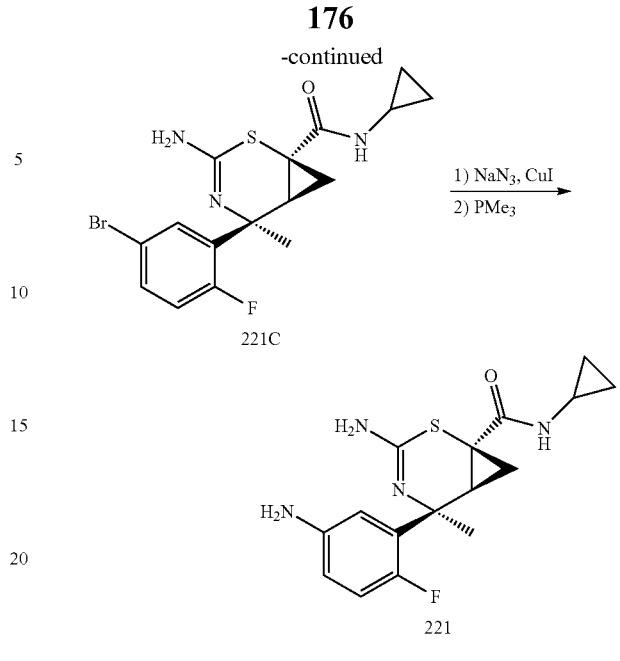

Preparation of acid 221A. A mixture of (1S,5S,6S)-methyl 5-(5-bromo-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylate (217I, 4.0 g, 6.63 mmol), and lithium hydroxide (19.88 mL of 1 M aqueous solution, 19.88 mmol) in MeOH (60 mL) was stirred at RT in 16 h. The reaction mixture was concentrated, diluted with H₂O, cooled in an ice bath and acidified with 5 N HCl. The solid (3.9 g, 100%) was collected, washed with H₂O, dried and used in the next step. MS (ESI, positive ion) m/z: 589/591 (M+1).

Preparation of tert-butyl((1S,5S,6S)-5-(5-bromo-2-fluorophenyl)-1-(cyclopropylcarbamoyl)-5-methyl-2-thia-4-azabicyclo[4.1.0]hept-3-en-3-yl)((2-(trimethylsilyl)ethoxy)methyl)carbamate (221B). To a solution of (1S,5S)-5-(5-bromo-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylic acid (221A, 5.3 g, 9.0 mmol) in 40 mL dry THF was added 1,1'-carbonyldiimidazole (2.2 g, 13.5 mmol), and the resulting cloudy mixture was stirred for 1 h. Additional 1,1'-carbonyldiimidazole (0.7 g) was added. It was stirred for 30 min then treated with cyclopropylamine (5 mL, 71.3 mmol). After the mixture was stirred for 1.5 h, it was treated with 100 mL of EtOAc and 100 mL of brine. The layers were separated. The organic layer was washed 1 N HCl (10 mL) followed by with brine (2×10 mL), dried over Na₂SO₄, filtered, and concentrated to give the title compound (221B, 5.4 g, 96%). MS (ESI, positive ion) m/z: 628/630 (M+1).

Preparation of (1S,5S,6S)-3-amino-5-(5-bromo-2-fluorophenyl)-N-cyclopropyl-5-methyl-2-thia-4-azabicyclo[4.1.0]hept-3-ene-1-carboxamide (221C). At RT, concentrated sulfuric acid (20 mL) was added to tert-butyl((1S,5S)-5-(5-bromo-2-fluorophenyl)-1-(cyclopropylcarbamoyl)-5-methyl-2-thia-4-azabicyclo[4.1.0]hept-3-en-3-yl)((2-(trimethylsilyl)ethoxy)methyl)carbamate (221B, 5.43 g, 8.64 mmol) dropwise. After the brown sticky mixture was stirred for 10 min, it was added slowly to a mixture of 400 mL of DCM and 200 g of ice cooled with an ice bath. Solid K₃PO₄ was added in small portions until pH was about 7. 500 mL of water was added, and the mixtured was partitioned. The layers were separated. The aqueous solution was extracted with a mixed solvent of (400 mL DCM+50 mL MeOH). The combined organic extracts were dried over $Na_2SO_4$ and evaporated to give the title compound (1.23 g, 36%). MS (ESI, positive ion) m/z: 398/400 (M+1).

Preparation of tert-butyl((1S,5S,6S)-5-(5-amino-2-fluorophenyl)-1-(cyclopropylcarbamoyl)-5-methyl-2-thia-4-azabicyclo[4.1.0]hept-3-en-3-yl)((2-(trimethylsilyl)ethoxy)methyl)carbamate (221D). A mixture of tert-butyl((1S,5S,6S)-5-(5-bromo-2-fluorophenyl)-1-(cyclopropylcarbamoyl)-5-methyl-2-thia-4-azabicyclo[4.1.0]hept-3-en-3-yl)((2-(trimethylsilyl)ethoxy)methyl)carbamate (221B, 3.5 g, 5.57 mmol), sodium azide (1.08 g, 16.70 mmol), copper(i) iodide (318 mg, 1.67 mmol), (+)-sodium L-ascorbate (0.33 g, 1.67 mmol), and (1R,2R)-(–)-N,N''-dimethylcyclohexane-1,2-diamine (0.26 mL, 1.67 mmol) in EtOH/$H_2O$ (4:1, 50 mL) was heated at 90° C. for 2 h. The reaction mixture was cooled to RT and treated with $NH_4Cl/NH_4OH$ (9:1, 20 mL) and stirred for 10 min. The mixture was extracted with $CHCl_3$ (3×). The organic extracts were concentrated to dryness and dissolved in THF/$H_2O$ (9:1, 40 mL) and added trimethylphosphine (1.0 M solution in THF, 8.35 mL, 8.35 mmol) and the mixture was stirred at RT overnight. It was treated with saturated aqueous $NH_4Cl$ and extracted with $CHCl_3$ (3×). The extracts were dried over $Na_2SO_4$ and concentrated to give the title compound (3.1 g, 99%). MS (ESI, positive ion) m/z: 564/566 (M+1).

Preparation of (1S,5S,6S)-3-amino-5-(5-amino-2-fluorophenyl)-N-cyclopropyl-5-methyl-2-thia-4-azabicyclo[4.1.0]hept-3-ene-1-carboxamide (221). A mixture of (1S,5S,6S)-3-amino-5-(5-bromo-2-fluorophenyl)-N-cyclopropyl-5-methyl-2-thia-4-azabicyclo[4.1.0]hept-3-ene-1-carboxamide (221C, 1.2 g, 3.01 mmol), sodium azide (0.59 g, 9.04 mmol), copper(I) iodide (0.14 g, 0.75 mmol), sodium (R)-2-((S)-1,2-dihydroxyethyl)-4-hydroxy-5-oxo-2,5-dihydrofuran-3-olate (0.15 g, 0.75 mmol), and (1R,2R)—N1,N2-dimethylcyclohexane-1,2-diamine (0.147 ml, 0.753 mmol) in EtOH/$H_2O$ (5:1, 18 mL) was heated at 90° C. for 16 h. The reaction mixture was cooled to RT and partitioned between $NH_4Cl/NH_4OH$ (9:1, 10 mL) and DCM (100 mL). The organic layer was concentrated and the residue was dissolved in THF/$H_2O$ (9:1, 20 mL). To this stirring solution was added trimethylphosphine (3.01 mL of 1 M in THF solution, 3.01 mmol). After the addition, the mixture was stirred for 1 h, diluted with EtOAc, washed with $H_2O$, brine, dried over $MgSO_4$, concentrated and the residue was purified by silica gel column (10-20% MeOH/DCM) to give the title product (0.41 g, 41%). MS (ESI, positive ion) m/z: 335 (M+1).

((1S,5S,6S)-3-Amino-5-(5-amino-2,3-difluorophenyl)-5-methyl-2-thia-4-azabicyclo[4.1.0]hept-3-en-1-yl)(pyrrolidin-1-yl)methanone (222)

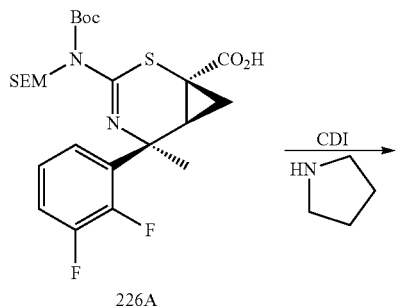

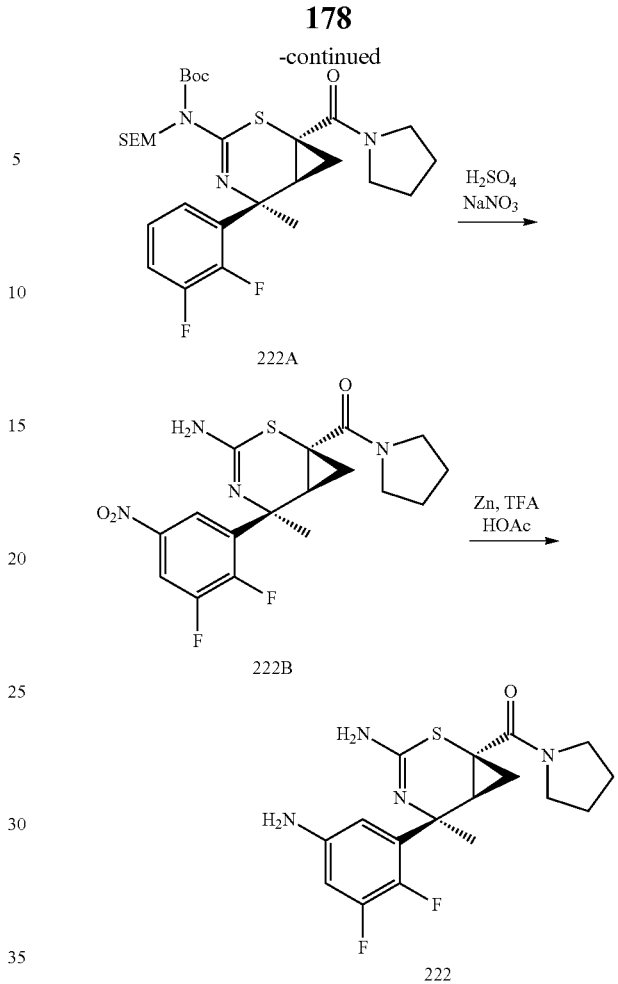

tert-Butyl((1S,5S,6S)-5-(2,3-difluorophenyl)-5-methyl-1-(pyrrolidine-1-carbonyl)-2-thia-4-azabicyclo[4.1.0]hept-3-en-3-yl)((2-(trimethylsilyl)ethoxy)methyl)carbamate (222A, 3.1 g, 5.30 mmol, 100% yield) as colorless oil was prepared according to the procedures described for intermediate 226B, starting from (1S,5S,6S)-3-((tert-butoxycarbonyl)((2-(trimethylsilyl)ethoxy)methyl)amino)-5-(2,3-difluorophenyl)-5-methyl-2-thia-4-azabicyclo[4.1.0]hept-3-ene-1-carboxylic acid (226A, 2.8 g, 5.30 mmol), CDI (1.29 g, 7.94 mmol) and pyrrolidine (1.33 mL, 15.89 mmol). LC/MS (ESI$^-$) m/z=582.2 (M+H)$^+$.

((1S,5S,6S)-3-Amino-5-(2,3-difluoro-5-nitrophenyl)-5-methyl-2-thia-4-azabicyclo[4.1.0]hept-3-en-1-yl)(pyrrolidin-1-yl)methanone (222B, 1.29 g, 3.25 mmol, 63% yield) as off white solid was prepared according to the procedures described for intermediate 226C, starting from tert-butyl ((1S,5S,6S)-5-(2,3-difluorophenyl)-5-methyl-1-(pyrrolidine-1-carbonyl)-2-thia-4-azabicyclo[4.1.0]hept-3-en-3-yl)((2-(trimethylsilyl)ethoxy)methyl)carbamate (222A, 3.0 g, 5.16 mmol). LC/MS (ESI$^-$) m/z=397.1 (M+H)$^+$. $^1$H NMR (400 MHz, DMSO-d$_6$) δ 8.31-8.38 (m, 2H), 6.51 (s, 2H), 3.60 (br., 2H), 3.28 (br., 2H), 2.14-2.20 (m, 1H), 1.83-1.93 (m, 2H), 1.81 (m, 2H), 1.70 (s, 3H), 1.31 (dd, J=5.58, 9.49 Hz, 1H), 0.71-0.76 (m, 1H).

((1S,5S,6S)-3-Amino-5-(5-amino-2,3-difluorophenyl)-5-methyl-2-thia-4-azabicyclo[4.1.0]hept-3-en-1-yl)(pyrrolidin-1-yl)methanone (222) (0.78 g, 2.1 mmol, 98% yield) as white solid was prepared according to the procedures described for intermediate 226, starting from ((1S,5S,6S)-

3-amino-5-(2,3-difluoro-5-nitrophenyl)-5-methyl-2-thia-4-azabicyclo[4.1.0]hept-3-en-1-yl)(pyrrolidin-1-yl)methanone (222B, 850 mg, 2.14 mmol). LC/MS (ESI⁻) m/z=367.1 (M+H). ¹H NMR (400 MHz, DMSO-d₆) δ 6.47-6.52 (m, 1H), 6.34 (ddd, J=2.84, 6.31, 12.57 Hz, 1H), 6.17 (br. s., 2H), 5.11 (s, 2H), 3.59 (d, J=18.78 Hz, 2H), 3.29 (d, J=9.00 Hz, 2H), 1.95-2.03 (m, 1H), 1.86 (br. s., 2H), 1.80 (br. s., 2H), 1.63 (s, 3H), 1.30 (dd, J=5.28, 9.39 Hz, 1H), 0.60-0.67 (m, 1H).

(1S,5S,6S)-3-Amino-5-(5-amino-2,3-difluorophenyl)-N,5-dimethyl-2-thia-4-azabicyclo[4.1.0]hept-3-ene-1-carboxamide (223)

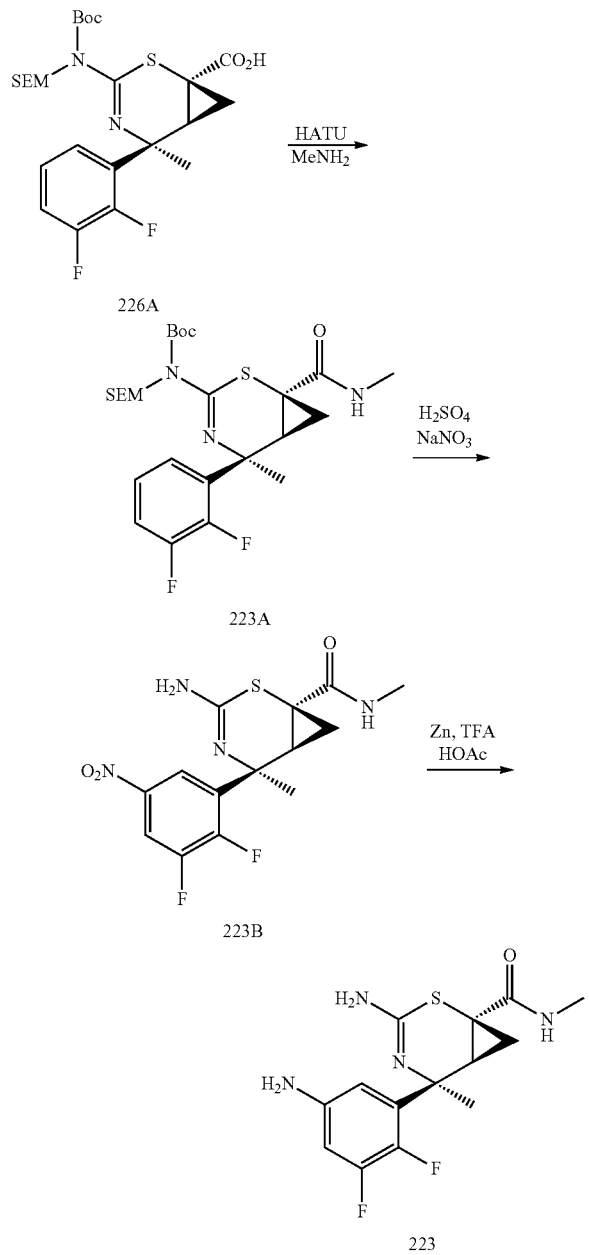

Preparation of Compound 223A. To a stirring solution of (1S,5S,6S)-3-(((tert-butoxycarbonyl)((2-(trimethylsilyl)ethoxy)methyl)amino)-5-(2,3-difluorophenyl)-5-methyl-2-thia-4-azabicyclo[4.1.0]hept-3-ene-1-carboxylic acid (226A, 13.0 g, 24.59 mmol) and N,N-diisopropylethylamine (5.35 ml, 30.7 mmol) in CHCl₃ (50 mL) and ACN (50 mL) at 20° C. was added HATU (10.75 g, 28.3 mmol). The solution was stirred for 45 min at 20° C. To the reaction was added methylamine (2.0 M in THF, 36.9 mL, 73.8 mmol). After 30 min the reaction was partitioned between EtOAc (300 mL) and sat. NaHCO₃ (200 mL). The organic layer was washed sequentially with 1 M NaOH (150 mL), 1 M HCl (150 mL), and brine (50 mL). The organic extract was then dried over MgSO₄, filtered, then concentrated under reduced pressure to afford light oil. The material was then purified by silica gel chromatography (330 g) eluting products with 0-25% EtOAc/heptane to afford tert-butyl((1S,5S,6S)-5-(2,3-difluorophenyl)-5-methyl-1-(methylcarbamoyl)-2-thia-4-azabicyclo[4.1.0]hept-3-en-3-yl)((2-(trimethylsilyl)ethoxy)methyl)carbamate (223A, 11.1 g, 20.49 mmol, 83% yield) as colorless tar. LC/MS (ESI⁻) m/z=542.2 (M+H).

Preparation of Compound 223B. To a 500 mL flask containing tert-butyl((1S,5S,6S)-5-(2,3-difluorophenyl)-5-methyl-1-(methylcarbamoyl)-2-thia-4-azabicyclo[4.1.0]hept-3-en-3-yl)((2-(trimethylsilyl)ethoxy)methyl)carbamate (223A, 5.5 g, 10.15 mmol) at 0° C. under nitrogen was added sulfuric acid (16.24 mL, 305 mmol). Gas evolution was evident. After 15 min, the reaction flask was removed from cooling bath, swirled by hand, then allowed to stir at 20° C. for 30 min. The mixture was chilled to 0° C. and sodium nitrate (0.86 g, 10.15 mmol) was added. The reaction was stirred for 15 min at 0° C. then more sodium nitrate (0.86 g, 10.15 mmol) added. The reaction was stirred at 20° C. for 45 min. The reaction was then slowly poured onto wet ice (700 mL) and the mixture along with CH₂Cl₂ (150 mL). To a rapidly stirred mixture was added potassium phosphate tribasic monohydrate (105 g, 457 mmol) over 40 min (pH~8). The suspension was filtered and the filtrate was transferred to a separatory funnel. The organic layer was separated, and the aqueous layer was extracted with CH₂Cl₂ (100 mL). The combined organic extracts were dried over MgSO₄, filtered, concentrated under reduced pressure, then purified via silica gel chromatography (120 g) eluting the products with a gradient of 0-50% EtOAc/CH₂Cl₂ to afford (1S,5S,6S)-3-amino-5-(2,3-difluoro-5-nitrophenyl)-N,5-dimethyl-2-thia-4-azabicyclo[4.1.0]hept-3-ene-1-carboxamide (223B, 2.2 g, 6.17 mmol, 60.8% yield) as off white solid. LC/MS (ESI⁻) m/z=357.0 (M+H). ¹H NMR (400 MHz, DMSO-d₆) δ 8.45-8.50 (m, 1H), 8.36 (ddd, J=2.93, 6.36, 9.49 Hz, 1H), 7.73 (t, J=5.63 Hz, 1H), 6.41 (s, 2H), 2.64 (d, J=4.50 Hz, 3H), 2.25 (t, J=8.22 Hz, 1H), 1.64 (s, 3H), 1.39 (dd, J=5.28, 9.59 Hz, 1H), 0.84 (dd, J=5.48, 7.04 Hz, 1H). ¹⁹F NMR (377 MHz, DMSO-d₆) δ −126.77 (d, J=21.16 Hz, 1F), −134.13 (d, J=21.16 Hz, 1F).

Preparation of Compound 223. To a stirring solution of (1S,5S,6S)-3-amino-5-(2,3-difluoro-5-nitrophenyl)-N,5-dimethyl-2-thia-4-azabicyclo[4.1.0]hept-3-ene-1-carboxamide (223B, 2.2 g, 6.17 mmol) in HOAc (20 mL) and TFA (5 mL) at 20° C. was added zinc dust (1.61 g, 24.69 mmol) in 4 portions over the period of 15 min. After 1 h, the suspension was filtered through a pad of Celite® filter aid and the metallic residue was extensively washed with CH₂Cl₂ (100 mL). The filtrate was then chilled to 0° C. and 30% NH₄OH (50 mL) was added drop wise via addition funnel over a 10 min period. The mixture was partitioned, and the aqueous portion was further extracted with CH₂Cl₂ (50 mL). The combined organic extracts were dried over MgSO₄, filtered, and concentrated under reduced pressure to afford (1S,5S,6S)-3-amino-5-(5-amino-2,3-difluorophenyl)-

N,5-dimethyl-2-thia-4-azabicyclo[4.1.0]hept-3-ene-1-carboxamide (223, 1.91 g, 5.85 mmol, 95% yield) as yellow foam. LC/MS (ESI⁻) m/z=327.1 (M+H).

(1S,5S,6S)-3-Amino-5-(5-amino-2,3-difluorophenyl)-5-methyl-2-thia-4-azabicyclo[4.1.0]hept-3-ene-1-carbonitrile (224)

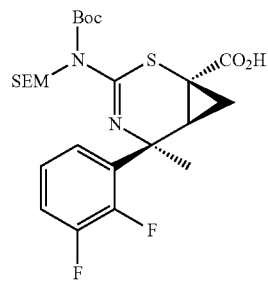

226A

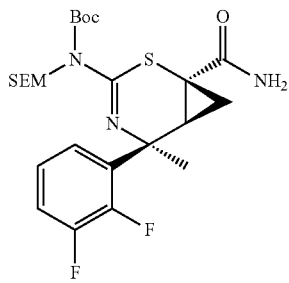

224A

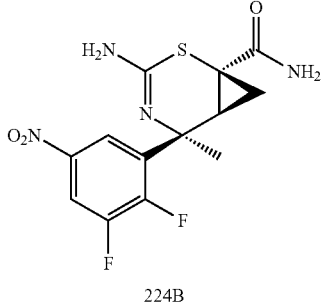

224B

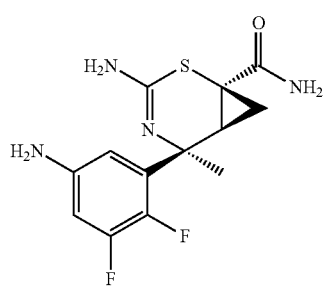

224C

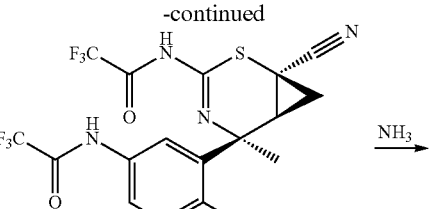

224D

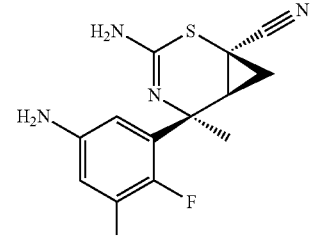

224

Preparation of Compound 224A. To a solution of (1S,5S,6S)-3-((tert-butoxycarbonyl)((2-(trimethylsilyl)ethoxy)methyl)amino)-5-(2,3-difluorophenyl)-5-methyl-2-thia-4-azabicyclo[4.1.0]hept-3-ene-1-carboxylic acid (226A, 4 g, 7.57 mmol) in THF (40 mL) at 20° C. was added 1,1'-carbonyldiimidazole (1.84 g, 11.35 mmol). The suspension was stirred for 1 h at 20° C. The solution was chilled to 0° C. and ammonia was introduced from a lecture bottle. After 30 min, the reaction was partitioned between EtOAc (30 mL) and 1 M HCl (30 mL). The organic extracts were washed with brine (25 mL), dried over MgSO₄, filtered, and concentrated under reduced pressure to afford tert-butyl((1S,5S,6S)-1-carbamoyl-5-(2,3-difluorophenyl)-5-methyl-2-thia-4-azabicyclo[4.1.0]hept-3-en-3-yl)((2-(trimethylsilyl)ethoxy)methyl)carbamate (224A, 4 g, 7.58 mmol, 100% yield) as colorless oil. LC/MS (ESI⁻) m/z=528.2 (M+H).

(1S,5S,6S)-3-Amino-5-(2,3-difluoro-5-nitrophenyl)-5-methyl-2-thia-4-azabicyclo[4.1.0]hept-3-ene-1-carboxamide (224B, 1.4 g, 4.1 mmol, 54% yield) as tan foam was prepared according to the procedures described for intermediate 223B, starting from tert-butyl((1S,5S,6S)-1-carbamoyl-5-(2,3-difluorophenyl)-5-methyl-2-thia-4-azabicyclo[4.1.0]hept-3-en-3-yl)((2-(trimethylsilyl)ethoxy)methyl)carbamate (224A, 4.0 g, 7.58 mmol). LC/MS (ESI⁻) m/z=343.0 (M+H). ¹H NMR (400 MHz, DMSO-d₆) δ 8.49 (d, J=5.60 Hz, 1H), 8.35 (ddd, J=2.93, 6.36, 9.49 Hz, 1H), 7.32 (br. s., 1H), 7.25 (br. s., 1H), 6.36 (s, 2H), 2.28 (t, J=8.41 Hz, 1H), 1.63 (s, 3H), 1.37 (dd, J=5.28, 9.59 Hz, 1H), 0.86 (dd, J=5.58, 6.94 Hz, 1H).

Preparation of Compound 224C. To a stirring solution of (1S,5S,6S)-3-amino-5-(2,3-difluoro-5-nitrophenyl)-5-methyl-2-thia-4-azabicyclo[4.1.0]hept-3-ene-1-carboxamide (224B, 280 mg, 0.82 mmol) in glacial HOAc (3 mL) and TFA (0.5 mL) at 20° C. was added zinc dust (270 mg, 4.09 mmol) in 5 portions. The suspension was stirred for 30 min at 20° C. then filtered. The metal residue was extensively washed with CH₂Cl₂ (10 mL). The filtrate was then chilled to 0° C. and 30% NH₄OH (5 mL) was added drop wise via addition funnel over a 10 min period. After separation of the organic the aqueous was further extracted with 9:1 CHCl₃/IPA (3×20 mL). The combined organics were dried over MgSO₄ and concentrated under reduced pressure to afford (1S,5S,6S)-3-amino-5-(5-amino-2,3-difluorophenyl)-5-methyl-2-thia-4-azabicyclo[4.1.0]hept-3-ene-1-carboxamide (224C, 295 mg, 0.944 mmol, 115% yield) as yellow foam. LC/MS (ESI⁻) m/z=313.1 (M+H).

Preparation of Compound 224D. To a stirring solution of (1S,5S,6S)-3-amino-5-(5-amino-2,3-difluorophenyl)-5-methyl-2-thia-4-azabicyclo[4.1.0]hept-3-ene-1-carboxamide (224C, 250 mg, 0.80 mmol) and N,N-diisopropylethylamine (2.08 mL, 12.01 mmol) in THF (10 mL) at −70° C. under nitrogen was added trifluoroacetic anhydride (1.33 mL, 9.60 mmol). After 1 h, the reaction was quenched with sat. NH₄Cl (1 mL). The mixture was partitioned between EtOAc (10 mL) and 5% NaHCO₃ (10 mL). The organic layer was dried over MgSO₄, filtered, then concentrated under reduced pressure to afford N-((1S,5S,6S)-1-cyano-5-(2,3-difluoro-5-(2,2,2-trifluoroacetamido)phenyl)-5-methyl-2-thia-4-azabicyclo[4.1.0]hept-3-en-3-yl)-2,2,2-trifluoroacetamide (224D, 450 mg, 0.92 mmol, 116% yield) as tan oil. LC/MS (ESI⁻) m/z=487.0 (M+H).

Preparation of Compound 224. A solution of N-((1S,5S,6S)-1-cyano-5-(2,3-difluoro-5-(2,2,2-trifluoroacetamido)phenyl)-5-methyl-2-thia-4-azabicyclo[4.1.0]hept-3-en-3-yl)-2,2,2-trifluoroacetamide (224D, 375 mg, 0.771 mmol) in 2 M NH₃ in MeOH (10 mL) was stirred for 18 h at 42° C. in a closed screw top vial. The solvent was removed under reduced pressure and the residue was purified by silica gel chromatography (12 g) eluting products with a gradient of 1-5% 2 M NH₃ in MeOH/CH₂Cl₂ to afford (1S,5S,6S)-3-amino-5-(5-amino-2,3-difluorophenyl)-5-methyl-2-thia-4-azabicyclo[4.1.0]hept-3-ene-1-carbonitrile (224, 100 mg, 0.34 mmol, 44% yield) as yellow film. LC/MS (ESI⁻) m/z=295.1 (M+H). ¹H NMR (400 MHz, DMSO-d₆) δ 6.49 (br. s., 2H), 6.34-6.44 (m, 2H), 5.11-5.21 (m, 2H), 2.29 (dd, J=8.02, 9.59 Hz, 1H), 1.87 (dd, J=5.87, 9.78 Hz, 1H), 1.68 (s, 3H), 0.96 (t, J=6.65 Hz, 1H).

tert-butyl((1S,5S,6S)-5-(5-Amino-2-fluorophenyl)-1-(tert-butylcarbamoyl)-5-methyl-2-thia-4-azabicyclo[4.1.0]hept-3-en-3-yl)((2-(trimethylsilyl)ethoxy)methyl)carbamate (225)

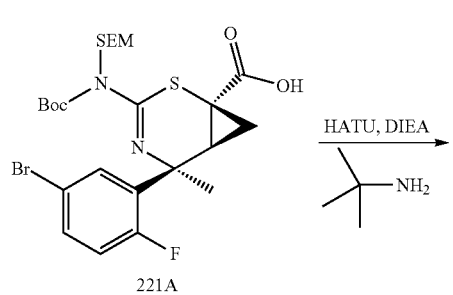

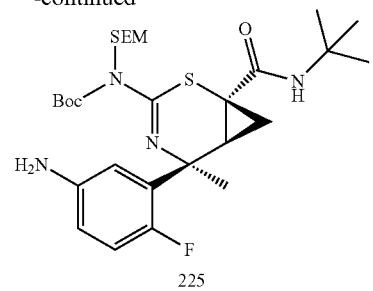

Preparation of tert-butyl((1S,5S,6S)-5-(5-bromo-2-fluorophenyl)-1-(tert-butylcarbamoyl)-5-methyl-2-thia-4-azabicyclo[4.1.0]hept-3-en-3-yl)((2-(trimethylsilyl)ethoxy)methyl)carbamate (225A). To a mixture of (1S,5S,6S)-5-(5-bromo-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylic acid (221A, 5.19 g, 8.82 mmol), tert-butylamine (1.20 mL, 11.47 mmol), and DIEA (2.03 mL, 11.47 mmol) in DMF (30 ML) was added HATU (4.02 g, 10.58 mmol). After the addition, the mixture was stirred for 2 h. It was partitioned between H₂O (50 mL) and DCM (150). The extracts were dried over Na₂SO₄, and concentrated to give the title compound (5.6 g, 100%). MS (ESI, positive ion) m/z: 644/646 (M+1).

Preparation of tert-butyl((1S,5S,6S)-5-(5-amino-2-fluorophenyl)-1-(tert-butylcarbamoyl)-5-methyl-2-thia-4-azabicyclo[4.1.0]hept-3-en-3-yl)((2-(trimethylsilyl)ethoxy)methyl)carbamate (225). The title compound (3.63 g, 71%) was prepared according to the procedures described for intermediate 221D, starting from tert-butyl((1S,5S,6S)-5-(5-bromo-2-fluorophenyl)-1-(tert-butylcarbamoyl)-5-methyl-2-thia-4-azabicyclo[4.1.0]hept-3-en-3-yl)((2-(trimethylsilyl)ethoxy)methyl)carbamate (225A, 5.69 g, 8.83 mmol). MS (ESI, positive ion) m/z: 581 (M+1).

(1S,5S,6S)-3-Amino-5-(5-amino-2,3-difluorophenyl)-N,N,5-trimethyl-2-thia-4-azabicyclo[4.1.0]hept-3-ene-1-carboxamide (226)

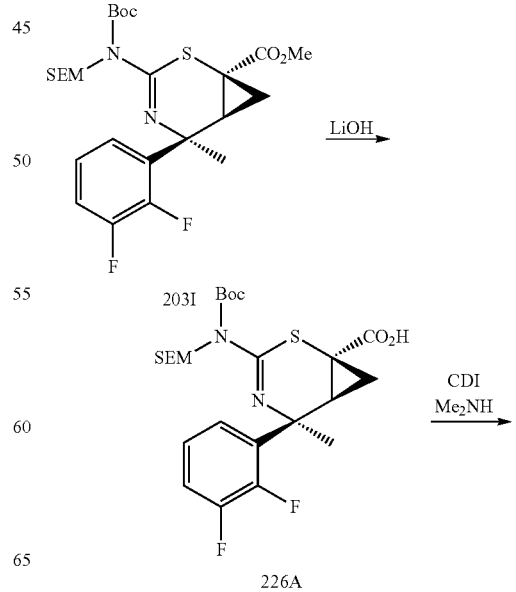

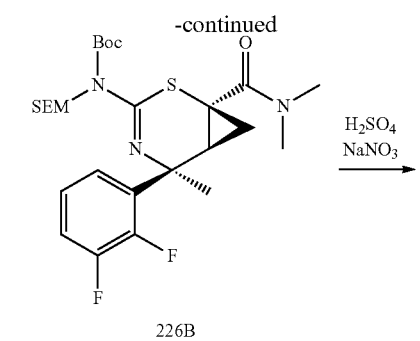

226B

226C

226

Preparation of Compound 226A. To a stirring solution of (1S,5S,6S)-methyl 3-((tert-butoxycarbonyl)((2-(trimethylsilyl)ethoxy)methyl)amino)-5-(2,3-difluorophenyl)-5-methyl-2-thia-4-azabicyclo[4.1.0]hept-3-ene-1-carboxylate (203I, 13.4 g, 24.7 mmol) in THF (100 mL) and MeOH (50 mL) was added a solution of lithium hydroxide monohydrate (3.1 g, 74.1 mmol) in water (50 mL). The reaction was rapidly stirred at 35° C. for 1 h. The reaction mixture was then partitioned between EtOAc (400 mL) and 1 M HCl (200 mL). The organic layer was washed with brine (2×50 mL), dried over MgSO$_4$, filtered, then concentrated under reduced pressure to afford (1S,5S,6S)-3-((tert-butoxycarbonyl)((2-(trimethylsilyl)ethoxy)methyl)amino)-5-(2,3-difluorophenyl)-5-methyl-2-thia-4-azabicyclo[4.1.0]hept-3-ene-1-carboxylic acid (226A, 13 g, 24.59 mmol, 100% yield) as colorless oil. LC/MS (ESI$^-$) m/z=529.1 (M+H)$^+$.

Preparation of Compound 226B. To a stirring solution of (1S,5S,6S)-3-((tert-butoxycarbonyl)((2-(trimethylsilyl)ethoxy)methyl)amino)-5-(2,3-difluorophenyl)-5-methyl-2-thia-4-azabicyclo[4.1.0]hept-3-ene-1-carboxylic acid (226A, 2.0 g, 3.8 mmol) in THF (20 mL) at RT under nitrogen was added 1,1'-carbonyldiimidazole (0.9 g, 5.6 mmol). The cloudy solution was stirred for 90 min at RT followed by addition of dimethylamine (2.0 M in THF, 9.46 mL, 18.91 mmol). After 2 h the reaction mixture was partitioned between EtOAc (60 mL) and 1 M HCl (60 mL). The organic layer was washed with brine (25 mL), dried over MgSO$_4$, filtered, and concentrated under reduced pressure to afford tert-butyl((1S,5S,6S)-5-(2,3-difluorophenyl)-1-(dimethylcarbamoyl)-5-methyl-2-thia-4-azabicyclo[4.1.0]hept-3-en-3-yl)((2-(trimethylsilyl)ethoxy)methyl)carbamate (226B, 2.1 g, 3.78 mmol) as colorless oil. LC/MS (ESI$^-$) m/z=556.3 (M+H)$^+$.

Preparation of Compound 226C. To a 500 mL flask containing tert-butyl((1S,5S,6S)-5-(2,3-difluorophenyl)-1-(dimethylcarbamoyl)-5-methyl-2-thia-4-azabicyclo[4.1.0]hept-3-en-3-yl)((2-(trimethylsilyl)ethoxy)methyl)carbamate (226B, 2.0 g, 3.60 mmol) at 0° C. was added sulfuric acid (14.39 mL, 270 mmol). The reaction was periodically removed from cooling bath, swirled by hand, and then allowed to stir at RT for 1 hr. The material was chilled to 0° C. and sodium nitrate (0.31 g, 3.60 mmol) was added. The reaction was stirred for 15 min at 0° C. then more sodium nitrate (0.31 g, 3.60 mmol) added. The reaction was stirred at RT for 45 min, then poured onto wet ice (700 mL) and the mixture along with CH$_2$Cl$_2$ (150 mL). To a rapidly stirred mixture was added potassium phosphate tribasic monohydrate (83 g, 360 mmol) over 20 min. The suspension was filtered and the filtrate transferred to a separatory funnel. The organic layer was separated, and the aqueous layer was extracted with 9:1 CHCl$_3$/IPA (2×50 mL). The combined organic layers were dried over MgSO$_4$, filtered, concentrated under reduced pressure, then purified via silica gel flash column chromatography (40 g) eluting the products with a gradient of 0-50% EtOAc/CH$_2$Cl$_2$ to afford (1S,5S,6S)-3-amino-5-(2,3-difluoro-5-nitrophenyl)-N,N,5-trimethyl-2-thia-4-azabicyclo[4.1.0]hept-3-ene-1-carboxamide (226C, 0.89 g, 2.40 mmol, 66.8% yield) as off white solid. LC/MS (ESI$^-$) m/z=371.0 (M+H)$^+$. $^1$H NMR (400 MHz, CHLOROFORM-d) δ 8.32 (br. s., 1H), 8.01 (ddd, J=2.74, 6.26, 9.00 Hz, 1H), 3.05 (br. s., 6H), 2.43 (t, J=8.31 Hz, 1H), 1.90 (s, 3H), 1.40 (br. s., 1H), 0.99 (t, J=6.65 Hz, 1H).

Preparation of Compound 226. To a stirring solution of (1S,5S,6S)-3-amino-5-(2,3-difluoro-5-nitrophenyl)-N,N,5-trimethyl-2-thia-4-azabicyclo[4.1.0]hept-3-ene-1-carboxamide (226C, 200 mg, 0.540 mmol) in glacial HOAc (2 mL) and TFA (0.5 mL) was added zinc nano powder (177 mg, 2.70 mmol) in five portions. The reaction was stirred for 2 h at 20° C. The reaction was then partitioned between 9:1 CHCl$_3$/IPA (30 mL) and 30% NH$_4$OH (20 mL). The aqueous was further extracted with 9:1 CHCl$_3$/IPA (2×15 mL). The organics were then washed with brine (10 mL), dried over MgSO$_4$, filtered, then concentrated under reduced pressure to afford (1S,5S,6S)-3-amino-5-(5-amino-2,3-difluorophenyl)-N,N,5-trimethyl-2-thia-4-azabicyclo[4.1.0]hept-3-ene-1-carboxamide (226, 170 mg, 0.50 mmol, 92% yield) as colorless film. LC/MS (ESI$^-$) m/z=341.0 (M+H)$^+$.

((1S,5S,6S)-3-Amino-5-(5-amino-2-fluorophenyl)-5-methyl-2-thia-4-azabicyclo[4.1.0]hept-3-en-1-yl)(pyrrolidin-1-yl)methanone (227)

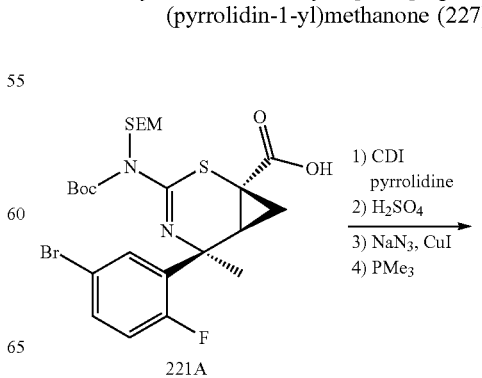

221A

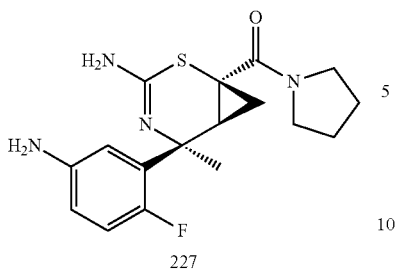

227

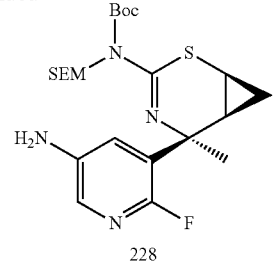

228

The title compound was prepared according to the synthetic sequence described for intermediate 221, starting from (1S,5S,6S)-5-(5-bromo-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylic acid (221A). MS (ESI, positive ion) m/z: 349.0 (M+1). $^1$H NMR (CHLOROFORM-d) δ: 6.82 (dd, J=11.6, 8.5 Hz, 1H), 6.76 (dd, J=6.6, 2.8 Hz, 1H), 6.49 (dt, J=8.2, 3.2 Hz, 1H), 3.65 (d, J=16.6 Hz, 4H), 3.46 (br. s., 2H), 2.11-2.26 (m, 1H), 1.91 (d, J=18.6 Hz, 4H), 1.81 (s, 3H), 1.43 (dd, J=9.7, 5.6 Hz, 1H), 0.79 (t, J=6.3 Hz, 1H).

tert-Butyl((1S,5S,6S)-5-(5-amino-2-fluoropyridin-3-yl)-5-methyl-2-thia-4-azabicyclo[4.1.0]hept-3-en-3-yl)((2-(trimethylsilyl)ethoxy)methyl)carbamate (228)

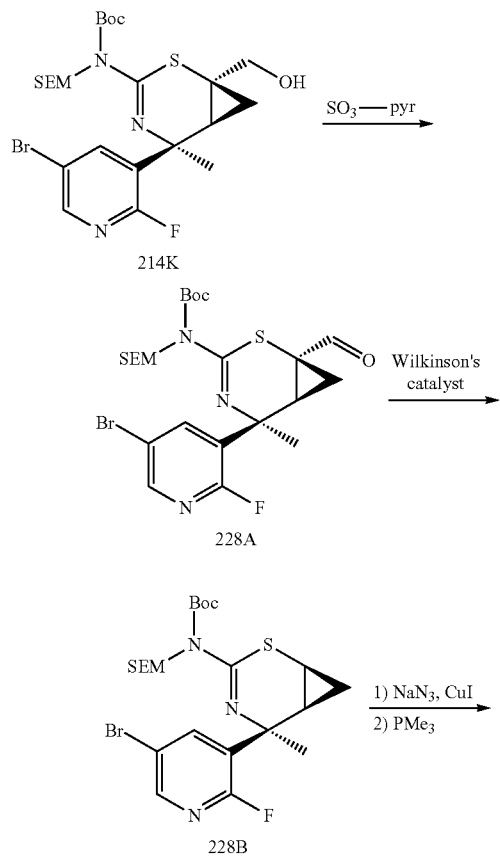

Preparation of tert-butyl((1S,5S,6S)-5-(5-bromo-2-fluoropyridin-3-yl)-1-formyl-5-methyl-2-thia-4-azabicyclo[4.1.0]hept-3-en-3-yl)((2-(trimethylsilyl)ethoxy)methyl)carbamate (228A). To a solution of tert-butyl ((1S,5S,6S)-5-(5-bromo-2-fluoropyridin-3-yl)-1-(hydroxymethyl)-5-methyl-2-thia-4-azabicyclo[4.1.0]hept-3-en-3-yl)((2-(trimethylsilyl)ethoxy)methyl)carbamate (214K, 3.0 g, 5.20 mmol) in DCM (30 mL) and DMSO (10 mL) was added diisopropylethylamine (3.8 mL, 21.85 mmol) and pyridine sulfur trioxide (1.8 g, 11.31 mmol). After 18 h, the mixture was diluted with EtOAc (200 mL) and washed with water (4×50 mL), brine, dried over MgSO$_4$, filtered, and concentrated. The residue was purified by chromatography on silica using EtOAc in heptane (5-35%) as eluent to give the desired product as a colorless oil (2.31 g, 77%). LCMS (ESI, pos.) 574.0/576.0 (M+1). $^1$H NMR (400 MHz, CHLOROFORM-d) δ 8.96 (s, 1H), 8.25 (dd, J=2.54, 8.61 Hz, 1H), 8.15-8.20 (m, 1H), 5.23-5.33 (m, 1H), 5.03 (d, J=10.56 Hz, 1H), 3.58-3.70 (m, 2H), 2.59 (ddd, J=1.17, 7.82, 9.59 Hz, 1H), 1.71 (d, J=0.98 Hz, 3H), 1.58 (dd, J=5.97, 9.88 Hz, 1H), 1.52 (s, 9H), 1.30-1.41 (m, 1H), 0.91-1.01 (m, 2H), 0.00 (s, 9H). $^{19}$F NMR (376 MHz, CHLOROFORM-d) δ −67.51 (s).

Preparation of tert-butyl((1S,5S,6S)-5-(5-amino-2-fluoropyridin-3-yl)-5-methyl-2-thia-4-azabicyclo[4.1.0]hept-3-en-3-yl)((2-(trimethylsilyl)ethoxy)methyl)carbamate (228B). A stream of Ar was bubbled through a solution of tert-butyl((1S,5S,6S)-5-(5-bromo-2-fluoropyridin-3-yl)-1-formyl-5-methyl-2-thia-4-azabicyclo[4.1.0]hept-3-en-3-yl)((2-(trimethylsilyl)ethoxy)methyl)carbamate (0.99 g, 1.72 mmol) in 1,2-dichloroethane (8 mL) for 5 min before Wilkinson's catalyst (1.59 g, 1.72 mmol) was added. The mixture was heated at 90° C. under N$_2$. After 18 h, the mixture was allowed to cool to RT and filtered. The filtrate was loaded directly on a 220 g silica gel column. The remaining solids were washed with DCM (5×3 mL) and the mother liquid was concentrated and the residue was loaded to the silica gel column. The column was eluted with EtOAc in heptane (5-25%) to give the title compound as a colorless oil (0.60 g, 64%). LCMS (ESI, pos.) 546.0/548.0 (M+1). $^1$H NMR (400 MHz, CHLOROFORM-d) δ 8.20 (dd, J=2.45, 8.51 Hz, 1H), 8.14 (s, 1H), 5.26 (d, J=10.56 Hz, 1H), 4.99 (d, J=10.56 Hz, 1H), 3.61-3.73 (m, 2H), 2.21 (dt, J=5.18, 8.26 Hz, 1H), 1.97-2.08 (m, 1H), 1.74 (s, 3H), 1.52 (s, 9H), 0.98 (dd, J=7.43, 9.19 Hz, 2H), 0.81-0.92 (m, 1H), 0.63 (q, J=5.74 Hz, 1H), 0.01 (s, 9H). $^{19}$F NMR (377 MHz, CHLOROFORM-d) δ −67.82 (s).

Preparation of tert-butyl((1S,5S,6S)-5-(5-amino-2-fluoropyridin-3-yl)-5-methyl-2-thia-4-azabicyclo[4.1.0]hept-3-en-3-yl)((2-(trimethylsilyl)ethoxy)methyl)carbamate (228). A mixture of (+)-sodium L-ascorbate (50 mg, 0.25 mmol), sodium azide (200 mg, 3.08 mmol), trans-N,N'-dimethyl-1,2-cyclohexanediamine (20 mg, 0.14 mmol), copper(I) iodide (30 mg, 0.16 mmol) and tert-butyl((5 S)-5-(5-bromo-2- fluoropyridin-3-yl)-5-methyl-2-thia-4-azabicyclo[4.1.0]hept-3-en-3-yl)((2-(trimethylsilyl)ethoxy)methyl)carbamate (600 mg, 1.10 mmol) was purged with $N_2$ through vacuum-back fill three times. EtOH (10 mL) and water 2.5 mL) were added. The blue mixture was heated at 95° C. under $N_2$. After 1 h, more (+)-sodium L-ascorbate (50 mg, 0.25 mmol), sodium azide (200 mg, 3.08 mmol), trans-N,N'-dimethyl-1,2-cyclohexanediamine (20 mg, 0.14 mmol) and copper(I) iodide (30 mg, 0.158 mmol) were added. The mixture was degassed with a stream of Ar for 5 min. The mixture was heated at 95° C. under $N_2$. After 30 min, the mixture was allowed to cool to RT. EtOAc (50 mL) was added and the mixture was washed with ammonium hydroxide (5 mL) followed by saturated $NH_4Cl$ (20 mL). The aqueous layer was extracted with DCM (2×10 mL). The combined organic phases were concentrated. The crude residue was suspended in THF (10 mL) and treated with trimethylphosphine (1.0 M solution in THF, 1.5 mL, 1.5 mmol). After 2 h at RT, EtOAc (50 mL) was added. The mixture was washed with saturated $NH_4Cl$ (20 mL) and brine (10 mL). The aqueous layer was washed with DCM (2×10 mL). The combined organic phases were dried over $MgSO_4$, filtered, and concentrated. The residue was purified by chromatography on silica using EtOAc in heptane (10-70%) as eluent to give the title compound (0.49 g, 86%). $^1$H NMR (400 MHz, CHLOROFORM-d) δ 7.51 (d, J=2.35 Hz, 1H), 7.44 (dd, J=2.93, 8.41 Hz, 1H), 5.27 (d, J=10.56 Hz, 1H), 5.01 (d, J=10.56 Hz, 1H), 3.58-3.72 (m, 2H), 2.19 (dt, J=4.89, 8.31 Hz, 1H), 1.99-2.08 (m, 1H), 1.73 (d, J=0.78 Hz, 3H), 0.91-1.00 (m, 2H), 0.85 (dd, J=7.53, 15.16 Hz, 1H), 0.65 (q, J=5.87 Hz, 1H), 0.02 (s, 9H). $^{19}$F NMR (376 MHz, CHLOROFORM-d) δ −77.66 (br. s.).

((1S,5S,6R)-3-Amino-5-(5-amino-2-fluorophenyl)-7,7-difluoro-5-methyl-2-thia-4-azabicyclo[4.1.0]hept-3-en-1-yl)methanol (229)

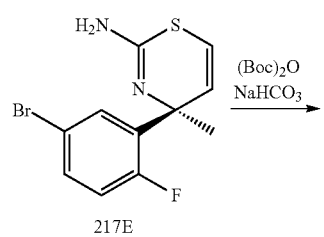

217E

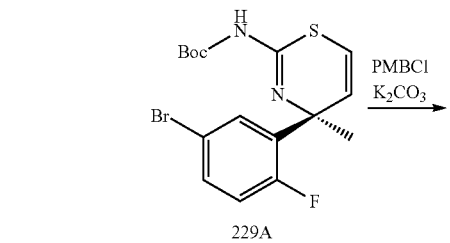

229A

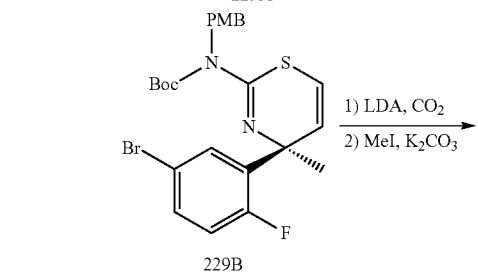

229B

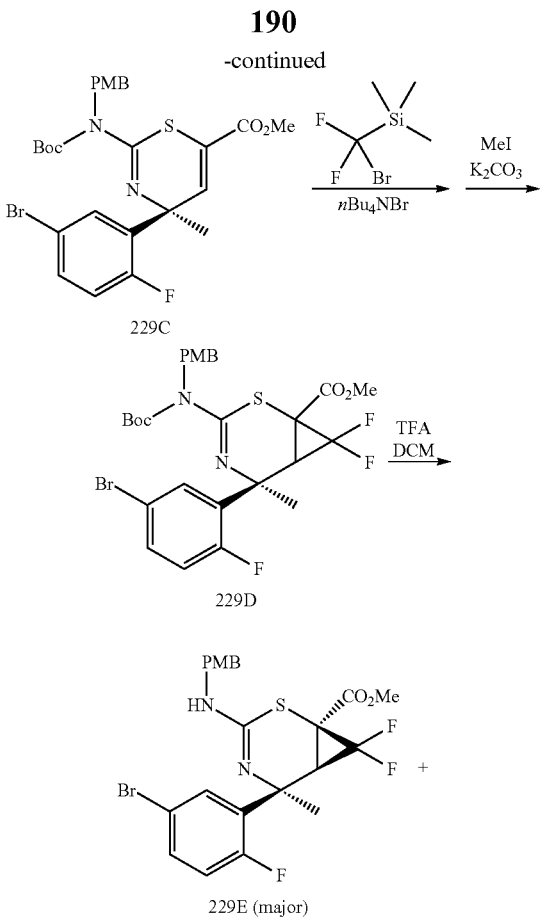

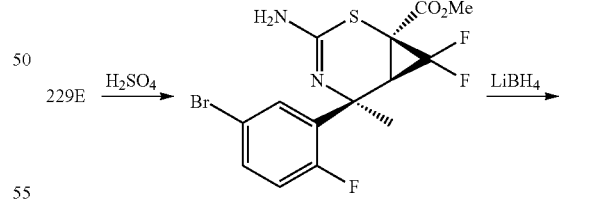

229G

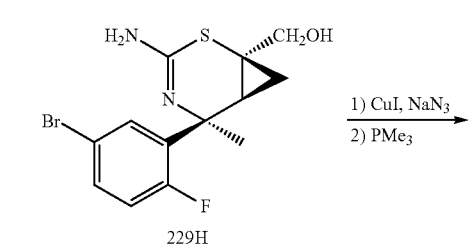

229H

-continued

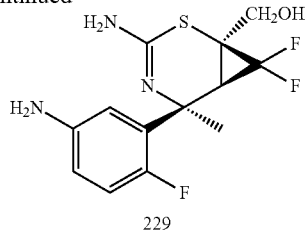

229

Preparation of (S)-tert-butyl(4-(5-bromo-2-fluorophenyl)-4-methyl-4H-1,3-thiazin-2-yl)carbamate (229A). To a 250 mL round bottom flask charged with (S)-4-(5-bromo-2-fluorophenyl)-4-methyl-4H-1,3-thiazin-2-amine (213E, 1.66 g, 5.51 mmol) and di-tert-butyl dicarbonate (1.20 g, 5.50 mmol, Sigma-Aldrich) was added THF (36 mL) and saturated sodium bicarbonate aqueous solution (36 mL). The reaction was stirred under Nitrogen for 48 h at RT. The reaction mixture was diluted with water and EtOAc. The organic layer was separated, washed with brine, dried over MgSO$_4$ and concentrated under reduced pressure. The crude residue was purified via silica gel flash chromatography eluting with a gradient of 0-30% EtOAc in hexanes to afford Compound 229A (2.08 g, 5.18 mmol, 94% yield) as a light yellow oil. MS m/z=401.0/403 [M+H]$^+$.

Preparation of (S)-tert-butyl(4-(5-bromo-2-fluorophenyl)-4-methyl-4H-1,3-thiazin-2-yl)(4-methoxybenzyl)carbamate (229B). To a solution of (S)-tert-butyl(4-(5-bromo-2-fluorophenyl)-4-methyl-4H-1,3-thiazin-2-yl)carbamate (229A, 2.00 g, 4.98 mmol) in DMF (12.46 mL) was added potassium carbonate (0.96 g, 6.98 mmol, Sigma-Aldrich), followed by 4-methoxybenzyl chloride (0.81 mL, 5.98 mmol, Sigma-Aldrich). The reaction stirred at ambient temperature for 6 h. The reaction was diluted with water and EtOAc and allowed to sit at RT for 72 h. The organic layer was separated, washed with brine, dried over MgSO$_4$ and concentrated under reduced pressure. The crude residue was purified via silica gel flash chromatography eluting with a gradient of 0-25% EtOAc in hexanes to afford (S)-tert-butyl (4-(5-bromo-2-fluorophenyl)-4-methyl-4H-1,3-thiazin-2-yl)(4-methoxybenzyl)carbamate (2.4 g, 4.60 mmol, 92% yield) as a clear oil. MS m/z=521.0/523 [M+H]$^+$.

Preparation of (S)-methyl 4-(5-bromo-2-fluorophenyl)-2-((tert-butoxycarbonyl)(4-methoxybenzyl)amino)-4-methyl-4H-1,3-thiazine-6-carboxylate (229C). A flame dried round bottom flask was charged with (S)-tert-butyl(4-(5-bromo-2-fluorophenyl)-4-methyl-4H-1,3-thiazin-2-yl)(4-methoxybenzyl)carbamate (0.53 g, 1.02 mmol) and THF (6 ml). The solution was cooled to −78° C. Lithium diisopropylamide (2.0 M in heptane/THF/ethylbenzene, 0.66 mL, 1.33 mmol, Sigma-Aldrich) was added drop wise and the mixture was stirred for 15 min. CO$_2$ (generated by evaporation of dry ice) was passed over the reaction head space for 15 min. The reaction was carefully quenched with saturated ammonium chloride aqueous solution and the mixture was warmed to RT. The mixture was diluted with 1.0 N HCl and extracted with EtOAc. The organic layer was separated, washed with brine, dried over MgSO$_4$ and concentrated under reduced pressure. The material was taken up in DMF (10 mL). Potassium carbonate (0.14 g, 1.02 mmol, Sigma-Aldrich) and methyl iodide (0.06 mL, 1.02 mmol, Sigma-Aldrich) were added. The reaction was stirred at ambient temperature for 1.5 h. The reaction was diluted with water and EtOAc. The organic layer was separated and washed sequentially with 1 M LiCl aqueous solution and brine, dried over MgSO$_4$ and concentrated under reduced pressure. The crude residue was purified via silica gel flash chromatography eluting with a gradient of 0-30% EtOAc in hexanes to afford (S)-methyl 4-(5-bromo-2-fluorophenyl)-2-((tert-butoxycarbonyl)(4-methoxybenzyl)amino)-4-methyl-4H-1,3-thiazine-6-carboxylate (0.44 g, 0.75 mmol, 73% yield). MS m/z=578.9/580.9 [M+H]$^+$.

Preparation of diastereomers 229D. A flame dried sealed tube was charged with a solution of (S)-methyl 4-(5-bromo-2-fluorophenyl)-2-((tert-butoxycarbonyl)(4-methoxybenzyl)amino)-4-methyl-4H-1,3-thiazine-6-carboxylate (229C, 3.03 g, 5.23 mmol) in toluene (20.9 mL). The vial was sealed and nitrogen was bubbled through the solution for 5 min. Tetrabutylammonium bromide (0.08 g, 0.26 mmol, Sigma-Aldrich) was added followed by trimethyl(bromodifluoromethyl)silane (2.12 g, 10.46 mmol, SynQuest Laboratories). The reaction was flushed with nitrogen and tightly sealed. The reaction was heated to 110° C. for 16 h then cooled to RT. It was diluted with water and EtOAc. The organic layer was separated, washed with brine, dried over MgSO$_4$ and concentrated under reduced pressure to afford an approximately 2:1:1 ratio of gemdifluorocyclopropyl carboxylic acid to gemdifluorocyclopropyl methyl ester to unreacted starting material by LC/MS. The crude material was taken up in DMF (35 mL). Potassium carbonate (0.72 g, 5.23 mmol, Sigma-Aldrich) was added followed by methyl iodide (0.33 mL, 5.23 mmol, Sigma-Aldrich). The reaction was stirred at RT for 2 h. The reaction was diluted with water and EtOAc. The organic layer was separated, washed with brine, and dried over MgSO$_4$. The crude material was purified via silica gel flash chromatography eluting with a gradient of 0-30% EtOAc in hexanes to afford 3.3 g of a mixture of (1S,5S,6R)-methyl 5-(5-bromo-2-fluorophenyl)-3-((tert-butoxycarbonyl)(4-methoxybenzyl)amino)-7,7-difluoro-5-methyl-2-thia-4-azabicyclo[4.1.0]hept-3-ene-1-carboxylate (229D: MS m/z=572.8/574.8 [M+H]$^+$) as a mixture of diastereomers and (S)-methyl 4-(5-bromo-2-fluorophenyl)-2-((tert-butoxycarbonyl)(4-methoxybenzyl)amino)-4-methyl-4H-1,3-thiazine-6-carboxylate (229C: MS m/z=578.9/580.9 M$^+$). Note: the observed mass to charge ratio of 572.8/574.8 corresponds to the mass of the desired product (629.5) minus the tert-butyl group of the Boc which is commonly observed under the standard LC/MS method. The mixture was carried forward without further purification.

Preparation of (1S,5S,6R)-methyl 5-(5-bromo-2-fluorophenyl)-7,7-difluoro-3-((4-methoxybenzyl)amino)-5-methyl-2-thia-4-azabicyclo[4.1.0]hept-3-ene-1-carboxylate (229E) and (1R,5S,6R)-methyl 5-(5-bromo-2-fluorophenyl)-7,7-difluoro-3-((4-methoxybenzyl)amino)-5-methyl-2-thia-4-azabicyclo[4.1.0]hept-3-ene-1-carboxylate (229F). To a flask charged with 3.3 g of the mixture containing (5 S)-methyl 5-(5-bromo-2-fluorophenyl)-3-((tert-butoxycarbonyl)(4-methoxybenzyl)amino)-7,7-difluoro-5-methyl-2-thia-4-azabicyclo[4.1.0]hept-3-ene-1-carboxylate (229D) and 229C from the previous step was added DCM (35 mL) followed by TFA (13.3 mL, 173 mmol). The reaction was stirred at RT for 1 h. The reaction was concentrated under reduced pressure. The crude material was taken up in EtOAc (100 mL) and washed with saturated sodium bicarbonate aqueous solution and brine. The organic layer was dried over MgSO$_4$ and concentrated under reduced pressure. The crude residue was purified via silica gel flash chromatography eluting with DCM to afford (1S,5S,6R)-methyl 5-(5-bromo-2-fluorophenyl)-7,7-difluoro-3-((4-methoxybenzyl)amino)-5-methyl-2-thia-4-azabicyclo[4.1.0]hept-3-ene-1-carboxylate (1.4 g, 2.64 mmol, 229E, 50% yield and the diastereomer (1R,5S,6S)-methyl 5-(5-bromo-2-fluorophenyl)-7,7-difluoro-3-((4-methoxybenzyl)amino)-5-methyl-2-thia-4-azabicyclo[4.1.0]hept-3-ene-1-carboxylate (0.3 g, 0.567 mmol, 11% yield). For both diastereomers: MS m/z=528.9/530.9 [M+H]⁺.

Preparation of (1S,5S,6R)-methyl 3-amino-5-(5-bromo-2-fluorophenyl)-7,7-difluoro-5-methyl-2-thia-4-azabicyclo[4.1.0]hept-3-ene-1-carboxylate (229G). To a solution of (1S,5S,6R)-methyl 5-(5-bromo-2-fluorophenyl)-7,7-difluoro-3-((4-methoxybenzyl)amino)-5-methyl-2-thia-4-azabicyclo[4.1.0]hept-3-ene-1-carboxylate (229E, 1.4 g, 2.6 mmol) in TFA (17.6 mL) was added anisole (0.87 mL, 7.93 mmol) followed by drop wise addition of sulfuric acid (1.4 mL, 26.4 mmol). The reaction was stirred at RT for 2 h. The sticky mixture was poured into an Erlenmeyer flask containing wet ice. 10 N NaOH was added to basify the reaction to pH=14. The basic aqueous layer was extracted with EtOAc twice and the combined organic layers were washed with brine, dried over MgSO₄ and concentrated under reduced pressure. The crude residue was purified via silica gel flash chromatography eluting with a gradient of 10-55% EtOAc in hexanes to afford (1S,5S,6R)-methyl 3-amino-5-(5-bromo-2-fluorophenyl)-7,7-difluoro-5-methyl-2-thia-4-azabicyclo[4.1.0]hept-3-ene-1-carboxylate (229G, 0.94 g, 2.29 mmol, 87% yield) as a white solid. MS m/z=408.9/410.9 [M+H]⁺.

Preparation of ((1S,5S,6R)-3-amino-5-(5-bromo-2-fluorophenyl)-7,7-difluoro-5-methyl-2-thia-4-azabicyclo[4.1.0]hept-3-en-1-yl)methanol (229H). To a solution of (1S,5S,6R)-methyl 3-amino-5-(5-bromo-2-fluorophenyl)-7,7-difluoro-5-methyl-2-thia-4-azabicyclo[4.1.0]hept-3-ene-1-carboxylate (229G, 0.98 g, 2.40 mmol) in THF (17 mL) was added lithium borohydride (2.0 M solution in THF, 2.40 ml, 4.80 mmol) followed by MeOH (0.78 mL, 19.22 mmol). The solution was stirred at ambient temperature for 2 h. The reaction was quenched with water and EtOAc. The organic layer was separated, washed with brine, dried over MgSO₄ and concentrated under reduced pressure to afford ((1S,5S,6R)-3-amino-5-(5-bromo-2-fluorophenyl)-7,7-difluoro-5-methyl-2-thia-4-azabicyclo[4.1.0]hept-3-en-1-yl)methanol (0.83 g, 2.18 mmol, 91% yield) as a white solid. MS m/z=380.8/382.8 [M+H]⁺.

Preparation of ((1S,5S,6R)-3-amino-5-(5-amino-2-fluorophenyl)-7,7-difluoro-5-methyl-2-thia-4-azabicyclo[4.1.0]hept-3-en-1-yl)methanol (229). To a mixture of copper(I) iodide (0.05 g, 0.27 mmol, Sigma-Aldrich), sodium azide (0.27 g, 4.11 mmol, Sigma-Aldrich), and ((1S,5S,6R)-3-amino-5-(5-bromo-2-fluorophenyl)-7,7-difluoro-5-methyl-2-thia-4-azabicyclo[4.1.0]hept-3-en-1-yl)methanol (229H, 0.52 g, 1.37 mmol) at RT was added EtOH (4.8 mL) and water (2.1 mL). The reaction mixture was degassed by bubbling nitrogen through the solution for 5 min then (1R,2R)-(−)-N,N″-dimethylcyclohexane-1,2-diamine (0.04 mL, 0.27 mmol, Sigma-Aldrich) was added. The reaction mixture was heated to 80° C. for 1.5 h then cooled to RT. The reaction was poured into a separatory funnel containing a 9:1 solution of aqueous saturated ammonium chloride to ammonium hydroxide. EtOAc was added and the phases were mixed. The organic layer was separated, washed sequentially with 9:1 saturated ammonium chloride to saturated ammonium hydroxide solution and brine, then dried over MgSO₄ and concentrated under reduced pressure. The crude residue was taken up in THF (6 mL) and water (3 mL). Trimethylphosphine (1.37 mL of 1.0 M solution in THF, 1.37 mmol) was added and the reaction was stirred at RT for 1 h. It was diluted with water and EtOAc. The organic layer was separated, washed with brine and dried over MgSO₄ to afford ((1S,5S,6R)-3-amino-5-(5-amino-2-fluorophenyl)-7,7-difluoro-5-methyl-2-thia-4-azabicyclo[4.1.0]hept-3-en-1-yl)methanol (0.37 g, 1.12 mmol, 86% yield) as a glassy brown solid. MS m/z=318.0 [M+H]⁺. ¹⁹F NMR (282 MHz, CHLOROFORM-d) δ −126.35 (s, 1F), −130.07 (d, J=157.75 Hz, 1F), −141.94 (d, J=158.32 Hz, 1F). ¹H NMR (300 MHz, CDCl₃) δ 7.03 (dd, J=2.9, 6.7 Hz, 1H), 6.87 (dd, J=8.6, 11.9 Hz, 1H), 6.55 (td, J=3.4, 8.5 Hz, 1H), 4.04-3.85 (m, 2H), 2.47 (dd, J=3.7, 15.8 Hz, 1H), 1.64 (s, 3H).

((1R,5S,6S)-3-Amino-5-(5-amino-2-fluorophenyl)-7,7-difluoro-5-methyl-2-thia-4-azabicyclo[4.1.0]hept-3-en-1-yl)methanol (230)

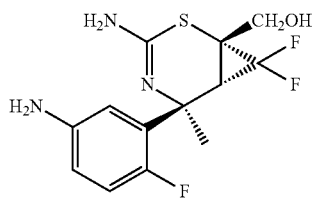

230

The title compound (230) was prepared following the procedures described for intermediate 229, starting with intermediate 229F. MS m/z=318.0 [M+H]⁺. ¹H NMR (300 MHz, CDCl₃) δ 6.87 (dd, J=8.6, 11.9 Hz, 1H), 6.68 (dd, J=3.0, 6.8 Hz, 1H), 6.54 (ddd, J=3.0, 3.8, 8.6 Hz, 1H), 3.91-3.76 (m, 2H), 2.41 (dd, J=3.2, 16.2 Hz, 1H), 1.74 (s, 3H).

(1S,5S,6R)-5-(5-Amino-2-fluorophenyl)-7,7-difluoro-1-(methoxymethyl)-5-methyl-2-thia-4-azabicyclo[4.1.0]hept-3-en-3-amine (231)

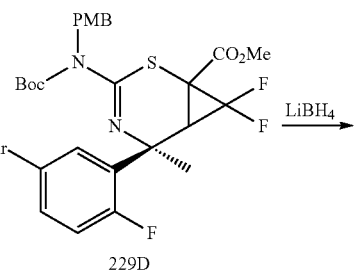

229D

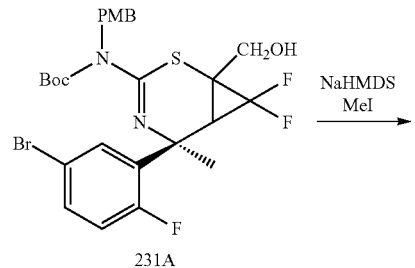

231A

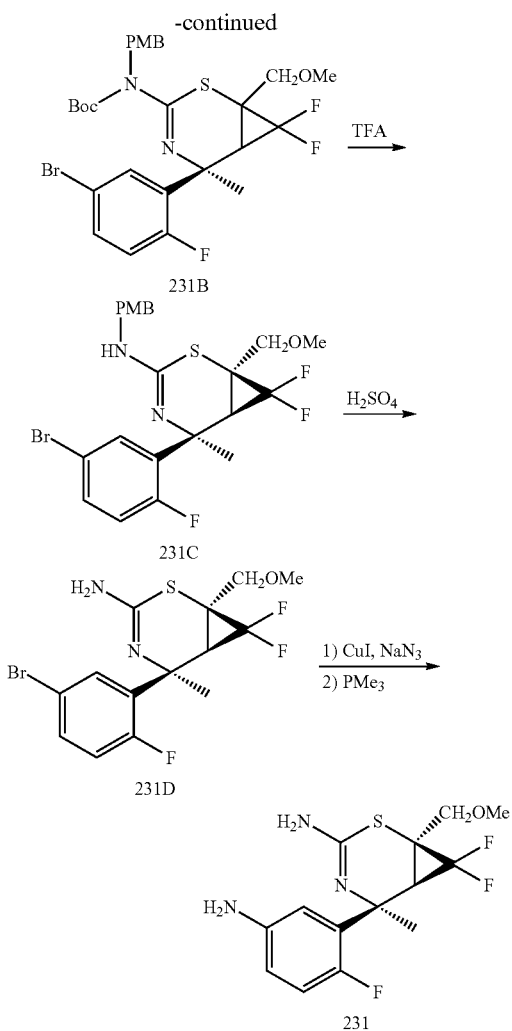

Preparation of tert-butyl((5S)-5-(5-bromo-2-fluorophenyl)-7,7-difluoro-1-(hydroxymethyl)-5-methyl-2-thia-4-azabicyclo[4.1.0]hept-3-en-3-yl)(4-methoxybenzyl)carbamate (231A). To a flask containing 0.94 g of intermediate 229D (not pure: contaminated with 229C) in THF (10 mL) at RT was added lithium borohydride (2.0 M solution in THF, 1.49 mL, 2.99 mmol). MeOH (0.48 mL, 11.95 mmol) was added dropwise. Evolution of gas was observed. The reaction was stirred at RT for 15 min. It was quenched with water and extracted with EtOAc. The organic layer was washed with brine, dried over MgSO₄ and concentrated under reduced pressure. The crude residue was purified via silica gel flash chromatography eluting with a gradient of 0-40% EtOAc in hexanes to afford 0.9 g of a mixture of tert-butyl((5S)-5-(5-bromo-2-fluorophenyl)-7,7-difluoro-1-(hydroxymethyl)-5-methyl-2-thia-4-azabicyclo[4.1.0]hept-3-en-3-yl)(4-methoxybenzyl)carbamate as a mixture of diastereomers (231A). MS m/z=544.8/546.8 [M+H]⁺. Note 1: the observed mass to charge ratio of 544.8/546.8 corresponds to the mass of the desired product (601.5) minus the tert-butyl group of the Boc which is commonly observed under the standard LC/MS method. Note 2: The product mixture contains some of the allylic alcohol resulting from the reduction of Compound 229C which was brought forward from the impure starting material.

Preparation of tert-butyl((5S)-5-(5-bromo-2-fluorophenyl)-7,7-difluoro-1-(methoxymethyl)-5-methyl-2-thia-4-azabicyclo[4.1.0]hept-3-en-3-yl)(4-methoxybenzyl)carbamate (231B). A solution of 0.9 g the above obtained intermediate 231A in THF (7.5 mL) was cooled to 0° C. Sodium bis(trimethylsilyl)amide (2.1 mL of 1.0 M solution in THF, 2.1 mmol, Sigma-Aldrich) was added drop wise to the stirring solution under nitrogen. The reaction was stirred for 20 min at 0° C. then methyl iodide (0.12 mL, 1.95 mmol) was added drop wise. The reaction was stirred at RT for 16 h. It was quenched with aqueous saturated ammonium chloride and diluted with water and EtOAc. The organic layer was separated, washed with brine, dried over MgSO₄ and concentrated under reduced pressure. The crude residue was purified via silica gel flash chromatography eluting with a gradient of 0-30% EtOAc in hexanes) to afford 0.77 g product mixture containing tert-butyl((5S)-5-(5-bromo-2-fluorophenyl)-7,7-difluoro-1-(methoxymethyl)-5-methyl-2-thia-4-azabicyclo[4.1.0]hept-3-en-3-yl)(4-methoxybenzyl)carbamate as a mixture of diastereomers (231B). MS m/z=615.0/617.0 [M+H]⁺.

Preparation of (1S,5S,6R)-5-(5-bromo-2-fluorophenyl)-7,7-difluoro-N-(4-methoxybenzyl)-1-(methoxymethyl)-5-methyl-2-thia-4-azabicyclo[4.1.0]hept-3-en-3-amine (231C). To a solution of 0.77 g of the above obtained intermediate 221C in DCM (10 mL) was added TFA (3.8 mL, 49.3 mmol). The reaction was stirred at RT for 30 min then concentrated under reduced pressure. The crude residue was taken up in EtOAc and washed with saturated sodium bicarbonate 3 times followed by brine, dried over MgSO₄ and concentrated under reduced pressure. The material was purified via silica gel flash chromatography eluting with DCM to afford (1S,5S,6R)-5-(5-bromo-2-fluorophenyl)-7,7-difluoro-N-(4-methoxybenzyl)-1-(methoxymethyl)-5-methyl-2-thia-4-azabicyclo[4.1.0]hept-3-en-3-amine (231C, 0.41 g, 0.79 mmol, 63% yield) as a single diastereomer MS m/z=515.0 [M+H]⁺.

Intermediate 231D was prepared following the procedure described in intermediate 229G, starting with intermediate 231C. MS m/z=395/397 [M+H]⁺.

Preparation of (1S,5S,6R)-5-(5-amino-2-fluorophenyl)-7,7-difluoro-1-(methoxymethyl)-5-methyl-2-thia-4-azabicyclo[4.1.0]hept-3-en-3-amine (231). This compound was prepared following the procedure described in intermediate 229, starting with intermediate 231D. MS m/z=332.0 [M+H]⁺. ¹H NMR (300 MHz, CDCl₃) δ 7.05 (dd, J=2.9, 6.7 Hz, 1H), 6.87 (dd, J=8.5, 12.0 Hz, 1H), 6.63-6.50 (m, 1H), 4.02-3.93 (m, 1H), 3.54 (dd, J=2.3, 11.3 Hz, 1H), 3.41 (s, 3H), 2.38 (dd, J=3.7, 15.4 Hz, 1H), 1.64 (d, J=1.0 Hz, 3H).

2-((1S,5S,6R)-3-Amino-5-(5-amino-2-fluorophenyl)-7,7-difluoro-5-methyl-2-thia-4-azabicyclo[4.1.0]hept-3-en-1-yl)propan-2-ol (232)

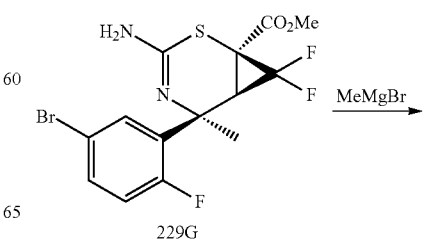

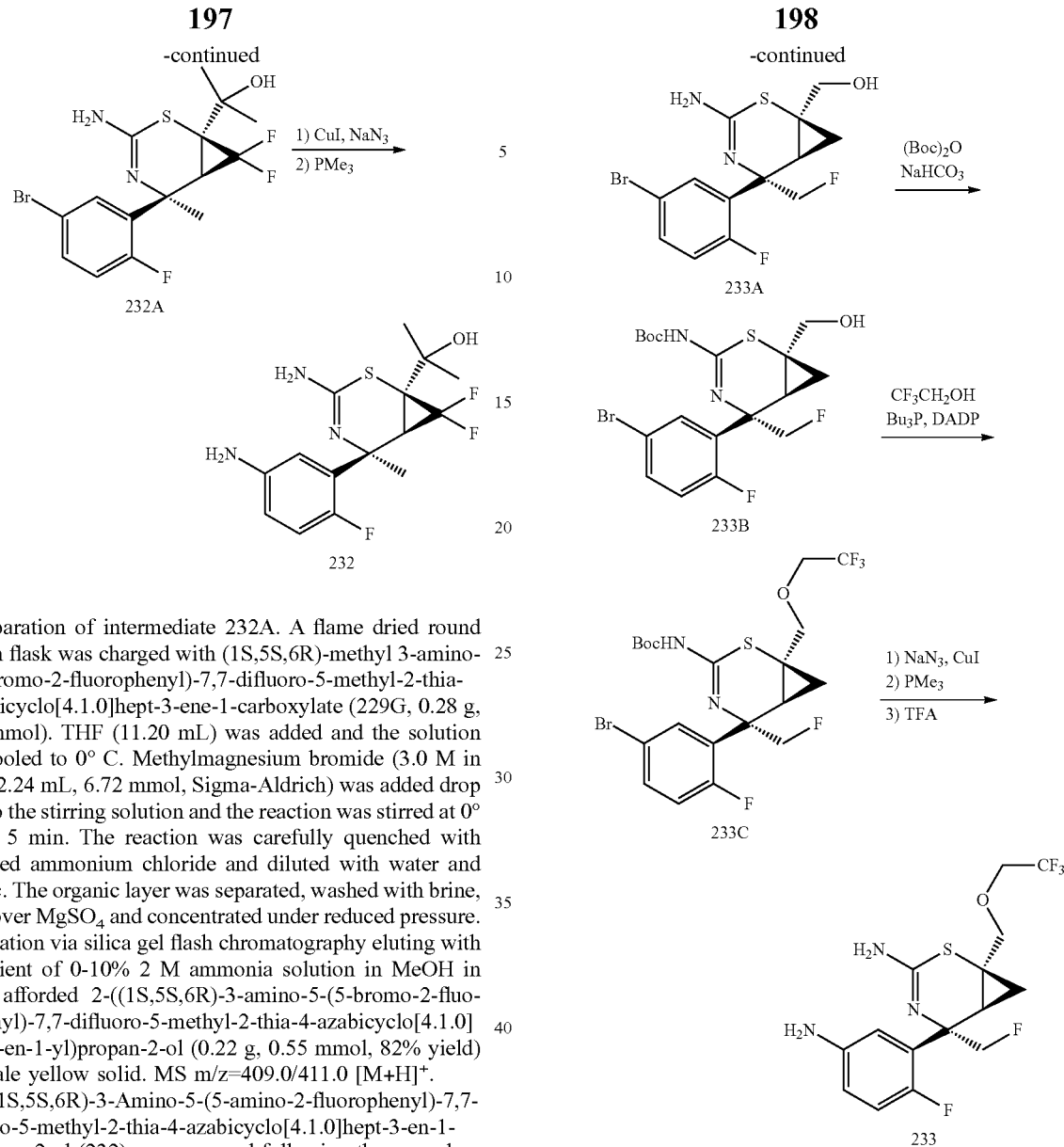

Preparation of intermediate 232A. A flame dried round bottom flask was charged with (1S,5S,6R)-methyl 3-amino-5-(5-bromo-2-fluorophenyl)-7,7-difluoro-5-methyl-2-thia-4-azabicyclo[4.1.0]hept-3-ene-1-carboxylate (229G, 0.28 g, 0.67 mmol). THF (11.20 mL) was added and the solution was cooled to 0° C. Methylmagnesium bromide (3.0 M in Et$_2$O, 2.24 mL, 6.72 mmol, Sigma-Aldrich) was added drop wise to the stirring solution and the reaction was stirred at 0° C. for 5 min. The reaction was carefully quenched with saturated ammonium chloride and diluted with water and EtOAc. The organic layer was separated, washed with brine, dried over MgSO$_4$ and concentrated under reduced pressure. Purification via silica gel flash chromatography eluting with a gradient of 0-10% 2 M ammonia solution in MeOH in DCM afforded 2-((1S,5S,6R)-3-amino-5-(5-bromo-2-fluorophenyl)-7,7-difluoro-5-methyl-2-thia-4-azabicyclo[4.1.0] hept-3-en-1-yl)propan-2-ol (0.22 g, 0.55 mmol, 82% yield) as a pale yellow solid. MS m/z=409.0/411.0 [M+H]$^+$.

2-((1S,5S,6R)-3-Amino-5-(5-amino-2-fluorophenyl)-7,7-difluoro-5-methyl-2-thia-4-azabicyclo[4.1.0]hept-3-en-1-yl)propan-2-ol (232) was prepared following the procedure described for intermediate 229, starting with intermediate 232A. MS m/z=346.0 [M+H]$^+$. $^1$H NMR (300 MHz, CDCl$_3$) δ 6.96 (dd, J=3.1, 6.8 Hz, 1H), 6.88 (dd, J=8.5, 11.8 Hz, 1H), 6.55 (td, J=3.6, 8.2 Hz, 1H), 3.12-3.01 (m, 1H), 1.68 (d, J=1.0 Hz, 3H), 1.49 (s, 3H), 1.47 (s, 3H).

(1S,5S,6S)-5-(5-Amino-2-fluorophenyl)-5-(fluoromethyl)-1-((2,2,2-trifluoroethoxy)methyl)-2-thia-4-azabicyclo[4.1.0]hept-3-en-3-amine (233)

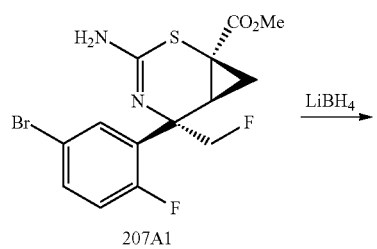

Preparation of Compound 233A. To a solution of (1S,5S,6S)-methyl 3-amino-5-(5-bromo-2-fluorophenyl)-5-(fluoromethyl)-2-thia-4-azabicyclo[4.1.0]hept-3-ene-1-carboxylate (207A1 purified from intermediate 207A via silica gel chromatography) (2.5 g, 6.39 mmol) in THF (60 mL) under N$_2$ was added lithium borohydride (2 M solution in THF, 6.39 mL, 12.78 mmol) via syringe followed by dropwise addition of MeOH (2.07 mL, 51.10 mmol). The mixture was stirred at RT for 30 min. It was quenched with saturated NH$_4$Cl, diluted with water, and then extracted with EtOAc (3×). The combined organic extracts were washed with water and brine, dried over Na$_2$SO$_4$ and then filtered. The filtrate was concentrated and purified by silica gel chromatography (1-8% MeOH (2 M NH$_3$) in DCM) to afford ((1S,5S,6S)-3-amino-5-(5-bromo-2-fluorophenyl)-5-(fluoromethyl)-2-thia-4-azabicyclo[4.1.0]hept-3-en-1-yl)methanol (233A, 1.85 g, 5.09 mmol, 80% yield) as white solid. LC/MS (ESI$^+$) m/z=363.0/365.0 (M+H).

Preparation of Compound 233B. To a solution of ((1S,5S,6S)-3-amino-5-(5-bromo-2-fluorophenyl)-5-(fluoromethyl)-2-thia-4-azabicyclo[4.1.0]hept-3-en-1-yl)methanol (1.5 g, 4.13 mmol) in 1,4-dioxane (30 mL) was added di-tert-butyl dicarbonate (4.74 mL, 20.65 mmol) followed by saturated sodium bicarbonate (12 mL). The reaction was stirred at ambient temperature for 16 h. The resulted mixture was diluted with water and then extracted with EtOAc. The organic layer was washed with brine, dried over $Na_2SO_4$ and filtered. The filtrate was concentrated and purified by silica gel chromatography (0-70% EtOAc/hexanes) to afford tert-butyl((1S,5S,6S)-5-(5-bromo-2-fluorophenyl)-5-(fluoromethyl)-1-(hydroxymethyl)-2-thia-4-azabicyclo[4.1.0]hept-3-en-3-yl)carbamate (1.77 g, 3.82 mmol, 93% yield) as white foam. LC/MS (ESI$^+$) m/z=463.0/465.0 (M+H).

Preparation of Compound 233C. To a solution of tert-butyl((1S,5S,6S)-5-(5-bromo-2-fluorophenyl)-5-(fluoromethyl)-1-(hydroxymethyl)-2-thia-4-azabicyclo[4.1.0]hept-3-en-3-yl)carbamate (0.10 g, 0.21 mmol) and (E)-diazene-1,2-diylbis(piperidin-1-ylmethanone) (0.11 g, 0.43 mmol) in toluene (5 mL) at ambient temperature was added tributylphosphine (0.11 mL, 0.43 mmol). After 10 min, 2,2,2-trifluoroethanol (0.16 mL, 2.16 mmol) was added and the mixture was heated at 65° C. for 2 h until the starting material was fully consumed. The mixture was concentrated and the residue was purified by Shimadzu HPLC to afford tert-butyl((1S,5S,6S)-5-(5-bromo-2-fluorophenyl)-5-(fluoromethyl)-1-((2,2,2-trifluoroethoxy)methyl)-2-thia-4-azabicyclo[4.1.0]hept-3-en-3-yl)carbamate (40 mg, 0.07 mmol, 34% yield). LC/MS (ESI$^+$) m/z=545.0/547.0 (M+H).

Preparation of Compound 233. To a pressure vial was charged tert-butyl((1S,5S,6S)-5-(5-bromo-2-fluorophenyl)-5-(fluoromethyl)-1-((2,2,2-trifluoroethoxy)methyl)-2-thia-4-azabicyclo[4.1.0]hept-3-en-3-yl)carbamate (0.040 g, 0.073 mmol), sodium azide (0.014 g, 0.220 mmol), copper (I) iodide (2.79 mg, 0.015 mmol), (+)-sodium L-ascorbate (3.34 mg, 0.017 mmol), water (0.400 mL) and EtOH (2 mL). After purged with $N_2$, (1R,2R)—N1,N2-dimethylcyclohexane-1,2-diamine (2 µL, 0.015 mmol) was added. The mixture was heated to 80° C. for 1.5 h. The reaction was quenched with saturated $NH_4Cl$ and extracted with EtOAc. The organic extracts were concentrated. The residue in THF (2 mL) and water (0.6 mL) was treated with trimethylphosphine (1.0 M solution in THF, 0.073 mL, 0.073 mmol). After stirred at RT for 5 min, the reaction was quenched with water and extracted with EtOAc. The organic extracts were washed with brine, dried over $Na_2SO_4$, filtered and concentrated. The residue was dissolved in DCM (3 mL) and treated with TFA (0.3 mL) at ambient temperature. After stirred for 25 min, the mixture was concentrated and purified by Shimadzu HPLC to afford (1S,5S,6S)-5-(5-amino-2-fluorophenyl)-5-(fluoromethyl)-1-((2,2,2-trifluoroethoxy)methyl)-2-thia-4-azabicyclo[4.1.0]hept-3-en-3-amine (6.0 mg, 0.016 mmol, 21% yield). LC/MS (ESI$^+$) m/z=382.1 [M+H]$^+$. $^1$H NMR (400 MHz, CHLOROFORM-d) δ 6.77-6.91 (m, 2H), 6.54 (td, J=3.42, 8.41 Hz, 1H), 4.51-4.97 (m, 2H), 3.84-3.97 (m, 2H), 3.79 (d, J=10.56 Hz, 1H), 3.62 (d, J=10.76 Hz, 1H), 1.79 (m, 1H), 1.13 (dd, J=5.87, 9.59 Hz, 1H), 0.73 (t, J=6.26 Hz, 1H). The 2 sets of $NH_2$ have broad peaks.

(1S,5S,6S)-5-(5-Amino-2-fluorophenyl)-5-(fluoromethyl)-1-(isopropoxymethyl)-2-thia-4-azabicyclo[4.1.0]hept-3-en-3-amine (234)

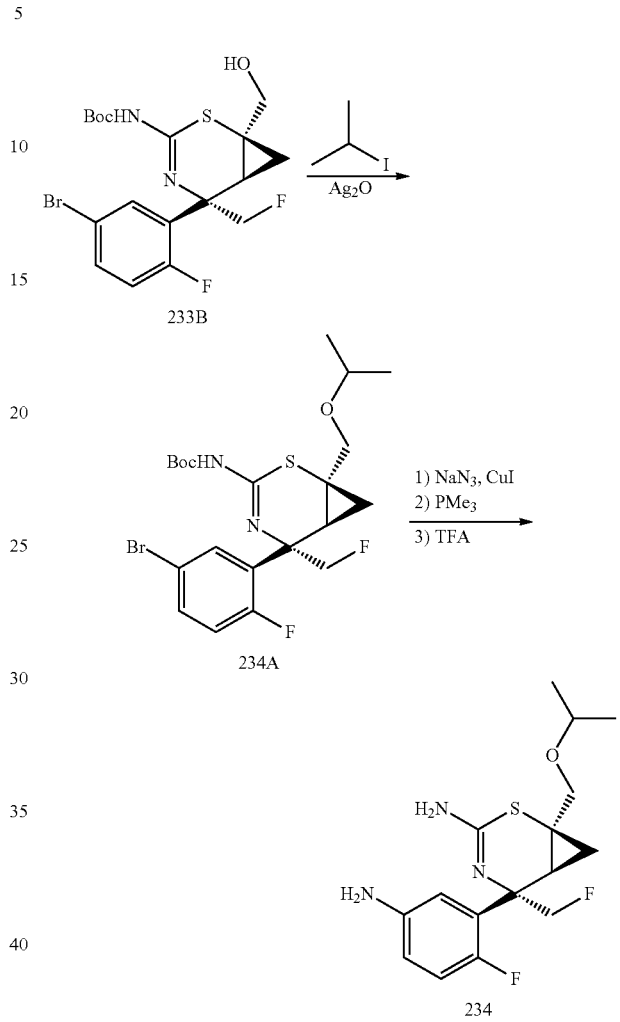

Preparation of Compound 234A. To a 20 mL pressure vial was charged tert-butyl((1S,5S,6S)-5-(5-bromo-2-fluorophenyl)-5-(fluoromethyl)-1-(hydroxymethyl)-2-thia-4-azabicyclo[4.1.0]hept-3-en-3-yl)carbamate (0.58 g, 1.252 mmol), 2-iodopropane (1.00 mL, 10.01 mmol) and silver(i) oxide (0.58 g, 2.50 mmol). After purged with $N_2$ for 5 min, the vial was sealed and stirred at ambient temperature with protection from light for 140 h. At this point, LCMS detected no starting material. The mixture was diluted with ether and DCM, and then filtered. The filtrate was concentrated and purified by silica gel chromatography (0-20% EtOAc/hexane) to afford tert-butyl((1S,5S,6S)-5-(5-bromo-2-fluorophenyl)-5-(fluoromethyl)-1-(isopropoxymethyl)-2-thia-4-azabicyclo[4.1.0]hept-3-en-3-yl)carbamate (0.20 g, 0.40 mmol, 31% yield). LC/MS (ESI$^+$) m/z=505.1/507.1 (M+H)$^+$.

Intermediate 234 was synthesized using procedures analogous to those described for intermediate 233, but using tert-butyl((1S,5S,6S)-5-(5-bromo-2-fluorophenyl)-5-(fluoromethyl)-1-(isopropoxymethyl)-2-thia-4-azabicyclo[4.1.0]hept-3-en-3-yl)carbamate (234A). LC/MS (ESI$^+$) m/z=342.2 (M+H)$^+$.

201

(1S,5S,6S)-5-(5-Amino-2-fluorophenyl)-5-(fluoromethyl)-1-(1H-1,2,3-triazol-4-yl)-2-thia-4-azabicyclo[4.1.0]hept-3-en-3-amine (235)

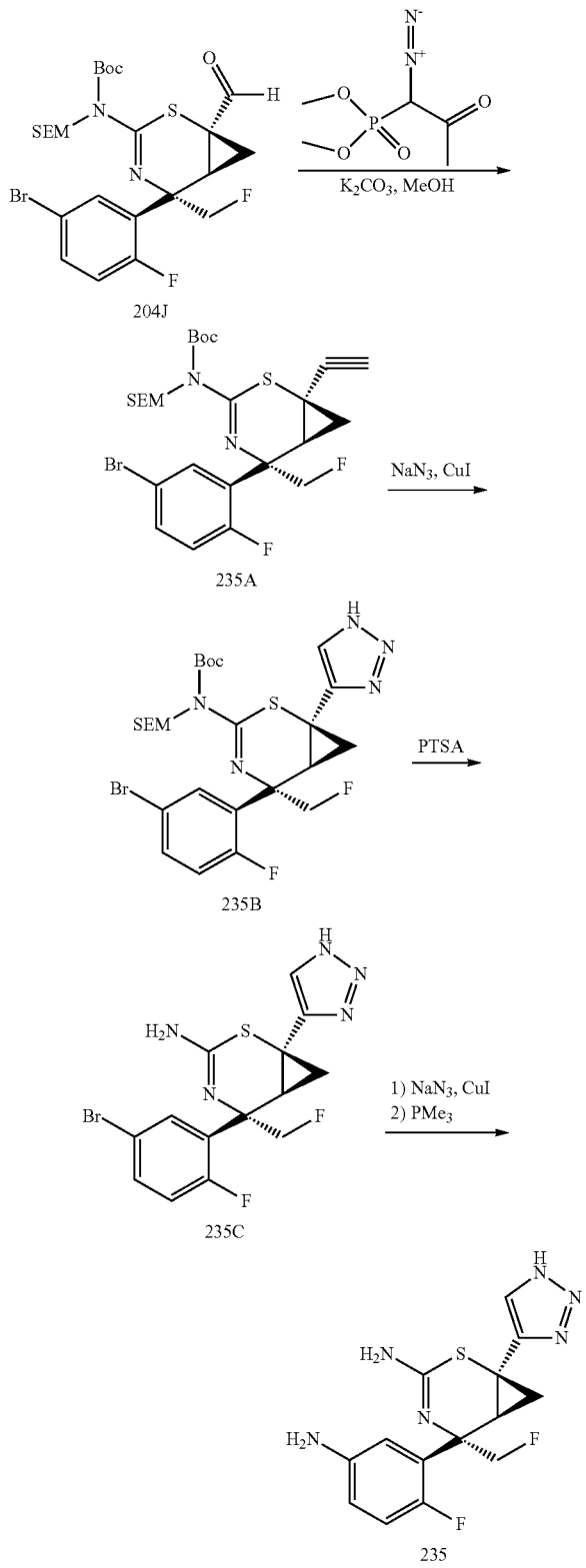

202

Preparation of Compound 235A. tert-butyl((1S,5S,6S)-5-(5-bromo-2-fluorophenyl)-5-(fluoromethyl)-1-formyl-2-thia-4-azabicyclo[4.1.0]hept-3-en-3-yl)((2-(trimethylsilyl)ethoxy)methyl)carbamate (204J, 3.85 g, 6.51 mmol) in MeOH (50 mL) was treated with potassium carbonate (1.80 g, 13.02 mmol) followed by dimethyl(1-diazo-2-oxopropyl)phosphonate (1.5 g, 7.81 mmol) at ambient temperature. After stirred for 1.5 h, the reaction was quenched with saturated NaHCO$_3$ and extracted with EtOAc (2×). The organic extracts were washed with brine, dried over Na$_2$SO$_4$ and filtered. The filtrate was concentrated and purified by silica gel chromatography (0-15% EtOAc in heptane) to afford tert-butyl((1S,5S,6S)-5-(5-bromo-2-fluorophenyl)-1-ethynyl-5-(fluoromethyl)-2-thia-4-azabicyclo[4.1.0]hept-3-en-3-yl)((2-(trimethylsilyl)ethoxy)methyl)carbamate (3.44 g, 5.86 mmol, 90% yield) as colorless oil. LC/MS (ESI$^+$) m/z=609.0/611.0 (M+Na)$^+$.

Preparation of Compound 235B. To a pressure flask charged with tert-butyl((1S,5S,6S)-5-(5-bromo-2-fluorophenyl)-1-ethynyl-5-(fluoromethyl)-2-thia-4-azabicyclo[4.1.0]hept-3-en-3-yl)((2-(trimethylsilyl)ethoxy)methyl)carbamate (2.19 g, 3.73 mmol), sodium azide (0.73 g, 11.18 mmol), copper(I) iodide (0.14 g, 0.74 mmol), (+)-sodium L-ascorbate (0.17 g, 0.85 mmol), water (4.00 mL) and EtOH (20 mL). After purged with N$_2$, (1R,2R)—N1,N2-dimethylcyclohexane-1,2-diamine (0.12 mL, 0.74 mmol) was added. The reaction was heated to 75° C. for 2 h, and then allowed to cool to RT. The reaction was quenched with saturated NH$_4$Cl and extracted with EtOAc. The organic extracts were washed with brine, dried over Na$_2$SO$_4$ and filtered. The filtrate was concentrated and purified by silica gel chromatography on ISCO (0-30% EtOAc in heptane) to afford tert-butyl((1S,5S,6S)-5-(5-bromo-2-fluorophenyl)-5-(fluoromethyl)-1-(1H-1,2,3-triazol-4-yl)-2-thia-4-azabicyclo[4.1.0]hept-3-en-3-yl)((2-(trimethylsilyl)ethoxy)methyl)carbamate (1.27 g, 2.01 mmol, 54% yield). LC/MS (ESI$^+$) m/z=630.2/632.2 (M+H)$^+$.

Preparation of Compound 235C. To a pressure flask was charged tert-butyl((1S,5S,6S)-5-(5-bromo-2-fluorophenyl)-5-(fluoromethyl)-1-(1H-1,2,3-triazol-4-yl)-2-thia-4-azabicyclo[4.1.0]hept-3-en-3-yl)((2-(trimethylsilyl)ethoxy)methyl)carbamate (1.26 g, 1.99 mmol), p-toluenesulfonic acid monohydrate (3.80 g, 19.98 mmol) and isopropanol (20 mL). The vial was then sealed and heated in an 80° C. oil bath for 16 h, then at 90° C. for additional 5 h until the reaction progressed no further. The reaction mixture was allowed to cool to RT and partitioned between EtOAc and water. The separated aqueous layer was back extracted with EtOAc. The organic layers were combined, washed with brine, dried over Na$_2$SO$_4$ and then filtered. The filtrate was concentrated and purified by silica gel chromatography (0-80% EtOAc in heptane) to afford (1S,5S,6S)-5-(5-bromo-2-fluorophenyl)-5-(fluoromethyl)-1-(1H-1,2,3-triazol-4-yl)-2-thia-4-azabicyclo[4.1.0]hept-3-en-3-amine (0.49 g, 1.22 mmol, 61% yield) as light yellow oil. LC/MS (ESI$^+$) m/z=400.0/402.0 (M+H)$^+$.

Preparation of Compound 235. To a pressure flask charged with (1S,5S,6S)-5-(5-bromo-2-fluorophenyl)-5-(fluoromethyl)-1-(1H-1,2,3-triazol-4-yl)-2-thia-4-azabicyclo[4.1.0]hept-3-en-3-amine (0.49 g, 1.22 mmol), sodium azide (0.24 g, 3.67 mmol), copper(I) iodide (47 mg, 0.24 mmol), (+)-sodium L-ascorbate (56 mg, 0.28 mmol), water (1.50 mL) and EtOH (7.50 mL). After purged with N$_2$, (1R,2R)—N1,N2-dimethylcyclohexane-1,2-diamine (0.04 mL, 0.24 mmol) was added. The mixture was heated to 75° C. for 23 h. The reaction was quenched with saturated NH$_4$Cl and extracted with EtOAc. The organic extracts were washed with brine and concentrated. To the residue in THF (10 mL) and water (3 mL) was added trimethylphosphine (1.0 M solution in THF, 1.22 mL, 1.22 mmol). After stirred for 50 min, the reaction was quenched with water and extracted with EtOAc. The organic extracts were concentrated. The residue was triturated with DCM and then filtered (repeated 3 times). The filter cake was rinsed with DCM and dried in air to afford (1S,5S,6S)-5-(5-amino-2-fluorophenyl)-5-(fluoromethyl)-1-(1H-1,2,3-triazol-4-yl)-2-thia-4-azabicyclo[4.1.0]hept-3-en-3-amine (0.31 g, 0.91 mmol, 74% yield) as brown solid. LC/MS (ESI$^+$) m/z=337.1 (M+H)$^+$.

tert-Butyl((1S,5S,6S)-5-(5-amino-2-fluorophenyl)-5-(fluoromethyl)-1-(prop-1-yn-1-yl)-2-thia-4-azabicyclo[4.1.0]hept-3-en-3-yl)((2-(trimethylsilyl)ethoxy)methyl)carbamate (236)

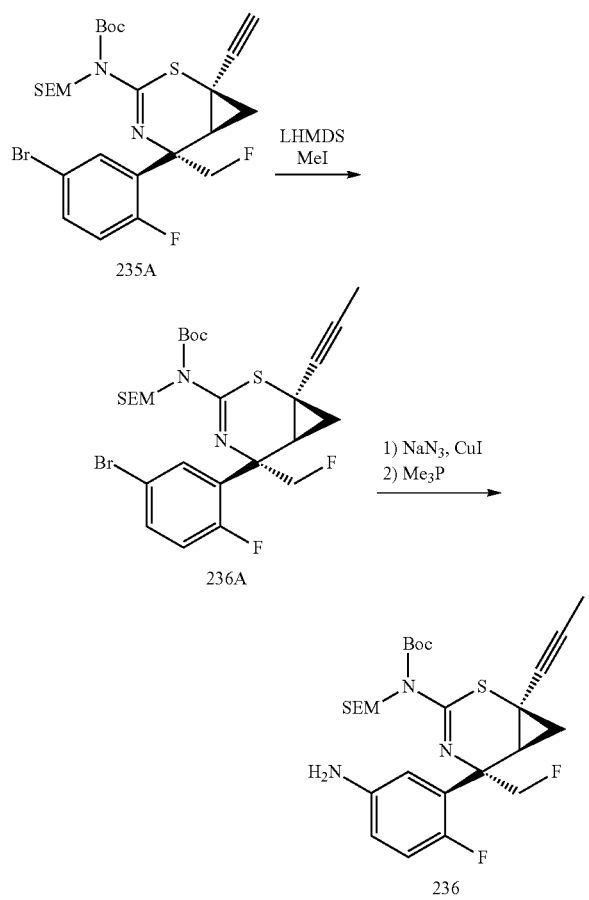

Preparation of Compound 236A. To a cooled (ice bath) solution of tert-butyl((1S,5S,6S)-5-(5-bromo-2-fluorophenyl)-1-ethynyl-5-(fluoromethyl)-2-thia-4-azabicyclo[4.1.0]hept-3-en-3-yl)((2-(trimethylsilyl)ethoxy)methyl)carbamate (235A, 0.24 g, 0.401 mmol) in THF (4.0 mL) was added lithium bis(trimethylsilyl)amide (0.61 mL of 1 M in THF, 0.61 mmol). After stirred for 10 min, iodomethane (0.04 mL, 0.61 mmol) was added and the mixture stirred for 1 h. The reaction was quenched with water and extracted with EtOAc. The organic extracts were washed with brine, dried over Na$_2$SO$_4$ and filtered. The filtrate was concentrated and purified by silica gel chromatography on ISCO (0-15% EtOAc in heptane) to afford tert-butyl((1S,5S,6S)-5-(5-bromo-2-fluorophenyl)-5-(fluoromethyl)-1-(prop-1-yn-1-yl)-2-thia-4-azabicyclo[4.1.0]hept-3-en-3-yl)((2-(trimethylsilyl)ethoxy)methyl)carbamate (0.25 g, 0.42 mmol, 100% yield) as light yellow oil, LC/MS (ESI$^+$) m/z=601.1/603.1 (M+H)$^+$.

Preparation of Compound 236. To a pressure flask charged with tert-butyl((1S,5S,6S)-5-(5-bromo-2-fluorophenyl)-5-(fluoromethyl)-1-(prop-1-yn-1-yl)-2-thia-4-azabicyclo[4.1.0]hept-3-en-3-yl)((2-(trimethylsilyl)ethoxy)methyl)carbamate (0.25 g, 0.41 mmol), sodium azide (0.08 g, 1.24 mmol), copper(I) iodide (16 mg, 0.08 mmol), (+)-sodium L-ascorbate (19 mg, 0.09 mmol), water (0.4 mL) and EtOH (2.0 mL). After purged with N$_2$, (1R,2R)—N1,N2-dimethylcyclohexane-1,2-diamine (0.013 mL, 0.083 mmol) was added. The mixture was heated at 75° C. for 2 h. The reaction was quenched with saturated NH$_4$Cl and extracted with EtOAc. The organic extracts were washed with brine and concentrated. The residue was purified by silica gel chromatography on ISCO (0-30% EtOAc in heptane) to afford tert-butyl((1S,5S,6S)-5-(5-bromo-2-fluorophenyl)-5-(fluoromethyl)-1-(5-methyl-1H-1,2,3-triazol-4-yl)-2-thia-4-azabicyclo[4.1.0]hept-3-en-3-yl)((2-(trimethylsilyl)ethoxy)methyl)carbamate as colorless oil. LC/MS (ESI$^+$) m/z=564.2 (M+H)$^+$. To the colorless oil in THF (2 mL) and water (0.6 mL) was added trimethylphosphine (0.41 mL of 1 M in THF, 0.41 mmol). After 50 min, the reaction was quenched with water and extracted with EtOAc. The organic extracts were concentrated and dried in vacuum to afford tert-butyl((1S,5S,6S)-5-(5-amino-2-fluorophenyl)-5-(fluoromethyl)-1-(prop-1-yn-1-yl)-2-thia-4-azabicyclo[4.1.0]hept-3-en-3-yl)((2-(trimethylsilyl)ethoxy)methyl)carbamate (114 mg, 0.21 mmol, 51% yield). This material was used without further purification. LC/MS (ESI$^+$) m/z=538.3 (M+H)$^+$.

(1S,5S,6S)-Methyl 3-amino-5-(5-amino-2,3-difluorophenyl)-5-methyl-2-thia-4-azabicyclo[4.1.0]hept-3-ene-1-carboxylate (237)

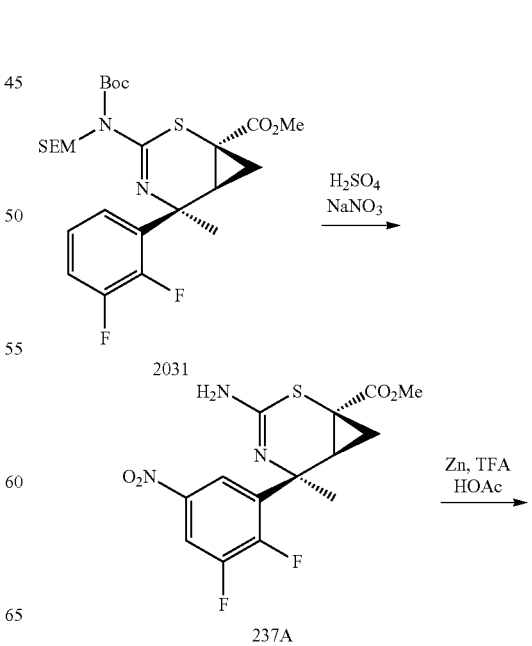

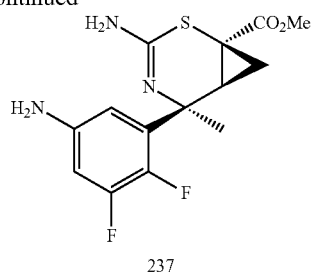

Preparation of Compound 237A. To a 250 mL flask containing (1S,5S,6S)-methyl 3-((tert-butoxycarbonyl)((2-(trimethylsilyl)ethoxy)methyl)amino)-5-(2,3-difluorophenyl)-5-methyl-2-thia-4-azabicyclo[4.1.0]hept-3-ene-1-carboxylate (203I, 2.00 g, 3.69 mmol) at 0° C. under nitrogen was added sulfuric acid (8.84 mL, 166 mmol). After 15 min, the ice bath was removed and syrup stirred for 30 min at 20° C. The reaction was cooled to 0° C. and sodium nitrate (0.44 g, 5.16 mmol) was added. It was stirred at 0° C. for 1 h then RT for 24 h. The sticky mixture was pour onto ice (100 g). The mixture was cooled with an ice bath, diluted with $CH_2Cl_2$ (50 mL) and rapidly stirred. Solid potassium phosphate tribasic (23.47 g, 111 mmol) was added in small portions (over 20 min), and the mixture was then brought to pH~8 with 1 M NaOH. The organic layer was separated, and the aqueous layer was extracted with $CH_2Cl_2$ (50 mL). The combined organic layers were dried over $MgSO_4$, filtered, concentrated under reduced pressure, then purified via silica gel flash column chromatography (0-25% EtOAc in heptane) to afford (1S,5S,6S)-methyl 3-amino-5-(2,3-difluoro-5-nitrophenyl)-5-methyl-2-thia-4-azabicyclo[4.1.0]hept-3-ene-1-carboxylate (237A, 1.17 g, 3.27 mmol, 89% yield) as tan oil. LC/MS (ESI⁻) m/z=485.1 (M+H)⁺. ¹H NMR (400 MHz, CHLOROFORM-d) δ 8.51 (br. s., 1H), 8.02 (ddd, J=2.84, 6.31, 9.05 Hz, 1H), 4.26-4.91 (m, 2H), 3.79-3.83 (m, 3H), 1.70-1.82 (m, 3H), 1.49-1.66 (m, 1H), 1.03-1.26 (m, 1H), 0.92 (br. s., 1H).

Preparation of Compound 237. To a stirring solution of (1S,5S,6S)-methyl 3-amino-5-(2,3-difluoro-5-nitrophenyl)-5-methyl-2-thia-4-azabicyclo[4.1.0]hept-3-ene-1-carboxylate (237A, 1.17 g, 3.27 mmol) in glacial HOAc (6 mL) and TFA (6 mL) at 20° C. was added zinc nanopowder (0.84 g, 13 mmol). After 90 min the reaction was concentrated under reduced pressure to a thick oil/suspension. The reaction was then partitioned between 9:1 $CHCl_3$/IPA (50 mL) and 10% $NH_4OH$ (50 mL). The separated aqueous layer was further extracted with 9:1 $CHCl_3$/IPA (20 mL). The combined organics were then washed with brine (20 mL). The organic was dried over $MgSO_4$, concentrated under reduced pressure, then purified by silica gel chromatography (1-5% of 2 M $NH_3$ in MeOH in $CH_2Cl_2$) to afford (1S,5S,6S)-Methyl 3-amino-5-(5-amino-2,3-difluorophenyl)-5-methyl-2-thia-4-azabicyclo[4.1.0]hept-3-ene-1-carboxylate (0.77 g, 2.35 mmol, 72% yield) as white foam. LC/MS (ESI⁻) m/z=328.1 (M+H)⁺. ¹H NMR (400 MHz, CHLOROFORM-d) δ 6.74 (d, J=5.24 Hz, 1H), 6.39 (ddd, J=2.93, 6.06, 11.35 Hz, 1H), 3.89-4.84 (m, 2H), 3.78 (s, 3H), 3.60 (br. s., 2H), 2.50-2.56 (m, 1H), 1.68-1.72 (m, 3H), 1.55 (dd, J=5.09, 9.78 Hz, 1H), 1.11 (dd, J=5.48, 7.43 Hz, 1H).

(1S,5S,6S)-3-Amino-5-(2,3-difluoro-5-nitrophenyl)-N-methoxy-N,5-dimethyl-2-thia-4-azabicyclo[4.1.0]hept-3-ene-1-carboxamide (238)

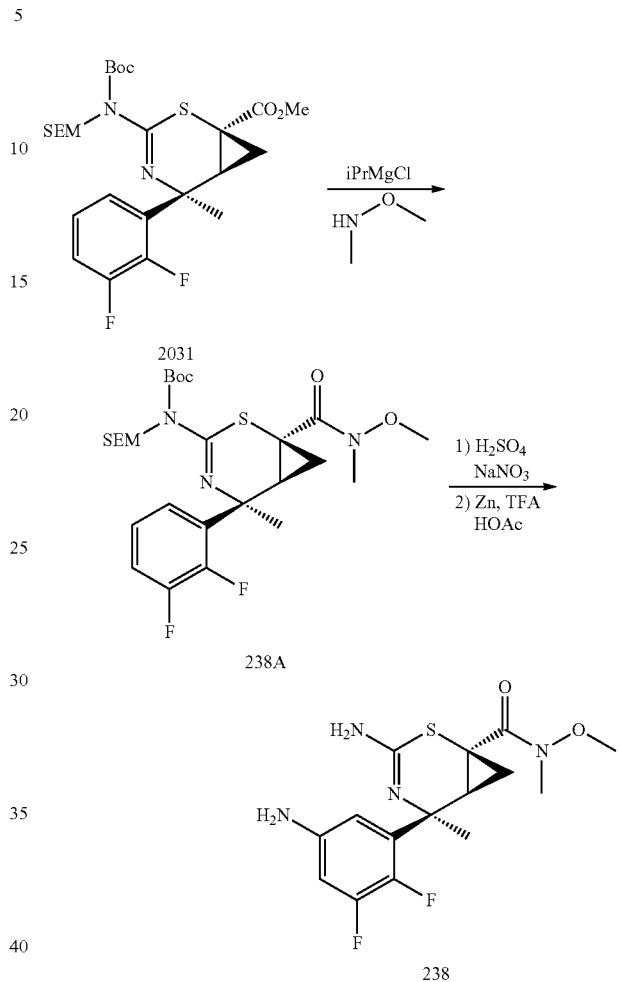

Preparation of Compound 238A. To a stirring suspension of (1S,5S,6S)-methyl 3-((tert-butoxycarbonyl)((2-(trimethylsilyl)ethoxy)methyl)amino)-5-(2,3-difluorophenyl)-5-methyl-2-thia-4-azabicyclo[4.1.0]hept-3-ene-1-carboxylate (203I, 90 mg, 0.16 mmol) and N,O-dimethylhydroxylamine hydrochloride (32 mg, 0.33 mmol) in THF (2 mL) at −20° C. under nitrogen was added isopropylmagnesium chloride (0.50 mL of 2 m in THF, 1.00 mmol) at a rate that did not exceed −15° C. internal temperature. After 15 min at −10° C. the reaction was quenched with sat $NH_4Cl$. The reaction was then portioned between 1:1 EtOAc/heptane (20 mL) and 5% $NaHCO_3$ (10 mL). The organic was dried over $MgSO_4$, concentrated under reduced pressure, then purified by silica gel chromatography (0-20% EtOAc in heptane) to afford tert-butyl((1S,5S,6S)-5-(2,3-difluorophenyl)-1-(methoxy(methyl)carbamoyl)-5-methyl-2-thia-4-azabicyclo[4.1.0]hept-3-en-3-yl)((2-(trimethylsilyl)ethoxy)methyl)carbamate (238A, 57 mg, 0.10 mmol, 60% yield) as colorless film. LC/MS (ESI⁻) m/z=572.2 (M+H)⁺.

Preparation of (1S,5S,6S)-3-amino-5-(5-amino-2,3-difluorophenyl)-N-methoxy-N,5-dimethyl-2-thia-4-azabicyclo[4.1.0]hept-3-ene-1-carboxamide (238). This compound (22 mg, 70 yield) as colorless film was prepared according to the procedures described for intermediate 237, but starting from tert-butyl((1S,5S,6S)-5-(2,3-difluorophenyl)-1-(methoxy (methyl)carbamoyl)-5-methyl-2-thia-4-azabicyclo[4.1.0] hept-3-en-3-yl)((2-(trimethylsilyl)ethoxy)methyl)carbamate (238A, 50 mg). LC/MS (ESI⁻) m/z=357.0 (M+H)⁺.

1-((1S,5S,6S)-3-Amino-5-(5-amino-2,3-difluorophenyl)-5-methyl-2-thia-4-azabicyclo[4.1.0]hept-3-en-1-yl)ethanone (239)

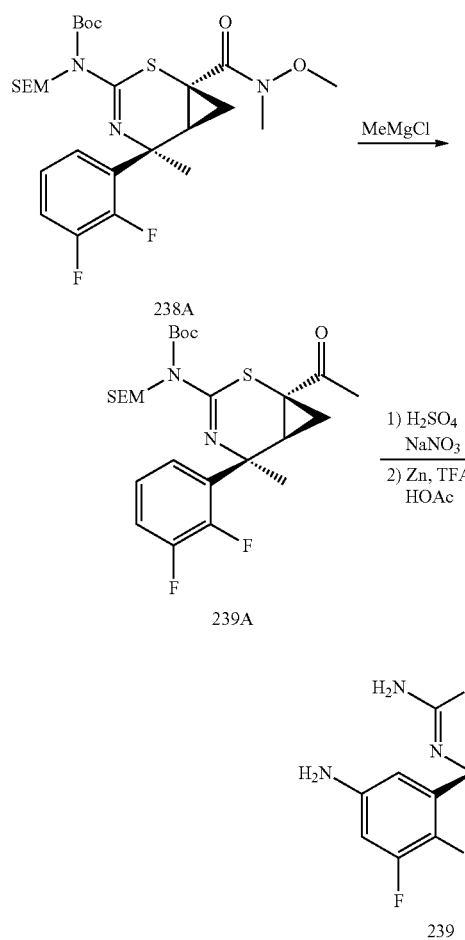

Preparation of Compound 239A. To a stirring solution of tert-butyl((1S,5S,6S)-5-(2,3-difluorophenyl)-1-(methoxy (methyl)carbamoyl)-5-methyl-2-thia-4-azabicyclo[4.1.0] hept-3-en-3-yl)((2-(trimethylsilyl)ethoxy)methyl)carbamate (238A, 1.04 g, 1.82 mmol) in THF (10 mL) at 0° C. under nitrogen was added methylmagnesium bromide (2.42 mL of 3.0 M in Et₂O, 7.28 mmol). After stirring for 15 min at 0° C. the reaction was slowly quenched with dropwise addition of sat. NH₄Cl (10 mL). The reaction was then partitioned between EtOAc (75 mL) and 5% NaHCO₃ (50 mL) along with water (50 mL). The separated aqueous was extracted with EtOAc (25 mL). The combined organics were dried over MgSO₄, filtered, then concentrated under reduced pressure to afford tert-butyl((1S,5S,6S)-1-acetyl-5-(2,3-difluorophenyl)-5-methyl-2-thia-4-azabicyclo[4.1.0]hept-3-en-3-yl)((2-(trimethylsilyl)ethoxy)methyl)carbamate (239A, 0.93 g, 1.76 mmol, 97% yield) as colorless oil. LC/MS (ESI⁻) m/z=527.2 (M+H)⁺. ¹H NMR (400 MHz, CHLOROFORM-d) δ 7.38 (t, J=6.89 Hz, 1H), 7.02-7.13 (m, 2H), 5.27 (d, J=10.56 Hz, 1H), 5.04 (d, J=10.56 Hz, 1H), 3.60-3.70 (m, 2H), 2.53 (dd, J=8.02, 9.19 Hz, 1H), 2.25 (s, 3H), 1.67-1.83 (m, 3H), 1.57 (dd, J=5.38, 9.88 Hz, 1H), 1.54 (d, J=5.48 Hz, 1H), 1.49-1.52 (m, 9H), 0.89-0.97 (m, 2H), −0.02-0.01 (m, 9H).

Preparation of 1-((1S,5S,6S)-3-amino-5-(5-amino-2,3-difluorophenyl)-5-methyl-2-thia-4-azabicyclo[4.1.0]hept-3-en-1-yl)ethanone (239). This compound (290 mg, 0.93 mmol, 51% yield) as tan foam was prepared according to the procedures described for intermediate 237, but starting from tert-butyl((1S,5S,6S)-1-acetyl-5-(2,3-difluorophenyl)-5-methyl-2-thia-4-azabicyclo[4.1.0]hept-3-en-3-yl)((2-(trimethylsilyl)ethoxy)methyl)carbamate (239A, 0.95 g, 1.80 mmol). LC/MS (ESI⁻) m/z=312.1 (M+H)⁺.

(S)-1-((1S,5S,6S)-3-amino-5-(5-amino-2,3-difluorophenyl)-5-methyl-2-thia-4-azabicyclo[4.1.0]hept-3-en-1-yl)ethanol (240A) and (R)-1-((1S,5S,6S)-3-amino-5-(5-amino-2,3-difluorophenyl)-5-methyl-2-thia-4-azabicyclo[4.1.0]hept-3-en-1-yl)ethanol (240B)

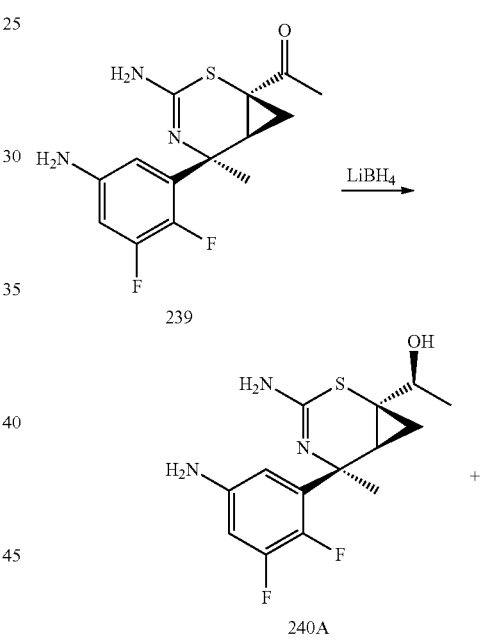

To a stirring solution of 1-((1S,5S,6S)-3-amino-5-(5-amino-2,3-difluorophenyl)-5-methyl-2-thia-4-azabicyclo [4.1.0]hept-3-en-1-yl)ethanone (intermediate 239, 104 mg, 0.33 mmol) in THF (3 mL) at RT under nitrogen was added lithium borohydride (0.33 mL of 2.0 M in THF, 0.66 mmol) at a rate that did not exceed an internal temperature of 25°

C. After 5 min, MeOH (0.13 mL, 3.34 mmol) was added drop wise. The reaction was cooled to 0° C. and quenched with sat'd aqueous NH₄Cl (2 mL). The mixture was then partitioned between 9:1 CHCl₃/IPA (30 mL) and 0.5 M K₂HPO₄ (10 mL). The aqueous was further extracted with 9:1 CHCl₃/IPA (2×5 mL). The organic solution was dried over MgSO₄, filtered, concentrated under reduced pressure. The residue was azeotroped with toluene (2×25 mL). The residue was then purified by silica gel chromatography (1-4% [2 M NH₃ in MeOH] in CH₂Cl₂) to afford separated diastereomers of arbitrary assignment. Oil observed: (R)-1-((1S,5S,6S)-3-amino-5-(5-amino-2,3-difluorophenyl)-5-methyl-2-thia-4-azabicyclo[4.1.0]hept-3-en-1-yl)ethanol (intermediate 240B, 45 mg, 0.14 mmol, 43% yield). LC/MS (ESI⁻) m/z=314.1 (M+H)⁺. ¹H NMR (400 MHz, CHLOROFORM-d) δ 6.59 (td, J=2.52, 4.94 Hz, 1H), 6.36 (ddd, J=2.93, 6.06, 11.35 Hz, 1H), 3.49-3.65 (m, 2H), 3.40-3.49 (m, 2H), 3.05-3.34 (m, 2H), 1.70-1.74 (m, 4H), 1.24-1.33 (m, 3H), 0.93 (dd, J=5.77, 9.49 Hz, 1H), 0.71 (t, J=6.26 Hz, 1H). Solid observed: (S)-1-((1S,5S,6S)-3-amino-5-(5-amino-2,3-difluorophenyl)-5-methyl-2-thia-4-azabicyclo[4.1.0]hept-3-en-1-yl)ethanol (intermediate 240A, 15 mg, 0.05 mmol, 14% yield). LC/MS (ESI⁻) m/z=314.1 (M+H)⁺. ¹H NMR (400 MHz, CHLOROFORM-d) δ 6.65-6.74 (m, 1H), 6.34-6.43 (m, 1H), 3.60 (br. s., 4H), 3.44-3.52 (m, 2H), 1.61-1.71 (m, 4H), 1.39 (d, J=6.26 Hz, 3H), 0.94 (dd, J=5.77, 9.49 Hz, 1H), 0.77 (t, J=6.06 Hz, 1H).

2-((1S,5S,6S)-3-Amino-5-(5-amino-2,3-difluorophenyl)-5-methyl-2-thia-4-azabicyclo[4.1.0]hept-3-en-1-yl)propan-2-ol (241)

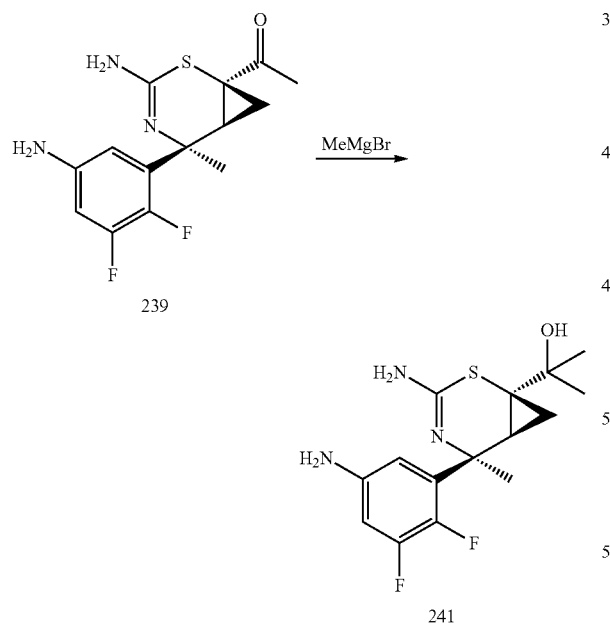

To a stirring solution of 1-((1S,5S,6S)-3-amino-5-(5-amino-2,3-difluorophenyl)-5-methyl-2-thia-4-azabicyclo[4.1.0]hept-3-en-1-yl)ethanone (intermediate 239, 82 mg, 0.26 mmol) in THF (3 mL) at 0° C. under nitrogen was added methylmagnesium bromide (3.0 M in Et₂O, 88 mL, 2.64 mmol) at a rate not to exceed an internal temperature of 7° C. After 15 min, the reaction was slowly quenched with sat NH₄Cl then partitioned between 0.1 M K₂PO₄ (20 mL) and 9:1 CHCl₃/IPA (15 mL). The organic layer was dried over MgSO₄, concentrated under reduced pressure, then purified by silica gel chromatography (0-5% [2 M NH₃ in MeOH] in CH₂Cl₂) to afford Compound 241 (9 mg, 0.03 mmol, 10% yield) as colorless film. LC/MS (ESI⁻) m/z=328.1 (M+H)⁺. ¹H NMR (400 MHz, CHLOROFORM-d) δ 6.62-6.69 (m, 1H), 6.33-6.40 (m, 1H), 3.85-4.77 (br., 2H), 3.60 (br. s., 2H), 1.86 (dd, J=7.34, 9.68 Hz, 1H), 1.59-1.79 (m, 3H), 1.30-1.36 (m, 6H), 1.23-1.30 (m, 1H), 1.12 (dd, J=5.67, 9.78 Hz, 1H), 0.61 (t, J=6.26 Hz, 1H).

tert-butyl((1S,5S,6S)-5-(5-Amino-2-fluoropyridin-3-yl)-1-(methoxymethyl)-5-methyl-2-thia-4-azabicyclo[4.1.0]hept-3-en-3-yl)((2-(trimethylsilyl)ethoxy)methyl)carbamate (242)

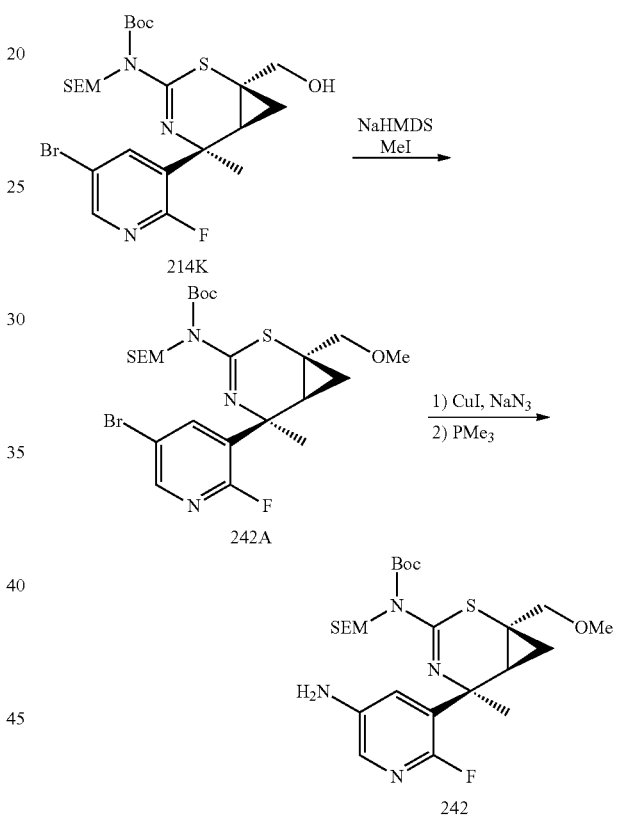

Preparation of Compound 242A. To a solution of tert-butyl((1S,5S,6S)-5-(5-bromo-2-fluoropyridin-3-yl)-1-(hydroxymethyl)-5-methyl-2-thia-4-azabicyclo[4.1.0]hept-3-en-3-yl)((2-(trimethylsilyl)ethoxy)methyl)carbamate (214K, 310 mg, 0.538 mmol) in THF (15 mL) under N₂ at 0° C. was added lithium bis(trimethylsilyl)amide (1.0 M solution in THF, 0.86 mL, 0.86 mmol) dropwise. After addition, the mixture was stirred at 0° C. for 30 min and iodomethane (0.053 mL, 0.860 mmol) was added. The mixture was stirred at 0° C. for 20 min and at RT for overnight, then quenched with saturated NH₄Cl and diluted with H₂O. The mixture was extracted with EtOAc (2×). The combined organic extracts were then washed with brine, dried over MgSO₄, and concentrated. The residue was purified by silica gel flash column chromatography (DCM/EtOAc=5:1) to give tert-butyl((1S,5S,6S)-5-(5-bromo-2-fluoropyridin-3-yl)-1-(methoxymethyl)-5-methyl-2-thia-4- azabicyclo[4.1.0]hept-3-en-3-yl)((2-(trimethylsilyl)ethoxy)methyl)carbamate (242A, 220 mg, 0.37 mmol, 69% yield) as a light yellow oil. LCMS (ESI+) m/z=590.5 (M+H).

Preparation of Compound 242. A microwave vial was charged with tert-butyl((1S,5S,6S)-5-(5-bromo-2-fluoropyridin-3-yl)-1-(methoxymethyl)-5-methyl-2-thia-4-azabicyclo[4.1.0]hept-3-en-3-yl)((2-(trimethylsilyl)ethoxy)methyl)carbamate (242A, 220 mg, 0.372 mmol), sodium azide (121 mg, 1.862 mmol), copper(I) iodide (14.19 mg, 0.074 mmol), sodium (R)-2-((S)-1,2-dihydroxyethyl)-4-hydroxy-5-oxo-2,5-dihydrofuran-3-olate (14.76 mg, 0.074 mmol), EtOH (3 mL) and water (1 mL). It was purged with N$_2$ and sealed. Then (1R,2R)—N$^1$,N$^2$-dimethylcyclohexane-1,2-diamine (23 µL, 0.15 mmol) was added. The mixture was heated to 80° C. The mixture was treated with saturated NH$_4$Cl and diluted with EtOAc. The organic layer was separated and the aqueous layer was extracted twice with EtOAc. The organic solution was washed with brine, dried over Na$_2$SO$_4$, and concentrated in vacuo. The residue was dissolved in THF (3 mL) and water (1 mL) and treated with trimethylphosphine (1.0 M solution in THF, 0.45 mL, 0.45 mmol). The mixture was evaporated to dryness purified by a silica gel chromatography (DCM/EtOAc=10:1 to 5:1) to give tert-butyl((1S,5S,6S)-5-(5-amino-2-fluoropyridin-3-yl)-1-(methoxymethyl)-5-methyl-2-thia-4-azabicyclo[4.1.0]hept-3-en-3-yl)((2-(trimethylsilyl)ethoxy)methyl)carbamate (242, 130 mg, 0.25 mmol, 66% yield). LCMS (ESI+) m/z=527.2 (M+H).

(1S,5S,6S)-3-Amino-5-(5-amino-2-fluorophenyl)-5-methyl-2-thia-4-azabicyclo[4.1.0]hept-3-ene-1-carbonitrile (243)

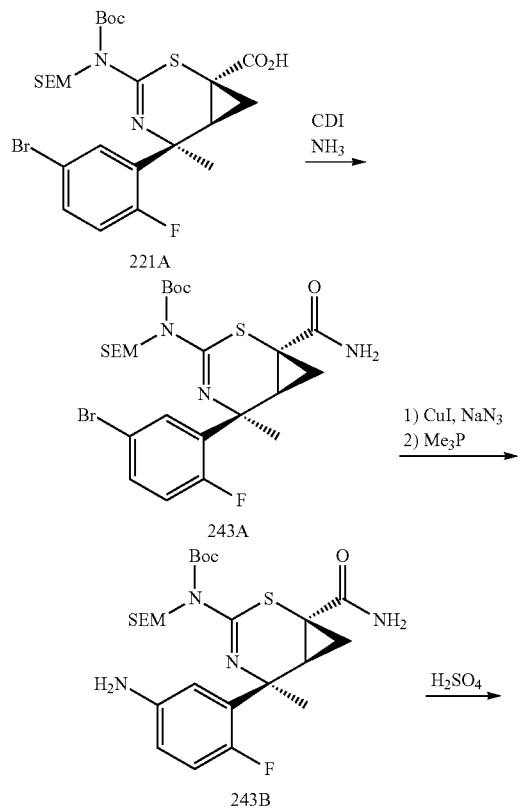

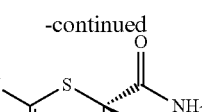

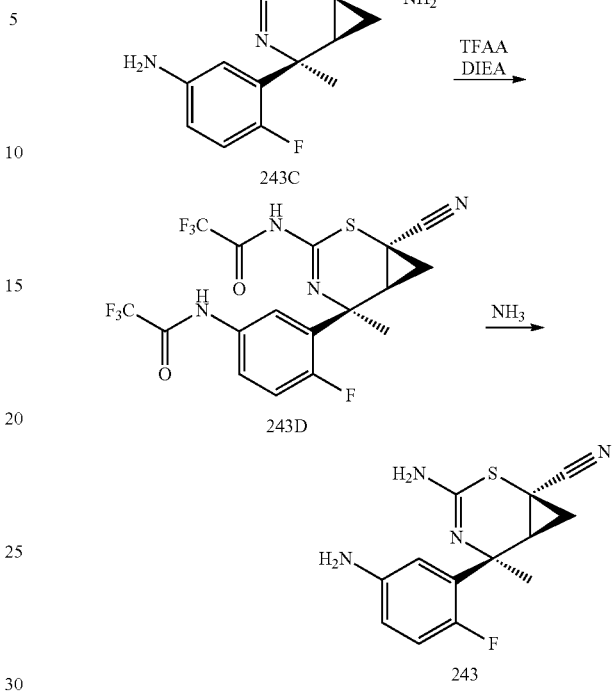

Preparation of Compound 243A. To a stirring solution of (1S,5S,6S)-5-(5-bromo-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylic acid (221A, 1.90 g, 3.22 mmol) in THF (20 mL) at 20° C. under nitrogen was added 1,1'-carbonyldiimidazole (0.784 g, 4.83 mmol). The cloudy solution was stirred for 1 hr at 20° C. followed by addition of ammonia (0.5 M in 1,4-dioxane, 19.34 mL, 9.67 mmol). After 1 h, the reaction mixture was partitioned between EtOAc (60 mL) and 1 M HCl (60 mL). The organic layer was washed with brine (25 mL), dried over MgSO$_4$, filtered and concentrated under reduced pressure to afford tert-butyl((1S,5S,6S)-5-(5-bromo-2-fluorophenyl)-1-carbamoyl-5-methyl-2-thia-4-azabicyclo[4.1.0]hept-3-en-3-yl)((2-(trimethylsilyl)ethoxy)methyl)carbamate (243A, 1.80 g, 3.06 mmol, 95% yield) as colorless oil. LC/MS (ESI$^-$) m/z=588.0/590.0 (M+H)$^+$.

Preparation of Compound 243B. A mixture of tert-butyl ((1S,5S,6S)-5-(5-bromo-2-fluorophenyl)-1-carbamoyl-5-methyl-2-thia-4-azabicyclo[4.1.0]hept-3-en-3-yl)((2-(trimethylsilyl)ethoxy)methyl)carbamate (243A, 1.90 g, 3.23 mmol), sodium azide (0.63 g, 9.68 mmol), copper(i) iodide (0.18 g, 0.97 mmol), (1R,2R)-(−)-N,N'''-dimethylcyclohexane-1,2-diamine (0.19 g, 0.97 mmol), (+)-sodium L-ascorbate (0.19 g, 0.97 mmol) in 5:1 EtOH/H$_2$O (20 mL) was purged with argon for 5 min. The blue suspension was then heated at 70° C. After 1 h, the reaction mixture was chilled to 10° C. and quenched with 9:1 (20 mL) sat. NH$_4$Cl/NH$_4$OH (30%). The mixture was then extracted with EtOAc (60 mL). The organic solution was washed with sat. NH$_4$Cl (10 mL) followed by brine (10 mL), dried over MgSO$_4$, and concentrated under reduced pressure. The residue was dissolved in 5:1 THF/water (20 mL), chilled to 0° C., then trimethylphosphine (4.84 mL of 1 M in THF, 4.84 mmol) was added. The ice bath was removed and reaction stirred for 20 min at 20° C. It was partitioned between EtOAc (40 mL) and 5% NaHCO$_3$ (20 mL). The organic layer was dried over MgSO$_4$, concentrated under reduced pressure, then purified by silica gel chromatography (0-60% EtOAc in heptane) to afford tert-butyl((1S,5S,6S)-5-(5-amino-2-fluorophenyl)-1-carbamoyl-5-methyl-2-thia-4-azabicyclo[4.1.0]hept-3-en-3-yl)((2-(trimethylsilyl)ethoxy)methyl)carbamate (243B, 0.81 g, 1.54 mmol, 48% yield) as colorless oil. LC/MS (ESI$^-$) m/z=525.2 (M+H)$^+$.

Preparation of Compound 243C. To a 100 mL flask containing tert-butyl((1S,5S,6S)-5-(5-amino-2-fluorophenyl)-1-carbamoyl-5-methyl-2-thia-4-azabicyclo[4.1.0]hept-3-en-3-yl)((2-(trimethylsilyl)ethoxy)methyl)carbamate (243B, 0.78 g, 1.48 mmol) at 0° C. under nitrogen was added sulfuric acid (5.95 mL). The flask was periodically removed from cooling bath, swirled by hand, then allowed to stir at 20° C. for 1 h. The reaction mixture was then poured onto wet ice (300 mL) and the mixture along with DCM (100 mL). To the rapidly stirred mixture was added potassium phosphate tribasic monohydrate (42.8 g, 186 mmol). The suspension was filtered and the filtrate transferred to a separatory funnel. The organic layer was separated, and the aqueous layer was extracted with 9:1 CHCl$_3$/IPA (2×50 mL). The combined organic layers were dried over MgSO$_4$, filtered, concentrated under reduced pressure, then purified via silica gel flash column chromatography (40 g) eluting the products with a gradient of 0-50% EtOAc/CH$_2$Cl$_2$ to afford (1S,5S,6S)-3-amino-5-(5-amino-2-fluorophenyl)-5-methyl-2-thia-4-azabicyclo[4.1.0]hept-3-ene-1-carboxamide (243C, 0.37 g, 1.25 mmol, 84% yield) as off white solid. LC/MS (ESI$^-$) m/z=295.1 (M+H)$^+$.

Preparation of Compound 243D. To a stirring solution of (1S,5S,6S)-3-amino-5-(5-amino-2-fluorophenyl)-5-methyl-2-thia-4-azabicyclo[4.1.0]hept-3-ene-1-carboxamide (0.38 g, 1.291 mmol) and N,N-diisopropylethylamine (243C, 1.80 mL, 10.33 mmol) in THF (10 mL) at −70° C. under nitrogen was added 2,2,2-trifluoroacetic anhydride (1.08 mL, 7.75 mmol). After 10 min, the reaction was quenched with sat. NH$_4$Cl (1 mL). The reaction was then partitioned between EtOAc (10 mL) and 5% NaHCO$_3$ (10 mL). The organic was dried over MgSO$_4$, filtered, then concentrated under reduced pressure to afford N-((1S,5S,6S)-1-cyano-5-(2-fluoro-5-(2,2,2-trifluoroacetamido)phenyl)-5-methyl-2-thia-4-azabicyclo[4.1.0]hept-3-en-3-yl)-2,2,2-trifluoroacetamide (243D, 0.60 g, 1.26 mmol) as tan solid. LC/MS (ESI$^-$) m/z=421.0 (M+H)$^+$.

Preparation of Compound 243. A solution of N-((1S,5S,6S)-1-cyano-5-(2-fluoro-5-(2,2,2-trifluoroacetamido)phenyl)-5-methyl-2-thia-4-azabicyclo[4.1.0]hept-3-en-3-yl)-2,2,2-trifluoroacetamide (243D, 600 mg, 1.28 mmol) in 2 M NH$_3$ in MeOH (10 mL) was stirred for 18 h at 37° C. The solvent was removed under reduced pressure and the residue was then purified by silica gel chromatography (12 g) eluting products with a gradient of 1-5% 2 M NH$_3$ in MeOH/DCM to afford (1S,5S,6S)-3-amino-5-(5-amino-2-fluorophenyl)-5-methyl-2-thia-4-azabicyclo[4.1.0]hept-3-ene-1-carbonitrile (235 mg, 0.85 mmol, 66% yield) as white foam. LC/MS (ESI$^-$) m/z=277.1 (M+H)$^+$. $^1$H NMR (400 MHz, DMSO-d$_6$) δ 6.80 (dd, J=8.41, 12.13 Hz, 1H), 6.63 (dd, J=2.93, 7.04 Hz, 1H), 6.38-6.50 (m, 3H), 4.84 (s, 2H), 2.28 (dd, J=7.92, 9.68 Hz, 1H), 1.83 (dd, J=5.87, 9.78 Hz, 1H), 1.67 (s, 3H), 0.92 (t, J=6.46 Hz, 1H).

(1R,5S,6R)-5-(5-Amino-2,3-difluorophenyl)-7,7-difluoro-5-methyl-2-thia-4-azabicyclo[4.1.0]hept-3-en-3-amine (244)

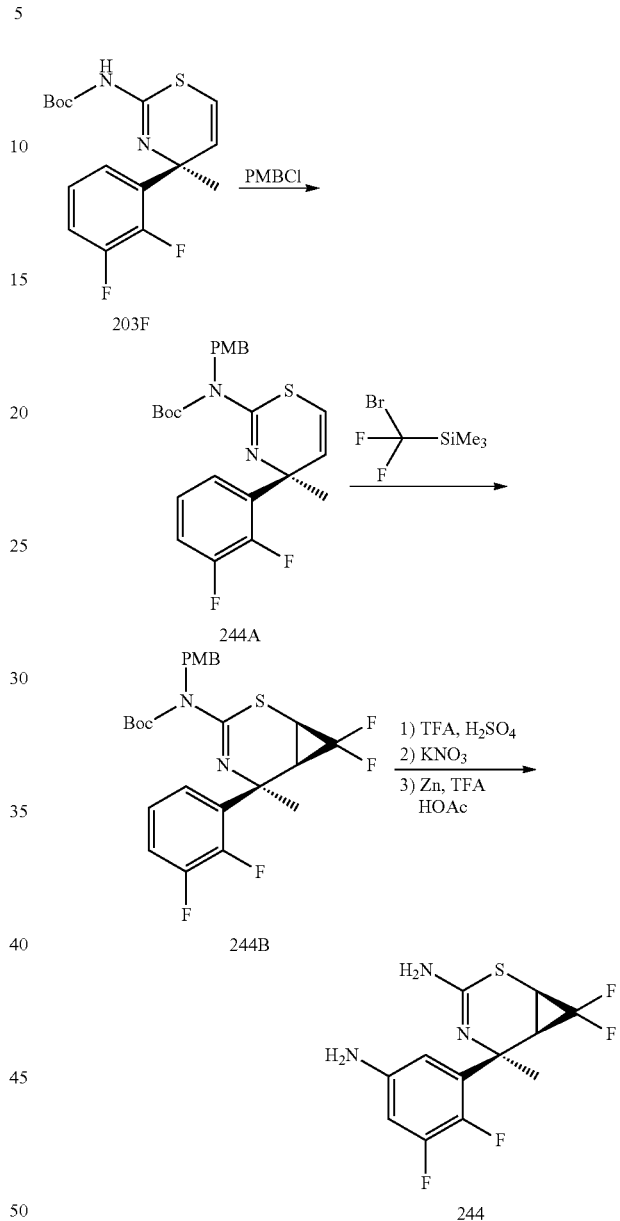

Synthesis of (S)-tert-butyl(4-(2,3-difluorophenyl)-4-methyl-4H-1,3-thiazin-2-yl)(4-methoxybenzyl)carbamate (244A). To a solution of (S)-tert-butyl(4-(2,3-difluorophenyl)-4-methyl-4H-1,3-thiazin-2-yl)carbamate (203F, 1.00 g, 2.94 mmol) in DMF (6 mL) was added potassium carbonate (568 mg, 4.1 mmol), followed by 4-methoxybenzyl chloride (0.5 mL, 3.5 mmol). The reaction mixture was stirred overnight at RT. It was partitioned between water and EtOAc. The aqueous phase was separated and was back-extracted with EtOAc. The combined organic extracts were dried over MgSO$_4$, filtered and concentrated in vacuo. The residue was purified by column chromatography (SiO$_2$, 0-30% EtOAc in hexanes) to afford the title compound (244A, 1.00 g, 2.25 mmol, 76% yield) as a yellow oil. LC/MS (ESI$^+$) m/z=461.1 (M+H)$^+$; $^1$H NMR (300 MHz, CHLOROFORM-d) δ ppm 1.49 (s, 9H) 1.69 (d, J=1.17 Hz, 3H) 3.79 (s, 3H) 5.06 (s, 2H) 6.07 (dd, J=9.50, 3.65 Hz, 1H) 6.26 (d, J=9.35 Hz, 1H) 6.84 (m, 2H) 6.89-7.13 (m, 3H) 7.27 (m, 2H).

Synthesis of tert-butyl((1R,5S,6R)-5-(2,3-difluorophenyl)-7,7-difluoro-5-methyl-2-thia-4-azabicyclo[4.1.0]hept-3-en-3-yl)(4-methoxybenzyl)carbamate (244B). A sealable vial was charged with (S)-tert-butyl(4-(2,3-difluorophenyl)-4-methyl-4H-1,3-thiazin-2-yl)(4-methoxybenzyl)carbamate (244A, 440 mg, 0.96 mmol) and toluene under nitrogen atmosphere. Tetrabutylammonium bromide (9 mg, 0.029 mmol) was added, followed by trimethyl(bromodifluoromethyl)silane (SynQuest Laboratories, 291 mg, 1.43 mmol). The vial was sealed and heated to 110° C. for 6 h. The residue was partitioned between water and EtOAc. The aqueous phase was separated and was back-extracted with EtOAc. The combined organic extracts were dried over MgSO₄, filtered and concentrated in vacuo. The residue was purified by column chromatography (SiO₂, 0-25% EtOAc in hexanes) to afford the title compound as an oil (244B, 116 mg, 0.23 mmol, 24%). LC/MS (ESI⁺) m/z=533.2 (M+Na)⁺.

Synthesis of Compound 244C. A solution of tert-butyl ((1R,5S,6R)-5-(2,3-difluorophenyl)-7,7-difluoro-5-methyl-2-thia-4-azabicyclo[4.1.0]hept-3-en-3-yl)(4-methoxybenzyl)carbamate (244B, 380 mg, 0.74 mmol) in DCM (2.5 mL) was treated with TFA (1.7 mL, 22 mmol) at RT. After 1 h, anisole (0.12 mL, 1.1 mmol) was added to the reaction mixture, followed by drop-wise addition of concentrates sulfuric acid (0.4 mL, 7.4 mmol). After 20 min, the reaction mixture was poured into water and neutralized with aqueous, saturated bicarbonate solution. The reaction mixture was partitioned between water and EtOAc. The aqueous phase was separated and was back-extracted with EtOAc. The combined organic extracts were dried over MgSO₄, filtered and concentrated in vacuo. The crude material was purified by column chromatography (SiO₂, 5-55% EtOAc in hexanes) to afford (1R,5S,6R)-5-(2,3-difluorophenyl)-7,7-difluoro-5-methyl-2-thia-4-azabicyclo[4.1.0]hept-3-en-3-amine (87 mg, 0.30 mmol, 40% yield) as a waxy yellow solid. LC/MS (ESI⁺) m/z=291.0 (M+H)⁺; ¹H NMR (300 MHz, CHLOROFORM-d) δ ppm 1.75 (d, J=1.17 Hz, 3H) 2.55-2.73 (m, 1H) 2.84-3.01 (m, 1H) 7.03-7.21 (m, 2H) 7.39-7.50 (m, 1H); ¹⁹F NMR (282 MHz, CHLOROFORM-d) δ ppm −149.49 (d, J=158.90 Hz, 1F) −140.44−−138.72 (m, 1F) −139.96−−139.68 (m, 1F) −139.26−−139.04 (m, 1F) −121.99 (d, J=158.90 Hz, 1F); The relative stereochemistry was confirmed by COSY, HMBC and NOESY correlations.

To a solution of (1R,5S,6R)-5-(2,3-difluorophenyl)-7,7-difluoro-5-methyl-2-thia-4-azabicyclo[4.1.0]hept-3-en-3-amine (87 mg, 0.30 mmol) in concentrated sulfuric acid (1 mL) at 0° C. was added potassium nitrate (45 mg, 0.45 mmol). The reaction was stirred at for 5 min at 0° C. and additional 5 min at RT. The reaction mixture was poured into ice-water and solid potassium carbonate was added portion wise until the reaction mixture reached pH>10. The aqueous phase was extracted with three times EtOAc. The combined organic extracts were dried over MgSO₄. The solution was filtered and concentrated in vacuo to give the crude (1R,5S,6R)-5-(2,3-difluoro-5-nitrophenyl)-7,7-difluoro-5-methyl-2-thia-4-azabicyclo[4.1.0]hept-3-en-3-amine (50 mg) as a yellow glass. The product was taken onto the next step without further purification. LC/MS (ESI⁺) m/z=336.0 (M+H)⁺.

A flask containing a solution of (1R,5S,6R)-5-(2,3-difluoro-5-nitrophenyl)-7,7-difluoro-5-methyl-2-thia-4-azabicyclo[4.1.0]hept-3-en-3-amine (50 mg, 0.15 mmol) in HOAc (1 mL) was cooled in a water bath. TFA (0.08 mL) was added, followed by zinc dust (50 mg, 0.75 mmol) in one portion. After 10 min, the reaction mixture was basified with 1 N NaOH and then extracted with EtOAc. The organic phase was washed with aqueous, saturated NaCl solution, dried over MgSO₄ and filtered. The filtrate was concentrated to afford intermediate 244 as a yellow residue which was taken on the next step without further purification. LC/MS (ESI⁺) m/z=306.0 (M+H)⁺.

(E)-3-((1R,5S,6S)-3-Amino-5-(5-amino-2-fluorophenyl)-5-(fluoromethyl)-2-thia-4-azabicyclo[4.1.0]hept-3-en-1-yl)-N,N-dimethylacrylamide (246)

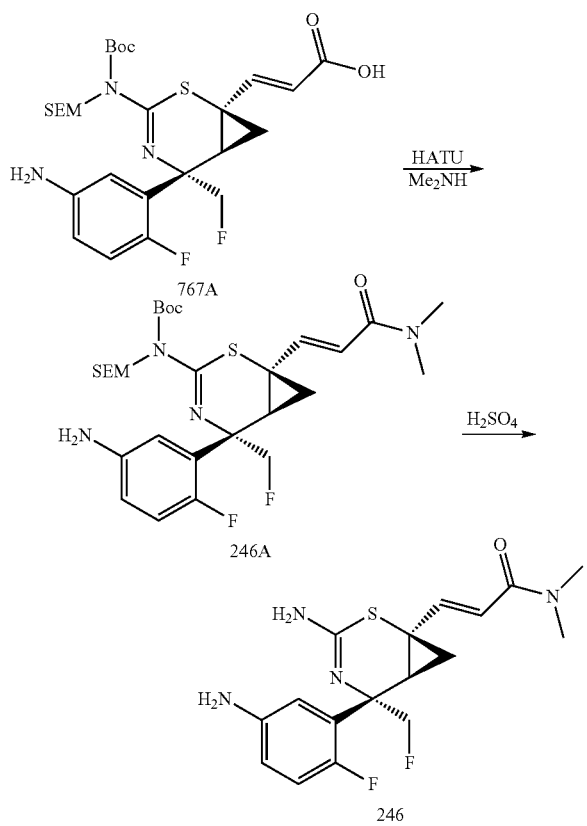

The title compound was prepared according to the procedures describe for intermediate 767C (see the synthesis of Example 767). MS (ESI, positive ion) m/z: 367 (M+1)⁺.

(E)-3-((1R,5S,6S)-3-Amino-5-(5-amino-2-fluorophenyl)-5-(fluoromethyl)-2-thia-4-azabicyclo[4.1.0]hept-3-en-1-yl)-1-(3,3-difluoroazetidin-1-yl)prop-2-en-1-one (247)

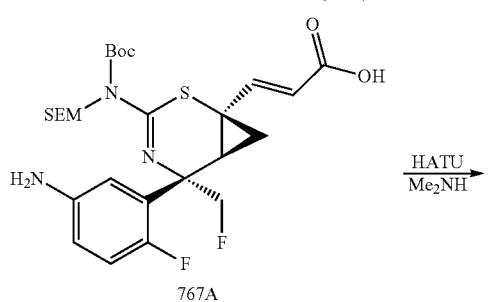

217

-continued

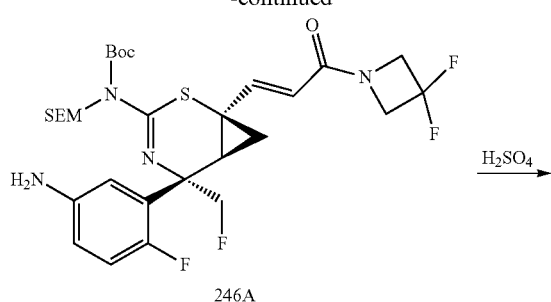

246A

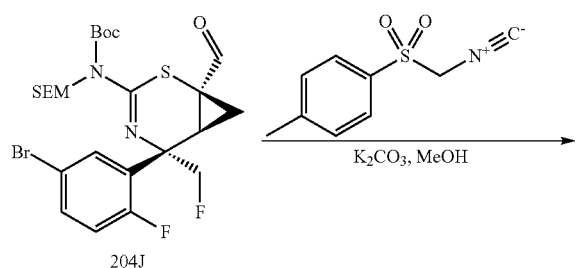

247

The title compound was prepared according to the procedures describe for intermediate 767C (see the synthesis of Example 767). MS (ESI, positive ion) m/z: 415 (M+1)⁺.

(1S,5S,6S)-5-(5-amino-2-fluorophenyl)-5-(fluoromethyl)-1-(oxazol-5-yl)-2-thia-4-azabicyclo[4.1.0]hept-3-en-3-amine (248)

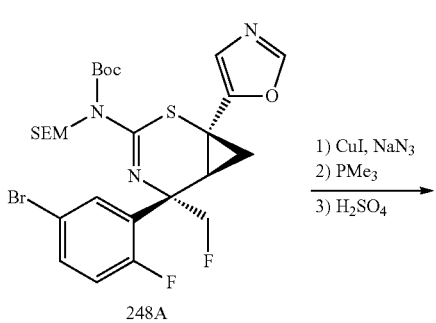

204J

218

-continued

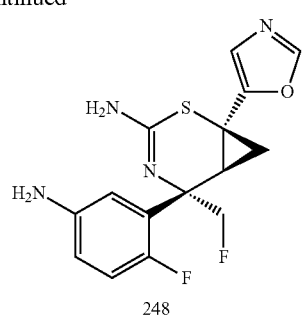

248

Preparation of Compound 248A. A mixture of p-toluenesulfonylmethyl isocyanide (0.79 g, 4.06 mmol), tert-butyl ((1S,5S,6S)-5-(5-bromo-2-fluorophenyl)-5-(fluoromethyl)-1-formyl-2-thia-4-azabicyclo[4.1.0]hept-3-en-3-yl)((2-(trimethylsilyl) ethoxy)methyl)carbamate (2.00 g, 3.38 mmol), and potassium carbonate (2.34 g, 16.90 mmol) in MeOH (4 mL) was stirred a RT for 16 h. The reaction mixture was concentrated to dryness. The residue was diluted with H₂O, and extracted with EtOAc (3×). The organic extracts were dried over Na₂SO₄, concentrated and purified by silica gel column to give tert-butyl((1S,5S,6S)-5-(5-bromo-2-fluorophenyl)-5-(fluoromethyl)-1-(oxazol-5-yl)-2-thia-4-azabicyclo[4.1.0]hept-3-en-3-yl)((2-(trimethylsilyl)ethoxy)methyl)carbamate (248A, 1.37 g, 64%). ¹H NMR (CHLOROFORM-d) δ: 7.86 (dd, J=6.8, 2.5 Hz, 1H), 7.80 (s, 1H), 7.42 (ddd, J=8.7, 4.3, 2.7 Hz, 1H), 7.01 (s, 1H), 6.98 (dd, J=11.5, 8.6 Hz, 1H), 5.36 (d, J=10.4 Hz, 1H), 5.10 (d, J=10.4 Hz, 1H), 4.89-5.06 (m, 1H), 4.68-4.85 (m, 1H), 3.62-3.72 (m, 2H), 2.30 (ddd, J=9.8, 7.4, 2.2 Hz, 1H), 1.53 (s, 9H), 1.50 (d, J=5.9 Hz, 1H), 1.12 (dd, J=7.0, 6.1 Hz, 1H), 0.98 (dd, J=9.0, 7.6 Hz, 2H), 0.00 (s, 9H). MS (ESI, positive ion) m/z: 630/632 (M+1)⁺.

Preparation of (1S,5S,6S)-5-(5-amino-2-fluorophenyl)-5-(fluoromethyl)-1-(oxazol-5-yl)-2-thia-4-azabicyclo[4.1.0]hept-3-en-3-amine (248). The title compound (0.58 g, 79%) was prepared in the same method as described for 243C, but starting from 248A (1.37 g, 2.17 mmol). MS (ESI, positive ion) m/z: 337 (M+1)⁺.

(1S,5S,6S)-5-(5-Amino-2-fluorophenyl)-5-(fluoromethyl)-1-(4-methyloxazol-5-yl)-2-thia-4-azabicyclo[4.1.0]hept-3-en-3-amine (249)

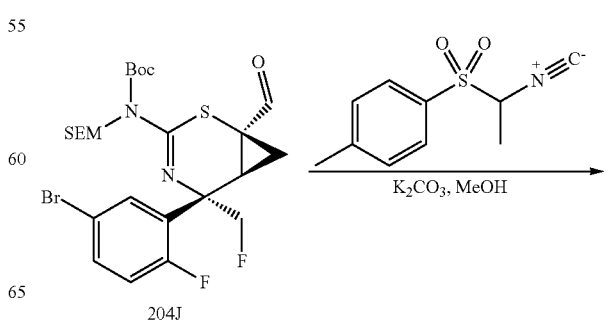

204J

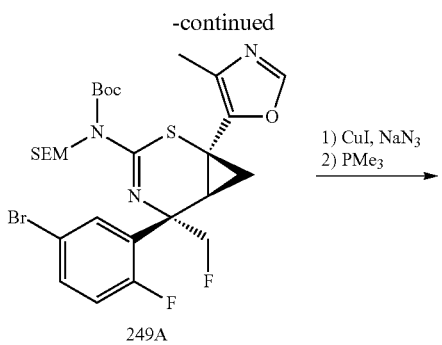

249A

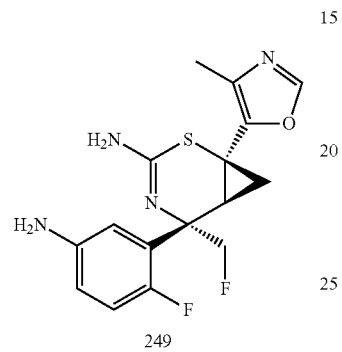

249

Preparation of tert-butyl((1S,5S,6S)-5-(5-bromo-2-fluorophenyl)-5-(fluoromethyl)-1-(4-methyloxazol-5-yl)-2-thia-4-azabicyclo[4.1.0]hept-3-en-3-yl)((2-(trimethylsilyl)ethoxy)methyl) carbamate (249A). The title compound (2.41 g, 88%) was prepared in the same method as that described for Example 248A, but starting from tert-butyl ((1S,5S,6S)-5-(5-bromo-2-fluorophenyl)-5-(fluoromethyl)-1-formyl-2-thia-4-azabicyclo[4.1.0]hept-3-en-3-yl)((2-(trimethylsilyl)ethoxy)methyl)carbamate (204J, 2.50 g, 4.23 mmol), and 1-methyl-1-tosylmethyl isocyanide (1.06 g, 5.07 mmol). MS (ESI, positive ion) m/z: 644/646 (M+1)⁺.

Compound 249 (2.41 g, 88%) was prepared in the same method as that described for intermediate 243C, but starting from Compound 249A (2.40 g, 3.71 mmol). MS (ESI, positive ion) m/z: 581 (M+1).

(1S,5S,6S)-5-(5-Amino-2-fluorophenyl)-1,5-bis(fluoromethyl)-2-thia-4-azabicyclo[4.1.0]hept-3-en-3-amine (450)

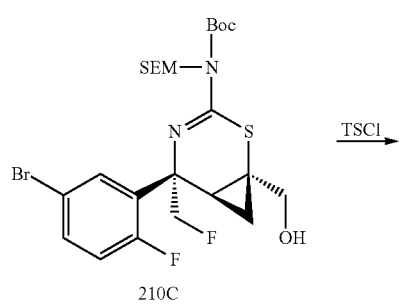

210C

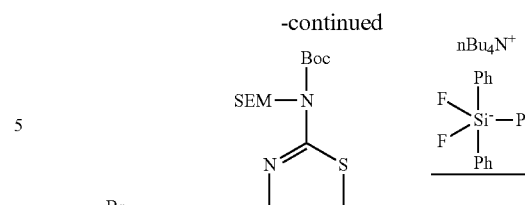

450A

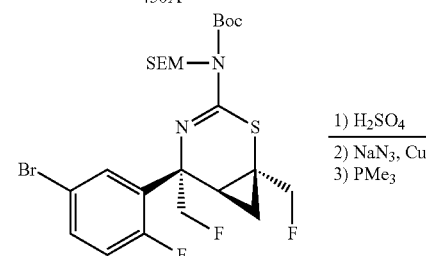

450B

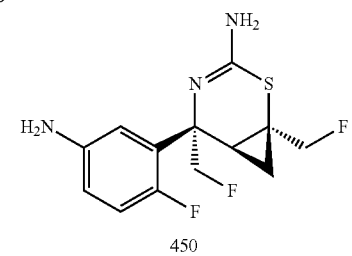

450

Preparation of Compound 450A. To a solution of tert-butyl((1S,5S,6S)-5-(5-bromo-2-fluorophenyl)-5-(fluoromethyl)-1-(hydroxymethyl)-2-thia-4-azabicyclo[4.1.0]hept-3-en-3-yl)((2-(trimethylsilyl)ethoxy)methyl)carbamate (210C, 1.4 g, 2.4 mmol) and TEA (0.5 mL, 3.5 mmol) in DCM (8 mL) at 0° C. was added 4-methylbenzenesulfonyl chloride (0.45 mL, 3.54 mmol) in DCM (7 mL). The resulting mixture was stirred at RT for 4 h. LCMS showed some starting material. 4-(dimethylamino)-pyridine (0.14 g, 1.18 mmol) was added and the mixture was stirred at RT for overnight. It was quenched saturated NaHCO₃. The organic layer was washed with brine, dried over MgSO₄, and concentrated. The residue was purified by silica gel flash column chromatography (0-70% EtOAc/heptane) to give ((1S,5S,6S)-5-(5-bromo-2-fluorophenyl)-3-((tert-butoxycarbonyl)((2-(trimethylsilyl)ethoxy)methyl)amino)-5-(fluoromethyl)-2-thia-4-azabicyclo[4.1.0]hept-3-en-1-yl)methyl 4-methylbenzenesulfonate (450A, 1.12 g, 1.50 mmol, 64% yield) as a colorless oil. MS (ESI, positive ion) m/z: 747/749 (M+1)⁺.

Preparation of Compound 450B. To a solution of ((1S,5S,6S)-5-(5-bromo-2-fluorophenyl)-3-((tert-butoxycarbonyl)((2-(trimethylsilyl)ethoxy)methyl)amino)-5-(fluoromethyl)-2-thia-4-azabicyclo[4.1.0]hept-3-en-1-yl)methyl 4-methylbenzenesulfonate (450A, 2.00 g, 2.67 mmol) (2.00 g, 2.67 mmol) in ACN (20 mL) at RT was added tetrabutylammonium difluorotriphenylsilicate (8.74 g, 16.19 mmol). The reaction mixture was heated to 75° C. for 1 d and cooled to RT. The mixture was diluted with EtOAc and transferred to a separatory funnel. The aqueous layer was discarded and the organic phase was washed with brine, dried over MgSO₄, filtered, and concentrated. Purification by flash column chromatography on silica gel (5-10% EtOAc in heptane) gave tert-butyl((1S,5S,6S)-5-(5-bromo-2-fluorophenyl)-1,5-bis(fluoromethyl)-2-thia-4-azabicyclo[4.1.0]hept-3-en-3-yl)((2-(trimethylsilyl)ethoxy)methyl)carbamate (1.17 g, 1.96 mmol, 73% yield). MS (ESI, positive ion) m/z: 594/596 (M+1)$^+$.

Preparation of (1S,5S,6S)-5-(5-amino-2-fluorophenyl)-1,5-bis(fluoromethyl)-2-thia-4-azabicyclo[4.1.0]hept-3-en-3-amine (450). The title compound was prepared in the same fashion as that described for intermediate 452. MS (ESI, positive ion) m/z: 302.0 (M+1)$^+$.

(1S,5S,6S)-5-(5-Amino-2-fluorophenyl)-1-(ethoxymethyl)-5-(fluoromethyl)-2-thia-4-azabicyclo[4.1.0]hept-3-en-3-amine (451)

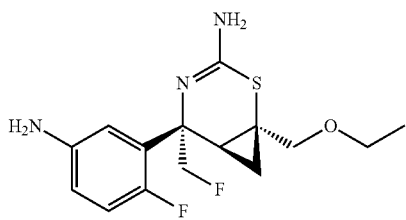

451

The title compound was prepared in a fashion similar to that described for intermediate 210. MS (ESI, positive ion) m/z: 328 (M+1)$^+$.

2-((1R,5S,6S)-3-Amino-5-(5-amino-2-fluorophenyl)-5-(fluoromethyl)-2-thia-4-azabicyclo[4.1.0]hept-3-en-1-yl)acetonitrile (452)

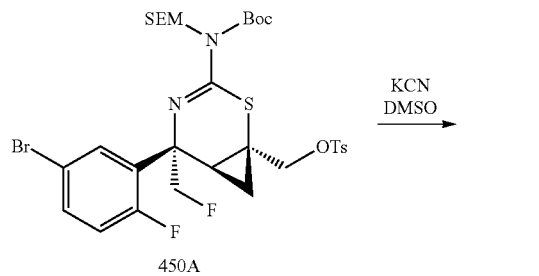

450A

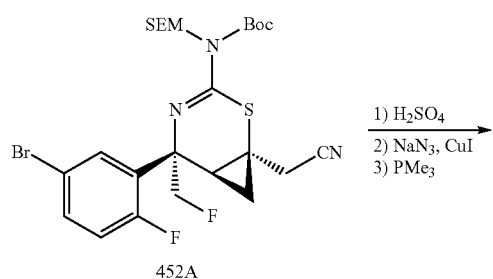

452A

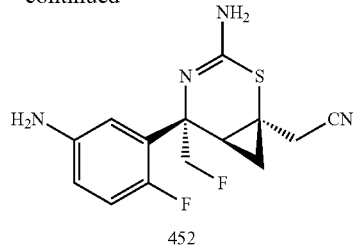

452

Preparation of Compound 452A. To a solution of ((1S,5S,6S)-5-(5-bromo-2-fluorophenyl)-3-((tert-butoxycarbonyl)((2-(trimethylsilyl)ethoxy)methyl)amino)-5-(fluoromethyl)-2-thia-4-azabicyclo[4.1.0]hept-3-en-1-yl)methyl 4-methylbenzenesulfonate (450A, 1.02 g, 1.36 mmol) in DMSO (anhydrous, 9 mL) was added potassium cyanide (0.13 g, 2.04 mmol). The resulting mixture was stirred at 55° C. under N$_2$ overnight. It was cooled to RT, quenched with saturated NaHCO$_3$ (30 mL) and extracted with EtOAc (2×40 mL). The organic layer was then collected, washed with brine, dried over MgSO$_4$, and concentrated. The residue was purified by silica gel flash column chromatography using ISCO instrument (0-100% EtOAc/heptane) to give 783 mg of tert-butyl((1R,5S,6S)-5-(5-bromo-2-fluorophenyl)-1-(cyanomethyl)-5-(fluoromethyl)-2-thia-4-azabicyclo[4.1.0]hept-3-en-3-yl)((2-(trimethylsilyl)ethoxy)methyl)carbamate as a colorless oil. MS (ESI, positive ion) m/z: 602.2/604.1 (M+1)$^+$. $^1$H NMR (CHLOROFORM-d) δ: 7.82 (dd, J=6.8, 2.5 Hz, 1H), 7.41 (dt, J=7.1, 4.3 Hz, 1H), 6.98 (dd, J=11.6, 8.7 Hz, 1H), 5.34 (d, J=10.4 Hz, 1H), 5.08 (d, J=10.4 Hz, 1H), 4.83-5.01 (m, 1H), 4.61-4.77 (m, 1H), 3.63-3.69 (m, 2H), 3.48 (s, 1H), 2.77 (q, J=17.4 Hz, 2H), 2.04 (t, J=7.5 Hz, 1H), 1.53 (s, 9H), 1.11 (dd, J=10.0, 6.3 Hz, 1H), 0.97 (dd, J=9.3, 7.3 Hz, 2H), 0.81 (t, J=6.7 Hz, 1H), 0.00 (s, 9H).

Preparation of Compound 452. To a round bottom flask containing tert-butyl((1R,5S,6S)-5-(5-bromo-2-fluorophenyl)-1-(cyanomethyl)-5-(fluoromethyl)-2-thia-4-azabicyclo[4.1.0]hept-3-en-3-yl)((2-(trimethylsilyl)ethoxy)methyl)carbamate (452A, 750 mg, 1.24 mmol) at 0° C. was added sulfuric acid (2 mL) dropwise. After addition, the mixture was stirred at 0° C. for 24 min and RT for 27 min. It was poured into 50 g of ice and the mixture was adjusted to pH>10 by saturated NaOH. The mixture was extracted with EtOAc (2×20 mL). The combined organic extracts were dried over MgSO$_4$ and concentrated. The residue was purified by silica gel flash column chromatography using ISCO instrument (0-100% EtOAc/heptane) to give 2-((1R,5S,6S)-3-amino-5-(5-bromo-2-fluorophenyl)-5-(fluoromethyl)-2-thia-4-azabicyclo[4.1.0]hept-3-en-1-yl)acetonitrile (83 mg, 0.223 mmol, 18% yield) as a light yellow solid. MS (ESI, positive ion) m/z: 372.0/374.0 (M+1)$^+$.

To a solution of 2-((1R,5S,6S)-3-amino-5-(5-bromo-2-fluorophenyl)-5-(fluoromethyl)-2-thia-4-azabicyclo[4.1.0]hept-3-en-1-yl)acetonitrile (83 mg, 0.223 mmol) in EtOH (0.5 mL) and water (0.25 mL) was added sodium azide (44 mg, 0.67 mmol), (+)-sodium L-ascorbate (11.0 mg, 0.05 mmol), copper(i) iodide (10.6 mg, 0.05 mmol), and trans-N,N'-dimethylcyclohexane-1,2-diamine (8.8 μL, 0.05 mmol). Then, N$_2$ was bubbled in the solution mixture for 5 min. Then, the mixture was then stirred at 70° C. under N$_2$ for 1 h. LCMS showed 80% conversion. Then, copper(i) iodide (10 mg), (+)-sodium L-ascorbate (11 mg), and trans-N,N'-dimethylcyclohexane-1,2-diamine (8.8 μL) were added and the mixture was stirred at 70° C. for 45 min. LCMS showed no starting material. The mixture was cooled to RT, quenched with saturated NH₄Cl/NH₄OH (9:1, 5 mL), and extracted with EtOAc (2×10 mL). The combined organic extracts were dried over MgSO₄ and concentrated in vacuo. The residue was dissolved in THF/H₂O (9:1, 1 mL) and trimethylphosphine (0.22 mL of 1.0 M solution in THF) was added. The resulting mixture was then stirred at RT overnight. It was diluted with EtOAc and washed with saturated NaHCO₃ (5 mL). The organic layer was collected, dried over MgSO₄, and concentrated in vacuo. The residue was purified by silica gel flash column chromatography using ISCO instrument (0-20% MeOH/DCM) to give 2-((1R,5S,6S)-3-amino-5-(5-amino-2-fluorophenyl)-5-(fluoromethyl)-2-thia-4-azabicyclo[4.1.0]hept-3-en-1-yl)acetonitrile (56 mg, 0.182 mmol, 81% yield) as a yellow solid. MS (ESI, positive ion) m/z: 309 (M+1)⁺.

3-((1S,5S,6S)-3-Amino-5-(5-bromo-2-fluorophenyl)-5-(fluoromethyl)-2-thia-4-azabicyclo[4.1.0]hept-3-en-1-yl)propanenitrile (453)

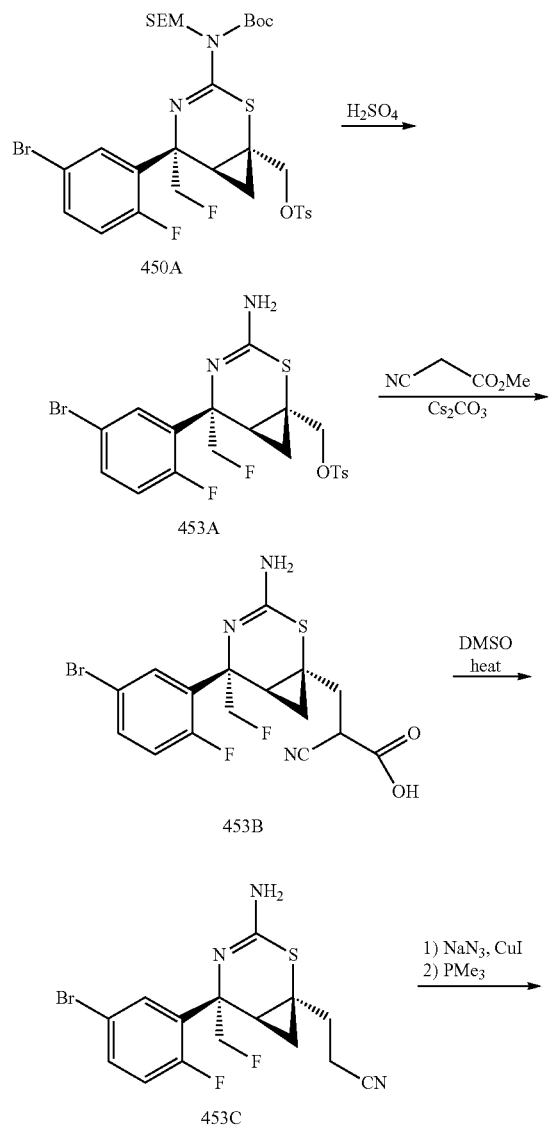

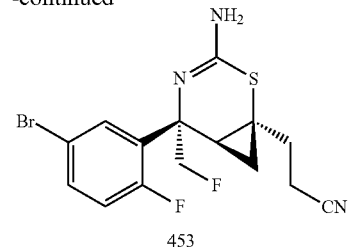

Preparation of Compound 453A. At 0° C., sulfuric acid (5 mL) was added dropwise to ((1S,5S,6S)-5-(5-bromo-2-fluorophenyl)-3-((tert-butoxycarbonyl)((2-(trimethylsilyl)ethoxy)methyl)amino)-5-(fluoromethyl)-2-thia-4-azabicyclo[4.1.0]hept-3-en-1-yl)methyl 4-methylbenzenesulfonate (250A, 1.7 g, 2.3 mmol). The mixture was stirred at RT for 5 min then pour onto 50 g of ice. The pH of the mixture was adjusted to >12 with the addition of 5 N NaOH. The mixture was extracted with EtOAc (2×50 mL). The combined organic extracts were dried over MgSO₄ and concentrated. The residue was purified by silica gel flash column chromatography using ISCO instrument (0-100% EtOAc/heptane) to give ((1S,5S,6S)-3-amino-5-(5-bromo-2-fluorophenyl)-5-(fluoromethyl)-2-thia-4-azabicyclo[4.1.0]hept-3-en-1-yl)methyl 4-methylbenzenesulfonate (851 mg, 1.64 mmol, 72% yield) as a light yellow solid. MS (ESI, positive ion) m/z: 517.0, 518.9 (M+1)⁺. ¹H NMR (CHLOROFORM-d) δ: 7.80 (d, J=8.2 Hz, 2H), 7.61 (d, J=6.3 Hz, 1H), 7.43 (br. s., 1H), 7.38 (d, J=8.0 Hz, 2H), 6.91-7.00 (m, 1H), 4.57-4.87 (m, 2H), 4.01-4.17 (m, 2H), 1.89 (br. s., 1H), 1.25 (br. s., 1H), 0.80 (t, J=6.7 Hz, 1H).

Preparation of Compound 453B. To a solution of ((1S,5S,6S)-3-amino-5-(5-bromo-2-fluorophenyl)-5-(fluoromethyl)-2-thia-4-azabicyclo[4.1.0]hept-3-en-1-yl)methyl 4-methylbenzenesulfonate (453A, 300 mg, 0.58 mmol) in DMF (3.7 mL) was added cesium carbonate (416 mg, 1.27 mmol) and methyl 2-cyanoacetate (86 mg, 0.87 mmol). The resulting mixture was stirred at RT overnight. It was quenched with saturated NaHCO₃ (7 mL) and extracted with EtOAc (2×20 mL). The combined organic extracts were dried over MgSO₄ and concentrated. The residue was purified by silica gel flash column chromatography using ISCO instrument (0-40% EtOAc/heptane), then by preparative HPLC (10% ACN 0.1% TFA/H₂O 0.1% TFA). The desired fractions were concentrated and the residue was treated with saturated NaHCO₃ and extracted with EtOAc (2×20 mL). The combined organic extracts were dried over MgSO₄, concentrated, and dried in vacuo to give a product as a mixture of (2R)-3-[(1R,5S,6S)-3-amino-5-(5-bromo-2-fluorophenyl)-5-(fluoromethyl)-2-thia-4-azabicyclo[4.1.0]hept-3-en-1-yl]-2-cyanopropanoic acid and (2S)-3-[(1R,5S,6S)-3-amino-5-(5-bromo-2-fluorophenyl)-5-(fluoromethyl)-2-thia-4-azabicyclo[4.1.0]hept-3-en-1-yl]-2-cyanopropanoic acid. MS (ESI, positive ion) m/z: 430, 432 (M+1)⁺.

Preparation of Compound 453C. A mixture of (2R)-3-[(1R,5S,6S)-3-amino-5-(5-bromo-2-fluorophenyl)-5-(fluoromethyl)-2-thia-4-azabicyclo[4.1.0]hept-3-en-1-yl]-2-cyanopropanoic acid and (2S)-3-[(1R,5S,6S)-3-amino-5-(5-bromo-2-fluorophenyl)-5-(fluoromethyl)-2-thia-4-azabicyclo[4.1.0]hept-3-en-1-yl]-2-cyanopropanoic acid (453B, 249 mg, 0.58 mmol) in DMSO (1 mL) was stirred at 70° C. overnight. It was cooled to RT and saturated NaHCO₃ (5 mL) was added. The mixture was extracted with EtOAc (2×10 mL). The combined organic extracts were dried over MgSO₄, concentrated and dried in vacuo to give 3-((1S,5S, 6S)-3-amino-5-(5-bromo-2-fluorophenyl)-5-(fluoromethyl)-2-thia-4-azabicyclo[4.1.0]hept-3-en-1-yl)propanenitrile as a light yellow oil which was used in the next step without purification requirement. MS (ESI, positive ion) m/z: 386, 388 (M+1)$^+$.

Preparation of 3-((1S,5S,6S)-3-amino-5-(5-amino-2-fluorophenyl)-5-(fluoromethyl)-2-thia-4-azabicyclo[4.1.0]hept-3-en-1-yl)propanenitrile (453). The title compound (13 mg) as a yellow solid was prepared from intermediate 453C (224 mg, 0.58 mmol) according to the procedures described for intermediate 452. MS (ESI, positive ion) m/z: 323 (M+1)$^+$.

(1S,5S,6S)-5-(5-Amino-2-fluorophenyl)-5-(fluoromethyl)-1-((5-methyl-1H-1,2,3-triazol-1-yl)methyl)-2-thia-4-azabicyclo[4.1.0]hept-3-en-3-amine (454)

methyl)-2-thia-4-azabicyclo[4.1.0]hept-3-en-3-yl)((2-(trimethylsilyl)ethoxy)methyl)carbamate (454A, 226 mg, 0.34 mmol, 14% yield) as a yellow solid. MS (ESI, positive ion) m/z: 658.1/660.2 (M+H)$^+$.

Preparation of (1S,5S,6S)-5-(5-amino-2-fluorophenyl)-5-(fluoromethyl)-1-((5-methyl-1H-1,2,3-triazol-1-yl)methyl)-2-thia-4-azabicyclo[4.1.0]hept-3-en-3-amine (454). The title compound (51 mg, 41% yield) as a yellow solid was prepared from intermediate 454A (226 mg, 0.34 mmol) according to the procedures described for intermediate 452. MS (ESI, positive ion) m/z: 365.0 (M+1)$^+$.

2-((1R,5S,6S)-3-Amino-5-(5-amino-2-fluorophenyl)-5-(fluoromethyl)-2-thia-4-azabicyclo[4.1.0]hept-3-en-1-yl)acetonitrile (455)

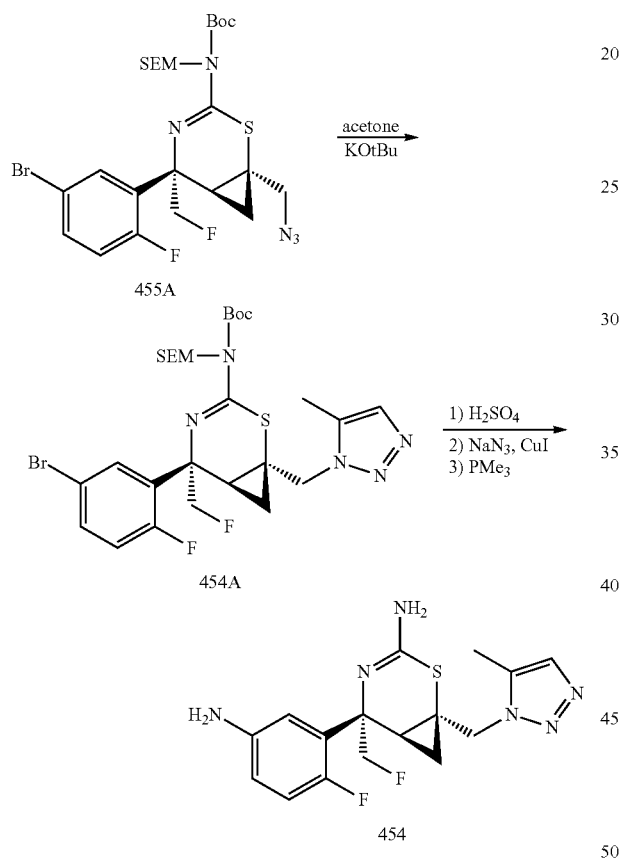

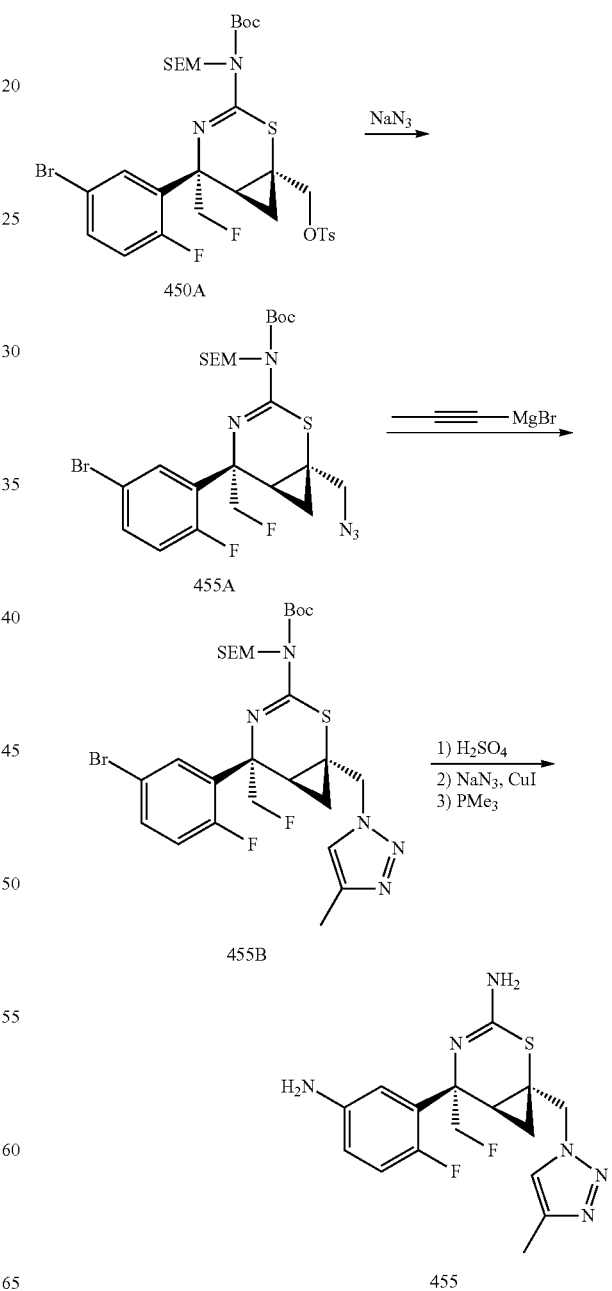

Preparation of Compound 454A. To a solution of potassium t-butoxide (0.82 g, 7.27 mmol) in THF (8 mL) at 0° C. under N$_2$ was added a solution of tert-butyl((1S,5S,6S)-1-(azidomethyl)-5-(5-bromo-2-fluorophenyl)-5-(fluoromethyl)-2-thia-4-azabicyclo[4.1.0]hept-3-en-3-yl)((2-(trimethylsilyl)ethoxy)methyl)carbamate (455A, 1.5 g, 2.42 mmol) in acetone (0.53 mL, 7.27 mmol) and THF (7 mL) dropwise. After addition, the mixture was stirred at 0° C. for 1 h and RT for 18 h. The mixture was poured onto ice bath (50 mL) and saturated NaHCO$_3$ (7 mL) was added. The mixture was extracted with EtOAc (2×10 mL). The combined organic extracts were washed with brine, dried over MgSO$_4$, and concentrated in vacuo. Chromatographic purification of the residue (silica gel, 0%-100% EtOAc/heptane) provided tert-butyl((1S,5S,6S)-5-(5-bromo-2-fluorophenyl)-5-(fluoromethyl)-1-((5-methyl-1H-1,2,3-triazol-1-yl)

Preparation of Compound 455A. To a solution of ((1S,5S,6S)-5-(5-bromo-2-fluorophenyl)-3-((tert-butoxycarbonyl)((2-(trimethylsilyl)ethoxy)methyl)amino)-5-(fluoromethyl)-2-thia-4-azabicyclo[4.1.0]hept-3-en-1-yl)methyl 4-methylbenzenesulfonate (450A, 606 mg, 0.81 mmol) in DMSO (4.0 mL) was added sodium azide (58 mg, 0.89 mmol). The resulting mixture was then stirred at RT overnight. The mixture was quenched with saturated NH$_4$Cl/NH$_4$OH (10:1, 10 mL) and extracted with EtOAc (2×15 mL). The combined organic extracts were dried over MgSO$_4$ and concentrated in vacuo. The residue was purified by silica gel flash column chromatography using ISCO instrument (0-100% EtOAc in heptane) to give tert-butyl((1S,5S,6S)-1-(azidomethyl)-5-(5-bromo-2-fluorophenyl)-5-(fluoromethyl)-2-thia-4-azabicyclo[4.1.0]hept-3-en-3-yl)((2-(trimethylsilyl)ethoxy)methyl)carbamate (501 mg, 0.81 mmol, 100% yield) as a colorless oil. MS (ESI, positive ion) m/z: 618.0/620.2 (M+1)$^+$.

Preparation of Compound 455B. To a solution of tert-butyl((1S,5S,6S)-1-(azidomethyl)-5-(5-bromo-2-fluorophenyl)-5-(fluoromethyl)-2-thia-4-azabicyclo[4.1.0]hept-3-en-3-yl)((2-(trimethylsilyl)ethoxy)methyl)carbamate (501 mg, 0.81 mmol) in MTBE (4 mL) under N$_2$ at 0° C. was added 1-propynylmagnesium bromide (0.5 M in THF, 2.43 mL, 1.21 mmol). After addition, the mixture was stirred at RT overnight. LCMS showed 15% conversion. Additional 1-propynylmagnesium bromide (0.5 M in THF, 2.43 mL, 1.21 mmol) was added and the mixture was then stirred at RT for 4 h. LCMS showed no starting material. The reaction was quenched with saturated NH$_4$Cl (50 mL) and extracted with EtOAc (2×70 mL). The combined organic extracts were dried over MgSO$_4$ and concentrated in vacuo. The residue was purified by silica gel flash column chromatography using ISCO instrument (0%-100% EtOAc/heptane) to give tert-butyl((1S,5S,6S)-5-(5-bromo-2-fluorophenyl)-5-(fluoromethyl)-1-((4-methyl-1H-1,2,3-triazol-1-yl)methyl)-2-thia-4-azabicyclo[4.1.0]hept-3-en-3-yl)((2-(trimethylsilyl)ethoxy)methyl)carbamate (449 mg, 0.68 mmol, 84% yield) as colorless oil. MS (ESI, positive ion) m/z: 658.1/660.0 (M+1)$^+$. $^1$H NMR (CHLOROFORM-d) δ: 7.77 (dd, J=6.9, 2.4 Hz, 1H), 7.50 (s, 1H), 7.40 (ddd, J=8.7, 4.3, 2.5 Hz, 1H), 6.97 (dd, J=11.5, 8.6 Hz, 1H), 5.27 (d, J=10.4 Hz, 1H), 5.03 (d, J=10.4 Hz, 1H), 4.57-4.82 (m, 2H), 4.39-4.50 (m, 2H), 3.64 (dd, J=9.1, 7.3 Hz, 2H), 2.43 (s, 3H), 2.24 (t, J=7.6 Hz, 1H), 1.50 (s, 9H), 1.22 (dd, J=9.9, 6.2 Hz, 1H), 0.95 (dd, J=9.1, 7.5 Hz, 2H), 0.85 (t, J=6.7 Hz, 1H), 0.00 (s, 9H).

Preparation of Compound 455. The title compound (185 mg, 87% yield) as a yellow solid was prepared from intermediate 455B (449 mg, 0.68 mmol) according to the procedures described for intermediate 452. MS (ESI, positive ion) m/z: 365.0 (M+1). $^1$H NMR (CHLOROFORM-d) δ: 7.46 (s, 1H), 6.84 (dd, J=11.7, 8.6 Hz, 1H), 6.75 (dd, J=6.6, 2.8 Hz, 1H), 6.51-6.58 (m, 1H), 4.73-4.90 (m, 1H), 4.52-4.69 (m, 1H), 4.33-4.51 (m, 2H), 2.38 (s, 3H), 2.04-2.06 (m, 1H), 1.35 (dd, J=9.8, 6.3 Hz, 1H), 1.26 (t, J=7.1 Hz, 1H). The 2 sets of NH$_2$ have very broad peaks.

8-Chloro-3-methoxy-1,7-naphthyridine (251)

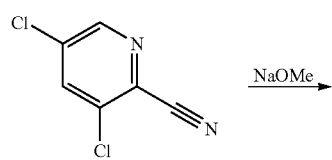

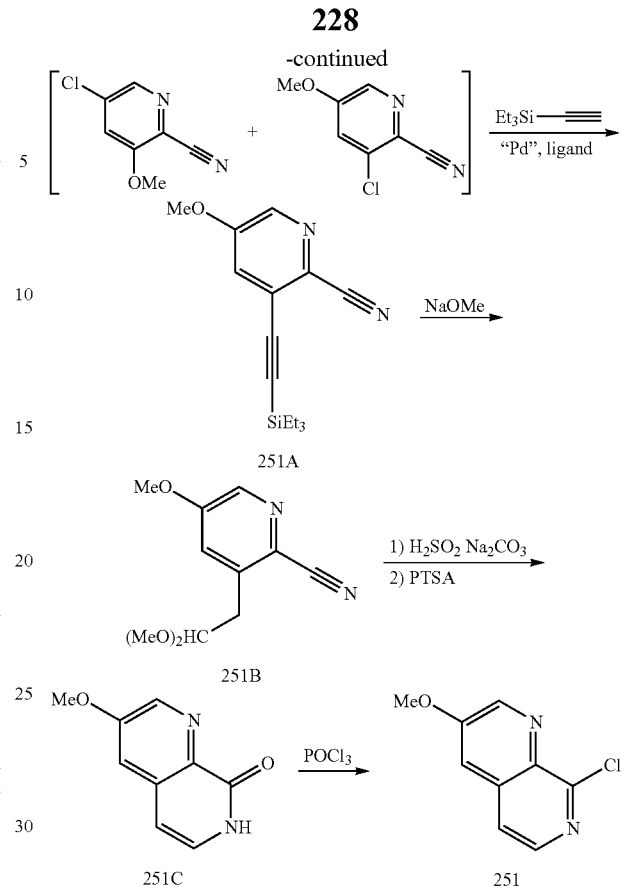

Preparation of 5-methoxy-3-((triethylsilyl)ethynyl)picolinonitrile (251A). To a solution of 3,5-dichloropicolinonitrile (22.5 g, 130 mmol) in DMF (500 mL) at 0° C. was added sodium methoxide (6.67 g, 124 mmol) slowly. The reaction was stirred for 5 min at 0° C. then stirred at RT for 30 min. The solution was partitioned between water and EtOAc. The organic layer was washed with water and concentrated. The crude product was purified via silica gel chromatography, eluting with 0-75% EtOAc in heptane, to afford a 1:1 ratio of the desired isomer 3-chloro-5-methoxypicolinonitrile and 5-chloro-3-methoxypicolinonitrile (7.0 g, 41.5 mmol). The material was used without further purification. MS m/z=169 (M+H). A sealed vessel was charged with bis(acetonitrile) palladium (II) chloride (0.154 g, 0.593 mmol), dicyclohexyl (2',4',6'-triisopropyl-[1,1'-biphenyl]-2-yl)phosphine (0.848 g, 1.780 mmol), cesium carbonate (25.1 g, 77 mmol), the mixture (1:1 ratio) of 3-chloro-5-methoxypicolinonitrile and 5-chloro-3-methoxypicolinonitrile (5 g, 29.7 mmol), and ACN (60 mL). The vessel was flushed with argon, and stirred at RT for 25 min. To the reaction was added triethyl (ethynyl)silane (5.41 g, 38.6 mmol), and the vessel was resealed and stirred at 90° C. for 3 h. The solution was concentrated, and the residue was purified via silica gel chromatography, eluting with 0-50% EtOAc in heptane, to afford the title compound (3.8 g, 13.9 mmol). MS m/z=273 (M+H)$^+$.

Preparation of 3-(2,2-dimethoxyethyl)-5-methoxypicolinonitrile (251B). A pressure vessel was charged with 5-methoxy-3-((triethylsilyl)ethynyl) picolinonitrile (251A, 3.8 g, 13.95 mmol) and sodium methoxide (0.5 M in MeOH, 69.7 mL, 34.9 mmol). The vessel was sealed and stirred at 55° C. for 2 h. The reaction was concentrated to afford the title intermediate (3.1 g, 13.95 mmol).

Preparation of 3-Methoxy-1,7-naphthyridin-8(7H)-one (251C). To a solution of 3-(2,2-dimethoxyethyl)-5-methoxypicolinonitrile (251B, 8.55 g, 38.5 mmol) in water (480 mL) and acetone (120 mL) was added an aqueous solution of sodium carbonate (3 M; 154 mL, 462 mmol) followed by hydrogen peroxide (35 wt. % solution in water; 138 mL, 1347 mmol). The tan mixture was stirred vigorously at RT for 2 h. The organic solvent was removed under reduced pressure and the aqueous residue was extracted with DCM (3×). The combined organic fractions were dried over sodium sulfate. The filtrate was concentrated under reduced pressure to afford 3-(2,2-dimethoxyethyl)-5-methoxypicolinamide (8.2 g, 34.1 mmol, 89% yield) as an off-white solid that was advanced without further purification. MS m/z=263.2 (M+Na)$^+$.

To a mixture of 3-(2,2-dimethoxyethyl)-5-methoxypicolinamide (6.74 g, 28.1 mmol) in toluene (112 mL) was added 4-methylbenzene sulfonic acid (monohydrate; 0.534 g, 2.81 mmol). The reaction mixture was heated to reflux for 20 h. The reaction mixture was cooled to RT and concentrated in vacuo to a volume of ca. 15 mL. The residue was triturated with heptane and filtered to afford 3-methoxy-1,7-naphthyridin-8(7H)-one (251C, 4.53 g, 25.7 mmol, 92% yield) as a crude, tan solid that was advanced without further purification. MS m/z=177.1 [M+H]$^+$ Preparation of 8-chloro-3-methoxy-1,7-naphthyridine (251). To a mixture of 3-methoxy-1,7-naphthyridin-8(7H)-one (4.50 g, 25.5 mmol) in ACN (102 mL) was added phosphorus oxychloride (11.69 mL, 128 mmol). The reaction mixture was heated to 85° C. for 5 h. The solution was cooled to RT and concentrated in vacuo. The resulting brown residue was partitioned between DCM and aqueous saturated NaHCO$_3$ solution; the aqueous layer was back-extracted with DCM (3×). The combined organic extracts were dried over sodium sulfate. The filtrate was concentrated in vacuo, and the residue was purified by silica gel chromatography (5-30% of (9:1 DCM:MeOH) in DCM) to give 8-chloro-3-methoxy-1,7-naphthyridine (3.00 g, 15.41 mmol, 60% yield) as an off-white solid. MS m/z=195 (M+H)$^+$.

3,8-Dichloro-1,7-naphthyridine (252)

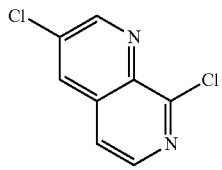

252

Preparation of 3-bromo-5-chloropicolinonitrile

A microwave vial was charged with copper(I) cyanide (1.089 g, 12.16 mmol), 2,3-dibromo-5-chloropyridine (3 g, 11.06 mmol), and propionitrile (15 mL). The vial was capped and irradiated in a microwave reactor at 150° C. for 2.5 h. The solution was concentrated, diluted with DCM (25 mL), and filtered. The filtrate was concentrated, and the residue was purified by silica gel chromatography, eluting with 0-30% EtOAc in heptane, to afford the title compound (2 g, 9.20 mmol). MS m/z=219 (M+H)$^+$.

Preparation of 5-chloro-3-((trimethylsilyl)ethynyl)picolinonitrile

A pressure vessel was charged with TEA (7.65 mL, 55.2 mmol), ethynyltrimethylsilane (2.32 mL, 16.6 mmol), copper(I) iodide (0.263 g, 1.380 mmol), palladium (0) tetrakis (triphenylphosphine) (0.558 g, 0.483 mmol), 3-bromo-5-chloropicolinonitrile (3.0 g, 13.8 mmol), and DMF (50 mL). The vessel was flushed with argon, sealed, stirred at ambient temperature for 15 minutes, and then heated at 50° C. for 4 h. The solution was diluted with water and extracted with EtOAc. The combined organic layers were concentrated, and the residue was purified by silica-gel chromatography, eluting 0-50% EtOAc in hexane, to afford the title compound (1.3 g, 5.5 mmol). MS m/z=235 (M+H)$^+$.

Preparation of 5-chloro-3-(2,2-dimethoxyethyl)picolinonitrile

A pressure vessel was charged with 5-chloro-3-((trimethylsilyl)ethynyl)picolinonitrile (2 g, 8.52 mmol) and sodium methoxide (0.5 M in MeOH, 42.6 mL, 21.30 mmol), sealed, and stirred at 55° C. for 1 h. The solution was concentrated, and the residue was purified via silica gel chromatography, eluting with 10% MeOH in DCM to afford the title compound (1.7 g, 7.50 mmol). MS m/z=227 (M+H)$^+$.

Preparation of 3-chloro-1,7-naphthyridin-8(7H)-one

To a solution of 5-chloro-3-(2,2-dimethoxyethyl)picolinonitrile (1.7 g, 7.50 mmol) in acetone (50 mL) and water (150 mL) was added aqueous saturated sodium carbonate (37.5 mL, 113 mmol) and 30% aqueous hydrogen peroxide (38.3 mL, 375 mmol). The reaction was stirred at RT for one hour, concentrated to remove most of the acetone, and extracted with DCM. The combined organic layers were concentrated.

To a solution of this intermediate (1.8 g, 7.36 mmol) in benzene (20 mL) was added p-toluenesulfonic acid (0.350 g, 1.839 mmol) and the reaction was sonicated for 10 minutes. The solution was stirred overnight at 80° C. and concentrated. The crude product was purified via silica gel, eluting with 0-100% (80/20/1 EtOAc/MeOH/ammonium hydroxide) in EtOAc, to the title intermediate (1.1 g, 6.1 mmol). MS m/z=181 (M+H)$^+$.

Preparation of 3,8-dichloro-1,7-naphthyridine

A suspension of -chloro-1,7-naphthyridin-8(7H)-one (250 mg, 1.384 mmol) in phosphorus oxychloride (1.94 mL, 20.8 mmol) was stirred at 95° C. for one hour. The solution was concentrated to afford the title compound (276 mg, 1.39 mmol). MS m/z=199 (M+H)$^+$.

5-Chloro-2-methoxypyrido[3,4-b]pyrazine (253)

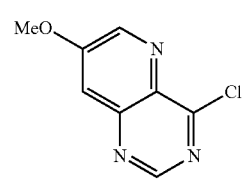

253

Preparation of 5-chloropyrido[3,4-b]pyrazin-2(1H)-one

A suspension 2-chloropyridine-3,4-diamine (2.5 g, 17.41 mmol) and a 50% solution of ethyl glyoxalate in toluene (3.45 mL, 17.41 mmol) in EtOH (34.8 mL) was stirred at reflux for 24 h. The solution was cooled to −20° C. for 16 hours, and the resulting precipitate was collected by vacuum filtration and rinsed with EtOH. The crude product was purified via reverse-phase HPLC, eluting with 5-50% ACN/0.1% TFA in water/0.1% TFA, to afford the title compound (570 mg, 3.14 mmol). MS m/z=182 (M+H)⁺.

Preparation of 2,5-dichloropyrido[3,4-b]pyrazine

A suspension of 5-chloropyrido[3,4-b]pyrazin-2(1H)-one (0.57 g, 3.14 mmol) in phosphorus oxychloride (10.24 mL, 110 mmol) was stirred at 110° C. for two hours, and then concentrated. The residue was dissolved in DCM, washed with saturated sodium bicarbonate, dried over anhydrous sodium sulfate, filtered, and concentrated to afford the title compound (580 mg, 2.90 mmol). MS m/z=200 (M+H)⁺.

Preparation of 5-chloro-2-methoxypyrido[3,4-b]pyrazine

To a solution of 2,5-dichloropyrido[3,4-b]pyrazine (580 mg, 2.90 mmol) in DMF (10 mL) was added a 0.5 M solution of sodium methoxide in MeOH (6.09 mL, 3.04 mmol), and the reaction was stirred at RT for 5 min. The solution was diluted with water and extracted with EtOAc. The organic layer was dried with sodium sulfate, filtered and concentrated to afford the title compound (550 mg, 2.81 mmol). MS m/z=196 (M+H)⁺.

8-Chloro-1,7-naphthyridine-3-carbonitrile (254)

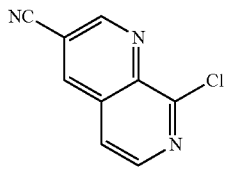

254

A screw-cap vial was charged with 3-chloro-1,7-naphthyridin-8(7H)-one (100 mg, 0.554 mmol), zinc cyanide (52.7 µL, 0.831 mmol), 2-dicyclohexylphosphino-2',6'-dimethoxybiphenyl (45.5 mg, 0.111 mmol), tris(dibenzylideneacetone)dipalladium(0) (40.6 mg, 0.044 mmol), DMF (2.74 mL) and water (28 OA The vial was purged with argon, sealed, and stirred at 110° C. for 1 hour. The mixture was filtered through a pad of Celite® filter aid, which was rinsed with MeOH and DMSO. The combined filtrates were concentrated, and a few drops of water were added. The resulting solids were collected by vacuum filtration, rinsed with water and dried. The solids were suspended in toluene (3.5 mL), and phosphorus oxychloride (98 µL, 1.052 mmol) and DIPEA (122 µL, 0.70 mmol) were added. The reaction was stirred at 120° C. for 1.5 hours, cooled to RT, diluted with EtOAc, and washed with 2 M aqueous sodium carbonate. The organic portion was dried over anhydrous sodium sulfate, filtered and concentrated. The crude material was purified by silica gel chromatography, eluting with 5-50% EtOAc in heptane, to provide the title compound (50 mg, 0.264 mmol) as a white solid. LC/MS (ESI⁺) m/z=190 (M+H)⁺.

4,7-Dichloropyrido[3,2-d]pyrimidine (255)

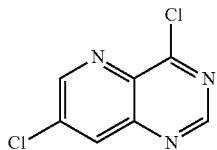

255

Preparation of 3-amino-5-chloropicolinamide

To a suspension of 5-chloro-2-cyano-3-nitropyridine (1.274 mL, 10.9 mmol) in water (22 mL) was added 28% aqueous NH₄OH (3.94 mL, 28.3 mmol), and the reaction was stirred at RT for 20 min. Sodium hydrosulfite (2.68 mL, 32.7 mmol) was added, and the reaction mixture was stirred at RT for 70 minutes. The yellow precipitate was collected by vacuum filtration to provide the title compound (1.097 g, 6.39 mmol) as yellow solid. ¹H-NMR (400 MHz, DMSO-d₆): δ 7.88 (br. s, 1H), δ 7.73 (s, 1H), δ 7.39 (br. s, 1H), δ 7.23 (s, 1H), δ 7.06 (br. s, 2H). LC/MS (ESI⁺) m/z=172 (M+H)⁺.

Preparation of 7-chloropyrido[3,2-d]pyrimidin-4(1H)-one

A suspension of 3-amino-5-chloropicolinamide (1.1 g, 6.41 mmol) in triethyl orthoformate (15.99 mL, 96 mmol) was stirred at 155° C. for 22 h. After cooling to RT, the yellow precipitate was collected by vacuum filtration and washed with hexanes to yield the title intermediate (1.03 g, 5.67 mmol) as a yellow solid. ¹H NMR (400 MHz, DMSO-d₆) δ ppm 8.20 (s, 1H) 8.27 (d, J=2.35 Hz, 1H) 8.80 (d, J=2.25 Hz, 1H) 12.68 (br. s., 1H). LC/MS (ESI⁺) m/z=182 (M+H)⁺.

Preparation of 4,7-dichloropyrido[3,2-d]pyrimidine

To a mixture of 7-chloropyrido[3,2-d]pyrimidin-4(1H)-one (250 mg, 1.377 mmol) in toluene (12 mL) were added DIPEA (0.73 mL, 4.20 mmol) and phosphorus oxychloride (0.391 mL, 4.27 mmol), and the reaction was stirred at reflux for 1 h. After cooling to RT, the reaction mixture was concentrated to provide the title compound. LC/MS (ESI⁺) m/z=200 (M+H)⁺.

4-Chloropyrido[3,2-d]pyrimidine-7-carbonitrile (256)

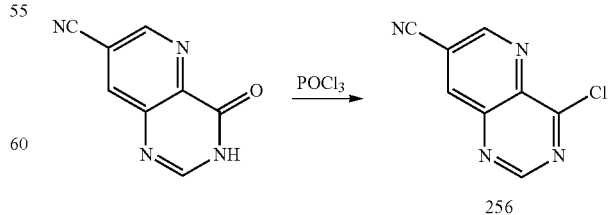

256

To a mixture of 4-oxo-1,4-dihydropyrido[3,2-d]pyrimidine-7-carbonitrile (prepared according to the procedures described in US20090036430) (7.7 g, 44.7 mmol) in toluene (249 mL) were added N,N-diisopropylethylamine (23.73 mL, 136 mmol) and phosphorus oxychloride (12.69 mL, 139 mmol). The resulting reaction mixture was refluxed at 130° C. for 20 min. It was concentrated under reduced pressure. The residue was dissolved in EtOAc (150 mL) and neutralized with sat. NaHCO$_3$ until pH=6-7. It was diluted with water and filtered through a pad of silica in a fritted funnel. The filtrate was extracted with EtOAc (3×150 mL). The combined organic extracts were washed sequentially with water, brine and dried over MgSO$_4$. The solution was filtered and concentrated in vacuo to give a dark brown solid. It was triturated with 160 mL of heptane and 20 mL of EtOAc to yield 4-chloropyrido[3,2-d]pyrimidine-7-carbonitrile (5.7 g, 29.9 mmol, 67% yield) as an orange solid. The filtrate was concentrated down to ~50 mL and the precipitated solid was collected to yield 0.3 g of 4-chloropyrido[3,2-d]pyrimidine-7-carbonitrile. MS m/z=191.0 [M+H]$^+$. $^1$H NMR (300 MHz, CHLOROFORM-d) δ 9.27 (d, J=2.0 Hz, 1H), 9.26 (s, 1H), 8.77 (d, J=2.0 Hz, 1H).

8-Chloro-5-fluoro-3-methoxy-1,7-naphthyridine (257)

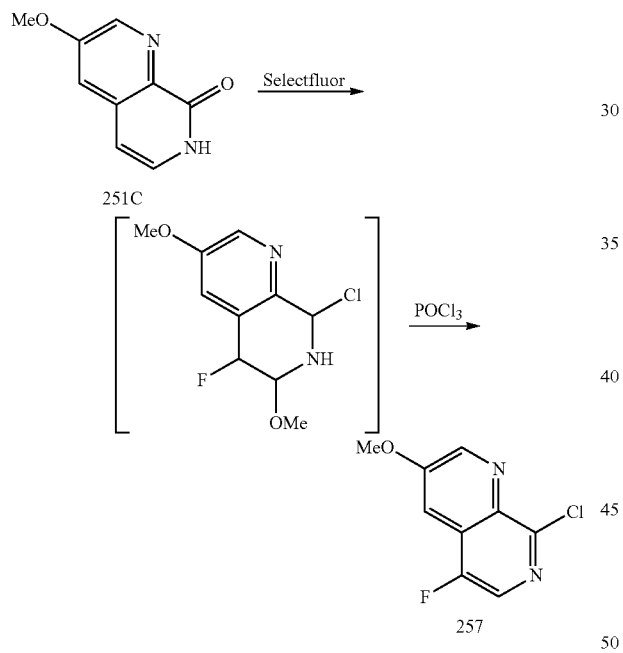

A mixture of 3-methoxy-1,7-naphthyridin-8(7H)-one (15.00 g, 85 mmol) and selectfluor fluorinating reagent (47.21 g, 133 mmol) in ACN (360 mL)/MeOH (90 mL) was heated at 45° C. for 3 h. It was cooled to RT and the solvents were removed in vacuo. The residue was partitioned between EtOAc (200 mL and saturated NaHCO$_3$ (200 mL). The aqueous layer was extracted with EtOAc (2×200 mL) and DCM (2×200 mL). A white solid precipitated from the combined organic layers and was filtered to give 5-fluoro-3,6-dimethoxy-6,7-dihydro-1,7-naphthyridin-8(5H)-one (10.20 g, MS m/z=227.0 [M+H]$^+$). The combined organic layers were dried over MgSO$_4$ where a white solid precipitate formed on the MgSO$_4$. The organic solution was filtered and the solid was washed consecutively with water then Et$_2$O. The remaining solid (1.24 g) contained product 5-fluoro-3,6-dimethoxy-6,7-dihydro-1,7-naphthyridin-8 (5H)-one (MS m/z=227.0 [M+H]$^+$). The combined dried organic layers were concentrated in vacuo to give 5-fluoro-3,6-dimethoxy-6,7-dihydro-1,7-naphthyridin-8(5H)-one (7.41 g) of a light-tan solid.

The three batches of solid (18.85 g) 5-fluoro-3,6-dimethoxy-6,7-dihydro-1,7-naphthyridin-8(5H)-one were slurried in toluene (150 mL), treated with phosphorus oxychloride (80 mL, 874 mmol) and heated at 75° C. overnight. The mixture was cooled to RT and the solvents were removed in vacuo. The residue was azeotroped with toluene, dissolved in DCM, evaporated onto silica gel and purified by flash chromatography eluting with EtOAc:hexanes (0:1→3:1) to give 8-chloro-5-fluoro-3-methoxy-1,7-naphthyridine (257) (11.21 g, 62% yield) of a sticky yellow solid. MS m/z=212.9 [M+H]$^+$. $^1$H NMR (300 MHz, CDCl$_3$) δ ppm 8.85 (d, J=2.92 Hz, 1H), 8.23 (s, 1H), 7.54 (d, J=2.92 Hz, 1H), 4.05 (s, 3H). $^{19}$F NMR (282 MHz, CDCl$_3$) δ ppm −140.46.

5-Chloro-2-methoxypyrido[3,4-b]pyrazine (258)

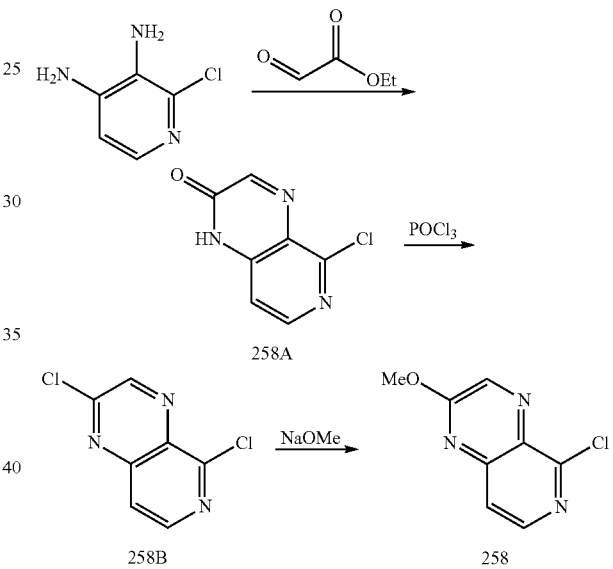

Preparation of 5-chloropyrido[3,4-b]pyrazin-2(1H)-one (258A). A suspension 2-chloropyridine-3,4-diamine (2.5 g, 17.41 mmol) and a 50% solution of ethyl glyoxalate in toluene (3.45 mL, 17.41 mmol) in EtOH (34.8 mL) was stirred at reflux for 24 h. The solution was cooled to −20° C. for 16 h, and the resulting precipitate was collected by vacuum filtration and rinsed with EtOH. The crude product was purified via reverse-phase HPLC, eluting with 5-50% ACN/0.1% TFA in water/0.1% TFA, to afford the title compound (570 mg, 3.14 mmol). MS m/z=182 (M+H)$^+$.

Preparation of 2,5-dichloropyrido[3,4-b]pyrazine (258B). A suspension of 5-chloropyrido[3,4-b]pyrazin-2(1H)-one (0.57 g, 3.14 mmol) in phosphorus oxychloride (10.24 mL, 110 mmol) was stirred at 110° C. for two h, and then concentrated. The residue was dissolved in DCM, washed with saturated sodium bicarbonate, dried over anhydrous sodium sulfate, filtered, and concentrated to afford the title compound (580 mg, 2.90 mmol). MS m/z=200 (M+H)$^+$.

Preparation of 5-chloro-2-methoxypyrido[3,4-b]pyrazine (258). To a solution of 2,5-dichloropyrido[3,4-b]pyrazine (580 mg, 2.90 mmol) in DMF (10 mL) was added a 0.5 M solution of sodium methoxide in MeOH (6.09 mL, 3.04 mmol), and the reaction was stirred at RT for 5 min. The solution was diluted with water and extracted with EtOAc. The organic layer was dried with sodium sulfate, filtered and concentrated to afford the title compound (550 mg, 2.81 mmol). MS m/z=196 (M+H)$^+$.

2-(((5-Chloropyrido[3,4-b]pyrazin-2-yl)oxy)methyl)oxazole (259)

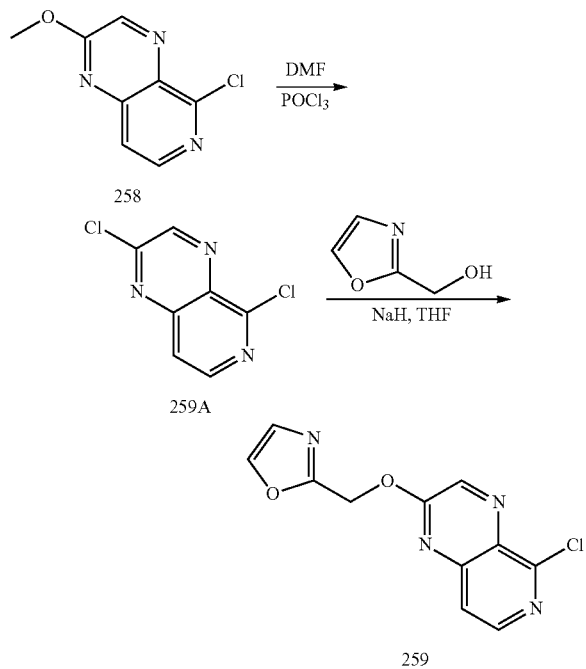

Preparation of Compound 259A. A mixture of 5-chloro-2-methoxypyrido[3,4-b]pyrazine (258, 2.76 g, 14.11 mmol), phosphorus oxychloride (17.10 mL, 183 mmol) and DMF (1.09 mL, 14.12 mmol) was heated at 100° C. overnight. The mixture was concentrated in vacuo. The residue was diluted with EtOAc (150 mL) and cooled to 0° C. It was treated with ice water followed by solid NaHCO$_3$ in small portions. The layers were separated. The basic aqueous layer was extracted with EtOAc. The combined organic solution was washed with brine, dried over Na$_2$SO$_4$ and concentrated in vacuo to afford 2,5-dichloropyrido[3,4-b]pyrazine (259A, 2.57 g, 12.85 mmol, 91% yield) as a brown solid. LC/MS (ESI$^-$) m/z=200, 202 (M+H)$^+$.

Preparation of Compound 259. At 0° C., to a mixture of 2,5-dichloropyrido[3,4-b]pyrazine (259A, 1.64 g, 8.20 mmol), oxazol-2-ylmethanol (1.19 g, 8.85 mmol) in THF (50 mL) under N$_2$ was added sodium hydride (60% wt. dispersion in mineral oil) (0.35 g, 8.85 mmol) in batches. After 40 min, the reaction was quenched with saturated NH$_4$Cl (20 mL) and water (20 mL). The mixture was diluted with EtOAc (150 mL) and the organic layer was washed with brine (50 mL), dried over Na$_2$SO$_4$, filtered, and concentrated in vacuo. The solid was suspended in heptane-EtOAc and filtered to afford 2-(((5-chloropyrido[3,4-b]pyrazin-2-yl)oxy)methyl)oxazole (259, 1.89 g, 7.20 mmol, 88% yield) as a brown powder. LC/MS (ESI$^-$) m/z=263, 265 (M+H)$^+$. $^1$H NMR (400 MHz, CHLOROFORM-d) δ=8.70 (s, 1H), 8.51 (d, J=5.7 Hz, 1H), 7.74 (d, J=0.8 Hz, 1H), 7.69-7.64 (m, 1H), 7.21 (s, 1H), 5.68 (s, 2H).

3-Bromo-8-chloropyrido[2,3-d]pyridazine (260)

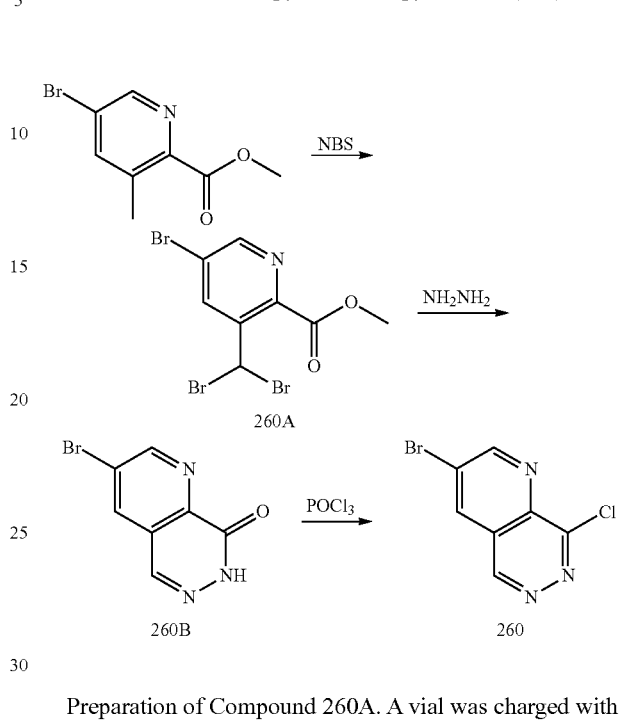

Preparation of Compound 260A. A vial was charged with methyl 5-bromo-3-methylpicolinate (2.03 g, 8.82 mmol), carbon tetrachloride (22 mL), benzoyl peroxide (0.107 g, 0.441 mmol) and NBS (3.14 g, 17.65 mmol). The mixture was heated at 80° C. for 2 h. Another equivalent of NBS and 50 mg benzoyl peroxide were added, and heating was continued for 16 h. Upon cooling to RT the mixture was filtered through Celite® filter aid and washed with DCM. The filtrate was concentrated, and the crude material was purified by silica gel chromatography (10-50% EtOAc/heptane) to provide methyl 5-bromo-3-(dibromomethyl)picolinate as a yellow oil (260A, 3.28 g, 8.46 mmol, 96% yield).

Preparation of 3-bromopyrido[2,3-d]pyridazin-8(7H)-one (260B). A pressure bottle was charged with methyl 5-bromo-3-(dibromomethyl)picolinate (3.28 g, 8.46 mmol), EtOH (16.91 mL) and hydrazine hydrate (4.19 mL, 85 mmol). The bottle was sealed, and the mixture was heated at 80° C. for 1.5 h. The mixture was heterogeneous upon cooling, so the solids were filtered, washed with MeOH and dried. The filtrate was concentrated and was triturated in MeOH. The solids were filtered, rinsed with MeOH and dried to give a second crop of product. The title compound (1.72 g, 7.61 mmol, 90% yield) was isolated as a yellow solid.

Preparation of 3-bromo-8-chloropyrido[2,3-d]pyridazine (260)

A vial was charged with 3-bromopyrido[2,3-d]pyridazin-8(7H)-one (500 mg, 2.212 mmol) and phosphorus oxychloride (4.1 mL, 44.2 mmol). The vial was capped and the mixture was heated at 90° C. for 2 h. The mixture was concentrated and used without further purification. MS m/z=241 (M+MeOH adduct)$^+$.

8-Chloro-3-(prop-2-yn-1-yloxy)-1,7-naphthyridine and 8-chloro-3-(prop-2-yn-1-yloxy)-1,7-naphthyridine (261)

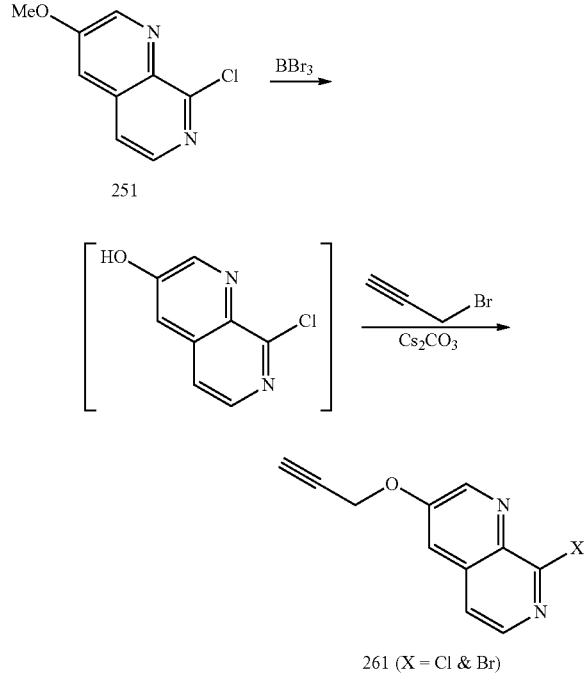

261 (X = Cl & Br)

To a stirring solution of 8-chloro-3-methoxy-1,7-naphthyridine (251) (0.75 g, 3.85 mmol) in 1,2-dichloroethane (40 mL) at 20° C. under nitrogen was added boron tribromide (3.71 mL, 38.5 mmol) dropwise. The reaction mixture was then heated to 70° C. for 2 h. The solvents were removed under reduced pressure. The resulting solid was suspended in CH$_2$Cl$_2$ (10 mL) and collected by filtration. The solid was further washed with CH$_2$Cl$_2$ (10 mL). The solid was air dried for 30 min to afford crude 8-chloro-1,7-naphthyridin-3-ol (1.8 g, 9.97 mmol, 259% yield) as a tan solid which was used without further purification.

To a stirring suspension of the above crude 8-chloro-1,7-naphthyridin-3-ol (700 mg, 3.88 mmol) and cesium carbonate (6.31 g, 19.38 mmol) in DMF (5 mL) at 20° C. under nitrogen was added propargyl bromide (691 µL, 7.75 mmol) in one portion and stirred for 18 h. The reaction mixture was partitioned between EtOAc (25 mL) and 5% NaHCO$_3$ (50 mL). The organic layer was separated, washed with 5% NaHCO$_3$ (50 mL) and brine (20 mL). The organic solution was dried over MgSO$_4$, concentrated under reduced pressure, then purified by silica gel chromatography eluting with a gradient of 0-30% EtOAc/heptane to afford 540 mg of off-white solid, as a mixture of 8-chloro-3-(prop-2-yn-1-yloxy)-1,7-naphthyridine (MS m/z=219.1 [M+H]$^+$) and 8-bromo-3-(prop-2-yn-1-yloxy)-1,7-naphthyridine (MS m/z=263/265 [M+H]$^+$) in a ratio of about 3:2. $^1$H NMR (400 MHz, CHLOROFORM-d) δ ppm 8.85 (d, J=2.74 Hz, 1H), 8.29-8.35 (m, 1H), 7.54-7.58 (m, 1H), 7.47-7.52 (m, 1H), 4.90 (d, J=2.54 Hz, 2H), 2.64 (t, J=2.45 Hz, 1H).

5-Chloro-2-(prop-2-yn-1-yloxy)pyrido[3,4-b]pyrazine (262)

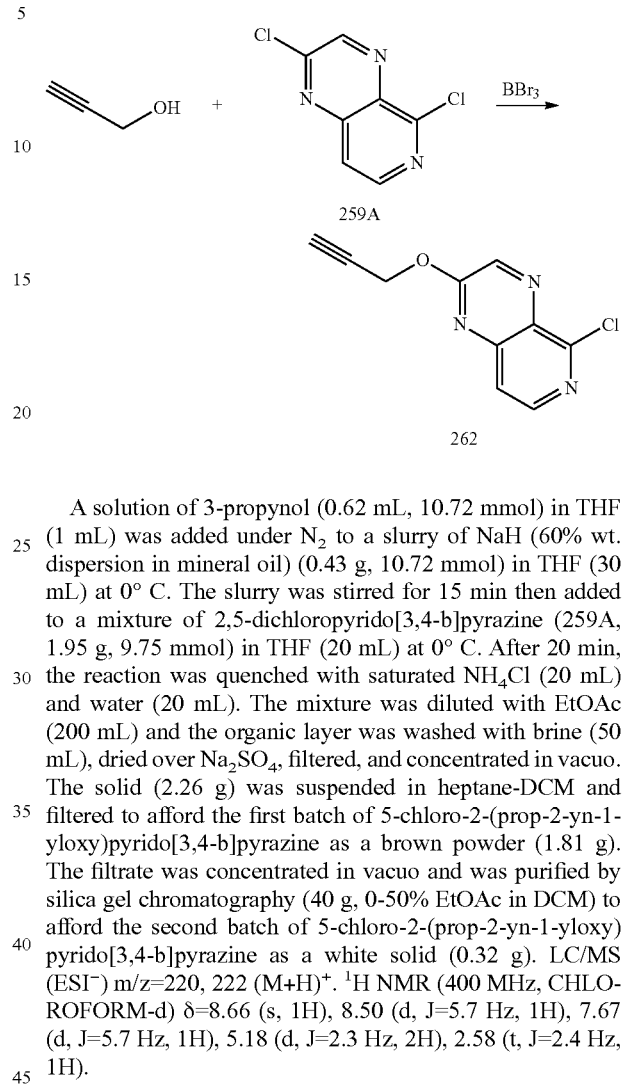

A solution of 3-propynol (0.62 mL, 10.72 mmol) in THF (1 mL) was added under N$_2$ to a slurry of NaH (60% wt. dispersion in mineral oil) (0.43 g, 10.72 mmol) in THF (30 mL) at 0° C. The slurry was stirred for 15 min then added to a mixture of 2,5-dichloropyrido[3,4-b]pyrazine (259A, 1.95 g, 9.75 mmol) in THF (20 mL) at 0° C. After 20 min, the reaction was quenched with saturated NH$_4$Cl (20 mL) and water (20 mL). The mixture was diluted with EtOAc (200 mL) and the organic layer was washed with brine (50 mL), dried over Na$_2$SO$_4$, filtered, and concentrated in vacuo. The solid (2.26 g) was suspended in heptane-DCM and filtered to afford the first batch of 5-chloro-2-(prop-2-yn-1-yloxy)pyrido[3,4-b]pyrazine as a brown powder (1.81 g). The filtrate was concentrated in vacuo and was purified by silica gel chromatography (40 g, 0-50% EtOAc in DCM) to afford the second batch of 5-chloro-2-(prop-2-yn-1-yloxy)pyrido[3,4-b]pyrazine as a white solid (0.32 g). LC/MS (ESI$^-$) m/z=220, 222 (M+H)$^+$. $^1$H NMR (400 MHz, CHLOROFORM-d) δ=8.66 (s, 1H), 8.50 (d, J=5.7 Hz, 1H), 7.67 (d, J=5.7 Hz, 1H), 5.18 (d, J=2.3 Hz, 2H), 2.58 (t, J=2.4 Hz, 1H).

8-Chloro-3-(cyclopropylmethoxy)-1,7-naphthyridine (400)

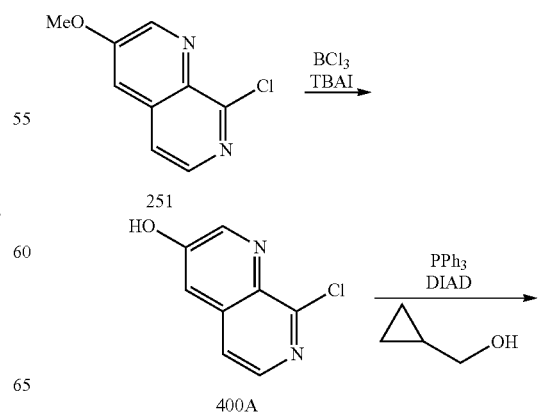

-continued

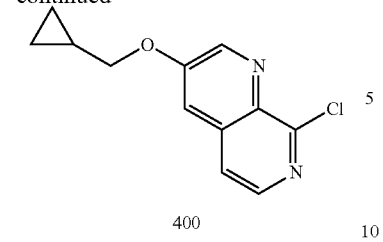

400

To a stirring solution of 8-chloro-3-methoxy-1,7-naphthyridine (251) (5.00 g, 25.7 mmol) and tetrabutylammonium iodide (12.3 g, 33.4 mmol) in DCM (86 mL) at RT under nitrogen was added a solution of boron trichloride (1.0 M in DCM, 128 mL, 128 mmol). The dark red solution was stirred at RT for 5 h and then cooled to 0° C. in an ice bath. The reaction was carefully quenched by dropwise addition of water until bubbling ceased with further addition of water. The ice bath was removed and the mixture was then stirred for 30 min. DCM (250 mL) and water (250 mL) were added and the mixture was carefully neutralized by portion wise addition of solid sodium bicarbonate. The layers were then separated and the aqueous layer was extracted with DCM (3×150 mL). The combined organic extracts were washed with brine (100 mL), dried over $Na_2SO_4$, filtered and concentrated in vacuo. The residue was purified by silica gel chromatography eluting with a gradient of 50-100% EtOAc/heptane to give 8-chloro-1,7-naphthyridin-3-ol as a yellow solid (400A, 3.5 g, 75%). LC/MS (ESI+) m/z=181.1 (M+H)+. $^1$H NMR (400 MHz, DMSO-$d_6$) δ 11.30 (s, 1H), 8.75 (d, J=2.74 Hz, 1H), 8.22 (d, J=5.48 Hz, 1H), 7.77 (d, J=5.67 Hz, 1H), 7.58 (d, J=2.74 Hz, 1H).

To a stirring suspension of 8-chloro-1,7-naphthyridin-3-ol (400A) (200 mg, 1.107 mmol) in THF (5 mL) under nitrogen, was added cyclopropanemethanol (0.27 mL, 3.32 mmol). The mixture was then cooled to 0° C. in an ice bath and triphenylphosphine (871 mg, 3.32 mmol) was added. The reaction mixture was stirred at 0° C. for 3 min then diisopropyl azodicarboxylate (0.65 mL, 3.32 mmol) was added dropwise by syringe over 2 min. The yellow solution was then stirred at RT for 10-120 min. The reaction was quenched with water (30 mL), and then diluted with EtOAc (25 mL). The layers were separated and the aqueous layer was extracted with EtOAc (20 mL). The combined organic extracts were washed with brine (20 mL), dried over $MgSO_4$, filtered through a fritted funnel and concentrated in vacuo. The residue was purified by silica gel chromatography eluting with a gradient of 0-80% EtOAc/heptane to give 8-chloro-3-(cyclopropylmethoxy)-1,7-naphthyridine (400), contaminated with DIAD byproduct as a white solid (280 mg, 108%). LC/MS (ESI+) m/z=235.1 (M+H)+. $^1$H NMR (400 MHz, chloroform-d) δ 8.85 (d, J=2.74 Hz, 1H), 8.28 (dd, J=5.67, 6.65 Hz, 1H), 7.50 (dd, J=2.35, 5.48 Hz, 1H), 7.28 (d, J=2.74 Hz, 1H), 3.99 (d, J=7.04 Hz, 2H), 1.32 (m, 1H), 0.71-0.79 (m, 2H), 0.45 (q, J=5.02 Hz, 2H).

8-Chloro-3-(2-methoxyethoxy)-1,7-naphthyridine (401)

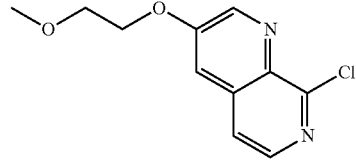

401

The title compound was synthesized according to the procedures similar to those described for intermediate 400, using 2-methoxyethanol to react with compound 400A. LC/MS (ESI+) m/z=239.1 (M+H)+. $^1$H NMR (400 MHz, chloroform-d) δ 8.88 (d, J=2.93 Hz, 1H), 8.30 (dd, J=5.67, 6.65 Hz, 1H), 7.52 (m, 1H), 7.36 (dd, J=2.93, 6.85 Hz, 1H), 4.27-4.35 (m, 2H), 3.82-3.90 (m, 2H), 3.50 (s, 3H).

5-(((8-Chloro-1,7-naphthyridin-3-yl)oxy)methyl)oxazole (402)

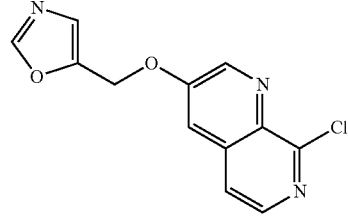

402

The title compound was synthesized according to the procedures similar to those described for intermediate 400, using 5-oxazolemethanol to react with compound 400A. LC/MS (ESI+) m/z=262.0 (M+H)+.

2-(((8-Chloro-1,7-naphthyridin-3-yl)oxy)methyl)oxazole (403)

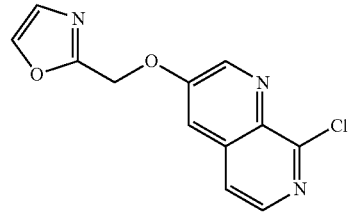

403

The title compound was synthesized according to the procedures similar to those described for intermediate 400, using 2-oxazolemethanol to react with compound 400A. LC/MS (ESI+) m/z=262.1 (M+H)+.

4-(((8-Chloro-1,7-naphthyridin-3-yl)oxy)methyl)oxazole (404)

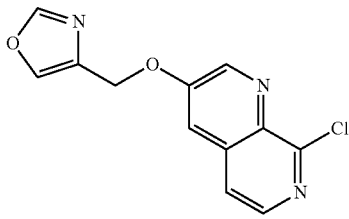

The title compound was synthesized according to intermediate 400, using oxazol-4-yl-methanol to react with compound 400A. The product precipitated from the reaction mixture and was collected by filtration, washed with THF and used without further purification. LC/MS (ESI$^+$) m/z=262.0 (M+H)$^+$. $^1$H NMR (400 MHz, DMSO-d$_6$) δ 8.87 (d, J=2.74 Hz, 1H), 8.46 (s, 1H), 8.30-8.38 (m, 2H), 8.07 (d, J=2.74 Hz, 1H), 7.85 (d, J=5.48 Hz, 1H), 5.29 (s, 2H).

5-Chloro-2-(((8-chloro-1,7-naphthyridin-3-yl)oxy)methyl)thiazole (405)

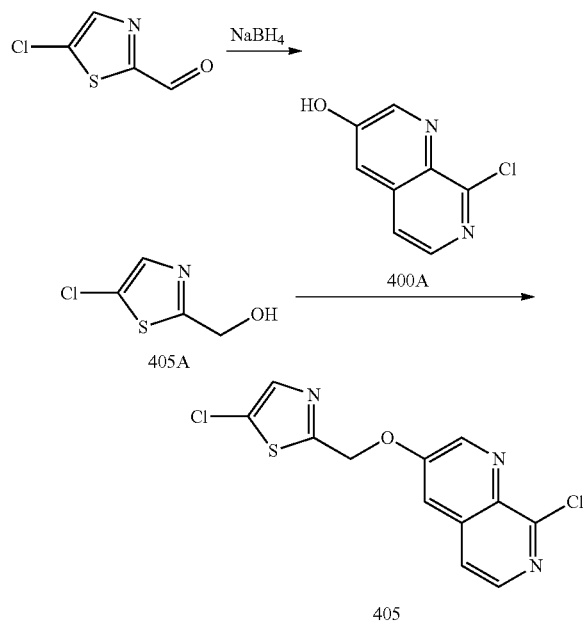

Sodium borohydride (0.128 g, 3.39 mmol) was added to a stirring solution of 5-chlorothiazole-2-carboxaldehyde (0.5 g, 3.39 mmol) in MeOH (6.78 mL) at RT. The mixture was stirred for 30 min at RT and then concentrated in vacuo. The residue was taken up in EtOAc (40 mL) and washed sequentially with water (30 mL) and brine (20 mL). The organic layer was then dried over Na$_2$SO$_4$, filtered and concentrated in vacuo to give (5-chlorothiazol-2-yl)methanol as a white solid that was used without further purification (405A, 511 mg, 101%). LC/MS (ESI$^+$) m/z=150.1 (M+H)$^+$. $^1$H NMR (400 MHz, chloroform-d) δ 7.54 (s, 1H), 4.88 (d, J=5.87 Hz, 2H), 2.57 (t, J=6.06 Hz, 1H).

The title compound was synthesized according to intermediate 400, using (5-chlorothiazol-2-yl)methanol (405A) to react with Compound 400A. LC/MS (ESI$^+$) m/z=311.0 (M+H)$^+$. $^1$H NMR (400 MHz, DMSO-d$_6$) δ 8.94 (d, J=2.93 Hz, 1H), 8.34 (d, J=5.67 Hz, 1H), 8.08 (d, J=2.74 Hz, 1H), 7.93 (s, 1H), 7.85 (d, J=5.67 Hz, 1H), 5.66 (s, 2H).

4-Bromo-2-(((8-chloro-1,7-naphthyridin-3-yl)oxy)methyl)thiazole (406)

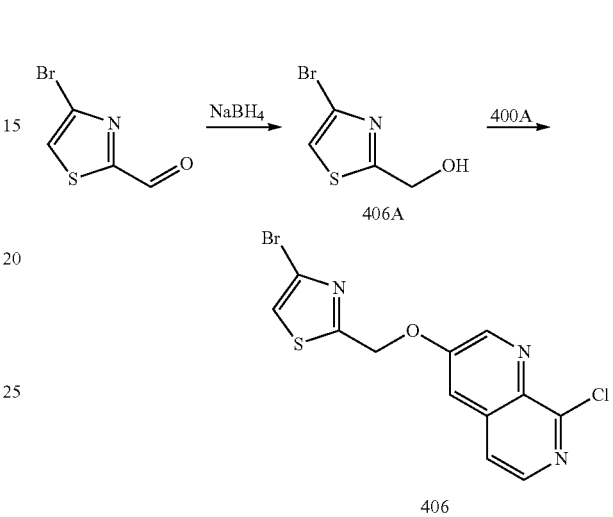

Sodium borohydride (99 mg, 2.60 mmol) was added to a stirring solution of 5-chlorothiazole-2-carboxaldehyde (500 mg, 2.60 mmol) in MeOH (5.2 mL) at RT. The mixture was stirred for 30 min at RT and then concentrated in vacuo. The residue was taken up in EtOAc (40 mL) and washed sequentially with water (30 mL) and brine (20 mL). The organic layer was then dried over Na$_2$SO$_4$, filtered and concentrated in vacuo to give (4-bromothiazol-2-yl)methanol as a brown oil that was used without further purification (406A, 499 mg, 99%). LC/MS (ESI$^+$) m/z=194.0 (M+H)$^+$. $^1$H NMR (400 MHz, chloroform-d) δ 7.23 (s, 1H), 4.97 (d, J=6.06 Hz, 2H), 2.51 (t, J=5.38 Hz, 1H).

The title compound was synthesized according to intermediate 400, using (4-bromothiazol-2-yl)methanol (406A) to react with Compound 400A. LC/MS (ESI$^+$) m/z=358.0 (M+H)$^+$. $^1$H NMR (400 MHz, DMSO-d$_6$) δ 8.96 (d, J=2.93 Hz, 1H), 8.35 (d, J=5.48 Hz, 1H), 8.09 (d, J=2.93 Hz, 1H), 7.97 (s, 1H), 7.86 (d, J=5.67 Hz, 1H), 5.71 (s, 2H).

2-(((8-Chloro-1,7-naphthyridin-3-yl)oxy)methyl)thiazole (407)

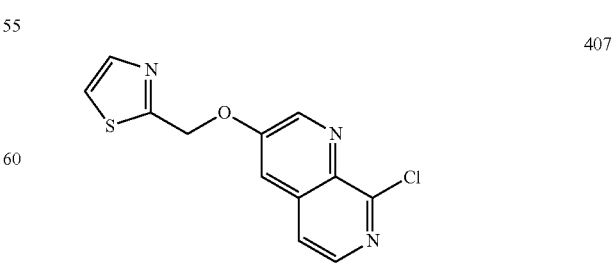

The title compound was synthesized according to intermediate 400, using 1,3-thiazol-2-ylmethanol to react with Compound 400A. LC/MS (ESI+) m/z=278.1 (M+H)+. $^1$H NMR (400 MHz, DMSO-$d_6$) δ 8.95 (d, J=2.93 Hz, 1H), 8.34 (d, J=5.48 Hz, 1H), 8.10 (d, J=2.93 Hz, 1H), 7.91 (d, J=3.13 Hz, 1H), 7.82-7.87 (m, 2H), 5.71 (s, 2H).

8-Chloro-3-((4,4,4-trideuterobut-2-yn-1-yl)oxy)-1,7-naphthyridine (408)

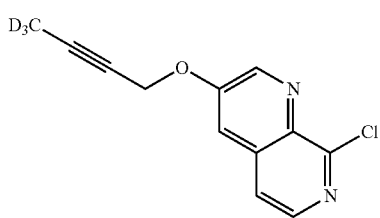

The title compound was synthesized according to intermediate 400, using 4,4,4-trideuterobut-2-yn-1-ol (prepared according to the procedures reported in: *J. Org. Chem.* 2014, 79, 3572) to react with Compound 400A. $^1$H NMR (400 MHz, chloroform-d) δ 8.86 (d, J=2.93 Hz, 1H), 8.32 (d, J=5.48 Hz, 1H), 7.56 (d, J=5.48 Hz, 1H), 7.48 (d, J=2.74 Hz, 1H), 4.86 (s, 2H).

2-((8-Chloro-1,7-naphthyridin-3-yl)oxy)acetonitrile (409) and 3-(((8-chloro-1,7-naphthyridin-3-yl)oxy)methyl)-1,2,4-oxadiazole (410)

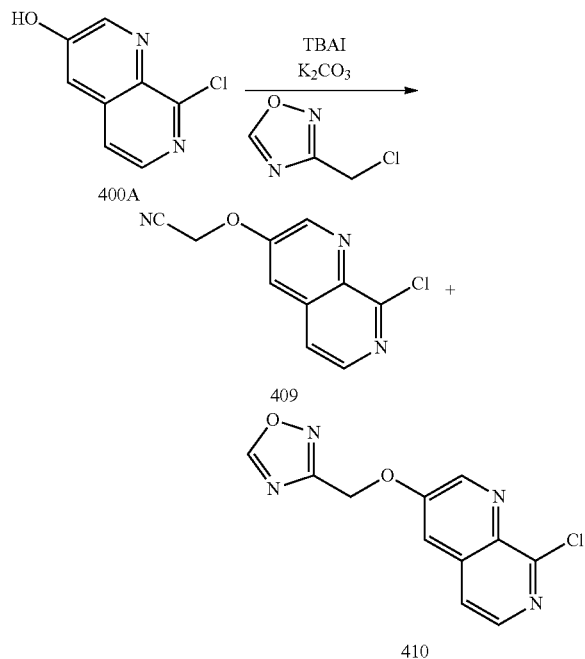

To a stirring solution of 3-(chloromethyl)-1,2,4-oxadiazole (361 mg, 3.05 mmol) in DMF (13.8 mL) was added 8-chloro-1,7-naphthyridin-3-ol (400A) (500 mg, 2.77 mmol), tetrabutylammonium iodide (102 mg, 0.27 mmol) and potassium carbonate (765 mg, 5.54 mmol). The suspension was heated at 70° C. for 45 min and then cooled to RT. The mixture was diluted with EtOAc (75 mL) and water (150 mL). The layers were separated and the aqueous layer was extracted with EtOAc (75 mL). The combined organic extracts were washed with brine (50 mL), dried over Na$_2$SO$_4$, filtered and concentrated in vacuo. The residue was purified by silica gel chromatography eluting with a gradient of 20-80% EtOAc/heptane to give two products: the 1$^{st}$ eluent, 2-((8-chloro-1,7-naphthyridin-3-yl)oxy)acetonitrile (409) as a white solid (325 mg, 53%). LC/MS (ESI+) m/z=220.1 (M+H)+. $^1$H NMR (400 MHz, chloroform-d) δ 8.89 (d, J=2.93 Hz, 1H), 8.40 (d, J=5.48 Hz, 1H), 7.61 (d, J=5.48 Hz, 1H), 7.52 (d, J=2.93 Hz, 1H), 5.00 (s, 2H). The 2$^{nd}$ eluent, 3-(((8-chloro-1,7-naphthyridin-3-yl)oxy)methyl)-1,2,4-oxadiazole (410) as a white solid (149 mg, 20%). LC/MS (ESI+) m/z=263.0 (M+H)+. $^1$H NMR (400 MHz, chloroform-d) δ 8.92 (d, J=2.93 Hz, 1H), 8.84 (s, 1H), 8.34 (d, J=5.67 Hz, 1H), 7.53-7.59 (m, 2H), 5.47 (s, 2H).

5-(((8-Chloro-1,7-naphthyridin-3-yl)oxy)methyl)-1,2,4-oxadiazole (411)

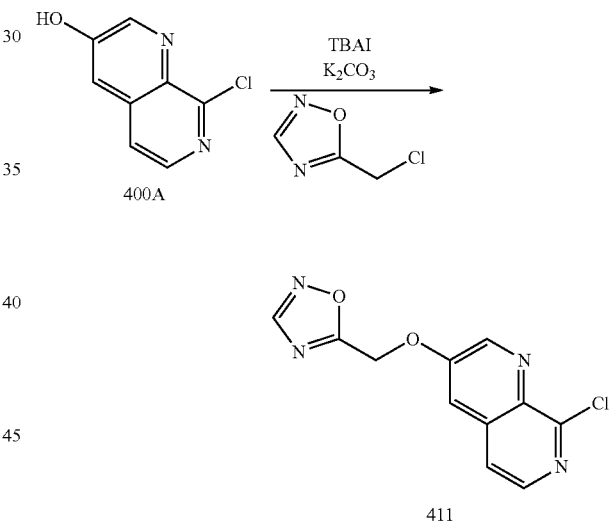

To a stirring solution of 5-(chloromethyl)-1,2,4-oxadiazole (361 mg, 3.05 mmol) in DMF (13.8 mL) was added 8-chloro-1,7-naphthyridin-3-ol (400A) (500 mg, 2.77 mmol), tetrabutylammonium iodide (205 mg, 0.554 mmol) and potassium carbonate (765 mg, 5.54 mmol). The suspension was heated at 70° C. for 4 h and then cooled to RT. The mixture was diluted with EtOAc (75 mL) and water (150 mL). The layers were separated and the aqueous layer was extracted with EtOAc (75 mL). The combined organic extracts were washed with brine (50 mL), dried over Na$_2$SO$_4$, filtered and concentrated in vacuo. The residue was purified by silica gel chromatography eluting with a gradient of 0-20% MeOH/DCM to give 5-(((8-chloro-1,7-naphthyridin-3-yl)oxy)methyl)-1,2,4-oxadiazole (411) as an oil (100 mg, 14%). LC/MS (ESI+) m/z=263.2 (M+H)+.

8-Chloro-3-(2,2,3,3-tetrafluoropropoxy)-1,7-naphthyridine (412)

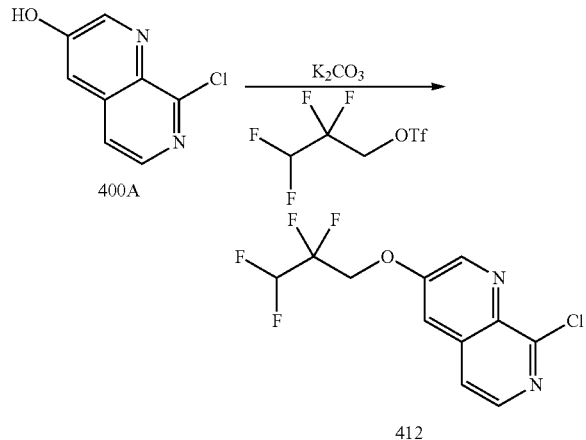

To a stirring suspension of 2,2,3,3-tetrafluoropropyl trifluoromethanesulfonate (377 mg, 1.43 mmol) and 8-chloro-1,7-naphthyridin-3-ol (400A) (258 mg, 1.43 mmol) in acetone (4.5 mL) was added potassium carbonate (592 mg, 4.29 mmol). The suspension was stirred at RT for 6 h, then diluted with MTBE (25 mL) and filtered to remove the solids. The filtrate was concentrated in vacuo and the residue was purified by silica gel chromatography eluting with a gradient of 10-70% EtOAc/heptane to give 8-chloro-3-(2,2,3,3-tetrafluoropropoxy)-1,7-naphthyridine (412) as an off-white solid (343 mg, 81%). LC/MS (ESI$^+$) m/z=295.1 (M+H)$^+$. $^1$H NMR (400 MHz, DMSO-d$_6$) δ 8.93 (d, J=2.93 Hz, 1H), 8.36 (d, J=5.48 Hz, 1H), 8.10 (d, J=2.93 Hz, 1H), 7.84 (d, J=5.67 Hz, 1H), 6.60-6.94 (m, 1H), 4.90 (t, J=13.50 Hz, 2H).

8-Chloro-3-((4,4,4-trifluorobut-2-yn-1-yl)oxy)-1,7-naphthyridine (413)

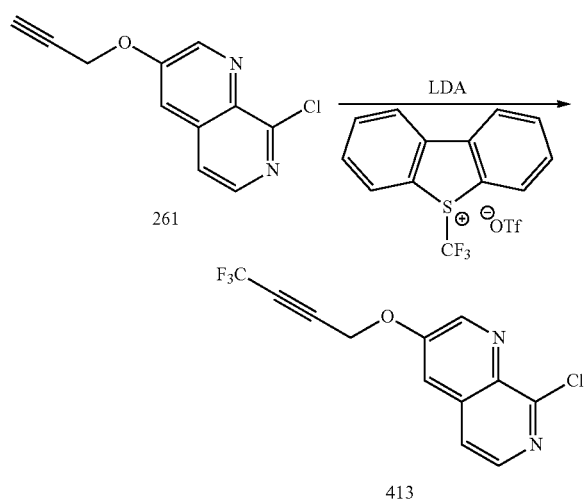

A solution of lithium diisopropylamide (2.0 M in THF/heptane/ethylbenzene) (0.73 mL, 1.47 mmol) was added dropwise to a stirring solution of 8-chloro-3-(prop-2-yn-1-yloxy)-1,7-naphthyridine (261) (292 mg, 1.33 mmol) in THF (13.4 mL) under nitrogen at −78° C. The solution was stirred at −78° C. for 5 min and then solid S-(trifluoromethyl)dibenzothiophenium triflate (913 mg, 2.27 mmol) was added in one portion. The cold bath was removed and the mixture was allowed to warm to RT. The reaction was quenched with saturated aqueous ammonium chloride solution (20 mL) and then diluted with water (30 mL) and EtOAc (50 mL). The layers were separated and the organic layer was dried over Na$_2$SO$_4$, filtered, and concentrated in vacuo. The residue was purified by silica gel chromatography eluting with a gradient of 10-35% EtOAc/heptane to give 8-chloro-3-((4,4,4-trifluorobut-2-yn-1-yl)oxy)-1,7-naphthyridine (413) as a white solid (88 mg, 23%). LC/MS (ESI$^+$) m/z=287.1 (M+H)$^+$. $^1$H NMR (400 MHz, chloroform-d) δ 8.88 (d, J=2.93 Hz, 1H), 8.37 (d, J=5.48 Hz, 1H), 7.59 (d, J=5.48 Hz, 1H), 7.44 (d, J=2.93 Hz, 1H), 5.02 (q, J=2.80 Hz, 2H). $^{19}$F NMR (376 MHz, chloroform-d) δ −51.2.

3-(But-2-yn-1-yloxy)-8-chloro-1,7-naphthyridine (414)

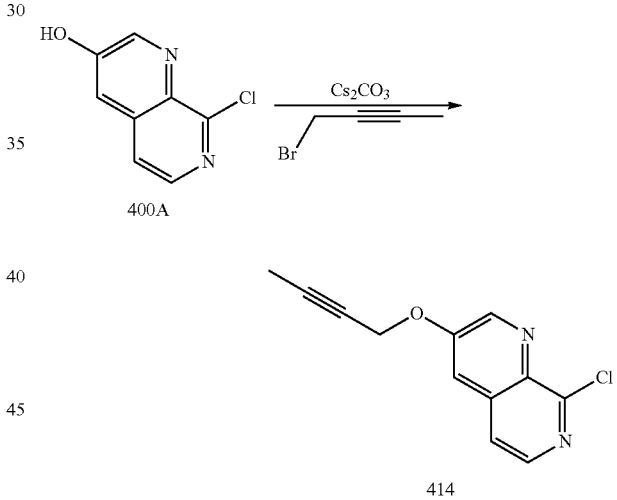

A suspension of 8-chloro-1,7-naphthyridin-3-ol (0.50 g, 2.77 mmol) with cesium carbonate (4.51 g, 13.84 mmol) and 1-bromo-2-butyne (0.73 g, 5.54 mmol) was stirred at RT for 15 min then placed in a 40° C. sand bath for 18 h. The reaction mixture was partitioned between EtOAc (25 mL) and 0.5 M K$_2$HPO$_4$ (50 mL). The organic layer was further washed with 0.5 M K$_2$HPO$_4$ (50 mL) and brine (20 mL). The organic layer was dried over MgSO$_4$, concentrated under reduced pressure, then purified by silica gel chromatography (40 g) eluting products with a gradient of 10-25% EtOAc/heptane to afford 3-(but-2-yn-1-yloxy)-8-chloro-1,7-naphthyridine (414) (370 mg) as a white solid: m/z (APCI, pos. ion) 233.0. This material contained a small amount of 8-bromo-3-(but-2-yn-1-yloxy)-1,7-naphthyridine: m/z (APCI, pos. ion) 277.

4-(((5-Chloropyrido[3,4-b]pyrazin-2-yl)oxy)methyl)oxazole (415)

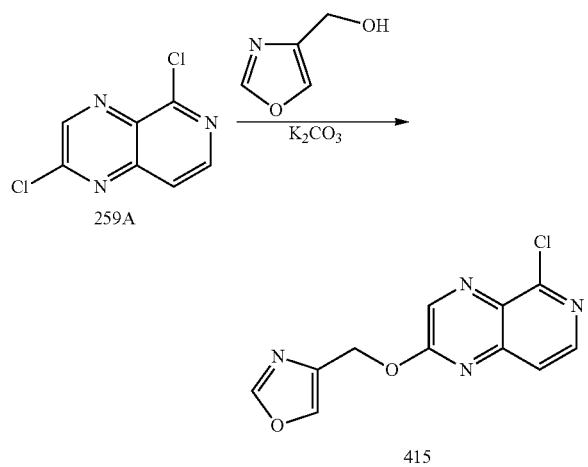

A mixture of 2,5-dichloropyrido[3,4-b]pyrazine (1.07 g, 5.35 mmol), oxazol-4-yl-methanol (0.42 mL, 5.35 mmol), and potassium carbonate (1.48 g, 10.70 mmol) in DMF (18 mL) was heated at 50° C. for 5 h. The reaction mixture was diluted with water and extracted with EtOAc. The organic extract was washed with brine, dried over $Na_2SO_4$, filtered and concentrated in vacuo. The crude product (1.2 g) was adsorbed onto a plug of silica gel and chromatographed through a Biotage SNAP Ultra silica gel column (50 g), eluting with isocratic 18% EtOH/EtOAc (25:75) in hexanes, to the title compound (0.74 g, 2.82 mmol, 53% yield). $^1$H NMR (300 MHz, DMSO-$d_6$) δ ppm 5.51 (s, 2H) 7.84 (d, J=5.70 Hz, 1H) 8.34 (d, J=0.73 Hz, 1H) 8.45 (s, 1H) 8.54 (d, J=5.70 Hz, 1H) 8.80 (s, 1H). LC/MS (ESI) m/z=263.0 [M+H]$^+$.

4-(((5-Chloropyrido[3,4-b]pyrazin-2-yl)oxy)methyl)-2-methyloxazole (416)

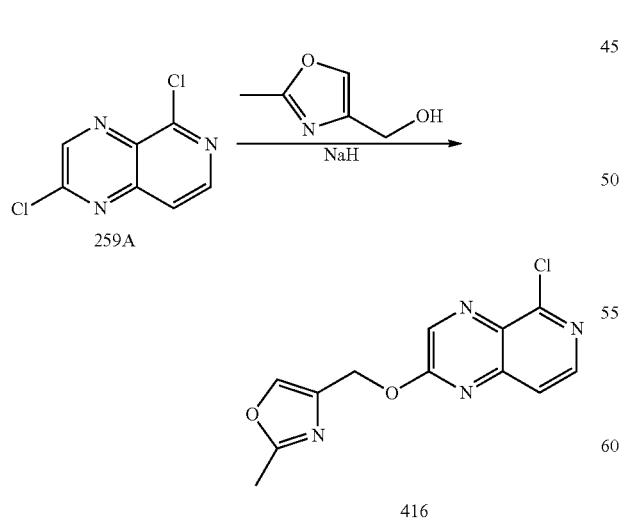

The title compound (0.94 g, 3.81 mmol, 73% yield) as a tan solid was prepared according to the procedures described for intermediate 259 using 2,5-dichloropyrido[3,4-b]pyrazine (259A, 0.99 g, 4.98 mmol) and (2-methyloxazol-4-yl)methanol (0.56 g, 4.98 mmol). $^1$H NMR (300 MHz, CHLOROFORM-d) δ ppm 2.50 (s, 3H) 5.48 (s, 2H) 7.66 (d, J=5.70 Hz, 1H) 7.70 (s, 1H) 8.50 (d, J=5.70 Hz, 1H) 8.64 (s, 1H). LC/MS (ESI$^+$) m/z=277.0 (M+H)$^+$.

4-(((5-chloropyrido[3,4-b]pyrazin-2-yl)oxy)methyl)-5-methyloxazole (417)

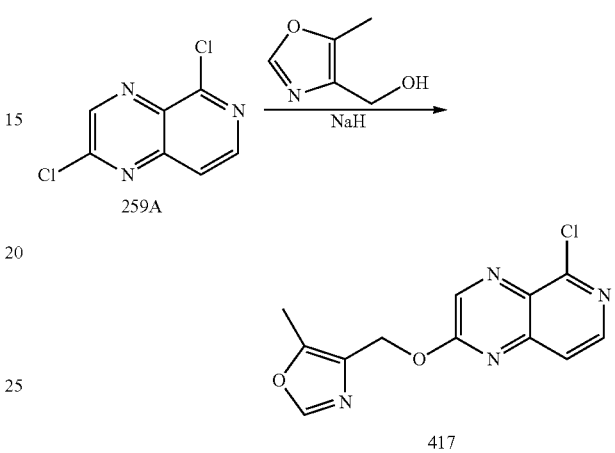

The title compound (0.16 g, 0.58 mmol, 22% yield) as an off-white solid was prepared according to the procedures described for intermediate 259 using 2,5-dichloropyrido[3,4-b]pyrazine (259A, 0.51 g, 2.56 mmol) and (5-methyloxazol-4-yl)methanol (0.29 g, 2.56 mmol). $^1$H NMR (400 MHz, DMSO-$d_6$) δ ppm 2.47 (s, 3H) 5.45 (s, 2H) 7.81 (d, J=5.67 Hz, 1H) 8.26 (s, 1H) 8.53 (d, J=5.67 Hz, 1H) 8.79 (s, 1H). LC/MS (ESI$^+$) m/z=277.1 (M+H)$^+$.

2-(But-2-yn-1-yloxy)-5-chloropyrido[3,4-b]pyrazine (418)

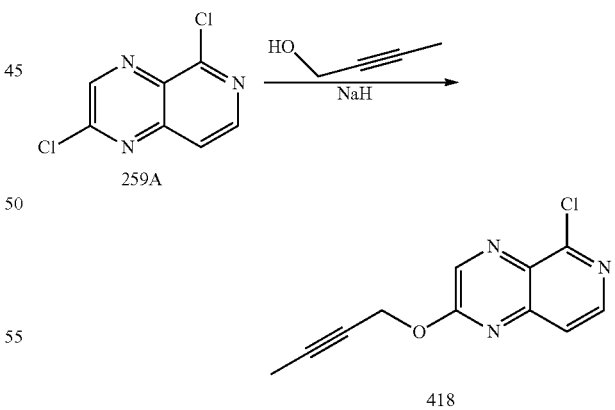

The title compound (0.59 g, 2.56 mmol, 50% yield) as a light brown solid was prepared according to the procedures described for intermediate 259 using 2,5-dichloropyrido[3,4-b]pyrazine (259A, 1.02 g, 5.11 mmol) and 3-pentyn-2-ol (0.48 mL, 5.11 mmol). $^1$H NMR (300 MHz, DMSO-$d_6$) δ ppm 1.88 (t, J=2.34 Hz, 3H) 5.19 (q, J=2.34 Hz, 2H) 7.81 (d, J=5.70 Hz, 1H) 8.53 (d, J=5.55 Hz, 1H) 8.82 (s, 1H). LC/MS (ESI$^+$) m/z=234.2 (M+H)$^+$.

249

5-Chloro-2-(pent-3-yn-2-yloxy)pyrido[3,4-b]pyrazine (419)

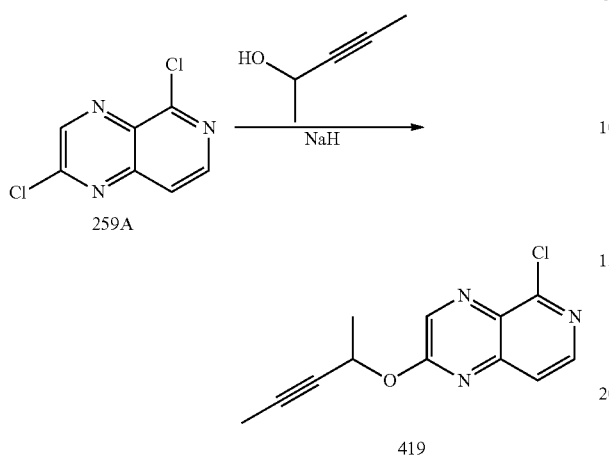

The title compound (0.64 g, 2.61 mmol, 51% yield) as a solid was prepared according to the procedures described for intermediate 259 using 2,5-dichloropyrido[3,4-b]pyrazine (259A, 1.03 g, 5.15 mmol) and 2-butyn-1-ol (0.38 mL, 5.15 mmol). $^1$H NMR (400 MHz, CHLOROFORM-d) δ ppm 1.70 (d, J=6.65 Hz, 3H) 1.86 (d, J=2.15 Hz, 3H) 5.98 (m, 1H) 7.67 (d, J=5.67 Hz, 1H) 8.49 (d, J=5.67 Hz, 1H) 8.60 (s, 1H). LC/MS (ESI$^+$) m/z=247.9 (M+H)$^+$.

5-Chloro-2-isopropoxypyrido[3,4-b]pyrazine (420)

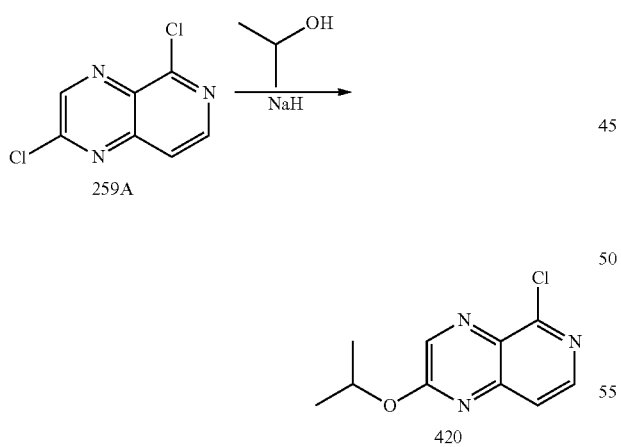

The title compound (0.56 g, 2.53 mmol, 100% yield) as a tan solid was prepared according to the procedures described for intermediate 259 using 2,5-dichloropyrido[3,4-b]pyrazine (259A, 0.50 g, 2.53 mmol) and isopropanol (0.19 mL, 2.53 mmol). $^1$H NMR (300 MHz, CHLOROFORM-d) δ ppm 1.47 (d, J=6.14 Hz, 6H) 5.56 (dt, J=12.39, 6.16 Hz, 1H) 7.61 (d, J=5.70 Hz, 1H) 8.46 (d, J=5.70 Hz, 1H) 8.53 (s, 1H). LC/MS (ESI$^+$) m/z=224.0 (M+H)$^+$.

250

5-Chloro-2-(3-fluoropropoxy)pyrido[3,4-b]pyrazine (421)

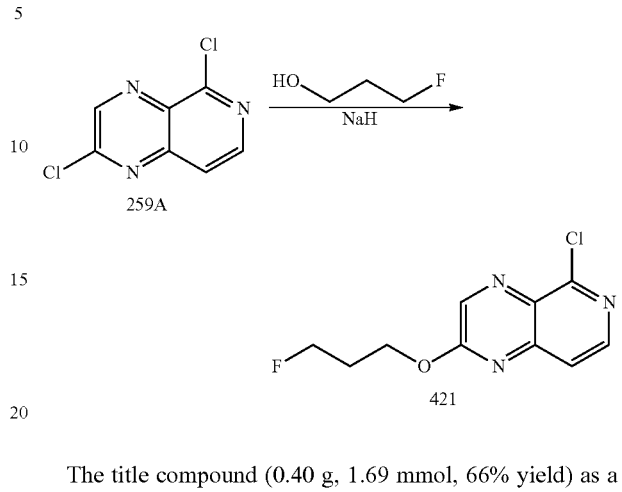

The title compound (0.40 g, 1.69 mmol, 66% yield) as a white solid was prepared according to the procedures described for intermediate 259 using 2,5-dichloropyrido[3,4-b]pyrazine (259A, 0.51 g, 2.54 mmol) and 3-fluoropropan-1-ol (0.19 mL, 2.54 mmol). 1H NMR (300 MHz, CHLOROFORM-d) δ ppm 2.18-2.41 (m, 2H) 4.56-4.83 (m, 4H) 7.64 (d, J=5.70 Hz, 1H) 8.49 (d, J=5.70 Hz, 1H) 8.61 (s, 1H). LC/MS (ESI$^+$) m/z=242.0 (M+H)$^+$.

5-Chloro-2-(2,2,3,3-tetrafluoropropoxy)pyrido[3,4-b]pyrazine (422)

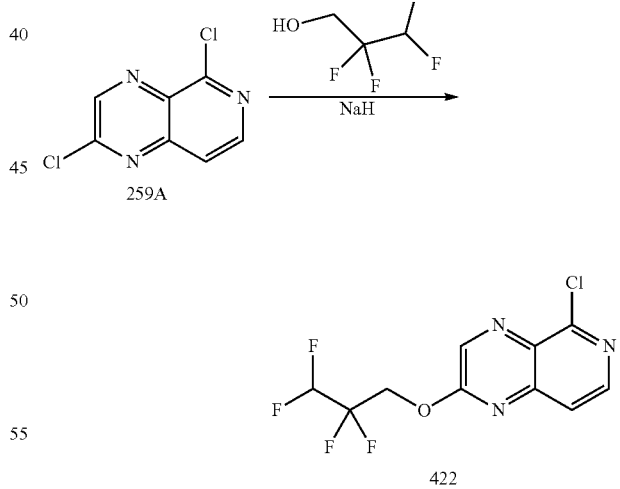

The title compound (0.63 g, 2.2 mmol, 85% yield) as a white solid was prepared according to the procedures described for intermediate 259 using 2,5-dichloropyrido[3,4-b]pyrazine (259A, 0.50 g, 2.53 mmol) and 1H,1H,3H-tetrafluoro-1-propanol (0.20 mL, 2.53 mmol). $^1$H NMR (300 MHz, DMSO-d$_6$) δ ppm 5.11 (t, J=14.10 Hz, 2H) 6.52-6.99 (m, 1H) 7.83 (d, J=5.70 Hz, 1H) 8.57 (d, J=5.70 Hz, 1H) 8.92 (s, 1H). LC/MS (ESI$^+$) m/z=295.9 (M+H)$^+$.

5-Chloro-2-(2,2-difluoropropoxy)pyrido[3,4-b]pyrazine (423)

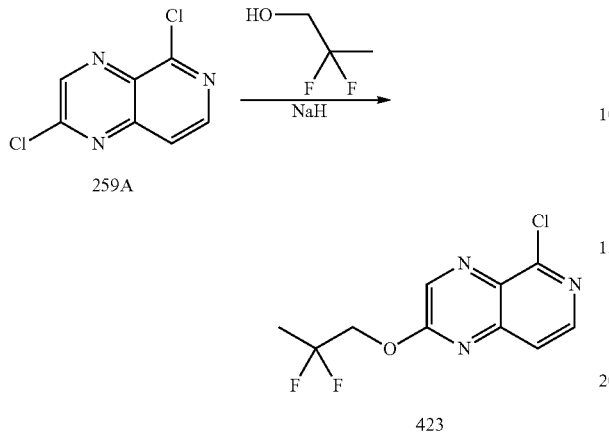

The title compound (0.34 g, 1.33 mmol, 52% yield) as a white solid was prepared according to the procedures described for intermediate 259 using 2,5-dichloropyrido[3,4-b]pyrazine (259A, 0.51 g, 2.56 mmol) and 2,2-difluoropropan-1-ol (0.20 mL, 2.56 mmol). $^1$H NMR (300 MHz, CHLOROFORM-d) δ ppm 1.83 (t, J=18.64 Hz, 3H) 4.72 (t, J=11.84 Hz, 2H) 7.65 (d, J=5.70 Hz, 1H) 8.52 (d, J=5.55 Hz, 1H) 8.71 (s, 1H). LC/MS (ESI$^+$) m/z=260.0 (M+H)$^+$.

4-(((5-Chloropyrido[3,4-b]pyrazin-2-yl)oxy)methyl)thiazole (424)

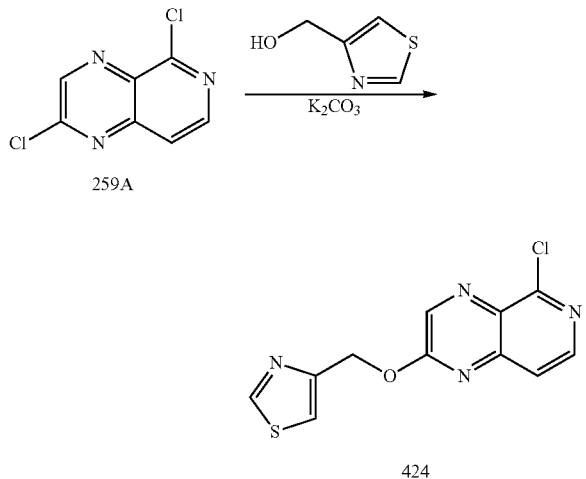

The title compound (0.22 g, 0.78 mmol, 39% yield) as a tan solid was prepared according to the procedures described for intermediate 415 using 2,5-dichloropyrido[3,4-b]pyrazine (259A, 0.40 g, 2.00 mmol) and thiazole-4-methanol (0.23 g, 2.00 mmol). $^1$H NMR (300 MHz, CHLOROFORM-d) δ ppm 5.78 (s, 2H) 7.55 (d, J=2.05 Hz, 1H) 7.68 (d, J=5.70 Hz, 1H) 8.51 (d, J=5.70 Hz, 1H) 8.68 (s, 1H) 8.91 (d, J=2.05 Hz, 1H). LC/MS (ESI$^+$) m/z=278.9 (M+H)$^+$.

(S)-2-(1-((5-Chloropyrido[3,4-b]pyrazin-2-yl)oxy)ethyl)oxazole (425A) and (R)-2-(1-((5-chloropyrido[3,4-b]pyrazin-2-yl)oxy)ethyl)oxazole (425B)

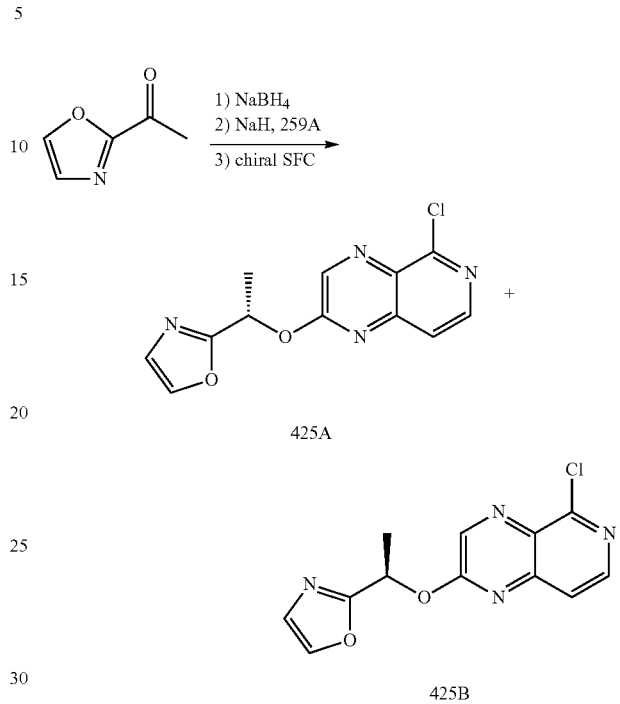

At 0° C., a solution of 1-(oxazol-2-yl)ethanone (1.0 g, 9.00 mmol, J&W Pharmlab) in MeOH (40 mL) was treated with sodium borohydride (0.39 g, 10.31 mmol) in 2 portions. After 15 min the reaction was allowed to warm to RT for 2 h. The reaction was quenched with water (5 mL). The mixture was partitioned between brine/DCM and the aqueous layer was extracted with DCM (2x). The combined organic layers were washed brine, dried over Na$_2$SO$_4$ and concentrated under reduced pressure to give 920 mg (90%) of a light-yellow oil. $^1$H NMR (300 MHz, CDCl$_3$) δ ppm 7.62 (d, J=0.88 Hz, 1H), 7.07 (s, 1H), 4.97 (q, J=6.58 Hz, 1H), 1.62 (d, J=6.72 Hz, 3H). LC/MS (ESI$^+$) m/z=114.1 (M+H)$^+$.

2-(1-((5-Chloropyrido[3,4-b]pyrazin-2-yl)oxy)ethyl)oxazole (6.00 g, 21.7 mmol, 88% yield) as a solid was prepared according to the procedures described for intermediate 259 using 2,5-dichloropyrido[3,4-b]pyrazine (259A, 4.91 g, 24.57 mmol) and 1-(oxazol-2-yl)ethanol (2.7794 g, 24.57 mmol). $^1$H NMR (300 MHz, CHLOROFORM-d) δ ppm 1.90 (d, J=6.72 Hz, 3H) 6.58 (q, J=6.72 Hz, 1H) 7.14 (s, 1H) 7.63 (d, J=5.70 Hz, 1H) 7.67 (d, J=0.73 Hz, 1H) 8.49 (d, J=5.55 Hz, 1H) 8.67 (s, 1H). LC/MS (ESI$^+$) m/z=277.1 (M+H)$^+$. The racemic mixture was chromatographed using supercritical CO$_2$ (Organic modifier, 40% MeOH) on a Chiracel AZ-H column (150×21 mm, 5 µm) eluting at a flow rate of 60 mL/min (220 bar pressure, 40° C. column temperature). The stereochemistry was arbitrarily assigned. (S)-2-(1-((5-Chloropyrido[3,4-b]pyrazin-2-yl)oxy)ethyl)oxazole (425A, the first eluent, 2.97 g) and (R)-2-(1-((5-chloropyrido[3,4-b]pyrazin-2-yl)oxy)ethyl)oxazole (425B, the second eluent, 3.02 g) were obtained.

5-Chloro-2-((4-methylpyrimidin-2-yl)methoxy)pyrido[3,4-b]pyrazine (426)

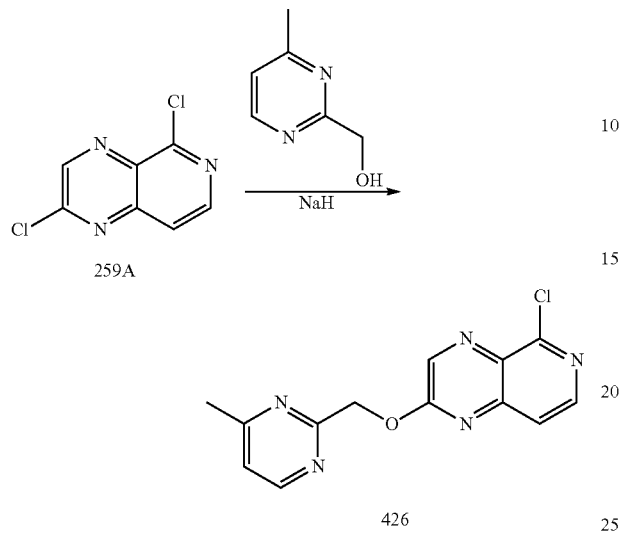

The title compound (0.45 g, 1.58 mmol, 56% yield) as a light yellow solid was prepared according to the procedures described for intermediate 259 using 2,5-dichloropyrido[3,4-b]pyrazine (259A, 0.56 g, 2.79 mmol) and 2-hydroxymethyl-4-methylpyrimidine (0.28 mL, 2.79 mmol). $^1$H NMR (400 MHz, DMSO-$d_6$) δ ppm 2.46 (s, 3H) 5.73 (s, 2H) 7.33 (d, J=5.28 Hz, 1H) 7.69 (d, J=5.67 Hz, 1H) 8.48 (d, J=5.67 Hz, 1H) 8.62 (d, J=5.09 Hz, 1H) 8.94 (s, 1H). LC/MS (ESI$^+$) m/z=287.9 (M+H)$^+$.

5-Chloro-2-((3-fluoropyridin-2-yl)methoxy)pyrido[3,4-b]pyrazine (427)

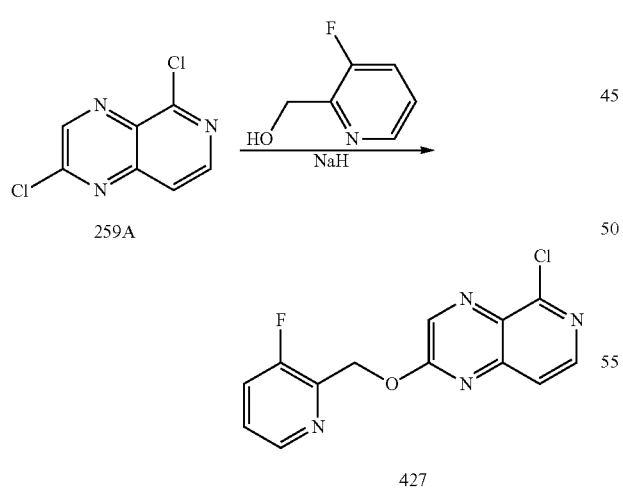

The title compound (0.74 g, 2.56 mmol, 101% yield) as a light yellow solid was prepared according to the procedures described for intermediate 259 using 2,5-dichloropyrido[3,4-b]pyrazine (259A, 0.51 g, 2.54 mmol) and (3-fluoropyridin-2-yl)methanol (0.25 mL, 2.54 mmol). $^1$H NMR (300 MHz, DMSO-$d_6$) δ ppm 5.74 (d, J=1.90 Hz, 2H) 7.55 (dt, J=8.59, 4.40 Hz, 1H) 7.74-7.90 (m, 2H) 8.46 (dt, J=4.60, 1.42 Hz, 1H) 8.52 (d, J=5.70 Hz, 1H) 8.86 (s, 1H). LC/MS (ESI$^+$) m/z=290.9 (M+H)$^+$.

4-(((5-chloropyrido[3,4-b]pyrazin-2-yl)oxy)methyl)-2-methylthiazole (428)

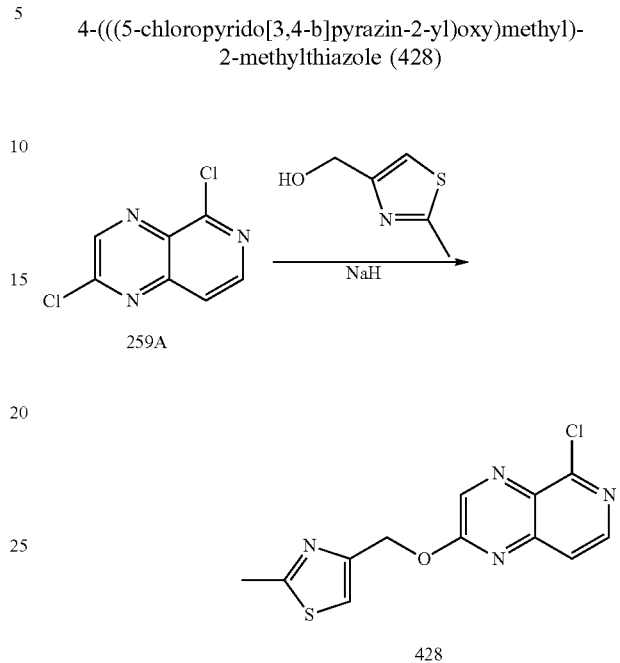

The title compound (0.72 g, 2.48 mmol, 100% yield) as a tan solid was prepared according to the procedures described for intermediate 259 using 2,5-dichloropyrido[3,4-b]pyrazine (259A, 0.50 g, 2.49 mmol) and (2-methyl-1,3-thiazol-4-yl)methanol (0.32 g, 2.49 mmol). $^1$H NMR (300 MHz, DMSO-$d_6$) δ ppm 5.59 (s, 2H) 7.71 (s, 1H) 7.83 (d, J=5.70 Hz, 1H) 8.53 (d, J=5.70 Hz, 1H). LC/MS (ESI$^+$) m/z=293.0 (M+H)$^+$.

5-Chloro-2-(pyrimidin-2-ylmethoxy)pyrido[3,4-b]pyrazine (429)

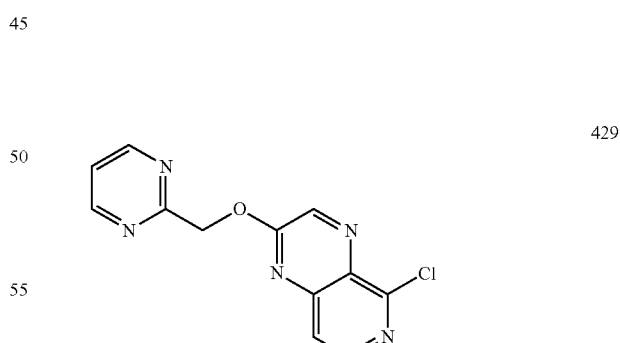

The title compound (1.11 g, 4.06 mmol, 77% yield) as a tan crystalline solid was prepared according to the procedure described for intermediate 259 using 2,5-dichloropyrido[3,4-b]pyrazine (259A, 1.06 g, 5.30 mmol) and pyrimidin-2-ylmethanol (0.59 g, 5.35 mmol, Synthonix). $^1$H NMR (400 MHz, CDCl$_3$) δ ppm 8.81 (s, 1H), 8.76 (d, J=4.89 Hz, 2H), 8.45 (d, J=5.67 Hz, 1H), 7.56 (d, J=5.67 Hz, 1H), 7.27-7.31 (m, 1H), 5.82 (s, 2H). LC/MS (ESI$^+$) m/z=274.1 (M+H)$^+$.

(S)-2-(But-3-yn-2-yloxy)-5-chloropyrido[3,4-b]pyrazine (430)

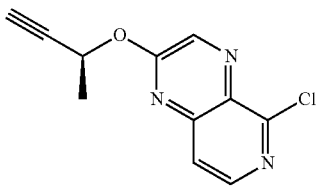

430

The title compound (0.87 g, 3.72 mmol, 62% yield) as a tan crystalline solid was prepared according to the procedure described for intermediate 259 using 2,5-dichloropyrido[3,4-b]pyrazine (259A, 1.2 g, 6.0 mmol) and (S)-(−)-3-butyn-2-ol (0.50 mL, 0.443 g, 6.31 mmol, Sigma-Aldrich). $^1$H NMR (300 MHz, CDCl$_3$) δ ppm 8.61 (s, 1H), 8.49 (d, J=5.70 Hz, 1H), 7.66 (d, J=5.70 Hz, 1H), 5.98 (qd, J=6.67, 2.05 Hz, 1H), 2.51 (d, J=2.05 Hz, 1H), 1.75 (d, J=6.72 Hz, 3H). LC/MS (ESI$^+$) m/z=234.1 (M+H)$^+$.

5-(((5-Chloropyrido[3,4-b]pyrazin-2-yl)oxy)methyl)-3-methyl-1,2,4-oxadiazole (431)

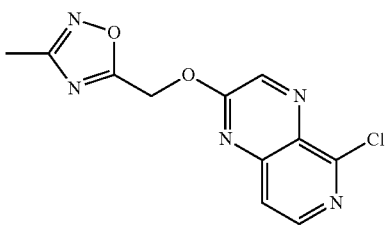

431

The title compound (0.95 g, 3.41 mmol, 68% yield) as a tan amorphous solid was prepared according to the procedure described for intermediate 259 using 2,5-dichloropyrido[3,4-b]pyrazine (259A, 1.0 g, 5.0 mmol) and (3-methyl-1,2,4-oxadiazol-5-yl)methanol (0.618 g, 5.42 mmol, Enamine). $^1$H NMR (300 MHz, CDCl$_3$) δ ppm 8.77 (s, 1H) 8.52 (d, J=5.55 Hz, 1H) 7.64 (d, J=5.70 Hz, 1H) 5.78 (s, 2H) 2.44 (s, 3H). LC/MS (ESI$^+$) m/z=278.0 (M+H)$^+$.

4-(((5-Chloropyrido[3,4-b]pyrazin-2-yl)oxy)methyl)-2,5-dimethyloxazole (432)

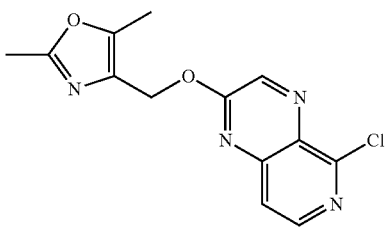

432

The title compound (0.631 g, 2.17 mmol, 83% yield) as a white crystalline solid was prepared according to the procedure described for intermediate 259 using 2,5-dichloropyrido[3,4-b]pyrazine (259A, 0.520 g, 2.60 mmol) and (2,5-dimethyloxazol-4-yl)methanol (0.380 g, 2.99 mmol, Frontier Scientific). $^1$H NMR (300 MHz, CDCl$_3$) δ ppm 8.63 (s, 1H), 8.49 (d, J=5.70 Hz, 1H), 7.64 (d, J=5.70 Hz, 1H), 5.41 (s, 2H), 2.44 (s, 3H), 2.43 (s, 3H). LC/MS (ESI$^+$) m/z=291.0 (M+H)$^+$.

2-(((5-Chloropyrido[3,4-b]pyrazin-2-yl)oxy)methyl)-5-methyloxazole (433)

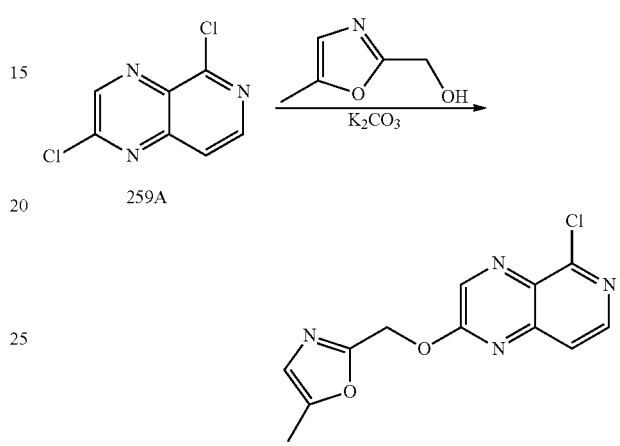

The title compound (0.87 g, 3.17 mmol, 80% yield) as a tan solid was prepared according to the procedures described for intermediate 415 using 2,5-dichloropyrido[3,4-b]pyrazine (259A, 0.79 g, 3.96 mmol) and (5-methyloxazol-2-yl)methanol (0.36 mL, 3.96 mmol). $^1$H NMR (300 MHz, CHLOROFORM-d) δ ppm 2.37 (d, J=1.02 Hz, 4H) 5.61 (s, 2H) 6.81 (d, J=1.17 Hz, 1H) 7.68 (d, J=5.70 Hz, 1H) 8.52 (d, J=5.70 Hz, 1H) 8.69 (s, 1H) LC/MS (ESI$^+$) m/z=2778.0 (M+H)$^+$.

3-(((5-Chloropyrido[3,4-b]pyrazin-2-yl)oxy)methyl)-5-methyl-1,2,4-oxadiazole (434)

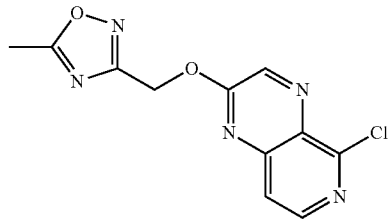

434

The title compound (1.349 g, 4.86 mmol, 88% yield) as a white crystalline solid was prepared according to the procedure described for intermediate 259 using 2,5-dichloropyrido[3,4-b]pyrazine (259A, 1.10, 5.50 mmol) and (5-methyl-1,2,4-oxadiazol-3-yl-methanol (0.656 g, 5.75 mmol, Enamine). $^1$H NMR (300 MHz, CDCl$_3$) δ ppm 8.72 (s, 1H), 8.51 (d, J=5.70 Hz, 1H), 7.66 (d, J=5.70 Hz, 1H), 5.69 (s, 2H), 2.65 (s, 3H). LC/MS (ESI$^+$) m/z=278.1 (M+H)$^+$.

1-(2-((5-Chloropyrido[3,4-b]pyrazin-2-yl)oxy)ethyl)pyrrolidin-2-one (435)

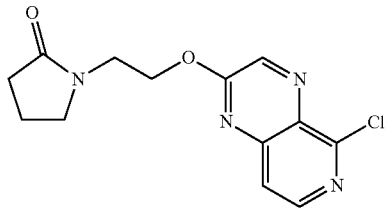

435

The title compound (0.822 g, 2.81 mmol, 75% yield) as a light-yellow crystalline solid was prepared according to the procedure described for intermediate 259 using 2,5-dichloropyrido[3,4-b]pyrazine (259A, 0.750 g, 3.75 mmol) and 1-(2-hydroxyethyl)-2-pyrrolidinone (0.450 mL, 3.98 mmol, Sigma-Aldrich). $^1$H NMR (300 MHz, CDCl$_3$) δ ppm 8.59 (s, 1H), 8.49 (d, J=5.55 Hz, 1H), 7.62 (d, J=5.70 Hz, 1H), 4.69 (t, J=5.41 Hz, 2H), 3.79 (t, J=5.41 Hz, 2H), 3.57 (t, J=7.02 Hz, 2H), 2.34-2.47 (m, 2H), 1.98-2.17 (m, 2H). LC/MS (ESI$^+$) m/z=293.0 (M+H)$^+$.

2-(((5-Chloropyrido[3,4-b]pyrazin-2-yl)oxy)methyl)-5-methyl-1,3,4-oxadiazole (436)

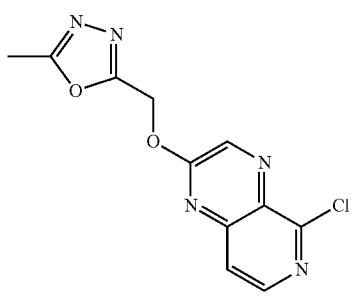

436

The title compound (0.860 g, 3.10 mmol, 68% yield) as a white crystalline solid was prepared according to the procedure described for intermediate 259 using 2,5-dichloropyrido[3,4-b]pyrazine (259A, 0.910 g, 4.55 mmol) and (5-methyl-1,3,4-oxadiazol-2-yl)methanol (0.597 g, 5.23 mmol, ChemBridge). $^1$H NMR (300 MHz, CDCl$_3$) δ ppm 8.71 (s, 1H) 8.54 (d, J=5.70 Hz, 1H) 7.69 (d, J=5.70 Hz, 1H) 5.77 (s, 2H) 2.60 (s, 3H) LC/MS (ESI$^+$) m/z=278.1 (M+H)$^+$.

2-((5-Chloropyrido[3,4-b]pyrazin-2-yl)oxy)-N,N-dimethylacetamide (437)

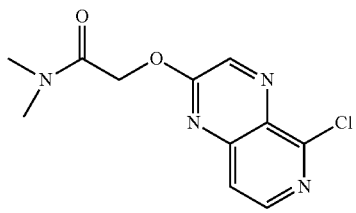

437

The title compound (0.555 g, 2.08 mmol, 59% yield) as a light-orange crystalline solid was prepared according to the procedure described for intermediate 259 using 2,5-dichloropyrido[3,4-b]pyrazine (259A, 0.706 g, 3.53 mmol) and 2-hydroxy-N,N-dimethylacetamide (0.372 g, 3.61 mmol, Enamine). LC/MS (ESI$^+$) m/z=267.0 (M+H)$^+$.

2-(((5-Chloropyrido[3,4-b]pyrazin-2-yl)oxy)methyl)-5-methyl-1,3,4-thiadiazole (438)

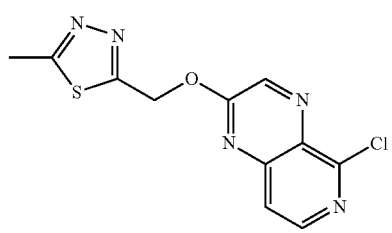

438

The title compound (0.191 g, 0.650 mmol, 34% yield) as a tan crystalline solid was prepared according to the procedure described for intermediate 259 using 2,5-dichloropyrido[3,4-b]pyrazine (259A, 0.380 g, 1.90 mmol) and (5-methyl-1,3,4-thiadiazol-2-yl)methanol (0.261 g, 2.00 mmol, Enamine). $^1$H NMR (300 MHz, CDCl$_3$) δ ppm 8.68 (s, 1H) 8.54 (d, J=5.70 Hz, 1H) 7.70 (d, J=5.70 Hz, 1H) 5.96 (s, 2H) 2.81 (s, 3H). LC/MS (ESI$^+$) m/z=294.2 (M+H)$^+$.

(S)-5-Chloro-2-((1-methoxypropan-2-yl)oxy)pyrido[3,4-b]pyrazine (439)

439

The title compound (0.794 g, 3.13 mmol, 84% yield) as a light-yellow crystalline solid was prepared according to the procedure described for intermediate 259 using 2,5-dichloropyrido[3,4-b]pyrazine (259A, 0.750 g, 3.75 mmol) and (S)-(+)-1-methoxy-2-propanol (0.380 mL, 3.88 mmol, Fluka). $^1$H NMR (300 MHz, CDCl$_3$) δ ppm 8.59 (s, 1H), 8.46 (d, J=5.70 Hz, 1H), 7.60 (d, J=5.55 Hz, 1H), 5.56-5.78 (m, 1H), 3.68 (dd, J=10.67, 5.99 Hz, 1H), 3.62 (dd, J=10.67, 3.80 Hz, 1H), 3.42 (s, 3H), 1.45 (d, J=6.43 Hz, 3H). LC/MS (ESI$^+$) m/z=254.0 (M+H)$^+$.

5-Chloro-2-(2-methoxyethoxy)pyrido[3,4-b]pyrazine (440)

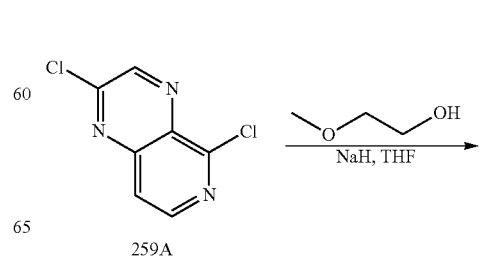

259A

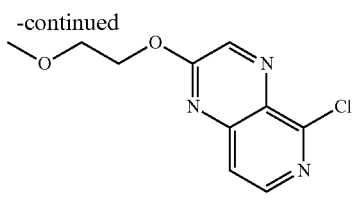

440

To a solution of 2-methoxyethanol (0.09 mL, 1.10 mmol) in THF (1 mL) under nitrogen was added to a slurry of sodium hydride (60% dispersion in mineral oil, 44 mg, 1.10 mmol) in THF (3 mL) at 0° C. The slurry was stirred for 15 min, then was added to the mixture of 2,5-dichloropyrido[3,4-b]pyrazine (0.20 g, 1.00 mmol) in THF (2 mL) at 0° C. After 20 min, the reaction was quenched with saturated NH$_4$Cl solution (20 mL) and water (20 mL). The mixture was diluted with EtOAc (100 mL) and the organic layer was washed with brine (50 mL), dried over Na$_2$SO$_4$, filtered, and concentrated to give 5-chloro-2-(2-methoxyethoxy)pyrido[3,4-b]pyrazine (0.24 g, 1.01 mmol, 100% yield). This material was used without further purification. LC/MS (ESI$^-$) m/z=240.1 (M+H)$^+$.

5-Chloro-2-((1,1-dideuteriumprop-2-yn-1-yl)oxy)pyrido[3,4-b]pyrazine (441)

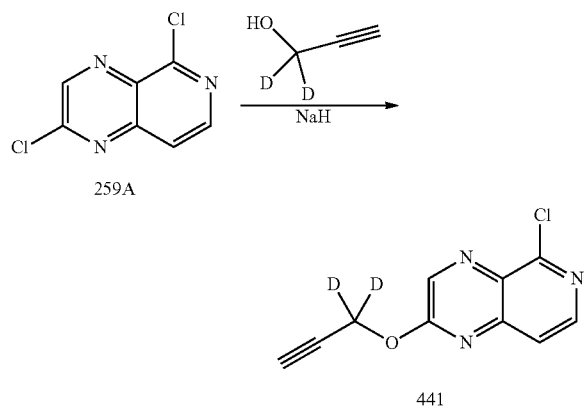

441

A solution of 1,1-dideuteriumprop-2-yn-1-ol (0.22 g, 3.8 mmol) in THF (1 mL) was added to a slurry of sodium hydride (60% dispersion in mineral oil, 0.11 g, 2.80 mmol) in THF (5 mL) at 0° C. The slurry was stirred for 10 min. Solid 2,5-dichloropyrido[3,4-b]pyrazine (259A, 500 mg, 2.50 mmol) was added to the alkoxide followed by THF rinsing of the stock flask (~5 mL). After 10 min at 0° C., the cooling bath was removed and the mixture was stirred at RT for 20 min. It was quenched with saturated NH$_4$Cl solution and was extracted with DCM (3×). The combined organic extracts were dried over Na$_2$SO$_4$ and was passed through a silica gel pad with excess of DCM/EtOAc=10:1. The filtrate was concentrated and the resulting solid was triturated with hexanes-EtOAc (2:1, 6 mL, 5 times) and dried under vacuum to afford intermediate 441 (350 mg, 1.58 mmol, 63% yield) as an off-white powder. LCMS (ESI$^+$) m/z=221.6 (M+H)$^+$. $^1$H NMR (300 MHz, CHLOROFORM-d) δ 8.66 (s, 1H), 8.50 (d, J=5.70 Hz, 1H), 7.67 (d, J=5.70 Hz, 1H), 2.57 (s, 1H).

5-Chloro-2-((1,1,4,4,4-pentadeuterobut-2-yn-1-yl)oxy)pyrido[3,4-b]pyrazine (442)

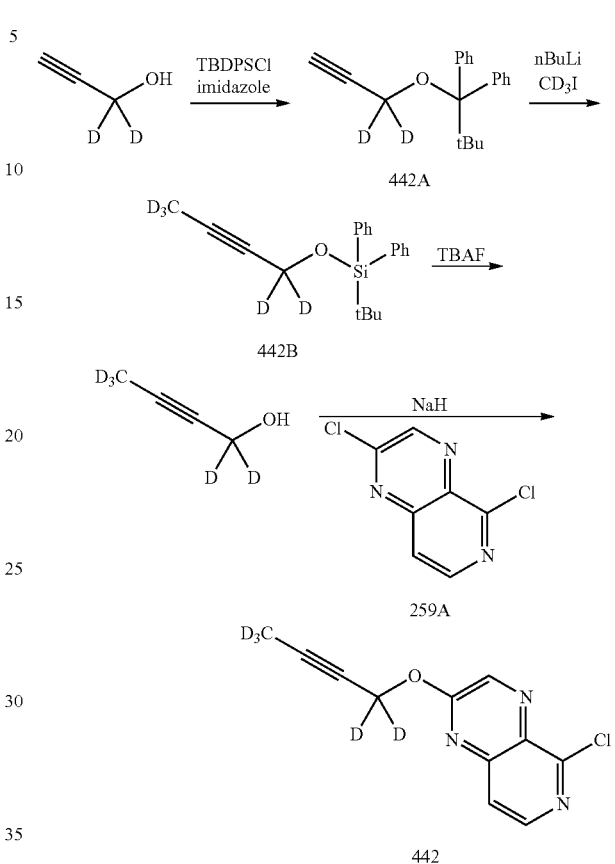

Preparation of Compound 442A. A solution of 1,1-dideutero-prop-2-yn-1-ol (0.8 g, 13.78 mmol) in DCM (5 mL) was added to a solution of tert-butyl(chloro)diphenylsilane (5.37 mL, 20.66 mmol) and imidazole (1.36 mL, 20.66 mmol) in DCM (5 mL) at RT. The mixture was stirred at RT for 18 h, diluted with water, and extracted with ether. The organic extract was washed with brine, dried over Na$_2$SO$_4$, filtered, and concentrated in vacuo. The residue was purified by silica gel chromatography eluting with a gradient of 0-10% EtOAc/heptane to give tert-butyl((1,1-dideutero-prop-2-yn-1-yl)oxy)diphenylsilane (1.7 g, 41.6%) as a colorless oil. $^1$H NMR (300 MHz, CHLOROFORM-d) δ 7.74 (dd, J=1.83, 7.67 Hz, 4H), 7.28-7.50 (m, 6H), 2.39 (s, 1H), 1.09 (s, 9H).

Preparation of Compound 442B. To a solution of tert-butyl((1,1-dideuteroprop-2-yn-1-yl)oxy)diphenylsilane (1.7 g, 5.73 mmol) in THF (10 mL) was slowly added n-butyllithium solution (1.6 M in hexanes) (4.66 mL, 7.45 mmol) at 0° C. After 10 min, iodomethane-D3 (0.47 mL, 7.45 mmol) was slowly added and the resulting mixture was stirred at RT overnight. The mixture was diluted with EtOAc and washed with saturated aqueous NH$_4$Cl solution and then brine. The organic layer was dried over Na$_2$SO$_4$ and concentrated under vacuum. The residue was purified by flash column chromatography on silica gel using 0-10% EtOAc in heptane to give tert-butyl((1,14,4,4-pentadeuterobut-2-yn-1-yl)oxy)diphenylsilane (1.23 g, 68.4%) as a pale yellow oil. LC/MS (ESI$^+$) m/z=314.0 (M+H)$^+$. $^1$H NMR (300 MHz, CHLOROFORM-d) δ 7.64-7.88 (m, 4H), 7.34-7.56 (m, 6H), 0.97-1.15 (m, 9H).

Preparation of 5-Chloro-2-((1,1,4,4,4-pentadeuterobut-2-yn-1-yl)oxy)pyrido[3,4-b]pyrazine (442). To a solution of tert-butyl((1,14,4,4-pentadeuterobut-2-yn-1-yl)oxy)diphenylsilane in THF (5 mL) was added TBAF solution (1M in THF) (1.91 mL, 1.9 mmol). The solution was stirred at RT for 1 h, quenched with water and extracted with Et$_2$O (2×). The combined organic extracts were washed with brine, dried over Na$_2$SO$_4$, filtered, and concentrated on the rotovap. The residue obtained which contained 1,1,4,4,4-pentadeutero-but-2-yn-1-ol was dissolved in THF (2 mL) at 0° C. and was added sodium hydride (38 mg, 0.96 mmol). The slurry was stirred for 10 min and solid 2,5-dichloropyrido[3,4-b]pyrazine (259A, 0.17 g, 0.83 mmol) was added. After stirring for 10 min at 0° C., the cooling bath was removed and the mixture was stirred at RT for 20 min. The reaction mixture was quenched with saturated NH$_4$Cl solution and extracted with DCM. The organic layer was washed with brine, dried over Na$_2$SO$_4$, filtered, and concentrated in vacuo. The residue was purified by silica gel chromatography eluting with a gradient of 0-60% EtOAc/heptane to give 5-chloro-2-((1,1,4,4,4-pentadeuterobut-2-yn-1-yl)oxy)pyrido[3,4-b]pyrazine (0.035 g, 22.95%). LCMS (ESI$^+$) m/z=239.0 (M+H)$^+$. $^1$H NMR (300 MHz, CHLOROFORM-d) δ 8.66 (s, 1H), 8.51 (d, J=5.70 Hz, 1H), 7.68 (d, J=5.70 Hz, 1H).

5-Chloro-2-(pent-2-yn-1-yloxy)pyrido[3,4-b]pyrazine (443)

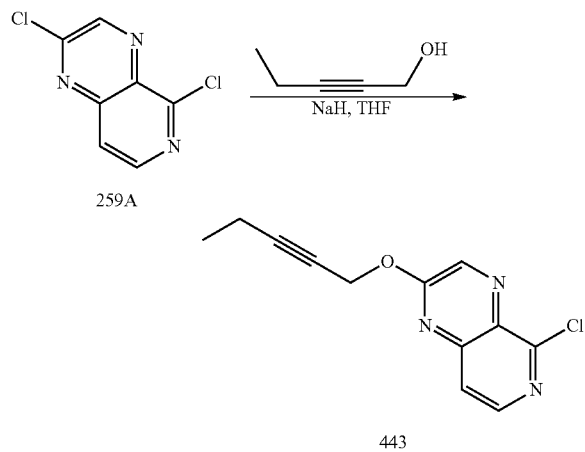

The title compound (0.94 g, 3.81 mmol, 73% yield) as an off-white solid was prepared according to the procedures described for intermediate 259 using 2,5-dichloropyrido[3,4-b]pyrazine (259A, 1.04 g, 5.20 mmol) and 2-pentyn-1-ol (0.50 mL, 5.46 mmol). $^1$H NMR (400 MHz, CHLOROFORM-d) δ ppm 1.18 (t, J=7.5 Hz, 3H), 2.28 (qt, J=7.5, 2.2 Hz, 2H), 5.17 (t, J=2.2 Hz, 2H), 7.66 (d, J=5.7 Hz, 1H), 8.49 (d, J=5.7 Hz, 1H), 8.65 (s, 1H). LC/MS (ESI$^+$) m/z=248.2 (M+H).

4-Chloro-7-fluoropyrido[3,2-d]pyrimidine (444)

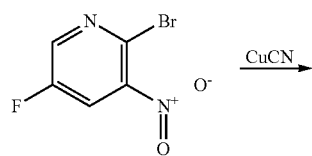

Preparation of 5-fluoro-3-nitropicolinonitrile (444A). Copper (I) cyanide (0.42 g, 4.73 mmol) was added to a solution of 2-bromo-5-fluoro-3-nitropyridine (0.95 g, 4.30 mmol) in DMF (15 mL) and the mixture was heated to 100° C. for 4 h. After cooling to RT, EtOAc (45 mL) was added followed by 9:1 NH$_4$Cl/NH$_4$OH (aq, 20 mL). The resulting biphasic mixture was stirred for 10 min, and then the layers were separated. The aqueous layer was extracted with EtOAc (2×) and then the combined extracts were washed with water (2×), dried over anhydrous MgSO$_4$, filtered, and concentrated in vacuo to give an oil. The oil was fused to silica gel and then purified by silica gel chromatography (0-60% EtOAc/heptane gradient) to give the title intermediate 444A (0.43 g, 2.60 mmol, 60% yield). $^1$H-NMR (400 MHz, CHLOROFORM-d): δ ppm 8.90 (s, 1H) 8.35 (d, J=5.1 Hz, 1H). LC/MS (ESI$^+$) m/z=168 (M+H)$^+$.

Preparation of 3-amino-5-fluoropicolinamide (444B). Ammonium hydroxide (28% wt., 0.25 mL, 6.42 mmol) was added to a suspension of 5-fluoro-3-nitropicolinonitrile (0.10 g, 0.62 mmol) in water (1.25 mL) and the mixture stirred for 20 min. Na$_2$S$_2$O$_4$ (0.33 g, 1.87 mmol) was added portion wise over 15 min. The resulting brown suspension was stirred for 2 h, then filtered. The brown solid was washed with water three times, then air-dried to give the title intermediate 444B (56 mg, 0.36 mmol, 58% yield). LC/MS (ESI$^+$) m/z=156 (M+H)$^+$.

Preparation of 7-fluoropyrido[3,2-d]pyrimidin-4(3H)-one (444C). 3-Amino-5-fluoropicolinamide (0.23 g, 1.49 mmol) was heated to reflux in triethyl orthoformate (3.0 mL) for 4 h while distillate was collected in a Dean-Stark trap. The mixture was cooled to RT and the resulting suspension was filtered. The collected solid was washed several times with heptane and then air dried to give the title intermediate 444C (0.21 g, 1.26 mmol, 85% yield) as a light brown solid. $^1$H NMR (400 MHz, DMSO-d$_6$) δ ppm 8.81 (d, J=2.74 Hz, 1H) 8.20 (s, 1H) 8.01 (dd, J=9.49, 2.64 Hz, 1H). LC/MS (ESI$^+$) m/z=166 (M+H)$^+$.

Preparation of 4-Chloro-7-fluoropyrido[3,2-d]pyrimidine (444). A mixture of 7-fluoropyrido[3,2-d]pyrimidin-4(3H)-one (0.20 g, 1.21 mmol), diisopropylethylamine (0.84 mL, 4.84 mmol), and phosphorus oxychloride (0.44 mL, 4.84 mmol) in toluene (3 mL) was heated to 110° C. for 3 h, then cooled to RT. The mixture was then carefully added to water that was being held at 10° C. This mixture was stirred vigorously for 30 min, and then the product was extracted into EtOAc (3×). The combined extracts were then dried over anhydrous MgSO₄, filtered, and concentrated in vacuo to give the title compound (68 mg, 31% yield) as a brown solid. LC/MS (ESI⁺) m/z=184 (M+H)⁺.

2-(((4-Chloropyrido[3,2-d]pyrimidin-7-yl)oxy)methyl)oxazole (445)

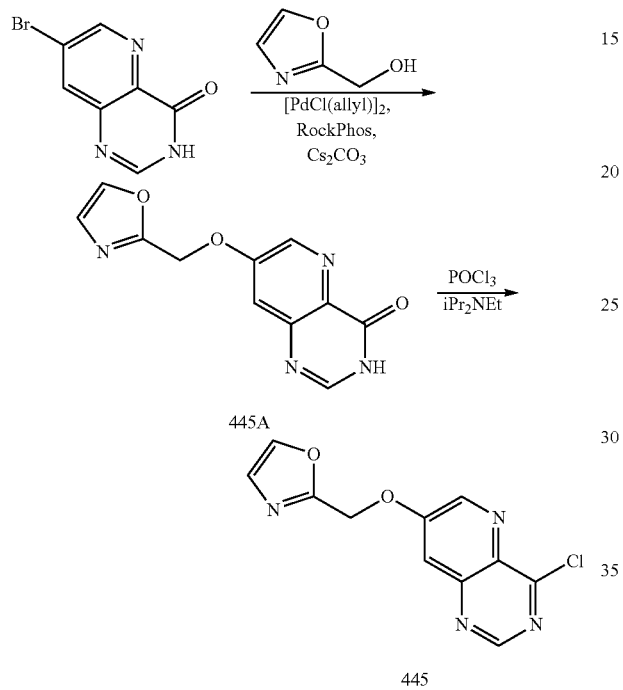

Preparation of 7-(oxazol-2-ylmethoxy)pyrido[3,2-d]pyrimidin-4(3H)-one (445A). To a resealable vial was added 7-bromopyrido[3,2-d]pyrimidin-4(3H)-one (2.0 g, 8.85 mmol, D-L Chiral Chemicals, LLC), cesium carbonate (8.65 g, 26.5 mmol), 2-(di-t-butylphosphono)-3-methoxy-6-methyl-2'-4'-6'-tri-i-propyl-1,1'-biphenyl (RockPhos) (0.21 g, 0.44 mmol, Strem Chemicals, Inc.), and allylpalladium(II) chloride dimer (55 mg, 0.15 mmol, Sigma-Aldrich Chemical Company, Inc.). The reaction vessel was carefully evacuated and backfilled with N₂. This was repeated twice. To this mixture was added 1,4-dioxane (10 mL) and 2-oxazolemethanol (2.81 mL, 35.4 mmol, Combi-Blocks, Inc.). Once again, the reaction vessel was carefully evacuated and backfilled with N₂. This was repeated twice. The reaction mixture was heated at 90° C. for 6 h. The mixture was treated with sat NH₄Cl and extracted with 25% iPrOH/CHCl₃. The solution needed to be filtered through Celite® filter aid to achieve good extraction. The combined extracts were dried and concentrated onto silica. Purification by silica gel chromatography (3-20% MeOH/DCM) afforded an off-white solid that was slurried with 50% EtOAc/heptane and then dried under vacuum to afford the title compound (0.91 g, 42%). MS m/z=245.0 (M+H)⁺. ¹H NMR (400 MHz, DMSO-d₆) δ ppm 5.50 (s, 2H) 7.31 (s, 1H) 7.70 (d, J=2.74 Hz, 1H) 8.13 (d, J=3.13 Hz, 1H) 8.21 (s, 1H) 8.54 (d, J=2.74 Hz, 1H) 12.43 (br s, 1H).

Preparation of 2-(((4-chloropyrido[3,2-d]pyrimidin-7-yl)oxy)methyl)oxazole (445). To a 25 mL round-bottomed flask was added 7-(oxazol-2-ylmethoxy)pyrido[3,2-d]pyrimidin-4(3H)-one (0.45 g, 1.8 mmol), toluene (10 mL), N,N-diisopropylethylamine (0.96 mL, 5.5 mmol) and phosphorus oxychloride (1.0 mL, 11 mmol). The solution was heated at 70° C. for 1 h. The reaction mixture was allowed to cool to RT and was pipetted into cold (-10° C.) sat NaHCO₃. It was extracted with DCM (2×) and the combined extracts were dried (Na₂SO₄) and concentrated. The resulting solid was washed with heptane and then dried under vacuum to afford the title compound as a tan solid (0.45 g, 1.7 mmol, 93% yield). MS m/z=263.1 (M+H)⁺. ¹H NMR (400 MHz, CDCl₃) δ ppm 5.39 (s, 2H), 7.22 (s, 1H), 7.75 (s, 1H), 7.79 (d, J=2.7 Hz, 1H), 8.92 (d, J=2.7 Hz, 1H), 9.05 (s, 1H).

4-Chloro-7-(prop-2-yn-1-yloxy)pyrido[3,2-d]pyrimidine (446)

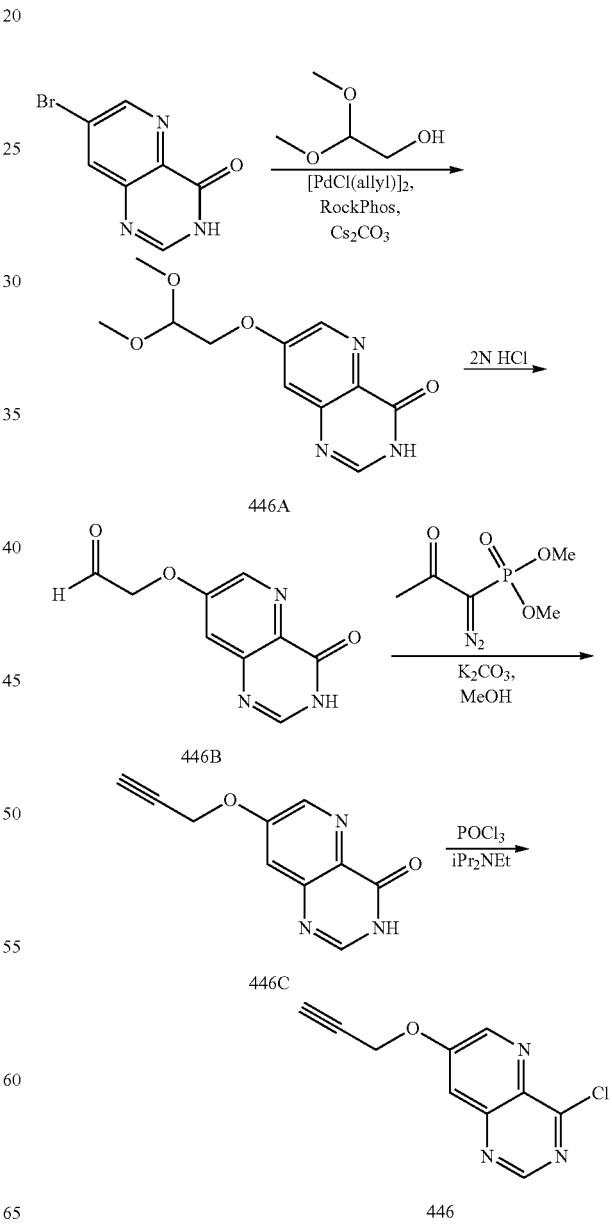

Preparation of 7-(2,2-dimethoxyethoxy)pyrido[3,2-d]pyrimidin-4(3H)-one (446A). To a resealable vial was added 7-bromopyrido[3,2-d]pyrimidin-4(3H)-one (0.50 g, 2.2 mmol, D-L Chiral Chemicals, LLC), cesium carbonate (2.2 g, 6.6 mmol), 2-(di-t-butylphosphono)-3-methoxy-6-methyl-2'-4'-6'-tri-i-propyl-1,1'-biphenyl (RockPhos) (0.062 g, 0.13 mmol, Strem Chemicals, Inc.) and allylpalladium(II) chloride dimer (0.016 g, 0.044 mmol, Sigma-Aldrich Chemical Company, Inc.). The reaction vessel was carefully evacuated and backfilled with $N_2$. This was repeated twice. To the mixture was added 1,4-dioxane (5 mL) followed by glycolaldehyde dimethyl acetal (1.41 g, 13.3 mmol). The reaction mixture was stirred at 90° C. for 2.5 h. After cooling to RT, the solution was treated with sat $NH_4Cl$ and extracted with 25% iPrOH/CHCl$_3$. The solution had to be filtered through Celite® filter aid to prevent emulsion formation during extraction. The combined extracts were dried and concentrated. Purification by silica gel chromatography (0-10% MeOH/DCM) afforded the title compound as a white solid (0.20 g, 36% yield). MS m/z=252.1 (M+H)$^+$. $^1$H NMR (400 MHz, DMSO-d$_6$) δ ppm 3.37 (s, 6H), 4.21 (d, J=5.1 Hz, 2H), 4.76 (t, J=5.1 Hz, 1H), 7.57 (d, J=2.7 Hz, 1H), 8.12 (s, 1H), 8.49 (d, J=2.7 Hz, 1H), 12.40 (br. s., 1H).

Preparation of 2-((4-oxo-3,4-dihydropyrido[3,2-d]pyrimidin-7-yl)oxy)acetaldehyde (446B). To a resealable vial was added 7-(2,2-dimethoxyethoxy)pyrido[3,2-d]pyrimidin-4(3H)-one (0.10 g, 0.40 mmol), THF (2 mL) and finally 2 N hydrochloric acid (2.0 mL). The reaction mixture was heated at 60° C. for 2 h. It was allowed to cool to RT and then concentrated to afford the title compound as a brown semi-solid which was carried on directly to the next step. MS m/z=224.0 (M+H$_2$O+H)$^+$.

Preparation of 7-(prop-2-yn-1-yloxy)pyrido[3,2-d]pyrimidin-4(3H)-one (446C). To a 150 mL round bottomed flask was added 2-((4-oxo-3,4-dihydropyrido[3,2-d]pyrimidin-7-yl)oxy)acetaldehyde (1.70 g, 8.29 mmol), potassium carbonate (4.58 g, 33.1 mmol) and MeOH (80 mL). To this solution was added dimethyl(1-diazo-2-oxopropyl)phosphonate (2.39 mL, 9.94 mmol, Astatech). The reaction mixture was stirred at RT for 3 h. The solution was poured into saturated NaHCO$_3$ and then the pH was adjusted to 7 with 5 N HCl. The solution was extracted with 25% iPrOH/CHCl$_3$. There was an emulsion present that contained some solid. LC/MS showed this solid to be product so it was filtered and dried under vacuum to afford 0.28 g of product. The combined extracts were dried (Na$_2$SO$_4$) and concentrated onto silica. Purification by silica gel chromatography (0-10% MeOH/DCM) afforded 1.07 g (in addition to the 0.28 g solid already isolated) of the title compound as a white solid (1.35 g, 6.71 mmol, 81% yield). MS m/z=201.9 (M+H)$^+$. $^1$H NMR (400 MHz, DMSO-d$_6$) δ ppm 3.71 (t, J=2.3 Hz, 1H), 5.06 (d, J=2.3 Hz, 2H), 7.58 (d, J=2.7 Hz, 1H), 8.13 (s, 1H), 8.50 (d, J=2.7 Hz, 1H), 12.43 (br s, 1H).

Preparation of 4-chloro-7-(prop-2-yn-1-yloxy)pyrido[3,2-d]pyrimidine (446). To a solution of 7-(prop-2-yn-1-yloxy)pyrido[3,2-d]pyrimidin-4(3H)-one (0.86 g, 4.27 mmol) in toluene (20 mL) was added N,N-diisopropylethylamine (2.31 mL, 13.3 mmol) followed by phosphorus oxychloride (1.17 mL, 12.8 mmol, Sigma-Aldrich Chemical Company, Inc.). The reaction mixture was heated at 65° C. for 2.5 h. The solution was allowed to cool to RT and then was slowly pipetted into sat NaHCO$_3$ that had been cooled to 10° C. The solution was stirred vigorously for 15 min and then was extracted with DCM (2×). The combined extracts were dried (Na$_2$SO$_4$), filtered and concentrated to afford the title compound as an off-white solid (0.86 g, 3.9 mmol, 92% yield). MS m/z=219.9 (M+H)$^+$. $^1$H NMR (400 MHz, CDCl$_3$) δ ppm 2.66 (t, J=2.3 Hz, 1H), 4.94 (d, J=2.3 Hz, 2H), 7.74 (d, J=2.7 Hz, 1H), 8.88 (d, J=2.7 Hz, 1H), 9.05 (s, 1H).

2-(((8-Chloro-5-fluoro-1,7-naphthyridin-3-yl)oxy)methyl)oxazole (447)

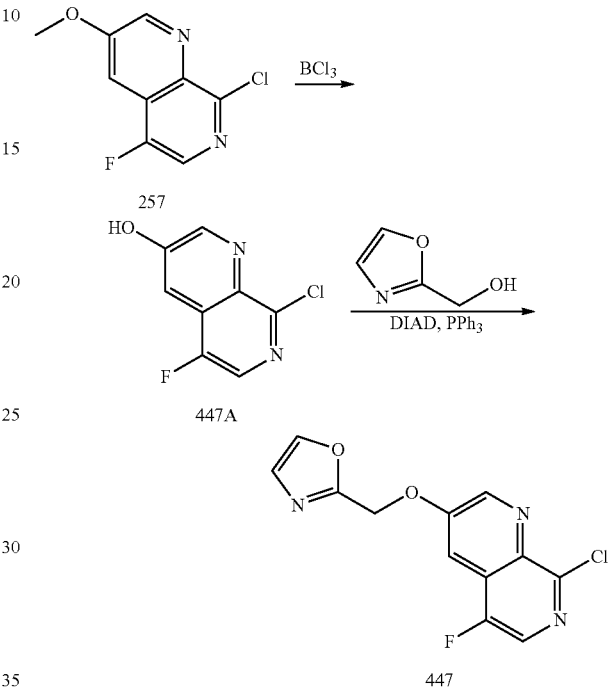

Boron trichloride (4.99 mL of 1.0 M solution in DCM, 4.99 mmol) was added by syringe over 2 min to a stirring yellow solution of 8-chloro-5-fluoro-3-methoxy-1,7-naphthyridine (212 mg, 0.99 mmol) and tetra-n-butylammonium iodide (479 mg, 1.29 mmol) in anhydrous DCM (3.5 mL) under a nitrogen atmosphere at RT. The mixture was stirred at RT for 4 h, then cooled with an ice bath before the careful addition of water. After bubbling ceased with addition of more water drops, the mixture was stirred for 30 min at RT. The mixture was then diluted with DCM and water, then carefully neutralized with portion wise addition of solid sodium bicarbonate. The layers were separated and the aqueous layer was extracted with DCM (3×150 mL). The combined extracts were washed with brine (100 mL), dried over Na$_2$SO$_4$, filtered and concentrated in vacuo to give a red oil. This oil was purified by ISCO (12 g Gold silica gel column, 50-100% EtOAc in heptane) to give compound 447A (123 mg, 62% yield) as a light yellow solid. $^1$H NMR (400 MHz, DMSO-d$_6$) δ ppm 11.72 (br. s., 1H), 8.83 (d, J=2.7 Hz, 1H), 8.34 (d, J=1.2 Hz, 1H), 7.56 (d, J=2.7 Hz, 1H). MS m/z=199.0 (M+H)$^+$.

To a 15 mL round-bottomed flask was added 8-chloro-5-fluoro-1,7-naphthyridin-3-ol (Intermediate 447A) (0.58 g, 2.9 mmol), triphenylphosphine (0.996 g, 3.80 mmol), THF (15 mL), and 2-oxazolemethanol (0.30 mL, 3.8 mmol, Combi-Blocks, Inc.). The solution was cooled to 0° C. and diisopropyl azodicarboxylate (0.75 mL, 3.8 mmol, Sigma-Aldrich Chemical Company, Inc.) was added slowly and then the solution was allowed to warm to RT. After 1 h, the reaction mixture was poured into water and extracted with EtOAc. The combined extracts were washed with water and brine and then dried (Na$_2$SO$_4$) and concentrated onto silica. Purification by silica gel chromatography (0-80% EtOAc/heptane) afforded the title compound (0.68 g, 2.4 mmol, 83% yield). MS m/z=280.0 (M+H)$^+$. $^1$H NMR (400 MHz, CDCl$_3$) δ ppm 5.40 (s, 2H), 7.23 (s, 1H), 7.76 (s, 1H), 7.80 (d, J=2.9 Hz, 1H), 8.25 (s, 1H), 8.93 (d, J=2.9 Hz, 1H).

4-(((4-Chloropyrido[3,2-d]pyrimidin-7-yl)oxy)methyl)-2,5-dimethyloxazole (448)

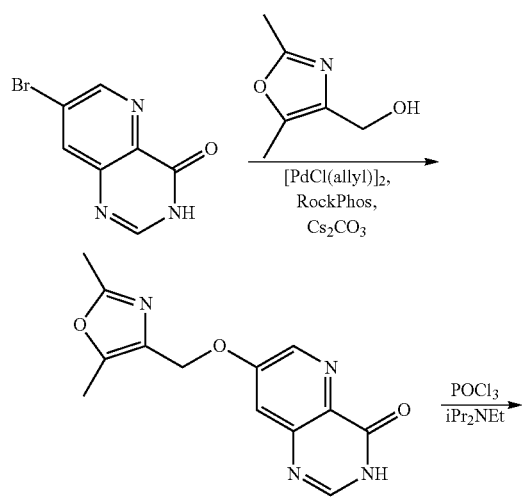

448A

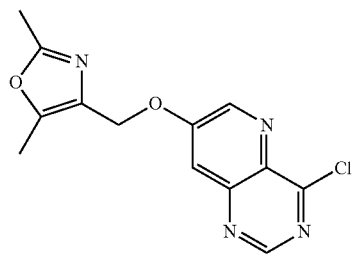

448A

Intermediate 448A (85 mg, 0.31 mmol, 35% yield) as a white solid was prepared according to the procedures described for intermediate 445A, starting from 7-bromopyrido[3,2-d]pyrimidin-4(3H)-one (0.20 g, 0.89 mmol) and (2,5-dimethyloxazol-4-yl)methanol (0.450 g, 3.54 mmol, Frontier Scientific, Inc.). MS m/z=273.2 (M+H)$^+$. $^1$H NMR (400 MHz, DMSO-d$_6$) δ ppm 2.35 (s, 3H) 2.35 (s, 3H) 5.12 (s, 2H) 7.66 (d, J=2.74 Hz, 1H) 8.12 (s, 1H) 8.48 (d, J=2.74 Hz, 1H) 12.40 (br s, 1H).

Intermediate 448 as a tan solid (0.057 g, 0.20 mmol, 86% yield) was prepared according to the procedures described for intermediate 445, starting from 7-((2,5-dimethyloxazol-4-yl)methoxy)pyrido[3,2-d]pyrimidin-4(3H)-one (448A, 62 mg, 0.23 mmol). MS m/z=290.9 (M+H)$^+$. $^1$H NMR (400 MHz, CDCl$_3$) δ ppm 2.39 (s, 3H), 2.45 (s, 3H), 5.08 (s, 2H), 7.72 (d, J=2.7 Hz, 1H), 8.89 (d, J=2.7 Hz, 1H), 9.04 (s, 1H).

5-Methoxy-3-methylpyrazine-2-carboxylic acid (265)

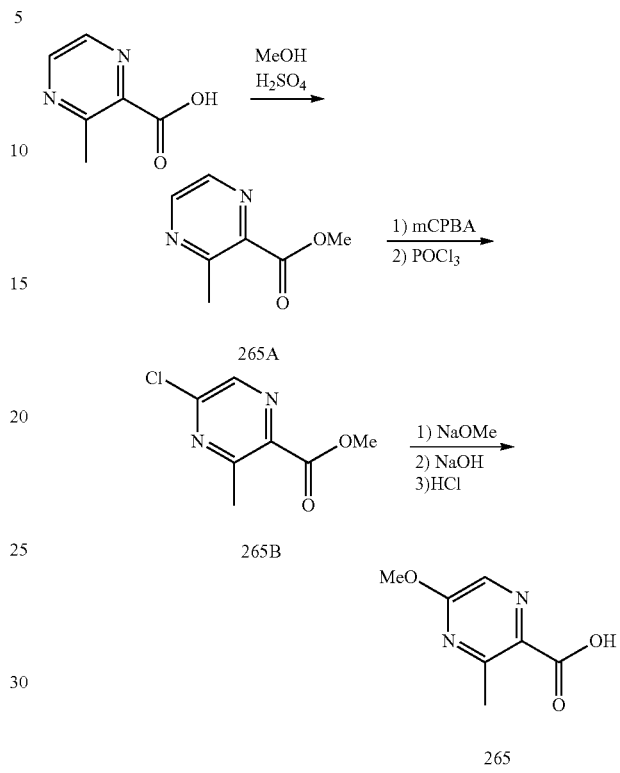

Preparation of Compound 265A. In a 2-L flask, 3-methylpyrazine-2-carboxylic acid (Matrix, 19.95 g, 144 mmol) was suspended in MeOH (500 mL). The suspension was cooled in an ice-water bath, and concentrated sulfuric acid (Fluka, 27.3 mL, 506 mmol) was added over a time period of 5 min. The reaction mixture was heated to 80° C. for 5 h. The reaction mixture was concentrated under reduced pressure and the residue was taken up in DCM (750 mL). The excess acid was neutralized carefully with of aqueous NaOH (5 M, 200 mL). The aqueous layer was separated and extracted with DCM (250 mL). The combined organic layers were combined, dried over MgSO$_4$ and concentrated to afford 16.15 g of methyl 3-methylpyrazine-2-carboxylate (265A, 106 mmol, 73%). MS m/z=153 [M+H]$^+$.

Preparation of Compound 265B. In a 1-L flask, the methyl 3-methylpyrazine-2-carboxylate (265A, 16.08 g, 106 mmol) was suspended in CHCl$_3$ (300 mL). 3-Chlorobenzoperoxoic acid (Aldrich, 24.62 g, 143 mmol) was added. The reaction mixture was heated to 70° C. for 16 h. The reaction mixture was quenched with saturated NaHCO$_3$ (200 mL). The layers were separated, and the aqueous layer was further extracted with DCM (2×100 mL). The combined organic layers were dried over MgSO$_4$, and the filtrate was concentrated to afford crude 3-(methoxycarbonyl)-2-methylpyrazine 1-oxide (17.77 g). MS m/z=169 [M+H]$^+$.

In a 1-L flask, the crude 3-(methoxycarbonyl)-2-methylpyrazine 1-oxide (17.77 g, 106 mmol) was dissolved in DMF (300 mL). Neat phosphoryl trichloride (29.6 mL, 317 mmol) was added. The reaction mixture was heated to 100° C. After 1 h, the reaction mixture was concentrated to remove most of the DMF. The flask was cooled in an ice water bath, and 1 M aqueous Na$_2$CO$_3$ (300 mL) was added slowly, followed by 80% EtOAc-hexane (400 mL). The mixture was filtered through Celite® filter aid. The resulting filtrate was partitioned and the aqueous phase was extracted further with 80% EtOAc-hexane (2×250 mL). The combined organic layers were dried over MgSO₄ and concentrated. The material was purified through silica gel using 11% EtOAc-hexane to afford methyl 5-chloro-3-methylpyrazine-2-carboxylate (265B, 4.29 g, 23 mmol, 22%). MS m/z=187 [M+H]⁺.

Preparation of Compound 265. A flask was charged with sodium (0.813 g, 35.4 mmol), purged with Argon, and placed in a room temperature water bath. MeOH (47.7 mL, 1179 mmol) was added slowly. After 40 min, methyl 5-chloro-3-methylpyrazine-2-carboxylate (265B, 2.2 g, 11.79 mmol) was added. The vessel was sealed and heated to 45° C. for 1.5 h. Sodium hydroxide (1 M, 12.97 mL, 12.97 mmol) was added and heating was continued for 1.5 h. The reaction mixture was concentrated under reduced pressure and the residue was dissolved in a minimum amount of water (50 mL). The aqueous phase was extracted with Et₂O (15 mL), which was discarded. The aqueous phase was acidified with HCl (5 M, 11 mL, 55 mmol). The mixture was extracted with DCM (3×60 mL). The combined organic extracts were dried over MgSO₄ and the filtrate was concentrated to afford 5-methoxy-3-methylpyrazine-2-carboxylic acid (265, 2.0 g, 100%). MS m/z=169 [M+H]⁺. ¹H NMR in CDCl₃ δ 10.70 (br, 1H), 7.98 (s, 1H), 4.00 (s, 3H), 2.91 (s, 3H).

3-Methyl-5-(2,2,2-trifluoroethoxy)pyrazine-2-carboxylic acid (266)

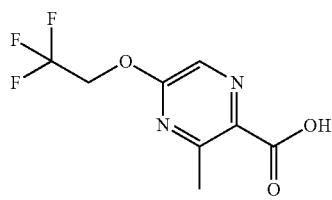

266

The title compound was synthesized according to Intermediate 265, using 2,2,2,-trifluoroethanol (Aldrich) to react with Compound 265B. MS m/z=237 (M+H)⁺.

5-Cyano-3-methylpicolinic acid (267)

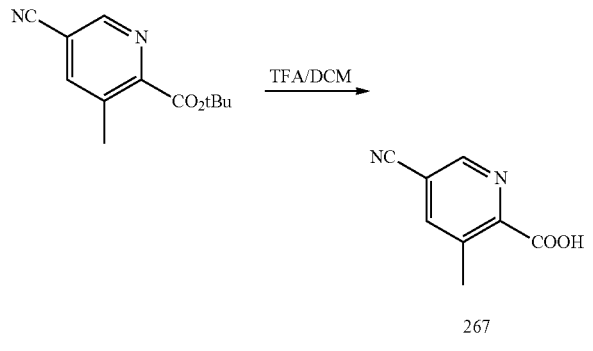

267

To a solution of tert-butyl 5-cyano-3-methylpicolinate (synthesized according to procedure described in WO2012095521; 4.18 g, 19.15 mmol) in DCM (96 mL) was added TFA (Aldrich, 148 mL, 1915 mmol). The reaction mixture was stirred at RT for 2 h. The reaction mixture was concentrated under reduced pressure and the residue was triturated with EtOAc. The yellow slurry was concentrated under reduced pressure. The residue was triturated with 30 mL of methyl tert-butyl ether (30 mL) and of hexanes (50 mL) to yield 5-cyano-3-methylpicolinic acid (2.91 g, 17.95 mmol, 94% yield) as yellow solid. MS m/z=163.2 [M+H]⁺.

5-Chloro-3-methylpicolinic acid (268)

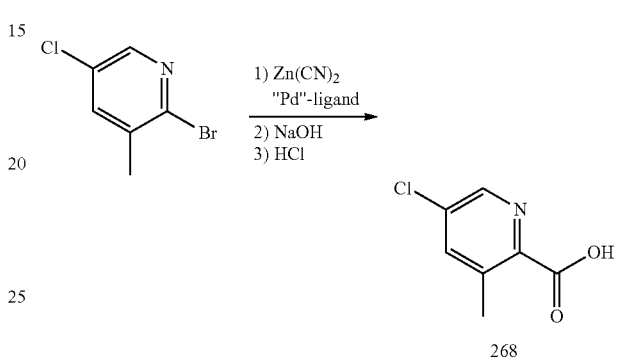

268

A mixture of 2-bromo-5-chloro-3-methylpyridine (45 g, 218 mmol), zinc cyanide (8.30 mL, 131 mmol), tris(dibenzylideneacetone)dipalladium (0) (4.99 g, 5.45 mmol), and 1,1'-bis(diphenylphosphino)ferrocene (6.04 g, 10.90 mmol) in dimethylacetamide (40 mL) was heated to 110° C. for 4 h. The reaction mixture was cooled to RT, diluted with water and extracted with EtOAc. The organic phase obtained was concentrated under reduced pressure and residue purified by chromatography on silica gel using ISCO eluting with 0-60% EtOAc/hexanes to afford 5-chloro-3-methylpicolinonitrile (25.4 g, 166 mmol, 76% yield). LC/MS (ESI⁺) m/z=153.1 (M+H).

To a solution of 5-chloro-3-methylpicolinonitrile (24.0 g, 157 mmol) in EtOH (100 mL) was added NaOH (110 mL of 5 N solution, 550 mmol). The resulting mixture was refluxed at 90° C. for 18 h. After cooling to RT, the reaction mixture was concentrated. The residue was diluted with water and the pH of the solution was adjusted to 4 by addition of 5 N HCl. The solid that precipitated was filtered and set aside. The filtrate was extracted with EtOAc (2×). The aqueous layer was again acidified with 5 N HCl to pH 4 and extracted with EtOAc (2×). The EtOAc extracts were combined, dried, and concentrated. The solid obtained from all the workup steps were combined and dried in a vacuum oven at 40° C. for 12 h to give 5-chloro-3-methylpicolinic acid (268) (24.1 g, 140 mmol, 89% yield). LC/MS (ESI⁺) m/z=172.0 (M+H)⁺. ¹H NMR (400 MHz, CHLOROFORM-d) δ ppm 11.29 (br. s., 1H), 8.41 (d, J=1.76 Hz, 1H), 7.73 (d, J=1.76 Hz, 1H), 2.75 (s, 3H).

5-(But-2-yn-1-yloxy)-3-methylpicolinic acid (269)

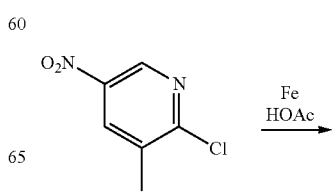

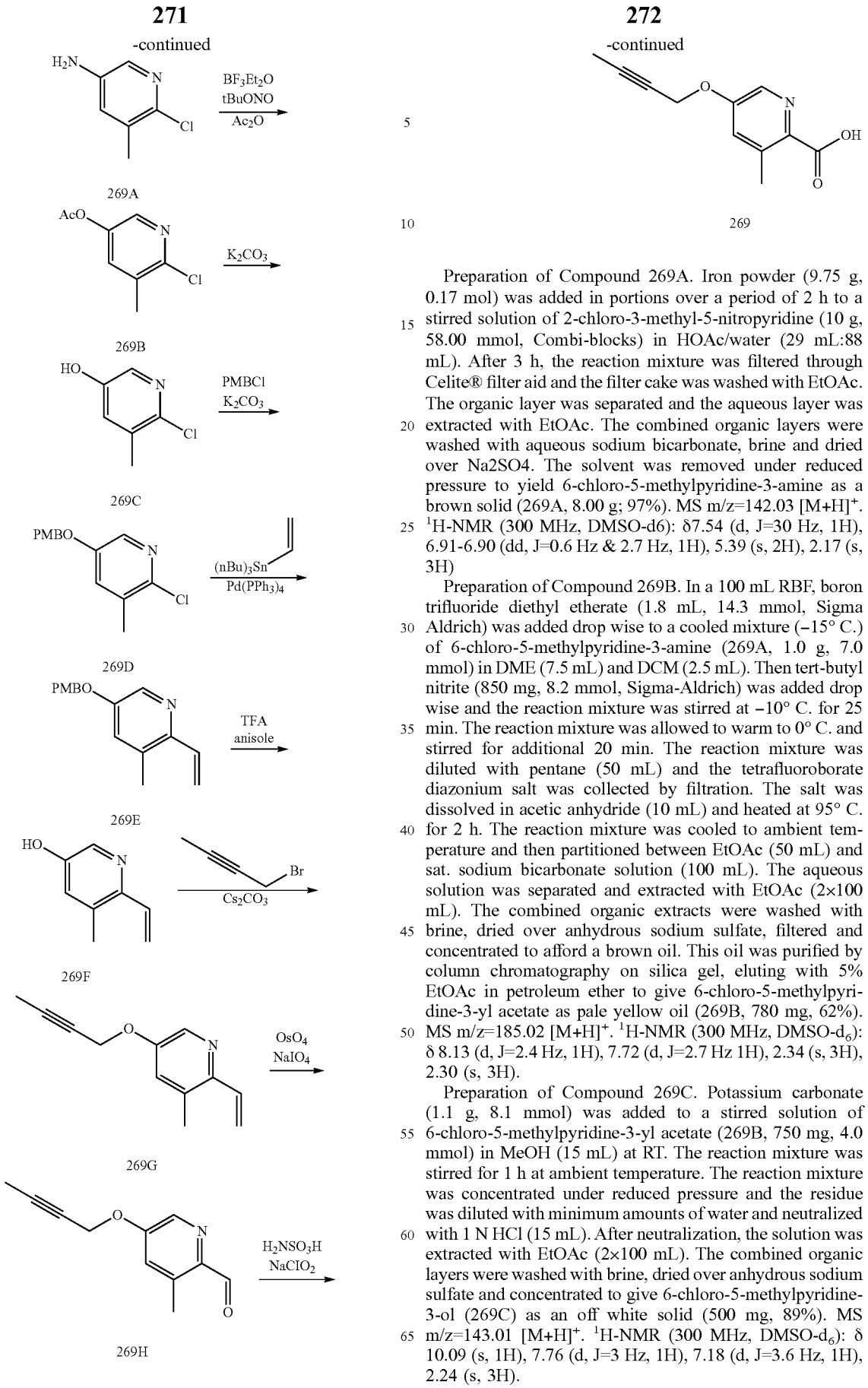

Preparation of Compound 269A. Iron powder (9.75 g, 0.17 mol) was added in portions over a period of 2 h to a stirred solution of 2-chloro-3-methyl-5-nitropyridine (10 g, 58.00 mmol, Combi-blocks) in HOAc/water (29 mL:88 mL). After 3 h, the reaction mixture was filtered through Celite® filter aid and the filter cake was washed with EtOAc. The organic layer was separated and the aqueous layer was extracted with EtOAc. The combined organic layers were washed with aqueous sodium bicarbonate, brine and dried over Na2SO4. The solvent was removed under reduced pressure to yield 6-chloro-5-methylpyridine-3-amine as a brown solid (269A, 8.00 g; 97%). MS m/z=142.03 [M+H]$^+$. $^1$H-NMR (300 MHz, DMSO-d6): δ7.54 (d, J=30 Hz, 1H), 6.91-6.90 (dd, J=0.6 Hz & 2.7 Hz, 1H), 5.39 (s, 2H), 2.17 (s, 3H)

Preparation of Compound 269B. In a 100 mL RBF, boron trifluoride diethyl etherate (1.8 mL, 14.3 mmol, Sigma Aldrich) was added drop wise to a cooled mixture (−15° C.) of 6-chloro-5-methylpyridine-3-amine (269A, 1.0 g, 7.0 mmol) in DME (7.5 mL) and DCM (2.5 mL). Then tert-butyl nitrite (850 mg, 8.2 mmol, Sigma-Aldrich) was added drop wise and the reaction mixture was stirred at −10° C. for 25 min. The reaction mixture was allowed to warm to 0° C. and stirred for additional 20 min. The reaction mixture was diluted with pentane (50 mL) and the tetrafluoroborate diazonium salt was collected by filtration. The salt was dissolved in acetic anhydride (10 mL) and heated at 95° C. for 2 h. The reaction mixture was cooled to ambient temperature and then partitioned between EtOAc (50 mL) and sat. sodium bicarbonate solution (100 mL). The aqueous solution was separated and extracted with EtOAc (2×100 mL). The combined organic extracts were washed with brine, dried over anhydrous sodium sulfate, filtered and concentrated to afford a brown oil. This oil was purified by column chromatography on silica gel, eluting with 5% EtOAc in petroleum ether to give 6-chloro-5-methylpyridine-3-yl acetate as pale yellow oil (269B, 780 mg, 62%). MS m/z=185.02 [M+H]$^+$. $^1$H-NMR (300 MHz, DMSO-d$_6$): δ 8.13 (d, J=2.4 Hz, 1H), 7.72 (d, J=2.7 Hz 1H), 2.34 (s, 3H), 2.30 (s, 3H).

Preparation of Compound 269C. Potassium carbonate (1.1 g, 8.1 mmol) was added to a stirred solution of 6-chloro-5-methylpyridine-3-yl acetate (269B, 750 mg, 4.0 mmol) in MeOH (15 mL) at RT. The reaction mixture was stirred for 1 h at ambient temperature. The reaction mixture was concentrated under reduced pressure and the residue was diluted with minimum amounts of water and neutralized with 1 N HCl (15 mL). After neutralization, the solution was extracted with EtOAc (2×100 mL). The combined organic layers were washed with brine, dried over anhydrous sodium sulfate and concentrated to give 6-chloro-5-methylpyridine-3-ol (269C) as an off white solid (500 mg, 89%). MS m/z=143.01 [M+H]$^+$. $^1$H-NMR (300 MHz, DMSO-d$_6$): δ 10.09 (s, 1H), 7.76 (d, J=3 Hz, 1H), 7.18 (d, J=3.6 Hz, 1H), 2.24 (s, 3H).

Preparation of Compound 269D. A mixture of 6-chloro-5-methylpyridin-3-ol (269C, 250 mg, 1.7 mmol), 1-(chloromethyl)-4-methoxybenzene (328 mg, 2.0 mmol, Sigma Aldrich), and potassium carbonate (482 mg, 3.4 mol) in DMF (5 mL) was allowed to stir for 3 h at 60° C. After completion of the reaction, reaction mixture was cooled to RT and poured into ice cold water (25 mL). The obtained solid was filtered, washed with water (2×10 mL) and dried to obtain 2-chloro-5-((4-methoxybenzyl)oxy)-3-methylpyridine as an off white solid (269D, 400 mg, 87%). MS m/z=263.9 [M+H]$^+$. $^1$H-NMR (300 MHz, CDCl$_3$): δ 7.96 (d, J=2.7 Hz, 1H), 7.34 (d, J=8.7 Hz, 2H), 7.15 (d, J=3 Hz, 1H), 6.94-6.89 (m, 2H), 4.99 (s, 2H), 3.81 (s, 3H), 2.33 (s, 3H).

Preparation of Compound 269E. A 25 mL sealable tube was charged with a mixture of 2-chloro-5-(difluoromethoxy)-3-methylpyridine (269D, 330 mg, 1.2 mmol), toluene (10 mL), and tributyl(vinyl)stannane (447 mg, 1.5 mmol). The reaction mixture was purged with Argon gas for 10 min. Then Pd(PPh$_3$)$_4$ (144 mg, 0.2 mmol, Alfa-Aesar) was added and the reaction mixture was allowed to stir for 16 h at 100° C. The reaction mixture was cooled to RT and filtered through Celite® filter aid. The filter cake was washed with EtOAc and concentrated to get a crude residue. The residue was purified by column chromatography using silica and eluting with 5-10% EtOAc in petroleum ether to give 5-((4-methoxybenzyl)oxy)-3-methyl-2-vinylpyridine as an off white solid (269E, 250 mg, 65%). MS m/z=256.1 [M+H]$^+$. $^1$H-NMR (300 MHz, CDCl$_3$): δ 8.20 (d, J=2.7 Hz, 1H), 7.37-7.33 (m, 2H), 7.02 (d, J=2.7 Hz, 1H), 6.94-6.87 (m, 3H), 6.21 (dd, J=1.8 Hz & 16.8 Hz, 1H), 5.39 (dd, J=2.1 Hz & 10.5 Hz, 1H), 5.01 (s, 2H), 3.81 (s, 3H), 2.33 (s, 3H).

Preparation of 5-methyl-6-vinylpyridin-3-ol (269F). TFA (1.25 mL, 5 times) was added to a stirred solution of 5-((4-methoxybenzyl)oxy)-3-methyl-2-vinylpyridine (269E, 250 mg, 9.8 mmol) in anisole (0.5 mL). The reaction mixture was stirred for 2 h at ambient temperature. After completion of the reaction, the mixture was concentrated and quenched with saturated NaHCO$_3$ solution (2 mL). The reaction mixture was extracted with EtOAc (2×10 mL) and the combined organic layers were washed with brine, dried over anhydrous sodium sulfate and concentrated under reduced pressure. The crude residue was triturated with pentane to afford 5-methyl-6-vinylpyridin-3-ol (269F) as an off white solid (100 mg, 76%). MS m/z=136.15 [M+H]$^+$. $^1$H-NMR (400 MHz, CDCl$_3$): δ 9.86 (s, 1H), 7.96 (d, J=2.8 Hz, 1H), 6.94-6.86 (m, 2H), 6.07 (dd, J=2.4 Hz, 16.8 Hz, 1H), 5.26 (dd, J=2.8 Hz, 10.4 Hz, 1H), 2.25 (s, 3H).

Preparation of 5-(but-2-yn-1-yloxy)-3-methyl-2-vinylpyridine (269G). A mixture of 5-methyl-6-vinylpyridin-3-ol (269F, 100 mg, 7.4 mmol), sodium 1-bromobut-2-yne (118 mg, 0.9 mmol, Alfa-Aesar) and cesium carbonate (361 mg, 1.1 mmol) in DMF (2 mL) was stirred for 2 h at 80° C. After completion of the reaction, reaction mixture was cooled to ambient temperature, poured into ice-cold water (10 mL) and extracted with EtOAc (3×10 mL). The combined organic layers were washed with brine, dried over sodium sulfate and concentrated under reduced pressure. The crude residue was purified by column chromatography using silica gel and eluting with 0-10% EtOAc in petroleum ether to give 5-(but-2-yn-1-yloxy)-3-methyl-2-vinylpyridine (269G) as an off white solid (85 mg, 61%). MS m/z=188.3 [M+H]$^+$. $^1$H-NMR (400 MHz, CDCl$_3$): δ 8.21 (d, J=2.8 Hz, 1H), 7.03 (d, J=2.4 Hz, 1H), 6.96-6.89 (m, 1H), 6.22 (dd, J=2.4 Hz & 17.2 Hz, 1H), 5.40 (dd, J=2 Hz & 10.8 Hz, 1H), 4.68-4.67 (m, 2H), 2.35 (s, 3H), 1.85 (t, J=2.4 Hz, 3H).

Preparation of 5-(but-2-yn-1-yloxy)-3-methylpicolinaldehyde (269H). OsO$_4$ (2.5 wt. % sol. in tert-butanol) (0.86 mL, 2.7 mmol) was added to a stirred solution of 5-(but-2-yn-1-yloxy)-3-methyl-2-vinylpyridine (5.1 g, 27 mmol) in acetone/water (100/100 mL) at 0° C. The reaction mixture was allowed to stir for 30 min at ambient temperature. Then NaIO$_4$ (23.2 g, 108.0 mmol) was added and the reaction mixture was allowed to stir for additional 4 h at ambient temperature. The reaction mixture was diluted with ice cold water (200 mL) and extracted with EtOAc (3×200 mL). The combined organic layers were washed with brine, dried over Na$_2$SO$_4$ and concentrated under reduced pressure. The crude residue was purified by flash column chromatography on silica gel, eluting with 5-10% EtOAc in petroleum ether to give 5-(but-2-yn-1-yloxy)-3-methylpicolinaldehyde (269H, 3.6 g, 70%) as an off white solid. MS m/z=189.9 [M+H]$^+$. $^1$H-NMR (400 MHz, CDCl$_3$): δ 10.10 (s, 1H), 8.37 (d, J=2.8 Hz, 1H), 7.13 (d, J=2.8 Hz, 1H), 4.77 (d, J=2.4 Hz, 2H), 2.67 (s, 3H), 1.86 (t, J=2 Hz, 3H).

Preparation of Compound 269. A stirred solution of 5-(but-2-yn-1-yloxy)-3-methylpicolinaldehyde (269H, 3.6 g, 19.0 mmol) in water (216 mL)/acetone (36 mL) was treated with sulphamic acid (2.5 g, 25.0 mmol) and 85% sodium chlorite (2.7 g, 29.0 mmol). The reaction mixture was allowed to stir for 2 h at ambient temperature. The reaction mixture was extracted with EtOAc (2×100 mL). The combined organic layer were washed with brine, dried over Na$_2$SO$_4$ and concentrated under reduced pressure. The crude residue was triturated with n-pentane to provide 5-(but-2-yn-1-yloxy)-3-methylpicolinaldehyde (269) as an off white solid (3.2 g, 82%). MS m/z=206.3 [M+H]$^+$. $^1$H-NMR (400 MHz, CD3OD): δ 8.16 (d, J=2.8 Hz, 1H), 7.38 (d, J=2.4 Hz, 1H), 4.84-4.82 (m, 2H), 2.63 (s, 3H), 1.83 (t, J=2 Hz, 3H).

3-Methyl-5-(prop-2-yn-1-yloxy)pyrazine-2-carboxylic acid

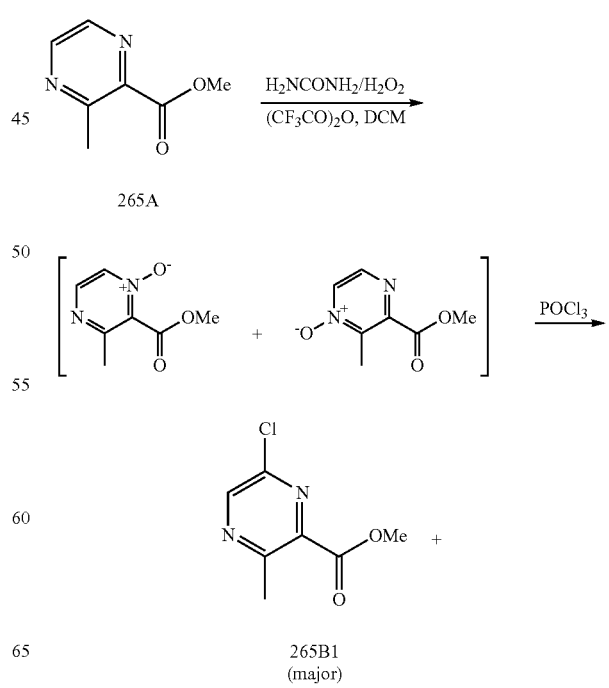

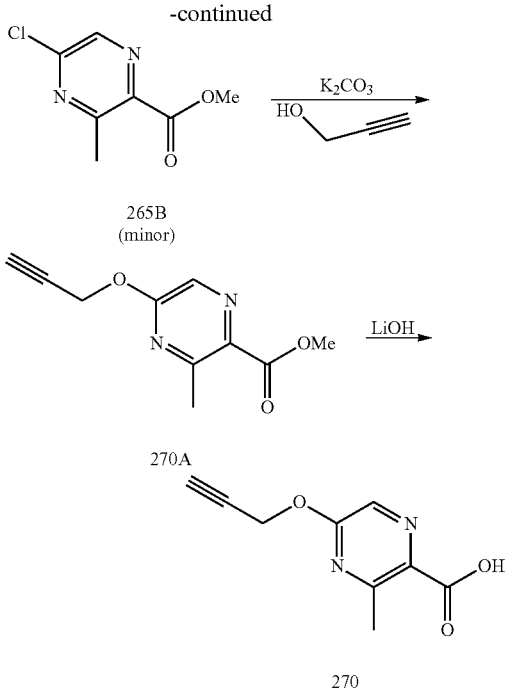

Preparation of Compound 265B. A solution of methyl 3-methylpyrazine-2-carboxylate (265A, 9.1 g, 59.8 mmol) in DCM (100 mL) was cooled to 0° C. was added urea hydrogen peroxide adduct (7.8 g, 83.0 mmol), followed by dropwise addition of trifluoroacetic acid anhydride (10.8 mL, 78.0 mmol). The resulting mixture was stirred at 0° C. for 1 h, and at RT for 18 h, during which LCMS indicated a mixture of two peaks corresponding to MS m/z=169.0 [M+H]⁺. The reaction was diluted with DCM and quenched with saturated Na₂SO₃ solution; the aqueous layer was back-extracted with DCM (2×). The combined organic extracts were dried (MgSO₄), filtered and concentrated in vacuo. ISCO purification (20-80% EtOAc/hexanes) afforded a mixture of two regioisomers, containing 3-(methoxycarbonyl)-2-methylpyrazine 1-oxide and 2-(methoxycarbonyl)-3-methylpyrazine 1-oxide (5.2 g, 30.9 mmol, 51.7% yield). The mixture of regioisomers was taken to next step without further purification. MS m/z=169.0 [M+H]⁺. A solution of the mixture of 3-(methoxycarbonyl)-2-methylpyrazine 1-oxide and 2-(methoxycarbonyl)-3-methylpyrazine 1-oxide (5.1 g, 15.2 mmol) in toluene (50 mL) was cooled to 0° C. and phosphorus oxychloride (2.8 mL, 30.3 mmol) was added under nitrogen followed by DMF (0.12 mL, 1.52 mmol). The reaction mixture was stirred at RT for 4 h, and heated to 65° C. for 18 h, cooled to RT, diluted with EtOAc and washed with saturated NaHCO₃ solution. The aqueous layer was back-extracted with EtOAc (2×). The combined organic extracts were dried (MgSO₄), filtered and concentrated in vacuo. ISCO purification (0-50% EtOAc/hexanes) with care afforded both isomers: methyl 5-chloro-3-methyl-pyrazine-2-carboxylate (265B, 0.68 g) (minor product) denoted by peak 1 and methyl 6-chloro-3-methylpyrazine-2-carboxylate (265B1, 1.50 g) (major product) denoted by peak 2. MS m/z=187.0 [M+H]⁺. Peak 1: ¹H NMR (300 MHz, DMSO-d₆) δ 8.73 (s, 1H), 3.91 (s, 3H), 2.71 (s, 3H). Peak 2: ¹H NMR (300 MHz, DMSO-d₆) δ 8.89 (s, 1H), 3.91 (s, 3H), 2.71 (s, 3H).

Preparation of compound 270A. To a solution of methyl 5-chloro-3-methylpyrazine-2-carboxylate (265B, 750 mg, 4.02 mmol) and propargyl alcohol (356 μL, 6.03 mmol) in 3 mL of DMF was added potassium carbonate (833 mg, 6.03 mmol). After 1 h, about 70% desired conversion was detected by LCMS. Additional propargyl alcohol (356 μL, 6.03 mmol) was added and the reaction was stirred overnight. The reaction was directly loaded to flash column (hexanes/EtOAc=10:1 to 5:1 to 4:1) to give methyl 3-methyl-5-(prop-2-yn-1-yloxy)pyrazine-2-carboxylate (270A, 800 mg, 3.88 mmol, 97% yield) as a white gum. MS m/z=207.0 [M+H]⁺. ¹H NMR (300 MHz, CHLOROFORM-d) δ 8.18 (s, 1H), 5.06 (d, J=2.48 Hz, 2H), 3.97 (s, 3H), 2.80 (s, 3H), 2.52 (t, J=2.41 Hz, 1H).

Preparation of compound 270. A solution of methyl 3-methyl-5-(prop-2-yn-1-yloxy)pyrazine-2-carboxylate (270A, 800 mg, 3.88 mmol) in THF (10 mL) was treated with lithium hydroxide hydrate (488 mg, 11.64 mmol) in 10 mL of water and the mixture was stirred at ambient temperature for 3 h. The mixture was treated with 5 M aqueous HCl (2.4 mL), and extracted with DCM (3×50 mL). The combined organic extracts were dried (Na₂SO₄) and concentrated to give 3-methyl-5-(prop-2-yn-1-yloxy)pyrazine-2-carboxylic acid (270) (380 mg, 1.98 mmol, 51% yield) as a white solid. MS m/z=193.0 [M+H]⁺. ¹H NMR (300 MHz, CHLOROFORM-d) δ 8.05 (s, 1H), 5.09 (d, J=2.48 Hz, 2H), 2.92 (s, 3H), 2.54 (t, J=2.41 Hz, 1H).

5-(2,2,2-Trifluoroethoxy)pyrazine-2-carboxylic acid (272)

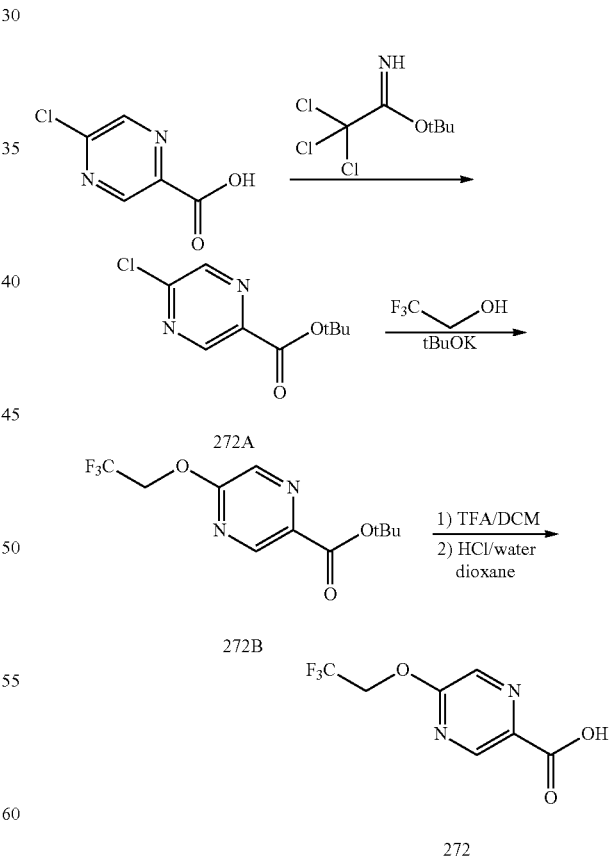

Preparation of tert-butyl 5-chloropyrazine-2-carboxylate (272A). A solution of 5-chloropyrazine-2-carboxylic acid (200.0 g, 1.26 mol) in THF (2.5 L) was treated with a solution of tert-butyl 2,2,2-trichloroacetimidate (460 mL, 2.57 mol) in cyclohexane (2.5 L). The reaction was stirred at 25° C. for 5 min and then treated with boron trifluoride dimethyl etherate (144.0 mL, 126 mmol). The resulting reaction mixture was stirred at 25° C. for 16 h and then diluted with EtOAc (5.0 L), washed with a saturated aqueous sodium bicarbonate solution (4.0 L) followed by water (5.0 L). The organic layer was dried over sodium sulfate, filtered, and concentrated under reduced pressure. The crude material was purified by column chromatography (Silica 60-120 mesh, 10% EtOAc in hexanes) to give tert-butyl 5-chloropyrazine-2-carboxylate (250 g, 92%) as a colorless oil. MS (ESI, positive ion) m/z: 215.2 (M+1)$^+$. $^1$H NMR (400 MHz, CDCl$_3$) δ 9.01 (d, J=1.3 Hz, 1H), 8.70 (d, J=1.3 Hz, 1H), 1.66 (s, 9H).

Preparation of tert-butyl 5-(2,2,2-trifluoroethoxy)pyrazine-2-carboxylate (272B). To a solution of 2,2,2-trifluoroethanol (2.70 mL, 37.00 mmol) in 30 mL of THF at 0° C. was added potassium tert-butoxide (4.47 g, 39.90 mmol) in small portions. The cloudy mixture was stirred at RT for 15 min then cannulated to a solution of tert-butyl 5-chloropyrazine-2-carboxylate (6.11 g, 28.50 mmol) in 50 mL of THF at 0° C. The mixture was stirred at 0° C. for 30 min then quenched with 50 mL of saturated NH$_4$Cl. It was extracted with 200 mL of EtOAc. The organic layer was washed with 25 mL of brine, dried (MgSO$_4$), filtered, and concentrated. The residue was purified on a silica gel column (5-25% EtOAc in heptane) to afford tert-butyl 5-(2,2,2-trifluoroethoxy)pyrazine-2-carboxylate (5.87 g, 21.10 mmol, 74% yield) as an off-white crystalline solid. $^{19}$F NMR (376 MHz, DMSO-d$_6$) δ −72.16 (s, 1F). $^1$H NMR (400 MHz, DMSO-d$_6$) δ 8.81 (d, J=1.37 Hz, 1H), 8.58 (d, J=1.17 Hz, 1H), 5.13 (q, J=8.80 Hz, 2H), 1.57 (s, 9H). m/z (ESI, +ve ion) 279.1

Preparation of 5-(2,2,2-trifluoroethoxy)pyrazine-2-carboxylic acid (272). At RT, a solution of tert-butyl 5-(2,2,2-trifluoroethoxy)pyrazine-2-carboxylate (5.85 g, 21.03 mmol) in 50 mL of DCM was treated with 2,2,2-trifluoroacetic acid (24.14 mL) drop wise. The resulting mixture was stirred at RT for 3 h. The reaction mixture was concentrated under reduced pressure and the crude product was azeotroped with toluene (3×5 mL). The crude product was stirred with 5% EtOAc in hexanes (20 mL) for 1 h and filtered. The filtrate was discarded. The white solid thus obtained was washed with hexanes (2×10 mL) and collected to afford 5-(oxazol-2-ylmethoxy)pyrazine-2-carboxylic acid as a white crystalline solid which was suspended in 10 mL of dioxane and treated with 4 N HCl in dioxane (40 mmol, 10 mL) followed by 5 mL of water. The mixture was stirred for 5 min at RT. It was concentrated to dryness, then azeotroped with toluene (3×5 mL) to provide 5-(2,2,2-trifluoroethoxy)pyrazine-2-carboxylic acid (4.41 g, 19.85 mmol, 94% yield) as a white crystalline solid. $^{19}$F NMR (377 MHz, DMSO-d$_6$) δ −72.16. $^1$H NMR (400 MHz, DMSO-d$_6$) δ 13.48 (br., 1H), 8.86 (d, J=1.17 Hz, 1H), 8.60 (d, J=1.17 Hz, 1H), 5.15 (q, J=9.00 Hz, 2H). m/z (ESI, +ve ion) 223.1

5-(Prop-2-yn-1-yloxy)pyrazine-2-carboxylic acid (273)

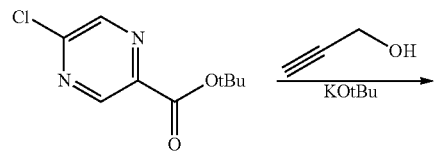

272A

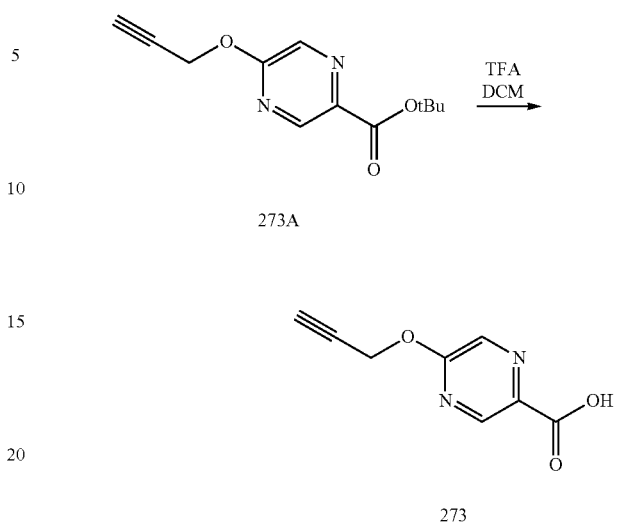

Preparation of tert-butyl 5-(prop-2-yn-1-yloxy)pyrazine-2-carboxylate. A solution of potassium tert-butoxide (272A, 78.0 g, 699 mmol) in 1,4-dioxane (2.5 L) was cooled to 0° C. and propargyl alcohol (39.2 g, 699 mmol) was added dropwise. The resulting mixture was allowed to stir for 10 min. A solution of tert-butyl 5-chloropyrazine-2-carboxylate (125 g, 582 mmol) in 1,4-dioxane (1.3 L) was added dropwise to the reaction mixture. The mixture was allowed to slowly warm to ambient temperature and stir for 4 h. The reaction mixture was quenched with sat. aq. NH$_4$Cl (2.0 L) and stirred for 10 min. The reaction mixture was diluted with EtOAc (3.0 L) and water (2.5 L). The layers were separated and the aqueous layer was extracted with EtOAc (3×2 L). The combined organic extract was dried over sodium sulfate, filtered and concentrated under reduced pressure to get the crude product which was purified by column chromatography (silica gel 60-120 mesh, 10% EtOAc in hexanes) to afford tert-butyl 5-(prop-2-yn-1-yloxy)pyrazine-2-carboxylate (70 g, 51%) as tan solid. MS (ESI, positive ion) m/z: 235.2 (M+H)$^+$. $^1$H NMR (400 MHz, CDCl$_3$) 8.83 (d, J=1.3 Hz, 1H), 8.35 (d, J=1.3 Hz, 1H), 5.06 (s, 2H), 2.54 (s, 1H), 1.64 (s, 9H).

Preparation of 5-(prop-2-yn-1-yloxy)pyrazine-2-carboxylic acid (273). A solution of tert-butyl 5-(prop-2-yn-1-yloxy)pyrazine-2-carboxylate (140 g, 598 mol) in DCM (480 mL) was cool to 0° C. and TFA (1.4 L) was added dropwise. The reaction mixture was stirred at ambient temperature for 4 h. The reaction mixture was concentrated under reduced pressure to obtain the crude material which was azeotroped with toluene (3×1.0 L). The crude material was stirred with 10% EtOAc in hexanes (2.0 L) for 1 h and filtered. The solid was washed with hexane (3.0 L) to provide tert-butyl 5-(prop-2-yn-1-yloxy)pyrazine-2-carboxylate (103 g, 97%) as white solid. MS (ESI, positive ion) m/z: 179.1 (M+H)$^+$. $^1$H NMR (400 MHz, DMSO-D$_6$) δ 13.41 (s, 1H), 8.83 (d, J=1.3 Hz, 1H), 8.46 (d, J=1.3 Hz, 1H), 5.11 (d, J=2.4 Hz, 2H), 3.64 (s, 1H).

5-((1,1-dideuteriumprop-2-yn-1-yl)oxy)pyrazine-2-carboxylic acid (274)

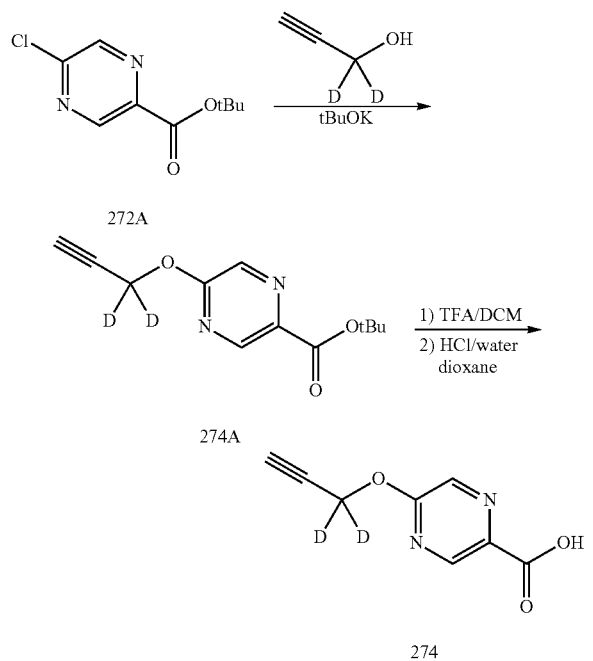

5-(2,2,3,3-Tetrafluoropropoxy)pyrazine-2-carboxylic acid (275)

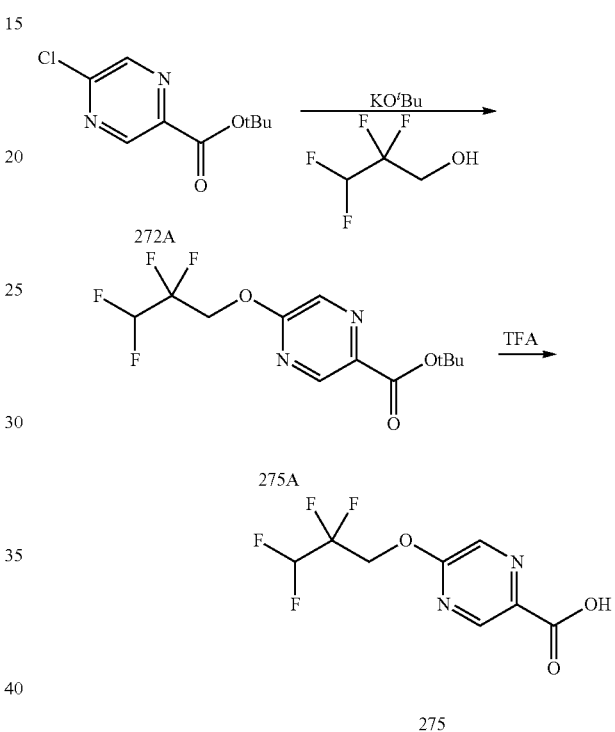

Preparation of tert-butyl 5-((1,1-dideuterium-prop-2-yn-1-yl)oxy)pyrazine-2-carboxylate (274A). To a solution of 1,1-dideuterium-prop-2-yn-1-ol (1.81 g, 31.1 mmol) [cat #AM1043, Adesis Inc.] in 30 mL of THF at 0° C. was added potassium tert-butoxide (3.77 g, 33.60 mmol) in small portions. The cloudy mixture was stirred at RT for 15 min then cannulated to a solution of tert-butyl 5-chloropyrazine-2-carboxylate (5.34 g, 24.88 mmol) in 50 mL of THF at 0° C. The mixture was stirred at 0° C. for 30 min then treated with 50 mL of saturated NH$_4$Cl followed by 200 mL of EtOAc. The mixture was transferred to a separatory funnel and the layers were separated. The organic layer was washed with 25 mL of brine, dried (MgSO$_4$), filtered, and concentrated. The residue was purified on a silica gel column (5-25% EtOAc in heptanes) to afford tert-butyl 5-((1,1-dideuterium-prop-2-yn-1-yl)oxy)pyrazine-2-carboxylate (1.40 g, 5.93 mmol, 24% yield) as a colorless viscous oil. $^1$H NMR (400 MHz, DMSO-d$_6$) δ 8.81 (d, J=1.37 Hz, 1H), 8.46 (d, J=1.37 Hz, 1H), 3.63 (s, 1H), 1.57 (s, 9H). m/z (ESI, +ve ion) 259.1 (M+23)$^+$.

Preparation of 5-((1,1-dideuteriumprop-2-yn-1-yl)oxy)pyrazine-2-carboxylic acid (274). At RT, a solution of tert-butyl 5-((1,1-dideuterium-prop-2-yn-1-yl)oxy)pyrazine-2-carboxylate (1.40 g, 5.93 mmol) in 10 mL of DCM was treated with 2,2,2-trifluoroacetic acid (5.44 mL, 71.1 mmol) drop wise. The resulting mixture was stirred at RT for 4 h. The reaction mixture was concentrated under reduced pressure and the crude product was azeotroped with toluene (2×5 mL). The crude product was stirred with 5% EtOAc in hexanes (20 mL) for 1 h and filtered. The filtrate was discarded. The white solid thus obtained was washed with hexanes (2×10 mL) and collected. $^{19}$F-NMR of the white solid indicated the presence of trace amount of 2,2,2-trifluoroacetic acid. The off white solid was suspended in 3 mL of dioxane and treated with 4 N HCl in dioxane (6 mmol, 1.5 mL) followed by 1 mL of water. The mixture was stirred for 5 min at RT. It was concentrated to dryness, then azeotroped with toluene (5 mL) to provide 5-((1,1-dideuteriumprop-2-yn-1-yl)oxy)pyrazine-2-carboxylic acid (1.0 g, 5.55 mmol, 94% yield) as a white crystalline solid. $^{19}$F-NMR of the white solid indicated the absence of 2,2,2-trifluoroacetic acid. $^1$H NMR (400 MHz, DMSO-d$_6$) δ 13.36 (br., 1H), 8.84 (d, J=1.17 Hz, 1H), 8.47 (d, J=1.17 Hz, 1H), 3.63 (s, 1H). m/z (ESI, +ve ion) 181.2 (M+H)$^+$.

To a solution of 2,2,3,3-tetrafluoro-1-propanol (1.1 mL, 8.4 mmol) in 5 mL of THF at 0° C. was added a solution of potassium tert-butoxide (1.0 M solution in THF (9.08 mL, 9.08 mmol)) by syringe over 2 min. The orange mixture was stirred at RT for 15 min then cannulated to a solution of tert-butyl 5-chloropyrazine-2-carboxylate (272A, 1.5 g, 6.99 mmol) in 15 mL of THF at 0° C. The mixture was stirred at 0° C. for 30 min. The reaction was quenched with saturated aqueous NH$_4$Cl (30 mL) and diluted with EtOAc (100 mL) and water (30 mL). The layers were separated and the organic layer was washed with brine (25 mL), dried over Na$_2$SO$_4$, filtered, and concentrated in vacuo. The residue was purified by silica gel chromatography eluting with a gradient of 0-30% EtOAc/heptane to give tert-butyl 5-(2,2,3,3-tetrafluoropropoxy)pyrazine-2-carboxylate as a yellow solid (275A, 1.88 g, 87%). LC/MS (ESI$^+$) m/z=333.1 (M+Na)$^+$. $^1$H NMR (400 MHz, chloroform-d) δ 8.81 (d, J=1.17 Hz, 1H), 8.41 (d, J=1.17 Hz, 1H), 5.83-6.17 (m, 1H), 4.84 (t, J=12.72 Hz, 2H), 1.65 (s, 9H).

2,2,2-Trifluoroacetic acid (6.66 mL, 87 mmol) was added at RT to a stirring solution of tert-butyl 5-(2,2,3,3-tetrafluoropropoxy)pyrazine-2-carboxylate (275A, 1.8 g, 5.8 mmol) in DCM (11.6 mL). The pink solution was stirred at RT for 3 h and then concentrated in vacuo. The residue was azeotroped with toluene (2×25 mL) to give 5-(2,2,3,3-tetrafluoropropoxy)pyrazine-2-carboxylic acid (275) as a white solid (1.38 g, 94%). LC/MS (ESI+) m/z=255.1 (M+H)+. ¹H NMR (400 MHz, DMSO-d₆) δ 13.44 (br. s., 1H), 8.83 (d, J=1.37 Hz, 1H), 8.53 (d, J=1.17 Hz, 1H), 6.54-6.87 (m, 1H), 5.00 (t, J=14.08 Hz, 2H).

5-(3,3,3-Trifluoropropoxy)pyrazine-2-carboxylic acid (276)

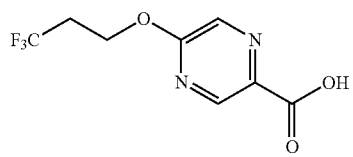

The title compound was synthesized according to intermediate 275, using 3,3,3-trifluoropropan-1-ol to react with tert-butyl 5-chloropyrazine-2-carboxylate 272A. LC/MS (ESI+) m/z=237.1 (M+H)+. ¹H NMR (400 MHz, DMSO-d₆) δ 13.32 (br. s., 1H), 8.83 (d, J=1.17 Hz, 1H), 8.41 (d, J=1.17 Hz, 1H), 4.63 (t, J=5.97 Hz, 2H), 2.88 (m, 2H). ¹⁹F NMR (376 MHz, DMSO-d₆) δ −63.2.

5-(2,2-Difluoropropoxy)pyrazine-2-carboxylic acid (277)

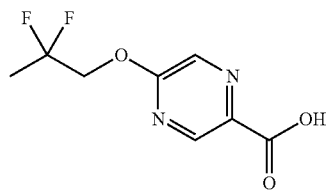

The title compound was synthesized according to intermediate 275, using 3,3,3-trifluoropropan-1-ol to react with tert-butyl 5-chloropyrazine-2-carboxylate 272A. LC/MS (ESI+) m/z=219.2 (M+H)+. ¹H NMR (400 MHz, DMSO-d₆) δ 13.38 (br. s., 1H), 8.82 (d, J=1.17 Hz, 1H), 8.51 (d, J=0.98 Hz, 1H), 4.70 (t, J=13.20 Hz, 2H), 1.76 (t, J=19.27 Hz, 3H); ¹⁹F NMR (376 MHz, DMSO-d₆) δ −97.3.

5-(3-Fluoropropoxy)pyrazine-2-carboxylic acid (278)

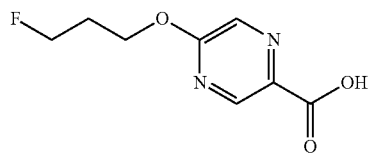

The title compound was synthesized according to intermediate 275, using 3,3,3-trifluoropropan-1-ol to react with tert-butyl 5-chloropyrazine-2-carboxylate 272A. LC/MS (ESI+) m/z=201.2 (M+H)+. ¹H NMR (400 MHz, DMSO-d₆) δ 8.80 (d, J=1.17 Hz, 1H), 8.38 (d, J=1.37 Hz, 1H), 4.67 (t, J=5.87 Hz, 1H), 4.55 (t, J=5.87 Hz, 1H), 4.49 (t, J=6.36 Hz, 2H), 2.08-2.23 (m, 2H); ¹⁹F NMR (376 MHz, DMSO-d₆) δ −74.5.

3-Methyl-5-(oxazol-2-ylmethoxy)pyrazine-2-carboxylic acid (279)

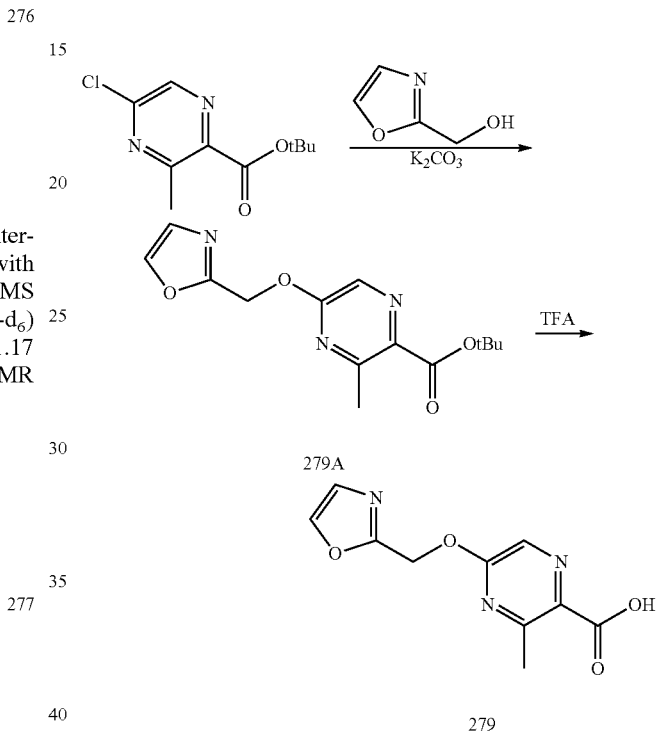

To a solution of tert-butyl 5-chloro-3-methylpyrazine-2-carboxylate (3.8 g, 16.62 mmol) and oxazol-2-ylmethanol ((Combi-Blocks Inc., 3.29 g, 33.2 mmol) in 3 mL of DMF was added potassium carbonate (4.59 g, 33.2 mmol). The reaction mixture was stirred overnight. The contents were loaded onto a flash column and eluted with a gradient of (hexanes: EtOAc=5:1 to 2:1) to give tert-butyl 3-methyl-5-(oxazol-2-ylmethoxy)pyrazine-2-carboxylate (279A, 4.16 g, 14.28 mmol, 86% yield) as a colorless oil. ¹H NMR (300 MHz, CHLOROFORM-d) δ 8.20 (s, 1H), 7.69 (d, J=0.88 Hz, 1H), 7.16 (s, 1H), 5.53 (s, 2H), 2.71 (s, 3H), 1.63 (s, 9H). To the ester was added TFA (18.52 mL, 249 mmol) dropwise and the mixture was stirred at RT overnight. The TFA was removed in vacuo. The residue was treated with 15 mL of 1 N aqueous HCl and azeotroped in vacuo to remove the residual TFA (repeated twice). The residue was dried under house vacuum overnight to give 3-methyl-5-(oxazol-2-ylmethoxy)pyrazine-2-carboxylic acid (3.6 g, 15.31 mmol, 92% yield) as a white solid. ¹H NMR (300 MHz, CHLOROFORM-d) δ 8.10 (s, 1H), 7.71 (d, J=0.88 Hz, 1H), 7.18 (s, 1H), 5.59 (s, 2H), 2.91 (s, 3H). LC/MS (ESI+) m/z=236.0 (M+H)+.

5-(Oxazol-2-ylmethoxy)pyrazine-2-carboxylic acid (280)

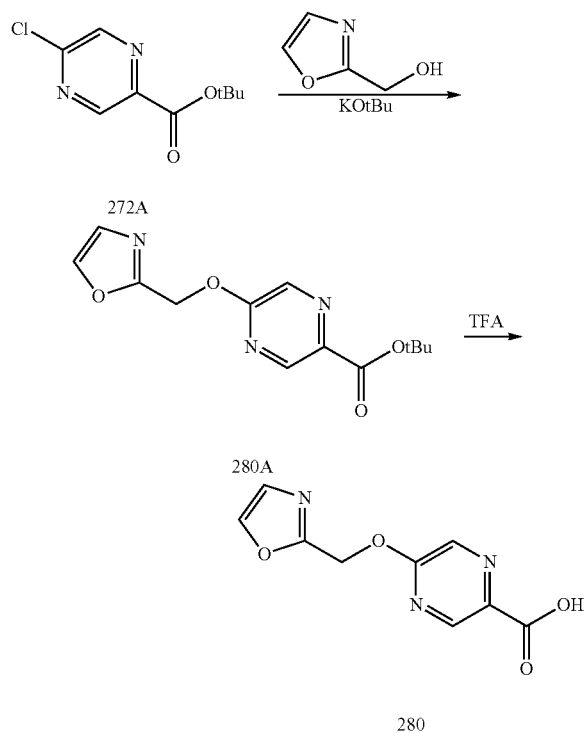

Compound 280A (3.07 g, 11.07 mmol, 66% yield) as an off white crystalline solid was prepared according to intermediate 272B starting from 272A (3.59 g, 16.72 mmol) and oxazol-2-ylmethanol (Combi-Blocks Inc., 1.99 g, 20.07 mmol). LC/MS (ESI+) m/z=278.1 (M+H)+.

Compound 280 (4.15 g, 18.76 mmol, 99% yield) as an off white crystalline solid was prepared according to intermediate 272 starting from 280A (5.26 g, 18.97 mmol). $^1$H NMR (400 MHz, DMSO-$d_6$) δ 8.81 (m, 1H), 8.50 (d, J=1.37 Hz, 1H), 8.18 (d, J=0.78 Hz, 1H), 7.28 (s, 1H), 5.58 (s, 2H), 4.55-5.55 (br., 1H). LC/MS (ESI+) m/z=222.0 (M+H)+.

3-Methyl-5-(oxazol-2-ylmethoxy)picolinic acid (281)

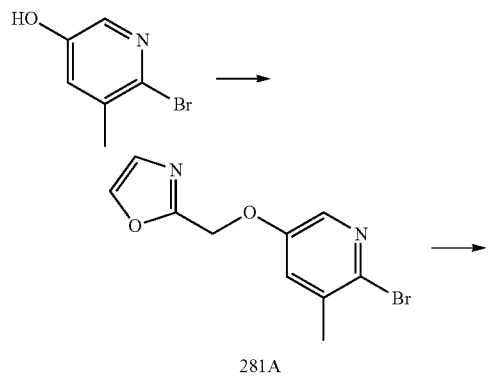

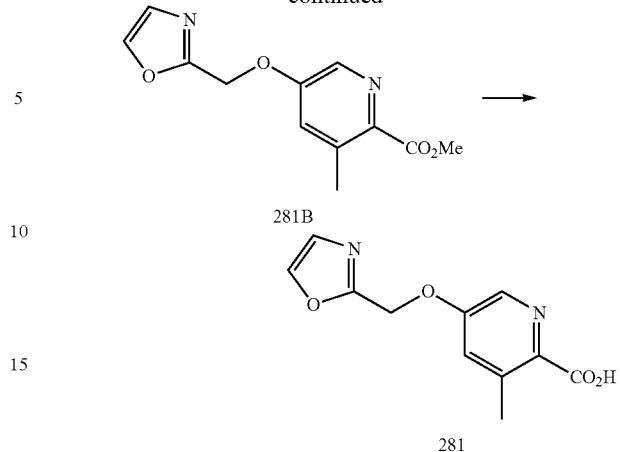

Preparation of 2-(((6-bromo-5-methylpyridin-3-yl)oxy)methyl)oxazole (281A). To a solution of 2-oxazolemethanol (1.12 g, 11.30 mmol, Combi-Blocks Inc.) and triphenylphosphine (3.72 g, 14.18 mmol) in THF (20 mL) was added 2-bromo-5-hydroxy-3-picoline (2.27 g, 12.07 mmol, AOB Chem USA). The mixture was cooled to 0° C. and 1,2-ethoxycarbonyl diazene (2.5 mL, 13.72 mmol) was added slowly. The solution was slowly allowed to warm to RT. After 21 h, diisopropyl azodicarboxylate (1.5 mL, 7.63 mmol) was added to the mixture. About 1.5 h later, a second batch of diisopropyl azodicarboxylate (1.5 mL, 7.63 mmol) was added. The mixture was stirred at RT for an additional 4 h and was diluted with EtOAc (50 mL). The solution was washed with NaOH (0.5 N, 10 mL), water, brine, and then dried over $Na_2SO_4$ and concentrated. The residue was purified by silica gel chromatography (10-50% EtOAc in DCM) to afford 2-(((6-bromo-5-methylpyridin-3-yl)oxy)methyl)oxazole (3.8 g, ~80% pure) as a white solid that contained the hydrazine by-product as impurities (based on $^1$H-NMR). LCMS (ESI, pos.) 269.0 (M+1)+. $^1$H NMR (400 MHz, CHLOROFORM-d) δ 8.02 (d, J=2.93 Hz, 1H), 7.70 (d, J=0.78 Hz, 1H), 7.23 (d, J=2.74 Hz, 1H), 7.17 (s, 1H), 5.18 (s, 2H), 2.37 (s, 3H).

Preparation of methyl 3-methyl-5-(oxazol-2-ylmethoxy)picolinate (281B). To a mixture of palladium (II) acetate (63 mg, 0.28 mmol) and 4,5-bis(diphenylphosphino)-9,9-dimethylxanthene (327 mg, 0.56 mmol) under $N_2$ was added 2-(((6-bromo-5-methylpyridin-3-yl)oxy)methyl)oxazole (281A, 3.8 g, 11.30 mmol, ~80% pure) in MeOH (50 mL, 1233 mmol) and TEA (18.90 mL, 136 mmol) in a 250 mL pressure tube. The mixture was evacuated-purged with CO gas (balloon) 3-times. The valves were closed and the mixture was heated at 70° C. for 24 h. The mixture was removed from the heater and was filtered through a pad of Celite® filter aid. The Celite® filter aid was washed with EtOAc (3×20 mL). The filtrate was concentrated in vacuo and partitioned between EtOAc (60 mL) and saturated $NaHCO_3$ (40 mL). The organic layer was dried over $Na_2SO_4$ and concentrated in vacuo. The crude material was purified by silica gel chromatography using a gradient of 0-5% MeOH in EtOAc. The product was obtained as a white solid (1.9 g, 68% over two steps). LCMS (ESI, pos.) 249.1 (M+1)+. $^1$H NMR (400 MHz, CHLOROFORM-d) δ 8.33 (d, J=2.74 Hz, 1H), 7.71 (s, 1H), 7.23 (d, J=2.54 Hz, 1H), 7.18 (s, 1H), 5.25 (s, 2H), 3.95 (s, 3H), 2.63 (s, 3H).

Preparation of 3-methyl-5-(oxazol-2-ylmethoxy)picolinic acid (281). To a solution of methyl 3-methyl-5-(oxazol-2- ylmethoxy)picolinate (281B, 1.9 g, 7.65 mmol) in THF (20 mL) was added water (6 mL) followed by lithium hydroxide monohydrate (350 mg, 8.34 mmol). After 3 h, the mixture was concentrated to remove most of the THF. The pH of the aqueous layer was adjusted to 3-4 by HCl (5 N). Solid NaCl was added to saturate the solution. The mixture was extracted with 2% IPA in CHCl$_3$ (5×30 mL). The combined organic phases were dried over Na$_2$SO$_4$, filtered, and concentrated to give a white solid (1.74 g, 95%). LCMS (ESI, pos.) 235.1 (M+1)$^+$. $^1$H NMR (400 MHz, CHLOROFORM-d) δ 8.21 (d, J=2.35 Hz, 1H), 7.73 (s, 1H), 7.31 (d, J=2.15 Hz, 1H), 7.19 (s, 1H), 5.28 (s, 2H), 2.76 (s, 3H).

3-Methyl-5-(2,2,2-trifluoroethoxy)picolinic acid (282)

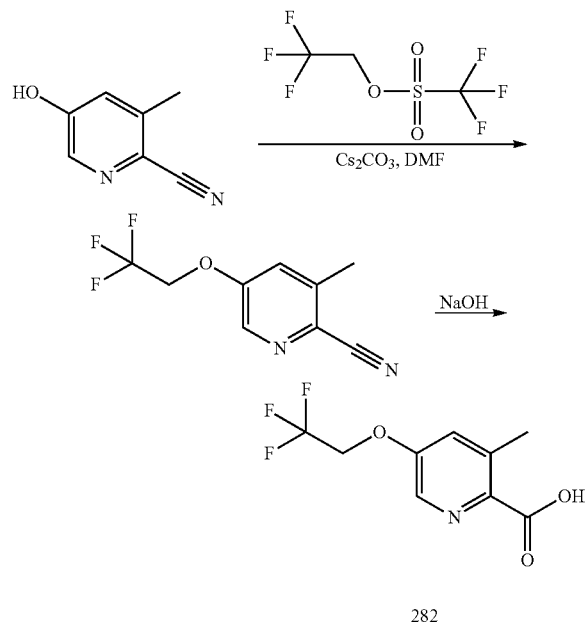

282

To a solution of 5-hydroxy-3-methylpicolinonitrile (0.49 g, 3.63 mmol) in DMF (5 mL) were added cesium carbonate (1.54 g, 4.72 mmol) and 2,2,2-trifluoroethyl trifluoromethanesulfonate (1.01 mL, 4.36 mmol). The resulting suspension was stirred at RT overnight. The reaction mixture was diluted with water and EtOAc. The organic layer was washed with 1 M LiCl solution and brine, dried over MgSO$_4$ and concentrating in vacuo. The crude 3-methyl-5-(2,2,2-trifluoroethoxy)picolinonitrile was taken up in EtOH (20 mL) and 1 M NaOH (10.89 mL, 10.89 mmol) was added. The reaction was heated at reflux until the conversion was complete. The mixture was cooled to RT and diluted with ether and water. The organic layer was washed with additional water and the combined aqueous layers were acidified to pH=1 by the addition of 1 M HCl. The aqueous layer was extracted with DCM twice and the combined organics were washed with brine, dried over MgSO$_4$ and concentrated in vacuo to afford 3-methyl-5-(2,2,2-trifluoroethoxy)picolinic acid (0.75 g, 88% yield). LC/MS (ESI$^-$) m/z=236 (M+H)$^+$. $^1$H NMR (300 MHz, DMSO-d6) δ ppm 2.50 (s, 3H) 4.94 (q, J=8.77 Hz, 2H) 7.53 (d, J=2.63 Hz, 1H) 8.28 (d, J=2.78 Hz, 1H).

3-Methyl-5-(prop-2-yn-1-yloxy)picolinic acid (283)

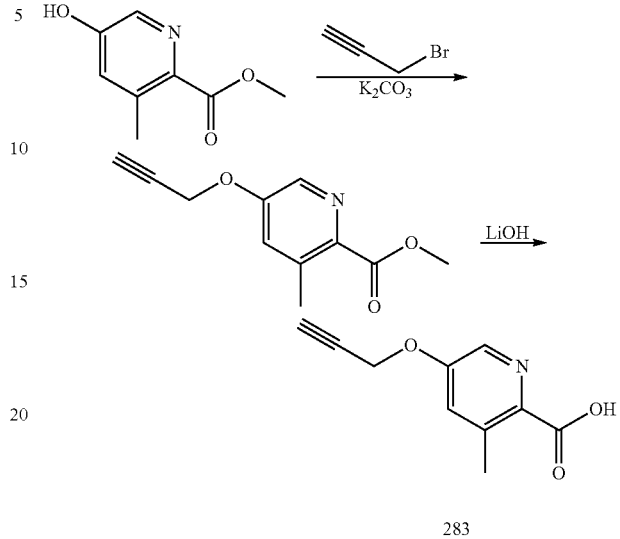

283

To a suspension of methyl 5-hydroxy-3-methylpicolinate (1.00 g, 5.98 mmol) and potassium carbonate (1.24 g, 8.97 mmol) in DMF (25 mL) was added propargyl bromide (80% solution in toluene, 0.80 mL, 7.18 mmol) dropwise at RT. The mixture was heated to 45° C. for 1 h, then diluted with EtOAc and washed with water and brine. The organic solution was dried over Na$_2$SO$_4$ and concentrated in vacuo. Purification by silica gel chromatography (40 g, 0-70% EtOAc in hexanes) afforded methyl 3-methyl-5-(prop-2-yn-1-yloxy)picolinate as yellow solid (1.21 g, 99% yield). LC/MS (ESI$^-$) m/z=206 (M+H)$^+$. $^1$H NMR (400 MHz, CHLOROFORM-d) δ ppm 2.58 (t, J=2.45 Hz, 1H) 2.64 (s, 3H) 3.96 (s, 3H) 4.79 (d, J=2.54 Hz, 2H) 7.16 (d, J=2.54 Hz, 1H) 8.31 (d, J=2.74 Hz, 1H).

To a suspension of methyl 3-methyl-5-(prop-2-yn-1-yloxy)picolinate (1.21 g, 5.90 mmol) and lithium hydroxide hydrate (0.26 g, 6.19 mmol) was added THF (16 mL) and water (4 mL). The mixture was stirred at RT for 1.5 h, then neutralized with 8.5 mL of 1 N HCl, and diluted with brine and a mixed solvent of i-PrOH:CHCl$_3$ (v/v 1:3). The aqueous layer was further extracted with the mixed solvent. The organic layer was dried over Na$_2$SO$_4$ and concentrated in vacuo to give 3-methyl-5-(prop-2-yn-1-yloxy)picolinic acid (1.10 g, 98% yield) as off-white solid. LC/MS (ESI$^-$) m/z=192 (M+H)$^+$. $^1$H NMR (400 MHz, CHLOROFORM-d) δ ppm 2.62 (br. s., 1H) 2.77 (s, 3H) 4.82 (br. s., 2H) 7.26 (br. s., 1H) 8.18 (br. s., 1H).

(S)-5-(But-3-yn-2-yloxy)-3-methylpyrazine-2-carboxylic acid (284)

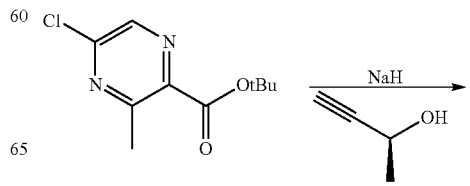

287

-continued

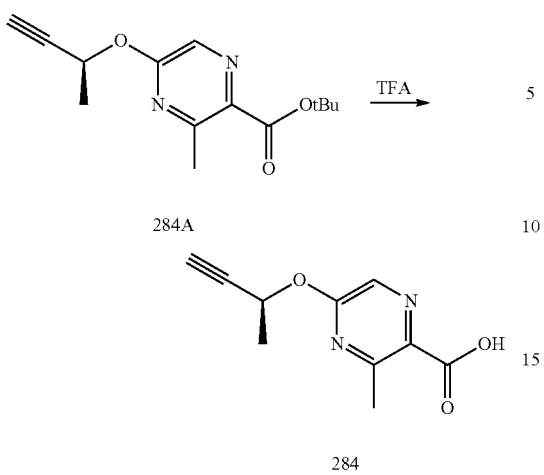

288

-continued

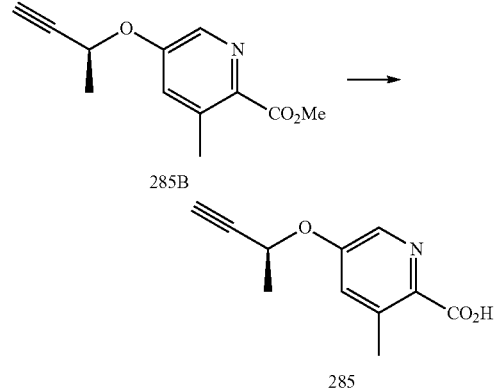

Preparation of (S)-tert-butyl 5-(but-3-yn-2-yloxy)-3-methylpyrazine-2-carboxylate (284A). To a solution of tert-butyl 5-chloro-3-methylpyrazine-2-carboxylate (2.50 g, 10.93 mmol) and (S)-3-butyn-2-ol (0.95 mL, 12.03 mmol) in THF (10 mL) at 0° C. was added in portion wise sodium hydride (60% wt. in oil, 0.48 g, 12.03 mmol). The reaction was stirred at 0° C. for 2 h, treated with saturated NH$_4$Cl solution (100 mL) and extracted with EtOAc (200 mL). The organic solution was concentrated under reduced pressure and the residue was purified via silica gel chromatography (0-10% EtOAc in heptane) to afford (S)-tert-butyl 5-(but-3-yn-2-yloxy)-3-methylpyrazine-2-carboxylate (1.25 g, 4.77 mmol, 43% yield) as a colorless oil. LC/MS (ESI$^+$) m/z=285.0 (M+23)$^+$. $^1$H NMR (300 MHz, CHLORO-FORM-d) δ 8.13 (s, 1H), 5.85 (dq, J=2.05, 6.67 Hz, 1H), 2.73 (s, 3H), 2.46 (d, J=2.05 Hz, 1H), 1.67 (d, J=6.72 Hz, 3H), 1.65 (s, 9H).

Preparation of Compound 284. TFA (20 mL, 269 mmol) was added at RT to a stirring solution of (S)-tert-butyl 5-(but-3-yn-2-yloxy)-3-methylpyrazine-2-carboxylate (1.85 g, 7.05 mmol) in DCM (20 mL). The reaction mixture was stirred at RT for 4 h and then concentrated in vacuo. The residue was dissolved in 4 N HCl in dioxane (5 mL) and 1 N HCl (10 mL), stirred at RT for 30 min and concentrated in vacuo to give (S)-5-(but-3-yn-2-yloxy)-3-methylpyrazine-2-carboxylic acid (1.3 g, 6.30 mmol, 89% yield). LC/MS (ESI$^+$) m/z=207.2 (M+H)$^+$. $^1$H NMR (400 MHz, DMSO-d$_6$) δ 13.10 (br. s., 1H), 8.22 (s, 1H), 5.80 (dq, J=2.05, 6.62 Hz, 1H), 3.56-3.59 (m, 1H), 2.69 (s, 3H), 1.60 (d, J=6.65 Hz, 3H).

Preparation of (S)-methyl 5-(but-3-yn-2-yloxy)-3-methylpicolinate (285)

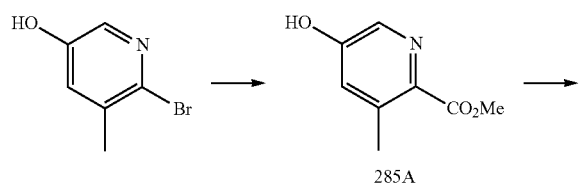

Preparation of methyl 5-hydroxy-3-methylpicolinate (285A). To a mixture of 2-bromo-5-hydroxy-3-picoline (2.18 g, 11.59 mmol), TEA (19.39 mL, 139 mmol), and MeOH (30 mL, 740 mmol) in a 250 mL pressure tube was added 4,5-bis(diphenylphosphino)-9,9-dimethylxanthene (335 mg, 0.58 mmol) and palladium (II) acetate (65 mg, 0.29 mmol). The mixture was evacuated-purged with CO gas (balloon) 3-times. The valves were closed and the mixture was heated at 70° C. for 24 h. The mixture was filtered through a pad of Celite® filter aid. The Celite® filter aid was washed with MeOH. The filtrate was concentrated in vacuo and dissolved in DCM (50 mL). The organic solution was washed with saturated NaHCO$_3$ (30 mL). The aqueous layer was saturated with NaCl and extracted with 2% IPA in CHCl$_3$ (3×20 mL). The combined organic layers were dried over Na$_2$SO$_4$ and concentrated in vacuo. The crude was purified by silica gel chromatography using 1-5% MeOH in DCM to give the product as an off-white solid (1.65 g, 85%). LCMS (ESI, pos.) 168.0 (M+1)$^+$. $^1$H NMR (400 MHz, DMSO-d$_6$) δ 10.57 (br. s., 1H), 8.02 (d, J=2.54 Hz, 1H), 7.08 (d, J=2.15 Hz, 1H), 3.79 (s, 3H), 2.44 (s, 3H).

Preparation of (S)-methyl 5-(but-3-yn-2-yloxy)-3-methylpicolinate (285B). To a solution of (R)-(+)-3-butyn-2-ol (Sigma-Aldrich, 0.294 mL, 4.19 mmol), triphenylphosphine (1.2 g, 4.58 mmol) and methyl 5-hydroxy-3-methylpicolinate (285A, 0.7 g, 4.19 mmol) in THF (20 mL) at 0° C. was added diisopropyl azodicarboxylate (1.0 mL, 5.09 mmol) slowly. The solution was allowed to warm to RT and stirred overnight. About ~¼ of the theoretical amount of the alcohol, PPh$_3$, and DIAD were added and the mixture was stirred for additional 1.5 h. The mixture was quenched with MeOH (2 mL) and concentrated. The residue was purified by silica gel chromatography (10-50% EtOAc/heptane) to afford (S)-methyl 5-(but-3-yn-2-yloxy)-3-methylpicolinate (1.9 g, 8.67 mmol, 207% yield) as a white foam that was contaminated by the hydrazine by-product. LCMS (ESI, pos.) 220.1 (M+1)$^+$. $^1$H NMR (400 MHz, CHLOROFORM-d) δ 8.32 (d, J=2.74 Hz, 1H), 7.21 (d, J=2.54 Hz, 1H), 4.98 (m, 1H, overlapping with DIAD OC-H), 3.96 (s, 3H), 2.64 (s, 3H), 2.54 (d, J=1.96 Hz, 1H), 1.71 (d, J=6.46 Hz, 4H).

Preparation of (S)-methyl 5-(but-3-yn-2-yloxy)-3-methylpicolinate (285). A mixture of (S)-methyl 5-(but-3-yn-2-yloxy)-3-methylpicolinate prepared above (285B, 1.9 g contaminated, theoretical 4.11 mmol) and lithium hydroxide (270 mg, 6.43 mmol) in MeOH (10 mL) and water (10 mL) was stirred at RT for 3 h. The mixture was concentrated to remove most of the MeOH. The aqueous layer was extracted with DCM (3×10 mL) to remove hydrazine carried from previous step. The aqueous layer was treated with HCl (5 N, 1.5 mL) to bring the pH of the solution to ~3-4. Solid NaCl was added to saturate the solution. The mixture was extracted with 2% IPA in CHCl₃ (3×10 mL). The combined organic phases were dried over Na₂SO₄, filtered, and concentrated to give a white solid that was still not pure. The solid was dissolved in EtOAc (30 mL) and extracted with saturated NaHCO₃ (3×10 mL). The combined aqueous layers were acidified with HCl (conc.) until the pH reached ~3. The solution was saturated with NaCl and extracted with 2% IPA in CHCl₃ (3×10 mL). The combined organic phases were dried over Na₂SO₄, filtered, and concentrated. The resulting solid was suspended in ACN (5 mL) and water (2 mL) and was lyophilized for 48 h to give a white powder (0.78 g, 92% yield over two steps). LCMS (ESI, pos.) 206.0 (M+1)⁺. ¹H NMR (400 MHz, CHLOROFORM-d) δ 8.17 (d, J=2.35 Hz, 1H), 7.27 (d, J=2.15 Hz, 1H), 4.97 (dq, J=1.96, 6.52 Hz, 1H), 4.75 (s, 1H), 2.76 (s, 3H), 2.57 (d, J=2.15 Hz, 1H), 1.73 (d, J=6.46 Hz, 3H).

(S)-3-Methyl-5-(1-(oxazol-2-yl)ethoxy)pyrazine-2-carboxylic acid (286)

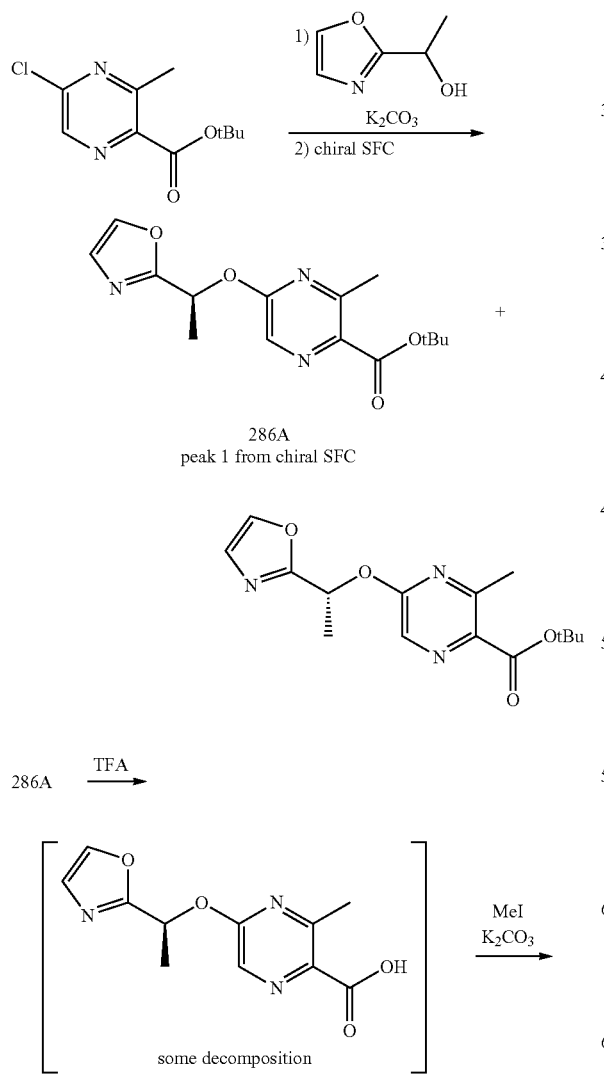

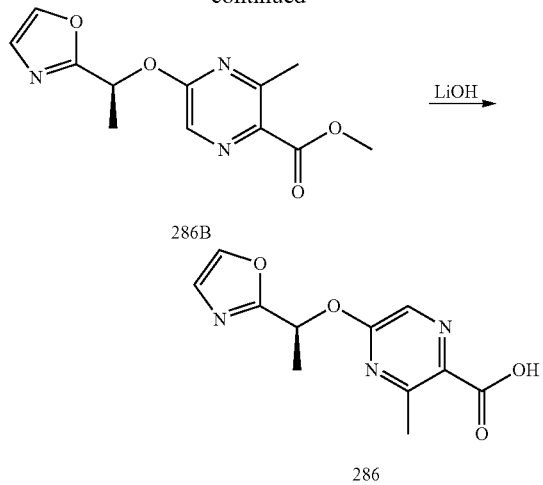

Preparation of Compound 286A. To a solution of tert-butyl 5-chloro-3-methylpyrazine-2-carboxylate (7.0 g, 30.6 mmol) and 1-(oxazol-2-yl)ethanol (5.19 g, 45.9 mmol) in 5 mL of DMF was added potassium carbonate (8.46 g, 61.2 mmol). The reaction was stirred overnight. LCMS showed about 10-20% conversion. It was heated at 55° C. for another 24 h. LCMS showed >90% conversion. The reaction was directly loaded onto a silica gel column and eluted with a gradient of (heptane/EtOAc=5:1 to 4:1 to 2:1) to give tert-butyl 3-methyl-5-(1-(oxazol-2-yl)ethoxy)pyrazine-2-carboxylate as a colorless oil. This material (5.5 g) was chromatographed using supercritical CO₂ (additives 10% of 20 mM NH₃ in IPOH) on a AY-H column (30×250 mm, 5 μm) eluting at a flow rate 100 mL/min (100 bar pressure). The absolute stereochemistry was arbitrarily assigned. The first peak (retention time=1.0 min) provided (S)-tert-butyl 3-methyl-5-(1-(oxazol-2-yl)ethoxy)pyrazine-2-carboxylate (286A, 2.25 g, 7.37 mmol, 24% yield). LCMS (ESI⁺) m/z=306 (M+H)⁺. ¹H NMR (300 MHz, CHLOROFORM-d) δ 8.16 (s, 1H), 7.62 (d, J=0.73 Hz, 1H), 7.10 (s, 1H), 6.40 (q, J=6.72 Hz, 1H), 2.67 (s, 3H), 1.79 (d, J=6.58 Hz, 3H), 1.62 (s, 9H). The second peak (retention time=3.2 min) provided (R)-tert-butyl 3-methyl-5-(1-(oxazol-2-yl)ethoxy) pyrazine-2-carboxylate (2.23 g, 7.30 mmol, 24% yield).

Preparation of Compound 286B. To (S)-tert-butyl 3-methyl-5-(1-(oxazol-2-yl)ethoxy)pyrazine-2-carboxylate (286A, 2.3 g, 7.53 mmol) was added TFA (8.39 mL, 113 mmol) dropwise and the mixture was stirred at RT overnight. The TFA was removed in vacuo. The residue was treated with 15 mL of 1 N aqueous HCl and azeotroped in vacuo to remove the residual TFA (repeated twice). The residue was dried under house vacuum overnight to give a gum. LCMS showed that the gum not pure (some decomposition). The gum was dissolved in DMF (3 mL), treated with iodomethane (0.56 mL, 9.04 mmol) and potassium carbonate (1.56 g, 11.30 mmol). After stirring overnight, the reaction was diluted with water, extracted with EtOAc, washed with sat. NaHCO₃, dried and evaporated to dryness. Flash column (DCM to DCM/EtOAc=10:1) gave (S)-methyl 3-methyl-5-(1-(oxazol-2-yl)ethoxy)pyrazine-2-carboxylate (286B, 540 mg, 2.051 mmol, 27% yield) as a gum. LCMS (ESI⁺) m/z=264.2 (M+H)⁺. ¹H NMR (300 MHz, CHLOROFORM-d) δ 8.18 (s, 1H), 7.63 (d, J=0.73 Hz, 1H), 7.11 (s, 1H), 6.43 (q, J=6.72 Hz, 1H), 3.97 (s, 3H), 2.76 (s, 3H), 1.80 (d, J=6.72 Hz, 3H).

Preparation of Compound 286. A solution of (S)-methyl 3-methyl-5-(1-(oxazol-2-yl)ethoxy)pyrazine-2-carboxylate (286B, 520 mg, 1.97 mmol) in THF (10 mL) was treated with lithium hydroxide hydrate (249 mg, 5.93 mmol) in 50 mL of water and the mixture was stirred at ambient temperature for 3 h. The mixture was treated with 5 M aqueous HCl (1.3 mL), and extracted with DCM (3×50 mL). The combined organic extracts were dried ($Na_2SO_4$) and concentrated to give (S)-3-methyl-5-(1-(oxazol-2-yl)ethoxy)pyrazine-2-carboxylic acid (286, 490 mg, 1.97 mmol, 100% yield) as a white solid. LCMS (ESI+) m/z=250.2 (M+H)+. $^1$H NMR (300 MHz, CHLOROFORM-d) δ 10.64 (br. s., 1H), 8.05 (s, 1H), 7.64 (d, J=0.73 Hz, 1H), 7.12 (d, J=0.73 Hz, 1H), 6.46 (q, J=6.67 Hz, 1H), 2.87 (s, 3H), 1.82 (d, J=6.72 Hz, 3H).

(S)-3-Methyl-5-(1-(oxazol-2-yl)ethoxy)picolinic acid (287) and (R)-3-methyl-5-(1-(oxazol-2-yl)ethoxy)picolinic acid (288)

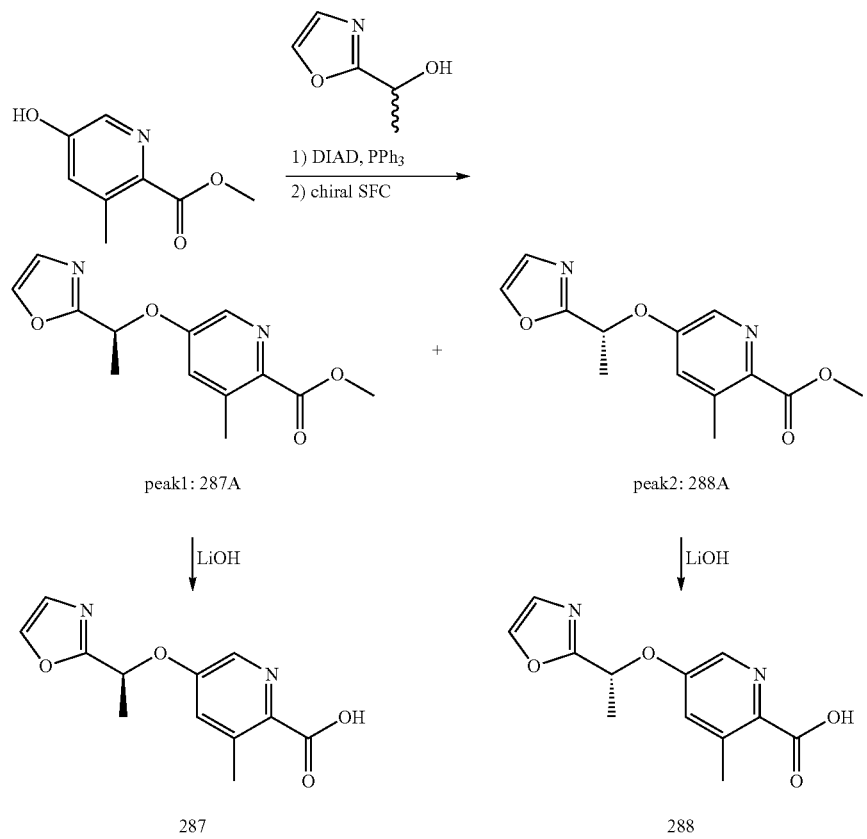

Preparation of Compounds 287A and 288A. To a mixture of methyl 5-hydroxy-3-methylpicolinate (1.66 g, 9.93 mmol), triphenylphosphine (3.91 g, 14.90 mmol), 1-(oxazol-2-yl)ethanol (1.42 g, 11.92 mmol) in THF (40 mL) at 0° C. was added diisopropyl azodicarboxylate (2.93 mL, 14.90 mmol) dropwise. The reaction was gradually warmed to RT and stirred overnight. The mixture was treated with MeOH (2 mL) and concentrated in vacuo. The residue was diluted with EtOAc (50 mL) and washed sequentially with NaOH (0.5 N, 10 mL), water, and brine, then dried over $Na_2SO_4$ and concentrated in vacuo. The residue was purified by silica gel chromatography (10-100% EtOAc in heptane). The mixture of two enantiomers was obtained and chromatographed using supercritical $CO_2$ (additives 15% of EtOH with 20 mM $NH_3$) on an AY-H column (150×4.6 mm, 5 μm) eluting at a flow rate of 4 mL/min (100 bar pressure). The stereochemistry was assigned arbitrarily. The first peak (retention time=1.5 min) provided (S)-methyl 3-methyl-5-(1-(oxazol-2-yl)ethoxy)picolinate (287A, 1.29 g, 49% yield). LC/MS (ESI−) m/z=263 (M+H)+. $^1$H NMR (400 MHz, CHLOROFORM-d) δ ppm 1.82 (d, J=6.65 Hz, 3H) 2.59 (s, 3H) 3.94 (s, 3H) 5.57 (q, J=6.65 Hz, 1H) 7.11 (s, 1H) 7.20 (d, J=2.54 Hz, 1H) 7.63 (s, 1H) 8.28 (d, J=2.74 Hz, 1H). The second peak (retention time=2.1 min) provided (R)-methyl 3-methyl-5-(1-(oxazol-2-yl)ethoxy)picolinate (288A, 1.11 g, 43% yield). LC/MS (ESI−) m/z=263 (M+H)+. $^1$H NMR (400 MHz, CHLOROFORM-d) δ ppm 1.82 (d, J=6.65 Hz, 3H) 2.59 (s, 3H) 3.94 (s, 3H) 5.57 (q, J=6.65 Hz, 1H) 7.11 (s, 1H) 7.20 (d, J=2.54 Hz, 1H) 7.63 (s, 1H) 8.28 (d, J=2.74 Hz, 1H).

Preparation of Compound 287. To a suspension of (S)-methyl 3-methyl-5-(1-(oxazol-2-yl)ethoxy)picolinate (287A, 1.29 g, 4.92 mmol) and lithium hydroxide hydrate (0.30 g, 7.28 mmol) was added THF (16 mL) and water (4 mL). The mixture was stirred at RT for 1.5 h, then 8.5 mL of 1 N HCl was added and the mixture was diluted with brine and a mixed solvent of i-PrOH:$CHCl_3$ (v/v 1:3). The aqueous layer was further extracted with the mixed solvent. The organic layer was dried over $Na_2SO_4$ and concentrated in vacuo to afford (S)-3-methyl-5-(1-(oxazol-2-yl)ethoxy)picolinic acid as off-white solid (1.20 g, 98% yield). LC/MS (ESI−) m/z=249 (M+H)+. $^1$H NMR (400 MHz, CHLOROFORM-d) δ ppm 1.84 (d, J=6.65 Hz, 3H) 2.72 (s, 3H)

5.51-5.67 (m, 1H) 7.13 (s, 1H) 7.28 (d, J=2.35 Hz, 1H) 7.66 (s, 1H) 8.17 (d, J=2.54 Hz, 1H). The acid-proton peak is broad.

Preparation of Compound 288. (R)-3-methyl-5-(1-(oxazol-2-yl)ethoxy)picolinic acid (288) (1.20 g, 98% yield) as an off-white solid was synthesized in a fashion similar to that of intermediate 287, but starting with (R)-methyl 3-methyl-5-(1-(oxazol-2-yl)ethoxy)picolinate (288A, 1.11 g, 4.23 mmol). LC/MS (ESI⁻) m/z=249 (M+H)⁺. ¹H NMR (400 MHz, CHLOROFORM-d) δ ppm 1.84 (d, J=6.46 Hz, 3H) 2.72 (s, 3H) 5.60 (q, J=6.52 Hz, 1H) 7.13 (s, 1H) 7.28 (d, J=1.76 Hz, 1H) 7.66 (s, 1H) 8.17 (d, J=2.35 Hz, 1H). The acid-proton peak is broad.

3-Chloro-5-(prop-2-yn-1-yloxy)picolinic acid (289)

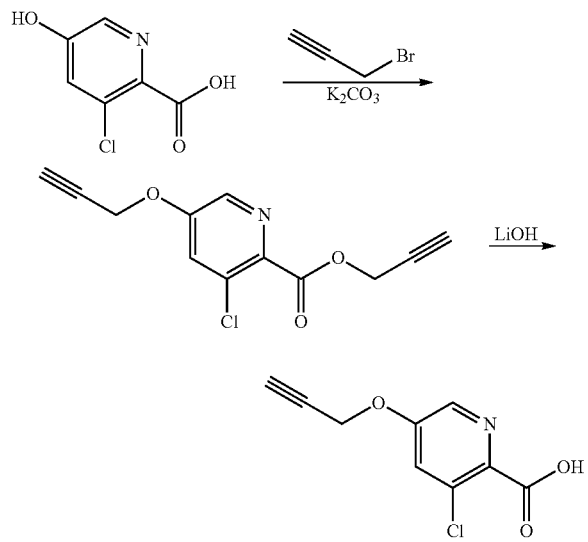

289

To a suspension of 3-chloro-5-hydroxypicolinic acid (Afferchem, 0.40 g, 2.30 mmol) and potassium carbonate (1.12 g, 8.07 mmol) in DMF (10 mL) was added propargyl bromide (0.56 mL, 5.07 mmol) dropwise at RT. The mixture was heated to 45° C. for 1 h. LCMS showed the reaction was complete. The mixture was diluted with EtOAc and washed with water and brine. The organic solution was dried over Na₂SO₄ and concentrated in vacuo. The residue was purified by silica gel chromatography: 0-50% EtOAc-Hexane. The product was obtained as yellow solid (0.45 g, 78% yield). LC/MS (ESI⁻) m/z=250 (M+H)⁺. ¹H NMR (400 MHz, CHLOROFORM-d) δ ppm 2.53 (t, J=2.35 Hz, 1H) 2.63 (t, J=2.25 Hz, 1H) 4.81 (d, J=2.15 Hz, 2H) 4.98 (d, J=2.35 Hz, 2H) 7.41 (d, J=2.54 Hz, 1H) 8.37 (d, J=2.54 Hz, 1H).

To a suspension of prop-2-yn-1-yl 3-chloro-5-(prop-2-yn-1-yloxy)picolinate (0.448 g, 1.795 mmol) and lithium hydroxide monohydrate (0.079 g, 1.884 mmol) was added THF (6 mL) and water (2 mL). The mixture was stirred at RT for 1 h. LCMS showed the reaction was complete. 0.08 mL of 1 N HCl was added and the mixture was concentrated in vacuo. The product was obtained as off-white solid (0.456 g, 100% yield). LC/MS (ESI⁻) m/z=212 (M+H)⁺.

5-(2,2,2-Trifluoroethoxy)picolinic acid (300)

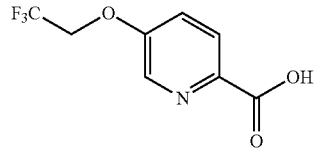 [SMILES: O=C(O)c1ccc(OCC(F)(F)F)cn1]

Preparation of ethyl 5-(2,2,2-trifluoroethoxy)picolinate. To a solution of methyl 5-hydroxypicolinate (0.50 g, 3.27 mmol, Frontier Scientific) in DMF (5 mL) were added cesium carbonate (1.383 g, 4.24 mmol, Aldrich) and 2,2,2-trifluoroethyl ester (0.909 ml, 3.92 mmol) and the resulting suspension was stirred at RT for 1 h. The reaction was diluted with water and EtOAc. The organic layer was washed with 1 M LiCl (aq) solution and brine before drying over magnesium sulfate and concentrating under reduced pressure to afford the crude title compound as a yellow oil, which was used directly in the next step without further purification. M/S m/z=236.0 [M+H]⁺.

Preparation of Compound 300. The crude material from the previous reaction was taken up in THF (5 mL) and lithium hydroxide (2.0 M of aq. Solution, 4.90 mL, 9.80 mmol) was added. The reaction was stirred at RT for 16 h. The reaction was diluted with water and acidified with 1.0 N HCl (aq.) solution was added until pH=1. The solution was extracted with DCM and the organic layer was washed with brine, dried over magnesium sulfate and concentrated under reduced pressure to afford the title compound as a white solid. (0.194 g, 0.877 mmol, 26.9% yield). M/S m/z=221.9 [M+H]⁺. ¹H NMR (300 MHz, DMSO-d₆) δ ppm 5.00 (q, J=8.77 Hz, 2H) 7.66 (dd, J=8.77, 2.92 Hz, 1H) 8.07 (d, J=8.77 Hz, 1H) 8.50 (d, J=2.92 Hz, 1H) 13.00 (br. S., 1H).

3,8-Dichloro-5-fluoro-1,7-naphthyridine (301)

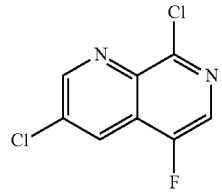 [SMILES: Fc1cnc(Cl)c2ncc(Cl)cc12]

A pressure bottle was charged with 3-chloro-1,7-naphthyridin-8(7H)-one (15 g, 83 mmol, Anichem), MeOH (34.6 mL), ACN (173 mL) and 1-chloromethyl-4-fluoro-1,4-diazoniabicyclo[2.2.2]octane bis(tetrafluoroborate) (30.9 g, 87 mmol), and the mixture was heated at 45° C. for 15 h. Water and EtOAc were added, and the layers were separated. The aqueous portion was extracted twice with EtOAc and once with DCM, and the combined organic layers were dried with anhydrous sodium sulfate, filtered and concentrated. The crude solid was triturated with a minimum amount of EtOAc and filtered. The title intermediate was isolated as an off-white solid (15.34 g, 80%) as a 3:1 mixture of diastereomers.

A vial was charged with 3-chloro-5-fluoro-6-methoxy-6,7-dihydro-1,7-naphthyridin-8(5H)-one (7.5 g, 32.5 mmol), ACN (130 mL) and phosphorus oxychloride (9.09 mL, 98 mmol), and the mixture was stirred at 75° C. for 15 hours.

The mixture was concentrated, and the crude material was purified by silica gel chromatography, eluting with 0-50% EtOAc in heptanes, to provide Compound 301 (5.57 g, 25.7 mmol, 79% yield) as a white solid. LC/MS (ESI$^+$) m/z=217 (M+H)$^+$.

4-Chloro-5-fluoro-7-methoxyquinazoline (302)

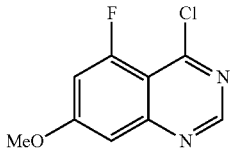

Preparation of 2-amino-6-fluoro-4-methoxybenzonitrile. Ammonia gas was bubbled through a solution of 2,6-difluoro-4-methoxybenzonitrile (1.0 g, 5.91 mmol) in DMSO (11.83 mL) for 10 minutes. The reaction was then sealed and stirred at 90° C. for 24 h. The reaction mixture was cooled to RT and concentrated in vacuo to afford a tan residue. The residue was triturated with water, collected be vacuum filtration, and dried in vacuo to afford the title intermediate (0.9 g, 5.42 mmol) as a white solid. LC/MS (ESI$^+$) m/z=167 (M+H)$^+$.

Preparation of 5-fluoro-7-methoxyquinazolin-4-ol. To a mixture of formic acid (11.43 mL, 298 mmol) and sulfuric acid (0.87 mL, 16.25 mmol) was added 2-amino-6-fluoro-4-methoxybenzonitrile (0.9 g, 5.42 mmol) in portions. The reaction mixture was stirred at 100° C. for 1 h, cooled to RT, and poured into 80 mL of an ice-water mixture. The resulting precipitate was collected by vacuum filtration and dried in vacuo to provide the title intermediate (0.8 g, 4.12 mmol) as an off-white solid. LC/MS (ESI$^+$) m/z=195 (M+H)$^+$.

Preparation of 4-chloro-5-fluoro-7-methoxyquinazoline. To a suspension of 5-fluoro-7-methoxyquinazolin-4-ol (0.12 g, 0.64 mmol) in thionyl chloride (1.41 mL, 19.31 mmol) was added DMF (0.028 mL, 0.36 mmol). The reaction was stirred at 80° C. for 6 h and concentrated in vacuo. The residue was suspended in saturated aqueous sodium bicarbonate and extracted with DCM. The organic layer was concentrated in vacuo to generate the title compound (0.13 g, 0.61 mmol) as a yellow solid. LC/MS (ESI$^+$) m/z=213 (M+H)$^+$.

Difluoromethyl)picolinic acid (303)

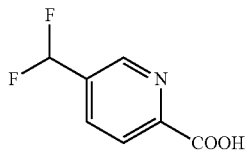 [SMILES: O=C(O)c1ccc(C(F)F)cn1]

Step 1: 5-Formylpicolinonitrile

A suspension of 2-bromo-5-formylpyridine (940 mg, 5.05 mmol) and copper (I) cyanide (233 µL, 7.58 mmol) in DMF (8.4 mL) was stirred at 120° C. for 1.5 hours, cooled to RT, and partitioned between water and EtOAc. The solids were removed from the aqueous layer by filtration, and the filtrate was extracted with EtOAc. The combined organic layers were washed with brine, dried over anhydrous magnesium sulfate, filtered and concentrated. The crude product was purified by silica-gel chromatography, eluting with a gradient of 40%-60% (40% EtOAc in heptane) in heptane, to provide the title compound (236 mg, 1.786 mmol) as white solid. LC/MS (ESI$^+$) m/z=133 (M+H)$^+$.

Step 2: 5-(Difluoromethyl)picolinonitrile

To a solution of 5-formylpicolinonitrile (74 mg, 0.560 mmol) in toluene (0.25 mL) was added bis(2-methoxyethyl) aminosulfur trifluoride (0.258 mL, 1.400 mmol), and the reaction was stirred at RT overnight. The reaction mixture was carefully quenched with saturated aqueous sodium bicarbonate, diluted with water, and extracted with DCM. The organic layer was washed with brine, dried over anhydrous magnesium sulfate, filtered, and concentrated. The crude material was purified by silica-gel chromatography, eluting with a gradient of 40% to 60% (40% EtOAc/heptane) in heptane, to provide the title compound (48 mg, 0.311 mmol) as white solid. LC/MS (ESI$^+$) m/z=155 (M+H).

Step 3: 5-(difluoromethyl)picolinic acid

A suspension of 5-(difluoromethyl) picolinonitrile (48 mg, 0.311 mmol) in 12 N aqueous hydrochloric acid (4.3 mL, 140 mmol) was stirred at 110° C. for 1.5 h. After cooling to ambient temperature, the reaction mixture was concentrated and treated with DIPEA (2 mL). The mixture was concentrated and dried in vacuo to provide the title compound in quantitative yield. LC/MS (ESI$^+$) m/z=174 (M+H)$^+$.

5-Methoxy-3-methylpyrazine-2-carboxylic acid (304)

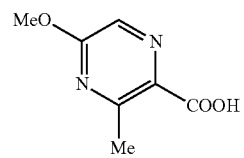

Step 1: Methyl 3-methylpyrazine-2-carboxylate

In a 2-L flask, 3-methylpyrazine-2-carboxylic acid (Matrix, 19.95 g, 144 mmol) was suspended in MeOH (500 mL). The suspension was cooled in an ice-water bath, and concentrated sulfuric acid (Fluka, 27.3 mL, 506 mmol) was added over a time period of 5 min. The reaction mixture was heated to 80° C. for 5 h. The reaction mixture was concentrated under reduced pressure and the residue was taken up in DCM (750 mL). The excess acid was neutralized carefully with of aqueous NaOH (5N or 5M, 200 mL). The aqueous layer was separated and extracted with DCM (250 mL). The combined organic layers were combined, dried over MgSO$_4$ and concentrated to afford 16.15 g of the title compound (106 mmol, 73%). MS m/z=153 [M+H]$^+$. Step 2: 3-(Methoxycarbonyl)-2-methylpyrazine 1-oxide In a 1-L flask, the methyl 3-methylpyrazine-2-carboxylate (step 1, 16.08 g, 106 mmol) was suspended in CHCl$_3$ (300 mL). 3-chlorobenzoperoxoic acid (Aldrich, 24.62 g, 143 mmol) was added. The reaction mixture was heated to 70° C. for 16 h. The reaction mixture was quenched with saturated NaHCO$_3$ (200 mL). The layers were separated, and the aqueous layer was further extracted with DCM (2×100 mL). The combined organic layers were dried over MgSO$_4$, and the filtrate was concentrated to afford the title compound. MS m/z=169 [M+H]$^+$.

Step 3: Methyl 5-chloro-3-methylpyrazine-2-carboxylate

In a 1-L flask, the crude 3-(methoxycarbonyl)-2-methylpyrazine 1-oxide (step 2, 17.77 g, 106 mmol) was dissolved in DMF (300 mL). Neat phosphoryl trichloride (29.6 mL, 317 mmol) was added. The reaction mixture was heated to 100° C. After 1 h, the reaction mixture was concentrated to remove most of the DMF. The flask was cooled in an ice water bath, and 1 M aqueous Na$_2$CO$_3$ (300 mL) was added slowly, followed by 80% EtOAc-hexane (400 mL). The mixture was filtered through Celite® filter aid. The resulting filtrate was partitioned and the aqueous phase was extracted further with 80% EtOAc-hexane (2×250 mL). The combined organic layers were dried over MgSO$_4$ and concentrated. The material was purified through silica gel using 11% EtOAc-hexane to afford the title compound (4.29 g, 23 mmol, 22%). MS m/z=187 [M+H]$^+$. $^1$H NMR in CDCl$_3$ δ: 8.51 (s, 1H), 4.01 (s, 3H), 2.86 (s, 3H).

Step 4: 5-Methoxy-3-methylpyrazine-2-carboxylic acid

A flask was charged with sodium (0.813 g, 35.4 mmol), purged with Argon. and placed in a room temperature water bath. MeOH (47.7 mL, 1179 mmol) was added slowly. After 40 min, methyl 5-chloro-3-methylpyrazine-2-carboxylate (step 3, 2.2 g, 11.79 mmol) was added. The vessel was sealed and heated to 45° C. for 1.5 hs. Sodium hydroxide (1M, 12.97 mL, 12.97 mmol) was added and heating was continued for 1.5 hs. The reaction mixture was concentrated uncle reduced pressure and the residue was dissolved in a minimum amount of water (50 mL). The aqueous phase was extracted with Et$_2$O (15 mL), which was discarded. The aqueous phase was acidified with HCl (5M, 11 mL, 55 mmol). The mixture was extracted with DCM (3×60 mL). The combined organic extracts were dried over MgSO$_4$ and the filtrate was concentrated to afford the title compound (2.0 g, 100%). MS m/z=169 [M+H]$^+$. $^1$H NMR in CDCl$_3$ δ: 10.70 (br, 1H), 7.98 (s, 1H), 4.00 (s, 3H), 2.91 (s, 3H).

5-Chloro-3-methoxypicolinic acid (305)

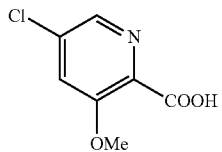 [SMILES: COc1cc(Cl)cnc1C(=O)O]

In a 1-L flask, 5-chloro-3-nitropicolinonitrile (Oakwood, 6.67 g, 36.3 mmol) was dissolved in MeOH (185 mL). The solution was cooled to 0° C., and sodium hydroxide (3 M, 36.3 mL, 109 mmol) was added. The reaction mixture was warmed to RT and stirred overnight. The reaction was concentrated under reduced pressure and the residue was taken up in absolute EtOH (100 mL). NaOH (5 M, 3 equiv, 109 mmol, 22 mL) was added, and the reaction mixture was heated to 100° C. for 1 h. The reaction mixture was concentrated under reduced pressure and the residue was taken up in water (100 mL). The aqueous layer was extracted with Et$_2$O (30 mL), which was discarded. The aqueous phase was acidified with HCl (5 M, 55 mL), saturated with NaCl, and extracted with EtOAc (5×75 mL). The combined organic extracts were dried over MgSO$_4$ and the filtrate was concentrated under reduced pressure. The resulting solid was triturated with Et$_2$O to afford the title compound (5.63 g, 30 mmol, 83%). MS m/z=188 [M+H]$^+$. $^1$H NMR in CDCl$_3$ δ: 8.18 (d, 1H, J=1.8), 7.49 (d, 1H, J=1.8), 4.03 (s, 3H).

5-Cyano-3-methoxypicolinic acid (306)

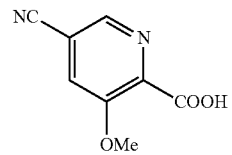 [SMILES: COc1cc(C#N)cnc1C(=O)O]

Step 1: Methyl 5-chloro-3-methoxypicolinate

In a 350-mL resealable vessel, 5-chloro-3-methoxypicolinic acid (intermediate 14, 7.51 g, 40.0 mmol) was dissolved in MeOH (120 mL). The solution was cooled to 0° C., and concentrated sulfuric acid (7.57 mL, 140 mmol) was added. The vessel was sealed and heated to 95° C. for 1.5 h. The reaction mixture was cooled to 0° C., and quenched with Na$_2$CO$_3$ (1M, 140 mL). The reaction mixture was concentrated under reduced pressure and the residue was extracted with EtOAc (3×100 mL). The combined organics extracts were dried over MgSO$_4$ and the filtrate was concentrated under reduced pressure. The residue was purified by silica gel chromatography (gradient 20%-33% EtOAc/hexane) to afford the title compound as a yellow solid (5.59 g, 27.7 mmol, 67%). MS m/z=202 [M+H]$^+$. $^1$H NMR in CDCl$_3$ δ: 8.24 (d, 1H, J=1.9), 7.37 (d, 1H, J=1.9), 3.97 (s, 3H), 3.94 (s, 3H).

Step 2: Methyl 5-cyano-3-methoxypicolinate

In a 350-mL resealable vessel, Pd$_2$dba$_3$ (1.487 g, 1.623 mmol), dicyclohexyl(2',6'-dimethoxy-[1,1'-biphenyl]-2-yl)phosphine (1.444 g, 3.52 mmol), dicyanozinc (3.18 g, 27.1 mmol), and methyl 5-chloro-3-methoxypicolinate (step 1, 5.455 g, 27.1 mmol) were taken up in DMF (80 mL). The reaction mixture was purged with Argon and subsequently heated to 120° C. for 2 h. Upon cooling, the reaction mixture was concentrated under reduced pressure. The residue was filtered through Celite® filter aid, and the filter cake was rinsed with 1% MeOH/DCM. The filtrate was concentrated under reduced pressure and the residue was purified by silica gel chromatography (33-40% EtOAc/hexane) to afford the title compound as a white solid (4.51 g, 23.5 mmol, 87%)., MS m/z=193 [M+H]$^+$. $^1$H NMR in CDCl$_3$ δ: 8.51 (d, 1H, J=1.6), 7.55 (d, 1H, J=1.6), 4.00 (s, 3H), 3.97 (s, 3H).

Step 3: 5-Cyano-3-methoxypicolinic acid

In a 1-L flask, the methyl 5-cyano-3-methoxypicolinate (step 2, 4.51 g, 23.5 mmol) was taken up in THF (74 mL). The suspension was cooled to 0° C., and sodium hydroxide (1M, 24.64 mL, 24.64 mmol) was added. After 1 h, the reaction was concentrated under reduced pressure. The residue was taken up in 100 mL of water, and the aqueous phase was extracted with Et₂O (50 mL), which was discarded. The aqueous phase was acidified with HCl (5M, 5.16 mL, 25.8 mmol). The aqueous phase was extracted with DCM (11×150 mL). The combined organic extracts were dried over MgSO₄ and the filtrate was concentrated under reduced pressure to afford the title compound as a white solid. MS m/z=179 [M+H]⁺. ¹H NMR in CDCl₃ δ: 8.48 (d, 1H, J=1.6), 7.71 (d, 1H, J=1.6), 4.08 (s, 3H).

5-Cyano-3-methylpicolinic acid (307)

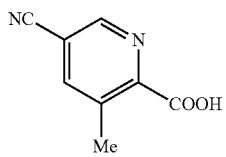 [SMILES: Cc1cc(C#N)cnc1C(=O)O]

To a solution of tert-butyl 5-cyano-3-methylpicolinate (synthesized according to procedure described in WO2012095521; 4.18 g, 19.15 mmol) in DCM (96 mL) was added TFA (Aldrich, 148 mL, 1915 mmol). The reaction mixture was stirred at room temperature for 2 hrs. The reaction mixture was concentrated under reduced pressure and the residue was triturated with EtOAc. The yellow slurry was concentrated under reduced pressure. The residue was triturated with 30 mL of methyl tert-butyl ether (30 mL) and hexanes (50 mL) to yield 5-cyano-3-methylpicolinic acid (2.91 g, 17.95 mmol, 94% yield) as yellow solid. MS m/z=163.2 [M+H]⁺.

8-Chloro-5-fluoro-1,7-naphthyridine-3-carbonitrile (308)

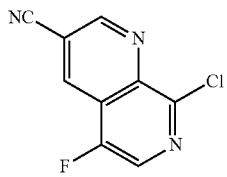 [SMILES: N#Cc1cnc2c(Cl)ncc(F)c2c1]

Step 1: 3-Chloro-5-fluoro-6-methoxy-6,7-dihydro-1,7-naphthyridin-8(5H)-one

A pressure bottle was charged with 3-chloro-1,7-naphthyridin-8(7H)-one (Anichem, 15 g, 83 mmol), MeOH (34 ml), ACN (173 ml) and 1-(chloromethyl)-4-fluoro-1,4-diazabicyclo[2.2.2]octane-1,4-diium tetrafluoroborate (Aldrich, 30.9 g, 87 mmol). The mixture was heated to 45-50° C. After 6 hs additional 1-(chloromethyl)-4-fluoro-1,4-diazabicyclo[2.2.2]octane-1,4-diium tetrafluoroborate (2.5 g) was added and heating was continued overnight. Water and EtOAc were added to the cooled reaction mixture and the layers were separated. The aqueous layer was extracted with EtOAc, and the combined organic layers were dried over MgSO₄. The filtrate was concentrated under reduced pressure and the residue was triturated with EtOAc. The solid was filtered off and the title compound (15.34 g, 66.5 mmol, 80% yield) was isolated as a white solid. MS m/z=231 [M+H]⁺.

Step 2: 5-Fluoro-6-methoxy-8-oxo-5,6,7,8-tetrahydro-1,7-naphthyridine-3-carbonitrile A pressure bottle was charged with Pd(dba)₃ (Strem, 1.032 g, 1.127 mmol), 2-dicyclohexylphosphino-2',6'-dimethoxybiphenyl (Strem 1.157 g, 2.82 mmol), zinc cyanide (Alfa Aesar, 2.482 g, 21.14 mmol), 3-chloro-5-fluoro-6-methoxy-6,7-dihydro-1,7-naphthyridin-8(5H)-one (step 1, 3.25 g, 14.09 mmol) and DMF (70 ml). The bottle was purged with Argon and the reaction mixture was heated to 110° C. for 1 h. The crude reaction mixture was filtered through a pad of Celite® filter aid and the filtercake was washed with MeOH. The combined filtrates were concentrated under reduced pressure. The residue was triturated with DCM. The solid was filtered off and washed with DCM. The title compound (2.27 g, 10.26 mmol, 73% yield) was obtained as an off white solid. MS m/z=222 [M+H]⁺.

Step 3: 8-Chloro-5-fluoro-1,7-naphthyridine-3-carbonitrile

A pressure bottle was charged with 5-fluoro-6-methoxy-8-oxo-5,6,7,8-tetrahydro-1,7-naphthyridine-3-carbonitrile (step 3, 2.27 g, 10.26 mmol), ACN (41 ml) and phosphorus oxychloride (Aldrich, 3.35 ml, 35.9 mmol). The bottle was sealed and the reaction mixture was heated to 75° C. overnight. The reaction mixture was concentrated and the crude material was purified by silica gel chromatography (gradient 0-20% (10 MeOH in DCM)/DCM to afford the title compound (1.2 g, 5.78 mmol, 56% yield) as a white solid. MS m/z=208 [M+H]⁺.

5-(Cyanomethoxy)-3-methylpicolinic acid (309)

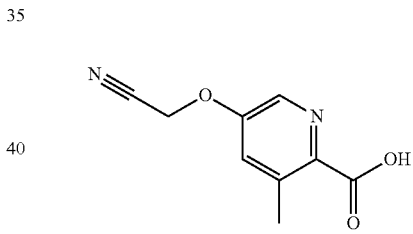

Step 1: Methyl 5-(cyanomethoxy)-3-methylpicolinate

To a suspension of methyl 5-hydroxy-3-methylpicolinate (0.8063 g, 4.82 mmol, step 3 intermediate 38) and cesium carbonate (0.77 ml, 9.65 mmol, Alfa Aesar) in DMF (48.2 mL) was added bromoacetonitrile (0.336 ml, 4.82 mmol, Sigma-Aldrich Chemical Company, Inc.). The reaction mixture was stirred for 4 h at RT. The reaction mixture was diluted with aqueous, saturated sodium bicarbonate solution and extracted with EtOAc. The organic extract was washed with aqueous, saturated sodium bicarbonate solution, brine and dried over MgSO₄. The filtrate was concentrated in vacuo. MS m/z=207.1 [M+H]⁺. ¹H NMR (400 MHz, CHLOROFORM-d) δ ppm 2.67 (s, 3H) 3.98 (s, 3H) 4.88 (s, 2H) 7.20 (d, J=2.35 Hz, 1H) 8.32 (br. s., 1H)

Step 2: 5-(Cyanomethoxy)-3-methylpicolinic acid

To a solution of methyl 5-(cyanomethoxy)-3-methylpicolinate (0.895 g, 4.34 mmol) and sodium iodide (0.354 ml, 8.68 mmol, Sigma-Aldrich Chemical Company, Inc.) in ACN (4.34 ml) was added chlorotrimethylsilane (1.102 ml, 8.68 mmol, Strem Chemicals, Inc.). The reaction mixture was heated to 70° C. and allowed to stir overnight. The reaction mixture was concentrated under reduced pressure and the residue was diluted with water and extracted with EtOAc. The organic extract was washed with water, 10% sodium thio sulfate solution and dried over MgSO$_4$. The filtrate was concentrated in vacuo to give 5-(cyanomethoxy)-3-methylpicolinic acid which was used without further purification. MS m/z=192.9 [M+H]$^+$.

The following carboxylic acid intermediates were synthesized according to existing literature procedures, as listed below:

| Intermediate No. | Structure | Literature Reference |
|---|---|---|
| 310 | [5-(difluoromethoxy)-3-methylpyridine-2-carboxylic acid] | WO2012095463 |
| 311 | [5-methoxy-3-methylpyridine-2-carboxylic acid] | WO2012095463 |
| 312 | [5-(difluoromethyl)-3-methylpyridine-2-carboxylic acid] | WO2012095521 |
| 313 | [3-chloro-5-(difluoromethyl)pyridine-2-carboxylic acid] | WO2012095521 |
| 314 | [5-(cyclopropylmethoxy)-3-methylpyridine-2-carboxylic acid] | WO2013061962 |
| 315 | [5-(difluoromethyl)pyrazine-2-carboxylic acid] | WO2012138734 |
| 316 | [2-(fluoromethyl)oxazole-4-carboxylic acid] | WO2011069934 |

| Intermediate No. | Structure | Literature Reference |
|---|---|---|
| 317 | 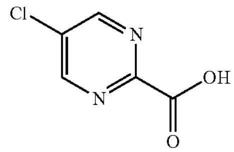 | WO 2011044181 |
| 318 | 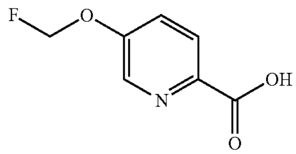 [SMILES: O=C(O)c1ccc(OCF)cn1] | WO 2011009898 |
| 319 | 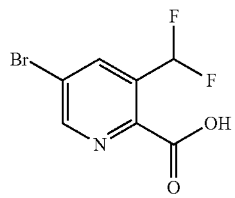 [SMILES: O=C(O)c1ncc(Br)cc1C(F)F] | WO 2012147763 |
| 320 | 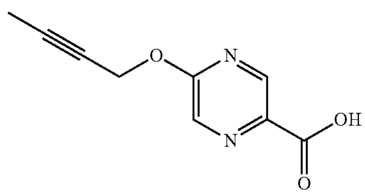 | J. Med. Chem. 2013, 56, 3980 |
| 321 | 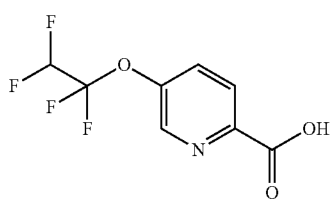 [SMILES: O=C(O)c1ccc(OC(F)(F)C(F)F)cn1] | J. Med. Chem. 2013, 56, 3980 |

5-Cyanopyrimidine-2-carboxylic acid (322)

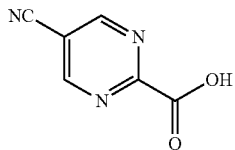 [SMILES: N#Cc1cnc(C(=O)O)nc1]

Step 1: methyl 5-bromopyrimidine-2-carboxylate

To a solution of 5-bromopyrimidine-2-carboxylic acid (3.22 g, 15.9 mmol) in MeOH (50 mL) at room temperature was added acetyl chloride (4.0 mL, 56.3 mmol). The reaction mixture was heated to reflux for 15 min, cooled to room temperature and concentrated under reduced pressure. The reaction mixture was diluted with saturated NaHCO$_3$ (30 mL) and EtOAc, and transferred to a separatory funnel. The aqueous phase was extracted with EtOAc (4×) and the combined organic extracts were washed with brine (1×), dried over MgSO$_4$, filtered, and concentrated to give methyl 5-bromopyrimidine-2-carboxylate (2.30 g, 10.6 mmol, 67% yield) as a white solid. LC/MS (ESI$^+$) m/z=216.9 (M+H). Calculated for C$_6$H$_5$BrN$_2$O$_2$ 216.0.

Step 2: methyl 5-cyanopyrimidine-2-carboxylate

To a mixture of methyl 5-bromopyrimidine-2-carboxylate (2.30 g, 10.6 mmol) and copper (I) cyanide (1.92 g, 21.4 mmol) in a 100 mL round bottom flask was added DMA (21 mL). The reaction mixture was degassed by bubbling nitrogen through the solution for 5 min. The reaction mixture was heated to 110° C. for 2 d and cooled to room temperature. The reaction mixture was diluted with EtOAc and water and filtered through a glass frit (medium). The filtrate was transferred to a separatory funnel. The aqueous phase was extracted with EtOAc (4×) and the combined organic extracts were washed with brine (1×), dried over MgSO$_4$, filtered, concentrated to give a yellow oil. Purification by flash column chromatography on silica gel (80 g, 5% to 50% EtOAc in heptane) gave methyl 5-cyanopyrimidine-2-carboxylate (0.83 g, 5.08 mmol, 48% yield) as a white solid. LC/MS (ESI$^+$) m/z=164.0 (M+H).

Step 3: 5-cyanopyrimidine-2-carboxylic acid

To a solution of methyl 5-cyanopyrimidine-2-carboxylate (0.11 g, 0.644 mmol) in THF (2.6 mL) at 0° C. was added a solution of lithium hydroxide monohydrate (30 mg, 0.715 mmol) in water (0.5 mL). The reaction mixture was stirred at 0° C. for 20 min and 1 M HCl (0.70 mL) was added. The reaction mixture was concentrated under reduced pressure and dried under high vacuum to give methyl 5-cyanopyrimidine-2-carboxylate (0.11 g, 0.644 mmol) as a white solid that was used without further purification. LC/MS (ESI⁺) m/z=148.0 (M−H).

5-Ethynylpicolinic acid (323)

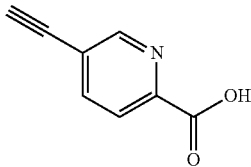

Step 1: Methyl 5-((triethylsilyl)ethynyl)picolinate

A glass microwave reaction vessel was charged with methyl 5-bromopyridine-2-carboxylate (0.95 mL, 6.94 mmol, Alfa Aesar), (triethylsilyl) acetylene (3.73 mL, 20.81 mmol, Sigma-Aldrich), tetrakis(triphenylphosphine) palladium (0.61 g, 0.527 mmol, Strem Chemicals), TEA (4.82 mL, 34.7 mmol, Sigma-Aldrich Chemical), and copper (I) iodide (198 mg, 1.04 mmol, Sigma-Aldrich). The reaction mixture was stirred and heated in a Biotage Initiator microwave reactor at 70° C. for 30 min. The reaction mixture was filtered through Celite® filter aid and concentrated. The reaction mixture was diluted with saturated NH₄Cl and extracted with EtOAc. The organic extract was washed with water and brine, dried over MgSO₄, filtered and concentrated in vacuo. The crude product was adsorbed onto a plug of silica gel and chromatographed through a silica gel column, eluting with a gradient of 0% to 40% EtOAc in hexane, to provide methyl 5-((triethylsilyl)ethynyl)picolinate (1.68 g, 6.09 mmol, 88% yield). MS m/z [M+H]⁺=276.0.

Step 2: 5-Ethynylpicolinic acid

To a solution of methyl 5-((triethylsilyl)ethynyl)picolinate (1.68 g, 6.05 mmol) in THF (12.11 ml) was added TBAF, 1.0M in THF (6.68 ml, 6.68 mmol, Sigma Aldrich). The reaction was allowed to stir for 6 hours at RT. The reaction was concentrated. The crude product was adsorbed onto a plug of silica gel and chromatographed through silica gel column eluting with a gradient of 10% to 100% EtOAc in hexane followed by 1% HOAc in EtOAc, to afford 5-ethynylpicolinic acid (0.05 g, 0.37 mmol, 6% yield). MS m/z [M+H]⁺=147.9.

5-(Prop-1-yn-1-yl)picolinic acid (324)

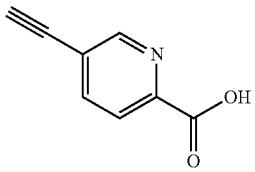

Step 1: Methyl 5-bromopicolinate

To a suspension of 5-bromopicolinic acid (2.0 g, 9.94 mmol) in MeOH (2 ml)/toluene (20 ml) was added TMS-diazomethane (20M in Et₂O; 5.47 ml, 10.94 mmol, Matrix Scientific) dropwise. The reaction was stirred at room temperature for 3 hours. An additional 0.2 eq (0.99 mL) of TMS-diazomethane was added and the reaction stirred for 1.5 hours. The reaction was concentrated and the brown solid was carried to next step without further work up. MS m/z [M+H]⁺=217.9.

Step 2: Methyl 5-(prop-1-yn-1-yl)picolinate

To a solution of methyl 5-bromopicolinate (0.60 g, 2.77 mmol) in toluene (50 mL) was added tributyl(prop-1-yn-1-yl)stannane (1.01 mL, 3.32 mmol, Sigma Aldrich) and tetrakis(triphenylphosphine)palladium (0.04 g, 0.036 mmol, Strem Chemicals, Inc.). The reaction was stirred overnight at 100° C. The reaction was allowed to cool to RT and concentrated. The residue was adsorbed onto a plug of 10% w/w KF Silica and chromatographed with a silica gel column eluting with a gradient of 10% to 100% EtOAc in hexane, to provide methyl 5-(prop-1-yn-1-yl)picolinate (0.18, 1.05 mmol, 38% yield). MS m/z [M+H]⁺=176.0.

Step 3: 5-(Prop-1-yn-1-yl)picolinic acid

To a solution of methyl 5-(prop-1-yn-1-yl)picolinate (0.18 g, 1.05 mmol) in THF (3.48 ml) was added sodium hydroxide 1.0 N solution (1.05 mL, 1.045 mmol, Sigma). The reaction was stirred for 1.5 hours at room temperature. Hydrogen chloride (4.0 M solution in 1,4-dioxane; 0.26 mL, 1.05 mmol, Sigma Aldrich) was added and the reaction stirred for an additional 10 minutes. The reaction was concentrated in vacuo to provide 5-(prop-1-yn-1-yl)picolinic acid as a light yellow solid. The material was used without further purification assuming theoretical yield. MS m/z [M+H]⁺=162.1.

(5S)-Methyl-3-((tert-butoxycarbonyl)((2-(trimethylsilyl)ethoxy)methyl)amino)-5-(2-fluoro-3-methylphenyl)-5-methyl-2-thia-4-azabicyclo[4.1.0]hept-3-ene-1-carboxylate (456M)

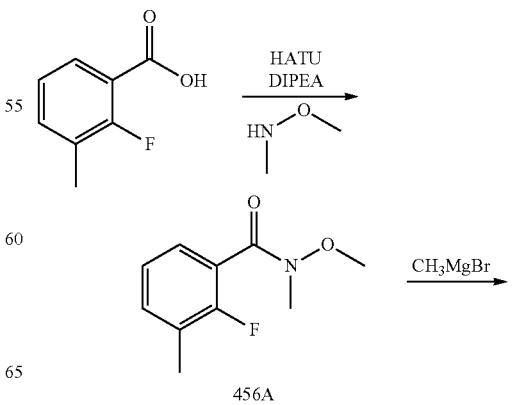

307
-continued
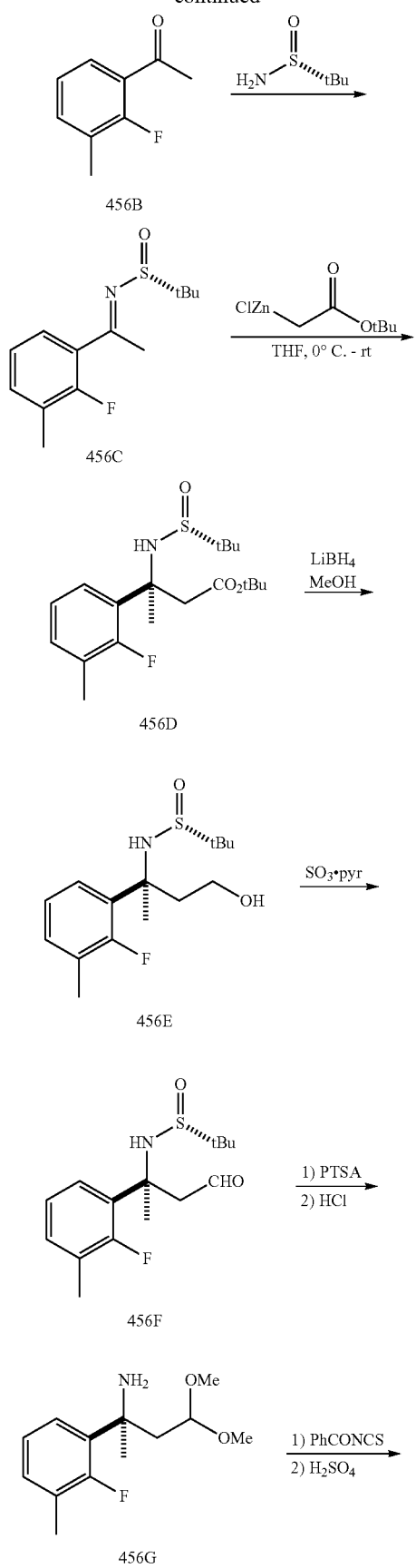
308
-continued
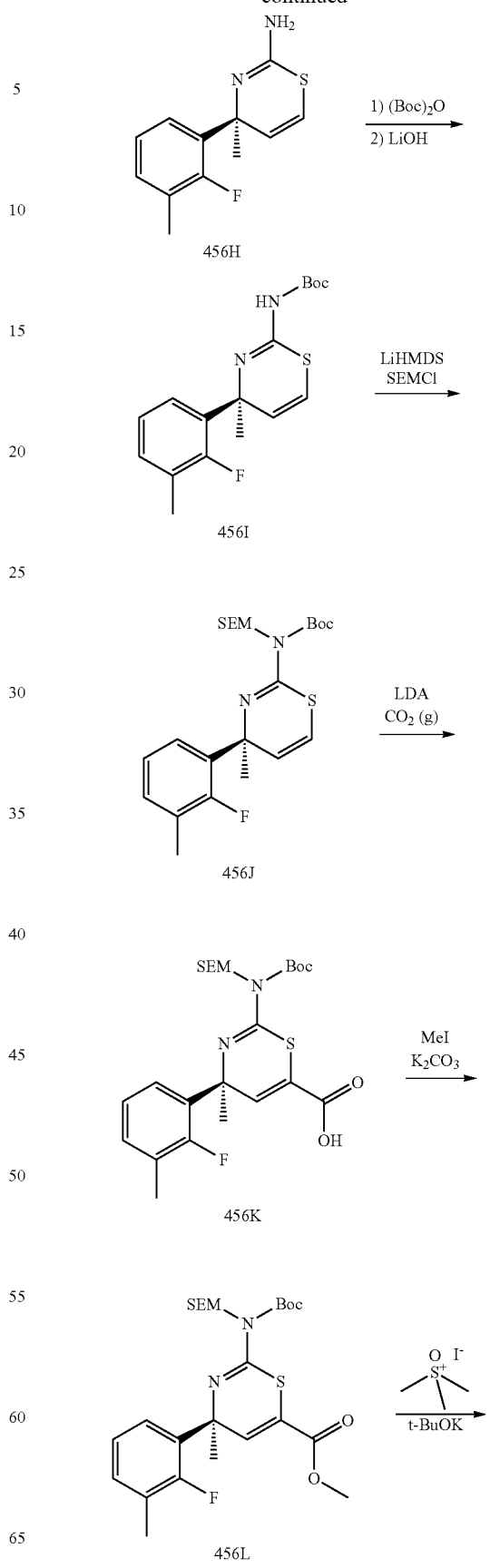

-continued

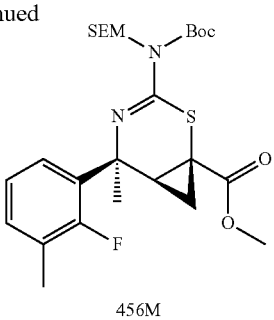

456M

Preparation of 2-fluoro-N-methoxy-N,3-dimethylbenzamide (456A). To a solution of 2-fluoro-3-methylbenzoic acid (240 g, 1.16 mol) in DMF (2.0 L) was added DIPEA (542 mL, 3.12 mol) followed by the addition of HATU (710 g, 1.87 mol) at 0° C. The reaction mixture was stirred for 10 min at 0° C. and N,O-dimethyl hydroxylamine hydrochloride (167 g, 1.71 mol) was added at 0° C. The resulting reaction mixture was then stirred for 12 h at RT. The reaction mixture was then quenched with water (3.0 L) and extracted with EtOAc (3×5.0 L). The combined organic layers were dried over sodium sulfate and concentrated under reduced pressure. The product thus obtained was purified using silica gel chromatography (30% EtOAc in hexanes) to provide compound 456A (270 g, 88%). $^1$H NMR (400 MHz, Chloroform-d) δ 7.25-7.19 (m, 2H), 7.05 (t, J=3.6 Hz, 1H), 3.53 (s, 3H), 3.32 (s, 3H), 2.29 (s, 3H).

Preparation of 1-(2-fluoro-3-methylphenyl)ethanone (456B). To a solution of compound 456A (270 g, 1.37 mol) in THF (2.7 L) was added methyl magnesium bromide (3.0 M in Et$_2$O, 1.82 L, 5.48 mol) drop wise at −78° C. The resulting mixture was stirred for 1 h at −78° C. The reaction mixture was then quenched with saturated ammonium chloride (5.0 L) and extracted with EtOAc (2×5.0 L). The combined organic layers were dried over sodium sulfate and concentrated under reduced pressure. The mixture thus obtained was purified by silica gel chromatography (10% EtOAc in hexanes) to give compound 456B (200 g, 96%). $^1$H NMR (400 MHz, Chloroform-d) δ 7.68-7.64 (m, 1H), 7.37-7.34 (m, 1H), 7.09 (t, J=7.0 Hz, 1H), 2.64 (s, 3H), 2.32 (s, 3H).

Preparation of (R)—N-(1-(2-fluoro-3-methylphenyl)ethylidene)-2-methylpropane-2-sulfinamide (456C). To a solution of compound 456B (200.0 g, 1.32 mol) in THF (2.0 L) was added (R)-2-methylpropane-2-sulfinamide (239 g, 1.97 mol) followed by addition of titanium tetraethoxide (899 g, 3.94 mol) at RT. The reaction mixture was stirred for 12 h at 70° C. It was then cooled to RT and quenched with brine (1 L). The precipitates thus obtained were filtered and washed thoroughly with EtOAc (3×1.0 L). The layers were separated, and the organic layer was concentrated under reduced pressure to afford the initial mixture which was purified by silica gel chromatography (30% EtOAc in hexanes) to give compound 456C (230 g, 68%). $^1$H NMR (300 MHz, Chloroform-d) δ 7.45 (t, J=7.0 Hz, 1H), 7.29-7.24 (m, 1H), 7.08-7.03 (m, 1H), 2.76 (s, 3H), 2.30 (s, 3H), 1.32 (s, 9H). MS (ESI+ve ion) m/z: [M+1]=256.2.

Preparation of (3S)-tert-butyl-3-(1,1-dimethylethylsulfinamido)-3-(2-fluoro-3-methylphenyl) butanoate (456D). To a suspension of zinc powder (589 g, 9.01 mol) in THF (2.5 L) was added TMSCl (92 mL, 721.5 mmol). The reaction mixture was then heated at 60° C. for 45 min. Next, the reaction mixture was cooled to 35° C., and t-butyl bromo acetate (284 mL, 2.25 mol) was added over 6 h (internal temperature did not go above 45° C.) and the reaction mixture was heated to 55° C. for 60 min. The reaction mixture was then allowed to cool to RT and stand for 30 min. The freshly prepared Zn-reagent was cannulated to a solution of compound 456C (230 g, 901 mmol) in THF (2.0 L) at 0° C. dropwise. The resulting reaction mixture was stirred for 12 h at RT. It was then quenched with saturated NH$_4$Cl (3.0 L) and stirred for 2 h (until all the white precipitates were dissolved). The layers were separated and the aqueous layer was extracted with EtOAc (3×3.0 L). The combined organic layers were dried (Na$_2$SO$_4$) and concentrated under reduced pressure to give an orange oil that was purified by silica gel chromatography (25% EtOAc in hexanes) to give compound 456D (270 g, 81%). $^1$H NMR: (300 MHz, CDCl$_3$) δ 7.32-7.29 (m, 1H), 7.12-7.08 (m, 1H), 7.00-6.95 (m, 1H), 5.42 (s, 1H), 3.27-3.25 (m, 1H), 2.97-2.95 (m, 1H), 2.35 (s, 3H), 1.84 (s, 3H), 1.28 (s, 9H), 1.24 (s, 9H). MS (ESI+ve ion) m/z: [M+1]=372.2.

Preparation of (R)—N—((S)-2-(2-fluoro-3-methylphenyl)-4-hydroxybutan-2-yl)-2-methyl propane-2-sulfinamide (456E). To a solution of compound 456D (270 g, 727.2 mmol) in dry THF (2.5 L) was added LiBH$_4$ (2.0 M solution in THF, 727 mL, 1454 mmol) dropwise at RT. The reaction mixture was stirred for 30 min at RT and was then cooled to 0° C. MeOH (294 mL) was slowly added. The reaction mixture was then stirred for 12 h at RT and quenched with saturated ammonium chloride (2.5 L). The reaction was then diluted with water and extracted with EtOAc (3×2.0 L). The organic layer was dried over sodium sulfate and concentrated under reduced pressure. The material thus obtained was triturated with hexanes (1.0 L) and filtered. The solid was purified by silica gel chromatography (10% EtOAc in hexanes) to give compound 456E (170 g, 78%). $^1$H NMR (300 MHz, DMSO) δ 7.31-7.28 (m, 1H), 7.19-7.17 (m, 1H), 7.04 (t, J=7.6 Hz, 1H), 5.56 (s, 1H), 4.74-4.71 (t, J=4.5 Hz, 1H), 3.46-3.43 (m, 1H), 3.26-3.22 (m, 1H), 2.20 (s, 3H), 2.17-2.08 (m, 2H), 1.71 (s, 3H), 1.11 (s, 9H). MS (ESI +ve ion) m/z: [M+1]=302.2.

Preparation of N—((S)-2-(2-fluoro-3-methylphenyl)-4-oxobutan-2-yl)-2-methylpropane-2-sulfinamide (456F). To a solution of compound 456E (170 g, 564.2 mmol, 1.0 equiv) in DMSO (850 mL) and DCM (1700 mL) at 0° C. was added DIPEA (295 mL, 1692.6 mmol) followed by pyridine sulphur trioxide (135 g, 846.3 mmol). The reaction mixture was then stirred overnight at RT, and then it was treated with water (2500 mL) and extracted with DCM (3×2000 mL). The combined organic layers were dried over sodium sulfate and concentrated under reduced pressure. The product thus obtained was purified by silica gel chromatography (50% EtOAc in hexanes) to give compound 456E (140 g, 83%). $^1$H NMR (300 MHz, CDCl$_3$) δ 9.62 (s, 1H), 7.30-7.20 (m, 1H), 7.06-7.04 (m, 1H), 6.99-6.96 (m, 1H), 4.81 (s, 1H), 3.40 (q, 2H), 2.20 (s, 3H), 1.74 (s, 3H), 1.21 (s, 9H). MS (ESI+ve ion) m/z: [M+1]=300.2.

Preparation of (S)-2-(2-fluoro-3-methylphenyl)-4,4-dimethoxybutan-2-amine (456G). To a solution of compound 456F (140 g, 468.6 mmol) in MeOH (700 mL) was added p-toluene sulfonic acid monohydrate (4.03 g, 23.38 mmol). The reaction mixture was stirred at 65° C. for 12 h. The solution was then allowed to cool to RT and treated with HCl (4.0 M solution in 1,4-dioxane, 129 mL, 516 mmol) dropwise. The reaction mixture was then stirred at RT for 3 h. The mixture was concentrated under reduced pressure and the material thus obtained was diluted with EtOAc (2 L) and treated with sat. aq. NaHCO$_3$ (2 L). The layers were separated and the aqueous layer was extracted with EtOAc (2×1 L). The combined organic extracts were washed with brine (1 L), dried over magnesium sulfate, filtered and concentrated under reduced pressure to give a light-yellow oil which was purified by silica gel chromatography (50% EtOAc in DCM) gave compound 456G (90 g, 80%). $^1$H NMR (400 MHz, CDCl$_3$) δ 7.34-7.32 (m, 1H), 7.11-7.09 (m, 1H), 7.03-7.01 (m, 1H), 4.88-4.86 (m, 1H), 3.21 (s, 3H), 3.17 (s, 3H) 2.40-2.30 (m, 5H), 2.15-2.00 (m, 3H). The NH$_2$ peak was very broad. MS (ESI+ve ion) m/z: [M+1]=242.2.

Preparation of (S)-4-(2-fluoro-3-methylphenyl)-4-methyl-4H-1,3-thiazin-2-amine (456H). To a stirring solution of compound 456G (60 g, 249.4 mmol) in THF (600 mL) at 0° C. under nitrogen, was added benzoyl isothiocyanate (36.9 mL, 274.6 mmol) dropwise. The reaction temperature was maintained between 0-5° C. during the addition. The reaction mixture was allowed to stir at 0° C. for 20 min. The solvents were then removed under reduced pressure, and the residue was chilled with an ice bath. Concentrated sulfuric acid (120 mL) was then added dropwise. The resulting solution was stirred for 2 h at 70° C. The mixture was then cooled to 0° C. and poured onto ice. To the slurry was added EtOAc (5.0 L), and the biphasic solution was chilled to 0° C. and basified to pH~12 with very slow addition of a 10 M aqueous NaOH solution. The organic layer was separated and the aqueous layer was extracted with EtOAc (3×5 L). The combined organic extracts were dried over Na$_2$SO$_4$, filtered and concentrated under reduced pressure. The residue was purified by flash column chromatography (hexanes:EtOAc=4:1) to give compound 456H (18.0 g, 31% yield). $^1$H NMR (400 MHz, CDCl$_3$) δ 7.27-7.25 (m, 1H), 7.09-7.05 (m, 1H), 6.97 (t, J=7.6 Hz, 1H), 6.35-6.20 (m, 2H), 2.26 (s, 3H), 1.72 (s, 3H). The NH$_2$ peak was very broad. MS (ESI+ve ion) m/z: [M+1]=237.0.

Preparation of (S)-tert-butyl(4-(2-fluoro-3-methylphenyl)-4-methyl-4H-1,3-thiazin-2-yl)carbamate (456I). To a solution of compound 456H (21 g, 89.6 mmol) in THF (200 mL) was added di-tert-butyl carbonate (42.7 g, 196.2 mmol) and DMAP (0.54 g, 4.4 mmol) at RT. The reaction mixture was then heated at 50° C. for 3 h. The resulting mixture was cooled to RT and treated with water (1 L) and extracted with EtOAc (3×1 L). The organic extracts were dried over sodium sulfate and concentrated under reduced pressure. The residue was taken in mixed solvents of THF: MeOH: water (200 mL: 100 mL: 100 mL) and treated with lithium hydroxide monohydrate (11.19 g, 269.0 mmol). The reaction mixture was heated at 50° C. for 40 min. The resulting mixture was then cooled to RT and diluted with water (1 L) and extracted with EtOAc (3×1 L). The combined organic layers were dried over sodium sulfate. The resulting mixture was concentrated under reduced pressure, and the product thus obtained was purified by flash chromatography using 10% EtOAc in hexanes to afford compound 456I (22 g, 73%). $^1$H NMR (300 MHz, CDCl$_3$) δ 7.15-7.10 (m, 2H), 7.01-6.96 (m, 1H), 6.24-6.17 (m, 2H), 2.27 (s, 3H), 1.80 (s, 3H), 1.53 (s, 9H). NH peak was not observed. MS (ESI+ve ion) m/z: [M+1]=337.0.

Preparation of (S)-tert-butyl(4-(2-fluoro-3-methylphenyl)-4-methyl-4H-1,3-thiazin-2-yl)((2-(trimethylsilyl)ethoxy)methyl)carbamate (456J). To a solution of compound 456I (22 g, 65.4 mmol) in THF (250 mL) was added LiHMDS (1.0 M in THF, 72 mL, 72 mmol) at −78° C. The reaction mixture was then stirred for 15 min at −78° C. and then treated with SEM chloride (12.0 g, 72.0 mmol). The reaction mixture was slowly warmed to RT and stirred for 3 h at RT. The resulting mixture was quenched with saturated ammonium chloride solution and extracted with EtOAc (3×1 L). The organic layers were combined and dried over sodium sulfate. The product thus obtained was purified by flash chromatography using 5% EtOAc in hexanes to afford compound 456J (25 g, 82%). $^1$H NMR (400 MHz, CDCl$_3$) δ 7.36 (t, J=7.7 Hz, 1H), 7.10 (t, J=6.9 Hz, 1H), 7.00 (t, J=7.5 Hz, 1H) 6.29 (d, J=9.3 Hz, 1H), 6.09 (dd, J=3.6 Hz, 9.3 Hz, 1H), 5.30 (d, J=10.4 Hz, 1H), 5.24 (d, J=10.4 Hz, 1H), 3.69-3.61 (m, 2H), 2.30 (s, 3H), 1.72 (s, 3H), 1.54 (s, 9H), 0.97-0.95 (m, 2H), 0.03 (s, 9H). MS (ESI+ve ion) m/z: [M+1]=467.2.

Preparation of (S)-2-((tert-butoxycarbonyl)((2-(trimethylsilyl)ethoxy)methyl)amino)-4-(2-fluoro-3-methylphenyl)-4-methyl-4H-1,3-thiazine-6-carboxylic acid (456K). To a solution of compound 456J (24.0 g, 51.4 mmol) in THF (250 mL) at −78° C. was added a solution of LDA (2 M in THF, 64.5 mL, 129 mmol) and the reaction mixture was stirred for 20 min at −78° C. Carbon dioxide gas was purged to the reaction mixture for 5 min and the resulting mixture was warm to RT. The resulting mixture was quenched with sat. NH$_4$Cl solution (200 mL) and extracted with EtOAc (3×500 mL). The combined organic layers were dried over sodium sulfate and concentrated under reduced pressure. The product thus obtained was purified by silica gel chromatography (50% EtOAc in hexanes) to afford compound 456K (17 g, 65%). $^1$H NMR (300 MHz, CDCl$_3$) δ 7.33-7.28 (m, 1H), 7.10-7.02 (m, 2H), 6.98-6.93 (m, 1H), 5.27 (d, J=10.6 Hz, 1H), 5.18 (d, J=10.6 Hz, 1H), 3.68-3.64 (m, 2H), 2.27 (s, 3H), 1.72 (s, 3H), 1.51 (s, 9H), 0.99-0.89 (m, 2H), 0.03 (s, 9H). —COOH proton was not observed. MS (ESI+ve ion) m/z: [M+1]=511.2.

Preparation of (S)-methyl-2-((tert-butoxycarbonyl)((2-trimethylsilyl)ethoxy)methyl)amino)-4-(2-fluoro-3-methylphenyl)-4-methyl-4H-1,3-thiazine-6-carboxylate (456L). To a solution of compound 456K (17.0 g, 33.3 mmol) in DMF (150 mL) at RT was added potassium carbonate (9.20 g, 66.6 mmol) followed by iodomethane (2.91 mL, 46.6 mmol). After the mixture was stirred for 3 h at RT, it was quenched with water (1 L) and extracted with Et$_2$O (3×500 mL). The combined organic layers were dried over sodium sulfate and concentrated under reduced pressure. The product thus obtained was purified by flash chromatography using 5% EtOAc in hexanes to give compound 456L (13.0 g, 74%). $^1$H NMR (300 MHz, CDCl$_3$) δ 7.36-7.30 (m, 1H), 7.15-7.10 (m, 2H), 7.00 (t, J=7.6 Hz, 1H), 5.31 (d, J=10.5 Hz, 1H), 5.22 (d, J=10.5 Hz, 1H), 3.82 (s, 3H), 3.68-3.64 (m, 2H), 2.28 (s, 3H), 1.75 (s, 3H), 1.53 (s, 9H), 0.92-0.89 (m, 2H), 0.02 (s, 9H). MS (ESI+ve ion) m/z: [M+1]=525.2.

Preparation of (5S)-methyl-3-((tert-butoxycarbonyl)((2-(trimethylsilyl)ethoxy)methyl)amino)-5-(2-fluoro-3-methylphenyl)-5-methyl-2-thia-4-azabicyclo[4.1.0]hept-3-ene-1-carboxylate (456M). To a solution of trimethylsulfoxonium iodide (6.0 g, 27.3 mmol) in DMSO (100 mL) at RT was added potassium tert-butoxide (3.06 g, 27.3 mmol). The resulting mixture was stirred for 30 min and then it was cannulated to a solution of compound 456L in THF (150 mL) at RT. The reaction mixture was stirred for 1 h at RT and then it was quenched with sat. NH$_4$Cl solution, and extracted with DCM (3×250 mL). The combined organic layers were dried over sodium sulfate and concentrated. The crude product was purified by flash column chromatography using 5% EtOAc in hexanes to afford compound 456M (7.5 g, 56%). $^1$H NMR: (400 MHz, CDCl$_3$) δ 7.45 (m, 1H), 7.15-7.11 (m, 1H), 7.03 (t, J=7.6 Hz, 1H), 5.30 (d, J=10.8 Hz, 1H), 5.06 (d, J=10.8 Hz, 1H), 3.83 (s, 3H), 3.71-3.67 (m, 2H), 2.71-2.67 (m, 1H), 2.32 (s, 3H), 1.77 (s, 3H), 1.54 (s, 9H), 1.26-1.22 (m, 2H), 0.98-0.94 (m, 2H), 0.02 (s, 9H). MS (ESI+ve ion) m/z: [M+1]=539.1

313

(1S,5S,6S)-5-(5-Amino-2-fluoro-3-methylphenyl)-1-(methoxymethyl)-5-methyl-2-thia-4-azabicyclo[4.1.0]hept-3-en-3-amine (456)

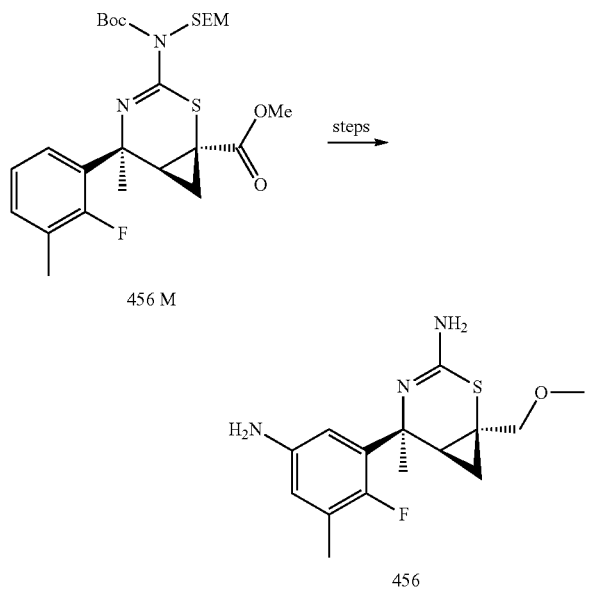

The title compound was prepared from 456M using the procedures described for intermediate 208. LC/MS (ESI⁻) m/z=310.0 (M+H)⁺. ¹H NMR (400 MHz, CHLOROFORM-d) δ 6.81 (dd, J=3.03, 6.16 Hz, 1H), 6.39 (dd, J=2.93, 5.67 Hz, 1H), 3.65 (d, J=10.56 Hz, 1H), 3.40 (s, 3H), 3.28-3.35 (m, 1H), 2.20 (d, J=2.35 Hz, 3H), 1.76 (dd, J=7.24, 9.00 Hz, 1H), 1.68 (d, J=1.37 Hz, 3H), 0.87 (dd, J=5.87, 9.59 Hz, 1H), 0.72-0.82 (m, 1H).

(1S,5S,6S)-3-Amino-5-(5-amino-2-methoxypyridin-3-yl)-5-methyl-2-thia-4-azabicyclo[4.1.0]hept-3-ene-1-carbonitrile (457)

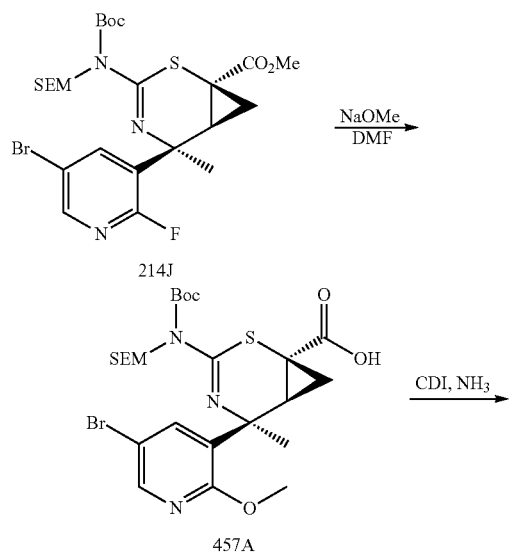

314

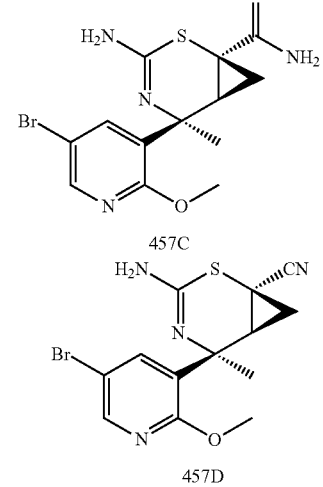

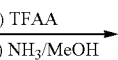

Preparation of (1S,5S,6S)-5-(5-bromo-2-methoxypyridin-3-yl)-3-((tert-butoxycarbonyl)((2-(trimethylsilyl)ethoxy)methyl)amino)-5-methyl-2-thia-4-azabicyclo[4.1.0]hept-3-ene-1-carboxylic acid (457A). To a solution of (1S,5S,6S)-methyl 5-(5-bromo-2-fluoropyridin-3-yl)-3-((tert-butoxycarbonyl)((2-(trimethylsilyl)ethoxy)methyl)amino)-5-methyl-2-thia-4-azabicyclo[4.1.0]hept-3-ene-1-carboxylate (214J, 2.80 g, 4.63 mmol) in DMF (10 mL) was added anhydrous sodium methoxide powder (2.50 g, 46.3 mmol) in small portions. The resulting suspension was stirred at RT for 18 h, and then it was diluted with water and acidified to pH 4 with 5 N HCl. The solid that formed was filtered and dried to give the title compound (457A, 2.07 g, 3.44 mmol, 74% yield). The product thus obtained was used in next step without further purification. LCMS (ESI⁺) m/z=604.2 (M+2H).

Preparation of tert-butyl((1S,5S,6S)-5-(5-bromo-2-methoxypyridin-3-yl)-1-carbamoyl-5-methyl-2-thia-4-azabicyclo[4.1.0]hept-3-en-3-yl)((2-(trimethylsilyl)ethoxy)methyl)carbamate (457B). The title compound 457B, (0.82 g, 1.36 mmol, 82% yield) was prepared according to the procedure described for intermediate 243A using (1S,5S,6S)-5-(5-bromo-2-methoxypyridin-3-yl)-3-((tert-butoxycarbonyl)((2-(trimethylsilyl)ethoxy)methyl)amino)-5-methyl-2-thia-4-azabicyclo[4.1.0]hept-3-ene-1-carboxylic acid, 457A, (1.00 g, 1.66 mmol) and 1,1'-carbonyldiimidazole (0.40 g, 2.49 mmol). LCMS (ESI+) m/z=602.1/603.1 (M+H). $^1$H NMR (300 MHz, CHLOROFORM-d) δ: 8.12 (d, J=2.49 Hz, 1H), 7.87 (d, J=2.34 Hz, 1H), 6.57-6.93 (m, 1H), 5.47-5.70 (m, 1H), 5.39 (d, J=10.52 Hz, 1H), 5.09 (d, J=10.52 Hz, 1H), 3.99-4.03 (m, 3H), 3.66-3.74 (m, 2H), 2.50 (dd, J=7.75, 9.65 Hz, 1H), 1.76-1.87 (m, 4H), 1.54-1.58 (m, 9H), 1.01 (ddd, J=1.61, 6.94, 9.72 Hz, 2H), 0.78 (dd, J=5.12, 7.60 Hz, 1H), −0.07 (s, 9H).

Preparation of (1S,5S,6S)-3-amino-5-(5-bromo-2-methoxypyridin-3-yl)-5-methyl-2-thia-4-azabicyclo[4.1.0]hept-3-ene-1-carboxamide (457C). The title compound 457C, (0.50 g, 1.34 mmol, 100% yield) was prepared according to the procedures described for intermediate 218C using tert-butyl((1S,5S,6S)-5-(5-bromo-2-methoxypyridin-3-yl)-1-carbamoyl-5-methyl-2-thia-4-azabicyclo[4.1.0]hept-3-en-3-yl)((2-(trimethylsilyl)ethoxy)methyl)carbamate, 457B (0.80 g, 1.33 mmol). LC/MS (ESI+) m/z=370.0/372.9 (M+H).

Preparation of (1S,5S,6S)-3-amino-5-(5-bromo-2-methoxypyridin-3-yl)-5-methyl-2-thia-4-azabicyclo[4.1.0]hept-3-ene-1-carbonitrile (457D). The title compound 457D, (0.20 g, 0.56 mmol, 42% yield) was prepared according to the procedure described for intermediate 243D using (1S,5S,6S)-3-amino-5-(5-bromo-2-methoxypyridin-3-yl)-5-methyl-2-thia-4-azabicyclo[4.1.0]hept-3-ene-1-carboxamide, 457C, (0.50 g, 1.34 mmol), diisopropylethylamine (1.64 mL, 9.43 mmol), 2,2,2-trifluoroacetic anhydride (0.75 mL, 5.39 mmol), and 2 M ammonia in MeOH. LCMS (ESI+) m/z=353.1/355.0 (M+H). $^1$H NMR (400 MHz, CHLOROFORM-d) δ: 8.11 (d, J=2.15 Hz, 1H), 7.95 (d, J=2.35 Hz, 1H), 5.20-4.20 (br.s, 2H), 4.01 (s, 3H), 2.75 (dd, J=8.02, 9.98 Hz, 1H), 1.76 (s, 3H), 1.56 (dd, J=6.06, 9.98 Hz, 1H), 1.04 (dd, J=6.16, 7.92 Hz, 1H).

Preparation of (1S,5S,6S)-3-amino-5-(5-amino-2-methoxypyridin-3-yl)-5-methyl-2-thia-4-azabicyclo[4.1.0]hept-3-ene-1-carbonitrile (457). The title compound 457, (0.05 g, 0.17 mmol, 30% yield) was prepared according to the procedure described for intermediate 218 using (1S,5S,6S)-3-amino-5-(5-bromo-2-methoxypyridin-3-yl)-5-methyl-2-thia-4-azabicyclo[4.1.0]hept-3-ene-1-carbonitrile, 457D, (0.20 g, 0.56 mmol), sodium azide (0.14 g, 2.26 mmol), copper(i) iodide (11 mg, 0.05 mmol), (+)-sodium L-ascorbate (22 mg, 0.11 mmol), (1R,2R)-(−)-N,N''-dimethylcyclohexane-1,2-diamine and 1 M trimethylphosphine solution in THF (1.13 mL, 1.13 mmol). LC/MS (ESI+) m/z=290.2 (M+H). $^1$H NMR (300 MHz, CHLOROFORM-d) δ: 7.56 (d, J=2.78 Hz, 1H), 7.24-7.30 (m, 1H), 3.95 (s, 3H), 3.78-4.04 (br.s, 4H), 2.70 (dd, J=8.11, 9.87 Hz, 1H), 1.78 (s, 3H), 1.60 (dd, J=6.14, 10.08 Hz, 1H), 0.99 (dd, J=6.14, 7.89 Hz, 1H).

(1S,5S,6S)-5-(5-Amino-2,3-difluorophenyl)-1-(methoxytrideuteriomethyl)-5-methyl-2-thia-4-azabicyclo[4.1.0]hept-3-en-3-amine (458)

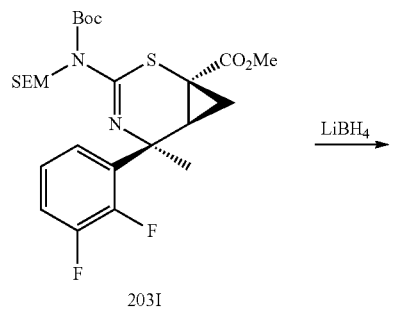

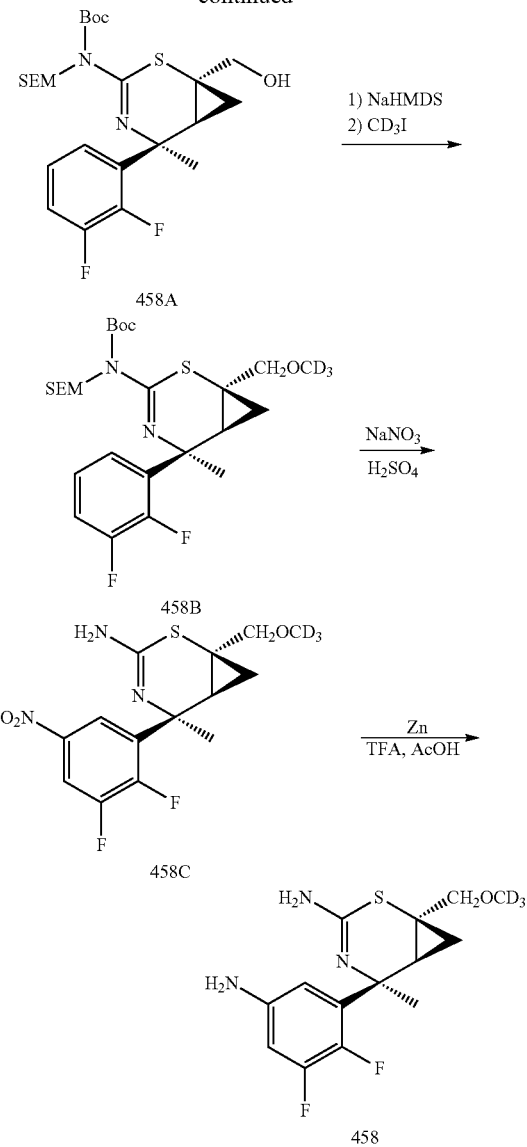

Preparation of compound 458A. To a stirred solution of (1S,5S,6S)-methyl 3-((tert-butoxycarbonyl)((2-(trimethylsilyl)ethoxy)methyl)amino)-5-(2,3-difluorophenyl)-5-methyl-2-thia-4-azabicyclo[4.1.0]hept-3-ene-1-carboxylate (203I, 36 g, 66.3 mmol) in THF (300 mL) at RT was added lithium borohydride (2.0 M in THF, 66.3 mL, 133 mmol). The vessel was then charged with MeOH (21.50 mL, 531 mmol) and gas evolution was evident with the reaction temperature rising to 33° C. The solution was stirred for 1 h, cooled to 0° C., and then it was slowly quenched with 150 mL of ½ sat. aqueous NH$_4$Cl added via addition funnel. The mixture was then extracted twice with 2:1 heptane/EtOAc (500 mL). The combined organic layers were washed with sat. NaCl (2×50 mL), 1 M HCl (100 mL), followed again by sat NaCl (2×50 mL). The organic layer was dried over MgSO$_4$, filtered, concentrated under reduced pressure, and then purified by silica gel chromatography (0-15% EtOAc/heptane) to afford tert-butyl((1S,5S,6S)-5-(2,3-difluorophenyl)-1-(hydroxymethyl)-5-methyl-2-thia-4-azabicyclo[4.1.0]hept-3-en-3-yl)((2-(trimethylsilyl)ethoxy)methyl)

carbamate (458A, 27.2 g, 52.8 mmol, 80% yield) as a light colorless oil that crystallized upon setting. LC/MS (ESI⁻) m/z=515.2 (M+H)⁺.

Preparation of compound 458B. To a stirred solution of tert-butyl((1S,5S,6S)-5-(2,3-difluorophenyl)-1-(hydroxymethyl)-5-methyl-2-thia-4-azabicyclo[4.1.0]hept-3-en-3-yl)((2-(trimethylsilyl)ethoxy)methyl)carbamate (458A, 1.05 g, 2.040 mmol) in THF (10 mL) at 0° C. was added sodium bis(trimethylsilyl)amide (1.0 M in THF, 2.44 mL, 2.44 mmol) dropwise at a rate that did not exceed an internal temp of 6° C. After 15 min, trideuteriomethyl iodide (0.17 mL, 2.65 mmol) was added. The resulting mixture was warmed to 20° C. and stirred for 18 h. The reaction was then quenched with aq. NH₄Cl (5 mL) and diluted with water (10 mL). The mixture was extracted with 2:1 heptane/EtOAc (50 mL). The organic layer was then washed with 1 M HCl (5 mL) followed by sat. NaCl (2×5 mL). The organic layer was then dried over MgSO₄. Filtration followed by concentration under reduced pressure afforded tert-butyl((1S,5S,6S)-5-(2,3-difluorophenyl)-1-(methoxytrideuteriomethyl)-5-methyl-2-thia-4-azabicyclo[4.1.0]hept-3-en-3-yl)((2-(trimethylsilyl)ethoxy)methyl)carbamate (458B, 1.02 g, 1.92 mmol, 94% yield) as a colorless oil. LC/MS (ESI⁻) m/z=532.3 (M+H)⁺.

Preparation of compound 458C. To a 100 mL single neck round bottom flask containing tert-butyl((1S,5S,6S)-5-(2,3-difluorophenyl)-1-(methoxytrideuteriomethyl)-5-methyl-2-thia-4-azabicyclo[4.1.0]hept-3-en-3-yl)((2-(trimethylsilyl)ethoxy)methyl)carbamate (458B, 1.02 g, 1.92 mmol) at 0° C. under nitrogen was added sulfuric acid (3.58 mL, 67.10 mmol). After 15 min, the reaction was removed from the cooling bath, swirled by hand, then allowed to stir at 20° C. for 30 min. The material was chilled to 0° C. and sodium nitrate (0.16 g, 1.92 mmol) was added. The reaction was stirred for 15 min at 0° C. and then more sodium nitrate (0.16 g, 1.92 mmol) was added. The reaction was stirred at 20° C. for 1 h, and then it was added dropwise to a mixture of wet ice (300 mL)/DCM (100 mL). After addition, water (500 mL) was added, and to the rapidly stirred mixture, was added potassium phosphate tribasic (14.25 g, 67.10 mmol) over 30 min periods (pH~7). The organic layer was separated, and the aqueous layer was extracted with DCM (2×20 mL). The combined organic layers were dried over MgSO₄, filtered, concentrated under reduced pressure, and then it was purified via silica gel chromatography (40 g) eluting the products with a gradient of 0-30% EtOAc/DCM to afford (1S,5S,6S)-5-(2,3-difluoro-5-nitrophenyl)-1-(methoxytrideuteriomethyl)-5-methyl-2-thia-4-azabicyclo[4.1.0]hept-3-en-3-amine (458C, 0.48 g, 1.38 mmol, 72% yield) as a yellow crystalline solid. LC/MS (ESI⁻) m/z=347.0 (M+H)⁺. ¹H NMR (400 MHz, CHLOROFORM-d) δ 8.47-8.52 (m, 1H), 7.98 (ddd, J=2.93, 6.31, 9.15 Hz, 1H), 4.53 (br. s., 2H), 3.63 (d, J=10.56 Hz, 1H), 3.38 (d, J=10.56 Hz, 1H), 1.78 (t, J=7.73 Hz, 1H), 1.73 (s, 3H), 0.90 (dd, J=6.06, 9.19 Hz, 1H), 0.79-0.84 (m, 1H).

Preparation of compound 458. To a stirring solution of (1S,5S,6S)-5-(2,3-difluoro-5-nitrophenyl)-1-(methoxytrideuteriomethyl)-5-methyl-2-thia-4-azabicyclo[4.1.0]hept-3-en-3-amine (458C, 480 mg, 1.38 mmol) in HOAc (4 mL) and TFA (1 mL) at 20° C. was added zinc (453 mg, 6.93 mmol) in 2 portions. After 1 h, the suspension was filtered and the metallic residue was extensively washed with DCM (20 mL). The filtrate was then added dropwise to a chilled (0° C.) mixture of 30% NH₄OH (10 mL) and DCM (10 mL). After separation of the organic and aqueous layers, the aqueous layer was further extracted with DCM (5 mL). The combined organic layers were dried over MgSO₄ and concentrated under reduced pressure to afford (1S,5S,6S)-5-(5-amino-2,3-difluorophenyl)-1-(methoxytrideuteriomethyl)-5-methyl-2-thia-4-azabicyclo[4.1.0]hept-3-en-3-amine as a yellow film. LC/MS (ESI⁻) m/z=317.1 (M+H)⁺.

tert-Butyl((1S,5S,6S)-5-(5-amino-2-fluorophenyl)-5-methyl-1-(methylcarbamoyl)-2-thia-4-azabicyclo [4.1.0]hept-3-en-3-yl)((2-(trimethylsilyl)ethoxy) methyl)carbamate (459)

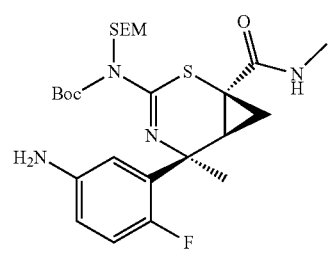

459

The title compound was synthesized according to the procedures described for intermediate 221D, using methylamine to react with (1S,5S)-5-(5-bromo-2-fluorophenyl)-3-((tert-butoxycarbonyl)((2-(trimethylsilyl)ethoxy)methyl) amino)-5-methyl-2-thia-4-azabicyclo[4.1.0]hept-3-ene-1-carboxylic acid 221A. LC/MS (ESI⁺) m/z=539 (M+H)⁺. ¹H NMR (400 MHz, CHLOROFORM-d) δ 6.92-7.03 (m, 1H), 6.85 (dd, J=8.61, 11.54 Hz, 1H), 6.70 (dd, J=2.93, 6.65 Hz, 1H), 6.50 (td, J=3.37, 8.51 Hz, 1H), 5.42 (d, J=10.56 Hz, 1H), 5.10 (d, J=10.76 Hz, 1H), 3.57-3.76 (m, 2H), 3.50 (br. s., 2H), 2.86 (d, J=4.69 Hz, 3H), 2.16 (dd, J=7.73, 9.29 Hz, 1H), 1.94 (dd, J=5.09, 9.59 Hz, 1H), 1.80 (d, J=0.78 Hz, 3H), 1.55 (s, 9H), 0.92-1.02 (m, 2H), 0.85 (dd, J=5.28, 6.46 Hz, 1H), 0.02 (s, 9H).

(1S,5S,6S)-5-(5-Amino-2-methoxypyridin-3-yl)-1-(difluoromethyl)-5-methyl-2-thia-4-azabicyclo [4.1.0]hept-3-en-3-amine (460)

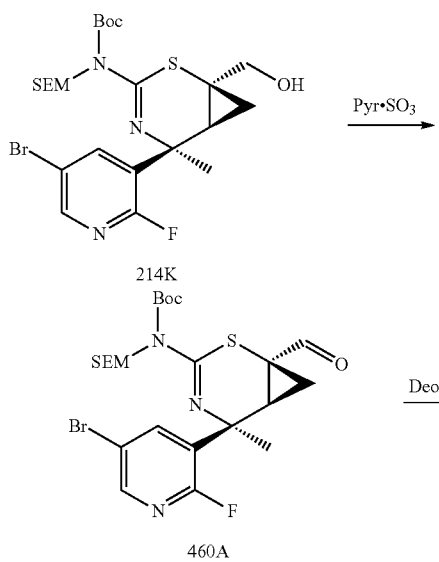

460A

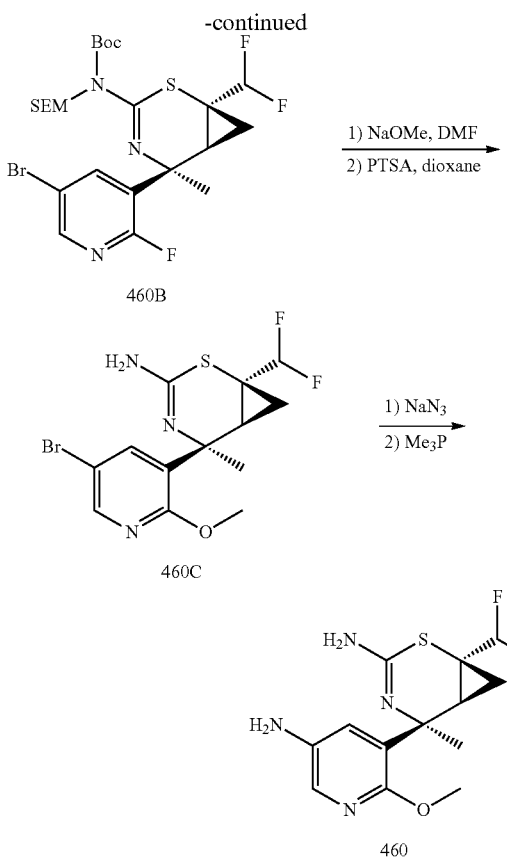

1) NaOMe, DMF
2) PTSA, dioxane

460B

1) NaN₃
2) Me₃P

460C

460

Preparation of tert-butyl((1S,5S,6S)-5-(5-bromo-2-fluoropyridin-3-yl)-1-formyl-5-methyl-2-thia-4-azabicyclo[4.1.0]hept-3-en-3-yl)((2-(trimethylsilyl)ethoxy)methyl)carbamate (460A). The title compound (7.59 g, 13.21 mmol, 76% yield) was prepared according to the procedure described for intermediate 218A using tert-butyl((1S,5S,6S)-5-(5-bromo-2-fluoropyridin-3-yl)-1-(hydroxymethyl)-5-methyl-2-thia-4-azabicyclo[4.1.0]hept-3-en-3-yl)((2-(trimethylsilyl)ethoxy)methyl)carbamate, 214K, (10 g, 17.34 mmol), TEA (12.06 mL, 87 mmol) and pyridine-sulfur trioxide complex (6.90 g, 43.40 mmol). LCMS (ESI⁺) m/z=574.1/576.1 (M+H).

Preparation of tert-butyl((1S,5S,6S)-5-(5-bromo-2-fluoropyridin-3-yl)-1-(difluoromethyl)-5-methyl-2-thia-4-azabicyclo[4.1.0]hept-3-en-3-yl)((2-(trimethylsilyl)ethoxy)methyl)carbamate (460B). The title compound (7.43 g, 12.45 mmol, 94% yield) was prepared according to the procedure described for intermediate 218B using tert-butyl ((1S,5S,6S)-5-(5-bromo-2-fluoropyridin-3-yl)-1-formyl-5-methyl-2-thia-4-azabicyclo[4.1.0]hept-3-en-3-yl)((2-(trimethylsilyl)ethoxy)methyl)carbamate (460A, 7.59 g, 13.21 mmol) and deoxo-fluor solution (8.51 mL, 46.2 mmol). LCMS (ESI⁺) m/z=596.0/598.1 (M+H). $^1$H NMR (300 MHz, CHLOROFORM-d) δ: 8.16-8.34 (m, 2H), 5.51-6.03 (m, 1H), 5.33 (d, J=10.08 Hz, 1H), 5.06 (d, J=10.52 Hz, 1H), 3.56-3.83 (m, 2H), 2.18 (t, J=8.62 Hz, 1H), 1.76 (s, 3H), 1.55 (s, 9H), 1.13-1.40 (m, 2H), 0.95-1.09 (m, 2H), −0.06 (s, 9H).

Preparation of (1S,5S,6S)-5-(5-bromo-2-methoxypyridin-3-yl)-1-(difluoromethyl)-5-methyl-2-thia-4-azabicyclo[4.1.0]hept-3-en-3-amine (460C). To a solution of tert-butyl ((1S,5S,6S)-5-(5-bromo-2-fluoropyridin-3-yl)-1-(difluoromethyl)-5-methyl-2-thia-4-azabicyclo[4.1.0]hept-3-en-3-yl)((2-(trimethylsilyl)ethoxy)methyl)carbamate, 460B, (4.68 g, 7.84 mmol) in DMF (15 mL) was added sodium methoxide (4.24 g, 78 mmol) portionwise. The suspension was stirred at RT for 30 min, diluted with water and extracted with EtOAc (2×). The combined organic layers were dried and concentrated under vacuum to afford tert-butyl((1S,5S,6S)-5-(5-bromo-2-methoxypyridin-3-yl)-1-(difluoromethyl)-5-methyl-2-thia-4-azabicyclo[4.1.0]hept-3-en-3-yl)((2-(trimethylsilyl)ethoxy)methyl)carbamate. The product thus obtained in 5 mL of dioxane was treated with p-toluenesulfonic acid monohydrate (1.87 g, 9.86 mmol). The reaction was heated to 85° C. for 2 h, and it was then diluted with water and extracted with EtOAc (2×). The combined organic layers were concentrated, and the residue was purified by flash column chromatography on silica gel (0-5% MeOH in DCM) to afford the title compound (460C, 0.55 g, 1.45 mmol, 73% yield). LCMS (ESI⁺) m/z=378.0/380.1 (M+H).

Preparation of (1S,5S,6S)-5-(5-amino-2-methoxypyridin-3-yl)-1-(difluoromethyl)-5-methyl-2-thia-4-azabicyclo[4.1.0]hept-3-en-3-amine (460). The title compound (0.17 g, 0.54 mmol, 41% yield) was prepared according to the procedure described for 218 using (1S,5S,6S)-5-(5-bromo-2-methoxypyridin-3-yl)-1-(difluoromethyl)-5-methyl-2-thia-4-azabicyclo[4.1.0]hept-3-en-3-amine (460C, 0.50 g, 1.32 mmol), sodium azide (0.34 g, 5.3 mmol), (1R,2R)-(−)-N,N″-dimethylcyclohexane-1,2-diamine (0.04 mL, 0.26 mmol), copper(I) iodide (25 mg, 0.13 mmol), and 1 M trimethylphosphine solution in THF (3.97 mL, 3.97 mmol). LC/MS (ESI⁺) m/z=315.2 (M+H). $^1$H NMR (300 MHz, CHLOROFORM-d) δ: 7.56 (s, 1H), 7.23 (br. s., 1H), 5.35-5.93 (m, 1H), 3.94 (s, 3H), 3.39 (br. s., 2H), 2.12-2.21 (m, 1H), 1.72-1.84 (m, 3H), 1.53 (s, 2H), 1.29 (d, J=13.59 Hz, 1H), 0.70 (br. s., 1H). $^{19}$F NMR (377 MHz, DMSO-d₆) δ: −116.63 (d, $^1$J=276.2 Hz, 1F), −119.21 (d, $^1$J=276.2 Hz, 1F).

(1S,5S,6S)-Methyl 3-(di-tert-butoxycarbonyl)amino-5-(2,3-difluoro-5aminophenyl)-5-methyl-2-thia-4-azabicyclo[4.1.0]hept-3-ene-1-(morpholino)methanone (461)

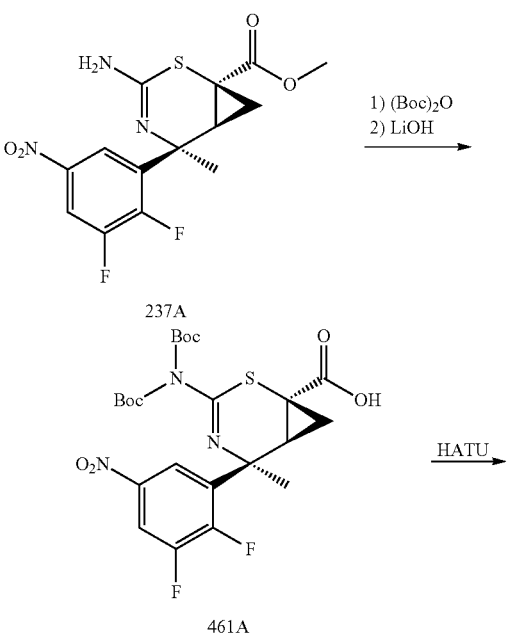

237A 1) (Boc)₂O
2) LiOH

461A

HATU

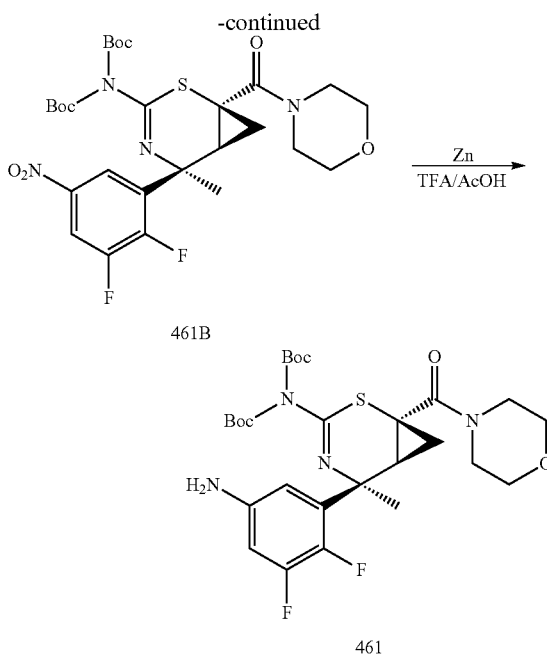

461B

461

Preparation of compound 461A. To a stirred solution of di-tert-butyl dicarbonate (3.82 g, 17.49 mmol) in THF (15 mL) was added (1S,5S,6S)-methyl 3-amino-5-(2,3-difluoro-5-nitrophenyl)-5-methyl-2-thia-4-azabicyclo[4.1.0]hept-3-ene-1-carboxylate (237A, 2.5 g, 7.00 mmol) in THF (15 mL) at 20° C. followed by DMAP (0.02 g, 0.17 mmol). After 30 min, MeOH (5 mL) was added to the mixture followed by an aqueous solution of lithium hydroxide monohydrate (0.88 g, 20.99 mmol) in water (10 mL). The suspension was stirred for 36 h at 20° C. The reaction was then partitioned between 1:1 EtOAc/heptane (150 mL) and 0.5 M KH$_2$PO$_4$ (50 mL). The organic layer was further washed with brine (2×25 mL). The organic layer was then dried over MgSO$_4$, and concentrated under reduced pressure to afford (1S,5S,6S)-methyl 3-(di-tert-butoxycarbonyl)amino-5-(2,3-difluoro-5-nitrophenyl)-5-methyl-2-thia-4-azabicyclo[4.1.0]hept-3-ene-1-carboxylic acid (461A, 3.76 g, 6.92 mmol, 99% yield) as white solid. LC/MS (ESI$^-$) m/z=566.2 (M+Na)$^+$. $^1$H NMR (400 MHz, DMSO-d$_6$) δ 8.40 (ddd, J=2.93, 6.50, 9.54 Hz, 1H), 8.12-8.21 (m, 1H), 3.60-3.66 (m, 1H), 2.29 (t, J=7.43 Hz, 1H), 1.63-1.71 (m, 3H), 1.42-1.52 (m, 18H), 1.06 (dd, J=3.91, 9.19 Hz, 1H), 0.75 (dd, J=4.11, 6.85 Hz, 1H).

Preparation of compound 461B. To a stirred solution of (1S,5S,6S)-methyl 3-(di-tert-butoxycarbonyl)amino-5-(2,3-difluoro-5-nitrophenyl)-5-methyl-2-thia-4-azabicyclo[4.1.0]hept-3-ene-1-carboxylic acid (461A, 270 mg, 0.49 mmol) and diisopropylethylamine (112 μL, 0.646\ mmol) in DMF (2 mL) at 20° C. was added HATU (246 mg, 0.64 mmol). The resulting solution was stirred for 20 min followed by addition of morpholine (60 μL, 0.69 mmol). Ater 18 h, the reaction was quenched with sat. NH$_4$Cl (2 mL) and was then partitioned between 2:1 EtOAc/heptane (30 mL) and water (75 mL). The organic layer was further washed with water (75 mL) and brine (10 mL), dried over MgSO$_4$, and concentrated under reduced pressure. The residue was purified by silica gel chromatography (20-50% EtOAc/heptane) to afford (1S,5S,6S)-methyl 3-(di-tert-butoxycarbonyl)amino-5-(2,3-difluoro-5-nitrophenyl)-5-methyl-2-thia-4-azabicyclo[4.1.0]hept-3-ene-1-(morpholino)methanone (461B, 300 mg, 0.49 mmol) as a white foam. LC/MS (ESI$^-$) m/z=636.2 (M+Na)$^+$.

Preparation of compound 461. To a stirred solution of (1S,5S,6S)-methyl 3-(di-tert-butoxycarbonyl)amino-5-(2,3-difluoro-5-nitrophenyl)-5-methyl-2-thia-4-azabicyclo[4.1.0]hept-3-ene-1-(morpholino)methanone (461C, 300 mg, 0.49 mmol) in glacial HOAc (2 mL) was added zinc (160 mg, 2.44 mmol). After 45 min, the reaction mixture was filtered, and the solid was washed with DCM (30 mL). The filtrate was then chilled to 0° C., and 30% NH$_4$OH (5 mL) was slowly added followed by water (50 mL). The organic layer was separated, washed with brine (10 mL), dried over MgSO$_4$, concentrated under reduced pressure, and then purified by silica gel chromatography (0-2.5% MeOH/DCM) to afford (1S,5S,6S)-methyl 3-(di-tert-butoxycarbonyl)amino-5-(2,3-difluoro-5aminophenyl)-5-methyl-2-thia-4-azabicyclo[4.1.0]hept-3-ene-1-(morpholino)methanone (461, 92 mg, 0.15 mmol, 32% yield) as a colorless film. LC/MS (ESI$^-$) m/z=605.2 (M+Na)$^+$. $^1$H NMR (400 MHz, CHLOROFORM-d) δ 6.62 (br. s., 1H), 6.48 (br. s., 1H), 3.70 (br. s., 8H), 2.43 (t, J=8.41 Hz, 1H), 1.81 (s, 3H), 1.51 (s, 18H), 1.33 (dd, J=5.58, 9.49 Hz, 1H), 1.13 (t, J=6.75 Hz, 1H).

(1S,5S,6S)-5-(5-Amino-2,3-difluorophenyl)-1-(ethoxymethyl)-5-methyl-2-thia-4-azabicyclo[4.1.0]hept-3-en-3-amine (462)

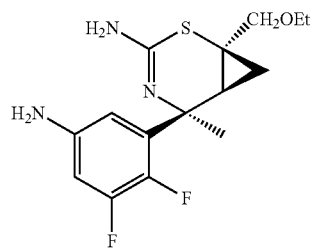

462

The title compound was prepared in a manner analogous to that described for intermediate 458 with the substitution of iodoethane. LC/MS (ESI$^-$) m/z=328.1 (M+H)$^+$.

(1S,5S,6S)-5-(5-Amino-2-fluoro-3-methylphenyl)-1-(difluoromethyl)-5-methyl-2-thia-4-azabicyclo[4.1.0]hept-3-en-3-amine (463)

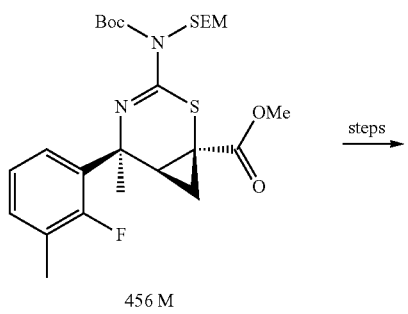

456M

-continued

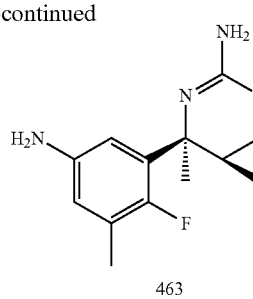

463

The title compound was prepared from 456 M using the procedures described for intermediate 211. LC/MS (ESI⁻) m/z=316.0 (M+H)⁺. ¹H NMR (400 MHz, CHLOROFORM-d) δ 6.57-6.64 (m, 1H), 6.39 (dd, J=3.03, 5.77 Hz, 1H), 5.48-5.81 (m, 1H), 3.44 (br. s., 2H), 2.20 (d, J=2.54 Hz, 3H), 1.93 (dd, J=7.34, 9.88 Hz, 1H), 1.73-1.76 (m, 3H), 1.33 (dd, J=6.16, 9.88 Hz, 1H), 0.79-0.86 (m, 1H).

(S)-5-(But-3-yn-2-yloxy)pyrazine-2-carboxylic acid (290)

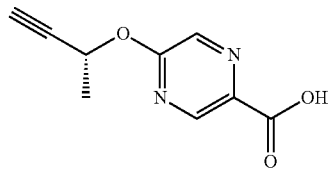

272A

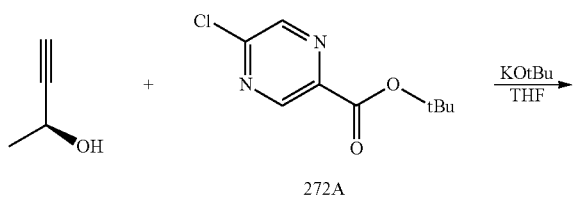

290A                290B

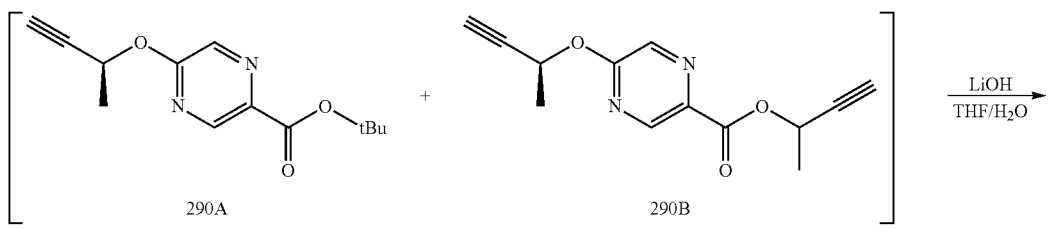

290

To a solution of (S)-(−)-3-butyn-2-ol (Alfa Aesar, 0.91 mL, 11.46 mmol) in THF (15 mL) was added potassium tert-butoxide (1.36 g, 12.11 mmol). The resulting solution was stirred at RT for 15 min and then a solution of tert-butyl 5-chloropyrazine-2-carboxylate (272A, 2.00 g, 9.32 mmol) in THF (20 mL) was added at 0° C. The mixture was gradually warmed to RT and stirred for 5 h. The reaction was quenched with sat. NH₄Cl, and the mixture was then extracted with EtOAc. The organic layer was dried over Na₂SO₄ and concentrated in vacuo. The material thus obtained was purified by silica gel chromatography (0-50% EtOAc in heptane) to provide a mixture of the desired product 290A and trans-esterification product 290B as a colorless oil (1.35 g).

A suspension of the above product (1.35 g), lithium hydroxide hydrate (0.46 g, 10.97 mmol), THF (30 mL) and water (10 mL) was heated at 50° C. until the conversion was complete. 1 N HCl (12 mL) was added, and the resulting mixture was extracted with DCM. The organic layer was dried over Na₂SO₄ and concentrated in vacuo to give (S)-5-(but-3-yn-2-yloxy)pyrazine-2-carboxylic acid (290) as a white solid (0.96 g, 54% yield over two steps). LC/MS (ESI⁺) m/z=193 (M+H)⁺. ¹H NMR (400 MHz, CHLOROFORM-d) δ 9.01 (d, J=1.17 Hz, 1H), 8.20 (d, J=0.98 Hz, 1H), 5.83 (dq, J=2.05, 6.68 Hz, 1H), 2.49 (d, J=2.15 Hz, 1H), 1.71 (d, J=6.65 Hz, 3H).

(R)-5-(But-3-yn-2-yloxy)pyrazine-2-carboxylic acid (291)

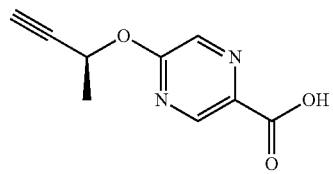

The title compound was synthesized according to the procedures described for intermediate 290, using (R)-but-3-yn-2-ol to react with tert-butyl 5-chloropyrazine-2-carboxylate 272A. LC/MS (ESI⁺) m/z=193 (M+H)⁺. ¹H NMR (400 MHz, CHLOROFORM-d) δ 9.01 (d, J=1.17 Hz, 1H), 8.21 (d, J=1.17 Hz, 1H), 5.83 (dq, J=2.05, 6.68 Hz, 1H), 2.50 (d, J=1.96 Hz, 1H), 1.71 (d, J=6.85 Hz, 3H).

325

(S)-5-((1-Methoxypropan-2-yl)oxy)pyrazine-2-carboxylic acid (292)

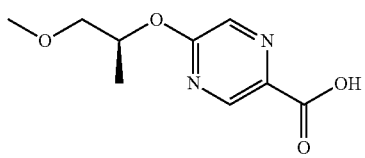

The title compound was synthesized according to the procedures described for intermediate 290, using (S)-(+)-1-methoxy-2-propanol to react with tert-butyl 5-chloropyrazine-2-carboxylate 272A. LC/MS (ESI$^+$) m/z=213 (M+H)$^+$. $^1$H NMR (400 MHz, CHLOROFORM-d) δ 8.95 (d, J=1.37 Hz, 1H), 8.17 (d, J=1.37 Hz, 1H), 5.53 (dquin, J=3.72, 6.36 Hz, 1H), 3.52-3.68 (m, 2H), 3.40 (s, 3H), 1.39 (d, J=6.46 Hz, 3H).

5-((1,1,1-Trifluoropropan-2-yl)oxy)pyrazine-2-carboxylic acid (293)

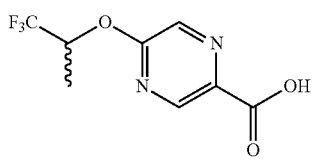

The title compound was synthesized according to the procedures described for intermediate 290, using 1,1,1-trifluoropropan-2-ol to react with tert-butyl 5-chloropyrazine-2-carboxylate 272A. LC/MS (ESI$^+$) m/z=237 (M+H)$^+$. $^1$H NMR (400 MHz, CHLOROFORM-d) δ 8.85-9.14 (m, 1H), 8.24-8.38 (m, 1H), 5.82 (m, 1H), 1.57 (d, J=6.46 Hz, 3H).

5-((3-Methyl-1,2,4-oxadiazol-5-yl)methoxy)pyrazine-2-carboxylic acid (294)

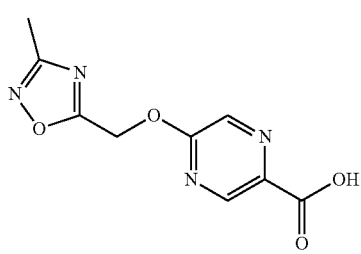

The title compound was synthesized according to the procedures described for intermediate 274, using (3-methyl-1,2,4-oxadiazol-5-yl)methanol to react with tert-butyl 5-chloropyrazine-2-carboxylate 272A. LC/MS (ESI$^+$) m/z=237 (M+H)$^+$. $^1$H NMR (400 MHz, CHLOROFORM-d) δ 8.97 (d, J=1.17 Hz, 1H), 8.39 (d, J=1.17 Hz, 1H), 5.70 (s, 2H), 2.43 (s, 3H).

326

(1S,5S,6S)-3-((tert-Butoxycarbonyl)((2-(trimethylsilyl)ethoxy)methyl)amino)-5-(2-fluoro-5-(5-(2,2,2-trifluoroethoxy)pyrazine-2-carboxamido)phenyl)-5-methyl-2-thia-4-azabicyclo[4.1.0]hept-3-ene-1-carboxylic acid (295)

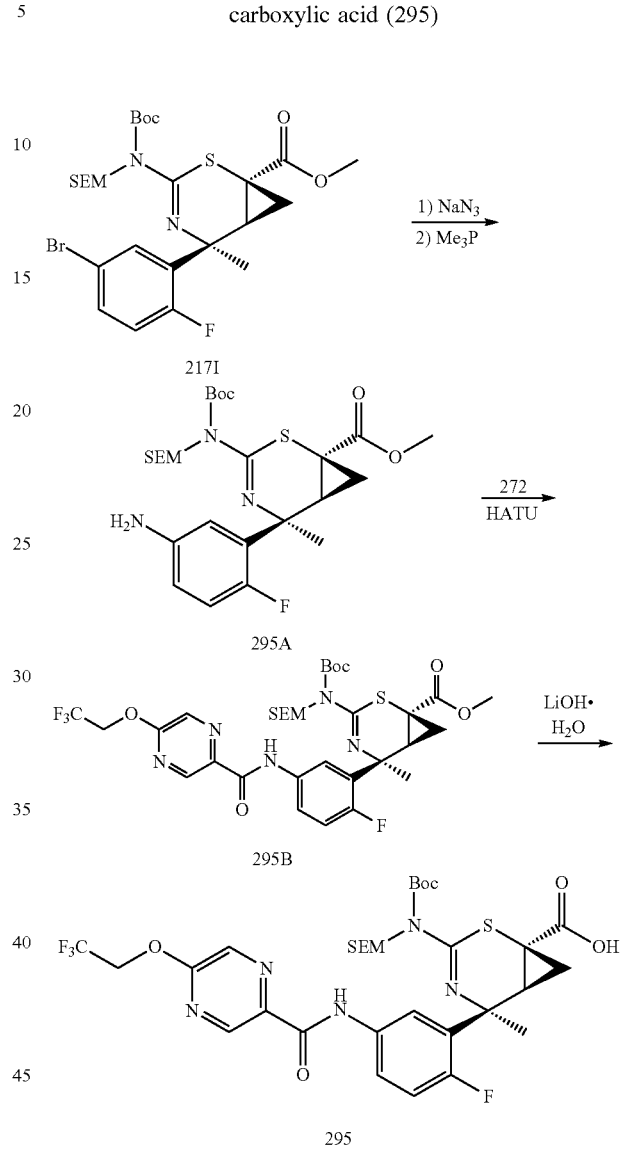

(1S,5S,6S)-Methyl 5-(5-amino-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylate (295A). The title compound (4.27 g, 7.91 mmol, 93% yield) was prepared according to the procedure described for intermediate 218 using (1S,5S,6S)-methyl 5-(5-bromo-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylate, 217I, (5.16 g, 8.55 mmol), sodium azide (2.78 g, 42.7 mmol), copper(i) iodide (0.24 g, 1.282 mmol), (1R,2R)-(−)-N,N"-dimethylcyclohexane-1,2-diamine (0.404 ml, 2.56 mmol), (+)-sodium L-ascorbate (0.508 g, 2.56 mmol) and 1.0 M trimethylphosphine solution in THF (17.10 ml, 17.10 mmol). LCMS (ESI$^+$) m/z=540.2 (M+H).

(1S,5S,6S)-Methyl 3-((tert-butoxycarbonyl)((2-(trimethylsilyl)ethoxy)methyl)amino)-5-(2-fluoro-5-(5-(2,2,2-trifluoroethoxy)pyrazine-2-carboxamido)phenyl)-5-methyl-2- thia-4-azabicyclo[4.1.0]hept-3-ene-1-carboxylate (295B). To a mixture of (1S,5S,6S)-methyl 5-(5-amino-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylate, 295A, (4.27 g, 7.91 mmol), 5-(2,2,2-trifluoroethoxy)pyrazine-2-carboxylic acid, 272, (2.28 g, 10.28 mmol) in DMF (15 mL) was added TEA (3.30 mL, 23.73 mmol) and HATU (6.02 g, 15.82 mmol). The reaction was stirred at RT for 2 h and was then diluted with water and extracted with EtOAc (2×). The organic layers were combined and concentrated, and the product was isolated using silica gel column chromatography (0-20% EtOAc/heptane) to afford the title compound (5.16 g, 6.94 mmol, 88% yield). LCMS (ESI$^+$) m/z=744.2 (M+H). $^1$H NMR (300 MHz, CHLOROFORM-d) δ 9.48 (s, 1H), 9.05 (s, 1H), 8.31 (s, 1H), 7.95-8.02 (m, 1H), 7.73 (dd, J=2.63, 6.72 Hz, 1H), 7.14 (dd, J=8.99, 11.62 Hz, 1H), 5.34 (d, J=10.52 Hz, 1H), 5.10 (d, J=10.52 Hz, 1H), 4.89 (q, J=8.18 Hz, 2H), 3.82 (s, 3H), 3.67-3.78 (m, 2H), 2.71 (t, J=8.70 Hz, 1H), 1.79 (s, 3H), 1.56 (s, 9H), 1.47-1.54 (m, 2H), 1.21-1.36 (m, 1H), 0.94-1.02 (m, 2H), 0.00 (s, 9H). $^{19}$F NMR (282 MHz, CHLOROFORM-d) δ −73.61 (s, 3F), −116.70 (s, 1F).

Compound 295 (1.3 g, 1.781 mmol, 96% yield) was prepared according to the procedure for 221A using (1S,5S,6S)-methyl 3-((tert-butoxycarbonyl)((2-(trimethylsilyl)ethoxy)methyl)amino)-5-(2-fluoro-5-(5-(2,2,2-trifluoroethoxy)pyrazine-2-carboxamido)phenyl)-5-methyl-2-thia-4-azabicyclo[4.1.0]hept-3-ene-1-carboxylate, 295B, (1.37 g, 1.85 mmol). LCMS (ESI$^+$) m/z=730.1 (M+H).

5-(2,2,2-Trifluoroethoxy)picolinic acid (296)

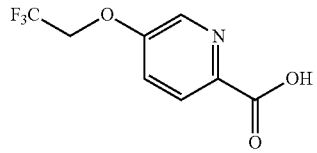

296

To a solution of methyl 5-hydroxypicolinate (0.50 g, 3.27 mmol, Frontier Scientific) in DMF (5 mL) were added cesium carbonate (1.38 g, 4.24 mmol) and 2,2,2-trifluoroethyl trifluoromethanesulfonate (0.91 mL, 3.92 mmol), The resulting suspension was stirred at RT for 1 h. The reaction mixture was then diluted with water and EtOAc. The organic layer was washed with brine before drying over magnesium sulfate and concentrating under reduced pressure to afford methyl 5-(2,2,2-trifluoroethoxy)picolinate as a yellow oil, which was used directly in the next step without further purification. M/S m/z=236.0 [M+H]$^+$.

The methyl 5-(2,2,2-trifluoroethoxy)picolinate from the above reaction was taken up in THF (5 mL) and lithium hydroxide (2.0 M, 4.90 mL, 9.80 mmol) was added. The reaction was stirred at RT for 16 h. The resulting mixture was diluted with water and acidified with 1.0 N HCl (aq) solution until pH=1 (by pH paper). The solution was extracted with DCM, and the organic layer was washed with brine, dried over magnesium sulfate and concentrated under reduced pressure to afford 5-(2,2,2-Trifluoroethoxy)picolinic acid (296) (0.19 g, 0.87 mmol, 27% yield) as a white solid. M/S m/z=221.9 [M+H]$^+$. $^1$H NMR (300 MHz, DMSO-d$_6$) δ ppm 5.00 (q, J=8.77 Hz, 2H) 7.66 (dd, J=8.77, 2.92 Hz, 1H) 8.07 (d, J=8.77 Hz, 1H) 8.50 (d, J=2.92 Hz, 1H) 13.00 (br., 1H).

General Amide Formation Procedures:
Method A, Method B, Method D, Method F1/2, Method H, and Method J were used to couple an aniline core intermediate to a desired acid as presented herein, to prepare the final compounds of the invention.

General SNAr Amination Procedures:
Method C, Method E and Method G were used for the SNAr displacement of the X in ArX intermediate (X=Cl or Br) with a desired aniline core intermediate as presented herein, to prepare the final compounds of the invention.

Method A: Propylphosphonic Anhydride (T3P) Procedure in DMF as Solvent

Example 3

Synthesis of N-(3-((1S,5S,6S)-3-amino-5-(fluoromethyl)-2-thia-4-azabicyclo[4.1.0]hept-3-en-5-yl)-4-fluorophenyl)-5-cyano-3-methylpicolinamide

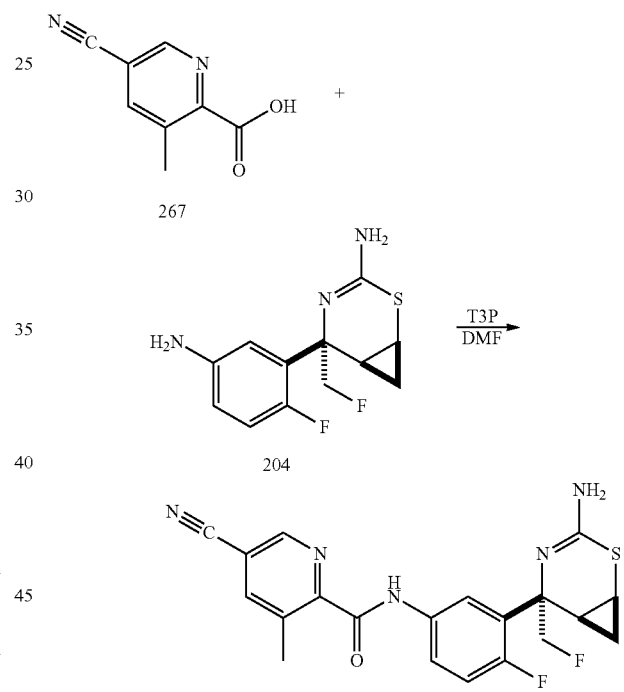

Example 3

To a solution of (1S,5S,6S)-5-(5-amino-2-fluorophenyl)-5-(fluoromethyl)-2-thia-4-azabicyclo[4.1.0]hept-3-en-3-amine (intermediate 204) (72 mg, 0.27 mmol) and 5-cyano-3-methylpicolinic acid (intermediate 267) (65 mg, 0.40 mmol) in DMF (5 mL) at 0° C. was added propylphosphonic anhydride solution (50 wt. % in EtOAc, 340 μL, 0.53 mmol). The reaction was stirred at 0° C. for 30 min. LC/MS showed the presence of the starting aniline (204). Another 34 μL of propylphosphonic anhydride solution (50 wt. % in EtOAc) was added. The reaction was stirred at 0° C. for another 30 min. It was quenched with saturated NaHCO$_3$ solution and extracted with DCM (2×). The combined organic extracts were concentrated. The residue was purified by flash chromatography (12 g ISCO RediSepRf column, 0-60% EtOAc/ hexanes) to provide N-(3-((1S,5S,6S)-3-amino-5-(fluoromethyl)-2-thia-4-azabicyclo[4.1.0]hept-3-en-5-yl)-4-fluorophenyl)-5-cyano-3-methylpicolinamide (Example 3, 72 mg, 0.17 mmol, 65% yield) as a white powder. MS m/z=414.2 [M+H]$^+$. $^1$H NMR (400 MHz, CHLOROFORM-d) δ=10.00 (s, 1H), 8.69 (d, J=1.4 Hz, 1H), 8.02 (ddd, J=3.0, 4.1, 8.8 Hz, 1H), 7.93 (d, J=1.2 Hz, 1H), 7.62 (dd, J=2.8, 6.7 Hz, 1H), 7.09 (dd, J=8.8, 11.5 Hz, 1H), 4.98-4.67 (m, 2H), 4.59 (br. s., 2H), 2.85 (s, 3H), 2.34-2.25 (m, 1H), 1.93 (ddt, J=2.1, 6.7, 9.1 Hz, 1H), 1.11-1.02 (m, 1H), 0.54 (q, J=5.7 Hz, 1H).

Using procedures analogous or similar to the general amidation Method A described above, the appropriate aniline and carboxylic acid intermediates were reacted to provide the 44 examples listed in Table 1 and Table 1'.

TABLE 1

| Ex.No. | Chemical Structure | Observed [M + H]$^+$ |
|---|---|---|
| 1 | 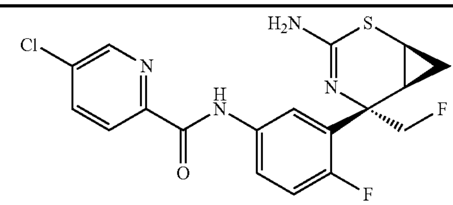 | 409.1 |
| 2 | 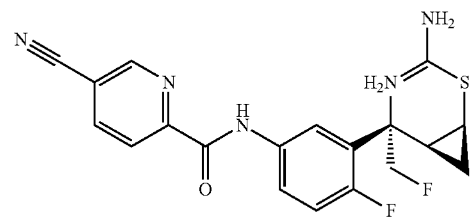 [SMILES: N#Cc1ccc(C(=O)Nc2ccc(F)c([C@@]3(CF)N=C(N)S[C@H]4C[C@H]43)c2)nc1] | 399.9 |
| 4 | 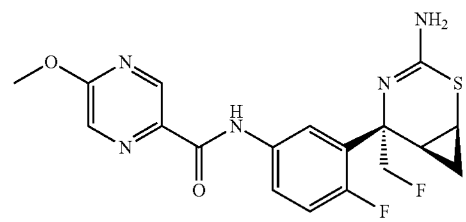 [SMILES: COc1cnc(C(=O)Nc2ccc(F)c([C@@]3(CF)N=C(N)S[C@H]4C[C@H]43)c2)cn1] | 406.1 |
| 5 | 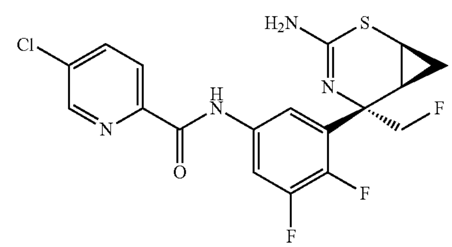 [SMILES: NC1=N[C@](CF)(c2cc(NC(=O)c3ccc(Cl)cn3)cc(F)c2F)[C@@H]2C[C@@H]2S1] | 427.0 |
| 6 | 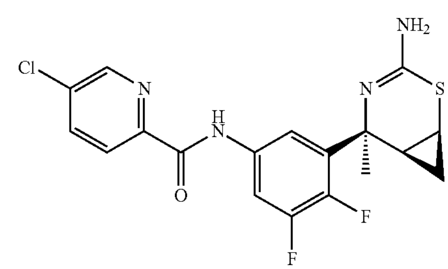 [SMILES: C[C@]1(c2cc(NC(=O)c3ccc(Cl)cn3)cc(F)c2F)N=C(N)S[C@H]2C[C@H]21] | 409.1 |
| 7 | 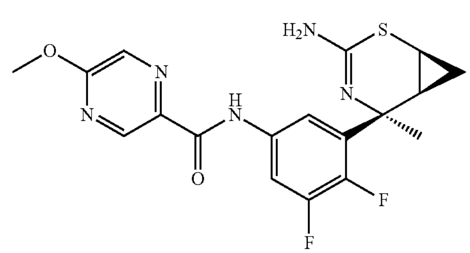 [SMILES: COc1cnc(C(=O)Nc2cc(F)c(F)c([C@@]3(C)N=C(N)S[C@H]4C[C@H]43)c2)cn1] | 406.1 |

TABLE 1-continued

| Ex.No. | Chemical Structure | Observed [M + H]+ |
|---|---|---|
| 8 | 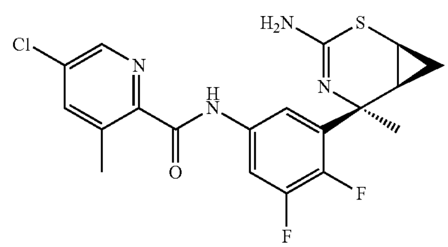 [SMILES: Cc1cc(Cl)cnc1C(=O)Nc1cc(F)c(F)c([C@@]2(C)N=C(N)S[C@H]3C[C@H]32)c1] | 423.0 |
| 11 | 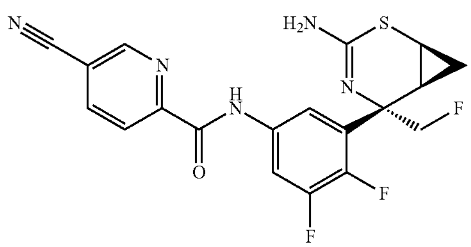 [SMILES: N#Cc1ccc(C(=O)Nc2cc(F)c(F)c([C@@]3(CF)N=C(N)S[C@H]4C[C@H]43)c2)nc1] | 418.1 |
| 13 | 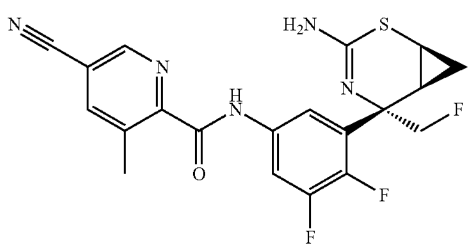 [SMILES: Cc1cc(C#N)cnc1C(=O)Nc1cc(F)c(F)c([C@@]2(CF)N=C(N)S[C@H]3C[C@H]32)c1] | 432.0 |
| 14 | 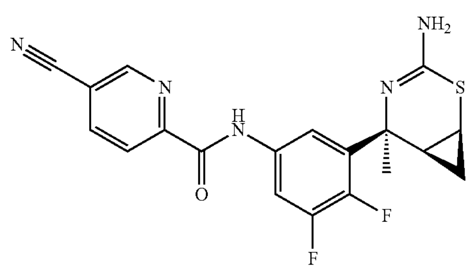 [SMILES: C[C@]1(c2cc(NC(=O)c3ccc(C#N)cn3)cc(F)c2F)N=C(N)S[C@H]2C[C@H]21] | 400.1 |
| 15 | 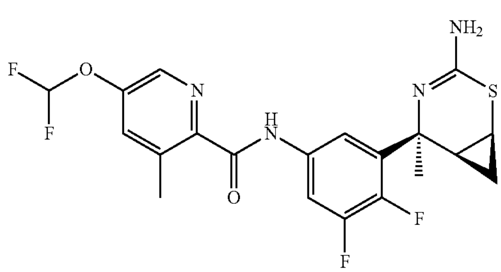 [SMILES: Cc1cc(OC(F)F)cnc1C(=O)Nc1cc(F)c(F)c([C@@]2(C)N=C(N)S[C@H]3C[C@H]32)c1] | 455.1 |
| 16 | 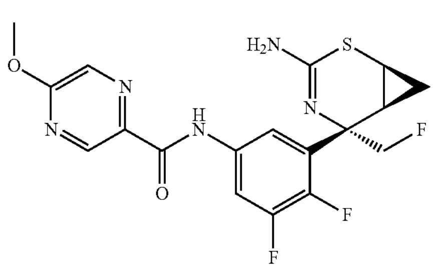 [SMILES: COc1cnc(C(=O)Nc2cc(F)c(F)c([C@@]3(CF)N=C(N)S[C@H]4C[C@H]43)c2)cn1] | 424.1 |

TABLE 1-continued

| Ex.No. | Chemical Structure | Observed [M + H]+ |
|---|---|---|
| 17 | 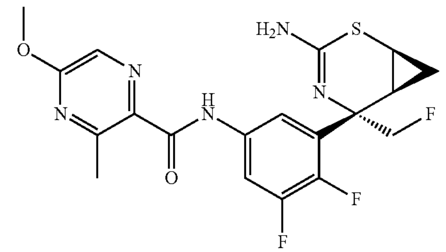 [SMILES: COc1cnc(C(=O)Nc2cc(F)c(F)c([C@@]3(CF)N=C(N)S[C@H]4C[C@H]43)c2)c(C)n1] | 438.0 |
| 18 | 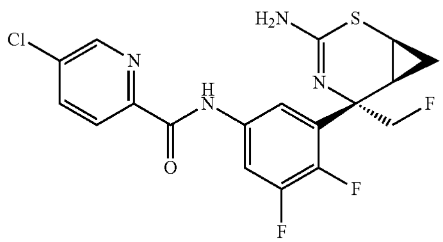 [SMILES: NC1=N[C@](CF)(c2cc(NC(=O)c3ccc(Cl)cn3)cc(F)c2F)[C@@H]2C[C@@H]2S1] | 427.1 |
| 19 | 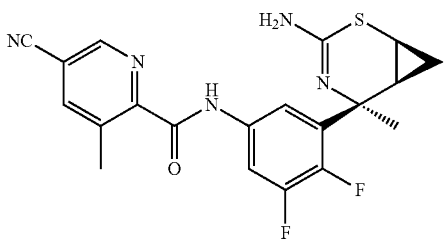 [SMILES: Cc1cc(C#N)cnc1C(=O)Nc1cc(F)c(F)c([C@@]2(C)N=C(N)S[C@H]3C[C@H]32)c1] | 414.2 |
| 20 | 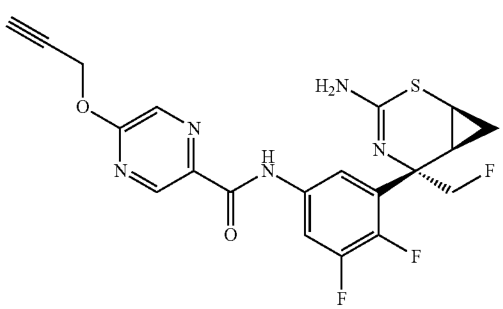 [SMILES: C#CCOc1cnc(C(=O)Nc2cc(F)c(F)c([C@@]3(CF)N=C(N)S[C@H]4C[C@H]43)c2)cn1] | 448.1 |
| 23 | 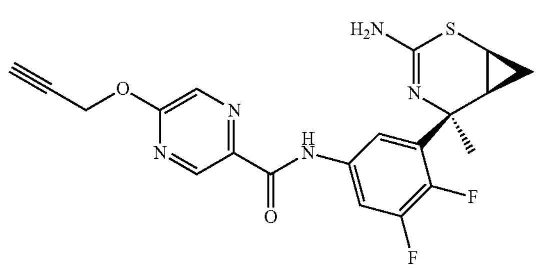 [SMILES: C#CCOc1cnc(C(=O)Nc2cc(F)c(F)c([C@@]3(C)N=C(N)S[C@H]4C[C@H]43)c2)cn1] | 430.0 |
| 29 | 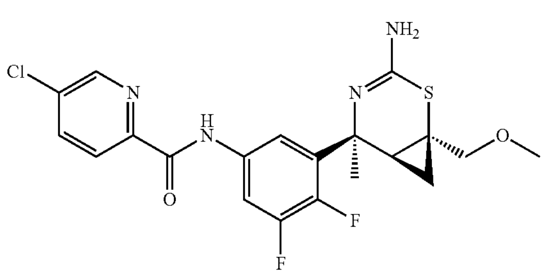 [SMILES: COC[C@]12C[C@H]1[C@@](C)(c1cc(NC(=O)c3ccc(Cl)cn3)cc(F)c1F)N=C(N)S2] | 453.0 |

TABLE 1-continued

| Ex.No. | Chemical Structure | Observed [M + H]+ |
|---|---|---|
| 40 | 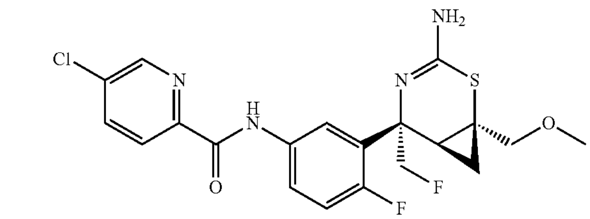 [SMILES: COC[C@]12C[C@H]1[C@@](CF)(c1cc(NC(=O)c3ccc(Cl)cn3)ccc1F)N=C(N)S2] | 453.0 |
| 61 | 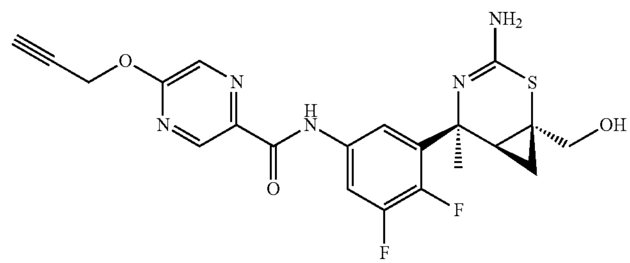 | 460.1 |
| 69 | 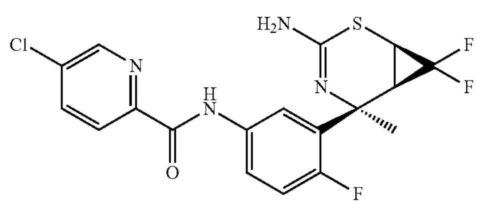 [SMILES: C[C@]1(c2cc(NC(=O)c3ccc(Cl)cn3)ccc2F)N=C(N)S[C@@H]2[C@H]1C2(F)F] | 427.0 |
| 71 | 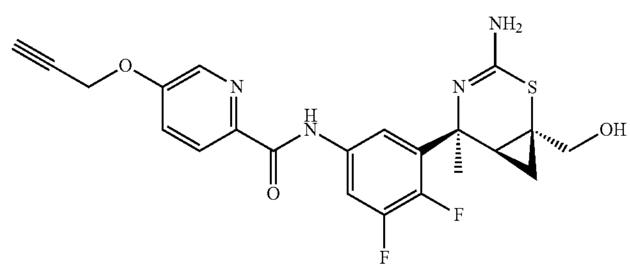 [SMILES: C#CCOc1ccc(C(=O)Nc2cc(F)c(F)c([C@@]3(C)N=C(N)S[C@@]4(CO)C[C@H]43)c2)nc1] | 459.0 |
| 74 | 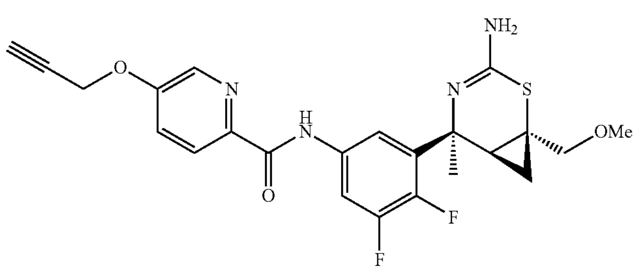 [SMILES: C#CCOc1ccc(C(=O)Nc2cc(F)c(F)c([C@@]3(C)N=C(N)S[C@@]4(COC)C[C@H]43)c2)nc1] | 473.1 |
| 77 | 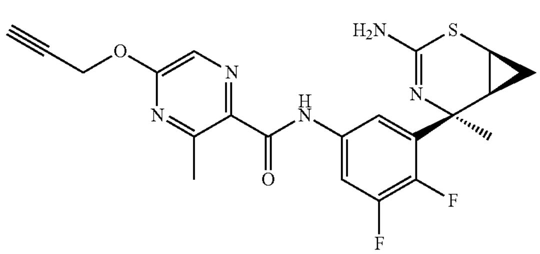 [SMILES: C#CCOc1cnc(C(=O)Nc2cc(F)c(F)c([C@@]3(C)N=C(N)S[C@H]4C[C@H]43)c2)c(C)n1] | 444.0 |

TABLE 1-continued

| Ex.No. | Chemical Structure | Observed [M + H]+ |
|---|---|---|
| 85 | 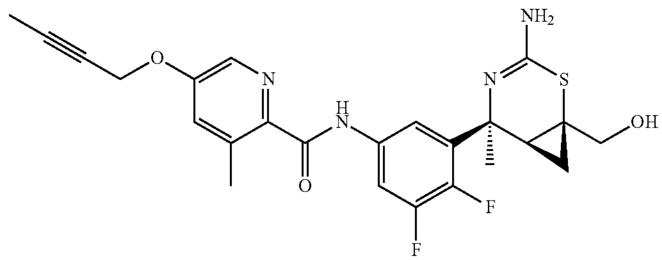 [SMILES: CC#CCOc1cnc(C(=O)Nc2cc(F)c(F)c([C@@]3(C)N=C(N)S[C@@]4(CO)C[C@H]43)c2)c(C)c1] | 487.1 |
| 102 | 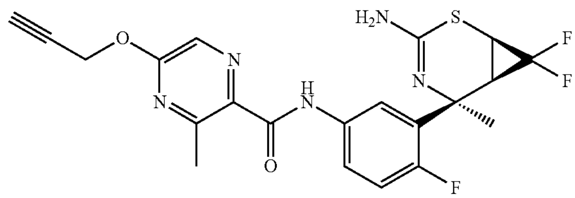 [SMILES: C#CCOc1cnc(C(=O)Nc2ccc(F)c([C@@]3(C)N=C(N)S[C@@H]4[C@H]3C4(F)F)c2)c(C)n1] | 462.0 |
| 603 | 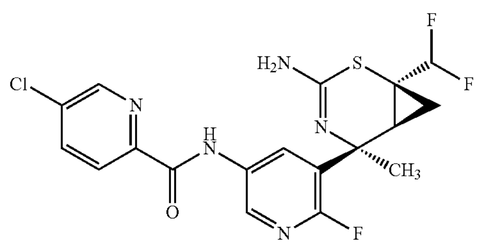 [SMILES: C[C@]1(c2cc(NC(=O)c3ccc(Cl)cn3)cnc2F)N=C(N)S[C@@]2(C(F)F)C[C@@H]12] | 459.1 |
| 655 | 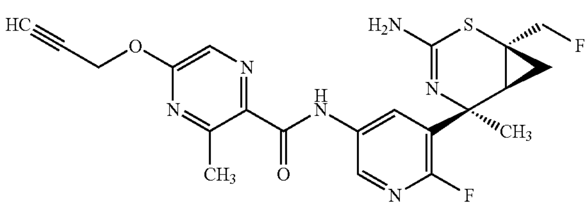 [SMILES: C#CCOc1cnc(C(=O)Nc2cnc(F)c([C@@]3(C)N=C(N)S[C@@]4(CF)C[C@H]43)c2)c(C)n1] | 442 |
| 704 | 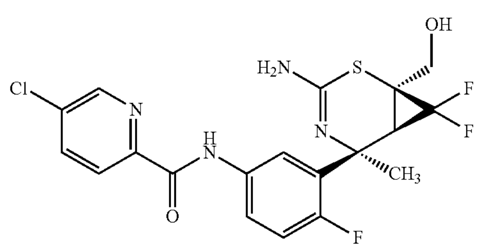 [SMILES: C[C@]1(c2cc(NC(=O)c3ccc(Cl)cn3)ccc2F)N=C(N)S[C@]2(CO)[C@H]1C2(F)F] | 457 |
| 708 | 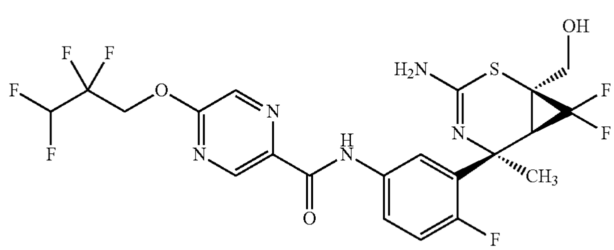 [SMILES: C[C@]1(c2cc(NC(=O)c3cnc(OCC(F)(F)C(F)F)cn3)ccc2F)N=C(N)S[C@]2(CO)[C@H]1C2(F)F] | 554 |

TABLE 1-continued

| Ex.No. | Chemical Structure | Observed [M + H]+ |
|---|---|---|
| 710 | 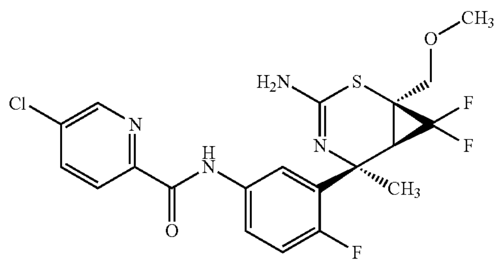 [SMILES: COC[C@@]12SC(N)=N[C@](C)(c3cc(NC(=O)c4ccc(Cl)cn4)ccc3F)[C@@H]1C2(F)F] | 471 |
| 711 | 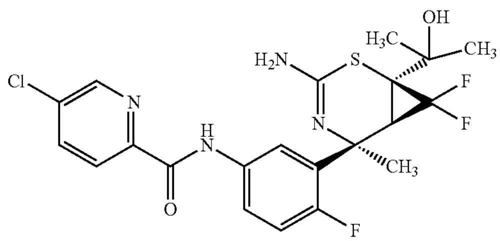 [SMILES: CC(C)(O)[C@@]12SC(N)=N[C@](C)(c3cc(NC(=O)c4ccc(Cl)cn4)ccc3F)[C@@H]1C2(F)F] | 485 |
| 748 | 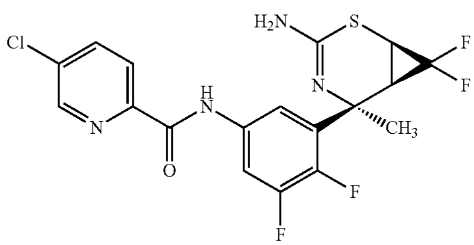 [SMILES: C[C@]1(c2cc(NC(=O)c3ccc(Cl)cn3)cc(F)c2F)N=C(N)S[C@@H]2[C@H]1C2(F)F] | 445.1 |
| 749 | 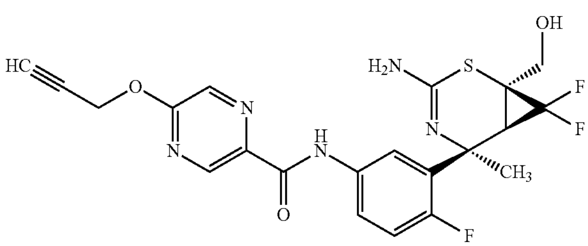 [SMILES: C#CCOc1cnc(C(=O)Nc2ccc(F)c([C@@]3(C)N=C(N)S[C@]4(CO)[C@H]3C4(F)F)c2)cn1] | 478.1 |
| 751 | 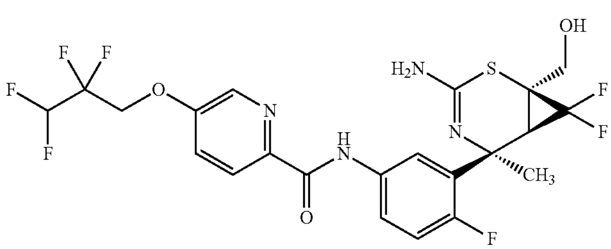 [SMILES: C[C@]1(c2cc(NC(=O)c3ccc(OCC(F)(F)C(F)F)cn3)ccc2F)N=C(N)S[C@]2(CO)[C@H]1C2(F)F] | 553.1 |
| 785 | 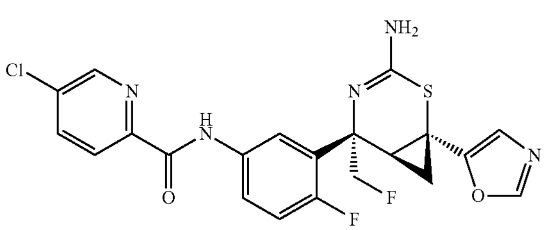 [SMILES: NC1=N[C@](CF)(c2cc(NC(=O)c3ccc(Cl)cn3)ccc2F)[C@@H]2C[C@]2(c2cnco2)S1] | 476 |

TABLE 1-continued

| Ex.No. | Chemical Structure | Observed [M + H]+ |
|---|---|---|
| 790 | 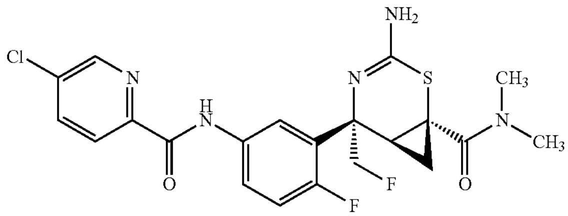 [SMILES: CN(C)C(=O)[C@]12C[C@H]1[C@@](CF)(c1cc(NC(=O)c3ccc(Cl)cn3)ccc1F)N=C(N)S2] | 480 |
| 906 | 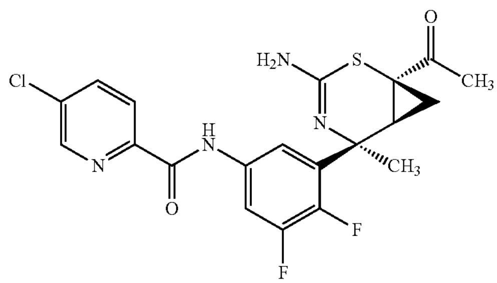 [SMILES: CC(=O)[C@]12C[C@H]1[C@@](C)(c1cc(NC(=O)c3ccc(Cl)cn3)cc(F)c1F)N=C(N)S2] | 451 |
| 910 | 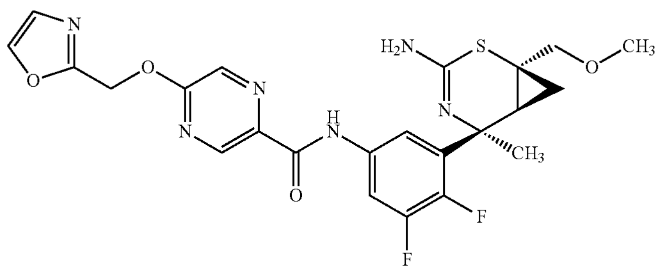 [SMILES: COC[C@]12C[C@H]1[C@@](C)(c1cc(NC(=O)c3cnc(OCc4ncco4)cn3)cc(F)c1F)N=C(N)S2] | 517 |
| 953 | 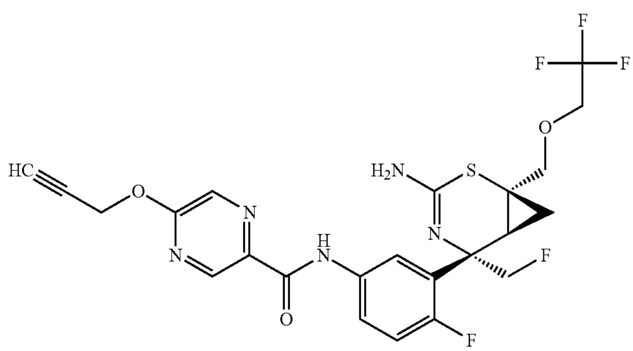 [SMILES: C#CCOc1cnc(C(=O)Nc2ccc(F)c([C@@]3(CF)N=C(N)S[C@@]4(COCC(F)(F)F)C[C@H]43)c2)cn1] | 542.2 |
| 954 | 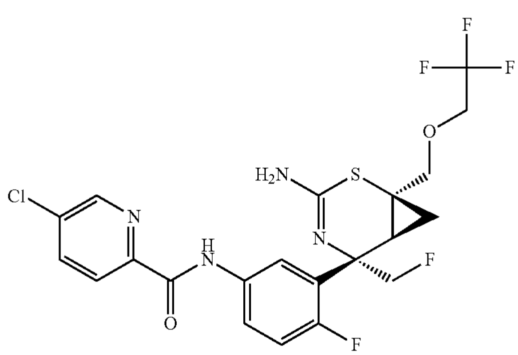 [SMILES: NC1=N[C@](CF)(c2cc(NC(=O)c3ccc(Cl)cn3)ccc2F)[C@@H]2C[C@]2(COCC(F)(F)F)S1] | 521.2 |

TABLE 1-continued

| Ex.No. | Chemical Structure | Observed [M + H]+ |
|---|---|---|
| 955 | 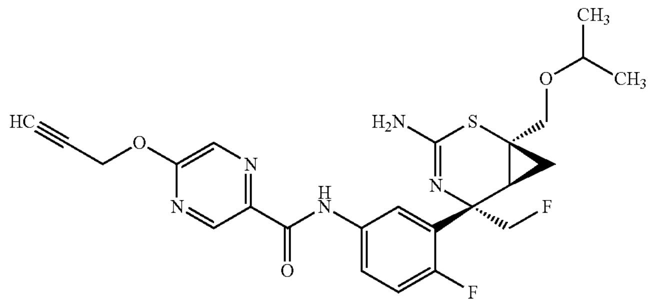 [SMILES: C#CCOc1cnc(C(=O)Nc2ccc(F)c([C@@]3(CF)N=C(N)S[C@@]4(COC(C)C)C[C@H]43)c2)cn1] | 502.2 |
| 956 | 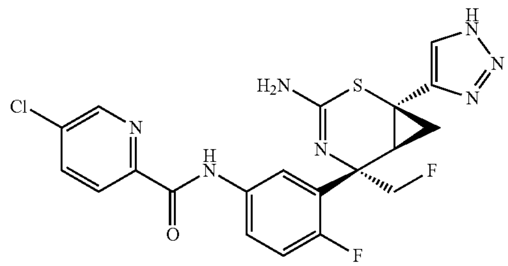 [SMILES: NC1=N[C@](CF)(c2cc(NC(=O)c3ccc(Cl)cn3)ccc2F)[C@@H]2C[C@]2(c2c[nH]nn2)S1] | 476.1 |
| 959 | 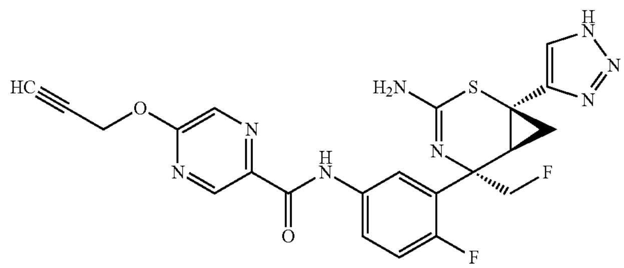 [SMILES: C#CCOc1cnc(C(=O)Nc2ccc(F)c([C@@]3(CF)N=C(N)S[C@@]4(c5c[nH]nn5)C[C@@H]34)c2)cn1] | 497.1 |

TABLE 1'

| Ex. No. | $^1$H-NMR | Chemical Name |
|---|---|---|
| 1 | $^1$H NMR (400 MHz, CHLOROFORM-d) δ = 9.82 (br. s., 1 H), 8.57-8.52 (m, 1 H), 8.24 (d, J = 8.4 Hz, 1 H), 8.01 (ddd, J = 2.9, 4.1, 8.8 Hz, 1 H), 7.87 (dd, J = 2.3, 8.4 Hz, 1 H), 7.69 (dd, J = 2.8, 6.7 Hz, 1 H), 7.09 (dd, J = 8.9, 11.6 Hz, 1 H), 4.98-4.83 (m, 1 H), 4.82-4.67 (m, 1 H), 4.60 (br s, 1 H), 2.30 (ddd, J = 5.1, 7.5, 8.9 Hz, 1 H), 1.93 (ddt, J = 2.0, 6.8, 9.1 Hz, 1 H), 1.60 (br s, 1 H), 1.11-1.03 (m, 1 H), 0.55 (q, J = 5.8 Hz, 1 H). | N-(3-((1S,5S,6S)-3-amino-5-(fluoromethyl)-2-thia-4-azabicyclo[4.1.0]hept-3-en-5-yl)-4-fluorophenyl)-5-chloro-2-pyridinecarboxamide |
| 2 | $^1$H NMR (300 MHz, CHLOROFORM-d) δ 9.85 (s, 1H), 8.88 (d, J = 1.17 Hz, 1H), 8.42 (d, J = 8.04 Hz, 1H), 8.20 (dd, J = 1.97, 8.11 Hz, 1H), 7.98-8.07 (m, 1H), 7.73 (dd, J = 2.85, 6.80 Hz, 1H), 7.12 (dd, J = 8.92, 11.55 Hz, 1H), 4.19-5.32 (m, 4H), 2.25-2.37 (m, 1H), 1.87-2.00 (m, 1H), 1.03-1.15 (m, 1H), 0.56 (q, J = 5.89 Hz, 1H). | N-(3-((1S,5S,6S)-3-amino-5-(fluoromethyl)-2-thia-4-azabicyclo[4.1.0]hept-3-en-5-yl)-4-fluorophenyl)-5-cyano-2-pyridinecarboxamide |
| 4 | $^1$H NMR (400 MHz, CHLOROFORM-d) δ 9.43-9.56 (m, 1H), 9.03 (s, 1H), 8.16 (s, 1H), 7.94-8.05 (m, 1H), 7.68 (dd, J = 2.84, 6.75 Hz, 1H), 7.10 (dd, J = 8.80, 11.54 Hz, 1H), 4.65-5.00 (m, 2H), 4.08 (s, 3H), 2.23-2.37 (m, 1H), 1.85-2.01 (m, 1H), 1.05-1.18 (m, 1H), 0.48-0.61 (m, 1H) | N-(3-((1S,5S,6S)-3-amino-5-(fluoromethyl)-2-thia-4-azabicyclo[4.1.0]hept-3-en-5-yl)-4-fluorophenyl)-5-methoxy-2-pyrazinecarboxamide |
| 5 | $^1$H NMR (400 MHz, DMSO-d6) δ ppm 10.80 (s, 1 H) 8.80 (d, J = 1.80 Hz, 1 H) 8.22 (dd, J = 8.61, 2.35 Hz, 1 H) 8.17 (d, J = 8.40 Hz, 1 H) 7.99 (ddd, J = 12.37, 6.80, 2.54 Hz, 1 H) 7.89-7.93 (m, 1 H) 6.25 (s, 2 H) 4.74 (d, J = 47.73 Hz, 2 H) 2.38-2.45 (m, 1 H) 1.73-1.81 (m, 1 H) 1.06 (ddd, J = 8.80, 7.63, 5.28 Hz, 1 H) 0.46 (q, J = 5.15 Hz, 1 H) | N-(3-((1S,5S,6S)-3-amino-5-(fluoromethyl)-2-thia-4-azabicyclo[4.1.0]hept-3-en-5-yl)-4,5-difluorophenyl)-5-chloro-2-pyridinecarboxamide |

TABLE 1'-continued

| Ex. No. | ¹H-NMR | Chemical Name |
|---|---|---|
| 6 | ¹H NMR (400 MHz, CHLOROFORM-d) δ 9.69-9.98 (m, 1H), 8.57 (d, J = 2.15 Hz, 1H), 8.25 (d, J = 8.41 Hz, 1H), 8.02-8.12 (m, 1H), 7.90 (dd, J = 2.35, 8.41 Hz, 1H), 7.37-7.49 (m, 1H), 4.33 (br. s., 2H), 2.21 (dt, J = 5.09, 8.31 Hz, 1H), 1.90-2.01 (m, 1H), 1.77 (s, 3H), 0.92 (dd, J = 7.43, 14.87 Hz, 1H), 0.63 (q, J = 5.87 Hz, 1H) | N-(3-((1S,5S,6S)-3-amino-5-methyl-2-thia-4-azabicyclo[4.1.0]hept-3-en-5-yl)-4,5-difluorophenyl)-5-chloro-2-pyridinecarboxamide |
| 7 | ¹H NMR (400 MHz, DMSO-d6) δ ppm 10.56 (s, 1 H), 8.89 (d, J = 1.37 Hz, 1 H), 8.41 (d, J = 1.17 Hz, 1 H), 7.85-7.93 (m, 2 H), 5.91 (s, 2 H), 4.02 (s, 3 H), 2.29-2.35 (m, 1 H), 1.67-1.74 (m, 1 H), 1.65 (s, 3 H), 0.83-0.90 (m, 1 H), 0.48 (q, J = 5.15 Hz, 1 H) | N-(3-((1S,5S,6S)-3-amino-5-methyl-2-thia-4-azabicyclo[4.1.0]hept-3-en-5-yl)-4,5-difluorophenyl)-5-methoxy-2-pyrazinecarboxamide |
| 8 | ¹H NMR (400 MHz, DMSO-d6) δ ppm 10.65 (s, 1 H), 8.57 (d, J = 1.96 Hz, 1 H), 8.02 (d, J = 1.56 Hz, 1 H), 7.91-7.95 (m, 1 H), 7.68-7.73 (m, 1 H), 5.92 (s, 2 H), 2.56 (s, 3 H), 2.29-2.36 (m, 1 H), 1.73 (q, J = 7.82 Hz, 1 H), 1.64 (s, 3 H), 0.82-0.90 (m, 1 H), 0.46 (q, J = 5.22 Hz, 1 H) | N-(3-((1S,5S,6S)-3-amino-5-methyl-2-thia-4-azabicyclo[4.1.0]hept-3-en-5-yl)-4,5-difluorophenyl)-5-chloro-3-methyl-2-pyridinecarboxamide |
| 11 | ¹H NMR (400 MHz, DMSO-d6) δ ppm 10.96 (s, 1 H) 9.22 (d, J = 1.17 Hz, 1 H) 8.60 (dd, J = 8.22, 1.96 Hz, 1 H) 8.30 (d, J = 8.22 Hz, 1 H) 7.99 (ddd, J = 12.18, 6.70, 2.25 Hz, 1 H) 7.91-7.96 (m, 1 H) 6.25 (s, 2 H) 4.74 (d, J = 47.54 Hz, 2 H) 2.38-2.46 (m, 1 H) 1.73-1.81 (m, 1 H) 1.06 (td, J = 8.07, 5.38 Hz, 1 H) 0.46 (q, J = 5.35 Hz, 1 H) | N-(3-((1S,5S,6S)-3-amino-5-(fluoromethyl)-2-thia-4-azabicyclo[4.1.0]hept-3-en-5-yl)-4,5-difluorophenyl)-5-cyano-2-pyridinecarboxamide |
| 13 | ¹H NMR (400 MHz, DMSO-d6) δ ppm 10.87 (s, 1 H) 8.98 (d, J = 1.17 Hz, 1 H) 8.40 (d, J = 0.78 Hz, 1 H) 7.96 (ddd, J = 12.18, 6.80, 2.54 Hz, 1 H) 7.68-7.73 (m, 1 H) 6.24 (s, 2 H) 4.73 (d, J = 47.54, 2 H) 2.56 (s, 3 H) 2.37-2.44 (m, 1 H) 1.75 (q, J = 7.96 Hz, 1 H) 1.04 (td, J = 8.22, 5.28 Hz, 1 H) 0.41 (q, J = 5.28 Hz, 1 H) | N-(3-((1S,5S,6S)-3-amino-5-(fluoromethyl)-2-thia-4-azabicyclo[4.1.0]hept-3-en-5-yl)-4,5-difluorophenyl)-5-cyano-3-methyl-2-pyridinecarboxamide |
| 14 | ¹H NMR (400 MHz, CHLOROFORM-d) Shift 9.88 (s, 1H), 8.85-8.94 (m, 1H), 8.41-8.48 (m, 1H), 8.17-8.26 (m, 1H), 8.07 (ddd, J = 2.84, 6.75, 11.74 Hz, 1H), 7.43 (td, J = 2.57, 5.23 Hz, 1H), 2.17-2.30 (m, 1H), 1.92-2.02 (m, 1H), 1.75-1.80 (m, 3H), 0.89-0.98 (m, 1H), 0.62 (q, J = 5.87 Hz, 1H) | N-(3-((1S,5S,6S)-3-amino-5-methyl-2-thia-4-azabicyclo[4.1.0]hept-3-en-5-yl)-4,5-difluorophenyl)-5-cyano-2-pyridinecarboxamide |
| 15 | ¹H NMR (400 MHz, CHLOROFORM-d) Shift 10.06 (br. s., 1H), 8.32 (s, 1H), 8.01-8.13 (m, 1H), 7.42 (s, 1H), 7.33 (br. s., 1H), 6.42-6.86 (m, 1H), 2.84 (s, 3H), 2.15-2.28 (m, 1H), 1.88-2.01 (m, 1H), 1.77 (s, 3H), 0.85-0.97 (m, 1H), 0.63 (q, J = 5.80 Hz, 1H) | N-(3-((1S,5S,6S)-3-amino-5-methyl-2-thia-4-azabicyclo[4.1.0]hept-3-en-5-yl)-4,5-difluorophenyl)-5-(difluoromethoxy)-3-methyl-2-pyridinecarboxamide |
| 16 | ¹H NMR (400 MHz, DMSO-d6) δ ppm 10.62 (s, 1 H) 8.90 (d, J = 0.98 Hz, 1 H) 8.42 (d, J = 1.17 Hz, 1 H) 7.96 (ddd, J = 12.37, 6.70, 2.45 Hz, 1 H) 7.87-7.91 (m, 1 H) 6.23 (s, 2 H) 4.73 (d, J = 47.54 Hz, 2 H) 4.03 (s, 3 H) 2.37-2.44 (m, 1 H) 1.71-1.79 (m, 1 H) 1.02-1.09 (m, 1 H) 0.45 (q, J = 5.28 Hz, 1H) | N-(3-((1S,5S,6S)-3-amino-5-(fluoromethyl)-2-thia-4-azabicyclo[4.1.0]hept-3-en-5-yl)-4,5-difluorophenyl)-5-methoxy-2-pyrazinecarboxamide |
| 17 | ¹H NMR (400 MHz, DMSO-d6) δ ppm 10.56 (s, 1 H) 8.24 (s, 1 H) 7.97 (ddd, J = 12.42, 6.85, 2.45 Hz, 1 H) 7.72-7.76 (m, 1 H) 6.23 (s, 2 H) 4.72 (d, J = 47.54 Hz, 2 H) 4.00 (s, 3 H) 2.77 (s, 3 H) 2.37-2.44 (m, 1 H) 1.75 (q, J = 8.15 Hz, 1 H) 1.01-1.08 (m, 1 H) 0.43 (q, J = 5.28 Hz, 1 H) | N-(3-((1S,5S,6S)-3-amino-5-(fluoromethyl)-2-thia-4-azabicyclo[4.1.0]hept-3-en-5-yl)-4,5-difluorophenyl)-5-methoxy-3-methyl-2-pyrazinecarboxamide |
| 18 | ¹H NMR (400 MHz, CHLOROFORM-d) δ ppm 10.87 (s, 1 H) 8.79 (d, J = 1.76 Hz, 1 H) 8.12-8.24 (m, 2 H) 7.94-8.07 (m, 2 H) 6.19 (s, 2 H) 4.73 (dd, J = 47.54, 8.61 Hz, 1 H) 4.49 (dd, J = 47.73, 8.22 Hz, 1 H) 2.41-2.48 (m, 1 H) 1.86-1.96 (m, 1 H) 1.04-1.15 (m, 1 H) 0.84 (q, J = 5.15 Hz, 1 H) | N-(3-((1S,5S,6S)-3-amino-5-(fluoromethyl)-2-thia-4-azabicyclo[4.1.0]hept-3-en-5-yl)-4,5-difluorophenyl)-5-chloropicolinamide |
| 19 | ¹H NMR (400 MHz, CHLOROFORM-d) Shift 10.06 (s, 1H), 8.72 (d, J = 1.17 Hz, 1H), 8.07 (ddd, J = 2.84, 6.75, 11.74 Hz, 1H), 7.95 (s, 1H), 7.31-7.41 (m, 1H), 2.88 (s, 3H), 2.22 (dt, J = 5.09, 8.41 Hz, 1H), 1.95 (td, J = 7.09, 8.90 Hz, 1H), 1.76 (s, 3H), 0.84-0.98 (m, 1H), 0.62 (q, J = 5.74 Hz, 1H) | N-(3-((1S,5S,6S)-3-amino-5-methyl-2-thia-4-azabicyclo[4.1.0]hept-3-en-5-yl)-4,5-difluorophenyl)-5-cyano-3-methyl-2-pyridinecarboxamide |
| 20 | ¹H NMR (400 MHz, DMSO-d6) δ ppm 10.67 (s, 1 H) 8.92 (d, J = 1.17 Hz, 1 H) 8.50 (d, J = 1.17 Hz, 1 H) 7.97 (ddd, J = 12.32, 6.75, 2.64 Hz, 1 H) 7.89-7.93 (m, 1 H) 6.24 (s, 2 H) 5.16 (d, J = 2.35 Hz, 2 H) 4.74 (d, J = 47.34 Hz, 2 H) 3.66 (t, J = 2.45 Hz, 1 | N-(3-((1S,5S,6S)-3-amino-5-(fluoromethyl)-2-thia-4-azabicyclo[4.1.0]hept-3-en-5-yl)-4,5-difluorophenyl)-5-(2-propyn-1-yloxy)-2- |

TABLE 1'-continued

| Ex. No. | ¹H-NMR | Chemical Name |
|---|---|---|
|  | H) 2.38-2.45 (m, 1 H) 1.72-1.80 (m, 1 H) 1.06 (ddd, J = 8.85, 7.58, 5.09 Hz, 1 H) 0.46 (q, J = 5.28 Hz, 1 H) | pyrazinecarboxamide |
| 23 | ¹H NMR (400 MHz, DMSO-d6) δ ppm 10.60 (s, 1 H) 8.90, (d, J = 1.17 Hz, 1 H), 8.48 (d, J = 0.98 Hz, 1 H), 7.85-7.93 (m, 2 H), 5.92 (br. s., 2 H), 5.14 (d, J = 2.35 Hz, 2 H), 3.64 (t, J = 2.35 Hz, 1 H), 2.32 (td, J = 8.26, 4.99 Hz, 1 H), 1.68-1.74 (m, 1 H), 1.65 (s, 3 H), 0.87 (td, J = 8.12, 5.28 Hz, 1 H), 0.48 (q, J = 5.28 Hz, 1 H) | N-(3-((1S,5S,6S)-3-amino-5-methyl-2-thia-4-azabicyclo[4.1.0]hept-3-en-5-yl)-4,5-difluorophenyl)-5-(2-propyn-1-yloxy)-2-pyrazinecarboxamide |
| 29 | ¹H NMR (400 MHz, DMSO-d6) δ 10.74 (br., 1H), 8.79 (d, J = 1.96 Hz, 1H), 8.14-8.23 (m, 2H), 7.87-7.97 (m, 2H), 6.00 (br., 2H), 3.57 (d, J = 10.95 Hz, 1H), 3.34 (m, 1H), 3.33 (s, 3H), 1.58 (m, 1H), 1.66 (s, 3H), 0.90 (m, 1H), 0.65 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-chloro-2-pyridinecarboxamide |
| 40 | ¹H NMR (DMSO-d6) δ: 10.58 (s, 1H), 8.78 (d, J = 2.0 Hz, 1H), 8.09-8.24 (m, 2H), 8.02 (d, J = 4.9 Hz, 1H), 7.83 (d, J = 8.4 Hz, 1H), 7.17 (dd, J = 11.7, 8.8 Hz, 1H), 6.25 (s, 2H), 4.57-4.78 (m, 2H), 3.32-3.60 (m, 2H), 3.28 (s, 3H), 1.64 (t, J = 8.2 Hz, 1H), 1.04 (dd, J = 9.3, 5.4 Hz, 1H), 0.58 (t, J = 5.8 Hz, 1H) | N-(3-((1S,5S,6S)-3-amino-5-(fluoromethyl)-1-(methoxymethyl)-2-thia-4-azabicyclo[4.1.0]hept-3-en-5-yl)-4-fluorophenyl)-5-chloro-2-pyridinecarboxamide |
| 61 | ¹H NMR (400 MHz, DMSO-d6) δ 10.62 (s, 1H), 8.92 (d, J = 1.37 Hz, 1H), 8.50 (d, J = 1.37 Hz, 1H), 7.89-7.98 (m, 2H), 5.95 (s, 2H), 5.16 (d, J = 2.35 Hz, 2H), 5.05 (t, J = 5.97 Hz, 1H), 3.66 (t, J = 2.35 Hz, 1H), 3.55 (dd, J = 6.36, 11.64 Hz, 1H), 3.45 (dd, J = 5.58, 11.64 Hz, 1H), 1.63 (m, 1H), 1.61 (s, 3H), 0.86 (dd, J = 5.09, 9.19 Hz, 1H), 0.57 (t, J = 5.77 Hz, 1H). | N-(3-((1S,5S,6S)-3-amino-1-(hydroxymethyl)-5-methyl-2-thia-4-azabicyclo[4.1.0]hept-3-en-5-yl)-4,5-difluorophenyl)-5-(2-propyn-1-yloxy)-2-pyrazinecarboxamide |
| 69 | ¹H NMR (300 MHz, CDCl3) Shift = 9.86 (br. s., 1H), 8.58 (d, J = 1.9 Hz, 1H), 8.26 (d, J = 7.9 Hz, 1H), 8.06 (ddd, J = 2.8, 4.2, 8.9 Hz, 1H), 7.90 (dd, J = 2.3, 8.3 Hz, 1H), 7.76 (dd, J = 2.8, 6.9 Hz, 1H), 7.12 (dd, J = 8.8, 11.8 Hz, 1H), 2.93 (dd, J = 8.3, 13.1 Hz, 1H), 2.79-2.64 (m, 1H), 1.73 (s, 3H) | N-(3-((1R,5S,6R)-3-amino-7,7-difluoro-5-methyl-2-thia-4-azabicyclo[4.1.0]hept-3-en-5-yl)-4-fluorophenyl)-5-chloro-2-pyridinecarboxamide |
| 71 | ¹H NMR (400 MHz, DMSO-d6) δ 10.56 (br., 1H), 8.45 (d, J = 2.54 Hz, 1H), 8.15 (d, J = 8.80 Hz, 1H), 7.915 (m, 1H), 7.88 (br., 1H), 7.69 (dd, J = 2.64, 8.71 Hz, 1H), 5.97 (br., 2H), 5.00-5.11 (m, 3H), 3.72 (s, 1H), 3.55 (m, 1H), 3.46 (m, 1H), 1.66 (m, 1H), 1.61 (s, 3H), 0.87 (m, 1H), 0.59 (m, 1H). | N-(3-((1S,5S,6S)-3-amino-1-(hydroxymethyl)-5-methyl-2-thia-4-azabicyclo[4.1.0]hept-3-en-5-yl)-4,5-difluorophenyl)-5-(2-propyn-1-yloxy)-2-pyridinecarboxamide |
| 74 | ¹H NMR (400 MHz, DMSO-d6) δ ppm 10.54 (s, 1 H), 8.43 (d, J = 2.74 Hz, 1 H), 8.13 (d, J = 8.61 Hz, 1 H), 7.89-7.99 (m, 1 H), 7.86 (d, J = 5.87 Hz, 1 H), 7.67 (dd, J = 8.80, 2.93 Hz, 1 H), 6.00 (br. s., 2 H), 5.04 (d, J = 2.35 Hz, 2 H), 3.71 (t, J = 2.35 Hz, 1 H), 3.56 (d, J = 10.95 Hz, 1 H), 3.36 (d, J = 11.15 Hz, 1 H), 3.29-3.32 (m, 3 H), 1.56-1.68 (m, 4 H), 0.90 (br. s., 1 H), 0.66 (d, J = 5.28 Hz, 1 H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-(2-propyn-1-yloxy)-2-pyridinecarboxamide |
| 77 | ¹H NMR (400 MHz, DMSO-d6) δ ppm 10.55 (s, 1 H), 8.29 (s, 1 H), 7.91 (ddd, J = 12.42, 6.75, 2.54, 1 H), 7.72 (d, J = 5.87 Hz, 1 H), 5.92 (s, 2 H), 5.11 (d, J = 2.35 Hz, 2 H), 3.61 (t, J = 2.35 Hz, 1 H), 2.75 (s, 3 H) 2.29-2.35 (m, 1 H), 1.67-1.78 (m, 1 H), 1.64 (s, 3 H), 0.86 (td, J = 8.07, 5.38 Hz, 1 H), 0.46 (q, J = 5.28 Hz, 1 H) | N-(3-((1S,5S,6S)-3-amino-5-methyl-2-thia-4-azabicyclo[4.1.0]hept-3-en-5-yl)-4,5-difluorophenyl)-3-methyl-5-(2-propyn-1-yloxy)-2-pyrazinecarboxamide |
| 85 | ¹H NMR (400 MHz, CHLOROFORM-d) Shift 10.10 (s, 1H), 8.17 (d, J = 2.54 Hz, 1H), 8.01-8.11 (m, 1H), 7.29 (br. s., 1H), 7.16 (d, J = 2.35 Hz, 1H), 4.55-4.82 (m, 2H), 3.59-3.80 (m, 2H), 2.80 (s, 3H), 1.88 (t, J = 2.35 Hz, 3H), 1.79-1.86 (m, 1H), 1.73 (s, 3H), 0.84-0.87 (m, 1H), 0.75-0.81 (m, 1H) | N-(3-((1S,5S,6S)-3-amino-1-(hydroxymethyl)-5-methyl-2-thia-4-azabicyclo[4.1.0]hept-3-en-5-yl)-4,5-difluorophenyl)-5-(2-butyn-1-yloxy)-3-methyl-2-pyridinecarboxamide |
| 102 | ¹H NMR (300 MHz, CHLOROFORM-d) δ ppm 1.72 (s, 3 H), 2.55 (s, 1 H), 2.65-2.82 (m, 1 H), 2.86-3.06 (m, 5 H), 4.58 (br., 2 H), 5.10 (s, 2 H), 7.03-7.19 (m, 1 H), 7.55-7.74 (m, 1 H), 7.96-8.18 (m, 2 H), 9.81 (s, 1 H). | N-(3-((1R,5S,6R)-3-amino-7,7-difluoro-5-methyl-2-thia-4-azabicyclo[4.1.0]hept-3-en-5-yl)-4-fluorophenyl)-3-methyl-5-(prop-2-yn-1-yloxy)pyrazine-2-carboxamide |
| 603 | ¹H NMR (300 MHz, CHLOROFORM-d) δ 9.83 (s, 1H), 8.55-8.75 (m, 1H), 8.32 (dd, J = 2.70, 8.70 Hz, 1H), 8.09 (s, 1H), 5.11 (d, J = 2.34 Hz, 2H), 4.97-5.26 (br. s., 2H), 4.44-4.65 (m, 1H), | N-(5-((1S,5S,6S)-3-amino-1-(fluoromethyl)-5-methyl-2-thia-4-azabicyclo[4.1.0]hept-3-en-5-yl)-6-fluoro-3-pyridinyl)-3- |

TABLE 1'-continued

| Ex. No. | ¹H-NMR | Chemical Name |
|---|---|---|
| | 4.07-4.43 (m, 1H), 2.98 (s, 3H), 2.56 (t, J = 2.41 Hz, 1H), 1.85-2.13 (m, 1H), 1.74 (s, 3H), 1.02 (dd, J = 6.14, 9.35 Hz, 1H), 0.84-0.93 (m, 1H). | methyl-5-(2-propyn-1-yloxy)-2-pyrazinecarboxamide |
| 655 | ¹H NMR (400 MHz, CHLOROFORM-d) δ ppm 0.84 (td, J = 6.60, 2.84 Hz, 1 H) 1.33 (dd, J = 9.88, 6.36 Hz, 1 H) 1.77 (s, 3 H) 1.97-2.08 (m, 1 H) 5.47-5.86 (m, 1 H) 7.90 (dd, J = 8.41, 2.35 Hz, 1 H) 8.23 (d, J = 8.22 Hz, 1 H) 8.35 (dd, J = 8.61, 2.74 Hz, 1 H) 8.53-8.63 (m, 2 H) 9.84 (s, 1 H). | N-(5-((1S,5S,6S)-3-amino-1-(difluoromethyl)-5-methyl-2-thia-4-azabicyclo[4.1.0]hept-3-en-5-yl)-6-fluoro-3-pyridinyl)-5-chloro-2-pyridinecarboxamide |
| 704 | ¹H NMR (300 MHz, CDCl3) δ = 9.85 (s, 1H), 8.58 (d, J = 2.3 Hz, 1H), 8.26 (d, J = 9.1 Hz, 1H), 8.03 (ddd, J = 2.9, 4.2, 8.8 Hz, 1H), 7.90 (dd, J = 2.3, 8.5 Hz, 1H), 7.77 (dd, J = 2.8, 6.9 Hz, 1H), 7.12 (dd, J = 8.8, 11.7 Hz, 1H), 4.04-3.97 (m, 1H), 3.97-3.90 (m, 1H), 2.58-2.49 (m, 1H), 1.68 (s, 3H) | N-(3-((1S,5S,6R)-3-amino-7,7-difluoro-1-(hydroxymethyl)-5-methyl-2-thia-4-azabicyclo[4.1.0]hept-3-en-5-yl)-4-fluorophenyl)-5-chloro-2-pyridinecarboxamide |
| 708 | ¹H NMR (300 MHz, DMSO) δ = 10.48 (s, 1H), 8.91 (d, J = 1.3 Hz, 1H), 8.56 (d, J = 1.3 Hz, 1H), 8.07 (dd, J = 2.7, 7.4 Hz, 1H), 7.83-7.73 (m, 1H), 7.19 (dd, J = 8.9, 12.0 Hz, 1H), 6.92-6.53 (m, 1H), 6.13 (s, 2H), 5.43 (t, J = 5.8 Hz, 1H), 5.03 (t, J = 14.3 Hz, 2H), 3.82 (br. s., 1H), 3.65 (dd, J = 5.2, 10.2 Hz, 1H), 1.52 (s, 3H) | N-(3-((1S,5S,6R)-3-amino-7,7-difluoro-1-(hydroxymethyl)-5-methyl-2-thia-4-azabicyclo[4.1.0]hept-3-en-5-yl)-4-fluorophenyl)-5-(2,2,3,3-tetrafluoropropoxy)-2-pyrazinecarboxamide |
| 710 | ¹H NMR (300 MHz, CDCl3) δ = 9.87 (br. s., 1H), 8.58 (s, 1H), 8.26 (d, J = 8.3 Hz, 1H), 8.13-8.02 (m, 1H), 7.96-7.86 (m, 1H), 7.82-7.72 (m, 1H), 7.21-7.05 (m, 1H), 3.98 (d, J = 11.0 Hz, 1H), 3.56 (d, J = 10.8 Hz, 1H), 3.42 (s, 3H), 2.44 (d, J = 15.9 Hz, 1H), 1.70 (s, 3H) | N-(3-((1S,5S,6R)-3-amino-7,7-difluoro-1-(methoxymethyl)-5-methyl-2-thia-4-azabicyclo[4.1.0]hept-3-en-5-yl)-4-fluorophenyl)-5-chloro-2-pyridinecarboxamide |
| 711 | ¹H NMR (300 MHz, CDCl3) δ = 9.85 (s, 1H), 8.62-8.53 (m, 1H), 8.27 (d, J = 9.1 Hz, 1H), 8.12-8.00 (m, 1H), 7.90 (dd, J = 2.3, 8.5 Hz, 1H), 7.72 (dd, J = 2.8, 7.0 Hz, 1H), 7.13 (dd, J = 8.8, 11.6 Hz, 1H), 3.17-3.06 (m, 1H), 1.68 (d, J = 0.9 Hz, 3H), 1.51 (s, 3H), 1.48 (s,3H) | N-(3-((1S,5S,6R)-3-amino-7,7-difluoro-1-(1-hydroxy-1-methylethyl)-5-methyl-2-thia-4-azabicyclo[4.1.0]hept-3-en-5-yl)-4-fluorophenyl)-5-chloro-2-pyridinecarboxamide |
| 748 | ¹H NMR (300 MHz, CHLOROFORM-d) δ ppm 1.75 (s, 3 H) 2.62-2.78 (m, 1 H) 2.90-3.02 (m, 1 H) 7.37-7.50 (m, 1 H) 7.85-7.95 (m, 1 H) 8.11-8.20 (m, 1 H) 8.22-8.29 (m, 1 H) 8.49-8.63 (m, 1 H) 9.77-9.96 (m, 1 H) | N-(3-((1R,5S,6R)-3-amino-7,7-difluoro-5-methyl-2-thia-4-azabicyclo[4.1.0]hept-3-en-5-yl)-4,5-difluorophenyl)-5-chloro-2-pyridinecarboxamide |
| 749 | ¹H NMR (300 MHz, DMSO-d6) δ ppm 1.52 (br. s., 3 H) 3.63 (br. s., 2 H) 3.82 (br. s., 1 H) 5.13 (br. s., 2 H) 5.42 (br. s., 1 H) 6.12 (br. s., 2 H) 7.03-7.28 (m, 1 H) 7.76 (br. s., 1 H) 8.06 (d, J = 4.82 Hz, 1 H) 8.47 (s, 1 H) 8.89 (s, 1 H) 10.43 (br. s., 1 H) | N-(3-((1S,5S,6R)-3-amino-7,7-difluoro-1-(hydroxymethyl)-5-methyl-2-thia-4-azabicyclo[4.1.0]hept-3-en-5-yl)-4-fluorophenyl)-5-(2-propyn-1-yloxy)-2-pyrazinecarboxamide |
| 751 | ¹H NMR (300 MHz, DMSO-d6) δ ppm 1.52 (s, 3 H) 2.38-2.48 (m, 1 H) 3.65 (dd, J = 12.57, 3.22 Hz, 1 H) 3.78-3.90 (m, 1 H) 4.85 (t, J = 13.52 Hz, 2 H) 5.43 (t, J = 5.77 Hz, 1 H) 6.14 (br. s., 2 H) 6.45-6.96 (m, 1 H) 7.18 (dd, J = 12.06, 8.84 Hz, 1 H) 7.76 (dd, J = 8.77, 2.92 Hz, 1 H) 7.81 (dt, J = 7.27, 4.26 Hz, 1 H) 8.03 (dd, J = 7.31, 2.78 Hz, 1 H) 8.14 (d, J = 8.77 Hz, 1 H) 8.49 (d, J = 2.63 Hz, 1 H) 10.31-10.46 (m, 1 H) 10.39 (s, 1 H) | N-(3-((1S,5S,6R)-3-amino-7,7-difluoro-1-(hydroxymethyl)-5-methyl-2-thia-4-azabicyclo[4.1.0]hept-3-en-5-yl)-4-fluorophenyl)-5-(2,2,3,3-tetrafluoropropoxy)-2-pyrazinecarboxamide |
| 785 | ¹H NMR(DMSO-d6) δ: 10.74 (s, 1H), 8.89 (d, J = 1.8 Hz, 1H), 8.43 (s, 1H), 8.28-8.33 (m, 1H), 8.22-8.28 (m, 1H), 8.13 (dd, J = 7.0, 2.7 Hz, 1H), 7.97 (dt, J = 7.3, 4.2 Hz, 1H), 7.31 (dd, J = 11.7, 8.8 Hz, 1H), 7.23 (s, 1H), 6.62 (s, 2H), 4.74-5.01 (m, 2H), 2.10-2.18 (m, 1H), 1.74 (dd, J = 9.7, 5.6 Hz, 1H), 1.03-1.11 (m, 1H), 1.03-1.11 (m, 1H) | N-(3-((1S,5S,6S)-3-amino-5-(fluoromethyl)-1-(1,3-oxazol-5-yl)-2-thia-4-azabicyclo[4.1.0]hept-3-en-5-yl)-4-fluorophenyl)-5-chloro-2-pyridinecarboxamide |
| 790 | ¹H NMR (DMSO-d6) δ: 10.62 (s, 1H), 9.73-10.99 (m, 1H), 8.80 (d, J = 1.8 Hz, 1H), 8.19-8.25 (m, 1H), 8.11-8.19 (m, 1H), 7.80-7.91 (m, 2H), 7.22 (dd, J = 11.7, 8.8 Hz, 1H), 6.57 (s, 2H), 4.82 (q, J = 8.1 Hz, 1H), 4.61-4.75 (m, 1H), 2.97-3.18 (m, 3H), 2.88 (br. s., 3H), 2.04-2.05 (m, 1H), 2.06 (t, J = 8.6 Hz, 1H), 1.50 (dd, J = 9.5, 5.4 Hz, 1H), 0.69 (t, J = 6.2 Hz, 1H). | (1S,5S,6S)-3-amino-5-(5-(((5-chloro-2-pyridinyl)carbonyl)amino)-2-fluorophenyl)-5-(fluoromethyl)-N,N-dimethyl-2-thia-4-azabicyclo[4.1.0]hept-3-ene-1-carboxamide |
| 906 | ¹H NMR (400 MHz, DMSO-d6) δ 10.79 (s, 1H), 8.79 (s, 1H), 8.15-8.23 (m, 2H), 7.92-8.02 (m, 2H), 6.17 (s, 2H), 2.33-2.41 (m, 3H), 2.11 (s, 3H), 1.74 (dd, J = 5.48, 9.78 Hz, 1H), 1.62 (s, 3H), 1.11-1.16 (m, 1H) | N-(3-((1S,5S,6S)-1-acetyl-3-amino-5-methyl-2-thia-4-azabicyclo[4.1.0]hept-3-en-5-yl)-4,5-difluorophenyl)-5-chloro-2-pyridinecarboxamide |
| 910 | ¹H NMR (400 MHz, DMSO-d6) δ 10.62 (s, 1H), 8.89 (d, J = 1.17 Hz, 1H), 8.54 (d, J = 1.17 Hz, 1H), 8.20 (s, 1H), 7.88-7.94 (m, 2H), 7.30 (s, 1H), | N-(3-((1S,5S,6S)-3-amino-1-(methoxymethyl)-5-methyl-2-thia-4-azabicyclo[4.1.0]hept-3- |

TABLE 1'-continued

| Ex. No. | ¹H-NMR | Chemical Name |
|---|---|---|
|  | 5.99 (s, 2H), 5.62 (s, 2H), 3.57 (d, J = 10.95 Hz, 1H), 3.36 (d, J = 10.95 Hz, 1H), 3.31 (d, J = 2.54 Hz, 3H), 1.58-1.65 (m, 4H), 0.90 (dd, J = 5.18, 9.10 Hz, 1H), 0.64 (t, J = 5.77 Hz, 1H) | en-5-yl)-4,5-difluorophenyl)-5-(1,3-oxazol-2-ylmethoxy)-2-pyrazinecarboxamide |
| 953 | ¹H NMR (400 MHz, CHLOROFORM-d) δ ppm 0.77 (t, J = 6.26 Hz, 1 H) 1.13 (dd, J = 9.68, 5.97 Hz, 1 H) 1.80-1.88 (m, 1 H) 2.55 (t, J = 2.35 Hz, 1 H) 3.60-3.84 (m, 2 H) 3.90 (q, J = 8.61 Hz, 2 H) 4.57-4.97 (m, 3 H) 5.09 (d, J = 2.35 Hz, 2 H) 7.09 (dd, J = 11.35, 8.80 Hz, 1 H) 7.68 (dd, J = 6.65, 2.74 Hz, 1 H) 7.96 (dt, J = 8.31, 3.67 Hz, 1 H) 8.20 (d, J = 0.98 Hz, 1 H) 9.02 (d, J = 0.98 Hz, 1 H) 9.48 (s, 1H) | N-(3-((1S,5S,6S)-3-amino-5-(fluoromethyl)-1-((2,2,2-trifluoroethoxy)methyl)-2-thia-4-azabicyclo[4.1.0]hept-3-en-5-yl)-4-fluorophenyl)-5-(2-propyn-1-yloxy)-2-pyrazinecarboxamide |
| 954 | ¹H NMR (400 MHz, CHLOROFORM-d) δ ppm 0.78 (t, J = 6.26 Hz, 1 H) 1.14 (dd, J = 9.68, 5.97 Hz, 1 H) 1.26 (br. s., 2 H) 1.83-1.89 (m, 1 H) 3.62-3.85 (m, 2 H) 3.90 (q, J = 8.74 Hz, 2 H) 4.60-4.96 (m, 2 H) 7.10 (dd, J = 11.54, 8.80 Hz, 1 H) 7.70 (dd, J = 6.85, 2.74 Hz, 1 H) 7.88 (dd, J = 8.41, 2.35 Hz, 1 H) 7.97 (dt, J = 8.75, 3.55 Hz, 1 H) 8.24 (d, J = 8.41 Hz, 1 H) 8.56 (d, J = 2.15 Hz, 1 H) 9.82 (s, 1 H) | N-(3-((1S,5S,6S)-3-amino-5-(fluoromethyl)-1-((2,2,2-trifluoroethoxy)methyl)-2-thia-4-azabicyclo[4.1.0]hept-3-en-5-yl)-4-fluorophenyl)-5-chloro-2-pyridinecarboxamide |
| 955 | ¹H NMR (400 MHz, CHLOROFORM-d) δ ppm 0.75 (t, J = 5.97 Hz, 1 H) 1.09 (dd, J = 9.49, 5.77 Hz, 1 H) 1.17 (t, J = 6.36 Hz, 6 H) 1.75-1.81 (m, 1 H) 2.55 (m, 1 H) 3.37 (d, J = 10.37 Hz, 1 H) 3.63 (dt, J = 12.13, 6.06 Hz, 1 H) 3.71 (d, J = 10.37 Hz, 1 H) 4.63-4.95 (m, 4 H) 5.08 (d, J = 1.96 Hz, 2 H) 7.09 (dd, J = 11.44, 9.10 Hz, 1 H) 7.70 (d, J = 4.30 Hz, 1 H) 7.93-8.05 (m, 1 H) 8.20 (s, 1 H) 9.02 (s, 1 H) 9.49 (br. s., 1 H) | N-(3-((1S,5S,6S)-3-amino-5-(fluoromethyl)-1-((1-methylethoxy)methyl)-2-thia-4-azabicyclo[4.1.0]hept-3-en-5-yl)-4-fluorophenyl)-5-(2-propyn-1-yloxy)-2-pyrazinecarboxamide |
| 956 | ¹H NMR (400 MHz, CHLOROFORM-d) δ ppm 1.14 (t, J = 6.36 Hz, 1 H) 1.77 (dd, J = 9.59, 5.87 Hz, 1 H) 2.27 (t, J = 8.31 Hz, 1 H) 4.68-5.07 (m, 2 H) 7.07-7.16 (m, 1 H) 7.66 (s, 1 H) 7.77 (d, J = 4.11 Hz, 1 H) 7.88 (d, J = 8.22 Hz, 1 H) 7.91-7.99 (m, 1 H) 8.24 (d, J = 8.22 Hz, 1 H) 8.56 (s, 1 H) 9.85 (s, 1 H) | N-(3-((1S,5S,6S)-3-amino-5-(fluoromethyl)-1-(1H-1,2,3-triazol-4-yl)-2-thia-4-azabicyclo[4.1.0]hept-3-en-5-yl)-4-fluorophenyl)-5-chloro-2-pyridinecarboxamide |
| 959 | ¹H NMR (400 MHz, CHLOROFORM-d) δ ppm 1.13 (t, J = 6.36 Hz, 1 H) 1.75 (dd, J = 9.39, 5.67 Hz, 1 H) 2.19-2.31 (m, 1 H) 2.55 (br. s., 1 H) 4.67-5.05 (m, 2 H) 5.09 (d, J = 2.15 Hz, 2 H) 7.11 (dd, J = 11.25, 9.29 Hz, 1 H) 7.66 (s, 1 H) 7.74 (d, J = 4.30 Hz, 1 H) 7.86-8.01 (m, 1 H) 8.21 (s, 1 H) 9.03 (s, 1 H) 9.51 (s, 1 H) | N-(3-((1S,5S,6S)-3-amino-5-(fluoromethyl)-1-(1H-1,2,3-triazol-4-yl)-2-thia-4-azabicyclo[4.1.0]hept-3-en-5-yl)-4-fluorophenyl)-5-(2-propyn-1-yloxy)-2-pyrazinecarboxamide |

Method B: Propylphosphonic Anhydride (T3P) Procedure in DMAc as Solvent

Example 94

N-(3-((1S,5S,6S)-3-amino-1-(difluoromethyl)-5-(fluoromethyl)-2-thia-4-azabicyclo[4.1.0]hept-3-en-5-yl)-4,5-difluorophenyl)-5-cyano-3-methylpicolinamide

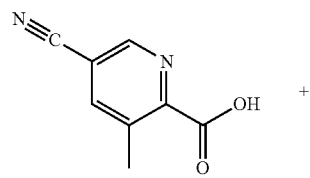

267

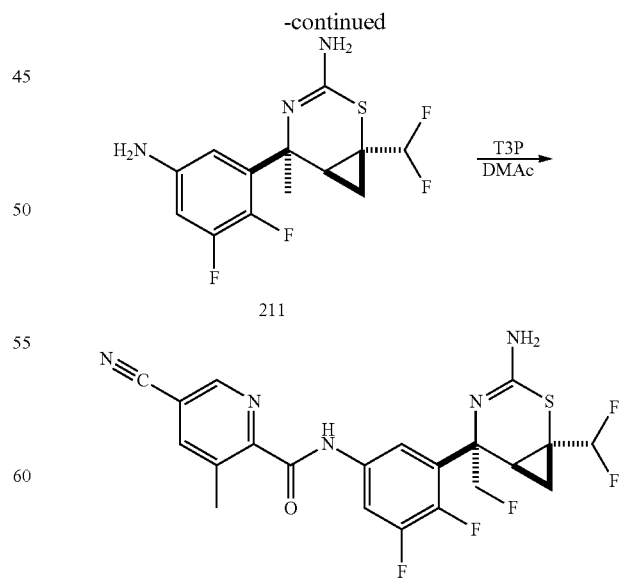

Example 94

Propylphosphonic anhydride solution (50 wt. % in EtOAc, 279 mg, 0.44 mmol) was added to a stirred solution of (1S,5S,6S)-5-(5-amino-2,3-difluorophenyl)-1-(difluoromethyl)-5-methyl-2-thia-4-azabicyclo[4.1.0]hept-3-en-3-amine (Intermediate 211, 70 mg, 0.22 mmol) and 5-cyano-3-methylpicolinic acid (Intermediate 267, 46 mg, 0.28 mmol) in DMAc (2 mL) at 0° C. The reaction mixture was stirred at 0° C. for 0.5 h then RT for 2 h. The reaction mixture was treated with additional 5-cyano-3-methylpicolinic acid (15 mg, 0.09 mmol) followed by T3P (50 wt. % in EtOAc, 100 mg, 0.15 mmol) and stirred at RT for 48 h. It was quenched with sat'd aqueous NaHCO$_3$ and extracted with EtOAc. The organic layer was separated, washed with brine, dried over MgSO$_4$, filtered, and concentrated. The resulting crude yellow oil was purified on a silica gel column (35-65% EtOAc in DCM) to afford N-(3-((1S,5S,6S)-3-amino-1-(difluoromethyl)-5-methyl-2-thia-4-azabicyclo[4.1.0]hept-3-en-5-yl)-4,5-difluorophenyl)-5-cyano-3-methylpicolinamide (Example 94, 65 mg, 0.14 mmol, 64% yield) as an off-white solid. MS m/z=464.0 [M+H]$^+$. $^1$H NMR (400 MHz, DMSO-d$_6$) δ 10.86 (br., 1H), 8.99 (d, J=1.57 Hz, 1H), 8.41 (d, J=1.17 Hz, 1H), 7.94 (ddd, J=2.64, 6.75, 12.32 Hz, 1H), 7.62 (m, 1H), 6.31 (br., 2H), 5.81-6.03 (m, 1H), 2.57 (s, 3H), 1.93 (m, 1H), 1.66 (s, 3H), 1.35 (m, 1H), 0.75 (m, 1H). $^{19}$F NMR (377 MHz, DMSO-d$_6$) δ −115.50 (d, $^1$J=273.96 Hz, 1F), −118.00 (d, $^1$J=273.90 Hz, 1F), −137.95 (d, $^2$J=22.56 Hz, 1F), −142.80 (d, $^2$J=22.66 Hz, 1F).

Using procedures analogous or similar to the general amidation Method B described above, the appropriate aniline and carboxylic acid intermediates were reacted to provide the 30 examples listed in Table 2 and Table 2'.

TABLE 2

| Ex.No. | Chemical Structure | Observed [M + H]$^+$ |
|---|---|---|
| 31 | 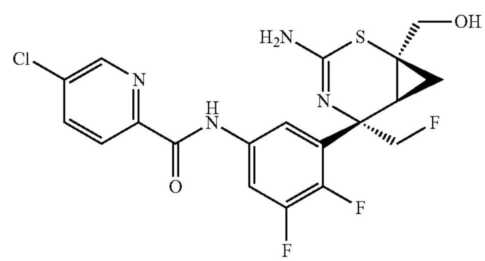 [SMILES: NC1=N[C@](CF)(c2cc(NC(=O)c3ccc(Cl)cn3)cc(F)c2F)[C@@H]2C[C@]2(CO)S1] | 457.1 |
| 37 | 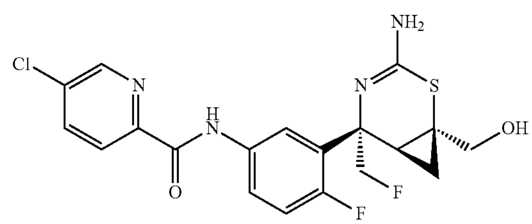 [SMILES: NC1=N[C@](CF)(c2cc(NC(=O)c3ccc(Cl)cn3)ccc2F)[C@@H]2C[C@]2(CO)S1] | 439.1 |
| 43 | 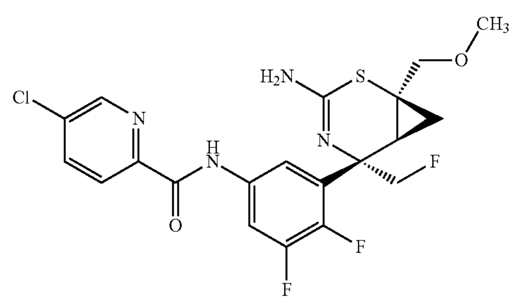 [SMILES: COC[C@]12C[C@H]1[C@@](CF)(c1cc(NC(=O)c3ccc(Cl)cn3)cc(F)c1F)N=C(N)S2] | 471.0 |
| 44 | 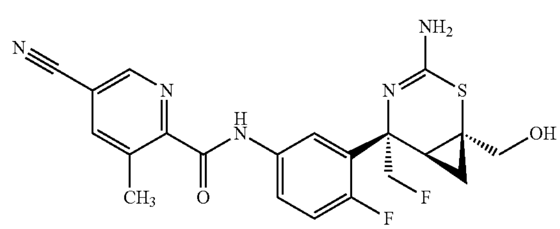 [SMILES: Cc1cc(C#N)cnc1C(=O)Nc1ccc(F)c([C@@]2(CF)N=C(N)S[C@@]3(CO)C[C@H]32)c1] | 444.0 |

TABLE 2-continued

| Ex.No. | Chemical Structure | Observed [M + H]+ |
|---|---|---|
| 53 | 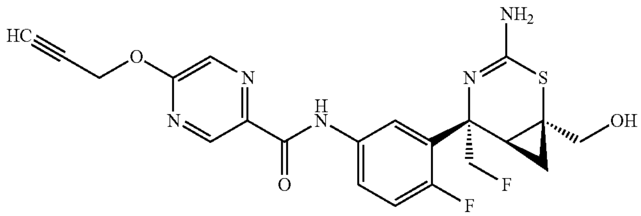 [SMILES: C#CCOc1cnc(C(=O)Nc2ccc(F)c([C@@]3(CF)N=C(N)S[C@@]4(CO)C[C@H]43)c2)cn1] | 460.1 |
| 70 | 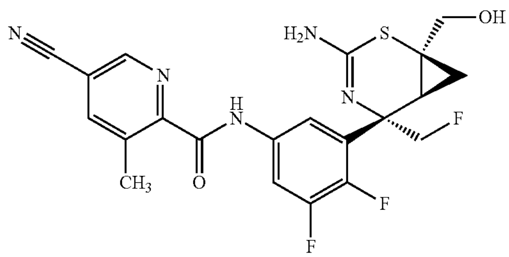 [SMILES: Cc1cc(C#N)cnc1C(=O)Nc1cc(F)c(F)c([C@@]2(CF)N=C(N)S[C@@]3(CO)C[C@H]32)c1] | 462.0 |
| 72 | 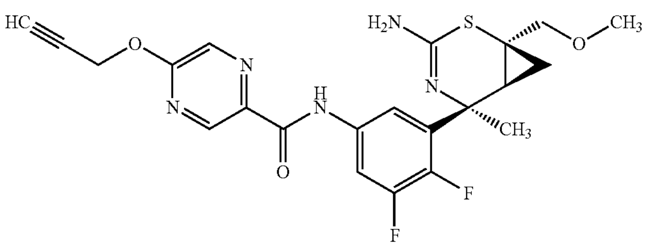 [SMILES: C#CCOc1cnc(C(=O)Nc2cc(F)c(F)c([C@@]3(C)N=C(N)S[C@@]4(COC)C[C@H]43)c2)cn1] | 474.0 |
| 75 | 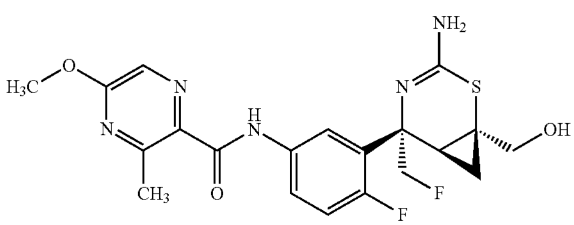 [SMILES: COc1cnc(C(=O)Nc2ccc(F)c([C@@]3(CF)N=C(N)S[C@@]4(CO)C[C@H]43)c2)c(C)n1] | 450.1 |
| 76 | 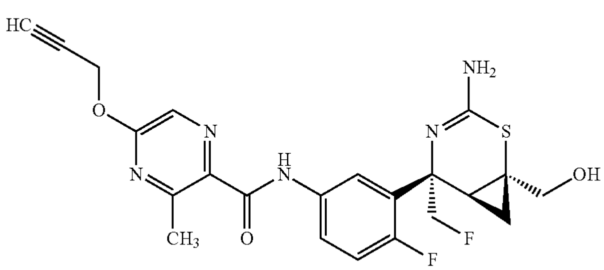 [SMILES: C#CCOc1cnc(C(=O)Nc2ccc(F)c([C@@]3(CF)N=C(N)S[C@@]4(CO)C[C@H]43)c2)c(C)n1] | 474.0 |
| 78 | 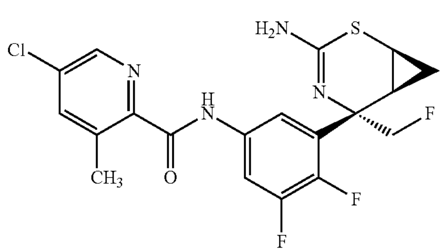 | 441.0 |

TABLE 2-continued

| Ex.No. | Chemical Structure | Observed [M + H]+ |
|---|---|---|
| 79 | 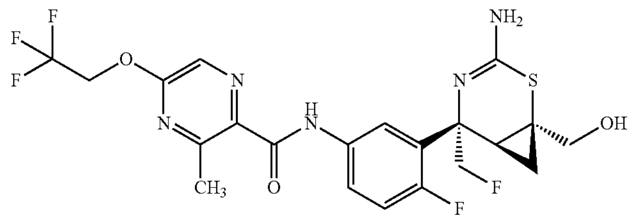 [SMILES: Cc1nc(OCC(F)(F)F)cnc1C(=O)Nc1ccc(F)c([C@@]2(CF)N=C(N)S[C@@]3(CO)C[C@H]32)c1] | 518.2 |
| 81 | 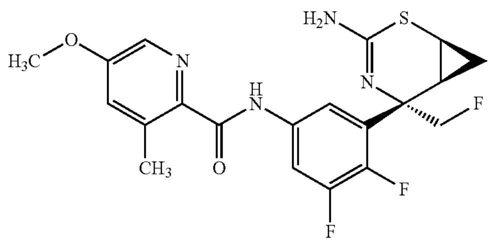 [SMILES: COc1cnc(C(=O)Nc2cc(F)c(F)c([C@@]3(CF)N=C(N)S[C@H]4C[C@H]43)c2)c(C)c1] | 437.1 |
| 83 | 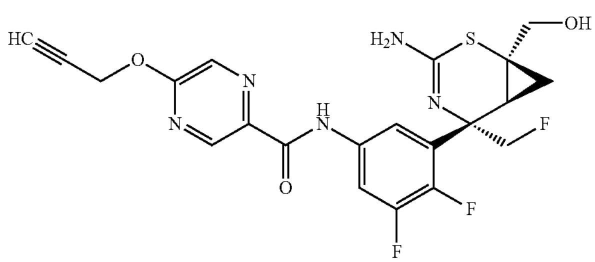 [SMILES: C#CCOc1cnc(C(=O)Nc2cc(F)c(F)c([C@@]3(CF)N=C(N)S[C@@]4(CO)C[C@H]43)c2)cn1] | 478.1 |
| 84 | 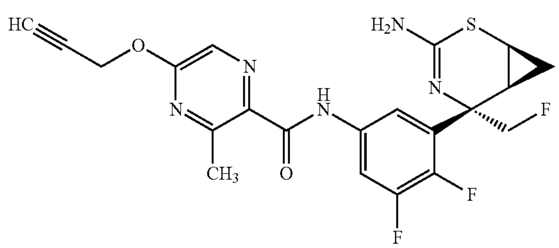 [SMILES: C#CCOc1cnc(C(=O)Nc2cc(F)c(F)c([C@@]3(CF)N=C(N)S[C@H]4C[C@H]43)c2)c(C)n1] | 462.0 |
| 86 | 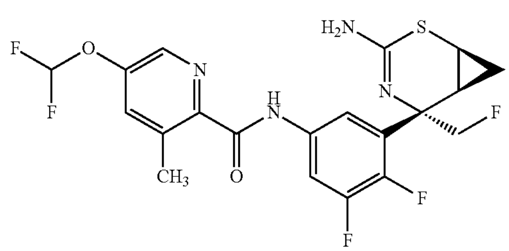 [SMILES: Cc1cc(OC(F)F)cnc1C(=O)Nc1cc(F)c(F)c([C@@]2(CF)N=C(N)S[C@H]3C[C@H]32)c1] | 473.1 |
| 96 | 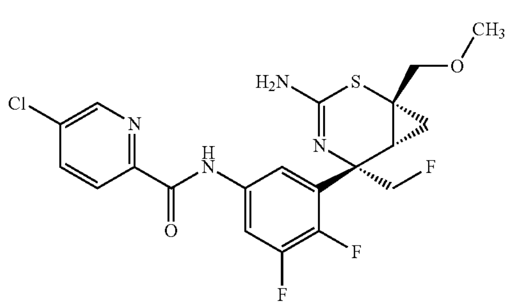 [SMILES: COC[C@@]12C[C@@H]1[C@@](CF)(c1cc(NC(=O)c3ccc(Cl)cn3)cc(F)c1F)N=C(N)S2] | 471.0 |

TABLE 2-continued

| Ex.No. | Chemical Structure | Observed [M + H]+ |
|---|---|---|
| 31 | 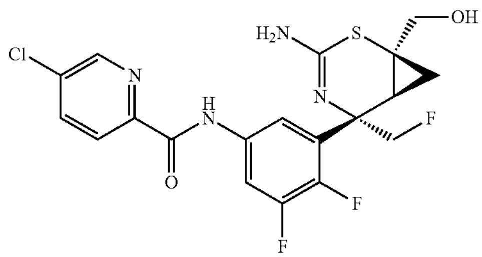 [SMILES: NC1=N[C@](CF)(c2cc(NC(=O)c3ccc(Cl)cn3)cc(F)c2F)[C@@H]2C[C@]2(CO)S1] | 457.1 |
| 37 | 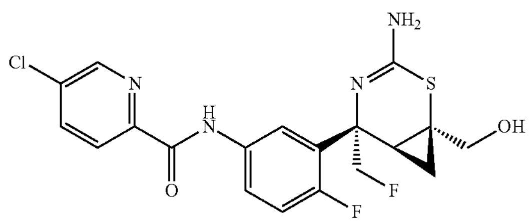 [SMILES: NC1=N[C@](CF)(c2cc(NC(=O)c3ccc(Cl)cn3)ccc2F)[C@@H]2C[C@]2(CO)S1] | 439.1 |
| 43 | 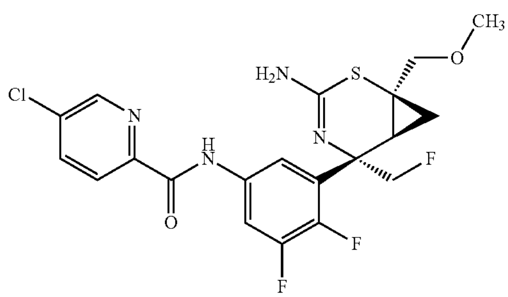 [SMILES: COC[C@]12C[C@H]1[C@@](CF)(c1cc(NC(=O)c3ccc(Cl)cn3)cc(F)c1F)N=C(N)S2] | 471.0 |
| 44 | 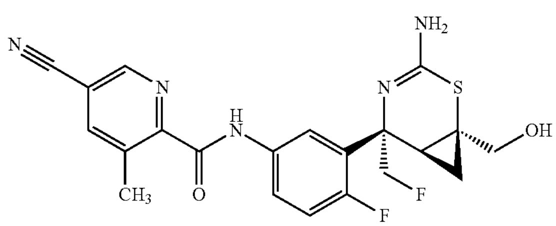 [SMILES: Cc1cc(C#N)cnc1C(=O)Nc1ccc(F)c([C@@]2(CF)N=C(N)S[C@@]3(CO)C[C@H]32)c1] | 444.0 |
| 673 | 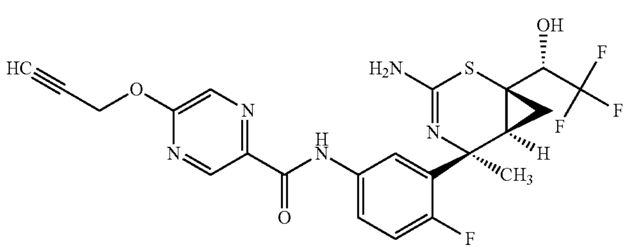 [SMILES: C#CCOc1cnc(C(=O)Nc2ccc(F)c([C@@]3(C)N=C(N)S[C@@]4([C@H](O)C(F)(F)F)C[C@H]43)c2)cn1] | 510 |
| 674 | 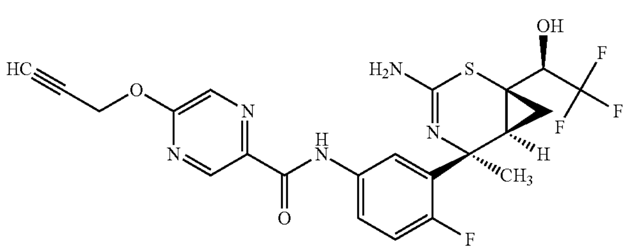 [SMILES: C#CCOc1cnc(C(=O)Nc2ccc(F)c([C@@]3(C)N=C(N)S[C@@]4([C@@H](O)C(F)(F)F)C[C@H]43)c2)cn1] | 510 |

TABLE 2-continued

| Ex.No. | Chemical Structure | Observed [M + H]+ |
|---|---|---|
| 675 | 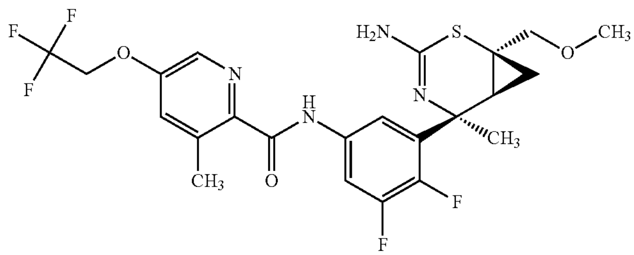 [SMILES: COC[C@]12C[C@H]1[C@@](C)(c1cc(NC(=O)c3ncc(OCC(F)(F)F)cc3C)cc(F)c1F)N=C(N)S2] | 531 |
| 678 | 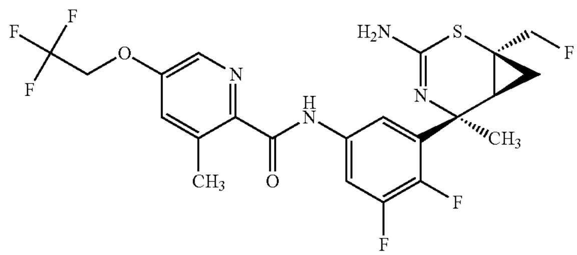 [SMILES: Cc1cc(OCC(F)(F)F)cnc1C(=O)Nc1cc(F)c(F)c([C@@]2(C)N=C(N)S[C@@]3(CF)C[C@H]32)c1] | 519 |
| 679 | 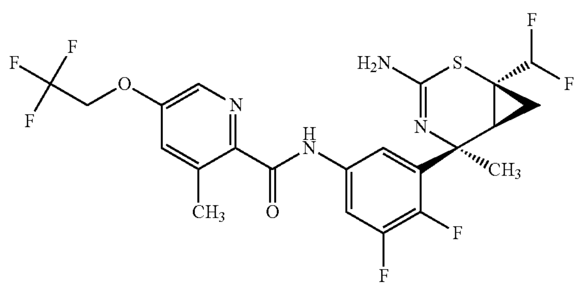 [SMILES: Cc1cc(OCC(F)(F)F)cnc1C(=O)Nc1cc(F)c(F)c([C@@]2(C)N=C(N)S[C@@]3(C(F)F)C[C@@H]23)c1] | 537 |
| 715 | 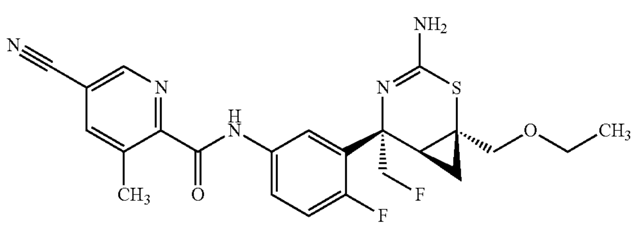 [SMILES: CCOC[C@]12C[C@H]1[C@@](CF)(c1cc(NC(=O)c3ncc(C#N)cc3C)ccc1F)N=C(N)S2] | 472.1 |
| 716 | 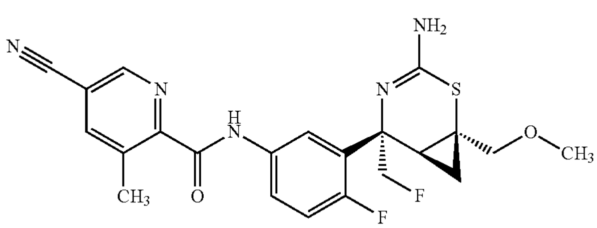 [SMILES: COC[C@]12C[C@H]1[C@@](CF)(c1cc(NC(=O)c3ncc(C#N)cc3C)ccc1F)N=C(N)S2] | 458.1 |
| 718 | 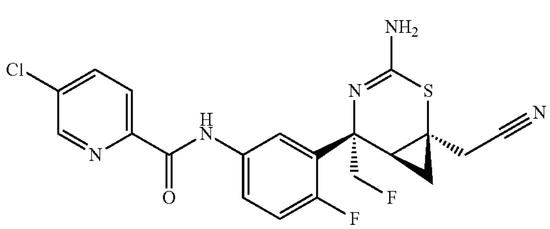 [SMILES: N#CC[C@]12C[C@H]1[C@@](CF)(c1cc(NC(=O)c3ccc(Cl)cn3)ccc1F)N=C(N)S2] | 448.1 |

TABLE 2-continued

| Ex.No. | Chemical Structure | Observed [M + H]+ |
|---|---|---|
| 723 | 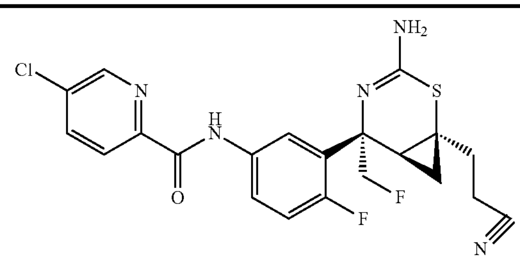 | 462 |
| 725 | 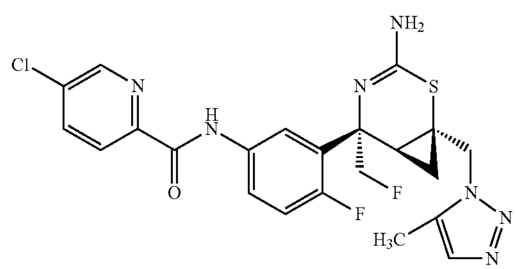 [SMILES: Cc1cnnn1C[C@]12C[C@H]1[C@@](CF)(c1cc(NC(=O)c3ccc(Cl)cn3)ccc1F)N=C(N)S2] | 504 |

TABLE 2'

| Ex. No. | $^1$H-NMR | Chemical Name |
|---|---|---|
| 31 | $^1$H NMR (400 MHz, DMSO-d6) δ ppm 10.79 (s, 1 H) 8.79 (d, J = 1.76 Hz, 1 H) 8.21 (dd, J = 8.41, 2.35 Hz, 1 H) 8.16 (d, J = 8.61 Hz, 1 H) 7.98 (ddd, J = 12.23, 6.75, 2.54 Hz, 1 H) 7.89-7.93 (m, 1 H) 6.26 (s, 2 H) 5.08 (t, J = 5.97 Hz, 1 H) 4.57-4.81 (m, 2 H) 3.54 (dd, J = 11.74, 6.26 Hz, 1 H) 3.44 (dd, J = 11.74, 5.67 Hz, 1 H) 1.61-1.67 (m, 1 H) 1.04 (dd, J = 9.29, 5.18 Hz, 1 H) 0.57 (t, J = 5.77 Hz, 1 H) | N-(3-((1S,5S,6S)-3-amino-5-(fluoromethyl)-1-(hydroxymethyl)-2-thia-4-azabicyclo[4.1.0]hept-3-en-5-yl)-4,5-difluorophenyl)-5-chloro-2-pyridinecarboxamide |
| 37 | $^1$H NMR (400 MHz, CHLOROFORM-d) δ ppm 9.80 (br s, 1H), 8.54 (d, J = 2.15 Hz, 1H), 8.23 (d, J = 8.41 Hz, 1H), 7.94-8.01 (m, 1H), 7.87 (dd, J = 8.41, 2.35 Hz, 1H), 7.71 (d, J = 4.30 Hz, 1 H), 7.09 (dd, J = 11.44, 8.90 Hz, 1H), 4.91 (dd, J = 46.95, 8.41 Hz, 1H), 4.77 (s br, 2H), 4.67 (dd, J = 47.54, 8.80 Hz, 1H), 3.76 (d, J = 11.93 Hz, 1H), 3.60 (d, J = 11.74 Hz, 1H), 1.85 (t, J = 9.00 Hz, 1H), 1.77 (s br, 1H), 1.08 (dd, J = 9.59, 5.87 Hz, 1H), 0.71 (t, J = 6.26 Hz, 1H) | N-(3-((1S,5S,6S)-3-amino-5-(fluoromethyl)-1-(hydroxymethyl)-2-thia-4-azabicyclo[4.1.0]hept-3-en-5-yl)-4-fluorophenyl)-5-chloro-2-pyridinecarboxamide |
| 43 | $^1$H NMR (400 MHz, DMSO-d6) δ ppm 10.79 (s, 1 H) 8.79 (d, J = 1.96 Hz, 1 H) 8.21 (dd, J = 8.41, 2.35 Hz, 1 H) 8.16 (d, J = 8.22 Hz, 1 H) 7.99 (ddd, J = 12.37, 6.80, 2.54 Hz, 1 H) 7.88-7.93 (m, 1 H) 6.30 (s, 2 H) 4.60-4.78 (m, 2 H) 3.56 (d, J = 10.76 Hz, 1 H) 3.35 (d, J = 10.95 Hz, 1 H) 3.30 (s, 3 H) 1.63-1.69 (m, 1 H) 1.10 (dd, J = 9.49, 5.18 Hz, 1 H) 0.64 (t, J = 5.87 Hz, 1 H) | N-(3-((1S,5S,6S)-3-amino-5-(fluoromethyl)-1-(methoxymethyl)-2-thia-4-azabicyclo[4.1.0]hept-3-en-5-yl)-4,5-difluorophenyl)-5-chloro-2-pyridinecarboxamide |
| 44 | $^1$H NMR (400 MHz, DMSO-d6) δ ppm 10.67 (s, 1H), 8.98 (d, J = 1.37 Hz, 1H), 8.40 (d, J = 1.96 Hz, 1H), 7.90 (dd, J = 7.04, 2.74 Hz, 1H), 7.81-7.87 (m, 1H), 7.19 (dd, J = 11.93, 8.80 Hz, 1H), 6.22 (s, 2H), 5.06 (t, J = 5.87 Hz, 1H), 4.77 (dd, J = 26.41, 8.61 Hz, 1H), 4.65 (dd, J = 26.41, 9.19 Hz, 1H), 3.54 (dd, J = 11.54, 6.26 Hz, 1H), 3.43 (dd, J = 11.74, 5.67 Hz, 1H), 2.56 (s, 3H), 1.64 (t, J = 7.82 Hz, 1H), 0.98 (dd, J = 9.49, 4.99 Hz, 1H), 0.50 (t, J = 5.67 Hz, 1H) | N-(3-((1S,5S,6S)-3-amino-5-(fluoromethyl)-1-(hydroxymethyl)-2-thia-4-azabicyclo[4.1.0]hept-3-en-5-yl)-4-fluorophenyl)-5-cyano-3-methyl-2-pyridinecarboxamide |
| 53 | $^1$H NMR (400 MHz, CHLOROFORM-d) δ ppm 9.48 (s, 1H), 9.02 (d, J = 1.37 Hz, 1H), 8.20 (d, J = 1.37 Hz, 1H), 7.94-8.01 (m, 1H), 7.68 (dd, J = 6.75, 2.64 Hz, 1H), 7.09 (dd, J = 11.54, 8.80 Hz, 1H), 5.09 (d, J = 2.35 Hz, 2H), 4.91 (dd, J = 46.75, 7.82 Hz, 1H), 4.72 (s br, 2H), 4.66 (dd, J = 47.73, 8.41 Hz, 1H), 3.76 (d, J = 11.74 Hz, 1H), 3.60 (d, J = 11.93 Hz, 1H), 2.55 (t, J = 2.35 Hz, | N-(3-((1S,5S,6S)-3-amino-5-(fluoromethyl)-1-(hydroxymethyl)-2-thia-4-azabicyclo[4.1.0]hept-3-en-5-yl)-4-fluorophenyl)-5-(2-propyn-1-yloxy)-2-pyrazinecarboxamide |

TABLE 2'-continued

| Ex. No. | ¹H-NMR | Chemical Name |
|---|---|---|
| | 1H), 1.84 (t, J = 8.80 Hz, 1H), 1.68 (s br, 1H), 1.07 (dd, J = 9.68, 5.77 Hz, 1H), 0.71 (t, J = 6.26 Hz, 1H) | |
| 70 | ¹H NMR (400 MHz, DMSO-d6) δ ppm 10.87 (s, 1 H) 8.98 (d, J = 1.17 Hz, 1 H) 8.40 (d, J = 1.17 Hz, 1 H) 7.97 (ddd, J = 12.37, 6.80, 2.54 Hz, 1 H) 7.70-7.74 (m, 1 H) 6.26 (s, 2 H) 5.08 (t, J = 5.97 Hz, 1 H) 4.57-4.82 (m, 2 H) 3.53 (dd, J = 11.74, 6.26 Hz, 1 H) 3.43 (dd, J = 11.74, 5.67 Hz, 1 H) 2.56 (s, 3 H) 1.60-1.66 (m, 1 H) 1.02 (dd, J = 9.39, 5.09 Hz, 1 H) 0.53 (t, J = 5.77 Hz, 1 H) | N-(3-((1S,5S,6S)-3-amino-5-(fluoromethyl)-1-(hydroxymethyl)-2-thia-4-azabicyclo[4.1.0]hept-3-en-5-yl)-4,5-difluorophenyl)-5-cyano-3-methyl-2-pyridinecarboxamide |
| 72 | ¹H NMR (400 MHz, DMSO-d₆) δ 10.42-10.79 (m, 1H), 8.90 (d, J = 1.17 Hz, 1H), 8.48 (d, J = 1.17 Hz, 1H), 7.70-8.03 (m, 2H), 5.99 (s, 2H), 5.14 (d, J = 2.35 Hz, 2H), 3.64 (t, J = 2.45 Hz, 1H), 3.57 (d, J = 10.95 Hz, 1H), 3.36 (d, J = 11.15 Hz, 1H), 3.30-3.31 (m, 3H), 1.57-1.70 (m, 4H), 0.90 (dd, J = 5.28, 9.19 Hz, 1H), 0.65 (t, J = 5.77 Hz, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-(2-propyn-1-yloxy)-2-pyrazinecarboxamide |
| 75 | ¹H NMR (400 MHz, CHLOROFORM-d) δ ppm 9.76 (s, 1H), 8.00 (dt, J = 8.56, 3.64 Hz, 1H), 7.97 (s, 1H), 7.58 (dd, J = 6.65, 2.74 Hz, 1H), 7.07 (dd, J = 11.54, 9.00 Hz, 1H), 4.91 (dd, J = 47.34, 8.22 Hz, 1H), 4.75 (s br, 2H), 4.64 (dd, J = 47.14, 8.41 Hz, 1H), 4.04 (s, 3H), 3.75 (d, J = 11.93 Hz, 1H), 3.60 (d, J = 11.93 Hz, 1H), 2.94 (s, 3H), 1.85 (t, J = 8.20 Hz, 1H), 1.72 (s br, 1H), 1.06 (dd, J = 9.68, 5.77 Hz, 1H), 0.70 (t, J = 6.16 Hz, 1H) | N-(3-((1S,5S,6S)-3-amino-5-(fluoromethyl)-1-(hydroxymethyl)-2-thia-4-azabicyclo[4.1.0]hept-3-en-5-yl)-4-fluorophenyl)-5-methoxy-3-methyl-2-pyrazinecarboxamide |
| 76 | ¹H NMR (400 MHz, CHLOROFORM-d) δ ppm 9.75 (s, 1H), 8.05 (s, 1H), 8.01 (dt, J = 8.80, 3.50 Hz, 1H), 7.58 (dd, J = 6.65, 2.54 Hz, 1H), 7.08 (dd, J = 11.54, 8.80 Hz, 1H), 5.08 (d, J = 2.35 Hz, 2H), 4.92 (dd, J = 47.34, 8.02 Hz, 1H), 4.70 (s br, 2H), 4.64 (dd, J = 46.95, 8.61 Hz, 1H), 3.76 (d, J = 11.93 Hz, 1H), 3.60 (d, J = 11.93 Hz, 1H), 2.95 (s, 3H), 2.53 (t, J = 2.35 Hz, 1H), 1.86 (t, J = 8.00 Hz, 1H), 1.70 (s br, 1H), 1.06 (dd, J = 9.68, 5.77 Hz, 1H), 0.71 (t, J = 6.36 Hz, 1H) | N-(3-((1S,5S,6S)-3-amino-5-(fluoromethyl)-1-(hydroxymethyl)-2-thia-4-azabicyclo[4.1.0]hept-3-en-5-yl)-4-fluorophenyl)-3-methyl-5-(2-propyn-1-yloxy)-2-pyrazinecarboxamide |
| 78 | ¹H NMR (400 MHz, DMSO-d6) δ ppm 10.70 (s, 1 H) 8.57 (d, J = 2.15 Hz, 1 H) 8.03 (d, J = 1.76 Hz, 1 H) 7.96 (ddd, J = 12.42, 6.85, 2.64 Hz, 1 H) 7.69-7.73 (m, 1 H) 6.22 (s, 2 H) 4.72 (d, J = 47.73 Hz, 2 H) 2.56 (s, 3 H) 2.39 (ddd, J = 9.00, 7.63, 5.09 Hz, 1 H) 1.74 (m, J = 7.76, 7.76, 7.76 Hz, 1 H) 1.03 (ddd, J = 8.80, 7.63, 5.28 Hz, 1 H) 0.41 (q, J = 5.15 Hz, 1 H) | N-(3-((1S,5S,6S)-3-amino-5-(fluoromethyl)-2-thia-4-azabicyclo[4.1.0]hept-3-en-5-yl)-4,5-difluorophenyl)-5-chloro-3-methyl-2-pyridinecarboxamide |
| 79 | ¹H NMR (400 MHz, CHLOROFORM-d) δ ppm 9.73 (s, 1H), 8.13 (s, 1H), 7.97-8.02 (m, 1H), 7.60 (d, J = 5.67 Hz, 1H), 7.08 (t, J = 10.04 Hz, 1H), 4.85 (q, J = 8.40 Hz, 2H), 4.82-4.98 (m, 1H), 4.71 (s br, 2H), 4.65 (dd, J = 47.14, 8.61 Hz, 1H), 3.76 (d, J = 11.74 Hz, 1H), 3.61 (d, J = 11.74 Hz, 1H), 2.95 (s, 3H), 1.85 (t, J = 8.12 Hz, 1H), 1.66 (s br, 1H), 1.06 (dd, J = 9.59, 5.67 Hz, 1H), 0.71 (t, J = 6.26 Hz, 1H) | N-(3-((1S,5S,6S)-3-amino-5-(fluoromethyl)-1-(hydroxymethyl)-2-thia-4-azabicyclo[4.1.0]hept-3-en-5-yl)-4-fluorophenyl)-3-methyl-5-(2,2,2-trifluoroethoxy)-2-pyrazinecarboxamide |
| 81 | ¹H NMR (400 MHz, DMSO-d6) δ ppm 10.51 (s, 1 H) 8.22 (d, J = 2.54 Hz, 1 H) 7.98 (ddd, J = 12.52, 6.85, 2.54 Hz, 1 H) 7.68-7.73 (m, 1 H) 7.41 (d, J = 2.54 Hz, 1 H) 6.23 (s, 2 H) 4.71 (d, J = 47.73 Hz, 2 H) 3.91 (s, 3 H) 2.62 (s, 3 H) 2.36-2.42 (m, 1 H) 1.69-1.81 (m, 1 H) 1.00-1.07 (m, 1 H) 0.43 (q, J = 5.15 Hz, 1 H) | N-(3-((1S,5S,6S)-3-amino-5-(fluoromethyl)-2-thia-4-azabicyclo[4.1.0]hept-3-en-5-yl)-4,5-difluorophenyl)-5-methoxy-3-methyl-2-pyridinecarboxamide |
| 83 | ¹H NMR (400 MHz, DMSO-d6) δ ppm 10.67 (s, 1 H) 8.92 (d, J = 1.17 Hz, 1 H) 8.50 (d, J = 1.37 Hz, 1 H) 7.97 (ddd, J = 12.32, 6.85, 2.74 Hz, 1 H) 7.90-7.94 (m, 1 H) 6.26 (s, 2 H) 5.16 (d, J = 2.35 Hz, 2 H) 5.09 (t, J = 5.87 Hz, 1 H) 4.58-4.82 (m, 2 H) 3.66 (t, J = 2.35 Hz, 1 H) 3.55 (dd, J = 11.74, 6.26 Hz, 1 H) 3.45 (dd, J = 11.74, 5.48 Hz, 1 H) 1.62-1.68 (m, 1 H) 1.05 (dd, J = 9.29, 5.18 Hz, 1 H) 0.58 (t, J = 5.67 Hz, 1 H) | N-(3-((1S,5S,6S)-3-amino-5-(fluoromethyl)-1-(hydroxymethyl)-2-thia-4-azabicyclo[4.1.0]hept-3-en-5-yl)-4,5-difluorophenyl)-5-(2-propyn-1-yloxy)-2-pyrazinecarboxamide |
| 84 | ¹H NMR (400 MHz, DMSO-d6) δ ppm 10.60 (s, 1 H) 8.30 (s, 1 H) 7.97 (ddd, J = 12.32, 6.75, 2.25 Hz, 1 H) 7.72-7.76 (m, 1 H) 6.23 (s, 2 H) 5.12 (d, J = 2.35 Hz, 2 H) 4.73 (d, J = 47.54 Hz, 2 H) | N-(3-((1S,5S,6S)-3-amino-5-(fluoromethyl)-2-thia-4-azabicyclo[4.1.0]hept-3-en-5-yl)-4,5-difluorophenyl)-3- |

TABLE 2'-continued

| Ex. No. | ¹H-NMR | Chemical Name |
|---|---|---|
|  | 3.62 (t, J = 2.15 Hz, 1 H) 2.76 (s, 3 H) 2.40 (td, J = 8.12, 5.28 Hz, 1 H) 1.75 (q, J = 8.28 Hz, 1 H) 1.04 (td, J = 8.07, 5.58 Hz, 1 H) 0.43 (q, J = 5.28 Hz, 1 H) | methyl-5-(2-propyn-1-yloxy)-2-pyrazinecarboxamide |
| 86 | ¹H NMR (400 MHz, DMSO-d6) δ ppm 10.67 (s, 1 H) 8.43 (d, J = 2.35 Hz, 1 H) 7.97 (ddd, J = 12.42, 6.94, 2.35 Hz, 1 H) 7.71-7.75 (m, 2 H) 7.44 (t, J = 73.20 Hz, 1 H) 6.23 (s, 2 H) 4.73 (d, J = 47.54 Hz, 2 H) 2.60 (s, 3 H) 2.37-2.44 (m, 1 H) 1.75 (q, J = 8.22 Hz, 1 H) 1.05 (td, J = 8.12, 5.48 Hz, 1 H) 0.43 (q, J = 5.35 Hz, 1 H) | N-(3-((1S,5S,6S)-3-amino-5-(fluoromethyl)-2-thia-4-azabicyclo[4.1.0]hept-3-en-5-yl)-4,5-difluorophenyl)-5-(difluoromethoxy)-3-methyl-2-pyridinecarboxamide |
| 96 | ¹H NMR (400 MHz, CHLOROFORM-d) δ ppm 9.80 (s, 1 H) 8.54 (d, J = 2.15 Hz, 1 H) 8.23 (d, J = 8.22 Hz, 1 H) 8.05 (ddd, J = 11.59, 6.80, 2.54 Hz, 1 H) 7.89 (dd, J = 8.41, 2.15 Hz, 1 H) 7.44-7.49 (m, 1 H) 4.56-4.91 (m, 2 H) 3.60 (d, J = 10.56 Hz, 1 H) 3.50 (d, J = 10.76 Hz, 1 H) 3.41 (s, 3 H) 2.03-2.09 (m, 1 H) 1.23-1.30 (m, 4 H) 1.11 (dd, J = 9.49, 6.16 Hz, 1 H) | N-(3-((1R,5S,6R)-3-amino-5-(fluoromethyl)-1-(methoxymethyl)-2-thia-4-azabicyclo[4.1.0]hept-3-en-5-yl)-4,5-difluorophenyl)-5-chloro-2-pyridinecarboxamide |
| 31 | ¹H NMR (400 MHz, DMSO-d6) δ ppm 10.79 (s, 1 H) 8.79 (d, J = 1.76 Hz, 1 H) 8.21 (dd, J = 8.41, 2.35 Hz, 1 H) 8.16 (d, J = 8.61 Hz, 1 H) 7.98 (ddd, J = 12.23, 6.75, 2.54 Hz, 1 H) 7.89-7.93 (m, 1 H) 6.26 (s, 2 H) 5.08 (t, J = 5.97 Hz, 1 H) 4.57-4.81 (m, 2 H) 3.54 (dd, J = 11.74, 6.26 Hz, 1 H) 3.44 (dd, J = 11.74, 5.67 Hz, 1 H) 1.61-1.67 (m, 1 H) 1.04 (dd, J = 9.29, 5.18 Hz, 1 H) 0.57 (t, J = 5.77 Hz, 1 H) | N-(3-((1S,5S,6S)-3-amino-5-(fluoromethyl)-1-(hydroxymethyl)-2-thia-4-azabicyclo[4.1.0]hept-3-en-5-yl)-4,5-difluorophenyl)-5-chloro-2-pyridinecarboxamide |
| 37 | ¹H NMR (400 MHz, CHLOROFORM-d) δ ppm 9.80 (br s, 1H), 8.54 (d, J = 2.15 Hz, 1H), 8.23 (d, J = 8.41 Hz, 1H), 7.94-8.01 (m, 1H), 7.87 (dd, J = 8.41, 2.35 Hz, 1H), 7.71 (d, J = 4.30 Hz, 1 H), 7.09 (dd, J = 11.44, 8.90 Hz, 1H), 4.91 (dd, J = 46.95, 8.41 Hz, 1H), 4.77 (s br, 2H), 4.67 (dd, J = 47.54, 8.80 Hz, 1H), 3.76 (d, J = 11.93 Hz, 1H), 3.60 (d, J = 11.74 Hz, 1H), 1.85 (t, J = 9.00 Hz, 1H), 1.77 (s br, 1H), 1.08 (dd, J = 9.59, 5.87 Hz, 1H), 0.71 (t, J = 6.26 Hz, 1H) | N-(3-((1S,5S,6S)-3-amino-5-(fluoromethyl)-1-(hydroxymethyl)-2-thia-4-azabicyclo[4.1.0]hept-3-en-5-yl)-4-fluorophenyl)-5-chloro-2-pyridinecarboxamide |
| 43 | ¹H NMR (400 MHz, DMSO-d6) δ ppm 10.79 (s, 1 H) 8.79 (d, J = 1.96 Hz, 1 H) 8.21 (dd, J = 8.41, 2.35 Hz, 1 H) 8.16 (d, J = 8.22 Hz, 1 H) 7.99 (ddd, J = 12.37, 6.80, 2.54 Hz, 1 H) 7.88-7.93 (m, 1 H) 6.30 (s, 2 H) 4.60-4.78 (m, 2 H) 3.56 (d, J = 10.76 Hz, 1 H) 3.35 (d, J = 10.95 Hz, 1 H) 3.30 (s, 3 H) 1.63-1.69 (m, 1 H) 1.10 (dd, J = 9.49, 5.18 Hz, 1 H) 0.64 (t, J = 5.87 Hz, 1 H) | N-(3-((1S,5S,6S)-3-amino-5-(fluoromethyl)-1-(methoxymethyl)-2-thia-4-azabicyclo[4.1.0]hept-3-en-5-yl)-4,5-difluorophenyl)-5-chloro-2-pyridinecarboxamide |
| 44 | ¹H NMR (400 MHz, DMSO-d6) δ ppm 10.67 (s, 1H), 8.98 (d, J = 1.37 Hz, 1H), 8.40 (d, J = 1.96 Hz, 1H), 7.90 (dd, J = 7.04, 2.74 Hz, 1H), 7.81-7.87 (m, 1H), 7.19 (dd, J = 11.93, 8.80 Hz, 1H), 6.22 (s, 2H), 5.06 (t, J = 5.87 Hz, 1H), 4.77 (dd, J = 26.41, 8.61 Hz, 1H), 4.65 (dd, J = 26.41, 9.19 Hz, 1H), 3.54 (dd, J = 11.54, 6.26 Hz, 1H), 3.43 (dd, J = 11.74, 5.67 Hz, 1H), 2.56 (s, 3H), 1.64 (t, J = 7.82 Hz, 1H), 0.98 (dd, J = 9.49, 4.99 Hz, 1H), 0.50 (t, J = 5.67 Hz, 1H) | N-(3-((1S,5S,6S)-3-amino-5-(fluoromethyl)-1-(hydroxymethyl)-2-thia-4-azabicyclo[4.1.0]hept-3-en-5-yl)-4-fluorophenyl)-5-cyano-3-methyl-2-pyridinecarboxamide |
| 673 | ¹H NMR (400 MHz, CHLOROFORM-d) δ ppm 0.84 (t, J = 6.46 Hz, 1 H) 1.04-1.13 (m, 1 H) 1.75 (s, 3 H) 2.00-2.08 (m, 1 H) 2.55 (t, J = 2.45 Hz, 1 H) 3.23-3.64 (m, 3 H) 3.70 (q, J = 6.39 Hz, 1 H) 5.08 (d, J = 2.35 Hz, 2 H) 7.06 (dd, J = 11.54, 8.80 Hz, 1 H) 7.63 (dd, J = 6.85, 2.74 Hz, 1 H) 7.75-7.86 (m, 1 H) 8.20 (d, J = 1.17 Hz, 1 H) 9.01 (d, J = 1.17 Hz, 1 H) 9.48 (s, 1 H). | N-(3-((1S,5S,6S)-3-amino-5-methyl-1-((1R)-2,2,2-trifluoro-1-hydroxyethyl)-2-thia-4-azabicyclo[4.1.0]hept-3-en-5-yl)-4-fluorophenyl)-5-(2-propyn-1-yloxy)-2-pyrazinecarboxamide |
| 674 | ¹H NMR (400 MHz, CHLOROFORM-d) δ ppm 0.91 (t, J = 6.65 Hz, 1 H) 1.16-1.25 (m, 1 H) 1.74-1.88 (m, 4 H) 2.55 (t, J = 2.35 Hz, 1 H) 3.49 (q, J = 6.78 Hz, 1 H) 3.58-3.83 (m, 3 H) 5.08 (d, J = 2.35 Hz, 2 H) 7.05 (dd, J = 11.54, 8.80 Hz, 1 H) 7.59 (dd, J = 6.85, 2.74 Hz, 1 H) 7.82 (dt, J = 8.46, 3.50 Hz, 1 H) 8.20 (d, J = 1.17 Hz, 1 H) 9.01 (d, J = 1.17 Hz, 1 H) 9.46 (s, 1 H). | N-(3-((1S,5S,6S)-3-amino-5-methyl-1-((1S)-2,2,2-trifluoro-1-hydroxyethyl)-2-thia-4-azabicyclo[4.1.0]hept-3-en-5-yl)-4-fluorophenyl)-5-(2-propyn-1-yloxy)-2-pyrazinecarboxamide |
| 675 | ¹H NMR (400 MHz, CHLOROFORM-d) δ ppm 0.78-0.83 (m, 1 H) 0.89 (dd, J = 9.39, 5.87 Hz, 1 H) 1.72 (s, 3 H) 1.77-1.85 (m, 1 H) 2.81 (s, 3 H) 3.35 (d, J = 10.76 Hz, 1 H) 3.41 (s, 3 H) 3.67 (d, J = 10.76 Hz, 1 H) 4.47 (q, J = 7.89 Hz, 2 H) 7.15 (d, J = 2.35 Hz, 1 H) 7.30-7.36 (m, 1 H) | N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-(2,2,2-trifluoroethoxy)-2- |

TABLE 2'-continued

| Ex. No. | ¹H-NMR | Chemical Name |
|---|---|---|
| | 8.09 (ddd, J = 12.03, 6.94, 2.74 Hz, 1 H) 8.18 (d, J = 2.54 Hz, 1 H) 10.05 (s, 1 H). | pyridinecarboxamide |
| 678 | ¹H NMR (400 MHz, CHLOROFORM-d) δ ppm 0.82-0.90 (m, 1 H) 1.00 (dd, J = 9.59, 6.06 Hz, 1 H) 1.73 (s, 3 H) 1.87-1.95 (m, 1 H) 2.81 (s, 3 H) 4.19-4.90 (m, 6 H) 7.15 (d, J = 2.54 Hz, 1 H) 7.30-7.36 (m, 1 H) 8.05 (ddd, J = 11.93, 6.85, 2.74 Hz, 1 H) 8.18 (d, J = 2.74 Hz, 1 H) 10.04 (s, 1 H). | N-(3-((1S,5S,6S)-3-amino-1-(fluoromethyl)-5-methyl-2-thia-4-azabicyclo[4.1.0]hept-3-en-5-yl)-4,5-difluorophenyl)-3-methyl-5-(2,2,2-trifluoroethoxy)-2-pyridinecarboxamide |
| 679 | ¹H NMR (400 MHz, CHLOROFORM-d) δ ppm 0.80-0.88 (m, 1 H) 1.36 (dd, J = 9.98, 6.26 Hz, 1 H) 1.79 (s, 3 H) 1.98 (dd, J = 9.68, 7.34 Hz, 1 H) 2.80 (s, 3 H) 4.47 (q, J = 7.96 Hz, 2 H) 5.49-5.86 (m, 1 H) 7.11-7.20 (m, 2 H) 8.02 (ddd, J = 11.93, 6.85, 2.74 Hz, 1 H) 8.14 (d, J = 2.74 Hz, 1 H) 9.97 (s, 1 H). | N-(3-((1S,5S,6S)-3-amino-1-(difluoromethyl)-5-methyl-2-thia-4-azabicyclo[4.1.0]hept-3-en-5-yl)-4,5-difluorophenyl)-3-methyl-5-(2,2,2-trifluoroethoxy)-2-pyridinecarboxamide |
| 715 | ¹H NMR (CHLOROFORM-d) δ: 10.02 (s, 1H), 8.71 (s, 1H), 7.99-8.07 (m, 1H), 7.93 (s, 1H), 7.62 (dd, J = 6.6, 2.4 Hz, 1H), 7.10 (dd, J = 11.4, 8.9 Hz, 1H), 4.64-4.96 (m, 2H), 3.71 (d, J = 10.8 Hz, 1H), 3.50-3.59 (m, 2H), 3.38 (d, J = 10.6 Hz, 1H), 2.86 (s, 3H), 1.83 (d, J = 7.6 Hz, 1H), 1.22 (t, J = 7.0 Hz, 3H), 1.12 (dd, J = 9.4, 5.9 Hz, 1H), 0.78 (t, J = 6.2 Hz, 1H) | N-(3-((1S,5S,6S)-3-amino-1-(ethoxymethyl)-5-(fluoromethyl)-2-thia-4-azabicyclo[4.1.0]hept-3-en-5-yl)-4-fluorophenyl)-5-cyano-3-methyl-2-pyridinecarboxamide |
| 716 | ¹H NMR (CHLOROFORM-d) δ: 10.02 (s, 1H), 8.71 (s, 1H), 7.98-8.08 (m, 1H), 7.93 (s, 1H), 7.63 (dd, J = 6.7, 2.7 Hz, 1H), 7.10 (dd, J = 11.5, 9.0 Hz, 1H), 4.64-4.96 (m, 2H), 3.64 (d, J = 10.6 Hz, 1H), 3.40 (s, 3H), 3.36 (d, J = 10.6 Hz, 1H), 2.86 (s, 3H), 1.82 (t, J = 8.1 Hz, 1H), 1.09 (dd, J = 9.7, 5.8 Hz, 1H), 0.76 (t, J = 6.3 Hz, 1H) | N-(3-((1S,5S,6S)-3-amino-5-(fluoromethyl)-1-(methoxymethyl)-2-thia-4-azabicyclo[4.1.0]hept-3-en-5-yl)-4-fluorophenyl)-5-cyano-3-methyl-2-pyridinecarboxamide |
| 718 | ¹H NMR (CHLOROFORM-d) δ: 9.81 (s, 1H), 8.55 (d, J = 2.2 Hz, 1H), 8.23 (d, J = 8.2 Hz, 1H), 7.92-7.99 (m, 1H), 7.88 (dd, J = 8.3, 2.2 Hz, 1H), 7.70 (dd, J = 6.7, 2.6 Hz, 1H), 7.10 (dd, J = 11.3, 8.8 Hz, 1H), 4.54-5.03 (m, 3H), 2.76 (s, 2H), 1.88-2.00 (m, 1H), 1.22 (dd, J = 9.8, 6.5 Hz, 1H), 0.82 (t, J = 6.7 Hz, 1H) | N-(3-((1R,5S,6S)-3-amino-1-(cyanomethyl)-5-(fluoromethyl)-2-thia-4-azabicyclo[4.1.0]hept-3-en-5-yl)-4-fluorophenyl)-5-chloro-2-pyridinecarboxamide |
| 723 | ¹H NMR (CHLOROFORM-d) δ: 9.84 (s, 1H), 8.56 (d, J = 2.0 Hz, 1H), 8.23 (d, J = 8.4 Hz, 1H), 7.93-8.01 (m, 1H), 7.88 (dd, J = 8.4, 2.3 Hz, 1H), 7.66 (dd, J = 6.7, 2.5 Hz, 1H), 7.12 (dd, J = 11.2, 8.9 Hz, 1H), 4.60-5.10 (m, 2H), 2.53-2.66 (m, 2H), 1.91-2.00 (m, 1H), 1.84 (dd, J = 15.0, 6.6 Hz, 2H), 1.12-1.20 (m, 1H), 0.81 (t, J = 6.6 Hz, 1H) | N-(3-((1S,5S,6S)-3-amino-1-(2-cyanoethyl)-5-(fluoromethyl)-2-thia-4-azabicyclo[4.1.0]hept-3-en-5-yl)-4-fluorophenyl)-5-chloro-2-pyridinecarboxamide |
| 725 | ¹H NMR (400 MHz, CHLOROFORM-d) δ ppm 9.79 (1 H, s) 8.54 (1 H, d, J = 2.35 Hz) 8.22 (1 H, d, J = 8.41 Hz) 7.92-7.99 (1 H, m) 7.87 (1 H, dd, J = 8.41, 2.35 Hz) 7.64 (1 H, dd, J = 6.65, 2.74 Hz) 7.47 (1 H, s) 7.10 (1 H, dd, J = 11.44, 8.90 Hz) 4.58-4.92 (2 H, m) 4.36-4.52 (2 H, m) 2.39 (3 H, s) 2.09-2.16 (1 H, m) 1.36 (1 H, dd, J = 9.78, 6.26 Hz) 1.26 (1 H, s) 0.85 (1 H, t, J = 6.65 Hz). MS (ESI, positive ion) m/z: 504 (M + H) | N-(3-((1S,5S,6S)-3-amino-5-(fluoromethyl)-1-((5-methyl-1H-1,2,3-triazol-1-yl)methyl)-2-thia-4-azabicyclo[4.1.0]hept-3-en-5-yl)-4-fluorophenyl)-5-chloro-2-pyridinecarboxamide |

Method C: SNAr in iPrOH

Example 54

8-((3-((1S,5S,6S)-3-amino-1-(hydroxymethyl)-5-methyl-2-thia-4-azabicyclo[4.1.0]hept-3-en-5-yl)-4,5-difluorophenyl)amino)-1,7-naphthyridine-3-carbonitrile

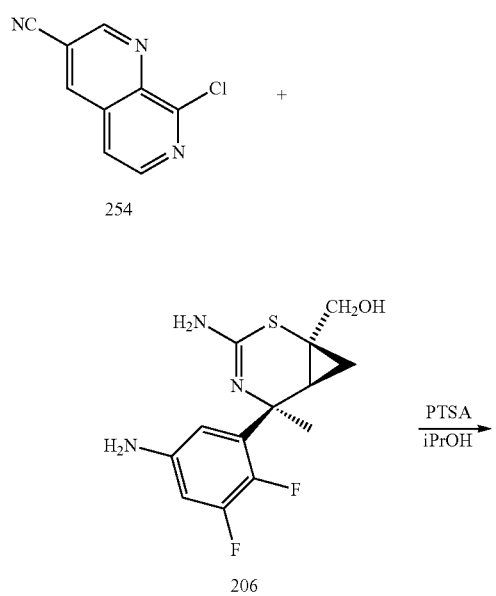

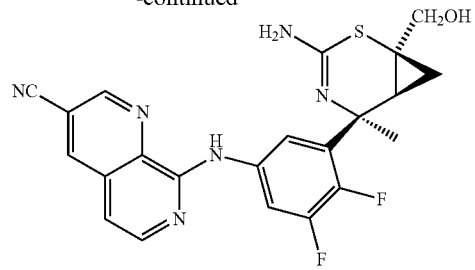

Example 54

A mixture of ((1S,5S,6S)-3-amino-5-(5-amino-2,3-difluorophenyl)-5-methyl-2-thia-4-azabicyclo[4.1.0]hept-3-en-1-yl)methanol (Intermediate 206, 75 mg, 0.25 mmol), 8-chloro-1,7-naphthyridine-3-carbonitrile (Intermediate 254, 52 mg, 0.27 mmol) and p-toluenesulfonic acid monohydrate (52 mg, 0.27 mmol) in isopropyl alcohol (2.0 mL) was heated to 75° C. in an oil bath for 1 h. The reaction mixture was cooled to RT and partitioned between $CHCl_3$/iPrOH=9/1 (40 mL) and sat. $NaHCO_3$ (10 mL). The organic layer was dried over $MgSO_4$, filtered, and then concentrated under reduced pressure to afford a yellow solid. It was purified by silica gel chromatography (12 g) eluting with 35-75% EtOAc in DCM to afford 8-((3-((1S,5S,6S)-3-amino-1-(hydroxymethyl)-5-methyl-2-thia-4-azabicyclo[4.1.0]hept-3-en-5-yl)-4,5-difluorophenyl)amino)-1,7-naphthyridine-3-carbonitrile (Example 54, 97 mg, 0.21 mmol, 86% yield) as yellow crystalline solid. MS m/z=453.2 $[M+H]^+$. $^1H$ NMR (400 MHz, DMSO-$d_6$) δ 9.76 (br., 1H), 9.24 (d, J=1.76 Hz, 1H), 9.01 (d, J=1.76 Hz, 1H), 8.30 (m, 2H), 7.93 (br., 1H), 7.28 (d, J=5.87 Hz, 1H), 6.00 (br., 2H), 5.05 (t, J=5.58 Hz, 1H), 3.55 (m, 1H), 3.45 (m, 1H), 1.68 (m, 1H), 1.63 (s, 3H), 0.89 (m., 1H), 0.60 (m, 1H). $^{19}F$ NMR (377 MHz, DMSO-$d_6$) δ −138.70 (d, J=22.59 Hz, 1F), −146.08 (d, J=22.59 Hz, 1F).

Using procedures analogous or similar to the general SNAr Method C described above, the appropriate aniline and ArX (X=Cl/Br) intermediates were reacted to provide the 195 examples listed in Table 3 and Table 3'.

TABLE 3

| Ex. No. | Chemical Structure | Observed [M + H]⁺ |
|---|---|---|
| 21 | 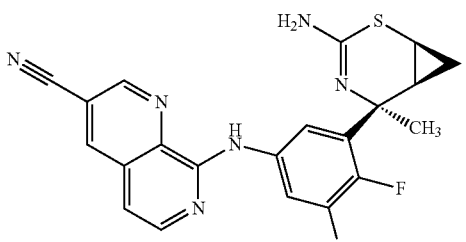 | 423.0 |
| 22 | 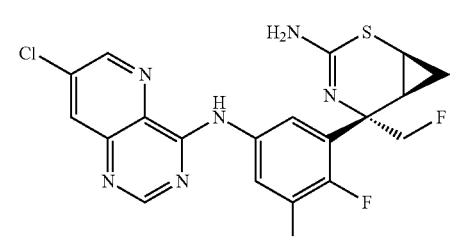 | 451.0 |

TABLE 3-continued
| Ex. No. | Chemical Structure | Observed [M + H]+ |
|---|---|---|
| 24 | 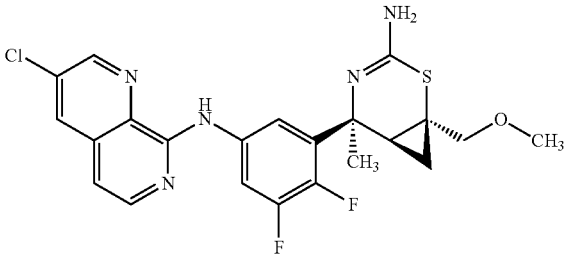 [SMILES: COC[C@]12C[C@H]1[C@@](C)(c1cc(Nc3nccc4cc(Cl)cnc34)cc(F)c1F)N=C(N)S2] | 476.1 |
| 25 | 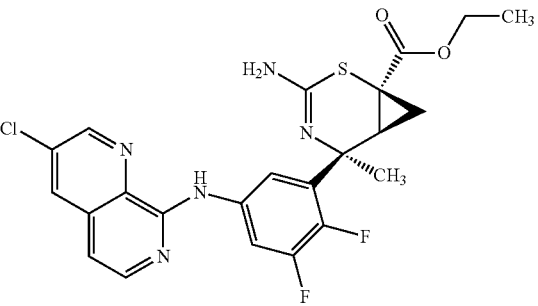 [SMILES: CCOC(=O)[C@]12C[C@H]1[C@@](C)(c1cc(Nc3nccc4cc(Cl)cnc34)cc(F)c1F)N=C(N)S2] | 504.0 |
| 26 | 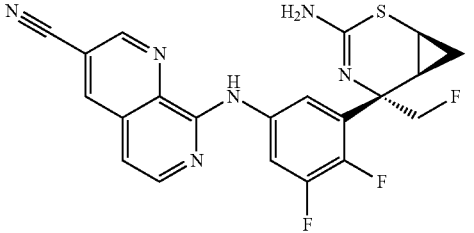 [SMILES: N#Cc1cnc2c(Nc3cc(F)c(F)c([C@@]4(CF)N=C(N)S[C@H]5C[C@H]54)c3)nccc2c1] | 441.0 |
| 27 | 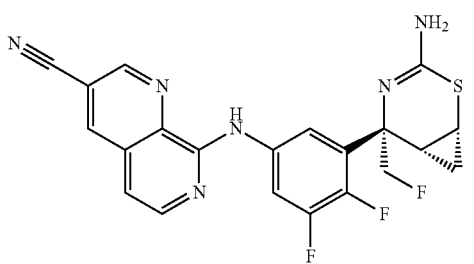 [SMILES: N#Cc1cnc2c(Nc3cc(F)c(F)c([C@@]4(CF)N=C(N)S[C@@H]5C[C@@H]54)c3)nccc2c1] | 441.0 |
| 32 | 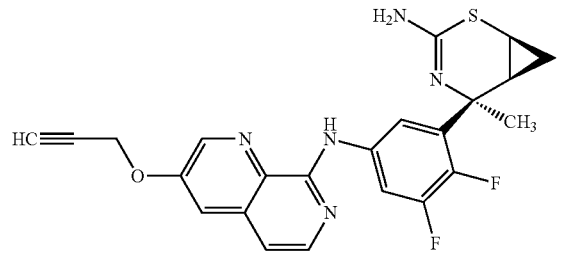 [SMILES: C#CCOc1cnc2c(Nc3cc(F)c(F)c([C@@]4(C)N=C(N)S[C@H]5C[C@H]54)c3)nccc2c1] | 452.0 |

TABLE 3-continued

| Ex. No. | Chemical Structure | Observed [M + H]+ |
|---|---|---|
| 33 | 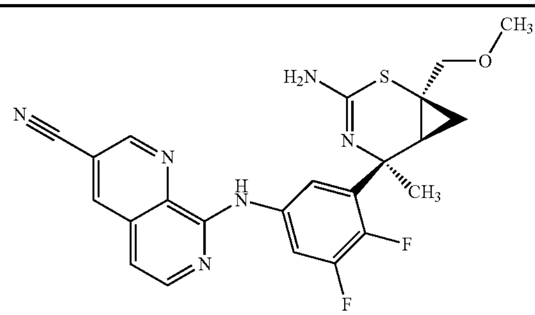 | 467.1 |
| 34 | 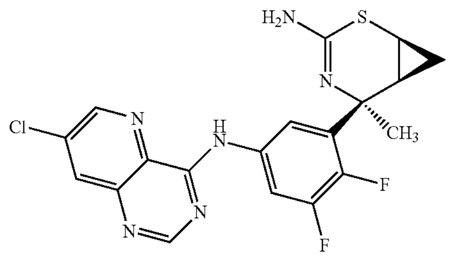 [SMILES: C[C@]1(c2cc(Nc3ncnc4cc(Cl)cnc34)cc(F)c2F)N=C(N)S[C@H]2C[C@H]21] | 433.0 |
| 35 | 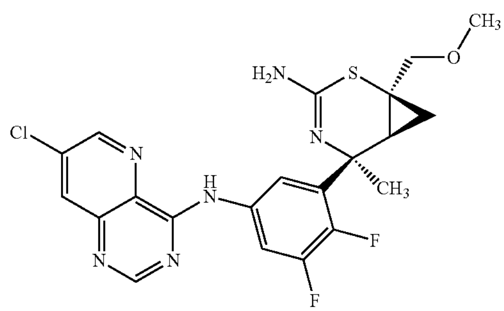 [SMILES: COC[C@]12C[C@H]1[C@@](C)(c1cc(Nc3ncnc4cc(Cl)cnc34)cc(F)c1F)N=C(N)S2] | 477.0 |
| 36 | 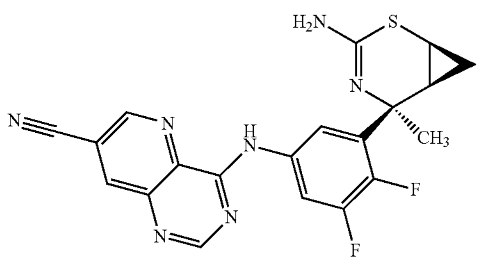 | 424.1 |
| 38 | 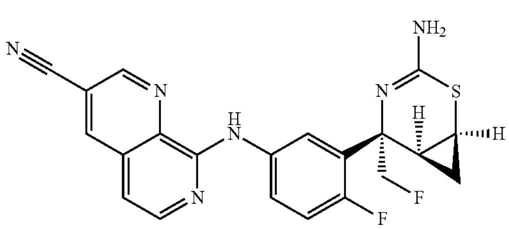 | 423.0 |
| 39 | 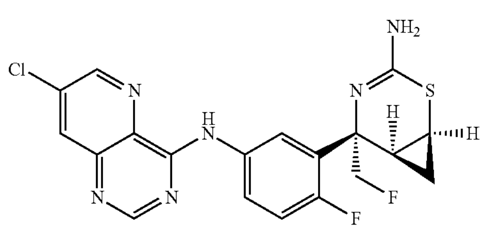 | 433.1 |

TABLE 3-continued

| Ex. No. | Chemical Structure | Observed [M + H]+ |
|---|---|---|
| 45 | 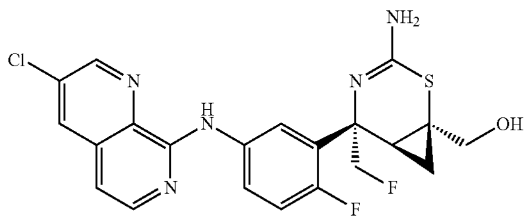 [SMILES: NC1=N[C@](CF)(c2cc(Nc3nccc4cc(Cl)cnc34)ccc2F)[C@@H]2C[C@]2(CO)S1] | 462.0 |
| 46 | 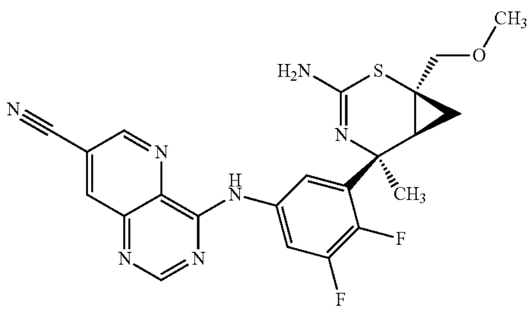 [SMILES: COC[C@]12C[C@H]1[C@@](C)(c1cc(Nc3ncnc4cc(C#N)cnc34)cc(F)c1F)N=C(N)S2] | 468.0 |
| 47 | 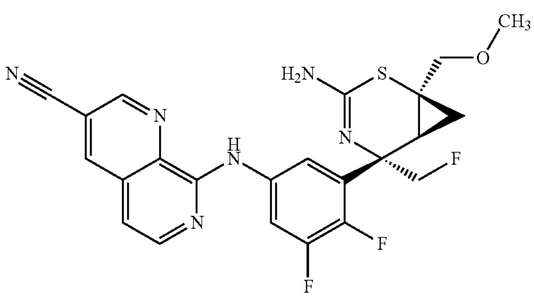 [SMILES: COC[C@]12C[C@H]1[C@@](CF)(c1cc(Nc3nccc4cc(C#N)cnc34)cc(F)c1F)N=C(N)S2] | 485.1 |
| 48 | 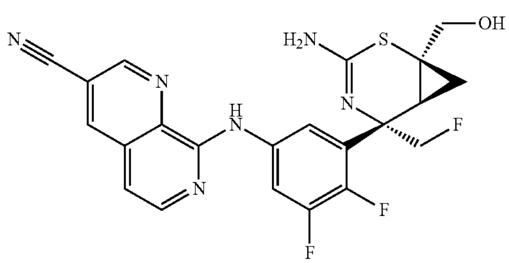 [SMILES: N#Cc1cnc2c(Nc3cc(F)c(F)c([C@@]4(CF)N=C(N)S[C@@]5(CO)C[C@H]54)c3)nccc2c1] | 471.0 |
| 49 | 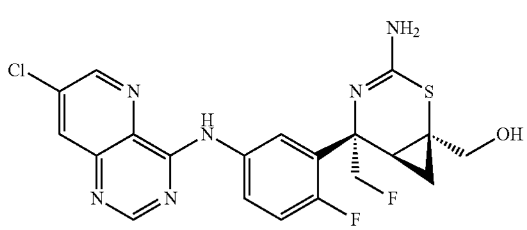 | 463.1 |
| 50 | 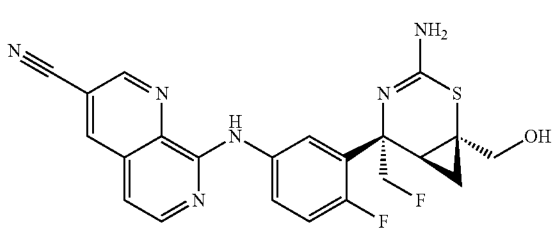 [SMILES: N#Cc1cnc2c(Nc3ccc(F)c([C@@]4(CF)N=C(N)S[C@@]5(CO)C[C@H]54)c3)nccc2c1] | 453.0 |

TABLE 3-continued
| Ex. No. | Chemical Structure | Observed [M + H]+ |
|---|---|---|
| 51 | 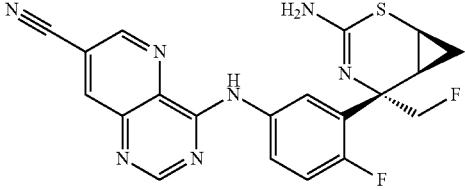 [SMILES: N#Cc1cnc2c(Nc3ccc(F)c([C@@]4(CF)N=C(N)S[C@H]5C[C@H]54)c3)ncnc2c1] | 424.1 |
| 52 | 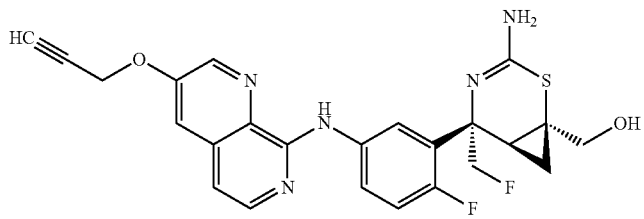 [SMILES: C#CCOc1cnc2c(Nc3ccc(F)c([C@@]4(CF)N=C(N)S[C@@]5(CO)C[C@H]54)c3)nccc2c1] | 482.1 |
| 55 | 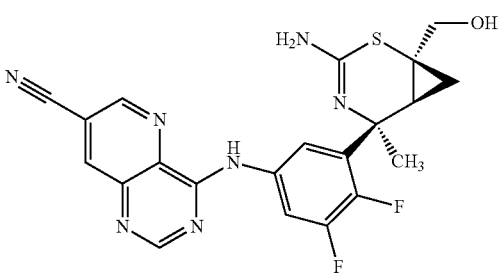 [SMILES: C[C@]1(c2cc(Nc3ncnc4cc(C#N)cnc34)cc(F)c2F)N=C(N)S[C@@]2(CO)C[C@H]21] | 454.2 |
| 56 | 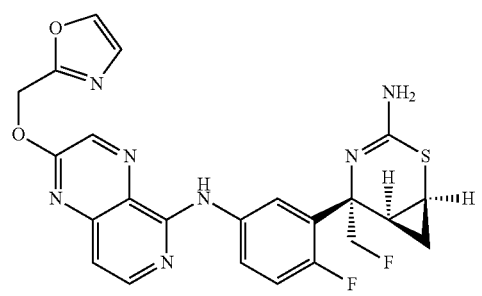 | 496.1 |
| 57 | 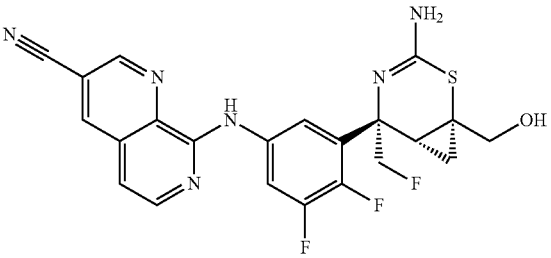 [SMILES: N#Cc1cnc2c(Nc3cc(F)c(F)c([C@@]4(CF)N=C(N)S[C@]5(CO)C[C@@H]54)c3)nccc2c1] | 471.0 |
| 58 | 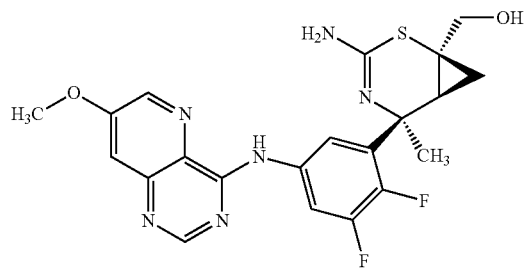 [SMILES: COc1cnc2c(Nc3cc(F)c(F)c([C@@]4(C)N=C(N)S[C@@]5(CO)C[C@H]54)c3)ncnc2c1] | 459.0 |

TABLE 3-continued

| Ex. No. | Chemical Structure | Observed [M + H]+ |
|---|---|---|
| 65 | 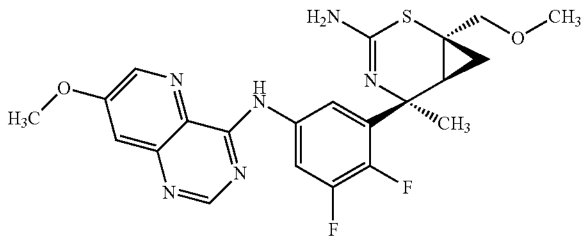 | 473.1 |
| 66 | 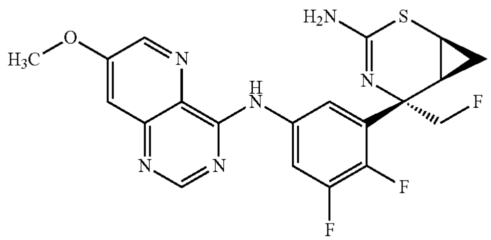 [SMILES: COc1cnc2c(Nc3cc(F)c(F)c([C@@]4(CF)N=C(N)S[C@H]5C[C@H]54)c3)ncnc2c1] | 447.0 |
| 67 | 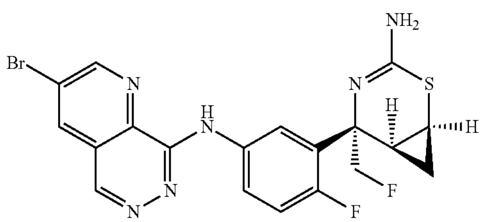 | 477.0<br>479.0 |
| 73 | 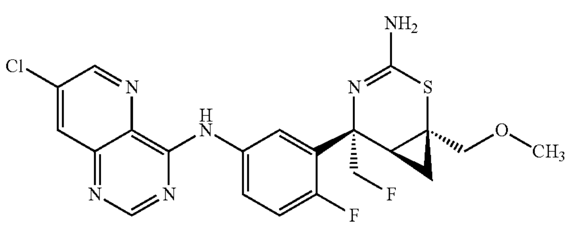 [SMILES: COC[C@]12C[C@H]1[C@@](CF)(c1cc(Nc3ncnc4cc(Cl)cnc34)ccc1F)N=C(N)S2] | 477.1 |
| 80 | 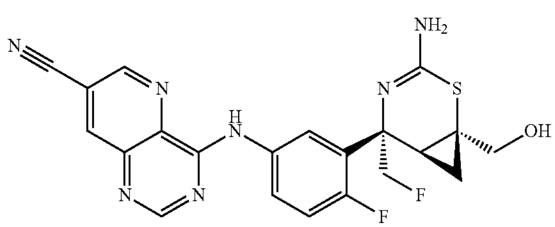 [SMILES: N#Cc1cnc2c(Nc3ccc(F)c([C@@]4(CF)N=C(N)S[C@@]5(CO)C[C@H]54)c3)ncnc2c1] | 454.1 |
| 82 | 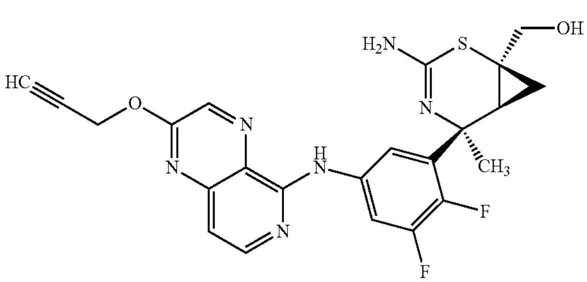 [SMILES: C#CCOc1cnc2c(Nc3cc(F)c(F)c([C@@]4(C)N=C(N)S[C@@]5(CO)C[C@H]54)c3)nccc2n1] | 483.0 |

TABLE 3-continued

| Ex. No. | Chemical Structure | Observed [M + H]+ |
|---|---|---|
| 87 | 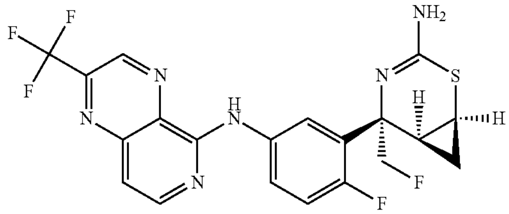 | 467.1 |
| 88 | 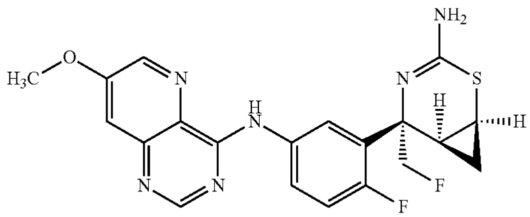 | 429.1 |
| 89 | 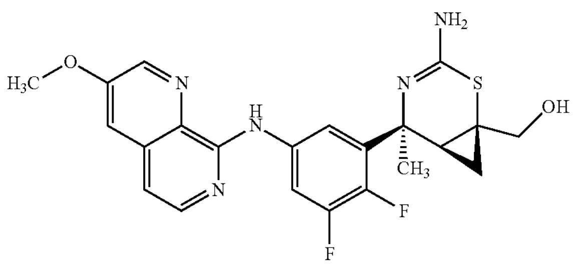 [SMILES: COc1cnc2c(Nc3cc(F)c(F)c([C@@]4(C)N=C(N)S[C@@]5(CO)C[C@H]54)c3)nccc2c1] | 458.1 |
| 90 | 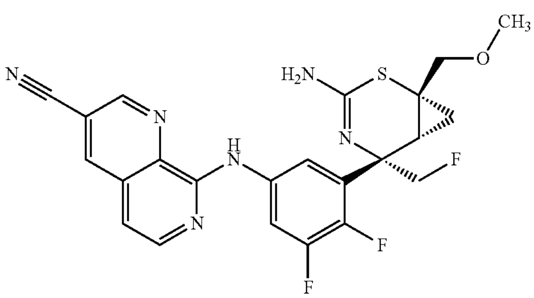 [SMILES: COC[C@@]12C[C@@H]1[C@@](CF)(c1cc(Nc3nccc4cc(C#N)cnc34)cc(F)c1F)N=C(N)S2] | 485.1 |
| 91 | 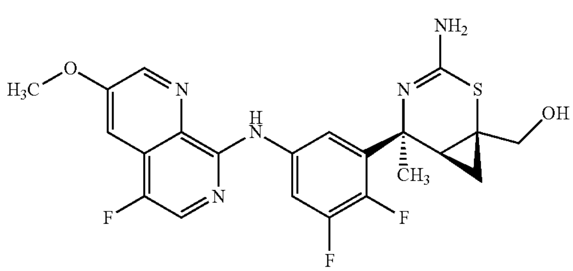 [SMILES: COc1cnc2c(Nc3cc(F)c(F)c([C@@]4(C)N=C(N)S[C@@]5(CO)C[C@H]54)c3)ncc(F)c2c1] | 476.1 |
| 92 | 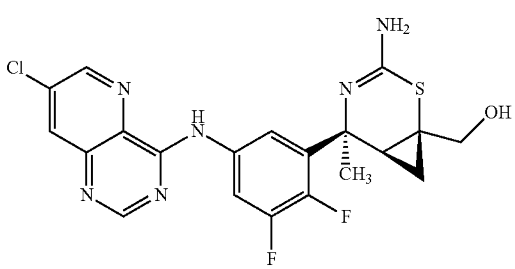 [SMILES: C[C@]1(c2cc(Nc3ncnc4cc(Cl)cnc34)cc(F)c2F)N=C(N)S[C@@]2(CO)C[C@H]21] | 463.1 |

TABLE 3-continued

| Ex. No. | Chemical Structure | Observed [M + H]+ |
|---|---|---|
| 95 | 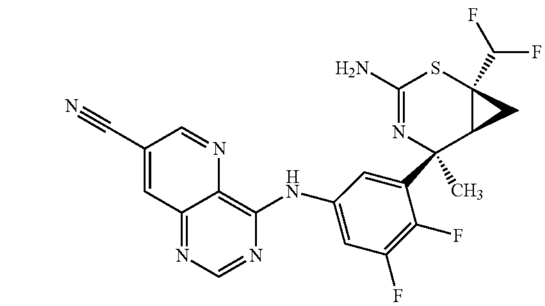 [SMILES: C[C@]1(c2cc(Nc3ncnc4cc(C#N)cnc34)cc(F)c2F)N=C(N)S[C@@]2(C(F)F)C[C@@H]12] | 474.0 |
| 101 | 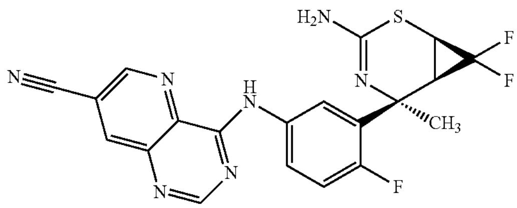 [SMILES: C[C@]1(c2cc(Nc3ncnc4cc(C#N)cnc34)ccc2F)N=C(N)S[C@@H]2[C@H]1C2(F)F] | 441.9 |
| 601 | 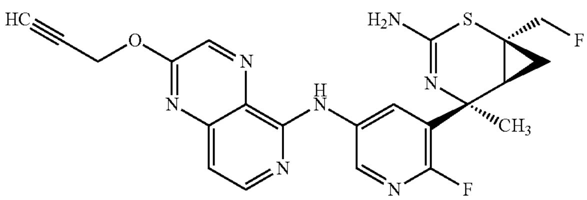 [SMILES: C#CCOc1cnc2c(Nc3cnc(F)c([C@@]4(C)N=C(N)S[C@@]5(CF)C[C@H]54)c3)nccc2n1] | 468 |
| 602 | 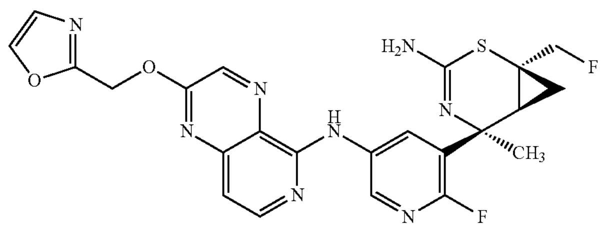 [SMILES: C[C@]1(c2cc(Nc3nccc4nc(OCc5ncco5)cnc34)cnc2F)N=C(N)S[C@@]2(CF)C[C@H]21] | 511 |
| 604 | 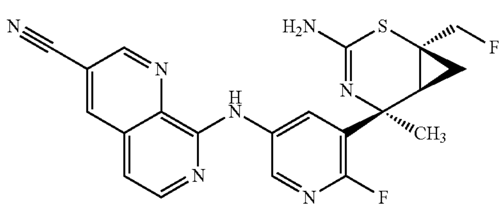 [SMILES: C[C@]1(c2cc(Nc3nccc4cc(C#N)cnc34)cnc2F)N=C(N)S[C@@]2(CF)C[C@H]21] | 437.9 |
| 605 | 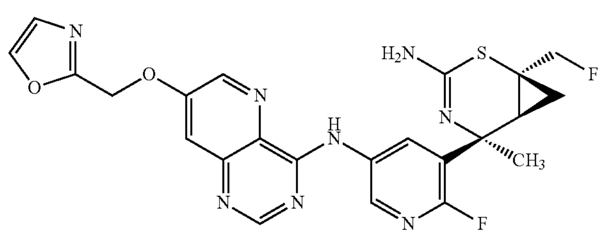 [SMILES: C[C@]1(c2cc(Nc3ncnc4cc(OCc5ncco5)cnc34)cnc2F)N=C(N)S[C@@]2(CF)C[C@H]21] | 510.9 |

TABLE 3-continued

| Ex. No. | Chemical Structure | Observed [M + H]+ |
|---|---|---|
| 608 | 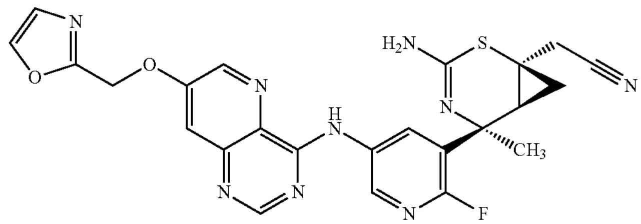 [SMILES: C[C@]1(c2cc(Nc3ncnc4cc(OCc5ncco5)cnc34)cnc2F)N=C(N)S[C@@]2(CC#N)C[C@H]21] | 518 |
| 611 | 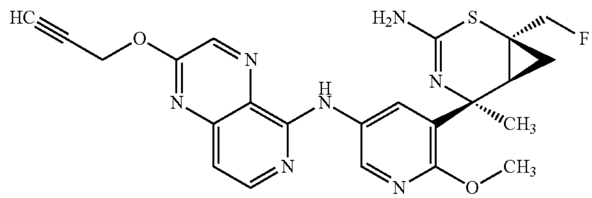 | 480.2 |
| 613 | 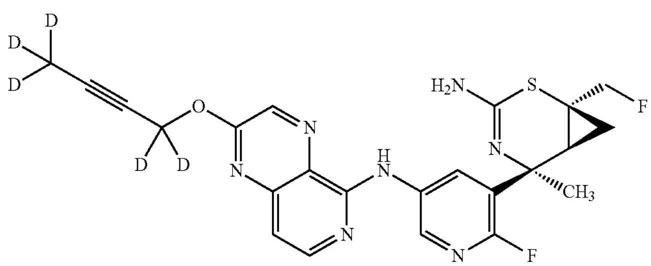 [SMILES: [2H]C([2H])([2H])C#CC([2H])([2H])Oc1cnc2c(Nc3cnc(F)c([C@@]4(C)N=C(N)S[C@@]5(CF)C[C@H]54)c3)nccc2n1] | 487.1 |
| 625 | 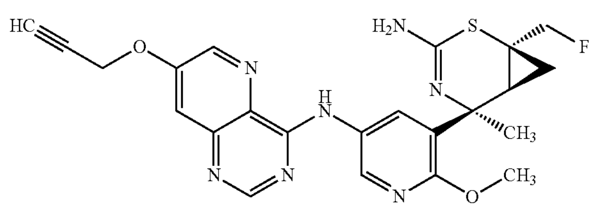 [SMILES: C#CCOc1cnc2c(Nc3cnc(OC)c([C@@]4(C)N=C(N)S[C@@]5(CF)C[C@H]54)c3)ncnc2c1] | 480.1 |
| 626 | 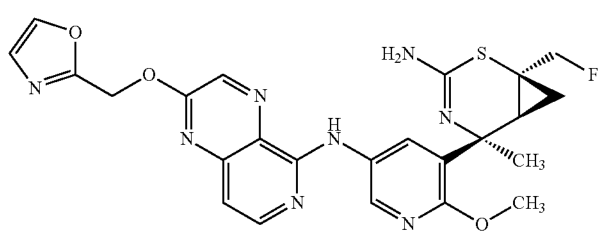 [SMILES: COc1ncc(Nc2nccc3nc(OCc4ncco4)cnc23)cc1[C@@]1(C)N=C(N)S[C@@]2(CF)C[C@H]21] | 523.1 |
| 627 | 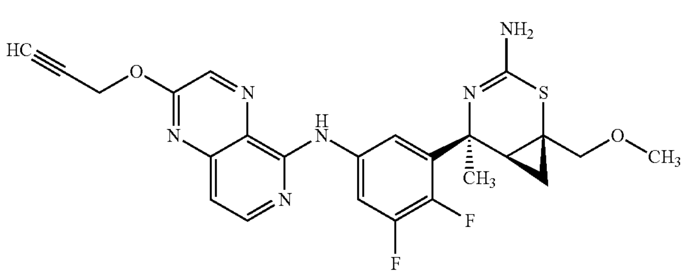 [SMILES: C#CCOc1cnc2c(Nc3cc(F)c(F)c([C@@]4(C)N=C(N)S[C@@]5(COC)C[C@H]54)c3)nccc2n1] | 497.1 |

TABLE 3-continued

| Ex. No. | Chemical Structure | Observed [M + H]+ |
|---|---|---|
| 628 | 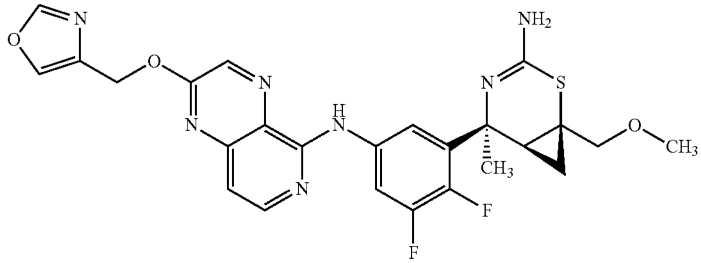 [SMILES: COC[C@]12C[C@H]1[C@@](C)(c1cc(Nc3nccc4nc(OCc5cocn5)cnc34)cc(F)c1F)N=C(N)S2] | 540 |
| 629 | 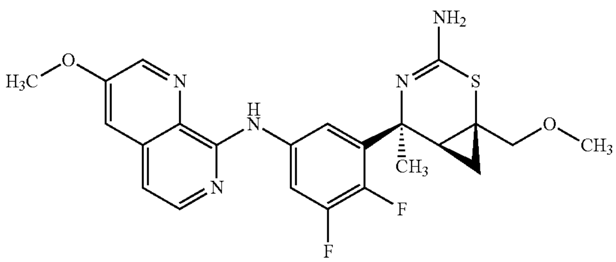 | 472.2 |
| 630 | 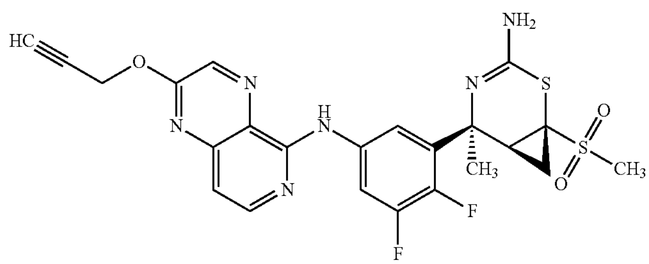 [SMILES: C#CCOc1cnc2c(Nc3cc(F)c(F)c([C@@]4(C)N=C(N)S[C@@]5(S(C)(=O)=O)C[C@H]54)c3)nccc2n1] | 531 |
| 631 | 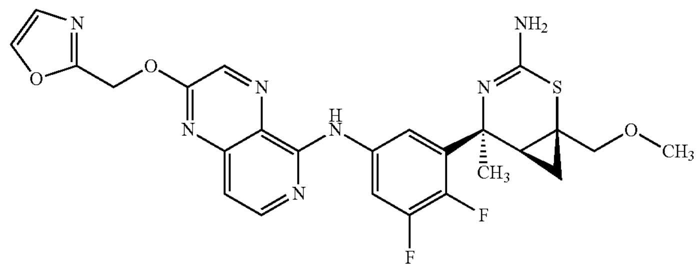 | 540.2 |
| 635 | 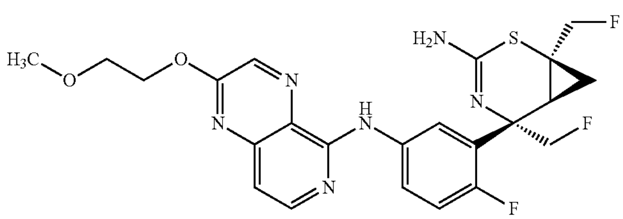 [SMILES: COCCOc1cnc2c(Nc3ccc(F)c([C@@]4(CF)N=C(N)S[C@@]5(CF)C[C@H]54)c3)nccc2n1] | 505.2 |
| 653 | 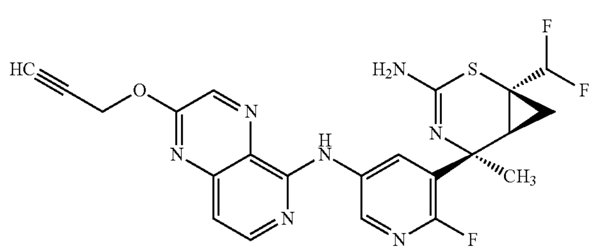 [SMILES: C#CCOc1cnc2c(Nc3cnc(F)c([C@@]4(C)N=C(N)S[C@@]5(C(F)F)C[C@@H]45)c3)nccc2n1] | 486 |

TABLE 3-continued

| Ex. No. | Chemical Structure | Observed [M + H]+ |
|---|---|---|
| 654 | 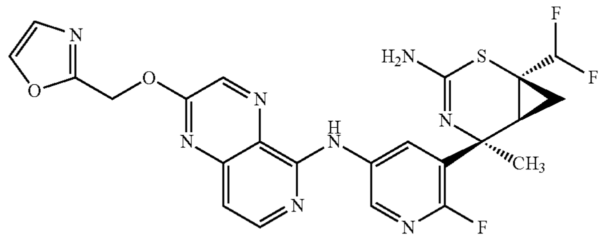 [SMILES: C[C@]1(c2cc(Nc3nccc4nc(OCc5ncco5)cnc34)cnc2F)N=C(N)S[C@@]2(C(F)F)C[C@@H]12] | 529 |
| 656 | 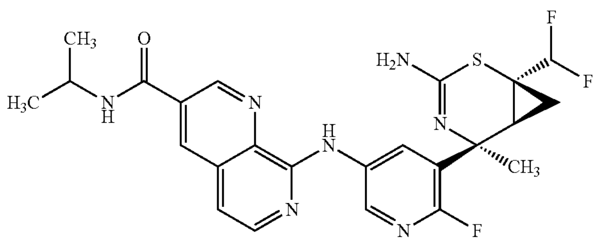 [SMILES: CC(C)NC(=O)c1cnc2c(Nc3cnc(F)c([C@@]4(C)N=C(N)S[C@@]5(C(F)F)C[C@@H]45)c3)nccc2c1] | 516 |
| 657 | 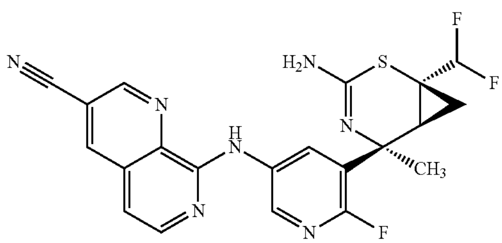 [SMILES: C[C@]1(c2cc(Nc3nccc4cc(C#N)cnc34)cnc2F)N=C(N)S[C@@]2(C(F)F)C[C@@H]12] | 456 |
| 658 | 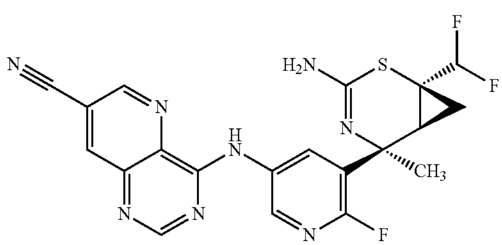 [SMILES: C[C@]1(c2cc(Nc3ncnc4cc(C#N)cnc34)cnc2F)N=C(N)S[C@@]2(C(F)F)C[C@@H]12] | 457 |
| 659 | 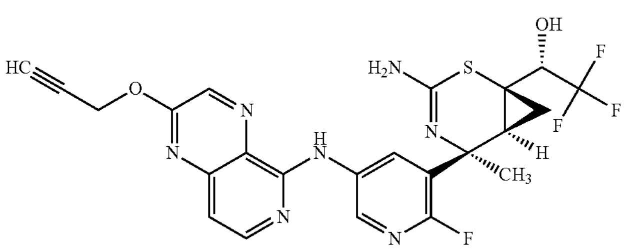 [SMILES: C#CCOc1cnc2c(Nc3cnc(F)c([C@@]4(C)N=C(N)S[C@@]5([C@H](O)C(F)(F)F)C[C@H]54)c3)nccc2n1] | 534 |
| 660 | 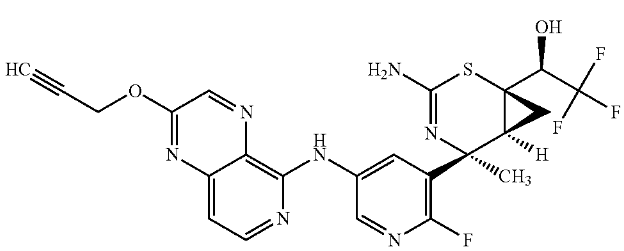 [SMILES: C#CCOc1cnc2c(Nc3cnc(F)c([C@@]4(C)N=C(N)S[C@@]5([C@@H](O)C(F)(F)F)C[C@H]54)c3)nccc2n1] | 534 |

TABLE 3-continued

| Ex. No. | Chemical Structure | Observed [M + H]+ |
|---|---|---|
| 662 | 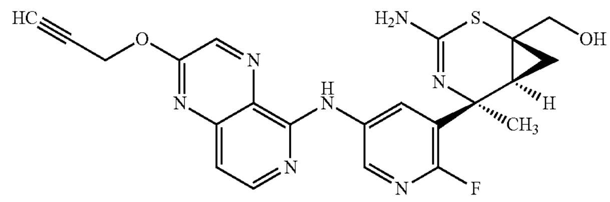 [SMILES: C#CCOc1cnc2c(Nc3cnc(F)c([C@@]4(C)N=C(N)S[C@@]5(CO)C[C@H]54)c3)nccc2n1] | 466 |
| 663 | 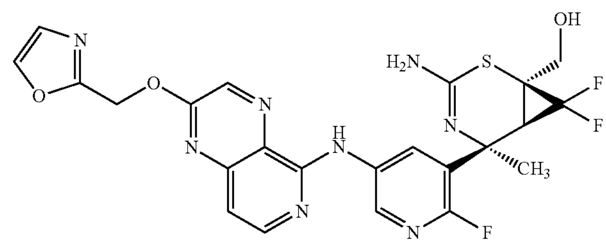 [SMILES: C[C@]1(c2cc(Nc3nccc4nc(OCc5ncco5)cnc34)cnc2F)N=C(N)S[C@]2(CO)[C@H]1C2(F)F] | 545 |
| 665 | 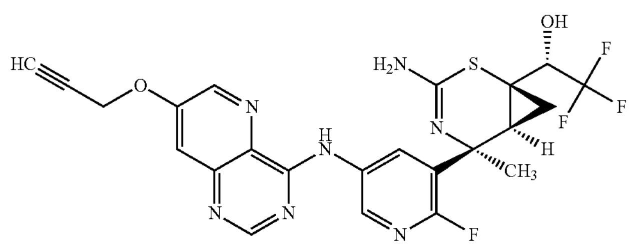 [SMILES: C#CCOc1cnc2c(Nc3cnc(F)c([C@@]4(C)N=C(N)S[C@@]5([C@H](O)C(F)(F)F)C[C@H]54)c3)ncnc2c1] | 534 |
| 666 | 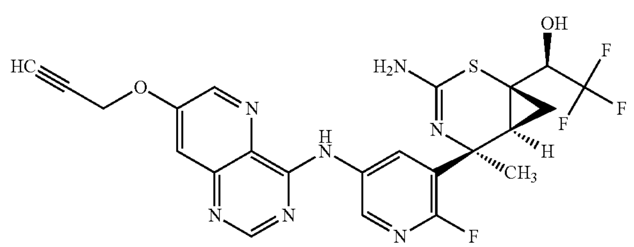 [SMILES: C#CCOc1cnc2c(Nc3cnc(F)c([C@@]4(C)N=C(N)S[C@@]5([C@@H](O)C(F)(F)F)C[C@H]54)c3)ncnc2c1] | 534 |
| 667 | 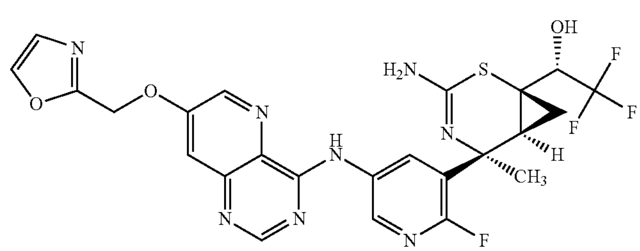 [SMILES: C[C@]1(c2cc(Nc3ncnc4cc(OCc5ncco5)cnc34)cnc2F)N=C(N)S[C@@]2([C@H](O)C(F)(F)F)C[C@H]21] | 534 |
| 668 | 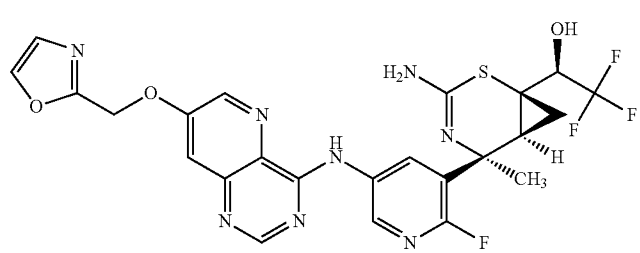 [SMILES: C[C@]1(c2cc(Nc3ncnc4cc(OCc5ncco5)cnc34)cnc2F)N=C(N)S[C@@]2([C@@H](O)C(F)(F)F)C[C@H]21] | 577 |

TABLE 3-continued

| Ex. No. | Chemical Structure | Observed [M + H]+ |
|---|---|---|
| 669 | 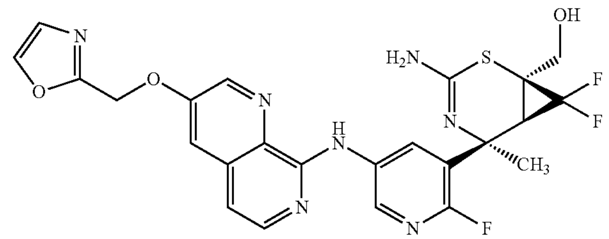 | 544 |
| 670 | 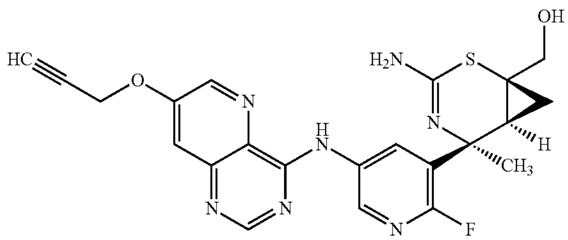 [SMILES: C#CCOc1cnc2c(Nc3cnc(F)c([C@@]4(C)N=C(N)S[C@@]5(CO)C[C@H]54)c3)ncnc2c1] | 466 |
| 671 | 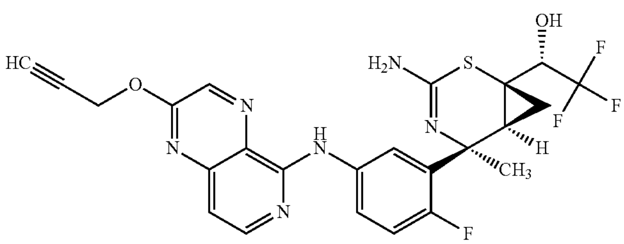 [SMILES: C#CCOc1cnc2c(Nc3ccc(F)c([C@@]4(C)N=C(N)S[C@@]5([C@H](O)C(F)(F)F)C[C@H]54)c3)nccc2n1] | 533 |
| 672 | 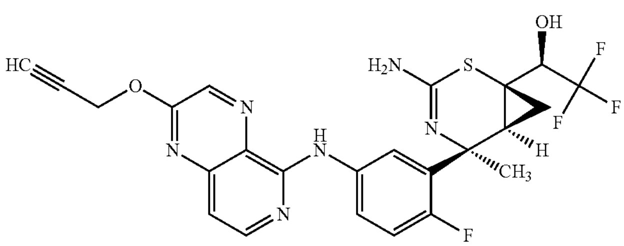 [SMILES: C#CCOc1cnc2c(Nc3ccc(F)c([C@@]4(C)N=C(N)S[C@@]5([C@@H](O)C(F)(F)F)C[C@H]54)c3)nccc2n1] | 533 |
| 676 | 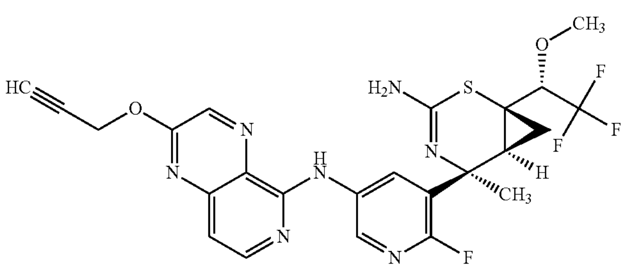 [SMILES: C#CCOc1cnc2c(Nc3cnc(F)c([C@@]4(C)N=C(N)S[C@@]5([C@H](OC)C(F)(F)F)C[C@H]54)c3)nccc2n1] | 548 |
| 677 | 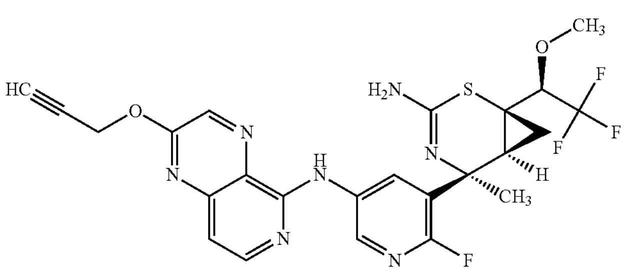 [SMILES: C#CCOc1cnc2c(Nc3cnc(F)c([C@@]4(C)N=C(N)S[C@@]5([C@@H](OC)C(F)(F)F)C[C@H]54)c3)nccc2n1] | 548 |

TABLE 3-continued

| Ex. No. | Chemical Structure | Observed [M + H]+ |
|---|---|---|
| 703 | 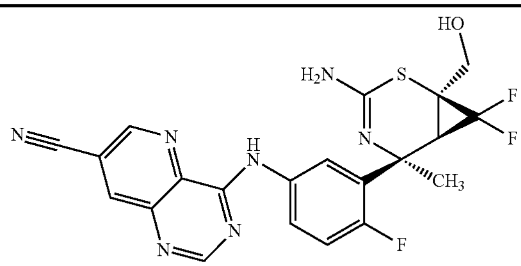 | 472 |
| 705 | 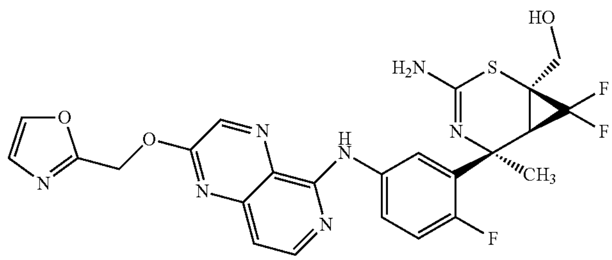 [SMILES: C[C@]1(c2cc(Nc3nccc4nc(OCc5ncco5)cnc34)ccc2F)N=C(N)S[C@]2(CO)[C@H]1C2(F)F] | 544 |
| 706 | 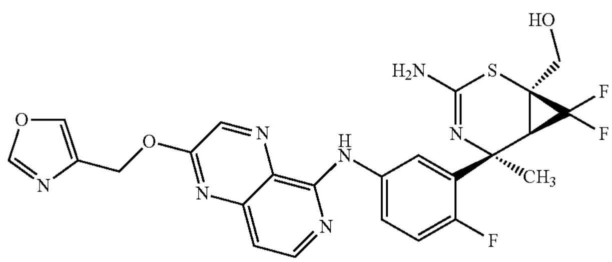 [SMILES: C[C@]1(c2cc(Nc3nccc4nc(OCc5cocn5)cnc34)ccc2F)N=C(N)S[C@]2(CO)[C@H]1C2(F)F] | 544 |
| 707 | 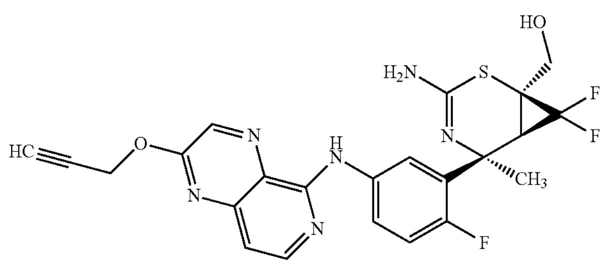 [SMILES: C#CCOc1cnc2c(Nc3ccc(F)c([C@@]4(C)N=C(N)S[C@]5(CO)[C@H]4C5(F)F)c3)nccc2n1] | 501 |
| 709 | 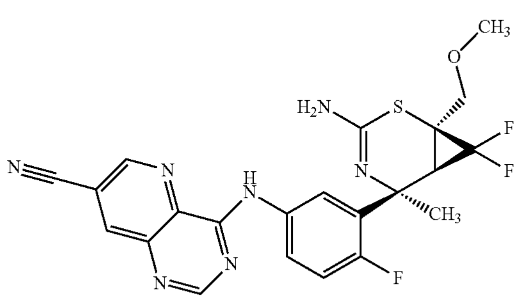 [SMILES: COC[C@@]12SC(N)=N[C@](C)(c3cc(Nc4ncnc5cc(C#N)cnc45)ccc3F)[C@@H]1C2(F)F] | 486 |
| 712 | 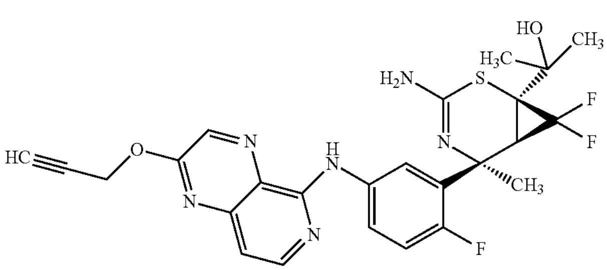 [SMILES: C#CCOc1cnc2c(Nc3ccc(F)c([C@@]4(C)N=C(N)S[C@]5(C(C)(C)O)[C@H]4C5(F)F)c3)nccc2n1] | 529 |

TABLE 3-continued

| Ex. No. | Chemical Structure | Observed [M + H]+ |
|---|---|---|
| 713 | 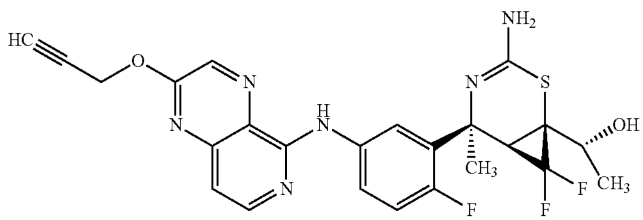 [SMILES: C#CCOc1cnc2c(Nc3ccc(F)c([C@@]4(C)N=C(N)S[C@]5([C@@H](C)O)[C@H]4C5(F)F)c3)nccc2n1] | 515 |
| 714 | 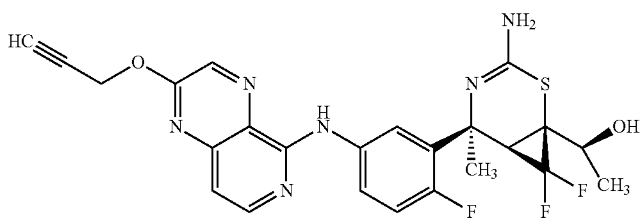 [SMILES: C#CCOc1cnc2c(Nc3ccc(F)c([C@@]4(C)N=C(N)S[C@]5([C@H](C)O)[C@H]4C5(F)F)c3)nccc2n1] | 515 |
| 717 | 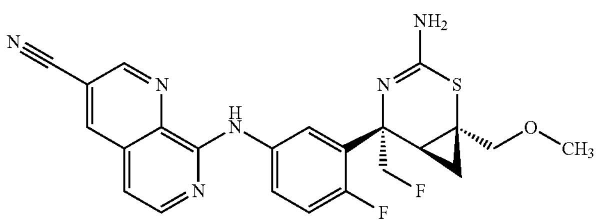 [SMILES: COC[C@]12C[C@H]1[C@@](CF)(c1cc(Nc3nccc4cc(C#N)cnc34)ccc1F)N=C(N)S2] | 467.1 |
| 719 | 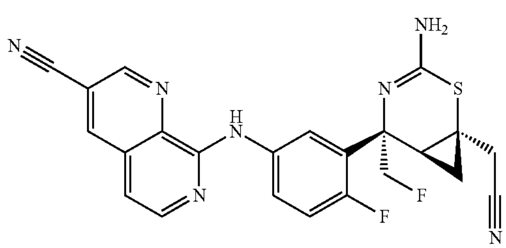 [SMILES: N#CC[C@]12C[C@H]1[C@@](CF)(c1cc(Nc3nccc4cc(C#N)cnc34)ccc1F)N=C(N)S2] | 462 |
| 720 | 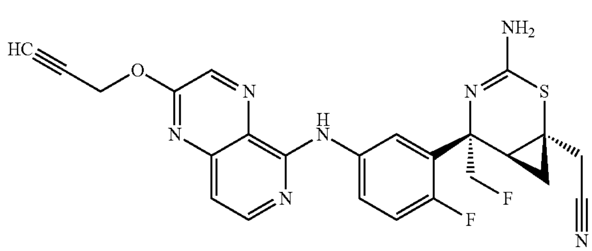 [SMILES: C#CCOc1cnc2c(Nc3ccc(F)c([C@@]4(CF)N=C(N)S[C@@]5(CC#N)C[C@H]54)c3)nccc2n1] | 492 |
| 721 | 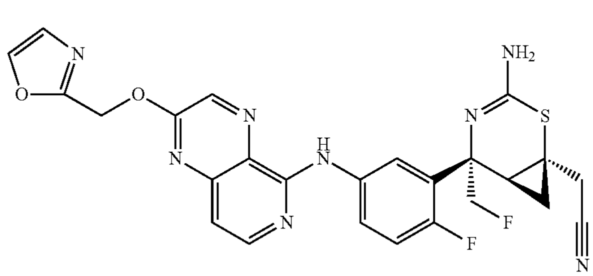 [SMILES: N#CC[C@]12C[C@H]1[C@@](CF)(c1cc(Nc3nccc4nc(OCc5ncco5)cnc34)ccc1F)N=C(N)S2] | 535.1 |

TABLE 3-continued

| Ex. No. | Chemical Structure | Observed [M + H]+ |
|---|---|---|
| 724 | 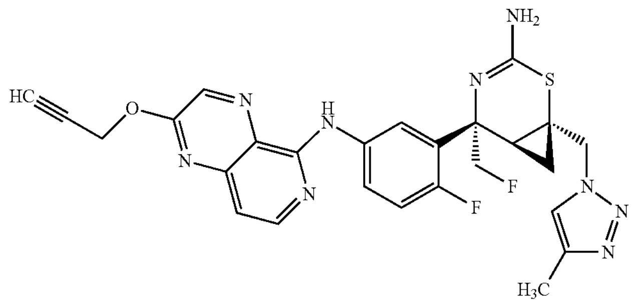 [SMILES: C#CCOc1cnc2c(Nc3ccc(F)c([C@@]4(CF)N=C(N)S[C@@]5(Cn6cc(C)nn6)C[C@H]54)c3)nccc2n1] | 548.2 |
| 726 | 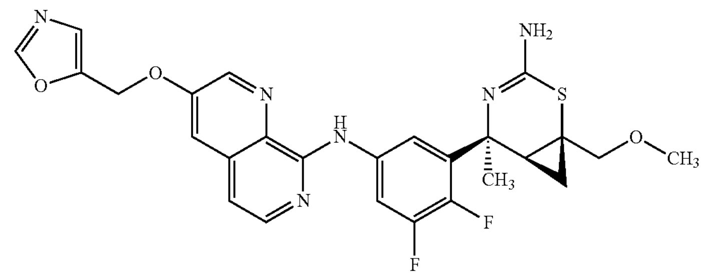 [SMILES: COC[C@]12C[C@H]1[C@@](C)(c1cc(Nc3nccc4cc(OCc5cnco5)cnc34)cc(F)c1F)N=C(N)S2] | 539.1 |
| 727 | 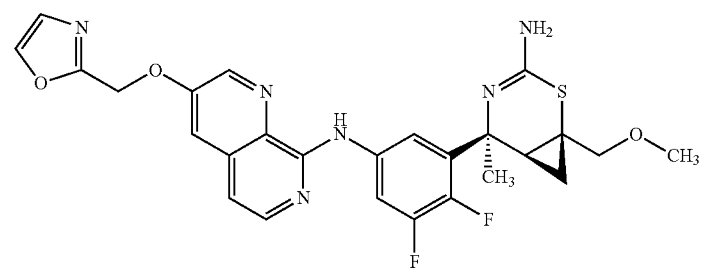 | 539.1 |
| 728 | 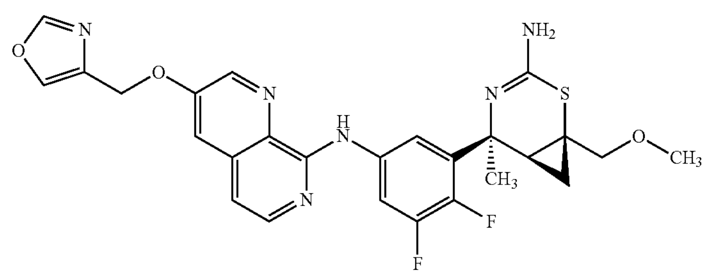 | 539.1 |
| 729 | 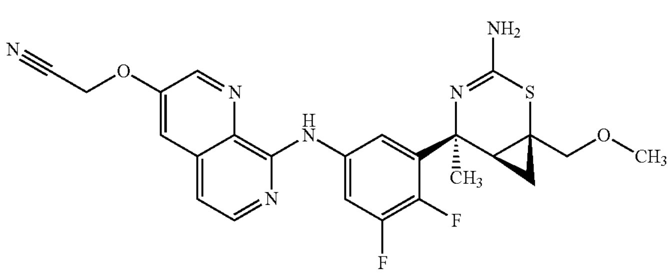 [SMILES: COC[C@]12C[C@H]1[C@@](C)(c1cc(Nc3nccc4cc(OCC#N)cnc34)cc(F)c1F)N=C(N)S2] | 497 |

TABLE 3-continued

| Ex. No. | Chemical Structure | Observed [M + H]+ |
|---|---|---|
| 730 | 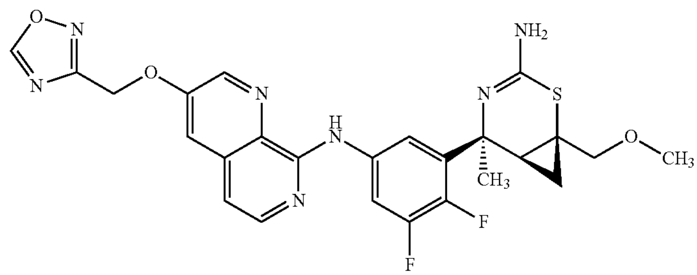 [SMILES: COC[C@]12C[C@H]1[C@@](C)(c1cc(Nc3nccc4cc(OCc5ncon5)cnc34)cc(F)c1F)N=C(N)S2] | 540.1 |
| 731 | 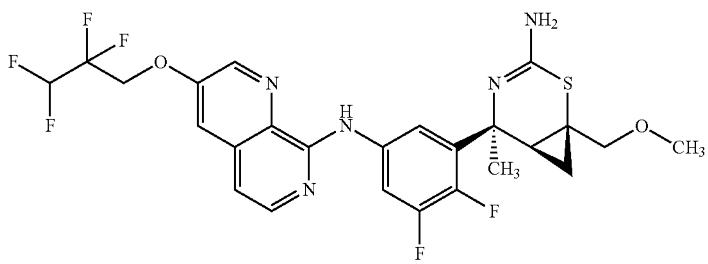 [SMILES: COC[C@]12C[C@H]1[C@@](C)(c1cc(Nc3nccc4cc(OCC(F)(F)C(F)F)cnc34)cc(F)c1F)N=C(N)S2] | 572.1 |
| 733 | 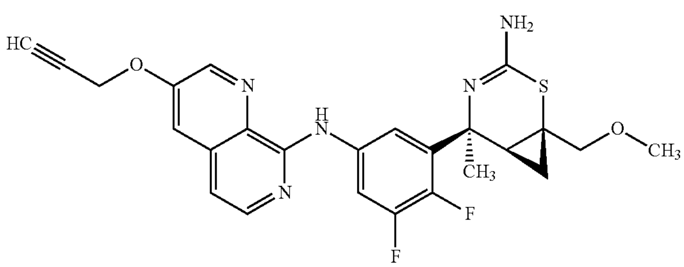 [SMILES: C#CCOc1cnc2c(Nc3cc(F)c(F)c([C@@]4(C)N=C(N)S[C@@]5(COC)C[C@H]54)c3)nccc2c1] | 496.1 |
| 735 | 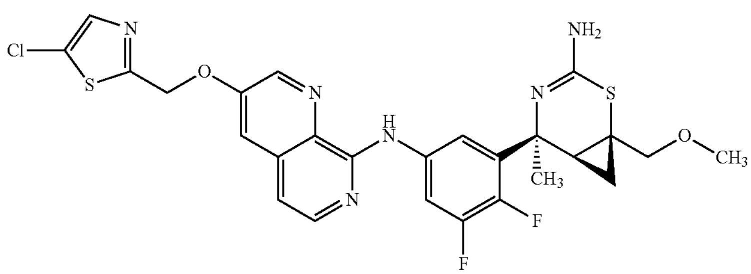 [SMILES: COC[C@]12C[C@H]1[C@@](C)(c1cc(Nc3nccc4cc(OCc5ncc(Cl)s5)cnc34)cc(F)c1F)N=C(N)S2] | 589.1 |
| 736 | 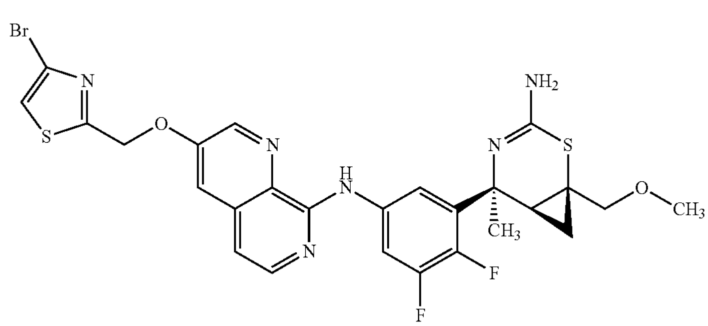 [SMILES: COC[C@]12C[C@H]1[C@@](C)(c1cc(Nc3nccc4cc(OCc5nc(Br)cs5)cnc34)cc(F)c1F)N=C(N)S2] | 633/635 |

TABLE 3-continued

| Ex. No. | Chemical Structure | Observed [M + H]+ |
|---|---|---|
| 737 | 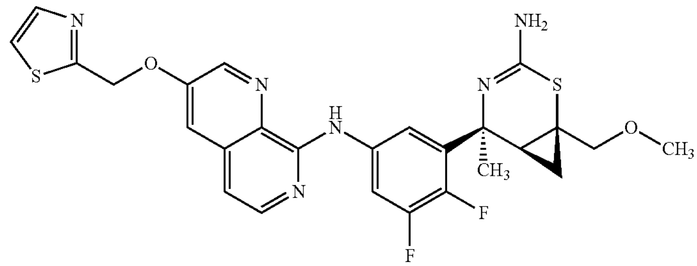 [SMILES: COC[C@]12C[C@H]1[C@@](C)(c1cc(Nc3nccc4cc(OCc5nccs5)cnc34)cc(F)c1F)N=C(N)S2] | 555.1 |
| 741 | 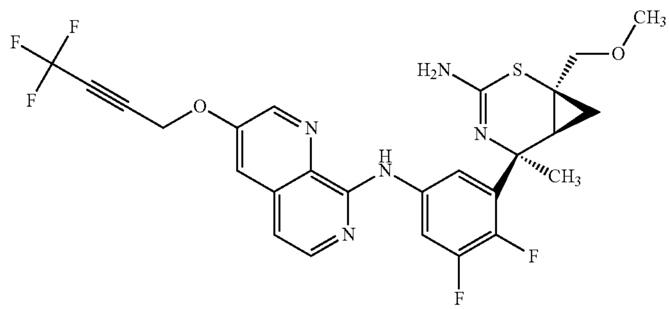 [SMILES: COC[C@]12C[C@H]1[C@@](C)(c1cc(Nc3nccc4cc(OCC#CC(F)(F)F)cnc34)cc(F)c1F)N=C(N)S2] | 564.1 |
| 750 | 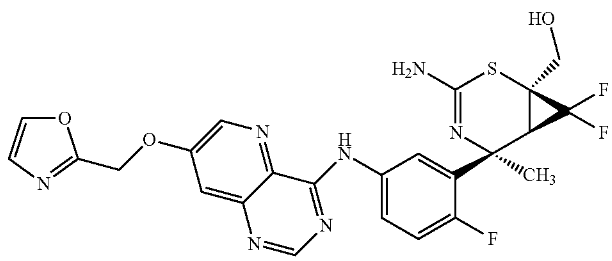 [SMILES: C[C@]1(c2cc(Nc3ncnc4cc(OCc5ncco5)cnc34)ccc2F)N=C(N)S[C@]2(CO)[C@H]1C2(F)F] | 544.1 |
| 762 | 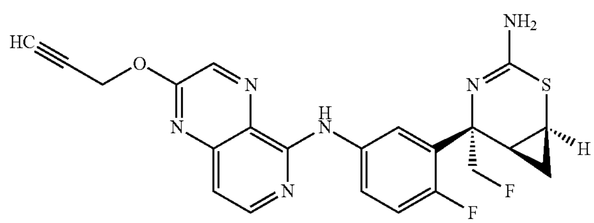 [SMILES: C#CCOc1cnc2c(Nc3ccc(F)c([C@@]4(CF)N=C(N)S[C@H]5C[C@H]54)c3)nccc2n1] | 453 |
| 763 | 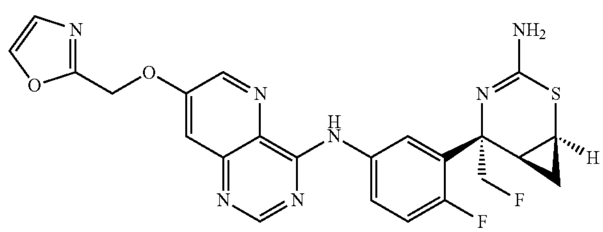 [SMILES: NC1=N[C@](CF)(c2cc(Nc3ncnc4cc(OCc5ncco5)cnc34)ccc2F)[C@@H]2C[C@@H]2S1] | 496 |
| 768 | 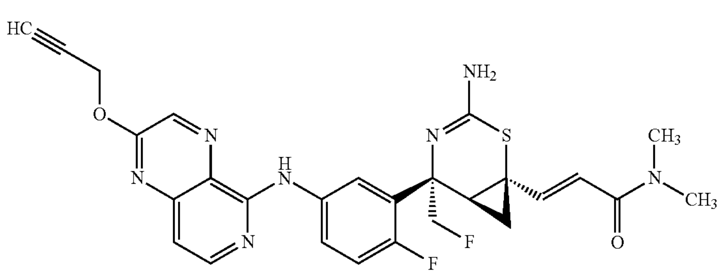 [SMILES: C#CCOc1cnc2c(Nc3ccc(F)c([C@@]4(CF)N=C(N)S[C@@]5(/C=C/C(=O)N(C)C)C[C@H]54)c3)nccc2n1] | 550.1 |

TABLE 3-continued

| Ex. No. | Chemical Structure | Observed [M + H]+ |
|---|---|---|
| 769 | 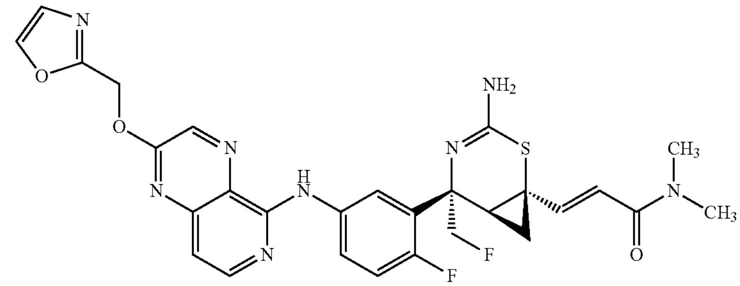 | 593 |
| 770 | 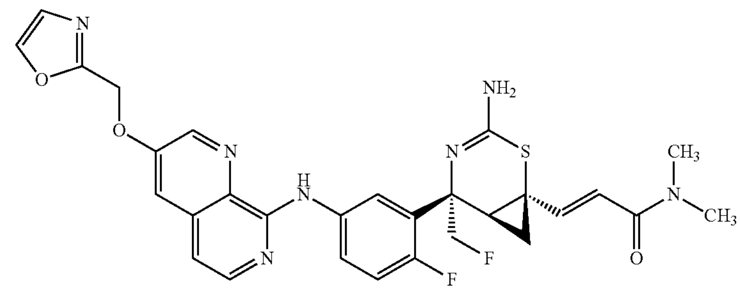 [SMILES: CN(C)C(=O)/C=C/[C@]12C[C@H]1[C@@](CF)(c1cc(Nc3nccc4cc(OCc5ncco5)cnc34)ccc1F)N=C(N)S2] | 592 |
| 771 | 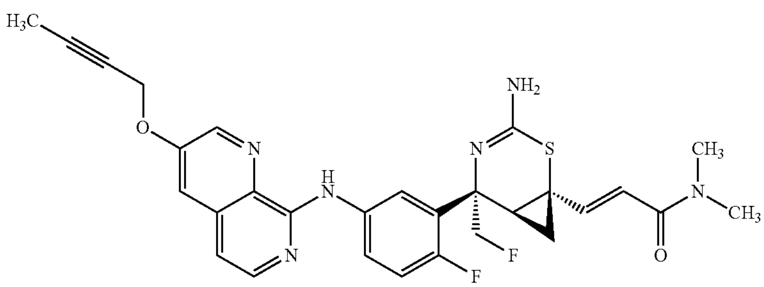 [SMILES: CC#CCOc1cnc2c(Nc3ccc(F)c([C@@]4(CF)N=C(N)S[C@@]5(/C=C/C(=O)N(C)C)C[C@H]54)c3)nccc2c1] | 563 |
| 773 | 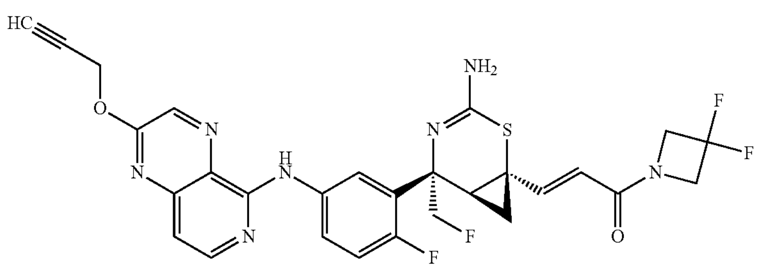 [SMILES: C#CCOc1cnc2c(Nc3ccc(F)c([C@@]4(CF)N=C(N)S[C@@]5(/C=C/C(=O)N6CC(F)(F)C6)C[C@H]54)c3)nccc2n1] | 598 |
| 775 | 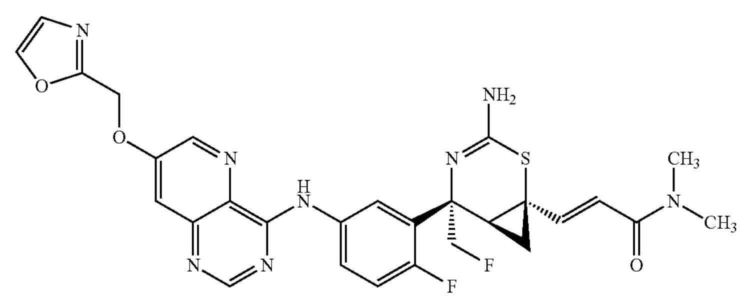 | |

TABLE 3-continued

| Ex. No. | Chemical Structure | Observed [M + H]+ |
|---|---|---|
| 776 | 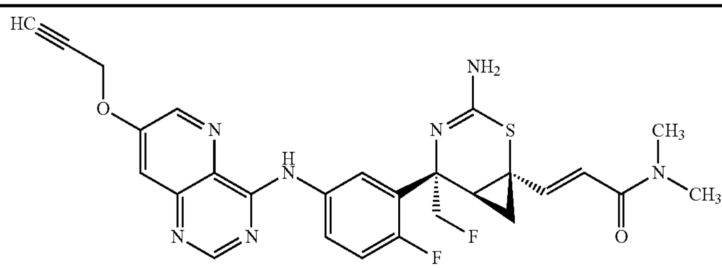 | 550 |
| 779 | 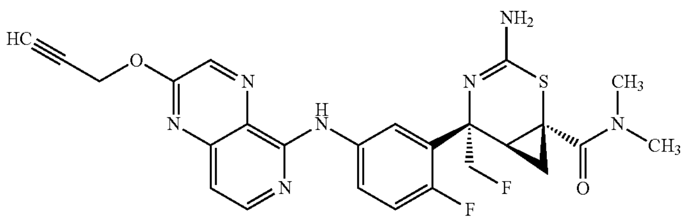 [SMILES: C#CCOc1cnc2c(Nc3ccc(F)c([C@@]4(CF)N=C(N)S[C@@]5(C(=O)N(C)C)C[C@H]54)c3)nccc2n1] | 524 |
| 781 | 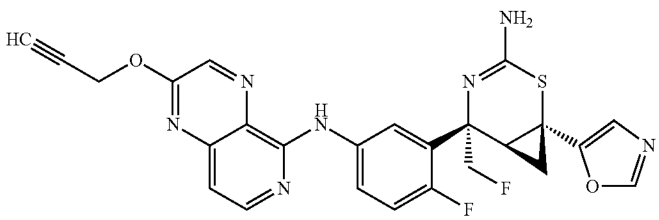 | 520 |
| 801 | 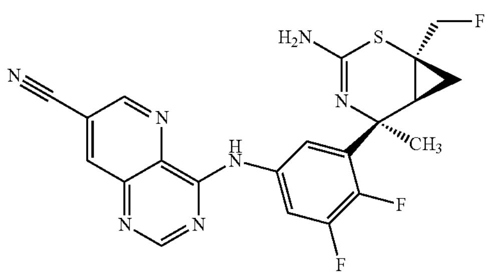 [SMILES: C[C@]1(c2cc(Nc3ncnc4cc(C#N)cnc34)cc(F)c2F)N=C(N)S[C@@]2(CF)C[C@H]21] | 456.2 |
| 802 | 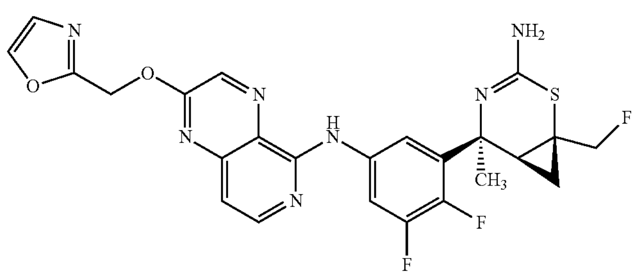 [SMILES: C[C@]1(c2cc(Nc3nccc4nc(OCc5ncco5)cnc34)cc(F)c2F)N=C(N)S[C@@]2(CF)C[C@H]21] | 528 |
| 805 | 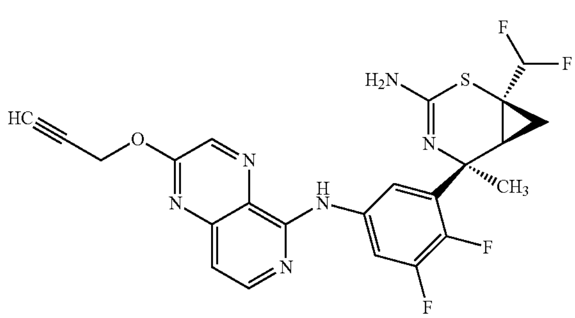 [SMILES: C#CCOc1cnc2c(Nc3cc(F)c(F)c([C@@]4(C)N=C(N)S[C@@]5(C(F)F)C[C@@H]45)c3)nccc2n1] | 503.1 |

TABLE 3-continued

| Ex. No. | Chemical Structure | Observed [M + H]+ |
|---|---|---|
| 806 | 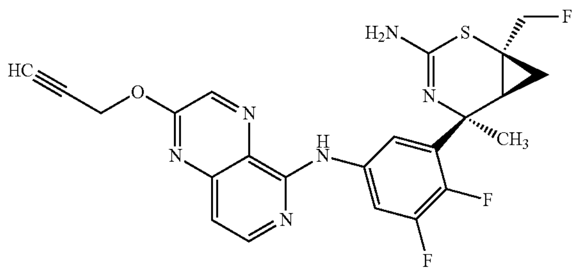 | 485 |
| 808 | 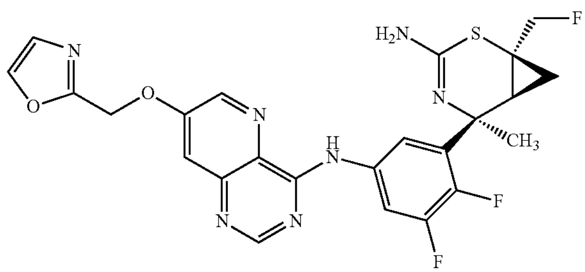 [SMILES: C[C@]1(c2cc(Nc3ncnc4cc(OCc5ncco5)cnc34)cc(F)c2F)N=C(N)S[C@@]2(CF)C[C@H]21] | 528.2 |
| 809 | 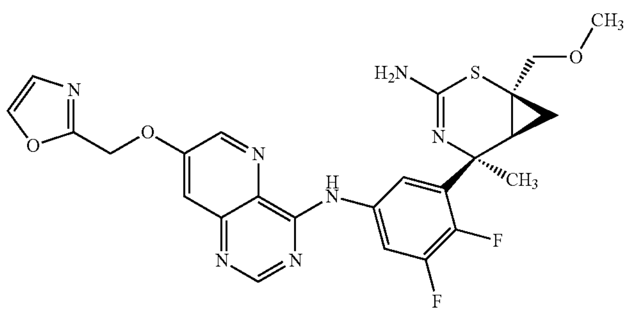 [SMILES: COC[C@]12C[C@H]1[C@@](C)(c1cc(Nc3ncnc4cc(OCc5ncco5)cnc34)cc(F)c1F)N=C(N)S2] | 540.1 |
| 812 | 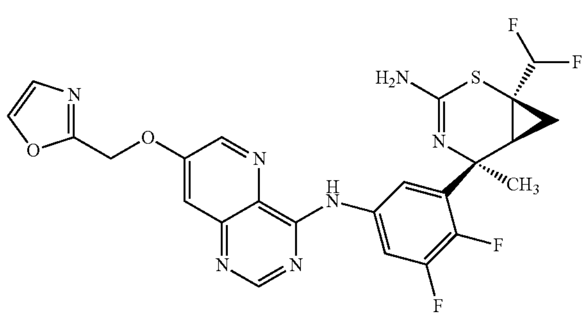 [SMILES: C[C@]1(c2cc(Nc3ncnc4cc(OCc5ncco5)cnc34)cc(F)c2F)N=C(N)S[C@@]2(C(F)F)C[C@@H]12] | 546 |
| 813 | 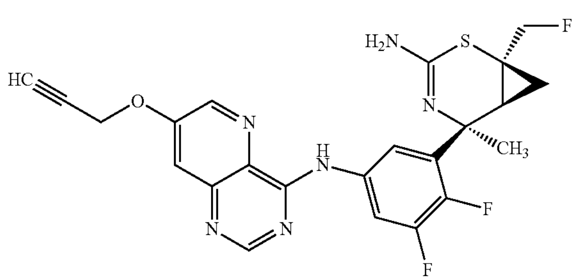 [SMILES: C#CCOc1cnc2c(Nc3cc(F)c(F)c([C@@]4(C)N=C(N)S[C@@]5(CF)C[C@H]54)c3)ncnc2c1] | 485.1 |

TABLE 3-continued

| Ex. No. | Chemical Structure | Observed [M + H]+ |
|---------|-------------------|-------------------|
| 816 | 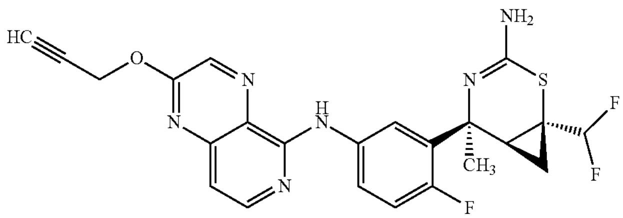 [SMILES: C#CCOc1cnc2c(Nc3ccc(F)c([C@@]4(C)N=C(N)S[C@@]5(C(F)F)C[C@@H]45)c3)nccc2n1] | 485 |
| 817 | 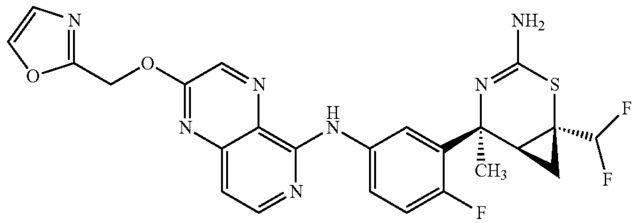 [SMILES: C[C@]1(c2cc(Nc3nccc4nc(OCc5ncco5)cnc34)ccc2F)N=C(N)S[C@@]2(C(F)F)C[C@@H]12] | 528 |
| 819 | 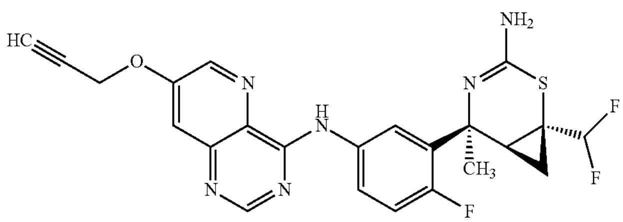 [SMILES: C#CCOc1cnc2c(Nc3ccc(F)c([C@@]4(C)N=C(N)S[C@@]5(C(F)F)C[C@@H]45)c3)ncnc2c1] | 485.1 |
| 823 | 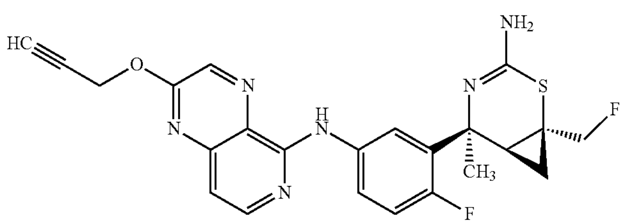 [SMILES: C#CCOc1cnc2c(Nc3ccc(F)c([C@@]4(C)N=C(N)S[C@@]5(CF)C[C@H]54)c3)nccc2n1] | 467 |
| 824 | 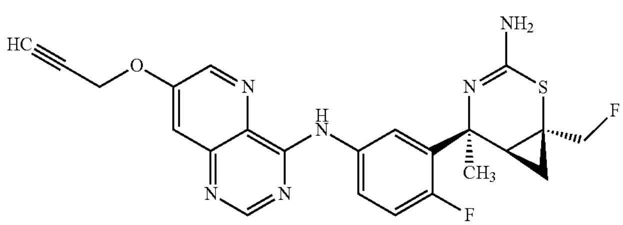 [SMILES: C#CCOc1cnc2c(Nc3ccc(F)c([C@@]4(C)N=C(N)S[C@@]5(CF)C[C@H]54)c3)ncnc2c1] | 467 |
| 825 | 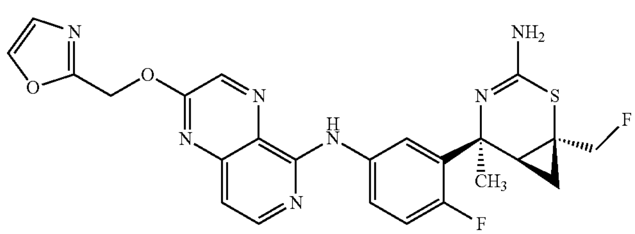 [SMILES: C[C@]1(c2cc(Nc3nccc4nc(OCc5ncco5)cnc34)ccc2F)N=C(N)S[C@@]2(CF)C[C@H]21] | 510 |
| 827 | 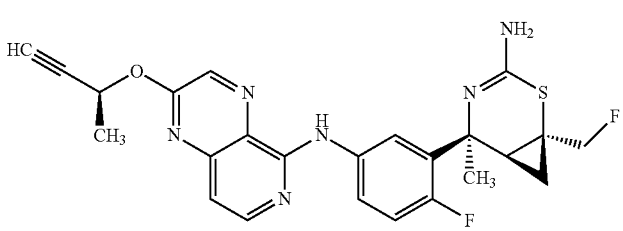 [SMILES: C#C[C@H](C)Oc1cnc2c(Nc3ccc(F)c([C@@]4(C)N=C(N)S[C@@]5(CF)C[C@H]54)c3)nccc2n1] | 481.1 |

TABLE 3-continued

| Ex. No. | Chemical Structure | Observed [M + H]+ |
|---|---|---|
| 828 | 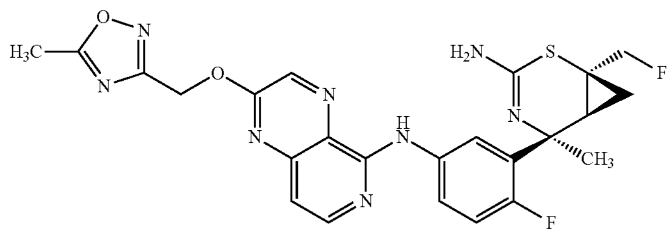 [SMILES: Cc1nc(COc2cnc3c(Nc4ccc(F)c([C@@]5(C)N=C(N)S[C@@]6(CF)C[C@H]65)c4)nccc3n2)no1] | 525 |
| 841 | 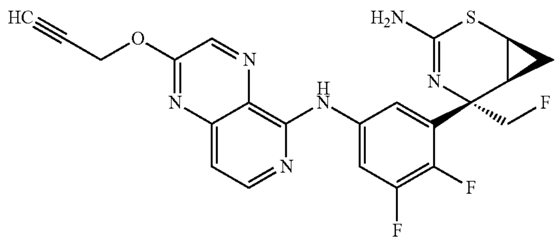 [SMILES: C#CCOc1cnc2c(Nc3cc(F)c(F)c([C@@]4(CF)N=C(N)S[C@H]5C[C@H]54)c3)nccc2n1] | 471 |
| 842 | 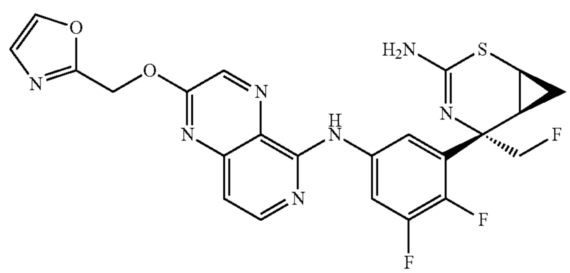 [SMILES: NC1=N[C@](CF)(c2cc(Nc3nccc4nc(OCc5ncco5)cnc34)cc(F)c2F)[C@@H]2C[C@@H]2S1] | 514.1 |
| 843 | 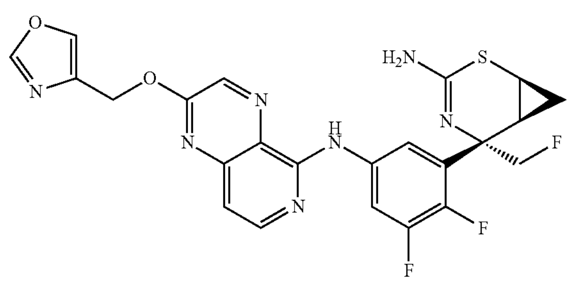 [SMILES: NC1=N[C@](CF)(c2cc(Nc3nccc4nc(OCc5cocn5)cnc34)cc(F)c2F)[C@@H]2C[C@@H]2S1] | 514.1 |
| 865 | 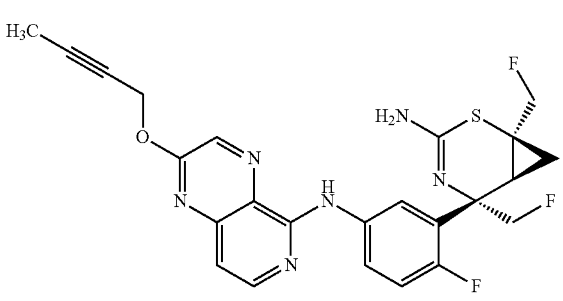 [SMILES: CC#CCOc1cnc2c(Nc3ccc(F)c([C@@]4(CF)N=C(N)S[C@@]5(CF)C[C@H]54)c3)nccc2n1] | 499 |

TABLE 3-continued
| Ex. No. | Chemical Structure | Observed [M + H]+ |
|---|---|---|
| 866 | 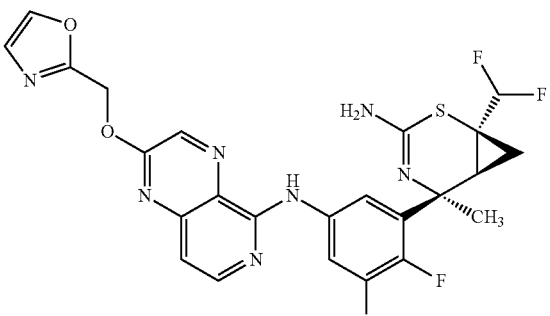 | 545.9 |
| 867 | 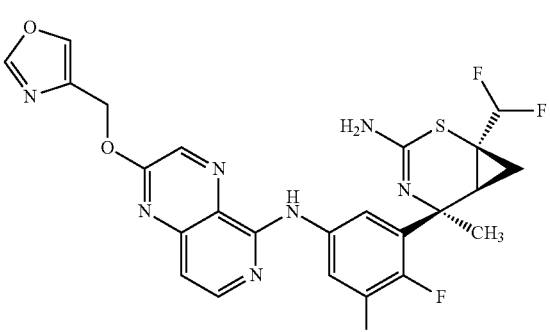 | 545.9 |
| 868 | 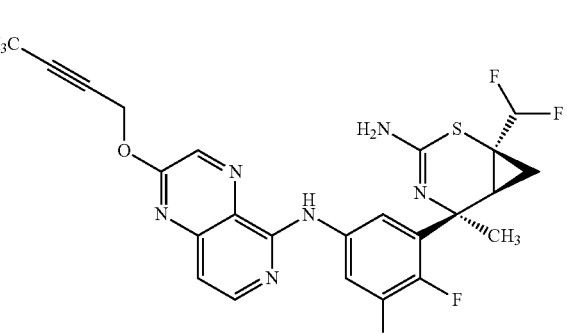 | 517 |
| 869 | 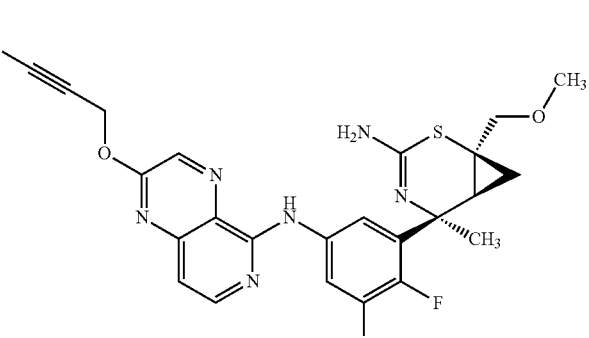 | 511 |

TABLE 3-continued

| Ex. No. | Chemical Structure | Observed [M + H]+ |
|---|---|---|
| 870 | 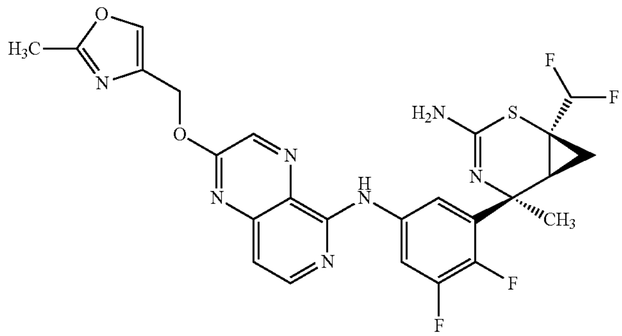 [SMILES: Cc1nc(COc2cnc3c(Nc4cc(F)c(F)c([C@@]5(C)N=C(N)S[C@@]6(C(F)F)C[C@@H]56)c4)nccc3n2)co1] | 560 |
| 871 | 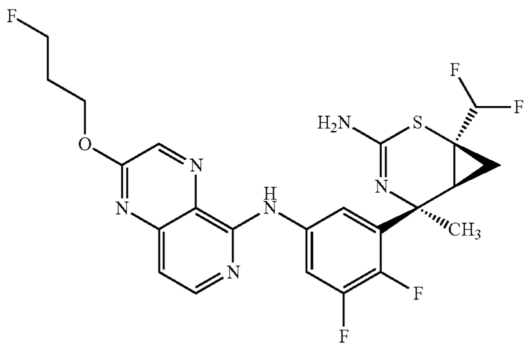 [SMILES: C[C@]1(c2cc(Nc3nccc4nc(OCCCF)cnc34)cc(F)c2F)N=C(N)S[C@@]2(C(F)F)C[C@@H]12] | 525 |
| 872 | 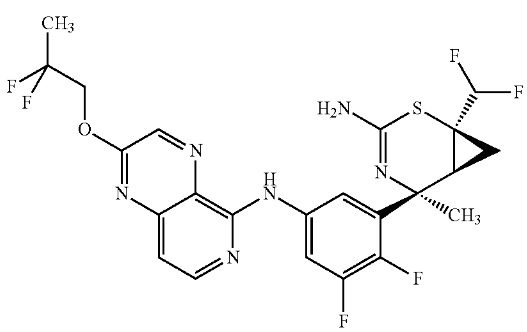 [SMILES: CC(F)(F)COc1cnc2c(Nc3cc(F)c(F)c([C@@]4(C)N=C(N)S[C@@]5(C(F)F)C[C@@H]45)c3)nccc2n1] | 542.9 |
| 873 | 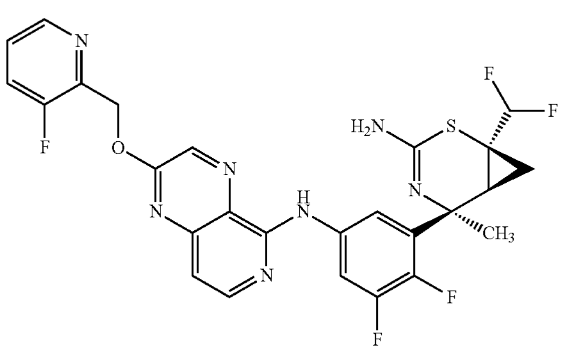 [SMILES: C[C@]1(c2cc(Nc3nccc4nc(OCc5ncccc5F)cnc34)cc(F)c2F)N=C(N)S[C@@]2(C(F)F)C[C@@H]12] | 574 |

TABLE 3-continued

| Ex. No. | Chemical Structure | Observed [M + H]+ |
|---|---|---|
| 874 | 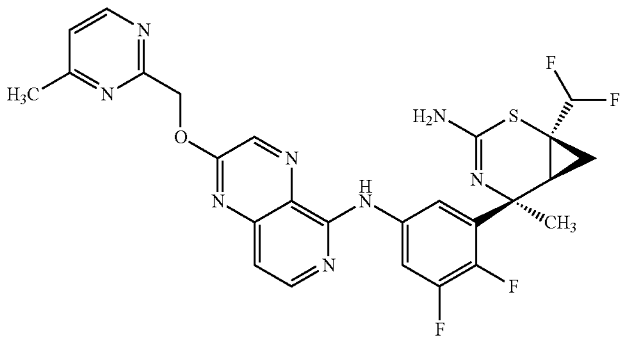 [SMILES: Cc1ccnc(COc2cnc3c(Nc4cc(F)c(F)c([C@@]5(C)N=C(N)S[C@@]6(C(F)F)C[C@@H]56)c4)nccc3n2)n1] | 571 |
| 875 | 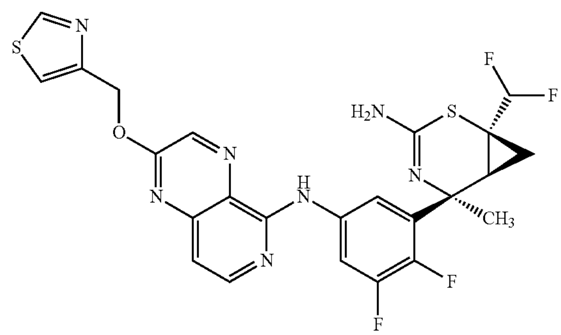 [SMILES: C[C@]1(c2cc(Nc3nccc4nc(OCc5cscn5)cnc34)cc(F)c2F)N=C(N)S[C@@]2(C(F)F)C[C@@H]12] | 562 |
| 876 | 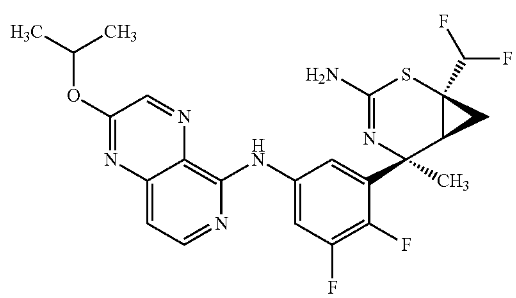 [SMILES: CC(C)Oc1cnc2c(Nc3cc(F)c(F)c([C@@]4(C)N=C(N)S[C@@]5(C(F)F)C[C@@H]45)c3)nccc2n1] | 506.9 |
| 877 | 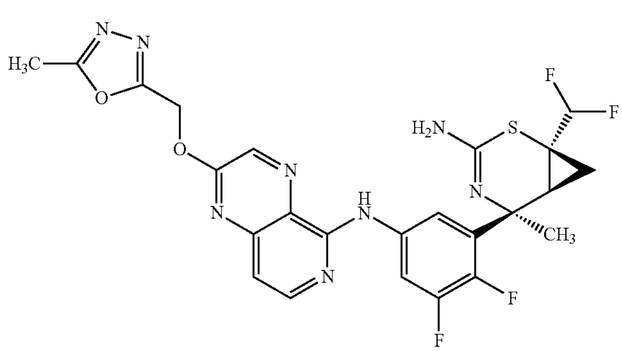 [SMILES: Cc1nnc(COc2cnc3c(Nc4cc(F)c(F)c([C@@]5(C)N=C(N)S[C@@]6(C(F)F)C[C@@H]56)c4)nccc3n2)o1] | 560.9 |

TABLE 3-continued

| Ex. No. | Chemical Structure | Observed [M + H]+ |
|---|---|---|
| 878 | 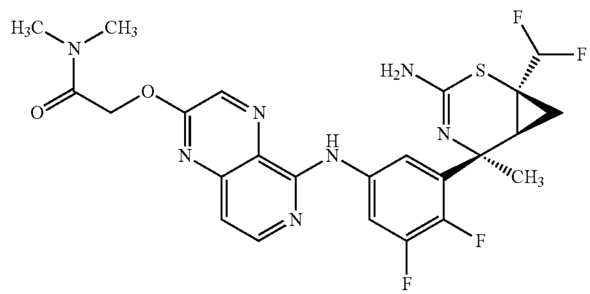 [SMILES: CN(C)C(=O)COc1cnc2c(Nc3cc(F)c(F)c([C@@]4(C)N=C(N)S[C@@]5(C(F)F)C[C@@H]45)c3)nccc2n1] | 550 |
| 879 | 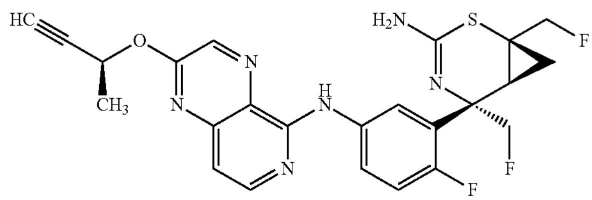 [SMILES: C#C[C@H](C)Oc1cnc2c(Nc3ccc(F)c([C@@]4(CF)N=C(N)S[C@@]5(CF)C[C@H]54)c3)nccc2n1] | 499 |
| 880 | 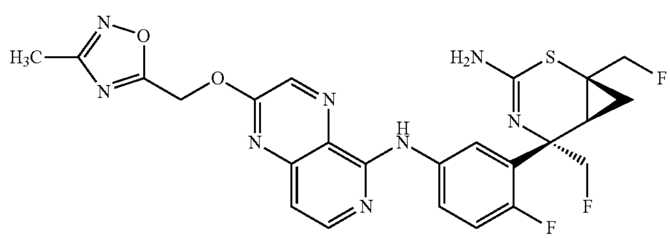 [SMILES: Cc1noc(COc2cnc3c(Nc4ccc(F)c([C@@]5(CF)N=C(N)S[C@@]6(CF)C[C@H]65)c4)nccc3n2)n1] | 543 |
| 881 | 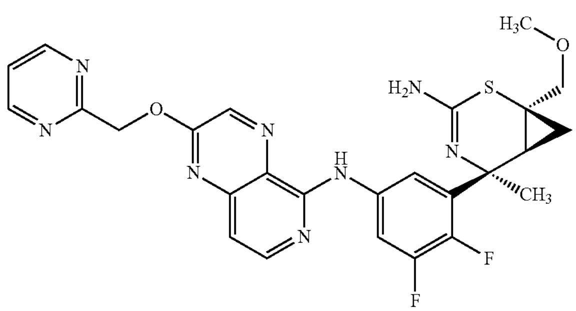 [SMILES: COC[C@]12C[C@H]1[C@@](C)(c1cc(Nc3nccc4nc(OCc5ncccn5)cnc34)cc(F)c1F)N=C(N)S2] | 551 |
| 882 | 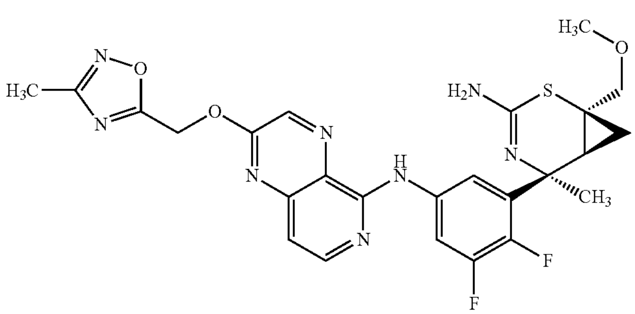 [SMILES: COC[C@]12C[C@H]1[C@@](C)(c1cc(Nc3nccc4nc(OCc5nc(C)no5)cnc34)cc(F)c1F)N=C(N)S2] | 555 |

TABLE 3-continued

| Ex. No. | Chemical Structure | Observed [M + H]+ |
|---|---|---|
| 883 | 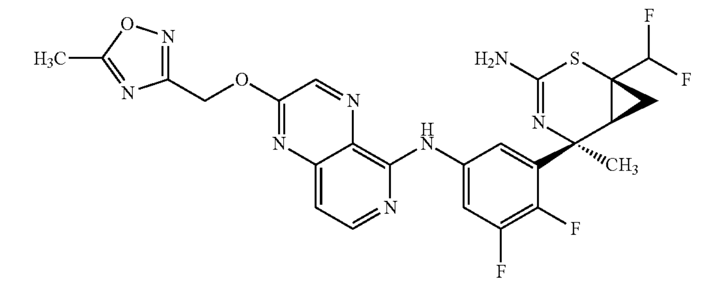 [SMILES: Cc1nc(COc2cnc3c(Nc4cc(F)c(F)c([C@@]5(C)N=C(N)S[C@@]6(C(F)F)C[C@@H]56)c4)nccc3n2)no1] | 561.2 |
| 884 | 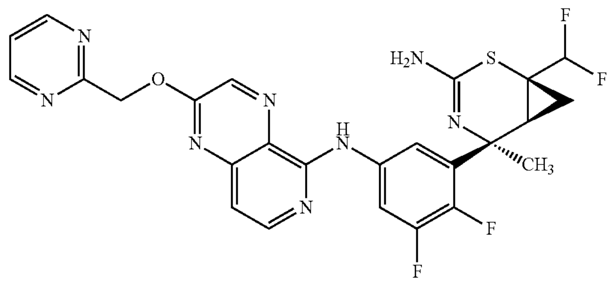 [SMILES: C[C@]1(c2cc(Nc3nccc4nc(OCc5ncccn5)cnc34)cc(F)c2F)N=C(N)S[C@@]2(C(F)F)C[C@@H]12] | 557.3 |
| 885 | 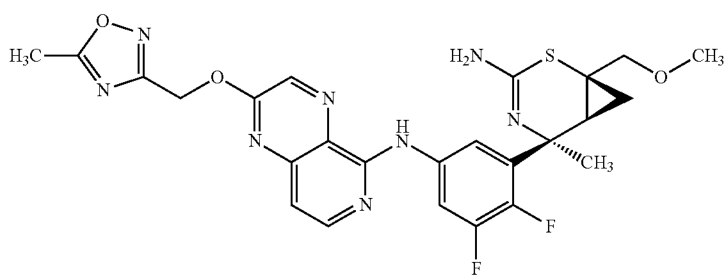 | 555.2 |
| 886 | 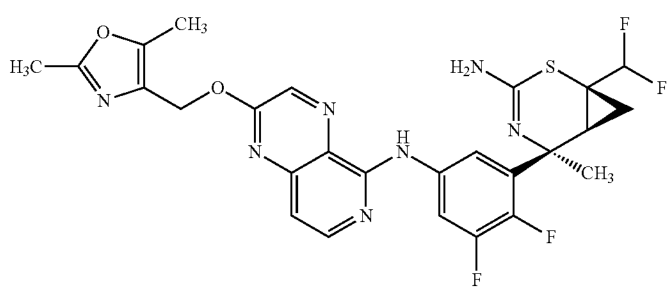 [SMILES: Cc1nc(COc2cnc3c(Nc4cc(F)c(F)c([C@@]5(C)N=C(N)S[C@@]6(C(F)F)C[C@@H]56)c4)nccc3n2)c(C)o1] | 574.2 |
| 887 | 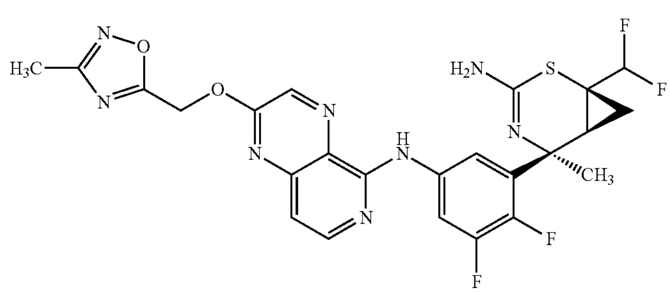 [SMILES: Cc1noc(COc2cnc3c(Nc4cc(F)c(F)c([C@@]5(C)N=C(N)S[C@@]6(C(F)F)C[C@@H]56)c4)nccc3n2)n1] | 561 |

TABLE 3-continued

| Ex. No. | Chemical Structure | Observed [M + H]+ |
|---|---|---|
| 888 | 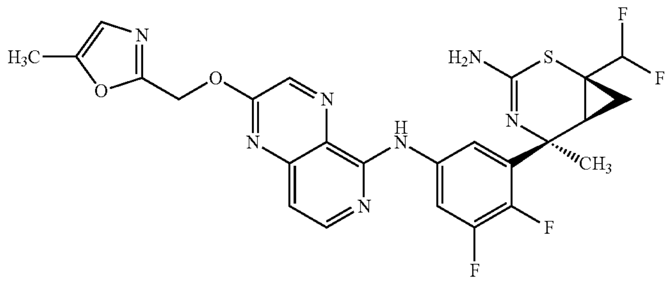 [SMILES: Cc1cnc(COc2cnc3c(Nc4cc(F)c(F)c([C@@]5(C)N=C(N)S[C@@]6(C(F)F)C[C@@H]56)c4)nccc3n2)o1] | 560.2 |
| 889 | 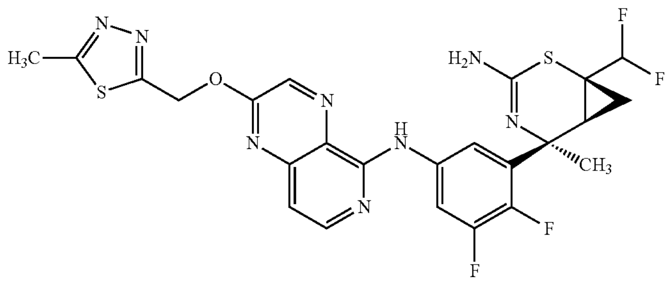 [SMILES: Cc1nnc(COc2cnc3c(Nc4cc(F)c(F)c([C@@]5(C)N=C(N)S[C@@]6(C(F)F)C[C@@H]56)c4)nccc3n2)s1] | 577.2 |
| 890 | 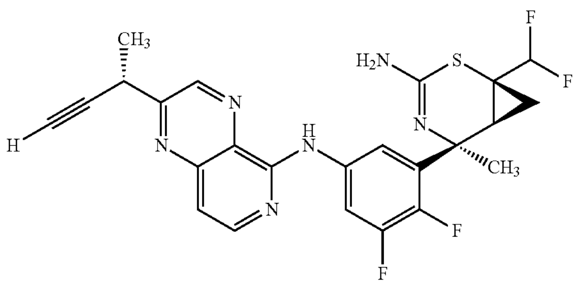 [SMILES: C#C[C@H](C)c1cnc2c(Nc3cc(F)c(F)c([C@@]4(C)N=C(N)S[C@@]5(C(F)F)C[C@@H]45)c3)nccc2n1] | 517.3 |
| 891 | 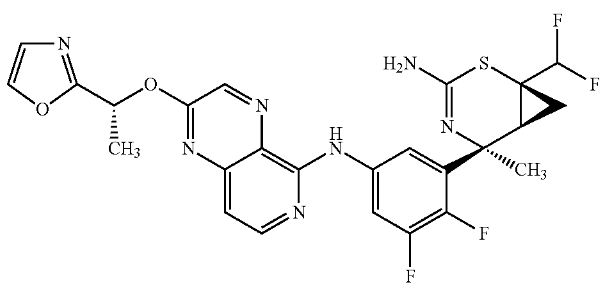 [SMILES: C[C@@H](Oc1cnc2c(Nc3cc(F)c(F)c([C@@]4(C)N=C(N)S[C@@]5(C(F)F)C[C@@H]45)c3)nccc2n1)c1ncco1] | 560 |
| 892 | 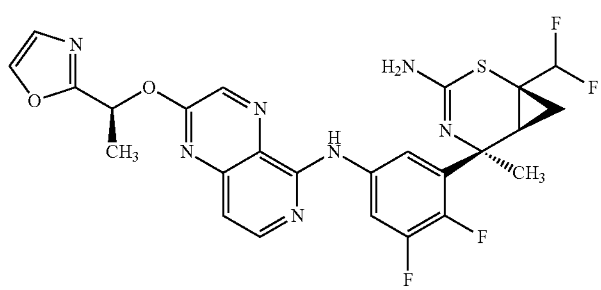 [SMILES: C[C@H](Oc1cnc2c(Nc3cc(F)c(F)c([C@@]4(C)N=C(N)S[C@@]5(C(F)F)C[C@@H]45)c3)nccc2n1)c1ncco1] | 560 |

TABLE 3-continued

| Ex. No. | Chemical Structure | Observed [M + H]+ |
|---|---|---|
| 893 | 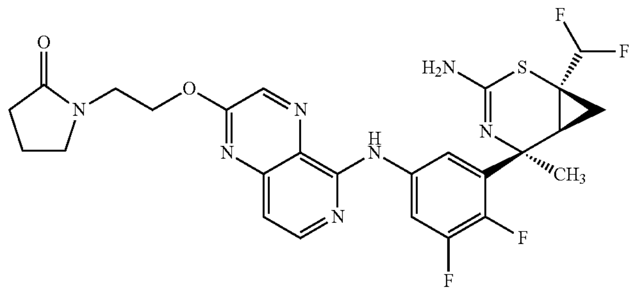 [SMILES: C[C@]1(c2cc(Nc3nccc4nc(OCCN5CCCC5=O)cnc34)cc(F)c2F)N=C(N)S[C@@]2(C(F)F)C[C@@H]12] | 576 |
| 894 | 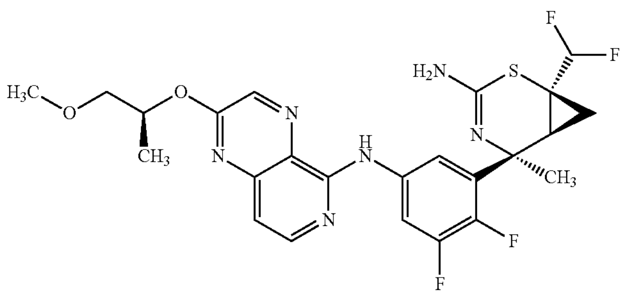 [SMILES: COC[C@H](C)Oc1cnc2c(Nc3cc(F)c(F)c([C@@]4(C)N=C(N)S[C@@]5(C(F)F)C[C@@H]45)c3)nccc2n1] | 536.9 |
| 895 | 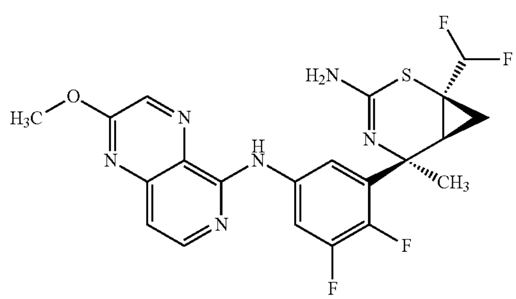 [SMILES: COc1cnc2c(Nc3cc(F)c(F)c([C@@]4(C)N=C(N)S[C@@]5(C(F)F)C[C@@H]45)c3)nccc2n1] | 479.1 |
| 896 | 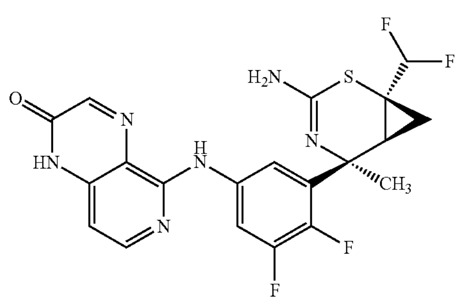 [SMILES: C[C@]1(c2cc(Nc3nccc4[nH]c(=O)cnc34)cc(F)c2F)N=C(N)S[C@@]2(C(F)F)C[C@@H]12] | 465.2 |
| 897 | 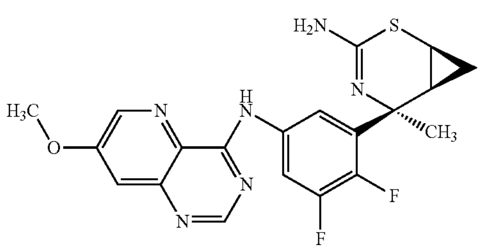 [SMILES: COc1cnc2c(Nc3cc(F)c(F)c([C@@]4(C)N=C(N)S[C@H]5C[C@H]54)c3)ncnc2c1] | 429 |

TABLE 3-continued

| Ex. No. | Chemical Structure | Observed [M + H]+ |
|---|---|---|
| 898 | 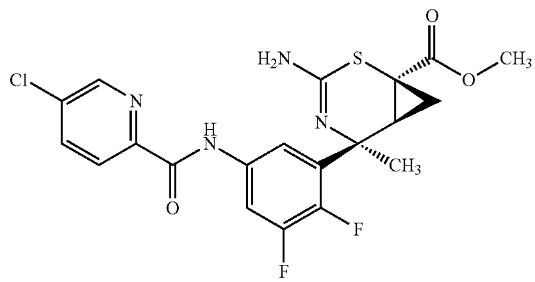 [SMILES: COC(=O)[C@]12C[C@H]1[C@@](C)(c1cc(NC(=O)c3ccc(Cl)cn3)cc(F)c1F)N=C(N)S2] | 467 |
| 900 | 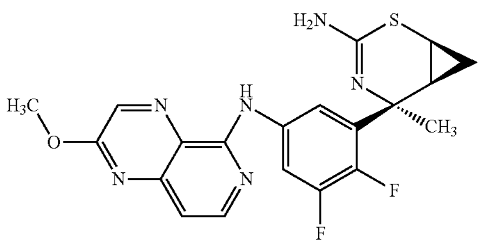 [SMILES: COc1cnc2c(Nc3cc(F)c(F)c([C@@]4(C)N=C(N)S[C@H]5C[C@H]54)c3)nccc2n1] | 429 |
| 901 | 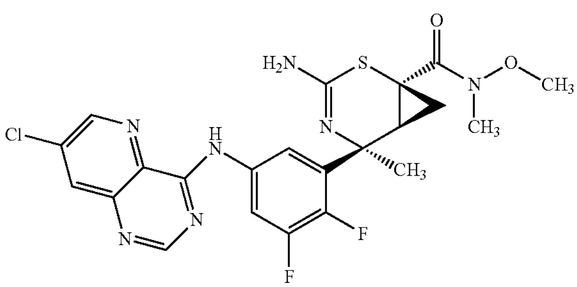 [SMILES: CON(C)C(=O)[C@]12C[C@H]1[C@@](C)(c1cc(Nc3ncnc4cc(Cl)cnc34)cc(F)c1F)N=C(N)S2] | 520.1 |
| 903 | 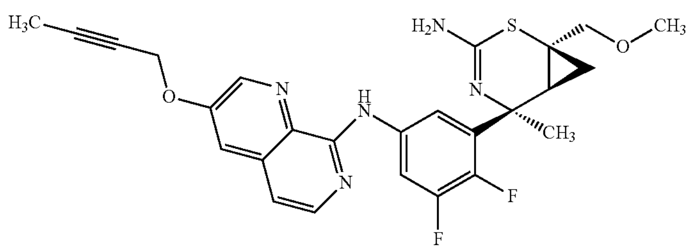 [SMILES: CC#CCOc1cnc2c(Nc3cc(F)c(F)c([C@@]4(C)N=C(N)S[C@@]5(COC)C[C@H]54)c3)nccc2c1] | 510 |
| 904 | 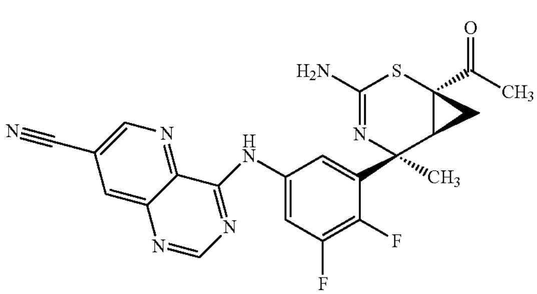 [SMILES: CC(=O)[C@]12C[C@H]1[C@@](C)(c1cc(Nc3ncnc4cc(C#N)cnc34)cc(F)c1F)N=C(N)S2] | 466.1 |

TABLE 3-continued

| Ex. No. | Chemical Structure | Observed [M + H]+ |
|---|---|---|
| 907 | 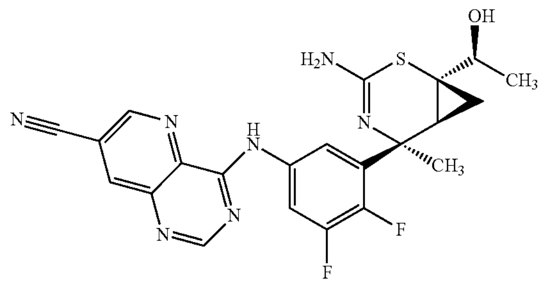 [SMILES: C[C@H](O)[C@]12C[C@H]1[C@@](C)(c1cc(Nc3ncnc4cc(C#N)cnc34)cc(F)c1F)N=C(N)S2] | 468.1 |
| 908 | 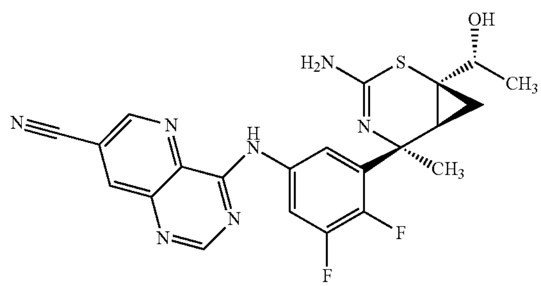 [SMILES: C[C@@H](O)[C@]12C[C@H]1[C@@](C)(c1cc(Nc3ncnc4cc(C#N)cnc34)cc(F)c1F)N=C(N)S2] | 468.1 |
| 909 | 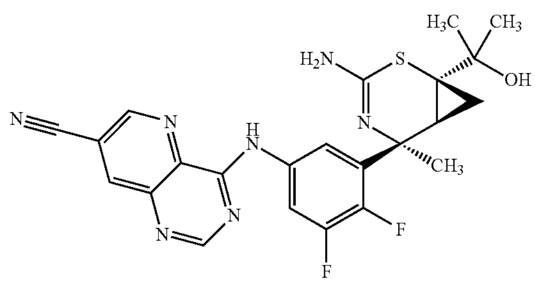 [SMILES: CC(C)(O)[C@]12C[C@H]1[C@@](C)(c1cc(Nc3ncnc4cc(C#N)cnc34)cc(F)c1F)N=C(N)S2] | 482 |
| 911 | 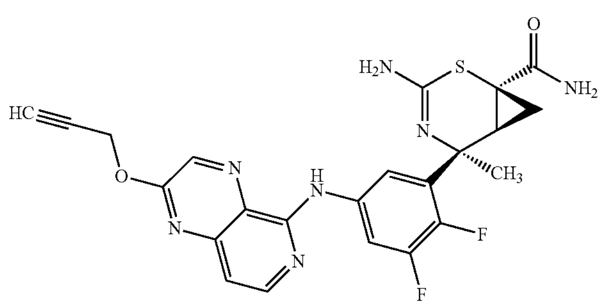 [SMILES: C#CCOc1cnc2c(Nc3cc(F)c(F)c([C@@]4(C)N=C(N)S[C@@]5(C(N)=O)C[C@H]54)c3)nccc2n1] | 496.1 |
| 912 | 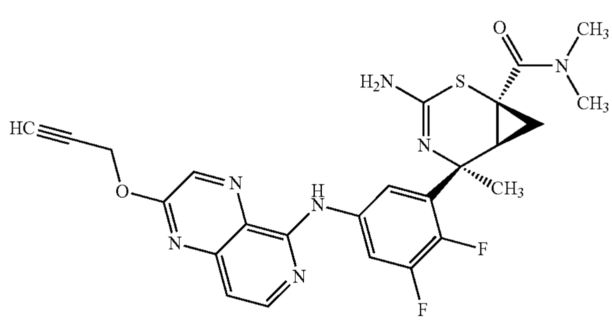 [SMILES: C#CCOc1cnc2c(Nc3cc(F)c(F)c([C@@]4(C)N=C(N)S[C@@]5(C(=O)N(C)C)C[C@H]54)c3)nccc2n1] | 524.1 |

TABLE 3-continued

| Ex. No. | Chemical Structure | Observed [M + H]+ |
|---|---|---|
| 917 | 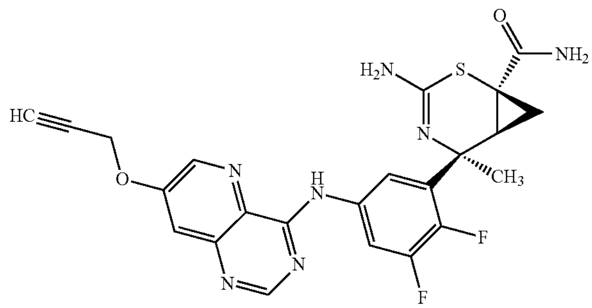 [SMILES: C#CCOc1cnc2c(Nc3cc(F)c(F)c([C@@]4(C)N=C(N)S[C@@]5(C(N)=O)C[C@H]54)c3)ncnc2c1] | 496 |
| 918 | 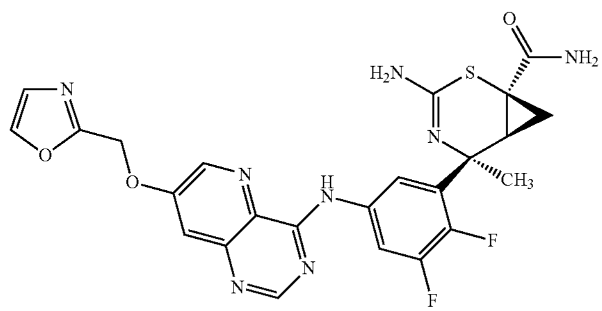 [SMILES: C[C@]1(c2cc(Nc3ncnc4cc(OCc5ncco5)cnc34)cc(F)c2F)N=C(N)S[C@@]2(C(N)=O)C[C@H]21] | 539 |
| 923 | 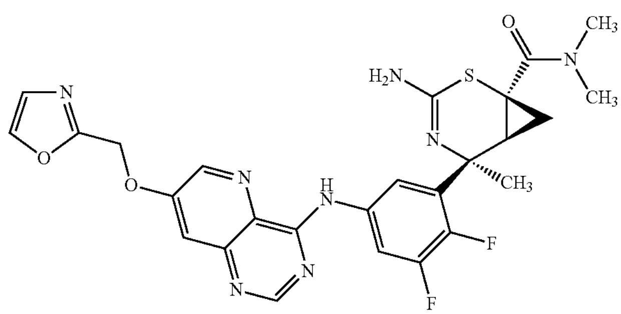 [SMILES: CN(C)C(=O)[C@]12C[C@H]1[C@@](C)(c1cc(Nc3ncnc4cc(OCc5ncco5)cnc34)cc(F)c1F)N=C(N)S2] | 567.1 |
| 928 | 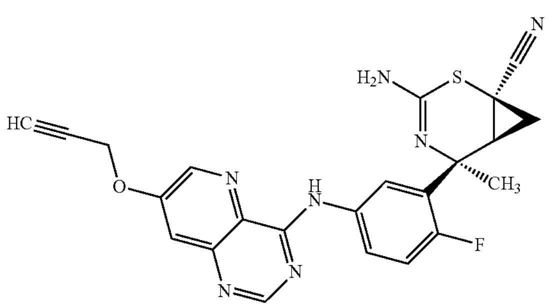 [SMILES: C#CCOc1cnc2c(Nc3ccc(F)c([C@@]4(C)N=C(N)S[C@@]5(C#N)C[C@H]54)c3)ncnc2c1] | 460.1 |
| 931 | 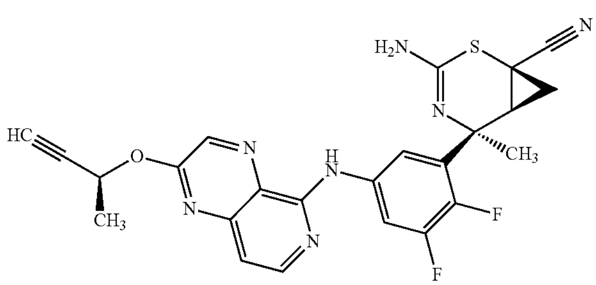 [SMILES: C#C[C@H](C)Oc1cnc2c(Nc3cc(F)c(F)c([C@@]4(C)N=C(N)S[C@@]5(C#N)C[C@H]54)c3)nccc2n1] | 492 |

TABLE 3-continued

| Ex. No. | Chemical Structure | Observed [M + H]+ |
|---|---|---|
| 933 | 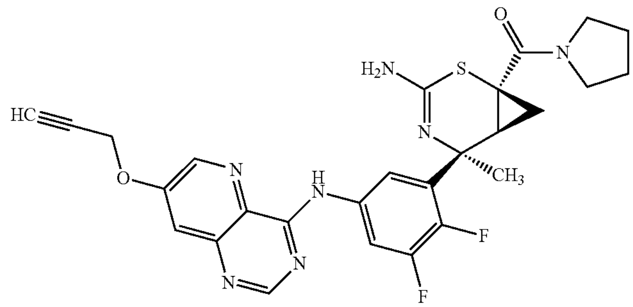 [SMILES: C#CCOc1cnc2c(Nc3cc(F)c(F)c([C@@]4(C)N=C(N)S[C@@]5(C(=O)N6CCCC6)C[C@H]54)c3)ncnc2c1] | 550.1 |
| 936 | 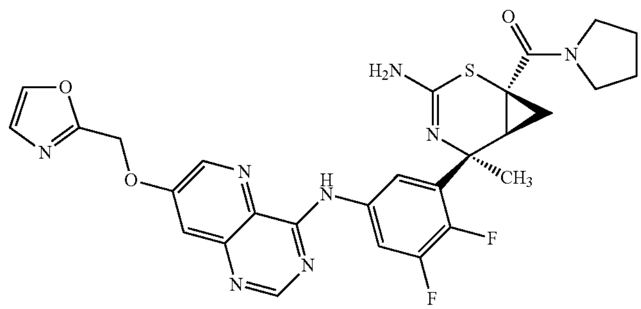 [SMILES: C[C@]1(c2cc(Nc3ncnc4cc(OCc5ncco5)cnc34)cc(F)c2F)N=C(N)S[C@@]2(C(=O)N3CCCC3)C[C@H]21] | 593.2 |
| 937 | 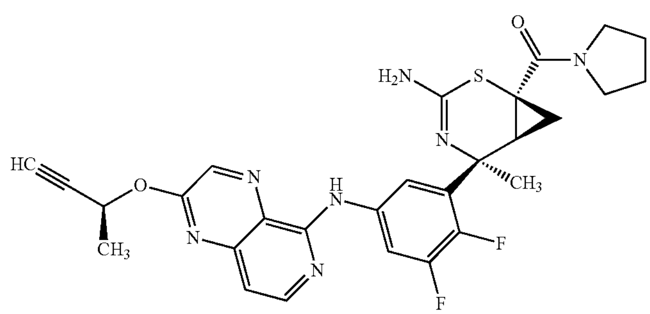 [SMILES: C#C[C@H](C)Oc1cnc2c(Nc3cc(F)c(F)c([C@@]4(C)N=C(N)S[C@@]5(C(=O)N6CCCC6)C[C@H]54)c3)nccc2n1] | 564 |
| 938 | 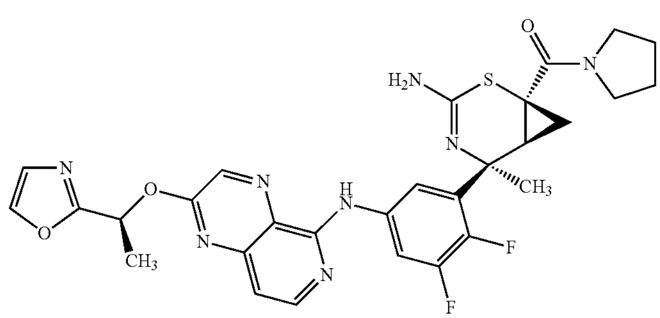 [SMILES: C[C@H](Oc1cnc2c(Nc3cc(F)c(F)c([C@@]4(C)N=C(N)S[C@@]5(C(=O)N6CCCC6)C[C@H]54)c3)nccc2n1)c1ncco1] | 607.1 |
| 941 | 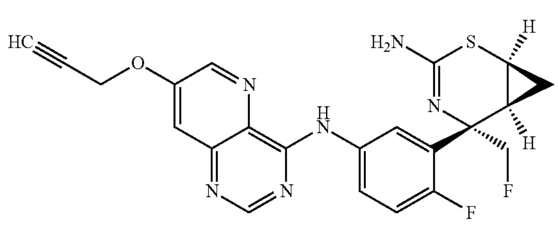 [SMILES: C#CCOc1cnc2c(Nc3ccc(F)c([C@@]4(CF)N=C(N)S[C@H]5C[C@H]54)c3)ncnc2c1] | 453.2 |

TABLE 3-continued
| Ex. No. | Chemical Structure | Observed [M + H]+ |
|---|---|---|
| 942 | 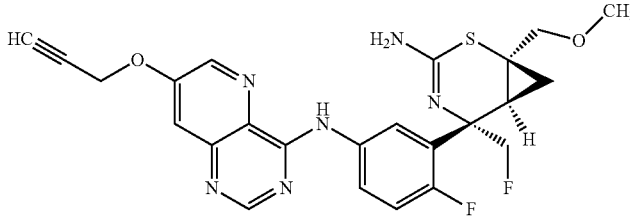 | 497 |
| 944 | 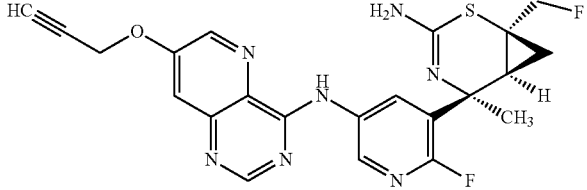 [SMILES: C#CCOc1cnc2c(Nc3cnc(F)c([C@@]4(C)N=C(N)S[C@@]5(CF)C[C@H]54)c3)ncnc2c1] | 468 |
| 945 | 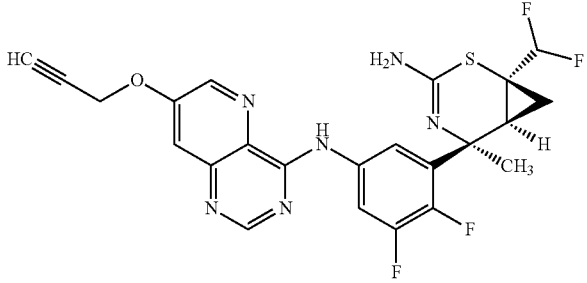 [SMILES: C#CCOc1cnc2c(Nc3cc(F)c(F)c([C@@]4(C)N=C(N)S[C@@]5(C(F)F)C[C@@H]45)c3)ncnc2c1] | 503 |
| 946 | 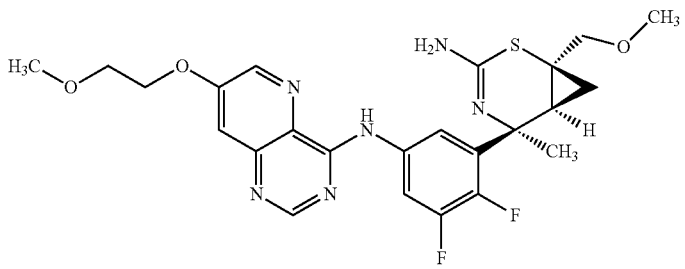 | 517 |
| 947 | 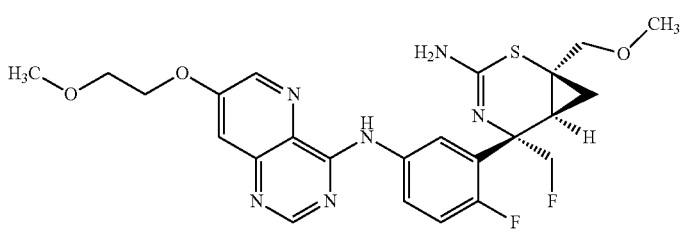 | 517.2 |
| 948 | 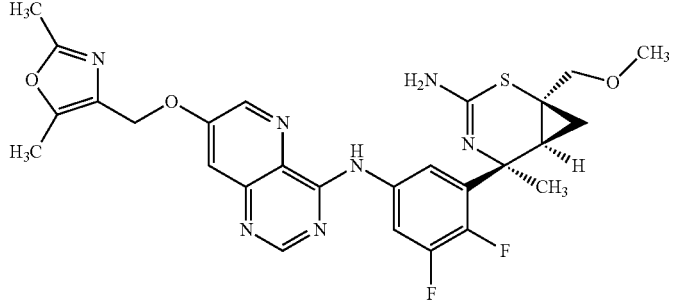 [SMILES: COC[C@]12C[C@H]1[C@@](C)(c1cc(Nc3ncnc4cc(OCc5nc(C)oc5C)cnc34)cc(F)c1F)N=C(N)S2] | 568 |

TABLE 3-continued

| Ex. No. | Chemical Structure | Observed [M + H]+ |
|---|---|---|
| 949 | 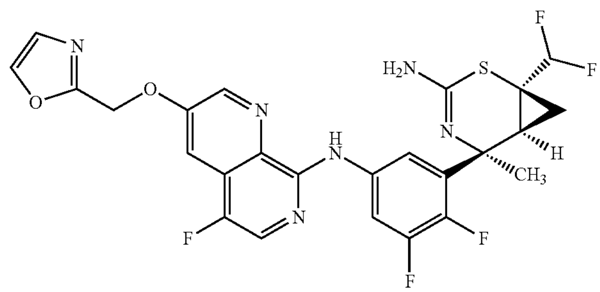 [SMILES: C[C@]1(c2cc(Nc3ncc(F)c4cc(OCc5ncco5)cnc34)cc(F)c2F)N=C(N)S[C@@]2(C(F)F)C[C@@H]12] | 563 |
| 950 | 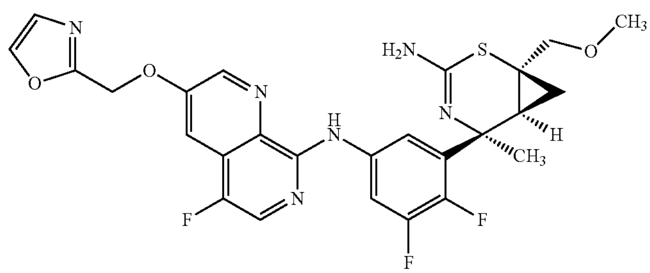 [SMILES: COC[C@]12C[C@H]1[C@@](C)(c1cc(Nc3ncc(F)c4cc(OCc5ncco5)cnc34)cc(F)c1F)N=C(N)S2] | 557.2 |
| 951 | 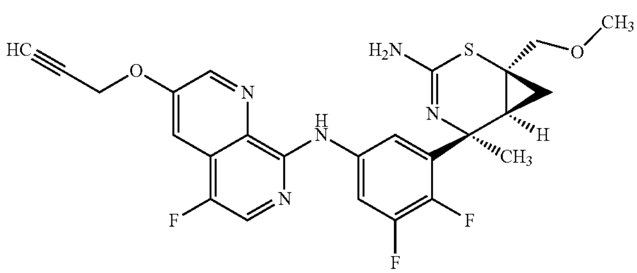 [SMILES: C#CCOc1cnc2c(Nc3cc(F)c(F)c([C@@]4(C)N=C(N)S[C@@]5(COC)C[C@H]54)c3)ncc(F)c2c1] | 514 |
| 952 | 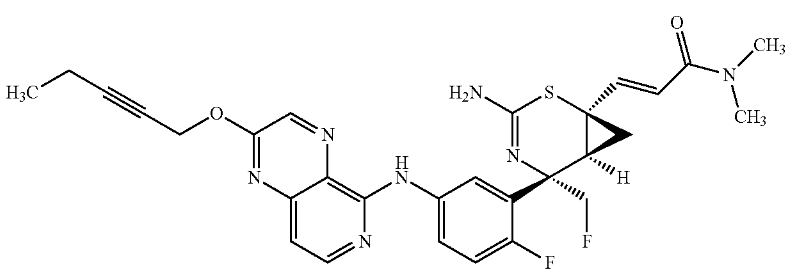 [SMILES: CCC#CCOc1cnc2c(Nc3ccc(F)c([C@@]4(CF)N=C(N)S[C@@]5(/C=C/C(=O)N(C)C)C[C@H]54)c3)nccc2n1] | 578 |
| 957 | 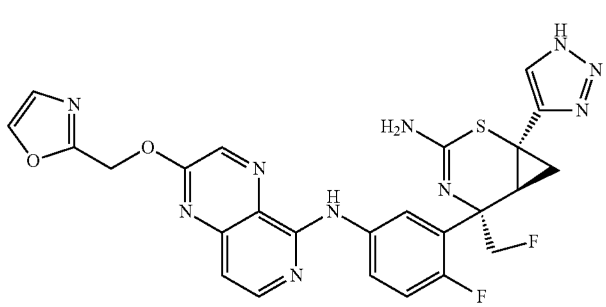 [SMILES: NC1=N[C@](CF)(c2cc(Nc3nccc4nc(OCc5ncco5)cnc34)ccc2F)[C@@H]2C[C@]2(c2c[nH]nn2)S1] | 463.2 |

TABLE 3-continued

| Ex. No. | Chemical Structure | Observed [M + H]+ |
|---|---|---|
| 958 | 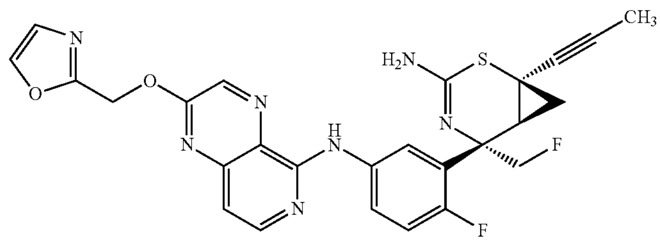 [SMILES: CC#C[C@]12C[C@H]1[C@@](CF)(c1cc(Nc3nccc4nc(OCc5ncco5)cnc34)ccc1F)N=C(N)S2] | 534.1 |
| 960 | 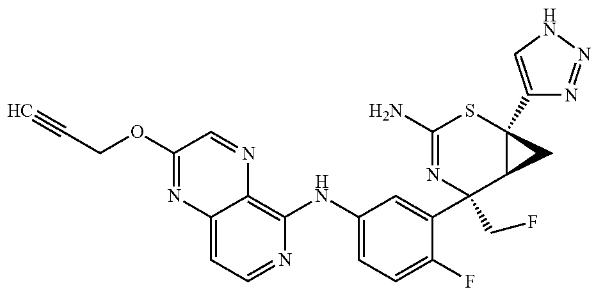 [SMILES: C#CCOc1cnc2c(Nc3ccc(F)c([C@@]4(CF)N=C(N)S[C@@]5(c6c[nH]nn6)C[C@@H]45)c3)nccc2n1] | 520.1 |
| 961 | 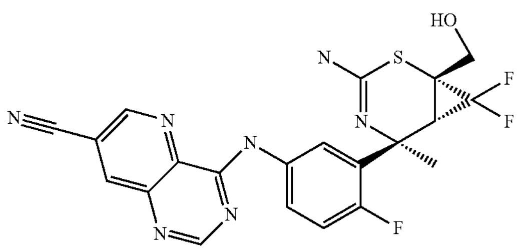 [SMILES: C[C@]1(c2cc(Nc3ncnc4cc(C#N)cnc34)ccc2F)N=C(N)S[C@@]2(CO)[C@@H]1C2(F)F] | 472 |

TABLE 3'

| Ex. No. | 1H-NMR | Chemical Name |
|---|---|---|
| 21 | 1H NMR (400 MHz, DMSO-d6) δ ppm 9.74 (s, 1 H), 9.23 (d, J = 1.96 Hz, 1 H), 9.00 (d, J = 1.96 Hz, 1 H), 8.34 (ddd, J = 12.96, 6.80, 2.74 Hz, 1 H), 8.27 (d, J = 5.87 Hz, 1 H), 7.91 (d, J = 5.35 Hz, 1 H), 7.27 (d, J = 5.67 Hz, 1 H), 5.96 (s, 2 H), 2.29-2.37 (m, 1 H), 1.69-1.80 (m, 1 H), 1.66 (s, 3 H), 0.89 (td, J = 8.12, 5.28 Hz, 1 H), 0.50 (q, J = 5.28 Hz, 1 H) | 8-((3-((1S,5S,6S)-3-amino-5-methyl-2-thia-4-azabicyclo[4.1.0]hept-3-en-5-yl)-4,5-difluorophenyl)amino)-1,7-naphthyridine-3-carbonitrile |
| 22 | 1H NMR (400 MHz, DMSO-d6) δ ppm 10.51 (s, 1 H) 8.96 (d, J = 2.35 Hz, 1 H) 8.75 (s, 1 H) 8.44 (d, J = 2.15 Hz, 1 H) 8.18 (ddd, J = 12.47, 6.80, 2.64 Hz, 1 H) 8.11-8.14 (m, 1 H) 6.28 (s, 2 H) 4.66-4.84 (m, 2 H) 2.40-2.47 (m, 1 H) 1.78 (q, J = 8.35 Hz, 1 H) 1.11 (ddd, J = 8.90, 7.53, 5.28 Hz, 1 H) 0.46 (q, J = 5.28 Hz, 1 H) | N-(3-((1S,5S,6S)-3-amino-5-(fluoromethyl)-2-thia-4-azabicyclo[4.1.0]hept-3-en-5-yl)-4,5-difluorophenyl)-7-chloropyrido[3,2-d]pyrimidin-4-amine |
| 24 | 1H NMR (400 MHz, CHLOROFORM-d) Shift 9.01 (s, 1H), 8.70 (d, J = 1.76 Hz, 1H), 8.41-8.55 (m, 1H), 8.16 (d, J = 5.87 Hz, 1H), 8.02 (d, J = 1.96 Hz, 1H), 7.40 (d, J = 3.52 Hz, 1H), 6.95 (d, J = 5.67 Hz, 1H), 3.69 (d, J = 10.76 Hz, 1H), 3.43 (s, 3H), 3.36 (d, J = 10.76 Hz, 1H), 1.78-1.90 (m, 1H), 1.75 (s, 3H), 0.92 (dd, J = 5.97, 9.29 Hz, 1H), 0.79-0.87 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-3-chloro-1,7-naphthyridin-8-amine |
| 25 | 1H NMR (400 MHz, DMSO-d6) δ 9.70 (s, 1H), 8.94 (d, J = 2.35 Hz, 1H), 8.56 (d, J = 2.15 Hz, 1H), 8.40-8.48 (m, 1H), 8.20 (d, J = 5.87 Hz, 1H), 7.93-7.99 (m, 1H), 7.23 (d, J = 5.67 Hz, 1H), 6.23 (s, 2H), 4.20 (q, J = 6.98 Hz, 2H), 2.35 (t, J = 8.61 Hz, 1H), 1.65 (s, 3H), 1.52 (dd, J = 4.99, 9.68 Hz, 1H), 1.24 (t, J = 7.14 Hz, 3H), 1.11 (dd, J = 5.09, 7.04 Hz, 1H) | ethyl (1S,5S,6S)-3-amino-5-(5-((3-chloro-1,7-naphthyridin-8-yl)amino)-2,3-difluorophenyl)-5-methyl-2-thia-4-azabicyclo[4.1.0]hept-3-ene-1-carboxylate |
| 26 | 1H NMR (400 MHz, DMSO-d6) δ ppm 9.82 (s, 1 H) 9.24 (d, J = 1.17 Hz, 1 H) 9.01 (d, J = 1.20 Hz, 1 H) 8.31-8.39 (m, 1 H) 8.28 (d, J = 5.67 Hz, 1 H) | 8-((3-((1S,5S,6S)-3-amino-5-(fluoromethyl)-2-thia-4-azabicyclo[4.1.0]hept-3-en-5- |

TABLE 3'-continued

| Ex. No. | ¹H-NMR | Chemical Name |
|---|---|---|
| | 7.98-8.03 (m, 1 H) 7.28 (d, J = 5.67 Hz, 1 H) 6.28 (s, 2 H) 4.65-4.84 (m, 2 H) 2.38-2.46 (m, 1 H) 1.73-1.82 (m, 1 H) 1.05-1.13 (m, 1 H) 0.42-0.49 (m, 1 H) | yl)-4,5-difluorophenyl)amino)-1,7-naphthyridine-3-carbonitrile |
| 27 | ¹H NMR (400 MHz, CHLOROFORM-d) 8.89-8.96 (m, 2 H) 8.39 (s, 1 H) 8.26-8.33 (m, 1 H) 8.22 (d, J = 5.87 Hz, 1 H) 7.38 (br. s., 1 H) 7.04 (d, J = 5.67 Hz, 1 H) 4.60-4.86 (m, 2 H) 2.17-2.24 (m, 1 H) 2.02-2.14 (m, 1 H) 1.07-1.21 (m, 2 H) | 8-((3-((1R,5S,6R)-3-amino-5-(fluoromethyl)-2-thia-4-azabicyclo[4.1.0]hept-3-en-5-yl)-4,5-difluorophenyl)amino)-1,7-naphthyridine-3-carbonitrile |
| 32 | ¹H NMR (400 MHz, CHLOROFORM-d) δ ppm 8.96 (s, 1 H), 8.47-8.56 (m, 2 H), 8.09 (d, J = 5.87 Hz, 1 H), 7.32-7.40 (m, 2 H), 7.13-7.20 (m, 1 H), 6.96 (d, J = 5.87 Hz, 1 H), 4.86 (d, J = 2.35 Hz, 2 H), 4.67 (br. s., 1 H), 2.62 (t, J = 2.45 Hz, 1 H), 2.17-2.28 (m, 1 H), 1.86-2.02 (m, 1 H), 1.74-1.85 (s, 3 H), 0.83-1.05 (m, 1 H) 0.64 (q, J = 5.80 Hz, 1 H) | N-(3-((1S,5S,6S)-3-amino-5-methyl-2-thia-4-azabicyclo[4.1.0]hept-3-en-5-yl)-4,5-difluorophenyl)-3-(2-propyn-1-yloxy)-1,7-naphthyridin-8-amine |
| 33 | ¹H NMR (400 MHz, DMSO-d6) δ 9.76 (s, 1H), 9.24 (d, J = 1.96 Hz, 1H), 9.01 (d, J = 1.96 Hz, 1H), 8.36 (m, 1H), 8.25 (m, 1H), 7.94 (m, 1H), 7.28 (d, J = 5.87 Hz, 1H), 6.03 (br., 2H), 3.58 (d, J = 10.95 Hz, 1H), 3.38 (m, 1H), 3.29 (s, 3H), 1.68 (m, 1H), 1.60 (s, 3H), 0.93 (dd, J = 5.18, 9.29 Hz, 1H), 0.67 (t, J = 5.77 Hz, 1H). | 8-((3-((1S,5S,6S)-3-amino-1-(methoxymethyl)-5-methyl-2-thia-4-azabicyclo[4.1.0]hept-3-en-5-yl)-4,5-difluorophenyl)amino)-1,7-naphthyridine-3-carbonitrile |
| 34 | ¹H NMR (400 MHz, DMSO-d6) δ ppm 10.43 (s, 1 H), 8.94 (d, J = 2.15 Hz, 1 H), 8.73 (s, 1 H), 8.42 (d, J = 2.15 Hz, 1 H), 8.13 (ddd, J = 12.42, 6.75, 2.74 Hz, 1 H), 8.04 (d, J = 5.91 Hz, 1 H), 5.94 (s, 2 H), 2.30-2.38 (m, 1 H), 1.70-1.76 (m, 1 H), 1.67 (s, 3 H), 0.90 (td, J = 8.17, 5.18 Hz, 1 H), 0.49 (q, J = 5.15 Hz, 1 H) | N-(3-((1S,5S,6S)-3-amino-5-methyl-2-thia-4-azabicyclo[4.1.0]hept-3-en-5-yl)-4,5-difluorophenyl)-7-chloropyrido[3,2-d]pyrimidin-4-amine |
| 35 | ¹H NMR (400 MHz, DMSO-d6) δ 10.46 (br., 1H), 8.96 (d, J = 2.15 Hz, 1H), 8.75 (s, 1H), 8.44 (d, J = 2.15 Hz, 1H), 8.16 (m, 1H), 8.07 (d, J = 5.84 Hz, 1H), 6.02 (br., 2H), 3.58 (d, J = 10.76 Hz, 1H), 3.39 (m, 1H), 3.32 (s, 3H), 1.69 (m, 1H), 1.65 (s, 3H), 0.94 (dd, J = 5.18, 9.29 Hz, 1H), 0.67 (t, J = 5.77 Hz, 1H). | N-(3-((1S,5S,6S)-3-amino-1-(methoxymethyl)-5-methyl-2-thia-4-azabicyclo[4.1.0]hept-3-en-5-yl)-4,5-difluorophenyl)-7-chloropyrido[3,2-d]pyrimidin-4-amine |
| 36 | ¹H NMR (400 MHz, DMSO-d6) δ ppm 10.58 (s, 1 H), 9.25 (d, J = 1.96 Hz, 1 H), 8.90 (d, J = 1.96 Hz, 1 H), 8.80 (s, 1 H), 8.05-8.16 (m, 2 H), 5.95 (s, 2 H), 2.30-2.37 (m, 1 H), 1.70-1.76 (m, 1 H), 1.67 (s, 3 H), 0.90 (td, J = 8.17, 5.38 Hz, 1 H), 0.49 (q, J = 5.28 Hz, 1 H) | 4-((3-((1S,5S,6S)-3-amino-5-methyl-2-thia-4-azabicyclo[4.1.0]hept-3-en-5-yl)-4,5-difluorophenyl)amino)pyrido[3,2-d]pyrimidine-7-carbonitrile |
| 38 | ¹H NMR (DMSO-d6) δ: 9.62 (s, 1H), 9.22 (d, J = 1.8 Hz, 1H), 8.98 (d, J = 2.0 Hz, 1H), 8.22 (d, J = 5.7 Hz, 1H), 8.07-8.16 (m, 2H), 7.22 (d, J = 5.9 Hz, 1H), 7.17 (dd, J = 11.8, 8.5 Hz, 1H), 6.24 (s, 2H), 4.74-4.86 (m, 1H), 4.61-4.74 (m, 1H), 2.35-2.43 (m, 1H), 1.77 (q, J = 7.8 Hz, 1H), 0.99-1.08 (m, 1H), 0.39 (q, J = 5.2 Hz, 1H) | 8-((3-((1S,5S,6S)-3-amino-5-(fluoromethyl)-2-thia-4-azabicyclo[4.1.0]hept-3-en-5-yl)-4-fluorophenyl)amino)-1,7-naphthyridine-3-carbonitrile |
| 39 | ¹H NMR (DMSO-d6) δ: 10.34 (s, 1H), 8.93 (d, J = 2.2 Hz, 1H), 8.67 (s, 1H), 8.39 (d, J = 2.0 Hz, 1H), 8.20 (dd, J = 7.0, 2.3 Hz, 1H), 7.78-7.99 (m, 1H), 7.21 (dd, J = 11.8, 8.7 Hz, 1H), 6.23 (s, 2H), 4.75-4.88 (m, 1H), 4.59-4.75 (m, 1H), 2.36-2.45 (m, 1H), 1.78 (q, J = 7.4 Hz, 1H), 1.05 (ddd, J = 8.9, 7.6, 5.2 Hz, 1H), 0.40 (q, J = 5.2 Hz, 1H) | N-(3-((1S,5S,6S)-3-amino-5-(fluoromethyl)-2-thia-4-azabicyclo[4.1.0]hept-3-en-5-yl)-4-fluorophenyl)-7-chloropyrido[3,2-d]pyrimidin-amine |
| 45 | ¹H NMR (400 MHz, DMSO-d6) δ ppm 9.49 (s, 1H), 8.92 (d, J = 2.35 Hz, 1H), 8.52 (d, J = 2.35 Hz, 1H), 8.13-8.19 (m, 2H), 8.10 (dd, J = 7.04, 2.74 Hz, 1H), 7.13-7.20 (m, 2H), 6.26 (s, 2H), 5.06 (t, J = 5.90 Hz, 1H), 4.78 (dd, J = 12.72, 8.80 Hz, 1H), 4.66 (dd, J = 12.91, 8.40 Hz, 1H), 3.56 (dd, J = 11.74, 6.06 Hz, 1H), 3.43 (dd, J = 11.64, 5.58 Hz, 1H), 1.67 (t, J = 8.20 Hz, 1H), 1.02 (dd, J = 9.19, 5.09 Hz, 1H), 0.53 (t, J = 5.70 Hz, 1H) | ((1S,5S,6S)-3-amino-5-(5-((3-chloro-1,7-naphthyridin-8-yl)amino)-2-fluorophenyl)-5-(fluoromethyl)-2-thia-4-azabicyclo[4.1.0]hept-3-en-1-yl)methanol |
| 46 | ¹H NMR (400 MHz, DMSO-d6) δ ppm 10.59 (s, 1 H), 9.25 (d, J = 1.96 Hz, 1 H), 8.90 (d, J = 1.96 Hz, 1 H), 8.80 (s, 1 H), 8.06-8.17 (m, 2 H), 6.01 (br. s., 2 H), 3.57 (d, J = 10.95 Hz, 1 H), 3.36 (d, J = 10.95 Hz, 1 H), 3.30 (s, 3 H), 1.60-1.68 (m, 4 H), 0.93 (dd, J = 9.19, 5.28 Hz, 1 H), 0.65 (t, J = 5.77 Hz, 1 H) | 4-((3-((1S,5S,6S)-3-amino-1-(methoxymethyl)-5-methyl-2-thia-4-azabicyclo[4.1.0]hept-3-en-5-yl)-4,5-difluorophenyl)amino)pyrido[3,2-d]pyrimidine-7-carbonitrile |
| 47 | ¹H NMR (400 MHz, DMSO-d6) δ ppm 9.84 (s, 1 H) 9.25 (d, J = 1.96 Hz, 1 H) 9.02 (d, J = 1.96 Hz, 1 H) 8.37 (ddd, J = 13.11, 6.85, 2.74 Hz, 1 H) 8.29 (d, J = 5.67 Hz, 1 H) 8.01-8.04 (m, 1 H) 7.30 (d, J = 5.87 Hz, 1 H) 6.35 (s, 2 H) 4.62-4.80 (m, 2 H) 3.58 (d, J = 10.95 Hz, 1 H) 3.37 (d, J = 10.95 Hz, 1 H) 3.31 (s, 3 H) 1.66-1.72 (m, 1 H) 1.15 (dd, J = 9.49, 5.18 Hz, 1 H) 0.67 (t, J = 5.87 Hz, 1 H) | 8-((3-((1S,5S,6S)-3-amino-5-(fluoromethyl)-1-(methoxymethyl)-2-thia-4-azabicyclo[4.1.0]hept-3-en-5-yl)-4,5-difluorophenyl)amino)-1,7-naphthyridine-3-carbonitrile |

TABLE 3'-continued

| Ex. No. | ¹H-NMR | Chemical Name |
|---|---|---|
| 48 | ¹H NMR (400 MHz, DMSO-d6) δ ppm 9.84 (br. s., 1 H) 9.24 (d, J = 1.17 Hz, 1 H) 9.01 (d, J = 1.17 Hz, 1 H) 8.37 (ddd, J = 12.91, 6.50, 2.15 Hz, 1 H) 8.28 (d, J = 5.67 Hz, 1 H) 8.02 (br. s., 1 H) 7.29 (d, J = 5.67 Hz, 1 H) 6.30 (br. s., 2 H) 5.10 (br. s., 1 H) 4.59-4.86 (m, 2 H) 3.55 (dd, J = 11.54, 6.06 Hz, 1 H) 3.45 (dd, J = 11.35, 5.28 Hz, 1 H) 1.68 (br. s., 1 H) 1.09 (br. s., 1 H) 0.60 (br. s., 1 H) | 8-((3-((1S,5S,6S)-3-amino-5-(fluoromethyl)-1-(hydroxymethyl)-2-thia-4-azabicyclo[4.1.0]hept-3-en-5-yl)-4,5-fluorophenyl)amino)-7-naphthyridine-3-carbonitrile |
| 49 | ¹H NMR (400 MHz, CHLOROFORM-d) δ ppm 9.00 (s, 1H), 8.72 (s, 1H), 8.68 (d, J = 2.15 Hz, 1H), 8.12-8.20 (m, 2H), 7.79 (dd, J = 6.65, 2.74 Hz, 1H), 7.13 (dd, J = 11.35, 8.80 Hz, 1H), 4.93 (dd, J = 46.56, 8.41 Hz, 1H), 4.79 (s br, 2H), 4.70 (dd, J = 47.34, 8.41 Hz, 1H), 3.76 (d, J = 11.93 Hz, 1H), 3.62 (d, J = 11.74 Hz, 1H), 1.85 (t, J = 7.92 Hz, 1H), 1.84 (s br, 1H), 1.10 (dd, J = 9.59, 5.87 Hz, 1H), 0.72 (t, J = 6.26 Hz, 1H) | ((1S,5S,6S)-3-amino-5-(5-((7-chloropyrido[3,2-d]pyrimidin-4-yl)amino)-2-fluorophenyl)-5-(fluoromethyl)-2-thia-4-azabicyclo[4.1.0]hept-3-en-1-yl)methanol |
| 50 | ¹H NMR (400 MHz, DMSO-d6) δ ppm 9.63 (s, 1H), 9.23 (d, J = 1.96 Hz, 1H), 8.99 (d, J = 1.96 Hz, 1H), 8.23 (d, J = 5.67 Hz, 1H), 8.11-8.17 (m, 2H), 7.23 (d, J = 5.86 Hz, 1H), 7.18 (dd, J = 11.74, 9.00 Hz, 1H), 6.26 (s, 2H), 5.06 (t, J = 5.97 Hz, 1H), 4.78 (dd, J = 13.11, 9.00 Hz, 1H), 4.66 (dd, J = 14.08, 9.00 Hz, 1H), 3.56 (dd, J = 11.35, 6.26 Hz, 1H), 3.43 (dd, J = 11.93, 5.67 Hz, 1H), 1.66 (t, J = 8.60 Hz, 1H), 1.02 (dd, J = 9.39, 4.30 Hz, 1H), 0.53 (t, J = 5.70 Hz, 1H) | 8-((3-((1S,5S,6S)-3-amino-5-(fluoromethyl)-1-(hydroxymethyl)-2-thia-4-azabicyclo[4.1.0]hept-3-en-5-yl)-4-fluorophenyl)amino)-1,7-naphthyridine-3-carbonitrile |
| 51 | ¹H NMR (DMSO-d6) δ: 10.50 (s, 1H), 9.25 (d, J = 1.8 Hz, 1H), 8.88 (d, J = 2.0 Hz, 1H), 8.74 (s, 1H), 8.23 (dd, J = 7.2, 2.7 Hz, 1H), 7.88-8.00 (m, 1H), 7.23 (dd, J = 11.7, 8.8 Hz, 1H), 6.23 (s, 2H), 4.75-4.87 (m, 1H), 4.64-4.75 (m, 1H), 2.37-2.46 (m, 1H), 1.73-1.86 (m, 1H), 1.05 (ddd, J = 9.0, 7.5, 5.2 Hz, 1H), 0.40 (q, J = 5.3 Hz, 1H) | 4-((3-((1S,5S,6S)-3-amino-5-(fluoromethyl)-2-thia-4-azabicyclo[4.1.0]hept-3-en-5-yl)-4-fluorophenyl)amino)pyrido[3,2-d]pyrimidine-7-carbonitrile |
| 52 | ¹H NMR (400 MHz, CHLOROFORM-d) δ ppm 8.89 (s, 1H), 8.52 (d, J = 2.74 Hz, 1H), 8.26 (dt, J = 8.36, 3.74 Hz, 1H), 8.05 (d, J = 5.67 Hz, 1H), 7.69 (dd, J = 6.85, 2.74 Hz, 1H), 7.37 (d, J = 2.74 Hz, 1H), 7.09 (dd, J = 11.54, 8.80 Hz, 1H), 6.92 (d, J = 5.87 Hz, 1H), 4.97 (dd, J = 47.34, 8.41 Hz, 1H), 4.85 (d, J = 2.35 Hz, 2H), 4.67 (s br, 2H), 4.66 (dd, J = 47.34, 8.61 Hz, 1H), 3.75 (d, J = 11.74 Hz, 1H), 3.60 (d, J = 11.93 Hz, 1H), 2.62 (t, J = 2.35 Hz, 1H), 1.86 (t, J = 8.20 Hz, 1H), 1.75 (s br, 1H), 1.08 (dd, J = 9.68, 5.77 Hz, 1H), 0.73 (t, J = 6.26 Hz, 1H) | ((1S,5S,6S)-3-amino-5-(2-fluoro-5-((3-(2-propyn-1-yloxy)-1,7-naphthyridin-8-yl)amino)phenyl)-2-thia-4-azabicyclo[4.1.0]hept-3-en-1-yl)methanol |
| 55 | ¹H NMR (400 MHz, DMSO-d6) δ 10.65 (br., 1H), 9.32 (d, J = 1.76 Hz, 1H), 8.96 (d, J = 1.96 Hz, 1H), 8.86 (s, 1H), 8.12-8.23 (m, 2H), 6.02 (br., 2H), 5.10 (t, J = 5.97 Hz, 1H), 3.60 (m, 1H), 3.51 (m, 1H), 1.65-1.73 (m, 4H), 0.94 (m, 1H), 0.63 (t, J = 5.67 Hz, 1H). | 4-((3-((1S,5S,6S)-3-amino-1-(hydroxymethyl)-5-methyl-2-thia-4-azabicyclo[4.1.0]hept-3-en-5-yl)-4,5-difluorophenyl)amino)pyrido[3,2-d]pyrimidine-7-carbonitrile |
| 56 | ¹H NMR (DMSO-d6) δ: 9.41 (s, 1H), 8.66 (s, 1H), 8.26 (d, J = 5.9 Hz, 1H), 8.23 (d, J = 0.8 Hz, 1H), 7.99-8.14 (m, 2H), 7.32 (d, J = 0.8 Hz, 1H), 7.15 (dd, J = 11.7, 8.8 Hz, 1H), 7.06 (d, J = 5.9 Hz, 1H), 6.23 (s, 2H), 5.68 (s, 2H), 4.75-4.88 (m, 1H), 4.61-4.74 (m, 1H), 2.36-2.45 (m, 1H), 1.77 (q, J = 7.5 Hz, 1H), 1.04 (ddd, J = 9.0, 7.4, 5.1 Hz, 1H), 0.39 (q, J = 5.1 Hz, 1H) | N-(3-((1S,5S,6S)-3-amino-5-(fluoromethyl)-2-thia-4-azabicyclo[4.1.0]hept-3-en-5-yl)-4-fluorophenyl)-2-(1,3-oxazol-2-ylmethoxy)pyrido[3,4-b]pyrazin-5-amine |
| 57 | ¹H NMR (DMSO-d6) δ 9.89 (s, 1 H) 9.25 (d, J = 1.96 Hz, 1 H) 9.03 (d, J = 1.96 Hz, 1 H) 8.28 (d, J = 5.67 Hz, 1 H) 8.15-8.22 (m, 2 H) 7.31 (d, J = 5.87 Hz, 1 H) 6.24 (s, 2 H) 5.13 (t, J = 5.77 Hz, 1 H) 4.80 (dd, J = 48.12, 9.39 Hz, 1 H) 4.51 (dd, J = 47.34, 9.19 Hz, 1 H) 3.77 (dd, J = 11.74, 6.65 Hz, 1 H) 3.56 (dd, J = 11.83, 5.18 Hz, 1 H) 1.89 (dd, J = 9.19, 6.06 Hz, 1 H) 1.08 (dd, J = 9.39, 5.28 Hz, 1 H) 0.93 (t, J = 5.58 Hz, 1 H) | 8-((3-((1R,5S,6R)-3-amino-5-(fluoromethyl)-1-(hydroxymethyl)-2-thia-4-azabicyclo[4.1.0]hept-3-en-5-yl)-4,5-difluorophenyl)amino)-1,7-naphthyridine-3-carbonitrile |
| 58 | ¹H NMR (400 MHz, DMSO-d6) δ 10.13 (br., 1H), 8.67 (m, 2H), 8.21 (m, 1H), 8.02 (br., 1H), 7.64 (br., 1H), 5.98 (br., 2H), 5.05 (t, J = 5.38 Hz, 1H), 4.02 (s, 3H), 3.56 (m, 1H), 3.46 (m, 1H), 1.66 (m, 1H), 1.63 (s, 3H), 0.90 (m, 1H), 0.60 (m, 1H). | ((1S,5S,6S)-3-amino-5-(2,3-difluoro-5-((7-methoxypyrido[3,2-d]pyrimidin-4-yl)amino)phenyl)-5-methyl-2-thia-4-azabicyclo[4.1.0]hept-3-en-1-yl)methanol |
| 65 | ¹H NMR (400 MHz, DMSO-d6) δ ppm 10.12 (s, 1 H), 8.66 (s, 1 H), 8.64 (s, 1 H) 8.18 (ddd, J = 12.62, 6.75, 2.74 Hz, 1 H), 7.98-8.03 (m, 1 H), 7.62 (d, J = 2.74 Hz, 1 H), 6.00 (s, 2 H), 4.01 (s, 3 H), 3.57 (d, J = 10.95 Hz, 1 H), 3.32-3.38 (m, 1 H), 3.30 (s, 3H), 1.58-1.68 (m, 4 H), 0.92 (dd, J = 9.29, 5.18 Hz, 1 H), 0.66 (t, J = 5.77 Hz, 1 H) | N-(3-((1S,5S,6S)-3-amino-1-(methoxymethyl)-5-methyl-2-thia-4-azabicyclo[4.1.0]hept-3-en-5-yl)-4,5-difluorophenyl)-7-methoxypyrido[3,2-d]pyrimidin-4-amine |

TABLE 3'-continued

| Ex. No. | ¹H-NMR | Chemical Name |
|---|---|---|
| 66 | ¹H NMR (400 MHz, DMSO-d6) δ ppm 10.19 (s, 1 H) 8.69 (s, 1H) 8.66 (d, J = 2.74 Hz, 1 H) 8.21 (ddd, J = 12.72, 6.85, 2.74 Hz, 1 H) 8.07-8.11 (m, 1 H) 7.64 (d, J = 2.74 Hz, 1 H) 6.27 (s, 2H) 4.66-4.84 (m, 2 H) 4.02 (s, 3 H) 2.40-2.46 (m, 1 H) 1.78 (m, J = 7.69, 7.69, 7.69 Hz, 1 H) 1.11 (ddd, J = 8.90, 7.53, 5.09 Hz, 1 H) 0.46 (q, J = 5.28 Hz, 1 H) | N-(3-((1S,5S,6S)-3-amino-5-(fluoromethyl)-2-thia-4-azabicyclo[4.1.0]hept-3-en-5-yl)-4,5-difluorophenyl)-7-methoxypyrido[3,2-d]pyrimidin-4-amine |
| 67 | ¹H NMR (DMSO-d6) δ: 9.45 (s, 1H), 9.30 (d, J = 2.2 Hz, 1H), 9.14 (s, 1H), 8.85 (d, J = 2.3 Hz, 1H), 8.17-8.26 (m, 1H), 7.98 (dd, J = 7.0, 2.7 Hz, 1H), 7.20 (dd, J = 11.8, 8.9 Hz, 1H), 6.18 (s, 2H), 4.76-4.87 (m, 1H), 4.63-4.75 (m, 1H), 2.35-2.44 (m, 1H), 1.74-1.85 (m, 1H), 0.97-1.07 (m, 1H), 0.44 (q, J = 5.2 Hz, 1H) | N-(3-((1S,5S,6S)-3-amino-5-(fluoromethyl)-2-thia-4-azabicyclo[4.1.0]hept-3-en-5-yl)-4-fluorophenyl)-3-bromopyrido[2,3-d]pyridazin-8-amine |
| 73 | ¹H NMR (DMSO-d6) δ: 10.35 (s, 1H), 8.94 (d, J = 2.3 Hz, 1H), 8.68 (s, 1H), 8.41 (d, J = 2.3 Hz, 1H), 8.22 (dd, J = 7.2, 2.7 Hz, 1H), 7.95 (dt, J = 8.8, 3.4 Hz, 1H), 7.22 (dd, J = 11.7, 8.8 Hz, 1H), 6.29 (s, 2H), 4.50-4.92 (m, 2H), 3.34-3.64 (m, 2H), 3.30 (s, 3H), 1.60-1.82 (m, 1H), 1.10 (dd, J = 9.5, 5.2 Hz, 1H), 0.60 (t, J = 5.9 Hz, 1H) | N-(3-((1S,5S,6S)-3-amino-5-(fluoromethyl)-1-(methoxymethyl)-2-thia-4-azabicyclo[4.1.0]hept-3-en-5-yl)-4-fluorophenyl)-7-chloropyrido[3,2-d]pyrimidin-4-amine |
| 80 | ¹H NMR (400 MHz, CHLOROFORM-d) δ ppm 9.09 (s, 1H), 8.92 (d, J = 1.76 Hz, 1H), 8.80 (s, 1H), 8.48 (d, J = 1.76 Hz, 1H), 8.19 (dt, J = 8.56, 3.55 Hz, 1H), 7.82 (dd, J = 6.65, 2.74 Hz, 1H), 7.16 (dd, J = 11.25, 8.90 Hz, 1H), 4.92 (dd, J = 47.14, 8.61 Hz, 1H), 4.78 (s br, 2H), 4.71 (dd, J = 47.54, 8.61 Hz, 1H), 3.76 (d, J = 11.93 Hz, 1H), 3.62 (d, J = 11.74 Hz, 1H), 1.85 (t, J = 8.02 Hz, 1H), 1.65 (s br, 1H), 1.10 (dd, J = 9.59, 5.87 Hz, 1H), 0.72 (t, J = 6.26 Hz, 1H) | 4-((3-((1S,5S,6S)-3-amino-5-(fluoromethyl)-1-(hydroxymethyl)-2-thia-4-azabicyclo[4.1.0]hept-3-en-5-yl)-4-fluorophenyl)amino)pyrido[3,2-d]pyrimidine-7-carbonitrile |
| 82 | ¹H NMR (400 MHz, DMSO-d6) δ 9.55 (br., 1H), 8.64 (s, 1H), 8.28-8.35 (m, 2H), 7.91 (d, J = 5.67 Hz, 1H), 7.14 (d, J = 5.87 Hz, 1H), 5.97 (br. s., 2H), 5.21 (d, J = 2.35 Hz, 2H), 5.05 (t, J = 5.77 Hz, 1H), 3.68 (t, J = 2.35 Hz, 1H), 3.56 (dd, J = 6.26, 11.54 Hz, 1H), 3.46 (dd, J = 5.67, 11.74 Hz, 1H), 1.68 (m, 1H), 1.63 (s, 3H), 0.89 (m, 1H), 0.60 (m, 1H). | ((1S,5S,6S)-3-amino-5-(2,3-difluoro-5-((2-(2-propyn-1-yloxy)pyrido[3,4-b]pyrazin-5-yl)amino)phenyl)-5-methyl-2-thia-4-azabicyclo[4.1.0]hept-3-en-1-yl)methanol |
| 87 | ¹H NMR (CHLOROFORM-d) δ: 9.02 (s, 1H), 8.90 (s, 1H), 8.41 (d, J = 5.9 Hz, 1H), 7.95-8.04 (m, 2H), 7.32 (d, J = 6.1 Hz, 1H), 7.15 (dd, J = 11.1, 9.1 Hz, 1H), 4.80-5.15 (m, 2H), 2.41-2.72 (m, 1H), 2.14-2.38 (m, 1H), 1.28-1.49 (m, 1H), 0.69 (q, J = 5.9 Hz, 1H) | N-(3-((1S,5S,6S)-3-amino-5-(fluoromethyl)-2-thia-4-azabicyclo[4.1.0]hept-3-en-5-yl)-4-fluorophenyl)-2-(trifluoromethyl)pyrido[3,4-b]pyrazin-5-amine |
| 88 | ¹H NMR (DMSO-d6) δ: 10.00 (s, 1H), 8.63 (d, J = 2.5 Hz, 1H), 8.60 (s, 1H), 8.17 (dd, J = 7.0, 2.7 Hz, 1H), 7.91-8.01 (m, 1H), 7.61 (d, J = 2.7 Hz, 1H), 7.19 (dd, J = 11.8, 8.9 Hz, 1H), 6.22 (s, 2H), 4.74-4.85 (m, 1H), 4.63-4.73 (m, 1H), 4.01 (s, 3H), 2.34-2.44 (m, 1H), 1.77 (q, J = 8.0 Hz, 1H), 0.99-1.10 (m, 1H), 0.39 (q, J = 5.3 Hz, 1H) | N-(3-((1S,5S,6S)-3-amino-5-(fluoromethyl)-2-thia-4-azabicyclo[4.1.0]hept-3-en-5-yl)-4-fluorophenyl)-7-methoxypyrido[3,2-d]pyrimidin-4-amine |
| 89 | ¹H NMR (400 MHz, CHLOROFORM-d) Shift 8.96 (s, 1H), 8.43-8.57 (m, 2H), 8.09 (d, J = 5.87 Hz, 1H), 7.31-7.41 (m, 1H), 7.25 (d, J = 2.74 Hz, 1H), 6.96 (d, J = 5.67 Hz, 1H), 3.98 (s, 3H), 3.66-3.76 (m, 2H), 3.50 (s, 1H), 1.82-1.87 (m, 1H), 1.76 (s, 3H), 0.92 (dd, J = 6.06, 9.19 Hz, 1H), 0.81 (t, J = 6.26 Hz, 1H) | ((1S,5S,6S)-3-amino-5-(2,3-difluoro-5-((3-methoxy-1,7-naphthyridin-8-yl)amino)phenyl)-5-methyl-2-thia-4-azabicyclo[4.1.0]hept-3-en-1-yl)methanol |
| 90 | ¹H NMR (400 MHz, DMSO-d6) δ ppm 9.80 (s, 1 H) 9.25 (d, J = 1.96 Hz, 1 H) 9.02 (d, J = 1.96 Hz, 1 H) 8.27 (d, J = 5.67 Hz, 1 H) 8.18-8.25 (m, 1 H) 8.15-8.18 (m, 1 H) 7.30 (d, J = 5.67 Hz, 1 H) 6.29 (s, 2 H) 4.44-4.87 (m, 2 H) 3.72 (d, J = 10.95 Hz, 1 H) 3.49 (d, J = 10.95 Hz, 1 H) 3.29 (s, 3 H) 1.92 (dd, J = 9.00, 6.26 Hz, 1 H) 1.10 (dd, J = 9.39, 5.48 Hz, 1 H) 1.01 (t, J = 5.70 Hz, 1 H) | 8-((3-((1R,5S,6R)-3-amino-5-(fluoromethyl)-1-(methoxymethyl)-2-thia-4-azabicyclo[4.1.0]hept-3-en-5-yl)-4,5-difluorophenyl)amino)-1,7-naphthyridine-3-carbonitrile |
| 91 | ¹H NMR (400 MHz, CHLOROFORM-d) Shift 8.78 (s, 1H), 8.55 (d, J = 2.74 Hz, 1H), 8.42 (ddd, J = 2.74, 6.85, 12.72 Hz, 1H), 7.99 (d, J = 1.56 Hz, 1H), 7.48 (d, J = 2.93 Hz, 1H), 7.31-7.40 (m, 1H), 3.98-4.05 (m, 3H), 3.65-3.79 (m, 2H), 3.50 (s, 1H), 1.81-1.88 (m, 1H), 1.76 (s, 3H), 0.92 (dd, J = 5.87, 9.39 Hz, 1H), 0.80 (t, J = 6.16 Hz, 1H) | ((1S,5S,6S)-3-amino-5-(2,3-difluoro-5-((5-fluoro-3-methoxy-1,7-naphthyridin-8-yl)amino)phenyl)-5-methyl-2-thia-4-azabicyclo[4.1.0]hept-3-en-1-yl)methanol |
| 92 | ¹H NMR (400 MHz, CHLOROFORM-d) Shift 9.07 (s, 1H), 8.79 (s, 1H), 8.72 (d, J = 2.15 Hz, 1H), 8.37-8.50 (m, 1H), 8.18 (d, J = 2.15 Hz, 1H), 7.44-7.57 (m, 1H), 3.61-3.81 (m, 2H), 1.84-1.90 (m, 1H), 1.76 (s, 3H), 0.92 (dd, J = 5.97, 9.10 Hz, 1H), 0.80 (t, J = 6.16 Hz, 1H) | ((1S,5S,6S)-3-amino-5-(5-((7-chloropyrido[3,2-d]pyrimidin-4-yl)amino)-2,3-difluorophenyl)-5-methyl-2-thia-4-azabicyclo[4.1.0]hept-3-en-1-yl)methanol |
| 95 | ¹H NMR (400 MHz, DMSO-d6) δ 10.64 (br., 1H), 9.27 (d, J = 1.96 Hz, 1H), 8.92 (d, J = 1.96 Hz, 1H), | 4-((3-((1S,5S,6S)-3-amino-1-(difluoromethyl)-5-methyl-2- |

TABLE 3'-continued

| Ex. No. | ¹H-NMR | Chemical Name |
|---|---|---|
| | 8.82 (s, 1H), 8.07-8.16 (m, 2H), 6.35 (s, 2H), 5.81-6.09 (m, 1H), 1.94 (m, 1H), 1.70 (s, 3H), 1.39 (m, 1H), 0.77 (m, 1H). | thia-4-azabicyclo[4.1.0]hept-3-en-5-yl)-4,5-difluorophenyl)amino)pyrido[3,2-d]pyrimidine-7-carbonitrile |
| 101 | ¹H NMR (300 MHz, CHLOROFORM-d) δ ppm 1.77 (s, 3 H) 2.67-2.80 (m, 1 H) 2.91-3.02 (m, 1 H) 4.66 (br., 2 H) 7.16-7.24 (m, 1 H) 7.86-7.94 (m, 1 H) 8.22-8.33 (m, 1 H) 8.47-8.57 (m, 1 H) 8.82-8.89 (m, 1 H) 8.92-9.00 (m, 1 H) 9.12-9.23 (m, 1 H) | 4-((3-((1R,5S,6R)-3-amino-7,7-difluoro-5-methyl-2-thia-4-azabicyclo[4.1.0]hept-3-en-5-yl)-4-fluorophenyl)amino)pyrido[3,2-d]pyrimidine-7-carbonitrile |
| 601 | ¹H NMR (300 MHz, CHLOROFORM-d) δ 8.92-8.96 (m, 1H), 8.58 (s, 1H), 8.35-8.41 (m, 2H), 8.29 (d, J = 5.99 Hz, 1H), 7.11 (d, J = 5.85 Hz, 1H), 5.18 (d, J = 2.34 Hz, 2H), 4.44-4.59 (m, 2H), 4.28-4.44 (m, 2H), 2.59 (t, J = 2.41 Hz, 1H), 1.88-2.02 (m, 1H), 1.76 (s, 3H), 1.03 (dd, J = 6.14, 9.50 Hz, 1H), 0.80-0.96 (m, 1H). | N-(5-((1S,5S,6S)-3-amino-1-(fluoromethyl)-5-methyl-2-thia-4-azabicyclo[4.1.0]hept-3-en-5-yl)-6-fluoro-3-pyridinyl)-2-(2-propyn-1-yloxy)pyrido[3,4-b]pyrazin-5-amine |
| 602 | ¹H NMR (300 MHz, CHLOROFORM-d) δ 8.92-8.96 (m, 1H), 8.58 (s, 1H), 8.33-8.44 (m, 2H), 8.29 (d, J = 5.99 Hz, 1H), 7.75 (d, J = 0.73 Hz, 1H), 7.21 (s, 1H), 7.02-7.16 (m, 1H), 5.67 (s, 2H), 4.46-4.58 (m, 1H), 4.28-4.43 (m, 1H), 3.75-5.00 (br. s, 2H), 1.94-2.03 (m, 1H), 1.76 (d, J = 1.02 Hz, 3H), 0.94-1.08 (m, 1H), 0.81-0.92 (m, 1H). | N-(5-((1S,5S,6S)-3-amino-1-(fluoromethyl)-5-methyl-2-thia-4-azabicyclo[4.1.0]hept-3-en-5-yl)-6-fluoro-3-pyridinyl)-2-(1,3-oxazol-2-ylmethoxy)pyrido[3,4-b]pyrazin-5-amine |
| 604 | ¹H NMR (300 MHz, CHLOROFORM-d) δ 8.92-9.04 (m, 3H), 8.40-8.47 (m, 2H), 8.29 (d, J = 5.70 Hz, 1H), 7.09 (d, J = 5.85 Hz, 1H), 4.45-4.60 (m, 1H), 4.30-4.43 (m, 1H), 3.75-5.00 (br. s, 2H), 1.90-2.12 (m, 1H), 1.82 (s, 3H), 1.11 (dd, J = 6.28, 9.50 Hz, 1H), 0.82-1.01 (m, 1H). | 8-((5-((1S,5S,6S)-3-amino-1-(fluoromethyl)-5-methyl-2-thia-4-azabicyclo[4.1.0]hept-3-en-5-yl)-6-fluoro-3-pyridinyl)amino)-1,7-naphthyridine-3-carbonitrile |
| 605 | ¹H NMR (400 MHz, CHLOROFORM-d) δ 8.92 (s, 1H), 8.89 (s, 1H), 8.74 (s, 1H), 8.59 (s, 1H), 8.45 (dd, J = 2.45, 8.51 Hz, 1H), 7.74 (s, 1H), 7.61-7.64 (m, 1H), 7.21 (s, 1H), 5.33 (s, 2H), 4.49 (q, J = 10.30 Hz, 1H), 4.37 (q, J = 10.30 Hz, 1H), 4.25-4.75 (br. s, 2H), 1.96 (t, J = 8.12 Hz, 1H), 1.74 (s, 3H), 1.01 (dd, J = 6.36, 9.29 Hz, 1H), 0.79-0.92 (m, 1H). | N-(5-((1S,5S,6S)-3-amino-1-(fluoromethyl)-5-methyl-2-thia-4-azabicyclo[4.1.0]hept-3-en-5-yl)-6-fluoro-3-pyridinyl)-7-(1,3-oxazol-2-ylmethoxy)pyrido[3,2-d]pyrimidin-4-amine |
| 608 | ¹H NMR (300 MHz, CHLOROFORM-d) δ 8.91 (s, 1H), 8.79-8.88 (m, 1H), 8.64-8.77 (m, 1H), 8.50-8.62 (m, 1H), 8.44 (dd, J = 2.78, 8.62 Hz, 1H), 7.68-7.82 (m, 1H), 7.50-7.67 (m, 1H), 7.10-7.25 (m, 1H), 5.32 (s, 2H), 4.33-5.09 (m, 2H), 2.56-2.90 (m, 2H), 1.96 (dd, J = 7.16, 9.06 Hz, 1H), 1.61-1.81 (m, 3H), 0.99 (dd, J = 6.36, 9.57 Hz, 1H), 0.81-0.94 (m, 1H) | ((1R,5S,6S)-3-amino-5-(2-fluoro-5-((7-(1,3-oxazol-2-ylmethoxy)pyrido[3,2-d]pyrimidin-4-yl)amino)-3-pyridinyl)-5-methyl-2-thia-4-azabicyclo[4.1.0]hept-3-en-1-yl)acetonitrile |
| 611 | ¹H NMR (300 MHz, CHLOROFORM-d) δ 8.84-8.99 (m, 1H), 8.37 (s, 2H), 8.18-8.31 (m, 1H), 7.99-8.19 (m, 1H), 6.95-7.09 (m, 1H), 5.17 (d, J = 2.34 Hz, 2H), 4.45-4.63 (m, 1H), 4.27-4.44 (m, 1H), 4.05 (s, 3H), 2.48-2.63 (m, 1H), 2.12-2.25 (m, 1H), 1.78 (s, 3H) 1.28 (br. s, 2H), 0.94-1.05 (m, 1H), 0.73-0.85 (m, 1H) | N-(5-((1S,5S,6S)-3-amino-1-(fluoromethyl)-5-methyl-2-thia-4-azabicyclo[4.1.0]hept-3-en-5-yl)-6-methoxy-3-pyridinyl)-2-(2-propyn-1-yloxy)pyrido[3,4-b]pyrazin-5-amine |
| 613 | ¹H NMR (300 MHz, CHLOROFORM-d) δ 8.81-9.06 (m, 1H), 8.56 (s, 1H), 8.33-8.44 (m, 2H), 8.27 (d, J = 5.99 Hz, 1H), 7.10 (d, J = 5.85 Hz, 1H), 4.45-4.64 (m, 1H), 4.26-4.44 (m, 1H), 3.50-5.00 (br. s., 2H), 1.85-2.02 (m, 1H), 1.60-1.82 (m, 3H), 1.03 (dd, J = 6.14, 9.50 Hz, 1H), 0.76-0.96 (m, 1H). | N-(5-((1S,5S,6S)-3-amino-1-(fluoromethyl)-5-methyl-2-thia-4-azabicyclo[4.1.0]hept-3-en-5-yl)-6-fluoro-3-pyridinyl)-2-((~2~H_5_)-2-butyn-1-yloxy)pyrido[3,4-b]pyrazin-5-amine |
| 625 | ¹H NMR (300 MHz, CHLOROFORM-d) δ 8.72-8.83 (m, 2H), 8.65 (s, 1H), 8.39-8.56 (m, 1H), 8.10-8.22 (m, 1H), 7.48-7.58 (m, 1H), 5.29 (s, 1H), 4.85 (s, 2H), 4.25-4.61 (m, 3H), 4.03 (s, 3H), 2.63 (s, 1H), 1.94-2.25 (m, 1H), 1.73 (s, 3H), 0.92 (dd, J = 6.07, 9.43 Hz, 1H), 0.71-0.82 (m, 1H) | N-(5-((1S,5S,6S)-3-amino-1-(fluoromethyl)-5-methyl-2-thia-4-azabicyclo[4.1.0]hept-3-en-5-yl)-6-methoxy-3-pyridinyl)-7-(2-propyn-1-yloxy)pyrido[3,2-d]pyrimidin-4-amine |
| 626 | ¹H NMR (300 MHz, CHLOROFORM-d) δ 8.92 (d, J = 2.19 Hz, 1H), 8.40 (s, 2H), 8.24 (d, J = 5.85 Hz, 1H), 8.12 (d, J = 2.19 Hz, 1H), 7.74 (s, 1H), 7.21 (s, 1H), 7.03 (d, J = 5.85 Hz, 1H), 5.66 (s, 2H), 4.46-4.59 (m, 1H), 4.19-4.43 (m, 3H), 4.05 (s, 3H), 2.15-2.24 (m, 1H), 1.77 (s, 3H), 0.98 (dd, J = 6.07, 9.43 Hz, 1H), 0.75-0.88 (m, 1H) | N-(5-((1S,5S,6S)-3-amino-1-(fluoromethyl)-5-methyl-2-thia-4-azabicyclo[4.1.0]hept-3-en-5-yl)-6-methoxy-3-pyridinyl)-2-(1,3-oxazol-2-ylmethoxy)pyrido[3,4-b]pyrazin-5-amine |
| 627 | ¹H NMR (400 MHz, CHLOROFORM-d) δ 8.67 (s, 1H), 8.45 (ddd, J = 2.84, 6.85, 12.62 Hz, 1H), 8.36 (s, 1H), 8.28 (d, J = 5.87 Hz, 1H), 7.34-7.38 (m, 1H), 7.08 (d, J = 5.87 Hz, 1H), 5.16 (d, J = 2.54 Hz, 2H), 3.65-3.72 (m, 1H), 3.43 (s, 3H), 3.36 (d, J = 10.56 Hz, 1H), 2.52-2.61 (m, 1H), 1.79-1.85 (m, 1H), 1.75 (s, 3H), 0.92 (dd, J = 5.87, 9.39 Hz, 1H), 0.78-0.86 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-2-(2-propyn-1-yloxy)pyrido[3,4-b]pyrazin-5-amine |

TABLE 3'-continued

| Ex. No. | ¹H-NMR | Chemical Name |
|---|---|---|
| 628 | ¹H NMR (400 MHz, CHLOROFORM-d) δ 8.67 (s, 1H), 8.46 (ddd, J = 2.74, 6.90, 12.67 Hz, 1H), 8.32-8.39 (m, 1H), 8.28 (d, J = 5.87 Hz, 1H), 7.95 (s, 1H), 7.85 (s, 1H), 7.32-7.39 (m, 1H), 7.09 (d, J = 5.87 Hz, 1H), 5.53 (s, 2H), 3.68 (d, J = 10.56 Hz, 1H), 3.42 (s, 3H), 3.28-3.39 (m, 1H), 1.79-1.85 (m, 1H), 1.75 (s, 3H), 0.91 (dd, J = 5.87, 9.59 Hz, 1H), 0.77-0.85 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-2-(1,3-oxazol-4-ylmethoxy)pyrido[3,4-b]pyrazin-5-amine |
| 629 | ¹H NMR (400 MHz, CHLOROFORM-d) δ 8.96 (s, 1H), 8.43-8.54 (m, 2H), 8.09 (d, J = 5.67 Hz, 1H), 7.38 (td, J = 2.47, 5.43 Hz, 1H), 7.25 (d, J = 2.74 Hz, 1H), 6.96 (d, J = 5.87 Hz, 1H), 3.98 (s, 3H), 3.68 (d, J = 10.56 Hz, 1H), 3.43 (s, 3H), 3.36 (d, J = 10.56 Hz, 1H), 1.81 (dd, J = 7.43, 8.61 Hz, 1H), 1.76 (d, J = 0.98 Hz, 3H), 0.91 (dd, J = 5.87, 9.59 Hz, 1H), 0.80-0.86 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-3-methoxy-1,7-naphthyridin-8-amine |
| 630 | ¹H NMR (400 MHz, CHLOROFORM-d) Shift 8.52-8.59 (m, 1H), 8.34 (s, 1H), 8.27-8.33 (m, 1H), 8.25 (d, J = 6.06 Hz, 1H), 7.11-7.18 (m, 1H), 7.09 (d, J = 6.06 Hz, 1H), 5.16 (d, J = 2.35 Hz, 2H), 3.03 (s, 3H), 2.57 (t, J = 2.35 Hz, 1H), 2.41 (dd, J = 7.63, 10.37 Hz, 1H), 2.15 (dd, J = 6.26, 10.37 Hz, 1H), 1.88 (s, 3H), 1.09 (t, J = 6.55 Hz, 1H) | N-(3-((1R,5S,6S)-3-amino-5-methyl-1-(methylsulfonyl)-2-thia-4-azabicyclo[4.1.0]hept-3-en-5-yl)-4,5-difluorophenyl)-2-(2-propyn-1-yloxy)pyrido[3,4-b]pyrazin-5-amine |
| 631 | ¹H NMR (400 MHz, CHLOROFORM-d) δ 8.68 (s, 1H), 8.46 (ddd, J = 2.74, 7.04, 12.72 Hz, 1H), 8.41 (s, 1H), 8.29 (d, J = 6.06 Hz, 1H), 7.64-7.81 (m, 1H), 7.33-7.43 (m, 1H), 7.20 (s, 1H), 7.05-7.13 (m, 1H), 5.59-5.71 (m, 2H), 3.68 (d, J = 10.56 Hz, 1H), 3.42 (s, 3H), 3.36 (d, J = 10.56 Hz, 1H), 1.78-1.84 (m, 1H), 1.75 (s, 3H), 0.92 (dd, J = 5.87, 9.39 Hz, 1H), 0.79-0.86 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-2-(1,3-oxazol-2-ylmethoxy)pyrido[3,4-b]pyrazin-5-amine |
| 635 | ¹H NMR (300 MHz, DMSO-d₆) δ 9.37 (br., 1H), 8.57 (s, 1H), 8.23 (d, J = 5.99 Hz, 1H), 7.97-8.13 (m, 2H), 7.15 (dd, J = 8.77, 11.84 Hz, 1H), 7.04 (d, J = 5.85 Hz, 1H), 6.41 (br., 2H), 4.80 (m, 1H), 4.64 (m, 1H), 4.60 (m, 2H), 4.55 (m, 1H), 4.35 (m, 1H), 3.75 (m, 2H), 3.31 (s, 3H), 1.80 (m, 1H), 0.86 (m, 1H), 0.60 (m, 1H). | N-(3-((1S,5S,6S)-3-amino-1,5-bis(fluoromethyl)-2-thia-4-azabicyclo[4.1.0]hept-3-en-5-yl)-4-fluorophenyl)-2-(2-methoxyethoxy)pyrido[3,4-b]pyrazin-5-amine |
| 653 | ¹H NMR (400 MHz, CHLOROFORM-d) δ ppm 0.84 (td, J = 6.60, 2.84 Hz, 1 H) 1.38 (dd, J = 9.88, 6.36 Hz, 1 H) 1.80 (s, 3 H) 2.01 (dd, J = 9.78, 7.24 Hz, 1 H) 2.58 (t, J = 2.45 Hz, 1 H) 5.15 (d, J = 2.54 Hz, 2 H) 5.48-5.88 (m, 1 H) 7.07 (d, J = 5.87 Hz, 1 H) 8.23 (d, J = 5.87 Hz, 1 H) 8.30 (dd, J = 8.71, 2.64 Hz, 1 H) 8.33 (s, 1 H) 8.50 (s, 1 H) 8.81 (t, J = 2.15 Hz, 1 H). | N-(5-((1S,5S,6S)-3-amino-1-(difluoromethyl)-5-methyl-2-thia-4-azabicyclo[4.1.0]hept-3-en-5-yl)-6-fluoro-3-pyridinyl)-2-(2-propyn-1-yloxy)pyrido[3,4-b]pyrazin-5-amine |
| 654 | ¹H NMR (400 MHz, CHLOROFORM-d) δ ppm 0.82-0.90 (m, 1 H) 1.30-1.40 (m, 1 H) 1.79 (s, 3 H) 1.99-2.05 (m, 1 H) 5.50-5.83 (m, 3 H) 7.10 (d, J = 6.06 Hz, 1 H) 7.20 (s, 1 H) 7.73 (s, 1 H) 8.27 (d, J = 5.87 Hz, 1 H) 8.33 (dd, J = 8.61, 2.74 Hz, 1 H) 8.41 (s, 1 H) 8.56 (s, 1 H) 8.85 (t, J = 2.25 Hz, 1 H). | N-(5-((1S,5S,6S)-3-amino-1-(difluoromethyl)-5-methyl-2-thia-4-azabicyclo[4.1.0]hept-3-en-5-yl)-6-fluoro-3-pyridinyl)-2-(1,3-oxazol-2-ylmethoxy)pyrido[3,4-b]pyrazin-5-amine |
| 656 | ¹H NMR (400 MHz, CHLOROFORM-d) δ ppm 0.83 (td, J = 6.55, 2.74 Hz, 1 H) 1.36 (d, J = 6.65 Hz, 6 H) 1.40 (dd, J = 9.88, 6.36 Hz, 1 H) 1.84 (s, 3 H) 2.01 (dd, J = 9.68, 7.34 Hz, 1 H) 4.37 (dq, J = 13.74, 6.70 Hz, 1 H) 5.50-5.86 (m, 1 H) 6.30 (d, J = 7.43 Hz, 1 H) 7.02 (d, J = 5.67 Hz, 1 H) 8.07 (d, J = 5.87 Hz, 1 H) 8.26-8.33 (m, 2 H) 8.81 (t, J = 2.15 Hz, 1 H) 8.89 (s, 1 H) 8.97-9.04 (m, 1 H). | 8-((5-((1S,5S,6S)-3-amino-1-(difluoromethyl)-5-methyl-2-thia-4-azabicyclo[4.1.0]hept-3-en-5-yl)-6-fluoro-3-pyridinyl)amino)-N-(1-methylethyl)-1,7-naphthyridine-3-carboxamide |
| 657 | ¹H NMR (400 MHz, METHANOL-d4) δ ppm 0.78 (br. s., 1 H) 1.42 (dd, J = 9.49, 6.55 Hz, 1 H) 1.80 (s, 3 H) 1.86-1.96 (m, 1 H) 5.46-5.85 (m, 1 H) 7.09 (d, J = 5.67 Hz, 1 H) 7.38 (d, J = 7.43 Hz, 1 H) 8.19 (d, J = 5.67 Hz, 1 H) 8.28 (d, J = 8.61 Hz, 1 H) 8.48 (br. s., 1 H) 8.80 (s, 1 H) 8.95 (s, 1 H). | 8-((5-((1S,5S,6S)-3-amino-1-(difluoromethyl)-5-methyl-2-thia-4-azabicyclo[4.1.0]hept-3-en-5-yl)-6-fluoro-3-pyridinyl)amino)-1,7-naphthyridine-3-carbonitrile |
| 658 | ¹H NMR (400 MHz, CHLOROFORM-d) δ ppm 0.81-0.90 (m, 1 H) 1.34-1.41 (m, 1 H) 1.81 (s, 3 H) 2.07 (dd, J = 9.78, 7.43 Hz, 1 H) 5.50-5.94 (m, 1 H) 8.44 (dd, J = 8.41, 2.74 Hz, 1 H) 8.53 (d, J = 1.96 Hz, 1 H) 8.84-8.86 (m, 1 H) 8.87 (s, 1 H) 8.97 (d, J = 1.96 Hz, 1 H) 9.06 (s, 1 H). | 4-((5-((1S,5S,6S)-3-amino-1-(difluoromethyl)-5-methyl-2-thia-4-azabicyclo[4.1.0]hept-3-en-5-yl)-6-fluoro-3-pyridinyl)amino)pyrido[3,2-d]pyrimidine-7-carbonitrile |
| 659 | ¹H NMR (400 MHz, CHLOROFORM-d) δ ppm 0.90 (t, J = 6.46 Hz, 1 H) 1.18-1.28 (m, 2 H) 1.82 (s, 3 H) 2.18 (t, J = 8.41 Hz, 1 H) 2.57 (t, J = 2.35 Hz, 1 H) 3.85 (br. s., 1 H) 5.16 (d, J = 2.54 Hz, 2 H) 7.11 (d, J = 5.87 Hz, 1 H) 8.27 (d, J = 5.87 Hz, 1 H) 8.32-8.39 (m, 2 H) 8.58 (s, 1 H) 8.86 (br. s., 1 H). | (1R)-1-((1S,5S,6S)-3-amino-5-(2-fluoro-5-((2-(2-propyn-1-yloxy)pyrido[3,4-b]pyrazin-5-yl)amino)-3-pyridinyl)-5-methyl-2-thia-4-azabicyclo[4.1.0]hept-3-en-1-yl)-2,2,2-trifluoroethanol |

TABLE 3'-continued

| Ex. No. | ¹H-NMR | Chemical Name |
|---|---|---|
| 660 | ¹H NMR (400 MHz, CHLOROFORM-d) δ ppm 0.95 (t, J = 6.85 Hz, 1 H) 1.23-1.30 (m, 2 H) 1.82 (s, 3 H) 1.92-1.99 (m, 1 H) 2.57 (t, J = 2.35 Hz, 1 H) 3.53 (q, J = 6.72 Hz, 1 H) 5.16 (d, J = 2.35 Hz, 2 H) 7.11 (d, J = 6.06 Hz, 1 H) 8.27 (d, J = 5.87 Hz, 1 H) 8.33-8.39 (m, 2 H) 8.57 (s, 1 H) 8.85 (s, 1 H). | (1S)-1-((1S,5S,6S)-3-amino-5-(2-fluoro-5-((2-(2-propyn-1-yloxy)pyrido[3,4-b]pyrazin-5-yl)amino)-3-pyridinyl)-5-methyl-2-thia-4-azabicyclo[4.1.0]hept-3-en-1-yl)-2,2,2-trifluoroethanol |
| 662 | ¹H NMR (400 MHz, CHLOROFORM-d) δ ppm 0.78 (t, J = 6.26 Hz, 1 H) 0.90 (dd, J = 9.29, 5.97 Hz, 1 H) 1.74 (s, 3 H) 1.84-1.92 (m, 1 H) 2.53-2.59 (m, 1 H) 3.65-3.76 (m, 2 H) 5.16 (d, J = 2.35 Hz, 2 H) 7.10 (d, J = 6.06 Hz, 1 H) 8.28 (d, J = 5.87 Hz, 1 H) 8.32-8.40 (m, 2 H) 8.56 (s, 1 H) 8.94 (s, 1 H). | ((1S,5S,6S)-3-amino-5-(2-fluoro-5-((2-(2-propyn-1-yloxy)pyrido[3,4-b]pyrazin-5-yl)amino)-3-pyridinyl)-5-methyl-2-thia-4-azabicyclo[4.1.0]hept-3-en-1-yl)methanol |
| 663 | ¹H NMR (400 MHz, CHLOROFORM-d) δ ppm 1.67 (s, 3 H) 2.52 (dd, J = 15.16, 2.64 Hz, 1 H) 3.88-4.05 (m, 2 H) 4.51 (br. s., 2 H) 5.65 (s, 2 H) 7.11 (d, J = 6.06 Hz, 1 H) 7.20 (s, 1 H) 7.73 (s, 1 H) 8.29 (d, J = 5.87 Hz, 1 H) 8.36 (dd, J = 8.61, 2.74 Hz, 1 H) 8.42 (s, 1 H) 8.59 (s, 1 H) 9.02 (t, J = 2.35 Hz, 1 H). | ((1S,5S,6R)-3-amino-7,7-difluoro-5-(2-fluoro-5-((2-(1,3-oxazol-2-ylmethoxy)pyrido[3,4-b]pyrazin-5-yl)amino)-3-pyridinyl)-5-methyl-2-thia-4-azabicyclo[4.1.0]hept-3-en-1-yl)methanol |
| 665 | ¹H NMR (400 MHz, CHLOROFORM-d) δ ppm 0.87 (t, J = 6.46 Hz, 1 H) 1.15 (dd, J = 9.78, 6.06 Hz, 1 H) 1.77 (s, 3 H) 2.10-2.19 (m, 1 H) 2.64 (t, J = 2.35 Hz, 1 H) 3.83 (q, J = 6.46 Hz, 1 H) 4.88 (d, J = 2.35 Hz, 2 H) 7.59 (d, J = 2.74 Hz, 1 H) 8.40-8.50 (m, 1 H) 8.55 (d, J = 2.74 Hz, 1 H) 8.72 (s, 1 H) 8.76-8.83 (m, 1 H) 8.95 (s, 1 H). | (1R)-1-((1S,5S,6S)-3-amino-5-(2-fluoro-5-((7-(2-propyn-1-yloxy)pyrido[3,2-d]pyrimidin-4-yl)amino)-3-pyridinyl)-5-methyl-2-thia-4-azabicyclo[4.1.0]hept-3-en-1-yl)-2,2,2-trifluoroethanol |
| 666 | ¹H NMR (400 MHz, CHLOROFORM-d) δ ppm 0.95 (t, J = 6.75 Hz, 1 H) 1.82 (s, 3 H) 1.92-1.99 (m, 2 H) 2.64 (d, J = 1.57 Hz, 1 H) 3.56 (q, J = 6.52 Hz, 1 H) 4.04 (br. s., 1 H) 4.89 (s, 2 H) 7.61 (s, 1 H) 8.44 (d, J = 8.61 Hz, 1 H) 8.56 (s, 1 H) 8.74 (s, 1 H) 8.82 (br. s., 1 H) 8.94 (s, 1 H). | (1S)-1-((1S,5S,6S)-3-amino-5-(2-fluoro-5-((7-(2-propyn-1-yloxy)pyrido[3,2-d]pyrimidin-4-yl)ammo)-3-pyridinyl)-5-methyl-2-thia-4-azabicyclo[4.1.0]hept-3-en-1-yl)-2,2,2-trifluoroethanol |
| 667 | ¹H NMR (400 MHz, CHLOROFORM-d) δ ppm 0.85 (t, J = 6.46 Hz, 1 H) 1.13 (dd, J = 9.59, 6.06 Hz, 1 H) 1.77 (s, 3 H) 2.09-2.17 (m, 1 H) 3.81 (q, J = 6.39 Hz, 1 H) 5.34 (s, 2 H) 7.17-7.23 (m, 1 H) 7.63 (d, J = 2.74 Hz, 1 H) 7.74 (s, 1 H) 8.44 (dd, J = 8.51, 2.64 Hz, 1 H) 8.60 (d, J = 2.74 Hz, 1 H) 8.72 (s, 1 H) 8.79 (s, 1 H) 8.94 (s, 1 H). | (1R)-1-((1S,5S,6S)-3-amino-5-(2-fluoro-5-((7-(1,3-oxazol-2-ylmethoxy)pyrido[3,2-d]pyrimidin-4-yl)amino)-3-pyridinyl)-5-methyl-2-thia-4-azabicyclo[4.1.0]hept-3-en-1-yl)-2,2,2-trifluoroethanol |
| 668 | ¹H NMR (400 MHz, CHLOROFORM-d) δ ppm 0.94 (t, J = 6.94 Hz, 1 H) 1.19-1.25 (m, 1 H) 1.80 (s, 3 H) 1.94 (dd, J = 9.29, 7.53 Hz, 1 H) 3.54 (q, J = 6.65 Hz, 1 H) 5.34 (s, 2 H) 7.21 (s, 1 H) 7.63 (d, J = 2.74 Hz, 1 H) 7.74 (s, 1 H) 8.42 (dd, J = 8.61, 2.74 Hz, 1 H) 8.61 (d, J = 2.74 Hz, 1 H) 8.74 (s, 1 H) 8.80-8.86 (m, 1 H) 8.92 (s, 1 H). | (1S)-1-((1S,5S,6S)-3-amino-5-(2-fluoro-5-((7-(1,3-oxazol-2-ylmethoxy)pyrido[3,2-d]pyrimidin-4-yl)amino)-3-pyridinyl)-5-methyl-2-thia-4-azabicyclo[4.1.0]hept-3-en-1-yl)-2,2,2-trifluoroethanol |
| 669 | ¹H NMR (400 MHz, CHLOROFORM-d) δ ppm 1.68 (s, 3 H) 2.51 (dd, J = 15.16, 2.84 Hz, 1 H) 3.87-4.05 (m, 2 H) 4.71 (br. s., 2 H) 5.32 (s, 2 H) 6.98 (d, J = 5.87 Hz, 1 H) 7.21 (s, 1 H) 7.46 (d, J = 2.74 Hz, 1 H) 7.74 (s, 1 H) 8.09 (d, J = 5.87 Hz, 1 H) 8.39 (dd, J = 8.61, 2.54 Hz, 1 H) 8.58 (d, J = 2.74 Hz, 1 H) 8.87 (s, 1 H) 9.03 (s, 1 H). | ((1S,5S,6R)-3-amino-7,7-difluoro-5-(2-fluoro-5-((3-(1,3-oxazol-2-ylmethoxy)-1,7-naphthyridin-8-yl)amino)-3-pyridinyl)-5-methyl-2-thia-4-azabicyclo[4.1.0]hept-3-en-1-yl)methanol |
| 670 | ¹H NMR (400 MHz, CHLOROFORM-d) δ ppm 0.78 (t, J = 6.26 Hz, 1 H) 0.85-0.96 (m, 1 H) 1.74 (s, 3 H) 1.86-1.92 (m, 1 H) 2.63 (t, J = 2.35 Hz, 1 H) 3.63-3.81 (m, 2 H) 4.31-4.76 (m, 2 H) 4.88 (d, J = 2.35 Hz, 2 H) 7.60 (d, J = 2.74 Hz, 1 H) 8.43 (dd, J = 8.61, 2.74 Hz, 1 H) 8.56 (d, J = 2.74 Hz, 1 H) 8.75 (s, 1 H) 8.88-8.98 (m, 2 H). | ((1S,5S,6S)-3-amino-5-(2-fluoro-5-((7-(2-propyn-1-yloxy)pyrido[3,2-d]pyrimidin-4-yl)amino)-3-pyridinyl)-5-methyl-2-thia-4-azabicyclo[4.1.0]hept-3-en-1-yl)methanol |
| 671 | ¹H NMR (400 MHz, CHLOROFORM-d) δ ppm 0.82 (t, J = 6.46 Hz, 1 H) 0.93 (dd, J = 9.59, 6.06 Hz, 1 H) 1.76 (s, 3 H) 1.97-2.03 (m, 1 H) 2.56 (t, J = 2.35 Hz, 1 H) 2.88-3.49 (m, 3 H) 3.59 (q, J = 6.39 Hz, 1 H) 5.14 (d, J = 2.35 Hz, 2 H) 6.98-7.09 (m, 2 H) 7.58 (dd, J = 6.94, 2.84 Hz, 1 H) 8.04 (dt, J = 8.51, 3.47 Hz, 1 H) 8.20 (d, J = 5.87 Hz, 1 H) 8.32 (s, 1 H) 8.55 (s, 1 H). | (1R)-1-((1S,5S,6S)-3-amino-5-(2-fluoro-5-((2-(2-propyn-1-yloxy)pyrido[3,4-b]pyrazin-5-yl)amino)phenyl)-5-methyl-2-thia-4-azabicyclo[4.1.0]hept-3-en-1-yl)-2,2,2,-trifluoroethanol |
| 672 | ¹H NMR (400 MHz, CHLOROFORM-d) δ ppm 0.92 (t, J = 6.65 Hz, 1 H) 1.20-1.27 (m, 1 H) 1.76-1.85 (m, 4 H) 2.56 (t, J = 2.35 Hz, 1 H) 3.46 (q, J = 6.65 Hz, 1 H) 3.66 (br. s., 3 H) 5.14 (d, J = 2.54 Hz, 2 H) 6.97-7.10 (m, 2 H) 7.60 (dd, J = 6.85, 2.74 Hz, 1 H) 8.03 (dt, J = 8.71, 3.37 Hz, 1 H) 8.20 (d, J = 5.87 Hz, 1 H) 8.31 (s, 1 H) 8.54 (s, 1 H). | (1S)-1-((1S,5S,6S)-3-amino-5-(2-fluoro-5-((2-(2-propyn-1-yloxy)pyrido[3,4-b]pyrazin-5-yl)amino)phenyl)-5-methyl-2-thia-4-azabicyclo[4.1.0]hept-3-en-1-yl)-2,2,2-trifluoroethanol |

TABLE 3'-continued

| Ex. No. | ¹H-NMR | Chemical Name |
|---|---|---|
| 676 | ¹H NMR (400 MHz, CHLOROFORM-d) δ ppm 0.94 (t, J = 6.46 Hz, 1 H) 1.09 (dd, J = 9.88, 5.97 Hz, 1 H) 1.75 (s, 3 H) 2.04-2.10 (m, 1 H) 2.57 (t, J = 2.45 Hz, 1 H) 3.29 (q, J = 6.06 Hz, 1 H) 3.61 (s, 3 H) 5.16 (d, J = 2.54 Hz, 2 H) 7.10 (d, J = 5.87 Hz, 1 H) 8.28 (d, J = 5.87 Hz, 1 H) 8.35 (dd, J = 8.71, 2.84 Hz, 1 H) 8.37 (s, 1 H) 8.56 (s, 1 H) 8.87-8.96 (m, 1 H). | N-(5-((1S,5S,6S)-3-amino-5-methyl-1-((1R)-2,2,2-trifluoro-1-methoxyethyl)-2-thia-4-azabicyclo[4.1.0]hept-3-en-5-yl)-6-fluoro-3-pyridinyl)-2-(2-propyn-1-yloxy)pyrido[3,4-b]pyrazin-5-amine |
| 677 | ¹H NMR (400 MHz, CHLOROFORM-d) δ ppm 0.87 (t, J = 6.65 Hz, 1 H) 1.08-1.17 (m, 1 H) 1.82 (s, 3 H) 1.99 (dd, J = 9.39, 7.24 Hz, 1 H) 2.57 (t, J = 2.35 Hz, 1 H) 3.23 (q, J = 6.46 Hz, 1 H) 3.67 (s, 3 H) 5.15 (d, J = 2.54 Hz, 2 H) 7.09 (d, J = 5.87 Hz, 1 H) 8.25 (d, J = 5.87 Hz, 1 H) 8.31 (dd, J = 8.70, 2.64 Hz, 1 H) 8.35 (s, 1 H) 8.54 (s, 1 H) 8.87 (t, J = 2.15 Hz, 1 H). | N-(5-((1S,5S,6S)-3-amino-5-methyl-1-((1S)-2,2,2-trifluoro-1-methoxyethyl)-2-thia-4-azabicyclo[4.1.0]hept-3-en-5-yl)-6-fluoro-3-pyridinyl)-2-(2-propyn-1-yloxy)pyrido[3,4-b]pyrazin-5-amine |
| 703 | ¹H NMR (300 MHz, CDCl3) δ = 9.16 (s, 1H), 8.96 (d, J = 1.9 Hz, 1H), 8.85 (s, 1H), 8.50 (d, J = 1.9 Hz, 1H), 8.28-8.19 (m, 1H), 7.90 (dd, J = 2.9, 6.9 Hz, 1H), 7.20 (dd, J = 8.9, 11.7 Hz, 1H), 4.06-3.92 (m, 2H), 2.64-2.54 (m, 1H), 1.76 (s, 3H) | 4-((3-((1S,5S,6R)-3-amino-7,7-difluoro-1-(hydroxymethyl)-5-methyl-2-thia-4-azabicyclo[4.1.0]hept-3-en-5-yl)-4-fluorophenyl)amino)pyrido[3,2-d]pyrimidine-7-carbonitrile |
| 705 | ¹H NMR (300 MHz, CDCl3) δ = 8.66 (s, 1H), 8.41 (s, 1H), 8.27 (d, J = 5.8 Hz, 2H), 7.78-7.71 (m, 2H), 7.21 (d, J = 0.7 Hz, 1H), 7.13 (dd, J = 8.9, 11.8 Hz, 1H), 7.06 (d, J = 6.0 Hz, 1H), 5.66 (s, 2H), 4.06-3.92 (m, 2H), 2.57 (dd, J = 2.6, 15.1 Hz, 1H), 1.73 (s, 3H) | ((1S,5S,6R)-3-amino-7,7-difluoro-5-(2-fluoro-5-((2-(1,3-oxazol-2-ylmethoxy)pyrido[3,4-b]pyrazin-5-yl)amino)phenyl)-5-methyl-2-thia-4-azabicyclo[4.1.0]hept-3-en-1-yl)methanol |
| 706 | ¹H NMR (300 MHz, DMSO) δ = 9.32 (s, 1H), 8.57 (s, 1H), 8.45 (s, 1H), 8.33-8.31 (m, 1H), 8.25 (d, J = 5.8 Hz, 1H), 8.15-8.03 (m, 2H), 7.16 (dd, J = 8.8, 11.9 Hz, 1H), 7.10 (d, J = 5.8 Hz, 1H), 6.15 (s, 2H), 5.48 (s, 2H), 5.43 (t, J = 5.8 Hz, 1H), 3.90-3.80 (m, 1H), 3.71-3.62 (m, 1H), 1.54 (s, 3H) | ((1S,5S,6R)-3-amino-7,7-difluoro-5-(2-fluoro-5-((2-(1,3-oxazol-4-ylmethoxy)pyrido[3,4-b]pyrazin-5-yl)amino)phenyl)-5-methyl-2-thia-4-azabicyclo[4.1.0]hept-3-en-1-yl)methanol |
| 707 | ¹H NMR (300 MHz, DMSO) δ = 9.34 (s, 1H), 8.60 (s, 1H), 8.25 (d, J = 5.8 Hz, 1H), 8.12 (dd, J = 2.8, 7.2 Hz, 1H), 8.08-8.02 (m, 1H), 7.16 (dd, J = 8.7, 11.9 Hz, 1H), 7.07 (d, J = 5.8 Hz, 1H), 6.15 (s, 2H), 5.43 (t, J = 5.8 Hz, 1H), 5.19 (d, J = 2.5 Hz, 2H), 3.91-3.79 (m, 1H), 3.72-3.60 (m, 2H), 1.54 (s, 3H) | ((1S,5S,6R)-3-amino-7,7-difluoro-5-(2-fluoro-5-((2-(2-propyn-1-yloxy)pyrido[3,4-b]pyrazin-5-yl)amino)phenyl)-5-methyl-2-thia-4-azabicyclo[4.1.0]hept-3-en-1-yl)methanol |
| 709 | ¹H NMR (300 MHz, CDCl3) δ = 9.18 (s, 1H), 8.96 (d, J = 1.9 Hz, 1H), 8.85 (s, 1H), 8.50 (d, J = 1.9 Hz, 1H), 8.33-8.26 (m, 1H), 7.90 (dd, J = 2.8, 6.7 Hz, 1H), 7.20 (dd, J = 8.9, 11.5 Hz, 1H), 4.04-3.97 (m, 1H), 3.58 (dd, J = 2.5, 11.3 Hz, 1H), 3.43 (s, 3H), 2.47 (dd, J = 2.3, 15.1 Hz, 1H), 1.74 (s, 3H) | 4-((3-((1S,5S,6R)-3-amino-7,7-difluoro-1-(methoxymethyl)-5-methyl-2-thia-4-azabicyclo[4.1.0]hept-3-en-5-yl)-4-fluorophenyl)amino)pyrido[3,2-d]pyrimidine-7-carbonitrile |
| 712 | ¹H NMR (300 MHz, CDCl3) δ = 8.65 (s, 1H), 8.37 (s, 1H), 8.33-8.25 (m, 2H), 7.70 (dd, J = 2.8, 6.9 Hz, 1H), 7.14 (dd, J = 8.9, 11.8 Hz, 1H), 7.05 (d, J = 5.8 Hz, 1H), 5.17 (d, J = 2.5 Hz, 2H), 3.17-3.07 (m, 1H), 2.58 (t, J = 2.4 Hz, 1H), 1.74 (s, 3H), 1.51 (s, 3H), 1.48 (s, 3H), 1.49-1.46 (m, 3H) | 2-((1S,5S,6R)-3-amino-7,7-difluoro-5-(2-fluoro-5-((2-(2-propyn-1-yloxy)pyrido[3,4-b]pyrazin-5-yl)amino)phenyl)-5-methyl-2-thia-4-azabicyclo[4.1.0]hept-3-en-1-yl)-2-propanol |
| 713 | ¹H NMR (300 MHz, CDCl3) δ = 8.66 (s, 1H), 8.37 (s, 1H), 8.34-8.28 (m, 1H), 8.27 (d, J = 5.8 Hz, 1H), 7.72 (dd, J = 2.9, 6.9 Hz, 1H), 7.13 (dd, J = 8.8, 11.8 Hz, 1H), 7.06 (d, J = 5.8 Hz, 1H), 5.17 (d, J = 2.5 Hz, 2H), 4.09-4.01 (m, 1H), 2.58 (t, J = 2.5 Hz, 1H), 2.38 (dd, J = 2.9, 15.6 Hz, 1H), 1.71 (s, 3H), 1.53 (d, J = 6.3 Hz, 3H) | (1R)-1-((1S,5S,6R)-3-amino-7,7-difluoro-5-(2-fluoro-5-((2-(2-propyn-1-yloxy)pyrido[3,4-b]pyrazin-5-yl)amino)phenyl)-5-methyl-2-thia-4-azabicyclo[4.1.0]hept-3-en-1-yl)ethanol |
| 714 | ¹H NMR (300 MHz, CDCl3) δ = 8.64 (s, 1H), 8.37 (s, 1H), 8.27 (d, J = 5.8 Hz, 2H), 7.71 (dd, J = 2.9, 6.9 Hz, 1H), 7.13 (dd, J = 8.9, 11.8 Hz, 1H), 7.05 (d, J = 6.0 Hz, 1H), 5.17 (d, J = 2.5 Hz, 2H), 3.92 (dd, J = 2.5, 6.3 Hz, 1H), 2.64 (dd, J = 2.4, 15.4 Hz, 1H), 2.58 (t, J = 2.5 Hz, 1H), 1.76 (s, 3H), 1.40 (d, J = 6.4 Hz, 3H) | (1S)-1-((1S,5S,6R)-3-amino-7,7-difluoro-5-(2-fluoro-5-((2-(2-propyn-1-yloxy)pyrido[3,4-b]pyrazin-5-yl)amino)phenyl)-5-methyl-2-thia-4-azabicyclo[4.1.0]hept-3-en-1-yl)ethanol |
| 717 | ¹H NMR (CHLOROFORM-d) δ 9.01 (s, 1H), 8.93 (s, 1H), 8.37 (d, J = 1.8 Hz, 1H), 8.17-8.30 (m, 2H), 7.78 (dd, J = 6.7, 2.6 Hz, 1H), 7.13 (dd, J = 11.6, 8.9 Hz, 1H), 7.00 (d, J = 5.7 Hz, 1H), 4.67-5.01 (m, 2H), 3.64 (d, | 8-((3-((1S,5S,6S)-3-amino-5-(fluoromethyl)-1-(methoxymethyl)-2-thia-4-azabicyclo[4.1.0]hept-3-en-5- |

TABLE 3'-continued

| Ex. No. | ¹H-NMR | Chemical Name |
|---|---|---|
| | J = 10.6 Hz, 1H), 3.40 (s, 3H), 3.37 (d, J = 10.6 Hz, 1H), 1.84-1.93 (m, 1H), 1.12-1.19 (m, 1H), 0.81 (t, J = 5.9 Hz, 1H) | yl)-4-fluorophenyl)amino)-1,7-naphthyridine-3-carbonitrile |
| 719 | ¹H NMR (DMSO-d6) δ 9.65 (s, 1H), 9.22 (d, J = 2.0 Hz, 1H), 8.98 (d, J = 2.0 Hz, 1H), 8.22 (d, J = 5.7 Hz, 1H), 8.08-8.18 (m, 2H), 7.14-7.24 (m, 2H), 6.46 (s, 2H), 4.58-4.85 (m, 2H), 2.89-3.14 (m, 2H), 1.76-1.88 (m, 1H), 1.16 (dd, J = 9.5, 5.4 Hz, 1H), 0.62 (t, J = 6.2 Hz, 1H) | 8-((3-((1R,5S,6S)-3-amino-1-(cyanomethyl)-5-(fluoromethyl)-2-thia-4-azabicyclo[4.1.0]hept-3-en-5-yl)-4-fluorophenyl)amino)-1,7-naphthyridine-3-carbonitrile |
| 720 | ¹H NMR (DMSO-d6) δ: 9.42 (s, 1H), 8.61 (s, 1H), 8.25 (d, J = 5.9 Hz, 1H), 8.12 (dd, J = 7.1, 2.6 Hz, 1H), 8.03-8.08 (m, 1H), 7.16 (dd, J = 11.8, 8.9 Hz, 1H), 7.07 (d, J = 5.9 Hz, 1H), 6.45 (s, 2H), 5.19 (d, J = 2.5 Hz, 2H), 4.43-4.95 (m, 2H), 3.66 (t, J = 2.3 Hz, 1H), 2.84-3.19 (m, 2H), 1.73-1.90 (m, 1H), 1.16 (dd, J = 9.6, 5.5 Hz, 1H), 0.61 (t, J = 6.0 Hz, 1H) | ((1R,5S,6S)-3-amino-5-(fluoromethyl)-5-((2-(2-propyn-1-yloxy)pyrido[3,4-b]pyrazin-5-yl)amino)phenyl)-2-thia-4-azabicyclo[4.1.0]hept-3-en-1-yl)acetonitrile |
| 721 | ¹H NMR (DMSO-d6) δ: 9.44 (s, 1H), 8.66 (s, 1H), 8.27 (d, J = 5.9 Hz, 1H), 8.23 (s, 1H), 8.13 (dd, J = 7.0, 2.7 Hz, 1H), 8.07 (dd, J = 8.3, 3.8 Hz, 1H), 7.32 (s, 1H), 7.17 (dd, J = 11.6, 8.9 Hz, 1H), 7.07 (d, J = 5.9 Hz, 1H), 6.46 (s, 2H), 5.68 (s, 2H), 4.62-4.83 (m, 2H), 2.94-3.11 (m, 2H), 1.79-1.85 (m, 1H), 1.15-1.22 (m, 1H), 0.63 (t, J = 6.0 Hz, 1H) | ((1R,5S,6S)-3-amino-5-(fluoromethyl)-5-(2-fluoro-5-((2-(1,3-oxazol-2-ylmethoxy)pyrido[3,4-b]pyrazin-5-yl)amino)phenyl)-2-thia-4-azabicyclo[4.1.0]hept-3-en-1-yl)acetonitrile |
| 724 | ¹H NMR (CHLOROFORM-d) δ: 8.60 (s, 1H), 8.34 (s, 1H), 8.23 (d, J = 6.1 Hz, 1H), 8.10-8.18 (m, 1H), 7.67 (dd, J = 6.9, 2.6 Hz, 1H), 7.48 (s, 1H), 7.10 (dd, J = 11.3, 8.8 Hz, 1H), 7.04 (d, J = 5.9 Hz, 1H), 5.14 (d, J = 2.5 Hz, 2H), 4.65-5.00 (m, 2H), 4.38-4.54 (m, 2H), 2.56 (t, J = 2.4 Hz, 1H), 2.40 (s, 3H), 2.18 (t, J = 8.1 Hz, 1H), 1.41-1.45 (m, 1H), 0.91-0.97 (m, 1H) | N-(3-((1S,5S,6S)-3-amino-5-(fluoromethyl)-1-((4-methyl-1H-1,2,3-triazol-1-yl)methyl)-2-thia-4-azabicyclo[4.1.0]hept-3-en-5-yl)-4-fluorophenyl)-2-(2-propyn-1-yloxy)pyrido[3,4-b]pyrazin-5-amine |
| 726 | ¹H NMR (400 MHz, CHLOROFORM-d) δ ppm 8.96 (s, 1H), 8.54 (d, J = 2.74 Hz, 1H), 8.50 (dt, J = 2.74, 6.36 Hz, 1H), 8.11 (d, J = 5.87 Hz, 1H), 7.97 (s, 1H), 7.37 (d, J = 2.74 Hz, 2H), 7.28 (s, 1H), 6.96 (d, J = 5.87 Hz, 1H), 5.24 (s, 2H), 3.68 (d, J = 10.56 Hz, 1H), 3.42 (s, 3H), 3.36 (d, J = 10.76 Hz, 1H), 1.79-1.85 (m, 1H), 1.76 (s, 3H), 0.92 (dd, J = 5.97, 9.49 Hz, 1H), 0.80-0.86 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-3-(1,3-oxazol-5-ylmethoxy)-1,7-naphthyridin-8-amine |
| 727 | ¹H NMR (400 MHz, CHLOROFORM-d) δ ppm 8.96 (s, 1H), 8.58 (d, J = 2.74 Hz, 1H), 8.50 (ddd, J = 2.93, 6.99, 12.76 Hz, 1H), 8.10 (d, J = 5.87 Hz, 1H), 7.74 (d, J = 0.78 Hz, 1H), 7.46 (d, J = 2.74 Hz, 1H), 7.37 (td, J = 2.52, 5.33 Hz, 1H), 7.21 (s, 1H), 6.96 (d, J = 5.67 Hz, 1H), 5.33 (s, 2H), 3.68 (d, J = 10.56 Hz, 1H), 3.42 (s, 3H), 3.36 (d, J = 10.56 Hz, 1H), 1.81 (dd, J = 7.34, 8.71 Hz, 1H), 1.76 (s, 3H), 0.92 (dd, J = 5.77, 9.49 Hz, 1H), 0.78-0.87 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-3-(1,3-oxazol-2-ylmethoxy)-1,7-naphthyridin-8-amine |
| 728 | ¹H NMR (400 MHz, CHLOROFORM-d) δ ppm 8.96 (s, 1H), 8.56 (d, J = 2.74 Hz, 1H), 8.50 (ddd, J = 2.93, 6.94, 12.81 Hz, 1H), 8.10 (d, J = 5.87 Hz, 1H), 7.97 (s, 1H), 7.83 (d, J = 0.78 Hz, 1H), 7.40 (d, J = 2.74 Hz, 1H), 7.38 (td, J = 2.54, 5.48 Hz, 1H), 6.96 (d, J = 5.87 Hz, 1H), 5.20 (s, 2H), 3.68 (d, J = 10.37 Hz, 1H), 3.42 (s, 3H), 3.36 (d, J = 10.76 Hz, 1H), 1.81 (ddd, J = 1.08, 6.75, 9.39 Hz, 1H), 1.75 (d, J = 0.98 Hz, 3H), 0.91 (dd, J = 5.87, 9.39 Hz, 1H), 0.79-0.86 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-3-(1,3-oxazol-4-ylmethoxy)-1,7-naphthyridin-8-amine |
| 729 | ¹H NMR (400 MHz, CHLOROFORM-d) δ ppm 8.97 (s, 1H), 8.57 (d, J = 2.74 Hz, 1H), 8.51 (ddd, J = 2.64, 6.94, 12.72 Hz, 1H), 8.15 (d, J = 5.67 Hz, 1H), 7.35-7.43 (m, 2H), 7.00 (d, J = 5.87 Hz, 1H), 4.95 (s, 2H), 3.68 (d, J = 10.56 Hz, 1H), 3.43 (s, 3H), 3.36 (d, J = 10.56 Hz, 1H), 1.79-1.86 (m, 1H), 1.76 (s, 3H), 0.92 (dd, J = 6.06, 9.39 Hz, 1H), 0.80-0.87 (m, 1H) | ((8-((3-((1S,5S,6S)-3-amino-1-(methoxymethyl)-5-methyl-2-thia-4-azabicyclo[4.1.0]hept-3-en-5-yl)-4,5-difluorophenyl)amino)-1,7-naphthyridin-3-yl)oxy)acetonitrile |
| 730 | ¹H NMR (400 MHz, DMSO-d6) δ 9.73 (s, 1H), 9.47 (s, 1H), 8.71 (d, J = 2.93 Hz, 1H), 8.43 (ddd, J = 2.74, 6.80, 13.16 Hz, 1H), 8.10 (d, J = 5.87 Hz, 1H), 7.91 (d, J = 2.74 Hz, 1H), 7.81 (br. s., 1H), 7.15 (d, J = 5.87 Hz, 1H), 6.03 (br. s., 2H), 5.62 (s, 2H), 3.57 (d, J = 10.76 Hz, 1H), 3.36 (d, J = 10.95 Hz, 1H), 3.30 (s, 3H), 1.58-1.71 (m, 4H), 0.92 (br. s., 1H), 0.67 (t, J = 5.58 Hz, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-3-(1,2,4-oxadiazol-3-ylmethoxy)-1,7-naphthyridin-8-amine |
| 731 | ¹H NMR (400 MHz, DMSO-d6) δ 9.50 (s, 1H), 8.72 (d, J = 2.74 Hz, 1H), 8.44 (ddd, J = 2.84, 6.85, 13.20 Hz, 1H), 8.12 (d, J = 5.87 Hz, 1H), 7.93 (d, J = 2.74 Hz, 1H), 7.79-7.87 (m, 1H), 7.15 (d, J = 5.87 Hz, | N-(3-((1S,5S,6S)-3-amino-1-(methoxymethyl)-5-methyl-2-thia-4-azabicyclo[4.1.0]hept-3-en-5-yl)-4,5-difluorophenyl)-3- |

TABLE 3'-continued

| Ex. No. | ¹H-NMR | Chemical Name |
|---|---|---|
|  | 1H), 6.59-6.96 (m, 1H), 6.04 (br. s., 2H), 4.88 (t, J = 13.50 Hz, 2H), 3.58 (d, J = 10.76 Hz, 1H), 3.37 (d, J = 11.15 Hz, 1H), 3.32 (s, 3H), 1.59-1.70 (m, 4H), 0.92 (dd, J = 5.28, 9.19 Hz, 1H), 0.68 (t, J = 5.87 Hz, 1H) | (2,2,3,3-tetrafluoropropoxy)-1,7-naphthyridin-8-amine |
| 733 | ¹H NMR (400 MHz, DMSO-d6) δ 9.45 (s, 1H), 8.66 (d, J = 2.74 Hz, 1H), 8.43 (ddd, J = 2.74, 6.85, 13.30 Hz, 1H), 8.10 (d, J = 5.87 Hz, 1H), 7.79-7.83 (m, 1H), 7.78 (d, J = 2.74 Hz, 1H), 7.17 (d, J = 5.87 Hz, 1H), 6.03 (br. s., 2H), 5.06 (d, J = 2.35 Hz, 2H), 3.72 (t, J = 2.35 Hz, 1H), 3.57 (d, J = 10.95 Hz, 1H), 3.36 (d, J = 10.95 Hz, 1H), 3.30 (s, 3H), 1.57-1.70 (m, 4H), 0.91 (dd, J = 5.28, 9.19 Hz, 1H), 0.66 (t, J = 5.77 Hz, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-3-(2-propyn-1-yloxy)-1,7-naphthyridin-8-amine |
| 735 | ¹H NMR (400 MHz, DMSO-d6) δ 9.47 (s, 1H), 8.73 (d, J = 2.74 Hz, 1H), 8.43 (ddd, J = 2.74, 6.65, 13.30 Hz, 1H), 8.10 (d, J = 5.67 Hz, 1H), 7.93 (s, 1H), 7.91 (d, J = 2.74 Hz, 1H), 7.82 (br. s., 1H), 7.15 (d, J = 5.87 Hz, 1H), 6.03 (br. s., 2H), 5.63 (s, 2H), 3.57 (d, J = 10.76 Hz, 1H), 3.36 (d, J = 10.95 Hz, 1H), 3.30 (s, 3H), 1.64-1.69 (m, 1H), 1.62 (s, 3H), 0.91 (d, J = 8.61 Hz, 1H), 0.67 (t, J = 5.77 Hz, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-3-((5-chloro-1,3-thiazol-2-yl)methoxy)-1,7-naphthyridin-8-amine |
| 736 | ¹H NMR (400 MHz, DMSO-d6) δ 9.47 (s, 1H), 8.74 (d, J = 2.93 Hz, 1H), 8.43 (ddd, J = 2.93, 6.90, 13.25 Hz, 1H), 8.10 (d, J = 5.87 Hz, 1H), 7.96 (s, 1H), 7.91 (d, J = 2.74 Hz, 1H), 7.82 (d, J = 5.67 Hz, 1H), 7.16 (d, J = 5.87 Hz, 1H), 6.03 (br. s., 2H), 5.69 (s, 2H), 3.57 (d, J = 10.76 Hz, 1H), 3.36 (d, J = 10.95 Hz, 1H), 3.31 (s, 3H), 1.64-1.69 (m, 1H), 1.62 (s, 3H), 0.88-0.95 (m, 1H), 0.67 (t, J = 5.67 Hz, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-3-((4-bromo-1,3-thiazol-2-yl)methoxy)-1,7-naphthyridin-8-amine |
| 737 | ¹H NMR (400 MHz, DMSO-d6) δ 9.46 (s, 1H), 8.73 (d, J = 2.74 Hz, 1H), 8.43 (ddd, J = 2.74, 6.75, 13.20 Hz, 1H), 8.10 (d, J = 5.67 Hz, 1H), 7.91 (dd, J = 3.13, 5.67 Hz, 2H), 7.85 (d, J = 3.13 Hz, 1H), 7.77-7.83 (m, 1H), 7.15 (d, J = 5.87 Hz, 1H), 6.04 (br. s., 2H), 5.69 (s, 2H), 3.57 (d, J = 10.95 Hz, 1H), 3.36 (d, J = 10.95 Hz, 1H), 3.30-3.32 (m, 3H), 1.67 (m, 1H), 1.62 (s, 3H), 0.91 (dd, J = 5.09, 9.19 Hz, 1H), 0.67 (t, J = 5.77 Hz, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-3-(1,3-thiazol-2-ylmethoxy)-1,7-naphthyridin-8-amine |
| 741 | ¹H NMR (400 MHz, DMSO-d6) δ 9.47 (s, 1H), 8.71 (d, J = 2.74 Hz, 1H), 8.42 (ddd, J = 2.84, 6.85, 13.20 Hz, 1H), 8.11 (d, J = 5.87 Hz, 1H), 7.85 (d, J = 2.93 Hz, 1H), 7.78-7.84 (m, 1H), 7.18 (d, J = 5.87 Hz, 1H), 6.03 (s, 2H), 5.39 (q, J = 3.06 Hz, 2H), 3.57 (d, J = 10.95 Hz, 1H), 3.36 (d, J = 10.95 Hz, 1H), 3.30 (s, 3H), 1.63-1.69 (m, 1H), 1.62 (s, 3H), 0.91 (dd, J = 5.18, 9.29 Hz, 1H), 0.66 (t, J = 5.77 Hz, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-3-((4,4,4-trifluoro-2-butyn-1-yl)oxy)-1,7-naphthyridin-8-amine |
| 750 | ¹H NMR (300 MHz, DMSO-d6) δ ppm 1.54 (s, 3 H) 3.61-3.72 (m, 1 H) 3.83 (d, J = 4.68 Hz, 1 H) 5.43 (t, J = 5.26 Hz, 1 H) 5.54 (s, 2 H) 6.14 (br. s., 2 H) 7.20 (dd, J = 11.91, 8.70 Hz, 1 H) 7.33 (s, 1 H) 7.80 (d, J = 2.63 Hz, 1 H) 7.92 (dd, J = 8.18, 3.51 Hz, 1 H) 8.16-8.24 (m, 2 H) 8.60 (s, 1 H) 8.70 (d, J = 2.63 Hz, 1 H) 10.01 (s, 1 H) | ((1S,5S,6R)-3-amino-7,7-difluoro-5-(2-fluoro-5-((7-(1,3-oxazol-2-ylmethoxy)pyrido[3,2-d]pyrimidin-4-yl)amino)phenyl)-5-methyl-2-thia-4-azabicyclo[4.1.0]hept-3-en-1-yl)methanol |
| 762 | ¹H NMR (DMSO-d6) δ: 9.39 (s, 1H), 8.61 (s, 1H), 8.25 (d, J = 5.9 Hz, 1H), 8.00-8.14 (m, 2H), 7.14 (dd, J = 11.8, 8.7 Hz, 1H), 7.07 (d, J = 5.9 Hz, 1H), 6.22 (s, 2H), 5.19 (d, J = 2.3 Hz, 2H), 4.73-4.87 (m, 1H), 4.59-4.73 (m, 1H), 3.66 (t, J = 2.4 Hz, 1H), 2.33-2.43 (m, 1H), 1.76 (q, J = 7.8 Hz, 1H), 0.97-1.08 (m, 1H), 0.38 (q, J = 5.1 Hz, 1H) | N-(3-((1S,5S,6S)-3-amino-5-(fluoromethyl)-2-thia-4-azabicyclo[4.1.0]hept-3-en-5-yl)-4-fluorophenyl)-2-(2-propyn-1-yloxy)pyrido[3,4-b]pyrazin-5-amine |
| 763 | ¹H NMR (DMSO-d6) δ: 10.05 (s, 1H), 8.69 (d, J = 2.7 Hz, 1H), 8.60 (s, 1H), 8.23 (d, J = 0.8 Hz, 1H), 8.17 (dd, J = 7.2, 2.7 Hz, 1H), 7.91-8.00 (m, 1H), 7.80 (d, J = 2.7 Hz, 1H), 7.33 (d, J = 0.8 Hz, 1H), 7.18 (dd, J = 11.7, 8.8 Hz, 1H), 6.21 (s, 2H), 5.54 (s, 2H), 4.73-4.85 (m, 1H), 4.61-4.72 (m, 1H), 2.34-2.42 (m, 1H), 1.69-1.82 (m, 1H), 1.03 (ddd, J = 8.9, 7.4, 5.2 Hz, 1H), 0.38 (q, J = 5.1 Hz, 1H) | N-(3-((1S,5S,6S)-3-amino-5-(fluoromethyl)-2-thia-4-azabicyclo[4.1.0]hept-3-en-5-yl)-4-fluorophenyl)-7-(1,3-oxazol-2-ylmethoxy)pyrido[3,2-d]pyrimidin-4-amine |
| 768 | ¹H NMR (DMSO-d6) δ: 9.44 (br. s., 1H), 8.61 (s, 1H), 8.26 (d, J = 5.9 Hz, 1H), 8.14 (br. s., 1H), 8.02-8.10 (m, 1H), 7.17 (t, J = 9.8 Hz, 1H), 7.08 (d, J = 5.9 Hz, 1H), 6.38-6.57 (m, 4H), 5.20 (d, J = 2.5 Hz, 2H), 4.57-4.89 (m, 2H), 3.66 (t, J = 2.3 Hz, 1H), 3.06 (s, 3H), 2.88 (s, | (2E)-3-((1R,5S,6S)-3-amino-5-(fluoromethyl)-5-(2-fluoro-5-((2-(2-propyn-1-yloxy)pyrido[3,4-b]pyrazin-5-yl)amino)phenyl)-2-thia-4- |

TABLE 3'-continued

| Ex. No. | ¹H-NMR | Chemical Name |
|---|---|---|
| | 3H), 1.93 (d, J = 12.3 Hz, 1H), 1.58 (br. s., 1H), 0.96 (br. s., 1H). | azabicyclo[4.1.0]hept-3-en-1-yl)-N,N-dimethyl-2-propenamide |
| 769 | ¹H NMR (DMSO-d6) δ: 9.45 (br. s., 1H), 8.66 (s, 1H), 8.26 (d, J = 5.9 Hz, 1H), 8.22 (s, 1H), 8.11-8.16 (m, 1H), 8.07 (dt, J = 8.4, 3.6 Hz, 1H), 7.31 (s, 1H), 7.13-7.22 (m, 1H), 7.06 (d, J = 5.9 Hz, 1H), 6.40-6.58 (m, 4H), 5.67 (s, 2H), 4.57-4.89 (m, 2H), 3.06 (s, 3H), 2.88 (s, 3H), 1.89-1.99 (m, 1H), 1.58 (d, J = 4.3 Hz, 1H), 0.95 (br. s., 1H). | (2E)-3-((1R,5S,6S)-3-amino-5-(fluoromethyl)-5-(2-fluoro-5-((2-(1,3-oxazol-2-ylmethoxy)pyrido[3,4-b]pyrazin-5-yl)amino)phenyl)-2-thia-4-azabicyclo[4.1.0]hept-3-en-1-yl)-N,N-dimethyl-2-propenamide |
| 770 | ¹H NMR (DMSO-d6) δ: 9.35 (s, 1H), 8.69 (d, J = 2.9 Hz, 1H), 8.23 (d, J = 0.8 Hz, 1H), 8.18 (dt, J = 8.9, 3.4 Hz, 1H), 8.03-8.10 (m, 2H), 7.87 (d, J = 2.9 Hz, 1H), 7.33 (s, 1H), 7.15 (dd, J = 11.7, 8.8 Hz, 1H), 7.10 (d, J = 5.9 Hz, 1H), 6.42-6.55 (m, 4H), 5.49 (s, 2H), 4.57-4.85 (m, 2H), 3.05 (s, 3H), 2.88 (s, 3H), 1.94 (t, J = 8.1 Hz, 1H), 1.56 (dd, J = 9.6, 5.5 Hz, 1H), 0.95 (t, J = 6.0 Hz, 1H). | (2E)-3-((1R,5S,6S)-3-amino-5-(fluoromethyl)-5-(2-fluoro-5-((3-(1,3-oxazol-2-ylmethoxy)-1,7-naphthyridin-8-yl)amino)phenyl)-2-thia-4-azabicyclo[4.1.0]hept-3-en-1-yl)-N,N-dimethyl-2-propenamide |
| 771 | ¹H NMR (DMSO-d6) δ: 9.34 (s, 1H), 8.64 (d, J = 2.7 Hz, 1H), 8.19 (dt, J = 8.4, 3.6 Hz, 1H), 8.01-8.11 (m, 2H), 7.73 (d, J = 2.7 Hz, 1H), 7.16 (dd, J = 11.7, 9.0 Hz, 1H), 7.12 (d, J = 5.9 Hz, 1H), 6.43-6.56 (m, 4H), 5.00 (d, J = 2.2 Hz, 2H), 4.59-4.86 (m, 2H), 3.06 (s, 3H), 2.89 (s, 3H), 1.96 (t, J = 8.2 Hz, 1H), 1.87 (t, J = 2.2 Hz, 3H), 1.57 (dd, J = 9.2, 5.1 Hz, 1H), 0.96 (t, J = 6.0 Hz, 1H). | (2E)-3-((1R,5S,6S)-3-amino-5-(5-((3-(2-butyn-1-yloxy)-1,7-naphthyridin-8-yl)amino)-2-fluorophenyl)-5-(fluoromethyl)-2-thia-4-azabicyclo[4.1.0]hept-3-en-1-yl)-N,N-dimethyl-2-propenamide |
| 773 | ¹H NMR (DMSO-d6) δ: 9.45 (s, 1H), 8.62 (s, 1H), 8.27 (d, J = 5.9 Hz, 1H), 8.14 (dd, J = 6.9, 2.6 Hz, 1H), 8.05-8.11 (m, 1H), 7.18 (dd, J = 11.7, 9.0 Hz, 1H), 7.09 (d, J = 5.9 Hz, 1H), 6.61 (d, J = 15.3 Hz, 1H), 6.49 (s, 2H), 6.05 (d, J = 15.1 Hz, 1H), 5.21 (d, J = 2.3 Hz, 2H), 4.58-4.87 (m, 4H), 4.35 (br. s., 2H), 3.68 (t, J = 2.3 Hz, 1H), 2.02 (t, J = 8.1 Hz, 1H), 1.61 (dd, J = 9.6, 5.1 Hz, 1H), 0.96-1.02 (m, 1H). | N-(3-((1R,5S,6S)-3-amino-1-((1E)-3-(3,3-difluoro-1-azetidinyl)-3-oxo-1-propen-1-yl)-5-(fluoromethyl)-2-thia-4-azabicyclo[4.1.0]hept-3-en-5-yl)-4-fluorophenyl)-2-(2-propyn-1-yloxy)pyrido[3,4-b]pyrazin-5-amine |
| 775 | ¹H NMR (DMSO-d6) δ: 10.11 (s, 1H), 8.72 (d, J = 2.7 Hz, 1H), 8.63 (s, 1H), 8.25 (s, 1H), 8.21 (dd, J = 7.0, 2.7 Hz, 1H), 7.98 (dt, J = 8.5, 3.5 Hz, 1H), 7.82 (d, J = 2.7 Hz, 1H), 7.35 (s, 1H), 7.22 (dd, J = 11.6, 8.9 Hz, 1H), 6.43-6.57 (m, 4H), 5.56 (s, 2H), 4.58-4.88 (m, 2H), 3.07 (s, 3H), 2.90 (s, 3H), 1.96 (t, J = 8.2 Hz, 1H), 1.59 (dd, J = 9.5, 5.2 Hz, 1H), 0.93-0.99 (m, 1H) | (2E)-3-((1R,5S,6S)-3-amino-5-(fluoromethyl)-5-(2-fluoro-5-((7-(1,3-oxazol-2-ylmethoxy)pyrido[3,2-d]pyrimidin-4-yl)amino)phenyl)-2-thia-4-azabicyclo[4.1.0]hept-3-en-1-yl)-N,N-dimethyl-2-propenamide |
| 776 | ¹H NMR (DMSO-d6) δ: 10.10 (s, 1H), 8.68 (d, J = 2.7 Hz, 1H), 8.63 (s, 1H), 8.21 (dd, J = 7.1, 2.6 Hz, 1H), 7.94-8.02 (m, 1H), 7.70 (d, J = 2.5 Hz, 1H), 7.22 (dd, J = 11.7, 8.8 Hz, 1H), 6.43-6.58 (m, 4H), 5.13 (d, J = 2.3 Hz, 2H), 4.60-4.88 (m, 2H), 3.75 (t, J = 2.3 Hz, 1H), 3.07 (s, 3H), 2.90 (s, 3H), 1.92-2.01 (m, 1H), 1.59 (dd, J = 9.6, 5.3 Hz, 1H), 0.91-1.01 (m, 1H) | (2E)-3-((1R,5S,6S)-3-amino-5-(fluoromethyl)-5-(2-fluoro-5-((7-(2-propyn-1-yloxy)pyrido[3,2-d]pyrimidin-4-yl)amino)phenyl)-2-thia-4-azabicyclo[4.1.0]hept-3-en-1-yl)-N,N-dimethyl-2-propenamide |
| 779 | ¹H NMR (DMSO-d6) δ: 9.43 (s, 1H), 8.60 (s, 1H), 8.25 (d, J = 5.9 Hz, 1H), 8.09 (dd, J = 7.1, 2.8 Hz, 1H), 7.97 (dt, J = 8.4, 3.7 Hz, 1H), 7.15 (dd, J = 11.5, 8.8 Hz, 1H), 7.07 (d, J = 5.9 Hz, 1H), 6.60 (s, 2H), 5.19 (d, J = 2.3 Hz, 2H), 4.75-4.89 (m, 1H), 4.62-4.75 (m, 1H), 3.66 (t, J = 2.3 Hz, 1H), 2.94-3.13 (m, 3H), 2.84 (br. s., 3H), 2.03 (t, J = 8.2 Hz, 1H), 1.50 (dd, J = 9.5, 5.4 Hz, 1H), 0.64 (t, J = 6.2 Hz, 1H) | (1S,5S,6S)-3-amino-5-(fluoromethyl)-5-(2-fluoro-5-((2-(2-propyn-1-yloxy)pyrido[3,4-b]pyrazin-5-yl)amino)phenyl)-N,N-dimethyl-2-thia-4-azabicyclo[4.1.0]hept-3-ene-1-carboxamide |
| 781 | ¹H NMR (DMSO-d6) δ: 9.47 (s, 1H), 8.62 (s, 1H), 8.33 (s, 1H), 8.27 (d, J = 5.9 Hz, 1H), 8.18 (dd, J = 7.1, 2.8 Hz, 1H), 8.07 (dt, J = 8.7, 3.6 Hz, 1H), 7.18 (dd, J = 11.6, 8.9 Hz, 1H), 7.13 (s, 1H), 7.09 (d, J = 5.9 Hz, 1H), 6.56 (s, 2H), 5.21 (d, J = 2.5 Hz, 2H), 4.62-4.96 (m, 2H), 3.68 (t, J = 2.4 Hz, 1H), 2.01-2.13 (m, 1H), 1.69 (dd, J = 9.7, 5.4 Hz, 1H), 0.88-1.04 (m, 1H) | N-(3-((1S,5S,6S)-3-amino-5-(fluoromethyl)-1-(1,3-oxazol-5-yl)-2-thia-4-azabicyclo[4.1.0]hept-3-en-5-yl)-4-fluorophenyl)-2-(2-propyn-1-yloxy)pyrido[3,4-b]pyrazin-5-amine |
| 801 | ¹H NMR (400 MHz, DMSO-d₆) δ 10.63 (s, 1H), 9.27 (d, J = 1.96 Hz, 1H), 8.92 (d, J = 1.76 Hz, 1H), 8.82 (s, 1H), 8.09-8.19 (m, 2H), 6.15 (s, 2H), 4.45-4.57 (m, 2H), 1.84 (m, 1H), 1.66 (s, 3H), 1.09 (m, 1H), 0.73 (m, 1H). ¹⁹F NMR (377 MHz, DMSO-d₆) δ −138.52 (d, J = 22.55 Hz, 1F), −143.20 (d, J = 22.55 Hz, 1F), −211.45 (s, 1F). | 4-((3-((1S,5S,6S)-3-amino-1-(fluoromethyl)-5-methyl-2-thia-4-azabicyclo[4.1.0]hept-3-en-5-yl)-4,5-difluorophenyl)amino)pyrido[3,2-d]pyrimidine-7-carbonitrile |
| 802 | ¹H NMR (400 MHz, DMSO-d₆) δ 9.57 (br., 1H), 8.67 (s, 1H), 8.30 (m, 2H), 8.22 (s, 1H), 7.91 (m, 1H), 7.32 (s, 1H), 7.11 (t, J = 11.97 Hz, 1H), 6.13 (br., 2H), 5.67 (s, 2H), 4.55-4.46 (m, 2H), 1.80 (t, J = 7.92 Hz, 1H), | N-(3-((1S,5S,6S)-3-amino-1-(fluoromethyl)-5-methyl-2-thia-4-azabicyclo[4.1.0]hept-3-en-5-yl)-4,5-difluorophenyl)-2-(1,3- |

TABLE 3'-continued

| Ex. No. | ¹H-NMR | Chemical Name |
|---|---|---|
|  | 1.64 (s, 3H), 1.07 (dd, J = 5.48, 9.19 Hz, 1H), 0.73 (d, J = 5.09 Hz, 1H). ¹⁹F NMR (376 MHz, DMSO-d₆) δ −138.80 (d, J = 22.53 Hz, 1F), −146.42 (d, J = 22.54 Hz, 1F), −211.42 (s, 1F). | oxazol-2-ylmethoxy)pyrido[3,4-b]pyrazin-5-amine |
| 805 | ¹H NMR (400 MHz, DMSO-d₆) δ 9.58 (br., 1H), 8.63 (s, 1H), 8.23-8.33 (m, 2H), 7.86-7.92 (m, 1H), 7.13 (d, J = 5.87 Hz, 1H), 6.32 (s, 2H), 5.79-6.07 (m, 1H), 5.20 (d, J = 2.35 Hz, 2H), 3.67 (t, J = 2.45 Hz, 1H), 1.90 (m, 1H), 1.68 (s, 3H), 1.37 (m, 1H), 0.77 (m, 1H). ¹⁹F NMR (377 MHz, DMSO-d₆) δ −115.43 (d, ¹J = 273.86 Hz, 1F), −117.97 (d, ¹J = 273.80 Hz, 1F), −138.76 (d, ²J = 22.53 Hz, 1F), −142.98 (d, ²J = 22.53 Hz, 1F). | N-(3-((1S,5S,6S)-3-amino-1-(difluoromethyl)-5-methyl-2-thia-4-azabicyclo[4.1.0]hept-3-en-5-yl)-4,5-difluorophenyl)-2-(2-propyn-1-yloxy)pyrido[3,4-b]pyrazin-5-amine |
| 806 | ¹H NMR (400 MHz, DMSO-d₆) δ 9.56 (br., 1H), 8.63 (s, 1H), 8.27-8.34 (m, 2H), 7.90 (m, 1H), 7.13 (d, J = 5.87 Hz, 1H), 6.13 (br., 1H), 5.20 (d, J = 2.35 Hz, 2H), 4.56 (m, 1H), 4.43 (m, 1H), 3.67 (t, J = 2.35 Hz, 1H), 1.80 (m, 1H), 1.63 (s, 3H), 1.07 (m, 1H), 0.73 (m, 1H). ¹⁹F NMR (376 MHz, DMSO-d₆) δ −138.80 (d, J = 23.41 Hz, 1F), −146.44 (d, J = 23.41 Hz, 1F), −211.42 (s, 1F). | N-(3-((1S,5S,6S)-3-amino-1-(fluoromethyl)-5-methyl-2-thia-4-azabicyclo[4.1.0]hept-3-en-5-yl)-4,5-difluorophenyl)-2-(2-propyn-1-yloxy)pyrido[3,4-b]pyrazin-5-amine |
| 808 | ¹H NMR (400 MHz, DMSO-d₆) δ 10.19 (br., 1H), 8.73 (m, 1H), 8.67 (s, 1H), 8.24 (s, 1H), 8.19 (m, 1H), 8.04 (d, J = 5.67 Hz, 1H), 7.84 (d, J = 2.74 Hz, 1H), 7.34 (s, 1H), 6.13 (br., 2H), 5.56 (s, 2H), 4.44-4.56 (m, 2H), 1.80 (m, 1H), 1.64 (s, 3H), 1.08 (m, 1H), 0.74 (m, 1H). ¹⁹F NMR (376 MHz, DMSO-d₆) δ −138.68 (d, J = 23.45 Hz, 1F), −144.36 (d, J = 23.45 Hz, 1F), −211.44 (s, 1F). | N-(3-((1S,5S,6S)-3-amino-1-(fluoromethyl)-5-methyl-2-thia-4-azabicyclo[4.1.0]hept-3-en-5-yl)-4,5-difluorophenyl)-7-(1,3-oxazol-2-ylmethoxy)pyrido[3,2-d]pyrimidin-4-amine |
| 809 | ¹H NMR (400 MHz, DMSO-d₆) δ 10.18 (br., 1H), 8.67-8.73 (m, 2H), 8.15-8.25 (m, 2H), 8.02 (m, 1H), 7.83 (d, J = 2.74 Hz, 1H), 7.34 (s, 1H), 6.01 (br., 2H), 5.56 (s, 2H), 3.57 (d, J = 10.95 Hz, 1H), 3.38 (d, J = 10.95 Hz, 1 H), 3.29 (s, 3H), 1.67 (m, 1H), 1.63 (s, 3H), 0.93 (m, 1H), 0.67 (m, 1H). ¹⁹F NMR (377 MHz, DMSO-d₆) δ −138.72 (d, J = 22.54 Hz, 1F), −144.51 (d, J = 22.55 Hz, 1F). | N-(3-((1S,5S,6S)-3-amino-1-(methoxymethyl)-5-methyl-2-thia-4-azabicyclo[4.1.0]hept-3-en-5-yl)-4,5-difluorophenyl)-7-(1,3-oxazol-2-ylmethoxy)pyrido[3,2-d]pyrimidin-4-amine |
| 812 | ¹H NMR (400 MHz, DMSO-d₆) δ 10.23 (br., 1H), 8.64-8.78 (m, 2H), 8.25 (d, J = 0.78 Hz, 1H), 8.15 (m, 1H), 8.04 (m, 1H), 7.85 (d, J = 2.74 Hz, 1H), 7.35 (s, 1H), 6.34 (br., 2H), 5.81-6.09 (m, 1H), 5.57 (s, 2H), 1.91 (m, 1H), 1.69 (s, 3H), 1.40 (m, 1H), 0.78 (m, 1H). ¹⁹F NMR (377 MHz, DMSO-d₆) δ −116.84 (d, J = 273.96 Hz, 1F), −117.94 (d, J = 273.96 Hz, 1F), −138.56 (d, J = 22.55 Hz, 1F), −143.80 (d, J = 22.55 Hz, 1F). | N-(3-((1S,5S,6S)-3-amino-1-(difluoromethyl)-5-methyl-2-thia-4-azabicyclo[4.1.0]hept-3-en-5-yl)-4,5-difluorophenyl)-7-(1,3-oxazol-2-ylmethoxy)pyrido[3,2-d]pyrimidin-4-amine |
| 813 | ¹H NMR (400 MHz, DMSO-d₆) δ 10.20 (br., 1H), 8.69-8.70 (m, 2H), 8.20 (m, 1H), 8.05 (m, 1H), 7.72 (d, J = 2.74 Hz, 1H), 6.15 (br., 2H), 5.13 (d, J = 2.35 Hz, 2H), 4.45-4.61 (m, 2H), 3.75 (t, J = 2.35 Hz, 1H), 1.82 (m, 1H), 1.66 (s, 3H), 1.09 (m, 1H), 0.74 (m, 1H). ¹⁹F NMR (377 MHz, DMSO-d₆) δ −138.66 (d, J = 22.54 Hz, 1F), −144.04 (d, J = 22.54 Hz, 1F), −211.42 (s, 1F). | N-(3-((1S,5S,6S)-3-amino-1-(fluoromethyl)-5-methyl-2-thia-4-azabicyclo[4.1.0]hept-3-en-5-yl)-4,5-difluorophenyl)-7-(2-propyn-1-yloxy)pyrido[3,2-d]pyrimidin-4-amine |
| 816 | ¹H NMR (400 MHz, DMSO-d₆) δ 9.37 (br., 1H), 8.62 (s, 1H), 8.26 (d, J = 5.87 Hz, 1H), 7.95-8.10 (m, 2H), 7.15 (dd, J = 8.80, 11.74 Hz, 1H), 7.08 (m, 1H), 6.30 (br., 2H), 5.69-6.13 (m, 1H), 5.09-5.28 (m, 2H), 3.67 (t, J = 2.35 Hz, 1H), 1.92 (m, 1H), 1.68 (s, 3H), 1.32 (m, 1H), 0.75 (m, 1H). ¹⁹F NMR (377 MHz, DMSO-d₆) δ −115.42 (d, ¹J = 273.10 Hz, 1F), −117.88 (d, ¹J = 273.10 Hz, 1F), −118.59 (s, 1F). | N-(3-((1S,5S,6S)-3-amino-1-(difluoromethyl)-5-methyl-2-thia-4-azabicyclo[4.1.0]hept-3-en-5-yl)-4-fluorophenyl)-2-(2-propyn-1-yloxy)pyrido[3,4-b]pyrazin-5-amine |
| 817 | ¹H NMR (400 MHz, DMSO-d₆) δ 9.38 (br., 1H), 8.65 (s, 1H), 8.15-8.32 (m, 2H), 8.03 (m, 2H), 7.31 (s, 1H), 7.14 (dd, J = 8.51, 11.84 Hz, 1H), 7.05 (d, J = 5.87 Hz, 1H), 6.29 (br., 2H), 5.71-6.09 (m, 1H), 5.66 (s, 2H), 1.91 (m, 1H), 1.66 (s, 3H), 1.30 (m, 1H), 0.70 (m, 1H). ¹⁹F NMR (376 MHz, DMSO-d₆) δ −115.10 (d, ¹J = 273.90 Hz, 1F), −118.10 (d, ¹J = 273.90 Hz, 1F), −118.57 (s, 1F). | N-(3-((1S,5S,6S)-3-amino-1-(difluoromethyl)-5-methyl-2-thia-4-azabicyclo[4.1.0]hept-3-en-5-yl)-4-fluorophenyl)-2-(1,3-oxazol-2-ylmethoxy)pyrido[3,4-b]pyrazin-5-amine |
| 819 | ¹H NMR (400 MHz, DMSO-d₆) δ 10.02 (br., 1H), 8.66 (d, J = 2.74 Hz, 1H), 8.61 (s, 1H), 8.12 (dd, J = 2.74, 7.43 Hz, 1H), 7.91 (td, J = 3.67, 8.31 Hz, 1H), 7.68 (d, J = 2.74 Hz, 1H), 7.20 (m, 1H), 6.28 (br., 2H), 5.77-6.10 (m, 1H), 5.11 (d, J = 2.35 Hz, 2H), 3.74 (m, 1H), 1.90 (m, 1H), 1.67 (s, 3H), 1.33 (m, 1H), 0.73 (m, 1H). ¹⁹F NMR (376 MHz, DMSO-d₆) δ −115.07 (d, ¹J = 273.70 Hz, 1F), −116.68 (s, 1F), −117.96 (d, ¹J = 273.70 Hz, 1F). | N-(3-((1S,5S,6S)-3-amino-1-(difluoromethyl)-5-methyl-2-thia-4-azabicyclo[4.1.0]hept-3-en-5-yl)-4-fluorophenyl)-7-(2-propyn-1-yloxy)pyrido[3,2-d]pyrimidin-4-amine |

TABLE 3'-continued

| Ex. No. | ¹H-NMR | Chemical Name |
|---|---|---|
| 823 | ¹H NMR (400 MHz, DMSO-d₆) δ 9.35 (br., 1H), 8.62 (s, 1H), 8.25 (d, J = 5.87 Hz, 1H), 8.01-8.12 (m, 2H), 7.14 (dd, J = 8.80, 11.93 Hz, 1H), 7.07 (d, J = 5.87 Hz, 1H), 6.11 (br., 2H), 5.21 (d, J = 2.35 Hz, 2H), 4.29-4.66 (m, 2H), 3.67 (t, J = 2.35 Hz, 1H), 1.82 (m, 1H), 1.63 (s, 3H), 1.03 (m, 1H), 0.70 (m, 1H). ¹⁹F NMR (377 MHz, DMSO-d₆) δ –119.06 (s, 1F), –211.28 (s, 1F). | N-(3-((1S,5S,6S)-3-amino-1-(fluoromethyl)-5-methyl-2-thia-4-azabicyclo[4.1.0]hept-3-en-5-yl)-4-fluorophenyl)-2-(2-propyn-1-yloxy)pyrido[3,4-b]pyrazin-5-amine |
| 824 | ¹H NMR (400 MHz, DMSO-d₆) δ 10.01 (br., 1H), 8.67 (d, J = 2.74 Hz, 1H), 8.62 (s, 1H), 8.15 (dd, J = 2.84, 7.34 Hz, 1H), 7.95 (td, J = 3.67, 8.31 Hz, 1H), 7.69 (d, J = 2.74 Hz, 1H), 7.19 (dd, J = 8.61, 11.93 Hz, 1H), 6.10 (br., 2H), 5.12 (d, J = 2.35 Hz, 2H), 4.37-4.63 (m, 2H), 3.76 (m, 1H), 1.84 (m, 1H), 1.64 (s, 3H), 1.03 (m, 1H), 0.70 (q, J = 5.35 Hz, 1H). ¹⁹F NMR (377 MHz, DMSO-d₆) δ –117.13 (s, 1F), –211.31 (s, 1F). | N-(3-((1S,5S,6S)-3-amino-1-(fluoromethyl)-5-methyl-2-thia-4-azabicyclo[4.1.0]hept-3-en-5-yl)-4-fluorophenyl)-2-(2-propyn-1-yloxy)pyrido[3,2-d]pyrimidin-4-amine |
| 825 | ¹⁹F NMR (377 MHz, DMSO-d₆) δ –119.04 (s, 1F), –211.28 (s, 1F). ¹H NMR (400 MHz, DMSO-d₆) δ 9.37 (br., 1H), 8.66 (s, 1H), 8.18-8.31 (m, 2H), 7.95-8.11 (m, 2H), 7.32 (s, 1H), 7.14 (dd, J = 9.19, 11.93 Hz, 1H), 7.06 (d, J = 5.67 Hz, 1H), 6.10 (br., 2H), 5.68 (s, 2H), 4.30-4.70 (m, 2H), 1.80 (m, 1H), 1.63 (s, 3H), 1.03 (m, 1H), 0.70 (m, 1H). | N-(3-((1S,5S,6S)-3-amino-1-(fluoromethyl)-5-methyl-2-thia-4-azabicyclo[4.1.0]hept-3-en-5-yl)-4-fluorophenyl)-2-(1,3-oxazol-2-ylmethoxy)pyrido[3,4-b]pyrazin-5-amine |
| 827 | ¹H NMR (400 MHz, DMSO-d₆) δ 9.33 (br., 1H), 8.57 (s, 1H), 8.24 (d, J = 5.87 Hz, 1H), 8.00-8.11 (m, 2H), 7.13 (dd, J = 8.80, 11.93 Hz, 1H), 7.01-7.08 (m, 1H), 6.10 (br., 2H), 5.92 (dq, J = 1.76, 6.59 Hz, 1H), 4.31-4.64 (m, 2H), 3.60 (d, J = 1.96 Hz, 1H), 1.83 (t, J = 7.82 Hz, 1H), 1.66 (d, J = 6.46 Hz, 3H), 1.62 (s, 3H), 1.02 (m, 1H), 0.69 (m, 1H). ¹⁹F NMR (376 MHz, DMSO-d₆) δ –119.12 (s, 1F), –211.30 (s, 1F). | N-(3-((1S,5S,6S)-3-amino-1-(fluoromethyl)-5-methyl-2-thia-4-azabicyclo[4.1.0]hept-3-en-5-yl)-4-fluorophenyl)-2-(((1S)-1-methyl-2-propyn-1-yl)oxy)pyrido[3,4-b]pyrazin-5-amine |
| 828 | ¹H NMR (400 MHz, DMSO-d₆) δ 9.37 (br., 1H), 8.67 (s, 1H), 8.25 (d, J = 5.87 Hz, 1H), 7.99-8.12 (m, 2H), 7.10-7.20 (m, 1H), 7.05 (d, J = 5.87 Hz, 1H), 6.11 (br., 2H), 5.58-5.71 (s, 2H), 4.35-4.70 (m, 2H), 2.65 (s, 3H), 1.87 (m, 1H), 1.63 (s, 3H), 1.03 (m, 1H), 0.70 (m, 1H). ¹⁹F NMR (377 MHz, DMSO-d₆) δ –119.02 (s, 1F), –211.28 (s, 1F). | N-(3-((1S,5S,6S)-3-amino-1-(fluoromethyl)-5-methyl-2-thia-4-azabicyclo[4.1.0]hept-3-en-5-yl)-4-fluorophenyl)-2-((5-methyl-1,2,4-oxadiazol-3-yl)methoxy)pyrido[3,4-b]pyrazin-5-amine |
| 841 | ¹H NMR (400 MHz, DMSO-d₆) δ ppm 9.61 (s, 1 H), 8.64 (s, 1 H), 8.28-8.36 (m, 2 H), 7.94-8.00 (m, 1 H), 7.14 (d, J = 5.87 Hz, 1 H), 6.27 (s, 2 H), 5.21 (d, J = 2.35 Hz, 2 H), 4.64-4.85 (m, 2 H), 3.68 (t, J = 2.35 Hz, 1 H), 2.38-2.47 (m, 1 H), 1.74-1.83 (m, 1 H), 1.10 (ddd, J = 8.75, 7.58, 5.18 Hz, 1 H), 0.46 (q, J = 5.28 Hz, 1 H) | N-(3-((1S,5S,6S)-3-amino-5-(fluoromethyl)-2-thia-4-azabicyclo[4.1.0]hept-3-en-5-yl)-4,5-difluorophenyl)-2-(2-propyn-1-yloxy)pyrido[3,4-b]pyrazin-5-amine |
| 842 | ¹H NMR (400 MHz, DMSO-d₆) δ ppm 9.62 (s, 1 H), 8.68 (s, 1 H), 8.27-8.36 (m, 2 H), 8.23 (d, J = 0.78 Hz, 1 H), 7.94-8.00 (m, 1 H), 7.33 (d, J = 0.78 Hz, 1 H), 7.13 (d, J = 5.87 Hz, 1 H), 6.27 (s, 2 H), 5.68 (s, 2 H), 4.64-4.85 (m, 2 H), 2.38-2.47 (m, 1 H), 1.72-1.84 (m, 1 H), 1.10 (ddd, J = 8.90, 7.53, 5.28 Hz, 1 H), 0.46 (q, J = 5.28 Hz, 1 H) | N-(3-((1S,5S,6S)-3-amino-5-(fluoromethyl)-2-thia-4-azabicyclo[4.1.0]hept-3-en-5-yl)-4,5-difluorophenyl)-2-(1,3-oxazol-2-ylmethoxy)pyrido[3,4-b]pyrazin-5-amine |
| 843 | ¹H NMR (400 MHz, DMSO-d₆) δ ppm 9.59 (s, 1 H), 8.61 (s, 1 H), 8.47 (s, 1 H), 8.28-8.37 (m, 3 H), 7.93-8.00 (m, 1 H), 7.17 (d, J = 5.87 Hz, 1 H), 6.27 (s, 2 H), 5.49 (s, 2 H), 4.64-4.85 (m, 2 H), 2.39-2.46 (m, 1 H), 1.78 (q, J = 8.22 Hz, 1 H), 1.06-1.14 (m, 1 H), 0.46 (q, J = 5.15 Hz, 1 H) | N-(3-((1S,5S,6S)-3-amino-5-(fluoromethyl)-2-thia-4-azabicyclo[4.1.0]hept-3-en-5-yl)-4,5-difluorophenyl)-2-(1,3-oxazol-4-ylmethoxy)pyrido[3,4-b]pyrazin-5-amine |
| 865 | ¹H NMR (400 MHz, DMSO-d6) δ ppm 0.57-0.68 (m, 1 H) 1.23 (dd, J = 9.59, 5.28 Hz, 1 H) 1.72-1.83 (m, 1 H) 1.87 (t, J = 2.25 Hz, 3 H) 4.32-4.57 (m, 2 H) 4.58-4.85 (m, 2 H) 5.15 (d, J = 2.35 Hz, 2 H) 6.40 (s, 2 H) 7.06 (d, J = 5.67 Hz, 1 H) 7.15 (dd, J = 11.84, 8.90 Hz, 1 H) 8.05 (dt, J = 8.56, 3.55 Hz, 1 H) 8.11 (dd, J = 7.24, 2.74 Hz, 1 H) 8.24 (d, J = 5.87 Hz, 1 H) 8.57 (s, 1 H) 9.39 (s, 1 H) | N-(3-((1S,5S,6S)-3-amino-1,5-bis(fluoromethyl)-2-thia-4-azabicyclo[4.1.0]hept-3-en-5-yl)-4-fluorophenyl)-2-(2-butyn-1-yloxy)pyrido[3,4-b]pyrazin-5-amine |
| 866 | ¹H NMR (300 MHz, DMSO-d6) δ ppm 0.70-0.82 (m, 1 H) 1.36 (dd, J = 9.50, 5.70 Hz, 1 H) 1.67 (s, 3 H) 1.82-1.97 (m, 1 H) 5.66 (s, 2 H) 5.71-6.16 (m, 1 H) 6.31 (s, 2 H) 7.11 (d, J = 5.85 Hz, 1 H) 7.31 (d, J = 0.73 Hz, 1 H) 7.83-7.93 (m, 1 H) 8.21 (d, J = 0.73 Hz, 1 H) 8.25 (td, J = 6.58, 4.09 Hz, 1 H) 8.30 (d, J = 5.85 Hz, 1 H) 8.67 (s, 1 H) 9.59 (s, 1 H) | N-(3-((1S,5S,6S)-3-amino-1-(difluoromethyl)-5-methyl-2-thia-4-azabicyclo[4.1.0]hept-3-en-5-yl)-4,5-difluorophenyl)-2-(1,3-oxazol-2-ylmethoxy)pyrido[3,4-b]pyrazin-5-amine |
| 867 | ¹H NMR (300 MHz, DMSO-d6) δ ppm 0.70-0.84 (m, 1 H) 1.36 (dd, J = 9.57, 5.92 Hz, 1 H) 1.66 (s, 3 H) 1.81-1.95 (m, 1 H) 5.47 (s, 2 H) 5.62-6.18 (m, 1 H) | N-(3-((1S,5S,6S)-3-amino-1-(difluoromethyl)-5-methyl-2-thia-4-azabicyclo[4.1.0]hept-3- |

TABLE 3'-continued

| Ex. No. | ¹H-NMR | Chemical Name |
|---|---|---|
| | 6.31 (s, 2 H) 7.15 (d, J = 5.85 Hz, 1 H) 7.82-7.94 (m, 1 H) 8.24 (td, J = 6.54, 2.85 Hz, 1 H) 8.29-8.35 (m, 2 H) 8.44 (d, J = 0.73 Hz, 1 H) 8.58 (s, 1 H) 9.55 (s, 1 H) | en-5-yl)-4,5-difluorophenyl)-2-(1,3-oxazol-4-ylmethoxy)pyrido[3,4-b]pyrazin-5-amine |
| 868 | ¹H NMR (300 MHz, DMSO-d6) δ ppm 0.77 (q, J = 5.75 Hz, 1 H) 1.29-1.44 (m, 1 H) 1.68 (s, 3 H) 1.88 (t, J = 2.34 Hz, 4 H) 5.16 (d, J = 2.48 Hz, 2 H) 5.69-6.16 (m, 1 H) 6.32 (s, 2 H) 7.12 (d, J = 5.99 Hz, 1 H) 7.81-7.94 (m, 1 H) 8.22-8.31 (m, 2 H) 8.60 (s, 1 H) 9.56 (s, 1 H) | N-(3-((1S,5S,6S)-3-amino-1-(difluoromethyl)-5-methyl-2-thia-4-azabicyclo[4.1.0]hept-3-en-5-yl)-4,5-difluorophenyl)-2-(2-butyn-1-yloxy)pyrido[3,4-b]pyrazin-5-amine |
| 869 | ¹H NMR (300 MHz, DMSO-d6) δ ppm 0.63-0.70 (m, 1 H) 0.92 (dd, J = 9.21, 5.26 Hz, 1 H) 1.60-1.70 (m, 4 H) 1.88 (t, J = 2.41 Hz, 3 H) 3.31 (s, 3 H) 3.31 (s, 3 H) 3.36 (d, J = 11.11 Hz, 1 H) 3.57 (d, J = 10.96 Hz, 1 H) 5.16 (d, J = 2.34 Hz, 2 H) 6.01 (br. s., 2 H) 7.12 (d, J = 5.85 Hz, 1 H) 7.83-7.94 (m, 1 H) 8.22-8.39 (m, 2 H) 8.60 (s, 1 H) 9.52 (s, 1 H) | N-(3-((1S,5S,6S)-3-amino-1-(methoxymethyl)-5-methyl-2-thia-4-azabicyclo[4.1.0]hept-3-en-5-yl)-4,5-difluorophenyl)-2-(2-butyn-1-yloxy)pyrido[3,4-b]pyrazin-5-amine |
| 870 | ¹H NMR (300 MHz, DMSO-d6) δ ppm 0.67-0.84 (m, 1 H) 1.36 (dd, J = 9.72, 6.21 Hz, 1 H) 1.67 (s, 3 H) 1.78-1.97 (m, 1 H) 2.42 (s, 3 H) 5.40 (s, 2 H) 5.69-6.14 (m, 1 H) 6.31 (s, 2 H) 7.15 (d, J = 5.99 Hz, 1 H) 7.88 (d, J = 5.85 Hz, 1 H) 8.14 (s, 1 H) 8.21-8.32 (m, 2 H) 8.58 (s, 1 H) 9.55 (s, 1 H) | N-(3-((1S,5S,6S)-3-amino-1-(difluoromethyl)-5-methyl-2-thia-4-azabicyclo[4.1.0]hept-3-en-5-yl)-4,5-difluorophenyl)-2-((2-methyl-1,3-oxazol-4-yl)methoxy)pyrido[3,4-b]pyrazin-5-amine |
| 871 | ¹H NMR (300 MHz, DMSO-d6) δ ppm 0.77 (q, J = 5.65 Hz, 1 H) 1.38 (td, J = 10.05, 5.92 Hz, 1 H) 1.68 (s, 3 H) 1.82-1.98 (m, 1 H) 2.12-2.34 (m, 2 H) 4.51-4.65 (m, 3 H) 4.75 (t, J = 5.85 Hz, 1 H) 5.68-6.18 (m, 1 H) 6.32 (s, 2 H) 7.11 (d, J = 5.85 Hz, 1 H) 7.88 (d, J = 6.14 Hz, 1 H) 8.20-8.35 (m, 2 H) 8.57 (s, 1 H) 9.55 (s, 1 H) | N-(3-((1S,5S,6S)-3-amino-1-(difluoromethyl)-5-methyl-2-thia-4-azabicyclo[4.1.0]hept-3-en-5-yl)-4,5-difluorophenyl)-2-(3-fluoropropoxy)pyrido[3,4-b]pyrazin-5-amine |
| 872 | ¹H NMR (300 MHz, DMSO-d6) δ ppm 0.76 (q, J = 5.65 Hz, 1 H) 1.36 (dd, J = 9.79, 5.70 Hz, 1 H) 1.67 (s, 3 H) 1.81 (t, J = 19.37 Hz, 4 H) 4.79 (t, J = 13.15 Hz, 2 H) 5.67-6.15 (m, 1 H) 6.32 (s, 2 H) 7.12 (d, J = 5.85 Hz, 1 H) 7.84-7.95 (m, 1 H) 8.17-8.36 (m, 2 H) 8.68 (s, 1 H) 9.61 (s, 1 H) | N-(3-((1S,5S,6S)-3-amino-1-(difluoromethyl)-5-methyl-2-thia-4-azabicyclo[4.1.0]hept-3-en-5-yl)-4,5-difluorophenyl)-2-(2,2-difluoropropoxy)pyrido[3,4-b]pyrazin-5-amine |
| 873 | ¹H NMR (300 MHz, DMSO-d6) δ ppm 0.76 (q, J = 5.85 Hz, 1 H) 1.36 (dd, J = 9.87, 5.92 Hz, 1 H) 1.67 (s, 3 H) 1.82-1.94 (m, 1 H) 5.71 (d, J = 1.90 Hz, 2 H) 5.72-6.14 (m, 1 H) 6.31 (s, 2 H) 7.10 (d, J = 5.85 Hz, 1 H) 7.50-7.60 (m, 1 H) 7.77-7.93 (m, 2 H) 8.19-8.33 (m, 2 H) 8.42-8.50 (m, 1 H) 8.64 (s, 1 H) 9.56 (s, 1 H) | N-(3-((1S,5S,6S)-3-amino-1-(difluoromethyl)-5-methyl-2-thia-4-azabicyclo[4.1.0]hept-3-en-5-yl)-4,5-difluorophenyl)-2-((3-fluoro-2-pyridinyl)methoxy)pyrido[3,4-b]pyrazin-5-amine |
| 874 | ¹H NMR (300 MHz, DMSO-d6) δ ppm 0.68-0.85 (m, 1 H) 1.36 (dd, J = 9.57, 5.77 Hz, 1 H) 1.67 (s, 3 H) 1.80-1.95 (m, 1 H) 2.46 (s, 3 H) 5.69 (s, 2 H) 5.72-6.15 (m, 1 H) 6.31 (s, 2 H) 7.00 (d, J = 5.85 Hz, 1 H) 7.33 (d, J = 5.12 Hz, 1 H) 7.88 (dd, J = 5.41, 2.78 Hz, 1 H) 8.17-8.33 (m, 2 H) 8.62 (d, J = 5.12 Hz, 1 H) 8.71 (s, 1 H) 9.56 (s, 1 H) | N-(3-((1S,5S,6S)-3-amino-1-(difluoromethyl)-5-methyl-2-thia-4-azabicyclo[4.1.0]hept-3-en-5-yl)-4,5-difluorophenyl)-2-((4-methyl-2-pyrimidinyl)methoxy)pyrido[3,4-b]pyrazin-5-amine |
| 875 | ¹H NMR (300 MHz, DMSO-d6) δ ppm 0.70-0.83 (m, 1 H) 1.36 (dd, J = 9.72, 5.63 Hz, 1 H) 1.67 (s, 3 H) 1.82-1.95 (m, 1 H) 5.67 (s, 2 H) 5.70-6.14 (m, 1 H) 6.31 (s, 2 H) 7.15 (d, J = 5.85 Hz, 1 H) 7.89 (d, J = 6.28 Hz, 1 H) 7.94 (d, J = 1.90 Hz, 1 H) 8.20-8.34 (m, 2 H) 8.62 (s, 1 H) 9.16 (d, J = 1.90 Hz, 1 H) 9.56 (s, 1 H) | N-(3-((1S,5S,6S)-3-amino-1-(difluoromethyl)-5-methyl-2-thia-4-azabicyclo[4.1.0]hept-3-en-5-yl)-4,5-difluorophenyl)-2-(1,3-thiazol-4-ylmethoxy)pyrido[3,4-b]pyrazin-5-amine |
| 876 | ¹H NMR (300 MHz, DMSO-d6) δ ppm 0.76 (d, J = 6.28 Hz, 1 H) 1.30-1.47 (m, 7 H) 1.67 (s, 3 H) 1.88 (t, J = 7.82 Hz, 1 H) 5.39-5.55 (m, 1 H) 5.70-6.16 (m, 1 H) 6.31 (s, 2 H) 7.08 (d, J = 5.85 Hz, 1 H) 7.87 (br. s., 1 H) 8.20-8.34 (m, 2 H) 8.48 (s, 1 H) 9.50 (s, 1 H) | N-(3-((1S,5S,6S)-3-amino-1-(difluoromethyl)-5-methyl-2-thia-4-azabicyclo[4.1.0]hept-3-en-5-yl)-4,5-difluorophenyl)-2-(1-methylethoxy)pyrido[3,4-b]pyrazin-5-amine |
| 877 | ¹H NMR (300 MHz, DMSO-d6) δ ppm 0.69-0.82 (m, 1 H) 1.36 (dd, J = 9.57, 5.63 Hz, 1 H) 1.67 (s, 3 H) 1.89 (t, J = 8.18 Hz, 1 H) 2.54 (s, 3 H) 5.71-6.14 (m, 3 H) 6.31 (s, 2 H) 7.12 (d, J = 5.85 Hz, 1 H) 7.89 (d, J = 5.99 Hz, 1 H) 8.19-8.29 (m, 1 H) 8.31 (d, J = 5.99 Hz, 1 H) 8.68 (s, 1 H) 9.61 (s, 1 H) | N-(3-((1S,5S,6S)-3-amino-1-(difluoromethyl)-5-methyl-2-thia-4-azabicyclo[4.1.0]hept-3-en-5-yl)-4,5-difluorophenyl)-2-((5-methyl-1,3,4-oxadiazol-2-yl)methoxy)pyrido[3,4-b]pyrazin-5-amine |
| 878 | ¹H NMR (300 MHz, DMSO-d6) δ ppm 0.77 (d, J = 4.82 Hz, 1 H) 1.38 (d, J = 6.43 Hz, 1 H) 1.67 (s, 3 H) 1.80-1.96 (m, 1 H) 2.85 (s, 4 H) 3.05 (s, 3 H) 5.30 (s, 2 H) 5.70-6.15 (m, 1 H) 6.32 (s, 2 H) 7.05 (d, J = 5.85 Hz, | 2-((5-(3-((1S,5S,6S)-3-amino-1-(difluoromethyl)-5-methyl-2-thia-4-azabicyclo[4.1.0]hept-3-en-5-yl)-4,5- |

TABLE 3'-continued

| Ex. No. | ¹H-NMR | Chemical Name |
|---|---|---|
| | 1 H) 7.87 (br. s., 1 H) 8.27 (d, J = 5.85 Hz, 2 H) 8.66 (s, 1 H) 9.56 (s, 1 H) | difluorophenyl)amino)pyrido[3,4-b]pyrazin-2-yl)oxy)-N,N-dimethylacetamide |
| 879 | ¹H NMR (300 MHz, DMSO-d6) δ ppm 9.40 (s, 1 H) 8.56 (s, 1 H) 8.24 (d, J = 5.85 Hz, 1 H) 8.00-8.15 (m, 2 H) 7.15 (dd, J = 11.84, 8.77 Hz, 1 H) 7.06 (d, J = 5.85 Hz, 1 H) 6.40 (s, 2 H) 5.91 (qd, J = 6.63, 2.05 Hz, 1 H) 4.69-4.86 (m, 1 H) 4.48-4.69 (m, 2 H) 4.30-4 | N-(3-((1S,5S,6S)-3-amino-1,5-bis(fluoromethyl)-2-thia-4-azabicyclo[4.1.0]hept-3-en-5-yl)-4-fluorophenyl)-2-(((1S)-1-methyl-2-propyn-1-yl)oxy)pyrido[3,4-b]pyrazin-5-amine |
| 880 | ¹H NMR (300 MHz, DMSO-d6) δ ppm 9.59 (s, 1 H), 8.85 (s, 1 H), 8.38 (d, J = 5.85 Hz, 1 H), 8.26 (dd, J = 7.16, 2.92 Hz, 1 H), 8.18 (ddd, J = 8.73, 4.13, 3.07 Hz, 1 H), 7.29 (dd, J = 11.84, 8.92 Hz, 1 H), 7.14 (d, J = 5.85 Hz, 1 H), 6.54 (s, 2 H), 6.00 (s, 2 H), 4.63-5.01 (m, 3 H), 4.46-4.59 (m, 1 H), 2.50 (s, 3 H), 1.86-2.01 (m, 1 H), 1.37 (dd, J = 9.50, 5.26 Hz, 1 H), 0.68-0.84 (m, 1 H) | N-(3-((1S,5S,6S)-3-amino-1,5-bis(fluoromethyl)-2-thia-4-azabicyclo[4.1.0]hept-3-en-5-yl)-4-fluorophenyl)-2-((3-methyl-1,2,4-oxadiazol-5-yl)methoxy)pyrido[3,4-b]pyrazin-5-amine |
| 881 | ¹H NMR (400 MHz, DMSO-d6) δ ppm 9.52 (s, 1 H), 8.81 (d, J = 4.89 Hz, 2 H), 8.72 (s, 1 H), 8.30 (ddd, J = 13.30, 6.65, 2.74 Hz, 1 H), 8.23 (d, J = 5.87 Hz, 1 H), 7.88 (m, J = 5.87 Hz, 1 H), 7.46 (t, J = 4.89 Hz, 1 H), 6.97 (d, J = 5.87 Hz, 1 H), 6.00 (br. s., 2 H), 5.76 (s, 2 H), 3.56 (d, J = 10.95 Hz, 1 H), 3.36 (d, J = 11.15 Hz, 1 H), 3.30 (s, 3 H), 1.57-1.69 (m, 4 H), 0.92 (dd, J = 8.61, 4.69 Hz, 1 H), 0.66 (t, J = 5.58 Hz, 1 H) | N-(3-((1S,5S,6S)-3-amino-1-(methoxymethyl)-5-methyl-2-thia-4-azabicyclo[4.1.0]hept-3-en-5-yl)-4,5-difluorophenyl)-2-(2-pyrimidinylmethoxy)pyrido[3,4-b]pyrazin-5-amine |
| 882 | ¹H NMR (400 MHz, DMSO-d6) δ ppm 9.58 (s, 1 H), 8.73 (s, 1 H), 8.23-8.35 (m, 2 H), 7.83-7.94 (m, 1 H), 7.06 (d, J = 5.87 Hz, 1 H), 6.00 (br. s., 2 H), 5.87 (s, 2 H), 3.56 (d, J = 10.95 Hz, 1 H), 3.36 (d, J = 10.95 Hz, 1 H), 3.27 (s, 3 H), 2.36 (s, 3 H), 1.55-1.71 (m, 4 H), 0.92 (dd, J = 9.10, 5.38 Hz, 1 H), 0.66 (t, J = 5.58 Hz, 1 H) | N-(3-((1S,5S,6S)-3-amino-1-(methoxymethyl)-5-methyl-2-thia-4-azabicyclo[4.1.0]hept-3-en-5-yl)-4,5-difluorophenyl)-2-((3-methyl-1,2,4-oxadiazol-5-yl)methoxy)pyrido[3,4-b]pyrazin-5-amine |
| 883 | ¹H NMR (400 MHz, DMSO-d6) δ ppm 9.59 (s, 1 H), 8.67 (s, 1 H), 8.30 (d, J = 5.87 Hz, 1 H), 8.25 (ddd, J = 13.06, 6.80, 2.64 Hz, 1 H), 7.82-7.93 (m, 1 H), 7.10 (d, J = 5.87 Hz, 1 H), 6.32 (br. s., 2 H), 5.93 (t, J = 55.40 Hz, 1 H), 5.69 (s, 2 H), 2.63 (s, 3 H), 1.81-1.96 (m, 1 H), 1.67 (s, 3 H), 1.37 (dd, J = 9.59, 5.87 Hz, 1 H), 0.76 (q, J = 5.67 Hz, 1 H) | N-(3-((1S,5S,6S)-3-amino-1-(difluoromethyl)-5-methyl-2-thia-4-azabicyclo[4.1.0]hept-3-en-5-yl)-4,5-difluorophenyl)-2-((5-methyl-1,2,4-oxadiazol-3-yl)methoxy)pyrido[3,4-b]pyrazin-5-amine |
| 884 | ¹H NMR (400 MHz, DMSO-d6) δ ppm 9.35-9.76 (m, 1 H), 8.81 (d, J = 4.89 Hz, 2 H), 8.72 (s, 1 H), 8.18-8.30 (m, 2 H), 7.83-7.92 (m, 1 H), 7.46 (t, J = 4.89 Hz, 1 H), 6.98 (d, J = 5.87 Hz, 1 H), 6.32 (br. s., 2 H), 5.93 (t, J = 55.60 Hz, 1 H), 5.75 (s, 2 H), 1.81-1.96 (m, 1 H), 1.67 (s, 3 H), 1.36 (dd, J = 9.78, 5.87 Hz, 1 H), 0.76 (q, J = 5.74 Hz, 1 H) | N-(3-((1S,5S,6S)-3-amino-1-(difluoromethyl)-5-methyl-2-thia-4-azabicyclo[4.1.0]hept-3-en-5-yl)-4,5-difluorophenyl)-2-(2-pyrimidinylmethoxy)pyrido[3,4-b]pyrazin-5-amine |
| 885 | ¹H NMR (400 MHz, CD3OD) δ ppm 8.56 (s, 1 H), 8.27 (d, J = 6.06 Hz, 1 H), 7.93-8.09 (m, 2 H), 7.16 (d, J = 5.87 Hz, 1 H), 5.73 (s, 2 H), 3.50-3.66 (m, 2 H), 3.45 (s, 3 H), 2.66 (s, 3 H), 2.16 (dd, J = 9.10, 6.75 Hz, 1 H), 2.08 (s, 3 H), 1.63 (dd, J = 9.00, 6.65 Hz, 1 H), 1.13 (t, J = 6.36 Hz, 1 H) | N-(3-((1S,5S,6S)-3-amino-1-(methoxymethyl)-5-methyl-2-thia-4-azabicyclo[4.1.0]hept-3-en-5-yl)-4,5-difluorophenyl)-2-((5-methyl-1,2,4-oxadiazol-3-yl)methoxy)pyrido[3,4-b]pyrazin-5-amine |
| 886 | ¹H NMR (300 MHz, DMSO-d6) δ ppm 9.53 (s, 1 H), 8.56 (s, 1 H), 8.20-8.35 (m, 2 H), 7.80-7.93 (m, 1 H), 7.12 (d, J = 5.85 Hz, 1 H), 6.31 (s, 2 H), 5.93 (t, J = 55.50 Hz, 1 H), 5.34 (s, 2 H), 2.41 (s, 3 H), 2.35 (s, 3 H), 1.88 (t, J = 8.40 Hz, 1 H), 1.67 (s, 3 H), 1.36 (dd, J = 9.50, 5.85 Hz, 1 H), 0.76 (q, J = 5.60 Hz, 1 H) | N-(3-((1S,5S,6S)-3-amino-1-(difluoromethyl)-5-methyl-2-thia-4-azabicyclo[4.1.0]hept-3-en-5-yl)-4,5-difluorophenyl)-2-((2,5-dimethyl-1,3-oxazol-4-yl)methoxy)pyrido[3,4-b]pyrazin-5-amine |
| 887 | ¹H NMR (300 MHz, CD3OD) δ ppm 8.59 (s, 1 H), 8.23 (d, J = 5.85 Hz, 1 H), 7.96 (dt, J = 5.96, 2.28 Hz, 1 H), 7.87 (ddd, J = 12.35, 6.80, 2.63 Hz, 1 H), 7.08 (d, J = 5.85 Hz, 1 H), 5.83 (s, 3 H), 5.81 (t, J = 55.80 Hz, 1 H), 2.43 (dd, J = 9.35, 7.02 Hz, 1 H), 2.37 (s, 3 H), 2.06 (s, 3 H), 1.91 (dd, J = 9.50, 6.87 Hz, 1 H), 1.04-1.20 (m, 1 H) | N-(3-((1S,5S,6S)-3-amino-1-(difluoromethyl)-5-methyl-2-thia-4-azabicyclo[4.1.0]hept-3-en-5-yl)-4,5-difluorophenyl)-2-((3-methyl-1,2,4-oxadiazol-5-yl)methoxy)pyrido[3,4-b]pyrazin-5-amine |
| 888 | ¹H NMR (400 MHz, DMSO-d6) δ ppm 9.59 (s, 1 H), 8.65 (s, 1 H), 8.30 (d, J = 5.87 Hz, 1 H), 8.25 (ddd, J = 13.01, 6.85, 2.64 Hz, 1 H), 7.89 (m, 1 H), 7.12 (d, J = 5.87 Hz, 1 H), 6.92 (d, J = 1.17 Hz, 1 H), 6.31 (br. s., 2 H), 5.93 (t, J = 55.60 Hz, 1 H), 5.58 (s, 2 H), 2.33 (d, J = 1.17 Hz, 3 H), 1.89 (t, J = 7.63 Hz, 1 H), 1.67 (s, 3 H), 1.31-1.44 (m, 1 H), 0.77 (m, 1 H) | N-(3-((1S,5S,6S)-3-amino-1-(difluoromethyl)-5-methyl-2-thia-4-azabicyclo[4.1.0]hept-3-en-5-yl)-4,5-difluorophenyl)-2-((5-methyl-2-yl)methoxy)pyrido[3,4-b]pyrazin-5-amine |
| 889 | ¹H NMR (300 MHz, DMSO-d6) δ ppm 9.61 (s, 1 H), 8.66 (s, 1 H), 8.32 (d, J = 5.99 Hz, 1 H), 8.25 (ddd, J = 13.12, 6.83, 2.70 Hz, 1 H), 7.89 (dt, J = 5.92, 2.16 Hz, | N-(3-((1S,5S,6S)-3-amino-1-(difluoromethyl)-5-methyl-2-thia-4-azabicyclo[4.1.0]hept-3- |

TABLE 3'-continued

| Ex. No. | ¹H-NMR | Chemical Name |
|---|---|---|
| | 1 H), 7.15 (d, J = 5.85 Hz, 1 H), 6.32 (s, 2 H), 5.69-6.15 (m, 3 H), 2.73 (s, 3 H), 1.80-1.96 (m, 1 H), 1.67 (s, 3 H), 1.36 (dd, J = 9.57, 5.92 Hz, 1 H), 0.76 (q, J = 5.75 Hz, 1 H) | en-5-yl)-4,5-difluorophenyl)-2-((5-methyl-1,3,4-thiadiazol-2-yl)methoxy)pyrido[3,4-b]pyrazin-5-amine |
| 890 | ¹H NMR (300 MHz, DMSO-d6) δ ppm 9.57 (s, 1 H), 8.58 (s, 1 H), 8.18-8.36 (m, 2 H), 7.81-7.95 (m, 1 H), 7.12 (d, J = 5.85 Hz, 1 H), 6.32 (br. s., 2 H), 5.70-6.15 (m, 2 H), 3.60 (d, J = 2.05 Hz, 1 H), 1.81-1.97 (m, 1 H), 1.56-1.78 (m, 6 H), 1.31-1.42 (m, 1 H), 0.77 (d, J = 5.55 Hz, 1 H) | N-(3-((1S,5S,6S)-3-amino-1-(chfluoromethyl)-5-methyl-2-thia-4-azabicyclo[4.1.0]hept-3-en-5-yl)-4,5-difluorophenyl)-2-(((1S)-1-methyl-2-propyn-1-yl)oxy)pyrido[3,4-b]pyrazin-5-amine |
| 891 | ¹H NMR (300 MHz, DMSO-d6) δ ppm 9.57 (s, 1 H), 8.63 (s, 1 H), 8.19-8.35 (m, 2 H), 8.15 (d, J = 0.88 Hz, 1 H), 7.89 (dt, J = 4.02, 2.08 Hz, 1 H), 7.25 (d, J = 0.73 Hz, 1 H), 7.07 (d, J = 5.85 Hz, 1 H), 6.43-6.59 (m, 1 H), 6.31 (s, 2 H), 5.93 (t, J = 55.50 Hz, 1 H), 1.83-1.95 (m, 1 H), 1.79 (d, J = 6.58 Hz, 3 H), 1.67 (s, 3 H), 1.31-1.41 (m, 1 H), 0.76 (q, J = 5.75 Hz, 1 H) | N-(3-((1S,5S,6S)-3-amino-1-(difluoromethyl)-5-methyl-2-thia-4-azabicyclo[4.1.0]hept-3-en-5-yl)-4,5-difluorophenyl)-2-((1 R)-1-(1,3-oxazol-2-yl)ethoxy)pyrido[3,4-b]pyrazin-5-amine |
| 892 | ¹H NMR (300 MHz, DMSO-d6) δ ppm 9.57 (s, 1 H), 8.63 (s, 1 H), 8.20-8.36 (m, 2 H), 8.15 (d, J = 0.88 Hz, 1 H), 7.88 (dt, J = 3.95, 2.12 Hz, 1 H), 7.25 (d, J = 0.73 Hz, 1 H), 7.07 (d, J = 5.85 Hz, 1 H), 6.43-6.60 (m, 1 H), 6.32 (br. s., 2 H), 5.93 (t, J = 55.50 Hz, 1 H), 1.83-1.95 (m, 1 H), 1.79 (d, J = 6.72 Hz, 3 H), 1.67 (s, 3 H), 1.32-1.42 (m, 1 H), 0.76 (q, J = 5.90 Hz, 1 H) | N-(3-((1S,5S,6S)-3-amino-1-(difluoromethyl)-5-methyl-2-thia-4-azabicyclo[4.1.0]hept-3-en-5-yl)-4,5-difluorophenyl)-2-((1 S)-1-(1,3-oxazol-2-yl)ethoxy)pyrido[3,4-b]pyrazin-5-amine |
| 893 | ¹H NMR (300 MHz, DMSO-d6) δ ppm 9.55 (s, 1 H), 8.53 (s, 1 H), 8.20-8.34 (m, 2 H), 7.88 (dt, J = 6.03, 2.17 Hz, 1 H), 7.09 (d, J = 5.85 Hz, 1 H), 6.31 (s, 2 H), 5.93 (t, J = 55.50 Hz, 1 H), 4.60 (t, J = 5.33 Hz, 2 H), 3.65 (t, J = 5.33 Hz, 2 H), 3.50 (t, J = 7.02 Hz, 2 H), 2.12-2.23 (m, 2 H), 1.81-2.03 (m, 3 H), 1.67 (s, 3 H), 1.36 (dd, J = 9.65, 5.85 Hz, 1 H), 0.76 (q, J = 5.70 Hz, 1 H) | 1-(2-((5-((3-((1S,5S,6S)-3-amino-1-(difluoromethyl)-5-methyl-2-thia-4-azabicyclo[4.1.0]hept-3-en-5-yl)-4,5-difluorophenyl)amino)pyrido[3,4-b]pyrazin-2-yl)oxy)ethyl)-2-pyrrolidinone |
| 894 | ¹H NMR (300 MHz, DMSO-d6) δ ppm 9.51 (s, 1 H), 8.52 (s, 1 H), 8.18-8.34 (m, 2 H), 7.78-7.92 (m, 1 H), 7.08 (d, J = 5.85 Hz, 1 H), 6.32 (s, 2 H), 5.93 (t, J = 55.70 Hz, 1 H), 5.47-5.64 (m, 1 H), 3.51-3.71 (m, 2 H), 1.83-1.95 (m, 1 H), 1.67 (s, 3 H), 1.29-1.43 (m, 4 H), 0.76 (q, J = 5.70 Hz, 1 H) | N-(3-((1S,5S,6S)-3-amino-1-(difluoromethyl)-5-methyl-2-thia-4-azabicyclo[4.1.0]hept-3-en-5-yl)-4,5-difluorophenyl)-2-((1S)-2-methoxy-1-methylethoxy)pyrido[3,4-b]pyrazin-5-amine |
| 895 | ¹H NMR (300 MHz, DMSO-d6) δ ppm 9.53 (s, 1 H), 8.56 (s, 1 H), 8.17-8.34 (m, 2 H), 7.87 (dt, J = 5.96, 2.28 Hz, 1 H), 7.12 (d, J = 5.85 Hz, 1 H), 6.31 (s, 2 H), 5.93 (t, J = 55.70 Hz, 1 H), 4.07 (s, 3 H), 1.82-1.95 (m, 1 H), 1.67 (s, 3 H), 1.36 (dd, J = 9.65, 5.85 Hz, 1 H), 0.76 (q, J = 5.80 Hz, 1 H) | N-(3-((1S,5S,6S)-3-amino-1-(difluoromethyl)-5-methyl-2-thia-4-azabicyclo[4.1.0]hept-3-en-5-yl)-4,5-difluorophenyl)-2-methoxypyrido[3,4-b]pyrazin-5-amine |
| 896 | ¹H NMR (300 MHz, DMSO-d6) δ ppm 12.58 (br. s., 1 H), 9.22 (s, 1 H), 8.06-8.22 (m, 3 H), 7.76 (dt, J = 3.98, 2.03 Hz, 1 H), 6.65 (d, J = 5.70 Hz, 1 H), 6.29 (br. s., 2 H), 5.92 (t, J = 55.50 Hz, 1 H), 1.80-1.94 (m, 1 H), 1.65 (s, 3 H), 1.35 (dd, J = 9.72, 5.92 Hz, 1 H), 0.75 (q, J = 5.75 Hz, 1 H) | 5-((3-((1S,5S,6S)-3-amino-1-(difluoromethyl)-5-methyl-2-thia-4-azabicyclo[4.1.0]hept-3-en-5-yl)-4,5-difluorophenyl)amino)pyrido[3,4-b]pyrazin-2(1H)-one |
| 897 | ¹H NMR (400 MHz, DMSO-d6) δ 10.11 (s, 1H), 8.65-8.67 (m, 1H), 8.64 (s, 1H), 8.17 (ddd, J = 2.54, 6.70, 12.67 Hz, 1H), 8.00 (d, J = 5.99 Hz, 1H), 7.62 (d, J = 2.74 Hz, 1H), 5.94 (br. s., 2H), 4.01 (s, 3H), 2.30-2.37 (m, 1H), 1.69-1.76 (m, 1H), 1.67 (s, 3H), 0.83-0.98 (m, 1H), 0.50 (q, J = 5.28 Hz, 1H) | N-(3-((1S,5S,6S)-3-amino-5-methyl-2-thia-4-azabicyclo[4.1.0]hept-3-en-5-yl)-4,5-difluorophenyl)-7-methoxypyrido[3,2-d]pyrimidin-4-amine |
| 898 | ¹H NMR (400 MHz, DMSO-d6) δ 10.79 (s, 1H), 8.79 (s, 1H), 8.14-8.22 (m, 2H), 7.93-8.00 (m, 2H), 6.20 (s, J = 4.64 Hz, 2H), 3.72 (s, 3H), 2.32 (t, J = 8.51 Hz, 1H), 1.62 (s, 3H), 1.50 (dd, J = 4.99, 9.68 Hz, 1H), 1.06 (dd, J = 5.09, 7.43 Hz, 1H) | methyl (1S,5S,6S)-3-amino-5-(5-(((5-chloro-2-pyridinyl)carbonyl)amino)-2,3-difluorophenyl)-5-methyl-2-thia-4-azabicyclo[4.1.0]hept-3-ene-1-carboxylate |
| 900 | ¹H NMR (400 MHz, DMSO-d6) δ 9.48 (s, 1H), 8.56 (s, 1H), 8.26-8.33 (m, 2H), 7.83-7.88 (m, 1H), 7.11 (d, J = 5.87 Hz, 1H), 5.95 (br. s, 2H), 4.08 (s, 3H), 2.29-2.36 (m, 1H), 1.74 (q, J = 7.89 Hz, 1H), 1.66 (s, 3H), 0.89 (dt, J = 5.18, 8.17 Hz, 1H), 0.49 (q, J = 5.09 Hz, 1H) | N-(3-((1S,5S,6S)-3-amino-5-methyl-2-thia-4-azabicyclo[4.1.0]hept-3-en-5-yl)-4,5-difluorophenyl)-2-methoxypyrido[3,4-b]pyrazin-5-amine |
| 901 | ¹H NMR (400 MHz, DMSO-d6) δ 10.46 (s, 1H), 8.94 (d, J = 2.35 Hz, 1H), 8.73 (s, 1H), 8.42 (d, J = 2.15 Hz, 1H), 8.08 (ddd, J = 2.64, 6.60, 12.47 Hz, 1H), 7.98-8.03 (m, 1H), 6.26 (s, 2H), 3.71 (s, 3H), 3.14-3.19 (m, 3H), 2.07-2.15 (m, 1H), 1.72 (s, 3H), 1.46 (dd, J = 5.48, 9.59 Hz, 1H), 0.72-0.77 (m, 1H) | (1S,5S,6S)-3-amino-5-(5-((7-chloropyrido[3,2-d]pyrimidin-4-yl)amino)-2,3-difluorophenyl)-N-methoxy-N,5-dimethyl-2-thia-4-azabicyclo[4.1.0]hept-3-ene-1-carboxamide |

TABLE 3'-continued

| Ex. No. | ¹H-NMR | Chemical Name |
|---|---|---|
| 903 | ¹H NMR (400 MHz, DMSO-d6) δ 9.43 (s, 1H), 8.65 (d, J = 2.93 Hz, 1H), 8.44 (ddd, J = 2.74, 6.85, 13.30 Hz, 1H), 8.09 (d, J = 5.87 Hz, 1H), 7.78-7.81 (m, 1H), 7.75 (s, 1H), 7.17 (d, J = 5.87 Hz, 1H), 6.03 (s, 2H), 4.99 (d, J = 2.35 Hz, 2H), 3.57 (d, J = 10.95 Hz, 1H), 3.36 (d, J = 10.95 Hz, 1H), 3.30 (s, 3H), 1.87 (t, J = 2.25 Hz, 3H), 1.66 (dd, J = 7.24, 8.80 Hz, 1H), 1.62 (s, 3H), 0.91 (dd, J = 5.18, 9.29 Hz, 1H), 0.66 (t, J = 5.87 Hz, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-3-(2-butyn-1-yloxy)-1,7-naphthyridin-8-amine |
| 904 | ¹H NMR (400 MHz, DMSO-d6) δ 10.64 (s, 1H), 9.27 (d, J = 1.76 Hz, 1H), 8.91 (d, J = 1.96 Hz, 1H), 8.82 (s, 1H), 8.20 (ddd, J = 2.74, 6.70, 12.47 Hz, 1H), 8.10-8.16 (m, 1H), 6.19 (s, 2H), 2.40 (dd, J = 7.73, 9.49 Hz, 1H), 2.13 (s, 3H), 1.77 (dd, J = 5.38, 9.68 Hz, 1H), 1.64 (s, 3H), 1.14 (dd, J = 5.87, 7.24 Hz, 1H) | 4-((3-((1S,5S,6S)-1-acetyl-3-amino-5-methyl-2-thia-4-azabicyclo[4.1.0]hept-3-en-5-yl)-4,5-difluorophenyl)amino)pyrido[3,2-d]pyrimidine-7-carbonitrile |
| 907 | ¹H NMR (400 MHz, DMSO-d6) δ 10.60 (s, J = 5.99 Hz, 1H), 9.26 (d, J = 1.96 Hz, 1H), 8.90 (d, J = 1.96 Hz, 1H), 8.80 (s, 1H), 8.13 (ddd, J = 2.64, 6.70, 12.37 Hz, 1H), 8.05-8.09 (m, 1H), 5.96 (br. s., 2H), 5.00 (d, J = 3.91 Hz, 1H), 3.34-3.45 (m, 1H), 1.61 (s, 3H), 1.54-1.59 (m, 1H), 1.19-1.28 (m, 3H), 0.93 (dd, J = 4.99, 9.29 Hz, 1H), 0.59 (t, J = 5.67 Hz, 1H) | 4-((3-((1S,5S,6S)-3-amino-1-(1-hydroxyethyl)-5-methyl-2-thia-4-azabicyclo[4.1.0]hept-3-en-5-yl)-4,5-difluorophenyl)amino)pyrido[3,2-d]pyrimidine-7-carbonitrile |
| 908 | ¹H NMR (400 MHz, DMSO-d6) δ 10.59 (s, 1H), 9.25 (d, J = 1.76 Hz, 1H), 8.89 (d, J = 1.76 Hz, 1H), 8.79 (s, 1H), 8.04-8.16 (m, 2H), 5.95 (br. s., 2H), 4.91-5.00 (m, 1H), 3.41-3.50 (m, 1H), 1.59-1.70 (m, 4H), 1.12-1.25 (m, 3H), 0.94 (dd, J = 4.99, 9.29 Hz, 1H), 0.53 (t, J = 5.77 Hz, 1H) | 4-((3-((1R,2S,6S)-4-amino-6-((R)-1-hydroxyethyl)-2-methyl-3-azabicyclo[4.1.0]hept-3-en-2-yl)-4,5-difluorophenyl)amino)pyrido[3,2-d]pyrimidine-7-carbonitrile |
| 909 | ¹H NMR (400 MHz, CHLOROFORM-d) δ 9.14 (br. s., 1H), 8.94 (d, J = 1.76 Hz, 1H), 8.86 (s, 1H), 8.50 (d, J = 1.96 Hz, 1H), 8.39 (ddd, J = 2.74, 6.75, 11.84 Hz, 1H), 7.48 (t, J = 3.65 Hz, 1H), 1.96 (dd, J = 7.43, 9.19 Hz, 1H), 1.67-1.81 (m, 3H), 1.38 (d, J = 5.28 Hz, 6H), 1.14 (dd, J = 5.77, 9.88 Hz, 1H), 0.64 (t, J = 6.16 Hz, 1H) | 4-((3-((1S,5S,6S)-3-amino-1-(1-hydroxy-1-methylethyl)-5-methyl-2-thia-4-azabicyclo[4.1.0]hept-3-en-5-yl)-4,5-difluorophenyl)amino)pyrido[3,2-d]pyrimidine-7-carbonitrile |
| 911 | ¹H NMR (400 MHz, DMSO-d6) δ 9.57 (s, 1H), 8.63 (s, 1H), 8.28-8.35 (m, 2H), 7.90 (d, J = 5.48 Hz, 1H), 7.15-7.32 (m, 2H), 7.13 (d, J = 5.87 Hz, 1H), 6.12 (br. s., 2H), 5.20 (d, J = 2.35 Hz, 2H), 3.67 (t, J = 2.35 Hz, 1H), 2.17 (t, J = 8.31 Hz, 1H), 1.65 (s, 3H), 1.46 (dd, J = 5.18, 9.49 Hz, 1H), 0.91 (t, J = 6.16 Hz, 1H) | (1S,5S,6S)-3-amino-5-(2,3-difluoro-5-((2-(2-propyn-1-yloxy)pyrido[3,4-b]pyrazin-5-yl)amino)phenyl)-5-methyl-2-thia-4-azabicyclo[4.1.0]hept-3-ene-1-carboxamide |
| 912 | ¹H NMR (400 MHz, DMSO-d6) δ 9.55 (s, 1H), 8.62 (s, 1H), 8.22-8.32 (m, 2H), 7.86-7.90 (m, 1H), 7.12 (d, J = 5.87 Hz, 1H), 6.28 (s, 2H), 5.20 (d, J = 2.35 Hz, 2H), 3.67 (t, J = 2.45 Hz, 1H), 3.05 (br. s., 3H), 2.90 (br. s., 3H), 1.99-2.07 (m, 1H), 1.72 (s, 3H), 1.36 (dd, J = 5.38, 9.49 Hz, 1H), 0.79 (t, J = 6.26 Hz, 1H) | (1S,5S,6S)-3-amino-5-(2,3-difluoro-5-((2-(2-propyn-1-yloxy)pyrido[3,4-b]pyrazin-5-yl)amino)phenyl)-N,N,5-trimethyl-2-thia-4-azabicyclo[4.1.0]hept-3-ene-1-carboxamide |
| 917 | ¹H NMR (400 MHz, DMSO-d6) δ 10.20 (s, 1H), 8.68 (s, 1H), 8.69 (d, J = 3.44 Hz, 2H), 8.20 (ddd, J = 2.45, 6.70, 12.57 Hz, 1H), 8.00-8.05 (m, 1H), 7.71 (d, J = 2.54 Hz, 1H), 7.29 (br. s., 1H), 7.22 (br. s., 1H), 6.13 (br. s., 2H), 5.12 (d, J = 2.35 Hz, 2H), 3.74 (t, J = 2.35 Hz, 1H), 2.17 (t, J = 8.31 Hz, 1H), 1.65 (s, 3H), 1.46 (dd, J = 5.18, 9.49 Hz, 1H), 0.91 (t, J = 5.97 Hz, 1H) | (1S,5S,6S)-3-amino-5-(2,3-difluoro-5-((7-(2-propyn-1-yloxy)pyrido[3,2-d]pyrimidin-4-yl)amino)phenyl)-5-methyl-2-thia-4-azabicyclo[4.1.0]hept-3-ene-1-carboxamide |
| 918 | ¹H NMR (400 MHz, DMSO-d6) δ 10.20 (s, 1H), 8.73 (s, 1H), 8.68 (s, 1H), 8.24 (s, 1H), 8.17-8.22 (m, 1H), 8.02 (d, J = 5.67 Hz, 1H), 7.84 (d, J = 2.74 Hz, 1H), 7.25-7.36 (m, 2H), 7.21 (br. s., 1H), 6.12 (br. s., 2H), 5.56 (s, 2H), 2.14-2.20 (m, 1H), 1.65 (s, 3H), 1.46 (dd, J = 5.09, 9.59 Hz, 1H), 0.85-0.96 (m, 1H) | (1S,5S,6S)-3-amino-5-(2,3-difluoro-5-((7-(1,3-oxazol-2-ylmethoxy)pyrido[3,2-d]pyrimidin-4-yl)amino)phenyl)-5-methyl-2-thia-4-azabicyclo[4.1.0]hept-3-ene-1-carboxamide |
| 923 | ¹H NMR (400 MHz, DMSO-d6) δ 10.19 (s, 1H), 8.72 (d, J = 2.74 Hz, 1H), 8.68 (s, 1H), 8.24 (s, 1H), 8.10-8.17 (m, 1H), 8.02 (br. s., 1H), 7.84 (d, J = 2.74 Hz, 1H), 7.34 (s, 1H), 6.28 (br. s., 2H), 5.56 (s, 2H), 2.99-3.21 (m, 3H), 2.91 (br. s., 3H), 2.00-2.07 (m, 1H), 1.72 (s, 3H), 1.36 (dd, J = 5.58, 9.29 Hz, 1H), 0.79 (t, J = 6.26 Hz, 1H). | (1S,5S,6S)-3-amino-5-(2,3-difluoro-5-((7-(1,3-oxazol-2-ylmethoxy)pyrido[3,2-d]pyrimidin-4-yl)amino)phenyl)-N,N,5-trimethyl-2-thia-4-azabicyclo[4.1.0]hept-3-ene-1-carboxamide |
| 928 | ¹H NMR (400 MHz, DMSO-d6) δ 10.06 (s, 1H), 8.66 (s, 1H), 8.61 (s, 1H), 8.10 (dd, J = 2.74, 7.24 Hz, 1H), 7.90 (td, J = 3.67, 8.51 Hz, 1H), 7.68 (d, J = 2.93 Hz, 1H), 7.19 (dd, J = 8.80, 11.74 Hz, 1H), 6.57 (s, 2H), 5.11 (d, J = 2.35 Hz, 2H), 3.74 (t, J = 2.25 Hz, 1H), 2.37 (dd, J = 8.02, 9.59 Hz, 1H), 1.92 (dd, J = 5.87, 9.78 Hz, 1H), 1.77 (s, 3H), 1.00 (t, J = 6.65 Hz, 1H) | (1S,5S,6S)-3-amino-5-(2-fluoro-5-((7-(2-propyn-1-yloxy)pyrido[3,2-d]pyrimidin-4-yl)amino)phenyl)-5-methyl-2-thia-4-azabicyclo[4.1.0]hept-3-ene-1-carbonitrile |

TABLE 3'-continued

| Ex. No. | ¹H-NMR | Chemical Name |
|---|---|---|
| 931 | ¹H NMR (400 MHz, DMSO-d6) δ 9.62 (s, 1H), 8.59 (s, 1H), 8.30 (d, J = 5.87 Hz, 1H), 8.25 (ddd, J = 2.74, 6.85, 13.11 Hz, 1H), 7.85-7.90 (m, 1H), 7.12 (d, J = 5.87 Hz, 1H), 6.60 (s, 2H), 5.92 (dq, J = 2.05, 6.62 Hz, 1H), 3.60 (d, J = 2.15 Hz, 1H), 2.37 (dd, J = 7.92, 9.68 Hz, 1H), 1.94 (dd, J = 5.97, 9.68 Hz, 1H), 1.78 (s, 3H), 1.66 (d, J = 6.65 Hz, 3H), 1.07 (t, J = 6.75 Hz, 1H) | (1S,5S,6S)-3-amino-5-(2,3-difluoro-5-((2-(((1S)-1-methyl-2-propyn-1-yl)oxy)pyrido[3,4-b]pyrazin-5-yl)amino)phenyl)-5-methyl-2-thia-4-azabicyclo[4.1.0]hept-3-ene-1-carbonitrile |
| 933 | ¹H NMR (400 MHz, DMSO-d6) δ 10.20 (s, 1H), 8.69 (s, 2H), 8.15 (ddd, J = 2.74, 6.80, 12.57 Hz, 1H), 7.98-8.04 (m, 1H), 7.72 (d, J = 2.93 Hz, 1H), 6.30 (s, 2H), 5.13 (d, J = 2.35 Hz, 2H), 3.75 (t, J = 2.35 Hz, 1H), 3.62 (d, J = 17.21 Hz, 2H), 3.32 (s, 2H), 2.03-2.10 (m, 1H), 1.89 (br. s., 2H), 1.82 (br. s., 2H), 1.74 (s, 3H), 1.39 (dd, J = 5.38, 9.49 Hz, 1H), 0.74 (t, J = 6.16 Hz, 1H) | N-(3-((1S,5S,6S)-3-amino-5-methyl-1-(1-pyrrolidinylcarbonyl)-2-thia-4-azabicyclo[4.1.0]hept-3-en-5-yl)-4,5-difluorophenyl)-7-(2-propyn-1-yloxy)pyrido[3,2-d]pyrimidin-4-amine |
| 936 | ¹H NMR (400 MHz, DMSO-d6) δ 10.20 (s, 1H), 8.73 (s, 1H), 8.69 (s, 1H), 8.25 (d, J = 0.78 Hz, 1H), 8.14 (ddd, J = 2.64, 6.65, 12.62 Hz, 1H), 8.01 (d, J = 5.92 Hz, 1H), 7.85 (d, J = 2.74 Hz, 1H), 7.35 (s, 1H), 6.30 (br. s., 2H), 5.57 (s, 2H), 3.62 (d, J = 15.26 Hz, 2H), 3.30 (br.s., 2H), 1.96-2.10 (m, 1H), 1.89 (br. s., 2H), 1.82 (br. s., 2H), 1.74 (s, 3H), 1.40 (dd, J = 5.38, 9.49 Hz, 1H), 0.74 (t, J = 6.06 Hz, 1H) | N-(3-((1S,5S,6S)-3-amino-5-methyl-1-(1-pyrrolidinylcarbonyl)-2-thia-4-azabicyclo[4.1.0]hept-3-en-5-yl)-4,5-difluorophenyl)-7-(1,3-oxazol-2-ylmethoxy)pyrido[3,2-d]pyrimidin-4-amine |
| 937 | ¹H NMR (400 MHz, DMSO-d6) δ 9.56 (s, 1H), 8.60 (s, 1H), 8.23-8.34 (m, 2H), 7.84-7.90 (m, 1H), 7.13 (d, J = 5.87 Hz, 1H), 6.29 (br. s., 2H), 5.90-5.97 (m, 1H), 3.62 (d, J = 2.15 Hz, 3H), 3.32 (br. s., 2H), 2.01-2.10 (m, 1H), 1.89 (br. s., 2H), 1.82 (br. s., 2H), 1.73 (s, 3H), 1.68 (d, J = 6.65 Hz, 3H), 1.35-1.44 (m, 1H), 0.74 (t, J = 6.06 Hz, 1H) | N-(3-((1S,5S,6S)-3-amino-5-methyl-1-(1-pyrrolidinylcarbonyl)-2-thia-4-azabicyclo[4.1.0]hept-3-en-5-yl)-4,5-difluorophenyl)-2-(((1S)-1-methyl-2-propyn-1-yl)oxy)pyrido[3,4-b]pyrazin-5-amine |
| 938 | ¹H NMR (400 MHz, DMSO-d6) δ 9.58 (s, 1H), 8.65 (s, 1H), 8.24-8.33 (m, 2H), 8.18 (s, 1H), 7.88 (d, J = 5.81 Hz, 1H), 7.28 (s, 1H), 7.09 (d, J = 5.87 Hz, 1H), 6.54 (q, J = 6.65 Hz, 1H), 6.31 (br. s., 2H), 3.63 (d, J = 15.65 Hz, 2H), 3.34 (s, 2H), 2.07 (t, J = 8.22 Hz, 1H), 1.90 (br. s., 2H), 1.82 (s, J = 6.65 Hz, 5H), 1.75 (s, 3H), 1.40 (dd, J = 5.48, 9.39 Hz, 1H), 0.75 (t, J = 6.06 Hz, 1H) | N-(3-((1S,5S,6S)-3-amino-5-methyl-1-(1-pyrrolidinylcarbonyl)-2-thia-4-azabicyclo[4.1.0]hept-3-en-5-yl)-4,5-difluorophenyl)-2-((1S)-1-(1,3-oxazol-2-yl)ethoxy)pyrido[3,4-b]pyrazin-5-amine |
| 941 | ¹H NMR (400 MHz, DMSO-d6) δ ppm 0.38 (q, J = 5.1 Hz, 1 H), 0.99-1.09 (m, 1 H), 1.76 (q, J = 8.3 Hz, 1 H), 2.35-2.43 (m, 1 H), 3.73 (t, J = 2.3 Hz, 1 H), 4.60-4.87 (m, 2 H), 5.11 (d, J = 2.3 Hz, 2 H), 6.21 (s, 2 H), 7.18 (dd, J = 11.9, 8.8 Hz, 1 H), 7.68 (d, J = 2.7 Hz, 1 H), 7.91-8.00 (m, 1 H), 8.17 (dd, J = 7.1, 2.8 Hz, 1 H), 8.60 (s, 1 H), 8.66 (d, J = 2.7 Hz, 1 H), 10.04 (s, 1 H) | N-(3-((1S,5S,6S)-3-amino-5-(fluoromethyl)-2-thia-4-azabicyclo[4.1.0]hept-3-en-5-yl)-4-fluorophenyl)-7 (2-propyn-1-yloxy)pyrido[3,2-d]pyrimidin-4-amine |
| 942 | ¹H NMR (400 MHz, DMSO-d6) δ ppm 0.58 (t, J = 5.9 Hz, 1 H), 1.08 (dd, J = 9.4, 5.3 Hz, 1 H), 1.62-1.70 (m, 1 H), 3.28 (s, 3 H), 3.34 (d, J = 10.8 Hz, 1 H), 3.55 (d, J = 10.8 Hz, 1 H), 3.73 (t, J = 2.3 Hz, 1 H), 4.58-4.81 (m, 2 H), 5.11 (d, J = 2.3 Hz, 2 H), 6.27 (s, 2 H), 7.18 (dd, J = 11.7, 8.8 Hz, 1 H), 7.68 (d, J = 2.7 Hz, 1 H), 7.94-7.99 (m, 1 H), 8.18 (dd, J = 7.2, 2.7 Hz, 1 H), 8.60 (s, 1 H), 8.66 (d, J = 2.7 Hz, 1 H), 10.05 (s, 1 H) | N-(3-((1S,5S,6S)-3-amino-5-(fluoromethyl)-1-(methoxymethyl)-2-thia-4-azabicyclo[4.1.0]hept-3-en-5-yl)-4-fluorophenyl)-7-(2-propyn-1-yloxy)pyrido[3,2-d]pyrimidin-4-amine |
| 944 | ¹H NMR (400 MHz, DMSO-d6) δ ppm 0.63-0.72 (m, 1 H), 1.05 (dd, J = 9.3, 5.4 Hz, 1 H), 1.61 (s, 3 H), 1.79-1.88 (m, 1 H), 3.74 (t, J = 2.2 Hz, 1 H), 4.40-4.48 (m, 1 H), 4.51-4.60 (m, 1 H), 5.12 (d, J = 2.3 Hz, 2 H), 6.17 (s, 2 H), 7.70 (d, J = 2.7 Hz, 1 H), 8.64 (s, 1 H), 8.66-8.68 (m, 1 H), 8.69 (d, J = 2.7 Hz, 1 H), 8.73 (dd, J = 9.2, 2.7 Hz, 1 H), 10.40 (s, 1 H) | N-(5-((1S,5S,6S)-3-amino-1-(fluoromethyl)-5-methyl-2-thia-4-azabicyclo[4.1.0]hept-3-en-5-yl)-6-fluoro-3-pyridinyl)-7-(2-propyn-1-yloxy)pyrido[3,2-d]pyrimidin-4-amine |
| 945 | ¹H NMR (400 MHz, DMSO-d6) δ ppm 0.77 (br. s., 1 H), 1.38 (br. s., 1 H), 1.68 (s, 3 H), 1.90 (br. s., 1 H), 3.73 (t, J = 2.3 Hz, 1 H), 5.11 (d, J = 2.3 Hz, 2 H), 5.93 (t, J = 55.5 Hz, 1 H), 6.32 (br. s., 2 H), 7.70 (d, J = 2.7 Hz, 1 H), 7.96-8.05 (m, 1 H), 8.15 (ddd, J = 12.6, 6.7, 2.5 Hz, 1 H), 8.62-8.74 (m, 2 H), 10.21 (s, 1 H) | N-(3-((1S,5S,6S)-3-amino-1-(difluoromethyl)-5-methyl-2-thia-4-azabicyclo[4.1.0]hept-3-en-5-yl)-4,5-difluorophenyl)-7-(2-propyn-1-yloxy)pyrido[3,2-d]pyrimidin-4-amine |
| 946 | ¹H NMR (400 MHz, CHLOROFORM-d) δ ppm 0.79-0.86 (m, 1 H), 0.92-1.01 (m, 1 H), 1.77 (s, 3 H), 1.79-1.87 (m, 1 H), 3.37 (d, J = 10.6 Hz, 1 H), 3.43 (s, 3 H), 3.50 (s, 3 H), 3.66 (d, J = 10.6 Hz, 1 H), 3.82-3.93 (m, 2 H), 4.25-4.35 (m, 2 H), 7.40-7.51 (m, 2 H), 8.41 (ddd, J = 12.0, 6.9, 2.6 Hz, 1 H), 8.57 (d, J = 2.7 Hz, 1 H), 8.73 (s, 1 H), 9.00 (s, 1 H). | N-(3-((1S,5S,6S)-3-amino-1-(methoxymethyl)-5-methyl-2-thia-4-azabicyclo[4.1.0]hept-3-en-5-yl)-4,5-difluorophenyl)-7-(2-methoxyethoxy)pyrido[3,2-d]pyrimidin-4-amine |
| 947 | ¹H NMR (400 MHz, CHLOROFORM-d) δ ppm 0.77 (t, J = 6.2 Hz, 1 H), 1.10 (dd, J = 9.7, 5.8 Hz, 1 H), 1.82 (t, J = 7.5 Hz, 1 H), 3.37 (d, J = 10.6 Hz, 1 H), 3.41 (s, 3 H), 3.50 (s, 3 H), 3.67 (d, J = 10.4 Hz, 1 H), 3.85-3.87 (m, 2 H), 4.25-4.36 (m, 2 H), 4.48-4.80 (m, 3 H), | N-(3-((1S,5S,6S)-3-amino-5-(fluoromethyl)-1-(methoxymethyl)-2-thia-4-azabicyclo[4.1.0]hept-3-en-5-yl)-4-fluorophenyl)-7-(2- |

TABLE 3'-continued

| Ex. No. | ¹H-NMR | Chemical Name |
|---|---|---|
| | 4.80-5.01 (m, 1 H), 7.14 (dd, J = 11.6, 8.9 Hz, 1 H), 7.43 (d, J = 2.7 Hz, 1 H), 7.78 (dd, J = 6.7, 2.8 Hz, 1 H), 8.24 (dt, J = 8.5, 3.6 Hz, 1 H), 8.56 (d, J = 2.5 Hz, 1 H), 8.69 (s, 1 H), 8.96 (s, 1 H). | methoxyethoxy)pyrido[3,2-d]pyrimidin-4-amine |
| 948 | ¹H NMR (400 MHz, CHLOROFORM-d) δ ppm 0.78-0.85 (m, 1 H), 0.91-1.00 (m, 1 H), 1.76 (s, 3 H), 1.79-1.87 (m, 1 H), 2.38 (s, 3 H), 2.45 (s, 3 H), 3.37 (d, J = 10.6 Hz, 1 H), 3.43 (s, 3 H), 3.67 (d, J = 10.6 Hz, 1 H), 5.03 (s, 2 H), 7.40-7.50 (m, 1 H), 7.56 (d, J = 2.7 Hz, 1 H), 8.42 (ddd, J = 12.0, 6.8, 2.8 Hz, 1 H), 8.56 (d, J = 2.5 Hz, 1 H), 8.75 (s, 1 H), 9.00 (s, 1 H) | N-(3-((1S,5S,6S)-3-amino-1-(methoxymethyl)-5-methyl-2-thia-4-azabicyclo[4.1.0]hept-3-en-5-yl)-4,5-difluorophenyl)-7-((2,5-dimethyl-1,3-oxazol-4-yl)methoxy)pyrido[3,2-d]pyrimidin-4-amine |
| 949 | ¹H NMR (400 MHz, DMSO-d6) δ ppm 0.75 (q, J = 5.8 Hz, 1 H), 1.36 (dd, J = 9.6, 5.9 Hz, 1 H), 1.67 (s, 3 H), 1.84-1.95 (m, 1 H), 5.59 (s, 2 H), 5.92 (t, J = 55.4 Hz, 1 H), 6.34 (br. s., 2 H), 7.34 (d, J = 0.8 Hz, 1 H), 7.84-7.92 (m, 1 H), 7.96 (d, J = 2.7 Hz, 1 H), 8.16 (d, J = 1.6 Hz, 1 H), 8.20-8.30 (m, 2 H), 8.78 (d, J = 2.9 Hz, 1 H), 9.47 (s, 1 H) | N-(3-((1S,5S,6S)-3-amino-1-(difluoromethyl)-5-methyl-2-thia-4-azabicyclo[4.1.0]hept-3-en-5-yl)-4,5-difluorophenyl)-5-fluoro-3-(1,3-oxazol-2-ylmethoxy)-1,7-naphthyridin-8-amine |
| 950 | ¹H NMR (400 MHz, DMSO-d6) δ ppm 0.65 (t, J = 5.8 Hz, 1 H), 0.92 (dd, J = 8.7, 5.4 Hz, 1 H), 1.58-1.68 (m, 4 H), 3.30 (s, 3 H), 3.36 (d, J = 11.0 Hz, 1 H), 3.56 (d, J = 11.0 Hz, 1 H), 5.59 (s, 2 H), 6.02 (br. s., 2 H), 7.34 (s, 1 H), 7.82-7.92 (m, 1 H), 7.96 (d, J = 2.7 Hz, 1 H), 8.16 (d, J = 1.6 Hz, 1 H), 8.24 (s, 1 H), 8.30 (ddd, J = 13.2, 6.7, 2.7 Hz, 1 H), 8.79 (d, J = 2.7 Hz, 1 H), 9.43 (s, 1 H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-fluoro-3-(1,3-oxazol-2-ylmethoxy)-1,7-naphthyridin-8-amine |
| 951 | ¹H NMR (400 MHz, DMSO-d₆) δ ppm 0.65 (t, J = 5.8 Hz, 1 H), 0.91 (dd, J = 9.3, 5.2 Hz, 1 H), 1.62 (s, 3 H), 1.64-1.68 (m, 1 H), 3.30 (s, 3 H), 3.36 (d, J = 11.0 Hz, 1 H), 3.56 (d, J = 11.0 Hz, 1 H), 3.75 (t, J = 2.3 Hz, 1 H), 5.16 (d, J = 2.3 Hz, 2 H), 6.02 (s, 2 H), 7.83 (d, J = 2.9 Hz, 1 H), 7.84-7.91 (m, 1 H), 8.16 (d, J = 1.8 Hz, 1 H), 8.31 (ddd, J = 13.2, 6.8, 2.7 Hz, 1 H), 8.75 (d, J = 2.9 Hz, 1 H), 9.43 (s, 1 H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-fluoro-3-(2-propyn-1-yloxy)-1,7-naphthyridin-8-amine |
| 952 | ¹H NMR (400 MHz, DMSO-d₆) δ ppm 0.94 (br. s., 1 H), 1.09 (t, J = 7.5 Hz, 3 H), 1.57 (br. s., 1 H), 1.94 (br. s., 1 H), 2.27 (qt, J = 7.5, 2.1 Hz, 2 H), 2.88 (s, 3 H), 3.05 (s, 3 H), 4.54-4.90 (m, 2 H), 5.16 (t, J = 2.1 Hz, 2 H), 6.35-6.60 (m, 4 H), 7.07 (d, J = 5.7 Hz, 1 H), 7.16 (t, J = 10.1 Hz, 1 H), 8.06 (dt, J = 8.6, 3.5 Hz, 1 H), 8.12 (br. s., 1 H), 8.24 (d, J = 5.9 Hz, 1 H), 8.59 (s, 1 H), 9.41 (br. s., 1 H) | (2E)-3-((1R,5S,6S)-3-amino-5-(fluoromethyl)-5-(2-fluoro-5-((2-(2-pentyn-1-yloxy)pyrido[3,4-b]pyrazin-5-yl)amino)phenyl)-2-thia-4-azabicyclo[4.1.0]hept-3-en-1-yl)-N,N-dimethyl-2-propenamide |
| 957 | ¹H NMR (400 MHz, CHLOROFORM-d) δ ppm 1.13 (br. s., 1 H) 1.75 (br. s., 1 H) 2.21 (t, J = 7.82 Hz, 1 H) 4.61-5.14 (m, 2 H) 5.65 (s, 2 H) 7.02 (d, J = 5.87 Hz, 1 H) 7.09 (t, J = 10.17 Hz, 1 H) 7.20 (s, 1 H) 7.61 (s, 1 H) 7.73 (br. s., 2 H) 8.12 (br. s., 1 H) 8.21 (d, J = 5.28 Hz, 1 H) 8.35 (s, 1 H) 8.60 (br. s., 1 H) | N-(3-((1S,5S,6S)-3-amino-5-(fluoromethyl)-1-(1H-1,2,3-triazol-4-yl)-2-thia-4-azabicyclo[4.1.0]hept-3-en-5-yl)-4-fluorophenyl)-2-(1,3-oxazol-2-ylmethoxy)pyrido[3,4-b]pyrazin-5-amine |
| 958 | ¹H NMR (400 MHz, CHLOROFORM-d) δ ppm 1.35 (br. s., 1 H) 1.75-1.93 (m, 4 H) 2.18 (d, J = 7.04 Hz, 1 H) 4.65-5.10 (m, 3 H) 5.64 (br. s., 2 H) 7.02 (d, J = 5.28 Hz, 1 H) 7.09 (t, J = 10.07 Hz, 1 H) 7.19 (br. s., 1 H) 7.65-7.80 (m, 2 H) 8.14-8.27 (m, 2 H) 8.36 (br. s., 1 H) 8.59 (br. s., 1 H) | N-(3-((1S,5S,6S)-3-amino-5-(fluoromethyl)-1-(1-propyn-1-yl)-2-thia-4-azabicyclo[4.1.0]hept-3-en-5-yl)-4-fluorophenyl)-2-(1,3-oxazol-2-ylmethoxy)pyrido[3,4-b]pyrazin-5-amine |
| 960 | ¹H NMR (400 MHz, CD3OD) δ ppm 1.17 (t, J = 6.06 Hz, 1 H) 1.81 (dd, J = 9.59, 5.67 Hz, 1 H) 2.16-2.24 (m, 1 H) 3.03 (t, J = 2.35 Hz, 1 H) 4.76-5.06 (m, 2 H) 5.21 (d, J = 2.54 Hz, 2 H) 7.08 (d, J = 5.87 Hz, 1 H) 7.15 (dd, J = 11.64, 8.90 Hz, 1 H) 7.80 (s, 1 H) 7.91-8.01 (m, 2 H) 8.19 (d, J = 5.87 Hz, 1 H) 8.46 (s, 1 H) | N-(3-((1S,5S,6S)-3-amino-5-(fluoromethyl)-1-(1H-1,2,3-triazol-4-yl)-2-thia-4-azabicyclo[4.1.0]hept-3-en-5-yl)-4-fluorophenyl)-2-(2-propyn-1-yloxy)pyrido[3,4-b]pyrazin-5-amine |
| 961 | ¹H NMR (CDCl3, 300 MHz) δ = 9.09 (s, 1H), 8.96 (d, J = 1.9 Hz, 1H), 8.83 (s, 1H), 8.51 (d, J = 1.9 Hz, 1H), 7.96 (dt, J = 8.8, 3.4 Hz, 1H), 7.86 (dd, J = 7.0, 2.9 Hz, 1H), 7.18 (dd, J = 11.5, 8.8 Hz, 1H), 3.81-3.94 (m, 2H), 2.43 (dd, J = 15.9, 2.9 Hz, 1H), 1.81 ppm (s, 3H) | 4-((3-((1R,5S,6S)-3-amino-7,7-difluoro-1-(hydroxymethyl)-5-methyl-2-thia-4-azabicyclo[4.1.0]hept-3-en-5-yl)-4-fluorophenyl)amino)pyrido[3,2-d]pyrimidine-7-carbonitrile |

Method D: Propylphosphonic Anhydride (T3P) procedure in DCM as solvent

Example 810

N-(3-((1S,5S,6S)-3-amino-1,5-bis(fluoromethyl)-2-thia-4-azabicyclo[4.1.0]hept-3-en-5-yl)-4,5-difluorophenyl)-5-(prop-2-yn-1-yloxy)pyrazine-2-carboxamide

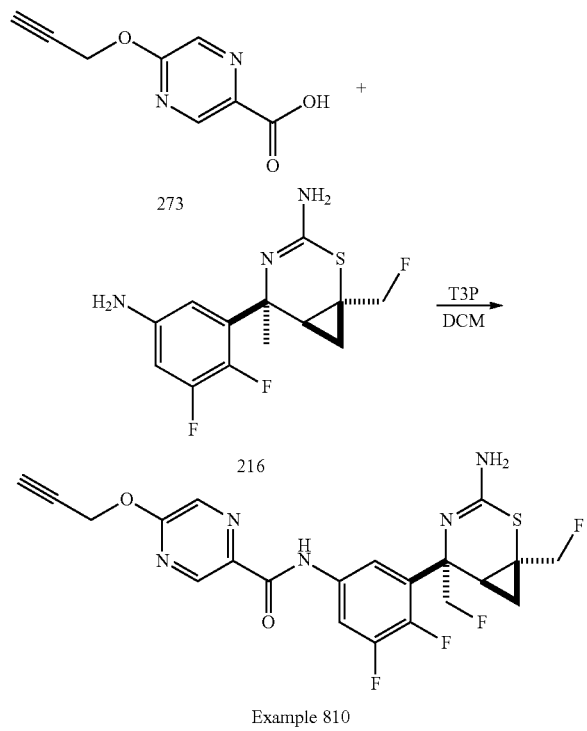

To a suspension of (1S,5S,6S)-5-(5-amino-2,3-difluorophenyl)-1-(fluoromethyl)-5-methyl-2-thia-4-azabicyclo[4.1.0]hept-3-en-3-amine (intermediate 216, 110 mg, 0.36 mmol) and 5-(prop-2-yn-1-yloxy)pyrazine-2-carboxylic acid (intermediate 273, 119 mg, 0.55 mmol) in DCM (4 mL) at 0° C. under nitrogen was added 1-propanephosphonic acid cyclic anhydride (50 wt. % solution in EtOAc, 465 mg, 0.73 mmol). After 1 h, the cooling bath was removed, and the hazy reaction mixture was stirred for 18 h at RT. The reaction mixture was diluted with DCM (30 mL) and poured into a 0.2 N NaOH solution (5 mL) that was cooled with an ice bath. The mixture was stirred for 15 min then transferred to a separatory funnel. The layers were separated. The aqueous layer was further extracted with DCM (10 mL). The organic extracts were combined and dried over $MgSO_4$ then concentrated under reduced pressure. The residue was purified by silica gel chromatography (12 g, using a gradient of 25-100% EtOAc in hexanes) to afford N-(3-((1S,5S,6S)-3-amino-1-(fluoromethyl)-5-methyl-2-thia-4-azabicyclo[4.1.0]hept-3-en-5-yl)-4,5-difluorophenyl)-5-(prop-2-yn-1-yloxy)pyrazine-2-carboxamide (Example 810, 101 mg, 0.219 mmol, 60% yield) as an off white crystalline solid. MS m/z=462.0 [M+H]+. $^1$H NMR (400 MHz, DMSO-$d_6$) δ 10.64 (br., 1H), 8.92 (d, J=1.37 Hz, 1H), 8.50 (d, J=1.17 Hz, 1H), 7.89-7.97 (m, 2H), 6.12 (br., 2H), 5.16 (d, J=2.35 Hz, 2H), 4.44-4.57 (m, 2H), 3.66 (t, J=2.45 Hz, 1H), 1.80 (m, 1H), 1.63 (s, 3H), 1.05 (m, 1H), 0.72 (m, 1H). $^{19}$F NMR (377 MHz, DMSO-$d_6$) δ -138.45 (d, J=22.54 Hz, 1F), -143.62 (d, J=22.54 Hz, 1F), -211.57 (s, 1F).

Using procedures analogous or similar to the general amidation Method D described above, the appropriate aniline and carboxylic acid intermediates were reacted to provide the 103 examples listed in Table 4 and Table 4'.

TABLE 4

| Ex. No. | Chemical Structure | Observed [M + H]+ |
| --- | --- | --- |
| 614 | 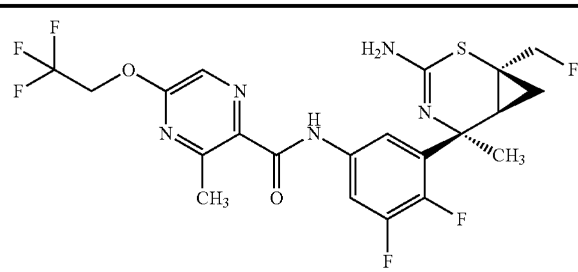 | 520.2 |
| 615 | 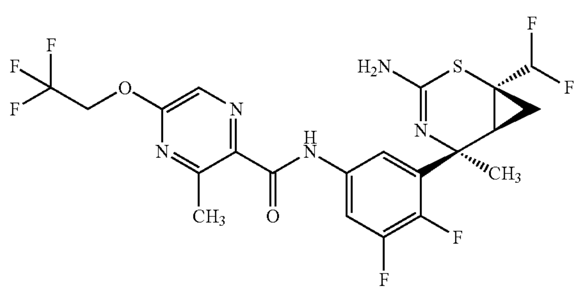 [SMILES: Cc1nc(OCC(F)(F)F)cnc1C(=O)Nc1cc(F)c(F)c([C@@]2(C)N=C(N)S[C@@]3(C(F)F)C[C@@H]23)c1] | 538.1 |

TABLE 4-continued

| Ex. No. | Chemical Structure | Observed [M + H]+ |
|---|---|---|
| 616 | 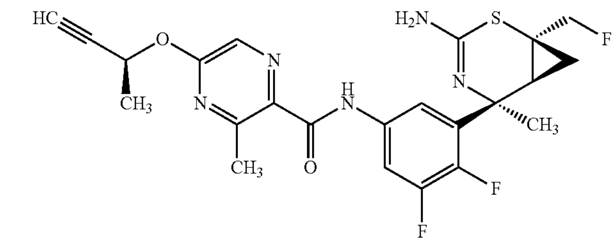 [SMILES: C#C[C@H](C)Oc1cnc(C(=O)Nc2cc(F)c(F)c([C@@]3(C)N=C(N)S[C@@]4(CF)C[C@H]43)c2)c(C)n1] | 590.2 |
| 617 | 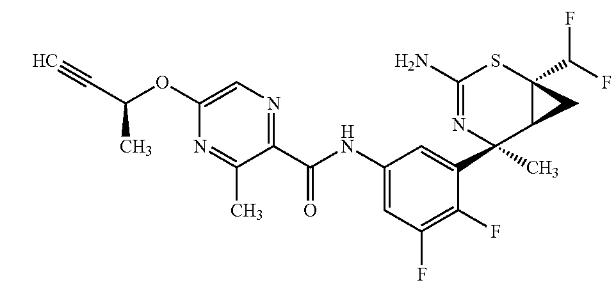 [SMILES: C#C[C@H](C)Oc1cnc(C(=O)Nc2cc(F)c(F)c([C@@]3(C)N=C(N)S[C@@]4(C(F)F)C[C@@H]34)c2)c(C)n1] | 508.1 |
| 618 | 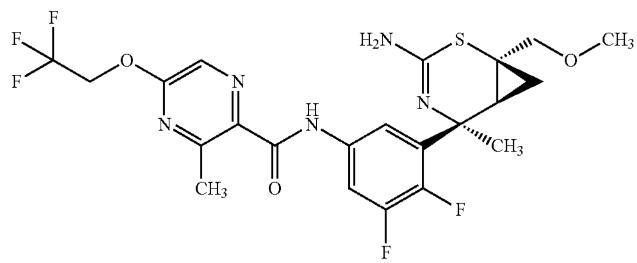 [SMILES: COC[C@]12C[C@H]1[C@@](C)(c1cc(NC(=O)c3ncc(OCC(F)(F)F)nc3C)cc(F)c1F)N=C(N)S2] | 532.2 |
| 619 | 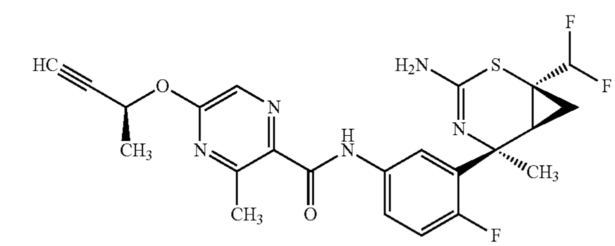 [SMILES: C#C[C@H](C)Oc1cnc(C(=O)Nc2ccc(F)c([C@@]3(C)N=C(N)S[C@@]4(C(F)F)C[C@@H]34)c2)c(C)n1] | 490.1 |
| 620 | 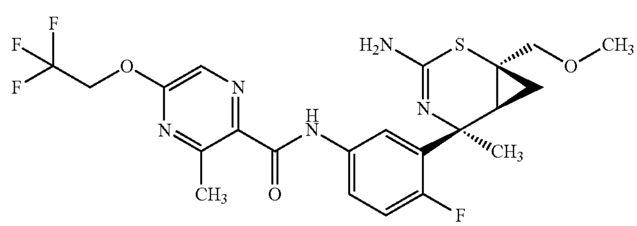 [SMILES: COC[C@]12C[C@H]1[C@@](C)(c1cc(NC(=O)c3ncc(OCC(F)(F)F)nc3C)ccc1F)N=C(N)S2] | 514.1 |
| 621 | 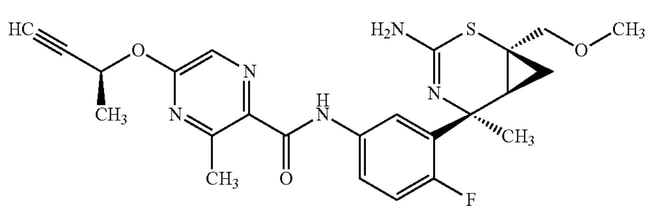 [SMILES: C#C[C@H](C)Oc1cnc(C(=O)Nc2ccc(F)c([C@@]3(C)N=C(N)S[C@@]4(COC)C[C@H]43)c2)c(C)n1] | 484.1 |

TABLE 4-continued

| Ex. No. | Chemical Structure | Observed [M + H]+ |
|---|---|---|
| 622 | 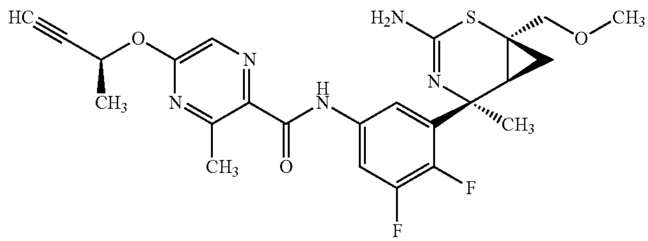 [SMILES: C#C[C@H](C)Oc1cnc(C(=O)Nc2cc(F)c(F)c([C@@]3(C)N=C(N)S[C@@]4(COC)C[C@H]43)c2)c(C)n1] | 592.1 |
| 623 | 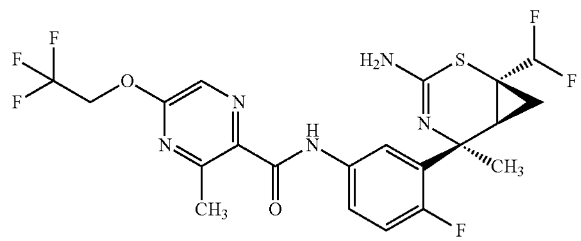 [SMILES: Cc1nc(OCC(F)(F)F)cnc1C(=O)Nc1ccc(F)c([C@@]2(C)N=C(N)S[C@@]3(C(F)F)C[C@@H]23)c1] | 520.1 |
| 633 | 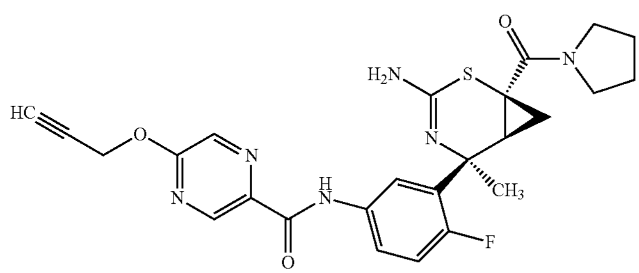 [SMILES: C#CCOc1cnc(C(=O)Nc2ccc(F)c([C@@]3(C)N=C(N)S[C@@]4(C(=O)N5CCCC5)C[C@H]43)c2)cn1] | 509.1 |
| 634 | 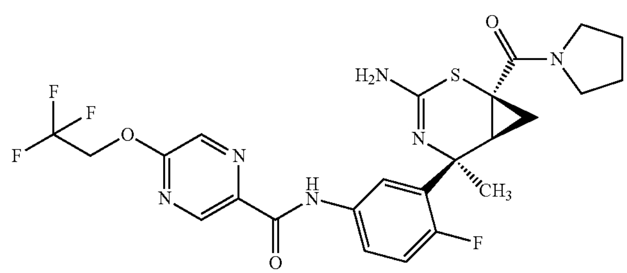 [SMILES: C[C@]1(c2cc(NC(=O)c3cnc(OCC(F)(F)F)cn3)ccc2F)N=C(N)S[C@@]2(C(=O)N3CCCC3)C[C@H]21] | 553.1 |
| 642 | 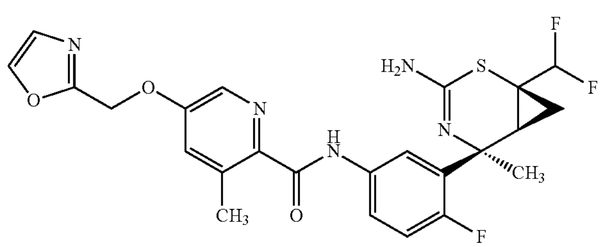 [SMILES: Cc1cc(OCc2ncco2)cnc1C(=O)Nc1ccc(F)c([C@@]2(C)N=C(N)S[C@@]3(C(F)F)C[C@@H]23)c1] | 518.2 |
| 643 | 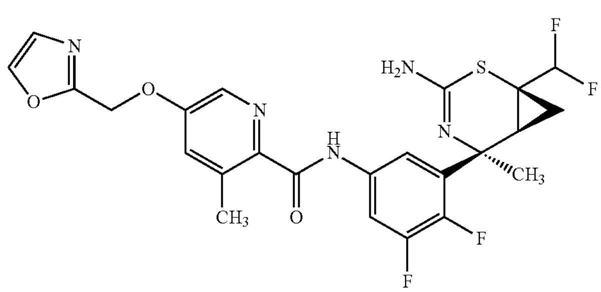 [SMILES: Cc1cc(OCc2ncco2)cnc1C(=O)Nc1cc(F)c(F)c([C@@]2(C)N=C(N)S[C@@]3(C(F)F)C[C@@H]23)c1] | 536.2 |

TABLE 4-continued

| Ex. No. | Chemical Structure | Observed [M + H]+ |
|---|---|---|
| 644 | 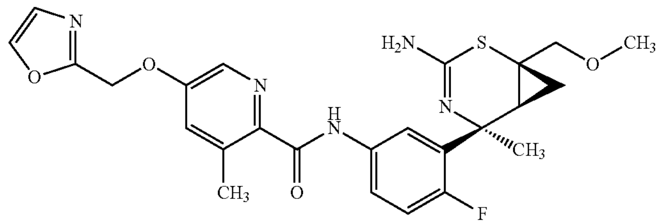 [SMILES: COC[C@]12C[C@H]1[C@@](C)(c1cc(NC(=O)c3ncc(OCc4ncco4)cc3C)ccc1F)N=C(N)S2] | 512.2 |
| 645 | 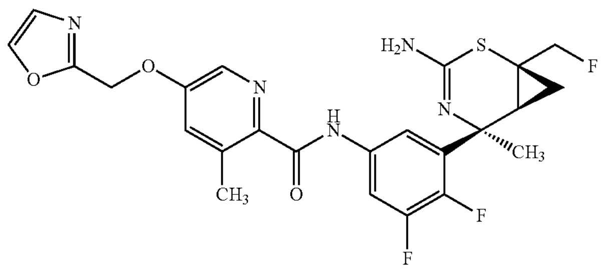 [SMILES: Cc1cc(OCc2ncco2)cnc1C(=O)Nc1cc(F)c(F)c([C@@]2(C)N=C(N)S[C@@]3(CF)C[C@H]32)c1] | 518.2 |
| 646 | 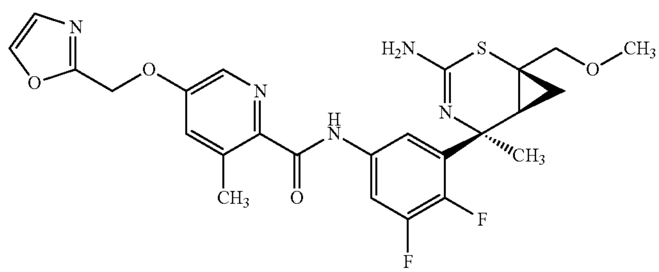 [SMILES: COC[C@]12C[C@H]1[C@@](C)(c1cc(NC(=O)c3ncc(OCc4ncco4)cc3C)cc(F)c1F)N=C(N)S2] | 530.2 |
| 647 | 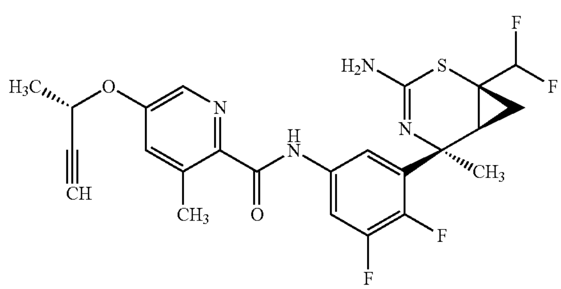 [SMILES: C#C[C@H](C)Oc1cnc(C(=O)Nc2cc(F)c(F)c([C@@]3(C)N=C(N)S[C@@]4(C(F)F)C[C@@H]34)c2)c(C)c1] | 507.2 |
| 648 | 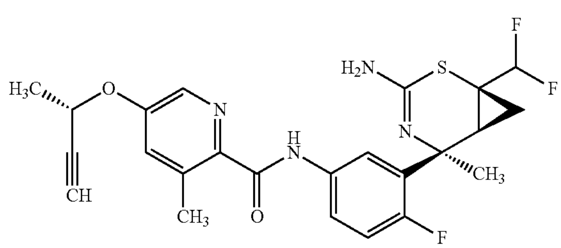 [SMILES: C#C[C@H](C)Oc1cnc(C(=O)Nc2ccc(F)c([C@@]3(C)N=C(N)S[C@@]4(C(F)F)C[C@@H]34)c2)c(C)c1] | 499 |
| 649 | 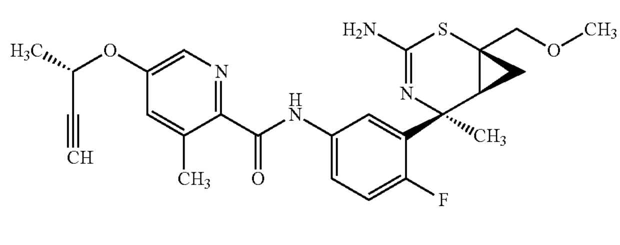 [SMILES: C#C[C@H](C)Oc1cnc(C(=O)Nc2ccc(F)c([C@@]3(C)N=C(N)S[C@@]4(COC)C[C@H]43)c2)c(C)c1] | 483.2 |

US 9,550,762 B2
TABLE 4-continued
| Ex. No. | Chemical Structure | Observed [M + H]+ |
|---|---|---|
| 650 | 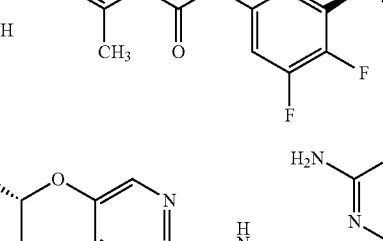 | 501.2 |
| 651 | 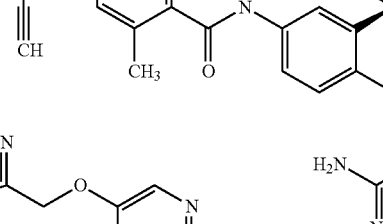 | 471 |
| 652 | 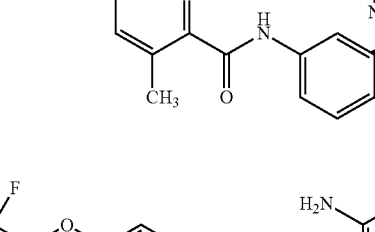 | 500.1 |
| 680 | 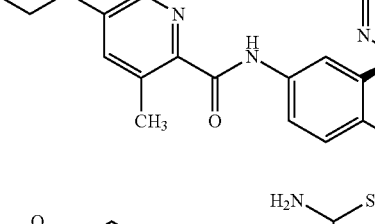 | 519 |
| 681 | 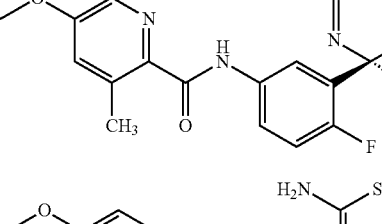 | 513 |
| 682 | 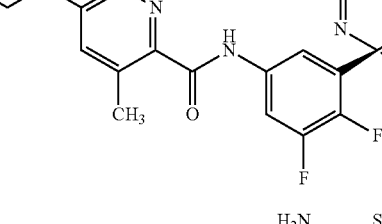 | 487 |
| 683 | 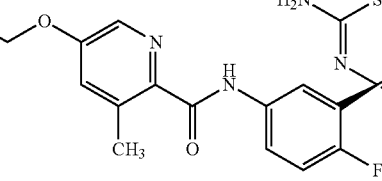 | 469 |

TABLE 4-continued

| Ex. No. | Chemical Structure | Observed [M + H]+ |
|---|---|---|
| 684 | 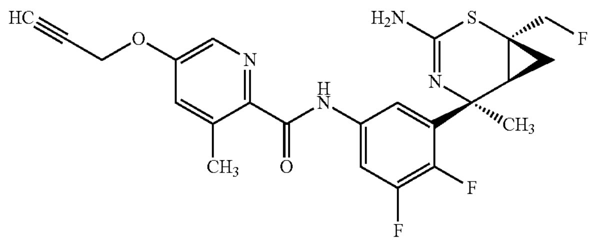 [SMILES: C#CCOc1cnc(C(=O)Nc2cc(F)c(F)c([C@@]3(C)N=C(N)S[C@@]4(CF)C[C@H]43)c2)c(C)c1] | 475 |
| 685 | 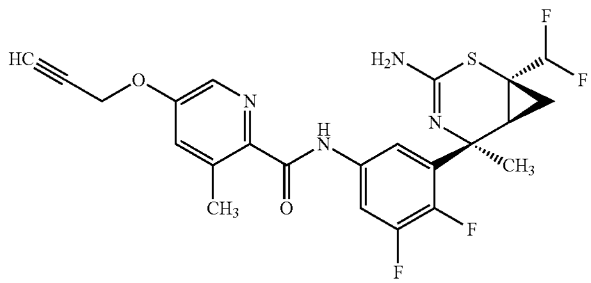 [SMILES: C#CCOc1cnc(C(=O)Nc2cc(F)c(F)c([C@@]3(C)N=C(N)S[C@@]4(C(F)F)C[C@@H]34)c2)c(C)c1] | 493 |
| 686 | 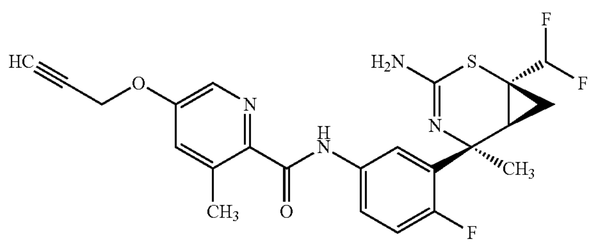 [SMILES: C#CCOc1cnc(C(=O)Nc2ccc(F)c([C@@]3(C)N=C(N)S[C@@]4(C(F)F)C[C@@H]34)c2)c(C)c1] | 475 |
| 687 | 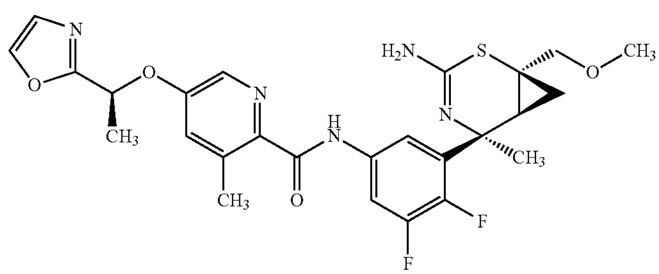 [SMILES: COC[C@]12C[C@H]1[C@@](C)(c1cc(NC(=O)c3ncc(O[C@@H](C)c4ncco4)cc3C)cc(F)c1F)N=C(N)S2] | 544 |
| 688 | 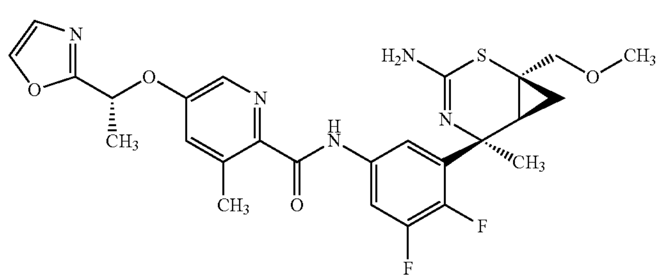 [SMILES: COC[C@]12C[C@H]1[C@@](C)(c1cc(NC(=O)c3ncc(O[C@H](C)c4ncco4)cc3C)cc(F)c1F)N=C(N)S2] | 544 |
| 689 | 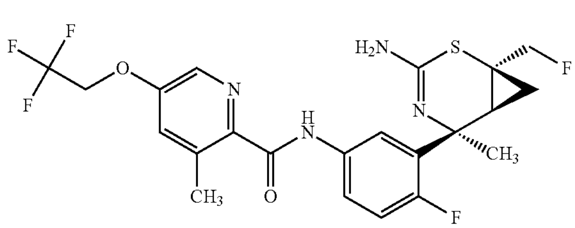 [SMILES: Cc1cc(OCC(F)(F)F)cnc1C(=O)Nc1ccc(F)c([C@@]2(C)N=C(N)S[C@@]3(CF)C[C@H]32)c1] | 501 |

TABLE 4-continued

| Ex. No. | Chemical Structure | Observed [M + H]+ |
|---|---|---|
| 690 | 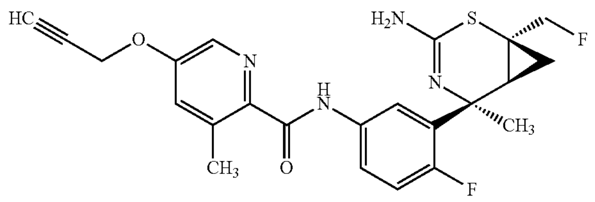 [SMILES: C#CCOc1cnc(C(=O)Nc2ccc(F)c([C@@]3(C)N=C(N)S[C@@]4(CF)C[C@H]43)c2)c(C)c1] | 457 |
| 691 | 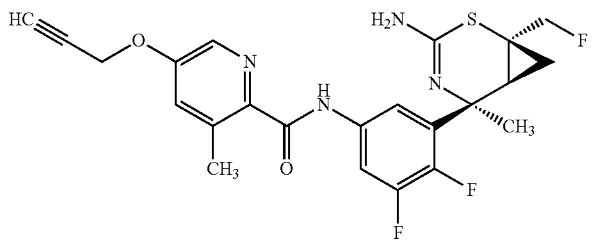 [SMILES: C#CCOc1cnc(C(=O)Nc2cc(F)c(F)c([C@@]3(C)N=C(N)S[C@@]4(CF)C[C@H]43)c2)c(C)c1] | 495 |
| 692 | 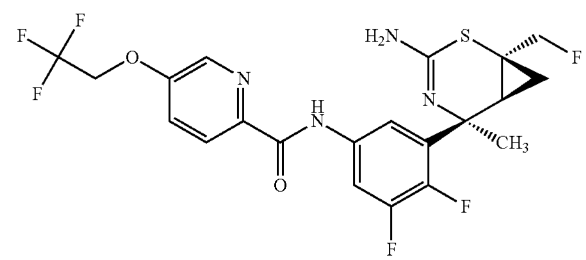 [SMILES: C[C@]1(c2cc(NC(=O)c3ccc(OCC(F)(F)F)cn3)cc(F)c2F)N=C(N)S[C@@]2(CF)C[C@H]21] | 505 |
| 693 | 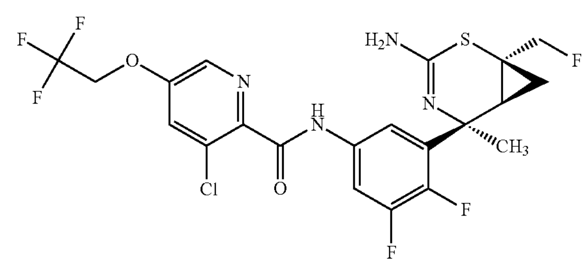 [SMILES: C[C@]1(c2cc(NC(=O)c3ncc(OCC(F)(F)F)cc3Cl)cc(F)c2F)N=C(N)S[C@@]2(CF)C[C@H]21] | 539 |
| 694 | 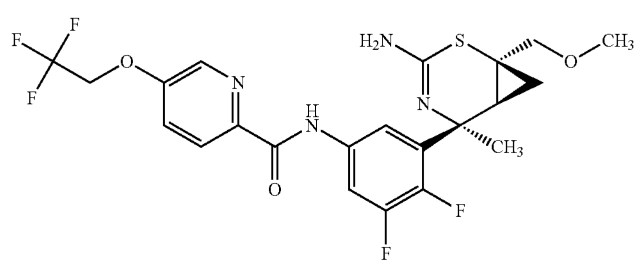 [SMILES: COC[C@]12C[C@H]1[C@@](C)(c1cc(NC(=O)c3ccc(OCC(F)(F)F)cn3)cc(F)c1F)N=C(N)S2] | 517 |
| 695 | 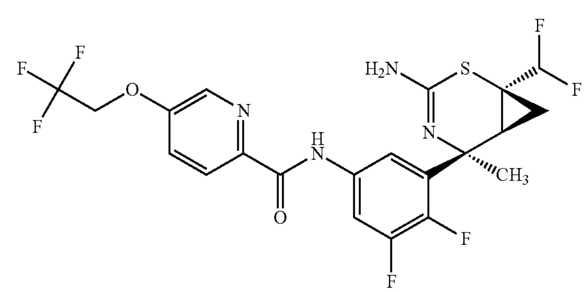 [SMILES: C[C@]1(c2cc(NC(=O)c3ccc(OCC(F)(F)F)cn3)cc(F)c2F)N=C(N)S[C@@]2(C(F)F)C[C@@H]12] | 523 |

TABLE 4-continued

| Ex. No. | Chemical Structure | Observed [M + H]+ |
|---|---|---|
| 696 | 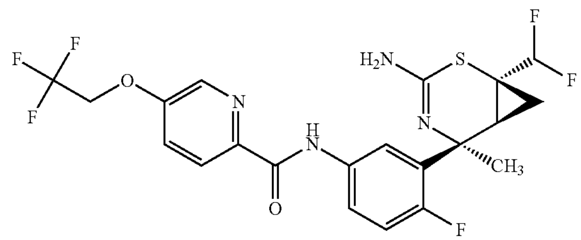 [SMILES: C[C@]1(c2cc(NC(=O)c3ccc(OCC(F)(F)F)cn3)ccc2F)N=C(N)S[C@@]2(C(F)F)C[C@@H]12] | 505 |
| 697 | 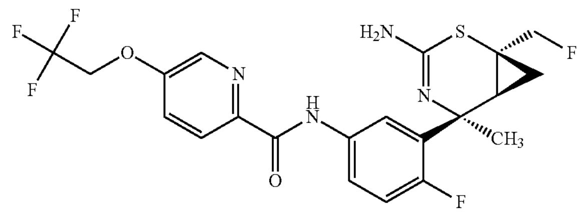 [SMILES: C[C@]1(c2cc(NC(=O)c3ccc(OCC(F)(F)F)cn3)ccc2F)N=C(N)S[C@@]2(CF)C[C@H]21] | 487 |
| 698 | 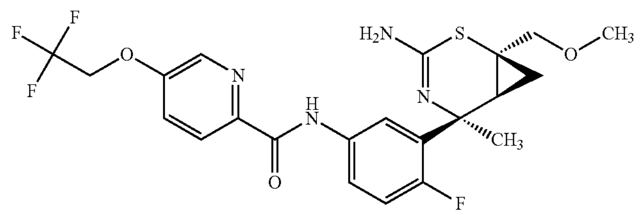 [SMILES: COC[C@]12C[C@H]1[C@@](C)(c1cc(NC(=O)c3ccc(OCC(F)(F)F)cn3)ccc1F)N=C(N)S2] | 499 |
| 699 | 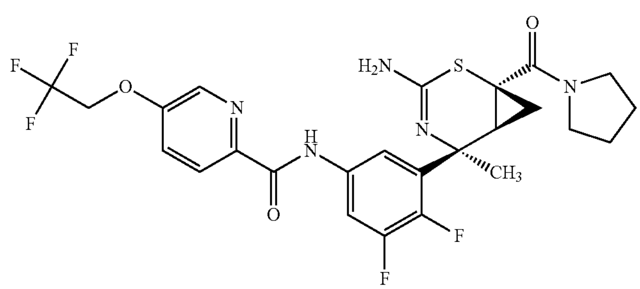 [SMILES: C[C@]1(c2cc(NC(=O)c3ccc(OCC(F)(F)F)cn3)cc(F)c2F)N=C(N)S[C@@]2(C(=O)N3CCCC3)C[C@H]21] | 570 |
| 700 | 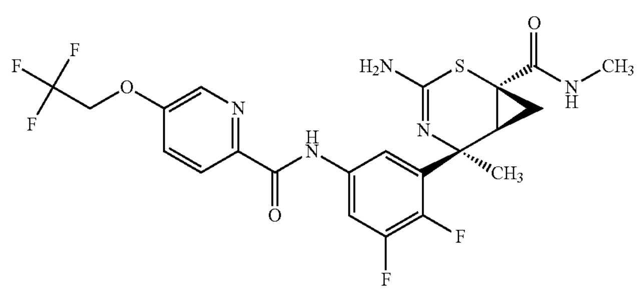 [SMILES: CNC(=O)[C@]12C[C@H]1[C@@](C)(c1cc(NC(=O)c3ccc(OCC(F)(F)F)cn3)cc(F)c1F)N=C(N)S2] | 530 |
| 701 | 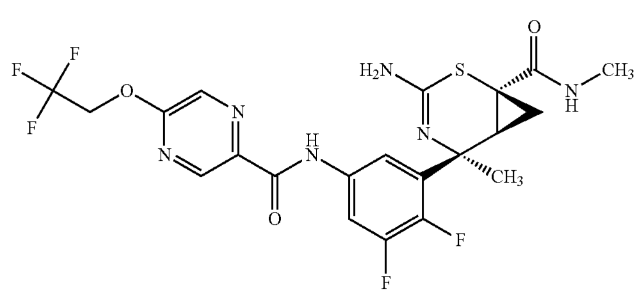 [SMILES: CNC(=O)[C@]12C[C@H]1[C@@](C)(c1cc(NC(=O)c3cnc(OCC(F)(F)F)cn3)cc(F)c1F)N=C(N)S2] | 531 |

TABLE 4-continued
| Ex. No. | Chemical Structure | Observed [M + H]+ |
|---|---|---|
| 702 | 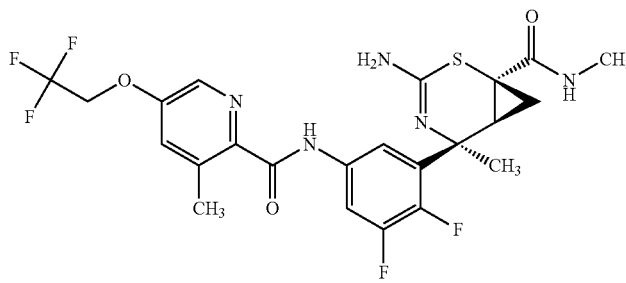 | 544 |
| 732 | 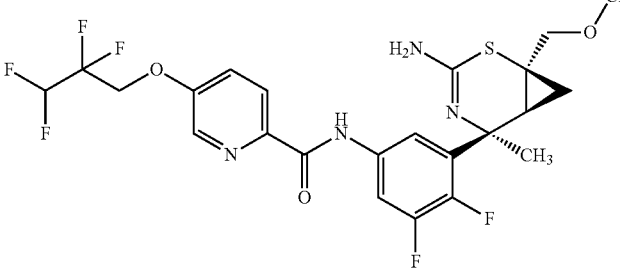 | 549.1 |
| 734 | 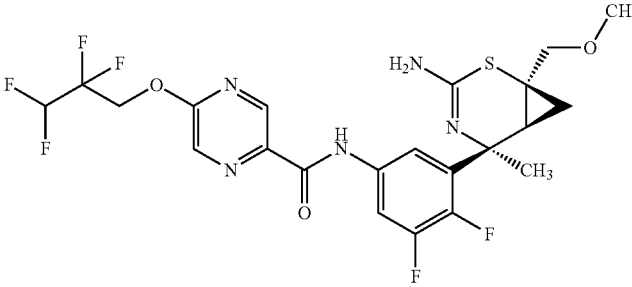 | 550.1 |
| 738 | 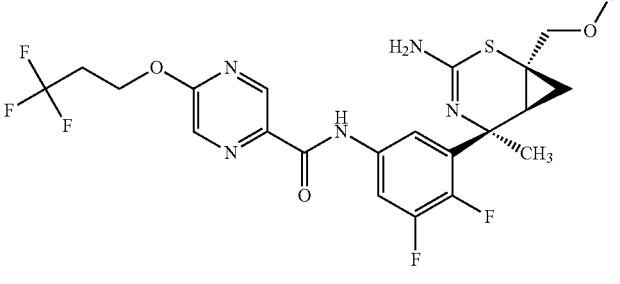 | 532 |
| 739 | 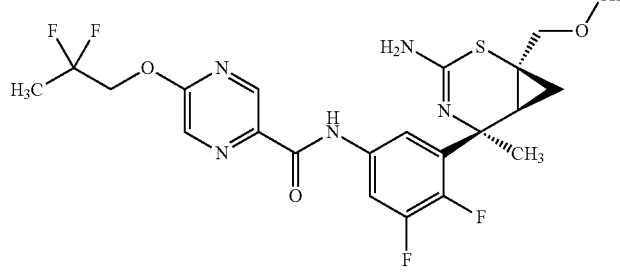 | 514.1 |

TABLE 4-continued

| Ex. No. | Chemical Structure | Observed [M + H]+ |
|---------|-------------------|-------------------|
| 740 | 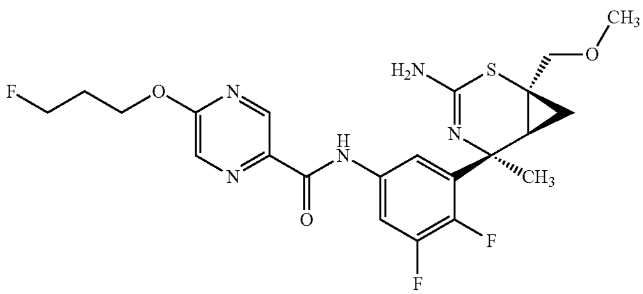 [SMILES: COC[C@]12C[C@H]1[C@@](C)(c1cc(NC(=O)c3cnc(OCCCF)cn3)cc(F)c1F)N=C(N)S2] | 496.1 |
| 742 | 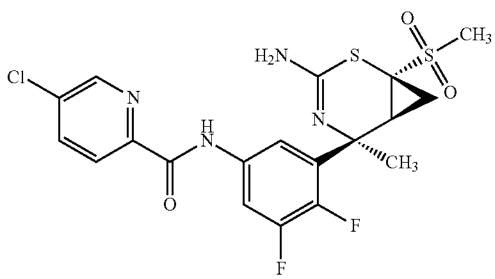 [SMILES: C[C@]1(c2cc(NC(=O)c3ccc(Cl)cn3)cc(F)c2F)N=C(N)S[C@@]2(S(C)(=O)=O)C[C@H]21] | 487 |
| 743 | 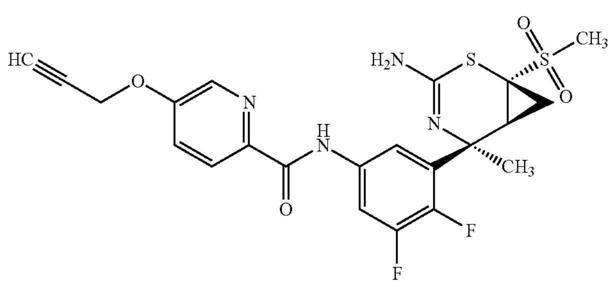 [SMILES: C#CCOc1ccc(C(=O)Nc2cc(F)c(F)c([C@@]3(C)N=C(N)S[C@@]4(S(C)(=O)=O)C[C@H]43)c2)nc1] | 507 |
| 744 | 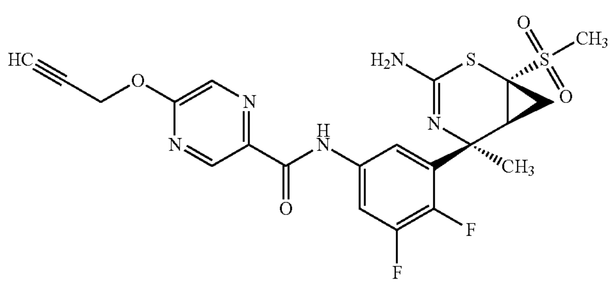 [SMILES: C#CCOc1cnc(C(=O)Nc2cc(F)c(F)c([C@@]3(C)N=C(N)S[C@@]4(S(C)(=O)=O)C[C@H]43)c2)cn1] | 508 |
| 745 | 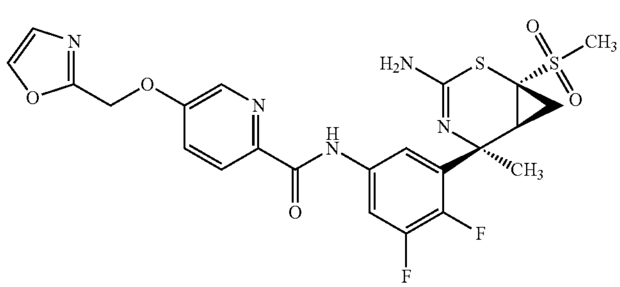 [SMILES: C[C@]1(c2cc(NC(=O)c3ccc(OCc4ncco4)cn3)cc(F)c2F)N=C(N)S[C@@]2(S(C)(=O)=O)C[C@H]21] | 550.1 |

TABLE 4-continued

| Ex. No. | Chemical Structure | Observed [M + H]+ |
|---|---|---|
| 746 | 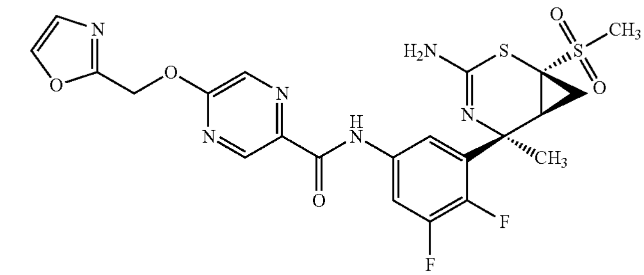 [SMILES: C[C@]1(c2cc(NC(=O)c3cnc(OCc4ncco4)cn3)cc(F)c2F)N=C(N)S[C@@]2(S(C)(=O)=O)C[C@H]21] | 551 |
| 772 | 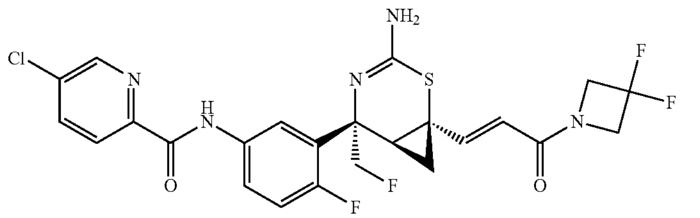 [SMILES: NC1=N[C@](CF)(c2cc(NC(=O)c3ccc(Cl)cn3)ccc2F)[C@@H]2C[C@]2(/C=C/C(=O)N2CC(F)(F)C2)S1] | 554 |
| 774 | 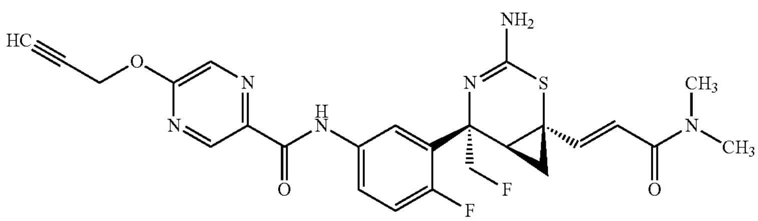 [SMILES: C#CCOc1cnc(C(=O)Nc2ccc(F)c([C@@]3(CF)N=C(N)S[C@@]4(/C=C/C(=O)N(C)C)C[C@H]43)c2)cn1] | 527 |
| 780 | 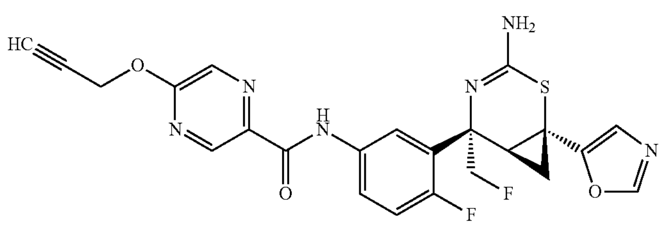 [SMILES: C#CCOc1cnc(C(=O)Nc2ccc(F)c([C@@]3(CF)N=C(N)S[C@@]4(c5cnco5)C[C@@H]34)c2)cn1] | 497 |
| 783 | 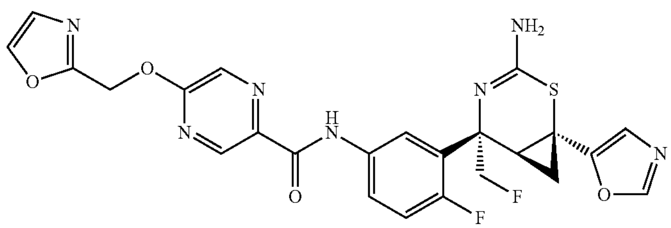 [SMILES: NC1=N[C@](CF)(c2cc(NC(=O)c3cnc(OCc4ncco4)cn3)ccc2F)[C@@H]2C[C@]2(c2cnco2)S1] | 540 |
| 792 | 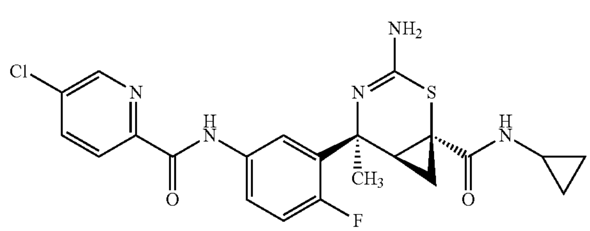 [SMILES: C[C@]1(c2cc(NC(=O)c3ccc(Cl)cn3)ccc2F)N=C(N)S[C@@]2(C(=O)NC3CC3)C[C@H]21] | 474 |

TABLE 4-continued

| Ex. No. | Chemical Structure | Observed [M + H]+ |
|---|---|---|
| 795 | 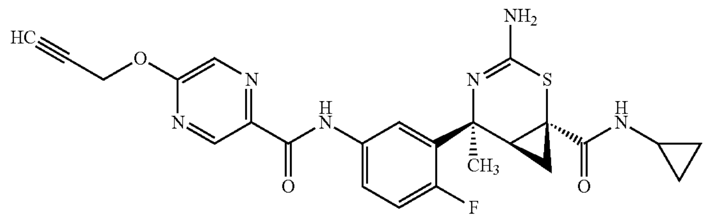 [SMILES: C#CCOc1cnc(C(=O)Nc2ccc(F)c([C@@]3(C)N=C(N)S[C@@]4(C(=O)NC5CC5)C[C@H]43)c2)cn1] | 495 |
| 803 | 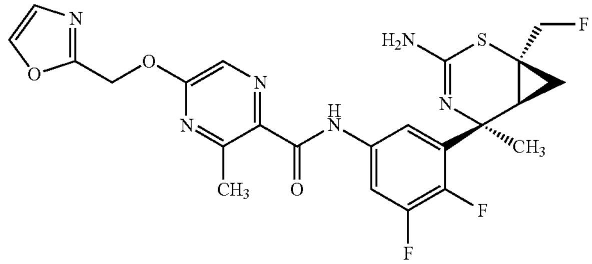 [SMILES: Cc1nc(OCc2ncco2)cnc1C(=O)Nc1cc(F)c(F)c([C@@]2(C)N=C(N)S[C@@]3(CF)C[C@H]32)c1] | 519.1 |
| 804 | 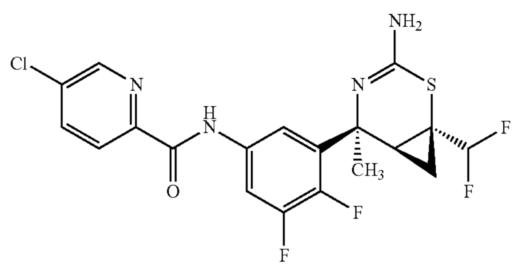 [SMILES: C[C@]1(c2cc(NC(=O)c3ccc(Cl)cn3)cc(F)c2F)N=C(N)S[C@@]2(C(F)F)C[C@@H]12] | 459 |
| 807 | 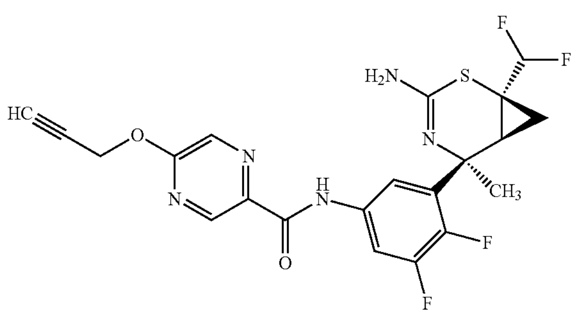 [SMILES: C#CCOc1cnc(C(=O)Nc2cc(F)c(F)c([C@@]3(C)N=C(N)S[C@@]4(C(F)F)C[C@@H]34)c2)cn1] | 480 |
| 811 | 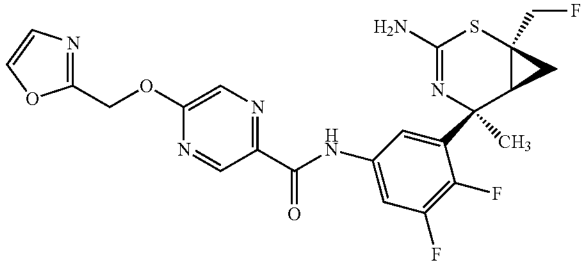 [SMILES: C[C@]1(c2cc(NC(=O)c3cnc(OCc4ncco4)cn3)cc(F)c2F)N=C(N)S[C@@]2(CF)C[C@H]21] | 505.1 |

TABLE 4-continued

| Ex. No. | Chemical Structure | Observed [M + H]+ |
|---|---|---|
| 814 | 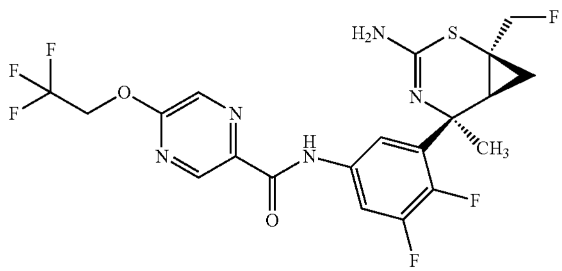 [SMILES: C[C@]1(c2cc(NC(=O)c3cnc(OCC(F)(F)F)cn3)cc(F)c2F)N=C(N)S[C@@]2(CF)C[C@H]21] | 506 |
| 815 | 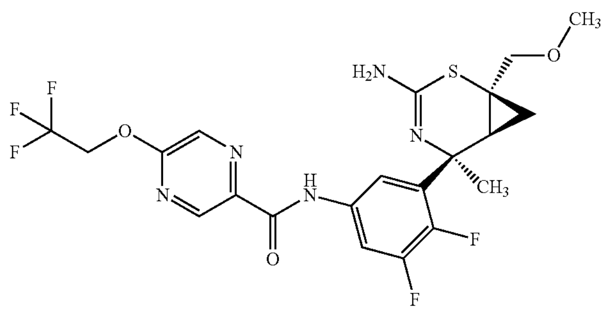 [SMILES: COC[C@]12C[C@H]1[C@@](C)(c1cc(NC(=O)c3cnc(OCC(F)(F)F)cn3)cc(F)c1F)N=C(N)S2] | 518 |
| 818 | 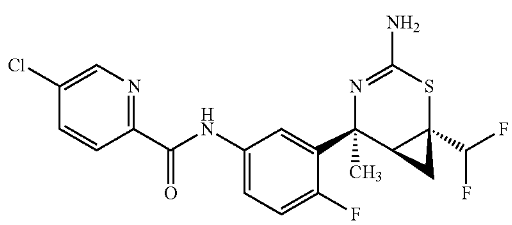 [SMILES: C[C@]1(c2cc(NC(=O)c3ccc(Cl)cn3)ccc2F)N=C(N)S[C@@]2(C(F)F)C[C@@H]12] | 441 |
| 820 | 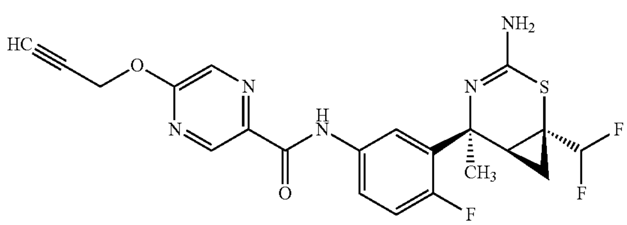 [SMILES: C#CCOc1cnc(C(=O)Nc2ccc(F)c([C@@]3(C)N=C(N)S[C@@]4(C(F)F)C[C@@H]34)c2)cn1] | 462 |
| 821 | 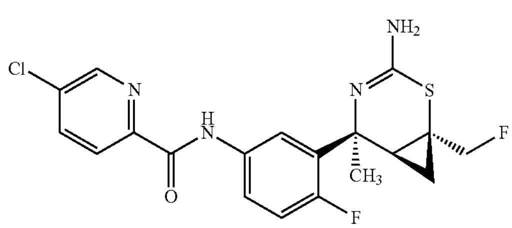 [SMILES: C[C@]1(c2cc(NC(=O)c3ccc(Cl)cn3)ccc2F)N=C(N)S[C@@]2(CF)C[C@H]21] | 423.2 |
| 822 | 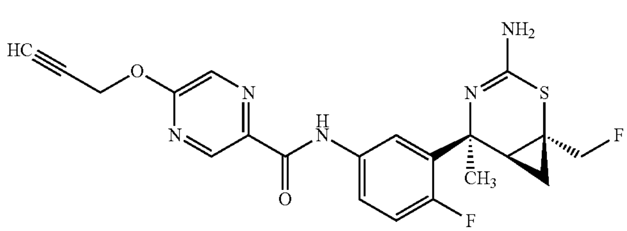 [SMILES: C#CCOc1cnc(C(=O)Nc2ccc(F)c([C@@]3(C)N=C(N)S[C@@]4(CF)C[C@H]43)c2)cn1] | 440 |

TABLE 4-continued

| Ex. No. | Chemical Structure | Observed [M + H]+ |
|---|---|---|
| 826 | 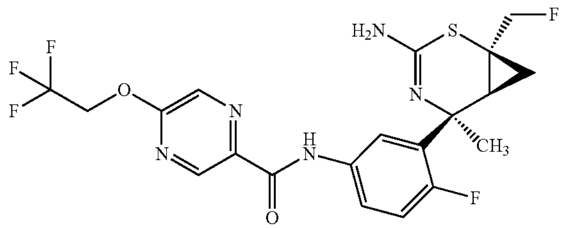 [SMILES: C[C@]1(c2cc(NC(=O)c3cnc(OCC(F)(F)F)cn3)ccc2F)N=C(N)S[C@@]2(CF)C[C@H]21] | 488 |
| 829 | 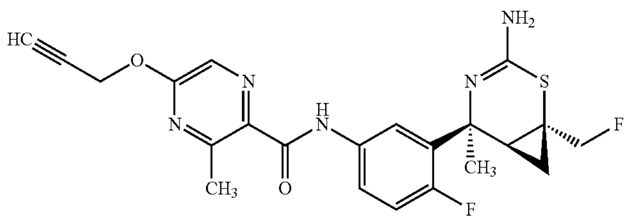 [SMILES: C#CCOc1cnc(C(=O)Nc2ccc(F)c([C@@]3(C)N=C(N)S[C@@]4(CF)C[C@H]43)c2)c(C)n1] | 458 |
| 830 | 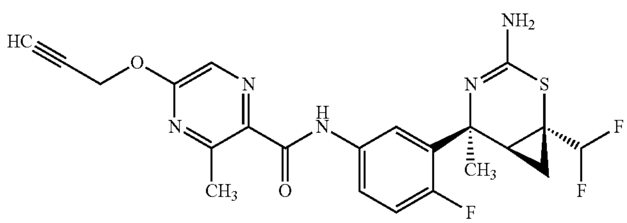 [SMILES: C#CCOc1cnc(C(=O)Nc2ccc(F)c([C@@]3(C)N=C(N)S[C@@]4(C(F)F)C[C@@H]34)c2)c(C)n1] | 476 |
| 831 | 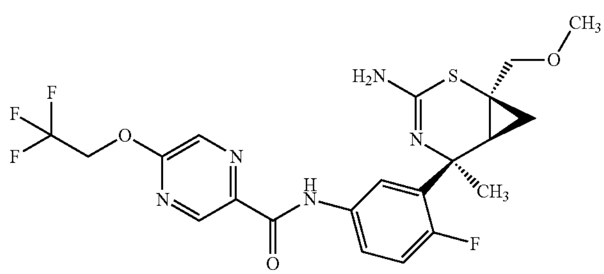 [SMILES: COC[C@]12C[C@H]1[C@@](C)(c1cc(NC(=O)c3cnc(OCC(F)(F)F)cn3)ccc1F)N=C(N)S2] | 500 |
| 832 | 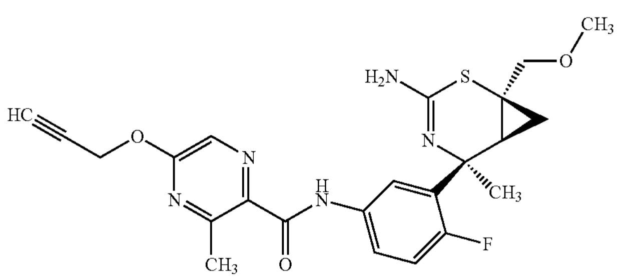 [SMILES: C#CCOc1cnc(C(=O)Nc2ccc(F)c([C@@]3(C)N=C(N)S[C@@]4(COC)C[C@H]43)c2)c(C)n1] | 470.1 |
| 833 | 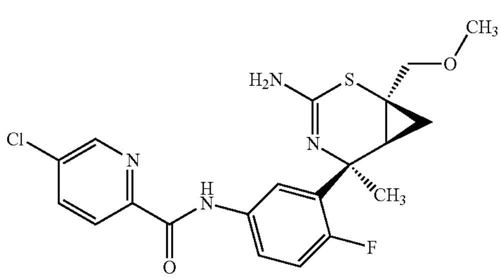 [SMILES: COC[C@]12C[C@H]1[C@@](C)(c1cc(NC(=O)c3ccc(Cl)cn3)ccc1F)N=C(N)S2] | 435 |

TABLE 4-continued

| Ex. No. | Chemical Structure | Observed [M + H]+ |
|---|---|---|
| 834 | 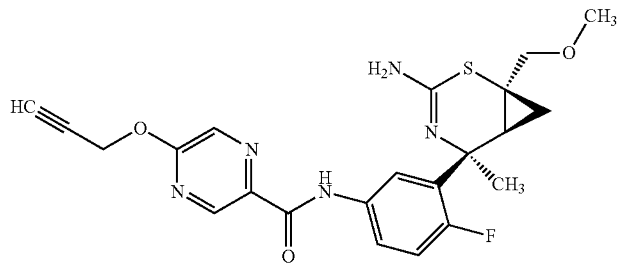 [SMILES: C#CCOc1cnc(C(=O)Nc2ccc(F)c([C@@]3(C)N=C(N)S[C@@]4(COC)C[C@H]43)c2)cn1] | 456 |
| 835 | 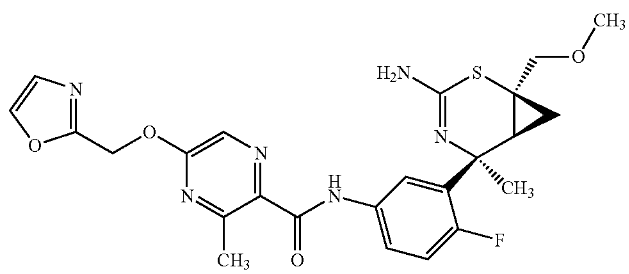 [SMILES: COC[C@]12C[C@H]1[C@@](C)(c1cc(NC(=O)c3ncc(OCc4ncco4)nc3C)ccc1F)N=C(N)S2] | 513 |
| 836 | 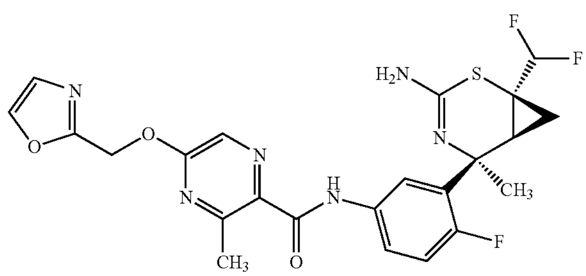 [SMILES: Cc1nc(OCc2ncco2)cnc1C(=O)Nc1ccc(F)c([C@@]2(C)N=C(N)S[C@@]3(C(F)F)C[C@@H]23)c1] | 519 |
| 837 | 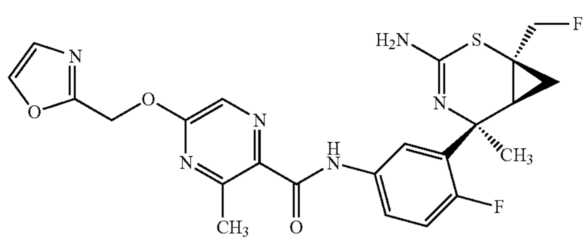 [SMILES: Cc1nc(OCc2ncco2)cnc1C(=O)Nc1ccc(F)c([C@@]2(C)N=C(N)S[C@@]3(CF)C[C@H]32)c1] | 501 |
| 838 | 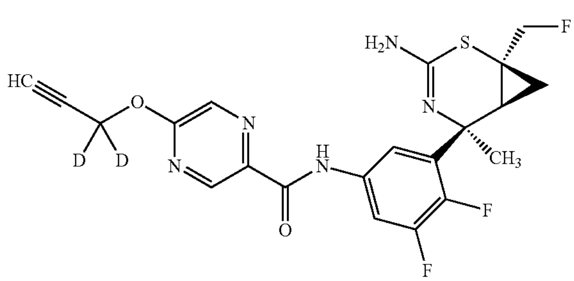 [SMILES: [2H]C([2H])(C#C)Oc1cnc(C(=O)Nc2cc(F)c(F)c([C@@]3(C)N=C(N)S[C@@]4(CF)C[C@H]43)c2)cn1] | 464 |

TABLE 4-continued

| Ex. No. | Chemical Structure | Observed [M + H]+ |
|---|---|---|
| 839 | 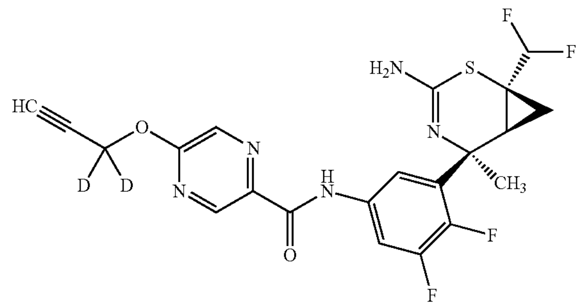 [SMILES: [2H]C([2H])(C#C)Oc1cnc(C(=O)Nc2cc(F)c(F)c([C@@]3(C)N=C(N)S[C@@]4(C(F)F)C[C@@H]34)c2)cn1] | 482 |
| 840 | 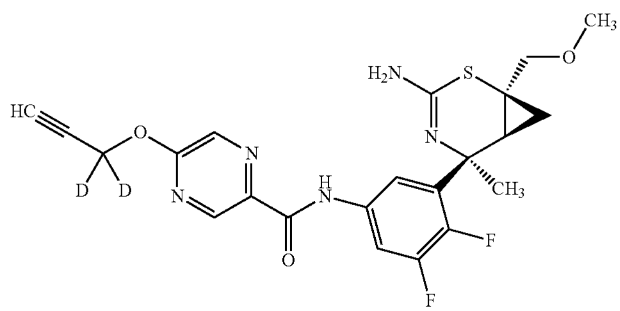 [SMILES: [2H]C([2H])(C#C)Oc1cnc(C(=O)Nc2cc(F)c(F)c([C@@]3(C)N=C(N)S[C@@]4(COC)C[C@H]43)c2)cn1] | 476 |
| 860 | 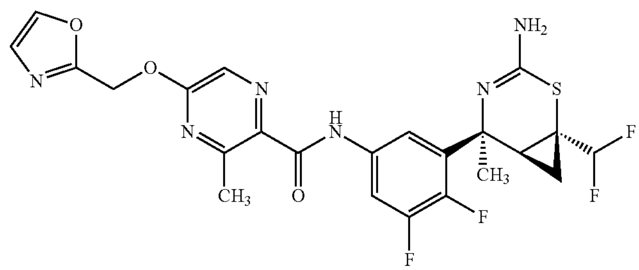 [SMILES: Cc1nc(OCc2ncco2)cnc1C(=O)Nc1cc(F)c(F)c([C@@]2(C)N=C(N)S[C@@]3(C(F)F)C[C@@H]23)c1] | 537.2 |
| 861 | 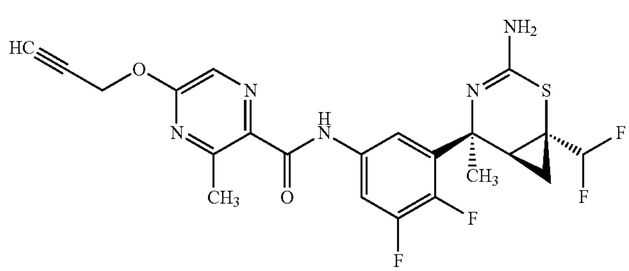 [SMILES: C#CCOc1cnc(C(=O)Nc2cc(F)c(F)c([C@@]3(C)N=C(N)S[C@@]4(C(F)F)C[C@@H]34)c2)c(C)n1] | 494 |
| 862 | 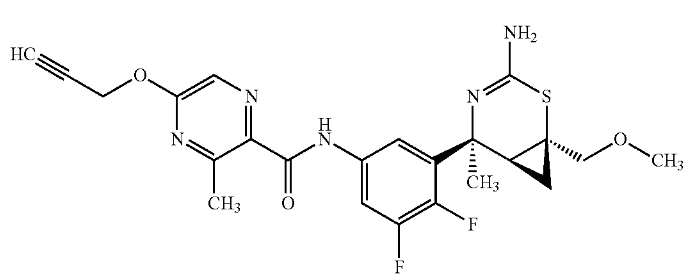 [SMILES: C#CCOc1cnc(C(=O)Nc2cc(F)c(F)c([C@@]3(C)N=C(N)S[C@@]4(COC)C[C@H]43)c2)c(C)n1] | 488.2 |

TABLE 4-continued

| Ex. No. | Chemical Structure | Observed [M + H]+ |
|---|---|---|
| 863 | 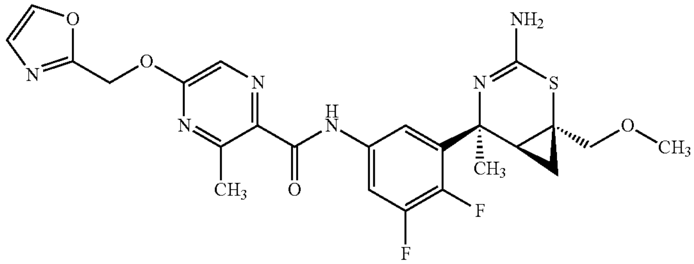 [SMILES: COC[C@]12C[C@H]1[C@@](C)(c1cc(NC(=O)c3ncc(OCc4ncco4)nc3C)cc(F)c1F)N=C(N)S2] | 531.2 |
| 864 | 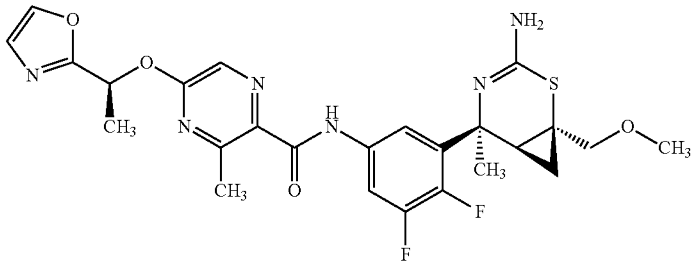 [SMILES: COC[C@]12C[C@H]1[C@@](C)(c1cc(NC(=O)c3ncc(O[C@@H](C)c4ncco4)nc3C)cc(F)c1F)N=C(N)S2] | 545 |
| 913 | 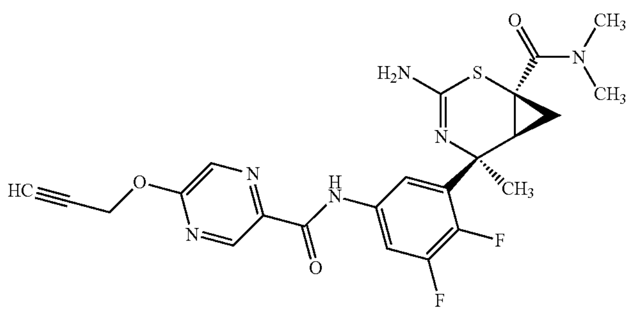 [SMILES: C#CCOc1cnc(C(=O)Nc2cc(F)c(F)c([C@@]3(C)N=C(N)S[C@@]4(C(=O)N(C)C)C[C@H]43)c2)cn1] | 501 |
| 914 | 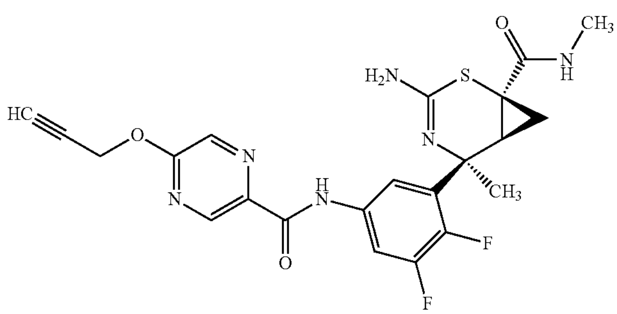 [SMILES: C#CCOc1cnc(C(=O)Nc2cc(F)c(F)c([C@@]3(C)N=C(N)S[C@@]4(C(=O)NC)C[C@H]43)c2)cn1] | 487.1 |
| 919 | 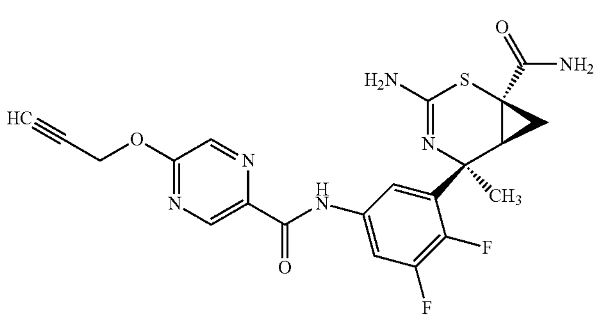 [SMILES: C#CCOc1cnc(C(=O)Nc2cc(F)c(F)c([C@@]3(C)N=C(N)S[C@@]4(C(N)=O)C[C@H]43)c2)cn1] | 473 |

TABLE 4-continued

| Ex. No. | Chemical Structure | Observed [M + H]+ |
|---|---|---|
| 922 | 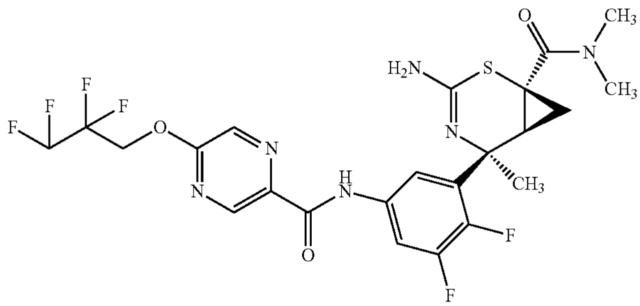 [SMILES: CN(C)C(=O)[C@]12C[C@H]1[C@@](C)(c1cc(NC(=O)c3cnc(OCC(F)(F)C(F)F)cn3)cc(F)c1F)N=C(N)S2] | 577.1 |
| 924 | 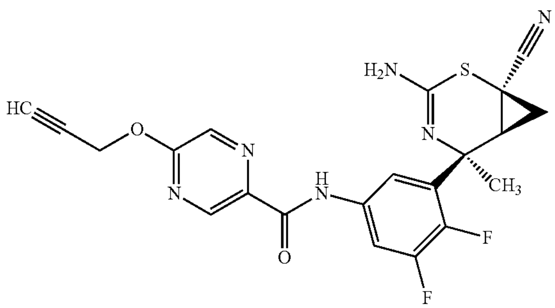 [SMILES: C#CCOc1cnc(C(=O)Nc2cc(F)c(F)c([C@@]3(C)N=C(N)S[C@@]4(C#N)C[C@H]43)c2)cn1] | 455.1 |
| 926 | 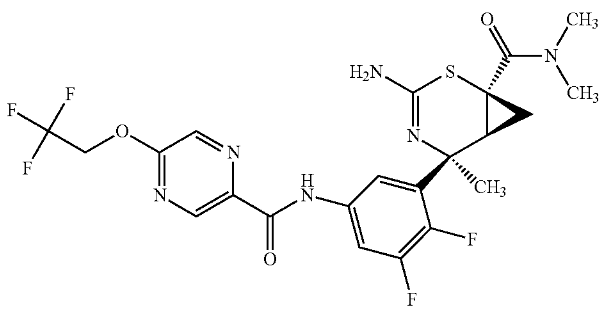 [SMILES: CN(C)C(=O)[C@]12C[C@H]1[C@@](C)(c1cc(NC(=O)c3cnc(OCC(F)(F)F)cn3)cc(F)c1F)N=C(N)S2] | 545 |
| 927 | 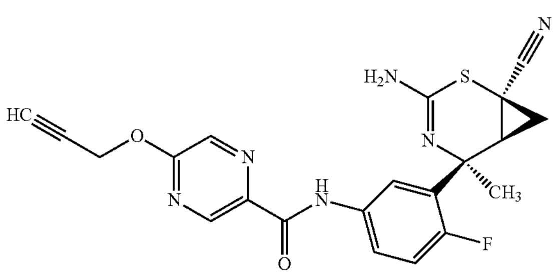 [SMILES: C#CCOc1cnc(C(=O)Nc2ccc(F)c([C@@]3(C)N=C(N)S[C@@]4(C#N)C[C@H]43)c2)cn1] | 437 |
| 929 | 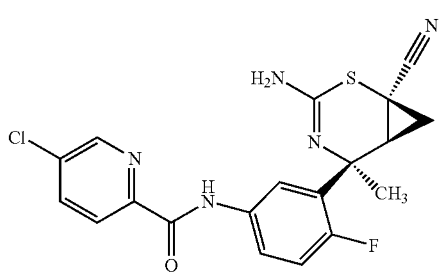 [SMILES: C[C@]1(c2cc(NC(=O)c3ccc(Cl)cn3)ccc2F)N=C(N)S[C@@]2(C#N)C[C@H]21] | 416 |

TABLE 4-continued

| Ex. No. | Chemical Structure | Observed [M + H]+ |
|---|---|---|
| 930 | 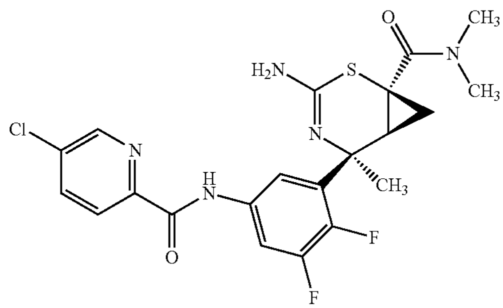 [SMILES: CN(C)C(=O)[C@]12C[C@H]1[C@@](C)(c1cc(NC(=O)c3ccc(Cl)cn3)cc(F)c1F)N=C(N)S2] | 480 |
| 932 | 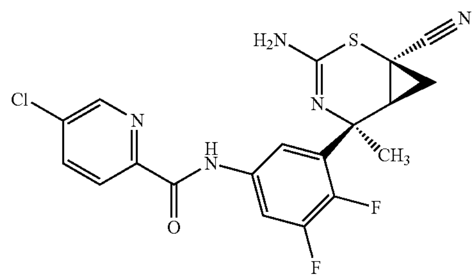 [SMILES: C[C@]1(c2cc(NC(=O)c3ccc(Cl)cn3)cc(F)c2F)N=C(N)S[C@@]2(C#N)C[C@H]21] | 434 |
| 934 | 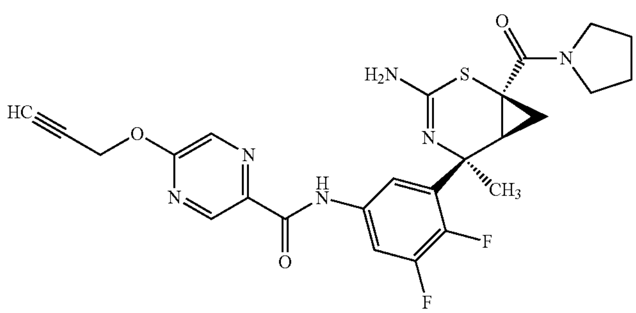 [SMILES: C#CCOc1cnc(C(=O)Nc2cc(F)c(F)c([C@@]3(C)N=C(N)S[C@@]4(C(=O)N5CCCC5)C[C@H]43)c2)cn1] | 527.1 |
| 935 | 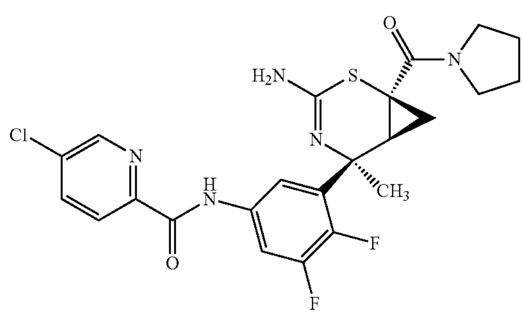 [SMILES: C[C@]1(c2cc(NC(=O)c3ccc(Cl)cn3)cc(F)c2F)N=C(N)S[C@@]2(C(=O)N3CCCC3)C[C@H]21] | 506 |
| 940 | 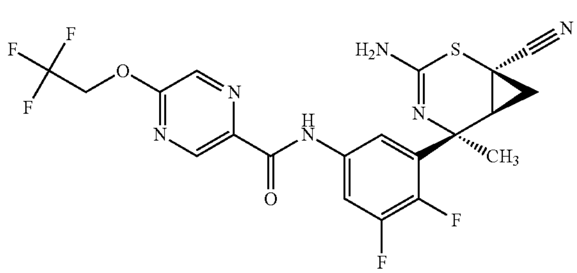 [SMILES: C[C@]1(c2cc(NC(=O)c3cnc(OCC(F)(F)F)cn3)cc(F)c2F)N=C(N)S[C@@]2(C#N)C[C@H]21] | 499 |

TABLE 4'

| Ex. No. | ¹H-NMR | Chemical Name |
|---|---|---|
| 614 | ¹H-NMR (300 MHz, CHLOROFORM-d) δ 9.79 (s, 1H), 8.16 (s, 1H), 8.08 (ddd, J = 2.78, 6.87, 11.98 Hz, 1H), 7.32 (br. s., 1H), 4.88 (q, J = 8.33 Hz, 2H), 4.44-4.62 (m, 1H), 4.21-4.44 (m, 1H), 4.00-5.00 (br. s., 2H), 2.97 (s, 3H), 1.87-2.00 (m, 1H), 1.75 (d, J = 1.17 Hz, 3H), 1.03 (dd, J = 5.99, 9.50 Hz, 1H), 0.84-0.93 (m, 1H). | N-(3-((1S,5S,6S)-3-amino-1-(fluoromethyl)-5-methyl-2-thia-4-azabicyclo[4.1.0]hept-3-en-5-yl)-4,5-difluorophenyl)-3-methyl-5-(2,2,2-trifluoroethoxy)-2-pyrazinecarboxamide |
| 615 | ¹H-NMR (300 MHz, CHLOROFORM-d) δ 9.77 (s, 1H), 8.16 (s, 1H), 8.06 (ddd, J = 2.70, 6.87, 11.91 Hz, 1H), 7.12-7.23 (m, 1H), 5.43-5.97 (m, 1H), 4.88 (q, J = 8.33 Hz, 2H), 2.85-3.07 (m, 3H), 2.04 (dd, J = 7.45, 9.65 Hz, 1H), 1.99 (br. s., 2H), 1.82 (s, 3H), 1.28-1.45 (m, 1H), 0.78-0.98 (m, 1H). | N-(3-((1S,5S,6S)-3-amino-1-(difluoromethyl)-5-methyl-2-thia-4-azabicyclo[4.1.0]hept-3-en-5-yl)-4,5-difluorophenyl)-3-methyl-5-(2,2,2-trifluoroethoxy)-2-pyrazinecarboxamide |
| 616 | ¹H-NMR (400 MHz, CHLOROFORM-d) δ 9.80 (s, 1H), 8.08 (ddd, J = 2.74, 6.85, 11.93 Hz, 1H), 8.02 (s, 1H), 7.25-7.27 (m, 3H), 5.89 (dd, J = 1.96, 6.65 Hz, 1H), 4.48 (d, J = 6.26 Hz, 1H), 4.35 (d, J = 6.06 Hz, 1H), 2.95 (s, 3H), 2.47 (d, J = 2.15 Hz, 1H), 1.76 (s, 3H), 1.68 (d, J = 6.85 Hz, 3H), 1.22-1.31 (m, 1H), 1.05 (dd, J = 6.16, 9.68 Hz, 1H), 0.85-0.91 (m, 1H). | N-(3-((1S,5S,6S)-3-amino-1-(fluoromethyl)-5-methyl-2-thia-4-azabicyclo[4.1.0]hept-3-en-5-yl)-4,5-difluorophenyl)-3-methyl-5-(((1S)-1-methyl-2-propyn-1-yl)oxy)-2-pyrazinecarboxamide |
| 617 | ¹H-NMR (300 MHz, CHLOROFORM-d) δ 9.78 (s, 1H), 8.01-8.11 (m, 2H), 7.18 (td, J = 2.36, 5.66 Hz, 1H), 5.86-5.95 (m, 1H), 5.22-5.75 (m, 1H), 3.36-4.84 (m, 2H), 2.96 (s, 3H), 2.49 (d, J = 2.19 Hz, 1H), 2.02 (dd, J = 7.53, 9.57 Hz, 1H), 1.77-1.83 (m, 3H), 1.70 (d, J = 6.72 Hz, 3H), 1.38 (dd, J = 6.28, 9.94 Hz, 1H), 0.84-0.93 (m, 1H) | N-(3-((1S,5S,6S)-3-amino-1-(difluoromethyl)-5-methyl-2-thia-4-azabicyclo[4.1.0]hept-3-en-5-yl)-4,5-difluorophenyl)-3-methyl-5-(((1S)-1-methyl-2-propyn-1-yl)oxy)-2-pyrazinecarboxamide |
| 618 | ¹H-NMR (300 MHz, CHLOROFORM-d) δ 9.80 (s, 1H), 8.16 (s, 1H), 8.10 (ddd, J = 2.78, 6.87, 11.98 Hz, 1H), 7.33 (td, J = 2.41, 5.70 Hz, 1H), 4.87 (q, J = 8.33 Hz, 2H), 4.00-4.50 (br. s., 2H), 3.67 (d, J = 10.52 Hz, 1H), 3.43 (s, 3H), 3.37 (d, J = 10.67 Hz, 1H), 2.97 (s, 3H), 1.83 (ddd, J = 1.39, 6.69, 9.32 Hz, 1H), 1.75 (d, J = 1.17 Hz, 3H), 0.94 (dd, J = 5.92, 9.43 Hz, 1H), 0.78-0.88 (m, 1H). | N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-(2,2,2-trifluoroethoxy)-2-pyrazinecarboxamide |
| 619 | ¹H-NMR (300 MHz, CHLOROFORM-d) δ 9.80 (s, 1H), 8.16 (s, 1H), 8.10 (ddd, J = 2.78, 6.87, 11.98 Hz, 1H), 7.33 (td, J = 2.41, 5.70 Hz, 1H), 4.87 (q, J = 8.33 Hz, 2H), 3.67 (d, J = 10.52 Hz, 1H), 3.43 (s, 3H), 3.37 (d, J = 10.67 Hz, 1H), 2.97 (s, 3H), 1.83 (ddd, J = 1.39, 6.69, 9.32 Hz, 1H), 1.75 (d, J = 1.17 Hz, 3H), 0.94 (dd, J = 5.92, 9.43 Hz, 1H), 0.78-0.88 (m, 1H), NH2 broad at 4.5-4.0. | N-(3-((1S,5S,6S)-3-amino-1-(difluoromethyl)-5-methyl-2-thia-4-azabicyclo[4.1.0]hept-3-en-5-yl)-4-fluorophenyl)-3-methyl-5-(((1S)-1-methyl-2-propyn-1-yl)oxy)-2-pyrazinecarboxamide |
| 620 | ¹H-NMR (300 MHz, CHLOROFORM-d) δ 9.75 (s, 1H), 8.13 (s, 1H), 7.86-8.04 (m, 1H), 7.66 (dd, J = 2.78, 7.02 Hz, 1H), 7.07 (dd, J = 8.77, 11.69 Hz, 1H), 4.86 (q, J = 8.33 Hz, 2H), 4.00-4.50 (br.s, 2H), 3.68 (d, J = 10.50 Hz, 1H), 3.42 (s, 3H), 3.35 (d, J = 10.52 Hz, 1H), 2.87-3.06 (m, 3H), 1.83 (ddd, J = 1.10, 6.80, 9.35 Hz, 1H), 1.73 (d, J = 1.17 Hz, 3H), 0.67-0.97 (m, 2H) | N-(3-((1S,5S,6S)-3-amino-1-(methoxymethyl)-5-methyl-2-thia-4-azabicyclo[4.1.0]hept-3-en-5-yl)-4-fluorophenyl)-3-methyl-5-(2,2,2-trifluoroethoxy)-2-pyrazinecarboxamide |
| 621 | ¹H-NMR (300 MHz, CHLOROFORM-d) δ 9.77 (s, 1H), 7.86-8.10 (m, 2H), 7.65 (dd, J = 2.85, 6.94 Hz, 1H), 6.90-7.15 (m, 1H), 5.89 (dq, J = 2.12, 6.65 Hz, 1H), 4.23-4.85 (br.s, 2H), 3.67 (d, J = 10.67 Hz, 1H), 3.39-3.49 (m, 3H), 3.35 (d, J = 10.67 Hz, 1H), 2.82-3.03 (m, 3H), 2.37-2.58 (m, 1H), 1.82 (ddd, J = 1.10, 6.83, 9.32 Hz, 1H), 1.72 (d, J = 1.17 Hz, 3H), 1.69 (d, J = 6.72 Hz, 3H), 0.74-0.92 (m, 2H) | N-(3-((1S,5S,6S)-3-amino-1-(methoxymethyl)-5-methyl-2-thia-4-azabicyclo[4.1.0]hept-3-en-5-yl)-4-fluorophenyl)-3-methyl-5-(((1S)-1-methyl-2-propyn-1-yl)oxy)-2-pyrazinecarboxamide |
| 622 | ¹H-NMR (300 MHz, CHLOROFORM-d) δ 9.82 (s, 1H), 8.11 (ddd, J = 2.78, 6.87, 11.98 Hz, 1H), 8.03 (s, 1H), 7.32 (d, J = 4.97 Hz, 1H), 5.91 (dd, J = 2.05, 6.72 Hz, 1H), 5.00-4.00 (br.s, 2H), 3.67 (d, J = 10.52 Hz, 1H), 3.43 (s, 3H), 3.37 (d, J = 10.67 Hz, 1H), 2.96 (s, 3H), 2.49 (d, J = 2.05 Hz, 1H), 1.82 (ddd, J = 1.46, 6.72, 9.35 Hz, 1H), 1.75 (d, J = 1.17 Hz, 3H), 1.70 (d, J = 6.72 Hz, 3H), 0.93 (dd, J = 5.85, 9.50 Hz, 1H), 0.79-0.88 (m, 1H). | N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-(((1S)-1-methyl-2-propyn-1-yl)oxy)-2-pyrazinecarboxamide |
| 623 | ¹H-NMR (300 MHz, CHLOROFORM-d) δ 9.73 (s, 1H), 8.15 (s, 1H), 7.82-8.02 (m, 1H), 7.42 (dd, J = 2.70, 6.94 Hz, 1H), 7.10 (dd, J = 8.77, 11.40 Hz, 1H), 5.50 (s, 1H), 4.66-4.95 (m, 4H), 2.96 (s, 3H), 2.06 (dd, J = 6.80, 10.16 Hz, 1H), 1.88 (d, J = 0.73 Hz, 3H), 1.46 (dd, J = 6.43, 9.79 Hz, 1H), 0.75-1.03 (m, 1H). | N-(3-((1S,5S,6S)-3-amino-1-(difluoromethyl)-5-methyl-2-thia-4-azabicyclo[4.1.0]hept-3-en-5-yl)-4-fluorophenyl)-3-methyl-5-(2,2,2-trifluoroethoxy)-2-pyrazinecarboxamide |
| 633 | ¹H-NMR (CHLOROFORM-d) Shift: 9.45 (br. s., 1H), 9.02 (br. s., 1H), 8.19 (br. s., 1H), 7.85 (br. s., | N-(3-((1S,5S,6S)-3-amino-5-methyl-1-(1- |

TABLE 4'-continued

| Ex. No. | ¹H-NMR | Chemical Name |
|---|---|---|
| | 1H), 7.60 (d, J = 3.9 Hz, 1H), 7.06 (t, J = 9.8 Hz, 1H), 5.08 (br. s., 2H), 3.35-3.81 (m, 4H), 2.28 (t, J = 7.7 Hz, 1H), 1.79-2.08 (m, 7H), 1.41 (d, J = 8.2 Hz, 1H), 0.83 (br. s., 1H). | pyrrolidinylcarbonyl)-2-thia-4-azabicyclo[4.1.0]hept-3-en-5-yl)-4-fluorophenyl)-5-(2-propyn-1-yloxy)-2-pyrazinecarboxamide |
| 634 | ¹H-NMR (CHLOROFORM-d) δ: 9.45 (br. s., 1H), 9.01 (br. s., 1H), 8.29 (br. s., 1H), 7.85 (br. s., 1H), 7.60 (d, J = 4.3 Hz, 1H), 7.07 (t, J = 10.0 Hz, 1H), 4.86 (q, J = 8.0 Hz, 2H), 3.39-3.82 (m, 4H), 2.30 (t, J = 7.6 Hz, 1H), 1.87-2.02 (m, 4H), 1.85 (br. s., 3H), 1.42 (d, J = 7.2 Hz, 1H), 0.84 (m, 1H). NH2 peak is broad. | N-(3-((1S,5S,6S)-3-amino-5-methyl-1-(1-pyrrolidinylcarbonyl)-2-thia-4-azabicyclo[4.1.0]hept-3-en-5-yl)-4-fluorophenyl)-5-(2,2,2-trifluoroethoxy)-2-pyrazinecarboxamide |
| 642 | ¹H-NMR (400 MHz, CHLOROFORM-d) Shift 9.99 (s, 1H), 8.21 (d, J = 2.54 Hz, 1H), 7.93 (ddd, J = 2.84, 4.11, 8.71 Hz, 1H), 7.72 (d, J = 0.78 Hz, 1H), 7.48 (dd, J = 2.74, 7.04 Hz, 1H), 7.23 (d, J = 2.54 Hz, 1H), 7.19 (s, 1H), 7.05 (dd, J = 8.80, 11.54 Hz, 1H), 5.58 (t, J = 54.20 Hz, 1H), 5.26 (s, 2H), 2.79 (s, 3H), 1.96-2.03 (m, 1H), 1.78 (d, J = 0.78 Hz, 3H), 1.33 (dd, J = 6.26, 9.98 Hz, 1H), 0.81-0.90 (m, 1H). | N-(3-((1S,5S,6S)-3-amino-1-(difluoromethyl)-5-methyl-2-thia-4-azabicyclo[4.1.0]hept-3-en-5-yl)-4-fluorophenyl)-3-methyl-5-(1,3-oxazol-2-ylmethoxy)-2-pyridinecarboxamide |
| 643 | ¹H-NMR (400 MHz, CHLOROFORM-d) δ 10.01 (s, 1H), 8.19 (s, 1H), 7.99-8.09 (m, 1H), 7.73 (s, 1H), 7.24 (d, J = 2.54 Hz, 1H), 7.19 (s, 1H), 7.12-7.17 (m, 1H), 5.66 (t, J = 57.10 Hz, 1H), 5.26 (s, 2H), 2.78 (s, 3H), 1.98 (dd, J = 7.73, 9.49 Hz, 1H), 1.78 (s, 3H), 1.35 (dd, J = 6.36, 9.88 Hz, 1H), 0.85 (br. s., 1H). | N-(3-((1S,5S,6S)-3-amino-1-(difluoromethyl)-5-methyl-2-thia-4-azabicyclo[4.1.0]hept-3-en-5-yl)-4,5-difluorophenyl)-3-methyl-5-(1,3-oxazol-2-ylmethoxy)-2-pyridinecarboxamide |
| 644 | ¹H-NMR (400 MHz, CHLOROFORM-d) δ 10.03 (s, 1H), 8.21 (d, J = 2.74 Hz, 1H), 7.94-7.99 (m, 1H), 7.72 (s, 1H), 7.62 (dd, J = 2.74, 7.04 Hz, 1H), 7.23 (d, J = 2.54 Hz, 1H), 7.19 (s, 1H), 7.04 (dd, J = 8.80, 11.93 Hz, 1H), 5.26 (s, 2H), 3.66 (d, J = 10.56 Hz, 1H), 3.41 (s, 3H), 3.34 (d, J = 10.76 Hz, 1H), 2.79 (s, 3H), 1.81 (dd, J = 7.43, 8.80 Hz, 1H), 1.72 (d, J = 0.98 Hz, 3H), 0.88 (dd, J = 5.87, 9.39 Hz, 1H), 0.76-0.84 (m, 1H). | N-(3-((1S,5S,6S)-3-amino-1-(methoxymethyl)-5-methyl-2-thia-4-azabicyclo[4.1.0]hept-3-en-5-yl)-4-fluorophenyl)-3-methyl-5-(1,3-oxazol-2-ylmethoxy)-2-pyridinecarboxamide |
| 645 | ¹H-NMR (400 MHz, CHLOROFORM-d) δ 10.08 (s, 1H), 8.22 (d, J = 2.74 Hz, 1H), 8.07 (ddd, J = 2.93, 6.94, 12.03 Hz, 1H), 7.73 (d, J = 0.78 Hz, 1H), 7.30 (dd, J = 2.25, 5.58 Hz, 1H), 7.24 (d, J = 2.54 Hz, 1H), 7.19 (s, 1H), 5.27 (s, 2H), 4.48 (q, J = 10.37 Hz, 1H), 4.35 (q, J = 10.30 Hz, 1H), 2.79 (s, 3H), 1.91 (dd, J = 7.63, 8.80 Hz, 1H), 1.74 (s, 3H), 1.01 (dd, J = 6.06, 9.39 Hz, 1H), 0.81-0.92 (m, 1H). | N-(3-((1S,5S,6S)-3-amino-1-(fluoromethyl)-5-methyl-2-thia-4-azabicyclo[4.1.0]hept-3-en-5-yl)-4,5-difluorophenyl)-3-methyl-5-(1,3-oxazol-2-ylmethoxy)-2-pyridinecarboxamide |
| 646 | ¹H-NMR (400 MHz, CHLOROFORM-d) δ 10.09 (s, 1H), 8.22 (d, J = 2.74 Hz, 1H), 8.05-8.15 (m, 1H), 7.72 (s, 1H), 7.24 (d, J = 2.15 Hz, 2H), 7.19 (s, 1H), 5.26 (s, 2H), 3.63 (d, J = 10.56 Hz, 1H), 3.41 (s, 3H), 3.35 (d, J = 10.56 Hz, 1H), 2.79 (s, 3H), 1.79-1.85 (m, 1H), 1.77 (s, 3H), 0.90-1.01 (m, 1H), 0.82 (t, J = 6.16 Hz, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-(1,3-oxazol-2-ylmethoxy)-2-pyridinecarboxamide |
| 647 | ¹H-NMR (400 MHz, CHLOROFORM-d) δ 10.07 (s, 1H), 8.18 (d, J = 2.54 Hz, 1H), 8.06 (ddd, J = 2.54, 6.94, 12.03 Hz, 1H), 7.21 (d, J = 2.54 Hz, 1H), 7.11-7.17 (m, 1H), 5.66 (t, J = 55.80 Hz, 1H), 4.97 (dq, J = 1.96, 6.52 Hz, 1H), 2.79 (s, 3H), 2.56 (d, J = 1.96 Hz, 1H), 2.07-2.08 (m, 1H), 1.80 (s, 3H), 1.73 (d, J = 6.46 Hz, 4H), 1.38 (dd, J = 6.26, 9.78 Hz, 2H), 0.88 (br. s., 1H). | N-(3-((1S,5S,6S)-3-amino-1-(difluoromethyl)-5-methyl-2-thia-4-azabicyclo[4.1.0]hept-3-en-5-yl)-4,5-difluorophenyl)-3-methyl-5-(((1S)-1-methyl-2-propyn-1-yl)oxy)-2-pyridinecarboxamide |
| 648 | ¹H-NMR (400 MHz, CHLOROFORM-d) δ 10.02 (br. s., 1H), 8.19 (d, J = 2.54 Hz, 1H), 7.95 (dd, J = 2.74, 9.39 Hz, 1H), 7.46 (dd, J = 2.64, 6.94 Hz, 1H), 7.21 (d, J = 2.54 Hz, 1H), 7.06 (dd, J = 8.80, 11.54 Hz, 1H), 5.65 (t, J = 56.50 Hz, 1H), 4.96 (dq, J = 1.86, 6.55 Hz, 1H), 2.79 (s, 3H), 2.56 (d, J = 1.96 Hz, 1H), 2.02 (dd, J = 7.43, 9.78 Hz, 1H), 1.81 (s, 3H), 1.72 (d, J = 9.19 Hz, 3H), 1.31-1.43 (m, 1H), 0.87 (t, J = 7.40 Hz, 1H) | N-(3-((1S,5S,6S)-3-amino-1-(difluoromethyl)-5-methyl-2-thia-4-azabicyclo[4.1.0]hept-3-en-5-yl)-4-fluorophenyl)-3-methyl-5-(((1S)-1-methyl-2-propyn-1-yl)oxy)-2-pyridinecarboxamide |
| 649 | ¹H-NMR (400 MHz, CHLOROFORM-d) δ 10.06 (s, 1H), 8.18 (d, J = 2.54 Hz, 1H), 7.99 (ddd, J = 2.93, 4.01, 8.71 Hz, 1H), 7.61 (dd, J = 2.74, 7.04 Hz, 1H), 7.20 (d, J = 2.54 Hz, 1H), 7.04 (dd, J = 8.80, 11.93 Hz, 1H), 4.96 (dq, J = 1.96, 6.52 Hz, 2H), 3.66 (d, J = 10.56 Hz, 1H), 3.41 (s, 3H), 3.34 (d, J = 10.76 Hz, 1H), 2.80 (s, 3H), 2.56 (d, J = 2.15 Hz, | N-(3-((1S,5S,6S)-3-amino-1-(methoxymethyl)-5-methyl-2-thia-4-azabicyclo[4.1.0]hept-3-en-5-yl)-4-fluorophenyl)-3-methyl-5-(((1S)-1-methyl-2-propyn-1-yl)oxy)-2-pyridinecarboxamide |

TABLE 4'-continued

| Ex. No. | ¹H-NMR | Chemical Name |
|---|---|---|
| | 1H), 1.81 (dd, J = 7.34, 8.90 Hz, 1H), 1.73 (s, 3H), 1.72 (d, J = 2.15 Hz, 3H), 0.89 (dd, J = 5.97, 9.29 Hz, 1H), 0.78-0.84 (m, 1H). | |
| 650 | ¹H-NMR (400 MHz, CHLOROFORM-d) δ 10.11 (s, 1H), 8.18 (d, J = 2.54 Hz, 1H), 8.10 (ddd, J = 2.74, 6.85, 12.13 Hz, 1H), 7.27-7.33 (m, 1H), 7.21 (d, J = 2.54 Hz, 1H), 4.97 (dq, J = 1.76, 6.52 Hz, 1H), 3.65 (d, J = 10.76 Hz, 1H), 3.41 (s, 3H), 3.35 (d, J = 10.76 Hz, 1H), 2.79 (s, 3H), 2.56 (d, J = 1.96 Hz, 1H), 1.80 (dd, J = 7.04, 8.22 Hz, 1H), 1.73 (s, 3H), 1.72 (d, 3H), 0.91 (dd, J = 5.97, 9.29 Hz, 1H), 0.81 (t, J = 6.16 Hz, 1H). | N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-(((1S)-1-methyl-2-propyn-1-yl)oxy)-2-pyridinecarboxamide |
| 651 | ¹H-NMR (400 MHz, CHLOROFORM-d) δ 10.06 (br. s., 1H), 8.20 (d, J = 2.35 Hz, 1H), 7.94-8.01 (m, 1H), 7.41 (d, J = 4.89 Hz, 1H), 7.20 (br. s., 1H), 7.07 (t, J = 9.86 Hz, 1H), 4.92-5.00 (m, J = 6.06 Hz, 1H), 4.38 (d, J = 49.30 Hz, 2H), 2.78 (s, 3H), 2.55 (s, 1H), 1.94-2.00 (m, J = 8.02 Hz, 1H), 1.90 (br. s., 3H), 1.72 (d, J = 6.46 Hz, 3H), 1.19-1.33 (m, 1H), 0.90-0.97 (m, 1H). | N-(3-((1S,5S,6S)-3-amino-1-(fluoromethyl)-5-methyl-2-thia-4-azabicyclo[4.1.0]hept-3-en-5-yl)-4-fluorophenyl)-3-methyl-5-(((1S)-1-methyl-2-propyn-1-yl)oxy)-2-pyridinecarboxamide |
| 652 | ¹H-NMR (400 MHz, CHLOROFORM-d) δ 10.03 (br. s., 1H), 8.22 (d, J = 2.54 Hz, 1H), 7.94-8.00 (m, 1H), 7.72 (s, 1H), 7.47 (dd, J = 2.45, 6.94 Hz, 1H), 7.23 (d, J = 2.35 Hz, 1H), 7.19 (s, 1H), 7.06 (dd, J = 8.90, 11.64 Hz, 1H), 5.26 (s, 2H), 4.39 (d, J = 46.17 Hz, 2H), 2.78 (s, 3H), 1.91-1.99 (m, 1H), 1.84 (s, 3H), 1.10-1.21 (m, J = 15.85 Hz, 1H), 0.87-0.95 (m, 1H). | N-(3-((1S,5S,6S)-3-amino-1-(fluoromethyl)-5-methyl-2-thia-4-azabicyclo[4.1.0]hept-3-en-5-yl)-4-fluorophenyl)-3-methyl-5-(1,3-oxazol-2-ylmethoxy)-2-pyridinecarboxamide |
| 680 | ¹H-NMR (400 MHz, CHLOROFORM-d) δ ppm 0.82-0.90 (m, 1 H) 1.32 (dd, J = 9.88, 6.16 Hz, 1 H) 1.77 (d, J = 0.98 Hz, 3 H) 1.96-2.05 (m, 1 H) 2.81 (s, 3 H) 4.47 (q, J = 7.82 Hz, 2 H) 5.48-5.91 (m, 1 H) 7.06 (dd, J = 11.54, 8.80 Hz, 1 H) 7.14 (d, J = 2.35 Hz, 1 H) 7.53 (dd, J = 7.04, 2.74 Hz, 1 H) 7.86-7.96 (m, 1 H) 8.18 (d, J = 2.54 Hz, 1 H) 9.97 (s, 1 H). | N-(3-((1S,5S,6S)-3-amino-1-(difluoromethyl)-5-methyl-2-thia-4-azabicyclo[4.1.0]hept-3-en-5-yl)-4-fluorophenyl)-3-methyl-5-(2,2,2-trifluoroethoxy)-2-pyridinecarboxamide |
| 681 | ¹H-NMR (400 MHz, CHLOROFORM-d) δ ppm 0.78-0.84 (m, 1 H) 0.88 (dd, J = 9.49, 5.77 Hz, 1 H) 1.72 (d, J = 1.17 Hz, 3 H) 1.77-1.85 (m, 1 H) 2.82 (s, 3 H) 3.34 (d, J = 10.56 Hz, 1 H) 3.41 (s, 3 H) 3.67 (d, J = 10.56 Hz, 1 H) 4.47 (q, J = 7.82 Hz, 2 H) 7.05 (dd, J = 11.83, 8.71 Hz, 1 H) 7.14 (d, J = 2.54 Hz, 1 H) 7.64 (dd, J = 6.94, 2.84 Hz, 1 H) 7.96 (ddd, J = 8.80, 4.11, 2.93 Hz, 1 H) 8.18 (d, J = 2.74 Hz, 1 H) 10.00 (s, 1 H). | N-(3-((1S,5S,6S)-3-amino-1-(methoxymethyl)-5-methyl-2-thia-4-azabicyclo[4.1.0]hept-3-en-5-yl)-4-fluorophenyl)-3-methyl-5-(2,2,2-trifluoroethoxy)-2-pyridinecarboxamide |
| 682 | ¹H-NMR (400 MHz, CHLOROFORM-d) δ ppm 0.77-0.83 (m, 1 H) 0.89 (dd, J = 9.39, 5.87 Hz, 1 H) 1.72 (s, 3 H) 1.76-1.84 (m, 1 H) 2.60 (t, J = 2.35 Hz, 1 H) 2.81 (s, 3 H) 3.35 (d, J = 10.56 Hz, 1 H) 3.41 (s, 3 H) 3.67 (d, J = 10.76 Hz, 1 H) 4.80 (d, J = 2.35 Hz, 2 H) 7.18 (d, J = 2.74 Hz, 1 H) 7.29-7.34 (m, 1 H) 8.09 (ddd, J = 12.08, 6.90, 2.93 Hz, 1 H) 8.18 (d, J = 2.74 Hz, 1 H) 10.10 (s, 1 H). | N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-(2-propyn-1-yloxy)-2-pyridinecarboxamide |
| 683 | ¹H-NMR (400 MHz, CHLOROFORM-d) δ ppm 0.77-0.91 (m, 2 H) 1.71 (d, J = 1.17 Hz, 3 H) 1.76-1.85 (m, 1 H) 2.60 (t, J = 2.35 Hz, 1 H) 2.81 (s, 3 H) 3.34 (d, J = 10.76 Hz, 1 H) 3.41 (s, 3 H) 3.67 (d, J = 10.56 Hz, 1 H) 4.80 (d, J = 2.54 Hz, 2 H) 7.04 (dd, J = 11.93, 8.80 Hz, 1 H) 7.18 (d, J = 2.35 Hz, 1 H) 7.64 (dd, J = 6.94, 2.84 Hz, 1 H) 7.97 (ddd, J = 8.75, 4.06, 2.84 Hz, 1 H) 8.18 (d, J = 2.74 Hz, 1 H) 10.04 (s, 1 H). | N-(3-((1S,5S,6S)-3-amino-1-(methoxymethyl)-5-methyl-2-thia-4-azabicyclo[4.1.0]hept-3-en-5-yl)-4-fluorophenyl)-3-methyl-5-(2-propyn-1-yloxy)-2-pyridinecarboxamide |
| 684 | ¹H-NMR (400 MHz, CHLOROFORM-d) δ ppm 0.83-0.90 (m, 1 H) 1.00 (dd, J = 9.59, 6.06 Hz, 1 H) 1.73 (d, J = 0.98 Hz, 3 H) 1.86-1.95 (m, 1 H) 2.61 (t, J = 2.35 Hz, 1 H) 2.81 (s, 3 H) 4.29-4.41 (m, 1 H) 4.42-4.53 (m, 1 H) 4.81 (d, J = 2.35 Hz, 2 H) 7.19 (d, J = 2.74 Hz, 1 H) 7.32 (dt, J = 5.72, 2.32 Hz, 1 H) 8.07 (ddd, J = 12.08, 6.90, 2.74 Hz, 1 H) 8.18 (d, J = 2.54 Hz, 1 H) 10.09 (s, 1 H). | N-(3-((1S,5S,6S)-3-amino-1-(fluoromethyl)-5-methyl-2-thia-4-azabicyclo[4.1.0]hept-3-en-5-yl)-4,5-difluorophenyl)-3-methyl-5-(2-propyn-1-yloxy)-2-pyridinecarboxamide |
| 685 | ¹H-NMR (400 MHz, CHLOROFORM-d) δ ppm 0.86 (br. s., 1 H) 1.35 (dd, J = 9.78, 6.26 Hz, 1 H) 1.78 (s, 3 H) 1.98 (dd, J = 9.39, 7.63 Hz, 1 H) 2.61 (s, 1 H) 2.80 (s, 3 H) 4.80 (d, J = 2.15 Hz, 2 H) 5.49-5.88 (m, 1 H) 7.15-7.21 (m, 2 H) 8.04 (ddd, J = 11.93, 6.94, 2.64 Hz, 1 H) 8.16 (d, J = 2.54 Hz, 1 H) 10.04 (s, 1 H). | N-(3-((1S,5S,6S)-3-amino-1-(difluoromethyl)-5-methyl-2-thia-4-azabicyclo[4.1.0]hept-3-en-5-yl)-4,5-difluorophenyl)-3-methyl-5-(2-propyn-1-yloxy)-2-pyridinecarboxamide |

TABLE 4'-continued

| Ex. No. | ¹H-NMR | Chemical Name |
|---|---|---|
| 686 | ¹H-NMR (400 MHz, CHLOROFORM-d) δ ppm 0.78-0.87 (m, 1 H) 1.31 (dd, J = 9.88, 6.16 Hz, 1 H) 1.77 (s, 3 H) 1.97 (dd, J = 9.78, 7.43 Hz, 1 H) 2.57-2.63 (m, 1 H) 2.77 (s, 3 H) 4.67-4.98 (m, 3 H) 5.42-5.89 (m, 1 H) 7.02 (dd, J = 11.64, 8.90 Hz, 1 H) 7.15 (d, J = 2.35 Hz, 1 H) 7.51 (dd, J = 6.85, 2.74 Hz, 1 H) 7.88 (dt, J = 8.46, 3.40 Hz, 1 H) 8.09 (d, J = 1.96 Hz, 1 H) 9.97 (s, 1 H). | N-(3-((1S,5S,6S)-3-amino-1-(difluoromethyl)-5-methyl-2-thia-4-azabicyclo[4.1.0]hept-3-en-5-yl)-4-fluorophenyl)-3-methyl-5-(2-propyn-1-yloxy)-2-pyridinecarboxamide |
| 687 | ¹H-NMR (400 MHz, CHLOROFORM-d) δ ppm 0.76-0.83 (m, 1 H) 0.88 (dd, J = 9.39, 5.87 Hz, 1 H) 1.71 (s, 3 H) 1.74-1.81 (m, 1 H) 1.83 (d, J = 6.46 Hz, 3 H) 2.75 (s, 3 H) 3.34 (d, J = 10.56 Hz, 1 H) 3.41 (s, 3 H) 3.66 (d, J = 10.76 Hz, 1 H) 4.11-4.11 (m, 1 H) 4.49 (br. s., 2 H) 5.58 (q, J = 6.52 Hz, 1 H) 7.13 (s, 1 H) 7.20 (d, J = 2.54 Hz, 1 H) 7.31 (dd, J = 5.09, 2.54 Hz, 1 H) 7.66 (s, 1 H) 8.07 (ddd, J = 11.93, 6.85, 2.54 Hz, 1 H) 8.15 (d, J = 2.35 Hz, 1 H) 10.07 (s, 1 H). | N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-((1S)-1-(1,3-oxazol-2-yl)ethoxy)-2-pyridinecarboxamide |
| 688 | ¹H NMR (400 MHz, CHLOROFORM-d) δ ppm 0.77-0.84 (m, 1 H) 0.88 (dd, J = 9.39, 5.87 Hz, 1 H) 1.71 (s, 3 H) 1.76-1.81 (m, 1 H) 1.83 (d, J = 6.46 Hz, 3 H) 2.76 (s, 3 H) 3.34 (d, J = 10.56 Hz, 1 H) 3.41 (s, 3 H) 3.66 (d, J = 10.56 Hz, 1 H) 4.23-4.60 (m, 2 H) 5.58 (q, J = 6.65 Hz, 1 H) 7.13 (s, 1 H) 7.21 (d, J = 2.54 Hz, 1 H) 7.31 (dd, J = 5.28, 2.54 Hz, 1 H) 7.66 (s, 1 H) 8.07 (ddd, J = 12.13, 6.85, 2.74 Hz, 1 H) 8.17 (d, J = 2.54 Hz, 1 H) 10.06 (s, 1 H). | N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-(1R)-1-(1,3-oxazol-2-yl)ethoxy)-2-pyridinecarboxamide |
| 689 | ¹H NMR (400 MHz, CHLOROFORM-d) δ ppm 0.82-0.91 (m, 1 H) 0.98 (dd, J = 9.49, 5.97 Hz, 1 H) 1.72 (d, J = 1.17 Hz, 3 H) 1.84-1.98 (m, 1 H) 2.82 (s, 3 H) 4.25-4.58 (m, 6 H) 7.06 (dd, J = 11.74, 8.80 Hz, 1 H) 7.14 (d, J = 2.54 Hz, 1 H) 7.64 (dd, J = 7.04, 2.74 Hz, 1 H) 7.90-8.01 (m, 1 H) 8.18 (d, J = 2.54 Hz, 1 H) 10.00 (s, 1 H). | N-(3-((1S,5S,6S)-3-amino-1-(fluoromethyl)-5-methyl-2-thia-4-azabicyclo[4.1.0]hept-3-en-5-yl)-4-fluorophenyl)-3-methyl-5-(2,2,2-trifluoroethoxy)-2-pyridinecarboxamide |
| 690 | ¹H NMR (400 MHz, CHLOROFORM-d) δ ppm 0.81-0.91 (m, 1 H) 0.98 (dd, J = 9.49, 6.16 Hz, 1 H) 1.72 (d, J = 0.98 Hz, 3 H) 1.85-1.97 (m, 1 H) 2.60 (t, J = 2.35 Hz, 1 H) 2.81 (s, 3 H) 4.26-4.59 (m, 4 H) 4.80 (d, J = 2.54 Hz, 2 H) 7.05 (dd, J = 11.74, 8.80 Hz, 1 H) 7.18 (d, J = 2.35 Hz, 1 H) 7.63 (dd, J = 7.04, 2.74 Hz, 1 H) 7.88-8.01 (m, 1 H) 8.19 (d, J = 2.54 Hz, 1 H) 10.04 (s, 1 H). | N-(3-((1S,5S,6S)-3-amino-1-(fluoromethyl)-5-methyl-2-thia-4-azabicyclo[4.1.0]hept-3-en-5-yl)-4-fluorophenyl)-3-methyl-5-(2-propyn-1-yloxy)-2-pyridinecarboxamide |
| 691 | ¹H NMR (400 MHz, CHLOROFORM-d) δ ppm 0.83-0.90 (m, 1 H) 1.00 (dd, J = 9.49, 6.16 Hz, 1 H) 1.72 (d, J = 0.98 Hz, 3 H) 1.91 (dd, J = 8.90, 7.53 Hz, 1 H) 2.65 (t, J = 2.45 Hz, 1 H) 4.27-4.57 (m, 4 H) 4.83 (d, J = 2.35 Hz, 2 H) 7.30-7.35 (m, 1 H) 7.45 (d, J = 2.54 Hz, 1 H) 8.10 (ddd, J = 11.93, 6.85, 2.74 Hz, 1 H) 8.26 (d, J = 2.54 Hz, 1 H) 9.85 (s, 1 H). | N-(3-((1S,5S,6S)-3-amino-1-(fluoromethyl)-5-methyl-2-thia-4-azabicyclo[4.1.0]hept-3-en-5-yl)-4,5-difluorophenyl)-3-chloro-5-(2-propyn-1-yloxy)-2-pyridinecarboxamide |
| 692 | ¹H NMR (400 MHz, CHLOROFORM-d) δ ppm 0.80-0.91 (m, 1 H) 1.01 (dd, J = 9.59, 6.06 Hz, 1 H) 1.74 (s, 3 H) 1.84-1.96 (m, 1 H) 4.31-4.54 (m, 4 H) 7.36-7.44 (m, 2 H) 8.02 (ddd, J = 11.88, 6.80, 2.64 Hz, 1 H) 8.26 (d, J = 8.61 Hz, 1 H) 8.32 (d, J = 2.93 Hz, 1 H) 9.81 (s, 1 H). | N-(3-((1S,5S,6S)-3-amino-1-(fluoromethyl)-5-methyl-2-thia-4-azabicyclo[4.1.0]hept-3-en-5-yl)-4,5-difluorophenyl)-5-(2,2,2-trifluoroethoxy)-2-pyridinecarboxamide |
| 693 | ¹H NMR (400 MHz, CHLOROFORM-d) δ ppm 0.84-0.91 (m, 1 H) 1.04 (dd, J = 9.49, 6.16 Hz, 1 H) 1.75 (s, 3 H) 1.89-1.96 (m, 1 H) 4.26-4.97 (m, 6 H) 7.30 (dt, J = 5.43, 2.47 Hz, 1 H) 7.40 (d, J = 2.54 Hz, 1 H) 8.11 (ddd, J = 11.93, 6.85, 2.74 Hz, 1 H) 8.28 (d, J = 2.54 Hz, 1 H) 9.80 (s, 1 H). | N-(3-((1S,5S,6S)-3-amino-1-(fluoromethyl)-5-methyl-2-thia-4-azabicyclo[4.1.0]hept-3-en-5-yl)-4,5-difluorophenyl)-3-chloro-5-(2,2,2-trifluoroethoxy)-2-pyridinecarboxamide |
| 694 | ¹H NMR (400 MHz, CHLOROFORM-d) δ ppm 0.00-0.00 (m, 1 H) 0.78-0.84 (m, 1 H) 0.90 (dd, J = 9.39, 5.87 Hz, 1 H) 1.72 (d, J = 1.17 Hz, 3 H) 1.80 (ddd, J = 9.34, 6.80, 1.27 Hz, 1 H) 3.35 (d, J = 10.56 Hz, 1 H) 3.41 (s, 3 H) 3.67 (d, J = 10.76 Hz, 1 H) 4.19-4.58 (m, 4 H) 7.36-7.46 (m, 2 H) 8.07 (ddd, J = 11.93, 6.85, 2.74 Hz, 1 H) 8.28 (d, J = 8.80 Hz, 1 H) 8.34 (d, J = 2.54 Hz, 1 H) 9.75-9.88 (m, 1 H). | N-(3-((1S,5S,6S)-3-amino-1-(methoxymethyl)-5-methyl-2-thia-4-azabicyclo[4.1.0]hept-3-en-5-yl)-4,5-difluorophenyl)-5-(2,2,2-trifluoroethoxy)-2-pyridinecarboxamide |
| 695 | ¹H NMR (400 MHz, CHLOROFORM-d) δ ppm 0.82-0.91 (m, 1 H) 1.35 (dd, J = 9.88, 6.36 Hz, 1 H) 1.78 (d, J = 0.78 Hz, 3 H) 1.99 (dd, J = 9.68, 7.53 Hz, 1 H) 4.49 (q, J = 7.82 Hz, 4 H) 5.51-5.84 (m, 1 H) 7.27-7.32 (m, 1 H) 7.41 (dd, J = 8.70, 2.84 Hz, 1 H) 8.02 (ddd, J = 11.79, 6.80, 2.74 Hz, 1 H) | N-(3-((1S,5S,6S)-3-amino-1-(difluoromethyl)-5-methyl-2-thia-4-azabicyclo[4.1.0]hept-3-en-5-yl)-4,5-difluorophenyl)-5-(2,2,2-trifluoroethoxy)-2-pyridinecarboxamide |

TABLE 4'-continued

| Ex. No. | ¹H-NMR | Chemical Name |
|---|---|---|
| | 8.27 (d, J = 8.61 Hz, 1 H) 8.33 (d, J = 2.93 Hz, 1 H) 9.78 (s, 1 H). | |
| 696 | ¹H NMR (400 MHz, CHLOROFORM-d) δ ppm 0.80-0.89 (m, 1 H) 1.33 (dd, J = 9.88, 6.16 Hz, 1 H) 1.78 (d, J = 0.78 Hz, 3 H) 2.00 (dd, J = 9.78, 7.24 Hz, 1 H) 4.22-4.88 (m, 4 H) 5.50-5.84 (m, 1 H) 7.07 (dd, J = 11.64, 8.71 Hz, 1 H) 7.40 (dd, J = 8.71, 2.84 Hz, 1 H) 7.63 (dd, J = 7.04, 2.74 Hz, 1 H) 7.85-7.94 (m, 1 H) 8.28 (d, J = 8.61 Hz, 1 H) 8.33 (d, J = 2.74 Hz, 1 H) 9.77 (s, 1 H). | N-(3-((1S,5S,6S)-3-amino-1-(difluoromethyl)-5-methyl-2-thia-4-azabicyclo[4.1.0]hept-3-en-5-yl)-4-fluorophenyl)-5-(2,2,2-trifluoroethoxy)-2-pyridinecarboxamide |
| 697 | ¹H NMR (400 MHz, CHLOROFORM-d) δ ppm 0.85-0.94 (m, 1 H) 1.05 (dd, J = 9.49, 6.16 Hz, 1 H) 1.77 (d, J = 0.78 Hz, 3 H) 1.88-2.00 (m, 1 H) 4.30-4.54 (m, 4 H) 7.08 (dd, J = 11.54, 8.80 Hz, 1 H) 7.40 (dd, J = 8.80, 2.93 Hz, 1 H) 7.69 (dd, J = 7.04, 2.74 Hz, 1 H) 7.94 (ddd, J = 8.80, 4.11, 2.93 Hz, 1 H) 8.28 (d, J = 8.61 Hz, 1 H) 8.34 (d, J = 2.74 Hz, 1 H) 9.80 (s, 1 H). | N-(3-((1S,5S,6S)-3-amino-1-(fluoromethyl)-5-methyl-2-thia-4-azabicyclo[4.1.0]hept-3-en-5-yl)-4-fluorophenyl)-5-(2,2,2-trifluoroethoxy)-2-pyridinecarboxamide |
| 698 | ¹H NMR (400 MHz, CHLOROFORM-d) δ ppm 0.84 (t, J = 6.36 Hz, 1 H) 0.94-1.02 (m, 1 H) 1.79 (s, 3 H) 1.84 (dd, J = 8.61, 6.85 Hz, 1 H) 3.36 (d, J = 10.76 Hz, 1 H) 3.41 (s, 3 H) 3.63 (d, J = 10.76 Hz, 1 H) 4.48 (q, J = 7.82 Hz, 2 H) 7.08 (dd, J = 11.74, 8.80 Hz, 1 H) 7.40 (dd, J = 8.80, 2.93 Hz, 1 H) 7.66 (dd, J = 6.85, 2.74 Hz, 1 H) 7.97 (ddd, J = 8.75, 4.06, 2.84 Hz, 1 H) 8.27 (d, J = 8.80 Hz, 1 H) 8.34 (d, J = 2.54 Hz, 1 H) 9.68-9.91 (m, 1 H). | N-(3-((1S,5S,6S)-3-amino-1-(methoxymethyl)-5-methyl-2-thia-4-azabicyclo[4.1.0]hept-3-en-5-yl)-4-fluorophenyl)-5-(2,2,2-trifluoroethoxy)-2-pyridinecarboxamide |
| 699 | ¹H NMR (400 MHz, CHLOROFORM-d) δ ppm 0.86 (t, J = 6.36 Hz, 1 H) 1.42 (dd, J = 9.59, 5.67 Hz, 1 H) 1.60 (br. s., 2 H) 1.85 (s, 3 H) 1.89 (br. s., 4 H) 2.25-2.34 (m, 1 H) 3.48 (br. s., 2 H) 3.67 (br. s., 2 H) 4.49 (q, J = 7.82 Hz, 2 H) 7.26-7.30 (m, 1 H) 7.40 (dd, J = 8.71, 2.84 Hz, 1 H) 8.01 (ddd, J = 11.79, 6.80, 2.74 Hz, 1 H) 8.27 (d, J = 8.61 Hz, 1 H) 8.33 (d, J = 2.74 Hz, 1 H) 9.78 (s, 1 H). | N-(3-((1S,5S,6S)-3-amino-5-methyl-1-(1-pyrrolidinylcarbonyl)-2-thia-4-azabicyclo[4.1.0]hept-3-en-5-yl)-4,5-difluorophenyl)-5-(2,2,2-trifluoroethoxy)-2-pyridinecarboxamide |
| 700 | ¹H NMR (400 MHz, CHLOROFORM-d) δ ppm 0.73-0.83 (m, 1 H) 1.89 (s, 3 H) 2.00 (dd, J = 9.68, 4.99 Hz, 1 H) 2.22 (dd, J = 9.39, 7.63 Hz, 1 H) 2.87 (d, J = 4.89 Hz, 3 H) 4.49 (q, J = 7.82 Hz, 2 H) 6.61 (d, J = 4.69 Hz, 1 H) 6.99-7.13 (m, 1 H) 7.39 (dd, J = 8.70, 2.84 Hz, 1 H) 7.77 (ddd, J = 11.74, 6.65, 2.74 Hz, 1 H) 8.18 (d, J = 8.61 Hz, 1 H) 8.24 (d, J = 2.74 Hz, 1 H) 9.53 (s, 1 H). | (1S,5S,6S)-3-amino-5-(2,3-difluoro-5-(((5-(2,2,2-trifluoroethoxy)-2-pyridinyl)carbonyl)amino)phenyl)-N,5-dimethyl-2-thia-4-azabicyclo[4.1.0]hept-3-ene-1-carboxamide |
| 701 | ¹H NMR (400 MHz, CHLOROFORM-d) δ ppm 0.74-0.85 (m, 1 H) 1.85 (s, 3 H) 1.98 (dd, J = 9.59, 5.09 Hz, 1 H) 2.23 (dd, J = 9.29, 7.73 Hz, 1 H) 2.87 (d, J = 4.89 Hz, 3 H) 4.81-4.93 (m, 2 H) 6.54 (d, J = 4.70 Hz, 1 H) 7.06-7.19 (m, 1 H) 7.81 (ddd, J = 11.39, 6.70, 2.64 Hz, 1 H) 8.25 (d, J = 1.17 Hz, 1 H) 8.96 (d, J = 1.17 Hz, 1 H) 9.29 (s, 1 H) | (1S,5S,6S)-3-amino-5-(2,3-difluoro-5-(((5-(2,2,2-trifluoroethoxy)-2-pyrazinyl)carbonyl)amino)phenyl)-N,5-dimethyl-2-thia-4-azabicyclo[4.1.0]hept-3-ene-1-carboxamide |
| 702 | ¹H NMR (400 MHz, CHLOROFORM-d) δ ppm 0.79 (t, J = 5.87 Hz, 1 H) 1.88 (s, 3 H) 2.00 (dd, J = 9.59, 5.09 Hz, 1 H) 2.22 (dd, J = 9.39, 7.63 Hz, 1 H) 2.77 (s, 3 H) 2.87 (d, J = 4.69 Hz, 3 H) 4.47 (q, J = 7.82 Hz, 2 H) 6.59 (d, J = 4.69 Hz, 1 H) 6.83-6.94 (m, 1 H) 7.14 (d, J = 2.54 Hz, 1 H) 7.88 (ddd, J = 12.03, 6.75, 2.54 Hz, 1 H) 8.04 (d, J = 2.74 Hz, 1 H) 9.75 (s, 1 H). | (1S,5S,6S)-3-amino-5-(2,3-difluoro-5-(((3-methyl-5-(2,2,2-trifluoroethoxy)-2-pyridinyl)carbonyl)amino)phenyl)-N,5-dimethyl-2-thia-4-azabicyclo[4.1.0]hept-3-ene-1-carboxamide |
| 732 | ¹H NMR (400 MHz, DMSO-d6) δ 10.57 (s, 1H), 8.49 (d, J = 2.74 Hz, 1H), 8.15 (d, J = 8.61 Hz, 1H), 7.94 (ddd, J = 2.74, 6.75, 12.42 Hz, 1H), 7.84-7.89 (m, 1H), 7.76 (dd, J = 2.84, 8.71 Hz, 1H), 6.56-6.89 (m, 1H), 5.99 (s, 2H), 4.85 (t, J = 13.40 Hz, 2H), 3.56 (d, J = 10.76 Hz, 1H), 3.35 (d, J = 10.95 Hz, 1H), 3.30 (s, 3H), 1.58-1.67 (m, 4H), 0.89 (dd, J = 5.18, 9.29 Hz, 1H), 0.65 (t, J = 5.87 Hz, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-(2,2,3,3-tetrafluoropropoxy)-2-pyridinecarboxamide |
| 734 | ¹H NMR (400 MHz, DMSO-d6) δ 10.67 (s, 1H), 8.92 (d, J = 1.37 Hz, 1H), 8.57 (d, J = 1.37 Hz, 1H), 7.86-7.97 (m, 2H), 6.56-6.89 (m, 1H), 5.99 (br. s., 2H), 5.04 (t, J = 14.08 Hz, 2H), 3.57 (d, J = 10.76 Hz, 1H), 3.36 (d, J = 10.95 Hz, 1H), 3.31 (s, 3H), 1.63-1.67 (m, 1H), 1.62 (s, 3H), 0.91 (br. s., 1H), 0.61-0.69 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-(2,2,3,3-tetrafluoropropoxy)-2-pyrazinecarboxamide |
| 738 | ¹H NMR (400 MHz, DMSO-d6) δ 10.60 (s, 1H), 8.89 (d, J = 1.37 Hz, 1H), 8.43 (d, J = 1.37 Hz, 1H), 7.84-7.96 (m, 2H), 5.98 (br. s., 2H), 4.65 (t, J = 5.87 Hz, 2H), 3.56 (d, J = 10.95 Hz, 1H), 3.35 (d, | N-(3-((1S,5S,6S)-3-amino-1-(methoxymethyl)-5-methyl-2-thia-4-azabicyclo[4.1.0]hept-3-en-5-yl)-4,5-difluorophenyl)-5- |

TABLE 4'-continued

| Ex. No. | ¹H-NMR | Chemical Name |
|---|---|---|
| | J = 10.95 Hz, 1H), 3.30 (s, 3H), 2.89 (tq, J = 5.67, 11.35 Hz, 2H), 1.64 (br. s., 1H), 1.61 (s, 3H), 0.89 (d, J = 8.41 Hz, 1H), 0.64 (t, J = 5.67 Hz, 1H) | (3,3,3-trifluoropropoxy)-2-pyrazinecarboxamide |
| 739 | ¹H NMR (400 MHz, DMSO-d6) δ 10.63 (s, 1H), 8.89 (d, J = 1.37 Hz, 1H), 8.54 (d, J = 1.17 Hz, 1H), 7.85-7.97 (m, 2H), 5.98 (s, 2H), 4.73 (t, J = 13.20 Hz, 2H), 3.56 (d, J = 10.95 Hz, 1H), 3.35 (d, J = 10.95 Hz, 1H), 3.30 (s, 3H), 1.78 (t, J = 19.27 Hz, 3H), 1.64 (br. s., 1H), 1.61 (s, 3H), 0.89 (dd, J = 5.28, 9.19 Hz, 1H), 0.64 (t, J = 5.67 Hz, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-(2,2-difluoropropoxy)-2-pyrazinecarboxamide |
| 740 | ¹H NMR (400 MHz, DMSO-d6) δ 10.58 (s, 1H), 8.88 (d, J = 1.37 Hz, 1H), 8.41 (d, J = 1.37 Hz, 1H), 7.86-7.95 (m, 2H), 5.99 (br. s., 2H), 4.70 (t, J = 5.87 Hz, 1H), 4.58 (t, J = 5.87 Hz, 1H), 4.52 (t, J = 6.36 Hz, 2H), 3.56 (d, J = 10.95 Hz, 1H), 3.36 (d, J = 11.15 Hz, 1H), 3.30 (s, 3H), 2.22 (quin, J = 6.11 Hz, 1H), 2.15 (quin, J = 6.11 Hz, 1H), 1.65 (br. s., 1H), 1.61 (s, 3H), 0.90 (dd, J = 5.18, 9.29 Hz, 1H), 0.64 (t, J = 5.67 Hz, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-(3-fluoropropoxy)-2-pyrazinecarboxamide |
| 742 | ¹H NMR (400 MHz, DMSO-d6) δ 10.82 (s, 1H), 8.78 (d, J = 2.35 Hz, 1H), 8.17-8.23 (m, 1H), 8.11-8.16 (m, 1H), 7.95 (ddd, J = 2.54, 6.80, 12.37 Hz, 1H), 7.66-7.75 (m, 1H), 6.61 (s, 2H), 3.13 (s, 3H), 2.18 (dd, J = 7.82, 10.17 Hz, 1H), 1.92 (dd, J = 6.06, 10.17 Hz, 1H), 1.73 (s, 3H), 0.95 (t, J = 6.75 Hz, 1H) | N-(3-((1R,5S,6S)-3-amino-5-methyl-1-(methylsulfonyl)-2-thia-4-azabicyclo[4.1.0]hept-3-en-5-yl)-4,5-difluorophenyl)-5-chloro-2-pyridinecarboxamide |
| 743 | ¹H NMR (400 MHz, DMSO-d6) δ 10.63 (s, 1H), 8.44 (d, J = 2.93 Hz, 1H), 8.13 (d, J = 8.61 Hz, 1H), 7.96 (ddd, J = 2.54, 6.85, 12.32 Hz, 1H), 7.63-7.72 (m, 2H), 6.61 (s, 2H), 5.04 (d, J = 2.35 Hz, 2H), 3.71 (t, J = 2.25 Hz, 1H), 3.13 (s, 3H), 2.19 (dd, J = 7.63, 10.17 Hz, 1H), 1.92 (dd, J = 6.06, 10.37 Hz, 1H), 1.73 (s, 3H), 0.96 (t, J = 6.85 Hz, 1H) | N-(3-((1R,5S,6S)-3-amino-5-methyl-1-(methylsulfonyl)-2-thia-4-azabicyclo[4.1.0]hept-3-en-5-yl)-4,5-difluorophenyl)-5-(2-propyn-1-yloxy)-2-pyridinecarboxamide |
| 744 | ¹H NMR (400 MHz, DMSO-d6) δ 10.69 (s, 1H), 8.90 (d, J = 1.17 Hz, 1H), 8.48 (d, J = 1.37 Hz, 1H), 7.93 (ddd, J = 2.64, 6.85, 12.23 Hz, 1H), 7.71 (d, J = 5.87 Hz, 1H), 6.61 (s, 2H), 5.14 (d, J = 2.35 Hz, 2H), 3.64 (t, J = 2.45 Hz, 1H), 3.13 (s, 3H), 2.19 (dd, J = 7.82, 10.17 Hz, 1H), 1.92 (dd, J = 6.06, 10.17 Hz, 1H), 1.73 (s, 3H), 0.95 (t, J = 6.75 Hz, 1H) | N-(3-((1R,5S,6S)-3-amino-5-methyl-1-(methylsulfonyl)-2-thia-4-azabicyclo[4.1.0]hept-3-en-5-yl)-4,5-difluorophenyl)-5-(2-propyn-1-yloxy)-2-pyrazinecarboxamide |
| 745 | ¹H NMR (400 MHz, DMSO-d6) δ 10.62 (s, 1H), 8.49 (d, J = 2.74 Hz, 1H), 8.21 (d, J = 0.78 Hz, 1H), 8.12 (d, J = 8.80 Hz, 1H), 7.95 (ddd, J = 2.64, 6.80, 12.47 Hz, 1H), 7.75 (dd, J = 2.74, 8.80 Hz, 1H), 7.64-7.71 (m, 1H), 7.31 (d, J = 0.78 Hz, 1H), 6.61 (s, 2H), 5.48 (s, 2H), 3.13 (s, 3H), 2.18 (dd, J = 7.82, 10.17 Hz, 1H), 1.92 (dd, J = 6.06, 10.17 Hz, 1H), 1.73 (s, 3H), 0.96 (t, J = 6.75 Hz, 1H) | N-(3-((1R,5S,6S)-3-amino-5-methyl-1-(methylsulfonyl)-2-thia-4-azabicyclo[4.1.0]hept-3-en-5-yl)-4,5-difluorophenyl)-5-(1,3-oxazol-2-ylmethoxy)-2-pyridinecarboxamide |
| 746 | ¹H NMR (400 MHz, DMSO-d6) δ 10.70 (s, 1H), 8.88 (d, J = 1.37 Hz, 1H), 8.53 (d, J = 1.17 Hz, 1H), 8.19 (d, J = 0.78 Hz, 1H), 7.93 (ddd, J = 2.64, 6.85, 12.42 Hz, 1H), 7.66-7.74 (m, 1H), 7.29 (s, 1H), 6.61 (s, 2H), 5.61 (s, 2H), 3.13 (s, 3H), 2.18 (dd, J = 7.73, 10.07 Hz, 1H), 1.92 (dd, J = 6.06, 10.17 Hz, 1H), 1.73 (s, 3H), 0.94 (t, J = 6.75 Hz, 1H) | N-(3-((1R,5S,6S)-3-amino-5-methyl-1-(methylsulfonyl)-2-thia-4-azabicyclo[4.1.0]hept-3-en-5-yl)-4,5-difluorophenyl)-5-(1,3-oxazol-2-ylmethoxy)-2-pyrazinecarboxamide |
| 772 | ¹H NMR (DMSO-d6) δ: 10.63 (s, 1H), 8.80 (d, J = 2.0 Hz, 1H), 8.20-8.24 (m, 1H), 8.15-8.19 (m 1H), 8.03 (dd, J = 7.0, 2.5 Hz, 1H), 7.83-7.90 (m, 1H), 7.21 (dd, J = 11.7, 8.8 Hz, 1H), 6.61 (d, J = 15.3 Hz, 1H), 6.46 (br. s., 2H), 6.04 (d, J = 15.1 Hz, 1H), 4.59-4.87 (m, 4H), 4.35 (m, 2H), 2.01 (t, J = 8.4 Hz, 1H), 1.56 (dd, J = 9.3, 4.8 Hz, 1H), 0.99 (t, J = 6.0 Hz, 1H). | N-(3-((1R,5S,6S)-3-amino-1-((1E)-3-(3,3-difluoro-1-azetidinyl)-3-oxo-1-propen-1-yl)-5-(fluoromethyl)-2-thia-4-azabicyclo[4.1.0]hept-3-en-5-yl)-4-fluorophenyl)-5-chloro-2-pyridinecarboxamide |
| 774 | ¹H NMR (DMSO-d6) δ: 10.49 (s, 1H), 8.90 (d, J = 1.4 Hz, 1H), 8.48 (d, J = 1.4 Hz, 1H), 8.02 (dd, J = 7.0, 2.5 Hz, 1H), 7.75-7.89 (m, 1H), 7.19 (dd, J = 11.5, 9.0 Hz, 1H), 6.40-6.55 (m, 4H), 5.14 (d, J = 2.3 Hz, 2H), 4.59-4.84 (m, 2H), 3.64 (t, J = 2.3 Hz, 1H), 3.06 (s, 3H), 2.88 (s, 3H), 1.87-1.97 (m, 1H), 1.53 (dd, J = 9.0, 4.9 Hz, 1H), 0.94 (t, J = 5.9 Hz, 1H). | N-(3-((1R,5S,6S)-3-amino-1-((1E)-3-(dimethylamino)-3-oxo-1-propen-1-yl)-5-(fluoromethyl)-2-thia-4-azabicyclo[4.1.0]hept-3-en-5-yl)-4-fluorophenyl)-5-(2-propyn-1-yloxy)-2-pyrazinecarboxamide |
| 780 | ¹H NMR (DMSO-d6) δ: 10.50 (s, 1H), 8.89 (d, J = 1.2 Hz, 1H), 8.48 (d, J = 1.4 Hz, 1H), 8.32 (s, 1H), 8.02 (dd, J = 7.0, 2.7 Hz, 1H), 7.78-7.91 (m, 1H), 7.19 (dd, J = 11.8, 8.7 Hz, 1H), 7.12 (s, 1H), 6.50 (s, 2H), 5.14 (d, J = 2.3 Hz, 2H), 4.61-4.90 (m, | N-(3-((1S,5S,6S)-3-amino-5-(fluoromethyl)-1-(1,3-oxazol-5-yl)-2-thia-4-azabicyclo[4.1.0]hept-3-en-5-yl)-4-fluorophenyl)-5-(2-propyn-1- |

TABLE 4'-continued

| Ex. No. | ¹H-NMR | Chemical Name |
|---|---|---|
| | 2H), 3.64 (t, J = 2.4 Hz, 1H), 1.98-2.08 (m, 1H), 1.63 (dd, J = 9.8, 5.5 Hz, 1H), 0.89-1.00 (m, 1H) | yloxy)-2-pyrazinecarboxamide |
| 783 | ¹H NMR (DMSO-d6) δ: 10.62 (s, 1H), 8.99 (d, J = 1.4 Hz, 1H), 8.64 (d, J = 1.4 Hz, 1H), 8.43 (s, 1H), 8.30 (s, 1H), 8.13 (dd, J = 7.2, 2.7 Hz, 1H), 7.95 (dt, J = 7.3, 4.2 Hz, 1H), 7.40 (d, J = 0.8 Hz, 1H), 7.30 (dd, J = 11.7, 8.8 Hz, 1H), 7.23 (s, 1H), 6.61 (s, 2H), 5.72 (s, 2H), 4.73-5.02 (m, 2H), 2.07-2.19 (m, 1H), 1.74 (dd, J = 9.7, 5.6 Hz, 1H), 0.96-1.12 (m, 1H) | N-(3-((1S,5S,6S)-3-amino-5-(fluoromethyl)-1-(1,3-oxazol-5-yl)-2-thia-4-azabicyclo[4.1.0]hept-3-en-5-yl)-4-fluorophenyl)-5-(1,3-oxazol-2-ylmethoxy)-2-pyrazinecarboxamide |
| 792 | ¹H NMR (DMSO-d6) δ: 10.55 (s, 1H), 8.78 (d, J = 2.3 Hz, 1H), 8.17-8.23 (m, 1H), 8.11-8.17 (m, 1H), 7.99 (dd, J = 7.4, 2.7 Hz, 1H), 7.77-7.85 (m, 1H), 7.64 (d, J = 3.7 Hz, 1H), 7.16 (dd, J = 11.9, 8.8 Hz, 1H), 6.09 (s, 2H), 2.65 (td, J = 7.3, 3.7 Hz, 1H), 2.15 (dd, J = 9.3, 7.5 Hz, 1H), 1.61 (s, 3H), 1.38 (dd, J = 9.7, 5.2 Hz, 1H), 0.79-0.87 (m, 1H), 0.56-0.65 (m, 2H), 0.43-0.51 (m, 2H) | (1S,5S,6S)-3-amino-5-(5-(((5-chloro-2-pyridinyl)carbonyl)amino)-2-fluorophenyl)-N-cyclopropyl-5-methyl-2-thia-4-azabicyclo[4.1.0]hept-3-en-1-carboxamide |
| 795 | ¹H NMR (DMSO-d6) d: 10.43 (br. s., 1H), 8.90 (s, 1H), 8.48 (s, 1H), 8.00 (d, J = 4.9 Hz, 1H), 7.78 (br. s., 1H), 7.64 (br. s., 1H), 7.16 (br. s., 1H), 6.07 (br. s., 1H), 5.14 (d, J = 2.3 Hz, 2H), 3.64 (t, J = 2.3 Hz, 1H), 0.83 (br. s., 1H), 2.61-2.72 (m, 1H), 2.15 (t, J = 8.4 Hz, 1H), 1.63 (s, 3H), 1.41 (dd, J = 9.7, 5.4 Hz, 1H), 0.84 (t, J = 6.0 Hz, 1H), 0.60 (d, J = 5.1 Hz, 2H), 0.39-0.51 (m, 2H) | (1S,5S,6S)-3-amino-N-cyclopropyl-5-(2-fluoro-5-(((5-(2-propyn-1-yloxy)-2-pyrazinyl)carbonyl)amino)phenyl)-5-methyl-2-thia-4-azabicyclo[4.1.0]hept-3-en-1-carboxamide |
| 803 | ¹H NMR (400 MHz, DMSO-d₆) δ 10.58 (br., 1H), 8.35 (s, 1H), 8.19 (s, 1H), 7.93 (ddd, J = 2.45, 6.70, 12.37 Hz, 1H), 7.74 (d, J = 6.06 Hz, 1H), 7.29 (s, 1H), 6.12 (s, 2H), 5.59 (s, 2H), 4.40-4.55 (m, 2H), 2.74 (s, 3H), 1.80 (m, 1H), 1.61 (s, 3H), 1.03 (dd, J = 5.48, 9.39 Hz, 1H), 0.69 (q, J = 5.35 Hz, 1H). ¹⁹F NMR (376 MHz, DMSO-d₆) δ −138.40 (d, J = 22.54 Hz, 1F), −143.92 (d, J = 22.55 Hz,, 1F), −211.59 (s, 1F). | N-(3-((1S,5S,6S)-3-amino-1-(fluoromethyl)-5-methyl-2-thia-4-azabicyclo[4.1.0]hept-3-en-5-yl)-4,5-difluorophenyl)-3-methyl-5-(1,3-oxazol-2-ylmethoxy)-2-pyrazinecarboxamide |
| 804 | ¹H NMR (400 MHz, DMSO-d₆) δ 10.78 (br., 1H), 8.80 (s, 1H), 8.22 (m, 1H), 8.17 (m, 1H), 7.96 (m, 1H), 7.83 (m, 1H), 6.30 (s, 2H), 5.81-6.09 (m, 1H), 1.91 (m, 1H), 1.66 (s, 3H), 1.34 (m, 1H), 0.78 (m, 1H). ¹⁹F NMR (376 MHz, CHLOROFORM-d) δ −115.56 (d, ¹J = 273.96 Hz, 1F), −118.27 (d, ¹J = 273.77 Hz, 1F), −140.28 (d, ²J = 22.54 Hz, 1F), −155.35 (d, ²J = 22.64 Hz, 1F). | N-(3-((1S,5S,6S)-3-amino-1-(difluoromethyl)-5-methyl-2-thia-4-azabicyclo[4.1.0]hept-3-en-5-yl)-4,5-difluorophenyl)-5-chloro-2-pyridinecarboxamide |
| 807 | ¹H NMR (400 MHz, DMSO-d₆) δ 10.65 (br., 1H), 8.91 (d, J = 1.17 Hz, 1H), 8.50 (d, J = 1.17 Hz, 1H), 7.93 (m, 1H), 7.83 (d, J = 5.87 Hz, 1H), 6.29 (br., 2H), 5.75-6.09 (m, 1H), 5.16 (d, J = 2.35 Hz, 2H), 3.66 (t, J = 2.35 Hz, 1H), 1.91 (m, 1H), 1.66 (s, 3H), 1.34 (m, 1H), 0.77 (m, 1H). ¹⁹F NMR (377 MHz, DMSO-d₆) δ −115.61 (d, ¹J = 273.96 Hz, 1F), −118.23 (d, ¹J = 273.90 Hz, 1F), −138.27 (d, ²J = 22.55 Hz, 1F), −143.09 (d, ²J = 22.55 Hz, 1F). | N-(3-((1S,5S,6S)-3-amino-1-(difluoromethyl)-5-methyl-2-thia-4-azabicyclo[4.1.0]hept-3-en-5-yl)-4,5-difluorophenyl)-5-(2-propyn-1-yloxy)-2-pyrazinecarboxamide |
| 811 | ¹H NMR (400 MHz, DMSO-d₆) δ 10.64 (br., 1H), 8.89 (d, J = 1.17 Hz, 1H), 8.54 (d, J = 1.17 Hz, 1H), 8.20 (d, J = 0.78 Hz, 1H), 7.81-8.01 (m, 2H), 7.30 (s, 1H), 6.11 (br., 2H), 5.62 (s, 2H), 4.23-4.77 (m, 2H), 1.80 (m, 1H), 1.62 (s, 3H), 1.04 (dd, J = 5.48, 9.39 Hz, 1H), 0.63-0.76 (m, 1H). ¹⁹F NMR (376 MHz, DMSO-d₆) δ −138.46 (d, J = 22.55 Hz, 1F), −143.62 (d, J = 22.54 Hz, 1F), −211.59 (s, 1F). | N-(3-((1S,5S,6S)-3-amino-1-(fluoromethyl)-5-methyl-2-thia-4-azabicyclo[4.1.0]hept-3-en-5-yl)-4,5-difluorophenyl)-5-(1,3-oxazol-2-ylmethoxy)-2-pyrazinecarboxamide |
| 814 | ¹H NMR (400 MHz, DMSO-d₆) δ 10.69 (s, 1H), 8.92 (d, J = 1.17 Hz, 1H), 8.62 (d, J = 1.37 Hz, 1H), 7.73-8.02 (m, 2H), 6.11 (s, 2H), 5.17 (q, J = 8.93 Hz, 2H), 4.11-4.73 (m, 2H), 1.79 (m, 1H), 1.62 (s, 3H), 1.04 (m, 1H), 0.71 (m, 1H). ¹⁹F NMR (376 MHz, DMSO-d₆) δ −72.13 (s, 3F), −138.44 (d, J = 22.54 Hz, 1F), −143.52 (d, J = 22.54 Hz, 1F), −211.59 (s, 1F). | N-(3-((1S,5S,6S)-3-amino-1-(fluoromethyl)-5-methyl-2-thia-4-azabicyclo[4.1.0]hept-3-en-5-yl)-4,5-difluorophenyl)-5-(2,2,2-trifluoroethoxy)-2-pyrazinecarboxamide |
| 815 | ¹H NMR (400 MHz, DMSO-d₆) δ 10.67 (br., 1H), 8.92 (d, J = 0.98 Hz, 1H), 8.62 (m, 1H), 7.95 (m, 2H), 5.99 (s, 2H), 5.17 (q, J = 9.00 Hz, 2H), 3.56 (d, J = 11.15 Hz, 1H), 3.36 (d, J = 11.15 Hz, 1H), 3.31 (s, 3H), 1.61 (m, 1H), 1.59 (s, 3H), 0.90 (m, 1H), 0.64 (m, 1H). ¹⁹F NMR (376 MHz, DMSO-d₆) δ −72.13 (s, 3F), −138.52 (d, J = 22.54 Hz, 1F), −143.68 (d, J = 22.55 Hz, 1F). | N-(3-((1S,5S,6S)-3-amino-1-(methoxymethyl)-5-methyl-2-thia-4-azabicyclo[4.1.0]hept-3-en-5-yl)-4,5-difluorophenyl)-5-(2,2,2-trifluoroethoxy)-2-pyrazinecarboxamide |
| 818 | ¹H NMR (400 MHz, DMSO-d₆) δ 10.55 (br., 1H), 8.78 (d, J = 2.35 Hz, 1H), 8.08-8.28 (m, 2H), | N-(3-((1S,5S,6S)-3-amino-1-(difluoromethyl)-5-methyl-2-thia- |

TABLE 4'-continued

| Ex. No. | ¹H-NMR | Chemical Name |
|---|---|---|
|  | 7.95 (dd, J = 2.64, 7.34 Hz, 1H), 7.80 (td, J = 3.52, 8.61 Hz, 1H), 7.17 (dd, J = 8.70, 11.84 Hz, 1H), 6.25 (br., 2H), 5.77-6.11 (m, 1H), 1.91 (m, 1H), 1.64 (s, 3H), 1.30 (m, 1H), 0.72 (m, 1H). ¹⁹F NMR (376 MHz, DMSO-d₆) δ −115.55 (d, ¹J = 273.77 Hz, 1F), −116.11 (s, 1F), −118.80 (d, ¹J = 273.77 Hz, 1F). | 4-azabicyclo[4.1.0]hept-3-en-5-yl)-4-fluorophenyl)-5-chloro-2-pyridinecarboxamide |
| 820 | ¹H NMR (400 MHz, DMSO-d₆) δ 10.44 (br., 1H), 8.91 (d, J = 1.37 Hz, 1H), 8.49 (d, J = 1.17 Hz, 1H), 7.97 (dd, J = 2.74, 7.24 Hz, 1H), 7.78 (td, J = 3.72, 8.22 Hz, 1H), 7.09 (m, 1H), 6.26 (br., 2H), 5.79-6.14 (m, 1H), 5.15 (d, J = 2.54 Hz, 2H), 3.65 (s, 1H), 1.93 (t, J = 8.22 Hz, 1H), 1.65 (s, 3H), 1.30 (m, 1H), 0.74 (m, 1H). ¹⁹F NMR (377 MHz, DMSO-d₆) δ −115.51 (d, ¹J = 273.97 Hz, 1F), −116.19 (s, 1F), −118.54 (d, ¹J = 273.97 Hz, 1F). | N-(3-((1S,5S,6S)-3-amino-1-(difluoromethyl)-5-methyl-2-thia-4-azabicyclo[4.1.0]hept-3-en-5-yl)-4-fluorophenyl)-5-(2-propyn-1-yloxy)-2-pyrazinecarboxamide |
| 821 | ¹H NMR (400 MHz, DMSO-d₆) δ 10.54 (br., 1H), 8.78 (d, J = 1.76 Hz, 1H), 8.10-8.28 (m, 2H), 7.97-8.07 (m, 1H), 7.80 (td, J = 3.67, 8.31 Hz, 1H), 7.16 (dd, J = 8.80, 12.13 Hz, 1H), 6.08 (br., 2H), 4.30-4.65 (m, 2H), 1.82 (m, 1H), 1.60 (s, 3H), 0.99 (m, 1H), 0.68 (q, J = 5.28 Hz, 1H). ¹⁹F NMR (376 MHz, DMSO-d₆) δ −116.55 (s, 1F), −211.46 (s, 1F). | N-(3-((1S,5S,6S)-3-amino-1-(fluoromethyl)-5-methyl-2-thia-4-azabicyclo[4.1.0]hept-3-en-5-yl)-4-fluorophenyl)-5-chloro-2-pyridinecarboxamide |
| 822 | ¹H NMR (400 MHz, DMSO-d6) δ 10.43 (br., 1H), 8.91 (d, J = 1.17 Hz, 1H), 8.49 (d, J = 1.37 Hz, 1H), 8.04 (dd, J = 2.74, 7.43 Hz, 1H), 7.78 (td, J = 3.47, 8.51 Hz, 1H), 7.16 (dd, J = 8.80, 11.93 Hz, 1H), 6.08 (br., 2H), 5.15 (d, J = 2.35 Hz, 2H), 4.34-4.65 (m, 2H), 3.65 (t, J = 2.45 Hz, 1H), 1.78-1.87 (m, 1H), 1.61 (s, 3H), 1.00 (m, 1H), 0.69 (m, 1H). | N-(3-((1S,5S,6S)-3-amino-1-(fluoromethyl)-5-methyl-2-thia-4-azabicyclo[4.1.0]hept-3-en-5-yl)-4-fluorophenyl)-5-(2-propyn-1-yloxy)-2-pyrazinecarboxamide |
| 826 | ¹H NMR (400 MHz, DMSO-d₆) δ 10.49 (br., 1H), 8.93 (d, J = 1.37 Hz, 1H), 8.63 (d, J = 1.17 Hz, 1H), 8.05 (dd, J = 2.74, 7.43 Hz, 1H), 7.79 (td, J = 3.72, 8.22 Hz, 1H), 7.17 (dd, J = 8.80, 12.13 Hz, 1H), 6.08 (br., 2H), 5.18 (q, J = 8.80 Hz, 2H), 4.33-4.66 (m, 2H), 1.83 (m, 1H), 1.61 (s, 3H), 1.00 (m, 1H), 0.68 (m, 1H). ¹⁹F NMR (377 MHz, DMSO-d₆) δ −72.12 (s, 3F), −116.54 (s, 1F), −211.45 (s, 1F). | N-(3-((1S,5S,6S)-3-amino-1-(fluoromethyl)-5-methyl-2-thia-4-azabicyclo[4.1.0]hept-3-en-5-yl)-4-fluorophenyl)-5-(2,2,2-trifluoroethoxy)-2-pyrazinecarboxamide |
| 829 | ¹H NMR (400 MHz, DMSO-d₆) δ 10.37 (br., 1H), 8.29 (s, 1H), 7.90-7.99 (m, 1H), 7.63-7.85 (m, 1H), 7.14 (dd, J = 8.80, 12.13 Hz, 1H), 6.08 (br., 2H), 5.11 (d, J = 2.35 Hz, 2H), 4.25-4.64 (m, 2H), 3.62 (t, J = 2.35 Hz, 1H), 2.76 (s, 3H), 1.82 (m, 1H), 1.60 (s, 3H), 0.99 (m, 1H), 0.66 (m, 1H). ¹⁹F NMR (376 MHz, DMSO-d₆) δ −116.96 (s, 1F), −211.47 (s, 1F). | N-(3-((1S,5S,6S)-3-amino-1-(fluoromethyl)-5-methyl-2-thia-4-azabicyclo[4.1.0]hept-3-en-5-yl)-4-fluorophenyl)-3-methyl-5-(2-propyn-1-yloxy)-2-pyrazinecarboxamide |
| 830 | ¹H NMR (400 MHz, DMSO-d₆) δ 10.39 (br., 1H), 8.30 (s, 1H), 7.71-7.81 (m, 2H), 7.17 (dd, J = 8.71, 11.84 Hz, 1H), 6.26 (br., 2H), 5.79-6.14 (m, 1H), 5.12 (d, J = 2.35 Hz, 2H), 3.63 (t, J = 2.35 Hz, 1H), 2.76 (s, 3H), 1.90 (m, 1H), 1.65 (s, 3H), 1.29 (m, 1H), 0.72 (m, 1H). ¹⁹F NMR (377 MHz, DMSO-d₆) δ −115.05 (d, ¹J = 273.09 Hz, 1F), −116.49 (s, 1F), −118.18 (d, ¹J = 273.09 Hz, 1F). | N-(3-((1S,5S,6S)-3-amino-1-(difluoromethyl)-5-methyl-2-thia-4-azabicyclo[4.1.0]hept-3-en-5-yl)-4-fluorophenyl)-3-methyl-5-(2-propyn-1-yloxy)-2-pyrazinecarboxamide |
| 831 | ¹H NMR (400 MHz, DMSO-d₆) δ 10.46 (br., 1H), 8.91 (d, J = 1.17 Hz, 1H), 8.61 (d, J = 1.17 Hz, 1H), 8.04 (dd, J = 2.74, 7.24 Hz, 1H), 7.76 (m, 1H), 7.15 (m, 1H), 5.95 (br., 2H), 5.15 (m, 2H), 3.56 (d, J = 10.76 Hz, 1H), 3.35 (d, J = 10.95 Hz, 2H), 3.32 (s, 3H), 1.67 (m, 1H), 1.60 (s, 3H), 0.87 (m, 1H), 0.62 (m, 1H). ¹⁹F NMR (376 MHz, DMSO-d₆) δ −76.94 (s, 3F), −116.69 (s, 1F). | N-(3-((1S,5S,6S)-3-amino-1-(methoxymethyl)-5-methyl-2-thia-4-azabicyclo[4.1.0]hept-3-en-5-yl)-4-fluorophenyl)-5-(2,2,2-trifluoroethoxy)-2-pyrazinecarboxamide |
| 832 | ¹H NMR (400 MHz, DMSO-d₆) δ 10.37 (br., 1H), 8.30 (s, 1H), 7.92 (dd, J = 2.74, 7.24 Hz, 1H), 7.78 (m, 1H), 7.14 (dd, J = 8.90, 12.03 Hz, 1H), 5.97 (br., 2H), 5.13 (d, J = 2.35 Hz, 2H), 3.63 (t, J = 2.35 Hz, 1H), 3.57 (d, J = 10.76 Hz, 1H), 3.36 (d, J = 11.15 Hz, 1H), 3.33 (s, 3H), 2.77 (s, 3H), 1.69 (m, 1H), 1.60 (s, 3H), 0.85 (dd, J = 5.28, 9.19 Hz, 1H), 0.61 (t, J = 5.77 Hz, 1H). ¹⁹F NMR (377 MHz, DMSO-d₆) δ −117.09 (s, 1F). | N-(3-((1S,5S,6S)-3-amino-1-(methoxymethyl)-5-methyl-2-thia-4-azabicyclo[4.1.0]hept-3-en-5-yl)-4-fluorophenyl)-3-methyl-5-(2-propyn-1-yloxy)-2-pyrazinecarboxamide |
| 833 | ¹H NMR (400 MHz, DMSO-d₆) δ 10.54 (br., 1H), 8.79 (d, J = 2.35 Hz, 1H), 8.13-8.28 (m, 2H), 8.04 (dd, J = 2.84, 7.34 Hz, 1H), 7.81 (td, J = 3.67, 8.31 Hz, 1H), 7.15 (m, 1H), 5.98 (br., 2H), 3.58 (d, J = 10.76 Hz, 1H), 3.40 (d, J = 10.76 Hz, 1H), 3.35 (s, 3H), 1.68 (t, J = 7.73 Hz, 1H), 1.61 (s, 3H), 0.86 (dd, J = 5.09, 8.61 Hz, 1H), 0.63 (t, J = 5.67 Hz, 1H). ¹⁹F NMR (377 MHz, DMSO-d₆) δ −116.67 (s, 1F). | N-(3-((1S,5S,6S)-3-amino-1-(methoxymethyl)-5-methyl-2-thia-4-azabicyclo[4.1.0]hept-3-en-5-yl)-4-fluorophenyl)-5-chloro-2-pyridinecarboxamide |

TABLE 4'-continued

| Ex. No. | $^1$H-NMR | Chemical Name |
|---|---|---|
| 834 | $^1$H NMR (400 MHz, DMSO-d$_6$) δ 10.41 (br., 1H), 8.91 (d, J = 1.37 Hz, 1H), 8.49 (d, J = 1.17 Hz, 1H), 8.05 (dd, J = 2.74, 7.43 Hz, 1H), 7.78 (td, J = 3.52, 8.41 Hz, 1H), 7.15 (dd, J = 8.80, 11.93 Hz, 1H), 5.97 (br., 2H), 5.15 (d, J = 2.35 Hz, 2H), 3.67 (m, 1H), 3.57 (d, J = 10.76 Hz, 1H), 3.42 (d, J = 10.76 Hz, 1H), 3.4 (s, 3H), 1.68 (m, 1H), 1.61 (s, 3H), 0.85 (m, 1H), 0.67 (m, 1H). $^{19}$F NMR (377 MHz, DMSO-d$_6$) δ −116.78 (s, 1F). | N-(3-((1S,5S,6S)-3-amino-1-(methoxymethyl)-5-methyl-2-thia-4-azabicyclo[4.1.0]hept-3-en-5-yl)-4-fluorophenyl)-5-(2-propyn-1-yloxy)-2-pyrazinecarboxamide |
| 835 | $^1$H NMR (400 MHz, DMSO-d$_6$) δ 10.38 (br., 1H), 8.35 (s, 1H), 8.20 (d, J = 0.78 Hz, 1H), 7.92 (dd, J = 2.74, 7.43 Hz, 1H), 7.78 (td, J = 3.50, 8.66 Hz, 1H), 7.30 (m, 1H), 7.10 (m, 1H), 5.97 (br., 2H), 5.60 (s, 2H), 3.56 (d, J = 10.70 Hz, 1H), 3.37 (d, J = 10.70 Hz, 1H), 3.31 (s, 3H), 2.75 (s, 3H), 1.70 (m, 1H), 1.60 (s, 3H), 0.80 (m, 1H), 0.60 (m, 1H). $^{19}$F NMR (377 MHz, DMSO-d$_6$) δ −113.44 (s, 1F). | N-(3-((1S,5S,6S)-3-amino-1-(methoxymethyl)-5-methyl-2-thia-4-azabicyclo[4.1.0]hept-3-en-5-yl)-4-fluorophenyl)-3-methyl-5-(1,3-oxazol-2-ylmethoxy)-2-pyrazinecarboxamide |
| 836 | $^{19}$F NMR (376 MHz, DMSO-d$_6$) δ −115.19 (d, J = 273.96 Hz, 1F), −116.49 (s, 1F), −118.19 (d, J = 273.96 Hz, 1F). $^1$H NMR (400 MHz, DMSO-d$_6$) δ 10.39 (br., 1H), 8.34 (s, 1H), 8.19 (m, 1H), 7.74-7.86 (m, 2H), 7.29 (m, 1H), 7.15 (dd, J = 8.71, 11.84 Hz, 1H), 6.25 (br., 2H), 5.69-6.11 (m, 1H), 5.58 (s, 2H), 2.73 (s, 3H), 1.90 (m, 1H), 1.63 (s, 3H), 1.27 (m, 1H), 0.68 (m, 1H). | N-(3-((1S,5S,6S)-3-amino-1-(difluoromethyl)-5-methyl-2-thia-4-azabicyclo[4.1.0]hept-3-en-5-yl)-4-fluorophenyl)-3-methyl-5-(1,3-oxazol-2-ylmethoxy)-2-pyrazinecarboxamide |
| 837 | $^1$H NMR (400 MHz, DMSO-d$_6$) δ 10.38 (br., 1H), 8.34 (s, 1H), 8.19 (s, 1H), 7.91 (dd, J = 2.74, 7.43 Hz, 1H), 7.78 (td, J = 3.64, 8.17 Hz, 1H), 7.29 (s, 1H), 7.14 (dd, J = 8.80, 12.13 Hz, 1H), 6.08 (br., 2H), 5.59 (s, 2H), 4.35-4.64 (m, 2H), 2.74 (s, 3H), 1.80 (m, 1H), 1.60 (s, 3H), 0.99 (dd, J = 5.38, 9.29 Hz, 1H), 0.66 (q, J = 5.28 Hz, 1H). $^{19}$F NMR (376 MHz, DMSO-d$_6$) δ −116.92 (s, 1F), −211.46 (s, 1F). | N-(3-((1S,5S,6S)-3-amino-1-(fluoromethyl)-5-methyl-2-thia-4-azabicyclo[4.1.0]hept-3-en-5-yl)-4-fluorophenyl)-3-methyl-5-(1,3-oxazol-2-ylmethoxy)-2-pyrazinecarboxamide |
| 838 | $^1$H NMR (400 MHz, DMSO-d$_6$) δ 10.62 (br., 1H), 8.91 (d, J = 0.98 Hz, 1H), 8.48 (d, J = 0.98 Hz, 1H), 7.79-7.97 (m, 2H), 6.11 (br., 2H), 4.32-4.63 (m, 2H), 3.63 (s, 1H), 1.78 (m, 1H), 1.62 (s, 3H), 1.06 (m, 1H), 0.73 (m, 1H). $^{19}$F NMR (376 MHz, DMSO-d$_6$) δ −138.46 (d, J = 22.55 Hz, 1F), −143.63 (d, J = 22.55 Hz, 1F), −211.58 (s, 1F). | N-(3-((1S,5S,6S)-3-amino-1-(fluoromethyl)-5-methyl-2-thia-4-azabicyclo[4.1.0]hept-3-en-5-yl)-4,5-difluorophenyl)-5-(1,1-dideuterium-prop-2-yn-1-yloxy)-2-pyrazinecarboxamide |
| 839 | $^{19}$F NMR (376 MHz, DMSO-d$_6$) δ −115.45 (d, $^1$J = 273.96 Hz, 1F), −118.24 (d, $^1$J = 273.96 Hz, 1F), −138.30 (d, $^2$J = 22.54 Hz, 1F), −143.10 (d, $^2$J = 22.54 Hz, 1F). $^1$H NMR (400 MHz, DMSO-d$_6$) δ 10.64 (br., 1H), 8.90 (d, J = 1.17 Hz, 1H), 8.48 (d, J = 1.17 Hz, 1H), 7.92 (ddd, J = 2.54, 6.85, 12.32 Hz, 1H), 7.82 (d, J = 5.87 Hz, 1H), 6.28 (br., 2H), 5.68-6.13 (m, 1H), 3.63 (s, 1H), 1.90 (m, 1H), 1.65 (s, 3H), 1.33 (m, 1H), 0.76 (m, 1H). | N-(3-((1S,5S,6S)-3-amino-1-(difluoromethyl)-5-methyl-2-thia-4-azabicyclo[4.1.0]hept-3-en-5-yl)-4,5-difluorophenyl)-5-(1,1-dideuterium-prop-2-yn-1-yloxy)-2-pyrazinecarboxamide |
| 840 | $^{19}$F NMR (376 MHz, DMSO-d$_6$) δ −138.54 (d, J = 22.54 Hz, 1F), −143.79 (d, J = 22.54 Hz, 1F). $^1$H NMR (400 MHz, DMSO-d$_6$) δ 10.61 (s, 1H), 8.90 (d, J = 0.98 Hz, 1H), 8.48 (d, J = 1.17 Hz, 1H), 7.70-7.99 (m, 2H), 5.99 (br., 2H), 3.63 (s, 1H), 3.57 (d, J = 10.95 Hz, 1H), 3.36 (d, J = 10.95 Hz, 1H), 3.32 (s, 3H), 1.63 (m, 1H), 1.61 (s, 3H), 0.90 (m, 1H), 0.65 (m, 1H). | N-(3-((1S,5S,6S)-3-amino-1-(methoxy)-5-methyl-2-thia-4-azabicyclo[4.1.0]hept-3-en-5-yl)-4,5-difluorophenyl)-5-(1,1-dideuterium-prop-2-yn-1-yloxy)pyrazine-2-carboxamide |
| 860 | $^1$H NMR (400 MHz, CHLOROFORM-d) δ 9.60-9.83 (m, 1H), 8.08 (s, 1H), 8.03 (ddd, J = 2.74, 6.85, 11.93 Hz, 1H), 7.71 (d, J = 0.78 Hz, 1H), 7.12-7.21 (m, 2H), 5.42-5.96 (m, 1H), 5.57 (s, 2H), 2.93 (s, 3H), 1.99 (dd, J = 7.34, 9.68 Hz, 1H), 1.78 (s, 3H), 1.35 (dd, J = 6.26, 9.98 Hz, 1H), 0.85 (dt, J = 3.03, 6.60 Hz, 1H) | N-(3-((1S,5S,6S)-3-amino-1-(difluoromethyl)-5-methyl-2-thia-4-azabicyclo[4.1.0]hept-3-en-5-yl)-4,5-difluorophenyl)-3-methyl-5-(1,3-oxazol-2-ylmethoxy)-2-pyrazinecarboxamide |
| 861 | $^1$H NMR (300 MHz, CHLOROFORM-d) δ 9.75 (s, 1H), 8.05 (s, 1H), 7.97-8.14 (m, 1H), 7.17 (td, J = 2.41, 5.70 Hz, 1H), 5.42-5.96 (m, 1H), 5.08 (d, J = 2.34 Hz, 2H), 2.95 (s, 3H), 2.54 (t, J = 2.41 Hz, 1H), 1.95-2.06 (m, 1H), 1.78 (d, J = 1.02 Hz, 3H), 1.35 (dd, J = 6.28, 9.79 Hz, 1H), 0.80-0.91 (m, 1H) | N-(3-((1S,5S,6S)-3-amino-1-(difluoromethyl)-5-methyl-2-thia-4-azabicyclo[4.1.0]hept-3-en-5-yl)-4,5-difluorophenyl)-3-methyl-5-(2-propyn-1-yloxy)-2-pyrazinecarboxamide |
| 862 | $^1$H NMR (300 MHz, CHLOROFORM-d) δ 9.81 (s, 1H), 8.02-8.14 (m, 2H), 7.21-7.30 (m, 1H), 5.08 (d, J = 2.48 Hz, 2H), 3.64 (d, J = 10.52 Hz, 1H), 3.41 (s, 3H), 3.35 (d, J = 10.67 Hz, 1H), 2.95 (s, 3H), 2.53 (t, J = 2.41 Hz, 1H), 1.77-1.87 (m, 1H), 1.75 (d, J = 1.17 Hz, 3H), 0.95 (dd, J = 5.85, 9.35 Hz, 1H), 0.77-0.84 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-(2-propyn-1-yloxy)-2-pyrazinecarboxamide |

TABLE 4'-continued

| Ex. No. | ¹H-NMR | Chemical Name |
|---|---|---|
| 863 | ¹H NMR (400 MHz, CHLOROFORM-d) δ 9.80 (s, 1H), 8.10 (s, 1H), 8.01-8.08 (m, 1H), 7.71 (d, J = 0.78 Hz, 1H), 7.30 (td, J = 2.37, 5.62 Hz, 1H), 7.18 (s, 1H), 5.57 (s, 2H), 3.65 (d, J = 10.56 Hz, 1H), 3.41 (s, 3H), 3.35 (d, J = 10.76 Hz, 1H), 2.94 (s, 3H), 1.80 (ddd, J = 1.17, 6.65, 9.39 Hz, 1H), 1.73 (d, J = 0.98 Hz, 3H), 0.91 (dd, J = 5.97, 9.49 Hz, 1H), 0.76-0.84 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-(1,3-oxazol-2-ylmethoxy)-2-pyrazinecarboxamide |
| 864 | ¹H NMR (300 MHz, CHLOROFORM-d) δ 9.79 (s, 1H), 8.00-8.19 (m, 2H), 7.64 (d, J = 0.88 Hz, 1H), 7.30 (td, J = 2.43, 5.52 Hz, 1H), 7.12 (d, J = 0.73 Hz, 1H), 6.45 (q, J = 6.72 Hz, 1H), 3.66 (d, J = 10.38 Hz, 1H), 3.41 (s, 3H), 3.35 (d, J = 10.67 Hz, 1H), 2.90 (s, 3H), 1.82 (d, J = 6.72 Hz, 4H), 1.72 (d, J = 1.02 Hz, 3H), 0.90 (dd, J = 5.85, 9.35 Hz, 1H), 0.75-0.84 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-((1S)-1-(1,3-oxazol-2-yl)ethoxy)-2-pyrazinecarboxamide |
| 913 | ¹H NMR (400 MHz, DMSO-d6) δ 10.62 (s, 1H), 8.90 (d, J = 1.17 Hz, 1H), 8.49 (d, J = 1.17 Hz, 1H), 7.90 (ddd, J = 2.54, 6.85, 12.52 Hz, 1H), 7.82 (d, J = 5.87 Hz, 1H), 6.24 (s, 2H), 5.14 (d, J = 2.35 Hz, 2H), 3.59-3.66 (m, 1H), 3.06 (br. s., 6H), 2.04 (t, J = 8.31 Hz, 1H), 1.69 (s, 3H), 1.32 (dd, J = 5.48, 9.59 Hz, 1H), 0.80 (t, J = 6.26 Hz, 1H) | (1S,5S,6S)-3-amino-5-(2,3-difluoro-5-(((5-(2-propyn-1-yloxy)-2-pyrazinyl)carbonyl)amino)phenyl)-N,N,5-trimethyl-2-thia-4-azabicyclo[4.1.0]hept-3-ene-1-carboxamide |
| 914 | ¹H NMR (400 MHz, DMSO-d6) δ 10.64 (s, 1H), 8.91 (d, J = 1.17 Hz, 1H), 8.49 (d, J = 1.37 Hz, 1H), 7.90-7.96 (m, 1H), 7.88 (d, J = 6.09 Hz, 1H), 7.68 (q, J = 4.17 Hz, 1H), 6.14 (s, 2H), 5.14 (d, J = 2.35 Hz, 2H), 3.65 (t, J = 2.35 Hz, 1H), 2.62 (d, J = 4.30 Hz, 3H), 2.09-2.16 (m, 1H), 1.63 (s, 3H), 1.43 (dd, J = 5.09, 9.59 Hz, 1H), 0.81-0.90 (m, 1H) | (1S,5S,6S)-3-amino-5-(2,3-difluoro-5-(((5-(2-propyn-1-yloxy)-2-pyrazinyl)carbonyl)amino)phenyl)-N,5-dimethyl-2-thia-4-azabicyclo[4.1.0]hept-3-ene-1-carboxamide |
| 919 | ¹H NMR (400 MHz, DMSO-d6) δ 10.64 (s, 1H), 8.91 (d, J = 1.17 Hz, 1H), 8.49 (d, J = 1.37 Hz, 1H), 7.87-7.97 (m, 2H), 7.28 (br. s., 1H), 7.21 (br. s., 1H), 6.10 (br. s., 2H), 5.15 (d, J = 2.54 Hz, 2H), 3.65 (t, J = 2.45 Hz, 1H), 2.16 (t, J = 8.51 Hz, 1H), 1.63 (s, 3H), 1.42 (dd, J = 4.99, 9.49 Hz, 1H), 0.89 (t, J = 6.06 Hz, 1H) | (1S,5S,6S)-3-amino-5-(2,3-difluoro-5-(((5-(2-propyn-1-yloxy)-2-pyrazinyl)carbonyl)amino)phenyl)-5-methyl-2-thia-4-azabicyclo[4.1.0]hept-3-ene-1-carboxamide |
| 922 | ¹H NMR (400 MHz, DMSO-d6) δ 10.69 (s, 1H), 8.93 (d, J = 1.37 Hz, 1H), 8.58 (d, J = 1.17 Hz, 1H), 7.92 (ddd, J = 2.64, 6.75, 12.13 Hz, 1H), 7.84 (d, J = 5.87 Hz, 1H), 6.57-6.90 (m, 1H), 6.25 (br. s., 2H), 5.05 (t, J = 14.18 Hz, 2H), 3.07 (br. s., 3H), 2.94 (br. s., 3H), 2.05 (t, J = 8.22 Hz, 1H), 1.71 (s, 3H), 1.34 (dd, J = 5.58, 9.49 Hz, 1H), 0.81 (t, J = 6.16 Hz, 1H) | (1S,5S,6S)-3-amino-5-(2,3-difluoro-5-(((5-(2,2,3,3-tetrafluoropropoxy)-2-pyrazinyl)carbonyl)amino)phenyl)-N,N,5-trimethyl-2-thia-4-azabicyclo[4.1.0]hept-3-ene-1-carboxamide |
| 924 | ¹H NMR (400 ¹H NMR (400 MHz, DMSO-d6) δ 10.66 (s, 1H), 8.90 (d, J = 1.37 Hz, 1H), 8.48 (d, J = 1.37 Hz, 1H), 7.91-7.94 (m, 1H), 7.75 (d, J = 5.67 Hz, 1H), 6.54 (s, 2H), 5.14 (d, J = 2.35 Hz, 2H), 3.64 (t, J = 2.45 Hz, 1H), 2.38 (dd, J = 7.82, 9.59 Hz, 1H), 1.85-1.93 (m, 1H), 1.75 (s, 3H), 1.03-1.10 (m, 1H) | N-(3-((1S,5S,6S)-3-amino-1-cyano-5-methyl-2-thia-4-azabicyclo[4.1.0]hept-3-en-5-yl)-4,5-difluorophenyl)-5-(2-propyn-1-yloxy)-2-pyrazinecarboxamide |
| 926 | ¹H NMR (400 MHz, DMSO-d6) δ 10.69 (s, 1H), 8.93 (d, J = 1.17 Hz, 1H), 8.63 (d, J = 1.37 Hz, 1H), 7.92 (ddd, J = 2.64, 6.80, 12.28 Hz, 1H), 7.84 (d, J = 5.87 Hz, 1H), 6.25 (s, 2H), 5.18 (q, J = 8.80 Hz, 2H), 3.07 (br. s., 3H), 2.92 (br. s., 3H), 2.05 (t, J = 8.31 Hz, 1H), 1.71 (s, 3H), 1.34 (dd, J = 5.38, 9.49 Hz, 1H), 0.77-0.85 (m, 1H) | (1S,5S,6S)-3-amino-5-(2,3-difluoro-5-(((5-(2,2,2-trifluoroethoxy)-2-pyrazinyl)carbonyl)amino)phenyl)-N,N,5-trimethyl-2-thia-4-azabicyclo[4.1.0]hept-3-ene-1-carboxamide |
| 927 | ¹H NMR (400 MHz, DMSO-d6) δ 10.47 (s, 1H), 8.90 (d, J = 1.37 Hz, 1H), 8.49 (d, J = 1.37 Hz, 1H), 7.90 (dd, J = 2.64, 7.34 Hz, 1H), 7.77-7.82 (m, 1H), 7.19 (dd, J = 8.80, 11.74 Hz, 1H), 6.53 (s, 2H), 5.15 (d, J = 2.35 Hz, 2H), 3.65 (t, J = 2.45 Hz, 1H), 2.38 (dd, J = 7.92, 9.68 Hz, 1H), 1.87 (dd, J = 5.87, 9.78 Hz, 1H), 1.75 (s, 3H), 1.03 (t, J = 6.55 Hz, 1H) | N-(3-((1S,5S,6S)-3-amino-1-cyano-5-methyl-2-thia-4-azabicyclo[4.1.0]hept-3-en-5-yl)-4-fluorophenyl)-5-(2-propyn-1-yloxy)-2-pyrazinecarboxamide |
| 929 | ¹H NMR (400 MHz, DMSO-d6) δ 10.60 (s, 1H), 8.79 (d, J = 5.87 Hz, 1H), 8.12-8.24 (m, 2H), 7.90 (dd, J = 2.74, 7.24 Hz, 1H), 7.80-7.86 (m, 1H), 7.20 (dd, J = 8.80, 11.74 Hz, 1H), 6.53 (s, 2H), 2.38 (dd, J = 7.92, 9.68 Hz, 1H), 1.87 (dd, J = 5.87, 9.78 Hz, 1H), 1.75 (s, 3H), 1.03 (t, J = 6.55 Hz, 1H) | N-(3-((1S,5S,6S)-3-amino-1-cyano-5-methyl-2-thia-4-azabicyclo[4.1.0]hept-3-en-5-yl)-4-fluorophenyl)-5-chloro 2-pyridinecarboxamide |
| 930 | ¹H NMR (400 MHz, DMSO-d6) δ 10.76 (s, 1H), 8.80 (s, 1H), 8.15-8.24 (m, 2H), 7.94 (ddd, J = 2.54, 6.80, 12.37 Hz, 1H), 7.83 (d, J = 5.58 Hz, 1H), 6.26 (br. s., 2H), 3.09 (br. s., 3H), 2.93 (br. s., 3H), 2.06 (t, J = 8.41 Hz, 1H), 1.71 (s, 3H), 1.34 (dd, J = 5.48, 9.59 Hz, 1H), 0.81 (t, J = 6.26 Hz, 1H) | (1S,5S,6S)-3-amino-5-(5-(((5-chloro-2-pyridinyl)carbonyl)amino)-2,3-difluorophenyl)-N,N,5-trimethyl-2-thia-4-azabicyclo[4.1.0]hept-3-ene-1-carboxamide |

TABLE 4'-continued

| Ex. No. | ¹H-NMR | Chemical Name |
|---|---|---|
| 932 | ¹H NMR (400 MHz, DMSO-d6) δ 10.81 (s, 1H), 8.80 (s, 1H), 8.19-8.24 (m, 1H), 8.14-8.19 (m, 1H), 7.97 (ddd, J = 2.54, 6.80, 12.37 Hz, 1H), 7.74-7.79 (m, 1H), 6.56 (s, 2H), 2.40 (dd, J = 7.82, 9.78 Hz, 1H), 1.90 (dd, J = 6.06, 9.78 Hz, 1H), 1.77 (s, 3H), 1.09 (t, J = 6.75 Hz, 1H). | N-(3-((1S,5S,6S)-3-amino-1-cyano-5-methyl-2-thia-4-azabicyclo[4.1.0]hept-3-en-5-yl)-4,5-difluorophenyl)-5-chloro-2-pyridinecarboxamide |
| 934 | ¹H NMR (400 MHz, DMSO-d6) δ 10.62 (s, 1H), 8.90 (d, J = 1.17 Hz, 1H), 8.48 (d, J = 1.37 Hz, 1H), 7.90 (ddd, J = 2.64, 6.75, 12.32 Hz, 1H), 7.78-7.82 (m, 1H), 6.24 (s, 2H), 5.14 (d, J = 2.35 Hz, 2H), 3.53-3.71 (m, 3H), 3.31 (bs, 2H), 2.00-2.08 (m, 1H), 1.87 (br. s., 2H), 1.81 (br. s., 2H), 1.70 (s, 3H), 1.34 (dd, J = 5.38, 9.49 Hz, 1H), 0.70-0.76 (m, 1H) | N-(3-((1S,5S,6S)-3-amino-5-methyl-1-(1-pyrrolidinylcarbonyl)-2-thia-4-azabicyclo[4.1.0]hept-3-en-5-yl)-4,5-difluorophenyl)-5-(2-propyn-1-yloxy)-2-pyrazinecarboxamide |
| 935 | ¹H NMR (400 MHz, DMSO-d6) δ 10.74 (s, 1H), 8.79 (d, J = 1.76 Hz, 1H), 8.13-8.23 (m, 2H), 7.92 (ddd, J = 2.54, 6.75, 12.42 Hz, 1H), 7.78-7.82 (m, 1H), 6.24 (s, 2H), 3.60 (br. s., 2H), 3.31 (s, 2H), 2.03-2.09 (m, 1H), 1.87 (br. s., 2H), 1.81 (br. s., 2H), 1.70 (s, 3H), 1.34 (dd, J = 5.48, 9.39 Hz, 1H), 0.71-0.76 (m, 1H) | N-(3-((1S,5S,6S)-3-amino-5-methyl-1-(1-pyrrolidinylcarbonyl)-2-thia-4-azabicyclo[4.1.0]hept-3-en-5-yl)-4,5-difluorophenyl)-5-chloro-2-pyridinecarboxamide |
| 940 | ¹H NMR (400 MHz, DMSO-d6) δ 10.72 (s, 1H), 8.92 (d, J = 1.17 Hz, 1H), 8.62 (d, J = 1.37 Hz, 1H), 7.94 (ddd, J = 2.64, 6.70, 12.37 Hz, 1H), 7.76 (d, J = 5.87 Hz, 1H), 6.54 (s, 2H), 5.17 (q, J = 9.00 Hz, 2H), 2.33-2.41 (m, 1H), 1.89 (dd, J = 5.87, 9.78 Hz, 1H), 1.75 (s, 3H), 1.07 (t, J = 6.85 Hz, 1H) | N-(3-((1S,5S,6S)-3-amino-1-cyano-5-methyl-2-thia-4-azabicyclo[4.1.0]hept-3-en-5-yl)-4,5-difluorophenyl)-5-(2,2,2-trifluoroethoxy)-2-pyrazinecarboxamide |

Method E: SNAr in 1,4-dioxane

Example 747

(1R,5S,6S)-5-(2,3-difluoro-5-((2-(oxazol-2-yl-methoxy)pyrido[3,4-b]pyrazin-5-yl)amino)phenyl)-5-methyl-1-(methylsulfonyl)-2-thia-4-azabicyclo[4.1.0]hept-3-en-3-amine

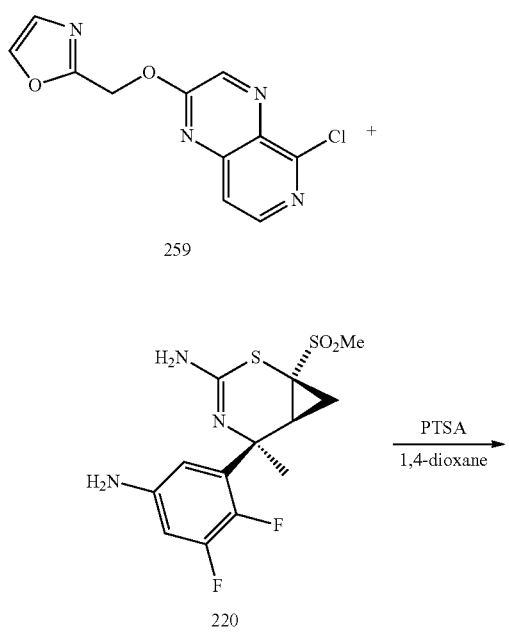

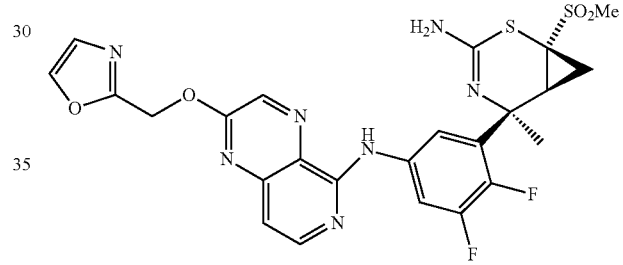

Example 747

A mixture of (1R,5S,6S)-5-(5-amino-2,3-difluorophenyl)-5-methyl-1-(methylsulfonyl)-2-thia-4-azabicyclo[4.1.0]hept-3-en-3-amine (intermediate 220, 50 mg, 0.14 mmol), 2-(((5-chloropyrido[3,4-b]pyrazin-2-yl)oxy)methyl)oxazole (intermediate 259, 42 mg, 0.16 mmol) and p-toluenesulfonic acid monohydrate (27 mg, 0.14 mmol) in 1,4-dioxane (1.1 mL) was heated to 60° C. in an aluminum heating block for 1 h. The reaction mixture was cooled to RT and diluted with EtOAc (25 mL) and saturated aqueous NaHCO₃ (20 mL). The layers were separated and the aqueous layer was extracted with EtOAc (20 mL). The combined organic layers were dried over Na₂SO₄, filtered, and then concentrated under reduced pressure to afford a yellow oil. It was purified by silica gel chromatography (0-8% MeOH in DCM) to afford (1R,5S,6S)-5-(2,3-difluoro-5-((2-(oxazol-2-ylmethoxy)pyrido[3,4-b]pyrazin-5-yl)amino)phenyl)-5-methyl-1-(methylsulfonyl)-2-thia-4-azabicyclo[4.1.0]hept-3-en-3-amine (Example 747, 20 mg, 0.035 mmol, 24% yield) as yellow solid. MS m/z=574.1 [M+H]⁺. ¹H NMR (400 MHz, DMSO-d₆) δ 9.67 (s, 1H), 8.66 (s, 1H), 8.30 (d, J=5.87 Hz, 1H), 8.13-8.23 (m, 2H), 7.89 (d, J=5.48 Hz, 1H), 7.31 (s, 1H), 7.11 (d, J=5.87 Hz, 1H), 6.66 (s, 2H), 5.66 (s, 2H), 3.11 (s, 3H), 2.17 (dd, J=7.63, 9.98 Hz, 1H), 1.91-2.00 (m, 1H), 1.76 (s, 3H), 0.94 (t, J=6.55 Hz, 1H).

Using procedures analogous or similar to the general SNAr Method E described above, the appropriate aniline and ArX (X=Cl/Br) intermediates were reacted to provide the 15 examples listed in Table 5 and Table 5'.

TABLE 5
| Ex. No. | Chemical Structure | Observed [M + H]+ |
|---|---|---|
| 632 | 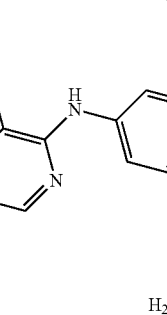 | 532.1 |
| 661 | 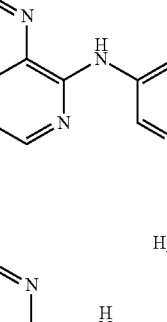 | 502 |
| 664 | 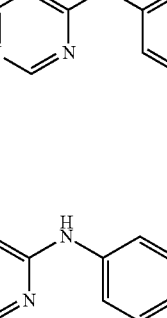 | 545 |
| 782 | 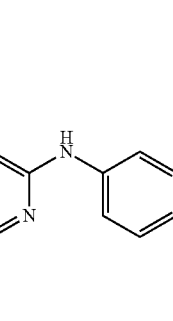 | 520 |
| 788 | 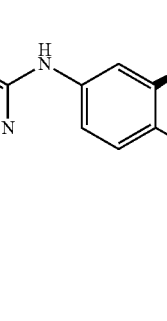 | 534 |
| 791 | 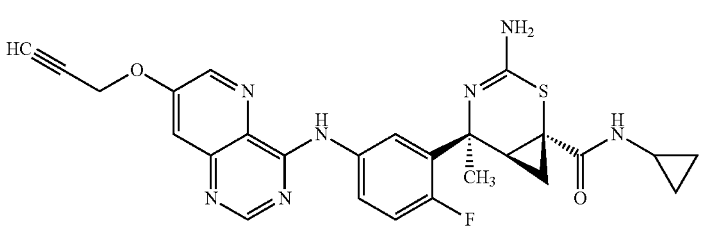 [SMILES: C#CCOc1cnc2c(Nc3ccc(F)c([C@@]4(C)N=C(N)S[C@@]5(C(=O)NC6CC6)C[C@H]54)c3)ncnc2c1] | 518 |

TABLE 5-continued

| Ex. No. | Chemical Structure | Observed [M + H]+ |
|---|---|---|
| 794 | 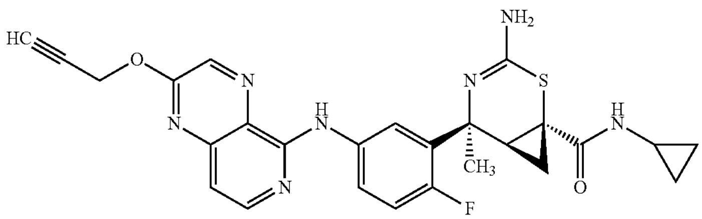 [SMILES: C#CCOc1cnc2c(Nc3ccc(F)c([C@@]4(C)N=C(N)S[C@@]5(C(=O)NC6CC6)C[C@H]54)c3)nccc2n1] | 518 |
| 796 | 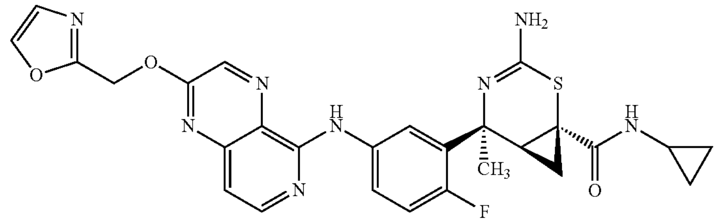 [SMILES: C[C@]1(c2cc(Nc3nccc4nc(OCc5ncco5)cnc34)ccc2F)N=C(N)S[C@@]2(C(=O)NC3CC3)C[C@H]21] | 561 |
| 915 | 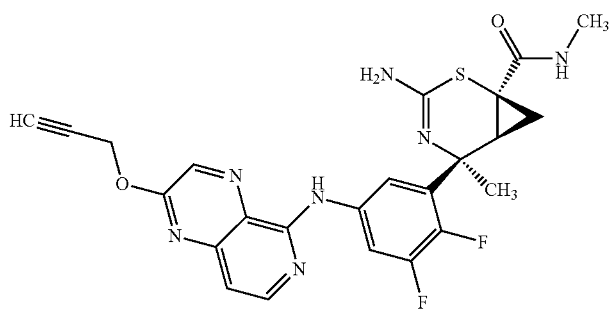 [SMILES: C#CCOc1cnc2c(Nc3cc(F)c(F)c([C@@]4(C)N=C(N)S[C@@]5(C(=O)NC)C[C@H]54)c3)nccc2n1] | 510 |
| 916 | 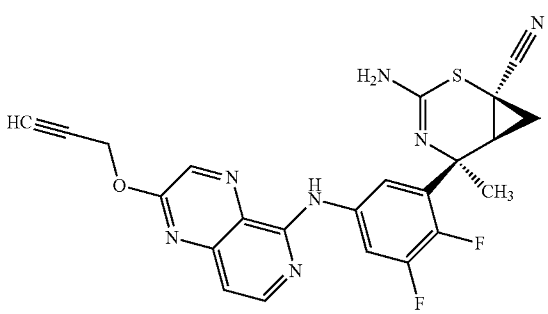 [SMILES: C#CCOc1cnc2c(Nc3cc(F)c(F)c([C@@]4(C)N=C(N)S[C@@]5(C#N)C[C@H]54)c3)nccc2n1] | 478 |
| 920 | 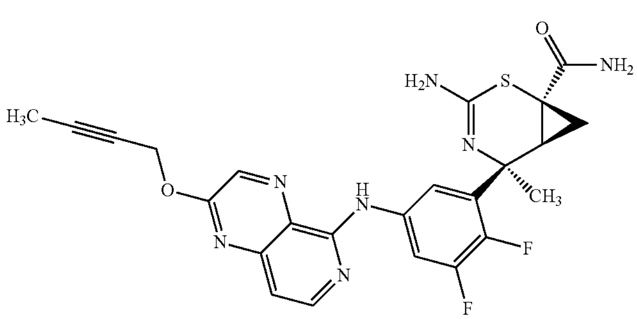 [SMILES: CC#CCOc1cnc2c(Nc3cc(F)c(F)c([C@@]4(C)N=C(N)S[C@@]5(C(N)=O)C[C@H]54)c3)nccc2n1] | 510 |

TABLE 5-continued

| Ex. No. | Chemical Structure | Observed [M + H]+ |
|---|---|---|
| 921 | 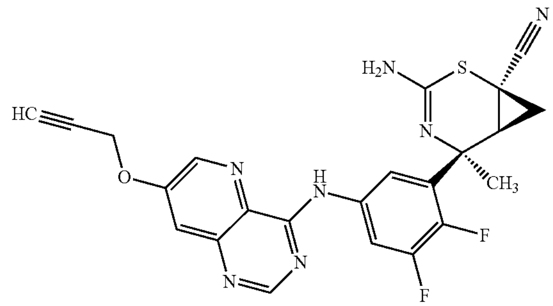 [SMILES: C#CCOc1cnc2c(Nc3cc(F)c(F)c([C@@]4(C)N=C(N)S[C@@]5(C#N)C[C@H]54)c3)ncnc2c1] | 478.1 |
| 925 | 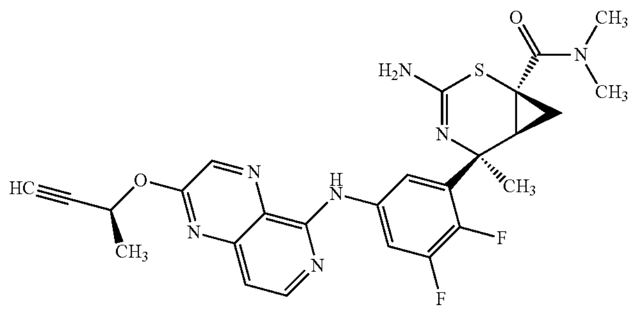 [SMILES: C#C[C@H](C)Oc1cnc2c(Nc3cc(F)c(F)c([C@@]4(C)N=C(N)S[C@@]5(C(=O)N(C)C)C[C@H]54)c3)nccc2n1] | 538.2 |
| 939 | 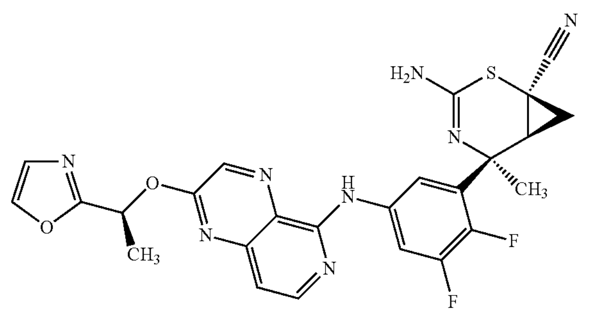 [SMILES: C[C@H](Oc1cnc2c(Nc3cc(F)c(F)c([C@@]4(C)N=C(N)S[C@@]5(C#N)C[C@H]54)c3)nccc2n1)c1ncco1] | 535.1 |
| 943 | 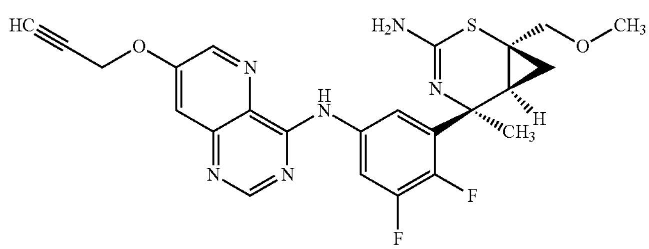 [SMILES: C#CCOc1cnc2c(Nc3cc(F)c(F)c([C@@]4(C)N=C(N)S[C@@]5(COC)C[C@H]54)c3)ncnc2c1] | 497 |

TABLE 5'

| Ex. No. | $^1$H-NMR | Chemical Name |
|---|---|---|
| 632 | $^1$H NMR (CHLOROFORM-d) Shift: 8.56 (s, 1H), 8.32 (s, 1H), 8.23 (d, J = 5.9 Hz, 1H), 8.04-8.16 (m, 1H), 7.57 (dd, J = 6.5, 2.3 Hz, 1H), 6.95-7.13 (m, 2H), 5.15 (d, J = 2.0 Hz, 2H), 3.42-3.82 (m, 4H), 2.28 (t, J = 8.2 Hz, 1H), 1.84-2.00 (m, 7H), 1.45 (dd, J = 9.7, 5.8 Hz, 1H), 0.85 (t, J = 6.2 Hz, 1H) | N-(3-((1S,5S,6S)-3-amino-5-methyl-1-(1-pyrrolidinylcarbonyl)-2-thia-4-azabicyclo[4.1.0]hept-3-en-5-yl)-4-fluorophenyl)-2-(2-propyn-1-yloxy)pyrido[3,4-b]pyrazin-5-amine |
| 661 | $^1$H NMR (400 MHz, CHLOROFORM-d) δ ppm 1.68 (s, 3 H) 2.51 (dd, J = 15.06, 2.54 Hz, 1 H) 2.57 (t, J = 2.45 Hz, 1 H) 3.89-4.05 (m, 2 H) 4.56 (br s, 2 H) 5.16 (d, J = 2.35 Hz, 2 H) 7.10 (d, J = 5.87 Hz, 1 H) | ((1S,5S,6R)-3-amino-7,7-difluoro-5-(2-fluoro-5-((2-(2-propyn-1-yloxy)pyrido[3,4-b]pyrazin-5-yl)amino)-3- |

TABLE 5'-continued

| Ex. No. | ¹H-NMR | Chemical Name |
|---|---|---|
| | 8.28 (d, J = 5.87 Hz, 1 H) 8.32-8.40 (m, 2 H) 8.58 (s, 1 H) 9.01 (t, J = 2.25 Hz, 1 H). | pyridinyl)-5-methyl-2-thia-4-azabicyclo[4.1.0]hept-3-en-1-yl)methanol |
| 664 | ¹H NMR (400 MHz, CHLOROFORM-d) δ ppm 1.68 (s, 3 H) 2.51 (dd, J = 14.96, 2.64 Hz, 1 H) 3.86-4.07 (m, 2 H) 4.56 (br. s., 2 H) 5.34 (s, 2 H) 7.21 (s, 1 H) 7.63 (d, J = 2.74 Hz, 1 H) 7.74 (s, 1 H) 8.44 (dd, J = 8.61, 2.74 Hz, 1 H) 8.61 (d, J = 2.74 Hz, 1 H) 8.75 (s, 1 H) 8.94 (s, 1 H) 8.96-8.98 (m, 1 H). | ((1S,5S,6R)-3-amino-7,7-difluoro-5-(2-fluoro-5-((7-(1,3-oxazol-2-ylmethoxy)pyrido[3,2-d]pyrimidin-4-yl)amino)-3-pyridinyl)-5-methyl-2-thia-4-azabicyclo[4.1.0]hept-3-en-1-yl)methanol |
| 782 | ¹H NMR (DMSO-d6) δ: 10.11 (s, 1H), 8.67 (d, J = 2.7 Hz, 1H), 8.62 (s, 1H), 8.32 (s, 1H), 8.23 (dd, J = 7.2, 2.7 Hz, 1H), 7.93-8.01 (m, 1H), 7.69 (d, J = 2.7 Hz, 1H), 7.22 (dd, J = 11.6, 8.9 Hz, 1H), 7.12 (s, 1H), 6.55 (s, 2H), 5.11 (d, J = 2.2 Hz, 2H), 4.64-4.93 (m, 2H), 3.74 (t, J = 2.3 Hz, 1H), 2.01-2.11 (m, 1H), 1.69 (dd, J = 9.6, 5.5 Hz, 1H), 0.89-1.02 (m, 1H) | N-(3-((1S,5S,6S)-3-amino-5-(fluoromethyl)-1-(1,3-oxazol-5-yl)-2-thia-4-azabicyclo[4.1.0]hept-3-en-5-yl)-4-fluorophenyl)-7-(2-propyn-1-yloxy)pyrido[3,2-d]pyrimidin-4-amine |
| 788 | ¹H NMR (DMSO-d6) δ: 10.10 (s, 1H), 8.67 (d, J = 2.7 Hz, 1H), 8.62 (s, 1H), 8.24 (dd, J = 7.2, 2.7 Hz, 1H), 8.19 (s, 1H), 8.00 (dt, J = 7.5, 4.3 Hz, 1H), 7.69 (d, J = 2.7 Hz, 1H), 7.21 (dd, J = 11.7, 8.8 Hz, 1H), 6.48 (s, 2H), 5.11 (d, J = 2.3 Hz, 2H), 4.68-5.00 (m, 2H), 3.74 (t, J = 2.3 Hz, 1H), 2.15 (s, 3H), 2.06-2.13 (m, 1H), 1.54 (dd, J = 9.7, 5.4 Hz, 1H), 0.94-1.03 (m, 1H) | N-(3-((1S,5S,6S)-3-amino-5-(fluoromethyl)-1-(4-methyl-1,3-oxazol-5-yl)-2-thia-4-azabicyclo[4.1.0]hept-3-en-5-yl)-4-fluorophenyl)-7-(2-propyn-1-yloxy)pyrido[3,2-d]pyrimidin-4-amine |
| 791 | ¹H NMR (DMSO-d6) δ: 10.02 (s, 1H), 8.66 (d, J = 2.7 Hz, 1H), 8.60 (s, 1H), 8.10 (dd, J = 7.2, 2.7 Hz, 1H), 7.94 (dt, J = 8.5, 3.6 Hz, 1H), 7.68 (d, J = 2.7 Hz, 1H), 7.65 (d, J = 3.7 Hz, 1H), 7.18 (dd, J = 11.8, 8.7 Hz, 1H), 6.11 (br. s., 2H), 5.11 (d, J = 2.3 Hz, 2H), 3.74 (t, J = 2.3 Hz, 1H), 2.65 (td, J = 7.3, 3.6 Hz, 1H), 2.16 (t, J = 8.4 Hz, 1H), 1.42 (dd, J = 9.3, 5.0 Hz, 1H), 0.84 (t, J = 6.0 Hz, 1H), 0.57-0.65 (m, 2H), 0.44-0.51 (m, 2H) | (1S,5S,6S)-3-amino-N-cyclopropyl-5-(2-fluoro-5-((7-(2-propyn-1-yloxy)pyrido[3,2-d]pyrimidin-4-yl)amino)phenyl)-5-methyl-2-thia-4-azabicyclo[4.1.0]hept-3-ene-1-carboxamide |
| 794 | ¹H NMR (DMSO-d6) δ: 9.36 (s, 1H), 8.60 (s, 1H), 8.24 (d, J = 5.7 Hz, 1H), 7.98-8.09 (m, 2H), 7.64 (d, J = 3.7 Hz, 1H), 7.10-7.19 (m, 1H), 7.06 (d, J = 5.9 Hz, 1H), 6.10 (s, 2H), 5.19 (d, J = 2.2 Hz, 2H), 3.66 (t, J = 2.45 Hz, 1H), 2.61-2.72 (m, 1H), 2.15 (t, J = 8.4 Hz, 1H), 1.63 (s, 3H), 1.41 (dd, J = 9.7, 5.4 Hz, 1H), 0.84 (t, J = 6.0 Hz, 1H), 0.61 (d, J = 4.7 Hz, 2H), 0.48 (d, J = 2.7 Hz, 2H) | (1S,5S,6S)-3-amino-N-cyclopropyl-5-(2-fluoro-5-((2-(2-propyn-1-yloxy)pyrido[3,4-b]pyrazin-5-yl)amino)phenyl)-5-methyl-2-thia-4-azabicyclo[4.1.0]hept-3-ene-1-carboxamide |
| 796 | ¹H NMR (DMSO-d6) δ: 9.38 (s, 1H), 8.66 (s, 1H), 8.25 (d, J = 5.7 Hz, 1H), 8.23 (d, J = 0.8 Hz, 1H), 7.94-8.13 (m, 2H), 7.66 (d, J = 3.9 Hz, 1H), 7.32 (d, J = 0.8 Hz, 1H), 7.15 (dd, J = 11.8, 8.7 Hz, 1H), 7.06 (d, J = 5.7 Hz, 1H), 6.12 (s, 2H), 5.68 (s, 2H), 2.61-2.72 (m, 1H), 2.16 (dd, J = 9.5, 7.5 Hz, 1H), 1.64 (s, 3H), 1.43 (dd, J = 9.6, 5.1 Hz, 1H), 0.80-0.89 (m, 1H), 0.58-0.67 (m, 2H), 0.45-0.52 (m, 2H) | (1S,5S,6S)-3-amino-N-cyclopropyl-5-(2-fluoro-5-((2-(1,3-oxazol-2-ylmethoxy)pyrido[3,4-b]pyrazin-5-yl)amino)phenyl)-5-methyl-2-thia-4-azabicyclo[4.1.0]hept-3-ene-1-carboxamide |
| 915 | ¹H NMR (400 MHz, DMSO-d6) δ 9.59 (s, 1H), 8.64 (s, 1H), 8.28-8.35 (m, 2H), 7.91 (d, J = 5.83 Hz, 1H), 7.69 (t, J = 5.68 Hz, 1H), 7.14 (d, J = 5.87 Hz, 1H), 6.17 (br. s., 2H), 5.21 (d, J = 2.35 Hz, 2H), 3.68 (t, J = 2.45 Hz, 1H), 2.64 (d, J = 4.50 Hz, 3H), 2.14 (dd, J = 7.63, 9.19 Hz, 1H), 1.66 (s, 3H), 1.48 (dd, J = 5.09, 9.59 Hz, 1H), 0.85-0.93 (m, 1H) | (1S,5S,6S)-3-amino-5-(2,3-difluoro-5-((2-(2-propyn-1-yloxy)pyrido[3,4-b]pyrazin-5-yl)amino)phenyl)-N,5-dimethyl-2-thia-4-azabicyclo[4.1.0]hept-3-ene-1-carboxamide |
| 916 | ¹H NMR (400 MHz, DMSO-d6) δ 9.63 (s, 1H), 8.62 (s, 1H), 8.30 (d, J = 5.87 Hz, 1H), 8.24 (ddd, J = 2.64, 6.80, 13.06 Hz, 1H), 7.88 (d, J = 5.81 Hz, 1H), 7.13 (d, J = 5.67 Hz, 1H), 6.60 (s, 2H), 5.20 (d, J = 2.35 Hz, 2H), 3.67 (t, J = 2.45 Hz, 1H), 2.32-2.42 (m, 1H), 1.94 (dd, J = 5.87, 9.78 Hz, 1H), 1.78 (s, 3H), 1.07 (t, J = 6.75 Hz, 1H) | (1S,5S,6S)-3-amino-5-(2,3-difluoro-5-((2-(2-propyn-1-yloxy)pyrido[3,4-b]pyrazin-5-yl)amino)phenyl)-5-methyl-2-thia-4-azabicyclo[4.1.0]hept-3-ene-1-carbonitrile |
| 920 | ¹H NMR (400 MHz, DMSO-d6) δ 9.57 (s, J = 5.25, 5.25 Hz, 1H), 8.62 (s, 1H), 8.29-8.37 (m, 2H), 7.91 (br. s., 1H), 7.30 (br. s., 1H), 7.22 (br. s., 1H), 7.14 (d, J = 5.80 Hz, 1H), 6.13 (br. s., 2H), 5.15-5.19 (m, 2H), 2.18 (t, J = 8.51 Hz, 1H), 1.89 (t, J = 2.35 Hz, 3H), 1.66 (s, 3H), 1.48 (d, J = 4.30 Hz, 1H), 0.92 (br. s., 1H) | (1S,5S,6S)-3-amino-5-(5-((2-(2-butyn-1-yloxy)pyrido[3,4-b]pyrazin-5-yl)amino)-2,3-difluorophenyl)-5-methyl-2-thia-4-azabicyclo[4.1.0]hept-3-ene-1-carboxamide |
| 921 | ¹H NMR (400 MHz, DMSO-d6) δ 10.25 (s, 1H), 8.68 (s, 2H), 8.15 (ddd, J = 2.74, 6.70, 12.67 Hz, 1H), 7.99 (d, J = 5.90 Hz, 1H), 7.71 (d, J = 2.93 Hz, 1H), 6.61 (s, 2H), 5.12 (d, J = 2.35 Hz, 2H), 3.74 (t, J = 2.25 Hz, 1H), | (1S,5S,6S)-3-amino-5-(2,3-difluoro-5-((7-(2-propyn-1-yloxy)pyrido[3,2-d]pyrimidin-4- |

TABLE 5'-continued

| Ex. No. | 1H-NMR | Chemical Name |
|---|---|---|
|  | 2.32-2.42 (m, 1H), 1.95 (dd, J = 6.06, 9.78 Hz, 1H), 1.78 (s, 3H), 1.07 (t, J = 6.75 Hz, 1H) | yl)amino)phenyl)-5-methyl-2-thia-4-azabicyclo[4.1.0]hept-3-ene-1-carbonitrile |
| 925 | 1H NMR (400 MHz, DMSO-d6) δ 9.56 (s, 1H), 8.60 (s, 1H), 8.24-8.33 (m, 2H), 7.88 (d, J = 5.48 Hz, 1H), 7.13 (d, J = 5.87 Hz, 1H), 6.29 (s, 2H), 5.94 (dq, J = 2.15, 6.59 Hz, 1H), 3.62 (d, J = 1.96 Hz, 1H), 3.04 (br. s., 3H), 2.92 (br. s., 3H), 2.03-2.09 (m, 1H), 1.73 (s, 3H), 1.68 (d, J = 6.65 Hz, 3H), 1.37 (dd, J = 5.48, 9.59 Hz, 1H), 0.81 (t, J = 6.16 Hz, 1H) | (1S,5S,6S)-3-amino-5-(2,3-difluoro-5-((2-(((1S)-1-methyl-2-propyn-1-yl)oxy)pyrido[3,4-b]pyrazin-5-yl)amino)phenyl)-N,N,5-trimethyl-2-thia-4-azabicyclo[4.1.0]hept-3-ene-1-carboxamide |
| 939 | 1H NMR (400 MHz, DMSO-d6) δ 9.63 (s, 1H), 8.63 (s, 1H), 8.21-8.31 (m, 2H), 8.15 (d, J = 0.78 Hz, 1H), 7.87 (d, J = 5.87 Hz, 1H), 7.26 (s, 1H), 7.08 (d, J = 5.87 Hz, 1H), 6.59 (s, 2H), 6.52 (q, J = 6.65 Hz, 1H), 2.37 (dd, J = 7.92, 9.68 Hz, 1H), | (1S,5S,6S)-3-amino-5-(2,3-difluoro-5-((2-((1S)-1-(1,3-oxazol-2-yl)ethoxy)pyrido[3,4-b]pyrazin-5-yl)amino)phenyl)-5-methyl-2-thia-4-azabicyclo[4.1.0]hept-3-ene-1-carbonitrile |
| 943 | 1H NMR (400 MHz, DMSO-d6) δ ppm 0.66 (t, J = 5.8 Hz, 1 H), 0.92 (dd, J = 9.2, 5.3 Hz, 1 H), 1.57-1.71 (m, 4 H), 3.30 (s, 3 H), 3.36 (d, J = 11.0 Hz, 1 H), 3.57 (d, J = 11.0 Hz, 1 H), 3.73 (t, J = 2.2 Hz, 1 H), 5.11 (d, J = 2.3 Hz, 2 H), 6.00 (s, 2 H), 7.70 (d, J = 2.7 Hz, 1 H), 7.97-8.06 (m, 1 H), 8.18 (ddd, J = 12.5, 6.8, 2.6 Hz, 1 H), 8.61-8.73 (m, 2 H), 10.16 (s, 1 H). | N-(3-((1S,5S,6S)-3-amino-1-(methoxymethyl)-5-methyl-2-thia-4-azabicyclo[4.1.0]hept-3-en-5-yl)-4,5-difluorophenyl)-7-(2-propyn-1-yloxy)pyrido[3,2-d]pyrimidin-4-amine |

Method F1: HATU Mediated Amide Formation Followed by Removal of the Protecting Groups SO$_4$ Example 606

N-(5-((1S,5S,6S)-3-amino-1-(fluoromethyl)-5-methyl-2-thia-4-azabicyclo[4.1.0]hept-3-en-5-yl)-6-fluoropyridin-3-yl)-5-(prop-2-yn-1-yloxy)pyrazine-2-carboxamide

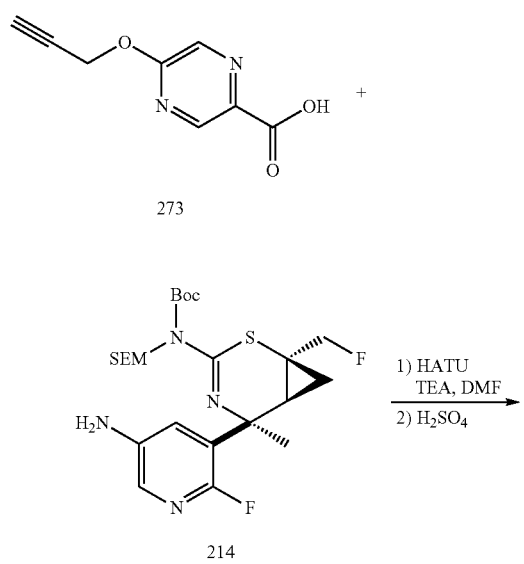

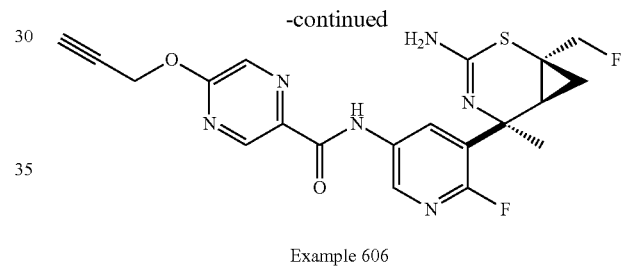

Example 606

To a mixture of tert-butyl((1S,5S,6S)-5-(5-amino-2-fluoropyridin-3-yl)-1-(fluoromethyl)-5-methyl-2-thia-4-azabicyclo[4.1.0]hept-3-en-3-yl)((2-(trimethylsilyl)ethoxy)methyl)carbamate (0.095 g, 0.185 mmol) and 5-(prop-2-yn-1-yloxy)pyrazine-2-carboxylic acid (0.049 g, 0.277 mmol) in 1.0 mL of DMF was added TEA (0.051 mL, 0.369 mmol) and HATU (0.140 g, 0.369 mmol). After stirring for 18 h, the reaction was quenched with saturated NH$_4$Cl solution, extracted with EtOAc, dried over Na$_2$SO$_4$, filtered and evaporated to dryness. It was purified by silica gel chromatography (12 g) eluting with 0-50% EtOAc in hexanes to afford tert-butyl((1S,5S,6S)-5-(2-fluoro-5-(5-(prop-2-yn-1-yloxy)pyrazine-2-carboxamido)pyridin-3-yl)-1-(fluoromethyl)-5-methyl-2-thia-4-azabicyclo[4.1.0]hept-3-en-3-yl)((2-(trimethylsilyl)ethoxy)methyl)carbamate as a brown solid. To the brown solid was added conc. H$_2$SO$_4$ (0.5 mL) and the mixture stirred at RT for 20 min. The reaction was poured onto iced water and pH adjusted to 10-14 with 10 N NaOH solution. The resulting basic solution was extracted with EtOAc (2×). The organic phase was concentrated and the residue purified by flash column chromatography on silica gel with ISCO eluting with 0-100% EtOAc in hexanes to afford N-(5-((1S,5S,6S)-3-amino-1-(fluoromethyl)-5-methyl-2-thia-4-azabicyclo[4.1.0]hept-3-en-5-yl)-6-fluoropyridin-3-yl)-5-(prop-2-yn-1-yloxy)pyrazine-2-carboxamide (Example 606, 18 mg, 22%). LCMS (ESI$^+$) m/z=445.2 (M+H). 1H NMR (300 MHz, CHLOROFORM-d) δ 9.55 (s, 1H), 9.05 (d, J=1.32 Hz, 1H), 8.60-8.65 (m, 1H), 8.42 (dd, J=2.78, 8.62 Hz, 1H), 8.23 (d, J=1.32 Hz, 1H), 5.11 (d, J=2.48 Hz, 2H), 4.44-4.64 (m, 1H), 4.27-4.42 (m, 1H), 2.57 (t, J=2.41 Hz, 1H), 1.90-2.02 (m, 1H), 1.73 (d, J=1.17 Hz, 3H), 0.94-1.16 (m, 1H), 0.83-0.93 (m, 1H). $NH_2$ peak is a broad peak between 3.25-4.75.

Using procedures analogous or similar to the general amidation Method F1 described above, the appropriate aniline and carboxylic acid intermediates were reacted to provide the 9 examples listed in Table 6 and Table 6'.

TABLE 6

| Ex. No. | Chemical Structure | Observed [M + H]+ |
|---|---|---|
| 607 | 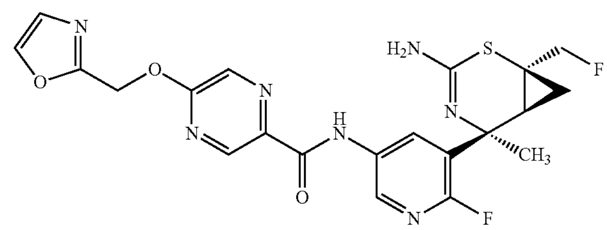 [SMILES: C[C@]1(c2cc(NC(=O)c3cnc(OCc4ncco4)cn3)cnc2F)N=C(N)S[C@@]2(CF)C[C@H]21] | 488 |
| 609 | 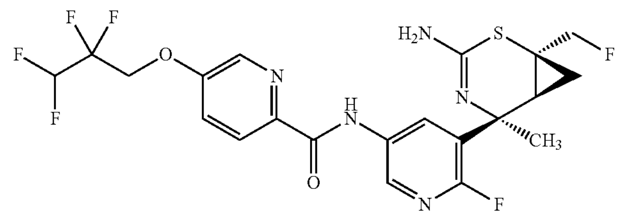 [SMILES: C[C@]1(c2cc(NC(=O)c3ccc(OCC(F)(F)C(F)F)cn3)cnc2F)N=C(N)S[C@@]2(CF)C[C@H]21] | 520.2 |
| 610 | 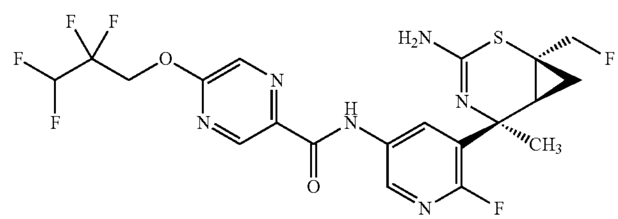 [SMILES: C[C@]1(c2cc(NC(=O)c3cnc(OCC(F)(F)C(F)F)cn3)cnc2F)N=C(N)S[C@@]2(CF)C[C@H]21] | 521 |
| 612 | 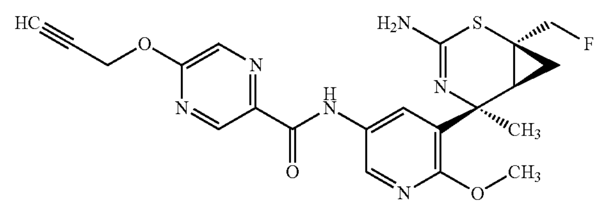 [SMILES: C#CCOc1cnc(C(=O)Nc2cnc(OC)c([C@@]3(C)N=C(N)S[C@@]4(CF)C[C@H]43)c2)cn1] | 457.2 |
| 624 | 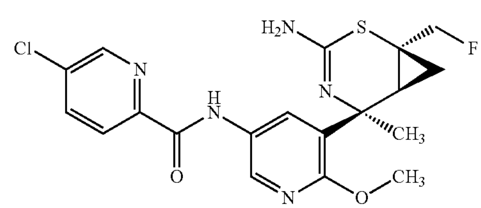 [SMILES: COc1ncc(NC(=O)c2ccc(Cl)cn2)cc1[C@@]1(C)N=C(N)S[C@@]2(CF)C[C@H]21] | 436.1 |
| 845 | 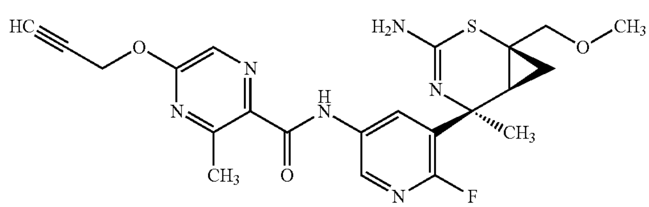 [SMILES: C#CCOc1cnc(C(=O)Nc2cnc(F)c([C@@]3(C)N=C(N)S[C@@]4(COC)C[C@H]43)c2)c(C)n1] | 471.2 |

TABLE 6-continued

| Ex. No. | Chemical Structure | Observed [M + H]+ |
|---|---|---|
| 850 | 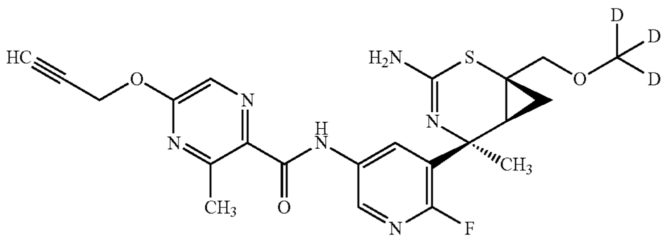 [SMILES: [2H]C([2H])([2H])OC[C@]12C[C@H]1[C@@](C)(c1cc(NC(=O)c3ncc(OCC#C)nc3C)cnc1F)N=C(N)S2] | 474 |
| 851 | 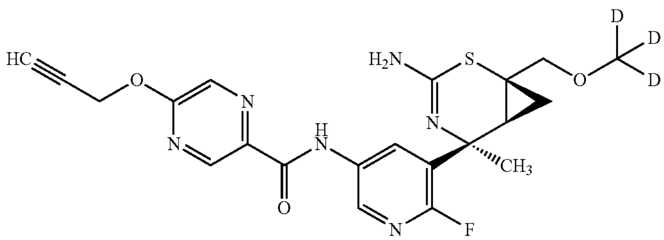 [SMILES: [2H]C([2H])([2H])OC[C@]12C[C@H]1[C@@](C)(c1cc(NC(=O)c3cnc(OCC#C)cn3)cnc1F)N=C(N)S2] | 460.2 |
| 859 | 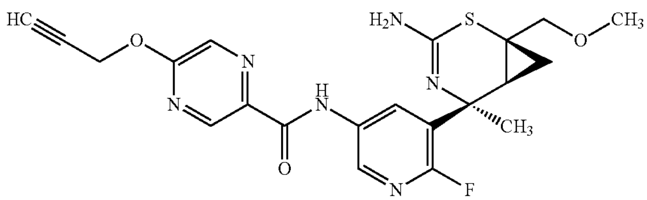 [SMILES: C#CCOc1cnc(C(=O)Nc2cnc(F)c([C@@]3(C)N=C(N)S[C@@]4(COC)C[C@H]43)c2)cn1] | 457.2 |

TABLE 6'

| Ex. No. | $^1$H-NMR | Chemical Name |
|---|---|---|
| 607 | $^1$H NMR (300 MHz, CHLOROFORM-d) δ 9.55 (s, 1H), 9.03 (d, J = 1.32 Hz, 1H), 8.59-8.65 (m, 1H), 8.42 (dd, J = 2.78, 8.62 Hz, 1H), 8.26 (d, J = 1.32 Hz, 1H), 7.72 (d, J = 0.73 Hz, 1H), 7.19 (s, 1H), 5.59 (s, 2H), 4.43-4.65 (m, 1H), 4.27-4.43 (m, 1H), 3.25-4.75 (br. s, 2H), 1.83-2.00 (m, 1H), 1.72 (d, J = 1.02 Hz, 3H), 0.99 (dd, J = 6.21, 9.57 Hz, 1H), 0.81-0.93 (m, 1H). | N-(5-((1S,5S,6S)-3-amino-1-(fluoromethyl)-5-methyl-2-thia-4-azabicyclo[4.1.0]hept-3-en-5-yl)-6-fluoro-3-pyridinyl)-5-(1,3-oxazol-2-ylmethoxy)-2-pyrazinecarboxamide |
| 609 | $^1$H NMR (300 MHz, CHLOROFORM-d) δ 9.85 (s, 1H), 8.65 (s, 1H), 8.66 (d, J = 3.18 Hz, 1H), 8.28-8.45 (m, 3H), 7.43 (dd, J = 2.85, 8.70 Hz, 1H), 6.08 (m, 1H), 4.0-4.72 (br.s, 2H), 4.44-4.62 (m, 2H), 4.21-4.44 (m, 1H), 1.93-2.06 (m, 1H), 1.75 (s, 3H), 1.01 (dd, J = 6.07, 9.43 Hz, 1H), 0.83-0.92 (m, 1H). | N-(5-((1S,5S,6S)-3-amino-1-(fluoromethyl)-5-methyl-2-thia-4-azabicyclo[4.1.0]hept-3-en-5-yl)-6-fluoro-3-pyridinyl)-5-(2,2,3,3-tetrafluoropropoxy)-2-pyridinecarboxamide |
| 610 | $^1$H NMR (400 MHz, DMSO-d6) δ 10.90 (s, 1H), 8.95 (d, J = 1.37 Hz, 1H), 8.55-8.64 (m, 3H), 6.74 (m, 1H), 6.18 (br. s., 2H), 5.06 (t, J = 14.08 Hz, 2H), 4.53-4.62 (m, 1H), 4.41-4.49 (m, 1H), 1.77-1.91 (m, 1H), 1.61 (s, 3H), 1.03 (dd, J = 5.48, 9.19 Hz, 1H), 0.68 (q, J = 5.28 Hz, 1H). | N-(5-((1S,5S,6S)-3-amino-1-(fluoromethyl)-5-methyl-2-thia-4-azabicyclo[4.1.0]hept-3-en-5-yl)-6-fluoro-3-pyridinyl)-5-(2,2,3,3-tetrafluoropropoxy)-2-pyrazinecarboxamide |
| 612 | $^1$H NMR (300 MHz, CHLOROFORM-d) δ 9.38 (s, 1H), 9.05 (d, J = 1.32 Hz, 1H), 8.66 (d, J = 2.63 Hz, 1H), 8.24 (d, J = 1.32 Hz, 1H), 8.14 (d, J = 2.63 Hz, 1H), 5.11 (d, J = 2.48 Hz, 2H), 4.53 (m, 3H), 4.36 (q, J = 10.23 Hz, 1H), 4.05 (s, 3H), 2.57 (t, J = 2.41 Hz, 1H), 2.16-2.25 (m, 1H), 1.74 (s, 3H), 0.95 (dd, J = 5.99, 9.65 Hz, 1H), 0.75-0.85 (m, 1H). | N-(5-((1S,5S,6S)-3-amino-1-(fluoromethyl)-5-methyl-2-thia-4-azabicyclo[4.1.0]hept-3-en-5-yl)-6-methoxy-3-pyridinyl)-5-(2-propyn-1-yloxy)-2-pyrazinecarboxamide |
| 624 | $^1$H NMR (400 MHz, CHLOROFORM-d) δ 9.69 (s, 1H), 8.66 (d, J = 2.54 Hz, 1H), 8.54 (d, J = 2.15 Hz, 1H), 8.23 (d, J = 8.22 Hz, 1H), 8.16 (d, J = 2.74 Hz, 1H), 7.86 (dd, J = 2.35, 8.41 Hz, 1H), 4.42-4.64 (m, 3H), 4.29-4.42 (m, 1H), 4.02 (s, 3H), | N-(5-((1S,5S,6S)-3-amino-1-(fluoromethyl)-5-methyl-2-thia-4-azabicyclo[4.1.0]hept-3-en-5-yl)-6-methoxy-3-pyridinyl)-5-chloro-2- |

TABLE 6'-continued

| Ex. No. | 1H-NMR | Chemical Name |
|---|---|---|
| | 2.18 (dd, J = 7.24, 9.00 Hz, 1H), 1.71 (s, 3H), 0.90 (dd, J = 5.97, 9.49 Hz, 1H), 0.72-0.83 (m, 1H). | pyridinecarboxamide |
| 845 | 1H NMR (300 MHz, CHLOROFORM-d) δ 9.81 (s, 1H), 8.62-8.78 (m, 1H), 8.26 (dd, J = 2.70, 8.70 Hz, 1H), 8.07 (s, 1H), 5.08 (d, J = 2.48 Hz, 2H), 3.65 (d, J = 10.67 Hz, 1H), 3.41 (s, 3H), 3.36 (d, J = 10.67 Hz, 1H), 2.96 (s, 3H), 2.54 (t, J = 2.41 Hz, 1H), 1.82-1.89 (m, 1H), 1.73 (d, J = 0.88 Hz, 3H), 0.92 (dd, J = 5.99, 9.35 Hz, 1H), 0.76-0.84 (m, 1H) | N-(5-((1S,5S,6S)-3-amino-1-(methoxymethyl)-5-methyl-2-thia-4-azabicyclo[4.1.0]hept-3-en-5-yl)-6-fluoro-3-pyridinyl)-3-methyl-5-(2-propyn-1-yloxy)-2-pyrazinecarboxamide |
| 850 | 1H NMR (300 MHz, CHLOROFORM-d) δ 9.81 (s, 1H), 8.59-8.74 (m, 1H), 8.28 (dd, J = 2.70, 8.70 Hz, 1H), 8.07 (s, 1H), 5.08 (d, J = 2.48 Hz, 2H), 3.66 (d, J = 10.08 Hz, 1H), 3.35 (d, J = 10.67 Hz, 1H), 2.96 (s, 3H), 2.54 (t, J = 2.41 Hz, 1H), 1.85 (ddd, J = 1.39, 6.72, 9.28 Hz, 1H), 1.71 (d, J = 1.17 Hz, 3H), 0.89 (dd, J = 5.99, 9.35 Hz, 1H), 0.74-0.83 (m, 1H) | N-(5-((1S,5S,6S)-3-amino-5-methyl-1-(((~2~H_3_)methyloxy)methyl)-2-thia-4-azabicyclo[4.1.0]hept-3-en-5-yl)-6-fluoro-3-pyridinyl)-3-methyl-5-(2-propyn-1-yloxy)-2-pyrazinecarboxamide |
| 851 | 1H NMR (300 MHz, CHLOROFORM-d) δ 9.52 (s, 1H), 9.04 (d, J = 1.32 Hz, 1H), 8.65 (dd, J = 1.90, 2.63 Hz, 1H), 8.36 (dd, J = 2.78, 8.62 Hz, 1H), 8.23 (d, J = 1.32 Hz, 1H), 5.10 (d, J = 2.48 Hz, 2H), 3.66 (d, J = 10.08 Hz, 1H), 3.36 (d, J = 10.67 Hz, 1H), 2.55 (t, J = 2.41 Hz, 1H), 1.79-1.92 (m, 2H), 1.71 (d, J = 1.17 Hz, 3H), 0.86-0.96 (m, 1H), 0.72-0.83 (m, 1H) | N-(5-((1S,5S,6S)-3-amino-5-methyl-1-(((~2~H_3_)methyloxy)methyl)-2-thia-4-azabicyclo[4.1.0]hept-3-en-5-yl)-6-fluoro-3-pyridinyl)-5-(2-propyn-1-yloxy)-2-pyrazinecarboxamide |
| 859 | 1H NMR (400 MHz, CHLOROFORM-d) δ 9.52 (s, 1H), 9.04 (s, 1H), 8.65 (s, 1H), 8.37 (dd, J = 2.15, 8.41 Hz, 1H), 8.22 (s, 1H), 5.10 (d, J = 2.54 Hz, 2H), 3.66 (d, J = 10.56 Hz, 1H), 3.41 (s, 3H), 3.36 (d, J = 10.56 Hz, 1H), 2.56 (t, J = 2.45 Hz, 1H), 1.80-1.90 (m, 1H), 1.71 (s, 3H), 0.86-0.92 (m, 1H), 0.74-0.82 (m, 1H) | N-(5-((1S,5S,6S)-3-amino-1-(methoxymethyl)-5-methyl-2-thia-4-azabicyclo[4.1.0]hept-3-en-5-yl)-6-fluoro-3-pyridinyl)-5-(2-propyn-1-yloxy)-2-pyrazinecarboxamide |

Method F2: HATU Mediated Amide Formation Followed by Removal of the Protecting Groups with PTSA Example 784

N-(3-((1S,5S,6S)-3-amino-5-(fluoromethyl)-1-(4-methyloxazol-5-yl)-2-thia-4-azabicyclo[4.1.0]hept-3-en-5-yl)-4-fluorophenyl)-5-(prop-2-yn-1-yloxy)pyrazine-2-carboxamide

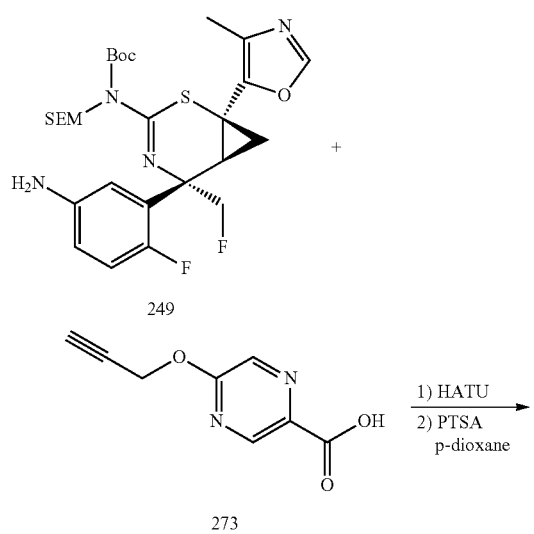

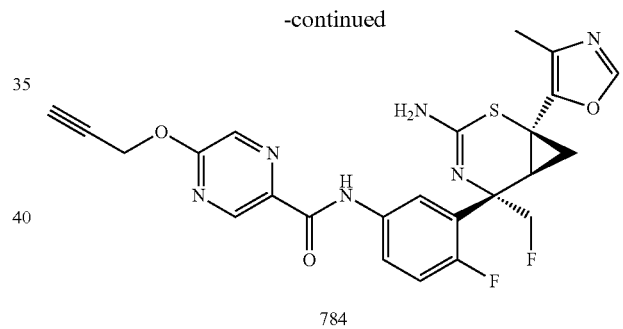

To a stirred mixture of tert-butyl((1S,5S,6S)-5-(5-amino-2-fluorophenyl)-5-(fluoromethyl)-1-(4-methyloxazol-5-yl)-2-thia-4-azabicyclo[4.1.0]hept-3-en-3-yl)((2-(trimethylsilyl)ethoxy)methyl)carbamate (189 mg, 0.325 mmol), 5-(prop-2-yn-1-yloxy)pyrazine-2-carboxylic acid (249, 70 mg, 0.39 mmol), and EtNiPr$_2$ (0.06 mL, 0.32 mmol) in DMF (4 mL) was added HATU (148 mg, 0.39 mmol). The reaction mixture was stirred at RT for 2 h. H$_2$O was added, the solid was collected, dried and dissolved in p-dioxane (4 mL) and added PTSA (186 mg, 0.97 mmol) and heated at 70° C. for 2 h. The mixture was concentrated, added H$_2$O, neutralized with saturated aqueous NaHCO$_3$. The solid was filtered, dried, purified by preparative reverse phase HPLC. The pure fractions were concentrated to dryness, dissolved in MeOH and passed through Pl-HCO$_3$ MP SPE (200 mg per tube) to give the title compound (69 mg, 48%). 1H NMR (DMSO-d6) δ: 10.49 (s, 1H), 8.90 (d, J=1.4 Hz, 1H), 8.48 (d, J=1.2 Hz, 1H), 8.20 (s, 1H), 8.06 (dd, J=7.2, 2.7 Hz, 1H), 7.84 (dt, J=8.6, 3.5 Hz, 1H), 7.20 (dd, J=11.7, 8.8 Hz, 1H), 6.45 (s, 2H), 5.14 (d, J=2.3 Hz, 2H), 4.66-4.99 (m, 2H), 3.64 (t, J=2.4 Hz, 1H), 2.15 (s, 3H), 2.04-2.11 (m, 1H), 1.50 (dd, J=9.7, 5.4 Hz, 1H), 0.94-1.02 (m, 1H). MS (ESI, positive ion) m/z: 511 (M+1).

Using procedures analogous or similar to the general amidation Method F2 described above, the appropriate aniline and carboxylic acid intermediates were reacted to provide the 7 examples listed in Table 7 and Table 7'.

TABLE 7

| Ex. No. | Chemical Structure | Observed [M + H]+ |
|---|---|---|
| 787 | 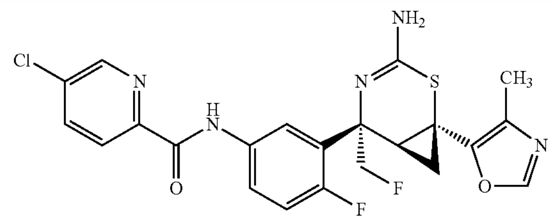 [SMILES: Cc1ncoc1[C@]12C[C@H]1[C@@](CF)(c1cc(NC(=O)c3ccc(Cl)cn3)ccc1F)N=C(N)S2] | 490 |
| 789 | 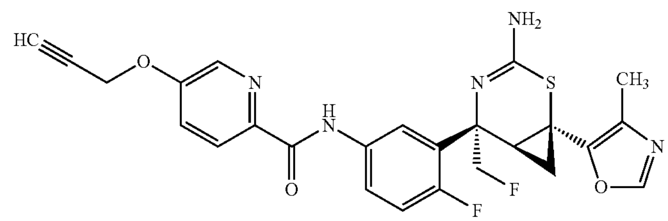 [SMILES: C#CCOc1ccc(C(=O)Nc2ccc(F)c([C@@]3(CF)N=C(N)S[C@@]4(c5ocnc5C)C[C@@H]34)c2)nc1] | 510 |
| 793 | 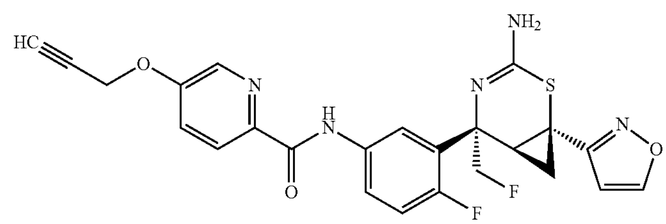 [SMILES: C#CCOc1ccc(C(=O)Nc2ccc(F)c([C@@]3(CF)N=C(N)S[C@@]4(c5ccon5)C[C@@H]34)c2)nc1] | 496 |
| 797 | 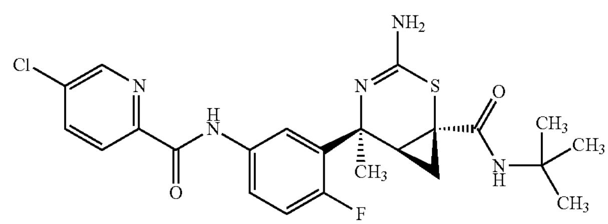 [SMILES: CC(C)(C)NC(=O)[C@]12C[C@H]1[C@@](C)(c1cc(NC(=O)c3ccc(Cl)cn3)ccc1F)N=C(N)S2] | 490 |
| 798 | 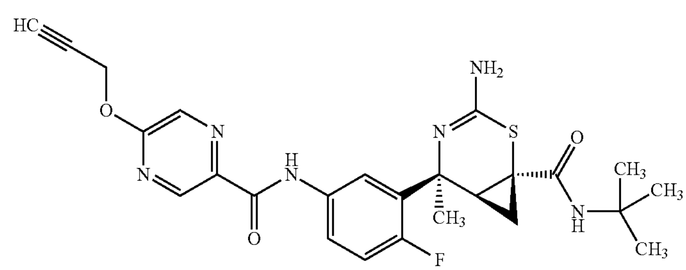 [SMILES: C#CCOc1cnc(C(=O)Nc2ccc(F)c([C@@]3(C)N=C(N)S[C@@]4(C(=O)NC(C)(C)C)C[C@H]43)c2)cn1] | 511 |
| 799 | 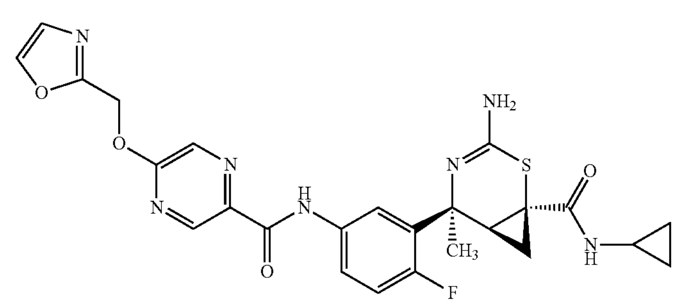 [SMILES: C[C@]1(c2cc(NC(=O)c3cnc(OCc4ncco4)cn3)ccc2F)N=C(N)S[C@@]2(C(=O)NC3CC3)C[C@H]21] | 538 |

TABLE 7-continued

| Ex. No. | Chemical Structure | Observed [M + H]⁺ |
|---|---|---|
| 800 | 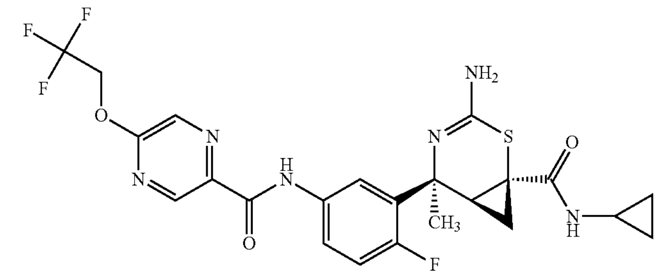 [SMILES: C[C@]1(c2cc(NC(=O)c3cnc(OCC(F)(F)F)cn3)ccc2F)N=C(N)S[C@@]2(C(=O)NC3CC3)C[C@H]21] | 539 |

TABLE 7'

| Ex. No. | ¹H-NMR | Chemical Name |
|---|---|---|
| 787 | ¹H NMR (DMSO-d6) δ: 10.62 (s, 1H), 8.78 (d, J = 2.3 Hz, 1H), 8.18-8.23 (m, 2H), 8.13-8.17 (m, 1H), 8.06 (dd, J = 7.2, 2.7 Hz, 1H), 7.84-7.90 (m, 1H), 7.20 (dd, J = 11.9, 8.8 Hz, 1H), 6.46 (s, 2H), 4.66-5.07 (m, 2H), 2.15 (s, 3H), 2.05-2.11 (m, 1H), 1.50 (dd, J = 9.6, 5.5 Hz, 1H), 0.94-1.01 (m, 1H) | N-(3-((1S,5S,6S)-3-amino-5-(fluoromethyl)-1-(4-methyl-1,3-oxazol-5-yl)-2-thia-4-azabicyclo[4.1.0]hept-3-en-5-yl)-4-fluorophenyl)-5-chloro-2-pyridinecarboxamide |
| 789 | ¹H NMR (DMSO-d6) δ: 10.44 (s, 1H), 8.44 (d, J = 2.7 Hz, 1H), 8.20 (s, 1H), 8.14 (d, J = 8.6 Hz, 1H), 8.04 (dd, J = 7.2, 2.7 Hz, 1H), 7.88 (dt, J = 8.7, 3.5 Hz, 1H), 7.67 (dd, J = 8.8, 2.9 Hz, 1H), 7.19 (dd, J = 11.9, 8.8 Hz, 1H), 6.46 (s, 2H), 5.04 (d, J = 2.3 Hz, 2H), 4.68-4.98 (m, 2H), 3.71 (t, J = 2.3 Hz, 1H), 2.15 (s, 3H), 2.06-2.12 (m, 1H), 1.50 (dd, J = 9.7, 5.4 Hz, 1H), 0.96-1.02 (m, 1H) | N-(3-((1S,5S,6S)-3-amino-5-(fluoromethyl)-1-(4-methyl-1,3-oxazol-5-yl)-2-thia-4-azabicyclo[4.1.0]hept-3-en-5-yl)-4-fluorophenyl)-5-(2-propyn-1-yloxy)-2-pyridinecarboxamide |
| 793 | ¹H NMR (CHLOROFORM-d) δ: 9.86 (s, 1H), 8.38 (d, J = 1.6 Hz, 1H), 8.34 (d, J = 2.7 Hz, 1H), 8.25 (d, J = 8.6 Hz, 1H), 7.97-8.03 (m, 1H), 7.74 (dd, J = 6.8, 2.7 Hz, 1H), 7.45 (dd, J = 8.7, 2.8 Hz, 1H), 7.11 (dd, J = 11.3, 8.8 Hz, 1H), 6.38 (d, J = 1.8 Hz, 1H), 4.89-5.06 (m, 1H), 4.83 (d, J = 2.3 Hz, 2H), 4.63-4.80 (m, 1H), 2.61 (t, J = 2.4 Hz, 1H), 2.30 (t, J = 8.7 Hz, 1H), 1.82-1.89 (m, J = 9.8, 6.1 Hz, 1H), 1.19 (t, J = 6.7 Hz, 1H) | N-(3-((1S,5S,6S)-3-amino-5-(fluoromethyl)-1-(3-isoxazolyl)-2-thia-4-azabicyclo[4.1.0]hept-3-en-5-yl)-4-fluorophenyl)-5-(2-propyn-1-yloxy)-2-pyridinecarboxamide |
| 797 | ¹H NMR (DMSO-d6) δ: 10.55 (s, 1H), 8.72-8.80 (m, 1H), 8.17-8.21 (m, 1H), 8.12-8.16 (m, 1H), 7.92 (dd, J = 7.3, 2.8 Hz, 1H), 7.76-7.82 (m, 1H), 7.15 (dd, J = 11.7, 8.8 Hz, 1H), 6.80 (s, 1H), 6.17 (s, 2H), 2.07 (dd, J = 9.3, 7.5 Hz, 1H), 1.63 (s, 3H), 1.45 (dd, J = 9.6, 4.9 Hz, 1H), 1.27 (s, 9H), 0.73 (dd, J = 6.7, 5.2 Hz, 1H) | (1S,5S,6S)-3-amino-N-tert-butyl-5-(5-(((5-chloro-2-pyridinyl)carbonyl)amino)-2-fluorophenyl)-5-methyl-2-thia-4-azabicyclo[4.1.0]hept-3-ene-1-carboxamide |
| 798 | ¹H NMR (DMSO-d6) δ: 10.42 (s, 1H), 8.89 (d, J = 1.4 Hz, 1H), 8.48 (d, J = 1.4 Hz, 1H), 7.93 (dd, J = 7.3, 2.6 Hz, 1H), 7.77 (dt, J = 8.4, 3.6 Hz, 1H), 7.16 (dd, J = 11.9, 8.8 Hz, 1H), 6.81 (s, 1H), 6.17 (s, 2H), 5.14 (d, J = 2.3 Hz, 2H), 3.64 (t, J = 2.3 Hz, 1H), 2.07 (dd, J = 9.2, 7.6 Hz, 1H), 1.63 (s, 3H), 1.46 (dd, J = 9.7, 5.0 Hz, 1H), 1.28 (s, 9H), 0.57-0.83 (m, 1H) | (1S,5S,6S)-3-amino-N-tert-butyl-5-(2-fluoro-5-(((5-(2-propyn-1-yloxy)-2-pyrazinyl)carbonyl)amino)phenyl)-5-methyl-2-thia-4-azabicyclo[4.1.0]hept-3-ene-1-carboxamide |
| 799 | ¹H NMR (DMSO-d6) δ: 10.57 (s, 1H), 9.00 (d, J = 1.4 Hz, 1H), 8.70 (d, J = 1.4 Hz, 1H), 8.09 (dd, J = 7.3, 2.8 Hz, 1H), 7.83-7.93 (m, 1H), 7.73 (d, J = 3.9 Hz, 1H), 7.25 (dd, J = 11.9, 8.8 Hz, 1H), 6.16 (s, 2H), 5.25 (q, J = 9.0 Hz, 2H), 2.69-2.81 (m, 1H), 2.23 (dd, J = 9.4, 7.6 Hz, 1H), 1.70 (s, 3H), 1.46 (dd, J = 9.7, 5.2 Hz, 1H), 0.91 (dd, J = 6.7, 5.4 Hz, 1H), 0.69 (dd, J = 7.2, 2.3 Hz, 2H), 0.46-0.60 (m, 2H). | (1S,5S,6S)-3-amino-N-cyclopropyl-5-(2-fluoro-5-(((5-(1,3-oxazol-2-ylmethoxy)-2-pyrazinyl)carbonyl)amino)phenyl)-5-methyl-2-thia-4-azabicyclo[4.1.0]hept-3-ene-1-carboxamide |
| 800 | ¹H NMR (DMSO-d6) δ: 10.57 (s, 1H), 9.00 (d, J = 1.4 Hz, 1H), 8.70 (d, J = 1.4 Hz, 1H), 8.09 (dd, J = 7.3, 2.8 Hz, 1H), 7.83-7.93 (m, 1H), 7.73 (d, J = 3.9 Hz, 1H), 7.25 (dd, J = 11.9, 8.8 Hz, 1H), 6.16 (s, 2H), 5.25 (q, J = 9.0 Hz, 2H), 2.69-2.81 (m, 1H), 2.23 (dd, J = 9.4, 7.6 Hz, 1H), 1.70 (s, 3H), 1.46 (dd, J = 9.7, 5.2 Hz, 1H), 0.91 (dd, J = 6.7, 5.4 Hz, 1H), 0.69 (dd, J = 7.2, 2.3 Hz, 2H), 0.46-0.60 (m, 2H) | (1S,5S,6S)-3-amino-N-cyclopropyl-5-(2-fluoro-5-(((5-(2,2,2-trifluoroethoxy)-2-pyrazinyl)carbonyl)amino)phenyl)-5-methyl-2-thia-4-azabicyclo[4.1.0]hept-3-ene-1-carboxamide |

Method G: SNAr in iPrOH Followed by Removal of the Protecting Groups with $H_2SO_4$ Example 844

(1S,5S,6S)-5-(5-((7-chloropyrido[3,2-d]pyrimidin-4-yl)amino)-2-fluoropyridin-3-yl)-1-(methoxymethyl)-5-methyl-2-thia-4-azabicyclo[4.1.0]hept-3-en-3-amine

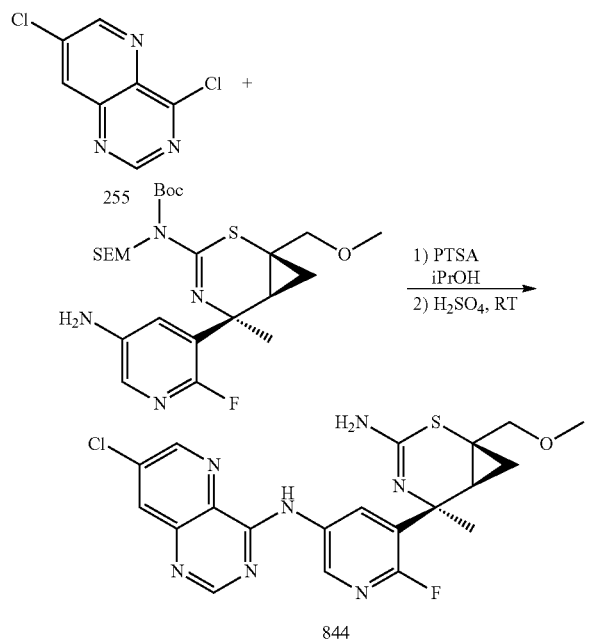

A mixture of 4,7-dichloropyrido[3,2-d]pyrimidine (31.3 mg, 0.157 mmol), tert-butyl((1S,5S,6S)-5-(5-amino-2-fluoropyridin-3-yl)-1-(methoxymethyl)-5-methyl-2-thia-4-azabicyclo[4.1.0]hept-3-en-3-yl)((2-(trimethylsilyl)ethoxy)methyl)carbamate (55 mg, 0.10 mmol), p-toluenesulfonic acid monohydrate (39 mg, 0.20 mmol) in isopropanol (3 mL) in a microwave vial was heated at 80° C. under $N_2$ for 1 h. LCMS showed the desired product peak, together with partial deprotections. The solvent was evaporated and the residue was treated with sulfuric acid (0.14 mL, 2.61 mmol) and was stirred at RT for 20 min. It was quenched by slow addition of saturated $NaHCO_3$ till pH=8. The aqueous layer was extracted with EtOAc. The organic phase was dried over $Na_2SO_4$, filtered, and concentrated. The residue was purified by chromatography on silica using EtOAc in DCM (30-100%) as eluent to give Example 844 (44 mg, 0.096 mmol, 92% yield) as a yellow solid. LCMS (ESI$^+$) m/z=459.2 (M+H). $^1$H NMR (300 MHz, CHLOROFORM-d) δ 9.00 (s, 1H), 8.93 (dd, J=1.97, 2.70 Hz, 1H), 8.79 (s, 1H), 8.73 (d, J=2.19 Hz, 1H), 8.44 (dd, J=2.78, 8.48 Hz, 1H), 8.19 (d, J=2.34 Hz, 1H), 3.67 (d, J=10.08 Hz, 1H), 3.42 (s, 3H), 3.37 (d, J=10.67 Hz, 1H), 1.86 (ddd, J=1.39, 6.69, 9.32 Hz, 1H), 1.74 (d, J=1.32 Hz, 3H), 0.91 (dd, J=5.85, 9.35 Hz, 1H), 0.75-0.84 (m, 1H).

Using procedures analogous or similar to the general SNAr Method G described above, the appropriate aniline and ArX (X=Cl/Br) intermediates were reacted to provide the 8 examples listed in Table 8 and Table 8'.

TABLE 8

| Ex. No. | Chemical Structure | Observed [M + H]+ |
|---|---|---|
| 641 | 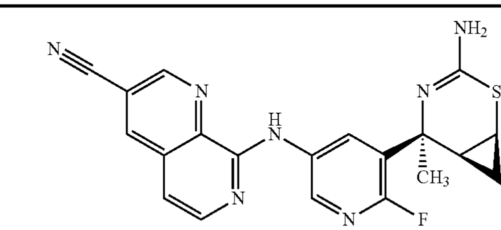 | 406 |
| 846 | 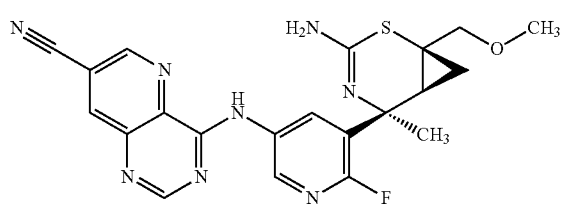 [SMILES: COC[C@]12C[C@H]1[C@@](C)(c1cc(Nc3ncnc4cc(C#N)cnc34)cnc1F)N=C(N)S2] | 451 |
| 847 | 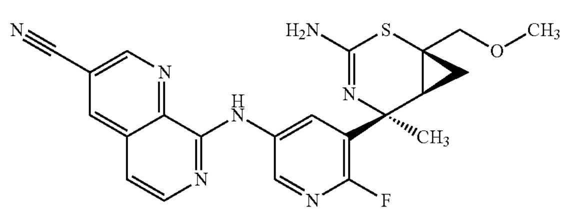 [SMILES: COC[C@]12C[C@H]1[C@@](C)(c1cc(Nc3nccc4cc(C#N)cnc34)cnc1F)N=C(N)S2] | 450.2 |

TABLE 8-continued

| Ex. No. | Chemical Structure | Observed [M + H]+ |
|---|---|---|
| 848 | 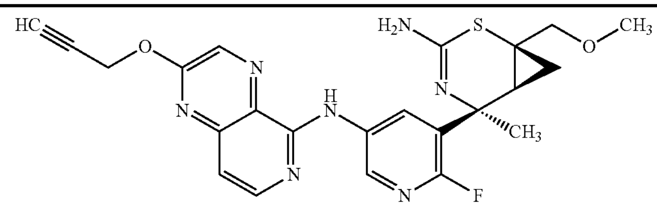 | 480.1 |
| 849 | 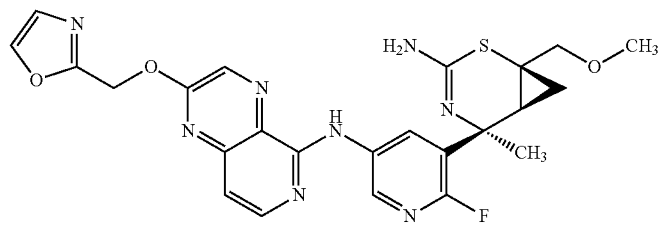 [SMILES: COC[C@]12C[C@H]1[C@@](C)(c1cc(Nc3nccc4nc(OCc5ncco5)cnc34)cnc1F)N=C(N)S2] | 523.2 |
| 852 | 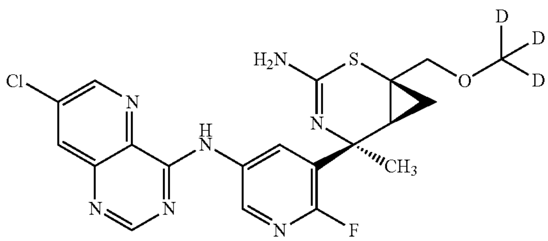 [SMILES: [2H]C([2H])([2H])OC[C@]12C[C@H]1[C@@](C)(c1cc(Nc3ncnc4cc(Cl)cnc34)cnc1F)N=C(N)S2] | 463 |
| 853 | 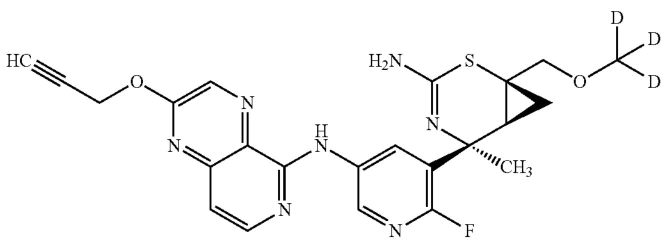 [SMILES: [2H]C([2H])([2H])OC[C@]12C[C@H]1[C@@](C)(c1cc(Nc3nccc4nc(OCC#C)cnc34)cnc1F)N=C(N)S2] | 483.2 |
| 854 | 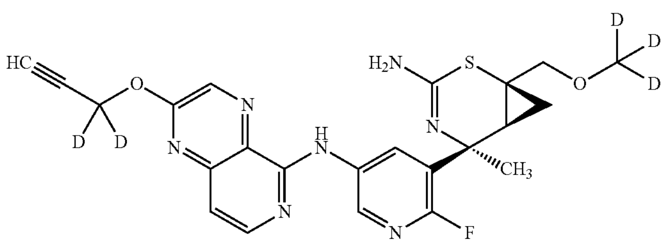 [SMILES: [2H]C([2H])([2H])OC[C@]12C[C@H]1[C@@](C)(c1cc(Nc3nccc4nc(OC([2H])([2H])C#C)cnc34)cnc1F)N=C(N)S2] | 485.2 |

TABLE 8'

| Ex. No. | ¹H-NMR | Chemical Name |
|---|---|---|
| 641 | ¹H NMR (400 MHz, DMSO-d6) δ 9.97 (s, 1H, NH), 9.92-10.02 (m, 1H), 9.92-10.02 (m, 1H), 9.23 (d, J = 1.96 Hz, 1H), 9.00 (d, J = 1.96 Hz, 1H), 8.78 (s, 1H), 8.70 (dd, J = 2.74, 9.00 Hz, 1H), 8.24 (d, J = 5.67 Hz, 1H), 7.26 (d, J = 5.67 Hz, 1H), 5.99 (br. s., 2H, NH2), 2.34 (d, J = 9.00 Hz, 1H), 1.73-1.82 (m, 1H), 1.65 (s, 3H), 0.88 (dd, J = 2.15, 10.17 Hz, 1H), 0.46 (d, J = 4.89 Hz, 1H). | 8-((5-((1S,5S,6S)-3-amino-5-methyl-2-thia-4-azabicyclo[4.1.0]hept-3-en-5-yl)-6-fluoro-3-pyridinyl)amino)-1,7-naphthyridine-3-carbonitrile |
| 846 | ¹H NMR (CHLOROFORM-d) δ: 9.08 (br. s., 1H), 8.97 (d, J = 1.9 Hz, 1H), 8.94 (dd, J = 2.8, 1.9 Hz, 1H), 8.87 (s, 1H), 8.53 (d, J = 1.9 Hz, 1H), 8.45 (dd, J = 8.4, 2.8 Hz, 1H), 3.67 (d, J = 10.7 Hz, 1H), 3.42 (s, 3H), 3.37 (d, J = 10.7 Hz, 1H), 1.87 (ddd, J = 9.4, 6.7, | 4-((5-((1S,5S,6S)-3-amino-1-(methoxymethyl)-5-methyl-2-thia-4-azabicyclo[4.1.0]hept-3-en-5-yl)-6-fluoro-3- |

TABLE 8'-continued

| Ex. No. | ¹H-NMR | Chemical Name |
|---|---|---|
|  | 1.5 Hz, 1H), 1.74 (d, J = 1.0 Hz, 3H), 0.92 (dd, J = 9.1, 6.1 Hz, 1H), 0.79 (t, J = 6.3 Hz, 1H) | pyridinyl)amino)pyrido[3,2-d]pyrimidine-7-carbonitrile |
| 847 | ¹H NMR (300 MHz, CHLOROFORM-d) δ 8.99-9.04 (m, 1H), 8.92-8.98 (m, 2H), 8.35-8.44 (m, 2H), 8.27 (d, J = 5.70 Hz, 1H), 7.07 (d, J = 5.85 Hz, 1H), 3.66 (d, J = 10.67 Hz, 1H), 3.42 (s, 3H), 3.37 (d, J = 10.67 Hz, 1H), 1.87 (ddd, J = 1.32, 6.72, 9.35 Hz, 1H), 1.76 (d, J = 1.02 Hz, 3H), 0.94 (dd, J = 5.99, 9.35 Hz, 1H), 0.76-0.85 (m, 1H). | 8-((5-((1S,5S,6S)-3-amino-1-(methoxymethyl)-5-methyl-2-thia-4-azabicyclo[4.1.0]hept-3-en-5-yl)-6-fluoro-3-pyridinyl)amino)-1,7-naphthyridine-3-carbonitrile |
| 848 | ¹H NMR (300 MHz, CHLOROFORM-d) δ 8.89-8.98 (m, 1H), 8.57 (s, 1H), 8.31-8.42 (m, 2H), 8.28 (d, J = 5.85 Hz, 1H), 7.10 (d, J = 5.85 Hz, 1H), 5.16 (d, J = 2.34 Hz, 2H), 3.66 (d, J = 10.52 Hz, 1H), 3.42 (s, 3H), 3.36 (d, J = 10.67 Hz, 1H), 2.57 (t, J = 2.41 Hz, 1H), 1.80-1.90 (m, 1H), 1.74 (s, 3H), 0.87-0.99 (m, 1H), 0.75-0.84 (m, 1H) | N-(5-((1S,5S,6S)-3-amino-1-(methoxymethyl)-5-methyl-2-thia-4-azabicyclo[4.1.0]hept-3-en-5-yl)-6-fluoro-3-pyridinyl)-2-(2-propyn-1-yloxy)pyrido[3,4-b]pyrazin-5-amine |
| 849 | ¹H NMR (300 MHz, CHLOROFORM-d) δ 8.89-8.99 (m, 1H), 8.58 (s, 1H), 8.41 (s, 1H), 8.35 (dd, J = 2.78, 8.62 Hz, 1H), 8.28 (d, J = 5.85 Hz, 1H), 7.73 (d, J = 0.73 Hz, 1H), 7.20 (s, 1H), 7.09 (d, J = 5.99 Hz, 1H), 5.65 (s, 2H), 3.66 (d, J = 10.38 Hz, 1H), 3.41 (s, 3H), 3.36 (d, J = 10.67 Hz, 1H), 1.80-1.90 (m, 1H), 1.74 (d, J = 1.02 Hz, 3H), 0.88-0.99 (m, 1H), 0.76-0.84 (m, 1H) | N-(5-((1S,5S,6S)-3-amino-1-(methoxymethyl)-5-methyl-2-thia-4-azabicyclo[4.1.0]hept-3-en-5-yl)-6-fluoro-3-pyridinyl)-2-(1,3-oxazol-2-ylmethoxy)pyrido[3,4-b]pyrazin-5-amine |
| 852 | ¹H NMR (300 MHz, CHLOROFORM-d) δ 9.00 (s, 1H), 8.93 (dd, J = 1.90, 2.78 Hz, 1H), 8.79 (s, 1H), 8.73 (d, J = 2.19 Hz, 1H), 8.44 (dd, J = 2.78, 8.62 Hz, 1H), 8.19 (d, J = 2.19 Hz, 1H), 3.67 (d, J = 10.67 Hz, 1H), 3.37 (d, J = 10.67 Hz, 1H), 1.86 (ddd, J = 1.39, 6.69, 9.32 Hz, 1H), 1.74 (d, J = 1.17 Hz, 3H), 0.87-0.99 (m, 1H), 0.75-0.84 (m, 1H) | N-(5-((1S,5S,6S)-3-amino-5-methyl-1-(((~2~H_3_)methyloxy)methyl)-2-thia-4-azabicyclo[4.1.0]hept-3-en-5-yl)-6-fluoro-3-pyridinyl)-7-chloropyrido[3,2-d]pyrimidin-4-amine |
| 853 | ¹H NMR (300 MHz, CHLOROFORM-d) δ 8.87-9.02 (m, 1H), 8.57 (s, 1H), 8.31-8.40 (m, 2H), 8.27 (d, J = 5.99 Hz, 1H), 7.09 (d, J = 5.99 Hz, 1H), 5.16 (d, J = 2.48 Hz, 2H), 3.66 (d, J = 10.23 Hz, 1H), 3.36 (d, J = 10.67 Hz, 1H), 2.57 (t, J = 2.48 Hz, 1H), 1.84 (ddd, J = 1.24, 6.72, 9.28 Hz, 1H), 1.74 (d, J = 1.17 Hz, 3H), 0.87-0.97 (m, 1H), 0.74-0.84 (m, 1H) | N-(5-((1S,5S,6S)-3-amino-5-methyl-1-(((~2~H_3_)methyloxy)methyl)-2-thia-4-azabicyclo[4.1.0]hept-3-en-5-yl)-6-fluoro-3-pyridinyl)-2-(2-propyn-1-yloxy)pyrido[3,4-b]pyrazin-5-amine |
| 854 | ¹H NMR (300 MHz, CHLOROFORM-d) δ 8.91-9.03 (m, 1H), 8.57 (s, 1H), 8.32-8.40 (m, 2H), 8.28 (d, J = 5.85 Hz, 1H), 7.10 (d, J = 5.85 Hz, 1H), 3.66 (d, J = 10.52 Hz, 1H), 3.36 (d, J = 10.67 Hz, 1H), 2.55 (s, 1H), 1.85 (ddd, J = 1.17, 6.65, 9.43 Hz, 1H), 1.75 (d, J = 1.02 Hz, 3H), 0.93 (dd, J = 5.92, 9.43 Hz, 1H), 0.77-0.84 (m, 1H) | N-(5-((1S,5S,6S)-3-amino-5-methyl-1-(((~2~H_3_)methyloxy)methyl)-2-thia-4-azabicyclo[4.1.0]hept-3-en-5-yl)-6-fluoro-3-pyridinyl)-2-((1,1-~2~H_2_)-2-propyn-1-yloxy)pyrido[3,4-b]pyrazin-5-amine |

Miscellaneous Methods

Example 12

N-(3-((1S,5S,6S)-3-amino-1-(fluoromethyl)-5-methyl-2-thia-4-azabicyclo[4.1.0]hept-3-en-5-yl)-4,5-difluorophenyl)-5-chloropicolinamide

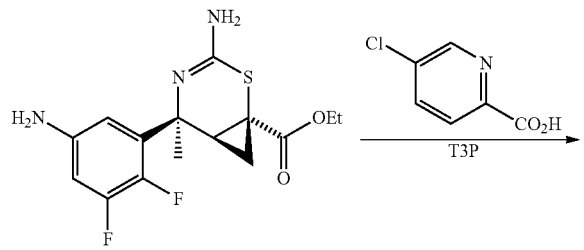

212

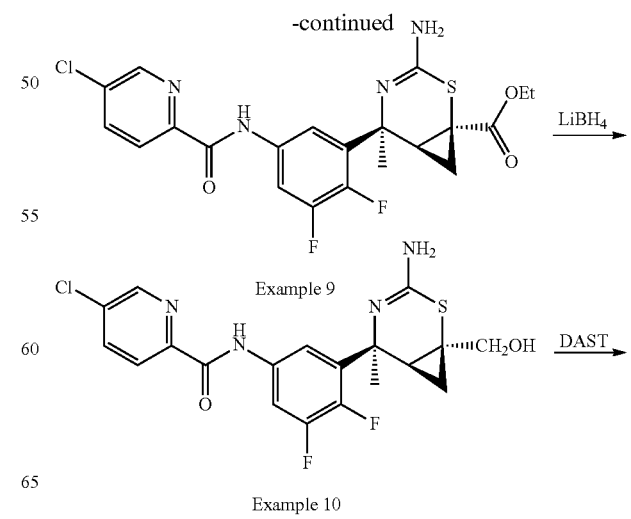

Example 9

Example 10

-continued

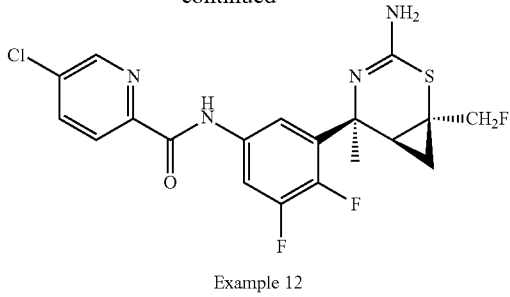

Example 12

Preparation of 3-amino-5-(5-(5-chloropicolinamido)-2,3-difluorophenyl)-5-methyl-2-thia-4-azabicyclo[4.1.0]hept-3-ene-1-carboxylate (Example 9). (1S,5S,6S)-ethyl 3-Amino-5-(5-amino-2,3-difluorophenyl)-5-methyl-2-thia-4-azabicyclo[4.1.0]hept-3-ene-1-carboxylate (intermediate 212, 225 mg, 0.66 mmol) was taken up in 3.2 mL of DMAc and chilled to 0° C. 5-Chloro-2-pyridinecarboxylic acid (125 mg, 0.79 mmol) and propylphosphonic anhydride solution (50 wt. % in EtOAc, 839 mg, 1.32 mmol) were added to the mixture. The mixture was stirred for 20 min at 0° C. then RT for 4 h. The reaction was diluted with 25 mL of EtOAc, cooled with an ice bath and quenched with 10 mL of aq. NaHCO$_3$. The organic layer was separated. The aqueous was extracted with 15 mL of EtOAc. The combine organic extracts were washed with 5 mL of brine, dried over sodium sulfate and concentrated. The residue was purified by silica gel flash chromatography (1-5% MeOH/DCM) to afford (1S,5S,6S)-ethyl 3-amino-5-(5-(5-chloropicolinamido)-2,3-difluorophenyl)-5-methyl-2-thia-4-azabicyclo[4.1.0]hept-3-ene-1-carboxylate (Example 9, 289 mg, 0.60 mmol, 91% yield) as an off white crystalline solid. MS m/z=481.0 [M+H]$^+$. $^1$H NMR (400 MHz, DMSO-d$_6$) δ 10.80 (s, 1H), 8.81 (d, J=1.76 Hz, 1H), 8.16-8.24 (m, 2H), 7.97 (m, 2H), 6.20 (br., 2H), 4.20 (q, J=7.17 Hz, 2H), 2.34 (d, J=8.22 Hz, 1H), 1.64 (s, 3H), 1.50 (m, 1H), 1.23 (t, J=7.14 Hz, 3H), 1.08 (m, 1H). $^{19}$F NMR (376 MHz, DMSO-d$_6$) δ −138.11 (d, J=20.20 Hz, 1F), −143.69 (d, J=20.20 Hz, 1F).

Preparation of N-(3-((1S,5S,6S)-3-amino-1-(hydroxymethyl)-5-methyl-2-thia-4-azabicyclo[4.1.0]hept-3-en-5-yl)-4,5-difluorophenyl)-5-chloropicolinamide (Example 10). At RT, (1S,5S,6S)-ethyl 3-amino-5-(5-(5-chloropicolinamido)-2,3-difluorophenyl)-5-methyl-2-thia-4-azabicyclo[4.1.0]hept-3-ene-1-carboxylate (Example 9, 289 mg, 0.60 mmol) in 5 mL of THF was treated with lithium borohydride (2.0 M solution in THF (0.60 mL, 1.20 mmol) followed by MeOH (0.24 mL, 6.01 mmol). After 1 h at RT, the reaction mixture was cooled with an ice bath and quenched with dropwise addition of 15 mL of aq. NH$_4$Cl. The resulting biphasic mixture was extracted with 2×40 mL of EtOAc. The organic extracts were washed with 20 mL of brine and dried over MgSO$_4$. Filtration and concentration under reduced pressure afforded a brown oil. It was purified on a silica gel column (15-45% EtOAc in hexanes) to provide N-(3-((1S,5S,6S)-3-amino-1-(hydroxymethyl)-5-methyl-2-thia-4-azabicyclo[4.1.0]hept-3-en-5-yl)-4,5-difluorophenyl)-5-chloropicolinamide (Example 10, 173 mg, 0.39 mmol, 66% yield) as an off-white crystalline solid. MS m/z=439.1 [M+H]$^+$. $^1$H NMR (400 MHz, DMSO-d$_6$) δ 10.74 (br., 1H), 8.79 (d, J=1.96 Hz, 1H), 8.14-8.23 (m, 2H), 7.87-7.98 (m, 2H), 5.95 (br., 2H), 5.05 (br., 1H), 3.55 (m, 1H), 3.44 (m, 1H), 1.70 (m, 1H), 1.61 (s, 3H), 0.86 (br., 1H), 0.58 (br., 1H). $^{19}$F NMR (376 MHz, DMSO-d$_6$) δ −138.50 (d, J=20.18 Hz, 1F), −143.58 (d, J=20.18 Hz, 1F).

Preparation of N-(3-((1S,5S,6S)-3-amino-1-(fluoromethyl)-5-methyl-2-thia-4-azabicyclo[4.1.0]hept-3-en-5-yl)-4,5-difluorophenyl)-5-chloropicolinamide (Example 12). To a solution of N-(3-((1S,5S,6S)-3-amino-1-(hydroxymethyl)-5-methyl-2-thia-4-azabicyclo[4.1.0]hept-3-en-5-yl)-4,5-difluorophenyl)-5-chloropicolinamide (Example 10, 75 mg, 0.17 mmol) in 3 mL of DCM at −30° C. (dry ice/acetone) was added diethylaminosulfur trifluoride (1 M in DCM) (342 µL, 0.34 mmol). The mixture was stirred at −30° C. for 5 min then RT for 0.5 h. The reaction mixture was cooled with an ice bath and treated with a saturated solution of NaHCO$_3$, extracted with DCM (3×50 mL), dried over MgSO$_4$, filtered and concentrated. The crude residue was purified on a silica gel column, using a gradient of 25-80% EtOAc in DCM, to provide N-(3-((1S,5S,6S)-3-amino-1-(fluoromethyl)-5-methyl-2-thia-4-azabicyclo[4.1.0]hept-3-en-5-yl)-4,5-difluorophenyl)-5-chloropicolinamide (Example 12, 31 mg, 0.07 mmol, 41% yield) as an off-white crystalline solid. MS m/z=441.0 [M+H]$^+$. $^1$H NMR (400 MHz, DMSO-d$_6$) δ 10.75 (s, 1H), 8.79 (d, J=1.96 Hz, 1H), 8.14-8.23 (m, 2H), 7.87-7.98 (m, 2H), 6.12 (br., 2H), 4.56 (m, 1H), 4.44 (m, 1H), 1.79 (m, 1H), 1.62 (s, 3H), 1.04 (dd, J=5.48, 9.19 Hz, 1H), 0.71 (m, 1H). $^{19}$F NMR (376 MHz, DMSO-d$_6$) δ −138.40 (d, J=20.22 Hz, 1F), −143.48 (d, J=20.22 Hz, 1F), −211.58 (s, 1F).

Example 28

4-((3-((1S,5S,6S)-3-amino-5-(fluoromethyl)-2-thia-4-azabicyclo[4.1.0]hept-3-en-5-yl)-4,5-difluorophenyl)amino)pyrido[3,2-d]pyrimidine-7-carbonitrile

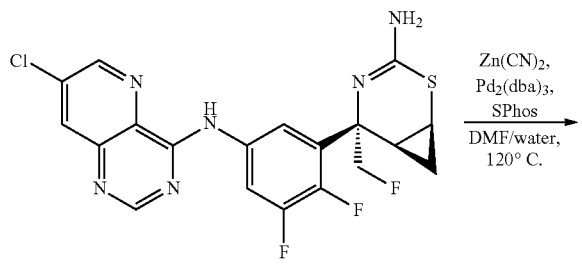

Example 22

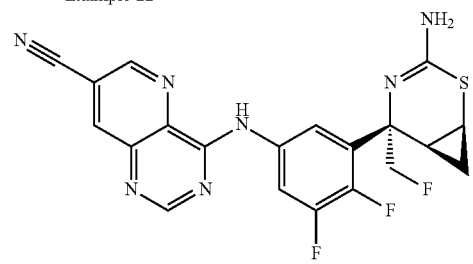

Example 28

(1S,5S,6S)-5-(5-((7-Chloropyrido[3,2-d]pyrimidin-4-yl)amino)-2,3-difluorophenyl)-5-(fluoromethyl)-2-thia-4-azabicyclo[4.1.0]hept-3-en-3-amine (Example 22, 84 mg, 0.19 mmol), zinc cyanide (33 mg, 0.28 mmol), tris(dibenzylideneacetone)dipalladium(0) (14 mg, 0.02 mmol), and 2-dicyclohexylphosphino-2',6'-dimethoxy-1,1'-biphenyl (15 mg, 0.04 mmol) were added to a round bottom flask and placed under an argon atmosphere. DMF (2 mL) and water (0.02 mL) were added, and the reaction mixture was stirred at 120° C. for 1 h. The reaction mixture was cooled to RT, diluted with water, and extracted with EtOAc. The organic layer was separated, washed with saturated aqueous sodium chloride, dried over magnesium sulfate, filtered, and concentrated in vacuo. The resulting crude residue was purified via silica gel flash column chromatography (0-100% EtOAc/heptane) to afford 4-((3-((1S,5S,6S)-3-amino-5-(fluoromethyl)-2-thia-4-azabicyclo[4.1.0]hept-3-en-5-yl)-4,5-difluorophenyl)amino)pyrido[3,2-d]pyrimidine-7-carbonitrile (Example 28, 68 mg, 0.15 mmol, 83% yield) as a light yellow solid. MS m/z=442.1 [M+H]$^+$. $^1$H NMR (400 MHz, DMSO-d$_6$) δ ppm 10.66 (s, 1H) 9.27 (d, J=1.76 Hz, 1H) 8.92 (d, J=1.96 Hz, 1H) 8.82 (s, 1H) 8.13-8.21 (m, 2H) 6.28 (s, 2H) 4.67-4.84 (m, 2H) 2.40-2.47 (m, 1H) 1.79 (q, J=7.89 Hz, 1H) 1.11 (ddd, J=8.85, 7.48, 5.18 Hz, 1H) 0.46 (q, J=5.28 Hz, 1H).

Example 30

((1S,5S,6S)-3-amino-5-(5-((3-chloro-1,7-naphthyridin-8-yl)amino)-2,3-difluorophenyl)-5-methyl-2-thia-4-azabicyclo[4.1.0]hept-3-en-1-yl)methanol

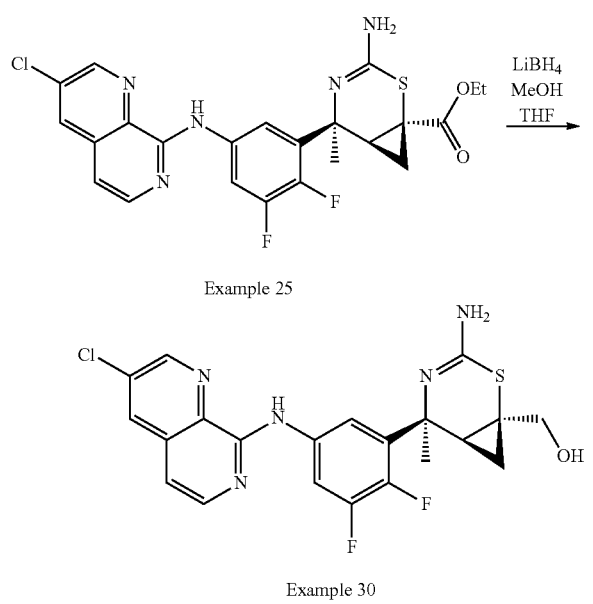

Example 30

At RT, (1S,5S,6S)-ethyl 3-amino-5-(5-((3-chloro-1,7-naphthyridin-8-yl)amino)-2,3-difluorophenyl)-5-methyl-2-thia-4-azabicyclo[4.1.0]hept-3-ene-1-carboxylate (Example 25, 236 mg, 0.47 mmol) in 4 mL of THF was treated with lithium borohydride (2.0 M solution in THF, 0.47 mL, 0.94 mmol) followed by MeOH (0.19 mL, 4.68 mmol). The reaction mixture was stirred at RT for 1 h. LCMS indicated the presence of the starting ester. Additional lithium borohydride (0.47 mL of the 2 M in THF solution, 0.94 mmol) and MeOH (0.19 mL, 4.68 mmol) were added to the reaction mixture. It was stirred at RT for 18 h. The reaction mixture was cooled with an ice bath and quenched with dropwise addition of 15 mL of aq. NH$_4$Cl. The resulting biphasic mixture was extracted with 2×40 mL of EtOAc. The organic extracts were washed with 20 mL of brine and dried over MgSO$_4$. Filtration and concentration under reduced pressure afforded a brown oil. The residue was purified on a silica gel column (15-45% EtOAc in hexanes) to provide ((1S,5S,6S)-3-amino-5-(5-((3-chloro-1,7-naphthyridin-8-yl)amino)-2,3-difluorophenyl)-5-methyl-2-thia-4-azabicyclo[4.1.0]hept-3-en-1-yl)methanol (29 mg, 0.06 mmol, 13% yield) as a yellow crystalline solid. m/z (ESI, +ve ion) 462.0 (M+1)$^+$. $^1$H NMR (400 MHz, DMSO-d$_6$) δ 9.65 (br., 1H), 8.93 (d, J=2.35 Hz, 1H), 8.55 (d, J=2.35 Hz, 1H), 8.39 (ddd, J=2.74, 6.85, 13.11 Hz, 1H), 8.20 (d, J=5.87 Hz, 1H), 7.90 (br., 1H), 7.22 (d, J=5.87 Hz, 1H), 6.01 (br., 2H), 5.07 (br., 1H), 3.56 (dd, J=6.26, 11.74 Hz, 1H), 3.47 (dd, J=5.48, 11.74 Hz, 1H), 1.68 (m, 1H), 1.64 (s, 3H), 0.91 (br., 1H), 0.62 (br., 1H).

Example 41

N-(3-((1S,5S,6S)-3-amino-1,5-bis(fluoromethyl)-2-thia-4-azabicyclo[4.1.0]hept-3-en-5-yl)-4-fluorophenyl)-5-chloro-2-pyridinecarboxamide

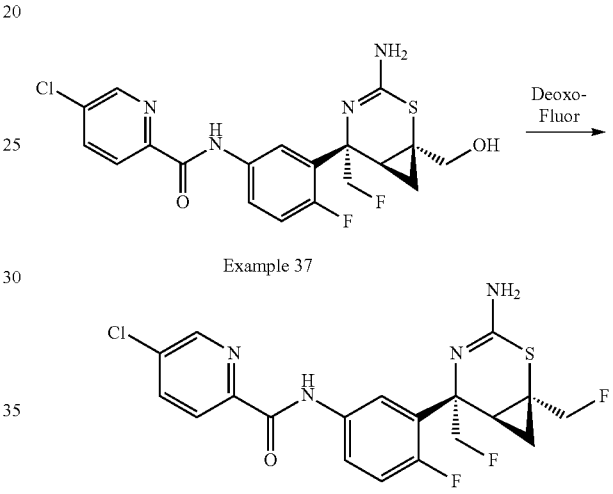

To a solution of N-(3-((1S,5S,6S)-3-amino-5-(fluoromethyl)-1-(hydroxymethyl)-2-thia-4-azabicyclo[4.1.0]hept-3-en-5-yl)-4-fluorophenyl)-5-chloropicolinamide (Example 37, 0.25 g, 0.58 mmol) in DCM (2.5 mL) at −78° C. was added Deoxo-Fluor (0.33 mL, 1.79 mmol). The reaction mixture was warmed from −78° C. to room temperature over 3 h, stirred at room temperature for 20 min and quenched with saturated NaHCO$_3$. After bubbling ceased, the mixture was transferred to a separatory funnel and diluted with water, EtOAc, and saturated NaHCO$_3$. The aqueous phase was extracted with EtOAc (3×) and the combined organic extracts were washed with brine (1×), dried over MgSO$_4$, filtered, and concentrated to give a light yellow solid. Purification by flash column chromatography on silica gel (24 g, eluted with 5-60% EtOAc in heptane) gave N-(3-((1S,5S,6S)-3-amino-1,5-bis(fluoromethyl)-2-thia-4-azabicyclo[4.1.0]hept-3-en-5-yl)-4-fluorophenyl)-5-chloropicolinamide (Example 41, 47 mg, 0.11 mmol, 18% yield) as an off-white solid. LC/MS (ESI) m/z=441.0 (M+H)$^+$. $^1$H NMR (400 MHz, CHLOROFORM-d) δ ppm 9.80 (br., 1H), 8.54 (s, 1H), 8.23 (d, J=8.61 Hz, 1H), 7.92-8.01 (m, 1H), 7.87 (d, J=8.41 Hz, 1H), 7.69 (d, J=6.85 Hz, 1H), 7.09 (t, J=11.20 Hz, 1H), 4.87 (dd, J=47.54, 9.00 Hz, 1H), 4.69 (dd, J=47.14, 8.61 Hz, 1H), 4.64 (br., 2H), 4.48 (dd, J=47.93, 10.17 Hz, 1H), 4.36 (dd, J=46.95, 9.78 Hz, 1H), 1.89 (t, J=8.02 Hz, 1H), 1.17-1.24 (m, 1H), 0.80 (br., 1H).

Example 42

N-(3-((1R,5S,6R)-3-amino-5-(fluoromethyl)-1-(hydroxymethyl)-2-thia-4-azabicyclo[4.1.0]hept-3-en-5-yl)-4-fluorophenyl)-5-chloro-2-pyridinecarboxamide

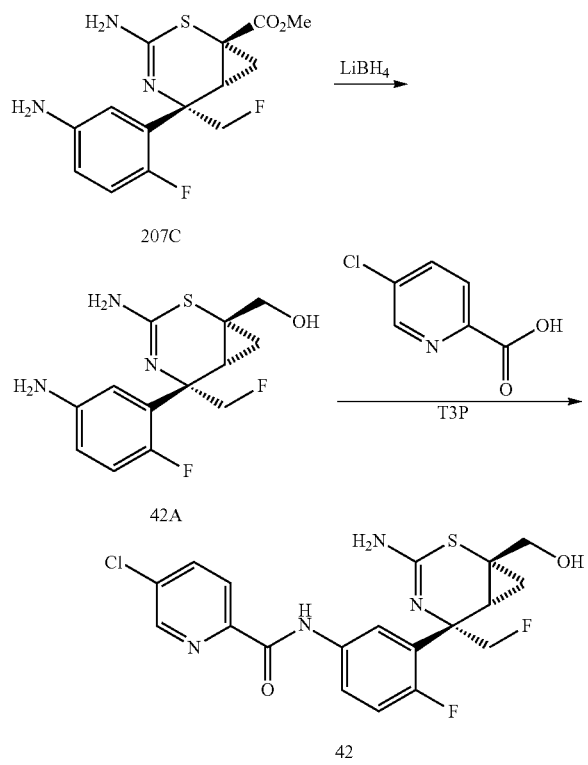

Preparation of ((1R,5S,6R)-3-amino-5-(5-amino-2-fluorophenyl)-5-(fluoromethyl)-2-thia-4-azabicyclo[4.1.0]hept-3-en-1-yl)methanol (42A). To a solution of (1R,5S,6R)-methyl 3-amino-5-(5-amino-2-fluorophenyl)-5-(fluoromethyl)-2-thia-4-azabicyclo[4.1.0]hept-3-ene-1-carboxylate (207C, 0.28 g, 0.86 mmol) in THF (3.5 mL) at room temperature was added lithium borohydride (2.0 M solution in THF, 1.30 mL, 2.60 mmol) and MeOH (0.28 mL, 6.91 mmol). The reaction mixture was stirred at room temperature for 4.5 h and quenched slowly with saturated $NH_4Cl$. After bubbling ceased, the mixture was transferred to a separatory funnel and diluted with water, EtOAc, and saturated $NH_4Cl$. The aqueous phase was extracted with EtOAc (3×) and the combined organic extracts were washed with brine (1×), dried over $MgSO_4$, filtered, concentrated. Purification by flash column chromatography on silica gel (24 g, eluted with 1-8% MeOH (2 M $NH_3$) in DCM) gave ((1R,5S,6R)-3-amino-5-(5-amino-2-fluorophenyl)-5-(fluoromethyl)-2-thia-4-azabicyclo[4.1.0]hept-3-en-1-yl)methanol (42A, 0.17 g, 0.57 mmol, 66% yield) as a white solid. LC/MS (ESI) m/z=300.0 $(M+H)^+$.

Preparation of N-(3-((1R,5S,6R)-3-amino-5-(fluoromethyl)-1-(hydroxymethyl)-2-thia-4-azabicyclo[4.1.0]hept-3-en-5-yl)-4-fluorophenyl)-5-chloro-2-pyridinecarboxamide (Example 42). To a solution of 5-chloro-2-pyridinecarboxylic acid (94 mg, 0.59 mmol) and ((1R,5S,6R)-3-amino-5-(5-amino-2-fluorophenyl)-5-(fluoromethyl)-2-thia-4-azabicyclo[4.1.0]hept-3-en-1-yl)methanol (42A, 159 mg, 0.53 mmol) in DMAc (1.5 mL) at room temperature was added 1-propylphosphonic acid cyclic anhydride (50 wt. % solution in EtOAc, 0.35 mL, 0.59 mmol). The reaction mixture was stirred at room temperature for 18 h and quenched with 1 M NaOH. The mixture was diluted with EtOAc and water (pH=10) and transferred to a separatory funnel. The aqueous phase was extracted with EtOAc (3×) and the combined organic extracts were washed with brine (1×), dried over $MgSO_4$, filtered, concentrated. Purification by flash column chromatography on silica gel (24 g, eluted with 60-100% EtOAc [10% MeOH (2 M $NH_3$)] in heptane) gave N-(3-((1R,5S,6R)-3-amino-5-(fluoromethyl)-1-(hydroxymethyl)-2-thia-4-azabicyclo[4.1.0]hept-3-en-5-yl)-4-fluorophenyl)-5-chloropicolinamide (Example 42, 145 mg, 0.33 mmol, 62% yield) as a white solid. LC/MS (ESI) m/z=439.1 $(M+H)^+$. $^1$H NMR (400 MHz, DMSO-d6) δ ppm 10.62 (s, 1H), 8.80 (d, J=2.35 Hz, 1H), 8.22 (dd, J=8.41, 2.35 Hz, 1H), 8.17 (dd, J=8.41, 0.78 Hz, 1H), 8.04 (dd, J=7.14, 2.64 Hz, 1H), 7.78-7.84 (m, 1H), 7.16 (dd, J=11.93, 8.80 Hz, 1H), 6.16 (s, 2H), 5.07 (dd, J=6.55, 5.18 Hz, 1H), 4.78 (dd, J=47.93, 8.41 Hz, 1H), 4.49 (dd, J=47.54, 8.61 Hz, 1H), 3.81 (dd, J=11.54, 6.65 Hz, 1H), 3.50 (dd, J=11.74, 5.09 Hz, 1H), 1.82 (dd, J=9.19, 6.26 Hz, 1H), 1.05 (dd, J=9.29, 5.18 Hz, 1H), 0.90 (t, J=5.58 Hz, 1H).

Example 59

N-(3-((1S,5S,6S)-3-amino-1,5-bis(fluoromethyl)-2-thia-4-azabicyclo[4.1.0]hept-3-en-5-yl)-4,5-difluorophenyl)-5-chloro-2-pyridinecarboxamide

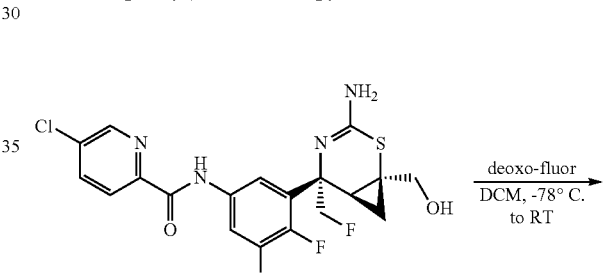

Example 31

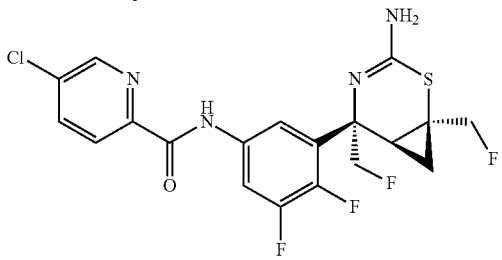

Example 59

Deoxo-fluor (0.13 mL, 0.71 mmol) was added to a stirred suspension of N-(3-((1S,5S,6S)-3-amino-5-(fluoromethyl)-1-(hydroxymethyl)-2-thia-4-azabicyclo[4.1.0]hept-3-en-5-yl)-4,5-difluorophenyl)-5-chloropicolinamide (Example 31, 108 mg, 0.24 mmol) in DCM (1 mL) at −78° C. under a nitrogen atmosphere. The reaction mixture was allowed to slowly warm up to room temperature over 1.5 h. The reaction mixture was quenched with saturated aqueous sodium bicarbonate and extracted with EtOAc. The organic layer was separated, washed with saturated aqueous sodium chloride, dried over magnesium sulfate, filtered, and concentrated in vacuo. The resulting crude residue was purified via silica gel flash column chromatography (0-70% EtOAc/ heptane) to afford N-(3-((1S,5S,6S)-3-amino-1,5-bis(fluoromethyl)-2-thia-4-azabicyclo[4.1.0]hept-3-en-5-yl)-4,5-difluorophenyl)-5-chloro-2-pyridinecarboxamide (Example 59, 33 mg, 0.07 mmol, 30% yield) as a white solid. MS m/z=459.0 [M+H]+. 1H NMR (400 MHz, CHLOROFORM-d) δ ppm 9.82 (s, 1H) 8.55 (d, J=1.96 Hz, 1H) 8.22 (d, J=8.22 Hz, 1H) 8.06-8.12 (m, 1H) 7.89 (dd, J=8.41, 2.15 Hz, 1H) 7.34-7.38 (m, 1H) 4.63-4.92 (m, 2H) 4.30-4.54 (m, 2H) 1.90 (t, J=8.22 Hz, 1H) 1.22-1.28 (m, 1H) 0.80-0.86 (m, 1H).

Example 60

8-((3-((1S,5S,6S)-3-amino-1-(fluoromethyl)-5-methyl-2-thia-4-azabicyclo[4.1.0]hept-3-en-5-yl)-4,5-difluorophenyl)amino)-1,7-naphthyridine-3-carbonitrile 1H), 9.01 (d, J=1.96 Hz, 1H), 8.25-8.39 (m, 2H), 7.95 (d, J=5.67 Hz, 1H), 7.29 (d, J=5.61 Hz, 1H), 6.15 (br., 2H), 4.56-4.41 (m, 2H), 1.86 (m, 1H), 1.64 (s, 3H), 1.07 (m, 1H), 0.75 (m, 1H). 19F NMR (376 MHz, DMSO-d6) δ −138.65 (d, J=22.70 Hz, 1F), −145.98 (d, J=22.69 Hz, 1F), −211.43 (s, 1F).

Example 62 and Example 63

N-(3-((1S,5S,6S)-3-amino-5-(fluoromethyl)-2-thia-4-azabicyclo[4.1.0]hept-3-en-5-yl)-4,5-difluorophenyl)-2-methoxypyrido[3,4-b]pyrazin-5-amine and N-(3-((1S,5S,6S)-3-amino-5-(fluoromethyl)-2-thia-4-azabicyclo[4.1.0]hept-3-en-5-yl)-4,5-difluorophenyl)-2-(1-methylethoxy)pyrido[3,4-b]pyrazin-5-amine

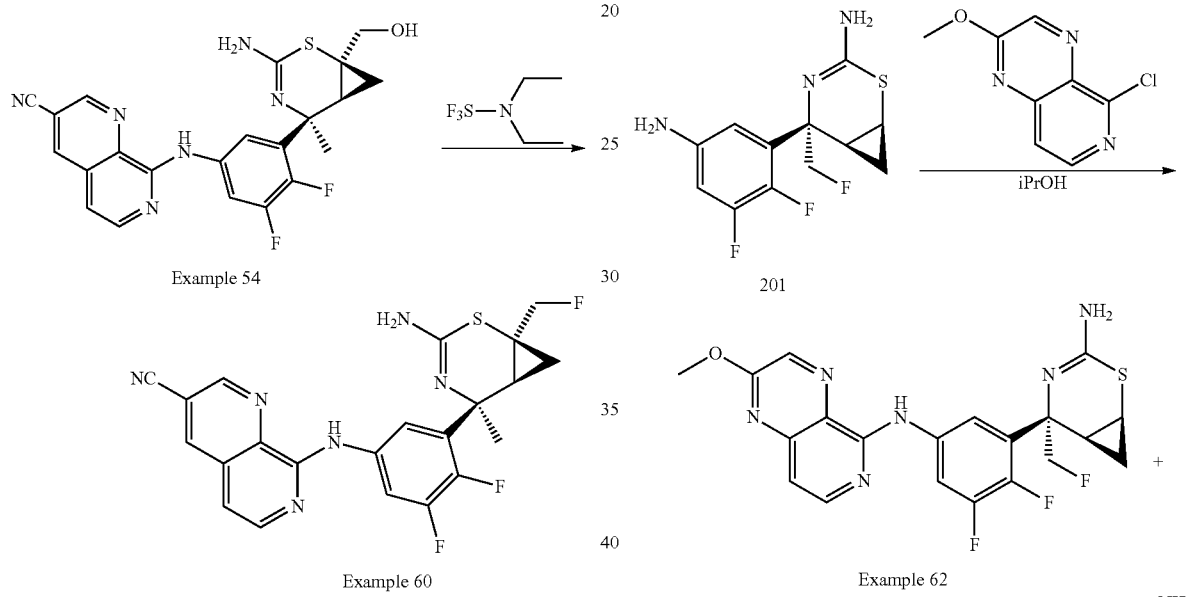

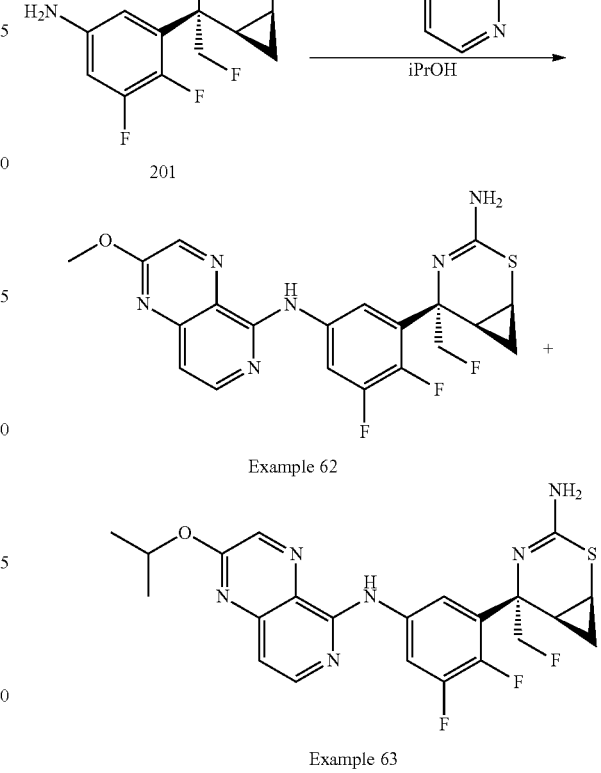

At 0° C., 8-((3-((1S,5S,6S)-3-amino-1-(hydroxymethyl)-5-methyl-2-thia-4-azabicyclo[4.1.0]hept-3-en-5-yl)-4,5-difluorophenyl)amino)-1,7-naphthyridine-3-carbonitrile (Example 54, 47 mg, 0.10 mmol) in 4 mL of DCM was treated with diethylaminosulfur trifluoride (1 M in DCM) (0.22 mL, 0.22 mmol). It was stirred at 0 OC for 30 min then RT for 1 h. LCMS indicated the presence of the staring alcohol. The reaction mixture was cooled with an ice bath and treated with additional diethylaminosulfur trifluoride (1 M in DCM) (55 μL, 55 μmol) and stirred at RT for 18 h. It was quenched with 10 mL of saturated NaHCO3 and extracted with CHCl3/iPrOH (2×15 mL, 9/1). The combined organic extracts was washed with 5 mL of brine, dried over Na2SO4 and concentrated. The residue was purified on a silica gel column (50-75% EtOAc in DCM) to afford 33 mg of yellow solid that contained the desired product [m/z (ESI, +ve ion) 455.1 (M+1)+] in about 91% purity as judged by LCMS. The material was purified on a silica gel column (65% EtOAc in DCM) to afford 8-((3-((1S,5S,6S)-3-amino-1-(fluoromethyl)-5-methyl-2-thia-4-azabicyclo[4.1.0]hept-3-en-5-yl)-4,5-difluorophenyl)amino)-1,7-naphthyridine-3-carbonitrile (Example 60, 10 mg, 0.02 mmol, 21% yield) as a brown crystalline solid. m/z (ESI, +ve ion) 455.1 (M+1)+. 1H NMR (400 MHz, DMSO-d6) δ 9.78 (br., 1H), 9.24 (d, J=4.66 Hz, (1S,5S,6S)-5-(5-amino-2,3-difluorophenyl)-5-(fluoromethyl)-2-thia-4-azabicyclo[4.1.0]hept-3-en-3-amine (Intermediate 201, 65 mg, 0.23 mmol), 5-chloro-2-methoxypyrido[3,4-b]pyrazine (49 mg, 0.25 mmol), and p-toluenesulfonic acid monohydrate (86 mg, 0.45 mmol) were mixed in isopropanol (1 mL) in a sealed tube. The reaction mixture was stirred at 80° C. for 2 h. It was cooled to RT, quenched with saturated aqueous sodium bicarbonate and extracted with EtOAc. The organic layer was separated, washed with saturated aqueous sodium chloride, dried over magnesium sulfate, filtered, and concentrated in vacuo. The resulting crude residue was purified via silica gel flash column chromatography (0-100% EtOAc/heptane) to afford two products. N-(3-((1S,5S,6S)-3-amino-5-(fluoromethyl)-2-thia-4-azabicyclo[4.1.0]hept-3-en-5-yl)-4,5-difluorophenyl)-2-(1-methylethoxy)pyrido[3,4-b]pyrazin-5-amine (Example 63, 17 mg, 36 μmol, 16% yield) was the first product to elute and was isolated as a yellow solid. MS m/z=475.1 [M+H]⁺. ¹H NMR (400 MHz, DMSO-d₆) δ ppm 9.53 (s, 1H) 8.49 (s, 1H) 8.33 (ddd, J=13.25, 6.80, 2.64 Hz, 1H) 8.27 (d, J=5.87 Hz, 1H) 7.92-7.96 (m, 1H) 7.09 (d, J=5.87 Hz, 1H) 6.26 (s, 2H) 5.48 (spt, J=6.19 Hz, 1H) 4.64-4.83 (m, 2H) 2.38-2.45 (m, 1H) 1.77 (q, J=8.35 Hz, 1H) 1.42 (d, J=6.26 Hz, 6H) 1.05-1.12 (m, 1H) 0.44 (q, J=5.22 Hz, 1H). N-(3-((1S,5S,6S)-3-amino-5-(fluoromethyl)-2-thia-4-azabicyclo[4.1.0]hept-3-en-5-yl)-4,5-difluorophenyl)-2-methoxypyrido[3,4-b]pyrazin-5-amine (Example 62, 25 mg, 56 μmol, 25% yield) was the second product to elute and was isolated as a yellow solid. MS m/z=447.0 [M+H]⁺. ¹H NMR (400 MHz, DMSO-d₆) δ ppm 9.56 (s, 1H) 8.57 (s, 1H) 8.30-8.35 (m, 1H) 8.29 (d, J=5.87 Hz, 1H) 7.93-7.97 (m, 1H) 7.13 (d, J=5.87 Hz, 1H) 6.26 (s, 2H) 4.64-4.83 (m, 2H) 4.08 (s, 3H) 2.38-2.45 (m, 1H) 1.73-1.81 (m, 1H) 1.05-1.12 (m, 1H) 0.44 (q, J=5.28 Hz, 1H).

Example 64

(1S,5S,6S)-5-(2,3-difluoro-5-((7-methoxypyrido[3,2-d]pyrimidin-4-yl)amino)phenyl)-1-(fluoromethyl)-5-methyl-2-thia-4-azabicyclo[4.1.0]hept-3-en-3-amine

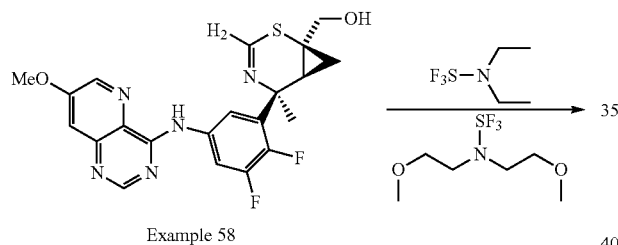

Example 58

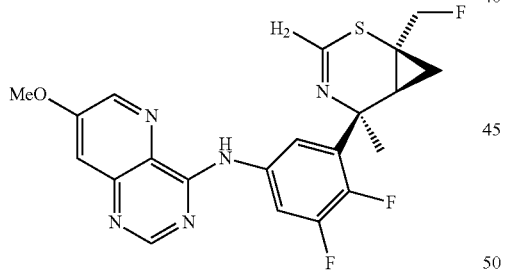

Example 64

At −60° C. to a solution of ((1S,5S,6S)-3-amino-5-(2,3-difluoro-5-((7-methoxypyrido[3,2-d]pyrimidin-4-yl)amino)phenyl)-5-methyl-2-thia-4-azabicyclo[4.1.0]hept-3-en-1-yl)methanol (Example 58, 75 mg, 0.16 mmol) in 4 mL of DCM was added diethylaminosulfur trifluoride (1 M in DCM) (0.22 mL, 0.22 mmol). The reaction mixture was slowly warmed to RT in 3 h. LCMS indicated the presence of the starting alcohol. The reaction mixture was cooled to −20° C. and treated with deoxo-fluor (0.03 mL, 0.16 mmol). The cold bath was removed and the mixture stirred at RT for 1 h. It was quenched with 10 mL of sat NaHCO₃ and extracted with CHCl₃/iPrOH (9/1, 2×15 mL). The combined organic extracts was washed with 5 mL of brine, dried over Na₂SO₄ and concentrated. The residue was purified on a silica gel column (50-100% EtOAc in hexanes followed by 5% MeOH in EtOAc) to afford (1S,5S,6S)-5-(2,3-difluoro-5-((7-methoxypyrido[3,2-d]pyrimidin-4-yl)amino)phenyl)-1-(fluoromethyl)-5-methyl-2-thia-4-azabicyclo[4.1.0]hept-3-en-3-amine (15 mg, 19% yield) as an off-white crystalline solid. m/z (ESI, +ve ion) 461.1 (M+1)⁺. ¹H NMR (400 MHz, DMSO-d₆) δ 10.16 (br., 1H), 8.68 (s, 1H), 8.66 (s, 1H), 8.20 (m, 1H), 8.04 (m, 1H), 7.64 (d, J=2.74 Hz, 1H), 6.14 (br., 2H), 4.41-4.57 (m, 2H), 4.02 (s, 3H), 1.80 (m, 1H), 1.65 (s, 3H), 1.09 (m, 1H), 0.74 (m, 1H). ¹⁹F NMR (377 MHz, DMSO-d₆) δ −138.67 (d, J=22.61 Hz, 1F), −144.46 (d, J=22.70 Hz, 1F), −211.43 (s, 1F).

Example 93

((1S,5S,6S)-3-Amino-5-(2,3-difluoro-5-((2-methoxypyrido[3,4-b]pyrazin-5-yl)amino)phenyl)-5-methyl-2-thia-4-azabicyclo[4.1.0]hept-3-en-1-yl)methanol

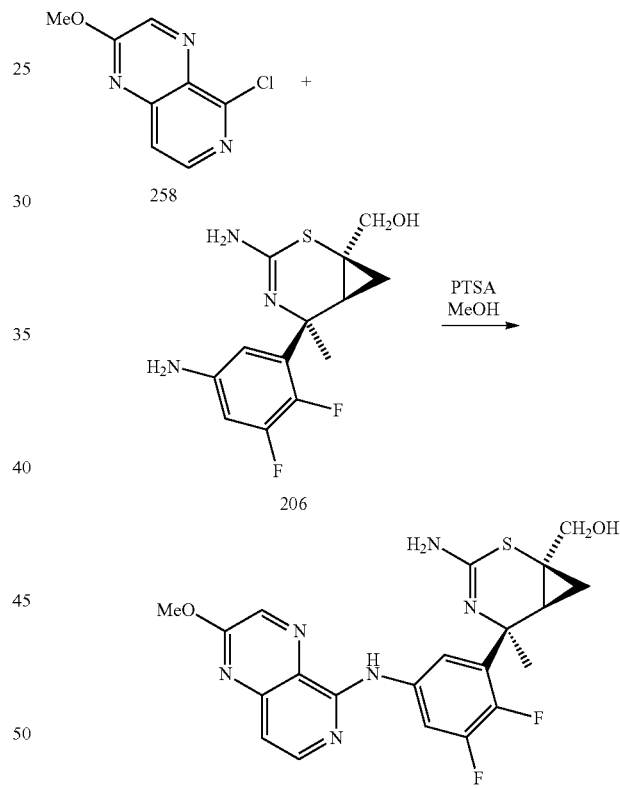

Example 93

A mixture of ((1S,5S,6S)-3-amino-5-(5-amino-2,3-difluorophenyl)-5-methyl-2-thia-4-azabicyclo[4.1.0]hept-3-en-1-yl)methanol (intermediate 206, 40 mg, 0.13 mmol), 5-chloro-2-methoxypyrido[3,4-b]pyrazine (intermediate 258, 29 mg, 0.15 mmol) and p-toluenesulfonic acid monohydrate (28 mg, 0.15 mmol) were taken up in 2 mL of MeOH in a sealable vial with a pressure relief septa. The vial was sealed and heated to 55° C. for 2 h. The mixture was cooled to RT and diluted with 20 mL of EtOAc. The mixture was washed with 10 mL of aq. NaHCO₃ and 10 mL of brine. The organic layer was dried over MgSO₄, filtered, then concentrated under reduced pressure. The residue was purified by silica gel chromatography (4 g) eluting with 1-5% MeOH in DCM to afford ((1S,5S,6S)-3-amino-5-(2,3-difluoro-5-((2-methoxypyrido[3,4-b]pyrazin-5-yl)amino)phenyl)-5-methyl-2-thia-4-azabicyclo[4.1.0]hept-3-en-1-yl)methanol (Example 93, 27 mg, 59 μmol, 44% yield) as a yellow solid. MS m/z=459.1 [M+H]$^+$. $^1$H NMR (400 MHz, CHLOROFORM-d) δ 8.65 (s, 1H), 8.46 (br. s., 1H), 8.31 (s, 1H), 8.24-8.28 (m, 1H), 7.34 (br. s., 1H), 7.08 (d, J=5.87 Hz, 1H), 4.13 (s, 3H), 3.62-3.77 (m, 2H), 3.50 (s, 1H), 1.82-1.89 (m, 1H), 1.76 (s, 3H), 0.86-0.97 (m, 1H), 0.73-0.83 (m, 1H).

Example 97

Synthesis of 4-((3-((1S,5S,6S)-3-amino-1,5-bis(fluoromethyl)-2-thia-4-azabicyclo[4.1.0]hept-3-en-5-yl)-4-fluorophenyl)amino)pyrido[3,2-d]pyrimidine-7-carbonitrile. (Method PH-3)

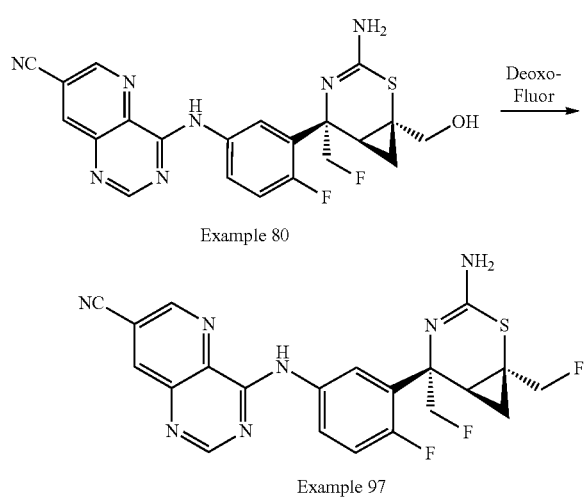

Example 97

To a suspension of 4-((3-((1S,5S,6S)-3-amino-5-(fluoromethyl)-1-(hydroxymethyl)-2-thia-4-azabicyclo[4.1.0]hept-3-en-5-yl)-4-fluorophenyl)amino)pyrido[3,2-d]pyrimidine-7-carbonitrile (Example 80, 0.30 g, 0.66 mmol) in hexanes (15 mL) at −78° C. was added bis(2-methoxyethyl)aminosulfur trifluoride (0.19 mL, 1.03 mmol). The reaction mixture was warmed from −78° C. to RT over 2 h. DCM (3 mL) was added and the reaction mixture was stirred at room temperature for 1.5 h and additional DCM (6 mL) was added. The reaction mixture was stirred at room temperature for 15 h and quenched with saturated NaHCO$_3$. The mixture was diluted with EtOAc and water and transferred to a separatory funnel. The aqueous phase was extracted with EtOAc (3×) and the combined organic extracts were washed with brine (1×), dried over MgSO$_4$, filtered, and concentrated to give a yellow solid. Purification by flash column chromatography on silica gel (40 g, eluted with 10% to 60% EtOAc (10% MeOH) in heptane) gave 4-((3-((1S,5S,6S)-3-amino-1,5-bis(fluoromethyl)-2-thia-4-azabicyclo[4.1.0]hept-3-en-5-yl)-4-fluorophenyl)amino)pyrido[3,2-d]pyrimidine-7-carbonitrile (Example 97, 0.12 g, 0.26 mmol, 40% yield) as a yellow solid. LC/MS (ESI) m/z=456.0 (M+H)$^+$. $^1$H NMR (400 MHz, CHLOROFORM-d) δ ppm 9.05 (s, 1H), 8.90 (d, J=1.76 Hz, 1H), 8.76-8.82 (m, 1H), 8.47 (d, J=1.56 Hz, 1H), 8.16 (dt, J=8.61, 3.50 Hz, 1H), 7.75-7.84 (m, 1H), 7.14 (dd, J=11.25, 8.90 Hz, 1H), 4.88 (dd, J=47.34, 8.22 Hz, 1H), 4.86 (br., 2H), 4.75 (dd, J=47.34, 8.61 Hz, 1H), 4.48 (dd, J=36.97, 9.98 Hz, 1H), 4.36 (dd, J=36.19, 9.98 Hz, 1H), 1.89 (t, J=8.12 Hz, 1H), 1.24 (dd, J=9.68, 5.97 Hz, 1H), 0.77-0.84 (m, 1H).

Example 98

N-(5-((1S,5S,6S)-3-amino-1-(fluoromethyl)-5-methyl-2-thia-4-azabicyclo[4.1.0]hept-3-en-5-yl)-6-fluoropyridin-3-yl)-5-chloropicolinamide

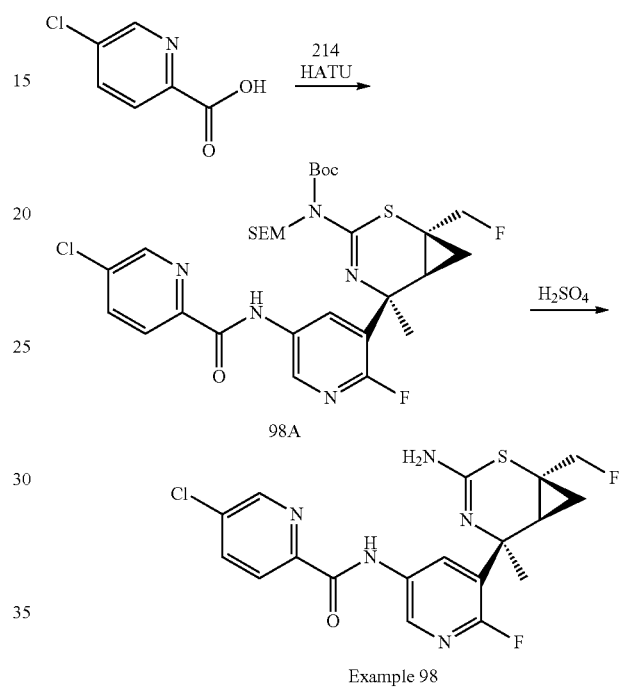

Preparation of Compound 98A. To a mixture of tert-butyl ((1S,5S,6S)-5-(5-amino-2-fluoropyridin-3-yl)-1-(fluoromethyl)-5-methyl-2-thia-4-azabicyclo[4.1.0]hept-3-en-3-yl)((2-(trimethylsilyl)ethoxy)methyl)carbamate (intermediate 214, 70 mg, 0.14 mmol), 5-chloropyridine-2-carboxylic acid (28 mg, 0.18 mmol), and TEA (0.06 mL, 0.41 mmol) in DMF (1.0 mL) at RT was added HATU (78 mg, 0.20 mmol). The reaction mixture was stirred at RT for 2 h, then diluted with water and extracted with EtOAc (2×). The organic extracts were dried over Na$_2$SO$_4$, filtered, and concentrated. The residue was purified by ISCO eluting with 0-40% EtOAc in heptane to afford tert-butyl((1S,5S,6S)-5-(5-(5-chloropicolinamido)-2-fluoropyridin-3-yl)-1-(fluoromethyl)-5-methyl-2-thia-4-azabicyclo[4.1.0]hept-3-en-3-yl)((2-(trimethylsilyl)ethoxy)methyl)carbamate (98A, 66 mg, 0.10 mmol, 74% yield). LCMS m/z=654.0 [M+H]$^+$. $^1$H NMR (300 MHz, CHLOROFORM-d) δ 9.85 (s, 1H), 8.68-8.76 (m, 1H), 8.57 (d, J=1.90 Hz, 1H), 8.38 (dd, J=2.78, 8.62 Hz, 1H), 8.26 (d, J=8.18 Hz, 1H), 7.91 (dd, J=2.41, 8.40 Hz, 1H), 5.31-5.44 (d, J=10.52 Hz, 1H), 5.14 (d, J=10.52 Hz, 1H), 4.50 (d, 2H), 3.70 (t, J=8.26 Hz, 2H), 2.01-2.14 (m, 1H), 1.77 (s, 3H), 1.56 (s, 9H), 0.88-1.06 (m, 4H), 0.01 (s, 9H). $^{19}$F NMR (282 MHz, CHLOROFORM-d) δ −69.42 (s, 1F), −213.24 (s, 1F).

Preparation of Example 98. At RT, concentrated sulfuric acid (0.4 mL, 7.2 mmol) was added to tert-butyl((1S,5S, 6S)-5-(5-(5-chloropicolinamido)-2-fluoropyridin-3-yl)-1-(fluoromethyl)-5-methyl-2-thia-4-azabicyclo[4.1.0]hept-3- en-3-yl)((2-(trimethylsilyl)ethoxy)methyl)carbamate (98A, 60 mg, 0.09 mmol) and the mixture stirred at RT for 15 min. It was poured onto ice and the pH was adjusted to 13 by addition of 5 N NaOH (~3.0 mL). The resulting solution was extracted with EtOAc (2×). The combined organic extracts were dried with sodium sulfate, filtered and concentrated in vacuo. The residue was purified by silica gel chromatography using ISCO (0-80% EtOAc in heptane) to afford N-(5-((1S,5S,6S)-3-amino-1-(fluoromethyl)-5-methyl-2-thia-4-azabicyclo[4.1.0]hept-3-en-5-yl)-6-fluoropyridin-3-yl)-5-chloropicolinamide (Example 98, 28 mg, 0.07 mmol, 72% yield). LC/MS (ESI$^+$) m/z=424.0 (M+H). $^1$H NMR (300 MHz, CHLOROFORM-d) δ 9.88 (s, 1H), 8.54-8.66 (m, 2H), 8.44 (dd, J=2.78, 8.62 Hz, 1H), 8.24 (d, J=8.33 Hz, 1H), 7.90 (dd, J=2.34, 8.33 Hz, 1H), 4.43-4.63 (m, 1H), 4.26-4.42 (m, 1H), 1.84-2.00 (m, 1H), 1.73 (d, J=1.17 Hz, 3H), 0.98 (d, J=6.14 Hz, 1H), 0.86 (dt, J=4.09, 6.36 Hz, 1H). The peak for NH$_2$ is broad, over 4.75-3.75 ppm. $^{19}$F NMR (282 MHz, CHLOROFORM-d) δ −68.62 (s, 1F), −212.75 (s, 1F).

Example 100

Synthesis of N-(5-((1S,5S,6S)-3-amino-1-(hydroxymethyl)-5-methyl-2-thia-4-azabicyclo[4.1.0]hept-3-en-5-yl)-6-fluoropyridin-3-yl)-5-chloropicolinamide

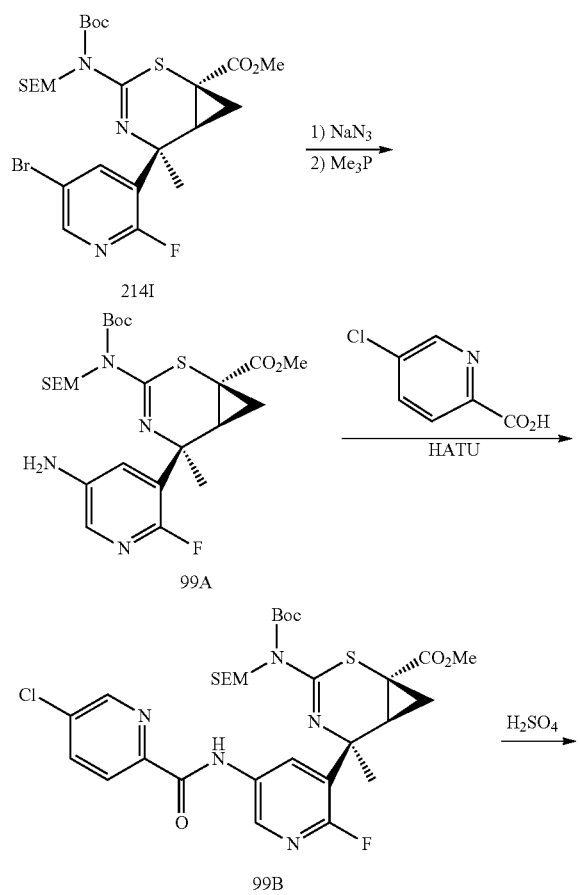

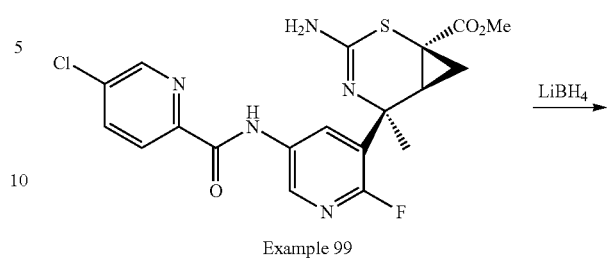

Example 99

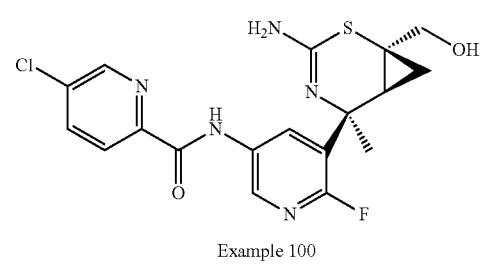

Example 100

Preparation of Compound 99A. A microwave vial was charged with (1S,5S,6S)-methyl 5-(5-bromo-2-fluoropyridin-3-yl)-3-((tert-butoxycarbonyl)((2-(trimethylsilyl)ethoxy)methyl)amino)-5-methyl-2-thia-4-azabicyclo[4.1.0]hept-3-ene-1-carboxylate (214I, 240 mg, 0.39 mmol), sodium azide (129 mg, 1.98 mmol), copper(I) iodide (30 mg, 0.16 mmol), sodium (R)-2-((S)-1,2-dihydroxyethyl)-4-hydroxy-5-oxo-2,5-dihydrofuran-3-olate (15 mg, 0.08 mmol), EtOH (2.0 mL) and water (0.2 mL), then purged with N$_2$ and sealed. Then (1R,2R)—N1,N2-dimethylcyclohexane-1,2-diamine (25 μL, 0.16 mmol) was added via a syringe. The mixture was heated at 80° C. for 1 h, cooled to RT, treated with saturated NH$_4$Cl and diluted with EtOAc. The organic layer was separated and the aqueous layer was extracted twice with EtOAc. The combined organic solution was washed with brine, dried over Na$_2$SO$_4$, and concentrated in vacuo. The crude material was used in next step directly.

To a solution of the above crude product in THF (3 mL) and water (1 mL) was added trimethylphosphine (1.0 M solution in THF, 0.47 mL, 0.47 mmol). After 10 min, LCMS showed the reaction was complete. The mixture was evaporated to dryness and the residue was purified by a quick silica gel chromatography (0-50% EtOAc in DCM) to give (1S,5S,6S)-methyl 5-(5-amino-2-fluoropyridin-3-yl)-3-((tert-butoxycarbonyl)((2-(trimethylsilyl)ethoxy)methyl)amino)-5-methyl-2-thia-4-azabicyclo[4.1.0]hept-3-ene-1-carboxylate (99A, 150 mg, 0.28 mmol, 70% yield) as a white solid (containing about 10% of the ethyl ester). LCMS m/z=540.72 [M+H]$^+$. $^1$H NMR (400 MHz, CHLOROFORM-d) δ 7.51 (d, J=2.35 Hz, 1H), 7.43 (dd, J=2.93, 8.41 Hz, 1H), 5.27 (d, J=10.76 Hz, 1H), 5.01 (d, J=10.56 Hz, 1H), 3.78 (s, 3H), 3.64 (t, J=8.22 Hz, 2H), 2.58-2.74 (m, 1H), 1.70 (s, 3H), 1.51 (s, 10H), 1.45 (dd, J=5.18, 9.88 Hz, 1H), 1.14 (dd, J=5.28, 7.43 Hz, 1H), 0.87-0.99 (m, 2H), 0.00 (s, 9H).

Preparation of Compound 99B. To a mixture of (1S,5S,6S)-methyl 5-(5-amino-2-fluoropyridin-3-yl)-3-((tert-butoxycarbonyl)((2-(trimethylsilyl)ethoxy)methyl)amino)-5-methyl-2-thia-4-azabicyclo[4.1.0]hept-3-ene-1-carboxylate (99A, 50 mg, 0.09 mmol) and 5-chloro-2-pyridinecarboxylic acid (29 mg, 0.18 mmol) in 0.5 mL of DMF was added HATU (70 mg, 0.18 mmol) and diisopropylethylamine (32 µL, 0.18 mmol). After stirring overnight, the reaction was quenched with sat. NH₄Cl, extracted with EtOAc, dried over Na₂SO₄, filtered, and evaporated to dryness. The residue was purified by flash column (10-100% EtOAc in DCM) to afford (1S,5S,6S)-methyl 3-((tert-butoxycarbonyl)((2-(trimethylsilyl)ethoxy)methyl)amino)-5-(5-(5-chloropicolinamido)-2-fluoropyridin-3-yl)-5-methyl-2-thia-4-azabicyclo[4.1.0]hept-3-ene-1-carboxylate (99B, 51 mg, 0.07 mmol, 81% yield) as a gum. LCMS m/z=680.0 [M+H]⁺. ¹H NMR (300 MHz, CHLOROFORM-d) δ 9.86 (s, 1H), 8.72 (d, J=1.90 Hz, 1H), 8.59 (d, J=1.90 Hz, 1H), 8.41 (dd, J=2.70, 8.55 Hz, 1H), 8.27 (d, J=8.33 Hz, 1H), 7.93 (dd, J=2.34, 8.33 Hz, 1H), 5.38 (d, J=10.52 Hz, 1H), 5.13 (d, J=10.52 Hz, 1H), 3.83 (s, 3H), 3.71 (t, J=8.26 Hz, 2H), 2.73 (t, J=8.70 Hz, 1H), 1.80 (s, 3H), 1.57 (s, 9H), 1.48-1.55 (m, 1H), 1.18-1.25 (m, 1H), 0.99 (dd, J=6.80, 9.43 Hz, 2H), 0.00 (s, 9H).

Preparation of Example 99. To (1S,5S,6S)-methyl 3-((tert-butoxycarbonyl)((2-(trimethylsilyl)ethoxy)methyl)amino)-5-(5-(5-chloropicolinamido)-2-fluoropyridin-3-yl)-5-methyl-2-thia-4-azabicyclo[4.1.0]hept-3-ene-1-carboxylate (99A, 50 mg, 0.07 mmol) at RT was added sulfuric acid (157 µL, 2.94 mmol). After stirring for 15 min, the reaction was quenched by slow addition of saturated NaHCO₃ solution (until pH was about 8). The mixture was extracted with EtOAc three times, dried over Na₂SO₄, filtered and evaporated to dryness. Flash chromatography (10-90% EtOAc in DCM) gave (1S,5S,6S)-methyl 3-amino-5-(5-(5-chloropicolinamido)-2-fluoropyridin-3-yl)-5-methyl-2-thia-4-azabicyclo[4.1.0]hept-3-ene-1-carboxylate (Example 99, 31 mg, 94% yield) as a white solid. LCMS m/z=449.9 [M+H]⁺. ¹H NMR (300 MHz, CHLOROFORM-d) δ 9.87 (s, 1H), 8.61-8.68 (m, 1H), 8.57 (d, J=2.34 Hz, 1H), 8.47 (dd, J=2.78, 8.62 Hz, 1H), 8.21-8.30 (m, 1H), 7.90 (dd, J=2.34, 8.33 Hz, 1H), 3.80 (s, 3H), 2.62 (ddd, J=1.24, 7.67, 9.79 Hz, 1H), 1.72 (d, J=1.32 Hz, 3H), 1.53 (dd, J=5.19, 9.72 Hz, 1H), 1.13 (dd, J=5.26, 7.45 Hz, 2H).

Preparation of Example 100. To a solution of (1S,5S,6S)-methyl 3-amino-5-(5-(5-chloropicolinamido)-2-fluoropyridin-3-yl)-5-methyl-2-thia-4-azabicyclo[4.1.0]hept-3-ene-1-carboxylate (Example 99, 26 mg, 0.06 mmol) in 5 mL of THF at RT was added lithium borohydride (72 µL of 2 M solution in THF, 0.14 mmol) followed by two drops of methanol. After stirring for 1 h, the reaction was quenched by the careful addition of satd. NH₄Cl. It was extracted with EtOAc (2×). The combined organic extracts were dried (Na₂SO₄), filtered, and concentrated in vacuo. Flash chromatography (10-90% EtOAc in DCM) gave N-(5-((1S,5S,6S)-3-amino-1-(hydroxymethyl)-5-methyl-2-thia-4-azabicyclo[4.1.0]hept-3-en-5-yl)-6-fluoropyridin-3-yl)-5-chloropicolinamide (Example 100, 12 mg, 49% yield) as a white solid. LCMS m/z=422.0 [M+H]⁺. ¹H NMR (300 MHz, MeOH) δ 8.74 (d, J=2.34 Hz, 1H), 8.62 (dd, J=1.75, 2.63 Hz, 1H), 8.52 (dd, J=2.63, 8.77 Hz, 1H), 8.20-8.28 (m, 1H), 8.11 (dd, J=2.34, 8.48 Hz, 1H), 3.59-3.76 (m, 2H), 1.79-1.86 (m, 1H), 1.78 (d, J=1.32 Hz, 3H), 1.03 (dd, J=5.70, 9.35 Hz, 1H), 0.77 (t, J=5.99 Hz, 1H).

Example 636

(1S,5S,6S)-5-(2,3-difluoro-5-((7-fluoropyrido[3,2-d]pyrimidin-4-yl)amino)phenyl)-5-methyl-2-thia-4-azabicyclo[4.1.0]hept-3-en-3-amine

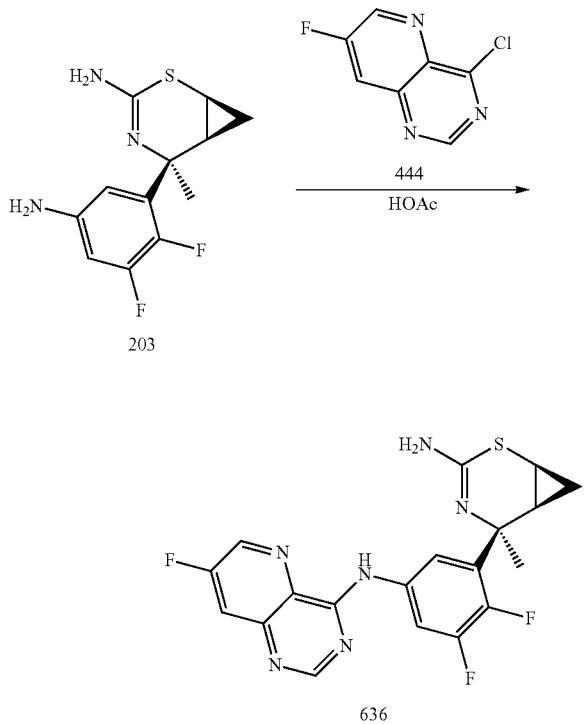

A mixture of (1S,5S,6S)-5-(5-amino-2,3-difluorophenyl)-5-methyl-2-thia-4-azabicyclo[4.1.0]hept-3-en-3-amine (0.05 g, 0.18 mmol) and 4-chloro-7-fluoropyrido[3,2-d]pyrimidine (0.068 g, 0.37 mmol) in HOAc (0.5 mL) was heated to 80° C. for 3 h. The mixture was cooled to RT, diluted with EtOAc, and then washed with saturated aqueous sodium bicarbonate solution several times. The resulting organic solution was then dried over anhydrous magnesium sulfate, filtered, and concentrated in vacuo to give an oil. The oil was purified by silica gel chromatography (0-5% MeOH in DCM) to give the title compound as a yellow solid. ¹H NMR (CHLOROFORM-d) δ ppm 9.08 (br. s., 1H) 8.78 (s, 1H) 8.67 (d, J=2.74 Hz, 1H) 8.34-8.41 (m, 1H) 7.82 (dd, J=8.80, 2.54 Hz, 1H) 7.47 (dd, J=5.38, 2.45 Hz, 1H) 2.20-2.27 (m, 1H) 1.91-2.01 (m, 1H) 1.80 (s, 3H) 0.90-1.01 (m, 1H) 0.63 (dd, J=11.35, 5.67 Hz, 1H). MS m/z=417.0 [M+H]⁺.

Example 637

N-(5-((1S,5S,6S)-3-Amino-5-methyl-2-thia-4-azabicyclo[4.1.0]hept-3-en-5-yl)-6-fluoropyridin-3-yl)-5-chloropicolinamide

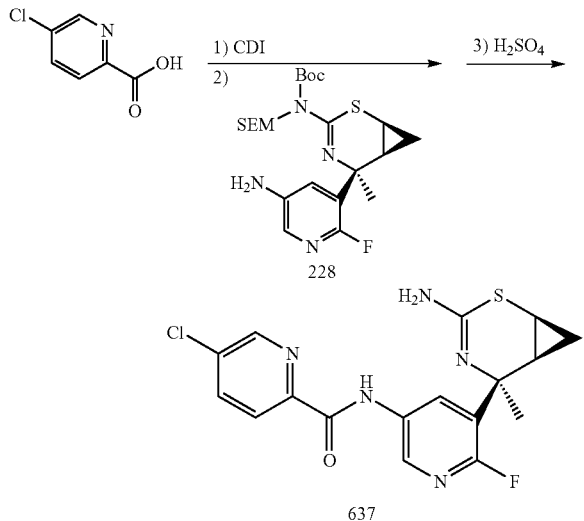

Flask A: A mixture of CDI (35 mg, 0.22 mmol) and 5-chloro-2-pyridinecarboxylic acid (34 mg, 0.22 mmol) in DMF (0.6 mL) was stirred as gas evolution occurred in ~1 min. The mixture was heated at 60° C. for 10 min then cooled to RT. Flask B: at RT, a solution of tert-butyl((1S,5S,6S)-5-(5-amino-2-fluoropyridin-3-yl)-5-methyl-2-thia-4-azabicyclo[4.1.0]hept-3-en-3-yl)((2-(trimethylsilyl)ethoxy)methyl)carbamate (intermediate 228) (30 mg, 0.06 mmol) in DMF (0.5 mL) was treated with the solution from Flask A (0.2 mL, ~1.15 equiv). The mixture in Flask B was heated at 60° C. for 30 min. Additional portion of the solution from Flask A (0.1 mL) was added to Flask B. After heating for 2 days, the mixture in Flask B was diluted with EtOAc (10 mL) and washed sequentially with water (2 mL), saturated $NaHCO_3$ (2 mL) and brine (2 mL). The aqueous layer was extracted with EtOAc (5 mL). The combined organic layer was dried over $Na_2SO_4$, filtered, and concentrated to give a yellow oil. LCMS (ESI, pos.) 622 (M+1). At RT, the yellow oil was treated with sulfuric acid (0.25 mL, 4.69 mmol). After 20 min, the mixture was quenched with ice (5 g) and treated with NaOH (5 N) until the pH reached >12. The mixture was extracted with DCM (3×5 mL). The combined organic extracts were dried over $Na_2SO_4$, filtered, and concentrated. The residue was purified by chromatography on silica using [10% (2 N $NH_3$ in MeOH) in DCM] in heptane (10-50%) as the eluent to give the product which was lyophilized (ACN-water) to afford Example 637 as a white flake (15 mg, 63%). LCMS (ESI, pos.) 392 (M+1). $^1$H NMR (400 MHz, ACETONITRILE-d3) δ 9.99 (br. s., 1H, NH), 8.67 (d, J=1.76 Hz, 1H), 8.52-8.57 (m, 1H), 8.48 (dd, J=2.74, 8.80 Hz, 1H), 8.19 (d, J=8.41 Hz, 1H), 8.02 (dd, J=2.35, 8.41 Hz, 1H), 4.88 (br., 2H, NH2), 2.26 (ddd, J=4.89, 7.63, 9.19 Hz, 2H), 1.84-1.92 (m, 1H), 1.67 (d, J=1.17 Hz, 3H), 0.80-0.90 (m, 1H), 0.43-0.51 (m, 1H).

Examples 5-((5-((1S,5S,6S)-3-amino-5-methyl-2-thia-4-azabicyclo[4.1.0]hept-3-en-5-yl)-6-fluoropyridin-3-yl)amino)pyrido[3,4-b]pyrazin-2(1H)-one (638) and (1S,5S,6S)-5-(2-fluoro-5-((2-(prop-2-yn-1-yloxy)pyrido[3,4-b]pyrazin-5-yl)amino)pyridin-3-yl)-5-methyl-2-thia-4-azabicyclo[4.1.0]hept-3-en-3-amine (639)

A mixture of tert-butyl((1S,5S,6S)-5-(5-amino-2-fluoropyridin-3-yl)-5-methyl-2-thia-4-azabicyclo[4.1.0]hept-3-en-3-yl)((2-(trimethylsilyl)ethoxy)methyl)carbamate (intermediate 228) (82 mg, 0.17 mmol), 5-chloro-2-(prop-2-yn-1-yloxy)pyrido[3,4-b]pyrazine (intermediate 262) (53 mg, 0.24 mmol), and p-toluenesulfonic acid (60 mg, 0.315 mmol) in IPA (2 mL) was heated at 80° C. for 1 h. The solvent was concentrated and the residue was treated with sulfuric acid (0.25 mL, 4.69 mmol) and heated at 50° C. for 1 h. The mixture was quenched with ice (5 g) and treated with NaOH (5 N) until the pH reached >12. The mixture was extracted with DCM (3×5 mL). The combined organic phase was dried over MgSO$_4$, filtered, and concentrated. The residue was purified by chromatography on silica using a gradient of [10% (2 N NH$_3$ in MeOH) in EtOAc] in DCM (10-70%) to give two fractions: 1$^{st}$ fraction was a mixture of Example 639 and Example 638; the 2$^{nd}$ fraction was the pure Example 638 (9 mg, 12% yield) as a yellow solid. The analytical data for Example 638: $^1$H NMR (400 MHz, DMSO-d6) δ 12.57 (br. s., 1H), 9.41 (s, 1H), 8.42-8.69 (m, 2H), 7.99-8.18 (m, 2H), 6.63 (d, J=5.67 Hz, 1H), 5.96 (br. s., 2H), 2.26-2.40 (m, 1H), 1.68-1.82 (m, 1H), 1.63 (s, 3H), 0.86 (d, J=4.69 Hz, 1H), 0.37-0.51 (m, 1H). LCMS (ESI, pos.) 398.0 (M+1).

The mixture of Example 639 and Example 638 was purified by reverse-phase preparative HPLC (Gilson GX281) using a Phenomenex Gemini column, 5 micron, C18, 110 Å, 150×30 mm, 0.1% TFA in CH$_3$CN/H$_2$O, gradient 5% to 60% over 16 min. The fraction containing Example 639 was concentrated and partitioned between saturated NaHCO$_3$ (5 mL) and IPA (3%)—CH$_3$Cl (10 mL). The organic phase was washed again with saturated NaHCO$_3$ (5 mL) and concentrated. This material was dried (lyophilized from ACN-water) to provide (1S,5S,6S)-5-(2-fluoro-5-((2-(prop-2-yn-1-yloxy)pyrido[3,4-b]pyrazin-5-yl)amino)pyridin-3-yl)-5-methyl-2-thia-4-azabicyclo[4.1.0]hept-3-en-3-amine (Example 639, 26 mg, 38% yield) as a yellow flake. $^1$H NMR (400 MHz, ACETONITRILE-d3) δ 8.83 (s, 1H), 8.75 (t, J=2.35 Hz, 1H), 8.62 (dd, J=2.74, 9.00 Hz, 1H), 8.47 (s, 1H), 8.29 (d, J=5.87 Hz, 1H), 7.11 (d, J=5.87 Hz, 1H), 5.19 (d, J=2.35 Hz, 2H), 4.85 (br. s., 1H), 2.90 (t, J=2.45 Hz, 1H), 2.30 (ddd, J=4.99, 7.58, 9.34 Hz, 1H), 1.86-1.94 (m, 1H), 1.71 (d, J=1.17 Hz, 3H), 0.90 (ddd, J=5.38, 7.58, 8.95 Hz, 1H), 0.48-0.57 (m, 1H). LCMS (ESI, pos.) 436.1 (M+1).

Example 722

N-(3-((1S,5S,6S)-3-amino-5-(fluoromethyl)-1-(1H-1,2,3-triazol-1-ylmethyl)-2-thia-4-azabicyclo[4.1.0]hept-3-en-5-yl)-4-fluorophenyl)-5-chloro-2-pyridinecarboxamide

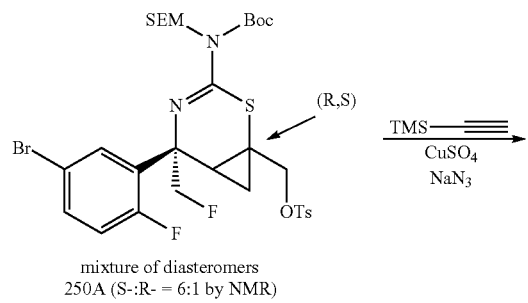

Preparation of Compound 722A. To a solution of Compound 250A, as a mixture of [(1S,5S,6S)-5-(5-bromo-2-fluorophenyl)-3-[(tert-butoxycarbonyl){[2-(trimethylsilyl)ethoxy]methyl}amino]-5-(fluoromethyl)-2-thia-4-azabicyclo[4.1.0]hept-3-en-1-yl]methyl 4-methylbenzenesulfonate (major) and [(1R,5S,6R)-5-(5-bromo-2-fluorophenyl)-3-[(tert-butoxycarbonyl){[2-(trimethylsilyl)ethoxy]methyl}amino]-5-(fluoromethyl)-2-thia-4-azabicyclo[4.1.0]hept-3-en-1-yl]methyl 4-methylbenzenesulfonate (minor), (1.1 g, 1.471 mmol) in DMSO (9 mL) was added sodium azide (0.115 g, 1.765 mmol). After addition, the mixture was then stirred at RT overnight. (+)-Sodium L-ascorbate (0.073 g, 0.368 mmol), copper (ii) sulfate pentahydrate (0.367 g, 1.471 mmol), and (trimethylsilyl)-acetylene (0.416 mL, 2.940 mmol) were added. After the mixture was then stirred at RT for 2 h, it was quenched with NH$_4$Cl/NH$_4$OH (10:1, 5 mL) and extracted with EtOAc (2×10 mL). The combined organic extracts were dried over MgSO$_4$ and concentrated. The residue was purified by silica gel flash column chromatography using ISCO instrument (0-100% EtOAc/heptane) to give Compound 722A as a mixture of diastereomers, tert-butyl((1S,5S,6S)-5-(5-bromo-2-fluorophenyl)-5-(fluoromethyl)-1-((4-(trimethylsilyl)-1H-1,2,3-triazol-1-yl)methyl)-2-thia-4-azabicyclo[4.1.0]hept-3-en-3-yl)((2-(trimethylsilyl)ethoxy)methyl)carbamate and tert-butyl((1R,5S,6R)-5-(5-bromo-2-fluorophenyl)-5-(fluoromethyl)-1-((4-(trimethylsilyl)-1H-1,2,3-triazol-1-yl)methyl)-2-thia-4-azabicyclo[4.1.0]hept-3-en-3-yl)((2-(trimethylsilyl)ethoxy)methyl)carbamate (725 mg, 1.011 mmol, 69% yield) as a colorless solid. MS (ESI, positive ion) m/z: 716, 718 (M+1).

Preparation of Compound 722B. To a solution of 722A (720 mg, 1.004 mmol) in EtOH (3.0 mL) and water (1.0 mL) was added sodium azide (196 mg, 3.01 mmol), copper(i) iodide (47.8 mg, 0.25 mmol) and (+)-sodium L-ascorbate (49.7 mg, 0.25 mmol). The mixture was then bubbled through N$_2$ for 5 min and then trans-N,N'-dimethylcyclohexane-1,2-diamine (0.040 mL, 0.251 mmol) was added. The resulting mixture was then stirred at 70° C. for 2 h under N$_2$. It was quenched with saturated NH$_4$Cl/NH$_4$OH (10:1, 5 mL), extracted with EtOAc (2×). The combined organic extracts were dried over MgSO$_4$ and concentrated. The residue was then dissolved in THF/H$_2$O (9:1, 5 mL) and trimethylphosphine (1.0 M solution in THF, 1.00 mL, 1.00 mmol) was added dropwise. After the addition, the mixture was stirred at RT under N$_2$ for 72 h. Trimethylphosphine (1.0 M solution in THF, 0.5 mL) was added to the mixture and stirring was continued for 30 min. The mixture was treated with saturated NaHCO$_3$ (5 mL) extracted with EtOAc (2×5 mL). The combined organic extracts were dried over MgSO$_4$ and concentrated. The residue was purified by silica gel flash column chromatography using ISCO instrument (0-100% EtOAc/heptane) to give a product (547 mg, 0.84 mmol, 83% yield) as a mixture of tert-butyl((1S,5S,6S)-5-(5-amino-2-fluorophenyl)-5-(fluoromethyl)-1-((4-(trimethylsilyl)-1H-1,2,3-triazol-1-yl)methyl)-2-thia-4-azabicyclo[4.1.0]hept-3-en-3-yl)((2-(trimethylsilyl)ethoxy)methyl)carbamate and tert-butyl((1R,5S,6R)-5-(5-amino-2-fluorophenyl)-5-(fluoromethyl)-1-((4-(trimethylsilyl)-1H-1,2,3-triazol-1-yl)methyl)-2-thia-4-azabicyclo[4.1.0]hept-3-en-3-yl)((2-(trimethylsilyl)ethoxy)methyl)carbamate as a colorless oil. MS (ESI, positive ion) m/z: 653.3 (M+1).

Preparation of Compound 722C. To a round bottom flask containing 722B (540 mg, 0.83 mmol) at 0° C. was added sulfuric acid (3.08 mL) dropwise. After the addition, the mixture was stirred at RT for 20 min, and treated with 20 g of ice. The mixture was cooled with an ice bath and treated with 5 N NaOH till pH>12. It was extracted with EtOAc (2×10 mL). The combined organic extracts were then dried over MgSO$_4$, concentrated, and dried in vacuo to give 722C as a yellow oil, as a mixture of (1S,5S,6S)-5-(5-amino-2-fluorophenyl)-5-(fluoromethyl)-1-((4-(trimethylsilyl)-1H-1,2,3-triazol-1-yl)methyl)-2-thia-4-azabicyclo[4.1.0]hept-3-en-3-amine and (1R,5S,6R)-5-(5-amino-2-fluorophenyl)-5-(fluoromethyl)-1-((4-(trimethylsilyl)-1H-1,2,3-triazol-1-yl)methyl)-2-thia-4-azabicyclo[4.1.0]hept-3-en-3-amine which was used in the next step without purification requirement. MS (ESI, positive ion) m/z: 423.0 (M+1).

Preparation of Compound 722D. To a solution of 722C (67 mg, 0.159 mmol) in THF (0.3 mL) was added TBAF solution (1.0 M in THF, 0.317 mL, 0.317 mmol). Then, the mixture was stirred at 60° C. for 9 h. It was cooled to RT, treated with saturated NaHCO$_3$ (1 mL) and saturated NH$_4$Cl (1 mL). The mixture was extracted with EtOAc (2×4 mL). The combined organic extracts were dried over MgSO$_4$, concentrated. The residue was purified by silica gel flash column chromatography using ISCO instrument (0-30% MeOH/DCM) to give 68 mg of 722D as a yellow oil, as a mixture of (1S,5S,6S)-1-((1H-1,2,3-triazol-1-yl)methyl)-5-(5-amino-2-fluorophenyl)-5-(fluoromethyl)-2-thia-4-azabicyclo[4.1.0]hept-3-en-3-amine and (1R,5S,6R)-1-((1H-1,2,3-triazol-1-yl)methyl)-5-(5-amino-2-fluorophenyl)-5-(fluoromethyl)-2-thia-4-azabicyclo[4.1.0]hept-3-en-3-amine. MS (ESI, positive ion) m/z: 351.0 (M+1).

Preparation of Example 722. To a solution of 722D (16.2 mg, 0.10 mmol) in DMA (1.2 mL) was added 5-chloro-2-pyridinecarboxylic acid (16.2 mg, 0.10 mmol). The mixture was cooled to 0° C. and propylphosphonic anhydride solution (50 wt. % in EtOAc, 0.082 mL, 0.128 mmol) was added. After addition, the mixture was stirred at RT overnight, then quenched with saturated NaHCO$_3$ (2 mL) and extracted with EtOAc (2×5 mL). The combined organic extracts were dried over MgSO$_4$ and concentrated. The residue was purified by preparative HPLC (0%-100% ACN 0.1% TFA/H$_2$O 0.1% TFA). The desired fractions were concentrated and the residue was treated with saturated NaHCO$_3$ (7 mL). The mixture was extracted with EtOAc (2×10 mL). The combined organic extracts were dried over MgSO$_4$, concentrated, and dried in vacuo to give N-(3-((1S,5S,6S)-1-((1H-1,2,3-triazol-1-yl)methyl)-3-amino-5-(fluoromethyl)-2-thia-4-azabicyclo[4.1.0]hept-3-en-5-yl)-4-fluorophenyl)-5-chloropicolinamide (15 mg, 0.031 mmol, 24% yield) as a yellow solid. MS (ESI, positive ion) m/z: 490 (M+1). 1H NMR (MeOH) δ: 8.70 (d, J=2.2 Hz, 1H), 8.19 (d, J=8.4 Hz, 1H), 8.04-8.10 (m, 2H), 7.80-7.86 (m, 1H), 7.74-7.80 (m, 2H), 7.17 (dd, J=11.5, 8.8 Hz, 1H), 4.50-4.83 (m, 4H), 2.18-2.26 (m, 1H), 1.52 (dd, J=9.6, 5.9 Hz, 1H), 0.85 (t, J=6.4 Hz, 1H).

Examples
752 (mixture of diastereomers), 753 and 962 N-(3-((4S,4aS,7aR)-2-amino-4-(fluoromethyl)-4a,4b,5,7-tetrahydro-4H-thieno[3',4':2,3]cyclopropa[1,2-e][1,3]thiazin-4-yl)-4-fluorophenyl)-5-chloropicolinamide (753) and N-(3-((4S,4aR,7aS)-2-amino-4-(fluoromethyl)-4a,4b,5,7-tetrahydro-4H-thieno[3',4':2,3]cyclopropa[1,2-e][1,3]thiazin-4-yl)-4-fluorophenyl)-5-chloropicolinamide (962)
5
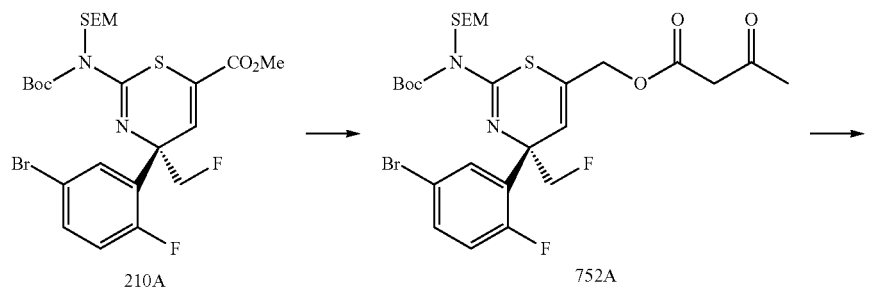
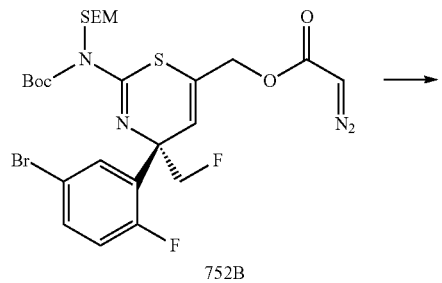
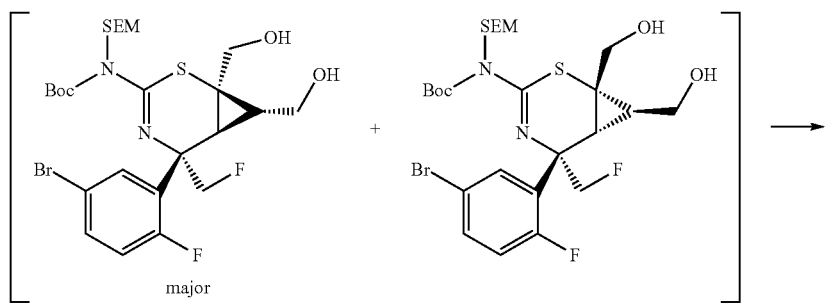
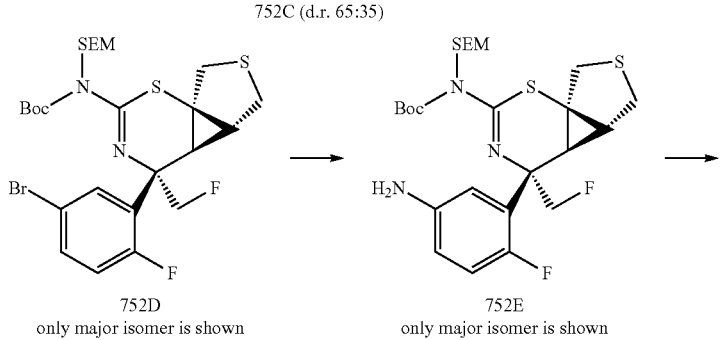

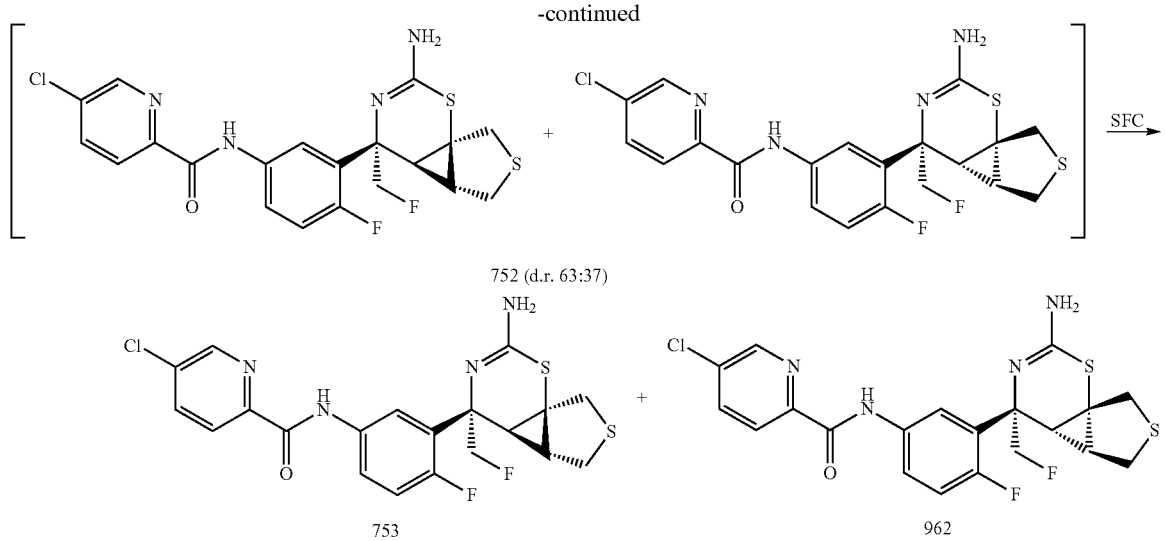

752 (d.r. 63:37)

753 + 962

Synthesis of (S)-(4-(5-bromo-2-fluorophenyl)-2-((tert-butoxycarbonyl)((2-(trimethylsilyl)ethoxy)methyl)amino)-4-(fluoromethyl)-4H-1,3-thiazin-6-yl)methyl 3-oxobutanoate (752A). A solution of diisobutylaluminum hydride in THF (1.0 M; 13.7 mL, 13.7 mmol) was added drop wise to a solution of (S)-methyl 4-(5-bromo-2-fluorophenyl)-2-((tert-butoxycarbonyl)((2-(trimethylsilyl)ethoxy)methyl)amino)-4-(fluoromethyl)-4H-1,3-thiazine-6-carboxylate (5.56 g, 9.15 mmol, 210A) in THF (100 ml) at 0° C. under nitrogen atmosphere. After 1 h, additional 13 mL DIBALH (1 M in THF) was added. The reaction mixture was allowed to stir for additional 20 min and was then slowly treated with MeOH. The reaction mixture was partitioned between EtOAc and water. The organic extract was separated, washed with brine and dried over MgSO$_4$. The solution was filtered and concentrated in vacuo to give the crude material. The crude material was absorbed onto a plug of silica gel and purified by column chromatography (SiO$_2$), eluting with a gradient of 10-80% (EtOAc in hexanes), to provide (S)-tert-butyl(4-(5-bromo-2-fluorophenyl)-4-(fluoromethyl)-6-(hydroxymethyl)-4H-1,3-thiazin-2-yl)((2-(trimethylsilyl)ethoxy)methyl)carbamate (5.3 g, 9.1 mmol, 99% yield) as a yellow oil. LC/MS (ESI$^+$) m/z=589.0/581.2 (M+H).

A round-bottom flask was charged with (S)-tert-butyl(4-(5-bromo-2-fluorophenyl)-4-(fluoromethyl)-6-(hydroxymethyl)-4H-1,3-thiazin-2-yl)((2-(trimethylsilyl)ethoxy)methyl)carbamate (5.37 g, 9.27 mmol), 2-xylene (4 mL) and 2,2,6-trimethyl-1,3-dioxin-4-one (1.4 mL, 11 mmol). The reaction mixture was heated to 135° C. (internal temp 123° C.) for 40 min. The reaction mixture was cooled to RT and absorbed onto a plug of silica gel. Purification by column chromatography (SiO$_2$), eluting with a gradient of 10-70% (EtOAc in hexanes), afforded the title compound as a red oil (752A; 4.4 g, 6.6 mmol, 71% yield). LC/MS (ESI$^+$) m/z=663.2/665.2 (M+H). The ketone compound exists in equilibrium with the corresponding enol.

Synthesis of (S)-(4-(5-bromo-2-fluorophenyl)-2-((tert-butoxycarbonyl)((2-(trimethylsilyl)ethoxy)methyl)amino)-4-(fluoromethyl)-4H-1,3-thiazin-6-yl)methyl 2-diazoacetate (752B). A solution of 4-acetamidobenzenesulfonyl azide (0.73 g, 3.0 mmol) in ACN (3 mL) was added drop wise to a stirred solution of (S)-(4-(5-bromo-2-fluorophenyl)-2-((tert-butoxycarbonyl)((2-(trimethylsilyl)ethoxy)methyl)amino)-4-(fluoromethyl)-4H-1,3-thiazin-6-yl)methyl 3-oxobutanoate (752A; 1.0 g, 1.5 mmol) and TEA (0.64 mL, 4.57 mmol) in ACN (5 mL). The reaction mixture was stirred at RT for 1.5 h. An aqueous LiOH solution (2 M, 2.3 mL, 4.57 mmol) was added and the reaction mixture was stirred overnight at RT. The reaction mixture was diluted with water and extracted with EtOAc. The organic phase was washed with aqueous saturated ammonium chloride solution and dried over MgSO$_4$. The solution was filtered and concentrated in vacuo to give the crude material. The crude material was absorbed onto a plug of silica gel and purified by column chromatography (SiO$_2$) eluting with a gradient of 5-60% (EtOAc in hexanes), to provide the title compound (752B; 700 mg, 1.08 mmol, 71% yield) as a yellow oil. LC/MS (ESI$^+$) m/z=647.2 (M+H). $^1$H NMR (300 MHz, CHLOROFORM-d) δ ppm −0.02-0.05 (m, 9H) 0.99 (dd, J=8.92, 7.60 Hz, 2H) 1.56 (s, 9H) 3.69 (td, J=8.22, 0.80 Hz, 2H) 4.50-4.94 (m, 5H) 5.26-5.34 (m, 1H) 5.36-5.44 (m, 1H) 6.19 (d, J=3.80 Hz, 1H) 6.96 (dd, J=11.25, 8.62 Hz, 1H) 7.41 (ddd, J=8.66, 4.28, 2.56 Hz, 1H) 7.67 (dd, J=6.87, 2.48 Hz, 1H)

Synthesis of 752C. A solution of (S)-(4-(5-bromo-2-fluorophenyl)-2-((tert-butoxycarbonyl)((2-(trimethylsilyl)ethoxy)methyl)amino)-4-(fluoromethyl)-4H-1,3-thiazin-6-yl)methyl 2-diazoacetate (752B, 0.32 g, 0.49 mmol) in dichloroethane (4 mL) was added drop wise (addition rate 1.3 mL/h) to a refluxing solution of bis(2-((E)-(tert-butylimino)methyl)phenoxy)copper (10.0 mg, 0.025 mmol, synthesized according to J. Org. Chem. 1957, 22, 677) in toluene (15 mL). The reaction mixture was allowed to stir for one more hour at the same temperature after completed addition (5 h total reaction time). The solvent was removed under reduced pressure and the residue was dissolved in THF (4 mL). A solution of lithium borohydride in THF (2.0 M in THF; 0.32 mL, 0.64 mmol) was added drop wise at 0° C. The reaction mixture was allowed to warm to RT. Additional lithium borohydride solution (0.32 mL, 0.64 mmol) were added drop wise. The reaction mixture was allowed to stir overnight. The reaction mixture was then cooled to 0° C. and quenched by the addition of aqueous HCl solution (1 M). The aqueous phase was extracted with EtOAc. The organic extract was washed with brine and dried over MgSO$_4$. The solution was filtered and concentrated in vacuo to give the crude material. The crude material was absorbed onto a plug of silica gel and purified by column chromatography (SiO$_2$), eluting with a gradient of 5-75% (EtOAc in hexanes), to provide a 65:35 mixture of tert-butyl ((1R,5S,6S)-5-(5-bromo-2-fluorophenyl)-5-(fluoromethyl)-1,7-bis(hydroxymethyl)-2-thia-4-azabicyclo[4.1.0]hept-3-en-3-yl)((2-(trimethylsilyl)ethoxy)methyl)carbamate and tert-butyl((1S,5S,6S)-5-(5-bromo-2-fluorophenyl)-5-(fluoromethyl)-1,7-bis(hydroxymethyl)-2-thia-4-azabicyclo[4.1.0]hept-3-en-3-yl)((2-(trimethylsilyl)ethoxy)methyl)carbamate (752C) (0.12 g, 0.20 mmol, 40% yield) as an oil. LC/MS (ESI$^+$) m/z=645.2/647.2 (M+Na, for both isomers). Retention time of minor isomer=1.58 min; Retention time of major isomer=1.61 min on LC.

Synthesis of 752D. A 65:35 mixture of tert-butyl((1R,5S,6S)-5-(5-bromo-2-fluorophenyl)-5-(fluoromethyl)-1,7-bis(hydroxymethyl)-2-thia-4-azabicyclo[4.1.0]hept-3-en-3-yl)((2-(trimethylsilyl)ethoxy)methyl)carbamate and tert-butyl((1S,5S,6S)-5-(5-bromo-2-fluorophenyl)-5-(fluoromethyl)-1,7-bis(hydroxymethyl)-2-thia-4-azabicyclo[4.1.0]hept-3-en-3-yl)((2-(trimethylsilyl)ethoxy)methyl)carbamate (752C; 143 mg, 0.22 mmol) was dissolved in DCM (1.5 mL) and cooled to 0° C. TEA (96 μL, 0.69 mmol) was added, followed by methanesulfonyl chloride (36 μL, 0.46 mmol). The reaction was warmed to RT and, aqueous saturated bicarbonate solution was added after 10 min, followed by EtOAc. The organic extract was washed with brine and dried over MgSO$_4$. The solution was filtered and concentrated in vacuo to give the crude material. The crude material was dissolved in DMSO (1 mL) and sodium sulfide (54 mg, 0.69 mmol) was added at RT. The suspension was diluted after 20 min with H$_2$O (30 mL) and extracted three times with EtOAc. The combined organic extracts were dried over MgSO$_4$, filtered and concentrated to under reduced pressure. The crude material was absorbed onto a plug of silica gel and purified by column chromatography (SiO$_2$), eluting with a gradient of 5-100% EtOAc in hexanes, to provide a mixture of tert-butyl((4S,4aS,7aR)-4-(5-bromo-2-fluorophenyl)-4-(fluoromethyl)-4a,4b,5,7-tetrahydro-4H-thieno[3',4':2,3]cyclopropa[1,2-e][1,3]thiazin-2-yl)((2-(trimethylsilyl)ethoxy)methyl)carbamate and tert-butyl((4S,4aR,7aS)-4-(5-bromo-2-fluorophenyl)-4-(fluoromethyl)-4a,4b,5,7-tetrahydro-4H-thieno[3',4':2,3]cyclopropa[1,2-e][1,3]thiazin-2-yl)((2-(trimethylsilyl)ethoxy)methyl)carbamate (752D) as a colorless oil. LC/MS (ESI$^+$) m/z=643.1/645.0 (M+Na, for both isomers, same retention time). The ratio of isomers was not determined.

Synthesis of 752E. A resealable tube was charged with a mixture of tert-butyl((4S,4aS,7aR)-4-(5-bromo-2-fluorophenyl)-4-(fluoromethyl)-4a,4b,5,7-tetrahydro-4H-thieno[3',4':2,3]cyclopropa[1,2-e][1,3]thiazin-2-yl)((2-(trimethylsilyl)ethoxy)methyl)carbamate and tert-butyl((4S,4aR,7aS)-4-(5-bromo-2-fluorophenyl)-4-(fluoromethyl)-4a,4b,5,7-tetrahydro-4H-thieno[3',4':2,3]cyclopropa[1,2-e][1,3]thiazin-2-yl)((2-(trimethylsilyl)ethoxy)methyl)carbamate (752D; 117 mg, 0.19 mmol), copper(I) iodide (7 mg, 0.04 mmol), sodium azide (37 mg, 0.57 mmol), (+)-sodium L-ascorbate (7.5 mg, 0.04 mmol). The reaction vessel was evacuated and backfilled with nitrogen. EtOH (1.3 mL) and water (0.57 mL) were added and the reaction mixture was degassed by bubbling nitrogen through the solution for 5 min. (1R,2R)-(−)-N,N"-dimethylcyclohexane-1,2-diamine (6.0 μL, 0.04 mmol) was added and the reaction mixture was heated to 80° C. for 30 min. The reaction mixture was cooled to RT and poured into a solution of saturated ammonium chloride and saturated ammonium hydroxide (9:1). The mixture was extracted three times with EtOAc. The organic layers were combined and concentrated under reduced pressure. The residue was dissolved in THF (3 mL) and H$_2$O (1.5 mL). A solution of trimethylphosphine in THF (0.21 mL of 1.0 M in THF, 0.21 mmol) was added at RT. The reaction was stirred for 15 min. The reaction was diluted with water and EtOAc. The organic layer was separated, washed with brine, dried over magnesium sulfate and concentrated under reduced pressure. The crude mixture (752E; 100 mg) was used directly in the next step without further purification. LC/MS (ESI$^+$) m/z=558.2 (M+H, same for both isomers same retention time). The ratio of isomers was not determined.

Synthesis of Example 752 (a mixture of diastereomers). A flask was charged with the crude product from the former step (752E; 100 mg, 0.18 mmol), 5-chloro-2-pyridinecarboxylic acid (34 mg, 0.21 mmol) and DMF (0.9 mL). The solution was cooled to 0° C. and N-[(dimethylamino)-1H-1,2,3-triazolo-[4,5-b]pyridin-1-ylmethylene]-N-methylmethanaminium hexafluorophosphate N-oxide (HATU, 119 mg, 0.31 mmol) and diisopropyl-ethyl-amine (55 μL, 0.31 mmol) were added. The reaction mixture was poured into water after 10 min reaction time. A white solid precipitated and was filtered off. The solid was washed with water and dried under reduced pressure. The solid was subsequently dissolved in concentrated H$_2$SO$_4$ (1 mL) and stirred vigorously at RT for 20 min. The reaction mixture was poured into water and the pH was adjusted to 10 with aqueous 5 M NaOH solution. A white solid precipitated and was filtered off. The solid was dissolved in EtOAc and dried over MgSO$_4$. The solution was filtered and concentrated in vacuo to give a mixture of N-(3-((4S,4aR,7aS)-2-amino-4-(fluoromethyl)-4a,4b,5,7-tetrahydro-4H-thieno[3',4':2,3]cyclopropa[1,2-e][1,3]thiazin-4-yl)-4-fluorophenyl)-5-chloropicolinamide and N-(3-((4S,4aS,7aR)-2-amino-4-(fluoromethyl)-4a,4b,5,7-tetrahydro-4H-thieno[3',4':2,3]cyclopropa[1,2-e][1,3]thiazin-4-yl)-4-fluorophenyl)-5-chloropicolinamide as a white solid (47 mg, 0.1 mmol, 56%). The ratio of isomers was determined to be 63:37 by analytical superfluid chromatography using supercritical CO$_2$ (additives 35% of 20 mM NH$_3$ in MeOH) on a Chiracel AD column (100×2.1 mm, 3 μm) eluting at a flow rate 1 mL/min (105 bar pressure, 25° C. column temperature). LC/MS (ESI$^+$) m/z=467.4 (M+H, for both isomers). $^1$H NMR (400 MHz, CHLOROFORM-d; overlapping signals) δ ppm 1.49 (t, J=4.89 Hz, 1H) 2.16-2.22 (m, 1H) 2.46 (d, J=2.93 Hz, 1H) 2.70 (d, J=5.28 Hz, 1H) 2.93 (d, J=11.15 Hz, 1H) 3.03-3.26 (m, 4H) 3.30-3.39 (m, 1H) 4.60-4.98 (m, 3H) 7.13 (dd, J=11.35, 8.80 Hz, 2H) 7.64-7.72 (m, 1H) 7.89 (dd, J=8.41, 2.35 Hz, 2H) 7.94-8.03 (m, 1H) 8.20-8.30 (m, 2H) 8.57 (d, J=1.96 Hz, 2H) 9.83 (s, 1H).

The mixture of N-(3-((4S,4aR,7aS)-2-amino-4-(fluoromethyl)-4a,4b,5,7-tetrahydro-4H-thieno[3',4':2,3]cyclopropa[1,2-e][1,3]thiazin-4-yl)-4-fluorophenyl)-5-chloropicolinamide and N-(3-((4S,4aS,7aR)-2-amino-4-(fluoromethyl)-4a,4b,5,7-tetrahydro-4H-thieno[3',4':2,3]cyclopropa[1,2-e][1,3]thiazin-4-yl)-4-fluorophenyl)-5-chloropicolinamide (Example 752) (39 mg) was chromatographed using supercritical CO$_2$ (additives 30% of 20 mM NH$_3$ in MeOH) on a Chiracel AD column (250×21 mm, 10 μm) eluting at a flow rate 70 mL/min (158 bar pressure, 40° C. column temperature). The first peak (retention time=3.1 min) provided N-(3-((4S,4aS,7aR)-2-amino-4-(fluoromethyl)-4a,4b,5,7-tetrahydro-4H-thieno[3',4':2,3]cyclopropa[1,2-e][1,3]thiazin-4-yl)-4-fluorophenyl)-5-chloropicolinamide (Example 753; 17 mg, >99% ee), and the second peak (retention time=3.8 min) provided N-(3-((4S,4aR,7aS)-2- amino-4-(fluoromethyl)-4a,4b,5,7-tetrahydro-4H-thieno[3',4':2,3]cyclopropa[1,2-e][1,3]thiazin-4-yl)-4-fluorophenyl)-5-chloropicolinamide (Example 962; 8 mg, >99% ee). LC/MS (ESI+) m/z=467.4 (M+H, for both isomers). ¹H NMR (400 MHz, DMSO-$d_6$, Example 753) δ ppm 1.40 (t, J=4.40 Hz, 1H) 2.16 (d, J=3.52 Hz, 1H) 2.85 (d, J=11.15 Hz, 1H) 3.00-3.08 (m, 1H) 3.10-3.22 (m, 3H) 4.52-4.79 (m, 2H) 6.39 (br. s., 2H) 7.19 (dd, J=11.74, 9.00 Hz, 1H) 7.82 (dt, J=8.71, 3.57 Hz, 1H) 8.00 (dd, J=7.14, 2.64 Hz, 1H) 8.13-8.16 (m, 1H) 8.17-8.23 (m, 1H) 8.78 (d, J=2.35 Hz, 1H) 10.61 (s, 1H); ¹H NMR (400 MHz, DMSO-$d_6$, Example 962) δ ppm 1.96 (br. s., 1H) 2.35 (br. s., 1H) 2.94-3.08 (m, 2H) 3.45 (d, J=10.95 Hz, 2H) 4.45-4.65 (m, 1H) 4.72-4.95 (m, 1H) 6.32 (br. s., 2H) 7.11-7.23 (m, 1H) 7.78 (br. s., 1H) 8.13-8.25 (m, 3H) 8.81 (d, J=1.37 Hz, 1H) 10.78 (s, 1H); The relative stereochemistry was confirmed by COSY, HMBC and NOESY correlations.

Example 754

(1S,5S,6S)-5-(5-((3-chloropyrido[2,3-d]pyridazin-8-yl)amino)-2-fluorophenyl)-5-(fluoromethyl)-2-thia-4-azabicyclo[4.1.0]hept-3-en-3-amine

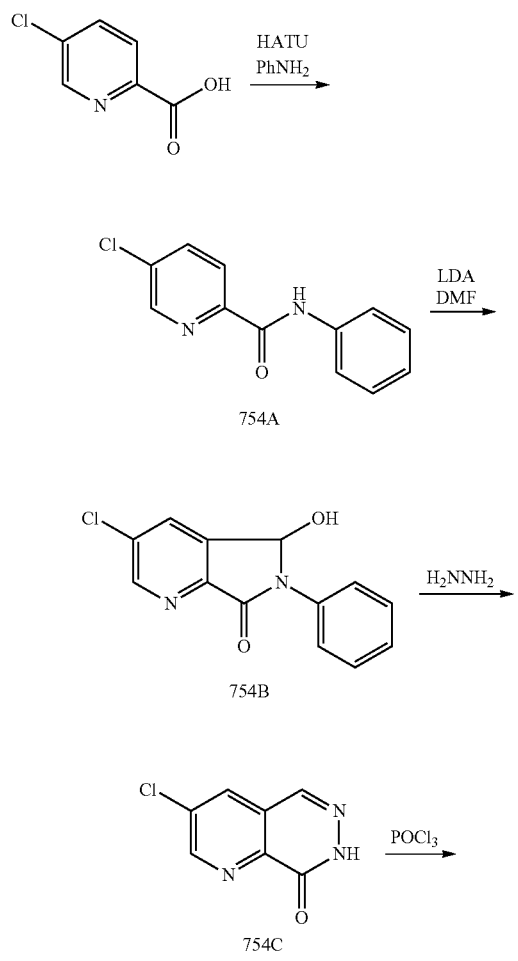

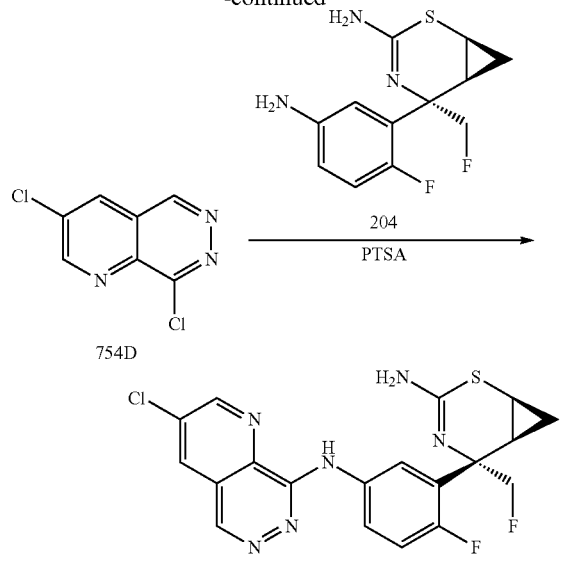

Preparation of 5-chloro-N-phenylpicolinamide (754A). To a stirred solution of 5-chloropicolinic acid (1.5 g, 9.52 mmol), aniline (1.13 mL, 12.38 mmol), and EtNiPr$_2$ (2.16 mL, 12.38 mmol) in DMF (15 mL) was added HATU (4.05 g, 10.66 mmol). After the addition, the mixture was stirred for 2 h. H$_2$O was added and the white solid was collected, washed with H$_2$O, dried to give the title compound (2.05 g, 93%). ¹H NMR (CHLOROFORM-d) δ: 9.82 (br. s., 1H), 8.57 (d, J=2.0 Hz, 1H), 8.26 (d, J=8.4 Hz, 1H), 7.88 (dd, J=8.4, 2.3 Hz, 1H), 7.76 (dd, J=8.6, 1.0 Hz, 2H), 7.39 (t, J=7.9 Hz, 2H), 7.07-7.21 (m, 1H). MS (ESI, positive ion) m/z: 233 (M+1).

Preparation of 3-chloro-5-hydroxy-6-phenyl-5H-pyrrolo[3,4-b]pyridin-7(6H)-one (754B). To a stirred solution of 5-chloro-N-phenylpicolinamide (754A, 1.00 g, 4.30 mmol) in THF (10 mL) at −78° C. was added lithium diisopropylamide (4.73 mL of 2 M in THF, 9.46 mmol) dropwise. After stirring at −78° C. for 1 h, DMF (1.99 mL, 25.8 mmol) was added and continued to stirred at −78° C. for another 2 h, then warmed to RT, and quenched with saturated NH$_4$Cl. The mixture was extracted with EtOAc (3×). The extracts were dried over Na$_2$SO$_4$, concentrated. The residue was triturated in EtOH, and the solid (0.78 g, 69%) was filtered, dried and used in the next step. MS (ESI, positive ion) m/z: 261 (M+1).

Preparation of 3-chloropyrido[2,3-d]pyridazin-8(7H)-one (754C). A mixture of 3-chloro-5-hydroxy-6-phenyl-5H-pyrrolo[3,4-b]pyridin-7(6H)-one (754B, 1.10 g, 4.22 mmol) and hydrazine (3.97 mL, 127 mmol) was stirred at RT overnight. The solid (0.65 g, 85%) was collected, washed with EtOH, and used in the next step. ¹H NMR (DMSO-d6) δ: 13.01 (br. s., 1H), 9.07 (d, J=2.3 Hz, 1H), 8.58 (d, J=2.3 Hz, 1H), 8.34 (s, 1H). MS (ESI, positive ion) m/z: 182 (M+1).

Preparation of 3,8-dichloropyrido[2,3-d]pyridazine (754D). A mixture of 3-chloropyrido[2,3-d]pyridazin-8(7H)-one (754C, 1.80 g, 9.91 mmol) and phosphorus oxychloride (9.24 mL, 99 mmol) was heated at 90° C. for 3 h. The reaction mixture was cooled, poured onto ice in a beaker and neutralized with saturated NaHCO$_3$. The solid (0.45 g, 22%) was collected dried and used in the next step. MS (ESI, positive ion) m/z: 200 (M+1).

Preparation of (1S,5S,6S)-5-(5-((3-chloropyrido[2,3-d]pyridazin-8-yl)amino)-2-fluorophenyl)-5-(fluoromethyl)-2-thia-4-azabicyclo[4.1.0]hept-3-en-3-amine (754). A mixture of (1S,5S,6S)-5-(5-amino-2-fluorophenyl)-5-(fluoromethyl)-2-thia-4-azabicyclo[4.1.0]hept-3-en-3-amine (754D, 0.10 g, 0.37 mmol), 3,8-dichloropyrido[2,3-d]pyridazine (204) (0.074 g, 0.371 mmol), 4-methylbenzenesulfonic acid hydrate (0.071 g, 0.371 mmol) in EtOH (4 mL) was heated at 80° C. in 4 h. The mixture was cooled, saturated aqueous NaHCO₃ was added, the solid was collected, dried and purified by silica gel column to give the title compound (25 mg, 16%). ¹H NMR (DMSO-d6) δ: 9.46 (s, 1H), 9.24 (d, J=2.3 Hz, 1H), 9.15 (s, 1H), 8.71 (d, J=2.3 Hz, 1H), 8.18-8.28 (m, 1H), 7.92-8.02 (m, 1H), 7.21 (dd, J=11.8, 9.1 Hz, 1H), 6.19 (br. s., 2H), 4.75-4.89 (m, 1H), 4.63-4.75 (m, 1H), 2.39 (d, J=4.5 Hz, 1H), 1.79 (d, J=7.2 Hz, 1H), 1.03 (d, J=6.1 Hz, 1H), 0.44 (d, J=5.3 Hz, 1H). MS (ESI, positive ion) m/z: 433/435 (M+1).

Example 755

(E)-ethyl 3-((1R,5S,6S)-3-amino-5-(5-(5-chloropicolinamido)-2-fluorophenyl)-5-(fluoromethyl)-2-thia-4-azabicyclo[4.1.0]hept-3-en-1-yl)acrylate

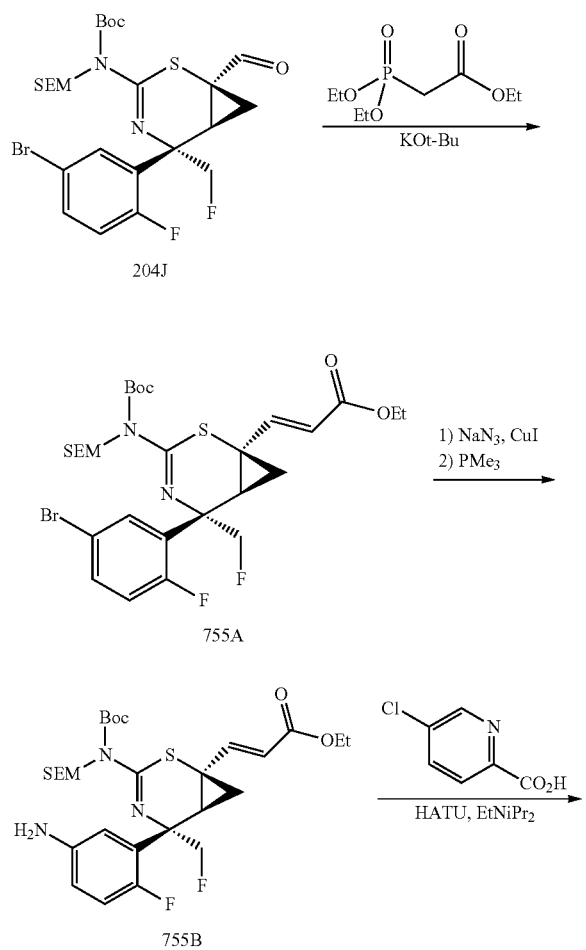

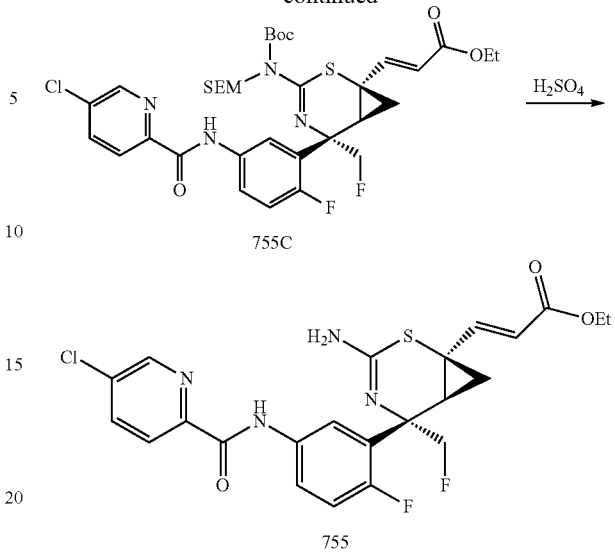

Preparation of (E)-ethyl 3-((1R,5S,6S)-5-(5-bromo-2-fluorophenyl)-3-((tert-butoxycarbonyl)((2-(trimethylsilyl)ethoxy)methyl)amino)-5-(fluoromethyl)-2-thia-4-azabicyclo[4.1.0]hept-3-en-1-yl)acrylate (755A). To a stirred solution of triethyl phosphonoacetate (0.227 mL, 1.014 mmol) in THF (5 mL) was added potassium tert-butoxide (1.0 M solution in THF, 1.014 mL, 1.014 mmol) dropwise. After the addition, the mixture was stirred for 30 min., then a solution of tert-butyl((1S,5S,6S)-5-(5-bromo-2-fluorophenyl)-5-(fluoromethyl)-1-formyl-2-thia-4-azabicyclo[4.1.0]hept-3-en-3-yl)((2-(trimethylsilyl)ethoxy)methyl)carbamate (4.01 mL, 0.84 mmol) was added and stirred for another 30 min. It was treated with saturated aqueous NH₄Cl and extracted with EtOAc (3×). The extracts were washed with brine, dried over Na₂SO₄, and concentrated to give Compound 755A (2.98 g, 100%). ¹H NMR (CHLOROFORM-d) δ: 7.82 (dd, J=6.8, 2.5 Hz, 1H), 7.41 (ddd, J=8.6, 4.3, 2.7 Hz, 1H), 6.97 (dd, J=11.7, 8.6 Hz, 1H), 6.66 (d, J=15.5 Hz, 1H), 6.03 (d, J=15.5 Hz, 1H), 5.31 (d, J=10.4 Hz, 1H), 5.06 (d, J=10.6 Hz, 1H), 4.78-4.97 (m, 1H), 4.62-4.78 (m, 1H), 4.20 (q, J=7.1 Hz, 2H), 3.67 (dd, J=9.4, 7.4 Hz, 2H), 2.16 (ddd, J=9.7, 7.5, 2.0 Hz, 1H), 1.54 (s, 8H), 1.25-1.35 (m, 4H), 1.12 (dd, J=7.1, 6.0 Hz, 1H), 0.97 (dd, J=9.3, 7.3 Hz, 2H), 0.00 (s, 9H). MS (ESI, positive ion) m/z: 661 (M+1).

Preparation of (E)-ethyl 3-((1R,5S,6S)-5-(5-amino-2-fluorophenyl)-3-((tert-butoxycarbonyl)((2-(trimethylsilyl)ethoxy)methyl)amino)-5-(fluoromethyl)-2-thia-4-azabicyclo[4.1.0]hept-3-en-1-yl)acrylate (755B). A mixture of (E)-ethyl 3-((1R,5S,6S)-5-(5-bromo-2-fluorophenyl)-3-((tert-butoxycarbonyl)((2-(trimethylsilyl)ethoxy)methyl)amino)-5-(fluoromethyl)-2-thia-4-azabicyclo[4.1.0]hept-3-en-1-yl)acrylate (2.98 g, 4.50 mmol), sodium (R)-2-((S)-1,2-dihydroxyethyl)-4-hydroxy-5-oxo-2,5-dihydrofuran-3-olate (0.223 g, 1.126 mmol), copper(I) iodide (0.214 g, 1.126 mmol), sodium azide (0.88 g, 13.51 mmol), and (1R,2R)—N1,N2-dimethylcyclohexane-1,2-diamine (0.178 ml, 1.126 mmol) in EtOH/H₂O (5:1, 33 mL) was heated at 85° C. in 2 h. The reaction mixture was cooled to RT, and partitioned between EtOAc and saturated NH₄Cl/NH₄OH (10/1). The organic phase was washed brine, dried over Na₂SO₄, and concentrated to give the oil. The oil was dissolved in 9:1 of THF/H₂O (30 mL) and treated with trimethylphosphine (6.99 mL of 1 M in THF solution, 6.99 mmol). After stirring for 30 min, it was diluted with EtOAc and H₂O. The organic solution was dried over Na₂SO₄, and concentrated. The resulting brown oil was purified on silica gel column to give Compound 755B as a light yellow gum (1.48 g, 53%). MS (ESI, positive ion) m/z: 598 (M+1).

Preparation of (E)-ethyl 3-((1R,5S,6S)-3-amino-5-(5-(5-chloropicolinamido)-2-fluorophenyl)-5-(fluoromethyl)-2-thia-4-azabicyclo[4.1.0]hept-3-en-1-yl)acrylate (755). To a stirred mixture of (E)-ethyl 3-((1R,5S,6S)-5-(5-amino-2-fluorophenyl)-3-((tert-butoxycarbonyl)((2-(trimethylsilyl)ethoxy)methyl)amino)-5-(fluoromethyl)-2-thia-4-azabicyclo[4.1.0]hept-3-en-1-yl)acrylate (2.02 g, 3.38 mmol), 5-chloro-2-pyridinecarboxylic acid (0.57 g, 3.72 mmol), EtNiPr₂ (0.76 mL, 4.39 mmol) in DMF (20 mL) was added HATU (1.54 g, 4.05 mmol). After the addition, the mixture was stirred at RT overnight, then treated with H₂O and extracted with EtOAc (3×). The organic extracts were dried over Na₂SO₄, and concentrated to give (E)-ethyl 3-((1R,5S,6S)-3-((tert-butoxycarbonyl)((2-(trimethylsilyl)ethoxy)methyl)amino)-5-(5-(5-chloropicolinamido)-2-fluorophenyl)-5-(fluoromethyl)-2-thia-4-azabicyclo[4.1.0]hept-3-en-1-yl)acrylate a light brown oil (755C, 2.44 g, 98%) as a brown oil, which was used in the next step without further purification. MS (ESI, positive ion) m/z: 737 (M+1).

Preparation of (E)-ethyl 3-((1R,5S,6S)-3-amino-5-(5-(5-chloropicolinamido)-2-fluorophenyl)-5-(fluoromethyl)-2-thia-4-azabicyclo[4.1.0]hept-3-en-1-yl)acrylate (755). To a stirred neat (E)-ethyl 3-((1R,5S,6S)-3-((tert-butoxycarbonyl)((2-(trimethylsilyl)ethoxy)methyl)amino)-5-(5-(5-chloropicolinamido)-2-fluorophenyl)-5-(fluoromethyl)-2-thia-4-azabicyclo[4.1.0]hept-3-en-1-yl)acrylate (77 mg, 0.10 mmol) at 0° C. was added H₂SO₄/TFA (1:4, 1 mL). The stirring was continued for 15 min at 0° C., then basified with saturated Na₂CO₃ until pH=9. It was extracted with DCM (3×). The organic extracts were dried over Na₂SO₄, and concentrated to give Example 755 (43 mg, 81%). ¹H NMR (DMSO-d6) δ: 10.61 (s, 1H), 8.78 (d, J=2.2 Hz, 1H), 8.17-8.21 (m, 1H), 8.12-8.16 (m, 1H), 7.97 (dd, J=7.1, 2.6 Hz, 1H), 7.85 (dd, J=8.0, 3.5 Hz, 1H), 7.08-7.26 (m, 1H), 6.73 (d, J=15.5 Hz, 1H), 6.50 (br. s., 2H), 5.92 (d, J=15.5 Hz, 1H), 4.51-4.84 (m, 2H), 4.09-4.17 (m, 2H), 1.60 (dd, J=9.0, 4.9 Hz, 1H), 1.22 (t, J=7.1 Hz, 3H), 0.93-1.01 (m, 1H), 0.82-0.89 (m, 1H). MS (ESI, positive ion) m/z: 507 (M+1).

Example 756

N-(3-((1R,5S,6S)-3-amino-5-(fluoromethyl)-1-((E)-3-hydroxyprop-1-en-1-yl)-2-thia-4-azabicyclo[4.1.0]hept-3-en-5-yl)-4-fluorophenyl)-5-chloropicolinamide

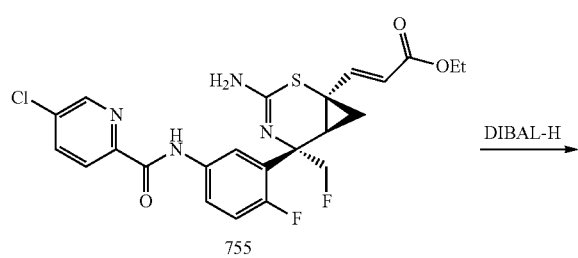

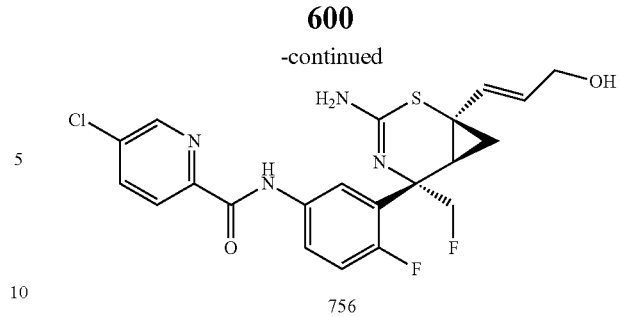

To a stirred solution of (E)-ethyl 3-((1R,5S,6S)-3-amino-5-(5-(5-chloropicolinamido)-2-fluorophenyl)-5-(fluoromethyl)-2-thia-4-azabicyclo[4.1.0]hept-3-en-1-yl)acrylate (35 mg, 0.07 mmol) in THF (2 mL) at 0° C. was added DIBAL-H (0.24 mL of 1 M in THF, 0.24 mmol). After the addition, the reaction mixture was stirred at RT for 2 h, then cooled with an ice bath and slowly quenched with saturated Rochelle's salt. It was extracted with EtOAc (3×). The organic extracts were dried over Na₂SO₄, concentrated and the residue purified on a silica gel column to give the title compound as an off white solid (15 mg, 16%). ¹H NMR (DMSO-d6) δ: 10.59 (s, 1H), 8.78 (d, J=2.3 Hz, 1H), 8.17-8.22 (m, 1H), 8.11-8.16 (m, 1H), 8.05 (dd, J=7.2, 2.9 Hz, 1H), 7.84 (dt, J=7.3, 4.3 Hz, 1H), 7.18 (dd, J=11.9, 8.8 Hz, 1H), 6.31 (s, 2H), 5.65-5.75 (m, 1H), 5.54-5.62 (m, 1H), 4.70-4.80 (m, 2H), 4.59-4.68 (m, 1H), 3.95 (t, J=4.4 Hz, 2H), 1.73 (t, J=8.0 Hz, 1H), 1.20 (dd, J=9.5, 5.2 Hz, 1H), 0.67-0.81 (m, 1H). MS (ESI, positive ion) m/z: 465 (M+1).

Example 757

(E)-3-((1R,5S,6S)-3-amino-5-(5-(5-chloropicolinamido)-2-fluorophenyl)-5-(fluoromethyl)-2-thia-4-azabicyclo[4.1.0]hept-3-en-1-yl)acrylic acid

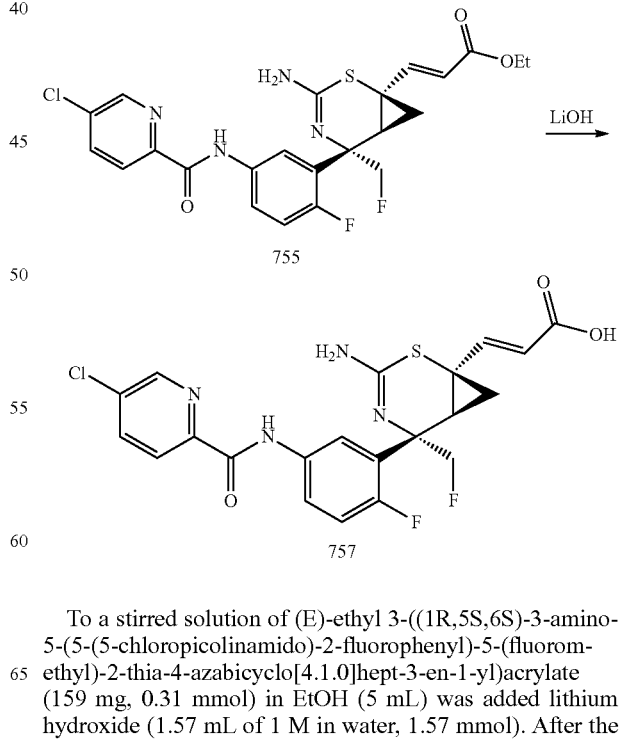

To a stirred solution of (E)-ethyl 3-((1R,5S,6S)-3-amino-5-(5-(5-chloropicolinamido)-2-fluorophenyl)-5-(fluoromethyl)-2-thia-4-azabicyclo[4.1.0]hept-3-en-1-yl)acrylate (159 mg, 0.31 mmol) in EtOH (5 mL) was added lithium hydroxide (1.57 mL of 1 M in water, 1.57 mmol). After the mixture was stirred for 16 h at RT, it was concentrated. The residue was diluted with H₂O and acidified with 1 N HCl. The precipitated tan solid was collected, washed with H₂O, and dried to give Example 757 (83 mg, 55%). $^1$H NMR (DMSO-d6) δ: 12.35 (br. s., 1H), 10.62 (s, 1H), 8.79 (d, J=1.8 Hz, 1H), 8.18-8.23 (m, 1H), 8.11-8.17 (m, 1H), 7.99 (dd, J=7.1, 2.6 Hz, 1H), 7.85 (dt, J=8.8, 3.4 Hz, 1H), 7.20 (dd, J=11.7, 8.8 Hz, 1H), 6.65 (d, J=15.5 Hz, 1H), 6.48 (s, 2H), 5.85 (d, J=15.5 Hz, 1H), 4.58-4.83 (m, 2H), 2.02 (t, J=8.8 Hz, 1H), 1.55 (dd, J=9.5, 5.2 Hz, 1H), 0.92-1.01 (m, 1H). MS (ESI, positive ion) m/z: 479 (M+1).

Example 758

N-(3-((1S,5S,6S)-3-amino-5-(fluoromethyl)-1-(3-hydroxypropyl)-2-thia-4-azabicyclo[4.1.0]hept-3-en-5-yl)-4-fluorophenyl)-5-chloropicolinamide

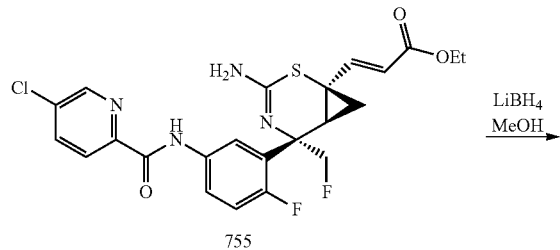

To a stirred solution of (E)-ethyl 3-((1R,5S,6S)-3-amino-5-(5-(5-chloropicolinamido)-2-fluorophenyl)-5-(fluoromethyl)-2-thia-4-azabicyclo[4.1.0]hept-3-en-1-yl)acrylate (34.7 mg, 0.07 mmol) in THF (2 mL) was added lithium borohydride (2.0 M solution in THF (0.05 mL, 0.10 mmol), followed by MeOH (0.023 mL, 0.55 mmol). After the addition, the mixture was stirred was stirred for 1 h. Another 0.05 mL of LiBH₄ was added and the mixture was continued to stir overnight. It was slowly quenched with saturated aqueous NH₄Cl, extracted with DCM (3×). The organic extracts were dried over Na₂SO₄, concentrated and the residue purified by ISCO (40-80% EtOAc in hexanes) to give the title compound (19 mg, 59%) as an off white solid. $^1$H NMR (DMSO-d6) δ: 10.57 (s, 1H), 8.74-8.80 (m, 1H), 8.17-8.23 (m, 1H), 8.12-8.16 (m, 1H), 8.03 (dd, J=7.1, 2.6 Hz, 1H), 7.78-7.88 (m, 1H), 7.16 (dd, J=11.8, 8.9 Hz, 1H), 6.21 (s, 2H), 4.75 (s, 1H), 4.63 (s, 1H), 4.42 (t, J=5.1 Hz, 1H), 3.41 (q, J=5.4 Hz, 2H), 1.45-1.73 (m, 5H), 0.85 (dd, J=9.3, 5.0 Hz, 1H), 0.53 (t, J=5.6 Hz, 1H). MS (ESI, positive ion) m/z: 467/469 (M+1).

Example 759

N-(3-((1R,5S,6S)-3-amino-1-((E)-3-amino-3-oxoprop-1-en-1-yl)-5-(fluoromethyl)-2-thia-4-azabicyclo[4.1.0]hept-3-en-5-yl)-4-fluorophenyl)-5-chloropicolinamide To a stirred mixture of (E)-3-((1R,5S,6S)-3-amino-5-(5-(5-chloropicolinamido)-2-fluorophenyl)-5-(fluoromethyl)-2-thia-4-azabicyclo[4.1.0]hept-3-en-1-yl)acrylic acid (45 mg, 0.10 mmol), DIEA (21.63 μL, 0.12 mmol), and ammonia (70.5 μL, 0.14 mmol) in DMF (2 mL) was added HATU (42.9 mg, 0.11 mmol). After the reaction mixture was stirred at RT for 2 h, it was treated with H₂O and extracted with EtOAc (3×). The organic extracts were dried over Na₂SO₄, concentrated, and the residue was purified by reverse phase HPLC. The pure fractions were concentrated to dryness. The residue was dissolved in MeOH, and passed through PL-HCO₃ MP SPE (200 mg per 6 mL tube) to give the title compound (24.3 mg, 54%) as a yellow solid. $^1$H NMR (DMSO-d6) δ: 10.62 (s, 1H), 8.80 (d, J=1.8 Hz, 1H), 8.19-8.25 (m, 1H), 8.14-8.19 (m, 1H), 8.07 (dd, J=7.2, 2.7 Hz, 1H), 7.83-7.93 (m, 1H), 7.49 (br. s., 1H), 7.21 (dd, J=11.7, 8.8 Hz, 1H), 7.01 (br. s., 1H), 6.39-6.49 (m, 3H), 6.04 (d, J=15.5 Hz, 1H), 4.59-4.84 (m, 2H), 1.97 (t, J=8.0 Hz, 1H), 1.41 (dd, J=9.7, 5.2 Hz, 1H), 0.89-1.02 (m, 1H). MS (ESI, positive ion) m/z: 478 (M+1).

Example 760

N-(3-((1R,5S,6S)-3-amino-5-(fluoromethyl)-1-((E)-3-(methylamino)-3-oxoprop-1-en-1-yl)-2-thia-4-azabicyclo[4.1.0]hept-3-en-5-yl)-4-fluorophenyl)-5-chloropicolinamide -continued

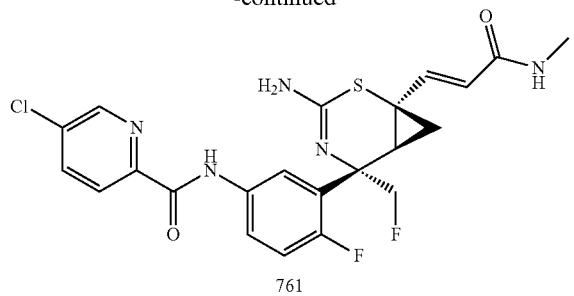

761

The title compound (23 mg, 59%) was prepared in the same method as described in Example 759. ¹H NMR (DMSO-d6) δ: 10.62 (s, 1H), 8.80 (d, J=1.8 Hz, 1H), 8.20-8.24 (m, 1H), 8.15-8.18 (m, 1H), 8.07 (dd, J=7.2, 2.7 Hz, 1H), 7.96-8.03 (m, 1H), 7.87 (dt, J=8.7, 3.5 Hz, 1H), 7.21 (dd, J=11.9, 8.8 Hz, 1H), 6.40-6.48 (m, 3H), 6.04 (d, J=15.3 Hz, 1H), 4.71-4.83 (m, 1H), 4.58-4.70 (m, 1H), 2.66 (d, J=4.7 Hz, 3H), 1.96 (t, J=8.3 Hz, 1H), 1.41 (dd, J=9.6, 5.3 Hz, 1H), 0.94-1.00 (m, 1H). MS (ESI, positive ion) m/z: 492 (M+1).

Example 761

N-(3-((1R,5S,6S)-3-amino-1-((E)-3-(dimethyl-amino)-3-oxoprop-1-en-1-yl)-5-(fluoromethyl)-2-thia-4-azabicyclo[4.1.0]hept-3-en-5-yl)-4-fluorophenyl)-5-chloropicolinamide

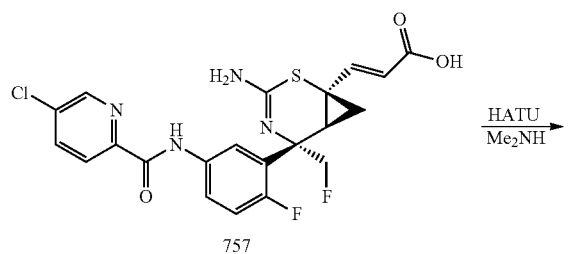

757

HATU / Me₂NH →

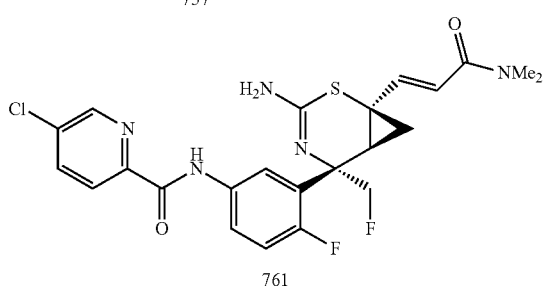

761

The title compound (16 mg, 36%) was prepared in the same method as described in Example 759. ¹H NMR (DMSO-d6) δ: 10.63 (s, 1H), 8.80 (d, J=1.8 Hz, 1H), 8.19-8.25 (m, 1H), 8.13-8.18 (m, 1H), 8.03 (dd, J=7.1, 2.6 Hz, 1H), 7.87 (dt, J=7.3, 4.2 Hz, 1H), 7.21 (dd, J=11.9, 8.8 Hz, 1H), 6.40-6.58 (m, 4H), 4.73-4.84 (m, 1H), 4.61-4.72 (m, 1H), 3.07 (s, 3H), 2.90 (s, 3H), 1.95 (t, J=8.2 Hz, 1H), 1.54 (dd, J=9.4, 5.3 Hz, 1H), 0.86-1.00 (m, 1H). MS (ESI, positive ion) m/z: 506 (M+1).

Example 764

N-(3-((1R,5S,6S)-3-amino-5-(fluoromethyl)-1-((E)-3-morpholino-3-oxoprop-1-en-1-yl)-2-thia-4-azabicyclo[4.1.0]hept-3-en-5-yl)-4-fluorophenyl)-5-chloropicolinamide

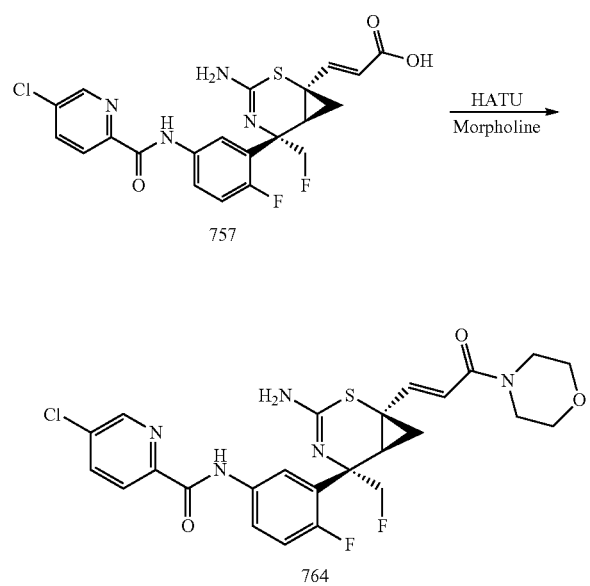

757

HATU / Morpholine →

764

The title compound (31 mg, 54%) was prepared in the same method as described in Example 759. ¹H NMR (DMSO-d6) δ: 10.61 (s, 1H), 10.59 (s, 1H), 8.79 (d, J=1.8 Hz, 1H), 8.18-8.23 (m, 1H), 8.12-8.17 (m, 1H), 8.00 (dd, J=7.1, 2.6 Hz, 1H), 7.85 (dt, J=8.7, 3.5 Hz, 1H), 7.20 (dd, J=11.7, 8.8 Hz, 1H), 6.56-6.62 (m, 1H), 6.45-6.50 (m, 1H), 6.44 (s, 2H), 4.71-4.84 (m, 1H), 4.60-4.71 (m, 1H), 3.47-3.64 (m, 8H), 1.88-1.98 (m, 1H), 1.55 (dd, J=9.7, 5.2 Hz, 1H), 0.90-0.97 (m, 1H). MS (ESI, positive ion) m/z: 548 (M+1).

Example 765

N-(3-((1S,5S,6S)-3-amino-1-(3-(dimethylamino)-3-oxopropyl)-5-(fluoromethyl)-2-thia-4-azabicyclo[4.1.0]hept-3-en-5-yl)-4-fluorophenyl)-5-chloropicolinamide

761

LiBH₄ →

-continued

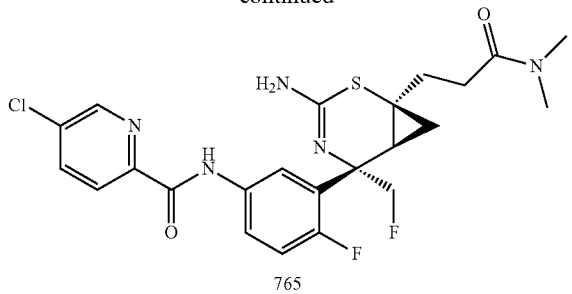
765

To a stirred solution of N-(3-((1R,5S,6S)-3-amino-1-((E)-3-(dimethylamino)-3-oxoprop-1-en-1-yl)-5-(fluoromethyl)-2-thia-4-azabicyclo[4.1.0]hept-3-en-5-yl)-4-fluorophenyl)-5-chloropicolinamide (31.5 mg, 0.062 mmol) in THF (2 mL) was added lithium borohydride (2.0 M solution in THF, 62.3 μL, 0.125 mmol). After 4 h, the reaction was slowly quenched with saturated NH₄Cl and extracted with DCM (3×). The organic extracts were dried over Na₂SO₄, concentrated and purified by reverse phase HPLC. The pure fractions were concentrated to dryness. The residue was dissolved in MeOH and passed through a PL-HCO3 MP SPE (200 mg per tube) to give the title compound (19.4 mg, 61%). ¹H NMR (DMSO-d6) δ: 10.60 (s, 1H), 8.80 (d, J=1.8 Hz, 1H), 8.20-8.25 (m, 1H), 8.15-8.19 (m, 1H), 8.04 (dd, J=7.1, 2.6 Hz, 1H), 7.86 (dt, J=8.5, 3.5 Hz, 1H), 7.19 (dd, J=11.7, 8.8 Hz, 1H), 6.26 (s, 2H), 4.62-4.80 (m, 2H), 3.01 (s, 3H), 2.85 (s, 3H), 2.41-2.50 (m, 2H), 1.84-1.98 (m, 1H), 1.68-1.78 (m, 1H), 1.59-1.67 (m, 1H), 0.92 (dd, J=9.4, 5.1 Hz, 1H), 0.54 (t, J=5.7 Hz, 1H). MS (ESI, positive ion) m/z: 508 (M+1).

Example 766

N-(3-((1R,5S,6S)-3-amino-5-(fluoromethyl)-1-((E)-3-(3-methoxyazetidin-1-yl)-3-oxoprop-1-en-1-yl)-2-thia-4-azabicyclo[4.1.0]hept-3-en-5-yl)-4-fluorophenyl)-5-chloropicolinamide

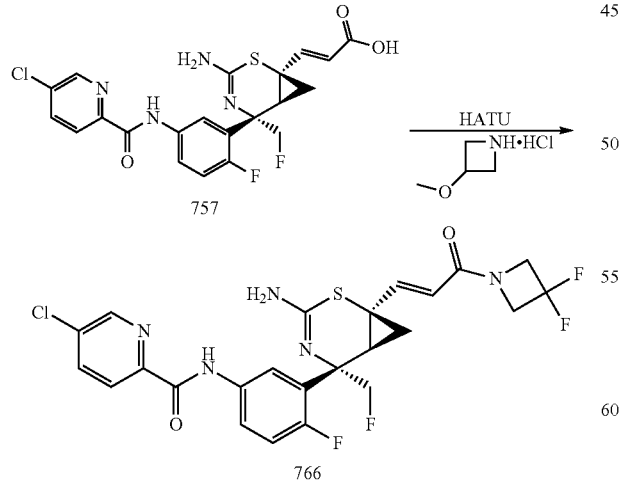

The title compound (14.5 mg, 25%) was prepared in the same method as described in Example 759. 1H NMR (DMSO-d6) δ: 10.64 (br. s., 1H), 8.81 (d, J=2.2 Hz, 1H), 8.21-8.26 (m, 1H), 8.15-8.20 (m, 1H), 8.03 (br. s., 1H), 7.89 (br. s., 1H), 7.22 (br. s., 1H), 6.54 (d, J=15.1 Hz, 1H), 6.47 (br. s., 2H), 6.04 (d, J=15.3 Hz, 1H), 4.78 (d, J=16.8 Hz, 1H), 4.66 (d, J=17.2 Hz, 1H), 4.41 (br. s., 1H), 4.24 (br. s., 1H), 4.09 (dd, J=17.3, 10.9 Hz, 2H), 3.72 (d, J=7.2 Hz, 1H), 3.25 (s, 3H), 1.98 (br. s., 1H), 1.46-1.62 (m, 1H), 0.98 (br. s., 1H). MS (ESI, positive ion) m/z: 548 (M+1).

Example 767

N-(3-((1R,5S,6S)-3-amino-5-(fluoromethyl)-1-((E)-3-((2-methoxyethyl)amino)-3-oxoprop-1-en-1-yl)-2-thia-4-azabicyclo[4.1.0]hept-3-en-5-yl)-4-fluorophenyl)-5-chloropicolinamide

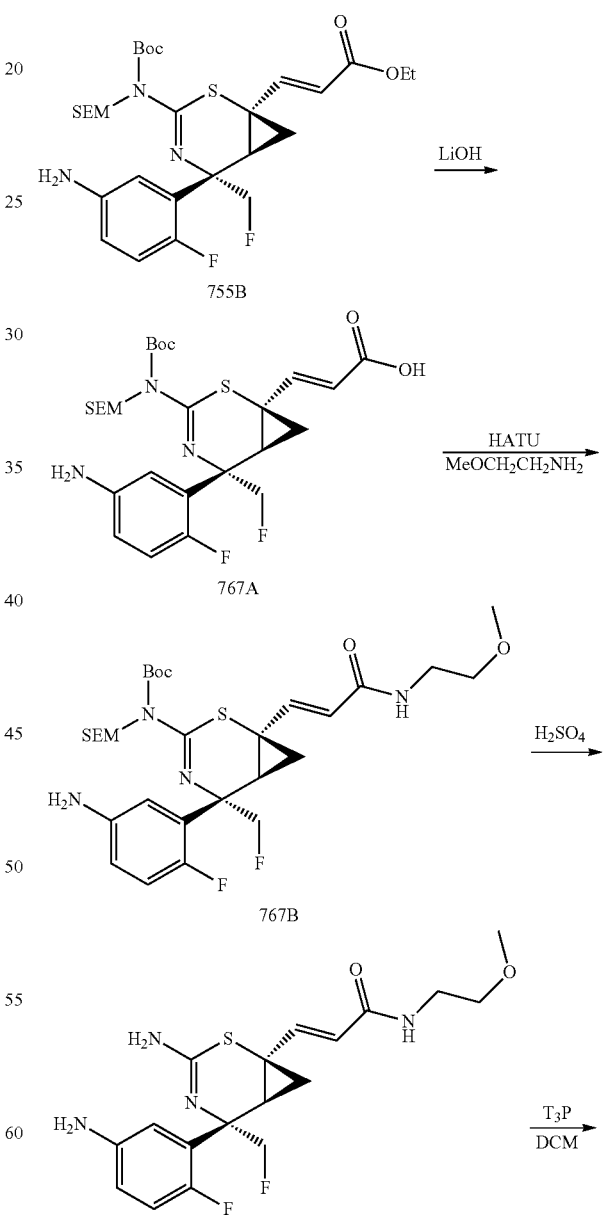

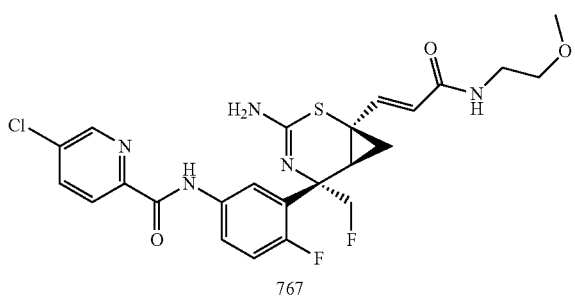

767

Preparation of (E)-3-((1R,5S,6S)-5-(5-amino-2-fluorophenyl)-3-((tert-butoxycarbonyl)((2-(trimethylsilyl)ethoxy)methyl)amino)-5-(fluoromethyl)-2-thia-4-azabicyclo[4.1.0]hept-3-en-1-yl)acrylic acid (767A). To a stirred solution of (E)-ethyl 3-((1R,5S,6S)-5-(5-amino-2-fluorophenyl)-3-((tert-butoxycarbonyl)((2-(trimethylsilyl)ethoxy)methyl)amino)-5-(fluoromethyl)-2-thia-4-azabicyclo[4.1.0]hept-3-en-1-yl)acrylate (2.60 g, 4.35 mmol) in EtOH (40 mL) was added lithium hydroxide (21.75 mL of 1 M in water, 21.75 mmol). The reaction mixture was stirred at RT in 16 h then concentrated. The residue was diluted with H₂O, cooled in an ice bath and neutralized with 5 N HCl. The solid (2.32 g, 94%) was collected, washed with H₂O, dried, and used in the next step. MS (ESI, positive ion) m/z: 570 (M+1).

Preparation of tert-butyl((1R,5S,6S)-5-(5-amino-2-fluorophenyl)-5-(fluoromethyl)-1-((E)-3-((2-methoxyethyl)amino)-3-oxoprop-1-en-1-yl)-2-thia-4-azabicyclo[4.1.0]hept-3-en-3-yl)((2-(trimethylsilyl)ethoxy)methyl)carbamate (767B). The title compound (154 mg, 54%) was prepared in the same method as described in Example 759. MS (ESI, positive ion) m/z: 627 (M+1).

Preparation of (E)-3-((1R,5S,6S)-3-amino-5-(5-amino-2-fluorophenyl)-5-(fluoromethyl)-2-thia-4-azabicyclo[4.1.0]hept-3-en-1-yl)-N-(2-methoxyethyl)acrylamide (767C). tert-Butyl((1R,5S,6S)-5-(5-amino-2-fluorophenyl)-5-(fluoromethyl)-1-((E)-3-((2-methoxyethyl)amino)-3-oxoprop-1-en-1-yl)-2-thia-4-azabicyclo[4.1.0]hept-3-en-3-yl)((2-(trimethylsilyl)ethoxy)methyl)carbamate (767B, 154 mg, 0.25 mmol) was cooled in an ice bath and treated with TFA/H₂SO₄ (4:1, 5 mL) and stirred for 15 min. The mixture was concentrated to remove all the excess of TFA, then cooled in an ice bath, basified with saturated Na₂CO₃, and extracted with DCM (3×). The organic extracts were dried over Na₂SO₄, concentrated and used in the next step. MS (ESI, positive ion) m/z: 397 (M+1).

Preparation of N-(3-((1R,5S,6S)-3-amino-5-(fluoromethyl)-1-((E)-3-((2-methoxyethyl)amino)-3-oxoprop-1-en-1-yl)-2-thia-4-azabicyclo[4.1.0]hept-3-en-5-yl)-4-fluorophenyl)-5-chloropicolinamide (767). The title compound (25.2 mg, 52%) was prepared using the amide formation Method D (T3P mediated amide formation in DCM as the solvent). ¹H NMR (DMSO-d6) δ: 10.61 (s, 1H), 8.79 (d, J=2.2 Hz, 1H), 8.19-8.23 (m, 1H), 8.12-8.18 (m, 2H), 8.06 (dd, J=7.2, 2.7 Hz, 1H), 7.84-7.89 (m, 1H), 7.20 (dd, J=11.9, 8.8 Hz, 1H), 6.42-6.46 (m, 1H), 6.41 (br. s., 2H), 6.09 (d, J=15.3 Hz, 1H), 4.70-4.82 (m, 1H), 4.58-4.70 (m, 1H), 3.34-3.41 (m, 2H), 3.26-3.30 (m, 2H), 3.25 (s, 3H), 1.96 (t, J=8.4 Hz, 1H), 1.40 (dd, J=9.7, 5.2 Hz, 1H), 0.93-1.00 (m, 1H). MS (ESI, positive ion) m/z: 536 (M+1).

Examples N-(3-((1R,5S,6S)-3-amino-5-(fluoromethyl)-1-((Z)-2-methyl-3-morpholino-3-oxoprop-1-en-1-yl)-2-thia-4-azabicyclo[4.1.0]hept-3-en-5-yl)-4-fluorophenyl)-5-chloropicolinamide (777) and N-(3-((1R,5S,6S)-3-amino-5-(fluoromethyl)-1-((E)-2-methyl-3-morpholino-3-oxoprop-1-en-1-yl)-2-thia-4-azabicyclo[4.1.0]hept-3-en-5-yl)-4-fluorophenyl)-5-chloropicolinamide (778)

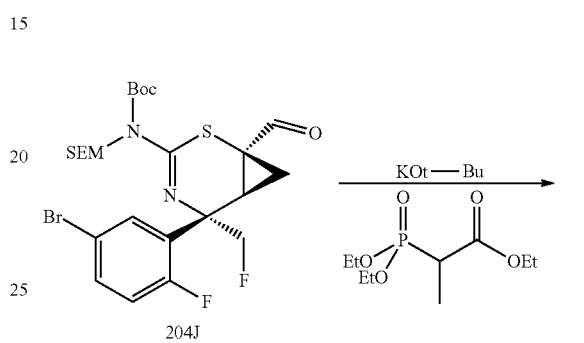

204J

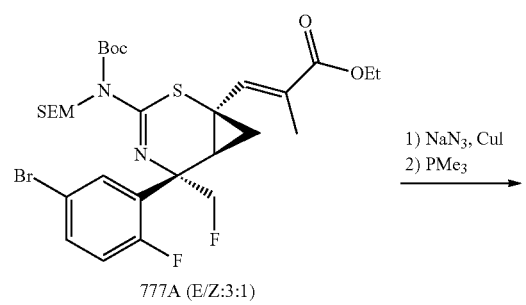

777A (E/Z:3:1)

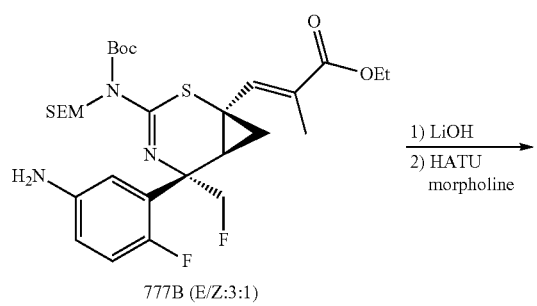

777B (E/Z:3:1)

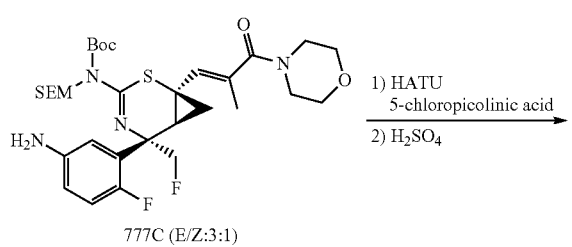

777C (E/Z:3:1)

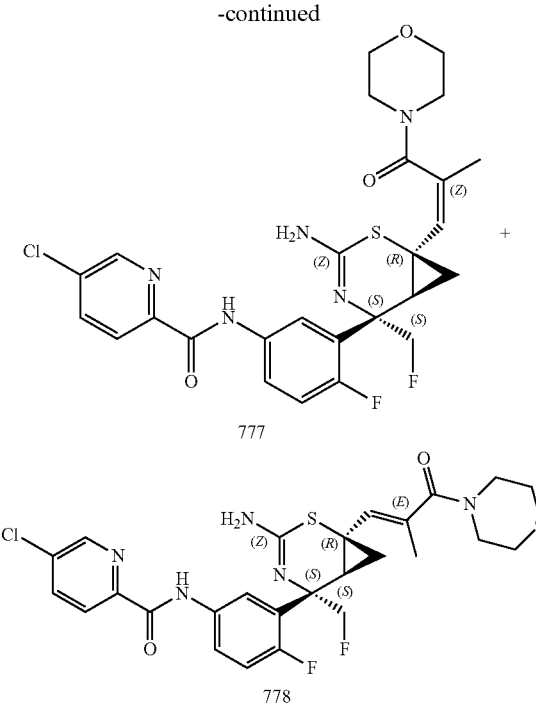

777

778

Preparation of (E/Z)-ethyl 3-((1R,5S,6S)-5-(5-bromo-2-fluorophenyl)-3-((tert-butoxycarbonyl)((2-(trimethylsilyl)ethoxy)methyl)amino)-5-(fluoromethyl)-2-thia-4-azabicyclo[4.1.0]hept-3-en-1-yl)-2-methylacrylate (777A). To a stirred solution of triethyl 2-phosphonopropionate (1.33 g, 5.58 mmol) in THF (20 mL) at 0° C. was added potassium tert-butoxide (1.0 M solution in THF, 5.32 mL, 5.32 mmol) dropwise. After stirring at 0° C. for 30 min., a solution of tert-butyl((1S,5S,6S)-5-(5-bromo-2-fluorophenyl)-5-(fluoromethyl)-1-formyl-2-thia-4-azabicyclo[4.1.0]hept-3-en-3-yl)((2-(trimethylsilyl)ethoxy)methyl)carbamate (3 g, 5.07 mmol) in THF (30 mL) was added dropwise from dropping funnel. The reaction mixture was stirred for 2 h. Saturated aqueous NH$_4$Cl was added and the mixture was extracted with EtOAc (3×). The organic extracts were dried over Na$_2$SO$_4$, concentrated and purified by silica gel column to give 777A (2.47, 72%) as a mixture of E and Z-isomers. MS (ESI, positive ion) m/z: 697/699 (M+1).

Compound 777B as a mixture of E and Z-isomers (1.55 g, 59%) was prepared in the same method as described in Example 755B, but starting from Compound 777A. MS (ESI, positive ion) m/z: 612 (M+1).

Compound 777C as a mixture of E and Z-isomers (0.58 g, 65%) was prepared in the same method as described for Example 767B, but starting from Compound 777B. MS (ESI, positive ion) m/z: 653 (M+1).

Preparation of Example 777 and Example 778. Intermediate 777C was converted to the amide as a mixture of E and Z-isomers following the general Method-F1 (HATU mediated amide formation followed by removal of protecting groups with H$_2$SO$_4$), which were separated by SFC (chiralPak OX-H). N-(3-((1R,5S,6S)-3-Amino-5-(fluoromethyl)-1-((Z)-2-methyl-3-morpholino-3-oxoprop-1-en-1-yl)-2-thia-4-azabicyclo[4.1.0]hept-3-en-5-yl)-4-fluorophenyl)-5-chloropicolinamide (777) (18 mg, 8%) was obtained. $^1$H NMR (DMSO-d6) δ: 10.68 (s, 1H), 8.85-8.91 (m, 1H), 8.27-8.34 (m, 1H), 8.21-8.27 (m, 1H), 8.10 (dd, J=7.1, 2.8 Hz, 1H), 7.93 (dt, J=7.3, 4.3 Hz, 1H), 7.27 (dd, J=11.9, 8.8 Hz, 1H), 6.39 (s, 2H), 5.65 (d, J=1.4 Hz, 1H), 4.87 (q, J=9.1 Hz, 1H), 4.60-4.79 (m, 1H), 3.59-3.76 (m, 4H), 3.44-3.59 (m, 4H), 1.91 (d, J=1.4 Hz, 3H), 1.81 (br. s., 1H), 1.25-1.32 (m, 1H), 0.76 (t, J=6.1 Hz, 1H). MS (ESI, positive ion) m/z: 562 (M+1). N-(3-((1R,5S,6S)-3-amino-5-(fluoromethyl)-1-((E)-2-methyl-3-morpholino-3-oxoprop-1-en-1-yl)-2-thia-4-azabicyclo[4.1.0]hept-3-en-5-yl)-4-fluorophenyl)-5-chloropicolinamide (778) (96.5 mg, 45%) was obtained. $^1$H NMR (DMSO-d6) δ: 10.59 (s, 1H), 8.67-8.84 (m, 1H), 8.17-8.23 (m, 1H), 8.10-8.17 (m, 1H), 8.02 (dd, J=7.2, 2.7 Hz, 1H), 7.80-7.87 (m, 1H), 7.18 (dd, J=11.9, 8.8 Hz, 1H), 6.32 (s, 2H), 5.67 (d, J=1.4 Hz, 1H), 4.78-4.88 (m, 1H), 4.66-4.76 (m, 1H), 3.51-3.63 (m, 4H), 3.41 (br. s., 4H), 1.90 (d, J=1.4 Hz, 3H), 1.77 (t, J=8.0 Hz, 1H), 1.15-1.22 (m, 1H), 0.81 (t, J=5.9 Hz, 1H). MS (ESI, positive ion) m/z: 562 (M+1).

Example 786

N-(3-((1S,5S,6S)-3-amino-5-(fluoromethyl)-1-(isoxazol-3-yl)-2-thia-4-azabicyclo[4.1.0]hept-3-en-5-yl)-4-fluorophenyl)-5-chloropicolinamide

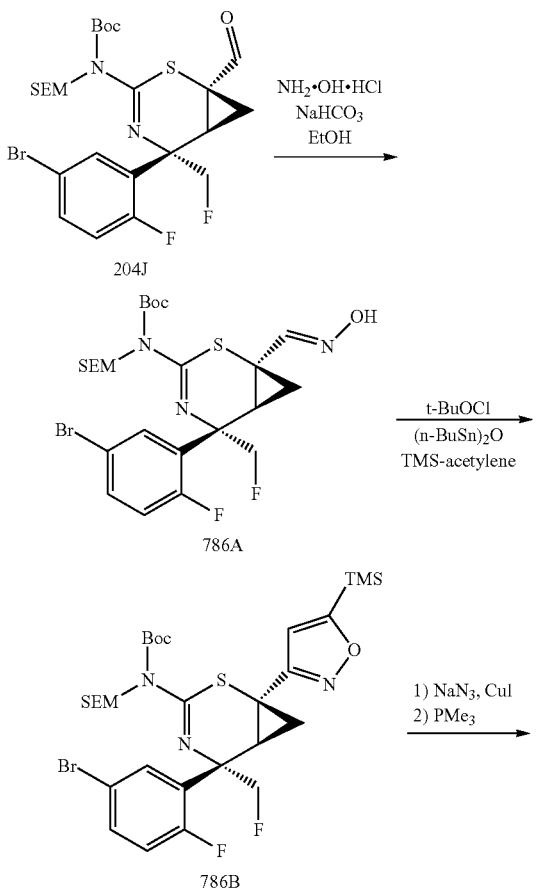

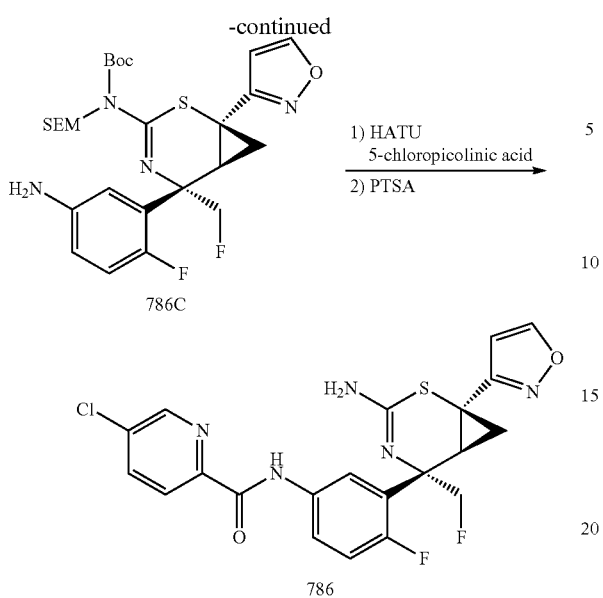

Preparation of tert-butyl((1S,5S,6S)-5-(5-bromo-2-fluorophenyl)-5-(fluoromethyl)-1-((E)-(hydroxyimino)methyl)-2-thia-4-azabicyclo[4.1.0]hept-3-en-3-yl)((2-(trimethylsilyl)ethoxy)methyl)carbamate (786A). A mixture of tert-butyl((1S,5S,6S)-5-(5-bromo-2-fluorophenyl)-5-(fluoromethyl)-1-formyl-2-thia-4-azabicyclo[4.1.0]hept-3-en-3-yl)((2-(trimethylsilyl)ethoxy)methyl)carbamate (2.00 g, 3.38 mmol), hydroxylamine hydrochloride (0.352 g, 5.07 mmol), and NaHCO₃ (0.71 g, 8.45 mmol) in EtOH (30 mL) was stirred at RT for 16 h. The reaction mixture was concentrated to dryness. The residue was added H₂O. The white solid (1.62 g, 80%) was collected, washed with H₂O, dried and used in the next step. ¹H NMR (CHLOROFORM-d) δ: 7.84 (dd, J=7.0, 2.5 Hz, 1H), 7.41 (ddd, J=8.7, 4.3, 2.7 Hz, 1H), 7.28 (s, 1H), 7.13 (br. s., 1H), 6.97 (dd, J=11.6, 8.7 Hz, 1H), 5.30 (d, J=10.6 Hz, 1H), 5.06 (d, J=10.6 Hz, 1H), 4.83-4.98 (m, 1H), 4.66-4.82 (m, 1H), 3.67 (td, J=8.3, 1.2 Hz, 2H), 2.19 (ddd, J=9.6, 7.4, 2.0 Hz, 1H), 1.52 (s, 9H), 1.38 (dd, J=9.9, 6.0 Hz, 1H), 1.04-1.12 (m, 1H), 0.98 (dd, J=9.2, 7.4 Hz, 2H), 0.00 (s, 9H). (ESI, positive ion) m/z: 606/608 (M+1).

Preparation of tert-butyl((1S,5S,6S)-5-(5-bromo-2-fluorophenyl)-5-(fluoromethyl)-1-(5-(trimethylsilyl)isoxazol-3-yl)-2-thia-4-azabicyclo[4.1.0]hept-3-en-3-yl)((2-(trimethylsilyl)ethoxy)methyl)carbamate (786B). To a stirred mixture of tert-butyl((1S,5S,6S)-5-(5-bromo-2-fluorophenyl)-5-(fluoromethyl)-1-((E)-(hydroxyimino)methyl)-2-thia-4-azabicyclo[4.1.0]hept-3-en-3-yl)((2-(trimethylsilyl)ethoxy)methyl)carbamate (1.62 g, 2.67 mmol), (trimethylsilyl)acetylene (1.13 mL, 8.00 mmol), and bis(tributylstannyl)oxide (2.04 mL, 4.00 mmol) in DCM (3 mL) at 0° C. was added tert-butyl hypochlorite (0.45 mL, 4.00 mmol). After the addition, the reaction mixture was gradually warmed to RT and stirred for 24 h. The reaction was diluted with DCM and washed with H₂O followed by brine, dried over Na₂SO₄, and concentrated. The residue was purified by silica gel column to give the title compound (1.15 g, 61%).

Preparation of tert-butyl((1S,5S,6S)-5-(5-amino-2-fluorophenyl)-5-(fluoromethyl)-1-(isoxazol-3-yl)-2-thia-4-azabicyclo[4.1.0]hept-3-en-3-yl)((2-(trimethylsilyl)ethoxy)methyl)carbamate (786C). The title compound (286 mg, 28%) was prepared in the same manner as described for Example 755B. MS (ESI, positive ion) m/z: 567 (M+1).

Preparation of N-(3-((1S,5S,6S)-3-amino-5-(fluoromethyl)-1-(isoxazol-3-yl)-2-thia-4-azabicyclo[4.1.0]hept-3-en-5-yl)-4-fluorophenyl)-5-chloropicolinamide (786). The title compound (25 mg, 60%) was prepared in the same manner as described for Example 784 (Method-F1: HATU mediated amide formation followed by removal of protecting groups with PTSA). ¹H NMR (DMSO-d6) δ: 10.63 (s, 1H), 8.92 (d, J=1.6 Hz, 1H), 8.79 (d, J=2.3 Hz, 1H), 8.19-8.23 (m, 1H), 8.13-8.18 (m, 1H), 8.08 (dd, J=7.0, 2.7 Hz, 1H), 7.89 (dt, J=8.2, 3.7 Hz, 1H), 7.21 (dd, J=11.7, 8.8 Hz, 1H), 6.63 (d, J=1.8 Hz, 1H), 6.49 (s, 2H), 4.62-4.89 (m, 2H), 2.08-2.16 (m, 1H), 1.63 (dd, J=9.8, 5.5 Hz, 1H), 1.08-1.16 (m, 1H). MS (ESI, positive ion) m/z: 476 (M+1).

Examples: 855, 856, 857 and 858

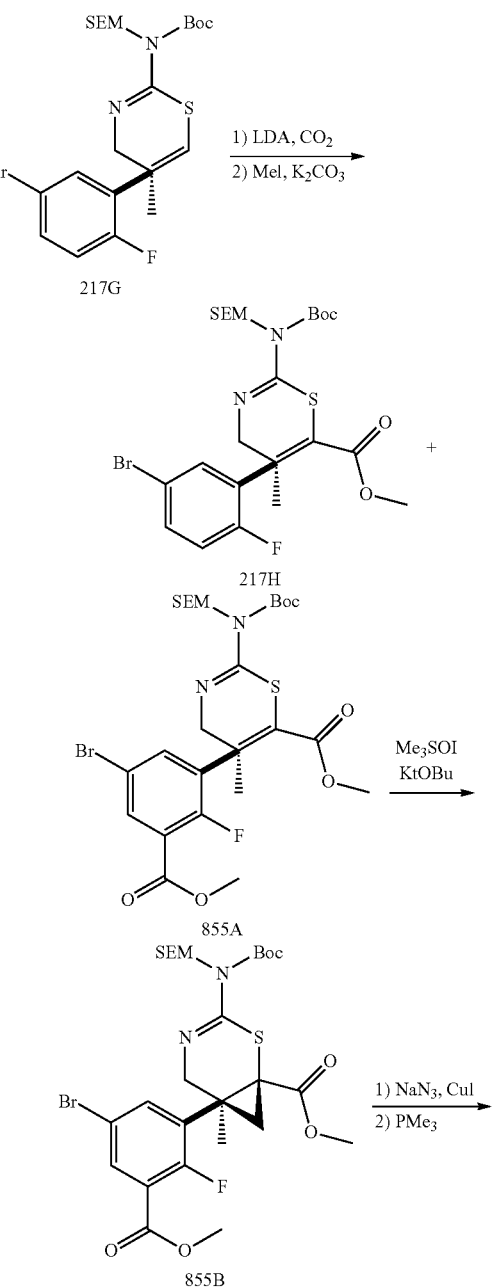

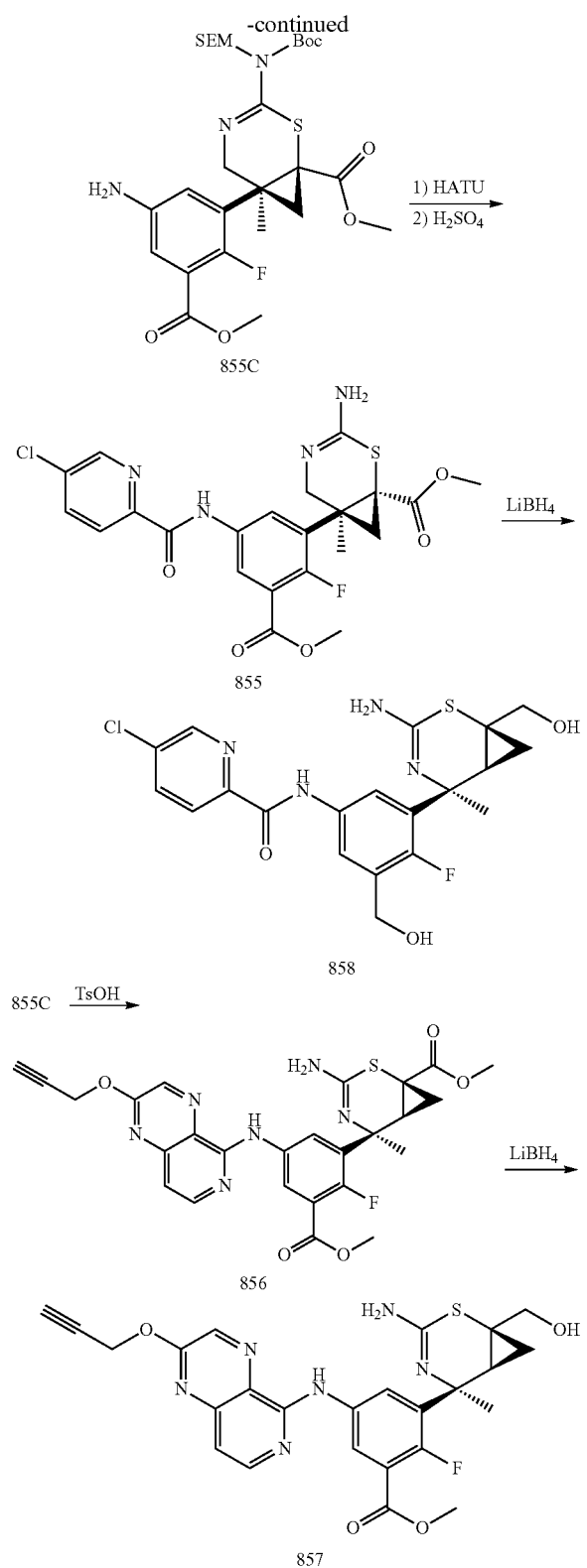

After addition, the mixture was then stirred at −78° C. for 45 min. Then, the mixture was bubbled CO₂ gas for 3 min. The mixture was warmed to RT and quenched with saturated ammonium chloride. It was extracted with EtOAc (3×20 mL). The combined organic extracts were dried over MgSO4, and concentrated. LCMS indicated that the crude material was a mixture of two products, in a ratio of about 2:1. To the residue in 2 mL of DMF was added potassium carbonate (1.92 g, 13.88 mmol) and methyl iodide (0.86 mL, 13.88 mmol). The reaction mixture was stirred overnight. It was quenched with sat. NH₄Cl, extracted with EtOAc, dried and concentrated. Flash column (5-20% EtOAc in DCM) gave (S)-methyl 4-(5-bromo-2-fluorophenyl)-2-((tert-butoxycarbonyl)((2-(trimethylsilyl)ethoxy)methyl)amino)-4-methyl-4H-1,3-thiazine-6-carboxylate (920 mg, 1.56 mmol, 67% yield) and (S)-methyl 4-(5-bromo-2-fluoro-3-(methoxycarbonyl)phenyl)-2-((tert-butoxycarbonyl)((2-(trimethylsilyl)ethoxy)methyl)amino)-4-methyl-4H-1,3-thiazine-6-carboxylate (855A, 470 mg, 0.726 mmol, 31% yield) as a yellow oil. LCMS (ESI⁺) m/z=647.5 (M+H). ¹H NMR (300 MHz, CHLOROFORM-d) δ 7.84-8.06 (m, 2H), 7.14 (d, J=3.65 Hz, 1H), 5.31-5.44 (m, 1H), 5.20 (d, J=10.38 Hz, 1H), 3.95 (s, 3H), 3.83 (s, 3H), 3.68 (dd, J=7.67, 8.84 Hz, 2H), 1.74 (d, J=1.02 Hz, 3H), 1.56 (s, 9H), 0.84-1.06 (m, 2H), 0.00 (s, 9H).

Preparation of Compound 855B. This intermediate was prepared from 855A in a fashion similar to that described for intermediate 217I. LCMS (ESI⁺) m/z=661.5 (M+H). ¹H NMR (400 MHz, CHLOROFORM-d) δ 7.99 (dd, J=2.74, 6.26 Hz, 1H), 7.95 (dd, J=2.64, 5.77 Hz, 1H), 5.26 (d, J=10.56 Hz, 1H), 4.99 (d, J=10.56 Hz, 1H), 3.94 (s, 3H), 3.78 (s, 3H), 3.60-3.70 (m, 2H), 2.70 (t, J=8.22 Hz, 1H), 1.74 (s, 3H), 1.52 (s, 9H), 1.45 (dd, J=5.28, 9.78 Hz, 1H), 1.13 (dd, J=5.38, 7.53 Hz, 1H), 0.91-1.01 (m, 2H), 0.00 (s, 9H).

Preparation of 855C. A microwave vial was charged with (1S,5S,6S)-methyl 5-(5-bromo-2-fluoro-3-(methoxycarbonyl)phenyl)-3-((tert-butoxycarbonyl)((2-(trimethylsilyl)ethoxy)methyl)amino)-5-methyl-2-thia-4-azabicyclo[4.1.0]hept-3-ene-1-carboxylate (855B, 320 mg, 0.48 mmol), sodium azide (94 mg, 1.45 mmol), copper(I) iodide (13.82 mg, 0.073 mmol), sodium (R)-2-((S)-1,2-dihydroxyethyl)-4-hydroxy-5-oxo-2,5-dihydrofuran-3-olate (14.37 mg, 0.07 mmol), EtOH (3 mL) and water (1 mL) was purged with N₂ and sealed. Then (1R,2R)—N₁,N₂-dimethylcyclohexane-1,2-diamine (0.023 mL, 0.145 mmol) was added. The mixture was heated to 80° C. After 60 min, LCMS showed most of the bromide was consumed. The mixture was treated with saturated NH₄Cl and diluted with EtOAc. The organic layer was separated and the aqueous layer was extracted twice with EtOAc. The organic solution was washed with brine, dried over Na₂SO₄, and concentrated in vacuo. To the residue in THF (3 mL) and water (1 mL) was added trimethylphosphine (1.0 M solution in THF, 0.58 mL, 0.58 mmol). After 10 min, the mixture was evaporated to dryness and purified by a quick silica gel chromatography (10-20% EtOAc in DCM) to give (1S,5S,6S)-methyl 5-(5-amino-2-fluoro-3-(methoxycarbonyl)phenyl)-3-((tert-butoxycarbonyl)((2-(trimethylsilyl)ethoxy)methyl)amino)-5-methyl-2-thia-4-azabicyclo[4.1.0]hept-3-ene-1-carboxylate (855C, 130 mg, 0.21 mmol, 45% yield) which was used directly in the next step.

Preparation of Example 855. To a mixture of (1S,5S,6S)-methyl 5-(5-amino-2-fluoro-3-(methoxycarbonyl)phenyl)-3-((tert-butoxycarbonyl)((2-(trimethylsilyl)ethoxy)methyl)amino)-5-methyl-2-thia-4-azabicyclo[4.1.0]hept-3-ene-1-carboxylate (50 mg, 0.084 mmol) and 5-chloro-2-

Preparation of Compound 855A. To a solution of (S)-tert-butyl(4-(5-bromo-2-fluorophenyl)-4-methyl-4H-1,3-thiazin-2-yl)((2-(trimethylsilyl)ethoxy)methyl)carbamate (217G, 1.23 g, 2.31 mmol) in THF (10 mL) under N₂ at −78° C. was added lithium diisopropylamide (2.0 M solution in THF/heptane/ethylbenzene, 3.47 mL, 6.94 mmol) dropwise.

pyridinecarboxylic acid (855C, 26.4 mg, 0.167 mmol) in 0.5 mL of DMF was added HATU (63.6 mg, 0.167 mmol) and diisopropylethylamine (29.1 μL, 0.167 mmol). After stirring overnight, LCMS showed about 80% conversion. The reaction was quenched with sat. NH₄Cl, extracted with EtOAc, dried over Na₂SO₄, filtered and evaporated to dryness. Flash column (0-10% EtOAc in DCM) afforded (1S,5S,6S)-methyl 3-((tert-butoxycarbonyl)((2-(trimethylsilyl)ethoxy)methyl)amino)-5-(5-(5-chloropicolinamido)-2-fluoro-3-(methoxycarbonyl)phenyl)-5-methyl-2-thia-4-azabicyclo[4.1.0]hept-3-ene-1-carboxylate (40 mg, 0.054 mmol, 64.9% yield) as a gum. ¹H NMR (300 MHz, CHLOROFORM-d) δ 9.88 (s, 1H), 8.58 (d, J=2.05 Hz, 1H), 8.49 (dd, J=2.92, 5.70 Hz, 1H), 8.28 (d, J=8.48 Hz, 1H), 8.10 (dd, J=3.00, 6.21 Hz, 1H), 7.92 (dd, J=2.34, 8.33 Hz, 1H), 5.38 (d, J=10.52 Hz, 1H), 5.13 (d, J=10.52 Hz, 1H), 3.99 (s, 3H), 3.82 (s, 3H), 3.72 (dd, J=7.75, 8.77 Hz, 2H), 2.79 (t, J=8.70 Hz, 1H), 1.82 (s, 3H), 1.57 (s, 9H), 1.52 (dd, J=5.26, 9.79 Hz, 1H), 1.21 (dd, J=5.33, 7.53 Hz, 1H), 0.93-1.07 (m, 2H), 0.00 (s, 9H).

To the neat (1S,5S,6S)-methyl 3-((tert-butoxycarbonyl)((2-(trimethylsilyl)ethoxy)methyl)amino)-5-(5-(5-chloropicolinamido)-2-fluoro-3-(methoxycarbonyl)phenyl)-5-methyl-2-thia-4-azabicyclo[4.1.0]hept-3-ene-1-carboxylate (40 mg, 0.054 mmol) was added 0.2 mL of concentrated H₂SO₄ and the mixture was stirred at RT for 20 min. It was quenched with sat NaHCO₃ to pH=8, extracted with EtOAc, dried and evaporated to dryness. Flash column (DCM/EtOAc=3:1 to 2:1 to 1:1) gave (1S,5S,6S)-methyl 3-amino-5-(5-(5-chloropicolinamido)-2-fluoro-3-(methoxycarbonyl)phenyl)-5-methyl-2-thia-4-azabicyclo[4.1.0]hept-3-ene-1-carboxylate (855, 33 mg, 0.065 mmol, 78% yield) as an off-white solid. LCMS (ESI⁺) m/z=507.0 (M+H). ¹H NMR (300 MHz, CHLOROFORM-d) δ 9.87 (s, 1H), 8.56 (d, J=2.34 Hz, 1H), 8.42 (dd, J=3.07, 5.70 Hz, 1H), 8.25 (d, J=8.48 Hz, 1H), 8.16 (dd, J=2.92, 6.28 Hz, 1H), 7.89 (dd, J=2.34, 8.33 Hz, 1H), 3.96 (s, 3H), 3.79 (s, 3H), 2.61-2.74 (m, 1H), 1.75 (d, J=1.32 Hz, 3H), 1.52 (dd, J=5.12, 9.79 Hz, 1H), 1.12 (dd, J=5.41, 7.45 Hz, 1H).

Preparation of Example 858. A solution of lithium tetrahydroborate (0.12 mL of 2 M in THF, 0.24 mmol) was added dropwise to a solution of (1S,5S,6S)-methyl 3-amino-5-(5-(5-chloropicolinamido)-2-fluoro-3-(methoxycarbonyl)phenyl)-5-methyl-2-thia-4-azabicyclo[4.1.0]hept-3-ene-1-carboxylate (Example 855, 30 mg, 0.06 mmol) under argon at RT, followed by addition of MeOH (15 mg, 0.47 mmol). The mixture was stirred for 1 h (slight exotherm), at which time LCMS suggested complete conversion. The reaction was quenched by the careful addition of satd. NH₄Cl and the product was extracted into EtOAc (2×). The combined extracts were dried (Na₂SO₄), filtered, and concentrated in vacuo and submit to flash column (DCM/MeOH=10:1 to 5:1) to give product as a solid N-(3-((1S,5S,6S)-3-amino-1-(hydroxymethyl)-5-methyl-2-thia-4-azabicyclo[4.1.0]hept-3-en-5-yl)-4-fluoro-5-(hydroxymethyl)phenyl)-5-chloropicolinamide (Example 858, 15 mg, 0.03 mmol, 56% yield). LCMS (ESI⁺) m/z=451.0 (M+H). ¹H NMR (400 MHz, MeOH) δ 8.73 (d, J=2.15 Hz, 1H), 8.22 (d, J=8.41 Hz, 1H), 8.10 (dd, J=2.45, 8.51 Hz, 1H), 7.83-7.94 (m, 2H), 4.75 (s, 2H), 3.66 (s, 2H), 1.88-1.97 (m, 4H), 1.25 (dd, J=6.06, 9.19 Hz, 1H), 0.90 (t, J=6.16 Hz, 1H).

Preparation of Example 856. To a mixture of 5-chloro-2-(prop-2-yn-1-yloxy)pyrido[3,4-b]pyrazine (38.6 mg, 0.176 mmol) and (5S)-methyl 5-(5-amino-2-fluoro-3-(methoxycarbonyl)phenyl)-3-((tert-butoxycarbonyl)((2-(trimethylsilyl)ethoxy)methyl)amino)-5-methyl-2-thia-4-azabicyclo[4.1.0]hept-3-ene-1-carboxylate (855C, 70 mg, 0.117 mmol) in 3 mL of iPrOH was added p-toluenesulfonic acid monohydrate (66.8 mg, 0.351 mmol) and the mixture was stirred at 80° C. for 2 h. The solvent was evaporated and the residue was treated with 0.2 mL of concentrated H₂SO₄ and stirred at RT for 20 min. The reaction was quenched with sat. NaHCO₃, extracted with EtOAc, dried and evaporated. Flash column (DCM/EtOAc=3:1 to 2:1) gave (1S,5S,6S)-methyl 3-amino-5-(2-fluoro-3-(methoxycarbonyl)-5-((2-(prop-2-yn-1-yloxy)pyrido[3,4-b]pyrazin-5-yl)amino)phenyl)-5-methyl-2-thia-4-azabicyclo[4.1.0]hept-3-ene-1-carboxylate (Example 856, 35 mg, 0.06 mmol, 54% yield) as a light yellow solid. LCMS (ESI⁺) m/z=551.0 (M+H). ¹H NMR (300 MHz, CHLOROFORM-d) δ 8.72 (ddd, J=1.46, 3.11, 5.66 Hz, 1H), 8.65 (s, 1H), 8.35 (d, J=1.75 Hz, 1H), 8.29 (dd, J=1.02, 5.85 Hz, 1H), 7.99-8.16 (m, 1H), 7.07 (dd, J=1.32, 5.99 Hz, 1H), 5.15 (dd, J=0.80, 2.41 Hz, 2H), 3.97 (s, 3H), 3.78 (s, 3H), 2.67 (t, J=8.77 Hz, 1H), 2.57 (t, J=2.48 Hz, 1H), 1.77 (s, 3H), 1.50-1.61 (m, 1H), 1.07-1.18 (m, 1H).

Preparation of Example 857. A solution of LiBH₄ (0.11 mL of 2 M THF solution, 0.22 mmol) was added dropwise to a solution of (1S,5S,6S)-methyl 3-amino-5-(2-fluoro-3-(methoxycarbonyl)-5-((2-(prop-2-yn-1-yloxy)pyrido[3,4-b]pyrazin-5-yl)amino)phenyl)-5-methyl-2-thia-4-azabicyclo[4.1.0]hept-3-ene-1-carboxylate (Example 856, 30 mg, 0.05 mmol) under argon at RT, followed by addition of MeOH (14 mg, 0.43 mmol). The mixture was stirred for 1 h, then quenched by the careful addition of sat. NH₄Cl. The mixture was extracted with EtOAc (2×). The combined extracts were dried (Na₂SO₄), filtered, and concentrated in vacuo and submit to flash column (DCM/MeOH=10:1 to 5:1) to give methyl 3-((1S,5S,6S)-3-amino-1-(hydroxymethyl)-5-methyl-2-thia-4-azabicyclo[4.1.0]hept-3-en-5-yl)-2-fluoro-5-((2-(prop-2-yn-1-yloxy)pyrido[3,4-b]pyrazin-5-yl)amino)benzoate (Example 857, 15 mg, 0.03 mmol, 53% yield) as an off-white solid. LCMS (ESI⁺) m/z=523.0 (M+H). ¹H NMR (400 MHz, CHLOROFORM-d) δ 8.68 (dd, J=2.93, 5.67 Hz, 1H), 8.64 (s, 1H), 8.35 (s, 1H), 8.29 (d, J=5.87 Hz, 1H), 8.03 (dd, J=2.93, 6.26 Hz, 1H), 7.07 (d, J=5.87 Hz, 1H), 5.15 (d, J=2.54 Hz, 2H), 3.97 (s, 3H), 3.61-3.74 (m, 2H), 2.57 (t, J=2.45 Hz, 1H), 1.91 (dd, J=7.34, 8.90 Hz, 1H), 1.79 (s, 3H), 0.90-0.98 (m, 1H), 0.76 (t, J=6.26 Hz, 1H).

Example 899

Lithium (1S,5S,6S)-3-amino-5-(5-(5-chloropicolinamido)-2,3-difluorophenyl)-5-methyl-2-thia-4-azabicyclo[4.1.0]hept-3-ene-1-carboxylate

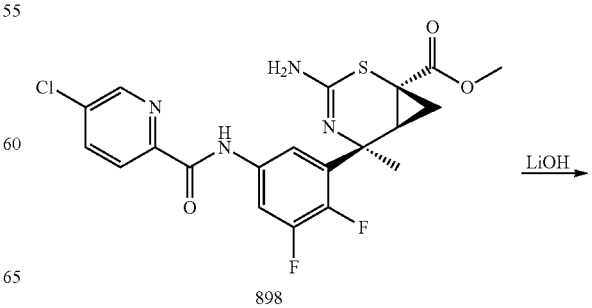

898

-continued

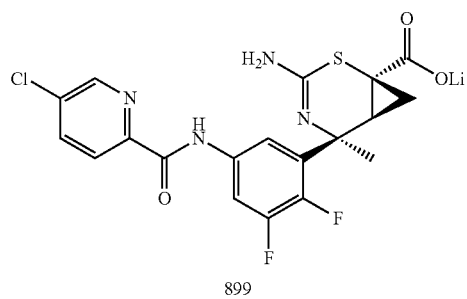

899

A suspension of (1S,5S,6S)-methyl 3-amino-5-(5-(5-chloropicolinamido)-2,3-difluorophenyl)-5-methyl-2-thia-4-azabicyclo[4.1.0]hept-3-ene-1-carboxylate (Example 898, 25 mg, 0.05 mmol) and lithium hydroxide monohydrate (3 mg, 0.05 mmol) in THF (0.4 mL), MeOH (0.2 mL), and water (0.2 mL) was stirred at 40° C. sand bath for 48 h. The solvents were then removed via positive pressure of nitrogen to afford lithium (1S,5S,6S)-3-amino-5-(5-(5-chloropicolinamido)-2,3-difluorophenyl)-5-methyl-2-thia-4-azabicyclo[4.1.0]hept-3-ene-1-carboxylate (899, 25 mg, 0.05 mmol, 100%) as white solid. LC/MS (ESI⁻) m/z=453.0 (M+H)⁺ [expected for the acid]. ¹H NMR (400 MHz, DMSO-d₆) δ 10.71 (s, 1H), 8.66 (br. s., 1H), 8.15-8.23 (m, 1H), 8.11 (br. s., 1H), 7.80-8.00 (m, 1H), 7.70 (br. s., 1H), 5.56 (br. s., 2H), 2.04 (t, J=7.53 Hz, 1H), 1.52 (s, 3H), 0.92 (dd, J=3.52, 9.00 Hz, 1H), 0.47 (dd, J=3.42, 6.36 Hz, 1H).

Example 902

1-((1S,5S,6S)-3-amino-5-(5-((7-chloropyrido[3,2-d]pyrimidin-4-yl)amino)-2,3-difluorophenyl)-5-methyl-2-thia-4-azabicyclo[4.1.0]hept-3-en-1-yl)ethanone

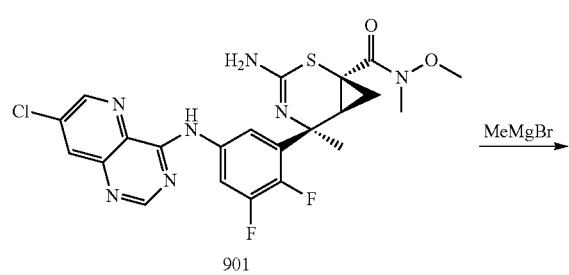

901

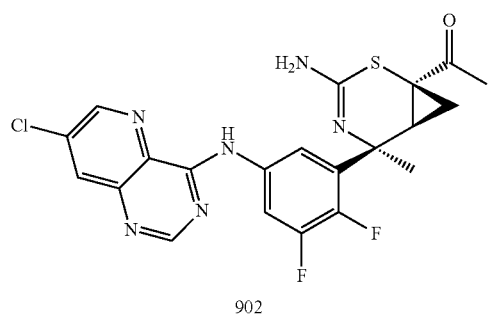

902

To a stirring solution of (1S,5S,6S)-3-amino-5-(5-((7-chloropyrido[3,2-d]pyrimidin-4-yl)amino)-2,3-difluorophenyl)-N-methoxy-N,5-dimethyl-2-thia-4-azabicyclo[4.1.0]hept-3-ene-1-carboxamide (901, 50 mg, 0.09 mmol) in THF (1 mL) at −8° C. (wet ice/ACN) under nitrogen was added methylmagnesium bromide (0.6 mL of 3.0 M in Et₂O, 1.8 mmol). The reaction was slowly quenched with sat NH₄Cl. The reaction was then partitioned between 5% NaHCO₃ (15 mL), water (15 mL) and EtOAc (15 mL). The organic layer was dried over MgSO₄, concentrated under reduced pressure, then purified by silica gel chromatography (0-60% ACN in CH₂Cl₂) to afford Example 902 (12 mg, 0.025 mmol, 26% yield) as white solid. LC/MS (ESI⁻) m/z=475.0 (M+H)⁺. ¹H NMR (400 MHz, DMSO-d₆) δ 10.49 (br. s., 1H), 8.95 (d, J=2.15 Hz, 1H), 8.75 (s, 1H), 8.43 (d, J=1.96 Hz, 1H), 8.22 (br. s., 1H), 8.11 (br. s., 1H), 6.18 (br. s., 2H), 2.12 (s, 3H), 1.77 (br. s., 1H), 1.64 (br. s., 3H), 1.25 (br. s., 1H), 1.15 (d, J=5.28 Hz, 1H), 0.86 (t, J=6.75 Hz, 1H).

Example 905

(1S,5S,6S)-3-amino-5-(5-(5-chloropicolinamido)-2,3-difluorophenyl)-5-methyl-2-thia-4-azabicyclo[4.1.0]hept-3-ene-1-carboxamide

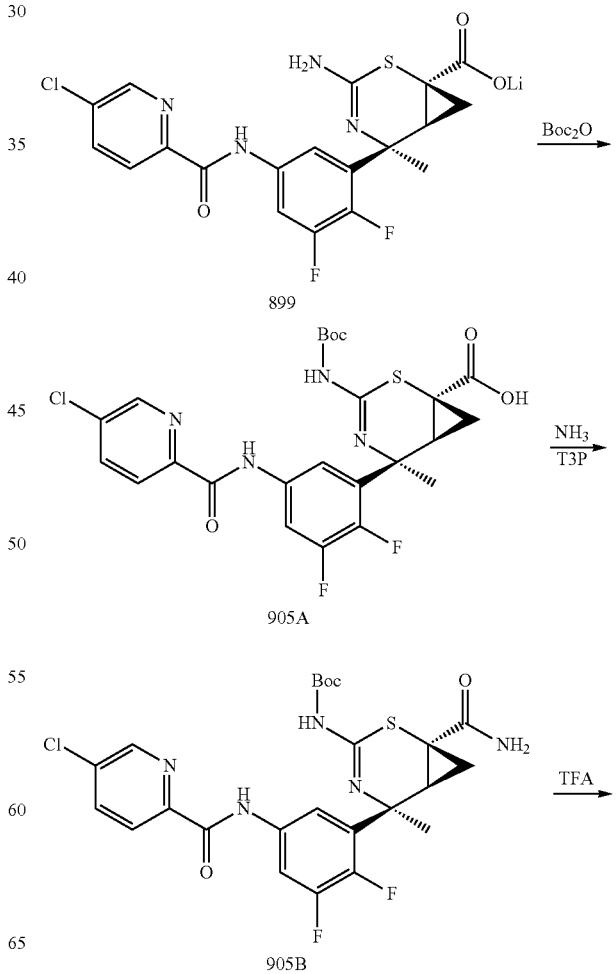

-continued

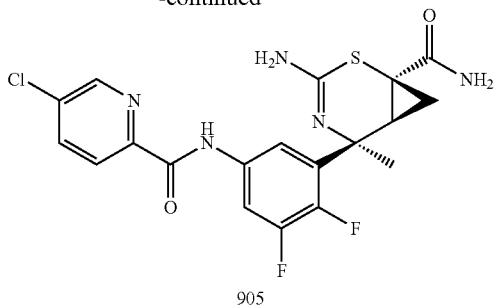

905

Preparation of Compound 905A. To a stirring suspension of lithium (1S,5S,6S)-3-amino-5-(5-(5-chloropicolinamido)-2,3-difluorophenyl)-5-methyl-2-thia-4-azabicyclo[4.1.0]hept-3-ene-1-carboxylate (899) (220 mg, 0.40 mmol) in DMF (2 mL) at 20° C. under nitrogen was added di-tert-butyl dicarbonate (131 mg, 0.60 mmol) and DMAP (2 mg). The suspension was heated in a 50° C. sand bath. After 15 min, the reaction was exposed to $K_2CO_3$ (150 mg) and MeOH (3 mL). After 10 min the reaction was partitioned between EtOAc (20 mL) and 1 M HCl (50 mL). The aqueous was further extracted with EtOAc (20 mL). The combined organics were dried over $MgSO_4$, filtered, then and concentrated under reduced pressure to afford (1S,5S,6S)-3-((tert-butoxycarbonyl)amino)-5-(5-(5-chloropicolinamido)-2,3-difluorophenyl)-5-methyl-2-thia-4-azabicyclo[4.1.0]hept-3-ene-1-carboxylic acid (905A, 265 mg, 0.48 mmol) as colorless oil. LC/MS (ESI$^-$) m/z=553.1 (M+H)$^+$.

Preparation of Compound 905B. To a stirring solution of (1S,5S,6S)-3-((tert-butoxycarbonyl)amino)-5-(5-(5-chloropicolinamido)-2,3-difluorophenyl)-5-methyl-2-thia-4-azabicyclo[4.1.0]hept-3-ene-1-carboxylic acid (905A, 250 mg, 0.452 mmol) in DMF (1 mL) was added 1-propanephosphonic acid cyclic anhydride (50% in EtOAc, 0.86 mL, 1.36 mmol). The solution was stirred for 20 min at 20° C. then ammonia (7 M in MeOH, 0.45 mL, 3.15 mmol) added. The resulting suspension was stirred for 3 days at 20° C. The reaction was then partitioned between 9:1 $CHCl_3$/IPA (20 mL) and 5% $NaHCO_3$ (10 mL). The organic was dried over $MgSO_4$, filtered, concentrated under reduced pressure, and then purified by silica gel chromatography (12 g) eluting products with 0-6% MeOH/$CH_2Cl_2$ to afford tert-butyl((1S,5S,6S)-1-carbamoyl-5-(5-(5-chloropicolinamido)-2,3-difluorophenyl)-5-methyl-2-thia-4-azabicyclo[4.1.0]hept-3-en-3-yl)carbamate (905B, 19 mg, 0.034 mmol, 7% yield) as white solid. LC/MS (ESI$^-$) m/z=552.0 (M+H)$^+$.

Preparation of Example 905. At RT, TFA (1 mL) was added to tert-butyl((1S,5S,6S)-1-carbamoyl-5-(5-(5-chloropicolinamido)-2,3-difluorophenyl)-5-methyl-2-thia-4-azabicyclo[4.1.0]hept-3-en-3-yl)carbamate (905B, 19 mg, 0.034 mmol). The solution was stirred for 20 min at 20° C. The TFA was removed under reduced pressure and the residue was partitioned between 9:1 $CHCl_3$/IPA (20 mL) and 1 M $K_2HPO_4$ (10 mL). The separated aqueous was further extracted with 9:1 $CHCl_3$/IPA (2×5 mL). The combined organics were dried over $MgSO_4$, filtered, and concentrated under reduced pressure. The resulting solid was suspended in 1:1 $H_2O$/ACN (2 mL), frozen, then lyophilized to afford (1S,5S,6S)-3-amino-5-(5-(5-chloropicolinamido)-2,3-difluorophenyl)-5-methyl-2-thia-4-azabicyclo[4.1.0]hept-3-ene-1-carboxamide (905, 14 mg, 0.031 mmol, 90% yield) as fluffy white powder. LC/MS (ESI$^-$) m/z=452.0 (M+H)$^+$. $^1$H NMR (400 MHz, DMSO-$d_6$) δ 10.77 (br. s., 1H), 8.79 (d, J=1.76 Hz, 1H), 8.11-8.25 (m, 2H), 7.95 (br. s., 1H), 7.88 (t, J=4.62 Hz, 1H), 7.28 (br. s., 1H), 7.21 (br. s., 1H), 6.10 (br. s., 2H), 2.17 (br. s., 1H), 1.57-1.69 (m, 3H), 1.45 (dd, J=7.43, 15.06 Hz, 1H), 0.79-0.92 (m, 1H).

Using procedures analogous or similar to the general amidation Method D described previously, the appropriate aniline and carboxylic acid intermediates were reacted to provide the 20 examples listed in Table 9 and Table 9'.

TABLE 9

| Ex.No. | Chemical Structure | Observed [M + H]$^+$ |
| --- | --- | --- |
| 963 | 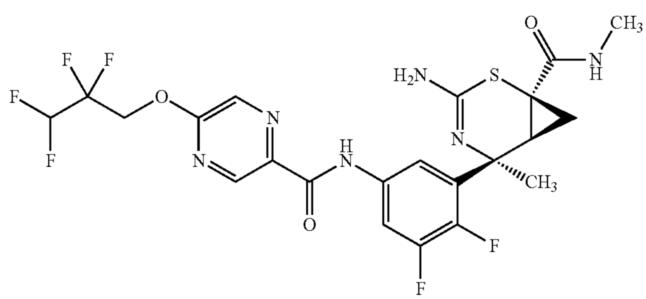 [SMILES: CNC(=O)[C@]12C[C@H]1[C@@](C)(c1cc(NC(=O)c3cnc(OCC(F)(F)C(F)F)cn3)cc(F)c1F)N=C(N)S2] | 563 |
| 964 | 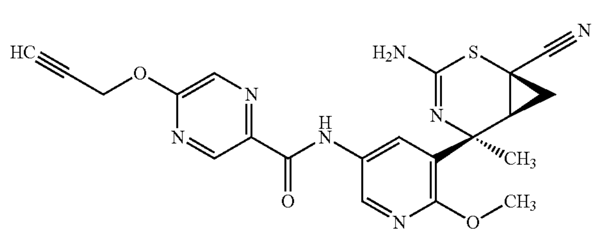 [SMILES: C#CCOc1cnc(C(=O)Nc2cnc(OC)c([C@@]3(C)N=C(N)S[C@@]4(C#N)C[C@H]43)c2)cn1] | 450.2 |

TABLE 9-continued

| Ex.No. | Chemical Structure | Observed [M + H]+ |
|---|---|---|
| 965 | 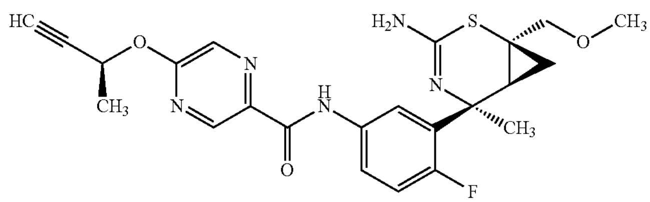 [SMILES: C#C[C@H](C)Oc1cnc(C(=O)Nc2ccc(F)c([C@@]3(C)N=C(N)S[C@@]4(COC)C[C@H]43)c2)cn1] | 470 |
| 966 | 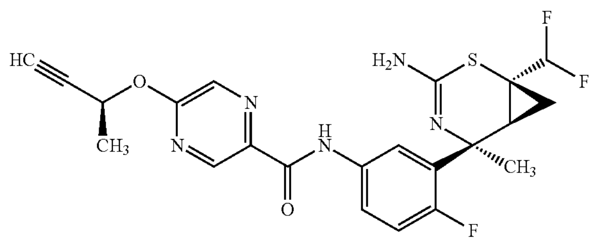 [SMILES: C#C[C@H](C)Oc1cnc(C(=O)Nc2ccc(F)c([C@@]3(C)N=C(N)S[C@@]4(C(F)F)C[C@@H]34)c2)cn1] | 476 |
| 967 | 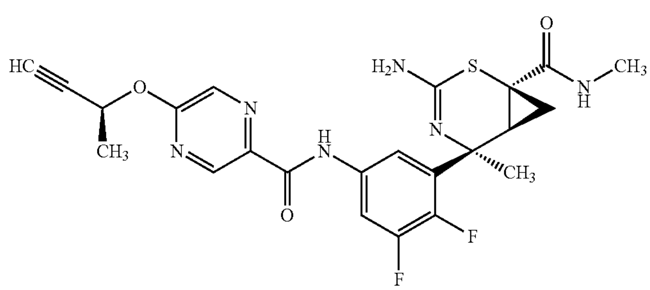 [SMILES: C#C[C@H](C)Oc1cnc(C(=O)Nc2cc(F)c(F)c([C@@]3(C)N=C(N)S[C@@]4(C(=O)NC)C[C@H]43)c2)cn1] | 501 |
| 968 | 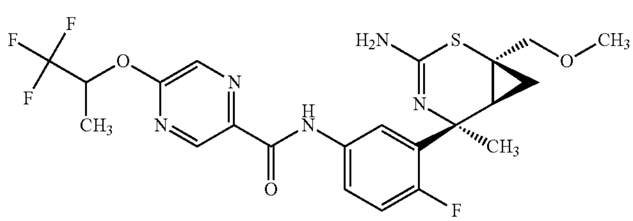 [SMILES: COC[C@]12C[C@H]1[C@@](C)(c1cc(NC(=O)c3cnc(OC(C)C(F)(F)F)cn3)ccc1F)N=C(N)S2] | 514 |
| 969 | 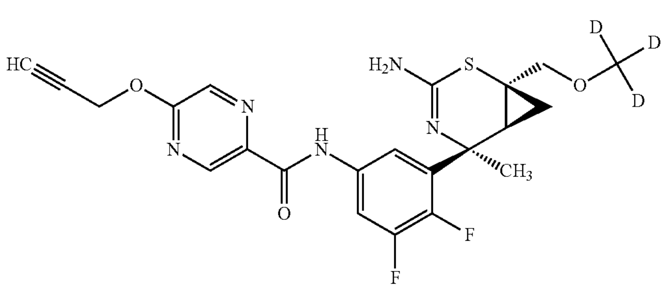 [SMILES: [2H]C([2H])([2H])OC[C@]12C[C@H]1[C@@](C)(c1cc(NC(=O)c3cnc(OCC#C)cn3)cc(F)c1F)N=C(N)S2] | 477 |
| 970 | 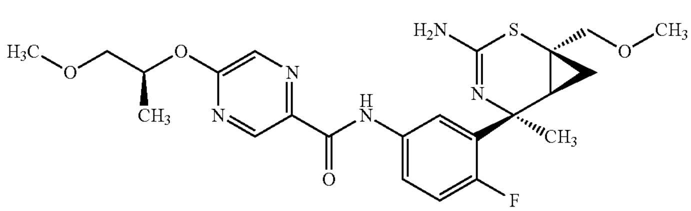 | 490 |

TABLE 9-continued
| Ex.No. | Chemical Structure | Observed [M + H]+ |
|---|---|---|
| 971 | 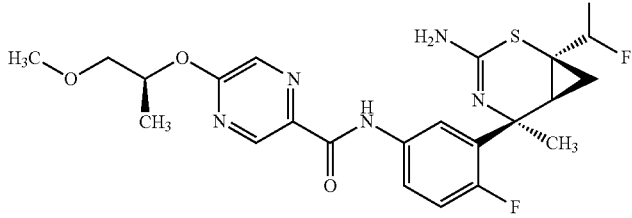 | 496 |
| 975 | 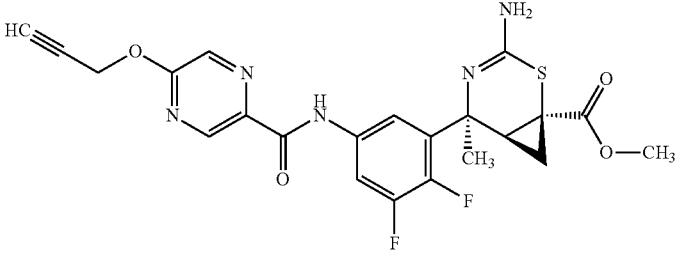 [SMILES: C#CCOc1cnc(C(=O)Nc2cc(F)c(F)c([C@@]3(C)N=C(N)S[C@@]4(C(=O)OC)C[C@H]43)c2)cn1] | 488 |
| 979 | 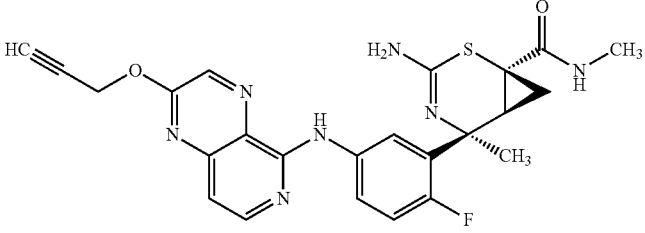 [SMILES: C#CCOc1cnc2c(Nc3ccc(F)c([C@@]4(C)N=C(N)S[C@@]5(C(=O)NC)C[C@H]54)c3)nccc2n1] | 492 |
| 988 | 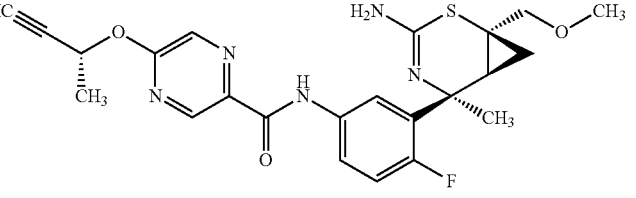 | 470 |
| 989 | 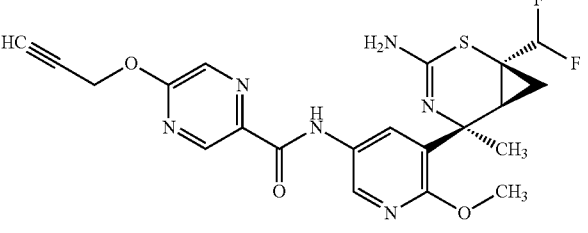 | 475.2 |
| 990 | 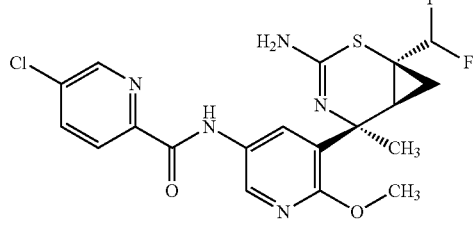 | 454.2 |

TABLE 9-continued

| Ex.No. | Chemical Structure | Observed [M + H]⁺ |
|---|---|---|
| 1007 | 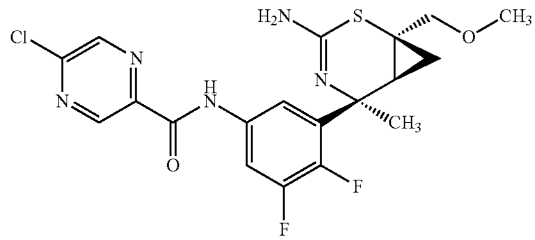 [SMILES: COC[C@]12C[C@H]1[C@@](C)(c1cc(NC(=O)c3cnc(Cl)cn3)cc(F)c1F)N=C(N)S2] | 454 |
| 1008 | 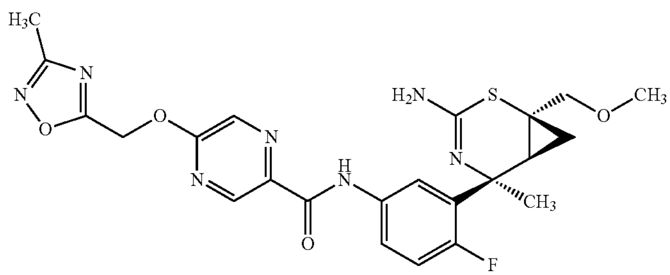 [SMILES: COC[C@]12C[C@H]1[C@@](C)(c1cc(NC(=O)c3cnc(OCc4nc(C)no4)cn3)ccc1F)N=C(N)S2] | 514 |
| 1009 | 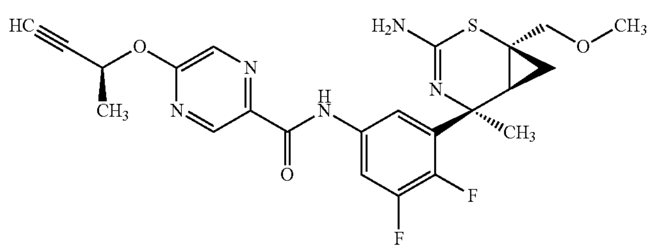 [SMILES: C#C[C@H](C)Oc1cnc(C(=O)Nc2cc(F)c(F)c([C@@]3(C)N=C(N)S[C@@]4(COC)C[C@H]43)c2)cn1] | 488 |
| 1014 | 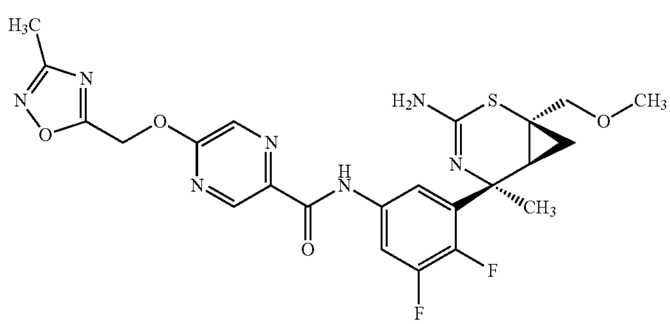 [SMILES: COC[C@]12C[C@H]1[C@@](C)(c1cc(NC(=O)c3cnc(OCc4nc(C)no4)cn3)cc(F)c1F)N=C(N)S2] | 532 |
| 1024 | 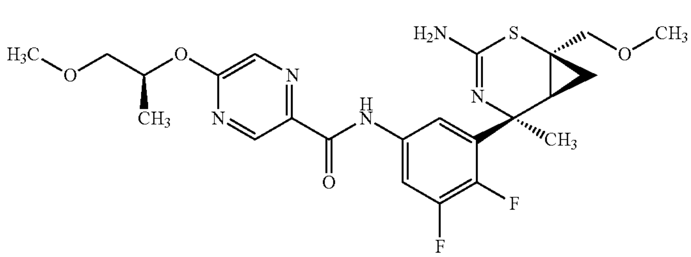 | 508 |

TABLE 9-continued

| Ex.No. | Chemical Structure | Observed [M + H]+ |
|---|---|---|
| 1039 | 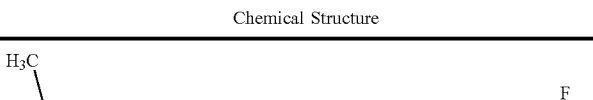 | 520 |

TABLE 9'

| Ex. No | ¹H-NMR | Chemical Name |
|---|---|---|
| 963 | 1H NMR (400 MHz, CHLOROFORM-d) δ 9.34-9.47 (m, 1H), 9.01 (d, J = 1.17 Hz, 1H), 8.26 (d, J = 1.17 Hz, 1H), 7.90 (ddd, J = 2.74, 6.65, 11.54 Hz, 1H), 7.10-7.18 (m, 1H), 6.46 (d, J = 4.30 Hz, 1H), 5.77-6.16 (m, 1H), 4.87 (t, J = 12.72 Hz, 2H), 2.88 (d, J = 4.89 Hz, 3H), 2.21-2.32 (m, 1H), 1.95 (dd, J = 5.09, 9.78 Hz, 1H), 1.81 (s, 3H), 0.75-0.87 (m, 1H) | (1S,5S,6S)-3-amino-5-(2,3-difluoro-5-(((5-(2,2,3,3-tetrafluoropropoxy)-2-pyrazinyl)carbonyl)amino)phenyl)-N,5-dimethyl-2-thia-4-azabicyclo[4.1.0]hept-3-ene-1-carboxamide |
| 964 | ¹H NMR (400 MHz, CHLOROFORM-d) δ 9.35 (s, 1H), 9.02 (s, 1H), 8.52 (d, J = 2.54 Hz, 1H), 8.21 (d, J = 1.17 Hz, 1H), 8.13 (d, J = 2.54 Hz, 1H), 5.09 (d, J = 2.35 Hz, 2H), 4.04 (s, 3H), 4.00-3.50 (br. s., 2H), 2.76 (dd, J = 8.02, 9.98 Hz, 1H), 2.55 (t, J = 2.45 Hz, 1H), 1.79-1.84 (m, 3H), 1.60 (dd, J = 6.26, 9.98 Hz, 1H), 1.06 (dd, J = 6.26, 7.82 Hz, 1H). | N-(5-((1S,5S,6S)-3-amino-1-cyano-5-methyl-2-thia-4-azabicyclo[4.1.0]hept-3-en-5-yl)-6-methoxy-3-pyridinyl)-5-(2-propyn-1-yloxy)-2-pyrazinecarboxamide |
| 965 | 1H NMR (400 MHz, CHLOROFORM-d) δ 9.49 (s, 1H), 9.02 (d, J = 1.17 Hz, 1H), 8.14 (d, J = 0.78 Hz, 1H), 7.94 (td, J = 3.52, 8.61 Hz, 1H), 7.73 (dd, J = 2.84, 6.94 Hz, 1H), 7.06 (dd, J = 8.80, 11.74 Hz, 1H), 5.83 (dq, J = 1.96, 6.65 Hz, 1H), 4.46 (br. s., 2H), 3.66 (d, J = 10.76 Hz, 1H), 3.41 (s, 3H), 3.34 (d, J = 10.76 Hz, 1H), 2.49 (d, J = 2.15 Hz, 1H), 1.80 (dd, J = 7.34, 8.71 Hz, 1H), 1.72 (d, J = 0.78 Hz, 3H), 1.70 (d, J = 6.65 Hz, 3H), 0.87 (dd, J = 5.87, 9.39 Hz, 1H), 0.77-0.83 (m, 1H) | N-(3-((1S,5S,6S)-3-amino-1-(methoxymethyl)-5-methyl-2-thia-4-azabicyclo[4.1.0]hept-3-en-5-yl)-4-fluorophenyl)-5-(((1S)-1-methyl-2-propyn-1-yl)oxy)-2-pyrazinecarboxamide |
| 966 | ¹H NMR (400 MHz, CHLOROFORM-d) δ 9.44 (s, 1H), 9.02 (d, J = 1.17 Hz, 1H), 8.14 (d, J = 1.17 Hz, 1H), 7.80-7.93 (m, 1H), 7.61 (dd, J = 2.74, 6.85 Hz, 1H), 7.06 (dd, J = 8.80, 11.54 Hz, 1H), 5.81-5.88 (m, 1H), 5.50-5.81 (m, 1H), 4.62 (br s, 2H), 2.49 (d, J = 2.15 Hz, 1H), 1.99 (dd, J = 7.24, 9.78 Hz, 1H), 1.78 (s, 3H), 1.70 (d, J = 6.65 Hz, 3H), 1.33 (dd, J = 6.16, 9.88 Hz, 1H), 0.84 (dt, J = 2.74, 6.46 Hz, 1H) | N-(3-((1S,5S,6S)-3-amino-1-(difluoromethyl)-5-methyl-2-thia-4-azabicyclo[4.1.0]hept-3-en-5-yl)-4-fluorophenyl)-5-(((1S)-1-methyl-2-propyn-1-yl)oxy)-2-pyrazinecarboxamide |
| 967 | 1H NMR (400 MHz, CHLOROFORM-d) δ 9.31 (s, 1H), 8.96 (d, J = 1.37 Hz, 1H), 8.11 (d, J = 1.37 Hz, 1H), 7.71-7.88 (m, 1H), 7.13 (dd, J = 2.45, 5.18 Hz, 1H), 6.55 (d, J = 4.69 Hz, 1H), 5.83 (dq, J = 2.05, 6.68 Hz, 1H), 2.87 (d, J = 4.69 Hz, 3H), 2.50 (d, J = 1.96 Hz, 1H), 2.22 (dd, J = 7.63, 9.39 Hz, 1H), 1.98 (dd, J = 5.09, 9.59 Hz, 1H), 1.85 (s, 3H), 1.70 (d, J = 6.65 Hz, 3H), 0.73-0.84 (m, 1H) | (1S,5S,6S)-3-amino-5-(2,3-difluoro-5-(((5-(((1S)-1-methyl-2-propyn-1-yl)oxy)-2-pyrazinyl)carbonyl)amino)phenyl)-N,5-dimethyl-2-thia-4-azabicyclo[4.1.0]hept-3-ene-1-carboxamide |
| 968 | 1H NMR (400 MHz, CHLOROFORM-d) δ 9.48 (s, 1H), 9.01 (d, J = 1.17 Hz, 1H), 8.24 (d, J = 0.98 Hz, 1H), 7.89-8.01 (m, 1H), 7.72 (td, J = 2.74, 6.85 Hz, 1H), 7.07 (dd, J = 8.71, 11.64 Hz, 1H), 5.81 (spt, J = 6.42 Hz, 1H), 3.67 (d, J = 10.76 Hz, 1H), 3.41 (s, 3H), 3.35 (d, J = 10.56 Hz, 1H), 1.81 (dd, J = 7.43, 8.80 Hz, 1H), 1.72 (d, J = 0.98 Hz, 3H), 1.56 (d, J = 6.65 Hz, 3H), 0.88 (dd, J = 5.87, 9.39 Hz, 1H), 0.78-0.83 (m, 1H) | N-(3-((1S,5S,6S)-3-amino-1-(methoxymethyl)-5-methyl-2-thia-4-azabicyclo[4.1.0]hept-3-en-5-yl)-4-fluorophenyl)-5-((1,1,1-trifluoropropan-2-yl)oxy)pyrazine-2-carboxamide |
| 969 | 1H NMR (400 MHz, DMSO-d6) δ 10.61 (s, 1H), 8.90 (d, J = 1.17 Hz, 1H), 8.48 (d, J = 1.17 Hz, 1H), 7.88-7.94 (m, 2H), 5.99 (s, 2H), 5.14 (d, J = 2.35 Hz, 2H), 3.64 (t, J = 2.45 Hz, 1H), 3.56 (d, J = 10.95 Hz, 1H), 3.36 (d, J = 10.95 Hz, 1H), 1.58-1.65 (m, 4H), 0.90 (dd, J = 5.28, 9.19 Hz, 1H), 0.64 (t, J = 5.77 Hz, 1H) | N-(3-((1S,5S,6S)-3-amino-5-methyl-1-(((trideuterium)methyloxy)methyl)-2-thia-4-azabicyclo[4.1.0]hept-3-en-5-yl)-4,5-difluorophenyl)-5-(2-propyn-1-yloxy)-2-pyrazinecarboxamide |
| 970 | 1H NMR (400 MHz, CHLOROFORM-d) δ 9.49 (s, 1H), 8.97 (s, 1H), 8.12 (s, 1H), 7.88-7.99 (m, 1H), 7.73 (dd, J = 2.45, 6.94 Hz, 1H), 7.06 (dd, J = 8.90, 11.64 Hz, | N-(3-((1S,5S,6S)-3-amino-1-(methoxymethyl)-5-methyl-2-thia-4-azabicyclo[4.1.0]hept-3- |

TABLE 9'-continued

| Ex. No | ¹H-NMR | Chemical Name |
|---|---|---|
|  | 1H), 5.45-5.56 (m, 1H), 4.45 (br. s., 2H), 3.54-3.69 (m, 3H), 3.41 (s, 6H), 3.34 (d, J = 10.76 Hz, 1H), 1.76-1.86 (m, 1H), 1.72 (s, 3H), 1.39 (d, J = 6.26 Hz, 3H), 0.87 (dd, J = 5.87, 9.39 Hz, 1H), 0.77-0.83 (m, 1H) | en-5-yl)-4-fluorophenyl)-5-((1S)-2-methoxy-1-methylethoxy)-2-pyrazinecarboxamide |
| 971 | 1H NMR (400 MHz, CHLOROFORM-d) δ 9.42 (s, 1H), 8.94 (d, J = 1.37 Hz, 1H), 8.08 (d, J = 1.37 Hz, 1H), 7.76-7.87 (m, 1H), 7.62 (dd, J = 2.84, 6.94 Hz, 1H), 7.03 (dd, J = 8.61, 11.54 Hz, 1H), 5.46-5.82 (m, 2H), 4.78 (br. s., 2H), 3.54-3.67 (m, 2H), 3.41 (s, 3H), 1.97 (dd, J = 7.24, 9.78 Hz, 1H), 1.79 (d, J = 0.98 Hz, 3H), 1.39 (d, J = 6.46 Hz, 3H), 1.33 (dd, J = 6.16, 9.88 Hz, 1H), 0.78-0.88 (m, 1H) | N-(3-((1S,5S,6S)-3-amino-1-(difluoromethyl)-5-methyl-2-thia-4-azabicyclo[4.1.0]hept-3-en-5-yl)-4-fluorophenyl)-5-((1S)-2-methoxy-1-methylethoxy)-2-pyrazinecarboxamide |
| 975 | ¹H NMR (400 MHz, CHLOROFORM-d) δ ppm 9.51 (br., 1 H), 9.02 (d, J = 1.37 Hz, 1 H), 8.20 (d, J = 1.37 Hz, 1 H), 8.02 (ddd, J = 11.74, 6.85, 2.74 Hz, 1 H), 7.47 (dt, J = 5.50, 2.50 Hz, 1 H), 5.09 (d, J = 2.54 Hz, 2 H), 3.79 (s, 3 H), 2.54-2.61 (m, 2 H), 1.73 (d, J = 0.78 Hz, 3 H), 1.54 (dd, J = 9.78, 5.28 Hz, 1 H), 1.13 (dd, J = 7.43, 5.28 Hz, 1 H). NH₂ peak is broad. ¹⁹F NMR (377 MHz, CHLOROFORM-d) δ ppm −135.85 (d, J = 20.86 Hz, 1 F) −142.34 (d, J = 21.46 Hz, 1 F). | methyl (1S,5S,6S)-3-amino-5-(2,3-difluoro-5-(((5-(2-propyn-1-yloxy)-2-pyrazinyl)carbonyl)amino)phenyl)-5-methyl-2-thia-4-azabicyclo[4.1.0]hept-3-ene-1-carboxylate |
| 979 | 1H NMR (400 MHz, CHLOROFORM-d) δ 8.48 (s, 1H), 8.29 (s, 1H), 8.19 (d, J = 5.87 Hz, 1H), 8.00 (td, J = 3.45, 8.75 Hz, 1H), 7.48 (dd, J = 2.74, 6.85 Hz, 1H), 7.05 (dd, J = 8.80, 11.35 Hz, 1H), 7.00 (d, J = 5.87 Hz, 1H), 6.59 (d, J = 4.69 Hz, 1H), 5.14 (d, J = 2.54 Hz, 2H), 2.87 (d, J = 4.89 Hz, 3H), 2.56 (t, J = 2.35 Hz, 1H), 2.24 (d, J = 7.73, 9.49 Hz, 1H), 1.99 (dd, J = 4.99, 9.68 Hz, 1H), 1.85 (s, 3H), 0.81-0.87 (m, 1H) | (1S,5S,6S)-3-amino-5-(2-fluoro-5-((2-(2-propyn-1-yloxy)pyrido[3,4-b]pyrazin-5-yl)amino)phenyl)-N,5-dimethyl-2-thia-4-azabicyclo[4.1.0]hept-3-ene-1-carboxamide |
| 988 | 1H NMR (400 MHz, CHLOROFORM-d) δ 9.50 (s, 1H), 9.02 (d, J = 1.37 Hz, 1H), 8.14 (d, J = 1.37 Hz, 1H), 7.89-7.99 (m, 1H), 7.74 (dd, J = 2.84, 6.94 Hz, 1H), 7.06 (dd, J = 8.80, 11.74 Hz, 1H), 5.83 (dq, J = 1.96, 6.65 Hz, 1H), 3.66 (d, J = 10.56 Hz, 1H), 3.41 (s, 3H), 3.34 (d, J = 10.76 Hz, 1H), 2.50 (d, J = 2.15 Hz, 1H), 1.80 (ddd, J = 0.88, 7.43, 8.71 Hz, 1H), 1.72 (d, J = 0.98 Hz, 3H), 1.69 (d, J = 6.65 Hz, 3H), 0.87 (dd, J = 5.87, 9.39 Hz, 1H), 0.76-0.83 (m, 1H) | N-(3-(1S,5S,6S)-3-amino-1-(methoxymethyl)-5-methyl-2-thia-4-azabicyclo[4.1.0]hept-3-en-5-yl)-4-fluorophenyl)-5-(((1R)-1-methyl-2-propyn-1-yl)oxy)-2-pyrazinecarboxamide |
| 989 | ¹H NMR (300 MHz, CHLOROFORM-d) δ: 9.36 (s, 1H), 9.04 (s, 1H), 8.60 (d, J = 2.48 Hz, 1H), 8.23 (s, 1H), 8.05 (d, J = 2.48 Hz, 1H), 5.42-5.92 (m, 1H), 5.10 (d, J = 2.19 Hz, 2H), 4.04 (s, 3H), 3.96-4.10 (br. s., 2H), 2.57 (t, J = 2.19 Hz, 1H), 2.18-2.32 (m, 1H), 1.80 (s, 3H), 1.29 (dd, J = 6.14, 10.23 Hz, 1H), 0.72-1.02 (m, 1H). ¹⁹F NMR (282 MHz, CHLOROFORM-d) δ: −116.81 (d, ¹J = 276.36 Hz, 1F), −119.51 (d, ¹J = 276.36 Hz, 1F). | N-(5-((1S,5S,6S)-3-amino-1-(difluoromethyl)-5-methyl-2-thia-4-azabicyclo[4.1.0]hept-3-en-5-yl)-6-methoxy-3-pyridinyl)-5-(2-propyn-1-yloxy)-2-pyrazinecarboxamide |
| 990 | ¹H NMR (300 MHz, CHLOROFORM-d) δ: 9.67 (s, 1H), 8.49-8.65 (m, 2H), 8.23 (d, J = 8.33 Hz, 1H), 8.07 (d, J = 2.05 Hz, 1H), 7.83-7.93 (m, 1H), 5.42-5.94 (m, 1H), 4.09-4.68 (br. s., 2H), 4.03 (s, 3H), 2.21 (dd, J = 7.60, 9.65 Hz, 1H), 1.79 (s, 3H), 1.23-1.35 (m, 1H), 0.69-0.92 (m, 1H). ¹⁹F NMR (282 MHz, CHLOROFORM-d) δ: −116.81 (d, ¹J = 277.07 Hz, 1F), −119.56 (d, ¹J = 277.07 Hz, 1F). | N-(5-((1S,5S,6S)-3-amino-1-(difluoromethyl)-5-methyl-2-thia-4-azabicyclo[4.1.0]hept-3-en-5-yl)-6-methoxy-3-pyridinyl)-5-chloro-2-pyridinecarboxamide |
| 1007 | 1H NMR (400 MHz, CHLOROFORM-d) δ 9.51 (s, 1H), 9.26 (d, J = 1.37 Hz, 1H), 8.57 (d, J = 1.37 Hz, 1H), 8.04 (ddd, J = 2.84, 6.70, 11.59 Hz, 1H), 7.43 (td, J = 2.47, 5.43 Hz, 1H), 4.41 (br. s., 2H), 3.66 (d, J = 10.56 Hz, 1H), 3.41 (s, 3H), 3.35 (d, J = 10.76 Hz, 1H), 1.80 (ddd, J = 1.37, 6.80, 9.24 Hz, 1H), 1.72 (d, J = 0.98 Hz, 3H), 0.90 (dd, J = 5.87, 9.39 Hz, 1H), 0.76-0.82 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-chloro-2-pyrazinecarboxamide |
| 1008 | 1H NMR (400 MHz, CHLOROFORM-d) δ 9.49 (s, 1H), 9.00 (d, J = 1.17 Hz, 1H), 8.33 (d, J = 1.17 Hz, 1H), 7.90-8.01 (m, 1H), 7.71 (dd, J = 2.74, 6.85 Hz, 1H), 7.07 (dd, J = 8.70, 11.64 Hz, 1H), 5.68 (s, 2H), 3.67 (d, J = 10.56 Hz, 1H), 3.41 (s, 3H), 3.35 (d, J = 10.76 Hz, 1H), 2.43 (s, 3H), 1.77-1.85 (m, 1H), 1.72 (s, 3H), 0.88 (dd, J = 5.87, 9.39 Hz, 1H), 0.77-0.84 (m, 1H) | N-(3-((1S,5S,6S)-3-amino-1-(methoxymethyl)-5-methyl-2-thia-4-azabicyclo[4.1.0]hept-3-en-5-yl)-4-fluorophenyl)-5-((3-methyl-1,2,4-oxadiazol-5-yl)methoxy)-2-pyrazinecarboxamide |
| 1009 | 1H NMR (400 MHz, CHLOROFORM-d) δ 9.51 (br. s., 1H), 9.03 (s, 1H), 8.17 (s, 1H), 8.00-8.12 (m, 1H), 7.39 (br. s., 1H), 5.84 (q, J = 6.19 Hz, 1H), 3.67 (d, J = 10.76 Hz, 1H), 3.41 (s, 3H), 3.35 (d, J = 10.37 Hz, 1H), 2.49 (s, 1H), 1.80 (t, J = 7.92 Hz, 1H), 1.69-1.73 (m, 6H), 0.85-0.93 (m, 1H), 0.76-0.84 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-(((1S)-1-methyl-2-propyn-1-yl)oxy)-2-pyrazinecarboxamide |
| 1014 | 1H NMR (400 MHz, CHLOROFORM-d) δ 9.50 (s, 1H), 8.98 (d, J = 1.37 Hz, 1H), 8.32 (d, J = 1.17 Hz, 1H), 8.03 (ddd, J = 2.74, 6.70, 11.69 Hz, 1H), 7.42 (dd, J = 2.45, 5.18 Hz, 1H), 5.68 (s, 2H), 5.63-5.74 (m, 2H), | N-(3-((1S,5S,6S)-3-amino-1-(methoxymethyl)-5-methyl-2-thia-4-azabicyclo[4.1.0]hept-3-en-5-yl)-4,5-difluorophenyl)-5- |

TABLE 9'-continued

| Ex. No | $^1$H-NMR | Chemical Name |
|---|---|---|
| | 3.66 (d, J = 10.56 Hz, 1H), 3.41 (s, 3H), 3.35 (d, J = 10.56 Hz, 1H), 2.43 (s, 3H), 1.75-1.83 (m, 1H), 1.72 (s, 3H), 0.89 (dd, J = 5.87, 9.39 Hz, 1H), 0.75-0.83 (m, 1H) | ((3-methyl-1,2,4-oxadiazol-5-yl)methoxy)-2-pyrazinecarboxamide |
| 1024 | 1H NMR (400 MHz, CHLOROFORM-d) δ 9.51 (s, 1H), 8.97 (d, J = 1.17 Hz, 1H), 8.12 (d, J = 1.17 Hz, 1H), 8.05 (ddd, J = 2.74, 6.80, 11.79 Hz, 1H), 7.40 (dd, J = 2.54, 5.28 Hz, 1H), 5.51 (dquin, J = 3.91, 6.26 Hz, 1H), 4.09-4.84 (m, 2H), 3.50-3.73 (m, 3H), 3.41 (s, 6H), 3.35 (d, J = 10.56 Hz, 1H), 1.75-1.83 (m, 1H), 1.72 (s, 3H), 1.39 (d, J = 6.46 Hz, 3H), 0.89 (dd, J = 5.87, 9.39 Hz, 1H), 0.77-0.83 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-((1S)-2-methoxy-1-methylethoxy)-2-pyrazinecarboxamide |
| 1039 | 1H NMR (400 MHz, CHLOROFORM-d) δ 9.44 (s, 1H), 8.98 (s, 1H), 8.32 (s, 1H), 7.81-7.92 (m, 1H), 7.61 (dd, J = 2.35, 6.85 Hz, 1H), 7.07 (dd, J = 9.00, 11.35 Hz, 1H), 5.49-5.87 (m, 3H), 2.43 (s, 3H), 1.95-2.05 (m, 1H), 1.78 (s, 3H), 1.33 (dd, J = 6.26, 9.78 Hz, 1H), 0.84 (br. s., 1H) | N-(3-((1S,5S,6S)-3-amino-1-(difluoromethyl)-5-methyl-2-thia-4-azabicyclo[4.1.0]hept-3-en-5-yl)-4-fluorophenyl)-5-((3-methyl-1,2,4-oxadiazol-5-yl)methoxy)-2-pyrazinecarboxamide |

Example 978

(1S,5S,6S)-3-amino-5-(5-(5-((S)-but-3-yn-2-yloxy)pyrazine-2-carboxamido)-2-fluorophenyl)-N,5-dimethyl-2-thia-4-azabicyclo[4.1.0]hept-3-ene-1-carboxamide

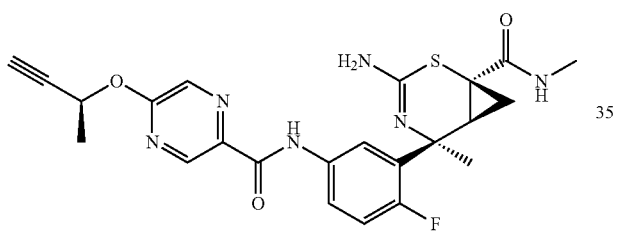

978

The title compound (67 mg, 0.14 mmol, 63% yield) was obtained as an off white crystalline solid and was made via General Method F2, using Intermediate 290 (51 mg, 0.26 mmol) and Intermediate 459 (120 mg, 0.22 mmol) as the starting materials. LC/MS (ESI$^+$) m/z=483 (M+H)$^+$. $^1$H NMR (400 MHz, CHLOROFORM-d) δ 9.25 (s, 1H), 8.92 (s, 1H), 8.05 (s, 1H), 7.58-7.73 (m, 1H), 7.44 (dd, J=2.54, 6.85 Hz, 1H), 6.90 (t, J=9.88 Hz, 1H), 6.67 (d, J=4.30 Hz, 1H), 5.82 (dq, J=1.86, 6.62 Hz, 1H), 2.85 (d, J=4.69 Hz, 3H), 2.51 (d, J=1.96 Hz, 1H), 2.20 (dd, J=7.82, 9.19 Hz, 1H), 1.98 (dd, J=4.89, 9.59 Hz, 1H), 1.87 (s, 3H), 1.70 (d, J=6.65 Hz, 3H), 0.76 (t, J=6.06 Hz, 1H).

Method H

Preformation of Acid Chloride with Ghosez Reagent Followed by Amide Coupling in ACN and Water Example 1010

N-(3-((1S,5S,6S)-3-amino-1-cyano-5-methyl-2-thia-4-azabicyclo[4.1.0]hept-3-en-5-yl)-4,5-difluorophenyl)-5-(((S)-1-methoxypropan-2-yl)oxy)pyrazine-2-carboxamide

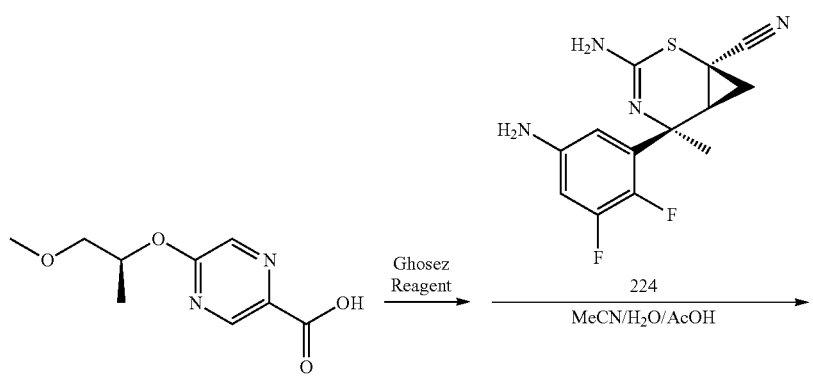

292

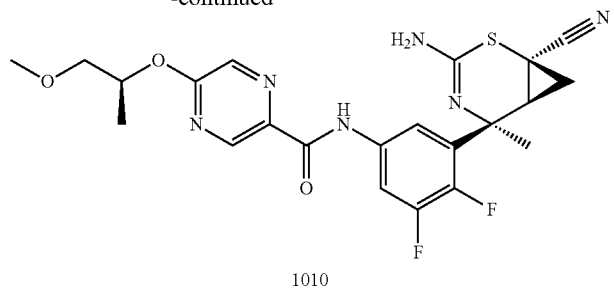

1010

A suspension of (S)-5-((1-methoxypropan-2-yl)oxy)pyrazine-2-carboxylic acid (292, 38.4 mg, 0.18 mmol) in ACN (0.25 mL) and 1-chloro-N,N,2-trimethyl-1-propenylamine (23.9 μL, 0.18 mmol) was stirred for 10 min at 20° C. and formed a solution. This freshly prepared acid chloride was then added to a solution of (1S,5S,6S)-3-amino-5-(5-amino-2,3-difluorophenyl)-5-methyl-2-thia-4-azabicyclo[4.1.0]hept-3-ene-1-carbonitrile (224, 38 mg, 0.13 mmol) and HOAc (7.5 μL, 0.13 mmol) in 1:1 ACN/water (1.0 mL) at 0° C. The reaction mixture was stirred for 5 min and then quenched with sat. NH₄Cl. The mixture was then partitioned between 9:1 CHCl₃/IPA (10 mL) and 1 M NaOH (4 mL). The aqueous layer was further extracted with 9:1 CHCl₃/IPA (5 mL). The organic layers were dried over MgSO₄, filtered, and concentrated under reduced pressure. The residue was purified by silica gel chromatography (0-6% MeOH in DCM) to afford Example 1010 (45 mg, 0.09 mmol, 71% yield) as a white solid. LCMS (ESI⁺) m/z=489.1 (M+H). ¹H NMR (400 MHz, DMSO-d₆) δ 10.62 (s, 1H), 8.86 (d, J=1.17 Hz, 1H), 8.37 (d, J=1.37 Hz, 1H), 7.94 (ddd, J=2.54, 6.80, 12.37 Hz, 1H), 7.74 (d, J=5.79 Hz, 1H), 6.54 (s, 2H), 5.38-5.48 (m, 1H), 3.51-3.62 (m, 2H), 3.30 (s, 3H), 2.38 (dd, J=7.82, 9.59 Hz, 1H), 1.89 (dd, J=5.87, 9.78 Hz, 1H), 1.75 (s, 3H), 1.29-1.34 (m, 3H), 1.07 (t, J=6.85 Hz, 1H).

Using procedures analogous or similar to the general amidation Method H described above, the appropriate aniline and carboxylic acid intermediates were reacted to provide the 15 examples listed in Table 10 and Table 10'.

TABLE 10

| Ex. No. | Chemical Structure | Observed [M + H]⁺ |
|---|---|---|
| 1011 | 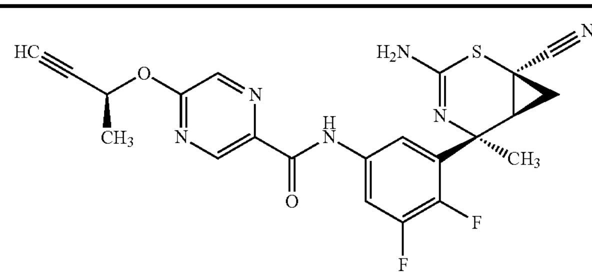 | 469.1 |
| 1012 | 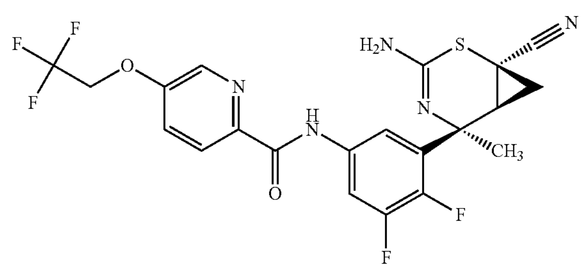 [SMILES: C[C@]1(c2cc(NC(=O)c3ccc(OCC(F)(F)F)cn3)cc(F)c2F)N=C(N)S[C@@]2(C#N)C[C@H]21] | 498 |
| 1015 | 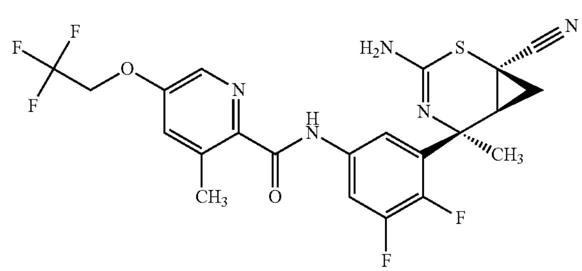 [SMILES: Cc1cc(OCC(F)(F)F)cnc1C(=O)Nc1cc(F)c(F)c([C@@]2(C)N=C(N)S[C@@]3(C#N)C[C@H]32)c1] | 512.1 |

TABLE 10-continued

| Ex. No. | Chemical Structure | Observed [M + H]+ |
|---|---|---|
| 1016 | 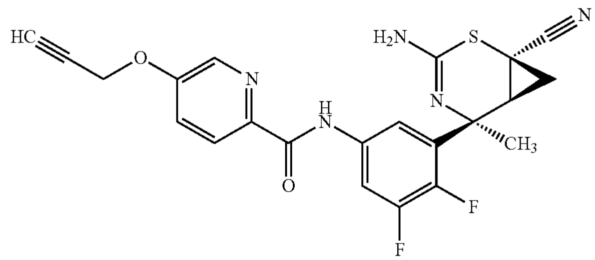 [SMILES: C#CCOc1ccc(C(=O)Nc2cc(F)c(F)c([C@@]3(C)N=C(N)S[C@@]4(C#N)C[C@H]43)c2)nc1] | 468 |
| 1043 | 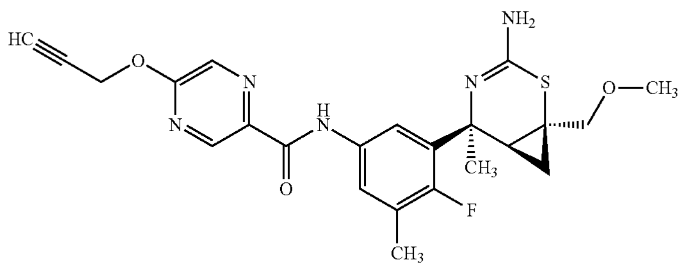 [SMILES: C#CCOc1cnc(C(=O)Nc2cc(C)c(F)c([C@@]3(C)N=C(N)S[C@@]4(COC)C[C@H]43)c2)cn1] | 470 |
| 1044 | 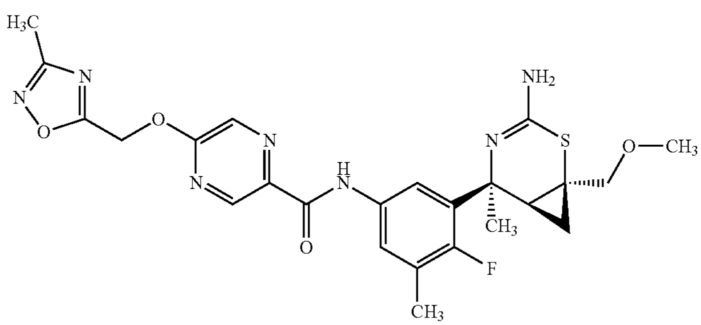 [SMILES: COC[C@]12C[C@H]1[C@@](C)(c1cc(NC(=O)c3cnc(OCc4nc(C)no4)cn3)cc(C)c1F)N=C(N)S2] | 528 |
| 1046 | 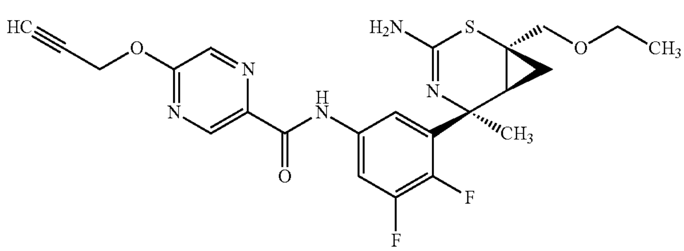 [SMILES: C#CCOc1cnc(C(=O)Nc2cc(F)c(F)c([C@@]3(C)N=C(N)S[C@@]4(COCC)C[C@H]43)c2)cn1] | 488 |
| 1065 | 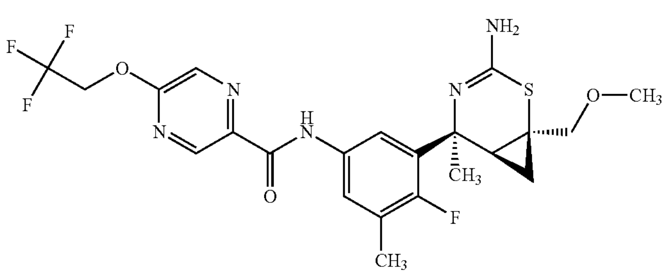 [SMILES: COC[C@]12C[C@H]1[C@@](C)(c1cc(NC(=O)c3cnc(OCC(F)(F)F)cn3)cc(C)c1F)N=C(N)S2] | 514 |

TABLE 10-continued

| Ex. No. | Chemical Structure | Observed [M + H]+ |
|---|---|---|
| 1066 | 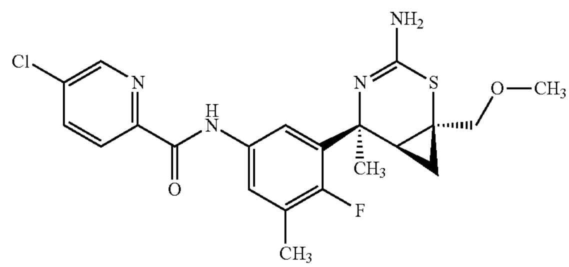 [SMILES: COC[C@]12C[C@H]1[C@@](C)(c1cc(NC(=O)c3ccc(Cl)cn3)cc(C)c1F)N=C(N)S2] | 449 |
| 1068 | 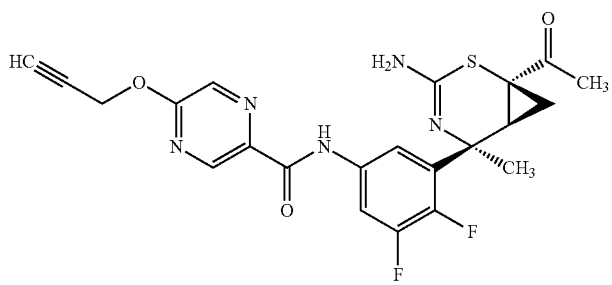 [SMILES: C#CCOc1cnc(C(=O)Nc2cc(F)c(F)c([C@@]3(C)N=C(N)S[C@@]4(C(C)=O)C[C@H]43)c2)cn1] | 472.1 |
| 1071 | 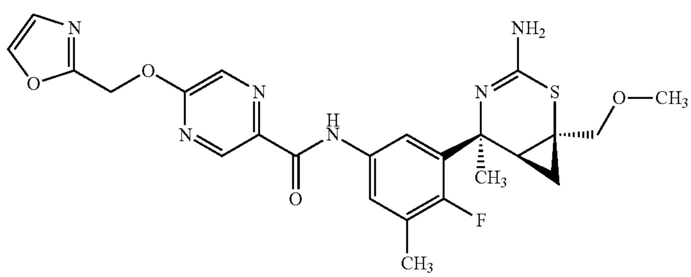 [SMILES: COC[C@]12C[C@H]1[C@@](C)(c1cc(NC(=O)c3cnc(OCc4ncco4)cn3)cc(C)c1F)N=C(N)S2] | 513 |
| 1072 | 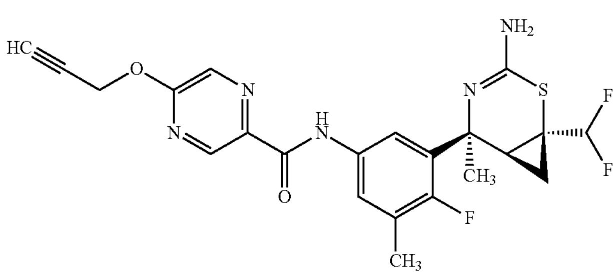 [SMILES: C#CCOc1cnc(C(=O)Nc2cc(C)c(F)c([C@@]3(C)N=C(N)S[C@@]4(C(F)F)C[C@@H]34)c2)cn1] | 476 |
| 1073 | 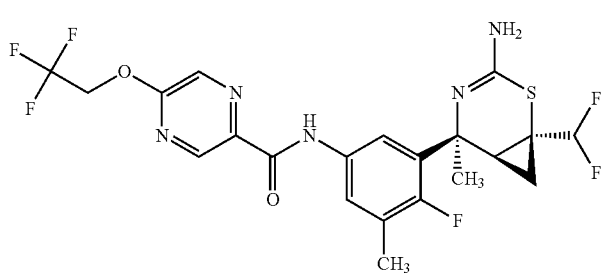 [SMILES: Cc1cc(NC(=O)c2cnc(OCC(F)(F)F)cn2)cc([C@@]2(C)N=C(N)S[C@@]3(C(F)F)C[C@@H]23)c1F] | 520 |

TABLE 10-continued

| Ex. No. | Chemical Structure | Observed [M + H]⁺ |
|---|---|---|
| 1074 | 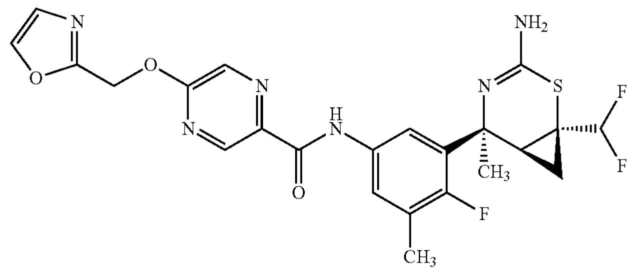 [SMILES: Cc1cc(NC(=O)c2cnc(OCc3ncco3)cn2)cc([C@@]2(C)N=C(N)S[C@@]3(C(F)F)C[C@@H]23)c1F] | 519 |
| 1075 | 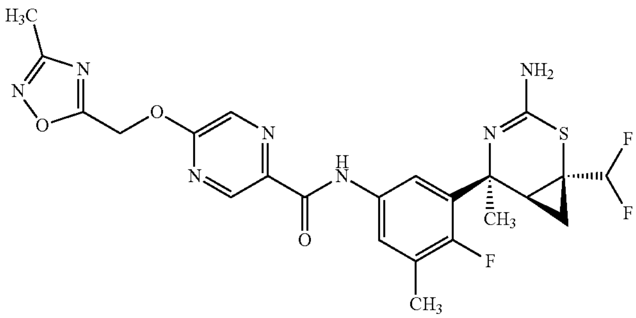 [SMILES: Cc1noc(COc2cnc(C(=O)Nc3cc(C)c(F)c([C@@]4(C)N=C(N)S[C@@]5(C(F)F)C[C@@H]45)c3)cn2)n1] | 534 |

TABLE 10'

| Ex. No | ¹H-NMR | Chemical Name |
|---|---|---|
| 1011 | ¹H NMR (400 MHz, DMSO-d6) δ 10.67 (s, 1H), 8.91 (d, J = 1.37 Hz, 1H), 8.46 (d, J = 1.37 Hz, 1H), 7.96 (ddd, J = 2.64, 6.80, 12.28 Hz, 1H), 7.76 (d, J = 5.78 Hz, 1H), 6.56 (s, 2H), 5.82 (dq, J = 1.96, 6.65 Hz, 1H), 3.61 (d, J = 2.15 Hz, 1H), 2.34-2.43 (m, 1H), 1.90 (dd, J = 5.97, 9.68 Hz, 1H), 1.76 (s, 3H), 1.64 (d, J = 6.65 Hz, 3H), 1.08 (t, J = 6.85 Hz, 1H) | N-(3-((1S,5S,6S)-3-amino-1-cyano-5-methyl-2-thia-4-azabicyclo[4.1.0]hept-3-en-5-yl)-4,5-difluorophenyl)-5-(((1S)-1-methyl-2-propyn-1-yl)oxy)-2-pyrazinecarboxamide |
| 1012 | ¹H NMR (400 MHz, DMSO-d6) δ 10.66 (s, 1H), 8.53 (d, J = 2.54 Hz, 1H), 8.17 (d, J = 8.80 Hz, 1H), 7.95-8.06 (m, 1H), 7.68-7.80 (m, 2H), 6.56 (s, 2H), 5.04 (q, J = 8.80 Hz, 2H), 2.40 (dd, J = 7.82, 9.59 Hz, 1H), 1.90 (dd, J = 5.87, 9.78 Hz, 1H), 1.76 (s, 3H), 1.10 (t, J = 6.85 Hz, 1H) | N-(3-((1S,5S,6S)-3-amino-1-cyano-5-methyl-2-thia-4-azabicyclo[4.1.0]hept-3-en-5-yl)-4,5-difluorophenyl)-5-(2,2,2-trifluoroethoxy)-2-pyridinecarboxamide |
| 1015 | ¹H NMR (400 MHz, DMSO-d6) δ 10.57 (s, 1H), 8.34 (d, J = 2.74 Hz, 1H), 7.96 (ddd, J = 2.45, 6.80, 12.47 Hz, 1H), 7.56-7.61 (m, 2H), 6.55 (s, 2H), 4.99 (q, J = 8.80 Hz, 2H), 2.61 (s, 3H), 2.38 (dd, J = 7.92, 9.68 Hz, 1H), 1.88 (dd, J = 6.06, 9.78 Hz, 1H), 1.75 (s, 3H), 1.08 (t, J = 6.85 Hz, 1H). | N-(3-((1S,5S,6S)-3-amino-1-cyano-5-methyl-2-thia-4-azabicyclo[4.1.0]hept-3-en-5-yl)-4,5-difluorophenyl)-3-methyl-5-(2,2,2-trifluoroethoxy)-2-pyridinecarboxamide |
| 1016 | ¹H NMR (400 MHz, DMSO-d6) δ 10.55 (s, 1H), 8.27 (d, J = 2.54 Hz, 1H), 7.93-8.00 (m, 1H), 7.58 (d, J = 5.67 Hz, 1H), 7.47 (d, J = 2.35 Hz, 1H), 6.54 (s, 2H), 5.00 (d, J = 2.35 Hz, 2H), 3.69 (t, J = 2.35 Hz, 1H), 2.61 (s, 3H), 2.38 (dd, J = 7.82, 9.59 Hz, 1H), 1.88 (dd, J = 5.87, 9.78 Hz, 1H), 1.75 (s, 3H), 1.08 (t, J = 6.85 Hz, 1H). | N-(3-((1S,5S,6S)-3-amino-1-cyano-5-methyl-2-thia-4-azabicyclo[4.1.0]hept-3-en-5-yl)-4,5-difluorophenyl)-3-methyl-5-(2-propyn-1-yloxy)-2-pyridinecarboxamide |
| 1043 | ¹H NMR (400 MHz, CHLOROFORM-d) Shift 9.44 (s, 1H), 8.91-9.08 (m, 1H), 8.20 (d, J = 1.37 Hz, 1H), 7.85 (dd, J = 2.64, 6.16 Hz, 1H), 7.52 (dd, J = 2.84, 6.36 Hz, 1H), 5.08 (d, J = 2.54 Hz, 2H), 3.67 (d, J = 10.56 Hz, 1H), 3.41 (s, 3H), 3.34 (d, J = 10.76 Hz, 1H), 2.54 (t, J = 2.45 Hz, 1H), 2.29-2.38 (m, 3H), 1.77-1.88 (m, 1H), 1.71 (s, 3H), 0.85-0.93 (m, 1H), 0.77-0.83 (m, 1H) | N-(3-((1S,5S,6S)-3-amino-1-(methoxymethyl)-5-methyl-2-thia-4-azabicyclo[4.1.0]hept-3-en-5-yl)-4-fluoro-5-methylphenyl)-5-(2-propyn-1-yloxy)-2-pyrazinecarboxamide |
| 1044 | ¹H NMR (400 MHz, CHLOROFORM-d) Shift 9.43 (s, 1H), 8.99 (d, J = 1.17 Hz, 1H), 8.33 (d, J = 1.37 Hz, 1H), 7.85 (dd, J = 2.74, 6.26 Hz, 1H), 7.52 (dd, J = 2.84, 6.36 Hz, 1H), 5.68 (s, 2H), 3.67 (d, J = 10.76 Hz, 1H), 3.41 (s, 3H), 3.35 (d, J = 10.76 Hz, | N-(3-((1S,5S,6S)-3-amino-1-(methoxymethyl)-5-methyl-2-thia-4-azabicyclo[4.1.0]hept-3-en-5-yl)-4-fluoro-5-methylphenyl)-5-((3-methyl- |

TABLE 10'-continued

| Ex. No | ¹H-NMR | Chemical Name |
|---|---|---|
|  | 1H), 2.43 (s, 3H), 2.32 (d, J = 2.35 Hz, 3H), 1.82 (dd, J = 7.24, 8.61 Hz, 1H), 1.71 (s, 4H), 0.88 (dd, J = 5.87, 9.39 Hz, 1H), 0.75-0.83 (m, 1H) | 1,2,4-oxadiazol-5-yl)methoxy)-2-pyrazinecarboxamide |
| 1046 | ¹H NMR (400 MHz, DMSO-d6) δ 10.62 (s, 1H), 8.92 (d, J = 1.17 Hz, 1H), 8.50 (d, J = 1.37 Hz, 1H), 7.89-7.96 (m, 2H), 5.99 (s, 2H), 5.16 (d, J = 2.35 Hz, 2H), 3.66 (td, J = 2.89, 5.18 Hz, 2H), 3.45-3.57 (m, 2H), 3.38 (d, J = 11.15 Hz, 1H), 1.59-1.66 (m, 4H), 1.14 (t, J = 6.94 Hz, 3H), 0.91 (dd, J = 5.28, 9.19 Hz, 1H), 0.66 (t, J = 5.77 Hz, 1H) | N-(3-((1S,5S,6S)-3-amino-1-(ethoxymethyl)-5-methyl-2-thia-4-azabicyclo[4.1.0]hept-3-en-5-yl)-4,5-difluorophenyl)-5-(2-propyn-1-yloxy)-2-pyrazinecarboxamide |
| 1065 | ¹H NMR (400 MHz, CHLOROFORM-d) δ 9.30-9.63 (m, 1H), 9.02 (d, J = 1.17 Hz, 1H), 8.30 (d, J = 1.37 Hz, 1H), 7.84 (dd, J = 2.74, 5.87 Hz, 1H), 7.54 (dd, J = 2.74, 6.46 Hz, 1H), 4.86 (q, J = 8.35 Hz, 2H), 3.67 (d, J = 10.56 Hz, 1H), 3.41 (s, 3H), 3.35 (d, J = 10.56 Hz, 1H), 2.33 (d, J = 2.35 Hz, 3H), 1.77-1.89 (m, 1H), 1.72 (s, 3H), 0.88 (dd, J = 5.87, 9.39 Hz, 1H), 0.76-0.82 (m, 1H) | N-(3-((1S,5S,6S)-3-amino-1-(methoxymethyl)-5-methyl-2-thia-4-azabicyclo[4.1.0]hept-3-en-5-yl)-4-fluoro-5-methylphenyl)-5-(2,2,2-trifluoroethoxy)-2-pyrazinecarboxamide |
| 1066 | ¹H NMR (400 MHz, CHLOROFORM-d) δ 9.63-9.87 (m, 1H), 8.55 (d, J = 2.15 Hz, 1H), 8.24 (d, J = 8.22 Hz, 1H), 7.81-7.89 (m, 2H), 7.52-7.62 (m, 1H), 3.67 (d, J = 10.56 Hz, 1H), 3.41 (s, 3H), 3.35 (d, J = 10.76 Hz, 1H), 2.27-2.39 (m, 3H), 1.82 (dd, J = 7.24, 8.80 Hz, 1H), 1.72 (d, J = 0.98 Hz, 3H), 1.69-1.74 (m, 3H), 0.88 (dd, J = 5.87, 9.39 Hz, 1H), 0.75-0.83 (m, 1H) | N-(3-((1S,5S,6S)-3-amino-1-(methoxymethyl)-5-methyl-2-thia-4-azabicyclo[4.1.0]hept-3-en-5-yl)-4-fluoro-5-methylphenyl)-5-chloro-2-pyridinecarboxamide |
| 1068 | ¹H NMR (400 MHz, DMSO-d6) δ 10.66 (s, 1H), 8.91 (d, J = 1.37 Hz, 1H), 8.49 (d, J = 1.37 Hz, 1H), 7.92-7.99 (m, 2H), 6.16 (s, 2H), 5.15 (d, J = 2.35 Hz, 2H), 3.65 (t, J = 2.45 Hz, 1H), 2.33-2.41 (m, 1H), 2.11 (s, 3H), 1.74 (dd, J = 5.48, 9.78 Hz, 1H), 1.62 (s, 3H), 1.11-1.17 (m, 1H) | N-(3-((1S,5S,6S)-1-acetyl-3-amino-5-methyl-2-thia-4-azabicyclo[4.1.0]hept-3-en-5-yl)-4,5-difluorophenyl)-5-(prop-2-yn-1-yloxy)pyrazine-2-carboxamide |
| 1071 | ¹H NMR (400 MHz, CHLOROFORM-d) δ 9.44 (s, 1H), 9.02 (d, J = 1.37 Hz, 1H), 8.17-8.28 (m, 1H), 8.17-8.28 (m, 1H), 7.87 (dd, J = 2.64, 6.16 Hz, 1H), 7.71 (d, J = 0.78 Hz, 1H), 7.52 (dd, J = 2.74, 6.46 Hz, 1H), 7.18 (s, 1H), 5.58 (s, 2H), 4.38 (br. s., 2H), 3.67 (d, J = 10.56 Hz, 1H), 3.41 (s, 3H), 3.34 (d, J = 10.76 Hz, 1H), 2.32 (d, J = 2.35 Hz, 3H), 1.82 (dd, J = 7.24, 8.80 Hz, 1H), 1.71 (d, J = 0.98 Hz, 3H), 0.88 (dd, J = 5.77, 9.49 Hz, 1H), 0.78-0.83 (m, 1H) | N-(3-((1S,5S,6S)-3-amino-1-(methoxymethyl)-5-methyl-2-thia-4-azabicyclo[4.1.0]hept-3-en-5-yl)-4-fluoro-5-methylphenyl)-5-(oxazol-2-ylmethoxy)pyrazine-2-carboxamide |
| 1072 | ¹H NMR (400 MHz, CHLOROFORM-d) δ 9.40 (s, 1H), 9.03 (d, J = 1.17 Hz, 1H), 8.21 (d, J = 1.17 Hz, 1H), 7.79 (dd, J = 2.54, 6.06 Hz, 1H), 7.41 (dd, J = 2.74, 6.26 Hz, 1H), 5.46-5.90 (m, 1H), 5.09 (d, J = 2.35 Hz, 2H), 2.55 (t, J = 2.45 Hz, 1H), 2.32 (d, J = 2.35 Hz, 3H), 2.00 (dd, J = 7.43, 9.78 Hz, 1H), 1.77 (s, 4H), 1.30-1.37 (m, 1H), 0.85 (br. s., 1H) | N-(3-((1S,5S,6S)-3-amino-1-(difluoromethyl)-5-methyl-2-thia-4-azabicyclo[4.1.0]hept-3-en-5-yl)-4-fluoro-5-methylphenyl)-5-(prop-2-yn-1-yloxy)pyrazine-2-carboxamide |
| 1073 | ¹H NMR (400 MHz, CHLOROFORM-d) δ 9.39 (s, 1H), 9.01 (d, J = 1.37 Hz, 1H), 8.30 (d, J = 1.37 Hz, 1H), 7.78 (dd, J = 2.93, 6.06 Hz, 1H), 7.43 (dd, J = 2.74, 6.46 Hz, 1H), 5.42-5.87 (m, 1H), 4.86 (q, J = 8.22 Hz, 2H), 2.25-2.40 (m, 3H), 2.01 (dd, J = 7.34, 9.88 Hz, 1H), 1.77 (s, 3H), 1.29-1.39 (m, 1H), 0.81-0.88 (m, 1H) | N-(3-((1S,5S,6S)-3-amino-1-(difluoromethyl)-5-methyl-2-thia-4-azabicyclo[4.1.0]hept-3-en-5-yl)-4-fluoro-5-methylphenyl)-5-(2,2,2-trifluoroethoxy)pyrazine-2-carboxamide |
| 1074 | ¹H NMR (400 MHz, CHLOROFORM-d) δ 9.41 (s, 1H), 9.02 (d, J = 1.17 Hz, 1H), 8.25 (d, J = 1.17 Hz, 1H), 7.79 (dd, J = 2.64, 6.16 Hz, 1H), 7.71 (s, 1H), 7.40 (dd, J = 2.84, 6.36 Hz, 1H), 7.18 (s, 1H), 5.48-5.84 (m, 3H), 2.27-2.37 (m, 3H), 2.00 (dd, J = 7.24, 9.78 Hz, 1H), 1.77 (s, 3H), 1.33 (dd, J = 6.16, 9.88 Hz, 1H), 0.85 (d, J = 9.39 Hz, 1H) | N-(3-((1S,5S,6S)-3-amino-1-(difluoromethyl)-5-methyl-2-thia-4-azabicyclo[4.1.0]hept-3-en-5-yl)-4-fluoro-5-methylphenyl)-5-(oxazol-2-ylmethoxy)pyrazine-2-carboxamide |
| 1075 | 1H NMR (400 MHz, CHLOROFORM-d) δ 9.40 (s, 1H), 8.99 (d, J = 1.37 Hz, 1H), 8.33 (d, J = 1.17 Hz, 1H), 7.78 (dd, J = 2.35, 6.06 Hz, 1H), 7.42 (dd, J = 2.93, 6.26 Hz, 1H), 5.42-5.90 (m, 3H), 2.43 (s, 3H), 2.28-2.36 (m, 3H), 2.01 (dd, J = 7.24, 9.78 Hz, 1H), 1.77 (s, 3H), 1.31-1.36 (m, 1H), 0.82-0.87 (m, 1H). | N-(3-((1S,5S,6S)-3-amino-1-(difluoromethyl)-5-methyl-2-thia-4-azabicyclo[4.1.0]hept-3-en-5-yl)-4-fluoro-5-methylphenyl)-5-((3-methyl-1,2,4-oxadiazol-5-yl)methoxy)pyrazine-2-carboxamide |

Method J

COMU Mediated Amide Formation Followed by Removal of the Protecting Groups with PTSA

Example 985

(1S,5S,6S)-3-amino-5-(5-(5-chloropicolinamido)-2-fluorophenyl)-N,5-dimethyl-2-thia-4-azabicyclo[4.1.0]hept-3-ene-1-carboxamide

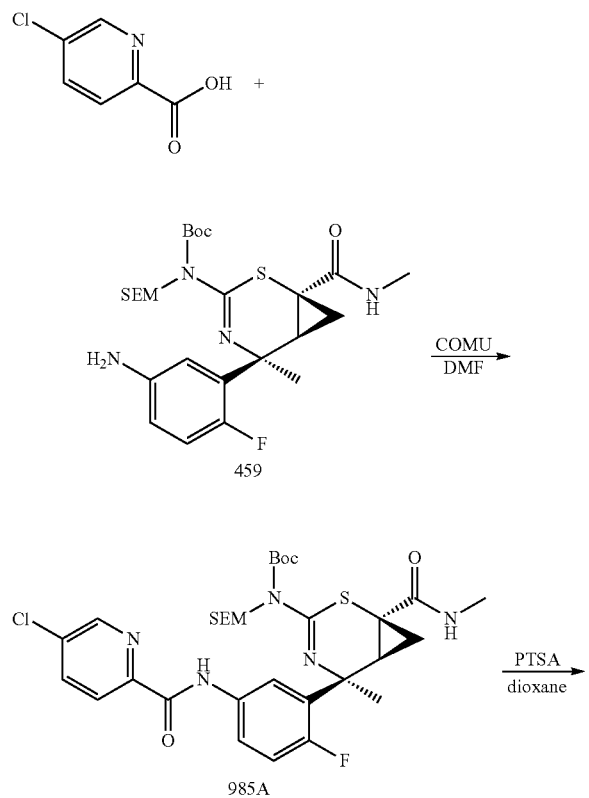

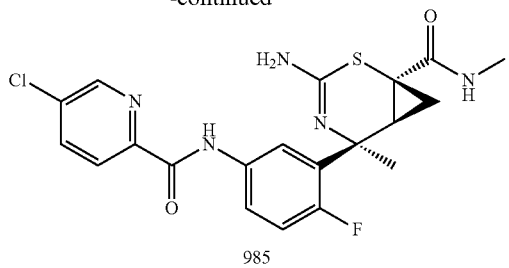

To a mixture of tert-butyl((1S,5S,6S)-5-(5-amino-2-fluorophenyl)-5-methyl-1-(methylcarbamoyl)-2-thia-4-azabicyclo[4.1.0]hept-3-en-3-yl)((2-(trimethylsilyl)ethoxy)methyl)carbamate (intermediate 459) (0.032 g, 0.059 mmol), 5-chloropicolinic acid (0.014 g, 0.089 mmol), and (1-cyano-2-ethoxy-2-oxoethylidenaminooxy)dimethylaminomorpholinocarbenium hexafluorophosphate (COMU, 0.038 g, 0.089 mmol) in DMF (0.5 mL) was added N-ethyl-N-isopropylpropan-2-amine (0.021 mL, 0.119 mmol) dropwise. The mixture was stirred at RT overnight. The reaction mixture was diluted with sat'd Na$_2$CO$_3$ and EtOAc. The organic layer was washed with water followed by brine, dried over Na$_2$SO$_4$, filtered, and concentrated in vacuo. The residue was purified by silica gel chromatography (0-100% EtOAc in heptane) to give product 985A (0.040 g, 0.059 mmol) as a white solid. LC/MS (ESI$^+$) m/z=678 (M+H)$^+$.

A mixture of 985A (0.040 g, 0.059 mmol) and p-toluenesulfonic acid monohydrate (0.024 g, 0.124 mmol) in 1,4-dioxane (1.5 mL) was stirred at 90° C. for 1 h. The mixture was diluted with saturated NaHCO$_3$ and extracted with EtOAc. The organic solution was washed with water and brine, dried over Na$_2$SO$_4$, and concentrated in vacuo. The residue was purified by silica gel chromatography (0-100% EtOAc in DCM) to provide Example 985 as an off-white solid (0.020 g, 78% yield over two steps). LC/MS (ESI$^+$) m/z=448 (M+H)$^+$. $^1$H NMR (400 MHz, CHLOROFORM-d) δ 9.67 (s, 1H), 8.48 (d, J=2.15 Hz, 1H), 8.17 (d, J=8.41 Hz, 1H), 7.84 (dd, J=2.35, 8.41 Hz, 1H), 7.72 (td, J=3.57, 8.31 Hz, 1H), 7.50 (dd, J=2.74, 6.85 Hz, 1H), 6.99 (dd, J=8.80, 11.15 Hz, 1H), 6.68 (d, J=4.30 Hz, 1H), 4.38 (br. s., 2H), 2.86 (d, J=4.69 Hz, 3H), 2.25 (dd, J=7.73, 9.29 Hz, 1H), 2.00 (dd, J=5.09, 9.59 Hz, 1H), 1.87 (s, 3H), 0.74-0.87 (m, 1H).

Using procedures analogous or similar to the general amidation Method J described above, the appropriate aniline and carboxylic acid intermediates were reacted to provide the 7 examples listed in Table 11 and Table 11'.

TABLE 11

| Ex. No. | Chemical Structure | Observed [M + H]$^+$ |
|---|---|---|
| 986 | 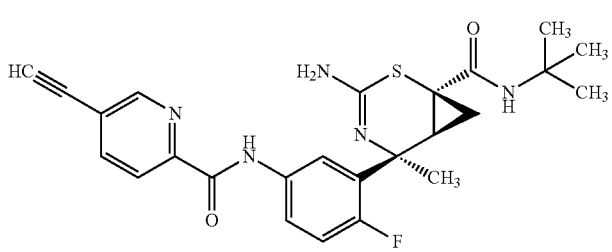 [SMILES: C#Cc1ccc(C(=O)Nc2ccc(F)c([C@@]3(C)N=C(N)S[C@@]4(C(=O)NC(C)(C)C)C[C@H]43)c2)nc1] | 481 |

TABLE 11-continued

| Ex. No. | Chemical Structure | Observed [M + H]+ |
|---|---|---|
| 987 | 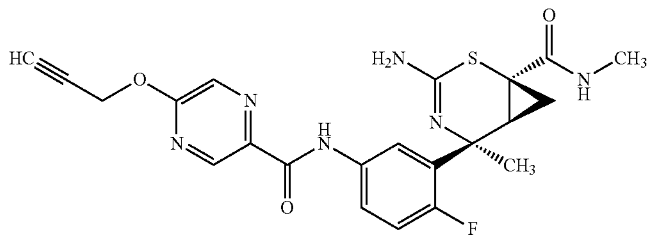 [SMILES: C#CCOc1cnc(C(=O)Nc2ccc(F)c([C@@]3(C)N=C(N)S[C@@]4(C(=O)NC)C[C@H]43)c2)cn1] | 469 |
| 993 | 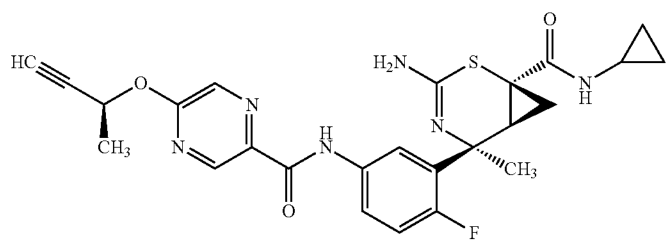 [SMILES: C#C[C@H](C)Oc1cnc(C(=O)Nc2ccc(F)c([C@@]3(C)N=C(N)S[C@@]4(C(=O)NC5CC5)C[C@H]43)c2)cn1] | 509 |
| 994 | 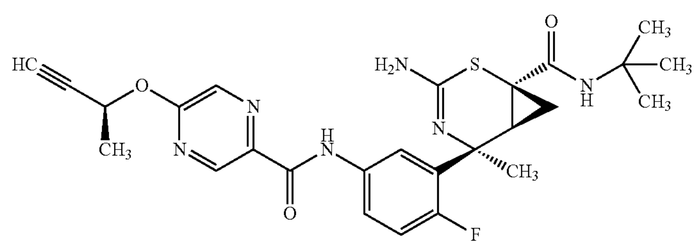 [SMILES: C#C[C@H](C)Oc1cnc(C(=O)Nc2ccc(F)c([C@@]3(C)N=C(N)S[C@@]4(C(=O)NC(C)(C)C)C[C@H]43)c2)cn1] | 525 |
| 1001 | 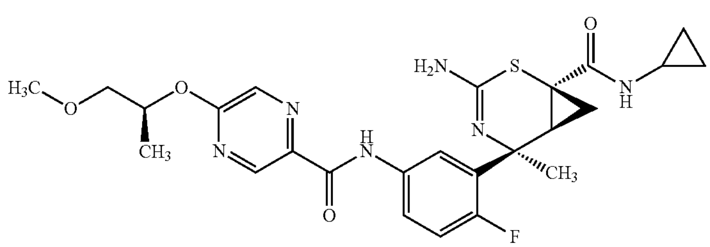 [SMILES: COC[C@H](C)Oc1cnc(C(=O)Nc2ccc(F)c([C@@]3(C)N=C(N)S[C@@]4(C(=O)NC5CC5)C[C@H]43)c2)cn1] | 529 |
| 1002 | 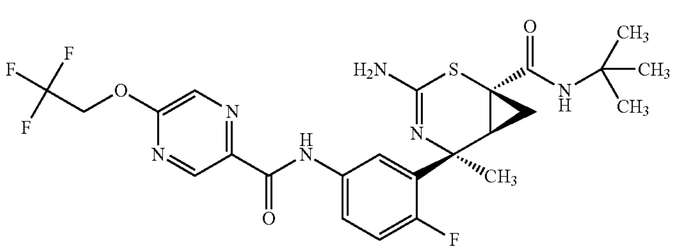 [SMILES: CC(C)(C)NC(=O)[C@]12C[C@H]1[C@@](C)(c1cc(NC(=O)c3cnc(OCC(F)(F)F)cn3)ccc1F)N=C(N)S2] | 555 |
| 1003 | 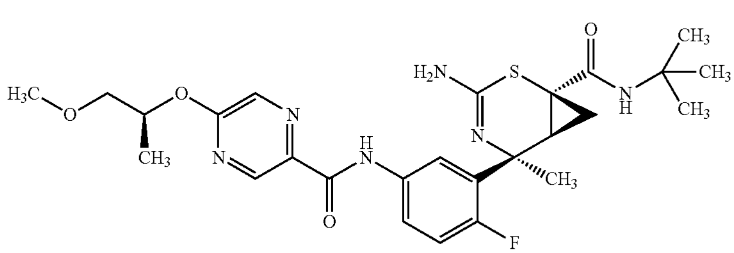 [SMILES: COC[C@H](C)Oc1cnc(C(=O)Nc2ccc(F)c([C@@]3(C)N=C(N)S[C@@]4(C(=O)NC(C)(C)C)C[C@H]43)c2)cn1] | 545 |

TABLE 11'

| Ex. No. | ¹H-NMR | Chemical Name |
|---|---|---|
| 986 | ¹H NMR (400 MHz, CHLOROFORM-d) δ 9.70 (s, 1H), 8.81 (d, J = 1.17 Hz, 1H), 8.35 (d, J = 8.02 Hz, 1H), 8.17 (dd, J = 1.96, 8.22 Hz, 1H), 7.69-7.82 (m, 1H), 7.52 (dd, J = 2.74, 6.85 Hz, 1H), 7.00 (dd, J = 8.80, 11.15 Hz, 1H), 6.36 (s, 1H), 4.39-4.83 (m, 2H), 2.19 (dd, J = 7.92, 9.29 Hz, 1H), 1.90 (dd, J = 4.99, 9.68 Hz, 1H), 1.86 (s, 3H), 1.36 (s, 9H), 0.72 (d, J = 5.38, 6.36 Hz, 1H) | (1S,5S,6S)-3-amino-N-tert-butyl-5-(5-(((5-cyano-2-pyridinyl)carbonyl)amino)-2-fluorophenyl)-5-methyl-2-thia-4-azabicyclo[4.1.0]hept-3-ene-1-carboxamide |
| 987 | ¹H NMR (400 MHz, CHLOROFORM-d) δ 9.39 (s, 1H), 9.00 (s, 1H), 8.19 (s, 1H), 7.70-7.87 (m, 1H), 7.49 (dd, J = 2.45, 6.75 Hz, 1H), 7.04 (dd, J = 9.00, 11.15 Hz, 1H), 6.54 (d, J = 4.11 Hz, 1H), 5.08 (d, J = 2.35 Hz, 2H), 2.87 (d, J = 4.69 Hz, 3H), 2.55 (s, 1H), 2.15-2.31 (m, 2H), 1.96 (dd, J = 4.89, 9.59 Hz, 1H), 1.83 (s, 3H), 0.73-0.88 (m, 1H) | (1S,5S,6S)-3-amino-5-(2-fluoro-5-(((5-(2-propyn-1-yloxy)-2-pyrazinyl)carbonyl)amino)phenyl)-N,5-dimethyl-2-thia-4-azabicyclo[4.1.0]hept-3-ene-1-carboxamide |
| 993 | ¹H NMR (400 MHz, CHLOROFORM-d) δ 9.38 (s, 1H), 9.00 (s, 1H), 8.14 (s, 1H), 7.76 (br. s., 1H), 7.48 (d, J = 4.69 Hz, 1H), 6.94-7.12 (m, 1H), 6.58 (br. s., 1H), 5.71-6.02 (m, 1H), 2.73 (d, J = 3.33 Hz, 1H), 2.49 (s, 1H), 2.19-2.29 (m, 2H), 1.95 (dd, J = 5.38, 9.88 Hz, 1H), 1.82 (s, 3H), 1.70 (d, J = 6.65 Hz, 3H), 0.80 (d, J = 6.65 Hz, 3H), 0.55 (d, J = 4.11 Hz, 2H) | (1S,5S,6S)-3-amino-N-cyclopropyl-5-(2-fluoro-5-(((5-(((1S)-1-methyl-2-propyn-1-yl)oxy)-2-pyrazinyl)carbonyl)amino)phenyl)-5-methyl-2-thia-4-azabicyclo[4.1.0]hept-3-ene-1-carboxamide |
| 994 | ¹H NMR (400 MHz, CHLOROFORM-d) δ 9.40 (s, 1H), 9.01 (s, 1H), 8.14 (s, 1H), 7.78 (br. s., 1H), 7.50 (d, J = 6.46 Hz, 1H), 6.98-7.12 (m, 1H), 6.30 (s, 1H), 5.84 (d, J = 7.63 Hz, 1H), 5.78-5.90 (m, 1H), 2.49 (s, 1H), 2.18 (t, J = 8.22 Hz, 1H), 1.86 (dd, J = 5.28, 9.59 Hz, 1H), 1.81 (s, 3H), 1.70 (d, J = 6.65 Hz, 3H), 1.37 (s, 10H), 0.75 (d, J = 6.65 Hz, 1H), 0.70-0.78 (m, 1H) | (1S,5S,6S)-3-amino-N-tert-butyl-5-(2-fluoro-5-(((5-(((1S)-1-methyl-2-propyn-1-yl)oxy)-2-pyrazinyl)carbonyl)amino)phenyl)-5-methyl-2-thia-4-azabicyclo[4.1.0]hept-3-ene-1-carboxamide |
| 1001 | ¹H NMR (400 MHz, CHLOROFORM-d) δ 9.39 (s, 1H), 8.95 (d, J = 1.37 Hz, 1H), 8.10 (d, J = 1.37 Hz, 1H), 7.70-7.83 (m, 1H), 7.49 (dd, J = 2.74, 6.85 Hz, 1H), 7.04 (dd, J = 8.80, 11.35 Hz, 1H), 6.59 (d, J = 2.15 Hz, 1H), 5.51 (dquin, J = 3.81, 6.28 Hz, 1H), 3.52-3.69 (m, 2H), 3.41 (s, 3H), 2.73 (qt, J = 3.62, 7.09 Hz, 1H), 2.24 (dd, J = 7.92, 9.29 Hz, 1H), 1.95 (dd, J = 5.09, 9.78 Hz, 1H), 1.82 (s, 3H), 1.39 (d, J = 6.46 Hz, 3H), 0.74-0.86 (m, 3H), 0.49-0.59 (m, 2H) | (1S,5S,6S)-3-amino-N-cyclopropyl-5-(2-fluoro-5-(((5-((1S)-2-methoxy-1-methylethoxy)-2-pyrazinyl)carbonyl)amino)phenyl)-5-methyl-2-thia-4-azabicyclo[4.1.0]hept-3-ene-1-carboxamide |
| 1002 | ¹H NMR (400 MHz, CHLOROFORM-d) δ 9.42 (s, 1H), 9.01 (d, J = 1.37 Hz, 1H), 8.29 (d, J = 1.37 Hz, 1H), 7.71-7.89 (m, 1H), 7.53 (dd, J = 2.64, 6.75 Hz, 1H), 7.07 (dd, J = 8.80, 11.15 Hz, 1H), 6.28 (s, 1H), 4.77-4.98 (m, 2H), 2.15-2.24 (m, 1H), 1.86 (dd, J = 4.89, 9.78 Hz, 1H), 1.80 (d, J = 0.98 Hz, 3H), 1.37 (s, 9H), 0.75 (dd, J = 5.48, 7.04 Hz, 1H) | (1S,5S,6S)-3-amino-N-tert-butyl-5-(2-fluoro-5-(((5-(2,2,2-trifluoroethoxy)-2-pyrazinyl)carbonyl)amino)phenyl)-5-methyl-2-thia-4-azabicyclo[4.1.0]hept-3-ene-1-carboxamide |
| 1003 | ¹H NMR (400 MHz, CHLOROFORM-d) δ 9.41 (s, 1H), 8.96 (d, J = 1.17 Hz, 1H), 8.12 (d, J = 1.17 Hz, 1H), 7.72-7.85 (m, 1H), 7.51 (dd, J = 2.74, 6.85 Hz, 1H), 7.05 (dd, J = 8.80, 11.35 Hz, 1H), 6.29 (s, 1H), 5.44-5.59 (m, 1H), 3.51-3.69 (m, 2H), 3.41 (s, 3H), 2.14-2.23 (m, 1H), 1.86 (dd, J = 5.09, 9.78 Hz, 1H), 1.80 (s, 3H), 1.39 (d, J = 6.46 Hz, 3H), 1.37 (s, 9H), 0.75 (dd, J = 5.18, 6.55 Hz, 1H) | (1S,5S,6S)-3-amino-N-tert-butyl-5-(2-fluoro-5-(((5-((1S)-2-methoxy-1-methylethoxy)-2-pyrazinyl)carbonyl)amino)phenyl)-5-methyl-2-thia-4-azabicyclo[4.1.0]hept-3-ene-1-carboxamide |

Example 972

(1S,5S,6S)-3-amino-5-(2-fluoro-5-(5-(2,2,2-trifluoroethoxy)pyrazine-2-carboxamido)phenyl)-5-methyl-N-(2,2,2-trifluoroethyl)-2-thia-4-azabicyclo[4.1.0]hept-3-ene-1-carboxamide

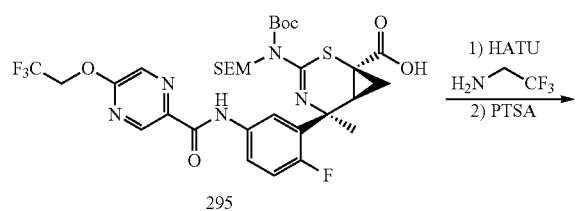

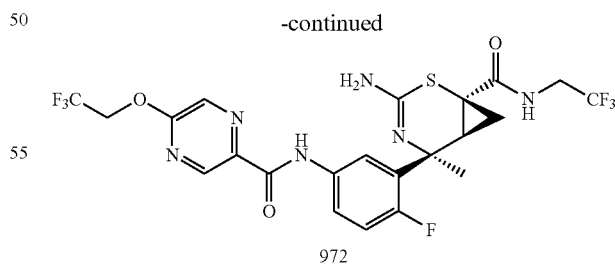

To a mixture of (1S,5S,6S)-3-((tert-butoxycarbonyl)((2-(trimethylsilyl)ethoxy)methyl)amino)-5-(2-fluoro-5-(5-(2,2,2-trifluoroethoxy)pyrazine-2-carboxamido)phenyl)-5-methyl-2-thia-4-azabicyclo[4.1.0]hept-3-ene-1-carboxylic acid, 295, (0.17 g, 0.27 mmol) and 2,2,2-trifluoroethylamine (0.04 mL, 0.40 mmol) in DMF (1.0 mL) was added TEA (0.11 mL, 0.81 mmol) and HATU (0.20 g, 0.53 mmol). The reaction mixture was stirred at RT for 2 h, and then it was quenched with saturated NH$_4$Cl solution and extracted with EtOAc. The organic layer was concentrated to dryness. The residue containing tert-butyl((1S,5S,6S)-5-(2-fluoro-5-(5-(2,2,2-trifluoroethoxy)pyrazine-2-carboxamido)phenyl)-5-methyl-1-((2,2,2-trifluoroethyl)carbamoyl)-2-thia-4-azabicyclo[4.1.0]hept-3-en-3-yl)((2-(trimethylsilyl)ethoxy)methyl)carbamate was dissolved in dioxane (2 mL) and treated with p-toluenesulfonic acid monohydrate (0.15 g, 0.80 mmol). The resulting mixture was heated at 85° C. for 2 h. The reaction mixture was diluted with water and extracted with EtOAc (2×). The organic phase was concentrated and the residue purified by flash column chromatography on silica gel (0-60% EtOAc in heptane) to afford (1S,5S,6S)-3-amino-5-(2-fluoro-5-(5-(2,2,2-trifluoroethoxy)pyrazine-2-carboxamido)phenyl)-5-methyl-N-(2,2,2-trifluoroethyl)-2-thia-4-azabicyclo[4.1.0]hept-3-ene-1-carboxamide (972) (72 mg, 0.12 mmol, 46% yield). LC/MS (ESI$^+$) m/z=581.2 (M+H). $^1$H NMR (300 MHz, CHLOROFORM-d) δ: 9.39 (s, 1H), 9.00 (s, 1H), 8.29 (s, 1H), 7.71-7.78 (m, 1H), 7.48-7.54 (m, 1H), 6.93-7.11 (m, 2H), 4.88 (q, J=8.28 Hz, 2H), 3.98-4.23 (m, 1H), 3.88 (ddd, J=5.99, 8.88, 14.94 Hz, 1H), 2.82 (s, 2H), 2.24-2.32 (m, 1H), 2.04-2.12 (m, 1H), 1.89 (s, 3H), 0.86-0.94 (m, 1H). $^{19}$F NMR (282 MHz, CHLOROFORM-d) δ: −72.37 (s, 3F), −73.64 (s, 3F), −113.23 (s, 1F).

Example 973

(1S,5S,6S)-3-amino-5-(2-fluoro-5-(5-(2,2,2-trifluoroethoxy)pyrazine-2-carboxamido)phenyl)-N,5-dimethyl-2-thia-4-azabicyclo[4.1.0]hept-3-ene-1-carboxamide The title compound 973 (45 mg, 0.09 mmol, 33% yield) was prepared according to the procedure described for 972 using compound 295 (0.20 g, 0.27 mmol) and 2.0 M methylamine solution in THF (0.20 mL, 0.40 mmol). LC/MS (ESI$^+$) m/z=513.2 (M+H). $^1$H NMR (300 MHz, CHLOROFORM-d) δ: 9.37 (s, 1H), 8.99 (s, 1H), 8.27 (s, 1H), 7.71-7.80 (m, 1H), 7.51 (dd, J=2.19, 6.72 Hz, 1H), 7.03 (dd, J=9.06, 10.82 Hz, 1H), 6.60 (d, J=4.38 Hz, 1H), 4.88 (q, J=8.28 Hz, 2H), 3.50-4.50 (br. s., 2H), 2.81-2.95 (m, 3H), 2.26 (t, J=8.55 Hz, 1H), 1.99 (dd, J=4.97, 9.65 Hz, 1H), 1.86 (s, 3H), 0.78-0.95 (m, 1H). $^{19}$F NMR (282 MHz, CHLOROFORM-d) δ: −73.64 (s, 3F), −113.35 (s, 1F).

Example 974

(1S,5S,6S)-3-amino-5-(2-fluoro-5-(5-(2,2,2-trifluoroethoxy)pyrazine-2-carboxamido)phenyl)-5-methyl-N—((S)-3-methylbutan-2-yl)-2-thia-4-azabicyclo[4.1.0]hept-3-ene-1-carboxamide The title compound 974 (0.045 g, 0.079 mmol, 29% yield) was prepared according to the procedure described for 972 using compound 295 (0.196 g, 0.269 mmol) and (S)-(+)-3-methyl-2-butylamine (0.035 mL, 0.403 mmol). LC/MS (ESI$^+$) m/z=569.3 (M+H). $^1$H NMR (300 MHz, CHLOROFORM-d) δ: 9.41 (s, 1H), 9.01 (s, 1H), 8.29 (s, 1H), 7.78-7.85 (m, 1H), 7.52-7.58 (m, 1H), 7.07 (t, J=9.90 Hz, 1H), 6.34 (d, J=8.62 Hz, 1H), 4.88 (q, J=8.28 Hz, 2H), 3.80-3.93 (m, 1H), 2.82 (s, 2H), 2.25 (t, J=8.62 Hz, 1H), 1.95 (dd, J=4.97, 9.65 Hz, 1H), 1.84 (s, 3H), 1.76 (dd, J=6.65, 13.23 Hz, 1H), 1.13 (d, J=6.72 Hz, 3H), 0.93 (dd, J=3.22, 6.58 Hz, 6H), 0.77-0.88 (m, 1H). $^{19}$F NMR (282 MHz, CHLOROFORM-d) δ: −73.63 (s, 3F), −113.78 (s, 1F).

Example 976

(1S,5S,6S)-3-amino-5-(2-fluoro-5-(5-(2,2,2-trifluoroethoxy)pyrazine-2-carboxamido)phenyl)-N-isopropyl-5-methyl-2-thia-4-azabicyclo[4.1.0]hept-3-ene-1-carboxamide

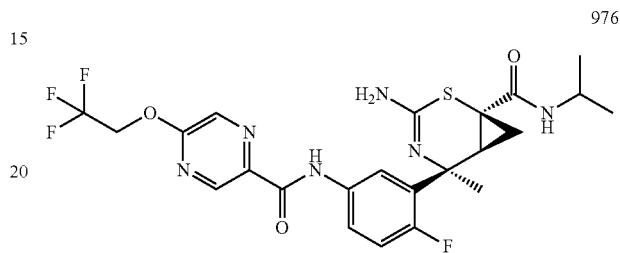

The title compound 976 (0.045 g, 0.083 mmol, 40% yield) was prepared according to the procedure described for 972 using compound 295 (0.150 g, 0.206 mmol) and isopropylamine (0.026 mL, 0.308 mmol). LCMS (ESI$^+$) m/z=541.3 (M+H). $^1$H NMR (300 MHz, CHLOROFORM-d) δ: 9.36 (s, 1H), 8.97 (s, 1H), 8.25 (s, 1H), 7.73-7.83 (m, 1H), 7.49 (dd, J=2.34, 6.72 Hz, 1H), 7.28 (s, 1H), 7.02 (dd, J=8.92, 10.96 Hz, 1H), 6.34 (d, J=7.60 Hz, 1H), 5.02-5.44 (m, 1H), 4.87 (q, J=8.28 Hz, 2H), 4.00-4.18 (m, 1H), 2.25 (t, J=8.55 Hz, 1H), 1.96 (dd, J=4.97, 9.65 Hz, 1H), 1.87 (s, 3H), 1.20 (dd, J=4.38, 6.28 Hz, 6H), 0.76-0.86 (m, 1H).

Example 977

(1S,5S,6S)-3-amino-N-ethyl-5-(2-fluoro-5-(5-(2,2,2-trifluoroethoxy)pyrazine-2-carboxamido)phenyl)-5-methyl-2-thia-4-azabicyclo[4.1.0]hept-3-ene-1-carboxamide

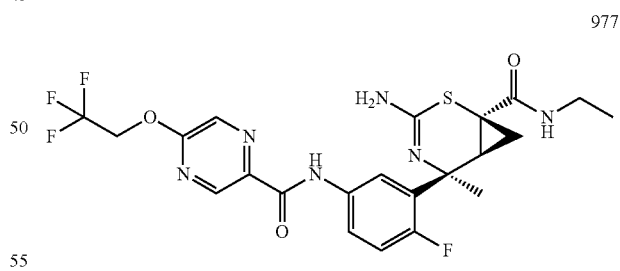

The title compound 977 (0.061 g, 0.116 mmol, 43% yield) was prepared according to the procedure for 972 using compound 295 (0.196 g, 0.269 mmol) and 2.0 M ethylamine solution in THF (0.671 mL, 1.343 mmol). LCMS (ESI$^+$) m/z=527.3 (M+H). $^1$H NMR (300 MHz, CHLOROFORM-d) δ: 9.29 (s, 1H), 8.92 (s, 1H), 8.20 (s, 1H), 7.62-7.72 (m, 1H), 7.47 (dd, J=2.34, 6.72 Hz, 1H), 6.94 (dd, J=9.13, 10.74 Hz, 1H), 6.63 (t, J=5.33 Hz, 1H), 5.43 (br. s., 2H), 4.87 (q, J=8.18 Hz, 2H), 3.23-3.42 (m, 2H), 2.23 (t, J=8.48 Hz, 1H), 1.93-2.07 (m, 1H), 1.89 (s, 3H), 1.17 (t, J=7.23 Hz, 3H), 0.78 (t, J=6.14 Hz, 1H).

Example 981

N-(3-((1S,5S,6S)-3-amino-1-(aminomethyl)-5-methyl-2-thia-4-azabicyclo[4.1.0]hept-3-en-5-yl)-4,5-difluorophenyl)-5-(prop-2-yn-1-yloxy)pyrazine-2-carboxamide

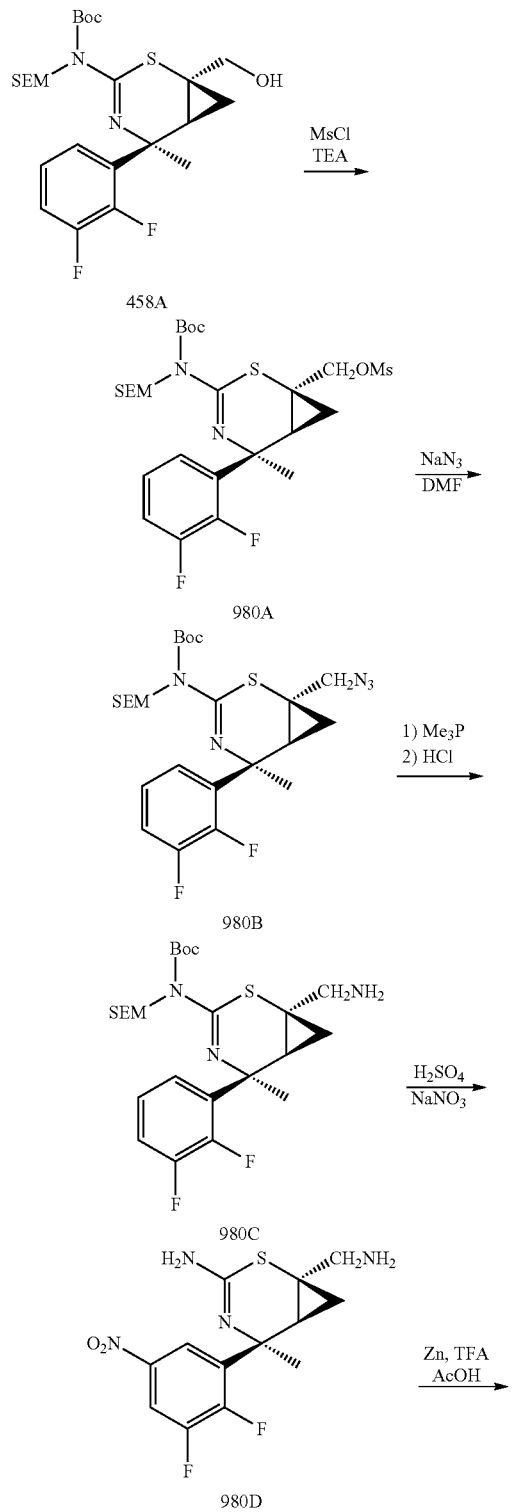

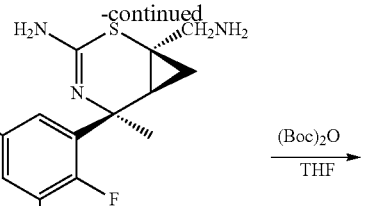

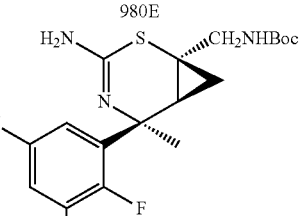

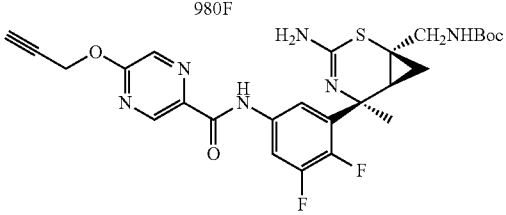

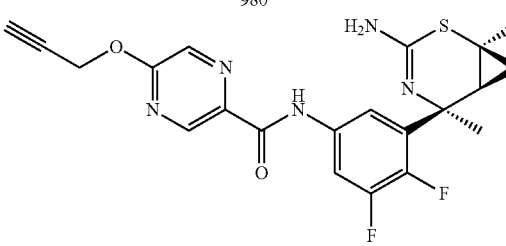

Preparation of compound 980A. To a stirred solution of tert-butyl((1S,5S,6S)-5-(2,3-difluorophenyl)-1-(hydroxymethyl)-5-methyl-2-thia-4-azabicyclo[4.1.0]hept-3-en-3-yl)((2-(trimethylsilyl)ethoxy)methyl)carbamate (458A, 4.60 g, 8.94 mmol) and TEA (1.49 mL, 10.72 mmol) in CH$_2$Cl$_2$ (100 mL) at 0° C. under nitrogen was added methanesulfonyl chloride (0.76 mL, 9.83 mmol). The resulting suspension was stirred for 20 min and then quenched with sat NH$_4$Cl (5 mL). The reaction was diluted with sat NaHCO$_3$ (200 mL) and CH$_2$Cl$_2$ (50 mL). The organic layer was further washed with brine (10 mL) and then it was dried over MgSO$_4$, filtered, and concentrated under reduced pressure to afford ((1S,5S,6S)-3-((tert-butoxycarbonyl)((2-(trimethylsilyl)ethoxy)methyl)amino)-5-(2,3-difluorophenyl)-5-methyl-2-thia-4-azabicyclo[4.1.0]hept-3-en-1-yl)methyl methanesulfonate (980A, 4.95 g, 8.35 mmol, 93% yield) as a colorless oil. LC/MS (ESI$^-$) m/z=593.2.

Preparation of compound 980B. A suspension of ((1S,5S,6S)-3-((tert-butoxycarbonyl)((2-(trimethylsilyl)ethoxy)methyl)amino)-5-(2,3-difluorophenyl)-5-methyl-2-thia-4-azabicyclo[4.1.0]hept-3-en-1-yl)methyl methanesulfonate (980A, 4.95 g, 8.35 mmol) and sodium azide (0.81 g, 12.53 mmol) in dry DMF (30 mL) was heated at 80° C. for 90 min. The reaction mixture was then partitioned between dimethylether (150 mL) and water (250 mL). The separated organic solution was washed with 1 M LiCl (100 mL) followed by brine (10 mL). It was dried over MgSO₄, filtered, and concentrated under reduced pressure. The residue was purified by silica gel chromatography (0-10% EtOAc in heptane) to afford tert-butyl((1S,5S,6S)-1-(azidomethyl)-5-(2,3-difluorophenyl)-5-methyl-2-thia-4-azabicyclo[4.1.0]hept-3-en-3-yl)((2-(trimethylsilyl)ethoxy)methyl)carbamate (980B, 4.40 g, 8.15 mmol, 98% yield) as a colorless oil. LC/MS (ESI⁻) m/z=540.2.

Preparation of compound 980C. To a stirred solution of tert-butyl((1S,5S,6S)-1-(azidomethyl)-5-(2,3-difluorophenyl)-5-methyl-2-thia-4-azabicyclo[4.1.0]hept-3-en-3-yl)((2-(trimethylsilyl)ethoxy)methyl)carbamate (980B, 4.2 g, 7.78 mmol) in THF (40 mL) at 20° C. was added trimethylphosphine (1 M in THF, 9.73 mL, 9.73 mmol) in 1 mL aliquots over a course of 10 min. To the reaction after 90 min was slowly added 1 M HCl (30 mL) and the resulting mixture was stirred at high speed for 1 h. The reaction mixture was then partitioned between EtOAc (250 mL) and water (300 mL). The organic layer was further washed with brine (2×50 mL), dried over MgSO₄, filtered, and then concentrated under reduce pressure to afford tert-butyl((1S,5S,6S)-1-(aminomethyl)-5-(2,3-difluorophenyl)-5-methyl-2-thia-4-azabicyclo[4.1.0]hept-3-en-3-yl)((2-(trimethylsilyl)ethoxy)methyl)carbamate (980C, 3.5 g, 6.81 mmol, 88% yield) as a white foam. LC/MS (ESI⁻) m/z=514.2.

Preparation of compound 980D. To tert-butyl((1S,5S,6S)-1-(aminomethyl)-5-(2,3-difluorophenyl)-5-methyl-2-thia-4-azabicyclo[4.1.0]hept-3-en-3-yl)((2-(trimethylsilyl)ethoxy)methyl)carbamate (980C, 3.50 g, 6.81 mmol) at 0° C. was added sulfuric acid (50.1 g, 511 mmol). The acid slowly digested the starting material and gas evolution was evident. After 15 min, the reaction was removed from the cooling bath, swirled by hand, and then allowed to stir at 20° C. for 30 min. The material was chilled to 0° C. and sodium nitrate (1.16 g, 13.63 mmol) was added in 2 portions over a course of 5 min. The reaction was then stirred for 45 min at 0° C. The reaction was then slowly poured onto wet ice (300 mL) along with CH₂Cl₂ (100 mL). Water (1200 mL) was added, followed by portion wise addition of potassium phosphate (181 g, 852 mmol) over 15-20 min period (pH~9). The organic layer was separated, and the aqueous layer was extracted with CH₂Cl₂ (2×50 mL). The combined organic layers were dried over MgSO₄, filtered, concentrated under reduced pressure, and then purified by silica gel chromatography (0-10% [2 M NH₃ in MeOH] in CH₂Cl₂ to give (1S,5S,6S)-1-(aminomethyl)-5-(2,3-difluoro-5-nitrophenyl)-5-methyl-2-thia-4-azabicyclo[4.1.0]hept-3-en-3-amine (980D, 1.48 g, 4.51 mmol, 66% yield) as a white foam. LC/MS (ESI⁻) m/z=329.1. ¹H NMR (400 MHz, DMSO-d₆) δ 8.46-8.51 (m, 1H), 8.31 (ddd, J=2.93, 6.36, 9.49 Hz, 1H), 6.21 (s, 2H), 2.64-2.77 (m, 2H), 1.72 (t, J=6.85 Hz, 1H), 1.61 (s, 3H), 1.58 (br. s., 2H), 0.79 (dd, J=5.28, 9.19 Hz, 1H), 0.48 (t, J=5.77 Hz, 1H).

Preparation of compound 980E. To a stirred solution of tert-butyl(((1S,5S,6S)-3-amino-5-(5-amino-2,3-difluorophenyl)-5-methyl-2-thia-4-azabicyclo[4.1.0]hept-3-en-1-yl)methyl)carbamate (980D, 1.50 g, 3.50 mmol) in glacial AcOH (15 mL) at 20° C. was added zinc (0.68 g, 10.50 mmol) in 0.20 g portions that kept the reaction temp in the range of 35-42° C. To the reaction, after 45 min, was added TFA (0.5 mL). After 4 h, the reaction was cooled to 0° C., CH₂Cl₂ (50 mL) added, and 30% NH₄OH (80 mL) was added dropwise to the reaction mixture. The organic layer was separated and the aqueous layer was extracted with CH₂Cl₂ (2×25 mL). The organic extracts were dried over MgSO₄, filtered, and then concentrated under reduced pressure to afford tert-butyl(((1S,5S,6S)-3-amino-5-(5-amino-2,3-difluorophenyl)-5-methyl-2-thia-4-azabicyclo[4.1.0]hept-3-en-1-yl)methyl)carbamate (980E, 1.3 g, 3.4 mmol, 98% yield) as a yellow foam. LC/MS (ESI⁻) m/z=399.2.

Preparation of compound 980F. To a stirred solution of (1S,5S,6S)-1-(aminomethyl)-5-(2,3-difluoro-5-nitrophenyl)-5-methyl-2-thia-4-azabicyclo[4.1.0]hept-3-en-3-amine (980E, 1.40 g, 4.26 mmol) in THF (20 mL) at 0° C. was added di-tert-butyl dicarbonate (2.88 g, 13.22 mmol) followed by DMAP (10 mg). The solution was stirred for 15 min and then quenched with sat NH₄Cl (10 mL). The reaction was diluted with EtOAc (50 mL) and water (20 mL). The separated organic was dried over MgSO₄, filtered, concentrated under reduced pressure, and then purified by silica gel chromatography (0-25% EtOAc in CH₂Cl₂) to afford tert-butyl(((1S,5S,6S)-3-amino-5-(2,3-difluoro-5-nitrophenyl)-5-methyl-2-thia-4-azabicyclo[4.1.0]hept-3-en-1-yl)methyl)carbamate (980F, 1.50 g, 3.50 mmol, 82% yield) as a yellow tar. The material thus obtained crystallized upon sitting overnight. LC/MS (ESI⁻) m/z=429.1. ¹H NMR (400 MHz, CHLOROFORM-d) δ 8.44 (br. s., 1H), 7.98 (ddd, J=2.93, 6.31, 9.15 Hz, 1H), 4.90 (br. s., 1H), 4.23-4.78 (bs, 2H), 3.33 (d, J=6.26 Hz, 2H), 1.99 (br. s., 1H), 1.72 (s, 3H), 1.47 (s, 9H), 0.90 (br. s., 1H), 0.75 (t, J=6.36 Hz, 1H).

Preparation of Example 980. To a stirred solution of tert-butyl(((1S,5S,6S)-3-amino-5-(5-amino-2,3-difluorophenyl)-5-methyl-2-thia-4-azabicyclo[4.1.0]hept-3-en-1-yl)methyl)carbamate (980F, 70 mg, 0.17 mmol) in CH₂Cl₂ (1 mL) at 0° C. under nitrogen was added 1-propanephosphonic acid cyclic anhydride (224 mg of 50% solution in EtOAc, 0.35 mmol) in CH₂Cl₂ (1 mL). The mixture was stirred for 18 h at 20° C. The reaction was then quenched with sat. NH₄Cl (2 mL) and stirred for 10 min. The reaction was then partitioned between 9:1 CHCl₃/IPA (10 mL) and 5% NaHCO₃ (10 mL). The aqueous layer was further extracted with 9:1 CHCl₃/IPA (2 mL). The combined organic layers were further washed with 1 M NaOH (10 mL). The aqueous layer was further extracted with 9:1 CHCl₃/IPA (2 mL). The combined organics were then dried over MgSO₄, concentrated under reduced pressure onto dry silica (5 g), and then purified by silica gel chromatography (12 g) eluting products with a gradient of 1-4% MeOH in CH₂Cl₂ to afford tert-butyl(((1S,5S,6S)-3-amino-5-(2,3-difluoro-5-(5-(prop-2-yn-1-yloxy)pyrazine-2-carboxamido)phenyl)-5-methyl-2-thia-4-azabicyclo[4.1.0]hept-3-en-1-yl)methyl)carbamate (980, 14 mg, 0.025 mmol, 14% yield) as a colorless film. This film was suspended in 1:1 ACN/water (1 mL), frozen, and then lyophilized to afford product as a white fluffy solid. LC/MS (ESI⁻) m/z=559.1. ¹H NMR (400 MHz, CHLOROFORM-d) δ 9.50 (s, 1H), 9.02 (d, J=1.37 Hz, 1H), 8.21 (s, 1H), 8.03 (ddd, J=2.64, 6.80, 11.69 Hz, 1H), 7.34-7.39 (m, 1H), 5.09 (d, J=2.54 Hz, 2H), 4.87 (br. s., 1H), 3.49 (s, 1H), 3.32 (d, J=5.87 Hz, 2H), 2.55 (t, J=2.45 Hz, 1H), 1.93 (t, J=7.63 Hz, 1H), 1.71 (s, 3H), 1.43-1.52 (m, 9H), 0.81-0.94 (m, 1H), 0.74 (t, J=6.26 Hz, 1H).

Preparation of Example 981. A solution of tert-butyl(((1S,5S,6S)-3-amino-5-(2,3-difluoro-5-(5-(prop-2-yn-1-yloxy)pyrazine-2-carboxamido)phenyl)-5-methyl-2-thia-4-azabicyclo[4.1.0]hept-3-en-1-yl)methyl)carbamate (980, 12 mg, 0.02 mmol) in TFA was stirred for 30 min at 20° C. The reaction was concentrated under reduced pressure then partitioned between 9:1 CHCl₃/IPA (10 mL) and 1 M NaCl (5 mL). The aqueous was further extracted with 9:1 CHCl₃/IPA (2×5 mL). The combined organics were dried over MgSO₄, and concentrated under reduced pressure. The resulting residue was suspended in 1:1 ACN/water (1 mL), frozen, and then lyophilized affording N-(3-((1S,5S,6S)-3-amino-1-(aminomethyl)-5-methyl-2-thia-4-azabicyclo[4.1.0]hept-3- en-5-yl)-4,5-difluorophenyl)-5-(prop-2-yn-1-yloxy)pyrazine-2-carboxamide (8 mg, 0.017 mmol, 81% yield) as a white fluffy powder. LC/MS (ESI⁻) m/z=459.0. $^1$H NMR (400 MHz, DMSO-$d_6$) δ 10.53 (s, 1H), 8.83 (d, J=1.17 Hz, 1H), 8.41 (d, J=1.17 Hz, 1H), 7.80-7.86 (m, 2H), 5.86 (s, 2H), 5.07 (d, J=2.54 Hz, 2H), 3.57 (t, J=2.45 Hz, 1H), 2.54-2.70 (m, 3H), 1.47-1.60 (m, 4H), 0.75 (dd, J=5.18, 9.49 Hz, 1H), 0.46 (t, J=5.67 Hz, 1H).

Example 982

(1S,5S,6S)-3-amino-N-(2,2-difluorocyclopropyl)-5-(2-fluoro-5-(5-(2,2,2-trifluoroethoxy)pyrazine-2-carboxamido)phenyl)-5-methyl-2-thia-4-azabicyclo[4.1.0]hept-3-ene-1-carboxamide The title compound 982 (0.008 g, 0.014 mmol, 5% yield) was prepared according to the procedure for 972 using compound 295 (0.196 g, 0.269 mmol) and 2,2-difluorocyclopropylamine hydrochloride (0.049 g, 0.376 mmol). LC/MS (ESI⁺) m/z=575.2 (M+H). $^1$H NMR (300 MHz, CHLOROFORM-d) δ: 9.39 (s, 1H), 9.00 (s, 1H), 8.29 (s, 1H), 7.72-7.81 (m, 1H), 7.49 (t, J=5.55 Hz, 1H), 6.98-7.12 (m, 1H), 6.94 (br. s., 1H), 4.88 (q, J=8.18 Hz, 2H), 4.00-4.50 (br. s., 2H), 3.38 (br. s., 1H), 2.29 (t, J=8.48 Hz, 1H), 1.97-2.11 (m, 1H), 1.81-1.94 (m, 4H), 1.34-1.68 (m, 1H), 0.81-0.99 (m, 1H). $^{19}$F NMR (282 MHz, CHLOROFORM-d) δ: −73.63 (s, 3F), −113.22 (s, 1F), −131.06 (d, J=160.74 Hz, 1F), −143.91 (d, J=160.74 Hz, 1F).

Example 983

(1S,5S,6S)-3-amino-N-(1-fluoro-2-methylpropan-2-yl)-5-(2-fluoro-5-(5-(2,2,2-trifluoroethoxy)pyrazine-2-carboxamido)phenyl)-5-methyl-2-thia-4-azabicyclo[4.1.0]hept-3-ene-1-carboxamide To a mixture of (1S,5S,6S)-3-((tert-butoxycarbonyl)((2-(trimethylsilyl)ethoxy)methyl)amino)-5-(2-fluoro-5-(5-(2,2,2-trifluoroethoxy)pyrazine-2-carboxamido)phenyl)-5-methyl-2-thia-4-azabicyclo[4.1.0]hept-3-ene-1-carboxylic acid, 295, (0.15 g, 0.20 mmol), 2-fluoro-1,1-dimethyl-ethylamine hydrochloride (52 mg, 0.41 mmol), and diisopropylethylamine (0.18 mL, 1.03 mmol) in DMF (2 mL) was added (1-cyano-2-ethoxy-2-oxoethylidenaminooxy)dimethylaminomorpholinocarbenium hexafluorophosphate, COMU, (0.17 g, 0.41 mmol). The reaction mixture was stirred at RT for 18 h, quenched with saturated NH$_4$Cl, and extracted with EtOAc. The organic layer was concentrated to dryness. The residue of tert-butyl((1S,5S,6S)-1-((1-fluoro-2-methylpropan-2-yl)carbamoyl)-5-(2-fluoro-5-(5-(2,2,2-trifluoroethoxy)pyrazine-2-carboxamido)phenyl)-5-methyl-2-thia-4-azabicyclo[4.1.0]hept-3-en-3-yl)((2-(trimethylsilyl)ethoxy)methyl)carbamate was dissolved in dioxane (2 mL) and added to p-toluenesulfonic acid monohydrate (0.15 g, 0.80 mmol). The resulting mixture was then heated at 85° C. for 2 h. The reaction was diluted with water and extracted with EtOAc (2×). The organic phase was concentrated and the residue purified by flash column chromatography on silica gel (0-5% MeOH in DCM) to afford (1S,5S,6S)-3-amino-N-(1-fluoro-2-methylpropan-2-yl)-5-(2-fluoro-5-(5-(2,2,2-trifluoroethoxy)pyrazine-2-carboxamido)phenyl)-5-methyl-2-thia-4-azabicyclo[4.1.0]hept-3-ene-1-carboxamide, 983, (0.04 g, 0.07 mmol, 34% yield). LCMS (ESI⁺) m/z=573.2 (M+H). $^1$H NMR (300 MHz, CHLOROFORM-d) δ: 9.41 (s, 1H), 9.01 (s, 1H), 8.29 (s, 1H), 7.77-7.85 (m, 1H), 7.50 (dd, J=2.34, 6.72 Hz, 1H), 7.07 (t, J=9.92 Hz, 1H), 6.45 (s, 1H), 4.88 (q, J=8.28 Hz, 2H), 4.45-4.62 (m, 1H), 4.28-4.43 (m, 1H), 3.88-4.26 (br. s., 2H), 2.18-2.27 (m, 1H), 1.80-1.96 (m, 4H), 1.33-1.45 (m, 6H), 0.76-0.88 (m, 1H). $^{19}$F NMR (282 MHz, CHLOROFORM-d) δ: −73.63 (s, 3F), −113.56 (s, 1F), −225.38 (s, 1F).

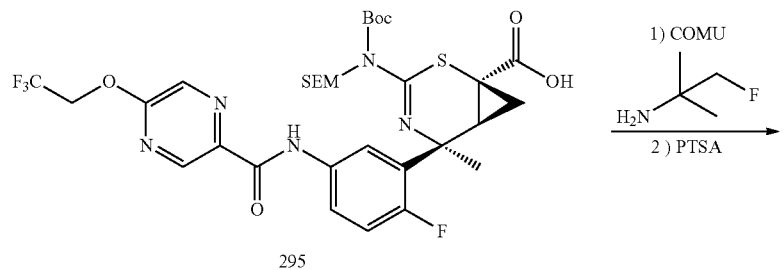

295

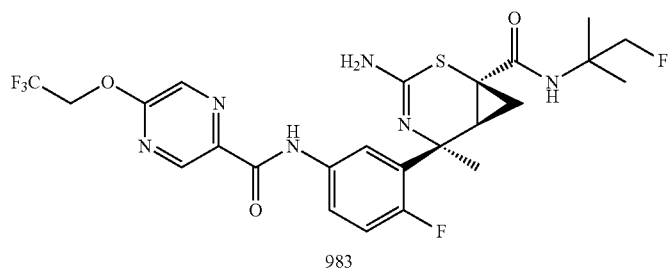

983

Example 984

(1S,5S,6S)-3-amino-5-(2-fluoro-5-(5-(2,2,2-trifluoroethoxy)pyrazine-2-carboxamido)phenyl)-N-methoxy-N,5-dimethyl-2-thia-4-azabicyclo[4.1.0]hept-3-ene-1-carboxamide

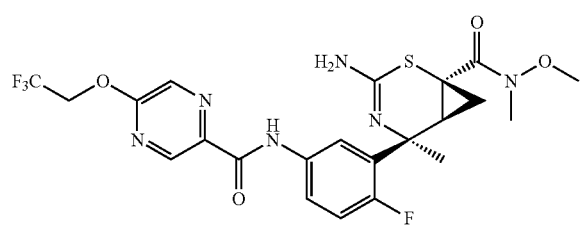 [SMILES: CON(C)C(=O)[C@]12C[C@H]1[C@@](C)(c1cc(NC(=O)c3cnc(OCC(F)(F)F)cn3)ccc1F)N=C(N)S2]

The title compound 984 (0.060 g, 0.111 mmol, 53% yield) was prepared according to the procedure for 983 using compound 295, (0.150 g, 0.206 mmol), and N,O-dimethyl hydroxylamine hydrochloride (0.040 g, 0.411 mmol). LCMS (ESI+) m/z=543.2 (M+H). $^1$H NMR (300 MHz, CHLOROFORM-d) δ: 9.45 (s, 1H), 9.02 (s, 1H), 8.31 (s, 1H), 7.86-7.93 (m, 1H), 7.55 (dd, J=2.48, 6.72 Hz, 1H), 6.96-7.18 (m, 1H), 4.88 (q, J=8.28 Hz, 2H), 3.92-4.65 (br. s., 2H), 3.79 (s, 3H), 3.26 (s, 3H), 2.46 (t, J=8.62 Hz, 1H), 1.88 (s, 3H), 1.51 (dd, J=5.55, 9.79 Hz, 1H), 0.93 (t, J=6.43 Hz, 1H). $^{19}$F NMR (282 MHz, CHLOROFORM-d) δ: −73.64 (s, 3F), −114.39 (s, 1F).

Example 991

N-(3-((1S,5S,6S)-3-amino-1-((R)-3-fluoropyrrolidine-1-carbonyl)-5-methyl-2-thia-4-azabicyclo[4.1.0]hept-3-en-5-yl)-4-fluorophenyl)-5-(2,2,2-trifluoroethoxy)pyrazine-2-carboxamide

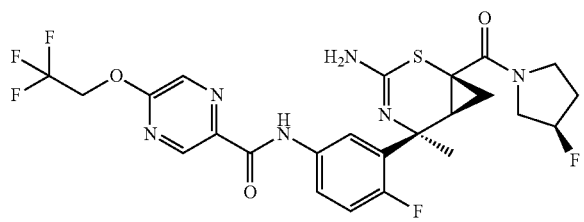

The title compound 991 (0.060 g, 0.105 mmol, 51% yield) was prepared according to the procedure for 983 using compound 295, (0.150 g, 0.206 mmol) and (R)-(−)-3-fluoropyrrolidine hydrochloride (0.052 g, 0.411 mmol). LCMS (ESI+) m/z=571.2 (M+H). $^1$H NMR (300 MHz, CHLOROFORM-d) δ: 9.47 (s, 1H), 9.03 (s, 1H), 8.31 (s, 1H), 7.83-7.91 (m, 1H), 7.57-7.64 (m, 1H), 6.99-7.19 (m, 1H), 5.10-5.55 (m, 1H), 4.88 (q, J=8.33 Hz, 2H), 3.28-4.46 (br. m., 7H), 2.35 (br. s., 1H), 2.15-2.31 (m, 1H), 1.91 (s, 3H), 1.60 (dd, J=5.92, 9.57 Hz, 1H), 0.86 (br. s., 1H). $^{19}$F NMR (282 MHz, CHLOROFORM-d) δ: −73.63 (s, 3F), −114.61 (s, 1F), −177.70 (s, 1F).

Example 992

N-(3-((1S,5S,6S)-3-amino-1-((S)-3-fluoropyrrolidine-1-carbonyl)-5-methyl-2-thia-4-azabicyclo[4.1.0]hept-3-en-5-yl)-4-fluorophenyl)-5-(2,2,2-trifluoroethoxy)pyrazine-2-carboxamide

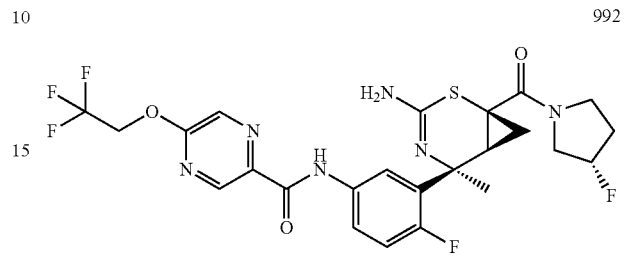

The title compound 992 (0.057 g, 0.100 mmol, 48% yield) was prepared according to the procedure for 983 using compound 295, (0.150 g, 0.206 mmol) and (S)-(−)-3-fluoropyrrolidine hydrochloride (0.052 g, 0.411 mmol). LCMS (ESI+) m/z=571.2 (M+H). $^1$H NMR (300 MHz, CHLOROFORM-d) δ: 9.47 (s, 1H), 9.03 (s, 1H), 8.31 (s, 1H), 7.84-7.92 (m, 1H), 7.62 (d, J=4.53 Hz, 1H), 7.09 (s, 1H), 5.10-5.50 (m, 1H), 4.88 (q, J=8.18 Hz, 2H), 3.90-4.62 (m, 3H), 3.76 (br. s., 4H), 2.46 (s, 2H), 1.89 (s, 3H), 1.42 (dd, J=5.63, 9.72 Hz, 1H), 0.93 (t, J=6.28 Hz, 1H). $^{19}$F NMR (282 MHz, CHLOROFORM-d) δ: −73.63 (s, 3F), −114.67 (s, 1F), −177.55 (s, 1F).

Example 995 and Example 996

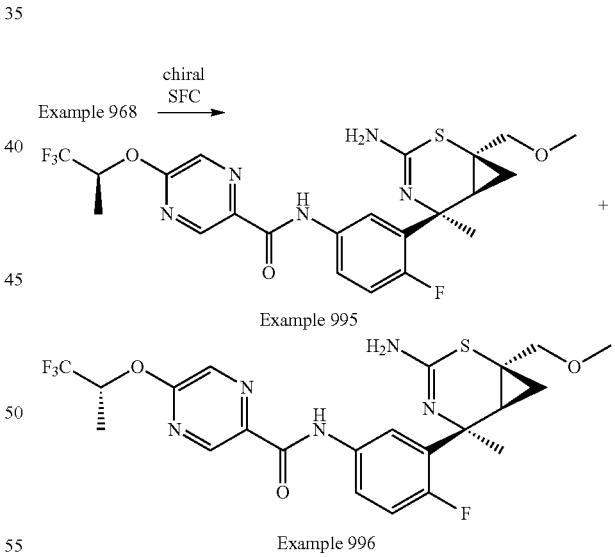

Example 968 (40 mg, a mixture of two diastereomers) was chromatographed using supercritical CO$_2$ (additives 15% of EtOH with 20 mM NH$_3$) on an OD-H column (250×21 mm, 5 μm) eluting at a flow rate of 70 mL/min. The first peak (retention time=3.6 min) provided N-(3-((1S,5S,6S)-3-amino-1-(methoxymethyl)-5-methyl-2-thia-4-azabicyclo[4.1.0]hept-3-en-5-yl)-4-fluorophenyl)-5-(((S)-1,1,1-trifluoropropan-2-yl)oxy)pyrazine-2-carboxamide 995 (18 mg, 45% yield). The second peak (retention time=4.5 min) provided N-(3-((1S,5S,6S)-3-amino-1-(methoxymethyl)-5-methyl-2-thia-4-azabicyclo[4.1.0]hept-3-en-5-yl)-4-fluorophenyl)-5-(((R)-1,1,1-trifluoropropan-2-yl)oxy)pyrazine-2-carboxamide 996 (18 mg, 45% yield). The absolute stereochemistry was arbitrarily assigned. Analytical data for Example 995: $^1$H NMR (400 MHz, CHLOROFORM-d) δ 9.48 (s, 1H), 9.01 (d, J=1.17 Hz, 1H), 8.23 (d, J=1.17 Hz, 1H), 7.87-8.00 (m, 1H), 7.72 (dd, J=2.74, 7.04 Hz, 1H), 7.07 (dd, J=8.80, 11.74 Hz, 1H), 5.81 (m, 1H), 3.67 (d, J=10.37 Hz, 1H), 3.41 (s, 3H), 3.35 (d, J=10.76 Hz, 1H), 1.81 (ddd, J=1.17, 6.70, 9.34 Hz, 1H), 1.72 (d, J=1.17 Hz, 3H), 1.56 (d, J=6.46 Hz, 3H), 0.88 (dd, J=5.87, 9.39 Hz, 1H), 0.77-0.84 (m, 1H). LC/MS (ESI$^+$) m/z=514 (M+H)$^+$. Analytical data for Example 996: $^1$H NMR (400 MHz, CHLOROFORM-d) δ 9.48 (s, 1H), 9.01 (d, J=1.37 Hz, 1H), 8.24 (d, J=1.17 Hz, 1H), 7.95 (td, J=3.47, 8.71 Hz, 1H), 7.71 (dd, J=2.74, 6.85 Hz, 1H), 7.08 (dd, J=8.61, 11.74 Hz, 1H), 5.74-5.89 (m, 1H), 3.67 (d, J=10.56 Hz, 1H), 3.41 (s, 3H), 3.35 (d, J=10.56 Hz, 1H), 1.82 (dd, J=7.04, 8.41 Hz, 1H), 1.73 (s, 3H), 1.57 (d, J=6.46 Hz, 3H), 0.89 (dd, J=5.87, 9.39 Hz, 1H), 0.76-0.83 (m, 1H). LC/MS (ESI$^+$) m/z=514 (M+H)$^+$.

Example 997

(1S,5S,6S)-3-amino-5-(2-fluoro-5-(5-(2,2,2-trifluoroethoxy)pyrazine-2-carboxamido)phenyl)-5-methyl-N—((R)-3-methylbutan-2-yl)-2-thia-4-azabicyclo[4.1.0]hept-3-ene-1-carboxamide

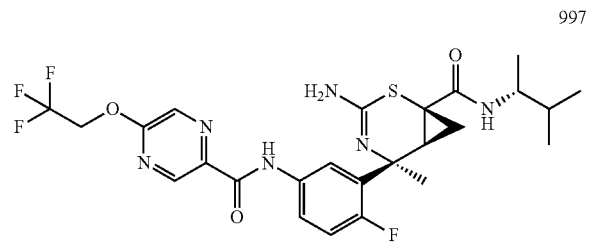 [SMILES: CC(C)[C@@H](C)NC(=O)[C@]12C[C@H]1[C@@](C)(c1cc(NC(=O)c3cnc(OCC(F)(F)F)cn3)ccc1F)N=C(N)S2]

997

The title compound 997 (0.042 g, 0.074 mmol, 36% yield) was prepared according to the procedure for 983 using compound 295, (0.150 g, 0.206 mmol) and (R)-(−)-2-amino-3-methylbutylamine (0.027 mL, 0.308 mmol). LCMS (ESI$^+$) m/z=569.3 (M+H). $^1$H NMR (300 MHz, CHLOROFORM-d) δ: 9.39 (s, 1H), 8.98 (s, 1H), 8.26 (s, 1H), 7.74-7.81 (m, 1H), 7.54 (dd, J=2.41, 6.80 Hz, 1H), 7.04 (dd, J=8.92, 10.96 Hz, 1H), 6.39 (d, J=8.77 Hz, 1H), 4.87 (q, J=8.33 Hz, 2H), 4.71 (br. s., 2H), 3.80-3.93 (m, 1H), 2.24 (t, J=8.55 Hz, 1H), 1.95 (dd, J=4.97, 9.65 Hz, 1H), 1.85 (s, 3H), 1.72-1.81 (m, 1H), 1.12 (d, J=6.72 Hz, 3H), 0.89-0.97 (m, 6H), 0.78-0.88 (m, 1H). $^{19}$F NMR (282 MHz, CHLOROFORM-d) δ: −73.63 (s, 3F), −113.63 (s, 1F).

Example 998

N-(3-((1S,5S,6S)-3-amino-5-methyl-1-(morpholine-4-carbonyl)-2-thia-4-azabicyclo[4.1.0]hept-3-en-5-yl)-4-fluorophenyl)-5-(2,2,2-trifluoroethoxy)pyrazine-2-carboxamide

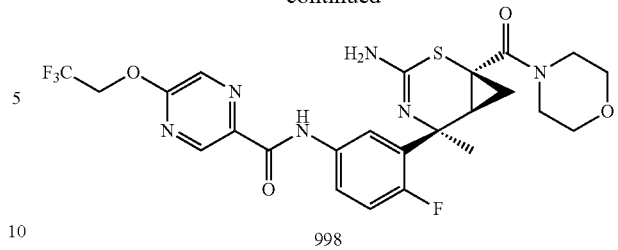

998

To a solution of (1S,5S,6S)-3-((tert-butoxycarbonyl)((2-(trimethylsilyl)ethoxy)methyl)amino)-5-(2-fluoro-5-(5-(2,2,2-trifluoroethoxy)pyrazine-2-carboxamido)phenyl)-5-methyl-2-thia-4-azabicyclo[4.1.0]hept-3-ene-1-carboxylic acid, 295, (0.15 g, 0.20 mmol) in DCM (3 mL) was added 1-chloro-N,N,2-trimethyl-1-propenylamine (0.20 mL, 1.49 mmol). After the reaction mixture was stirred at RT for 2 h, additional 1-chloro-N,N,2-trimethyl-1-propenylamine (0.20 mL, 1.49 mmol) was added and the reaction was stirred for another 12 h. The reaction mixture was then concentrated under vacuum. To the residue in DMF (1 mL) was added N,N-diisopropylethylamine (0.18 mL, 1.03 mmol) and morpholine (0.02 mL, 0.21 mmol). The reaction was stirred at RT for 30 min, diluted with water and extracted with EtOAc (2×). The combined organic extracts were concentrated to dryness. The residue was dissolved in dioxane (2 mL) and treated with p-toluenesulfonic acid monohydrate (0.12 g, 0.62 mmol). The resulting mixture was heated in an oil bath at 85° C. for 2 h. The reaction was then diluted with water and extracted with EtOAc (2×). The organic extracts were concentrated and the residue was purified by flash column chromatography on silica gel (0-5% MeOH in DCM) to afford N-(3-((1S,5S,6S)-3-amino-5-methyl-1-(morpholine-4-carbonyl)-2-thia-4-azabicyclo[4.1.0]hept-3-en-5-yl)-4-fluorophenyl)-5-(2,2,2-trifluoroethoxy)pyrazine-2-carboxamide, 998, (77 mg, 0.14 mmol, 66% yield). LCMS (ESI$^+$) m/z=569.2 (M+H). $^1$H NMR (300 MHz, CHLOROFORM-d) δ: 9.46 (s, 1H), 9.02 (s, 1H), 8.29 (s, 1H), 7.81-7.89 (m, 1H), 7.64-7.71 (m, 1H), 7.04-7.13 (m, 1H), 4.88 (q, J=8.18 Hz, 2H), 4.25 (br. s., 2H), 3.70 (br. s., 8H), 2.36 (t, J=8.48 Hz, 1H), 1.86 (s, 3H), 1.36 (dd, J=5.70, 9.65 Hz, 1H), 0.92 (t, J=6.43 Hz, 1H). $^{19}$F NMR (282 MHz, CHLOROFORM-d) δ: −73.36 (s, 3F), −114.91 (s, 1F).

Example 999

(1S,5S,6S)-3-amino-N-(2,2-difluoroethyl)-5-(2-fluoro-5-(5-(2,2,2-trifluoroethoxy)pyrazine-2-carboxamido)phenyl)-5-methyl-2-thia-4-azabicyclo[4.1.0]hept-3-ene-1-carboxamide

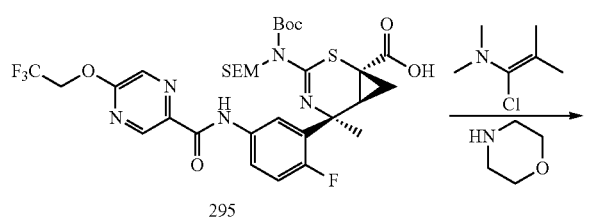

295

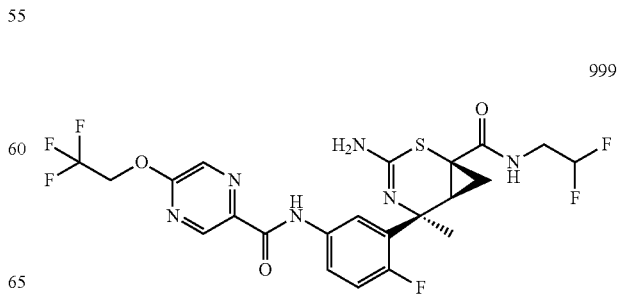

999

The title compound 999 (0.100 g, 0.178 mmol, 65% yield) was prepared according to the procedure for 998 using compound 295 (0.200 g, 0.274 mmol) and 2,2-difluoroethylamine (0.022 mL, 0.274 mmol). LCMS (ESI+) m/z=563.1 (M+H). $^1$H NMR (300 MHz, CHLOROFORM-d) δ: 9.28 (s, 1H), 8.93 (s, 1H), 8.22 (s, 1H), 7.62-7.73 (m, 1H), 7.46 (d, J=6.72 Hz, 1H), 6.87-7.04 (m, 2H), 5.60-6.14 (m, 1H), 5.26 (br. s., 2H), 4.88 (q, J=8.28 Hz, 2H), 3.51-3.82 (m, 2H), 2.18-2.28 (m, 1H), 2.04 (dd, J=5.12, 9.35 Hz, 1H), 1.90 (s, 3H), 0.84 (t, J=6.14 Hz, 1H). $^{19}$F NMR (282 MHz, CHLOROFORM-d) δ: −73.63 (s, 3F), −113.09 (s, 1F), −122.91 (s, 1F), −122.92 (s, 1F).

Example 1000

(1S,5S,6S)-3-amino-5-(2-fluoro-5-(5-(2,2,2-trifluoroethoxy)pyrazine-2-carboxamido)phenyl)-N,N,5-trimethyl-2-thia-4-azabicyclo[4.1.0]hept-3-ene-1-carboxamide

1000

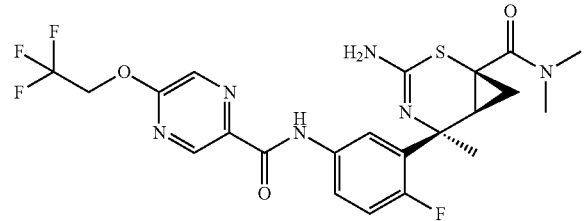

The title compound (0.109 g, 0.207 mmol, 76% yield) was prepared according to the procedure for 983 using compound 295, (0.200 g, 0.274 mmol) and dimethylamine hydrochloride (0.045 g, 0.548 mmol). LCMS (ESI+) m/z=527.2 (M+H). $^1$H NMR (300 MHz, CHLOROFORM-d) δ: 9.42 (s, 1H), 8.98 (s, 1H), 8.24 (s, 1H), 7.79-7.87 (m, 1H), 7.62 (dd, J=2.12, 6.65 Hz, 1H), 7.03 (dd, J=9.21, 10.96 Hz, 1H), 4.86 (q, J=8.28 Hz, 4H), 3.06 (br. s., 6H), 2.31 (t, J=8.40 Hz, 1H), 1.88 (s, 3H), 1.38 (dd, J=5.70, 9.65 Hz, 1H), 0.88 (t, J=6.43 Hz, 1H). $^{19}$F NMR (282 MHz, CHLOROFORM-d) δ: −73.63 (s, 3F), −114.70 (s, 1F).

Example 1004

N-(3-((1S,5S,6S)-3-amino-5-methyl-1-(morpholine-4-carbonyl)-2-thia-4-azabicyclo[4.1.0]hept-3-en-5-yl)-4,5-difluorophenyl)-5-(prop-2-yn-1-yloxy)pyrazine-2-carboxamide

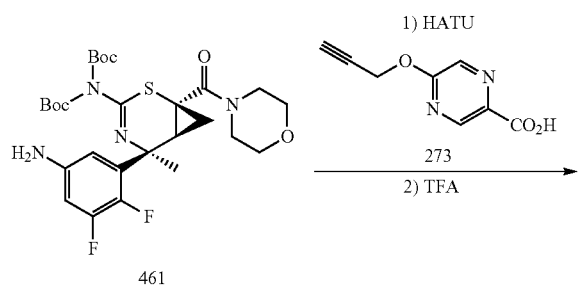

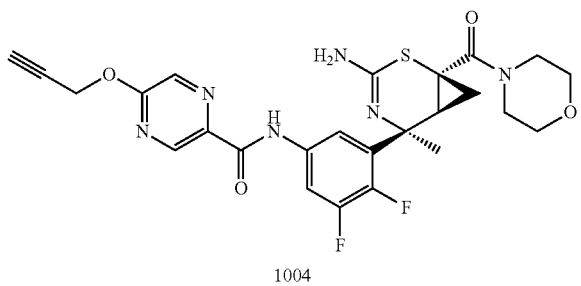

1004

To a stirred solution of (1S,5S,6S)-methyl 3-(di-tert-butoxycarbonyl)amino-5-(2,3-difluoro-5aminophenyl)-5-methyl-2-thia-4-azabicyclo[4.1.0]hept-3-ene-1-(morpholino)methanone (461, 83 mg, 0.142 mmol) and diisopropylethylamine (99 µL, 0.57 mmol) in DMF (0.5 mL) at 20° C. was added HATU (81 mg, 0.21 mmol). The solution was stirred for 30 min and then 5-(prop-2-yn-1-yloxy)pyrazine-2-carboxylic acid hydrochloride (273, 46 mg, 0.21 mmol) was added. The solution was stirred for 1 h and then partitioned between 9:1 CHCl$_3$/IPA (20 mL) and 5% NaHCO$_3$. The organic layer was washed with brine, dried over MgSO$_4$, filtered, and then concentrated under reduced pressure. The residue was azeotroped with toluene (3×5 mL) followed by stirring in TFA (1 mL) for 30 min. The solvent was removed under reduced pressure and the residue was partitioned between 9:1 CHCl$_3$/IPA (20 mL) and 1 M NaOH (10 mL). The organic layer was washed with brine, dried over MgSO$_4$, filtered, and then concentrated under reduced pressure. The resulting white solid was triturated with EtOH (2×2 mL) and then dried under reduced pressure to afford Example 1004 (42 mg, 0.08 mmol, 54% yield) as a white solid. LC/MS (ESI−) m/z=543.0 (M+H)+. $^1$H NMR (400 MHz, DMSO-d$_6$) δ 10.62 (s, 1H), 8.90 (d, J=1.17 Hz, 1H), 8.48 (d, J=1.37 Hz, 1H), 7.91 (ddd, J=2.54, 6.80, 12.37 Hz, 1H), 7.84 (d, J=5.87 Hz, 1H), 6.25 (s, 2H), 5.14 (d, J=2.35 Hz, 2H), 3.49-3.68 (m, 8H), 2.04-2.10 (m, 1H), 1.68 (s, 4H), 1.37 (dd, J=5.48, 9.59 Hz, 1H), 0.78-0.84 (m, 1H).

Example 1005

N-(3-((1S,5S,6S)-3-amino-5-methyl-1-(morpholine-4-carbonyl)-2-thia-4-azabicyclo[4.1.0]hept-3-en-5-yl)-4-fluorophenyl)-5-(prop-2-yn-1-yloxy)pyrazine-2-carboxamide

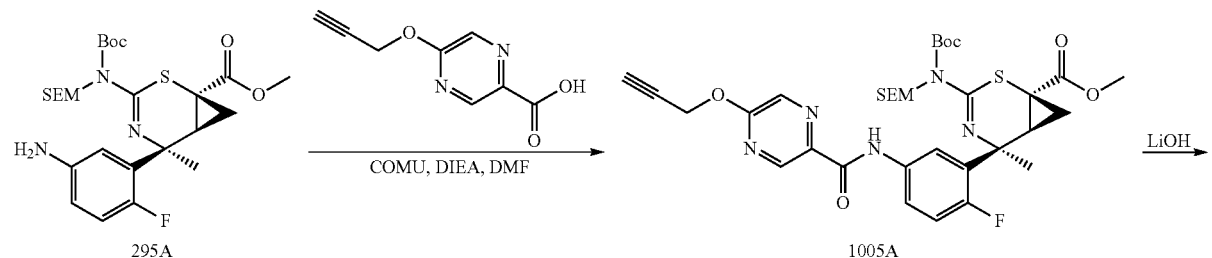

-continued

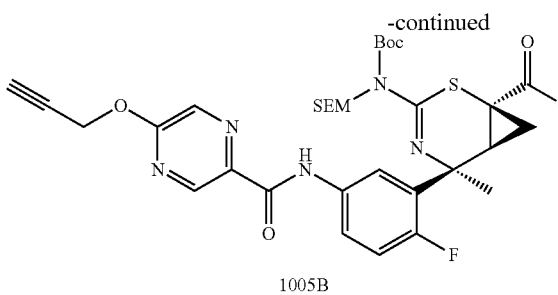

1005B

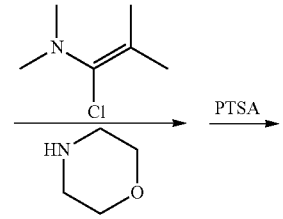

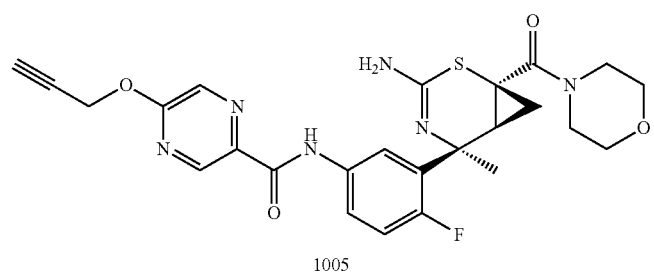

1005

Preparation of (1S,5S,6S)-methyl 3-((tert-butoxycarbonyl)((2-(trimethylsilyl)ethoxy)methyl)amino)-5-(2-fluoro-5-(5-(prop-2-yn-1-yloxy)pyrazine-2-carboxamido)phenyl)-5-methyl-2-thia-4-azabicyclo[4.1.0]hept-3-ene-1-carboxylate (1005A). To a mixture of (1S,5S,6S)-methyl 5-(5-amino-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylate, 295A, (0.570 g, 1.056 mmol), 5-(prop-2-yn-1-yloxy)pyrazine-2-carboxylic acid, 273, (0.226 g, 1.267 mmol), and diisopropylethylamine (0.551 mL, 3.17 mmol) in DMF (1 mL) was added (1-cyano-2-ethoxy-2-oxoethylidenaminooxy)dimethylaminomorpholinocarbenium hexafluorophosphate, COMU, (0.905 g, 2.112 mmol). The reaction mixture was stirred at RT for 2 h and was then quenched with saturated NH$_4$Cl solution and extracted with EtOAc. The organic layer was concentrated to dryness and the residue was purified by flash column chromatography on silica gel (0-40% EtOAc in heptane) to afford compound 1005A (0.510 g, 0.729 mmol, 69% yield). LCMS (ESI$^+$) m/z=700.3 (M+H).

Preparation of (1S,5S,6S)-3-((tert-butoxycarbonyl)((2-(trimethylsilyl)ethoxy)methyl)amino)-5-(2-fluoro-5-(5-(prop-2-yn-1-yloxy)pyrazine-2-carboxamido)phenyl)-5-methyl-2-thia-4-azabicyclo[4.1.0]hept-3-ene-1-carboxylic acid (1005B). The title compound (0.486 g, 0.709 mmol, 99% yield) was prepared according to the procedure for 221A using (1S,5S,6S)-methyl 3-((tert-butoxycarbonyl)((2-(trimethylsilyl)ethoxy)methyl)amino)-5-(2-fluoro-5-(5-(prop-2-yn-1-yloxy)pyrazine-2-carboxamido)phenyl)-5-methyl-2-thia-4-azabicyclo[4.1.0]hept-3-ene-1-carboxylate 1005A, (0.500 g, 0.714 mmol). LCMS (ESI$^+$) m/z=686.3 (M+H).

Example 1005 (0.043 g, 0.082 mmol, 70% yield) was prepared according to the procedure for 998 using compound (1S,5S,6S)-3-((tert-butoxycarbonyl)((2-(trimethylsilyl)ethoxy)methyl)amino)-5-(2-fluoro-5-(5-(prop-2-yn-1-yloxy)pyrazine-2-carboxamido)phenyl)-5-methyl-2-thia-4-azabicyclo[4.1.0]hept-3-ene-1-carboxylic acid, 1005B, (0.080 g, 0.117 mmol) and morpholine (0.020 mL, 0.233 mmol). LCMS (ESI$^+$) m/z=525.2 (M+H). $^1$H NMR (300 MHz, CHLOROFORM-d) δ: 9.46 (s, 1H), 9.02 (s, 1H), 8.20 (s, 1H), 7.81-7.88 (m, 1H), 7.68 (dd, J=2.41, 6.80 Hz, 1H), 7.07 (dd, J=8.99, 11.33 Hz, 1H), 5.09 (d, J=1.90 Hz, 2H), 4.39 (br. s., 2H), 3.70 (br. s., 8H), 2.56 (s, 1H), 2.35 (t, J=8.48 Hz, 1H), 1.85 (s, 3H), 1.35 (dd, J=5.77, 9.72 Hz, 1H), 0.91 (t, J=6.43 Hz, 1H). $^{19}$F NMR (282 MHz, CHLOROFORM-d) δ: −115.18 (s, 1F).

Example 1006

(1S,5S,6S)-3-amino-N-(1-fluoro-2-methylpropan-2-yl)-5-(2-fluoro-5-(5-(prop-2-yn-1-yloxy)pyrazine-2-carboxamido)phenyl)-5-methyl-2-thia-4-azabicyclo[4.1.0]hept-3-ene-1-carboxamide

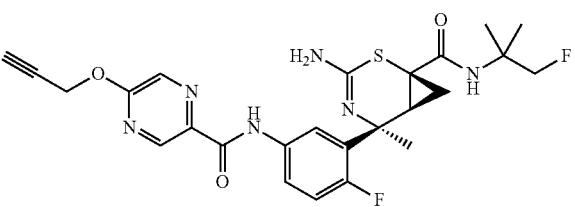

1006

The title compound (0.040 g, 0.076 mmol, 52% yield) was prepared according to the procedure for 998 using compound 1005B (0.100 g, 0.146 mmol) and 2-fluoro-1,1-dimethyl-ethylamine hydrochloride (0.026 g, 0.204 mmol). LCMS (ESI$^+$) m/z=529.1 (M+H). $^1$H NMR (300 MHz, CHLOROFORM-d) δ: 9.40 (s, 1H), 9.01 (s, 1H), 8.19 (s, 1H), 7.76-7.84 (m, 1H), 7.50 (dd, J=2.27, 6.65 Hz, 1H), 7.00-7.10 (m, 1H), 6.46 (s, 1H), 5.10 (s, 2H), 4.45-4.65 (m, 3H), 4.26-4.44 (m, 1H), 2.57 (s, 1H), 2.20 (t, J=8.55 Hz, 1H), 1.81-1.94 (m, 4H), 1.39 (s, 6H), 0.75-0.90 (m, 1H). $^{19}$F NMR (282 MHz, CHLOROFORM-d) δ: −113.80 (s, 1F), −225.37 (s, 1F).

Example 1017

(1S,5S,6S)-3-amino-N-ethyl-5-(2-fluoro-5-(5-(prop-2-yn-1-yloxy)pyrazine-2-carboxamido)phenyl)-5-methyl-2-thia-4-azabicyclo[4.1.0]hept-3-ene-1-carboxamide

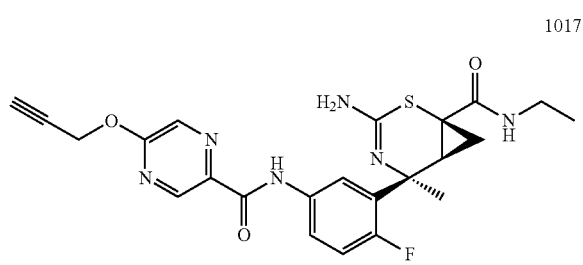 [SMILES: C#CCOc1cnc(C(=O)Nc2ccc(F)c([C@@]3(C)N=C(N)S[C@@]4(C(=O)NCC)C[C@H]43)c2)cn1]

The title compound 1017 (0.035 g, 0.073 mmol, 45% yield) was prepared according to the procedure for 998 using compound 1005B (0.110 g, 0.160 mmol) and 2.0 M ethylamine solution in THF (0.241 mL, 0.481 mmol). LCMS (ESI+) m/z=483.2 (M+H). ¹H NMR (300 MHz, CHLOROFORM-d) δ: 9.42 (s, 1H), 9.02 (s, 1H), 8.21 (s, 1H), 7.76-7.84 (m, 1H), 7.47-7.54 (m, 1H), 7.07 (dd, J=9.06, 10.96 Hz, 1H), 6.55 (br. s., 1H), 5.10 (d, J=2.19 Hz, 2H), 3.73-4.52 (br. s., 2H), 3.35 (m, 2H), 2.57 (s, 1H), 2.28 (t, J=8.55 Hz, 1H), 1.99 (dd, J=5.04, 9.57 Hz, 1H), 1.86 (s, 3H), 1.20 (t, J=7.23 Hz, 3H), 0.79-0.93 (m, 1H). ¹⁹F NMR (282 MHz, CHLOROFORM-d) δ: −113.63 (s, 1F).

Example 1018

(1S,5S,6S)-3-amino-5-(5-(5-cyanopicolinamido)-2-fluorophenyl)-N-(1-fluoro-2-methylpropan-2-yl)-5-methyl-2-thia-4-azabicyclo[4.1.0]hept-3-ene-1-carboxamide

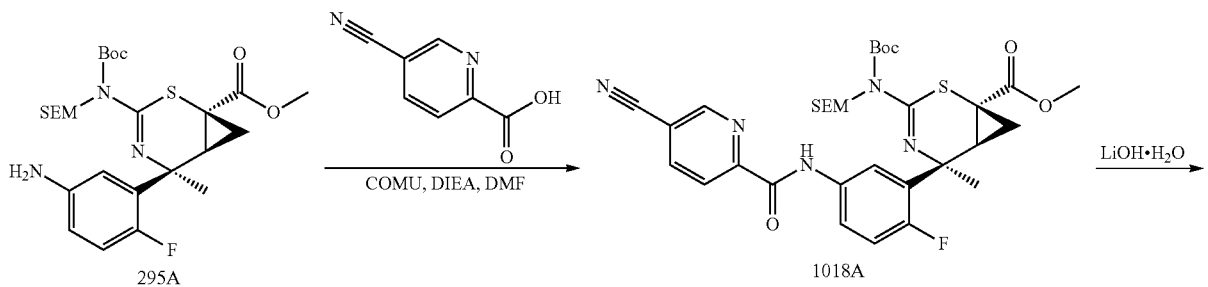

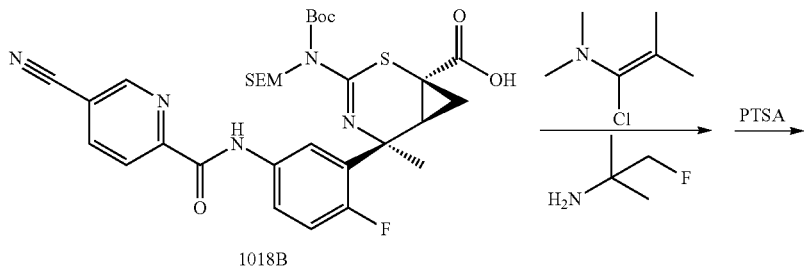

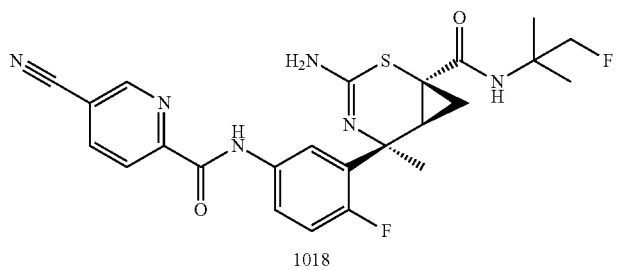

Preparation of (1S,5S,6S)-methyl 3-((tert-butoxycarbonyl)((2-(trimethylsilyl)ethoxy)methyl)amino)-5-(5-(5-cyanopicolinamido)-2-fluorophenyl)-5-methyl-2-thia-4-azabicyclo[4.1.0]hept-3-ene-1-carboxylate (1018A). The title compound (0.215 g, 0.321 mmol, 79% yield) was prepared according to the procedure described for 1005A using (1S,5S,6S)-methyl 5-(5-amino-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylate, 295A, (0.218 g, 0.404 mmol) and 5-cyano-2-pyridinecarboxylic acid (0.072 g, 0.485 mmol). LCMS (ESI⁺) m/z=670.2 (M+H).

Preparation of (1S,5S,6S)-3-((tert-butoxycarbonyl)((2-(trimethylsilyl)ethoxy)methyl)amino)-5-(5-(5-cyanopicolinamido)-2-fluorophenyl)-5-methyl-2-thia-4-azabicyclo[4.1.0]hept-3-ene-1-carboxylic acid (1018B). The title compound (0.181 g, 0.276 mmol, 98% yield) was prepared according to the procedure for 221A using (1S,5S,6S)-methyl 3-((tert-butoxycarbonyl)((2-(trimethylsilyl)ethoxy)methyl)amino)-5-(5-(5-cyanopicolinamido)-2-fluorophenyl)-5-methyl-2-thia-4-azabicyclo[4.1.0]hept-3-ene-1-carboxylate, 1018A, (0.188 g, 0.281 mmol). LCMS (ESI⁺) m/z=656.2 (M+H).

Example 1018 (0.039 g, 0.078 mmol, 34% yield) was prepared according to the procedure for 998 using (1S,5S,6S)-3-((tert-butoxycarbonyl)((2-(trimethylsilyl)ethoxy)methyl)amino)-5-(5-(5-cyanopicolinamido)-2-fluorophenyl)-5-methyl-2-thia-4-azabicyclo[4.1.0]hept-3-ene-1-carboxylic acid, 1018B, (0.150 g, 0.229 mmol) and 2-fluoro-1,1-dimethyl-ethylamine hydrochloride (0.041 g, 0.320 mmol). LCMS (ESI⁺) m/z=499.2 (M+H). ¹H NMR (300 MHz, CHLOROFORM-d) δ: 9.76 (s, 1H), 8.87 (s, 1H), 8.41 (d, J=8.18 Hz, 1H), 8.20 (d, J=8.01 Hz, 1H), 7.79-7.88 (m, 1H), 7.54 (dd, J=2.63, 6.87 Hz, 1H), 7.07 (dd, J=8.92, 11.11 Hz, 1H), 6.44 (s, 1H), 4.29-4.66 (m, 4H), 2.16-2.27 (m, 1H), 1.78-1.95 (m, 4H), 1.33-1.47 (m, 6H), 0.74-0.99 (m, 1H). ¹⁹F NMR (282 MHz, CHLOROFORM-d) δ: −113.05 (s, 1F), −225.39 (s, 1F).

Example 1019

(1S,5S,6S)-3-amino-5-(5-(5-((S)-but-3-yn-2-yloxy)pyrazine-2-carboxamido)-2-fluorophenyl)-N-(1-fluoro-2-methylpropan-2-yl)-5-methyl-2-thia-4-azabicyclo[4.1.0]hept-3-ene-1-carboxamide

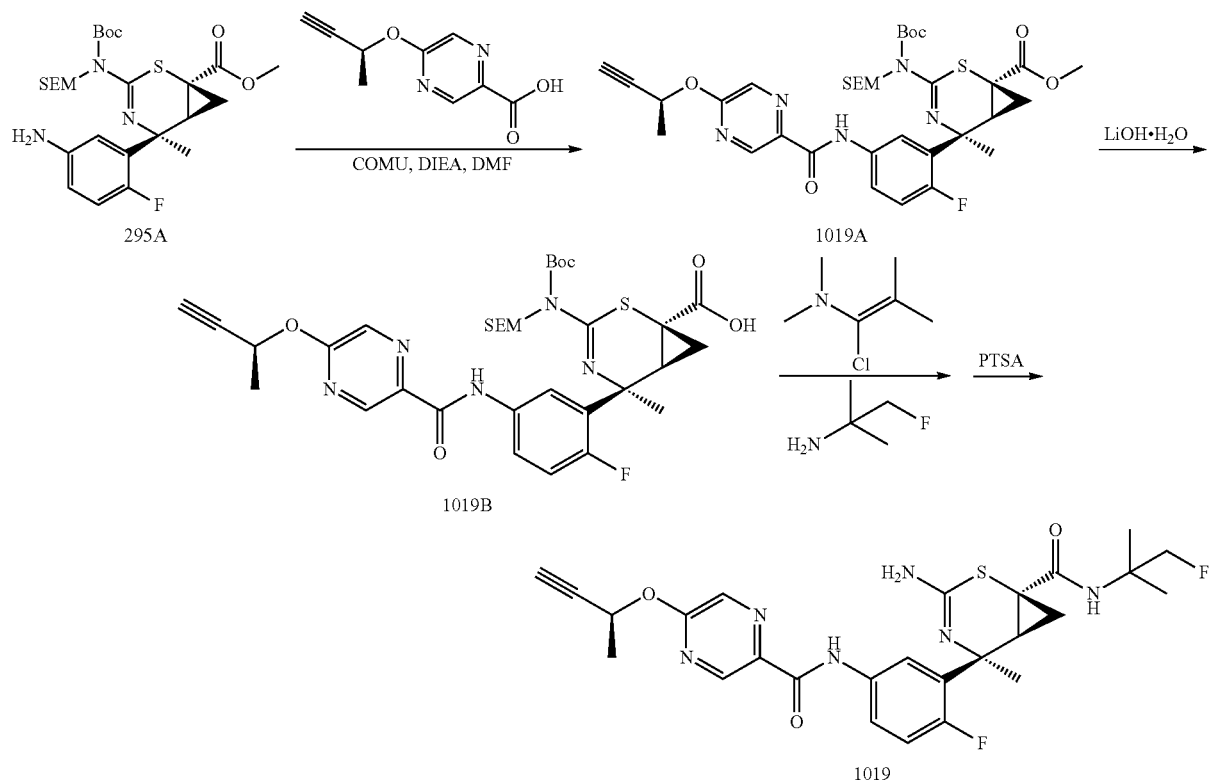

Preparation of (1S,5S,6S)-methyl 5-(5-(5-((S)-but-3-yn-2-yloxy)pyrazine-2-carboxamido)-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylate (1019A). The title compound (0.188 g, 0.263 mmol, 71% yield) was prepared according to the procedure described for 1005A using (1S,5S,6S)-methyl 5-(5-amino-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylate, 295A, (0.200 g, 0.371 mmol) and (S)-5-(but-3-yn-2-yloxy)pyrazine-2-carboxylic acid, 290, (0.085 g, 0.445 mmol). LCMS (ESI⁺) m/z=714.2 (M+H).

Preparation of (1S,5S,6S)-5-(5-(5-((S)-but-3-yn-2-yloxy)pyrazine-2-carboxamido)-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylic acid (1019B). The title compound 1019B (0.181 g, 0.259 mmol, 98% yield) was prepared according to the procedure for 221A using (1S,5S,6S)-methyl 5-(5-(5-((S)-but-3-yn-2- yloxy)pyrazine-2-carboxamido)-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylate, 1019A, (0.188 g, 0.263 mmol). LCMS (ESI⁺) m/z=700.3 (M+H).

Example 1019 (0.062 g, 0.114 mmol, 44% yield) was prepared according to the procedure for 998 using (1S,5S,6S)-5-(5-(5-((S)-but-3-yn-2-yloxy)pyrazine-2-carboxamido)-2-fluorophenyl)-3-((tert-butoxycarbonyl)((2-(trimethylsilyl)ethoxy)methyl)amino)-5-methyl-2-thia-4-azabicyclo[4.1.0]hept-3-ene-1-carboxylic acid, 1019B, (0.180 g, 0.257 mmol) and 2-fluoro-1,1-dimethyl-ethylamine hydrochloride (0.049 g, 0.386 mmol). LCMS (ESI⁺) m/z=543.2 (M+H). ¹H NMR (300 MHz, CHLOROFORM-d) δ: 9.40 (s, 1H), 9.02 (s, 1H), 8.15 (s, 1H), 7.78-7.86 (m, 1H), 7.46 (dd, J=2.34, 6.72 Hz, 1H), 7.05 (dd, J=8.99, 10.89 Hz, 1H), 6.47 (s, 1H), 5.85 (q, J=6.43 Hz, 1H), 4.45-4.62 (m, 1H), 4.26-4.44 (m, 2H), 2.51 (s, 1H), 2.21 (t, J=8.62 Hz, 1H), 1.92 (dd, J=4.97, 9.65 Hz, 1H), 1.86 (s, 3H), 1.72 (d, J=6.72 Hz, 3H), 1.39 (s, 6H), 1.08-1.24 (m, 1H), 0.75-0.88 (m, 1H). ¹⁹F NMR (282 MHz, CHLOROFORM-d) δ: -113.79 (s, 1F), -225.37 (s, 1F).

Example 1020

N-(3-((1S,5S,6S)-3-amino-1-(methoxymethyl)-5-methyl-2-thia-4-azabicyclo[4.1.0]hept-3-en-5-yl)-4,5-difluorophenyl)-5-(cyclobutylmethoxy)pyrazine-2-carboxamide

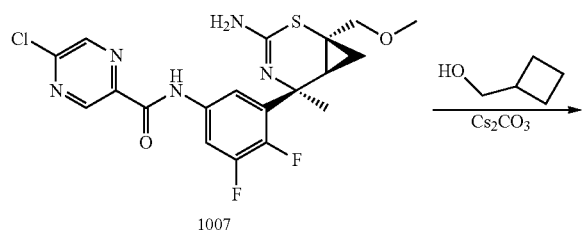

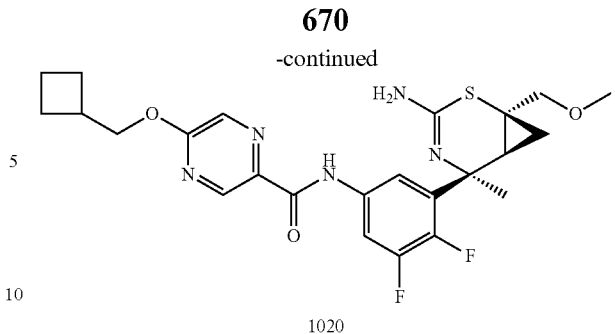

To a mixture of N-(3-((1S,5S,6S)-3-amino-1-(methoxymethyl)-5-methyl-2-thia-4-azabicyclo[4.1.0]hept-3-en-5-yl)-4,5-difluorophenyl)-5-chloropyrazine-2-carboxamide (Example 1007) (0.022 g, 0.047 mmol) and cyclobutanemethanol (0.061 mL, 0.711 mmol) in THF (0.5 mL) was added cesium carbonate (0.046 g, 0.142 mmol). The reaction mixture was then heated at 50° C. for 2 h. The resulting mixture was then diluted with water and extracted with EtOAc. The organic layer was washed with brine, dried over Na₂SO₄, filtered, and concentrated in vacuo. The residue was purified by silica gel chromatography (0-100% EtOAc in DCM) to afford Example 1020 (20 mg, 86% yield) as an off-white solid. LC/MS (ESI⁺) m/z=504 (M+H)⁺. ¹H NMR (400 MHz, CHLOROFORM-d) δ 9.51 (s, 1H), 8.97 (d, J=1.17 Hz, 1H), 8.12 (d, J=0.98 Hz, 1H), 8.05 (ddd, J=2.54, 6.75, 11.84 Hz, 1H), 7.35-7.42 (m, 1H), 4.40 (d, J=6.85 Hz, 2H), 3.66 (d, J=10.56 Hz, 1H), 3.41 (s, 3H), 3.35 (d, J=10.56 Hz, 1H), 2.81 (m, 1H), 2.10-2.22 (m, 2H), 1.84-2.05 (m, 4H), 1.76-1.82 (m, 1H), 1.72 (s, 3H), 0.90 (dd, J=5.77, 9.49 Hz, 1H), 0.77-0.83 (m, 1H).

Using procedures analogous or similar to the procedures described above for Example 1020, the appropriate alcohol and N-(3-((1S,5S,6S)-3-amino-1-(methoxymethyl)-5-methyl-2-thia-4-azabicyclo[4.1.0]hept-3-en-5-yl)-4,5-difluorophenyl)-5-chloropyrazine-2-carboxamide (Example 1007) were reacted to provide the 39 examples listed in Table 12 and Table 12'.

TABLE 12

| Ex. No. | Chemical Structure | Observed [M + H]⁺ |
|---|---|---|
| 1013 | 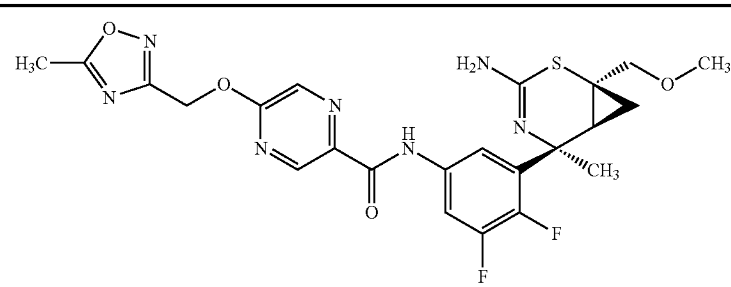 | 532 |
| 1021 | 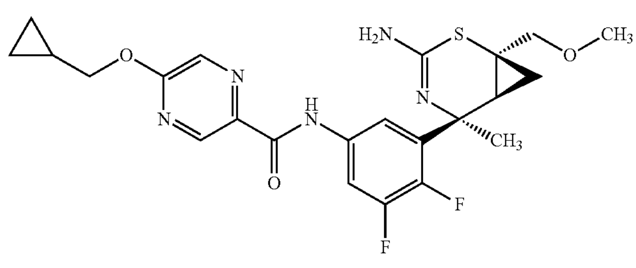 [SMILES: COC[C@]12C[C@H]1[C@@](C)(c1cc(NC(=O)c3cnc(OCC4CC4)cn3)cc(F)c1F)N=C(N)S2] | 490 |

TABLE 12-continued

| Ex. No. | Chemical Structure | Observed [M + H]+ |
|---|---|---|
| 1022 | 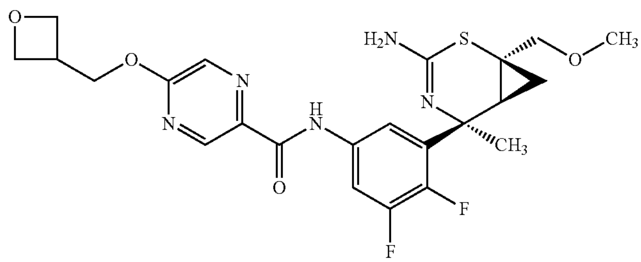 [SMILES: COC[C@]12C[C@H]1[C@@](C)(c1cc(NC(=O)c3cnc(OCC4COC4)cn3)cc(F)c1F)N=C(N)S2] | 506 |
| 1023 | 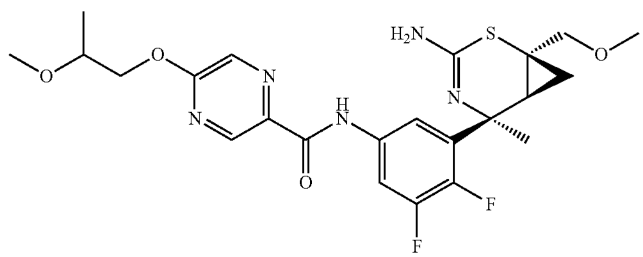 | 508 |
| 1025 | 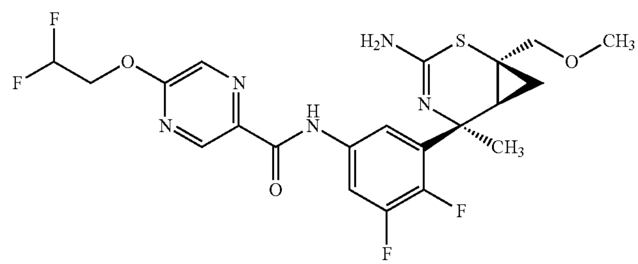 [SMILES: COC[C@]12C[C@H]1[C@@](C)(c1cc(NC(=O)c3cnc(OCC(F)F)cn3)cc(F)c1F)N=C(N)S2] | 500 |
| 1026 | 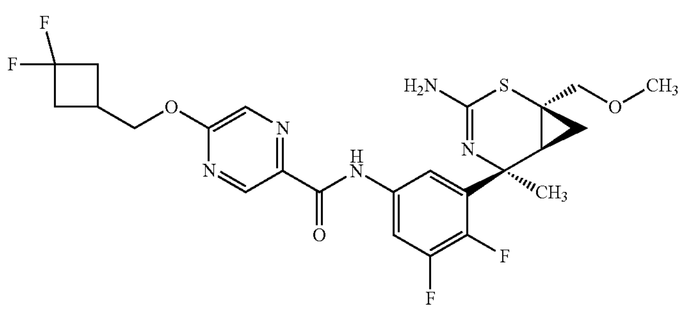 [SMILES: COC[C@]12C[C@H]1[C@@](C)(c1cc(NC(=O)c3cnc(OCC4CC(F)(F)C4)cn3)cc(F)c1F)N=C(N)S2] | 540 |
| 1027 | 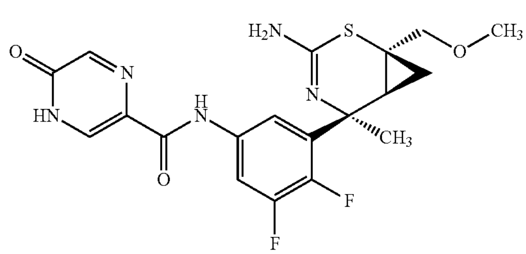 [SMILES: COC[C@]12C[C@H]1[C@@](C)(c1cc(NC(=O)c3c[nH]c(=O)cn3)cc(F)c1F)N=C(N)S2] | 436 |

TABLE 12-continued

| Ex. No. | Chemical Structure | Observed [M + H]+ |
|---|---|---|
| 1028 | 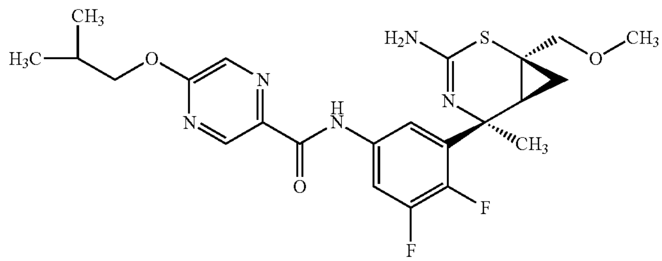 [SMILES: COC[C@]12C[C@H]1[C@@](C)(c1cc(NC(=O)c3cnc(OCC(C)C)cn3)cc(F)c1F)N=C(N)S2] | 492 |
| 1029 | 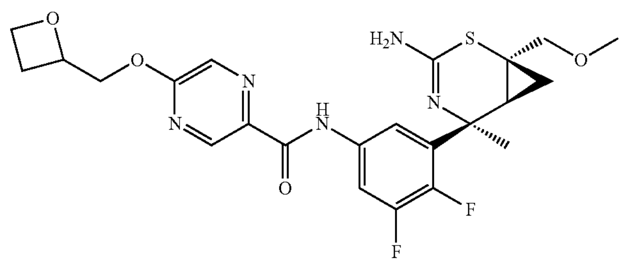 [SMILES: COC[C@]12C[C@H]1[C@@](C)(c1cc(NC(=O)c3cnc(OCC4CCO4)cn3)cc(F)c1F)N=C(N)S2] | 506 |
| 1030 | 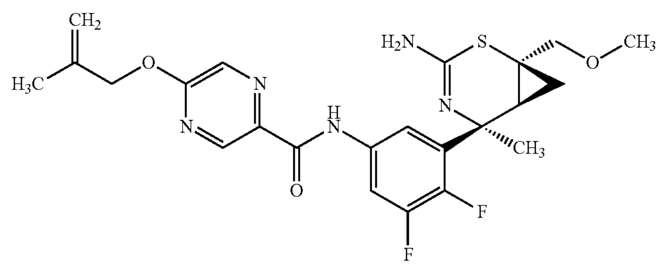 [SMILES: C=C(C)COc1cnc(C(=O)Nc2cc(F)c(F)c([C@@]3(C)N=C(N)S[C@@]4(COC)C[C@H]43)c2)cn1] | 490 |
| 1031 | 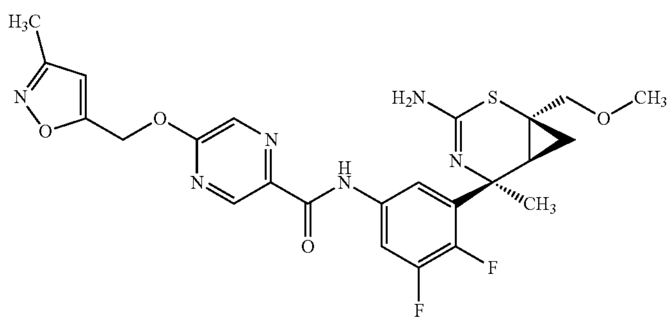 [SMILES: COC[C@]12C[C@H]1[C@@](C)(c1cc(NC(=O)c3cnc(OCc4cc(C)no4)cn3)cc(F)c1F)N=C(N)S2] | 531 |
| 1032 | 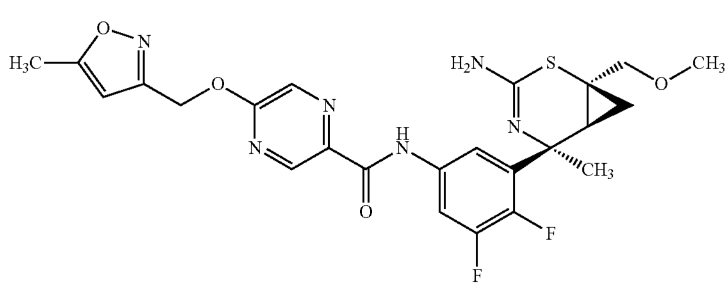 | 531 |

TABLE 12-continued

| Ex. No. | Chemical Structure | Observed [M + H]+ |
|---|---|---|
| 1033 | 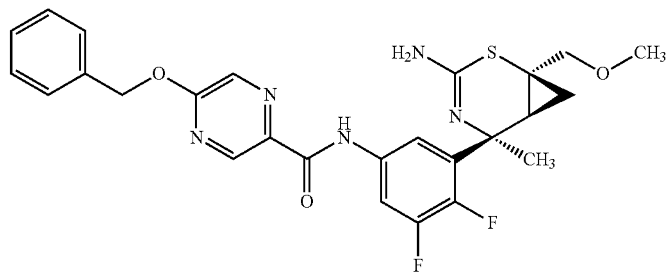 [SMILES: COC[C@]12C[C@H]1[C@@](C)(c1cc(NC(=O)c3cnc(OCc4ccccc4)cn3)cc(F)c1F)N=C(N)S2] | 526 |
| 1034 | 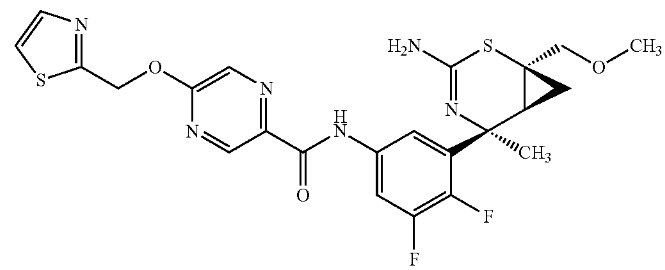 [SMILES: COC[C@]12C[C@H]1[C@@](C)(c1cc(NC(=O)c3cnc(OCc4nccs4)cn3)cc(F)c1F)N=C(N)S2] | 533 |
| 1035 | 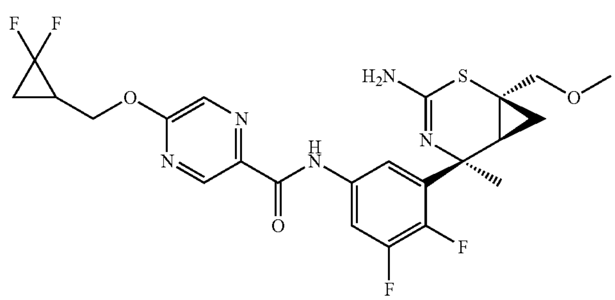 [SMILES: COC[C@]12C[C@H]1[C@@](C)(c1cc(NC(=O)c3cnc(OCC4CC4(F)F)cn3)cc(F)c1F)N=C(N)S2] | 526 |
| 1036 | 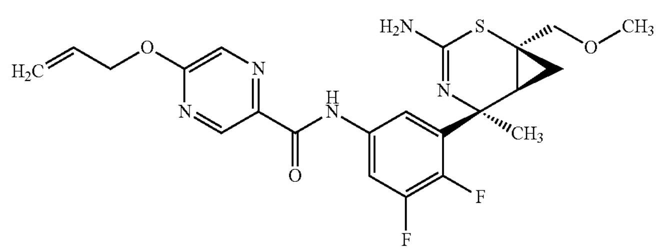 [SMILES: C=CCOc1cnc(C(=O)Nc2cc(F)c(F)c([C@@]3(C)N=C(N)S[C@@]4(COC)C[C@H]43)c2)cn1] | 476 |
| 1037 | 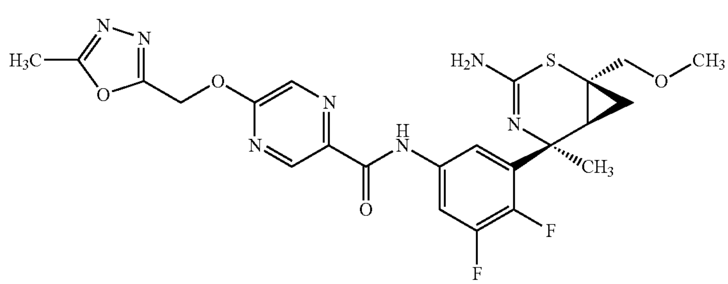 | 532 |

TABLE 12-continued

| Ex. No. | Chemical Structure | Observed [M + H]+ |
|---|---|---|
| 1038 | 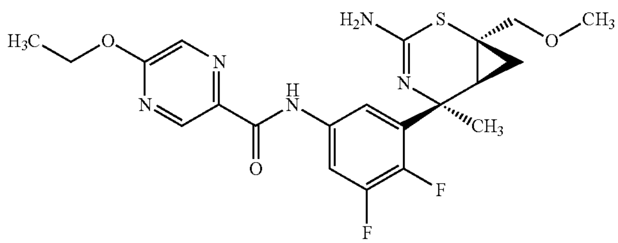 [SMILES: CCOc1cnc(C(=O)Nc2cc(F)c(F)c([C@@]3(C)N=C(N)S[C@@]4(COC)C[C@H]43)c2)cn1] | 464 |
| 1047 | 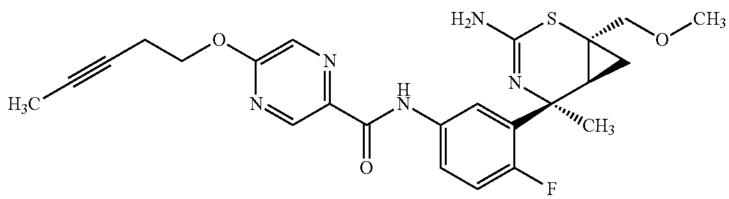 [SMILES: CC#CCCOc1cnc(C(=O)Nc2ccc(F)c([C@@]3(C)N=C(N)S[C@@]4(COC)C[C@H]43)c2)cn1] | 484 |
| 1048 | 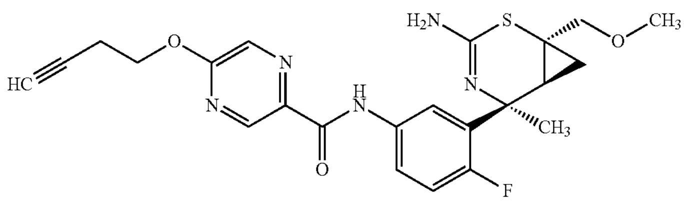 [SMILES: C#CCCOc1cnc(C(=O)Nc2ccc(F)c([C@@]3(C)N=C(N)S[C@@]4(COC)C[C@H]43)c2)cn1] | 470 |
| 1049 | 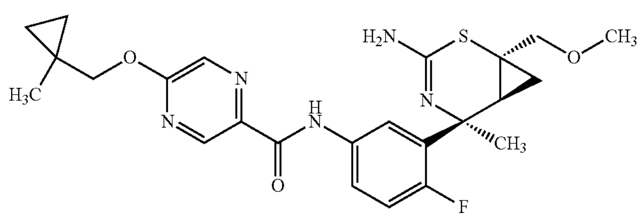 [SMILES: COC[C@]12C[C@H]1[C@@](C)(c1cc(NC(=O)c3cnc(OCC4(C)CC4)cn3)ccc1F)N=C(N)S2] | 486 |
| 1050 | 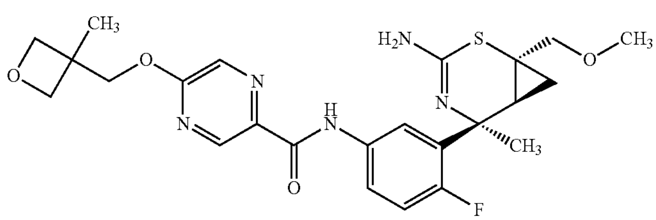 [SMILES: COC[C@]12C[C@H]1[C@@](C)(c1cc(NC(=O)c3cnc(OCC4(C)COC4)cn3)ccc1F)N=C(N)S2] | 502 |
| 1051 | Mixed | 472 |
| 1052 | 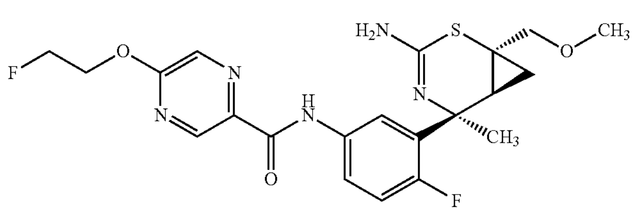 [SMILES: COC[C@]12C[C@H]1[C@@](C)(c1cc(NC(=O)c3cnc(OCCF)cn3)ccc1F)N=C(N)S2] | 464 |

TABLE 12-continued

| Ex. No. | Chemical Structure | Observed [M + H]+ |
|---|---|---|
| 1053 | 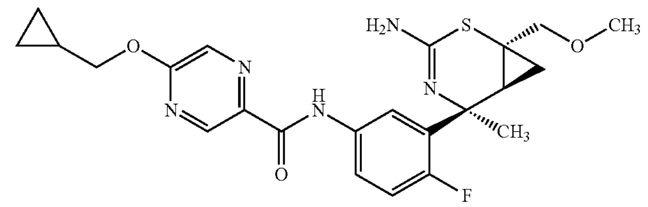 [SMILES: COC[C@]12C[C@H]1[C@@](C)(c1cc(NC(=O)c3cnc(OCC4CC4)cn3)ccc1F)N=C(N)S2] | 472 |
| 1054 | 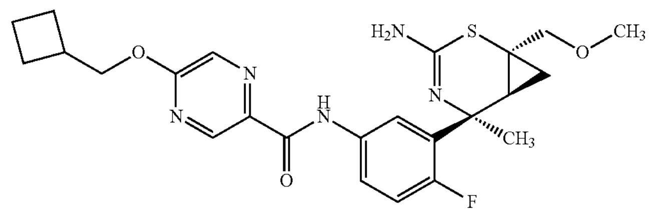 [SMILES: COC[C@]12C[C@H]1[C@@](C)(c1cc(NC(=O)c3cnc(OCC4CCC4)cn3)ccc1F)N=C(N)S2] | 486 |
| 1055 | 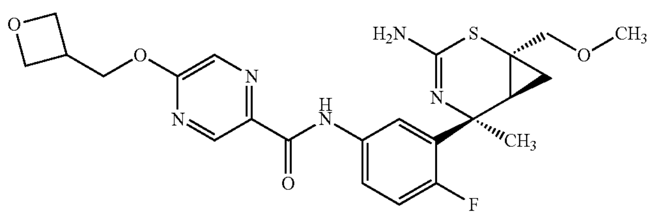 [SMILES: COC[C@]12C[C@H]1[C@@](C)(c1cc(NC(=O)c3cnc(OCC4COC4)cn3)ccc1F)N=C(N)S2] | 488 |
| 1056 | 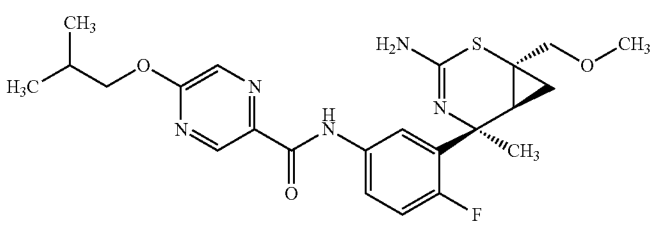 [SMILES: COC[C@]12C[C@H]1[C@@](C)(c1cc(NC(=O)c3cnc(OCC(C)C)cn3)ccc1F)N=C(N)S2] | 474 |
| 1057 | 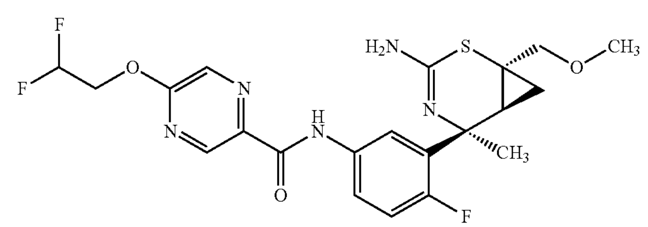 [SMILES: COC[C@]12C[C@H]1[C@@](C)(c1cc(NC(=O)c3cnc(OCC(F)F)cn3)ccc1F)N=C(N)S2] | 482 |
| 1058 | 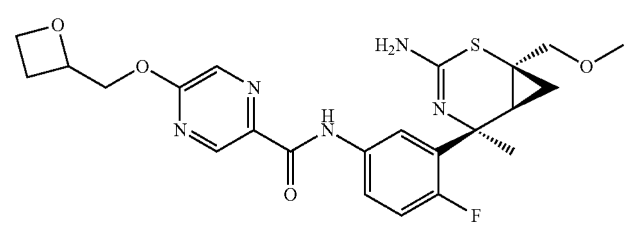 [SMILES: COC[C@]12C[C@H]1[C@@](C)(c1cc(NC(=O)c3cnc(OCC4CCO4)cn3)ccc1F)N=C(N)S2] | 488 |
| 1059 | 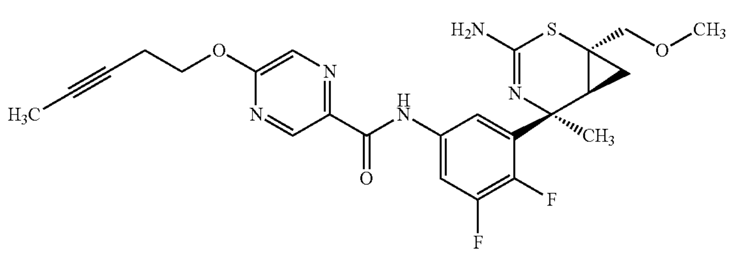 [SMILES: CC#CCCOc1cnc(C(=O)Nc2cc(F)c(F)c([C@@]3(C)N=C(N)S[C@@]4(COC)C[C@H]43)c2)cn1] | 502 |

TABLE 12-continued
| Ex. No. | Chemical Structure | Observed [M + H]+ |
|---|---|---|
| 1060 | 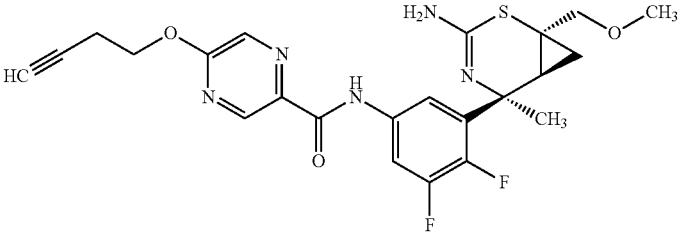 [SMILES: C#CCCOc1cnc(C(=O)Nc2cc(F)c(F)c([C@@]3(C)N=C(N)S[C@@]4(COC)C[C@H]43)c2)cn1] | 488 |
| 1061 | 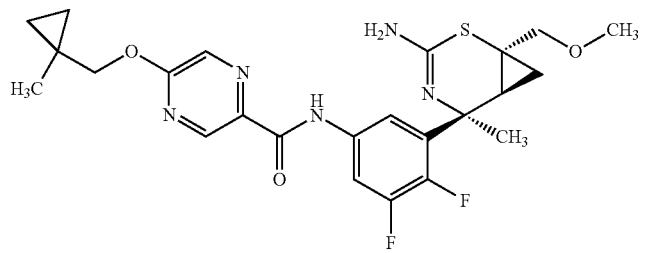 [SMILES: COC[C@]12C[C@H]1[C@@](C)(c1cc(NC(=O)c3cnc(OCC4(C)CC4)cn3)cc(F)c1F)N=C(N)S2] | 504 |
| 1062 | 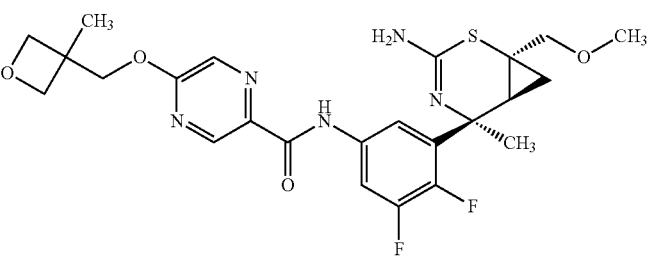 [SMILES: COC[C@]12C[C@H]1[C@@](C)(c1cc(NC(=O)c3cnc(OCC4(C)COC4)cn3)cc(F)c1F)N=C(N)S2] | 520 |
| 1063 | 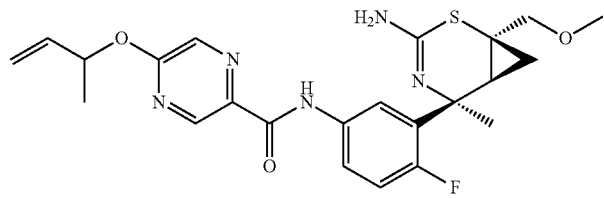 [SMILES: C=CC(C)Oc1cnc(C(=O)Nc2ccc(F)c([C@@]3(C)N=C(N)S[C@@]4(COC)C[C@H]43)c2)cn1] | 490 |
| 1064 | 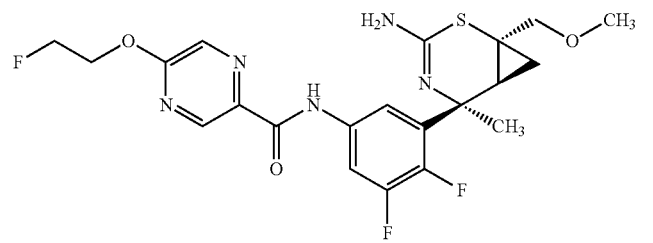 [SMILES: COC[C@]12C[C@H]1[C@@](C)(c1cc(NC(=O)c3cnc(OCCF)cn3)cc(F)c1F)N=C(N)S2] | 482 |
| 1067 | 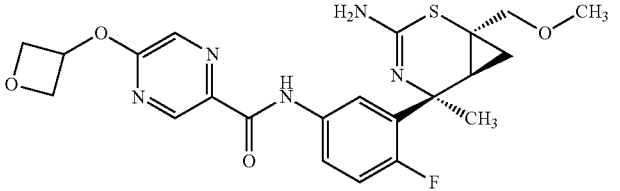 [SMILES: COC[C@]12C[C@H]1[C@@](C)(c1cc(NC(=O)c3cnc(OC4COC4)cn3)ccc1F)N=C(N)S2] | 474 |

TABLE 12-continued

| Ex. No. | Chemical Structure | Observed [M + H]+ |
|---|---|---|
| 1068 | (structure) | 492 |
| 1069 | (structure) | 506 |

TABLE 12'

| Ex. No. | ¹H-NMR | Chemical Name |
|---|---|---|
| 1013 | ¹H NMR (400 MHz, CHLOROFORM-d) δ 9.51 (s, 1H), 9.02 (d, J = 1.17 Hz, 1H), 8.27 (d, J = 1.17 Hz, 1H), 8.05 (ddd, J = 2.74, 6.80, 11.79 Hz, 1H), 7.40 (dd, J = 2.54, 5.28 Hz, 1H), 5.59 (s, 2H), 3.66 (d, J = 10.76 Hz, 1H), 3.62-3.71 (m, 1H), 3.41 (s, 3H), 3.35 (d, J = 10.56 Hz, 1H), 2.64 (s, 3H), 1.76-1.84 (m, 1H), 1.72 (s, 3H), 0.89 (dd, J = 5.87, 9.39 Hz, 1H), 0.76-0.84 (m, 1H), 0.76-0.84 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-((5-methyl-1,2,4-oxadiazol-3-yl)methoxy)-2-pyrazinecarboxamide |
| 1021 | ¹H NMR (400 MHz, CHLOROFORM-d) δ 9.51 (s, 1H), 8.96 (d, J = 1.17 Hz, 1H), 8.14 (d, J = 1.17 Hz, 1H), 8.05 (ddd, J = 2.74, 6.85, 11.93 Hz, 1H), 7.40 (td, J = 2.37, 5.23 Hz, 1H), 4.27 (d, J = 7.24 Hz, 2H), 3.66 (d, J = 10.56 Hz, 1H), 3.41 (s, 3H), 3.35 (d, J = 10.56 Hz, 1H), 1.76-1.83 (m, 1H), 1.72 (s, 3H), 1.27-1.38 (m, 1H), 0.89 (dd, J = 5.87, 9.39 Hz, 1H), 0.75-0.83 (m, 1H), 0.62-0.70 (m, 2H), 0.36-0.44 (m, 2H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-(cyclopropylmethoxy)-2-pyrazinecarboxamide |
| 1022 | ¹H NMR (400 MHz, CHLOROFORM-d) δ 9.50 (s, 1H), 8.98 (d, J = 1.37 Hz, 1H), 8.15 (d, J = 1.37 Hz, 1H), 8.04 (ddd, J = 2.74, 6.80, 11.79 Hz, 1H), 7.36-7.45 (m, 1H), 4.90 (dd, J = 6.26, 7.82 Hz, 2H), 4.67 (d, J = 6.65 Hz, 2H), 4.59 (t, J = 6.06 Hz, 2H), 3.66 (d, J = 10.56 Hz, 1H), 3.45-3.56 (m, 1H), 3.41 (s, 3H), 3.35 (d, J = 10.76 Hz, 1H), 1.76-1.82 (m, 1H), 1.72 (s, 3H), 0.90 (dd, J = 5.77, 9.49 Hz, 1H), 0.75-0.83 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-(3-oxetanylmethoxy)-2-pyrazinecarboxamide |
| 1023 | ¹H NMR (400 MHz, CHLOROFORM-d) δ 9.51 (s, 1H), 8.97 (d, J = 0.98 Hz, 1H), 8.18 (d, J = 0.78 Hz, 1H), 8.05 (ddd, J = 2.64, 6.80, 11.69 Hz, 1H), 7.33-7.45 (m, 1H), 4.34-4.51 (m, 2H), 3.72-3.83 (m, 1H), 3.66 (d, J = 10.56 Hz, 1H), 3.44 (s, 3H), 3.41 (s, 3H), 3.35 (d, J = 10.56 Hz, 1H), 1.76-1.82 (m, 1H), 1.72 (s, 3H), 1.29 (d, J = 6.46 Hz, 3H), 0.89 (dd, J = 5.87, 9.39 Hz, 1H), 0.76-0.84 (m, 1H). | N-(3-((1S,5S,6S)-3-amino-1-(methoxymethyl)-5-methyl-2-thia-4-azabicyclo[4.1.0]hept-3-en-5-yl)-4,5-difluorophenyl)-5-(2-methoxypropoxy)pyrazine-2-carboxamide |
| 1025 | ¹H NMR (400 MHz, CHLOROFORM-d) δ 9.50 (s, 1H), 9.00 (d, J = 1.17 Hz, 1H), 8.24 (d, J = 1.17 Hz, 1H), 8.04 (ddd, J = 2.74, 6.80, 11.79 Hz, 1H), 7.41 (dd, J = 2.25, 5.38 Hz, 1H), 5.93-6.37 (m, 1H), 4.66 (dt, J = 3.91, 13.40 Hz, 2H), 3.66 (d, J = 10.56 Hz, 1H), 3.41 (s, 3H), 3.35 (d, J = 10.76 Hz, 1H), 1.75-1.84 (m, 1H), 1.72 (s, 3H), 0.89 (dd, J = 5.87, 9.39 Hz, 1H), 0.80 (t, J = 6.16 Hz, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-(2,2-difluoroethoxy)-2-pyrazinecarboxamide |
| 1026 | ¹H NMR (400 MHz, CHLOROFORM-d) δ 9.50 (s, 1H), 8.98 (d, J = 0.78 Hz, 1H), 8.14 (d, J = 0.78 Hz, 1H), 8.04 (ddd, J = 2.64, 6.80, 11.69 Hz, 1H), 7.36-7.48 (m, 1H), 4.48 (d, J = 6.46 Hz, 2H), 3.66 (d, J = 10.76 Hz, 1H), 3.41 (s, 3H), 3.35 (d, J = 10.76 Hz, 1H), 2.62-2.86 (m, 3H), 2.41-2.57 (m, 2H), 1.76-1.83 (m, 1H), 1.72 (s, 3H), 0.90 (dd, J = 5.77, 9.29 Hz, 1H), 0.74-0.83 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-((3,3-difluorocyclobutyl)methoxy)-2-pyrazinecarboxamide |

TABLE 12'-continued

| Ex. No. | ¹H-NMR | Chemical Name |
|---|---|---|
| 1027 | ¹H NMR (400 MHz, CHLOROFORM-d) δ 9.27 (br. s., 1H), 7.90-8.57 (m, 4H), 7.55-7.74 (m, 2H), 7.23 (br. s., 1H), 3.44 (d, J = 9.78 Hz, 1H), 3.33 (s, 4H), 1.97 (br. s., 3H), 1.82 (d, J = 7.04 Hz, 1H), 1.16-1.50 (m, 1H), 0.80 (br. s., 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-oxo-4,5-dihydro-2-pyrazinecarboxamide |
| 1028 | ¹H NMR (400 MHz, CHLOROFORM-d) δ 9.51 (s, 1H), 8.97 (d, J = 0.98 Hz, 1H), 8.13 (d, J = 1.17 Hz, 1H), 8.05 (ddd, J = 2.74, 6.80, 11.79 Hz, 1H), 7.40 (dd, J = 2.45, 5.18 Hz, 1H), 4.20 (d, J = 6.65 Hz, 2H), 3.66 (d, J = 10.56 Hz, 1H), 3.41 (s, 3H), 3.35 (d, J = 10.76 Hz, 1H), 2.14 (quind, J = 6.67, 13.42 Hz, 1H), 1.76-1.82 (m, 1H), 1.72 (s, 3H), 1.05 (d, J = 6.85 Hz, 6H), 0.89 (dd, J = 5.87, 9.39 Hz, 1H), 0.77-0.84 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-(2-methylpropoxy)-2-pyrazinecarboxamide |
| 1029 | ¹H NMR (400 MHz, CHLOROFORM-d) δ 9.52 (s, 1H), 8.98 (d, J = 1.17 Hz, 1H), 8.22 (d, J = 1.17 Hz, 1H), 8.05 (ddd, J = 2.74, 6.65, 11.74 Hz, 1H), 7.41 (dd, J = 2.45, 5.18 Hz, 1H), 5.14-5.24 (m, 1H), 4.71-4.78 (m, 1H), 4.66 (td, J = 6.14, 9.05 Hz, 1H), 4.61 (d, J = 4.30 Hz, 2H), 3.66 (d, J = 10.56 Hz, 1H), 3.41 (s, 3H), 3.35 (d, J = 10.56 Hz, 1H), 2.75-2.88 (m, 1H), 2.65 (tdd, J = 7.04, 8.97, 11.17 Hz, 1H), 1.76-1.83 (m, 1H), 1.72 (s, 3H), 0.90 (dd, J = 5.87, 9.39 Hz, 1H), 0.76-0.84 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-(oxetan-2-ylmethoxy)pyrazine-2-carboxamide |
| 1030 | ¹H NMR (400 MHz, CHLOROFORM-d) δ 9.51 (s, 1H), 8.99 (d, J = 1.17 Hz, 1H), 8.17 (d, J = 1.17 Hz, 1H), 8.05 (ddd, J = 2.74, 6.80, 11.79 Hz, 1H), 7.40 (dd, J = 2.25, 5.38 Hz, 1H), 4.97-5.14 (m, 2H), 4.86 (s, 2H), 3.66 (d, J = 10.56 Hz, 1H), 3.41 (s, 3H), 3.35 (d, J = 10.76 Hz, 1H), 1.86 (s, 3H), 1.76-1.83 (m, 1H), 1.72 (s, 3H), 0.89 (dd, J = 5.87, 9.39 Hz, 1H), 0.76-0.83 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-((2-methyl-2-propen-1-yl)oxy)-2-pyrazinecarboxamide |
| 1031 | ¹H NMR (400 MHz, CHLOROFORM-d) δ 9.50 (s, 1H), 8.94-9.09 (m, 1H), 8.21 (d, J = 1.17 Hz, 1H), 8.05 (ddd, J = 2.74, 6.85, 11.74 Hz, 1H), 7.40 (td, J = 2.27, 5.43 Hz, 1H), 6.24 (s, 1H), 5.54 (s, 2H), 3.66 (d, J = 10.56 Hz, 1H), 3.41 (s, 3H), 3.35 (d, J = 10.56 Hz, 1H), 2.32 (s, 3H), 1.79 (dt, J = 0.98, 8.02 Hz, 1H), 1.72 (d, J = 0.78 Hz, 3H), 0.85-0.93 (m, 1H), 0.76-0.82 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-((3-methyl-5-isoxazolyl)methoxy)-2-pyrazinecarboxamide |
| 1032 | ¹H NMR (400 MHz, CHLOROFORM-d) δ 9.50 (s, 1H), 9.02 (s, 1H), 8.20 (s, 1H), 8.05 (ddd, J = 2.64, 6.80, 11.69 Hz, 1H), 7.34-7.48 (m, 1H), 6.11 (s, 1H), 5.53 (s, 2H), 4.40 (br s, 2H), 3.66 (d, J = 10.76 Hz, 1H), 3.41 (s, 3H), 3.35 (d, J = 10.56 Hz, 1H), 2.45 (s, 3H), 1.76-1.83 (m, 1H), 1.72 (s, 3H), 0.89 (dd, J = 5.87, 9.39 Hz, 1H), 0.77-0.83 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-((5-methyl-3-isoxazolyl)methoxy)-2-pyrazinecarboxamide |
| 1033 | ¹H NMR (400 MHz, CHLOROFORM-d) δ 9.51 (s, 1H), 9.02 (d, J = 1.17 Hz, 1H), 8.18 (d, J = 1.17 Hz, 1H), 8.06 (ddd, J = 2.74, 6.80, 11.79 Hz, 1H), 7.45-7.50 (m, 2H), 7.34-7.44 (m, 4H), 5.49 (s, 2H), 3.66 (d, J = 10.76 Hz, 1H), 3.41 (s, 3H), 3.35 (d, J = 10.56 Hz, 1H), 1.76-1.83 (m, 1H), 1.72 (s, 3H), 0.89 (dd, J = 5.77, 9.49 Hz, 1H), 0.77-0.83 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-(benzyloxy)-2-pyrazinecarboxamide |
| 1034 | ¹H NMR (400 MHz, CHLOROFORM-d) δ 9.51 (s, 1H), 9.04 (d, J = 1.17 Hz, 1H), 8.26 (d, J = 1.37 Hz, 1H), 8.05 (ddd, J = 2.74, 6.80, 11.79 Hz, 1H), 7.84 (d, J = 3.33 Hz, 1H), 7.35-7.44 (m, 2H), 5.80 (s, 2H), 3.66 (d, J = 10.76 Hz, 1H), 3.41 (s, 3H), 3.35 (d, J = 10.56 Hz, 1H), 1.79 (ddd, J = 1.08, 6.75, 9.19 Hz, 1H), 1.72 (d, J = 0.78 Hz, 3H), 0.86-0.93 (m, 1H), 0.76-0.83 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-(1,3-thiazol-2-ylmethoxy)-2-pyrazinecarboxamide |
| 1035 | ¹H NMR (400 MHz, CHLOROFORM-d) ™ 9.51 (s, 1H), 8.98 (d, J = 1.37 Hz, 1H), 8.17 (d, J = 1.37 Hz, 1H), 8.05 (ddd, J = 2.74, 6.75, 11.83 Hz, 1H), 7.34-7.45 (m, 1H), 4.53-4.65 (m, 1H), 4.37-4.48 (m, 1H), 3.66 (d, J = 10.56 Hz, 1H), 3.41 (s, 3H), 3.35 (d, J = 10.76 Hz, 1H), 2.16 (qt, J = 7.63, 12.03 Hz, 1H), 1.79 (ddd, J = 1.17, 6.80, 9.24 Hz, 1H), 1.72 (d, J = 0.78 Hz, 3H), 1.54-1.67 (m, 1H), 1.33 (tdd, J = 3.86, 7.65, 16.90 Hz, 1H), 0.89 (dd, J = 5.87, 9.39 Hz, 1H), 0.76-0.83 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-((2,2-difluorocyclopropyl)methoxy)pyrazine-2-carboxamide |
| 1036 | ¹H NMR (400 MHz, CHLOROFORM-d) δ 9.53 (s, 1H), 8.98 (d, J = 1.37 Hz, 1H), 8.15 (d, J = 1.17 Hz, 1H), 8.05 (ddd, J = 2.74, 6.85, 11.74 Hz, 1H), 7.37 (dd, J = 2.45, 5.18 Hz, 1H), 6.02-6.17 (m, 1H), 5.45 (dd, J = 1.37, 17.21 Hz, 1H), 5.34 (dd, J = 1.17, 10.37 Hz, 1H), 4.95 (d, J = 5.67 Hz, 2H), 3.64 (d, J = 10.56 Hz, 1H), 3.41 (s, 3H), 3.35 (d, J = 10.76 Hz, 1H), 1.80 (dd, J = 7.43, 8.61 Hz, 1H), 1.75 (s, 3H), 0.94 (dd, J = 5.87, 9.39 Hz, 1H), 0.78-0.84 (m, 1H), 0.00-0.00 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-(2-propen-1-yloxy)-2-pyrazinecarboxamide |

TABLE 12'-continued

| Ex. No. | ¹H-NMR | Chemical Name |
|---|---|---|
| 1037 | ¹H NMR (400 MHz, CHLOROFORM-d) δ 9.51 (s, 1H), 9.03 (d, J = 1.37 Hz, 1H), 8.27 (d, J = 1.37 Hz, 1H), 8.06 (ddd, J = 2.74, 6.85, 11.74 Hz, 1H), 7.29-7.37 (m, 1H), 5.66 (s, 2H), 3.64 (d, J = 10.56 Hz, 1H), 3.41 (s, 3H), 3.35 (d, J = 10.76 Hz, 1H), 2.58 (s, 3H), 1.77-1.82 (m, 1H), 1.75 (d, J = 0.78 Hz, 3H), 0.92-1.00 (m, 1H), 0.80 (t, J = 6.26 Hz, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-((5-methyl-1,3,4-oxadiazol-2-yl)methoxy)-2-pyrazinecarboxamide |
| 1038 | ¹H NMR (400 MHz, CHLOROFORM-d) δ 9.51 (s, 1H), 8.98 (d, J = 1.17 Hz, 1H), 8.11 (d, J = 1.17 Hz, 1H), 8.06 (ddd, J = 2.74, 6.80, 11.79 Hz, 1H), 7.39 (td, J = 2.40, 5.38 Hz, 1H), 4.49 (q, J = 7.04 Hz, 2H), 3.66 (d, J = 10.56 Hz, 1H), 3.41 (s, 3H), 3.35 (d, J = 10.76 Hz, 1H), 1.79 (ddd, J = 0.98, 7.38, 8.66 Hz, 1H), 1.72 (d, J = 0.78 Hz, 3H), 1.45 (t, J = 7.04 Hz, 3H), 0.89 (dd, J = 5.87, 9.39 Hz, 1H), 0.75-0.84 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-ethoxy-2-pyrazinecarboxamide |
| 1047 | ¹H NMR (500 MHz, DMSO-d6) δ 10.36 (s, 1H), 8.86 (s, 1H), 8.42 (s, 1H), 8.02 (dd, J = 2.59, 7.20 Hz, 1H), 7.64-7.86 (m, 1H), 7.13 (dd, J = 8.95, 11.87 Hz, 1H), 5.94 (br. s., 2H), 4.45 (t, J = 6.59 Hz, 2H), 3.55 (d, J = 10.96 Hz, 1H), 3.33-3.36 (m, 1H), 3.30 (br. s., 3H), 2.66 (d, J = 2.60 Hz, 2H), 1.75 (t, J = 2.21 Hz, 3H), 1.66 (t, J = 7.66 Hz, 1H), 1.59 (s, 3H), 0.84 (br. s., 1H), 0.61 (br. s., 1H) | N-(3-((1S,5S,6S)-3-amino-1-(methoxymethyl)-5-methyl-2-thia-4-azabicyclo[4.1.0]hept-3-en-5-yl)-4-fluorophenyl)-5-(3-pentyn-1-yloxy)-2-pyrazinecarboxamide |
| 1048 | ¹H NMR (500 MHz, DMSO-d₆) δ 10.36 (s, 1H), 8.87 (s, 1H), 8.42 (s, 1H), 8.02 (dd, J = 2.53, 7.20 Hz, 1H), 7.71-7.79 (m, 1H), 7.12 (dd, J = 8.86, 11.84 Hz, 1H), 5.94 (br. s., 2H), 4.49 (t, J = 6.46 Hz, 2H), 3.55 (d, J = 10.96 Hz, 1H), 3.34 (d, J = 10.96 Hz, 1H), 3.30 (br. s., 3H), 2.91 (t, J = 2.50 Hz, 1H), 2.72 (dt, J = 2.47, 6.39 Hz, 2H), 1.61-1.72 (m, 1H), 1.59 (s, 3H), 0.84 (dd, J = 5.03, 8.99 Hz, 1H), 0.61 (t, J = 5.55 Hz, 1H) | N-(3-((1S,5S,6S)-3-amino-1-(methoxymethyl)-5-methyl-2-thia-4-azabicyclo[4.1.0]hept-3-en-5-yl)-4-fluorophenyl)-5-(3-butyn-1-yloxy)-2-pyrazinecarboxamide |
| 1049 | ¹H NMR (500 MHz, DMSO-d6) δ 10.34 (s, 1H), 8.83 (s, 1H), 8.43 (s, 1H), 8.02 (dd, J = 2.50, 7.23 Hz, 1H), 7.67-7.86 (m, 1H), 7.12 (dd, J = 8.82, 11.87 Hz, 1H), 5.94 (br. s., 2H), 4.22 (s, 2H), 3.55 (d, J = 10.90 Hz, 1H), 3.34 (d, J = 11.22 Hz, 1H), 3.30 (br. s., 3H), 1.62-1.69 (m, 1H), 1.59 (s, 3H), 1.14-1.25 (m, 3H), 0.84 (dd, J = 5.29, 9.24 Hz, 1H), 0.55-0.65 (m, 3H), 0.43 (s, 2H) | N-(3-((1S,5S,6S)-3-amino-1-(methoxymethyl)-5-methyl-2-thia-4-azabicyclo[4.1.0]hept-3-en-5-yl)-4-fluorophenyl)-5-((1-methylcyclopropyl)methoxy)-2-pyrazinecarboxamide |
| 1050 | ¹H NMR (500 MHz, DMSO-d6) δ 10.37 (s, 1H), 8.88 (s, 1H), 8.44 (s, 1H), 8.03 (dd, J = 2.56, 7.17 Hz, 1H), 7.74-7.80 (m, 1H), 7.12 (dd, J = 8.89, 11.87 Hz, 1H), 5.94 (br. s., 2H), 4.47-4.58 (m, 4H), 4.33 (d, J = 5.84 Hz, 2H), 3.55 (d, J = 10.90 Hz, 1H), 3.33-3.36 (m, 1H), 3.30 (br. s., 3H), 1.62-1.69 (m, 1H), 1.59 (s, 3H), 1.39 (s, 3H), 0.84 (dd, J = 5.19, 9.15 Hz, 1H), 0.61 (t, J = 5.68 Hz, 1H) | N-(3-((1S,5S,6S)-3-amino-1-(methoxymethyl)-5-methyl-2-thia-4-azabicyclo[4.1.0]hept-3-en-5-yl)-4-fluorophenyl)-5-((3-methyl-3-oxetanyl)methoxy)-2-pyrazinecarboxamide |
| 1051 | ¹H NMR (500 MHz, DMSO-d6) δ 10.34 (s, 1H), 8.84 (s, 1H), 8.38 (s, 1H), 8.02 (d, J = 5.06 Hz, 1H), 7.76 (d, J = 8.43 Hz, 1H), 7.12 (dd, J = 8.79, 11.90 Hz, 1H), 5.97-6.07 (m, 1H), 5.94 (br. s., 2H), 5.70-5.78 (m, 1H), 5.34 (d, J = 17.32 Hz, 1H), 5.20 (d, J = 10.64 Hz, 1H), 3.55 (d, J = 10.90 Hz, 1H), 3.33-3.36 (m, 1H), 3.30 (br. s., 3H), 1.61-1.70 (m, 1H), 1.59 (s, 3H), 1.45 (d, J = 6.42 Hz, 3H), 0.83 (dd, J = 5.13, 9.28 Hz, 1H), 0.60 (t, J = 5.77 Hz, 1H) | N-(3-((1S,5S,6S)-3-amino-1-(methoxymethyl)-5-methyl-2-thia-4-azabicyclo[4.1.0]hept-3-en-5-yl)-4-fluorophenyl)-5-(((1R)-1-methyl-2-propen-1-yl)oxy)-2-pyrazinecarboxamide, N-(3-((1S,5S,6S)-3-amino-1-(methoxymethyl)-5-methyl-2-thia-4-azabicyclo[4.1.0]hept-3-en-5-yl)-4-fluorophenyl)-5-(((1S)-1-methyl-2-propen-1-yl)oxy)-2-pyrazinecarboxamide |
| 1052 | ¹H NMR (500 MHz, DMSO-d6) δ 10.37 (s, 1H), 8.87 (s, 1H), 8.47 (s, 1H), 8.02 (dd, J = 2.56, 7.10 Hz, 1H), 7.73-7.79 (m, 1H), 7.13 (dd, J = 8.79, 11.97 Hz, 1H), 5.94 (br. s., 2H), 4.83-4.90 (m, 1H), 4.73-4.80 (m, 1H), 4.67-4.73 (m, 1H), 4.62-4.67 (m, 1H), 3.55 (d, J = 10.83 Hz, 1H), 3.34 (d, J = 11.03 Hz, 1H), 3.30 (br. s., 3H), 1.61-1.68 (m, 1H), 1.59 (s, 3H), 0.84 (dd, J = 5.16, 9.24 Hz, 1H), 0.60 (t, J = 5.68 Hz, 1H) | N-(3-((1S,5S,6S)-3-amino-1-(methoxymethyl)-5-methyl-2-thia-4-azabicyclo[4.1.0]hept-3-en-5-yl)-4-fluorophenyl)-5-(2-fluoroethoxy)-2-pyrazinecarboxamide |
| 1053 | ¹H NMR (500 MHz, DMSO-d6) δ 10.34 (s, 1H), 8.84 (s, 1H), 8.41 (s, 1H), 7.95-8.10 (m, 1H), 7.68-7.84 (m, 1H), 7.12 (dd, J = 8.76, 11.87 Hz, 1H), 5.94 (br. s., 2H), 4.26 (d, J = 7.27 Hz, 2H), 3.55 (d, J = 10.90 Hz, 1H), 3.33-3.36 (m, 1H), 3.30 (br. s., 3H), 1.66 (t, J = 7.72 Hz, 1H), 1.59 (s, 3H), 1.30 (br. s., 1H), 0.84 (br. s., 1H), 0.56-0.65 (m, 3H), 0.39 (d, J = 4.41 Hz, 2H) | N-(3-((1S,5S,6S)-3-amino-1-(methoxymethyl)-5-methyl-2-thia-4-azabicyclo[4.1.0]hept-3-en-5-yl)-4-fluorophenyl)-5-(cyclopropylmethoxy)-2-pyrazinecarboxamide |
| 1054 | ¹H NMR (500 MHz, DMSO-d6) δ 10.36 (s, 1H), 8.86 (s, 1H), 8.42 (s, 1H), 8.02 (dd, J = 2.59, 7.20 Hz, 1H), 7.64-7.86 (m, 1H), 7.13 (dd, J = 8.95, 11.87 Hz, 1H), 5.94 (br. s., 2H), 4.45 (t, J = 6.59 Hz, 2H), 3.55 (d, J = 10.96 Hz, | N-(3-((1S,5S,6S)-3-amino-1-(methoxymethyl)-5-methyl-2-thia-4-azabicyclo[4.1.0]hept-3-en-5-yl)-4-fluorophenyl)-5- |

TABLE 12'-continued

| Ex. No. | ¹H-NMR | Chemical Name |
|---|---|---|
| | 1H), 3.33-3.36 (m, 1H), 3.30 (br. s., 3H), 2.66 (d, J = 2.60 Hz, 2H), 1.75 (t, J = 2.21 Hz, 3H), 1.66 (t, J = 7.66 Hz, 1H), 1.59 (s, 3H), 0.84 (br. s., 1H), 0.61 (br. s., 1H) | (cyclobutylmethoxy)-2-pyrazinecarboxamide |
| 1055 | ¹H NMR (500 MHz, DMSO-d6) δ 10.36 (s, 1H), 8.87 (s, 1H), 8.41 (s, 1H), 8.02 (d, J = 6.99 Hz, 1H), 7.76 (d, J = 8.21 Hz, 1H), 7.12 (dd, J = 8.82, 12.00 Hz, 1H), 5.94 (br. s., 2H), 4.72 (dd, J = 6.20, 7.75 Hz, 2H), 4.64 (d, J = 6.68 Hz, 2H), 4.47 (t, J = 6.07 Hz, 2H), 3.55 (d, J = 10.96 Hz, 1H), 3.46 (td, J = 6.86, 13.27 Hz, 1H), 3.33-3.36 (m, 1H), 3.30 (br. s., 3H), 1.63-1.68 (m, 1H), 1.59 (s, 3H), 0.81-0.88 (m, J = 4.80 Hz, 1H), 0.59-0.67 (m, 1H) | N-(3-((1S,5S,6S)-3-amino-1-(methoxymethyl)-5-methyl-2-thia-4-azabicyclo[4.1.0]hept-3-en-5-yl)-4-fluorophenyl)-5-(3-oxetanylmethoxy)-2-pyrazinecarboxamide |
| 1056 | ¹H NMR (500 MHz, DMSO-d6) δ 10.34 (s, 1H), 8.85 (s, 1H), 8.40 (s, 1H), 8.02 (dd, J = 2.34, 7.20 Hz, 1H), 7.73-7.79 (m, 1H), 7.12 (dd, J = 8.86, 11.97 Hz, 1H), 5.94 (br. s., 2H), 4.19 (d, J = 6.62 Hz, 2H), 3.55 (d, J = 10.96 Hz, 1H), 3.34 (d, J = 10.96 Hz, 1H), 3.29 (br. s., 3H), 2.10 (td, J = 6.60, 13.40 Hz, 1H), 1.61-1.71 (m, 1H), 1.59 (s, 3H), 1.00 (d, J = 6.68 Hz, 6H), 0.84 (dd, J = 4.93, 9.02 Hz, 1H), 0.61 (t, J = 5.84 Hz, 1H) | N-(3-((1S,5S,6S)-3-amino-1-(methoxymethyl)-5-methyl-2-thia-4-azabicyclo[4.1.0]hept-3-en-5-yl)-4-fluorophenyl)-5-(2-methylpropoxy)-2-pyrazinecarboxamide |
| 1057 | ¹H NMR (500 MHz, DMSO-d6) δ 10.41 (s, 1H), 8.89 (s, 1H), 8.53 (s, 1H), 8.01-8.08 (m, 1H), 7.74-7.79 (m, 1H), 7.13 (dd, J = 8.82, 11.94 Hz, 1H), 6.47 (t, J = 54.17 Hz, 1H), 5.94 (br. s., 2H), 4.74 (dt, J = 3.15, 15.07 Hz, 2H), 3.55 (d, J = 10.83 Hz, 1H), 3.33-3.36 (m, 1H), 3.30 (br. s., 3H), 1.61-1.68 (m, 1H), 1.59 (s, 3H), 0.84 (dd, J = 5.22, 9.12 Hz, 1H), 0.60 (t, J = 5.64 Hz, 1H) | N-(3-((1S,5S,6S)-3-amino-1-(methoxymethyl)-5-methyl-2-thia-4-azabicyclo[4.1.0]hept-3-en-5-yl)-4-fluorophenyl)-5-(2,2-difluoroethoxy)-2-pyrazinecarboxamide |
| 1058 | ¹H NMR (500 MHz, DMSO-d6) δ 10.37 (s, 1H), 8.86 (s, 1H), 8.46 (s, 1H), 7.98-8.05 (m, 1H), 8.02 (dd, J = 2.47, 7.27 Hz, 1H), 7.73-7.80 (m, 1H), 7.13 (dd, J = 8.92, 11.77 Hz, 1H), 5.95 (br. s., 2H), 5.08 (br. s., 1H), 4.46-4.63 (m, 4H), 3.55 (d, J = 10.96 Hz, 1H), 3.34 (d, J = 11.09 Hz, 1H), 3.30 (br. s., 3H), 2.73 (td, J = 8.35, 17.16 Hz, 1H), 2.54-2.62 (m, 1H), 1.64-1.70 (m, 1H), 1.59 (s, 3H), 0.84 (br. s., 1H), 0.61 (br. s., 1H) | N-(3-((1S,5S,6S)-3-amino-1-(methoxymethyl)-5-methyl-2-thia-4-azabicyclo[4.1.0]hept-3-en-5-yl)-4-fluorophenyl)-5-(oxetan-2-ylmethoxy)pyrazine-2-carboxamide |
| 1059 | ¹H NMR (500 MHz, DMSO-d6) δ 10.57 (s, 1H), 8.87 (s, 1H), 8.42 (s, 1H), 7.86-7.94 (m, 2H), 5.98 (br. s., 2H), 4.45 (t, J = 6.58 Hz, 2H), 3.56 (d, J = 10.90 Hz, 1H), 3.35 (d, J = 11.09 Hz, 1H), 3.30 (br. s., 3H), 2.66 (d, J = 2.53 Hz, 2H), 1.71-1.80 (m, 3H), 1.56-1.66 (m, 4H), 0.89 (dd, J = 5.32, 9.08 Hz, 1H), 0.64 (t, J = 5.81 Hz, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-(3-pentyn-1-yloxy)-2-pyrazinecarboxamide |
| 1060 | ¹H NMR (500 MHz, DMSO-d6) δ 10.58 (s, 1H), 8.87 (s, 1H), 8.43 (s, 1H), 7.84-7.93 (m, 2H), 5.97 (br. s., 2H), 4.50 (t, J = 6.46 Hz, 2H), 3.56 (d, J = 10.96 Hz, 1H), 3.34-3.37 (m, 1H), 3.30 (br. s., 3H), 2.91 (t, J = 2.43 Hz, 1H), 2.72 (dt, J = 2.59, 6.39 Hz, 2H), 1.58-1.65 (m, 4H), 0.89 (dd, J = 5.03, 9.18 Hz, 1H), 0.62-0.68 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-(3-butyn-1-yloxy)-2-pyrazinecarboxamide |
| 1061 | ¹H NMR (500 MHz, DMSO-d6) δ 10.56 (s, 1H), 8.84 (s, 1H), 8.43 (s, 1H), 7.87-7.93 (m, 2H), 5.98 (br. s., 2H), 4.22 (s, 2H), 3.56 (d, J = 10.96 Hz, 1H), 3.35 (d, J = 11.16 Hz, 1H), 3.30 (br. s., 3H), 1.60 (s, 4H), 1.20 (s, 3H), 0.89 (dd, J = 5.22, 9.18 Hz, 1H), 0.58-0.65 (m, 3H), 0.43 (s, 2H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-((1-methylcyclopropyl)methoxy)-2-pyrazinecarboxamide |
| 1062 | ¹H NMR (500 MHz, DMSO-d6) δ 10.59 (s, 1H), 8.88 (s, 1H), 8.45 (s, 1H), 7.84-7.94 (m, 2H), 5.98 (br. s., 2H), 4.46-4.59 (m, 4H), 4.33 (d, J = 5.90 Hz, 2H), 3.56 (d, J = 10.77 Hz, 1H), 3.33-3.39 (m, 1H), 3.30 (br. s., 3H), 1.57-1.66 (m, 4H), 1.39 (s, 3H), 0.89 (dd, J = 5.19, 9.21 Hz, 1H), 0.64 (t, J = 5.74 Hz, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-((3-methyl-3-oxetanyl)methoxy)-2-pyrazinecarboxamide |
| 1063 | ¹H NMR (500 MHz, DMSO-d6) δ 10.55 (s, 1H), 8.85 (s, 1H), 8.39 (s, 1H), 7.83-7.93 (m, 2H), 5.92-6.07 (m, 3H), 5.74 (t, J = 6.10 Hz, 1H), 5.34 (d, J = 17.32 Hz, 1H), 5.20 (d, J = 10.64 Hz, 1H), 3.56 (d, J = 10.96 Hz, 1H), 3.35 (d, J = 11.16 Hz, 1H), 3.30 (br. s., 3H), 1.57-1.66 (m, 4H), 1.45 (d, J = 6.42 Hz, 3H), 0.89 (dd, J = 5.29, 9.31 Hz, 1H), 0.64 (t, J = 5.81 Hz, 1H) | N-(3-((1S,5S,6S)-3-amino-1-(methoxymethyl)-5-methyl-2-thia-4-azabicyclo[4.1.0]hept-3-en-5-yl)-4-fluorophenyl)-5-(but-3-en-2-yloxy)pyrazine-2-carboxamide |
| 1064 | ¹H NMR (500 MHz, DMSO-d6) δ 10.59 (s, 1H), 8.87 (s, 1H), 8.47 (s, 1H), 7.85-7.93 (m, 2H), 5.97 (s, 2H), 4.83-4.89 (m, 1H), 4.74-4.81 (m, 1H), 4.67-4.73 (m, 1H), 4.61-4.67 (m, 1H), 3.56 (d, J = 10.96 Hz, 1H), 3.34-3.37 (m, 1H), 3.30 (br. s., 3H), 1.58-1.65 (m, 4H), 0.89 (dd, J = 5.13, 9.28 Hz, 1H), 0.62-0.68 (m, 1H) | N-(3-((1S,5S,6S)-3-amino-1-(methoxymethyl)-5-methyl-2-thia-4-azabicyclo[4.1.0]hept-3-en-5-yl)-4,5-difluorophenyl)-5-(2-fluoroethoxy)-2-pyrazinecarboxamide |

TABLE 12'-continued

| Ex. No. | ¹H-NMR | Chemical Name |
|---|---|---|
| 1067 | ¹H NMR (400 MHz, CHLOROFORM-d) δ 9.51 (s, 1H), 8.89-8.97 (m, 1H), 8.93 (d, J = 1.17 Hz, 1H), 8.23 (d, J = 1.17 Hz, 1H), 7.94 (td, J = 3.57, 8.31 Hz, 1H), 7.64 (dd, J = 2.74, 7.04 Hz, 1H), 7.08 (dd, J = 8.90, 11.64 Hz, 1H), 5.71 (quin, J = 5.72 Hz, 1H), 5.03 (t, J = 7.14 Hz, 2H), 4.77 (dd, J = 5.28, 7.82 Hz, 2H), 3.62 (d, J = 10.56 Hz, 1H), 3.41 (s, 3H), 3.36 (d, J = 10.76 Hz, 1H), 1.83 (dd, J = 7.14, 9.10 Hz, 1H), 1.79 (s, 3H), 0.99 (dd, J = 5.87, 9.39 Hz, 1H), 0.82 (t, J = 6.26 Hz, 1H). | N-(3-((1S,5S,6S)-3-amino-1-(methoxymethyl)-5-methyl-2-thia-4-azabicyclo[4.1.0]hept-3-en-5-yl)-4-fluorophenyl)-5-(oxetan-3-yloxy)pyrazine-2-carboxamide |
| 1068 | ¹H NMR (400 MHz, CHLOROFORM-d) δ 9.50 (s, 1H), 8.94 (d, J = 1.17 Hz, 1H), 8.23 (d, J = 1.37 Hz, 1H), 8.05 (ddd, J = 2.84, 6.75, 11.74 Hz, 1H), 7.39 (dd, J = 2.25, 5.58 Hz, 1H), 5.72 (quin, J = 5.67 Hz, 1H), 5.04 (t, J = 7.14 Hz, 2H), 4.77 (dd, J = 5.28, 8.22 Hz, 2H), 3.66 (d, J = 10.56 Hz, 1H), 3.41 (s, 3H), 3.35 (d, J = 10.56 Hz, 1H), 1.77-1.82 (m, 1H), 1.72 (s, 3H), 0.86-0.94 (m, 1H), 0.76-0.83 (m, 1H). | N-(3-((1S,5S,6S)-3-amino-1-(methoxymethyl)-5-methyl-2-thia-4-azabicyclo[4.1.0]hept-3-en-5-yl)-4,5-difluorophenyl)-5-(oxetan-3-yloxy)pyrazine-2-carboxamide |
| 1069 | ¹H NMR (400 MHz, CHLOROFORM-d) δ 9.51 (s, 1H), 8.98 (d, J = 1.37 Hz, 1H), 8.15 (d, J = 1.37 Hz, 1H), 8.05 (ddd, J = 2.74, 6.75, 11.83 Hz, 1H), 7.35-7.45 (m, 1H), 4.10 (s, 2H), 3.67 (d, J = 10.56 Hz, 1H), 3.41 (s, 3H), 3.35 (d, J = 10.56 Hz, 1H), 1.79 (dd, J = 7.24, 8.80 Hz, 1H), 1.72 (s, 3H), 1.06 (s, 9H), 0.90 (dd, J = 5.87, 9.39 Hz, 2H), 0.76-0.84 (m, 1H). | N-(3-((1S,5S,6S)-3-amino-1-(methoxymethyl)-5-methyl-2-thia-4-azabicyclo[4.1.0]hept-3-en-5-yl)-4,5-difluorophenyl)-5-(neopentyloxy)pyrazine-2-carboxamide |

Example 1040

(1S,5S,6S)-3-amino-5-(2-fluoro-5-(5-(2,2,2-trifluoroethoxy)pyrazine-2-carboxamido)phenyl)-N-(2-fluoroethyl)-5-methyl-2-thia-4-azabicyclo[4.1.0]hept-3-ene-1-carboxamide Example 1041

(1S,5S,6S)-3-amino-5-(2-fluoro-5-(5-(2,2,2-trifluoroethoxy)pyrazine-2-carboxamido)phenyl)-5-methyl-N-(1-methylcyclopropyl)-2-thia-4-azabicyclo[4.1.0]hept-3-ene-1-carboxamide

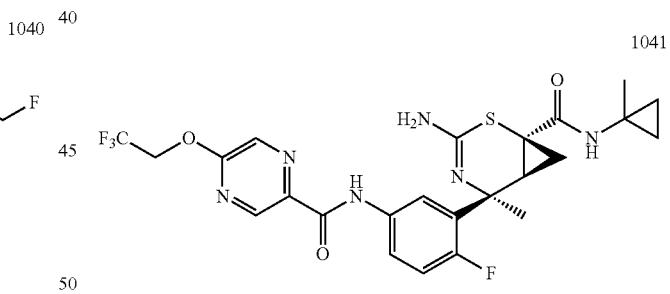

The title compound 1040 (0.024 g, 0.044 mmol, 30% yield) was prepared according to the procedure for 998 using compound 295 (0.106 g, 0.145 mmol) and 2-fluoroethylamine hydrochloride (0.019 g, 0.189 mmol). LCMS (ESI⁺) m/z=545.2 (M+H). ¹H NMR (300 MHz, CHLOROFORM-d) δ: 9.38 (s, 1H), 8.99 (d, J=1.32 Hz, 1H), 8.28 (d, J=1.32 Hz, 1H), 7.78 (ddd, J=2.85, 4.06, 8.73 Hz, 1H), 7.49 (dd, J=2.70, 6.80 Hz, 1H), 6.91-7.10 (m, 2H), 4.74-5.22 (m, 4H), 4.62 (t, J=4.75 Hz, 1H), 4.46 (t, J=4.75 Hz, 1H), 3.50-3.77 (m, 2H), 2.19-2.31 (m, 1H), 1.95-2.07 (m, 1H), 1.84-1.92 (m, 3H), 0.81-0.94 (m, 1H). ¹⁹F NMR (282 MHz, CHLOROFORM-d) δ: −73.63 (s, 3F), −113.22 (s, 1F), −224.15 (s, 1F).

The title compound 1041 (0.031 g, 0.056 mmol, 38% yield) was prepared according to the procedure for 998 using compound 295 (0.106 g, 0.145 mmol) and (1-methylcyclopropyl)amine (0.015 g, 0.218 mmol). LCMS (ESI⁺) m/z=553.1 (M+H). ¹H NMR (300 MHz, CHLOROFORM-d) δ: 9.34 (s, 1H), 8.96 (d, J=1.17 Hz, 1H), 8.24 (d, J=1.31 Hz, 1H), 7.67-7.82 (m, 1H), 7.49 (dd, J=2.70, 6.80 Hz, 1H), 7.00 (dd, J=8.77, 11.25 Hz, 1H), 6.82 (s, 1H), 4.87 (q, J=8.18 Hz, 4H), 2.21 (dd, J=7.75, 9.35 Hz, 1H), 1.95 (dd, J=4.90, 9.72 Hz, 1H), 1.86 (s, 3H), 1.38 (s, 3H), 0.72-0.87 (m, 3H), 0.63-0.72 (m, 2H). ¹⁹F NMR (282 MHz, CHLOROFORM-d) δ: −73.63 (s, 3F), −113.37 (s, 1F).

Example 1042

N-(3-((1S,5S,6S)-1-(acetamidomethyl)-3-amino-5-methyl-2-thia-4-azabicyclo[4.1.0]hept-3-en-5-yl)-4,5-difluorophenyl)-5-(prop-2-yn-1-yloxy)pyrazine-2-carboxamide

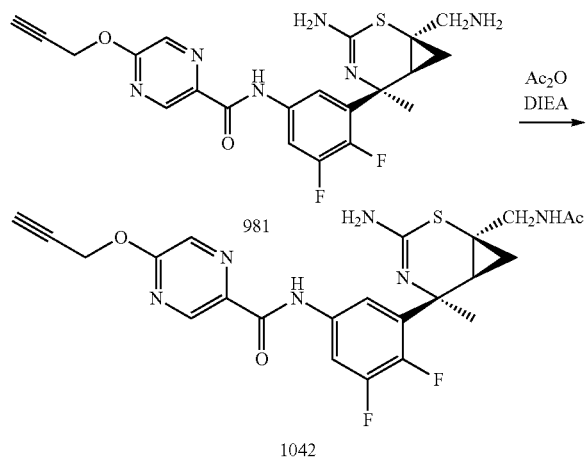

To a stirred solution of N-(3-((1S,5S,6S)-3-amino-1-(aminomethyl)-5-methyl-2-thia-4-azabicyclo[4.1.0]hept-3-en-5-yl)-4,5-difluorophenyl)-5-(prop-2-yn-1-yloxy)pyrazine-2-carboxamide (Example 981, 120 mg, 0.26 mmol) and diisopropylethylamine (0.045 mL, 0.262 mmol) in CH$_2$Cl$_2$ (4 mL) at −30° C. was added acetic anhydride (0.025 mL, 0.262 mmol) in CH$_2$Cl$_2$ (0.5 mL). The reaction was stirred for 2 h at −30° C. then quenched with sat. NH$_4$Cl (1 mL). The reaction mixture was then partitioned between CH$_2$Cl$_2$ (10 mL) and 1 M NaOH (5 mL). The organic layer was dried over MgSO$_4$, concentrated under reduced pressure, and then purified by silica gel chromatography (4 g) eluting products with a gradient of 20-50% of (3:1 EtOAc/EtOH) in heptane to afford N-(3-((1S,5S,6S)-1-(acetamidomethyl)-3-amino-5-methyl-2-thia-4-azabicyclo[4.1.0]hept-3-en-5-yl)-4,5-difluorophenyl)-5-(prop-2-yn-1-yloxy)pyrazine-2-carboxamide (1042, 52 mg, 0.104 mmol, 40% yield) as a white solid. LC/MS (ESI⁻) m/z=501.1. $^1$H NMR (400 MHz, DMSO-d$_6$) δ 10.61 (s, 1H), 8.90 (d, J=1.17 Hz, 1H), 8.48 (d, J=1.17 Hz, 1H), 8.14 (t, J=6.06 Hz, 1H), 7.87-7.94 (m, 2H), 5.96 (s, 2H), 5.14 (d, J=2.35 Hz, 2H), 3.64 (t, J=2.35 Hz, 1H), 3.32-3.38 (m, 1H), 3.21 (dd, J=5.58, 14.38 Hz, 1H), 1.85 (s, 3H), 1.74 (dd, J=7.04, 8.61 Hz, 1H), 1.59 (s, 3H), 0.86 (dd, J=5.28, 9.19 Hz, 1H), 0.57 (t, J=5.77 Hz, 1H).

Example 1045

(1S,5S,6S)-3-amino-N-(1,1-difluoropropan-2-yl)-5-(2-fluoro-5-(5-(2,2,2-trifluoroethoxy)pyrazine-2-carboxamido)phenyl)-5-methyl-2-thia-4-azabicyclo[4.1.0]hept-3-ene-1-carboxamide

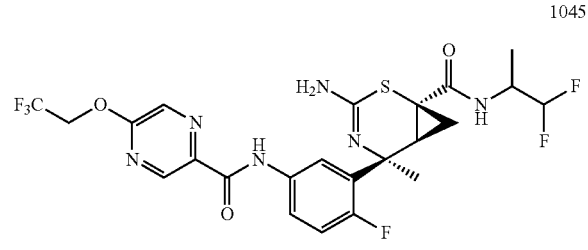 [SMILES: CC(NC(=O)[C@]12C[C@H]1[C@@](C)(c1cc(NC(=O)c3cnc(OCC(F)(F)F)cn3)ccc1F)N=C(N)S2)C(F)F]

The title compound 1045 (0.022 g, 0.038 mmol, 26% yield) was prepared according to the procedure for 983 using compound 295 (0.106 g, 0.145 mmol) and 1,1-difluoropropan-2-amine hydrochloride (0.029 g, 0.218 mmol). LCMS (ESI⁺) m/z=577.1 (M+H). $^1$H NMR (300 MHz, CHLOROFORM-d) δ: 9.34 (s, 1H), 8.97 (d, J=1.32 Hz, 1H), 8.25 (d, J=1.32 Hz, 1H), 7.73 (ddd, J=2.78, 3.98, 8.73 Hz, 1H), 7.48 (dd, J=2.70, 6.80 Hz, 1H), 7.01 (dd, J=8.84, 11.18 Hz, 1H), 6.63 (d, J=8.62 Hz, 1H), 5.83 (dt, J=2.05, 55.10 Hz, 1H), 4.88 (q, J=8.33 Hz, 2H), 4.23-4.61 (m, 3H), 2.24 (dd, J=7.89, 9.50 Hz, 1H), 2.00 (dd, J=4.97, 9.65 Hz, 1H), 1.88 (s, 3H), 1.23-1.34 (m, 3H), 0.81-0.95 (m, 1H). $^{19}$F NMR (282 MHz, CHLOROFORM-d) δ: −73.63 (s, 3F), −113.31 (s, 1F), −126.66 (d, J=283 Hz, 1F), −132.70 (d, J=283 Hz, 1F).

Table 13A contains representative compounds of the invention (Examples 1-102 presented herein), Table 13B contains representative compounds of the invention (Examples 601-962 presented herein), and Table 13C contain representative compounds of the invention (Examples 963-1075 presented herein). These tables also include the mass observed and associated biological data. The data presented includes BACE1 enzyme assay, BACE1 cell assay, BACE2 enzyme assay and Cathepsin D (Cat D) assay, inhibitory data expressed as µM IC$_{50}$'s. The assays procedures and data measurements are described below.

TABLE 13A

| Ex. No. | Oberved [M + H]⁺ | IC$_{50}$ IP (µM) BACE1 enzyme | IC$_{50}$ IP (µM) BACE1 cell | IC$_{50}$ IP (µM) BACE2 enzyme | IC$_{50}$ IP (µM) CatD |
|---|---|---|---|---|---|
| 1 | 409.1 | 0.00551 | 0.00871 | 0.0022 | 74.5 |
| 2 | 399.9 | 0.00747 | 0.00437 | 0.0129 | >400 |
| 3 | 414.2 | 0.00838 | 0.00522 | 0.0108 | 437 |
| 4 | 406.1 | 0.0696 | 0.0164 | | 1845 |
| 5 | 427.0 | 0.00855 | 0.0326 | 0.00154 | 1421 |
| 6 | 409.1 | 0.0123 | 0.0124 | 0.00184 | 750 |
| 7 | 406.1 | 0.0141 | 0.00636 | | 719 |
| 8 | 423.0 | 0.00528 | 0.0563 | | 418 |
| 9 | 481.0 | 0.00679 | 0.0232 | | 366 |
| 10 | 439.1 | 0.00235 | 0.00196 | | 1246 |
| 11 | 418.1 | 0.0104 | 0.0119 | 0.0275 | >400 |
| 12 | 441.0 | 0.00128 | 0.00242 | <0.00203 | 425 |
| 13 | 432.0 | 0.00548 | 0.00899 | 0.00618 | >400 |
| 14 | 400.1 | 0.0109 | 0.00569 | | 797 |
| 15 | 455.1 | 0.0124 | 0.00994 | | 506 |
| 16 | 424.1 | 0.0145 | 0.00908 | | 875 |
| 17 | 438.0 | 0.026 | 0.0548 | | 863 |
| 18 | 427.1 | 0.0172 | 0.0169 | | 34.3 |
| 19 | 414.2 | 0.00545 | 0.00431 | | 669 |
| 20 | 448.1 | 0.0006 | 0.00064 | 0.0394 | 47.1 |
| 21 | 423.0 | 0.0145 | 0.0164 | 0.00534 | >133 |
| 22 | 451.0 | 0.0149 | 0.0533 | | 331 |
| 23 | 430.0 | 0.00047 | 0.00062 | 0.0374 | 81.9 |
| 24 | 476.1 | 0.00188 | 0.0191 | | 189 |
| 25 | 504.0 | 0.0025 | 0.571 | | 48.7 |
| 26 | 441.0 | 0.0107 | 0.0213 | | >133 |
| 27 | 441.0 | 0.0235 | 0.013 | | 33.5 |
| 28 | 442.1 | 0.0276 | 0.0204 | 0.0497 | 466 |
| 29 | 453.0 | 0.00209 | 0.00212 | <0.00203 | 282 |
| 30 | 462.0 | 0.00152 | 0.00851 | <0.00203 | 958 |
| 31 | 457.1 | 0.00206 | 0.00226 | 0.00109 | 1396 |
| 32 | 452.0 | 0.0212 | 0.0836 | 0.304 | 138 |
| 33 | 467.1 | 0.00203 | 0.00383 | 0.00169 | >400 |
| 34 | 433.0 | 0.0198 | 0.0317 | 0.0136 | 295 |
| 35 | 477.0 | 0.00386 | 0.00288 | 0.00363 | 213 |
| 36 | 424.1 | 0.0267 | 0.00767 | 0.0562 | 250 |
| 37 | 439.1 | 0.00332 | 0.0014 | 0.00161 | >400 |
| 38 | 423.0 | 0.0157 | 0.0144 | 0.00728 | >133 |
| 39 | 433.1 | 0.0234 | 0.024 | 0.0278 | 1222 |
| 40 | 453.0 | 0.00553 | 0.0065 | 0.00121 | 2806 |
| 41 | 441.0 | 0.00227 | 0.00596 | <0.00203 | >400 |
| 42 | 439.1 | 0.00601 | 0.00576 | 0.0039 | 95.6 |

TABLE 13A-continued

| Ex. No. | Oberved [M + H]+ | IC$_{50}$ IP (μM) BACE1 enzyme | IC$_{50}$ IP (μM) BACE1 cell | IC$_{50}$ IP (μM) BACE2 enzyme | IC$_{50}$ IP (μM) CatD |
|---|---|---|---|---|---|
| 43 | 471.0 | 0.00235 | 0.00995 | 0.00163 | 755 |
| 44 | 444.0 | 0.00255 | 0.00215 | 0.00147 | >400 |
| 45 | 462.0 | 0.00299 | 0.00427 | <0.00203 | >400 |
| 46 | 468.0 | 0.00631 | 0.00352 | 0.0301 | 252 |
| 47 | 485.1 | 0.00318 | 0.0162 | 0.00187 | >400 |
| 48 | 471.0 | 0.00357 | 0.0149 | 0.00323 | >400 |
| 49 | 463.1 | 0.00631 | 0.0084 | 0.00749 | 1764 |
| 50 | 453.0 | 0.00225 | 0.00505 | 0.00286 | >133 |
| 51 | 424.1 | 0.033 | 0.00344 | 0.0983 | 1346 |
| 52 | 482.1 | 0.0105 | 0.00455 | 0.23 | >400 |
| 53 | 460.1 | 0.00045 | 0.00045 | 0.0156 | 349 |
| 54 | 453.2 | 0.00139 | 0.00196 | <0.00203 | >44.4 |
| 55 | 454.2 | 0.00399 | 0.00457 | 0.014 | 227 |
| 56 | 496.1 | 0.00538 | 0.0135 | 0.27 | >400 |
| 57 | 471.0 | 0.00563 | 0.0225 | 0.0235 | 29.5 |
| 58 | 459.0 | 0.00397 | 0.00306 | 0.0308 | 975 |
| 59 | 459.0 | 0.00114 | 0.0229 | <0.00203 | >400 |
| 60 | 455.1 | 0.00135 | 0.00767 | 0.00174 | 204 |
| 61 | 460.1 | 0.0003 | 0.00035 | 0.0201 | 59.7 |
| 62 | 447.0 | 0.0289 | 0.14 | 0.0885 | 295 |
| 63 | 475.1 | 0.1365 | 4.65 | 3.75 | 494 |
| 64 | 461.1 | 0.00448 | 0.00281 | 0.025 | 268 |
| 65 | 473.1 | 0.0133 | 0.00781 | 0.0836 | 1229 |
| 66 | 447.0 | 0.0171 | 0.0525 | 0.132 | >400 |
| 67 | 477.0/479.0 | 0.0137 | 0.0208 | 0.00616 | 738 |
| 68 | 457.0 | 0.00588 | 0.0201 | 0.00568 | 47.0 |
| 69 | 427.0 | 0.0152 | 0.114 | 0.00302 | 939 |
| 70 | 462.0 | 0.00116 | 0.0035 | 0.00247 | >400 |
| 71 | 459.0 | 0.00047 | 0.00156 | 0.0375 | 329 |
| 72 | 474.0 | 0.00044 | 0.00082 | 0.0212 | 81.6 |
| 73 | 477.1 | 0.00911 | 0.0177 | 0.00296 | >400 |
| 74 | 473.1 | 0.00095 | 0.00219 | 0.0473 | 932 |
| 75 | 450.1 | 0.012 | 0.0136 | 0.0295 | >400 |
| 76 | 474.0 | 0.00095 | 0.00271 | 0.0174 | 1494 |
| 77 | 444.0 | 0.0047 | 0.0217 | 0.0461 | 949 |
| 78 | 441.0 | 0.00464 | 0.0917 | 0.00126 | 627 |
| 79 | 518.2 | 0.00489 | 0.0284 | 0.143 | >400 |
| 80 | 454.1 | 0.00913 | 0.00851 | 0.0251 | >400 |
| 81 | 437.1 | 0.0219 | 0.047 | 0.0116 | 1392 |
| 82 | 483.0 | 0.00043 | 0.00354 | 0.0099 | >133 |
| 83 | 478.1 | 0.00046 | 0.00092 | 0.0138 | 105 |
| 84 | 462.0 | 0.00125 | 0.0216 | 0.0228 | 974 |
| 85 | 487.1 | 0.00062 | 0.00216 | 0.0435 | 1550 |
| 86 | 473.1 | 0.00763 | 0.0501 | 0.0206 | 715 |
| 87 | 467.1 | 0.114 | 22.6 | 0.271 | 2809 |
| 88 | 429.1 | 0.0416 | 0.0264 | 0.137 | >400 |
| 89 | 458.1 | 0.0228 | 0.0198 | 0.0364 | >400 |
| 90 | 485.1 | 0.00682 | 0.128 | 0.0112 | 34.1 |
| 91 | 476.1 | 0.00524 | 0.0256 | 0.0111 | 1208 |
| 92 | 463.1 | 0.00520 | 0.0102 | 0.00373 | 414 |
| 93 | 459.1 | 0.01 | 0.0108 | 0.0342 | 1376 |
| 94 | 464.0 | 0.00053 | 0.00304 | <0.00203 | 559 |
| 95 | 474.0 | 0.00426 | 0.0138 | 0.00837 | 133 |
| 96 | 471.0 | 0.00726 | 0.0174 | 0.0024 | 40.4 |
| 97 | 456.0 | 0.0118 | 0.0312 | 0.0632 | 752 |
| 98 | 424.0 | 0.00665 | 0.0056 | 0.0032 | 3140 |
| 99 | 449.9 | 0.00659 | 0.0659 | 0.00824 | 1130 |
| 100 | 422.0 | 0.0225 | 0.0112 | 0.0038 | >400 |
| 101 | 441.9 | 0.0197 | 0.094 | 0.023 | 720 |
| 102 | 462.0 | 0.00433 | 0.058 | 0.019 | 361 |

TABLE 13B

| Ex. No. | Oberved [M + H]+ | IC$_{50}$ IP (μM) BACE1 enzyme | IC$_{50}$ IP (μM) BACE1 cell | IC$_{50}$ IP (μM) BACE2 enzyme | IC$_{50}$ IP (μM) CatD |
|---|---|---|---|---|---|
| 601 | 468 | 0.000589 | 0.00235 | 0.0361 | 1679 |
| 602 | 511 | 0.000871 | 0.00204 | 0.0371 | 605 |
| 603 | 459.1 | 0.0016 | 0.0037 | 0.0132 | 336 |
| 604 | 437.9 | 0.00624 | 0.00933 | 0.00378 | 571 |
| 605 | 510.9 | 0.00178 | 0.00149 | 0.114 | 1290 |
| 606 | 445.2 | 0.00032 | 0.000849 | 0.00931 | 278 |
| 607 | 488 | 0.000975 | 0.000956 | 0.0237 | >400 |
| 608 | 518 | 0.00285 | 0.00174 | 0.154 | >400 |
| 609 | 520.2 | 0.00344 | 0.0194 | 0.466 | >400 |
| 610 | 521 | 0.00178 | 0.00597 | 0.193 | >400 |
| 611 | 480.2 | 0.00663 | 0.00649 | 0.208 | >400 |
| 612 | 457.2 | 0.00115 | 0.00103 | 0.0544 | 196 |
| 613 | 487.1 | 0.000555 | 0.00098 | 0.0123 | 709 |
| 614 | 520.2 | 0.00361 | 0.0755 | 0.101 | 340 |
| 615 | 538.1 | 0.00273 | 0.0788 | 0.117 | 102 |
| 616 | 590.2 | 0.00342 | 0.0329 | 0.124 | 905 |
| 617 | 508.1 | 0.00357 | 0.0652 | 0.158 | >400 |
| 618 | 532.2 | 0.00606 | 0.0557 | 0.0161 | 1015 |
| 619 | 490.1 | 0.00439 | 0.0352 | 0.175 | 655 |
| 620 | 514.1 | 0.00832 | 0.0437 | 0.245 | >400 |
| 621 | 484.1 | 0.0113 | 0.0197 | 0.148 | 710 |
| 622 | 592.1 | 0.00492 | 0.0438 | 0.225 | 946 |
| 623 | 520.1 | 0.00575 | 0.0671 | 0.0485 | 641 |
| 624 | 436.1 | 0.0298 | 0.0435 | 0.00394 | >400 |
| 625 | 480.1 | 0.0309 | 0.014 | 0.401 | 730 |
| 626 | 523.1 | 0.0164 | 0.00509 | 0.2 | 1077 |
| 627 | 497.1 | 0.00114 | 0.00428 | 0.0384 | 1389 |
| 628 | 540 | 0.00324 | 0.0148 | 0.0383 | 443 |
| 629 | 472.2 | 0.0365 | 0.0205 | 0.0582 | 2884 |
| 630 | 531 | 0.000443 | 0.00528 | 0.00547 | 74.9 |
| 631 | 540.2 | 0.00173 | 0.00325 | 0.055 | 475 |
| 632 | 532.1 | 0.000715 | 0.000535 | 0.00302 | 961 |
| 633 | 509.1 | 0.00036 | 0.000224 | 0.00165 | 67.5 |
| 634 | 553.1 | 0.000758 | 0.000616 | 0.00951 | 660 |
| 635 | 505.2 | 0.00832 | 0.0208 | 0.192 | >400 |
| 636 | 417 | 0.0918 | 0.411 | 0.0298 | 996 |
| 637 | 392 | 0.0213 | 0.0121 | 0.00261 | >400 |
| 638 | 398 | 0.0625 | 0.0517 | 0.0314 | >400 |
| 639 | 436.1 | 0.00157 | 0.00213 | 0.0401 | 381 |
| 640 | 479 | 0.00553 | 0.00251 | 0.101 | 646 |
| 641 | 406 | 0.0188 | 0.00799 | 0.00815 | 1428 |
| 642 | 518.2 | 0.00642 | 0.0351 | 0.114 | 434 |
| 643 | 536.2 | 0.00246 | 0.0328 | 0.134 | 751 |
| 644 | 512.2 | 0.014 | 0.0137 | 0.207 | >400 |
| 645 | 518.2 | 0.00337 | 0.0246 | 0.143 | 477 |
| 646 | 530.2 | 0.00656 | 0.013 | 0.211 | 865 |
| 647 | 507.2 | 0.0236 | 0.259 | 0.342 | 389 |
| 648 | 499 | 0.0433 | 0.222 | 0.522 | 196 |
| 649 | 483.2 | 0.0646 | 0.131 | 0.284 | 803 |
| 650 | 501.2 | 0.0389 | 0.344 | 0.556 | 777 |
| 651 | 471 | 0.0589 | 0.139 | 0.397 | 1033 |
| 652 | 500.1 | 0.00756 | 0.0256 | 0.142 | >400 |
| 653 | 486 | 0.000544 | 0.00151 | 0.0192 | 260 |
| 654 | 529 | 0.000931 | 0.00166 | 0.0291 | 861 |
| 655 | 442 | 0.00455 | 0.006 | <0.00203 | 1723 |
| 656 | 516 | 0.387 | 0.624 | 2.35 | 998 |
| 657 | 456 | 0.00369 | 0.00533 | 0.00303 | 306 |
| 658 | 457 | 0.0107 | 0.0136 | 0.0293 | 705 |
| 659 | 534 | 0.000774 | 0.0013 | 0.00425 | 462 |
| 660 | 534 | 0.00133 | 0.00345 | 0.0235 | 554 |
| 661 | 502 | 0.000765 | 0.00244 | 0.00392 | 795 |
| 662 | 466 | 0.000437 | 0.00049 | 0.0199 | 1060 |
| 663 | 545 | 0.00048 | 0.00338 | 0.0174 | 601 |
| 664 | 545 | 0.000274 | 0.0143 | 0.046 | >400 |
| 665 | 534 | 0.00165 | 0.00737 | 0.0383 | 1110 |
| 666 | 534 | 0.00201 | 0.00772 | 0.177 | 1693 |
| 667 |  | 0.00262 | 0.00362 | 0.0599 | 1162 |
| 668 | 577 | 0.0033 | 0.00697 | 0.233 | 1966 |
| 669 | 544 | 0.00119 | 0.00593 | 0.036 | 1136 |
| 670 | 466 | 0.0024 | 0.000969 | 0.17 | 730 |
| 671 | 533 | 0.000943 | 0.00177 | 0.0236 | 1045 |
| 672 | 533 | 0.00142 | 0.007 | 0.0685 | 638 |
| 673 | 510 | 0.000389 | 0.000398 | 0.00602 | 101 |
| 674 | 510 | 0.000368 | 0.000776 | 0.0133 | 149 |
| 675 | 531 | 0.0124 | 0.0519 | 0.703 | 1014 |
| 676 | 548 | 0.00155 | 0.0033 | 0.0157 | 337 |
| 677 | 548 | 0.0016 | 0.00305 | 0.00948 | 306 |
| 678 | 519 | 0.00612 | 0.0286 | 0.579 | 747 |
| 679 | 537 | 0.00435 | 0.0495 | 0.746 | 375 |
| 680 | 519 | 0.0139 | 0.0153 | 0.846 | 1110 |
| 681 | 513 | 0.0109 | 0.0555 | 0.789 | 1454 |

TABLE 13B-continued

| Ex. No. | Observed [M + H]+ | IC$_{50}$ IP (μM) BACE1 enzyme | IC$_{50}$ IP (μM) BACE1 cell | IC$_{50}$ IP (μM) BACE2 enzyme | IC$_{50}$ IP (μM) CatD |
|---|---|---|---|---|---|
| 682 | 487 | 0.00182 | 0.0175 | 0.0195 | 800 |
| 683 | 469 | 0.00391 | 0.008 | 0.0267 | 2099 |
| 684 | 475 | 0.00146 | 0.00684 | 0.0332 | 1038 |
| 685 | 493 | 0.00112 | 0.0197 | 0.018 | 463 |
| 686 | 475 | 0.00167 | 0.00967 | 0.0221 | 496 |
| 687 | 544 | 0.117 | 0.569 | 2.52 | >400 |
| 688 | 544 | 0.548 | 3.89 | 0.709 | 1320 |
| 689 | 501 | 0.0105 | 0.0464 | 0.819 | >400 |
| 690 | 457 | 0.00418 | 0.00779 | 0.026 | 675 |
| 691 | 495 | 0.000673 | 0.00563 | 0.0231 | 728 |
| 692 | 505 | 0.0053 | 0.0453 | 0.29 | >400 |
| 693 | 539 | 0.00294 | 0.0489 | 0.246 | 1197 |
| 694 | 517 | 0.00615 | 0.0517 | 0.401 | 1691 |
| 695 | 523 | 0.00272 | 0.0883 | 0.263 | >400 |
| 696 | 505 | 0.0062 | 0.0707 | 0.324 | 846 |
| 697 | 487 | 0.00629 | 0.0315 | 0.338 | >400 |
| 698 | 499 | 0.0086 | 0.0116 | 0.316 | >400 |
| 699 | 570 | 0.00106 | 0.0352 | 0.0524 | 138 |
| 700 | 530 | 0.00115 | 0.00826 | 0.224 | 569 |
| 701 | 531 | 0.000943 | 0.00309 | 0.0782 | 587 |
| 702 | 544 | 0.000986 | 0.0344 | 0.269 | 362 |
| 703 | 472 | 0.00594 | 0.0153 | 0.011 | 340 |
| 704 | 457 | 0.002 | 0.00557 | <0.00203 | 141 |
| 705 | 544 | 0.00186 | 0.0035 | 0.0184 | 183 |
| 706 | 544 | 0.00292 | 0.0086 | 0.0294 | 354 |
| 707 | 501 | 0.000636 | 0.00422 | 0.0185 | 550 |
| 708 | 554 | 0.000969 | 0.0215 | 0.107 | 438 |
| 709 | 486 | 0.0092 | 0.104 | 0.0257 | 148 |
| 710 | 471 | 0.00599 | 0.055 | <0.00203 | 379 |
| 711 | 485 | 0.00311 | 0.014 | <0.00203 | 753 |
| 712 | 529 | 0.000782 | 0.00904 | 0.0516 | 476 |
| 713 | 515 | 0.000864 | 0.00543 | 0.00394 | 547 |
| 714 | 515 | 0.00102 | 0.0109 | 0.00913 | 613 |
| 715 | 472.1 | 0.00409 | 0.00635 | 0.00881 | 918 |
| 716 | 458.1 | 0.00216 | 0.00431 | 0.00196 | 2288 |
| 717 | 467.1 | 0.0072 | 0.0239 | 0.00332 | >400 |
| 718 | 448.1 | 0.00367 | 0.04 | 0.00131 | 921 |
| 719 | 462 | 0.00442 | 0.0138 | 0.00397 | 1490 |
| 720 | 492 | 0.000935 | 0.00151 | 0.0273 | 648 |
| 721 | 535.1 | 0.00162 | 0.00474 | 0.0677 | 2126 |
| 722 | 490.1 | 0.0118 | 0.0209 | <0.00203 | 684 |
| 723 | 462 | 0.00169 | 0.00431 | <0.00203 | 282 |
| 724 | 548.2 | 0.00208 | 0.00712 | 0.0746 | 1080 |
| 725 | 504 | 0.00565 | 0.0148 | 0.00251 | 1164 |
| 726 | 539.1 | 0.179 | 0.406 | 0.641 | >400 |
| 727 | 539.1 | 0.00798 | 0.009625 | 0.359 | 779 |
| 728 | 539.1 | 0.0238 | 0.0127 | 0.553 | 859 |
| 729 | 497 | 0.0282 | 0.0457 | 0.385 | 856 |
| 730 | 540.1 | 0.0157 | 0.0759 | 1.03 | 1376 |
| 731 | 572.1 | 0.0668 | 1.3 | 3.83 | 1097 |
| 732 | 549.1 | 0.00339 | 0.034 | 0.737 | 600 |
| 733 | 496.1 | 0.00638 | 0.014 | 0.0642 | 1520 |
| 734 | 550.1 | 0.00173 | 0.017 | 0.188 | 2107 |
| 735 | 589.1 | 0.0412 | 1.76 | 0.978 | 1646 |
| 736 | 633/635 | 0.0317 | 1.07 | 0.765 | 151 |
| 737 | 555.1 | 0.0325 | 0.274 | 0.693 | 1497 |
| 738 | 532 | 0.0169 | 0.0667 | 0.562 | 648 |
| 739 | 514.1 | 0.00421 | 0.0169 | 0.158 | 1464 |
| 740 | 496.1 | 0.0055 | 0.0194 | 0.209 | 927 |
| 741 | 564.1 | 0.0269 | 1.14 | 0.658 | 94.4 |
| 742 | 487 | 0.000719 | 0.0149 | <0.00203 | 846 |
| 743 | 507 | 0.000395 | 0.00971 | 0.00543 | >133 |
| 744 | 508 | 0.00029 | 0.000872 | 0.0183 | 46.5 |
| 745 | 550.1 | 0.000898 | 0.0175 | 0.0257 | 972 |
| 746 | 551 | 0.000628 | 0.00356 | 0.00522 | 880 |
| 747 | 574.1 | 0.00242 | 0.0123 | 0.0115 | 1186 |
| 748 | 445.1 | 0.00807 | 0.597 | 0.00284 | 129 |
| 749 | 478.1 | 0.000319 | 0.00121 | 0.00979 | 101 |
| 750 | 544.1 | 0.0019 | 0.00301 | 0.0404 | 246 |
| 751 | 553.1 | 0.00203 | 0.0338 | 0.255 | 292 |
| 752 | 467.4 | 0.0068 | 0.0522 | 0.00709 | 26.4 |
| 753 | 467.4 | 0.00339 | 0.0964 | 0.00304 | 420 |
| 754 | 433 | 0.0454 | 0.0781 | 0.00588 | 844 |
| 755 | 507 | 0.00147 | 0.00838 | <0.00203 | 250 |
| 756 | 465 | 0.00373 | 0.00659 | <0.00203 | >400 |
| 757 | 479 | 0.000176 | 0.0498 | <0.00203 | 458 |
| 758 | 467 | 0.00156 | 0.00195 | <0.00203 | 2066 |
| 759 | 478 | 0.00101 | 0.00265 | <0.00203 | >400 |
| 760 | 492 | 0.000415 | 0.00265 | <0.00203 | 779 |
| 761 | 506 | 0.000794 | 0.00152 | <0.00203 | 364 |
| 762 | 453 | 0.00303 | 0.0142 | 0.0384 | 669 |
| 763 | 496 | 0.00849 | 0.0048 | 0.239 | 1110 |
| 764 | 548 | 0.00073 | 0.000856 | <0.00203 | 518 |
| 765 | 508 | 0.000706 | 0.0011 | <0.00203 | 1074 |
| 766 | 548 | 0.00105 | 0.0031 | <0.00203 | 848 |
| 767 | 536 | 0.00102 | 0.00143 | <0.00203 | 602 |
| 768 | 550.1 | 0.00119 | 0.00113 | 0.00612 | 406 |
| 769 | 593 | 0.00143 | 0.00121 | 0.023 | 224 |
| 770 | 592 | 0.00294 | 0.00281 | 0.143 | 311 |
| 771 | 563 | 0.00204 | 0.00146 | 0.0786 | 282 |
| 772 | 554 | 0.000429 | 0.000972 | <0.00203 | 82 |
| 773 | 598 | 0.000423 | 0.00148 | <0.00203 | 113 |
| 774 | 527 | 0.000313 | 0.000583 | 0.00575 | 7.95 |
| 775 |  | 0.00112 | 0.00323 | 0.0602 | 22.8 |
| 776 | 550 | 0.001197 | 0.00305 | 0.0264 | 293 |
| 777 | 562 | 0.000274 | 0.000416 | <0.00203 | 834 |
| 778 | 562 | 0.00558 | 0.0134 | 0.026 | 557 |
| 779 | 524 | 0.000728 | 0.00082 | <0.00203 | >400 |
| 780 | 497 | 0.00022 | 0.00126 | <0.0061 | 116 |
| 781 | 520 | 0.000422 | 0.00577 | 0.00329 | 397 |
| 782 | 520 | 0.000577 | 0.0197 | 0.0245 | 792 |
| 783 | 540 | 0.000501 | 0.00485 | 0.00245 | >400 |
| 784 | 511 | 0.000318 | 0.00152 | <0.00203 | 166 |
| 785 | 476 | 0.00112 | 0.0102 | <0.00203 | 621 |
| 786 | 476 | 0.000976 | 0.0464 | <0.00203 | 584 |
| 787 | 490 | 0.000847 | 0.0139 | <0.00203 | 1233 |
| 788 | 534 | 0.00127 | 0.0161 | 0.0122 | 485 |
| 789 | 510 | 0.000528 | 0.0259 | 0.00936 | 835 |
| 790 | 480 | 0.000338 | 0.0028 | <0.00203 | 792 |
| 791 | 518 | 0.000658 | 0.00183 | 0.0712 | 317 |
| 792 | 474 | 0.00075 | 0.000971 | <0.00203 | 134 |
| 793 | 496 | 0.000293 | 0.0153 | 0.00477 | 482 |
| 794 | 518 | 0.000846 | 0.0012 | 0.0397 | 316 |
| 795 | 495 | 0.0003 | 0.000608 | 0.0104 | 16.6 |
| 796 | 561 | 0.000859 | 0.00354 | 0.0628 | 543 |
| 797 | 490 | 0.00452 | 0.0211 | <0.00203 | 147 |
| 798 | 511 | 0.000294 | 0.000715 | 0.0272 | 4.72 |
| 799 | 538 | 0.000382 | 0.00075 | 0.015 | 349 |
| 800 | 539 | 0.000711 | 0.00659 | 0.0841 | 293 |
| 801 | 456.2 | 0.00613 | 0.0137 | 0.0163 | 145 |
| 802 | 528 | 0.000992 | 0.00497 | 0.0334 | 310 |
| 803 | 519.1 | 0.000643 | 0.00228 | 0.0157 | 1063 |
| 804 | 459 | 0.00111 | 0.008 | <0.00203 | 319 |
| 805 | 503.1 | 0.000222 | 0.00497 | 0.0189 | 27 |
| 806 | 485 | 0.000489 | 0.00772 | 0.0242 | 122 |
| 807 | 480 | 0.000228 | 0.000722 | 0.00736 | 43.9 |
| 808 | 528.2 | 0.000866 | 0.00111 | 0.0383 | 127 |
| 809 | 540.1 | 0.000974 | 0.00181 | 0.0358 | 123 |
| 810 | 462 | 0.000268 | 0.141 | 0.012 | 67.8 |
| 811 | 505.1 | 0.000676 | 0.00126 | 0.0207 | 297 |
| 812 | 546 | 0.000827 | 0.00167 | 0.0642 | 118 |
| 813 | 485.1 | 0.0009 | 0.002 | 0.0258 | 447 |
| 814 | 506 | 0.000829 | 0.00608 | 0.0601 | 595 |
| 815 | 518 | 0.000847 | 0.00349 | 0.0395 | 396 |
| 816 | 485 | 0.000244 | 0.00122 | 0.0183 | 73.6 |
| 817 | 528 | 0.000706 | 0.00171 | 0.0319 | 124 |
| 818 | 441 | 0.000587 | 0.00164 | <0.00203 | 152 |
| 819 | 485.1 | 0.000821 | 0.00175 | 0.0412 | 34.2 |
| 820 | 462 | 0.000319 | 0.000495 | 0.0162 | 60.4 |
| 821 | 423.2 | 0.00298 | 0.00428 | <0.00203 | 1174 |
| 822 | 440 | 0.000264 | 0.000378 | 0.0147 | 150 |
| 823 | 467 | 0.000791 | 0.00186 | 0.0296 | 351 |
| 824 | 467 | 0.00299 | 0.00128 | 0.0842 | 1840 |
| 825 | 510 | 0.00357 | 0.00111 | 0.0542 | 526 |
| 826 | 488 | 0.00174 | 0.00331 | 0.0778 | 395 |
| 827 | 481.1 | 0.000771 | 0.0207 | 0.263 | 810 |
| 828 | 525 | 0.00496 | 0.00446 | 0.207 | 995 |
| 829 | 458 | 0.000776 | 0.0019 | 0.00801 | 354 |
| 830 | 476 | 0.000566 | 0.00221 | 0.0101 | 121 |
| 831 | 500 | 0.00299 | 0.00359 | 0.118 | >400 [2] |
| 832 | 470.1 | 0.00299 | 0.00213 | 0.013 | 778 |
| 833 | 435 | 0.0041 | 0.0137 | 0.0061 | >400 |

TABLE 13B-continued

| Ex. No. | Oberved [M + H]+ | IC$_{50}$ IP (μM) BACE1 enzyme | IC$_{50}$ IP (μM) BACE1 cell | IC$_{50}$ IP (μM) BACE2 enzyme | IC$_{50}$ IP (μM) CatD |
|---|---|---|---|---|---|
| 834 | 456 | 0.000404 | 0.000489 | 0.0127 | 318 |
| 835 | 513 | 0.00305 | 0.00392 | 0.0249 | >400 |
| 836 | 519 | 0.00209 | 0.00389 | 0.0362 | >400 |
| 837 | 501 | 0.00253 | 0.00325 | 0.0259 | 1074 |
| 838 | 464 | 0.000209 | 0.000355 | 0.00751 | 49.1 |
| 839 | 482 | <0.00203 | 0.00105 | 0.0106 | 56.6 |
| 840 | 476 | <0.00203 | 0.0006 | 0.0163 | 153 |
| 841 | 471 | 0.00114 | 0.0216 | 0.0449 | 598 |
| 842 | 514.1 | 0.00256 | 0.0217 | 0.119 | >400 |
| 843 | 514.1 | 0.00378 | 0.0493 | 0.115 | 432 |
| 844 | 460.2 | 0.0219 | 0.0145 | 0.0108 | 1784 |
| 845 | 471.2 | 0.0026 | 0.00473 | 0.0257 | 1709 |
| 846 | 451 | 0.0282 | 0.0111 | 0.0494 | >400 |
| 847 | 450.2 | 0.0113 | 0.00675 | 0.00955 | 1906 |
| 848 | 480.1 | 0.00136 | 0.00134 | 0.0335 | 773 |
| 849 | 523.2 | 0.00343 | 0.0017 | 0.0463 | 1534 |
| 850 | 474 | 0.00121 | 0.00207 | 0.00886 | 1146 |
| 851 | 460.2 | 0.000574 | 0.000624 | 0.0184 | 468 |
| 852 | 463 | 0.0127 | 0.0101 | 0.00758 | 1685 |
| 853 | 483.2 | 0.000878 | 0.000961 | 0.0244 | 791 |
| 854 | 485.2 | 0.00144 | 0.00134 | 0.0383 | 1236 |
| 855 | 507.2 | 0.198 | 0.294 | 0.0224 | >400 |
| 856 | 551 | 0.071 | 0.249 | 0.657 | 116 |
| 857 | 523 | 0.0678 | 0.0156 | 0.346 | 2523 |
| 858 | 451 | 0.00085 | 0.000487 | <0.00203 | >400 |
| 859 | 457.2 | 0.000799 | 0.000762 | 0.0194 | 590 |
| 860 | 537.2 | 0.00276 | 0.00853 | 0.0286 | 1007 |
| 861 | 494 | 0.000889 | 0.00754 | 0.0176 | 146 |
| 862 | 488.2 | 0.000598 | 0.0072 | 0.017 | 129 |
| 863 | 531.2 | 0.00228 | 0.00635 | 0.0249 | 467 |
| 864 | 545 | 0.0609 | 0.172 | 0.652 | 621 |
| 865 | 499 | 0.000236 | 0.00301 | 0.0123 | 325 |
| 866 | 545.9 | 0.000941 | 0.0115 | 0.0285 | >400 |
| 867 | 545.9 | 0.00171 | 0.011 | 0.0549 | 299 |
| 868 | 517 | 0.000671 | 0.0147 | 0.0211 | >400 |
| 869 | 511 | 0.000725 | 0.00155 | 0.0173 | 127 |
| 870 | 560 | 0.00156 | 0.02 | 0.0326 | 91.3 |
| 871 | 525 | 0.0183 | 1.17 | 0.517 | 352 |
| 872 | 542.9 | 0.0193 | 2.66 | 0.441 | 239 |
| 873 | 574 | 0.00175 | 0.287 | 0.0358 | 95.1 |
| 874 | 571 | 0.00361 | 0.0245 | 0.0755 | 956 |
| 875 | 562 | 0.000296 | 0.0272 | 0.0352 | 295 |
| 876 | 506.9 | 0.0801 | 0.587 | 0.912 | 223 |
| 877 | 560.9 | 0.011 | 0.0294 | 0.338 | 343 |
| 878 | 550 | 0.231 | 1.07 | 0.353 | 171 |
| 879 | 499 | 0.00107 | 0.0179 | 0.282 | 2688 |
| 880 | 543 | 0.00452 | 0.0193 | 0.27 | 1106 |
| 881 | 551 | 0.00936 | 0.00819 | 0.14 | 349 |
| 882 | 555 | 0.00778 | 0.0204 | 0.381 | 911 |
| 883 | 561.2 | 0.000316 | 0.0133 | 0.091 | 363 |
| 884 | 557.3 | 0.00427 | 0.0119 | 0.13 | >400 |
| 885 | 555.2 | 0.00223 | 0.00823 | 0.143 | 592 |
| 886 | 574.2 | 0.0011 | 0.0411 | 0.0278 | 136 |
| 887 | 561 | 0.00295 | 0.0442 | 0.317 | >400 |
| 888 | 560.2 | 0.00209 | 0.0218 | 0.0581 | 71.9 |
| 889 | 577.2 | 0.0418 | 0.252 | 1.41 | 306 |
| 890 | 517.3 | 0.001 | 0.0257 | 0.2 | 517 |
| 891 | 560 | 0.177 | 2.88 | 1.09 | 984 |
| 892 | 560 | 0.00278 | 0.056 | 0.848 | 873 |
| 893 | 576 | 0.149 | 1.66 | 3.86 | 518 |
| 894 | 536.9 | 0.00372 | 0.05 | 0.464 | >133 |
| 895 | 479.1 | 0.0053 | 0.113 | 0.0254 | 167 |
| 896 | 465.2 | 0.018 | 0.135 | 0.0223 | 128 |
| 897 | 429 | 0.035 | 0.038 | 0.184 | 1443 |
| 898 | 467 | 0.00454 | 0.111 | 0.00268 | 673 |
| 899 | 453 | 0.00889 | 2.45 | 0.00258 | >400 |
| 900 | 429 | 0.0324 | 0.195 | 0.0972 | 559 |
| 901 | 520.1 | 0.00192 | 0.0167 | 0.00203 | 603 |
| 902 | 475 | 0.0148 | 0.0796 | 0.0125 | 479 |
| 903 | 510 | 0.00195 | 0.00785 | 0.109 | 1219 |
| 904 | 466.1 | 0.0141 | 0.0132 | 0.0355 | 380 |
| 905 | 452.2 | 0.000606 | 0.000893 | <0.00203 | 856 |
| 906 | 451 | 0.00404 | 0.014 | 0.00174 | 693 |
| 907 | 468.1 | 0.00747 | 0.00413 | 0.0102 | 381 |
| 908 | 468.1 | 0.00801 | 0.00812 | 0.0255 | 360 |
| 909 | 482 | 0.0257 | 0.0144 | 0.183 | 6.84 |
| 910 | 517 | 0.00124 | 0.00117 | 0.0337 | 1459 |
| 911 | 496.1 | 0.000649 | 0.0038 | 0.00714 | >400 |
| 912 | 524.1 | 0.000467 | 0.000795 | 0.00101 | >400 |
| 913 | 501 | 0.000303 | 0.000278 | 0.000795 | 45.1 |
| 914 | 487.1 | 0.000464 | 0.000534 | 0.0108 | 79.4 |
| 915 | 510 | 0.000426 | 0.00195 | 0.0101 | >400 |
| 916 | 478 | 0.000515 | 0.00974 | 0.00399 | 84.2 |
| 917 | 496 | 0.000633 | 0.000857 | 0.0355 | 373 |
| 918 | 539 | 0.000861 | 0.000733 | 0.0389 | 86.9 |
| 919 | 473 | 0.000199 | 0.000298 | 0.00428 | 21.2 |
| 920 | 510 | 0.000201 | 0.000644 | 0.00604 | 1077 |
| 921 | 478.1 | 0.00198 | 0.0206 | 0.0627 | 172 |
| 922 | 577.1 | 0.00155 | 0.00155 | 0.00839 | 1089 |
| 923 | 567.1 | 0.000863 | 0.000338 | 0.00253 | 121 |
| 924 | 455.1 | 0.000249 | 0.00138 | <0.00203 | 17.8 |
| 925 | 538.2 | 0.001405 | 0.00308 | 0.00387 | >400 |
| 926 | 545 | 0.0021 | 0.00113 | 0.00491 | 695 |
| 927 | 437 | 0.000266 | 0.000667 | 0.00448 | 126 |
| 928 | 460.1 | 0.00141 | 0.00723 | 0.0129 | 439 |
| 929 | 416 | 0.000567 | 0.00363 | <0.00203 | >400 |
| 930 | 480 | 0.000417 | 0.000688 | <0.00203 | 797 |
| 931 | 492 | 0.000902 | 0.0386 | 0.0551 | 633 |
| 932 | 434 | 0.00188 | 0.045 | <0.00203 | >400 |
| 933 | 550.1 | 0.000526 | 0.000709 | 0.00491 | 315 |
| 934 | 527.1 | 0.000393 | 0.000378 | <0.00203 | 12.9 |
| 935 | 506 | 0.000498 | 0.000889 | <0.00203 | 254 |
| 936 | 593.2 | 0.00385 | 0.000847 | 0.0182 | 115 |
| 937 | 564 | 0.00207 | 0.00624 | 0.0102 | 872 |
| 938 | 607.1 | 0.00129 | 0.00508 | 0.0633 | 162 |
| 939 | 535.1 | 0.000867 | 0.165 | 0.127 | 209 |
| 940 | 499 | 0.004 | 0.015 | 0.0224 | 1388 |
| 941 | 453.2 | 0.00962 | 0.0129 | 0.2 | 780 |
| 942 | 497 | 0.00314 | 0.00518 | 0.0417 | 1090 |
| 943 | 497 | 0.00223 | 0.00593 | 0.101 | 571 |
| 944 | 468 | 0.00102 | 0.00216 | 0.0696 | >400 |
| 945 | 503 | 0.00105 | 0.00709 | 0.0661 | 381 |
| 946 | 517 | 0.0268 | 0.0174 | 0.517 | 352 |
| 947 | 517.2 | 0.0282 | 0.0337 | 0.519 | 595 |
| 948 | 568 | 0.00304 | 0.0102 | 0.144 | 80.9 |
| 949 | 563 | 0.00245 | 0.0841 | 0.0588 | 336 |
| 950 | 557.2 | 0.0051 | 0.104 | 0.118 | 384 |
| 951 | 514 | 0.00233 | 0.0603 | 0.0497 | 915 |
| 952 | 578 | 0.00126 | 0.0108 | 0.00755 | 16.3 |
| 953 | 542.2 | 0.00028 | 0.00149 | 0.0267 | 61.9 |
| 954 | 521.2 | 0.00579 | 0.0144 | 0.00382 | 715 |
| 955 | 502.2 | 0.000805 | 0.00178 | 0.0501 | 48 |
| 956 | 476.1 | 0.000927 | 0.019 | <0.00203 | 341 |
| 957 | 463.2 | 0.000621 | 0.00616 | 0.00538 | 1255 |
| 958 | 534.1 | 0.0012 | 0.04 | 0.0662 | 354 |
| 959 | 497.1 | 0.0000901 | 0.00152 | <0.00203 | 44.1 |
| 960 | 520.1 | 0.000507 | 0.00624 | 0.00422 | >400 |
| 961 | 472 | 0.012 | 0.0214 | 0.0223 | 171 |
| 962 | 467.4 | 0.01 | 0.104 | 0.0199 | 21 |

TABLE 13C

| Ex. No. | Oberved [M + H]+ | IC$_{50}$ IP (μM) BACE1 enzyme | IC$_{50}$ IP (μM) BACE1 cell | IC$_{50}$ IP (μM) BACE2 enzyme | IC$_{50}$ IP (μM) CatD |
|---|---|---|---|---|---|
| 963 | 563 | 0.000194 | 0.0026 | 0.0631 | 267 |
| 964 | 450.2 | 0.000737 | 0.00154 | 0.00887 | 98.9 |
| 965 | 470 | 0.000618 | 0.00287 | 0.0638 | >400 |
| 966 | 476 | 0.000385 | 0.00182 | 0.0419 | 735 |
| 967 | 501 | 0.00011 | 0.000539 | 0.0149 | 269 |
| 968 | 514 | 0.129 | 0.12 | 1.1 | >400 |
| 969 | 477 | 0.000197 | 0.000687 | 0.0115 | 158 |
| 970 | 490 | 0.0085 | 0.021 | 0.333 | >400 |
| 971 | 496 | 0.00522 | 0.0185 | 0.38 | 611 |
| 972 | 581 | 0.000454 | 0.00455 | 0.0794 | 138 |
| 973 | 513 | 0.000404 | 0.00192 | 0.0476 | 1568 |
| 974 | 569.1 | 0.00132 | 0.00257 | 0.014 | 14.5 |
| 975 | 488 | 0.000565 | 0.00551 | 0.0562 | 212 |

TABLE 13C-continued

| Ex. No. | Oberved [M + H]+ | IC50 IP (μM) BACE1 enzyme | IC50 IP (μM) BACE1 cell | IC50 IP (μM) BACE2 enzyme | IC50 IP (μM) CatD |
|---|---|---|---|---|---|
| 976 | 541 | 0.000527 | 0.0101 | 0.268 | 260 |
| 977 | 527 | 0.000782 | 0.00439 | 0.0876 | 577 |
| 978 | 483 | 0.000344 | 0.000648 | 0.0195 | >400 |
| 979 | 492 | 0.000315 | 0.000859 | 0.0201 | >400 |
| 980 | 559.1 | 0.000455 | 0.000747 | 0.013 | 19.8 |
| 981 | 459.1 | 0.00315 | 0.00074 | 0.0575 | 106 |
| 982 | 575 | 0.000679 | 0.00329 | 0.032 | 175 |
| 983 | 573.1 | 0.00151 | 0.00736 | 0.174 | 172 |
| 984 | 543 | 0.000858 | 0.00125 | 0.0217 | 1111 |
| 985 | 448 | 0.000276 | 0.000709 | <0.00203 | 1119 |
| 986 | 481 | 0.00113 | 0.00141 | 0.00598 | 172 |
| 987 | 469 | 0.00014 | 0.000229 | 0.0079 | 49.9 |
| 988 | 470 | 0.0216 | 0.0532 | 0.336 | >400 |
| 989 | 475.2 | 0.000518 | 0.00067 | 0.0406 | 174 |
| 990 | 454.2 | 0.02075 | 0.026 | 0.00465 | 67 |
| 991 | 571 | 0.000297 | 0.000265 | 0.0097 | 664 |
| 992 | 571 | 0.000776 | 0.000338 | 0.0125 | 954 |
| 993 | 509 | 0.00048 | 0.000566 | 0.061 | 255 |
| 994 | 525 | 0.00069 | 0.00116 | 0.0689 | 215 |
| 995 | 514 | 0.10105 | 0.164 | 1.77 | 1943 |
| 996 | 514 | 0.123 | 0.1202 | 0.807 | 1636 |
| 997 | 569.3 | 0.000893 | 0.00672 | 0.0509 | 9.48 |
| 998 | 569.3 | 0.000146 | 0.0017 | 0.0754 | >400 |
| 999 | 563.1 | 0.00009 | 0.00613 | 0.0755 | 180 |
| 1000 | 527.2 | 0.00007 | 0.000921 | 0.00345 | 1003 |
| 1001 | 529 | 0.000059 | 0.00589 | 0.356 | 492 |
| 1002 | 555 | 0.00177 | 0.00484 | 0.165 | 82.7 |
| 1003 | 545 | 0.00565 | 0.021 | 0.48 | 297 |
| 1004 | 543 | 0.0001 | 0.000324 | 0.00235 | 14.9 |
| 1005 | 525.2 | 0.000384 | 0.00108 | 0.00516 | 72.1 |
| 1006 | 529.2 | 0.000885 | 0.000575 | 0.0213 | 7.08 |
| 1007 | 454 | 0.00702 | 0.73 | 0.00484 | 460 |
| 1008 | 514 | 0.00471 | 0.0022 | 0.195 | >400 |
| 1009 | 488 | 0.000695 | 0.00254 | 0.0436 | 936 |
| 1010 | 489.1 | 0.0032 | 0.0309 | 0.0669 | >400 |
| 1011 | 469.1 | 0.000465 | 0.00353 | 0.00908 | 741 |
| 1012 | 498 | 0.00399 | 0.111 | 0.095 | >400 |
| 1013 | 532 | 0.00139 | 0.00144 | 0.0541 | 959 |
| 1014 | 532 | 0.000879 | 0.00289 | 0.192 | 2555 |
| 1015 | 512.1 | 0.00497 | 0.00686 | 0.185 | >400 |
| 1016 | 468 | 0.00104 | 0.0119 | 0.00764 | >400 |
| 1017 | 483.1 | 0.000266 | 0.000106 | 0.00982 | 22.5 |
| 1018 | 499.2 | 0.00116 | 0.00113 | 0.00651 | 211 |
| 1019 | 543.2 | 0.000937 | 0.00109 | 0.073 | 271 |
| 1020 | 504.2 | 0.00118 | 0.0248 | 0.0998 | 783 |
| 1021 | 490 | 0.000918 | 0.0116 | 0.0808 | 776 |
| 1022 | 506 | 0.00572 | 0.0331 | 0.579 | >400 |
| 1023 | 508 | 0.00319 | 0.0135 | 0.204 | 1357 |
| 1024 | 508 | 0.00214 | 0.0222 | 0.313 | 884 |
| 1025 | 500 | 0.00169 | 0.0142 | 0.13 | 1697 |
| 1026 | 540 | 0.00496 | 0.0936 | 0.115 | 475 |
| 1027 | 436 | 0.0196 | 0.136 | 0.0565 | 981 |
| 1028 | 492 | 0.00195 | 0.0293 | 0.226 | 135 |
| 1029 | 506 | 0.00741 | 0.0541 | 0.459 | 1139 |
| 1030 | 490 | 0.00213 | 0.0414 | 0.072 | 243 |
| 1031 | 531 | 0.00107 | 0.152 | 0.0897 | 775 |
| 1032 | 531 | 0.00106 | 0.0323 | 0.0465 | 1017 |
| 1033 | 526 | 0.00105 | 0.101 | 0.0323 | 230 |
| 1034 | 533 | 0.0014 | 0.0109 | 0.0118 | 1395 |
| 1035 | 526 | 0.00258 | 0.022 | 0.1 | 1207 |
| 1036 | 476 | 0.00184 | 0.0445 | 0.0681 | 1275 |
| 1037 | 532 | 0.000803 | 0.0467 | 0.128 | 785 |
| 1038 | 464 | 0.00363 | 0.0364 | 0.0947 | 1295 |
| 1039 | 520 | 0.000941 | 0.00251 | 0.171 | 725 |
| 1040 | 545 | 0.000426 | 0.00284 | 0.0555 | 212 |
| 1041 | 553.2 | 0.00176 | 0.00692 | 0.222 | 324 |
| 1042 | 501 | 0.000317 | 0.00621 | 0.0159 | 55.6 |
| 1043 | 470 | 0.000352 | 0.0138 | 0.00931 | 196 |
| 1044 | 528 | 0.001 | 0.017 | 0.0987 | 291 |
| 1045 | 577.2 | 0.00181 | 0.0738 | 0.288 | 194 |
| 1046 | 488 | 0.00037 | 0.0162 | 0.0307 | 43.5 |
| 1047 | 484 | 0.0054 | 0.015 | 0.189 | >400 |
| 1048 | 470 | 0.0078 | 0.0095 | 0.152 | — |
| 1049 | 486 | 0.0054 | 0.0035 | 0.180 | >400 |
| 1050 | 502 | 0.030 | 0.035 | 1.19 | >400 |
| 1051 | 472 | 0.033 | 0.035 | 0.345 | >400 |
| 1052 | 464 | 0.016 | 0.0083 | 0.146 | >400 |
| 1053 | 472 | 0.0059 | 0.0029 | 0.108 | 1420 |
| 1054 | 486 | 0.0014 | 0.011 | 0171 | 862 |
| 1055 | 488 | 0.0079 | 0.022 | 0.498 | 1330 |
| 1056 | 474 | 0.0014 | 0.018 | 0.317 | 1240 |
| 1057 | 482 | 0.0023 | 0.0033 | 0.158 | >400 |
| 1058 | 488 | >0.016 | 0.010 | 0.498 | >400 |
| 1059 | 502 | 0.011 | 0.020 | 0.069 | 1320 |
| 1060 | 488 | 0.0074 | 0.0076 | 0.130 | >400 |
| 1061 | 504 | 0.0047 | 0.0039 | 0.170 | >400 |
| 1062 | 520 | >16 | 0.022 | 0.658 | >400 |
| 1063 | 490 | 0.037 | 0.100 | 0.555 | >400 |
| 1064 | 482 | 0.0027 | 0.0047 | 0.081 | >400 |
| 1065 | 514 | 0.000256 | 0.00294 | 0.0636 | 1578 |
| 1066 | 449 | 0.00161 | 0.00347 | 0.00099 | >400 |
| 1067 | 474 | 0.0264 | 0.0238 | 1.63 | 2051 |
| 1068 | 492 | 0.0165 | 0.0271 | 1.51 | >400 |
| 1069 | 506 | 0.0174 | 0.2145 | 0.878 | 1058 |
| 1068 | 472.1 | 0.000178 | 0.000127 | 0.0136 | 170 |
| 1071 | 513 | 0.000768 | 0.00025 | 0.0304 | 1429 |
| 1072 | 476 | 0.00032 | 0.000345 | 0.00983 | 143 |
| 1073 | 520 | 0.000842 | 0.00323 | 0.0515 | 1296 |
| 1074 | 519 | 0.00057 | 0.000489 | 0.0167 | 1328 |
| 1075 | 534 | 0.00152 | 0.00153 | 0.198 | 1250 |

The present invention also provides methods for making compounds of Formulas I-III, and sub-formulas therein. For example, the compounds of the present invention and additional examples may be made by the following methods, as similarly described in the literature references mentioned below.

In one embodiment of the invention, there is provided a method of making a compound of Formula I-A having a general structure of

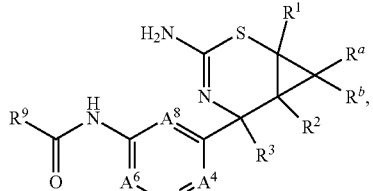

the method comprising the step of reacting a compound 20

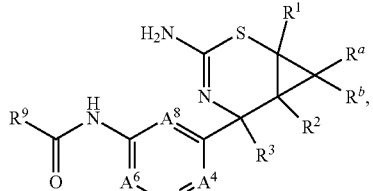

wherein $A^4$, $A^5$, $A^6$, $A^8$, each of $R^a$, $R^b$, $R^1$, $R^2$ and $R^3$ of Formula I-A are as defined herein, with a compound having the structure $R^9$—COOH, wherein $R^9$ is as defined herein, to make a compound of Formula I-A.

In one embodiment of the invention, there is provided a method of making a compound of Formula I-B having a general structure of

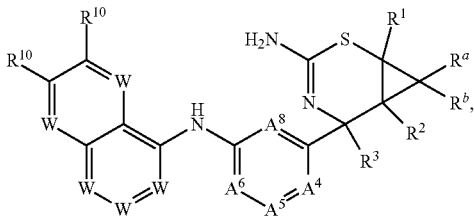

the method comprising the step of reacting a compound 20

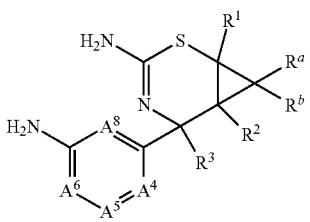

wherein $A^4$, $A^5$, $A^6$, $A^8$, each of $R^a$, $R^b$, $R^1$, $R^2$ and $R^3$ of Formula I-B are as defined herein, with a compound having the structure

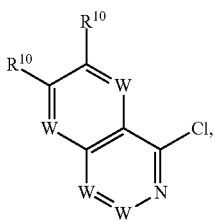

wherein each W and each $R^{10}$ are, independently, as defined herein, in the presence of acid to make a compound of Formula I-B.

In another embodiment of the invention, there is provided a method of making a compound of Formula II having a general formula of

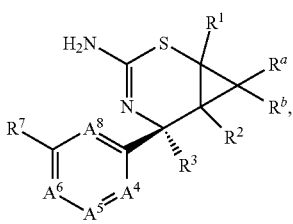

the method comprising the step of reacting a compound 30

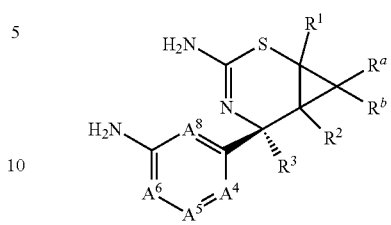

wherein $A^4$, $A^5$, $A^6$, $A^8$, each of $R^a$, $R^b$, $R^1$, $R^2$ and $R^3$ of Formula II are as defined herein, with a compound having either structure of $R^9$—COOH in the presence of a base or $R^9$—Cl in the presence of an acid or phosphonic anhydride, wherein $R^9$ is as defined herein, to make a compound of Formula II.

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

Salts, including pharmaceutically acceptable salts, of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary and suitable salts, and their preparation, are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the H+ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., $Et_2O$ and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including $CH_3CN$; halogenated hydrocarbons, including $CH_2Cl_2$, $CHCl_3$ and $CCl_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, $H_2SO_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

The invention further encompasses "intermediate" compounds, including structures produced from the synthetic procedures described, whether isolated or generated in-situ and not isolated, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

The invention also provides new starting materials and/or intermediates, as well as processes for the preparation thereof. In select embodiments, such starting materials are used and reaction conditions so selected as to obtain the desired compound(s). Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. While shown without respect to stereochemistry in Formulas I-III, the present invention includes such optical isomers and diastereomers, as well as the racemic and resolved, enantiomerically pure R and S stereoisomers, as well as other mixtures of R and S stereoisomers and pharmaceutically acceptable salts thereof.

The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. All such isomeric forms of such compounds are expressly included in the present invention.

The compounds of the invention may also be represented in multiple tautomeric forms. Tautomers often exist in equilibrium with each other, and interconvert under environmental and physiological conditions. The compounds of the invention may also occur in cis- or trans- or E- or Z-double bond isomeric forms. The invention expressly includes all tautomeric forms of the compounds described herein.

All crystal forms of the compounds described herein are expressly included in the present invention.

The present invention also includes isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$ (deuterium), $^{3}H$ (tritium), $^{13}C$, $^{14}C$, $^{15}N$, $^{16}O$, $^{17}O$, $^{31}P$, $^{32}P$, $^{35}S$, $^{18}F$, and $^{36}Cl$.

Compounds of the present invention that contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Deuterated ($^{2}H$), Tritiated ($^{3}H$) and carbon-14, i.e., $^{14}C$, isotopes are particularly preferred for their ease of preparation and detection. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of this invention can generally be prepared by substituting a readily available isotopically labeled reagent for a non-isotopically labeled reagent.

BIOLOGICAL EVALUATION

The compounds of the invention may be modified by appending appropriate functionalities to enhance selective biological properties. The pharmacokinetic and pharmacodynamic properties of a compound relate, directly and indirectly, to the ability of the compound to be effective for its intended use.

Although the pharmacological properties of the compounds of the invention (Formulas I-III) vary with structural change, in general, activity possessed by compounds of Formulas I-III may be demonstrated both in vitro as well as in vivo. The following exemplified pharmacological assays have been carried out with the compounds according to the invention, to assess and characterize the compound's ability to modulate BACE activity and to regulate the cleavage of amyloid beta precursor protein, thereby reducing or inhibiting the production of amyloid beta.

In Vitro Enzymatic BACE1 and BACE2 FRET (Fluorescence Resonance Energy Transfer) Assays (Enzyme Assay Data in the Example Tables)

The cDNAs for both human recombinant BACE1 and BACE2 with C-terminal 6-His Tags were cloned into transient protein expression vectors, which were subsequently transfected into mammalian cell lines. These recombinant proteins were further purified using Ni-NTA affinity chromatography (Qiagen). The assay buffer used in these screens is 0.05 M acetate, pH 4.5, 8% DMSO final, 100 uM genapol (which is a nonionic detergent, below its Critical Micelle Concentration). The Beta Secretase enzyme (0.02 nM for BACE1 and 0.64 nM for BACE2) is pre-incubated for one hour with inhibitors, typically in about 1 uL of DMSO according to a serial dilution, are added thereto. This assay is effectively started by the addition of FRET substrate (50 nM) and the combination is incubated for one hour. The FRET assay is terminated by addition of Tris buffer, which raises the pH to neutrality, and the fluorescence is determined. The FRET substrate is a peptide with commercially available fluorophore and quencher, on opposite sides of the BACE cleavage site. Proteolytic cleavage of the FRET substrate releases quenching of fluorescence (excitation 488 nm and emission 590 nm).

Where available, the in-vitro BACE FRET enzyme data for each of the Examples is provided in Tables 13A, 13B, and 13C.

In Vitro BACE-1 Cell-Based Assay

The cell-based assay measures inhibition or reduction of Aβ40 in conditioned medium of test compound treated cells expressing amyloid precursor protein. Cells stably expressing Amyloid Precursor Protein (APP) were plated at a density of 40K cells/well in 96 well plates (Costar). The cells were cultivated for 24 hours at 37° C. and 5% $CO_2$ in DMEM supplemented with 10% FBS. The test compounds were then added to cells in 10-point dose response concentrations with the starting concentration being either 100 μM or 10 μM. The compounds were diluted from stock solutions in DMSO and the final DMSO concentration of the test compounds on cells was 0.1%. After 24 h of incubation with the test compounds the supernatant conditioned media was collected and the Aβ40 levels were determined using a sandwich ELISA. The $IC_{50}$ of the compound was calculated from the percent of control or percent inhibition of Aβ40 as a function of the concentration of the test compound.

The sandwich ELISA to detect Aβ40 was performed in 96 well microtiter plates, which were pre-treated with goat anti-rabbit IgG (Pierce). The capture and detecting antibody pair that were used to detect Aβ40 from cell supernatants were affinity purified pAb40 (Biosource) and biotinylated 6E10 (Signet Labs Inc.), respectively. The optimal concentration for the pAb40 antibody was 3 μg/ml in Superblock/TBS (Pierce) that was supplemented with 0.05% Tween 20 (Sigma). Optimal concentration for the detection antibody 6E10-biotinylated was 0.5 μg/ml in Superblock/TBS (Pierce) that had been supplemented with 2% normal goat serum and 2% normal mouse serum. Cellular supernatants were incubated with the capture antibody for 3 h at 4° C., followed by 3 wash steps in TBS-tween (0.05%). The detecting antibody incubation was for 2 h at 4° C., again followed by the wash steps as described previously. The final readout of the ELISA is Time-Resolved Fluorescence (counts per minute) using Delfia reagents Streptavidin-Europium and Enhancement solutions (Perkin Elmer) and the Victor 2 multilabel counter (Perkin Elmer).

Where available, the in-vitro BACE cell based data for each of the Examples is provided in Tables 13A, 13B, and 13C.

In Vitro Enzymatic Cathepsin D (Cat D) FRET (Fluorescence Resonance Energy Transfer) Assay Recombinant Cat D was expressed in CHO cells. The assay buffer for CathepsinD is 0.05 M citrate pH 3.5, 10% DMSO final, 5 mM CHAPS. The Cat D enzyme (9 nM) is pre-incubated for one hour with inhibitors, typically in about 1 uL of DMSO according to a serial dilution, is added thereto. The assays are effectively started by the addition of different FRET substrates (20 nM for Cat D) and the combination is incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. The Cat D substrate peptide sequence is based on sequence #1 of Table 1 from Gulnik et al. FEBS Letters v413 p 379-384 1997. Proteolytic cleavage of the FRET substrate releases quenching of fluorescence (Cat D excitation 500 nm and emission 580 nm).

Alternatively, a Cat D assay may also be run according to the procedure described in the article, Characterization of new fluorogenic substrates for the rapid and sensitive assay of cathepsin E and cathepsin D, *J. Biochem.*, 125:1137, 1999. In addition, the cathepsin D and cathepsin E assays are described in PCT publication WO2011069934. This WIPO publication describes BACE inhibitor compounds having an amide linker connecting two aromatic groups with extremely poor cathepsin D and/or cathepsin E inhibitory activity (see Table 2).

Where available, the in-vitro Cat D FRET assay data for each of the Examples, conducted by the first procedure, is provided. For example, the compound of Example 43 has a Cat D $IC_{50}$ value of >400 uM. As shown by the high micromolar Cat D data (very poorly active or inactive against cat D), the compounds of the present invention possess the unexpected property of little to no ability to inhibit the activity of Cat D. It was surprisingly found that incorporation of an amino- or amido-linker between the core of the compounds and the $R^7$ and $R^9$ groups, respectively, has conferred a significantly reduced, poor or no potency on the protein Cat D. Thus, with this surprising selectivity profile, the compounds of the present invention are believed to minimize, reduce or completely eliminate any risk of retinal atrophy and abnormal development of the eye and of the retinal pigmented epithelium as it relates to the normal function and activity of Cat D.

In Vivo Inhibition of Beta-Secretase

Several animal models, including mouse, rat, dog, and monkey, may be used to screen for inhibition of beta-secretase activity in vivo following administration of a test compound sample. Animals used in this invention can be wild type, transgenic, or gene knockout animals. For example, the Tg2576 mouse model, prepared and conducted as described in Hsiao et al., 1996, *Science* 274, 99-102, and other non-transgenic or gene knockout animals are useful to analyze in vivo inhibition of Amyloid beta peptide (Abeta) production in the presence of inhibitory test compounds. Generally, 2 to 18 month old Tg2576 mice, gene knockout mice or non-transgenic animals are administered test compounds formulated in vehicles, such as cyclodextran, phosphate buffers, hydroxypropyl methylcellulose or other suitable vehicles. One to twenty-four hours following the administration of compound, animals are sacrificed, and brains as well as cerebrospinal fluid (CSF) and plasma are removed for analysis of A-beta levels and drug or test compound concentrations (Dovey et al., 2001, *Journal of Neurochemistry*, 76, 173-181) Beginning at time 0, animals are administered by oral gavage, or other means of delivery such as intravenous injection, an inhibitory test compound of up to 100 mg/kg in a standard, conventional formulation, such as 2% hydroxypropyl methylcellulose, 1% Tween80. A separate group of animals receive 2% hydroxypropyl methylcellulose, 1% Tween80 alone, containing no test compound, and serve as a vehicle-control group. At the end of the test period, animals are sacrificed and brain tissues, plasma or cerebrospinal fluid are collected. Brains are either homogenized in 10 volumes (w/v) of 0.2% diethylamine (DEA) in 50 mM NaCl (Best et al., 2005, *Journal of Pharmacology and Experimental Therapeutics*, 313, 902-908), or in 10 volumes of 0.5% TritonX-100 in Tris-buffered saline (pH at about 7.6). Homogenates are centrifuged at 355,000 g, 4° C. for 30 minutes. CSF or brain supernatants are then analyzed for the presence of A-beta peptide by specific sandwich ELISA assays based on ECL (Electrochemiluminescence) technology. For example, rat Abeta40 is measured using biotinylated-4G8 (Signet) as a capture antibody and Fab40 (an in-house antibody specific to the C-terminal of Abeta40) as a detection antibody. For example, 4 hours after administration of 30 mg/kg oral dose of the test compound in 2% hydroxypropyl methylcellulose, 1% Tween80 (pH2.2) to 200 g male Sprague Dawley rats, amyloid beta peptide levels are measured for reduction by X % and Y % in cerebrospinal fluid and brain, respectively, when compared to the levels measured in the vehicle-treated or control mice.

Actual vehicles used: Oral: 2% HPMC, 1% Tween80, pH 2.2

IV: 5% EtOH, 45% Propylene Glycol in 5% Dextrose

The compounds of the invention may be shown to reduce the formation and/or deposition of amyloid beta peptide in the cerebrospinal fluid (CSF) as well as in the brain of a mouse or rat at either 3 mpk, 10 mpk or 30 mpk (mpk=mg compound per kg weight of the animal) dosing concentrations after 4 h. The following examples in Table 14A, Table 14B, and Table 14C exhibited the following percent Abeta 40 reductions at 10 mpk (unless otherwise noted) in the CSF and brain of the rat, respectively.

TABLE 14A

| Ex. No. | % Aβ 40 reduction in rat CSF at 10 mpk | % Aβ 40 reduction in rat brain at 10 mpk |
|---|---|---|
| 1 | 58 | 28 |
| 2 | 72 | 67 |
| 4 | 40 | 18 |
| 5 | 43 | 19 |
| 6 | 78 | 68 |
| 11 | 41 (3 mpk) | 25 (3 mpk) |
| 12 | 75 | 65 |
| 13 | 70 | 56 |
| 20 | 80 | 76 |
| 21 | 61 | 40 |
| 23 | 70 (3 mpk) | 61 (3 mpk) |
| 26 | 38 | 34 |
| 28 | 42 | 26 |
| 33 | 65 | 53 |
| 35 | 63 | 50 |
| 36 | 74 | 46 |
| 38 | 66 | 44 |
| 39 | 50 | 23 |
| 45 | 17 | 0 |
| 46 | 73 | 67 |
| 49 | 24 | 14 |
| 51 | 23 (3 mpk) | 17 (3 mpk) |
| 52 | 16 | 0 |
| 54 | 18 | 19 |
| 56 | 50 | 32 |
| 72 | 85 | 84 |
| 82 | 48 | 23 |
| 84 | 40 | 8 |
| 95 | 69 | 60 |

TABLE 14B

| Ex. No. | % Aβ 40 reduction in rat CSF at 10 mpk | % Aβ 40 reduction in rat brain at 10 mpk |
|---|---|---|
| 707 | 27 | 25 |
| 712 | 52 | 32 |
| 708 | 13 | −4 |
| 660 | 38 | 26 |
| 689 | 38 | 10 |
| 678 | 40 | 11 |
| 662 | 40 | 37 |
| 679 | 20 | 6 |
| 680 | 30 | 8 |
| 631 | 52 | 47 |
| 698 | 15 | −7 |
| 931 | 8 | 3 |
| 770 | 22 | 6 |

TABLE 14B-continued

| Ex. No. | % Aβ 40 reduction in rat CSF at 10 mpk | % Aβ 40 reduction in rat brain at 10 mpk |
|---|---|---|
| 941 | 41 | 2 |
| 911 | 21 | 20 |
| 803 | 59 | 45 |
| 915 | 51 | 47 |
| 945 | 68 | 55 |
| 924 | 84 | 76 |
| 913 | 84 | 78 |
| 612 | 84 | 82 |
| 697 | 35 | 13 |
| 645 | 53 | 34 |
| 627 | 59 | 50 |
| 628 | 59 | 50 |
| 921 | 70 | 64 |
| 795 | 76 | 70 |
| 843 | 51 | 16 |
| 842 | 51 | 25 |
| 841 | 58 | 44 |
| 705 | 28 | 1 |
| 828 | 24 | 10 |
| 831 | 49 | 16 |
| 727 | 38 | 18 |
| 827 | 41 | 19 |
| 728 | 31 | 23 |
| 808 | 44 | 26 |
| 812 | 52 | 38 |
| 815 | 50 | 43 |
| 802 | 59 | 50 |
| 813 | 68 | 50 |
| 805 | 59 | 53 |
| 806 | 70 | 65 |
| 801 | 74 | 68 |
| 814 | 76 | 68 |
| 823 | 78 | 78 |
| 834 | 83 | 83 |
| 807 | 80 (3 mpk) | 66 (3 mpk) |
| 810 | 79 (3 mpk) | 74 (3 mpk) |

TABLE 14C

| Ex. No. | % Aβ 40 reduction in rat CSF at 10 mpk | % Aβ 40 reduction in rat brain at 10 mpk |
|---|---|---|
| 965 | 33 | 20 |
| 966 | 67 | 68 |
| 969 | 79 (3 mpk) | 79 (3 mpk) |
| 976 | 36 | 16 |
| 1021 | 44 | 25 |
| 1039 | 13 | 16 |

INDICATIONS

According to the amyloid cascade hypothesis, cerebral deposition of amyloid-beta peptide (Aβ) is critical for Alzheimer's disease (AD) pathogenesis. Aβ generation is initiated when β-secretase (BACE1) cleaves the amyloid precursor protein. De Meyer et al re-affirm the believed role which the accumulation of beta-amyloid protein (A-beta) in cerebral spinal fluid (CSF) in a subject plays in the progression of symptoms, initially revealed as mild cognitive impairment, which ultimately leads to AD. *Arch Neurol.* 67(8):949-956, 2010. Amyloid-b (Aβ) peptides generated from amyloid precursor protein (APP) by proteolytic cleavage, such as by aspartyl protease enzymes including beta-secreatase (BACE) and gamma-secretase, likely play a causal role in AD pathogenesis (Tanzi and Bertram, *Cell*, (120): 545-555, 2005; Walsh and Selkoe, *Neuron*, (44): 181-193, 2004). Although the precise mechanisms of Aβ toxicity are unclear, oligomeric forms of Aβ may contribute to cognitive decline by altering synaptic structure and function (Palop and Mucke, *Nat. Neuroscience*, (13): 812-818, 2010; Selkoe, *Behavioral Brain Res.*, (192): 106-113, 2008; Shankar et al., *Nat. Medicine* (14): 837-842, 2008). Transgenic mouse models that overexpress mutant APP and produce high levels of Ab show amyloid plaque deposition, synaptic deficits, learning and memory impairments, and other behavioral abnormalities (Games et al., *Nature*, (373): 523-527, 1995; Götz et al., *Molecular Psychiatry* (9): 664-683, 2004; Hsia et al., *Proc. Natl. Academy of Science* USA (96): 3228-3233, 1999; Hsiao et al., *Science* (274): 99-102, 1996, citing Harris et al, *Neuron* (68): 428-441, 2010).

For more than a decade, BACE1 has been a prime target for designing drugs to prevent or treat AD. However, development of such agents has turned out to be extremely challenging, with major hurdles in cell penetration, oral bioavailability/metabolic clearance, and brain access.

MK-8931, a small molecule inhibitor of BACE (structure unknown) was tested in a two-part randomised, double-blind, placebo-controlled phase 1 clinical trial in 88 healthy individuals (18-45 years old). MK-8931 seemed to be generally well tolerated (66 patients), and no serious adverse events were reported. A major goal of the trial was to determine whether MK-8931 was able to enter the brain and block β secretase. To monitor this, biomarkers of BACE1 activity in the CSF were measured, including Aβ40 and Aβ42, as was soluble peptide APP (sAPPβ), a direct product of BACE1 cleavage of APP. MK-8931 significantly reduced CSF Aβ concentrations in a sustained and dose-dependent manner. At 36 h post-dose, a single dose of 100 mg reduced CSF Aβ40 concentrations by 75% and a single dose of 550 mg by 92%. Similar reductions of CSF concentrations of Aβ42 and sAPPβ, the BACE1-cleaved ectodomain of APP, were also observed. Vassar & Yan, *Lancet Neurology*, 13:319-329 (2014). Currently, MK-8931 is enrolling mild-to-moderate Alzheimer's Disease patients in a Ph 2/3 trial; and enrolling participants with prodomal Alzheimer's disease in a Ph III safety and efficacy trial. (US clinical trials; Merck Newsroom, 2014).

Bapineuzamab, a monoclonal amino-terminus specific anti-amyloid antibody was in Phase III clinical trials for the treatment of AD. *Alzheimer's Research & Therapy*, 1:2, 2009. Each of the known genetic causes of AD is linked to A-beta. Dementia, Down's Syndrome to APP over-production, are all believed to be linked to the deposition of A-beta on the brain. With methods for identifying brain amyloid deposition, positron emission scanning (PET) and CSF measurements of Ab42, identification of AD suffering individuals needing treatment is becoming easier and more common. It is firmly believed that by reducing the formation of A-beta, one can begin to pre-treat AD. Vassar et al, *Journal of Neuroscience*, 29 (41):12787-12794, 2009. One published pathway for treatment of AD is inhibition of beta-secretase. Tirrell, *Bloomberg News, The Boston Globe*, Jan. 7, 2010.

The US biotech company CoMentis has been developing an orally bioavailable small molecule CTS-21166, a highly potent, highly selective and efficacious brain-penetrating beta-secretase inhibitor. CoMentis successfully completed a Phase I study of CTS-21166 in healthy volunteers in 2008. Results indicated that CTS-21166 was safe, well-tolerated and pharmacodynamically active at all dose levels. All clinical subjects administered CTS-21166 showed area-under-curve (AUC) reduction in plasma A-Beta40 reductions ranging from 40-75%. Because of the urgent need for AD treatment, Phase II studies for CTS-2166 are planned, or ongoing, for AD patients. In preclinical studies, CTS-21166 exhibits excellent efficacy, selectivity, brain penetration and pharmacologic activity.

Using a fragment-based chemistry strategy, Eli Lilly and company generated LY2811376 [(S)-4-(2,4-difluoro-5-pyrimidin-5-yl-phenyl)-4-methyl-5,6-dihydro-4H-[1,3]thiazin-2-ylamine], an orally available non-peptidic BACE1 inhibitor that produces profound Aβ-lowering effects in animals. The biomarker changes obtained in preclinical animal models translate into man at doses of LY2811376 that were safe and well tolerated in healthy volunteers (US Ph I Clinical trial—www.clinicaltrials.gov). Prominent and long-lasting Aβ reductions in lumbar CSF were measured after oral dosing of 30 or 90 mg of LY2811376. This represents the first translation of BACE1-driven biomarker changes in CNS from preclinical animal models to man. Because of toxicology findings identified in longer-term preclinical studies, this compound is no longer progressing in clinical development. However, BACE1 remains a viable target because the adverse effects reported here were recapitulated in LY2811376-treated BACE1 KO mice and thus are unrelated to BACE 1 inhibition. The magnitude and duration of central Aβ reduction obtainable with BACE1 inhibition positions this protease as a tractable small-molecule target through which to test the amyloid hypothesis in man. *Neuroscience,* 31(46):16507-16515, 2011

The compounds of the invention have been shown to modulate, and specifically inhibit the activity of the beta-secretase enzyme, thereby reducing the A-beta peptide fragments. Accordingly, compounds of the invention are useful for, but not limited to, the prevention or treatment of beta-secretase related diseases, including Alzheimer's disease. The compounds of the invention have the ability to modulate the activity of beta secretase enzyme, thereby regulating the production of amyloid beta (Abeta peptide) and reducing the formation and deposition of Abeta peptide in both the cerebral spinal fluid as well as in the brain, resulting in a decrease of amyloid plaque on the brain. In one embodiment of the invention, there is provided a method of treating a disorder related to a beta-secretase enzyme in a subject, the method comprising administering to the subject an effective dosage amount of a compound of Formulas I, II, III, and sub-formulae thereof. In another embodiment, there is provided a method of reducing production of amyloid beta, and of reducing plaque formation on the brain. In another embodiment, there is provided a method for the treatment, prevention or amelioration of a disease or disorder characterized by the elevated beta-amyloid deposits or beta-amyloid levels in a subject, the method comprising administering to the subject a therapeutically effective amount of a compound according to any of Formulas I-III. In yet another embodiment, the invention provides a method of treating Alzheimer's disease, cognitive impairment including mild, moderate and/or severe, Down's Syndrome, cognitive decline, senile dementia, cerebral amyloid angiopathy or a neurodegenerative disorder. Accordingly, the compounds of the invention would be useful in therapy as CNS agents in treating neurological disorders and related conditions in subjects.

In one embodiment, the compounds of the invention are provided for the manufacture of a medicament, or a pharmaceutical composition, for the therapeutic and/or prophylactic treatment of diseases and disorders characterized by elevated levels of amyloid and/or β-amyloid oligomers and/or b-amyloid plaques and further deposits, including Alzheimer's Disease (AD). In another embodiment, the invention provides compounds, in effective dosage amounts, for the therapeutic and/or prophylactic treatment of AD. The compounds of the invention are useful for treating various stages and degrees of AD, including without limitation, mild, moderate and sever AD. Additionally, the compounds of the invention may be used to treat prodomal patients, i.e., subjects exhibiting the biomarkers and/or hallmarks of developing AD, without exhibiting any symptoms of AD.

Besides being useful for human treatment, the compounds of the invention may be useful for veterinary treatment of companion animals, exotic animals and farm animals, including mammals, rodents, and the like. For example, animals including horses, dogs, and cats may be treated with compounds provided herein.

FORMULATIONS AND METHOD OF USE

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating neurological disorders and beta-secretase mediated diseases with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, and even more advantageously between about 0.1 and about 10 mg/kg body weight may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable excipient, which includes diluents, carriers, adjuvants and the like (collectively referred to herein as "excipient" materials) as described herein, and, if desired, other active ingredients. A pharmaceutical composition of the invention may comprise an "effective amount" of a compound of the invention or an "effective dosage amount" of a compound of the invention. An "effective dosage amount" of a compound of the invention includes an amount less than, equal to or greater than an effective amount of the compound. For example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, advantageously from about 1 to 500 mg, and typically from about 5 to 150 mg. A suitable daily dose for a human or other mammal may vary widely depending on the condition of the patient and other factors, but, once again, can be determined using routine methods and practices.

For therapeutic purposes, the active compounds of this invention are ordinarily combined with one or more adjuvants or other "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, and preferably from about 0.1 to about 10 mg/kg.

For pulmonary administration, the pharmaceutical composition may be administered in the form of an aerosol or with an inhaler including dry powder aerosol.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents. Accordingly, in yet another embodiment of the present invention, there is provided a method of manufacturing a medicament, the method comprising combining an amount of a compound according to Formulas I-III with a pharmaceutically acceptable carrier to manufacture the medicament.

In yet another embodiment, the invention provides a method of manufacturing a medicament for the treatment of Alzheimer's disease, the method comprising combining an amount of a compound according to Formulas I-III with a pharmaceutically acceptable carrier to manufacture the medicament.

COMBINATIONS

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of beta-secretase, gamma-secretase and/or other reagents known in influence the formation and/or deposition of amyloid beta, otherwise responsible for the formation of plaque on the brain.

If formulated as a fixed dose, such combination products employ the compounds of this invention within the accepted dosage ranges. Compounds of Formulas I, II and III may also be administered sequentially with other known medicinal agents. The invention is not limited in the sequence of administration; compounds of the invention may be administered either prior to, simultaneous with or after administration of the known anti-inflammatory agent.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:
1. A compound of Formula I

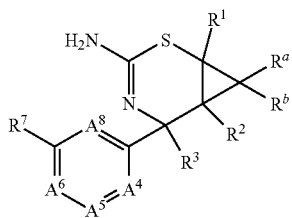

I or a stereoisomer, tautomer, hydrate, solvate or pharmaceutically acceptable salt thereof, wherein
$A^4$ is $CR^4$ or N;
$A^5$ is $CR^5$ or N;
$A^6$ is $CR^6$ or N;
$A^8$ is $CR^8$ or N, provided that no more than two of $A^4$, $A^5$, $A^6$ and $A^8$ is N;
each of $R^a$ and $R^b$, independently, is H, F, Cl, $C_{1-6}$-alkyl, $C_{2-4}$-alkenyl, $C_{2-4}$-alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$-alkenyl, $C_{2-4}$-alkynyl, and the $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;
$R^1$ and either $R^a$ or $R^b$ may optionally join to form a 5-membered saturated ring that includes one S heteroatom;
$R^1$ is H, F, Cl, $C_{1-6}$-alkyl, $C_{2-4}$-alkenyl, $C_{2-4}$-alkynyl, CN, —$CH_2OC_{1-6}$-alkyl, —$OC_{1-6}$-alkyl, —$S(O)_oC_{1-6}$-alkyl, —$NHC_{1-6}$-alkyl, —$C_{1-6}$-alkylNH$_2$, —$C_{1-6}$-alkyl-NHC$_{1-6}$-alkyl, —$C_{1-6}$-alkylNHC(O)OC$_{1-6}$-alkyl, —$C_{1-6}$-alkylNHC(O)NHC$_{1-6}$-alkyl, —$C_{1-6}$-alkylNHC(O)C$_{1-6}$-alkyl, —C(O)NH$_2$, —CH=CHC(O)NH$_2$, —CH=CHC(O)NHC$_{1-6}$-alkyl, —CH=CHC(O)N(C$_{1-6}$-alkyl)$_2$, —CH=CHC(O)NHC$_{1-6}$-alkyl-OC$_{1-6}$-alkyl, —CH=CHC(O)-heterocyclyl, —CH=C(CH$_3$)C(O)-heterocyclyl, —CH=CHC(O)$_2$H, —CH=CHC(O)OC$_{1-6}$-alkyl, —CH=CHCH$_2$OH, $C_{1-6}$-alkyl-C(O)NHC$_{1-6}$-alkyl, $C_{1-6}$-alkyl-C(O)N(C$_{1-6}$-alkyl)$_2$, —C(O)C$_{1-6}$-alkyl, —C(O)C$_{2-6}$-alkenyl, —C(O)OH, —C(O)OC$_1$-C$_6$-alkyl, —C(O)NHC$_{1-6}$-alkyl, —C(O)N(C$_{1-6}$-alkyl)$_2$, —C(O)NHC$_{3-6}$-cycloalkyl, —C(O)NHOC$_{1-6}$-alkyl, —C(O)N(C$_{1-6}$-alkyl)OC$_{1-6}$-alkyl, —C(O)-heterocyclyl, —$CH_2$-heteroaryl, or heteroaryl, wherein the heterocyclyl groups of the —CH=CHC(O)-heterocyclyl, —CH=C(CH$_3$)C(O)-heterocyclyl, and —C(O)-heterocyclyl groups are fully or partially saturated 3-, 4-, 5-, 6- or 7-membered monocyclic rings that include 1 heteroatom selected from N, O, or S if the ring is a 3-membered ring, that include 1 or 2 heteroatoms independently selected from N, O, or S if the ring is a 4- or 5-membered ring, and include 1, 2, or 3 heteroatoms independently selected from N, O, or S if the ring is a 6- or 7-membered ring, wherein the heteroaryl groups of the —$CH_2$-heteroaryl and heteroaryl groups is a 5- or 6-membered ring that includes 1, 2, 3, or 4 heteroatoms selected from N, O, or S, wherein each of the $C_{1-6}$-alkyl, $C_{2-4}$-alkenyl, $C_{2-4}$-alkynyl, and the $C_{1-6}$-alkyl, $C_{2-6}$-alkenyl, and $C_{3-6}$-cycloalkyl portion of —$CH_2OC_{1-6}$-alkyl, —$OC_{1-6}$-alkyl, —$S(O)_oC_{1-6}$-alkyl, —$NHC_{1-6}$-alkyl, $C(O)C_{1-6}$-alkyl, —$C(O)C_{2-6}$-alkenyl, —$C(O)NHC_{1-6}$-alkyl, —$C(O)N(C_{1-6}$-alkyl)$_2$, —$C(O)NHC_{3-6}$-cycloalkyl, —CH=CHC(O)NHC$_{1-6}$-alkyl and $C_{1-6}$-alkyl-C(O)NHC$_{1-6}$-alkyl groups are optionally substituted with 1-4 substituents of F, CN, methyl, oxo, or OH, and further wherein each of the heterocyclyl groups of the —CH=CHC(O)-heterocyclyl, —CH=C(CH$_3$)C(O)-heterocyclyl, and —C(O)heterocyclyl groups is optionally substituted with 1-4 substituents independently selected from F, methyl, OH, or OCH$_3$, and further wherein each of the heteroaryl groups of the —$CH_2$-heteroaryl and heteroaryl groups is optionally substituted with 1-3 substituents independently selected from halo, methyl, or OH;
$R^2$ is H, F, Cl, $C_{1-6}$-alkyl, $C_{2-4}$-alkenyl, $C_{2-4}$-alkynyl, CN, —$CH_2OC_{1-6}$-alkyl, —$OC_{1-6}$-alkyl, —$S(O)_oC_{1-6}$-alkyl, —$NHC_{1-6}$-alkyl, —C(O)NH$_2$, —CH=CHC(O)NHC$_{1-6}$-alkyl, —CH=CHC(O)$_2$H, —CH=CHCH$_2$OH, $C_{1-6}$-alkyl-C(O)NHC$_{1-6}$-alkyl, —$C(O)C_{1-6}$-alkyl or —$C(O)C_{2-6}$-alkenyl, wherein each of the $C_{1-6}$-alkyl, $C_{2-4}$-alkenyl, $C_{2-4}$-alkynyl, and the $C_{1-6}$-alkyl and $C_{2-6}$-alkenyl portion of —$CH_2OC_{1-6}$-alkyl, —$OC_{1-6}$-alkyl, —$S(O)_oC_{1-6}$-alkyl, —$NHC_{1-6}$-alkyl, $C(O)C_{1-6}$-alkyl, —$C(O)C_{2-6}$-alkenyl, —CH=CHC(O)NHC$_{1-6}$-alkyl and $C_{1-6}$-alkyl-C(O)NHC$_{1-6}$-alkyl, are optionally substituted with 1-4 substituents of F, CN, oxo or OH;
$R^3$ is $C_{1-4}$-alkyl, $CH_2OC_{1-4}$-alkyl, $CH_2OH$, $C_{1-4}$-haloalkyl or cyclopropyl, wherein each of the $C_{1-4}$-alkyl, $CH_2OC_{1-4}$-alkyl, $C_{1-4}$-haloalkyl and cyclopropyl is optionally substituted with 1-4 F atoms;
each of $R^4$, $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl, $C(O)C_{1-4}$-alkyl, $C(O)OC_{1-4}$-alkyl, or $CH_2OH$;
$R^7$ is NH—$R^9$, —NH—C(=O)—$R^9$,

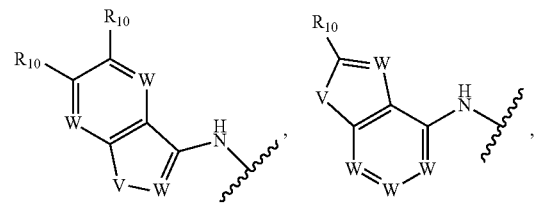

-continued

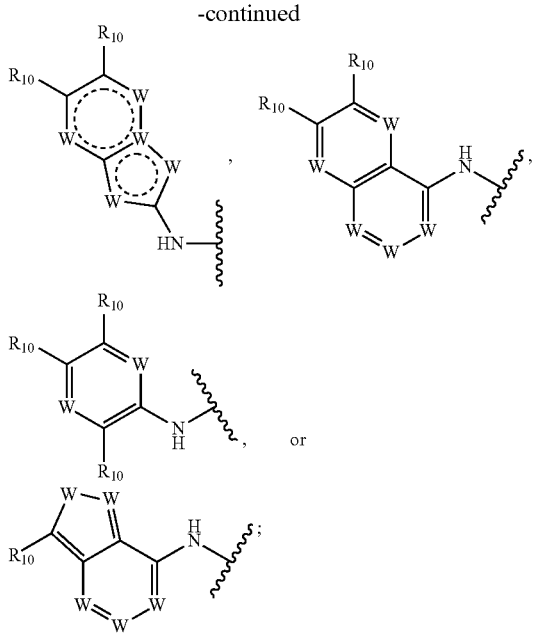

wherein V is NR$^{10}$, O or S; and
each W, independently, is CH, CF, CCl, CCH$_3$ or N;
R$^9$ is a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the ring is optionally substituted, independently, with 1-5 substituents of R$^{10}$;
each R$^{10}$, independently, is H, halo, haloalkyl, CN, OH, NO$_2$, NH$_2$, SF$_5$, acetyl, —C(O)NHC$_{1-6}$-alkyl, —OCH$_2$C(O)NHC$_{1-6}$-alkyl, —OCH$_2$C(O)N(C$_{1-6}$-alkyl)$_2$, —OCH$_2$CH$_2$-pyrrolidinonyl, oxo, cyclopropylmethoxy, 2-propynyloxy, 2-butynyloxy, 3-butynyloxy, 3-pentynyloxy, 2-pentyloxy, C$_{1-6}$-alkyl, C$_{2-6}$-alkenyl, C$_{2-6}$-alkynyl, C$_{3-6}$-cycloalkyl, C$_{1-6}$-alkylamino-, C$_{1-6}$-dialkylamino-, C$_{1-6}$-alkoxyl, —OC$_{2-6}$-alkenyl, C$_{1-6}$-thioalkoxyl, —OCH$_2$C$_{3-6}$-cycloalkyl, morpholinyl, pyrazolyl, isoxazolyl, dihydropyranyl, pyrrolyl, pyrrolidinyl, piperazinyl, oxetan-3-yl, imidazo-pyridinyl, dioxolyl, —O-heterocyclyl, or —OCH$_2$-heteroaryl, wherein the heterocyclyl of the —O-heterocyclyl group is a 3-, 4-, 5-, 6- or 7-membered monocyclic saturated ring that includes 1 heteroatom selected from N, O, or S if the heterocyclyl ring is a 3-membered ring, that includes 1 or 2 heteroatoms independently selected from N, O, or S if the heterocyclyl ring is a 4- or 5-membered ring, and includes 1, 2, or 3 heteroatoms independently selected from N, O, or S if the heterocyclyl ring is a 6- or 7-membered ring wherein the heteroaryl group of the —OCH$_2$-heteroaryl group is a 5- or 6-membered ring that includes 1, 2, 3, or 4 heteroatoms selected from N, O, or S, and further wherein each of the cyclopropylmethoxy, 2-propynyloxy, 2-butynyloxy, 2-pentyloxy, C$_{1-6}$-alkyl, C$_{2-6}$-alkenyl, C$_{2-6}$-alkynyl, C$_{3-6}$-cycloalkyl, C$_{1-6}$-alkylamino-, C$_{1-6}$-dialkylamino-, C$_{1-6}$-alkoxyl, C$_{1-6}$-thioalkoxyl, —OCH$_2$C$_{3-6}$-cycloalkyl, morpholinyl, pyrazolyl, isoxazolyl, dihydropyranyl, pyrrolidinyl, oxetan-3-yl, dioxolyl, or —OCH$_2$-heteroaryl is optionally substituted independently with 1-5 substituents of F, Cl, Br, CN, NO$_2$, NH$_2$, OH, oxo, CF$_3$, CHF$_2$, CH$_2$F, methyl, methoxy, ethyl, ethoxy, CH$_2$CF$_3$, CH$_2$CHF$_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, phenyl, C$_{1-3}$-alkylamino-, C$_{1-3}$-dialkylamino-, C$_{1-3}$-thioalkoxyl, oxazolyl, isoxazolyl, thiazolyl, isothiazolyl, thiadiazolyl, thienyl, furyl, pyrrolyl, tetrahydropyranyl, pyrrolidinyl, oxetan-2-yl, or oxetan-3-yl; and
the subscript o is selected from 0, 1, or 2.

2. The compound according to claim 1, or a stereoisomer or pharmaceutically acceptable salt thereof, wherein R$^1$ is a —CH$_2$-heteroaryl or a heteroaryl and the heteroaryl groups of the —CH$_2$-heteroaryl and heteroaryl is selected from triazolyl, oxazolyl, or isoxazolyl optionally substituted with 1 or 2 methyl groups.

3. The compound according to claim 1, or a stereoisomer or pharmaceutically acceptable salt thereof, wherein R$^{10}$ is a —OCH$_2$-heteroaryl and the heteroaryl group of the —OCH$_2$-heteroaryl is selected from an oxadiazolyl, thiadiazolyl, oxazolyl, isoxazolyl, thiazolyl, pyridinyl, or pyrimidinyl optionally substituted independently with 1 or 2 F, Cl, Br, or methyl groups.

4. A compound of Formula I

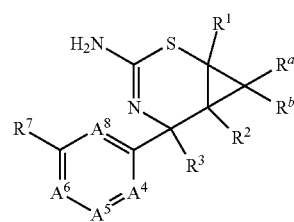

or a stereoisomer, tautomer, hydrate, solvate or pharmaceutically acceptable salt thereof, wherein
A$^4$ is CR$^4$ or N;
A$^5$ is CR$^5$ or N;
A$^6$ is CR$^6$ or N;
A$^8$ is CR$^8$ or N, provided that no more than two of A$^4$, A$^5$, A$^6$ and A$^8$ is N;
each of R$^a$ and R$^b$, independently, is H, F, Cl, C$_{1-6}$-alkyl, C$_{2-4}$-alkenyl, C$_{2-4}$-alkynyl, CN, —CH$_2$OC$_{1-6}$-alkyl, —OC$_{1-6}$-alkyl, —S(O)$_o$C$_{1-6}$-alkyl, —NHC$_{1-6}$-alkyl or —C(O)C$_{1-6}$-alkyl, wherein each of the C$_{1-6}$-alkyl, C$_{2-4}$-alkenyl, C$_{2-4}$-alkynyl, and C$_{1-6}$-alkyl portion of —CH$_2$OC$_{1-6}$-alkyl, —OC$_{1-6}$-alkyl, —S(O)$_o$C$_{1-6}$-alkyl, —NHC$_{1-6}$-alkyl and —C(O)C$_{1-6}$-alkyl are optionally substituted with 1-4 substituents of F, oxo or OH;
each of R$^1$ and R$^2$, independently, is H, F, Cl, C$_{1-6}$-alkyl, C$_{2-4}$-alkenyl, C$_{2-4}$-alkynyl, CN, —CH$_2$OC$_{1-6}$-alkyl, —OC$_{1-6}$-alkyl, —S(O)$_o$C$_{1-6}$-alkyl, —NHC$_{1-6}$-alkyl, —C(O)NH$_2$, —CH=CHC(O)NHC$_{1-6}$-alkyl, —CH=CHC(O)$_2$H, —CH=CHCH$_2$OH, C$_{1-6}$-alkyl-C(O)NHC$_{1-6}$-alkyl, —C(O)C$_{1-6}$-alkyl or —C(O)C$_{2-6}$-alkenyl, wherein each of the C$_{1-6}$-alkyl, C$_{2-4}$-alkenyl, C$_{2-4}$-alkynyl, and the C$_{1-6}$-alkyl and C$_{2-6}$-alkenyl portion of —CH$_2$OC$_{1-6}$-alkyl, —OC$_{1-6}$-alkyl, —S(O)$_o$C$_{1-6}$-alkyl, —NHC$_{1-6}$-alkyl, C(O)C$_{1-6}$-alkyl, —C(O)C$_{2-6}$-alkenyl, —CH=CHC(O)NHC$_{1-6}$-alkyl and C$_{1-6}$-alkyl-C(O)NHC$_{1-6}$-alkyl, are optionally substituted with 1-4 substituents of F, CN, oxo or OH;
R$^3$ is C$_{1-4}$-alkyl, CH$_2$OC$_{1-4}$-alkyl, CH$_2$OH, C$_{1-4}$-haloalkyl or cyclopropyl, wherein each of the C$_{1-4}$-alkyl, CH₂OC$_{1-4}$-alkyl, C$_{1-4}$-haloalkyl and cyclopropyl is optionally substituted with 1-4 F atoms;

each of R⁴, R⁵, R⁶ and R⁸, independently, is H, halo, haloalkyl, haloalkoxyl, CN, OH, OC$_{1-4}$-alkyl, S(O)$_o$C$_{1-4}$-alkyl, NHC$_{1-4}$-alkyl or C(O)C$_{1-4}$-alkyl;

R⁷ is —NH—R⁹ or —NH—C(=O)—R⁹;

R⁹ is a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the ring is optionally substituted, independently, with 1-5 substituents of R¹⁰;

each R¹⁰, independently, is H, halo, haloalkyl, CN, OH, NO₂, NH₂, SF₅, acetyl, —C(O)NHCH₃, oxo, cyclopropylmethoxy, 2-propynyloxy, 2-butynyloxy, C$_{1-6}$-alkyl, C$_{2-6}$-alkenyl, C$_{2-6}$-alkynyl, C$_{3-6}$-cycloalkyl, C$_{1-6}$-alkylamino-, C$_{1-6}$-alkoxyl, C$_{1-6}$-thioalkoxyl, morpholinyl, pyrazolyl, isoxazolyl, dihydropyranyl, pyrrolyl, pyrrolidinyl, piperazinyl, oxetan-3-yl, imidazopyridinyl or dioxolyl, wherein each of the cyclopropylmethoxy, 2-propynyloxy, 2-butynyloxy, C$_{1-6}$-alkyl, C$_{2-6}$-alkenyl, C$_{2-6}$-alkynyl, C$_{3-6}$-cycloalkyl, C$_{1-6}$-alkylamino-, C$_{1-6}$-dialkylamino-, C$_{1-6}$-alkoxyl, C$_{1-6}$-thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO₂, NH₂, OH, oxo, CF₃, CHF₂, CH₂F, methyl, methoxy, ethyl, ethoxy, CH₂CF₃, CH₂CHF₂, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, C$_{1-3}$-alkylamino-, C$_{1-3}$-dialkylamino-, C$_{1-3}$-thioalkoxyl, oxazolyl, isoxazolyl, thiazolyl, isothiazolyl, thiadiazolyl, thienyl, furyl, pyrrolyl, tetrahydropyranyl, pyrrolidinyl or oxetan-3-yl; and the subscript o is selected from 0, 1, or 2.

5. The compound according to claim 1, or a stereoisomer or pharmaceutically acceptable salt thereof, wherein each of R¹ and R², independently, is H, F, CH₃, CH₂OCH₃, CH₂F, CHF₂, CF₃, —C(O)NH₂, —CH=CHC(O)NHC$_{1-6}$-alkyl, —CH=CHC(O)₂H, —CH=CHCH₂OH or C$_{1-6}$-alkyl-C(O)NHC$_{1-6}$-alkyl.

6. The compound according to claim 1, or a stereoisomer or pharmaceutically acceptable salt thereof, wherein each of R$^a$ and R$^b$, independently, is H, F, CH₃, CH₂F, CHF₂ or CF₃.

7. The compound according to claim 1, or a stereoisomer or pharmaceutically acceptable salt thereof, wherein each of R¹ and R², independently, is H, F, CH₂OCH₃, or CF₃.

8. The compound according to claim 1, or a stereoisomer or pharmaceutically acceptable salt thereof, wherein each of R$^a$ and R$^b$, independently, is H or F.

9. The compound according to claim 1, or a stereoisomer or pharmaceutically acceptable salt thereof, wherein each of R¹ and R², independently, is H, F, CH₂OCH₃, or CF₃; and each of R$^a$ and R$^b$, independently, is H or F.

10. The compound according to claim 1, or a stereoisomer or pharmaceutically acceptable salt thereof, wherein each of R¹ and R² is, independently, H or CH₂OCH₃, and each of R$^a$ and R$^b$, independently, is H.

11. The compound according to claim 1, or a stereoisomer or pharmaceutically acceptable salt thereof, wherein R³ is CH₃, CF₃, CH₂F or CHF₂.

12. The compound according to claim 1, or a stereoisomer or pharmaceutically acceptable salt thereof, wherein R⁷ is —NH—C(=O)—R⁹;

or R⁷ is

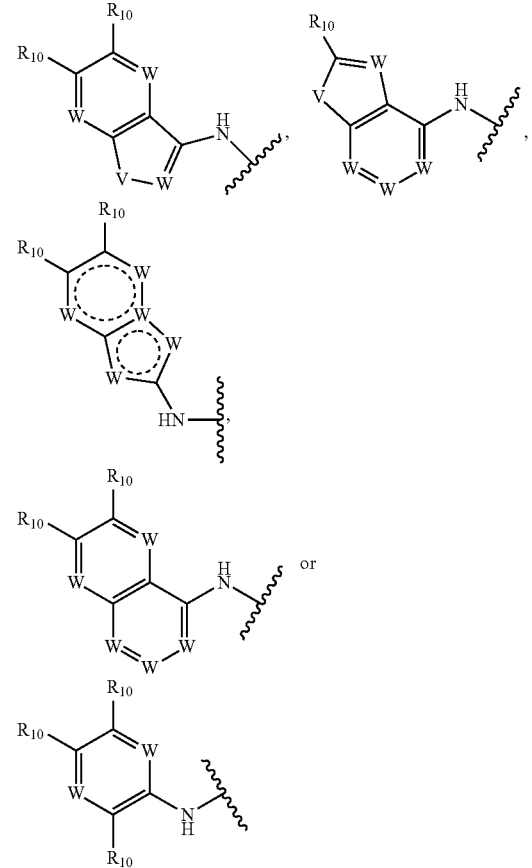

wherein V is NR¹⁰, O or S; and
each W, independently, is CH, CF, CCl, CCH₃ or N.

13. The compound according to claim 1, or a stereoisomer or pharmaceutically acceptable salt thereof, wherein A⁴ is CR⁴ or N;

A⁵ is CR⁵ or N;

A⁶ is CR⁶ or N;

A⁸ is CR⁸ or N, provided that no more than one of A⁴, A⁵, A⁶ and A⁸ is N;

each of R$^a$ and R$^b$, independently, is H, F, Cl, CF₃, OCF₃, methyl, ethyl, CN, OCH₃, SCH₃, NHCH₃, C(O)CH₃ or CH₂OCHF₂;

each of R¹ and R², independently, is H, F, Cl, CF₃, OCF₃, methyl, ethyl, CN, OCH₃, SCH₃, NHCH₃, C(O)CH₃, CH₂OCH₃ or CH₂OCHF₂;

R³ is C$_{1-4}$-alkyl, CH₂OH, CH₂OCHF₂ or cyclopropyl; and each of R⁴, R⁵, R⁶ and R⁸, independently, is H, F, Cl, CF₂H, CH₂F, CF₃, OCF₃, methyl, ethyl, CN, OH, OCH₃, SCH₃, NHCH₃ or C(O)CH₃.

14. The compound according to claim 1, or a stereoisomer or pharmaceutically acceptable salt thereof, wherein each of R¹ and R², independently, is H, F, CH₂OCH₃ or CF₃;

each of R$^a$ and R$^b$, independently, is H or F;

R³ is CH₃, CF₃, CH₂F or CHF₂; and

R⁷ is —NH—C(=O)—R⁹ or

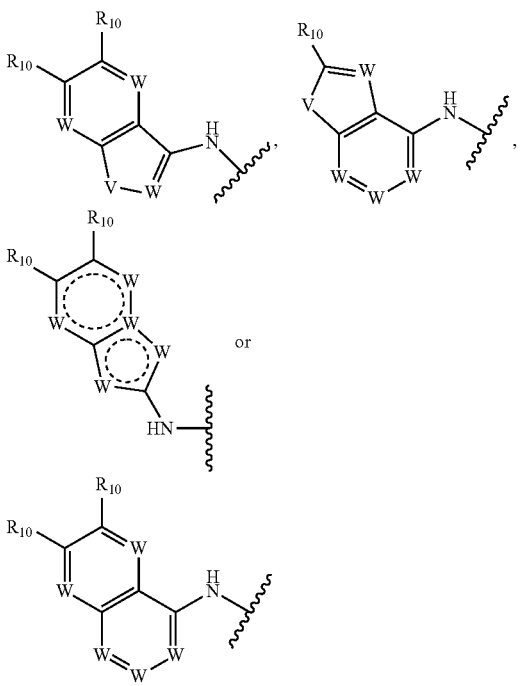

wherein V is NR[10], O or S; and
each W, independently, is CH, CF, CCl, CCH$_3$ or N.

15. The compound according to claim 1, or a stereoisomer or pharmaceutically acceptable salt thereof, wherein R$^7$ is —NH—C(=O)—R$^9$.

16. The compound according to claim 1, or a stereoisomer or pharmaceutically acceptable salt thereof, wherein R$^7$ is

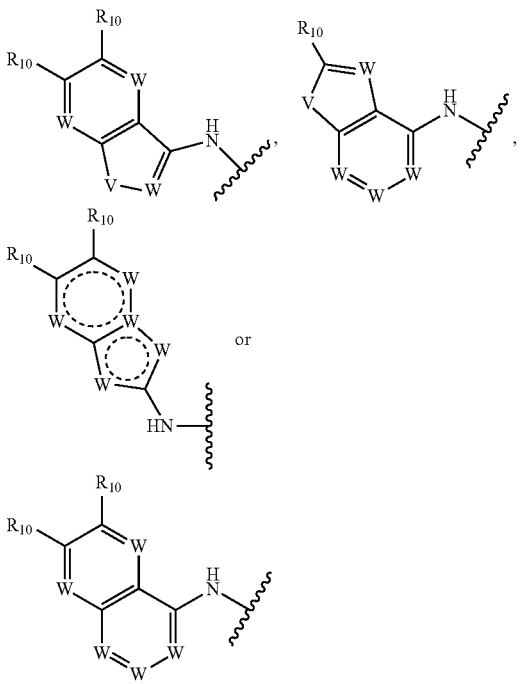

wherein V is NR[10], O or S; and
each W, independently, is CH, CF, CCl, CCH$_3$ or N.

17. The compound according to claim 1, or a stereoisomer or pharmaceutically acceptable salt thereof, wherein
A$^4$ is CR$^4$;
A$^5$ is CR$^5$ or N;
A$^6$ is CR$^6$; and
A$^8$ is CR$^8$ or N, provided only one of A$^5$ and A$^8$ is N, and wherein each of R$^4$, R$^5$, R$^6$ and R$^8$, independently, is H, F, Cl, CF$_3$, CF$_2$H, CH$_2$F or CH$_3$.

18. A compound according to claim 1, or a stereoisomer, tautomer, hydrate, solvate or pharmaceutically acceptable salt thereof, of Formula II:

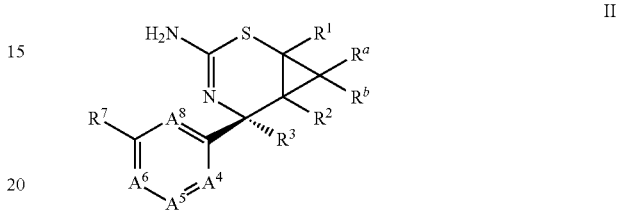

II wherein
A$^4$ is CR$^4$ or N;
A$^5$ is CR$^5$ or N;
A$^6$ is CR$^6$ or N;
A$^8$ is CR$^8$ or N, provided that no more than two of A$^4$, A$^5$, A$^6$ and A$^8$ is N;
each of R$^a$ and R$^b$, independently, is H, F, Cl, C$_{1-6}$-alkyl, C$_{2-4}$-alkenyl, C$_{2-4}$-alkynyl, CN, —CH$_2$OC$_{1-6}$-alkyl, —OC$_{1-6}$-alkyl, —S(O)$_o$C$_{1-6}$-alkyl, —NHC$_{1-6}$-alkyl or —C(O)C$_{1-6}$-alkyl, wherein each of the C$_{1-6}$-alkyl, C$_{2-4}$-alkenyl, C$_{2-4}$-alkynyl, and C$_{1-6}$-alkyl portion of —CH$_2$OC$_{1-6}$-alkyl, —OC$_{1-6}$-alkyl, —S(O)$_o$C$_{1-6}$-alkyl, —NHC$_{1-6}$-alkyl and —C(O)C$_{1-6}$-alkyl are optionally substituted with 1-4 substituents of F, oxo or OH;
each of R$^1$ and R$^2$, independently, is H, F, Cl, C$_{1-6}$-alkyl, C$_{2-4}$-alkenyl, C$_{2-4}$-alkynyl, CN, —CH$_2$OC$_{1-6}$-alkyl, —OC$_{1-6}$-alkyl, —S(O)$_o$C$_{1-6}$-alkyl, —NHC$_{1-6}$-alkyl, —C(O)NH$_2$, —CH=CHC(O)NHC$_{1-6}$-alkyl, —CH=CHC(O)$_2$H, —CH=CHCH$_2$OH, C$_{1-6}$-alkyl-C(O)NHC$_{1-6}$-alkyl, C(O)C$_{1-6}$-alkyl or —C(O)C$_{2-6}$-alkenyl, wherein each of the C$_{1-6}$-alkyl, C$_{2-4}$-alkenyl, C$_{2-4}$-alkynyl, and the C$_{1-6}$-alkyl and C$_{2-6}$-alkenyl portion of —CH$_2$OC$_{1-6}$-alkyl, —OC$_{1-6}$-alkyl, —S(O)$_o$C$_{1-6}$-alkyl, —NHC$_{1-6}$-alkyl, C(O)C$_{1-6}$-alkyl, C(O)C$_{2-6}$-alkenyl, —CH=CHC(O)NHC$_{1-6}$-alkyl and C$_{1-6}$-alkyl-C(O)NHC$_{1-6}$-alkyl, are optionally substituted with 1-4 substituents of F, CN, oxo or OH;
R$^3$ is C$_{1-4}$-alkyl, CH$_2$OC$_{1-4}$-alkyl, CH$_2$OH, C$_{1-4}$-haloalkyl or cyclopropyl, wherein each of the C$_{1-4}$-alkyl, CH$_2$OC$_{1-4}$-alkyl, C$_{1-4}$-haloalkyl and cyclopropyl is optionally substituted with 1-4 F atoms;
each of R$^4$, R$^5$, R$^6$ and R$^8$, independently, is H, halo, haloalkyl, haloalkoxyl, C$_{1-4}$-alkyl, CN, OH, OC$_{1-4}$-alkyl, S(O)$_o$C$_{1-4}$-alkyl, NHC$_{1-4}$-alkyl or C(O)C$_{1-4}$-alkyl;
R$^7$ is —NH—C(=O)—R$^9$; or R$^7$ is

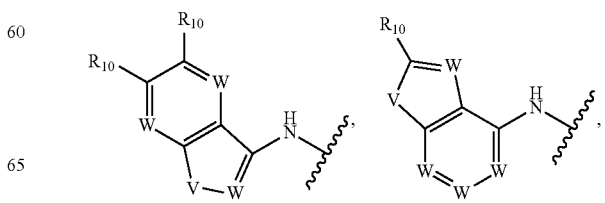

-continued

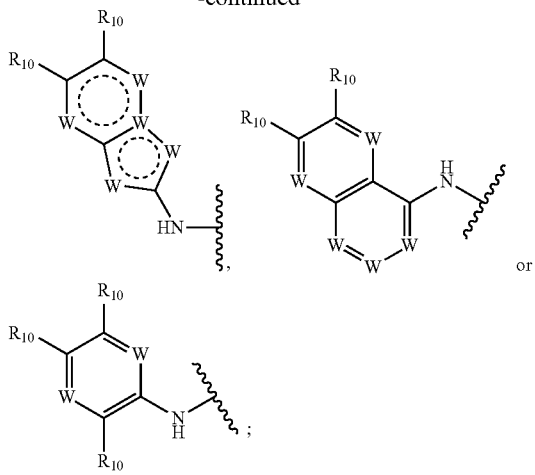

wherein V is NR$^{10}$, O or S; and
each W, independently, is CH, CF, CCl, CCH$_3$ or N;
R$^9$ is a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein ring is optionally substituted, independently, with 1-5 substituents of R$^{10}$;
each R$^{10}$, independently, is H, halo, haloalkyl, CN, OH, NO$_2$, NH$_2$, SF$_5$, acetyl, —C(O)NHCH$_3$, oxo, cyclopropylmethoxy, 2-propynyloxy, 2-butynyloxy, C$_{1-6}$-alkyl, C$_{2-6}$-alkenyl, C$_{2-6}$-alkynyl, C$_{3-6}$-cycloalkyl, C$_{1-6}$-alkylamino-, C$_{1-6}$-dialkylamino-, C$_{1-6}$-alkoxyl, C$_{1-6}$-thioalkoxyl, morpholinyl, pyrazolyl, isoxazolyl, dihydropyranyl, pyrrolyl, pyrrolidinyl, piperazinyl, oxetan-3-yl, imidazo-pyridinyl or dioxolyl, wherein each of the cyclopropylmethoxy, 2-propynyloxy, 2-butynyloxy, C$_{1-6}$-alkyl, C$_{2-6}$-alkenyl, C$_{2-6}$-alkynyl, C$_{3-6}$-cycloalkyl, C$_{1-6}$-alkylamino-, C$_{1-6}$-dialkylamino-, C$_{1-6}$-alkoxyl, C$_{1-6}$-thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO$_2$, NH$_2$, OH, oxo, CF$_3$, CHF$_2$, CH$_2$F, methyl, methoxy, ethyl, ethoxy, CH$_2$CF$_3$, CH$_2$CHF$_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, C$_{1-3}$-alkylamino-, C$_{1-3}$-dialkylamino-, C$_{1-3}$-thioalkoxyl, oxazolyl, isoxazolyl, thiazolyl, isothiazolyl, thiadiazolyl, thienyl, furyl, pyrrolyl, tetrahydropyranyl, pyrrolidinyl or oxetan-3-yl; and
the subscript o is selected from 0, 1, or 2.

19. The compound according to claim 1, or a stereoisomer, tautomer or pharmaceutically acceptable salt thereof, wherein
A$^4$ is CR$^4$ or N;
A$^5$ is CR$^5$ or N;
A$^6$ is CR$^6$ or N;
A$^8$ is CR$^8$ or N, provided no more than one of A$^4$, A$^5$, A$^6$ and A$^8$ is N;
each of R$^a$ and R$^b$, independently, is H, F, CH$_3$, CH$_2$F, CHF$_2$ or CF$_3$;
each of R$^1$ and R$^2$, independently, is H, F, CH$_3$, CH$_2$OCH$_3$, CH$_2$F, CHF$_2$ or CF$_3$;

R$^3$ is C$_{1-4}$-alkyl, C$_{1-4}$haloalkyl, CH$_2$OH, CH$_2$OCHF$_2$ or cyclopropyl; and
each of R$^4$, R$^5$, R$^6$ and R$^8$, independently, is H, F, Cl, CF$_2$H, CH$_2$F, CF$_3$, OCF$_3$, methyl, ethyl, CN, OH, OCH$_3$, SCH$_3$, NHCH$_3$ or C(O)CH$_3$.

20. The compound according to claim 1, or a stereoisomer or pharmaceutically acceptable salt thereof, wherein
A$^4$ is CR$^4$;
A$^5$ is CR$^5$;
A$^6$ is CR$^6$; and
A$^8$ is CR$^8$; wherein each of R$^4$, R$^5$, R$^6$ and R$^8$, independently, is H, F, CF$_3$, CF$_2$H, CH$_2$F or CH$_3$;
R$^3$ is CH$_3$, CF$_3$, CH$_2$F or CHF$_2$; and
R$^7$ is —NH—C(=O)—R$^9$ or

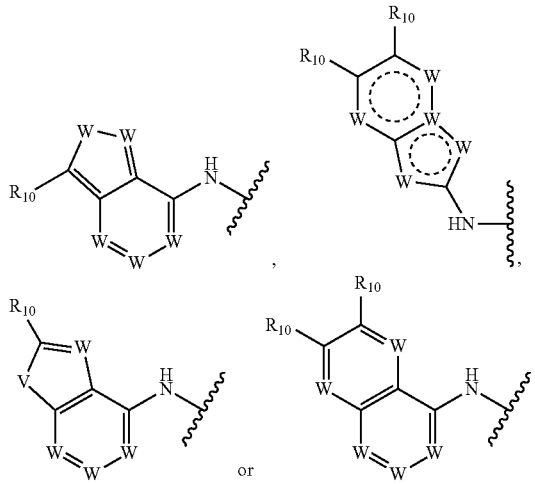

wherein V is NR$^{10}$, O or S; and
each W, independently, is CH, CF, CCl or N.

21. The compound according to claim 18, or a stereoisomer or pharmaceutically acceptable salt thereof, wherein R$^7$ is —NH—C(=O)—R$^9$.

22. The compound according to claim 1, or a stereoisomer or pharmaceutically acceptable salt thereof, wherein R$^7$ is

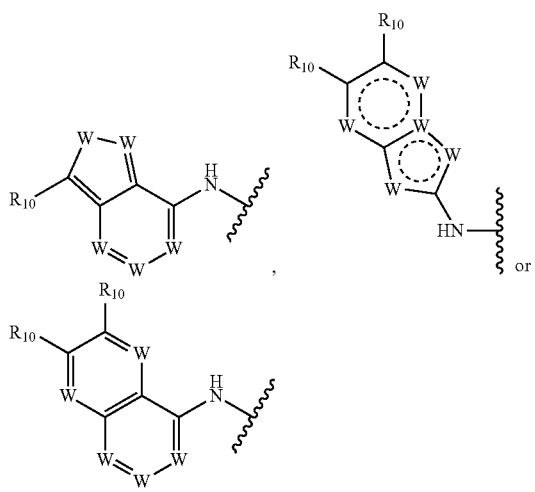

wherein V is NR$^{10}$, O or S; and
each W, independently, is CH, CF, CCl, CCH$_3$ or N.

23. The compound according to claim 18, or a stereoisomer or pharmaceutically acceptable salt thereof, wherein each of $R^1$ and $R^2$, independently, is H, F, $CH_2OCH_3$ or $CF_3$; and each of $R^a$ and $R^b$, independently, is H or F.

24. The compound according to claim 1, or a stereoisomer or pharmaceutically acceptable salt thereof, having a Formula I-A

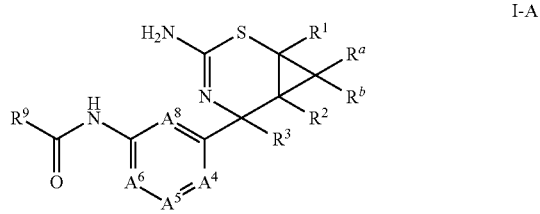

wherein
$A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N;
each of $R^a$ and $R^b$, independently, is H, F, Cl, $C_{1-6}$-alkyl, $C_{2-4}$-alkenyl, $C_{2-4}$-alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$-alkenyl, $C_{2-4}$-alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;
each of $R^1$ and $R^2$, independently, is H, F, Cl, $C_{1-6}$-alkyl, $C_{2-4}$-alkenyl, $C_{2-4}$-alkynyl, CN, —$CH_2OC_{1-6}$-alkyl, —$OC_{1-6}$-alkyl, —$S(O)_oC_{1-6}$-alkyl, —$NHC_{1-6}$-alkyl, —$C(O)NH_2$, —CH=$CHC(O)NHC_{1-6}$-alkyl, —CH=$CHC(O)_2H$, —CH=$CHCH_2OH$, $C_{1-6}$-alkyl-C(O)$NHC_{1-6}$-alkyl, $C(O)C_{1-6}$-alkyl or —$C(O)C_{2-6}$-alkenyl, wherein each of the $C_{1-6}$-alkyl, $C_{2-4}$-alkenyl, $C_{2-4}$-alkynyl, and the $C_{1-6}$-alkyl portion and $C_{2-6}$-alkenyl of —$CH_2OC_{1-6}$-alkyl, —$OC_{1-6}$-alkyl, —$S(O)_o$ $C_{1-6}$-alkyl, —$NHC_{1-6}$-alkyl, $C(O)C_{1-6}$-alkyl, —$C(O)$ $C_{2-6}$-alkenyl, —CH=$CHC(O)NHC_{1-6}$-alkyl and $C_{1-6}$-alkyl-C(O)$NHC_{1-6}$-alkyl, are optionally substituted with 1-4 substituents of F, CN, oxo or OH;
$R^3$ is $C_{1-4}$-alkyl, $CH_2OC_{1-4}$-alkyl, $CH_2OH$, $C_{1-4}$-haloalkyl or cyclopropyl, wherein each of the $C_{1-4}$-alkyl, $CH_2OC_{1-4}$-alkyl, $C_{1-4}$-haloalkyl and cyclopropyl is optionally substituted with 1-4 F atoms;
each of $R^4$, $R^5$, $R^6$ and $R^8$, independently, is H, F, Cl or $CH_3$;
$R^9$ is a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the ring is optionally substituted, independently, with 1-5 substituents of $R^{10}$;
each $R^{10}$, independently, is H, halo, haloalkyl, CN, OH, $NO_2$, $NH_2$, $SF_5$, acetyl, —C(O)$NHCH_3$, oxo, cyclopropylmethoxy, 2-propynyloxy, 2-butynyloxy, $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl, morpholinyl, pyrazolyl, isoxazolyl, dihydropyranyl, pyrrolyl, pyrrolidinyl, piperazinyl, oxetan-3-yl, imidazo-pyridinyl or dioxolyl, wherein each of the cyclopropylmethoxy, 2-propynyloxy, 2-butynyloxy, $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$-thioalkoxyl, oxazolyl, isoxazolyl, thiazolyl, isothiazolyl, thiadiazolyl, thienyl, furyl, pyrrolyl, tetrahydropyranyl, pyrrolidinyl or oxetan-3-yl; and the subscript o is selected from 0, 1, or 2.

25. The compound according to claim 1, or a stereoisomer, tautomer or pharmaceutically acceptable salt thereof, wherein
$A^4$ is $CR^4$;
$A^5$ is $CR^5$;
$A^6$ is $CR^6$;
$A^8$ is $CR^8$; wherein each of $R^4$, $R^5$, $R^6$ and $R^8$, independently, is H, F, Cl, $CF_2H$, $CH_2F$, $CF_3$, $OCF_3$, methyl, ethyl, CN, OH, $OCH_3$, $SCH_3$, $NHCH_3$ or $C(O)CH_3$;
each of $R^a$ and $R^b$, independently, is H, F, $CH_3$, $CH_2F$, $CHF_2$ or $CF_3$;
each of $R^1$ and $R^2$, independently, is H, F, $CH_3$, $CH_2OCH_3$, $CH_2F$, $CHF_2$ or $CF_3$;
$R^3$ is $CH_3$, $C_2H_5$, $CF_2H$ or $CH_2F$;
$R^9$ is a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the ring is optionally substituted, independently, with 1-5 substituents of $R^{10}$; and
each $R^{10}$, independently, is H, halo, haloalkyl, CN, OH, $NO_2$, $NH_2$, $SF_5$, acetyl, —C(O)$NHCH_3$, oxo, cyclopropylmethoxy, 2-propynyloxy, 2-butynyloxy, $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl, morpholinyl, pyrazolyl, isoxazolyl, dihydropyranyl, pyrrolyl, pyrrolidinyl piperazinyl, oxetan-3-yl, imidazo-pyridinyl or dioxolyl, wherein each of the cyclopropylmethoxy, 2-propynyloxy, 2-butynyloxy, $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$-alkylamino-, $C_{1-3}$-dialkylamino, $C_{1-3}$-thioalkoxyl, oxazolyl, isoxazolyl, thiazolyl, isothiazolyl, thiadiazolyl, thienyl, furyl, pyrrolyl, tetrahydropyranyl, pyrrolidinyl or oxetan-3-yl.

26. The compound according to claim 24, or a stereoisomer or pharmaceutically acceptable salt thereof, wherein
$A^4$ is $CR^4$ or N;
$A^5$ is $CR^5$ or N;
$A^6$ is $CR^6$ or N;

$A^8$ is $CR^8$ or N, wherein each of $R^4$, $R^5$, $R^6$ and $R^8$, independently, is H, F, Cl or $CH_3$, provided no more than one of $A^4$, $A^5$, $A^6$ and $A^8$ is N;

each of $R^1$ and $R^2$, independently, is H, F, $CH_2OCH_3$ or $CF_3$;

each of $R^a$ and $R^b$, independently, is H or F; and $R^3$ is $CF_3$, $CH_3$, $CF_2H$ or $CH_2F$.

27. The according to claim 1, or a stereoisomer or pharmaceutically acceptable salt thereof, having a Formula II-A

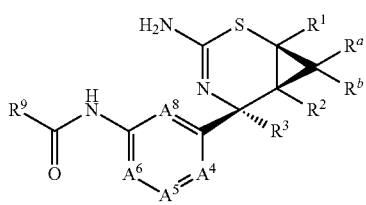

wherein $A^4$ is $CR^4$, wherein $R^4$ is H, F or Cl;

$A^5$ is $CR^5$ or N, wherein $R^5$ is H, F, Cl or $CH_3$;

$A^6$ is CH;

$A^8$ is $CR^8$ or N, wherein $R^8$ is H or F, provided that no more than one of $A^5$ and $A^8$ is N;

each of $R^1$ and $R^2$, independently, is H, F, $CH_2OCH_3$ or $CF_3$;

each of $R^a$ and $R^b$, independently, is H or F;

$R^3$ is $CH_3$, $CF_3$, $CH_2F$ or $CHF_2$;

$R^9$ is a fully unsaturated 5- or 6-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the ring is optionally substituted, independently, with 1-5 substituents of $R^{10}$; and each $R^{10}$, independently, is H, halo, haloalkyl, CN, OH, $NO_2$, $NH_2$, $SF_5$, acetyl, —C(O)$NHCH_3$, oxo, cyclopropylmethoxy, 2-propynyloxy, 2-butynyloxy, $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl, morpholinyl, pyrazolyl, isoxazolyl, dihydropyranyl, pyrrolyl, pyrrolidinyl, piperazinyl, oxetan-3-yl, imidazo-pyridinyl or dioxolyl, wherein each of the cyclopropylmethoxy, 2-propynyloxy, 2-butynyloxy, $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$-alkylamino-, $C_{1-3}$-dialkylamino-, $C_{1-3}$-thioalkoxyl, oxazolyl, isoxazolyl, thiazolyl, isothiazolyl, thiadiazolyl, thienyl, furyl, pyrrolyl, tetrahydropyranyl, pyrrolidinyl or oxetan-3-yl.

28. The compound according to claim 27, or a stereoisomer or pharmaceutically acceptable salt thereof, wherein each of $R^a$, $R^b$, $R^1$ and $R^2$ is H.

29. The compound according to claim 27, or a stereoisomer or pharmaceutically acceptable salt thereof, wherein $R^3$ is $CH_3$, $CH_2F$ or $CHF_2$.

30. The compound according to claim 27, or a stereoisomer or pharmaceutically acceptable salt thereof, wherein $R^3$ is $CH_2F$ or $CHF_2$.

31. The compound according to claim 27, or a stereoisomer or pharmaceutically acceptable salt thereof, wherein $A^4$ is CF or CCl;

$A^5$ is CH, CF, $CCH_3$ or N;

$A^6$ is CH; and $A^8$ is CH.

32. The compound according to claim 27, or a stereoisomer or pharmaceutically acceptable salt thereof, wherein $A^4$ is CF;

$A^5$ is CH, CF or N;

$A^6$ is CH; and $A^8$ is CH.

33. The compound according claim 27, or a stereoisomer or pharmaceutically acceptable salt thereof, wherein $A^4$ is CCl;

$A^5$ is CH or CF;

$A^6$ is CH; and $A^8$ is CH.

34. The compound according to claim 27, or a stereoisomer or pharmaceutically acceptable salt thereof, wherein $R^9$ is a ring selected from phenyl, pyridyl, pyrimidyl, pyrazinyl, pyridazinyl, pyrazolyl, pyrazolo[3,4-c]pyridinyl, oxazolyl, isoxazolyl, thiazolyl, isothiazolyl or thienyl, wherein the ring is optionally substituted with 1-5 substituents of $R^{10}$; and each $R^{10}$, independently, is H, halo, haloalkyl, CN, OH, $NO_2$, $NH_2$, $SF_5$, acetyl, —C(O)$NHCH_3$, oxo, cyclopropylmethoxy, 2-propynyloxy, 2-butynyloxy, $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl, morpholinyl, pyrazolyl, isoxazolyl, dihydropyranyl, pyrrolyl, pyrrolidinyl, piperazinyl, oxetan-3-yl, imidazo-pyridinyl or dioxolyl, wherein each of the cyclopropylmethoxy, 2-propynyloxy, 2-butynyloxy, $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$-alkylamino-, $C_{1-3}$-dialkylamino-, $C_{1-3}$-thioalkoxyl, oxazolyl, isoxazolyl, thiazolyl, isothiazolyl, thiadiazolyl, thienyl, furyl, pyrrolyl, tetrahydropyranyl, pyrrolidinyl or oxetan-3-yl.

35. The compound according to claim 27, or a stereoisomer or pharmaceutically acceptable salt thereof, wherein $R^9$ is a ring selected from pyridyl, pyrimidyl, pyrazinyl, pyridazinyl, pyrazolyl, pyrazolo[3,4-c]pyridinyl, oxazolyl, isoxazolyl, thiazolyl, isothiazolyl or thienyl, wherein the ring is optionally substituted with 1-5 substituents of $R^{10}$.

36. The compound according to claim 27, or a stereoisomer or pharmaceutically acceptable salt thereof, wherein $R^9$ is

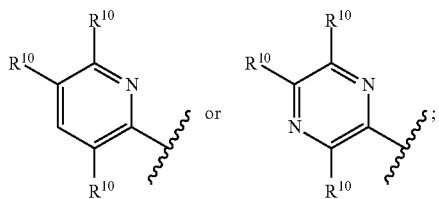

and
each $R^{10}$, independently, is H, F, Cl, Br, $CF_3$, $CHF_2$, $CH_2F$, CN, OH, —C(O)NHCH$_3$, cyclopropylmethoxy, 2-propynyloxy, 2-butynyloxy, $C_{1-6}$-alkyl, $C_{2-6}$-alkenyl, $C_{2-6}$-alkynyl, $C_{3-6}$-cycloalkyl, $C_{1-6}$-alkoxyl or $C_{1-6}$-thioalkoxyl, wherein each of the cyclopropylmethoxy, 2-propynyloxy, 2-butynyloxy, $C_{1-6}$-alkyl, $C_{2-6}$-alkenyl, $C_{2-6}$-alkynyl, $C_{3-6}$-cycloalkyl, $C_{1-6}$-alkoxyl and $C_{1-6}$-thioalkoxyl is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$-alkylamino-, $C_{1-3}$-dialkylamino-, $C_{1-3}$-thioalkoxyl, oxazolyl or thiazolyl.

37. The compound according to claim 27, or a stereoisomer or pharmaceutically acceptable salt thereof, wherein $R^3$ is $CHF_2$; $R^9$ is

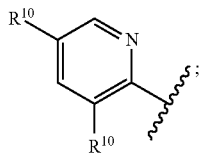

and
each $R^{10}$, independently, is H, F, Cl, Br, $CH_3$, $CHF_2$, $CH_2F$, CN, 2-propynyloxy, 2-butynyloxy or $C_{1-2}$-alkoxyl, wherein the $C_{1-2}$-alkoxyl is optionally substituted independently with 1-5 substituents of F, Cl, methyl, methoxy, ethyl, ethoxy, oxazolyl or thiazolyl.

38. The compound according to claim 27, or a stereoisomer or pharmaceutically acceptable salt thereof, wherein $R^3$ is $CH_2F$; $R^9$ is

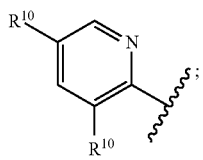

and
each $R^{10}$, independently, is H, F, Cl, Br, $CH_3$, $CHF_2$, $CH_2F$, CN, 2-propynyloxy, 2-butynyloxy or $C_{1-2}$-alkoxyl, wherein the $C_{1-2}$-alkoxyl is optionally substituted independently with 1-5 substituents of F, Cl, methyl, methoxy, ethyl, ethoxy, oxazolyl or thiazolyl.

39. The compound according to claim 27, or a stereoisomer or pharmaceutically acceptable salt thereof, wherein $R^3$ is $CHF_2$; $R^9$ is

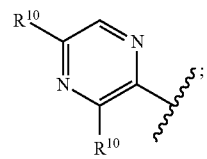

and
each $R^{10}$, independently, is H, F, Cl, Br, $CH_3$, $CHF_2$, $CH_2F$, CN, 2-propynyloxy, 2-butynyloxy or $C_{1-2}$-alkoxyl, wherein the $C_{1-2}$-alkoxyl is optionally substituted independently with 1-5 substituents of F, Cl, methyl, methoxy, ethyl, ethoxy, oxazolyl or thiazolyl.

40. The compound according to claim 27, or a stereoisomer or pharmaceutically acceptable salt thereof, wherein $R^3$ is $CH_2F$; $R^9$ is

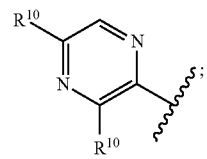

and
each $R^{10}$, independently, is H, F, Cl, Br, $CH_3$, $CHF_2$, $CH_2F$, CN, 2-propynyloxy, 2-butynyloxy or $C_{1-2}$-alkoxyl, wherein the $C_{1-2}$-alkoxyl is optionally substituted independently with 1-5 substituents of F, Cl, methyl, methoxy, ethyl, ethoxy, oxazolyl or thiazolyl.

41. The compound according to claim 1, or a stereoisomer, tautomer, hydrate, solvate or pharmaceutically acceptable salt thereof, having a Formula II-B:

II-B wherein
$A^4$ is $CR^4$, wherein $R^4$ is H, F or Cl;
$A^5$ is $CR^5$ or N, wherein $R^5$ is H, F, Cl or $CH_3$;
$A^6$ is CH;
$A^8$ is $CR^8$ or N, wherein $R^8$ is H or F,
provided that no more than one of $A^5$ and $A^8$ is N;
each of $R^1$ and $R^2$, independently, is H, F, $CH_2OCH_3$ or $CF_3$;
each of $R^a$ and $R^b$, independently, is H or F;
$R^3$ is $CH_3$, $CF_3$, $CH_2F$ or $CHF_2$;
$R^9$ is a fully unsaturated 5- or 6-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the ring is optionally substituted, independently, with 1-5 substituents of $R^{10}$;
each $R^{10}$ independently, is H, halo, haloalkyl, CN, OH, $NO_2$, $NH_2$, $SF_5$, acetyl, —C(O)NHCH$_3$, oxo, cyclopropylmethoxy, 2-propynyloxy, 2-butynyloxy, $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl, morpholinyl, pyrazolyl, isoxazolyl, dihydropyranyl, pyrrolyl, pyrrolidinyl, piperazinyl, oxetan-3-yl, imidazo-pyridinyl or dioxolyl, wherein each of the cyclopropylmethoxy, 2-propynyloxy, 2-butynyloxy, $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$-alkylamino-, $C_{1-3}$-dialkylamino-, $C_{1-3}$-thioalkoxyl, oxazolyl, isoxazolyl, thiazolyl, isothiazolyl, thiadiazolyl, thienyl, furyl, pyrrolyl, tetrahydropyranyl, pyrrolidinyl or oxetan-3-yl; and each W, independently, is CH, CF, CCl, $CCH_3$ or N.

42. The compound according to claim 41, or a stereoisomer or pharmaceutically acceptable salt thereof, wherein each of $R^a$, $R^b$, $R^1$ and $R^2$ is H.

43. The compound according to claim 41, or a stereoisomer or pharmaceutically acceptable salt thereof, wherein $R^3$ is $CH_3$, $CH_2F$ or $CHF_2$.

44. The compound according to claim 41, or a stereoisomer or pharmaceutically acceptable salt thereof, wherein
$A^4$ is CF or CCl;
$A^5$ is CH, CF, $CCH_3$ or N;
$A^6$ is CH; and
$A^8$ is CH.

45. The compound according to claim 41, or a stereoisomer or pharmaceutically acceptable salt thereof, wherein
$A^4$ is CF;
$A^5$ is CH, CF or N;
$A^6$ is CH; and
$A^8$ is CH.

46. The compound according to claim 41, or a stereoisomer or pharmaceutically acceptable salt thereof, wherein
$A^4$ is CCl;
$A^5$ is CH, CF, CCl or $CCH_3$;
$A^6$ is CH; and
$A^8$ is CH.

47. The compound according to claim 41, or a stereoisomer or pharmaceutically acceptable salt thereof, wherein

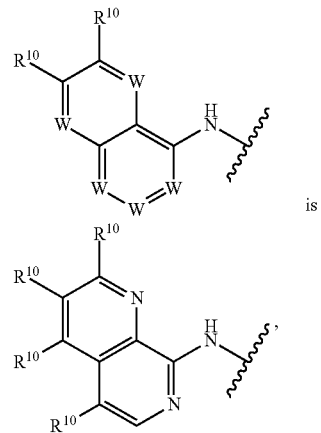

is

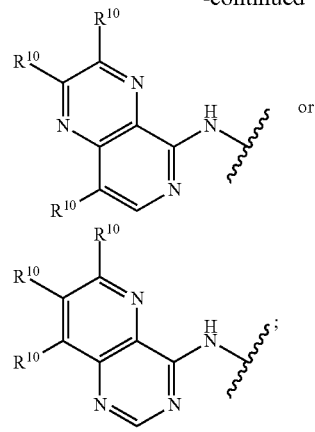

and each $R^{10}$, independently, is H, F, Cl, Br, $CH_3$, $CHF_2$, $CH_2F$, CN, 2-propynyloxy, 2-butynyloxy or $C_{1-2}$-alkoxyl, wherein the $C_{1-2}$-alkoxyl is optionally substituted independently with 1-5 substituents of F, Cl, methyl, methoxy, ethyl, ethoxy, oxazolyl or thiazolyl.

48. The compound of claim 1, or a stereoisomer or pharmaceutically acceptable salt thereof, selected from

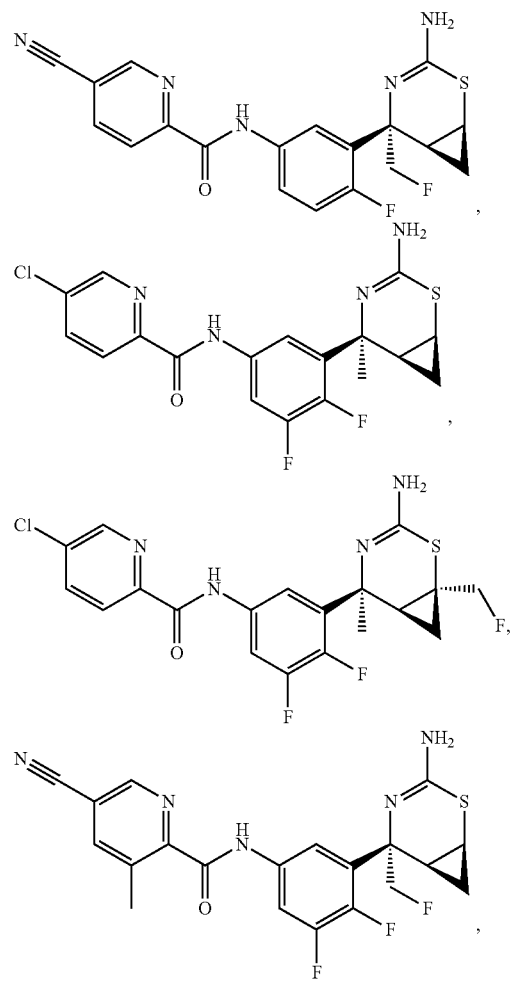

735
-continued
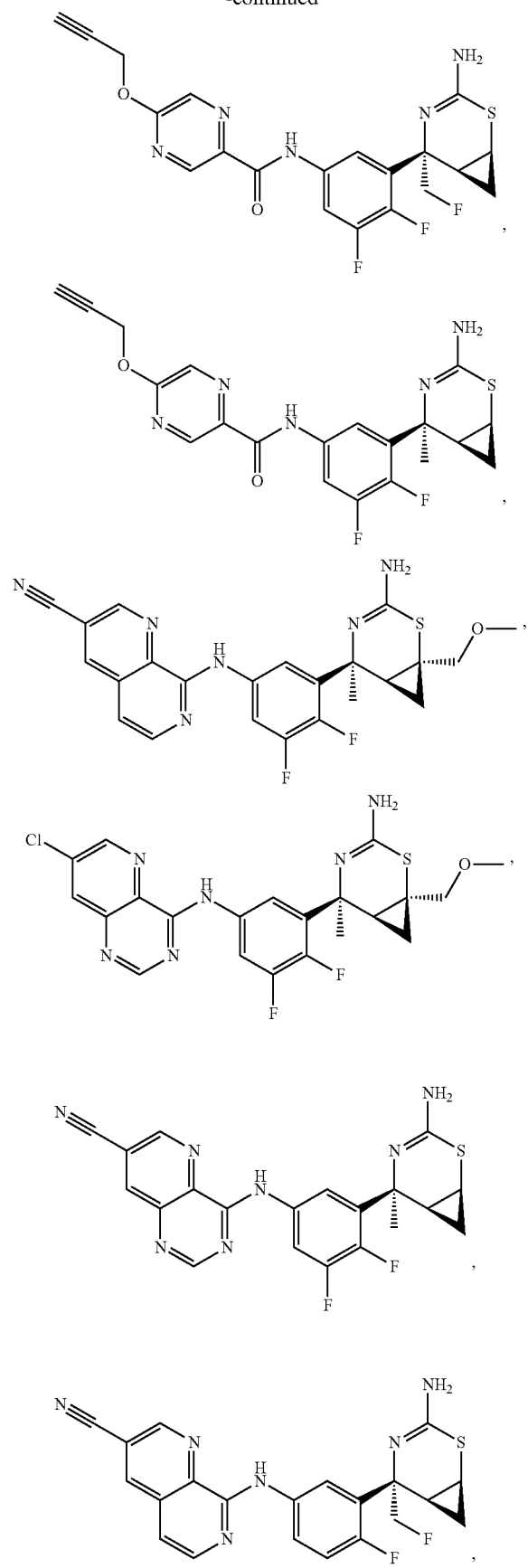
736
-continued
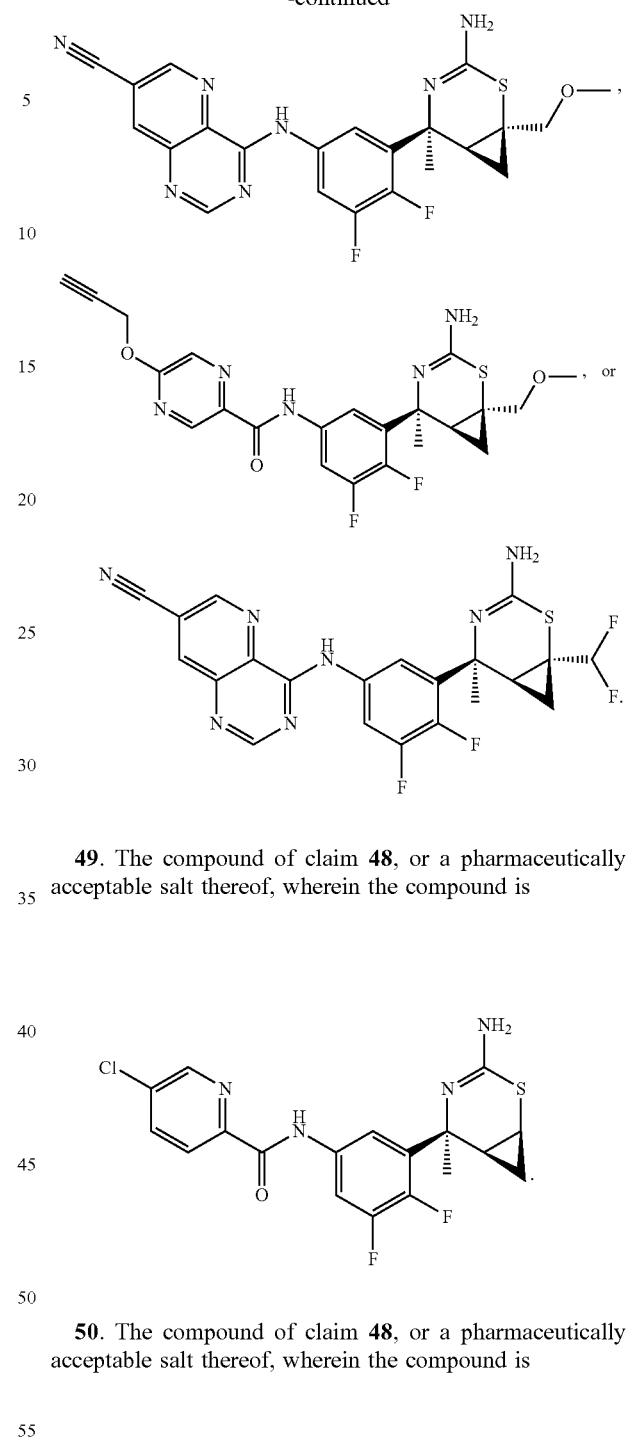
49. The compound of claim 48, or a pharmaceutically acceptable salt thereof, wherein the compound is
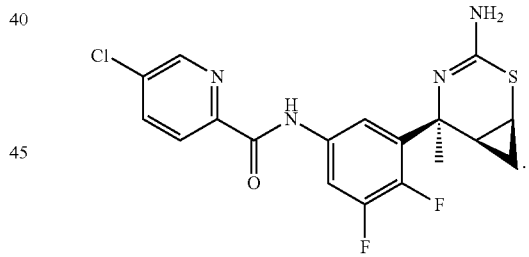
50. The compound of claim 48, or a pharmaceutically acceptable salt thereof, wherein the compound is
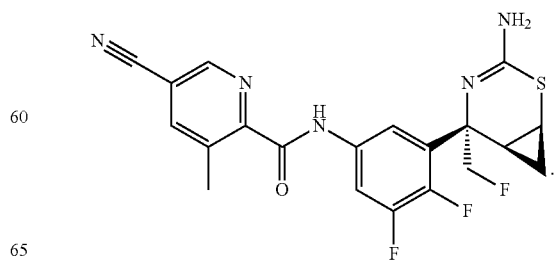

51. The compound of claim 48, or a pharmaceutically acceptable salt thereof, wherein the compound is

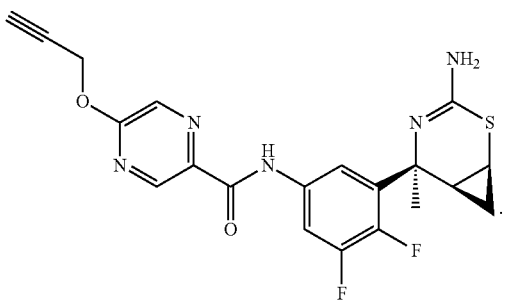 [SMILES: C#CCOc1cnc(C(=O)Nc2cc(F)c(F)c([C@@]3(C)N=C(N)S[C@H]4C[C@H]43)c2)cn1]

52. The compound of claim 48, or a pharmaceutically acceptable salt thereof, wherein the compound is

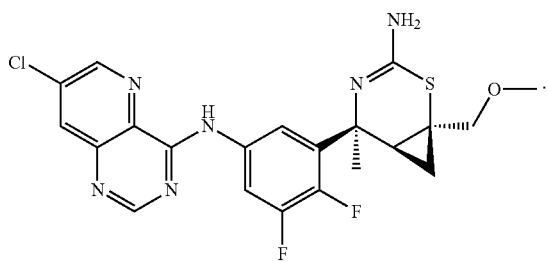 [SMILES: COC[C@]12C[C@H]1[C@@](C)(c1cc(Nc3ncnc4cc(Cl)cnc34)cc(F)c1F)N=C(N)S2]

53. The compound of claim 48, or a pharmaceutically acceptable salt thereof, wherein the compound is

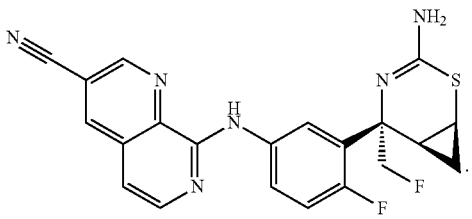 [SMILES: N#Cc1cnc2c(Nc3ccc(F)c([C@@]4(CF)N=C(N)S[C@H]5C[C@H]54)c3)nccc2c1]

54. The compound of claim 48, or a pharmaceutically acceptable salt thereof, wherein the compound is

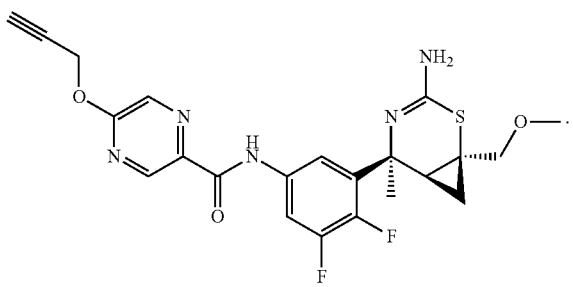 [SMILES: C#CCOc1cnc(C(=O)Nc2cc(F)c(F)c([C@@]3(C)N=C(N)S[C@@]4(COC)C[C@H]43)c2)cn1]

55. The compound of claim 1, or a tautomer or pharmaceutically acceptable salt thereof, selected from N-(3-((1S,5S,6S)-3-amino-5-(fluoromethyl)-2-thia-4-azabicyclo[4.1.0]hept-3-en-5-yl)-4-fluorophenyl)-5-chloro-2-pyridinecarboxamide;

N-(3-((1S,5S,6S)-3-amino-5-(fluoromethyl)-2-thia-4-azabicyclo[4.1.0]hept-3-en-5-yl)-4-fluorophenyl)-5-cyano-2-pyridinecarboxamide;

N-(3-((1S,5S,6S)-3-amino-5-(fluoromethyl)-2-thia-4-azabicyclo[4.1.0]hept-3-en-5-yl)-4-fluorophenyl)-5-cyano-3-methyl-2-pyridinecarboxamide;

N-(3-((1S,5S,6S)-3-amino-5-(fluoromethyl)-2-thia-4-azabicyclo[4.1.0]hept-3-en-5-yl)-4-fluorophenyl)-5-methoxy-2-pyrazinecarboxamide;

N-(3-((1S,5S,6S)-3-amino-5-(fluoromethyl)-2-thia-4-azabicyclo[4.1.0]hept-3-en-5-yl)-4,5-difluorophenyl)-5-chloro-2-pyridinecarboxamide;

N-(3-((1S,5S,6S)-3-amino-5-methyl-2-thia-4-azabicyclo[4.1.0]hept-3-en-5-yl)-4,5-difluorophenyl)-5-chloro-2-pyridinecarboxamide;

N-(3-((1S,5S,6S)-3-amino-5-(fluoromethyl)-2-thia-4-azabicyclo[4.1.0]hept-3-en-5-yl)-4,5-difluorophenyl)-5-cyano-2-pyridinecarboxamide;

N-(3-((1S,5S,6S)-3-amino-1-(fluoromethyl)-5-methyl-2-thia-4-azabicyclo[4.1.0]hept-3-en-5-yl)-4,5-difluorophenyl)-5-chloro-2-pyridinecarboxamide;

N-(3-((1S,5S,6S)-3-amino-5-(fluoromethyl)-2-thia-4-azabicyclo[4.1.0]hept-3-en-5-yl)-4,5-difluorophenyl)-5-cyano-3-methyl-2-pyridinecarboxamide;

N-(3-((1S,5S,6S)-3-amino-5-(fluoromethyl)-2-thia-4-azabicyclo[4.1.0]hept-3-en-5-yl)-4,5-difluorophenyl)-5-(2-propyn-1-yloxy)-2-pyrazinecarboxamide;

8-((3-((1S,5S,6S)-3-amino-5-methyl-2-thia-4-azabicyclo[4.1.0]hept-3-en-5-yl)-4,5-difluorophenyl)amino)-1,7-naphthyridine-3-carbonitrile;

N-(3-((1S,5S,6S)-3-amino-5-methyl-2-thia-4-azabicyclo[4.1.0]hept-3-en-5-yl)-4,5-difluorophenyl)-5-(2-propyn-1-yloxy)-2-pyrazinecarboxamide;

8-((3-((1S,5S,6S)-3-amino-5-(fluoromethyl)-2-thia-4-azabicyclo[4.1.0]hept-3-en-5-yl)-4,5-difluorophenyl)amino)-1,7-naphthyridine-3-carbonitrile;

4-((3-((1S,5S,6S)-3-amino-5-(fluoromethyl)-2-thia-4-azabicyclo[4.1.0]hept-3-en-5-yl)-4,5-difluorophenyl)amino)pyrido[3,2-d]pyrimidine-7-carbonitrile;

8-((3-((1S,5S,6S)-3-amino-1-(methoxymethyl)-5-methyl-2-thia-4-azabicyclo[4.1.0]hept-3-en-5-yl)-4,5-difluorophenyl)amino)-1,7-naphthyridine-3-carbonitrile;

N-(3-((1S,5S,6S)-3-amino-1-(methoxymethyl)-5-methyl-2-thia-4-azabicyclo [4.1.0]hept-3-en-5-yl)-4,5-difluorophenyl)-7-chloropyrido[3,2-d]pyrimidin-4-amine;

4-((3-((1S,5S,6S)-3-amino-5-methyl-2-thia-4-azabicyclo[4.1.0]hept-3-en-5-yl)-4,5-difluorophenyl)amino)pyrido[3,2-d]pyrimidine-7-carbonitrile;

8-((3-((1S,5S,6S)-3-amino-5-(fluoromethyl)-2-thia-4-azabicyclo[4.1.0]hept-3-en-5-yl)-4-fluorophenyl)amino)-1,7-naphthyridine-3-carbonitrile;

N-(3-((1S,5S,6S)-3-amino-5-(fluoromethyl)-2-thia-4-azabicyclo[4.1.0]hept-3-en-5-yl)-4-fluorophenyl)-7-chloropyrido[3,2-d]pyrimidin-4-amine;

4-((3-((1S,5S,6S)-3-amino-1-(methoxymethyl)-5-methyl-2-thia-4-azabicyclo [4.1.0]hept-3-en-5-yl)-4,5-difluorophenyl)amino)pyrido[3,2-d]pyrimidine-7-carbonitrile;

((1S,5S,6S)-3-amino-5-(5-((7-chloropyrido[3,2-d]pyrimidin-4-yl)amino)-2-fluorophenyl)-5-(fluoromethyl)-2-thia-4-azabicyclo[4.1.0]hept-3-en-1-yl)methanol;

4-((3-((1S,5S,6S)-3-amino-5-(fluoromethyl)-2-thia-4-azabicyclo[4.1.0]hept-3-en-5-yl)-4-fluorophenyl)amino)pyrido[3,2-d]pyrimidine-7-carbonitrile;

((1S,5S,6S)-3-amino-5-(fluoromethyl)-5-(2-fluoro-5-((3-(2-propyn-1-yloxy)-1,7-naphthyridin-8-yl)amino)phenyl)-2-thia-4-azabicyclo[4.1.0]hept-3-en-1-yl)methanol;

8-((3-(((1S,5S,6S)-3-amino-1-(hydroxymethyl)-5-methyl-2-thia-4-azabicyclo [4.1.0]hept-3-en-5-yl)-4,5-difluorophenyl)amino)-1,7-naphthyridine-3-carbonitrile;

N-(3-((1S,5S,6S)-3-amino-5-(fluoromethyl)-2-thia-4-azabicyclo[4.1.0]hept-3-en-5-yl)-4-fluorophenyl)-2-(1,3-oxazol-2-ylmethoxy)pyrido[3,4-b]pyrazin-5-amine;

N-(3-((1S,5S,6S)-3-amino-1-(methoxymethyl)-5-methyl-2-thia-4-azabicyclo [4.1.0]hept-3-en-5-yl)-4,5-difluorophenyl)-5-(2-propyn-1-yloxy)-2-pyrazinecarboxamide;

((1S,5S,6S)-3-amino-5-(2,3-difluoro-5-((2-(2-propyn-1-yloxy)pyrido[3,4-b]pyrazin-5-yl)amino)phenyl)-5-methyl-2-thia-4-azabicyclo[4.1.0]hept-3-en-1-yl)methanol;

N-(3-((1S,5S,6S)-3-amino-5-(fluoromethyl)-2-thia-4-azabicyclo[4.1.0]hept-3-en-5-yl)-4,5-difluorophenyl)-3-methyl-5-(2-propyn-1-yloxy)-2-pyrazinecarboxamide; or 4-((3-((1S,5S,6S)-3-amino-1-(difluoromethyl)-5-methyl-2-thia-4-azabicyclo [4.1.0]hept-3-en-5-yl)-4,5-difluorophenyl)amino)pyrido[3,2-d]pyrimidine-7-carbonitrile.

56. The compound of claim 1, or a tautomer or pharmaceutically acceptable salt thereof, selected from N-(5-((1S,5S,6 S)-3-amino-1-(fluoromethyl)-5-methyl-2-thia-4-azabicyclo[4.1.0]hept-3-en-5-yl)-6-fluoro-3-pyridinyl)-2-(2-propyn-1-yloxy)pyrido[3,4-b]pyrazin-5-amine;

N-(5-((1S,5S,6 S)-3-amino-1-(fluoromethyl)-5-methyl-2-thia-4-azabicyclo[4.1.0]hept-3-en-5-yl)-6-fluoro-3-pyridinyl)-2-(1,3-oxazol-2-ylmethoxy)pyrido[3,4-b]pyrazin-5-amine;

N-(5-((1S,5S,6 S)-3-amino-1-(fluoromethyl)-5-methyl-2-thia-4-azabicyclo[4.1.0]hept-3-en-5-yl)-6-fluoro-3-pyridinyl)-3-methyl-5-(2-propyn-1-yloxy)-2-pyrazinecarboxamide;

8-((5-((1S,5S,6S)-3-amino-1-(fluoromethyl)-5-methyl-2-thia-4-azabicyclo[4.1.0]hept-3-en-5-yl)-6-fluoro-3-pyridinyl)amino)-1,7-naphthyridine-3-carbonitrile;

N-(5-((1S,5S,6S)-3-amino-1-(fluoromethyl)-5-methyl-2-thia-4-azabicyclo[4.1.0]hept-3-en-5-yl)-6-fluoro-3-pyridinyl)-7-(1,3-oxazol-2-ylmethoxy)pyrido[3,2-d]pyrimidin-4-amine;

N-(5-((1S,5S,6S)-3-amino-1-(fluoromethyl)-5-methyl-2-thia-4-azabicyclo[4.1.0]hept-3-en-5-yl)-6-fluoro-3-pyridinyl)-5-(2-propyn-1-yloxy)-2-pyrazinecarboxamide;

N-(5-((1S,5S,6S)-3-amino-1-(fluoromethyl)-5-methyl-2-thia-4-azabicyclo[4.1.0]hept-3-en-5-yl)-6-fluoro-3-pyridinyl)-5-(1,3-oxazol-2-ylmethoxy)-2-pyrazinecarboxamide;

((1R,5S,6S)-3-amino-5-(2-fluoro-5-((7-(1,3-oxazol-2-ylmethoxy)pyrido[3,2-d]pyrimidin-4-yl)amino)-3-pyridinyl)-5-methyl-2-thia-4-azabicyclo[4.1.0]hept-3-en-1-yl)acetonitrile;

N-(5-((1S,5S,6S)-3-amino-1-(fluoromethyl)-5-methyl-2-thia-4-azabicyclo[4.1.0]hept-3-en-5-yl)-6-fluoro-3-pyridinyl)-5-(2,2,3,3-tetrafluoropropoxy)-2-pyridinecarboxamide;

N-(5-((1S,5S,6S)-3-amino-1-(fluoromethyl)-5-methyl-2-thia-4-azabicyclo[4.1.0]hept-3-en-5-yl)-6-fluoro-3-pyridinyl)-5-(2,2,3,3-tetrafluoropropoxy)-2-pyrazinecarboxamide;

N-(5-((1S,5S,6S)-3-amino-1-(fluoromethyl)-5-methyl-2-thia-4-azabicyclo[4.1.0]hept-3-en-5-yl)-6-methoxy-3-pyridinyl)-2-(2-propyn-1-yloxy)pyrido[3,4-b]pyrazin-5-amine;

N-(5-((1S,5S,6S)-3-amino-1-(fluoromethyl)-5-methyl-2-thia-4-azabicyclo[4.1.0]hept-3-en-5-yl)-6-methoxy-3-pyridinyl)-5-(2-propyn-1-yloxy)-2-pyrazinecarboxamide;

N-(5-((1S,5S,6S)-3-amino-1-(fluoromethyl)-5-methyl-2-thia-4-azabicyclo[4.1.0]hept-3-en-5-yl)-6-fluoro-3-pyridinyl)-2-((~2-H_5_)-2-butyn-1-yloxy)pyrido[3,4-b]pyrazin-5-amine;

N-(3-((1S,5S,6S)-3-amino-1-(fluoromethyl)-5-methyl-2-thia-4-azabicyclo[4.1.0]hept-3-en-5-yl)-4,5-difluorophenyl)-3-methyl-5-(2,2,2-trifluoroethoxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-3-methyl-5-(2,2,2-trifluoroethoxy)-2-pyrazinecarboxamide;

N-(3-((1S,5S,6S)-3-amino-1-(fluoromethyl)-5-methyl-2-thia-4-azabicyclo[4.1.0]hept-3-en-5-yl)-4,5-difluorophenyl)-3-methyl-5-(((1S)-1-methyl-2-propyn-1-yl)oxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-3-methyl-5-(((1S)-1-methyl-2-propyn-1-yl)oxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-(2,2,2-trifluoroethoxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-3-methyl-5-(((1S)-1-methyl-2-propyn-1-yl)oxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-3-methyl-5-(2,2,2-trifluoroethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-3-methyl-5-(((1S)-1-methyl-2-propyn-1-yl)oxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-(((1S)-1-methyl-2-propyn-1-yl)oxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-3-methyl-5-(2,2,2-trifluoroethoxy)-2-pyrazinecarboxamide;

N-(5-((1S,5S,6S)-3-amino-1-(fluoromethyl)-5-methyl-2-thia-4-azabicyclo[4.1.0]hept-3-en-5-yl)-6-methoxy-3-pyridinyl)-5-chloro-2-pyridinecarboxamide;

N-(5-((1S,5S,6S)-3-amino-1-(fluoromethyl)-5-methyl-2-thia-4-azabicyclo[4.1.0]hept-3-en-5-yl)-6-methoxy-3-pyridinyl)-7-(2-propyn-1-yloxy)pyrido[3,2-d]pyrimidin-4-amine;

N-(5-((1S,5S,6S)-3-amino-1-(fluoromethyl)-5-methyl-2-thia-4-azabicyclo[4.1.0]hept-3-en-5-yl)-6-methoxy-3-pyridinyl)-2-(1,3-oxazol-2-ylmethoxy)pyrido[3,4-b]pyrazin-5-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-2-(2-propyn-1-yloxy)pyrido[3,4-b]pyrazin-5-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-2-(1,3-oxazol-4-ylmethoxy)pyrido[3,4-b]pyrazin-5-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-3-methoxy-1,7-naphthyridin-8-amine;

N-(3-((1R,5S,6S)-3-amino-5-methyl-1-(methyl sulfonyl)-2-thia-4-azabicyclo[4.1.0]hept-3-en-5-yl)-4,5-difluorophenyl)-2-(2-propyn-1-yloxy)pyrido[3,4-b]pyrazin-5-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-2-(1,3-oxazol-2-ylmethoxy)pyrido[3,4-b]pyrazin-5-amine;

N-(3-((1S,5S,6S)-3-amino-5-methyl-1-(1-pyrrolidinylcarbonyl)-2-thia-4-azabicyclo[4.1.0]hept-3-en-5-yl)-4-fluorophenyl)-2-(2-propyn-1-yloxy)pyrido[3,4-b]pyrazin-5-amine;

N-(3-((1S,5S,6S)-3-amino-5-methyl-1-(1-pyrrolidinylcarbonyl)-2-thia-4-azabicyclo[4.1.0]hept-3-en-5-yl)-4-fluorophenyl)-5-(2-propyn-1-yloxy)-2-pyrazinecarboxamide;

N-(3-((1S,5S,6S)-3-amino-5-methyl-1-(1-pyrrolidinylcarbonyl)-2-thia-4-azabicyclo[4.1.0]hept-3-en-5-yl)-4-fluorophenyl)-5-(2,2,2-trifluoroethoxy)-2-pyrazinecarboxamide;

N-(3-((1S,5S,6S)-3-amino-1,5-bis(fluoromethyl)-2-thia-4-azabicyclo[4.1.0]hept-3-en-5-yl)-4-fluorophenyl)-2-(2-methoxyethoxy)pyrido[3,4-b]pyrazin-5-amine;

N-(3-((1S,5S,6S)-3-amino-5-methyl-2-thia-4-azabicyclo[4.1.0]hept-3-en-5-yl)-4,5-difluorophenyl)-7-fluoropyrido[3,2-d]pyrimidin-4-amine;

N-(5-((1S,5S,6S)-3-amino-5-methyl-2-thia-4-azabicyclo[4.1.0]hept-3-en-5-yl)-6-fluoro-3-pyridinyl)-5-chloro-2-pyridinecarboxamide;

5-((5-((1S,5S,6S)-3-amino-5-methyl-2-thia-4-azabicyclo[4.1.0]hept-3-en-5-yl)-6-fluoro-3-pyridinyl)amino)pyrido[3,4-b]pyrazin-2(1H)-one;

N-(5-((1S,5S,6S)-3-amino-5-methyl-2-thia-4-azabicyclo[4.1.0]hept-3-en-5-yl)-6-fluoro-3-pyridinyl)-2-(2-propyn-1-yloxy)pyrido[3,4-b]pyrazin-5-amine;

N-(5-((1S,5S,6S)-3-amino-5-methyl-2-thia-4-azabicyclo[4.1.0]hept-3-en-5-yl)-6-fluoro-3-pyridinyl)-2-(1,3-oxazol-2-ylmethoxy)pyrido[3,4-b]pyrazin-5-amine;

8-((5-((1S,5S,6S)-3-amino-5-methyl-2-thia-4-azabicyclo[4.1.0]hept-3-en-5-yl)-6-fluoro-3-pyridinyl)amino)-1,7-naphthyridine-3-carbonitrile;

N-(3-((1S,5S,6S)-3-amino-1-(difluoromethyl)-5-methyl-2-thia-4-azabicyclo[4.1.0]hept-3-en-5-yl)-4-fluorophenyl)-3-methyl-5-(1,3-oxazol-2-ylmethoxy)-2-pyridinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-3-methyl-5-(1,3-oxazol-2-ylmethoxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-3-methyl-5-(1,3-oxazol-2-ylmethoxy)-2-pyridinecarboxamide;

N-(3-((1S,5S,6S)-3-amino-1-(fluoromethyl)-5-methyl-2-thia-4-azabicyclo[4.1.0]hept-3-en-5-yl)-4,5-difluorophenyl)-3-methyl-5-(1,3-oxazol-2-ylmethoxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-(1,3-oxazol-2-ylmethoxy)-2-pyridinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-3-methyl-5-(((1S)-1-methyl-2-propyn-1-yl)oxy)-2-pyridinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-3-methyl-5-(((1S)-1-methyl-2-propyn-1-yl)oxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-3-methyl-5-(((1S)-1-methyl-2-propyn-1-yl)oxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-(((1S)-1-methyl-2-propyn-1-yl)oxy)-2-pyridinecarboxamide;

N-(3-((1S,5S,6S)-3-amino-1-(fluoromethyl)-5-methyl-2-thia-4-azabicyclo[4.1.0]hept-3-en-5-yl)-4-fluorophenyl)-3-methyl-5-(((1S)-1-methyl-2-propyn-1-yl)oxy)-2-pyridinecarboxamide;

N-(3-((1S,5S,6S)-3-amino-1-(fluoromethyl)-5-methyl-2-thia-4-azabicyclo[4.1.0]hept-3-en-5-yl)-4-fluorophenyl)-3-methyl-5-(1,3-oxazol-2-ylmethoxy)-2-pyridinecarboxamide;

N-(5-((1S,5S,6S)-3-amino-1-(difluoromethyl)-5-methyl-2-thia-4-azabicyclo[4.1.0]hept-3-en-5-yl)-6-fluoro-3-pyridinyl)-2-(2-propyn-1-yloxy)pyrido[3,4-b]pyrazin-5-amine;

N-(5-((1S,5S,6S)-3-amino-1-(difluoromethyl)-5-methyl-2-thia-4-azabicyclo[4.1.0]hept-3-en-5-yl)-6-fluoro-3-pyridinyl)-2-(1,3-oxazol-2-ylmethoxy)pyrido[3,4-b]pyrazin-5-amine;

N-(5-((1S,5S,6S)-3-amino-1-(difluoromethyl)-5-methyl-2-thia-4-azabicyclo[4.1.0]hept-3-en-5-yl)-6-fluoro-3-pyridinyl)-5-chloro-2-pyridinecarboxamide;

8-((5-((1S,5S,6S)-3-amino-1-(difluoromethyl)-5-methyl-2-thia-4-azabicyclo[4.1.0]hept-3-en-5-yl)-6-fluoro-3-pyridinyl)amino)-N-(1-methylethyl)-1,7-naphthyridine-3-carboxamide;

8-((5-((1S,5S,6S)-3-amino-1-(difluoromethyl)-5-methyl-2-thia-4-azabicyclo[4.1.0]hept-3-en-5-yl)-6-fluoro-3-pyridinyl)amino)-1,7-naphthyridine-3-carbonitrile;

4-((5-((1S,5S,6S)-3-amino-1-(difluoromethyl)-5-methyl-2-thia-4-azabicyclo[4.1.0]hept-3-en-5-yl)-6-fluoro-3-pyridinyl)amino)pyrido[3,2-d]pyrimidine-7-carbonitrile;

(1R)-1-((1S,5S,6S)-3-amino-5-(2-fluoro-5-((2-(2-propyn-1-yloxy)pyrido[3,4-b]pyrazin-5-yl)amino)-3-pyridinyl)-5-methyl-2-thia-4-azabicyclo[4.1.0]hept-3-en-1-yl)-2,2,2-trifluoroethanol;

(1S)-1-((1S,5S,6S)-3-amino-5-(2-fluoro-5-((2-(2-propyn-1-yloxy)pyrido[3,4-b]pyrazin-5-yl)amino)-3-pyridinyl)-5-methyl-2-thia-4-azabicyclo[4.1.0]hept-3-en-1-yl)-2,2,2-trifluoroethanol;

((1S,5S,6R)-3-amino-7,7-difluoro-5-(2-fluoro-5-((2-(2-propyn-1-yloxy)pyrido[3,4-b]pyrazin-5-yl)amino)-3-pyridinyl)-5-methyl-2-thia-4-azabicyclo[4.1.0]hept-3-en-1-yl)methanol;

((1S,5S,6S)-3-amino-5-(2-fluoro-5-((2-(2-propyn-1-yloxy)pyrido[3,4-b]pyrazin-5-yl)amino)-3-pyridinyl)-5-methyl-2-thia-4-azabicyclo[4.1.0]hept-3-en-1-yl)methanol;

((1S,5S,6R)-3-amino-7,7-difluoro-5-(2-fluoro-5-((2-(1,3-oxazol-2-ylmethoxy)pyrido[3,4-b]pyrazin-5-yl)amino)-3-pyridinyl)-5-methyl-2-thia-4-azabicyclo[4.1.0]hept-3-en-1-yl)methanol;

((1S,5S,6R)-3-amino-7,7-difluoro-5-(2-fluoro-5-((7-(1,3-oxazol-2-ylmethoxy)pyrido[3,2-d]pyrimidin-4-yl)amino)-3-pyridinyl)-5-methyl-2-thia-4-azabicyclo[4.1.0]hept-3-en-1-yl)methanol;

(1R)-1-((1S,5S,6S)-3-amino-5-(2-fluoro-5-((7-(2-propyn-1-yloxy)pyrido[3,2-d]pyrimidin-4-yl)amino)-3-pyridinyl)-5-methyl-2-thia-4-azabicyclo[4.1.0]hept-3-en-1-yl)-2,2,2-trifluoroethanol;

(1S)-1-((1S,5S,6S)-3-amino-5-(2-fluoro-5-((7-(2-propyn-1-yloxy)pyrido[3,2-d]pyrimidin-4-yl)amino)-3-pyridinyl)-5-methyl-2-thia-4-azabicyclo[4.1.0]hept-3-en-1-yl)-2,2,2-trifluoroethanol;

(1R)-1-((1S,5S,6S)-3-amino-5-(2-fluoro-5-((7-(1,3-oxazol-2-ylmethoxy)pyrido[3,2-d]pyrimidin-4-yl)amino)-3-pyridinyl)-5-methyl-2-thia-4-azabicyclo[4.1.0]hept-3-en-1-yl)-2,2,2-trifluoroethanol;

(1S)-1-((1S,5S,6S)-3-amino-5-(2-fluoro-5-((7-(1,3-oxazol-2-ylmethoxy)pyrido[3,2-d]pyrimidin-4-yl)amino)-3-pyridinyl)-5-methyl-2-thia-4-azabicyclo[4.1.0]hept-3-en-1-yl)-2,2,2-trifluoroethanol;

((1S,5S,6R)-3-amino-7,7-difluoro-5-(2-fluoro-5-((3-(1,3-oxazol-2-ylmethoxy)-1,7-naphthyridin-8-yl)amino)-3-pyridinyl)-5-methyl-2-thia-4-azabicyclo[4.1.0]hept-3-en-1-yl)methanol;

((1S,5S,6S)-3-amino-5-(2-fluoro-5-((7-(2-propyn-1-yloxy)pyrido[3,2-d]pyrimidin-4-yl)amino)-3-pyridinyl)-5-methyl-2-thia-4-azabicyclo[4.1.0]hept-3-en-1-yl)methanol;

(1R)-1-((1S,5S,6S)-3-amino-5-(2-fluoro-5-((2-(2-propyn-1-yloxy)pyrido[3,4-b]pyrazin-5-yl)amino)phenyl)-5-methyl-2-thia-4-azabicyclo[4.1.0]hept-3-en-1-yl)-2,2,2-trifluoroethanol;

(1S)-1-((1S,5S,6S)-3-amino-5-(2-fluoro-5-((2-(2-propyn-1-yloxy)pyrido[3,4-b]pyrazin-5-yl)amino)phenyl)-5-methyl-2-thia-4-azabicyclo[4.1.0]hept-3-en-1-yl)-2,2,2-trifluoroethanol;

N-(3-((1S,5S,6S)-3-amino-5-methyl-1-((1R)-2,2,2-trifluoro-1-hydroxyethyl)-2-thia-4-azabicyclo[4.1.0]hept-3-en-5-yl)-4-fluorophenyl)-5-(2-propyn-1-yloxy)-2-pyrazinecarboxamide;

N-(3-((1S,5S,6S)-3-amino-5-methyl-1-((1S)-2,2,2-trifluoro-1-hydroxyethyl)-2-thia-4-azabicyclo[4.1.0]hept-3-en-5-yl)-4-fluorophenyl)-5-(2-propyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-(2,2,2-trifluoroethoxy)-2-pyridinecarboxamide;

N-(5-((1S,5S,6S)-3-amino-5-methyl-1-((1R)-2,2,2-trifluoro-1-methoxyethyl)-2-thia-4-azabicyclo[4.1.0]hept-3-en-5-yl)-6-fluoro-3-pyridinyl)-2-(2-propyn-1-yloxy)pyrido[3,4-b]pyrazin-5-amine;

N-(5-((1S,5S,6S)-3-amino-5-methyl-1-((1S)-2,2,2-trifluoro-1-methoxyethyl)-2-thia-4-azabicyclo[4.1.0]hept-3-en-5-yl)-6-fluoro-3-pyridinyl)-2-(2-propyn-1-yloxy)pyrido[3,4-b]pyrazin-5-amine;

N-(3-((1S,5S,6S)-3-amino-1-(fluoromethyl)-5-methyl-2-thia-4-azabicyclo[4.1.0]hept-3-en-5-yl)-4,5-difluorophenyl)-3-methyl-5-(2,2,2-trifluoroethoxy)-2-pyridinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-3-methyl-5-(2,2,2-trifluoroethoxy)-2-pyridinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-3-methyl-5-(2,2,2-trifluoroethoxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-3-methyl-5-(2,2,2-trifluoroethoxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-(2-propyn-1-yloxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-3-methyl-5-(2-propyn-1-yloxy)-2-pyridinecarboxamide;

N-(3-((1S,5S,6S)-3-amino-1-(fluoromethyl)-5-methyl-2-thia-4-azabicyclo[4.1.0]hept-3-en-5-yl)-4,5-difluorophenyl)-3-methyl-5-(2-propyn-1-yloxy)-2-pyridinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-3-methyl-5-(2-propyn-1-yloxy)-2-pyridinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-3-methyl-5-(2-propyn-1-yloxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-((1S)-1-(1,3-oxazol-2-yl)ethoxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-((1R)-1-(1,3-oxazol-2-yl)ethoxy)-2-pyridinecarboxamide;

N-(3-((1S,5S,6S)-3-amino-1-(fluoromethyl)-5-methyl-2-thia-4-azabicyclo[4.1.0]hept-3-en-5-yl)-4-fluorophenyl)-3-methyl-5-(2,2,2-trifluoroethoxy)-2-pyridinecarboxamide;

N-(3-((1S,5S,6S)-3-amino-1-(fluoromethyl)-5-methyl-2-thia-4-azabicyclo[4.1.0]hept-3-en-5-yl)-4-fluorophenyl)-3-methyl-5-(2-propyn-1-yloxy)-2-pyridinecarboxamide;

N-(3-((1S,5S,6S)-3-amino-1-(fluoromethyl)-5-methyl-2-thia-4-azabicyclo[4.1.0]hept-3-en-5-yl)-4,5-difluorophenyl)-3-chloro-5-(2-propyn-1-yloxy)-2-pyridinecarboxamide;

N-(3-((1S,5S,6S)-3-amino-1-(fluoromethyl)-5-methyl-2-thia-4-azabicyclo[4.1.0]hept-3-en-5-yl)-4,5-difluorophenyl)-5-(2,2,2-trifluoroethoxy)-2-pyridinecarboxamide;

N-(3-((1S,5S,6S)-3-amino-1-(fluoromethyl)-5-methyl-2-thia-4-azabicyclo[4.1.0]hept-3-en-5-yl)-4,5-difluorophenyl)-3-chloro-5-(2,2,2-trifluoroethoxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(2,2,2-trifluoroethoxy)-2-pyridinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-5-(2,2,2-trifluoroethoxy)-2-pyridinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-5-(2,2,2-trifluoroethoxy)-2-pyridinecarboxamide;

N-(3-((1S,5S,6S)-3-amino-1-(fluoromethyl)-5-methyl-2-thia-4-azabicyclo[4.1.0]hept-3-en-5-yl)-4-fluorophenyl)-5-(2,2,2-trifluoroethoxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(2,2,2-trifluoroethoxy)-2-pyridinecarboxamide;

N-(3-((1S,5S,6 S)-3-amino-5-methyl-1-(1-pyrrolidinylcarbonyl)-2-thia-4-azabicyclo[4.1.0]hept-3-en-5-yl)-4,5-difluorophenyl)-5-(2,2,2-trifluoroethoxy)-2-pyridinecarboxamide;

(1S,5S,6S)-3-amino-5-(2,3-difluoro-5-(((5-(2,2,2-trifluoroethoxy)-2-pyridinyl)carbonyl)amino)phenyl)-N,5-dimethyl-2-thia-4-azabicyclo[4.1.0]hept-3-ene-1-carboxamide;

(1S,5S,6S)-3-amino-5-(2,3-difluoro-5-(((5-(2,2,2-trifluoroethoxy)-2-pyrazinyl)carbonyl)amino)phenyl)-N,5-dimethyl-2-thia-4-azabicyclo[4.1.0]hept-3-ene-1-carboxamide;

(1S,5S,6S)-3-amino-5-(2,3-difluoro-5-(((3-methyl-5-(2,2,2-trifluoroethoxy)-2-pyridinyl)carbonyl)amino)phenyl)-N,5-dimethyl-2-thia-4-azabicyclo[4.1.0]hept-3-ene-1-carboxamide;

4-((3-((1S,5S,6R)-3-amino-7,7-difluoro-1-(hydroxymethyl)-5-methyl-2-thia-4-azabicyclo[4.1.0]hept-3-en-5-yl)-4-fluorophenyl)amino)pyrido[3,2-d]pyrimidine-7-carbonitrile;

N-(3-((1S,5S,6R)-3-amino-7,7-difluoro-1-(hydroxymethyl)-5-methyl-2-thia-4-azabicyclo[4.1.0]hept-3-en-5-yl)-4-fluorophenyl)-5-chloro-2-pyridinecarboxamide;

((1S,5S,6R)-3-amino-7,7-difluoro-5-(2-fluoro-5-((2-(1,3-oxazol-2-ylmethoxy)pyrido[3,4-b]pyrazin-5-yl)amino)phenyl)-5-methyl-2-thia-4-azabicyclo[4.1.0]hept-3-en-1-yl)methanol;

((1S,5S,6R)-3-amino-7,7-difluoro-5-(2-fluoro-5-((2-(1,3-oxazol-4-ylmethoxy)pyrido[3,4-b]pyrazin-5-yl)amino)phenyl)-5-methyl-2-thia-4-azabicyclo[4.1.0]hept-3-en-1-yl)methanol;

((1S,5S,6R)-3-amino-7,7-difluoro-5-(2-fluoro-5-((2-(2-propyn-1-yloxy)pyrido[3,4-b]pyrazin-5-yl)amino)phenyl)-5-methyl-2-thia-4-azabicyclo[4.1.0]hept-3-en-1-yl)methanol;

N-(3-((1S,5S,6R)-3-amino-7,7-difluoro-1-(hydroxymethyl)-5-methyl-2-thia-4-azabicyclo[4.1.0]hept-3-en-5-yl)-4-fluorophenyl)-5-(2,2,3,3-tetrafluoropropoxy)-2-pyrazinecarboxamide;

4-((3-((1S,5S,6R)-3-amino-7,7-difluoro-1-(methoxymethyl)-5-methyl-2-thia-4-azabicyclo[4.1.0]hept-3-en-5-yl)-4-fluorophenyl)amino)pyrido[3,2-d]pyrimidine-7-carbonitrile;

N-(3-((1S,5S,6R)-3-amino-7,7-difluoro-1-(methoxymethyl)-5-methyl-2-thia-4-azabicyclo[4.1.0]hept-3-en-5-yl)-4-fluorophenyl)-5-chloro-2-pyridinecarboxamide;

N-(3-((1S,5S,6R)-3-amino-7,7-difluoro-1-(1-hydroxy-1-methylethyl)-5-methyl-2-thia-4-azabicyclo[4.1.0]hept-3-en-5-yl)-4-fluorophenyl)-5-chloro-2-pyridinecarboxamide;

2-((1S,5S,6R)-3-amino-7,7-difluoro-5-(2-fluoro-5-((2-(2-propyn-1-yloxy)pyrido[3,4-b]pyrazin-5-yl)amino)phenyl)-5-methyl-2-thia-4-azabicyclo[4.1.0]hept-3-en-1-yl)-2-propanol;

(1R)-1-((1S,5S,6R)-3-amino-7,7-difluoro-5-(2-fluoro-5-((2-(2-propyn-1-yloxy)pyrido[3,4-b]pyrazin-5-yl)amino)phenyl)-5-methyl-2-thia-4-azabicyclo[4.1.0]hept-3-en-1-yl)ethanol;

(1S)-1-((1S,5S,6R)-3-amino-7,7-difluoro-5-(2-fluoro-5-((2-(2-propyn-1-yloxy)pyrido[3,4-b]pyrazin-5-yl)amino)phenyl)-5-methyl-2-thia-4-azabicyclo[4.1.0]hept-3-en-1-yl)ethanol;

N-(3-((1S,5S,6S)-3-amino-1-(ethoxymethyl)-5-(fluoromethyl)-2-thia-4-azabicyclo[4.1.0]hept-3-en-5-yl)-4-fluorophenyl)-5-cyano-3-methyl-2-pyridinecarboxamide;

N-(3-((1S,5S,6S)-3-amino-5-(fluoromethyl)-1-(methoxymethyl)-2-thia-4-azabicyclo[4.1.0]hept-3-en-5-yl)-4-fluorophenyl)-5-cyano-3-methyl-2-pyridinecarboxamide;

8-((3-((1S,5S,6S)-3-amino-5-(fluoromethyl)-1-(methoxymethyl)-2-thia-4-azabicyclo[4.1.0]hept-3-en-5-yl)-4-fluorophenyl)amino)-1,7-naphthyridine-3-carbonitrile;

N-(3-((1R,5S,6S)-3-amino-1-(cyanomethyl)-5-(fluoromethyl)-2-thia-4-azabicyclo[4.1.0]hept-3-en-5-yl)-4-fluorophenyl)-5-chloro-2-pyridinecarboxamide;

8-((3-((1R,5S,6S)-3-amino-1-(cyanomethyl)-5-(fluoromethyl)-2-thia-4-azabicyclo[4.1.0]hept-3-en-5-yl)-4-fluorophenyl)amino)-1,7-naphthyridine-3-carbonitrile;

((1R,5S,6S)-3-amino-5-(fluoromethyl)-5-(2-fluoro-5-((2-(2-propyn-1-yloxy)pyrido[3,4-b]pyrazin-5-yl)amino)phenyl)-2-thia-4-azabicyclo[4.1.0]hept-3-en-1-yl)acetonitrile;

((1R,5S,6S)-3-amino-5-(fluoromethyl)-5-(2-fluoro-5-((2-(1,3-oxazol-2-ylmethoxy)pyrido[3,4-b]pyrazin-5-yl)amino)phenyl)-2-thia-4-azabicyclo[4.1.0]hept-3-en-1-yl)acetonitrile;

N-(3-((1S,5S,6S)-3-amino-5-(fluoromethyl)-1-(1H-1,2,3-triazol-1-ylmethyl)-2-thia-4-azabicyclo[4.1.0]hept-3-en-5-yl)-4-fluorophenyl)-5-chloro-2-pyridinecarboxamide;

N-(3-((1S,5S,6S)-3-amino-1-(2-cyanoethyl)-5-(fluoromethyl)-2-thia-4-azabicyclo[4.1.0]hept-3-en-5-yl)-4-fluorophenyl)-5-chloro-2-pyridinecarboxamide;

N-(3-((1S,5S,6S)-3-amino-5-(fluoromethyl)-1-((4-methyl-1H-1,2,3-triazol-1-yl)methyl)-2-thia-4-azabicyclo[4.1.0]hept-3-en-5-yl)-4-fluorophenyl)-2-(2-propyn-1-yloxy)pyrido[3,4-b]pyrazin-5-amine;

N-(3-((1S,5S,6S)-3-amino-5-(fluoromethyl)-1-((5-methyl-1H-1,2,3-triazol-1-yl)methyl)-2-thia-4-azabicyclo[4.1.0]hept-3-en-5-yl)-4-fluorophenyl)-5-chloro-2-pyridinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-(1,3-oxazol-5-ylmethoxy)-1,7-naphthyridin-8-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-3-(1,3-oxazol-2-ylmethoxy)-1,7-naphthyridin-8-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-3-(1,3-oxazol-4-ylmethoxy)-1,7-naphthyridin-8-amine;

((8-((3-((1S,5S,6S)-3-amino-1-(methoxymethyl)-5-methyl-2-thia-4-azabicyclo[4.1.0]hept-3-en-5-yl)-4,5-difluorophenyl)amino)-1,7-naphthyridin-3-yl)oxy)acetonitrile;

N-(3-((1S,5S,6S)-3-amino-1-(methoxymethyl)-5-methyl-2-thia-4-azabicyclo[4.1.0]hept-3-en-5-yl)-4,5-difluorophenyl)-3 (1,2,4-oxadiazol-3-ylmethoxy)-1,7-naphthyridin-8-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-3-(2,2,3,3-tetrafluoropropoxy)-1,7-naphthyridin-8-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(2,2,3,3-tetrafluoropropoxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3 (2-propyn-1-yloxy)-1,7-naphthyridin-8-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(2,2,3,3-tetrafluoropropoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-((5-chloro-1,3-thiazol-2-yl)methoxy)-1,7-naphthyridin-8-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-3-((4-bromo-1,3-thiazol-2-yl)methoxy)-1,7-naphthyridin-8-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-3-(1,3-thiazol-2-ylmethoxy)-1,7-naphthyridin-8-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(3,3,3-trifluoropropoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(2,2-difluoropropoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(3-fluoropropoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-((4,4,4-trifluoro-2-butyn-1-yl)oxy)-1,7-naphthyridin-8-amine;

N-(3-((1R,5S,6S)-3-amino-5-methyl-1-(methylsulfonyl)-2-thia-4-azabicyclo[4.1.0]hept-3-en-5-yl)-4,5-difluorophenyl)-5-chloro-2-pyridinecarboxamide;

N-(3-((1R,5S,6S)-3-amino-5-methyl-1-(methylsulfonyl)-2-thia-4-azabicyclo[4.1.0]hept-3-en-5-yl)-4,5-difluorophenyl)-5-(2-propyn-1-yloxy)-2-pyridinecarboxamide;

N-(3-((1R,5S,6S)-3-amino-5-methyl-1-(methylsulfonyl)-2-thia-4-azabicyclo[4.1.0]hept-3-en-5-yl)-4,5-difluorophenyl)-5-(2-propyn-1-yloxy)-2-pyrazinecarboxamide;

N-(3-((1R,5S,6S)-3-amino-5-methyl-1-(methylsulfonyl)-2-thia-4-azabicyclo[4.1.0]hept-3-en-5-yl)-4,5-difluorophenyl)-5-(1,3-oxazol-2-ylmethoxy)-2-pyridinecarboxamide;

N-(3-((1R,5S,6S)-3-amino-5-methyl-1-(methylsulfonyl)-2-thia-4-azabicyclo[4.1.0]hept-3-en-5-yl)-4,5-difluorophenyl)-5-(1,3-oxazol-2-ylmethoxy)-2-pyrazinecarboxamide;

N-(3-((1R,5S,6S)-3-amino-5-methyl-1-(methylsulfonyl)-2-thia-4-azabicyclo[4.1.0]hept-3-en-5-yl)-4,5-difluorophenyl)-2-(1,3-oxazol-2-ylmethoxy)pyrido[3,4-b]pyrazin-5-amine;

N-(3-((1R,5S,6R)-3-amino-7,7-difluoro-5-methyl-2-thia-4-azabicyclo[4.1.0]hept-3-en-5-yl)-4,5-difluorophenyl)-5-chloro-2-pyridinecarboxamide;

N-(3-((1S,5S,6R)-3-amino-7,7-difluoro-1-(hydroxymethyl)-5-methyl-2-thia-4-azabicyclo[4.1.0]hept-3-en-5-yl)-4-fluorophenyl)-5-(2-propyn-1-yloxy)-2-pyrazinecarboxamide;

((1S,5S,6R)-3-amino-7,7-difluoro-5-(2-fluoro-5-((7-(1,3-oxazol-2-ylmethoxy)pyrido[3,2-d]pyrimidin-4-yl)amino)phenyl)-5-methyl-2-thia-4-azabicyclo[4.1.0]hept-3-en-1-yl)methanol;

N-(3-((1S,5S,6R)-3-amino-7,7-difluoro-1-(hydroxymethyl)-5-methyl-2-thia-4-azabicyclo[4.1.0]hept-3-en-5-yl)-4-fluorophenyl)-5-(2,2,3,3-tetrafluoropropoxy)-2-pyridinecarboxamide;

N-(3-((4S,4aR,7aS)-2-amino-4-(fluoromethyl)-4,4a,4b,5-tetrahydrothieno[3',4':2,3]cyclopropa[1,2-e][1,3]thiazin-4-yl)-4-fluorophenyl)-5-chloro-2-pyridinecarboxamide;

N-(3-((4S,4aS,7aR)-2-amino-4-(fluoromethyl)-4,4a,4b,5-tetrahydrothieno[3',4':2,3]cyclopropa[1,2-e][1,3]thiazin-4-yl)-4-fluorophenyl)-5-chloro-2-pyridinecarboxamide;

N-(3-((4S,4aS,7aR)-2-amino-4-(fluoromethyl)-4,4a,4b,5-tetrahydrothieno[3',4':2,3]cyclopropa[1,2-e][1,3]thiazin-4-yl)-4-fluorophenyl)-5-chloro-2-pyridinecarboxamide;

N-(3-((1S,5S,6S)-3-amino-5-(fluoromethyl)-2-thia-4-azabicyclo[4.1.0]hept-3-en-5-yl)-4-fluorophenyl)-3-chloropyrido[2,3-d]pyridazin-8-amine;

ethyl (2E)-3-((1R,5S,6S)-3-amino-5-(5-(((5-chloro-2-pyridinyl)carbonyl)amino)-2-fluorophenyl)-5-(fluoromethyl)-2-thia-4-azabicyclo[4.1.0]hept-3-en-1-yl)-2-propenoate;

N-(3-((1R,5S,6S)-3-amino-5-(fluoromethyl)-1-((1E)-3-hydroxy-1-propen-1-yl)-2-thia-4-azabicyclo[4.1.0]hept-3-en-5-yl)-4-fluorophenyl)-5-chloro-2-pyridinecarboxamide;

(2E)-3-((1R,5S,6S)-3-amino-5-(5-(((5-chloro-2-pyridinyl)carbonyl)amino)-2-fluorophenyl)-5-(fluoromethyl)-2-thia-4-azabicyclo[4.1.0]hept-3-en-1-yl)-2-propenoic acid;

N-(3-((1S,5S,6S)-3-amino-5-(fluoromethyl)-1-(3-hydroxypropyl)-2-thia-4-azabicyclo[4.1.0]hept-3-en-5-yl)-4-fluorophenyl)-5-chloro-2-pyridinecarboxamide;

N-(3-((1R,5S,6S)-3-amino-1-((1E)-3-amino-3-oxo-1-propen-1-yl)-5-(fluoromethyl)-2-thia-4-azabicyclo[4.1.0]hept-3-en-5-yl)-4-fluorophenyl)-5-chloro-2-pyridinecarboxamide;

N-(3-((1R,5S,6S)-3-amino-5-(fluoromethyl)-1-((1E)-3-(methylamino)-3-oxo-1-propen-1-yl)-2-thia-4-azabicyclo[4.1.0]hept-3-en-5-yl)-4-fluorophenyl)-5-chloro-2-pyridinecarboxamide;

N-(3-((1R,5S,6S)-3-amino-1-((1E)-3-(dimethylamino)-3-oxo-1-propen-1-yl)-5-(fluoromethyl)-2-thia-4-azabicyclo[4.1.0]hept-3-en-5-yl)-4-fluorophenyl)-5-chloro-2-pyridinecarboxamide;

N-(3-((1S,5S,6S)-3-amino-5-(fluoromethyl)-2-thia-4-azabicyclo[4.1.0]hept-3-en-5-yl)-4-fluorophenyl)-2-(2-propyn-1-yloxy)pyrido[3,4-b]pyrazin-5-amine;

N-(3-((1S,5S,6S)-3-amino-5-(fluoromethyl)-2-thia-4-azabicyclo[4.1.0]hept-3-en-5-yl)-4-fluorophenyl)-7-(1,3-oxazol-2-ylmethoxy)pyrido[3,2-d]pyrimidin-4-amine;

N-(3-((1R,5S,6S)-3-amino-5-(fluoromethyl)-1-((1E)-3-(4-morpholinyl)-3-oxo-1-propen-1-yl)-2-thia-4-azabicyclo[4.1.0]hept-3-en-5-yl)-4-fluorophenyl)-5-chloro-2-pyridinecarboxamide;

N-(3-((1S,5S,6S)-3-amino-1-(3-(dimethylamino)-3-oxopropyl)-5-(fluoromethyl)-2-thia-4-azabicyclo[4.1.0]hept-3-en-5-yl)-4-fluorophenyl)-5-chloro-2-pyridinecarboxamide;

N-(3-((1R,5S,6S)-3-amino-5-(fluoromethyl)-1-((1E)-3-(3-methoxy-1-azetidinyl)-3-oxo-1-propen-1-yl)-2-thia-4-azabicyclo[4.1.0]hept-3-en-5-yl)-4-fluorophenyl)-5-chloro-2-pyridinecarboxamide;

N-(3-((1R,5S,6S)-3-amino-5-(fluoromethyl)-1-((1E)-3-((2-methoxyethyl)amino)-3-oxo-1-propen-1-yl)-2-thia-4-azabicyclo[4.1.0]hept-3-en-5-yl)-4-fluorophenyl)-5-chloro-2-pyridinecarboxamide;

(2E)-3-((1R,5S,6S)-3-amino-5-(fluoromethyl)-5-((2-fluoro-5-((2-(2-propyn-1-yloxy)pyrido[3,4-b]pyrazin-5-yl)amino)phenyl)-2-thia-4-azabicyclo[4.1.0]hept-3-en-1-yl)-N,N-dimethyl-2-propenamide;

(2E)-3-((1R,5S,6S)-3-amino-5-(fluoromethyl)-5-((2-fluoro-5-((2-(1,3-oxazol-2-ylmethoxy)pyrido[3,4-b]pyrazin-5-yl)amino)phenyl)-2-thia-4-azabicyclo[4.1.0]hept-3-en-1-yl)-N,N-dimethyl-2-propenamide;

(2E)-3-((1R,5S,6S)-3-amino-5-(fluoromethyl)-5-((2-fluoro-5-((3-(1,3-oxazol-2-ylmethoxy)-1,7-naphthyridin-8-yl)amino)phenyl)-2-thia-4-azabicyclo[4.1.0]hept-3-en-1-yl)-N,N-dimethyl-2-propenamide;

(2E)-3-((1R,5S,6S)-3-amino-5-(5-(((3-(2-butyn-1-yloxy)-1,7-naphthyridin-8-yl)amino)-2-fluorophenyl)-5-(fluoromethyl)-2-thia-4-azabicyclo[4.1.0]hept-3-en-1-yl)-N,N-dimethyl-2-propenamide;

N-(3-((1R,5S,6S)-3-amino-1-((1E)-3-(3,3-difluoro-1-azetidinyl)-3-oxo-1-propen-1-yl)-5-(fluoromethyl)-2-thia-4-azabicyclo[4.1.0]hept-3-en-5-yl)-4-fluorophenyl)-5-chloro-2-pyridinecarboxamide;

N-(3-((1R,5S,6S)-3-amino-1-((1E)-3-(3,3-difluoro-1-azetidinyl)-3-oxo-1-propen-1-yl)-5-(fluoromethyl)-2-thia-4-azabicyclo[4.1.0]hept-3-en-5-yl)-4-fluorophenyl)-2-(2-propyn-1-yloxy)pyrido[3,4-b]pyrazin-5-amine;

N-(3-((1R,5S,6S)-3-amino-1-((1E)-3-(dimethylamino)-3-oxo-1-propen-1-yl)-5-(fluoromethyl)-2-thia-4-azabicyclo[4.1.0]hept-3-en-5-yl)-4-fluorophenyl)-5-(2-propyn-1-yloxy)-2-pyrazinecarboxamide;

(2E)-3-((1R,5 S,6 S)-3-amino-5-(fluoromethyl)-5-(2-fluoro-5-((7-(1,3-oxazol-2-ylmethoxy)pyrido[3,2-d]pyrimidin-4-yl)amino)phenyl)-2-thia-4-azabicyclo[4.1.0]hept-3-en-1-yl)-N,N-dimethyl-2-propenamide;

(2E)-3-((1R,5 S,6 S)-3-amino-5-(fluoromethyl)-5-(2-fluoro-5-((7-(2-propyn-1-yloxy)pyrido[3,2-d]pyrimidin-4-yl)amino)phenyl)-2-thia-4-azabicyclo[4.1.0]hept-3-en-1-yl)-N,N-dimethyl-2-propenamide;

N-(3-((1R,5S,6S)-3-amino-5-(fluoromethyl)-1-((1Z)-2-methyl-3-(4-morpholinyl)-3-oxo-1-propen-1-yl)-2-thia-4-azabicyclo[4.1.0]hept-3-en-5-yl)-4-fluorophenyl)-5-chloro-2-pyridinecarboxamide;

N-(3-((1R,5S,6S)-3-amino-5-(fluoromethyl)-1-((1E)-2-methyl-3-(4-morpholinyl)-3-oxo-1-propen-1-yl)-2-thia-4-azabicyclo[4.1.0]hept-3-en-5-yl)-4-fluorophenyl)-5-chloro-2-pyridinecarboxamide;

(1S,5S,6S)-3-amino-5-(fluoromethyl)-5-(2-fluoro-5-((2-(2-propyn-1-yloxy)pyrido[3,4-b]pyrazin-5-yl)amino)phenyl)-N,N-dimethyl-2-thia-4-azabicyclo[4.1.0]hept-3-ene-1-carboxamide;

N-(3-((1S,5S,6S)-3-amino-5-(fluoromethyl)-1-(1,3-oxazol-5-yl)-2-thia-4-azabicyclo[4.1.0]hept-3-en-5-yl)-4-fluorophenyl)-5-(2-propyn-1-yloxy)-2-pyrazinecarboxamide;

N-(3-((1S,5S,6S)-3-amino-5-(fluoromethyl)-1-(1,3-oxazol-5-yl)-2-thia-4-azabicyclo[4.1.0]hept-3-en-5-yl)-4-fluorophenyl)-2-(2-propyn-1-yloxy)pyrido[3,4-b]pyrazin-5-amine;

N-(3-((1S,5S,6S)-3-amino-5-(fluoromethyl)-1-(1,3-oxazol-5-yl)-2-thia-4-azabicyclo[4.1.0]hept-3-en-5-yl)-4-fluorophenyl)-7-(2-propyn-1-yloxy)pyrido[3,2-d]pyrimidin-4-amine;

N-(3-((1S,5S,6S)-3-amino-5-(fluoromethyl)-1-(1,3-oxazol-5-yl)-2-thia-4-azabicyclo[4.1.0]hept-3-en-5-yl)-4-fluorophenyl)-5-(1,3-oxazol-2-ylmethoxy)-2-pyrazinecarboxamide;

N-(3-((1S,5S,6S)-3-amino-5-(fluoromethyl)-1-(4-methyl-1,3-oxazol-5-yl)-2-thia-4-azabicyclo[4.1.0]hept-3-en-5-yl)-4-fluorophenyl)-5-(2-propyn-1-yloxy)-2-pyrazinecarboxamide;

N-(3-((1S,5S,6S)-3-amino-5-(fluoromethyl)-1-(1,3-oxazol-5-yl)-2-thia-4-azabicyclo[4.1.0]hept-3-en-5-yl)-4-fluorophenyl)-5-chloro-2-pyridinecarboxamide;

N-(3-((1S,5S,6S)-3-amino-5-(fluoromethyl)-1-(3-isoxazolyl)-2-thia-4-azabicyclo[4.1.0]hept-3-en-5-yl)-4-fluorophenyl)-5-chloro-2-pyridinecarboxamide;

N-(3-((1S,5S,6S)-3-amino-5-(fluoromethyl)-1-(4-methyl-1,3-oxazol-5-yl)-2-thia-4-azabicyclo[4.1.0]hept-3-en-5-yl)-4-fluorophenyl)-5-chloro-2-pyridinecarboxamide;

N-(3-((1S,5S,6S)-3-amino-5-(fluoromethyl)-1-(4-methyl-1,3-oxazol-5-yl)-2-thia-4-azabicyclo[4.1.0]hept-3-en-5-yl)-4-fluorophenyl)-7-(2-propyn-1-yloxy)pyrido[3,2-d]pyrimidin-4-amine;

N-(3-((1S,5S,6S)-3-amino-5-(fluoromethyl)-1-(4-methyl-1,3-oxazol-5-yl)-2-thia-4-azabicyclo[4.1.0]hept-3-en-5-yl)-4-fluorophenyl)-5-(2-propyn-1-yloxy)-2-pyridinecarboxamide;

(1S,5S,6S)-3-amino-5-(5-(((5-chloro-2-pyridinyl)carbonyl)amino)-2-fluorophenyl)-5-(fluoromethyl)-N,N-dimethyl-2-thia-4-azabicyclo[4.1.0]hept-3-ene-1-carboxamide;

(1S,5S,6S)-3-amino-N-cyclopropyl-5-(2-fluoro-5-((7-(2-propyn-1-yloxy)pyrido[3,2-d]pyrimidin-4-yl)amino)phenyl)-5-methyl-2-thia-4-azabicyclo[4.1.0]hept-3-ene-1-carboxamide;

(1S,5S,6S)-3-amino-5-(5-(((5-chloro-2-pyridinyl)carbonyl)amino)-2-fluorophenyl)-N-cyclopropyl-5-methyl-2-thia-4-azabicyclo[4.1.0]hept-3-ene-1-carboxamide;

N-(3-((1S,5S,6S)-3-amino-5-(fluoromethyl)-1-(3-isoxazolyl)-2-thia-4-azabicyclo[4.1.0]hept-3-en-5-yl)-4-fluorophenyl)-5-(2-propyn-1-yloxy)-2-pyridinecarboxamide;

(1S,5S,6S)-3-amino-N-cyclopropyl-5-(2-fluoro-5-((2-(2-propyn-1-yloxy)pyrido[3,4-b]pyrazin-5-yl)amino)phenyl)-5-methyl-2-thia-4-azabicyclo[4.1.0]hept-3-ene-1-carboxamide;

(1S,5S,6S)-3-amino-N-cyclopropyl-5-(2-fluoro-5-(((5-(2-propyn-1-yloxy)-2-pyrazinyl)carbonyl)amino)phenyl)-5-methyl-2-thia-4-azabicyclo[4.1.0]hept-3-ene-1-carboxamide;

(1S,5S,6S)-3-amino-N-cyclopropyl-5-(2-fluoro-5-((2-(1,3-oxazol-2-ylmethoxy)pyrido[3,4-b]pyrazin-5-yl)amino)phenyl)-5-methyl-2-thia-4-azabicyclo[4.1.0]hept-3-ene-1-carboxamide;

(1S,5S,6S)-3-amino-N-tert-butyl-5-(5-(((5-chloro-2-pyridinyl)carbonyl)amino)-2-fluorophenyl)-5-methyl-2-thia-4-azabicyclo[4.1.0]hept-3-ene-1-carboxamide;

(1S,5S,6S)-3-amino-N-tert-butyl-5-(2-fluoro-5-(((5-(2-propyn-1-yloxy)-2-pyrazinyl)carbonyl)amino)phenyl)-5-methyl-2-thia-4-azabicyclo[4.1.0]hept-3-ene-1-carboxamide;

(1S,5S,6S)-3-amino-N-cyclopropyl-5-(2-fluoro-5-(((5-(1,3-oxazol-2-ylmethoxy)-2-pyrazinyl)carbonyl)amino)phenyl)-5-methyl-2-thia-4-azabicyclo[4.1.0]hept-3-ene-1-carboxamide;

(1S,5S,6S)-3-amino-N-cyclopropyl-5-(2-fluoro-5-(((5-(2,2,2-trifluoroethoxy)-2-pyrazinyl)carbonyl)amino)phenyl)-5-methyl-2-thia-4-azabicyclo[4.1.0]hept-3-ene-1-carboxamide;

4-((3-((1S,5S,6S)-3-amino-1-(fluoromethyl)-5-methyl-2-thia-4-azabicyclo[4.1.0]hept-3-en-5-yl)-4,5-difluorophenyl)amino)pyrido[3,2-d]pyrimidine-7-carbonitrile;

N-(3-((1S,5S,6S)-3-amino-1-(fluoromethyl)-5-methyl-2-thia-4-azabicyclo[4.1.0]hept-3-en-5-yl)-4,5-difluorophenyl)-2-(1,3-oxazol-2-ylmethoxy)pyrido[3,4-b]pyrazin-5-amine;

N-(3-((1S,5S,6S)-3-amino-1-(fluoromethyl)-5-methyl-2-thia-4-azabicyclo[4.1.0]hept-3-en-5-yl)-4,5-difluorophenyl)-3-methyl-5-(1,3-oxazol-2-ylmethoxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-5-chloro-2-pyridinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-2-(2-propyn-1-yloxy)pyrido[3,4-b]pyrazin-5-amine;

N-(3-((1S,5S,6S)-3-amino-1-(fluoromethyl)-5-methyl-2-thia-4-azabicyclo[4.1.0]hept-3-en-5-yl)-4,5-difluorophenyl)-2-(2-propyn-1-yloxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-5-(2-propyn-1-yloxy)-2-pyrazinecarboxamide;

N-(3-((1S,5S,6S)-3-amino-1-(fluoromethyl)-5-methyl-2-thia-4-azabicyclo[4.1.0]hept-3-en-5-yl)-4,5-difluorophenyl)-7-(1,3-oxazol-2-ylmethoxy)pyrido[3,2-d]pyrimidin-4-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-7-(1,3-oxazol-2-ylmethoxy)pyrido[3,2-d]pyrimidin-4-amine;

N-(3-((1S,5S,6S)-3-amino-1-(fluoromethyl)-5-methyl-2-thia-4-azabicyclo[4.1.0]hept-3-en-5-yl)-4,5-difluorophenyl)-5-(2-propyn-1-yloxy)-2-pyrazinecarboxamide;

N-(3-((1S,5S,6S)-3-amino-1-(fluoromethyl)-5-methyl-2-thia-4-azabicyclo[4.1.0]hept-3-en-5-yl)-4,5-difluorophenyl)-5-(1,3-oxazol-2-ylmethoxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-7-(1,3-oxazol-2-ylmethoxy)pyrido[3,2-d]pyrimidin-4-amine;

N-(3-((1S,5S,6S)-3-amino-1-(fluoromethyl)-5-methyl-2-thia-4-azabicyclo[4.1.0]hept-3-en-5-yl)-4,5-difluorophenyl)-7-(2-propyn-1-yloxy)pyrido[3,2-d]pyrimidin-4-amine;

N-(3-((1S,5S,6S)-3-amino-1-(fluoromethyl)-5-methyl-2-thia-4-azabicyclo[4.1.0]hept-3-en-5-yl)-4,5-difluorophenyl)-5-(2,2,2-trifluoroethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(2,2,2-trifluoroethoxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-2-(2-propyn-1-yloxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4-fluorophenyl)-2-(1,3-oxazol-2-ylmethoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4-fluorophenyl)-5-chloro-2-pyridinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-7-(2-propyn-1-yloxy)pyrido[3,2-d]pyrimidin-4-amine;

N-(3-((1S,5S,6S)-3-amino-1-(difluoromethyl)-5-methyl-2-thia-4-azabicyclo[4.1.0]hept-3-en-5-yl)-4-fluorophenyl)-5-(2-propyn-1-yloxy)-2-pyrazinecarboxamide;

N-(3-((1S,5S,6S)-3-amino-1-(fluoromethyl)-5-methyl-2-thia-4-azabicyclo[4.1.0]hept-3-en-5-yl)-4-fluorophenyl)-5-chloro-2-pyridinecarboxamide;

N-(3-((1S,5S,6S)-3-amino-1-(fluoromethyl)-5-methyl-2-thia-4-azabicyclo[4.1.0]hept-3-en-5-yl)-4-fluorophenyl)-5-(2-propyn-1-yloxy)-2-pyrazinecarboxamide;

N-(3-((1S,5S,6S)-3-amino-1-(fluoromethyl)-5-methyl-2-thia-4-azabicyclo[4.1.0]hept-3-en-5-yl)-4-fluorophenyl)-2-(2-propyn-1-yloxy)pyrido[3,4-b]pyrazin-5-amine;

N-(3-((1S,5S,6S)-3-amino-1-(fluoromethyl)-5-methyl-2-thia-4-azabicyclo[4.1.0]hept-3-en-5-yl)-4-fluorophenyl)-7-(2-propyn-1-yloxy)pyrido[3,2-d]pyrimidin-4-amine;

N-(3-((1S,5S,6S)-3-amino-1-(fluoromethyl)-5-methyl-2-thia-4-azabicyclo[4.1.0]hept-3-en-5-yl)-4-fluorophenyl)-2-(1,3-oxazol-2-ylmethoxy)pyrido[3,4-b]pyrazin-5-amine;

N-(3-((1S,5S,6S)-3-amino-1-(fluoromethyl)-5-methyl-2-thia-4-azabicyclo[4.1.0]hept-3-en-5-yl)-4-fluorophenyl)-5-(2,2,2-trifluoroethoxy)-2-pyrazinecarboxamide;

N-(3-((1S,5S,6S)-3-amino-1-(fluoromethyl)-5-methyl-2-thia-4-azabicyclo[4.1.0]hept-3-en-5-yl)-4-fluorophenyl)-2-(((1S)-1-methyl-2-propyn-1-yl)oxy)pyrido[3,4-b]pyrazin-5-amine;

N-(3-((1S,5S,6S)-3-amino-1-(fluoromethyl)-5-methyl-2-thia-4-azabicyclo[4.1.0]hept-3-en-5-yl)-4-fluorophenyl)-2-((5-methyl-1,2,4-oxadiazol-3-yl)methoxy)pyrido[3,4-b]pyrazin-5-amine;

N-(3-((1S,5S,6S)-3-amino-1-(fluoromethyl)-5-methyl-2-thia-4-azabicyclo[4.1.0]hept-3-en-5-yl)-4-fluorophenyl)-3-methyl-5-(2-propyn-1-yloxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-3-methyl-5-(2-propyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(2,2,2-trifluoroethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-3-methyl-5-(2-propyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-chloro-2-pyridinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(2-propyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-3-methyl-5-(1,3-oxazol-2-ylmethoxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-3-methyl-5-(1,3-oxazol-2-ylmethoxy)-2-pyrazinecarboxamide;

N-(3-((1S,5S,6S)-3-amino-1-(fluoromethyl)-5-methyl-2-thia-4-azabicyclo[4.1.0]hept-3-en-5-yl)-4-fluorophenyl)-3-methyl-5-(1,3-oxazol-2-ylmethoxy)-2-pyrazinecarboxamide;

N-(3-((1S,5S,6S)-3-amino-1-(fluoromethyl)-5-methyl-2-thia-4-azabicyclo[4.1.0]hept-3-en-5-yl)-4,5-difluorophenyl)-5-(1, 1-dideuterium-prop-2-yn-1-yloxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-5-(1, 1-dideuterium-prop-2-yn-1-yloxy)-2-pyrazinecarboxamide;

N-(3-((1S,5S,6S)-3-amino-1-(methoxy)-5-methyl-2-thia-4-azabicyclo[4.1.0]hept-3-en-5-yl)-4,5-difluorophenyl)-5-(1, 1-dideuterium-prop-2-yn-1-yloxy)pyrazine-2-carboxamide;

N-(3-((1S,5S,6S)-3-amino-5-(fluoromethyl)-2-thia-4-azabicyclo[4.1.0]hept-3-en-5-yl)-4,5-difluorophenyl)-2-(2-propyn-1-yloxy)pyrido[3,4-b]pyrazin-5-amine;

N-(3-((1S,5S,6S)-3-amino-5-(fluoromethyl)-2-thia-4-azabicyclo[4.1.0]hept-3-en-5-yl)-4,5-difluorophenyl)-2-(1,3-oxazol-2-ylmethoxy)pyrido[3,4-b]pyrazin-5-amine;

N-(3-((1S,5S,6S)-3-amino-5-(fluoromethyl)-2-thia-4-azabicyclo[4.1.0]hept-3-en-5-yl)-4,5-difluorophenyl)-2-(1,3-oxazol-4-ylmethoxy)pyrido[3,4-b]pyrazin-5-amine;

N-(5-((1S,5S,6S)-3-amino-1-(methoxymethyl)-5-methyl-2-thia-4-azabicyclo[4.1.0]hept-3-en-5-yl)-6-fluoro-3-pyridinyl)-7-chloropyrido[3,2-d]pyrimidin-4-amine;

N-(5-((1S,5S,6S)-3-amino-1-(methoxymethyl)-5-methyl-2-thia-4-azabicyclo[4.1.0]hept-3-en-5-yl)-6-fluoro-3-pyridinyl)-3-methyl-5-(2-propyn-1-yloxy)-2-pyrazinecarboxamide;

4-((5-((1S,5S,6S)-3-amino-1-(methoxymethyl)-5-methyl-2-thia-4-azabicyclo[4.1.0]hept-3-en-5-yl)-6-fluoro-3-pyridinyl)amino)pyrido[3,2-d]pyrimidine-7-carbonitrile;

8-((5-((1S,5S,6S)-3-amino-1-(methoxymethyl)-5-methyl-2-thia-4-azabicyclo[4.1.0]hept-3-en-5-yl)-6-fluoro-3-pyridinyl)amino)-1,7-naphthyridine-3-carbonitrile;

N-(5-((1S,5S,6S)-3-amino-1-(methoxymethyl)-5-methyl-2-thia-4-azabicyclo[4.1.0]hept-3-en-5-yl)-6-fluoro-3-pyridinyl)-2-(2-propyn-1-yloxy)pyrido[3,4-b]pyrazin-5-amine;

N-(5-((1S,5S,6S)-3-amino-1-(methoxymethyl)-5-methyl-2-thia-4-azabicyclo[4.1.0]hept-3-en-5-yl)-6-fluoro-3-pyridinyl)-2-(1,3-oxazol-2-ylmethoxy)pyrido[3,4-b]pyrazin-5-amine;

N-(5-((1S,5S,6S)-3-amino-5-methyl-1-(((~2~H_3_)methyloxy)methyl)-2-thia-4-azabicyclo[4.1.0]hept-3-en-5-yl)-6-fluoro-3-pyridinyl)-3-methyl-5-(2-propyn-1-yloxy)-2-pyrazinecarboxamide;

N-(5-((1S,5S,6S)-3-amino-5-methyl-1-(((~2~H_3_)methyloxy)methyl)-2-thia-4-azabicyclo[4.1.0]hept-3-en-5-yl)-6-fluoro-3-pyridinyl)-5-(2-propyn-1-yloxy)-2-pyrazinecarboxamide;

N-(5-((1S,5S,6S)-3-amino-5-methyl-1-(((~2~H_3_)methyloxy)methyl)-2-thia-4-azabicyclo[4.1.0]hept-3-en-5-yl)-6-fluoro-3-pyridinyl)-7-chloropyrido[3,2-d]pyrimidin-4-amine;

N-(5-((1S,5S,6S)-3-amino-5-methyl-1-(((~2~H_3_)methyloxy)methyl)-2-thia-4-azabicyclo[4.1.0]hept-3-en-5-yl)-6-fluoro-3-pyridinyl)-2-(2-propyn-1-yloxy)pyrido[3,4-b]pyrazin-5-amine;

N-(5-((1S,5S,6S)-3-amino-5-methyl-1-(((~2~H_3_)methyloxy)methyl)-2-thia-4-azabicyclo[4.1.0]hept-3-en-5-yl)-6-fluoro-3-pyridinyl)-2-((1,1-~2~H_2_)-2-propyn-1-yloxy)pyrido[3,4-b]pyrazin-5-amine;

methyl (1S,5S,6S)-3-amino-5-(((5-chloro-2-pyridinyl)carbonyl)amino)-2-fluoro-3-(methoxycarbonyl)phenyl)-5-methyl-2-thia-4-azabicyclo[4.1.0]hept-3-ene-1-carboxylate;

methyl (1S,5S,6S)-3-amino-5-(2-fluoro-3-(methoxycarbonyl)-5-((2-(2-propyn-1-yloxy)pyrido[3,4-b]pyrazin-5-yl)amino)phenyl)-5-methyl-2-thia-4-azabicyclo[4.1.0]hept-3-ene-1-carboxylate;

methyl 3-((1S,5S,6S)-3-amino-1-(hydroxymethyl)-5-methyl-2-thia-4-azabicyclo[4.1.0]hept-3-en-5-yl)-2-fluoro-5-((2-(2-propyn-1-yloxy)pyrido[3,4-b]pyrazin-5-yl)amino)benzoate;

N-(3-((1S,5S,6S)-3-amino-1-(hydroxymethyl)-5-methyl-2-thia-4-azabicyclo[4.1.0]hept-3-en-5-yl)-4-fluoro-5-(hydroxymethyl)phenyl)-5-chloro-2-pyridinecarboxamide;

N-(5-((1S,5S,6S)-3-amino-1-(methoxymethyl)-5-methyl-2-thia-4-azabicyclo[4.1.0]hept-3-en-5-yl)-6-fluoro-3-pyridinyl)-5-(2-propyn-1-yloxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-3-methyl-5-(1,3-oxazol-2-ylmethoxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4,5-difluorophenyl)-3-methyl-5-(2-propyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-(2-propyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-(1,3-oxazol-2-ylmethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-3-methyl-5-((1S)-1-(1,3-oxazol-2-yl)ethoxy)-2-pyrazinecarboxamide;

N-(3-((1S,5S,6S)-3-amino-1,5-bis(fluoromethyl)-2-thia-4-azabicyclo[4.1.0]hept-3-en-5-yl)-4-fluorophenyl)-2-(2-butyn-1-yloxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-(1,3-oxazol-2-ylmethoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-(1,3-oxazol-4-ylmethoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-(2-butyn-1-yloxy)pyrido[3,4-b]pyrazin-5-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-2-(2-butyn-1-yloxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-((2-methyl-1,3-oxazol-4-yl)methoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-((3-fluoropropoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-(2,2-difluoropropoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-((3-fluoro-2-pyridinyl)methoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-((4-methyl-2-pyrimidinyl)methoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-(1,3-thiazol-4-ylmethoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-(1-methylethoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-((5-methyl-1,3,4-oxadiazol-2-yl)methoxy)pyrido[3,4-b]pyrazin-5-amine;

2-((5-((3-((1S,5S,6S)-3-amino-1-(difluoromethyl)-5-methyl-2-thia-4-azabicyclo[4.1.0]hept-3-en-5-yl)-4,5-difluorophenyl)amino)pyrido[3,4-b]pyrazin-2-yl)oxy)-N,N-dimethylacetamide;

N-(3-((1S,5S,6S)-3-amino-1,5-bis(fluoromethyl)-2-thia-4-azabicyclo[4.1.0]hept-3-en-5-yl)-4-fluorophenyl)-2-(((1S)-1-methyl-2-propyn-1-yl)oxy)pyrido[3,4-b]pyrazin-5-amine;

N-(3-((1S,5S,6S)-3-amino-1,5-bis(fluoromethyl)-2-thia-4-azabicyclo[4.1.0]hept-3-en-5-yl)-4-fluorophenyl)-2-((3-methyl-1,2,4-oxadiazol-5-yl)methoxy)pyrido[3,4-b]pyrazin-5-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-2-(2-pyrimidinylmethoxy)pyrido[3,4-b]pyrazin-5-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-2-((3-methyl-1,2,4-oxadiazol-5-yl)methoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-((5-methyl-1,2,4-oxadiazol-3-yl)methoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-(2-pyrimidinylmethoxy)pyrido[3,4-b]pyrazin-5-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-2-((5-methyl-1,2,4-oxadiazol-3-yl)methoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-((2,5-dimethyl-1,3-oxazol-4-yl)methoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-((3-methyl-1,2,4-oxadiazol-5-yl)methoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-((5-methyl-1,3-oxazol-2-yl)methoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-((5-methyl-1,3,4-thiadiazol-2-yl)methoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-(((1S)-1-methyl-2-propyn-1-yl)oxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-((1R)-1-(1,3-oxazol-2-yl)ethoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-((1S)-1-(1,3-oxazol-2-yl)ethoxy)pyrido[3,4-b]pyrazin-5-amine;

1-(2-((5-((3-((1S,5S,6S)-3-amino-1-(difluoromethyl)-5-methyl-2-thia-4-azabicyclo[4.1.0]hept-3-en-5-yl)-4,5-difluorophenyl)amino)pyrido[3,4-b]pyrazin-2-yl)oxy)ethyl)-2-pyrrolidinone;

N-(3-((1S,5S,6S)-3-amino-1-(difluoromethyl)-5-methyl-2-thia-4-azabicyclo[4.1.0]hept-3-en-5-yl)-4,5-difluorophenyl)-2-((1S)-2-methoxy-1-methylethoxy)pyrido[3,4-b]pyrazin-5-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-2-methoxypyrido[3,4-b]pyrazin-5-amine;

5-((3-((1S,5S,6S)-3-amino-1-(difluoromethyl)-5-methyl-2-thia-4-azabicyclo[4.1.0]hept-3-en-5-yl)-4,5-difluorophenyl)amino)pyrido[3,4-b]pyrazin-2(1H)-one;

N-(3-((1S,5S,6S)-3-amino-5-methyl-2-thia-4-azabicyclo[4.1.0]hept-3-en-5-yl)-4,5-difluorophenyl)-7-methoxypyrido[3,2-d]pyrimidin-4-amine;

methyl (1S,5S,6S)-3-amino-5-(5-(((5-chloro-2-pyridinyl)carbonyl)amino)-2,3-difluorophenyl)-5-methyl-2-thia-4-azabicyclo[4.1.0]hept-3-ene-1-carboxylate;

(1S,5S,6S)-3-amino-5-(5-(((5-chloro-2-pyridinyl)carbonyl)amino)-2,3-difluorophenyl)-5-methyl-2-thia-4-azabicyclo[4.1.0]hept-3-ene-1-carboxylic acid;

N-(3-((1S,5S,6S)-3-amino-5-methyl-2-thia-4-azabicyclo[4.1.0]hept-3-en-5-yl)-4,5-difluorophenyl)-2-methoxypyrido[3,4-b]pyrazin-5-amine;

(1S,5S,6S)-3-amino-5-(5-((7-chloropyrido[3,2-d]pyrimidin-4-yl)amino)-2,3-difluorophenyl)-N-methoxy-N,5-dimethyl-2-thia-4-azabicyclo[4.1.0]hept-3-ene-1-carboxamide;

1-((1S,5S,6S)-3-amino-5-(5-((7-chloropyrido[3,2-d]pyrimidin-4-yl)amino)-2,3-difluorophenyl)-5-methyl-2-thia-4-azabicyclo[4.1.0]hept-3-en-1-yl)ethanone;

N-(3-((1S,5S,6S)-3-amino-1-(methoxymethyl)-5-methyl-2-thia-4-azabicyclo[4.1.0]hept-3-en-5-yl)-4,5-difluorophenyl)-3-(2-butyn-1-yloxy)-1,7-naphthyridin-8-amine;

4-((3-((1S,5S,6S)-1-acetyl-3-amino-5-methyl-2-thia-4-azabicyclo[4.1.0]hept-3-en-5-yl)-4,5-difluorophenyl)amino)pyrido[3,2-d]pyrimidine-7-carbonitrile;

(1S,5S,6S)-3-amino-5-(5-(((5-chloro-2-pyridinyl)carbonyl)amino)-2,3-difluorophenyl)-5-methyl-2-thia-4-azabicyclo[4.1.0]hept-3-ene-1-carboxamide;

N-(3-((1S,5S,6S)-1-acetyl-3-amino-5-methyl-2-thia-4-azabicyclo[4.1.0]hept-3-en-5-yl)-4,5-difluorophenyl)-5-chloro-2-pyridinecarboxamide;

4-((3-((1S,5S,6S)-3-amino-1-(1-hydroxyethyl)-5-methyl-2-thia-4-azabicyclo[4.1.0]hept-3-en-5-yl)-4,5-difluorophenyl)amino)pyrido[3,2-d]pyrimidine-7-carbonitrile;

4-((3-((1R,2S,6S)-4-amino-6-((R)-1-hydroxyethyl)-2-methyl-3-azabicyclo[4.1.0]hept-3-en-2-yl)-4,5-difluorophenyl)amino)pyrido[3,2-d]pyrimidine-7-carbonitrile;

4-((3-((1S,5S,6S)-3-amino-1-(1-hydroxy-1-methylethyl)-5-methyl-2-thia-4-azabicyclo[4.1.0]hept-3-en-5-yl)-4,5-difluorophenyl)amino)pyrido[3,2-d]pyrimidine-7-carbonitrile;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(1,3-oxazol-2-ylmethoxy)-2-pyrazinecarboxamide;

(1S,5S,6S)-3-amino-5-(2,3-difluoro-5-((2-(2-propyn-1-yloxy)pyrido[3,4-b]pyrazin-5-yl)amino)phenyl)-5-methyl-2-thia-4-azabicyclo[4.1.0]hept-3-ene-1-carboxamide;

(1S,5S,6S)-3-amino-5-(2,3-difluoro-5-((2-(2-propyn-1-yloxy)pyrido[3,4-b]pyrazin-5-yl)amino)phenyl)-N,N,5-trimethyl-2-thia-4-azabicyclo[4.1.0]hept-3-ene-1-carboxamide;

(1S,5S,6S)-3-amino-5-(2,3-difluoro-5-(((5-(2-propyn-1-yloxy)-2-pyrazinyl)carbonyl)amino)phenyl)-N,N,5-trimethyl-2-thia-4-azabicyclo[4.1.0]hept-3-ene-1-carboxamide;

(1S,5S,6S)-3-amino-5-(2,3-difluoro-5-(((5-(2-propyn-1-yloxy)-2-pyrazinyl)carbonyl)amino)phenyl)-N,5-dimethyl-2-thia-4-azabicyclo[4.1.0]hept-3-ene-1-carboxamide;

(1S,5S,6S)-3-amino-5-(2,3-difluoro-5-((2-(2-propyn-1-yloxy)pyrido[3,4-b]pyrazin-5-yl)amino)phenyl)-N,5-dimethyl-2-thia-4-azabicyclo[4.1.0]hept-3-ene-1-carboxamide;

(1S,5S,6S)-3-amino-5-(2,3-difluoro-5-((2-(2-propyn-1-yloxy)pyrido[3,4-b]pyrazin-5-yl)amino)phenyl)-5-methyl-2-thia-4-azabicyclo[4.1.0]hept-3-ene-1-carbonitrile;

(1S,5S,6S)-3-amino-5-(2,3-difluoro-5-((7-(2-propyn-1-yloxy)pyrido[3,2-d]pyrimidin-4-yl)amino)phenyl)-5-methyl-2-thia-4-azabicyclo[4.1.0]hept-3-ene-1-carboxamide;

(1S,5S,6S)-3-amino-5-(2,3-difluoro-5-((7-(1,3-oxazol-2-ylmethoxy)pyrido[3,2-d]pyrimidin-4-yl)amino)phenyl)-5-methyl-2-thia-4-azabicyclo[4.1.0]hept-3-ene-1-carboxamide;

(1S,5S,6S)-3-amino-5-(2,3-difluoro-5-(((5-(2-propyn-1-yloxy)-2-pyrazinyl)carbonyl)amino)phenyl)-5-methyl-2-thia-4-azabicyclo[4.1.0]hept-3-ene-1-carboxamide;

(1S,5S,6S)-3-amino-5-(5-((2-(2-butyn-1-yloxy)pyrido[3,4-b]pyrazin-5-yl)amino)-2,3-difluorophenyl)-5-methyl-2-thia-4-azabicyclo[4.1.0]hept-3-ene-1-carboxamide;

(1S,5S,6S)-3-amino-5-(2,3-difluoro-5-((7-(2-propyn-1-yloxy)pyrido[3,2-d]pyrimidin-4-yl)amino)phenyl)-5-methyl-2-thia-4-azabicyclo[4.1.0]hept-3-ene-1-carbonitrile;

(1S,5S,6S)-3-amino-5-(2,3-difluoro-5-(((5-(2,2,3,3-tetrafluoropropoxy)-2-pyrazinyl)carbonyl)amino)phenyl)-N,N,5-trimethyl-2-thia-4-azabicyclo[4.1.0]hept-3-ene-1-carboxamide;

(1S,5S,6S)-3-amino-5-(2,3-difluoro-5-((7-(1,3-oxazol-2-ylmethoxy)pyrido[3,2-d]pyrimidin-4-yl)amino)phenyl)-N,N,5-trimethyl-2-thia-4-azabicyclo[4.1.0]hept-3-ene-1-carboxamide;

N-(3-((1S,5S,6S)-3-amino-1-cyano-5-methyl-2-thia-4-azabicyclo[4.1.0]hept-3-en-5-yl)-4,5-difluorophenyl)-5-(2-propyn-1-yloxy)-2-pyrazinecarboxamide;

(1S,5S,6S)-3-amino-5-(2,3-difluoro-5-((2-(((1S)-1-methyl-2-propyn-1-yl)oxy)pyrido[3,4-b]pyrazin-5-yl)amino)phenyl)-N,N, 5-trimethyl-2-thia-4-azabicyclo[4.1.0]hept-3-ene-1-carboxamide;

(1S,5S,6S)-3-amino-5-(2,3-difluoro-5-(((5-(2,2,2-trifluoroethoxy)-2-pyrazinyl)carbonyl)amino)phenyl)-N,N,5-trimethyl-2-thia-4-azabicyclo[4.1.0]hept-3-ene-1-carboxamide;

N-(3-((1S,5S,6S)-3-amino-1-cyano-5-methyl-2-thia-4-azabicyclo[4.1.0]hept-3-en-5-yl)-4-fluorophenyl)-5-(2-propyn-1-yloxy)-2-pyrazinecarboxamide;

(1S,5S,6S)-3-amino-5-(2-fluoro-5-((7-(2-propyn-1-yloxy)pyrido[3,2-d]pyrimidin-4-yl)amino)phenyl)-5-methyl-2-thia-4-azabicyclo[4.1.0]hept-3-ene-1-carbonitrile;

N-(3-((1S,5S,6S)-3-amino-1-cyano-5-methyl-2-thia-4-azabicyclo[4.1.0]hept-3-en-5-yl)-4-fluorophenyl)-5-chloro-2-pyridinecarboxamide;

(1S,5S,6S)-3-amino-5-(5-(((5-chloro-2-pyridinyl)carbonyl)amino)-2,3-difluorophenyl)-N,N,5-trimethyl-2-thia-4-azabicyclo[4.1.0]hept-3-ene-1-carboxamide;

(1S,5S,6S)-3-amino-5-(2,3-difluoro-5-((2-(((1S)-1-methyl-2-propyn-1-yl)oxy)pyrido[3,4-b]pyrazin-5-yl)amino)phenyl)-5-methyl-2-thia-4-azabicyclo[4.1.0]hept-3-ene-1-carbonitrile;

N-(3-((1S,5S,6S)-3-amino-1-cyano-5-methyl-2-thia-4-azabicyclo[4.1.0]hept-3-en-5-yl)-4,5-difluorophenyl)-5-chloro-2-pyridinecarboxamide;

N-(3-((1S,5S,6S)-3-amino-5-methyl-1-(1-pyrrolidinylcarbonyl)-2-thia-4-azabicyclo[4.1.0]hept-3-en-5-yl)-4,5-difluorophenyl)-7-(2-propyn-1-yloxy)pyrido[3,2-d]pyrimidin-4-amine;

N-(3-((1S,5S,6S)-3-amino-5-methyl-1-(1-pyrrolidinylcarbonyl)-2-thia-4-azabicyclo[4.1.0]hept-3-en-5-yl)-4,5-difluorophenyl)-5-(2-propyn-1-yloxy)-2-pyrazinecarboxamide;

N-(3-((1S,5S,6S)-3-amino-5-methyl-1-(1-pyrrolidinylcarbonyl)-2-thia-4-azabicyclo[4.1.0]hept-3-en-5-yl)-4,5-difluorophenyl)-5-chloro-2-pyridinecarboxamide;

N-(3-((1S,5S,6S)-3-amino-5-methyl-1-(1-pyrrolidinylcarbonyl)-2-thia-4-azabicyclo[4.1.0]hept-3-en-5-yl)-4,5-difluorophenyl)-7-(1,3-oxazol-2-ylmethoxy)pyrido[3,2-d]pyrimidin-4-amine;

N-(3-((1S,5S,6S)-3-amino-5-methyl-1-(1-pyrrolidinylcarbonyl)-2-thia-4-azabicyclo[4.1.0]hept-3-en-5-yl)-4,5-difluorophenyl)-2-(((1S)-1-methyl-2-propyn-1-yl)oxy)pyrido[3,4-b]pyrazin-5-amine;

N-(3-((1S,5S,6S)-3-amino-5-methyl-1-(1-pyrrolidinylcarbonyl)-2-thia-4-azabicyclo[4.1.0]hept-3-en-5-yl)-4,5-difluorophenyl)-2-((1S)-1-(1,3-oxazol-2-yl)ethoxy)pyrido[3,4-b]pyrazin-5-amine;

(1S,5S,6S)-3-amino-5-(2,3-difluoro-5-((2-((1S)-1-(1,3-oxazol-2-yl)ethoxy)pyrido[3,4-b]pyrazin-5-yl)amino)phenyl)-5-methyl-2-thia-4-azabicyclo[4.1.0]hept-3-ene-1-carbonitrile;

N-(3-((1S,5S,6S)-3-amino-1-cyano-5-methyl-2-thia-4-azabicyclo[4.1.0]hept-3-en-5-yl)-4,5-difluorophenyl)-5-(2,2,2-trifluoroethoxy)-2-pyrazinecarboxamide;

N-(3-((1S,5S,6S)-3-amino-5-(fluoromethyl)-2-thia-4-azabicyclo[4.1.0]hept-3-en-5-yl)-4-fluorophenyl)-7-(2-propyn-1-yloxy)pyrido[3,2-d]pyrimidin-4-amine;

N-(3-((1S,5S,6S)-3-amino-5-(fluoromethyl)-1-(methoxymethyl)-2-thia-4-azabicyclo[4.1.0]hept-3-en-5-yl)-4-fluorophenyl)-7-(2-propyn-1-yloxy)pyrido[3,2-d]pyrimidin-4-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-7-(2-propyn-1-yloxy)pyrido[3,2-d]pyrimidin-4-amine;

N-(5-((1S,5S,6S)-3-amino-1-(fluoromethyl)-5-methyl-2-thia-4-azabicyclo[4.1.0]hept-3-en-5-yl)-6-fluoro-3-pyridinyl)-7-(2-propyn-1-yloxy)pyrido[3,2-d]pyrimidin-4-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-7-(2-propyn-1-yloxy)pyrido[3,2-d]pyrimidin-4-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-7-(2-methoxyethoxy)pyrido[3,2-d]pyrimidin-4-amine;

N-(3-((1S,5S,6S)-3-amino-5-(fluoromethyl)-1-(methoxymethyl)-2-thia-4-azabicyclo[4.1.0]hept-3-en-5-yl)-4-fluorophenyl)-7-(2-methoxyethoxy)pyrido[3,2-d]pyrimidin-4-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-7-(2,5-dimethyl-1,3-oxazol-4-yl)methoxy)pyrido[3,2-d]pyrimidin-4-amine;

N-(3-((1S,5S,6S)-3-amino-1-(difluoromethyl)-5-methyl-2-thia-4-azabicyclo[4.1.0]hept-3-en-5-yl)-4,5-difluorophenyl)-5-fluoro-3-(1,3-oxazol-2-ylmethoxy)-1,7-naphthyridin-8-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-5-fluoro-3-(1,3-oxazol-2-ylmethoxy)-1,7-naphthyridin-8-amine;

N-(3-((1S,5S,6S)-3-amino-1-(methoxymethyl)-5-methyl-2-thia-4-azabicyclo[4.1.0]hept-3-en-5-yl)-4,5-difluorophenyl)-5-fluoro-3-(2-propyn-1-yloxy)-1,7-naphthyridin-8-amine;

(2E)-3-((1R,5S,6S)-3-amino-5-(fluoromethyl)-5-(2-fluoro-5-((2-(2-pentyn-1-yloxy)pyrido[3,4-b]pyrazin-5-yl)amino)phenyl)-2-thia-4-azabicyclo[4.1.0]hept-3-en-1-yl)-N,N-dimethyl-2-propenamide;

N-(3-((1S,5S,6S)-3-amino-5-(fluoromethyl)-1-((2,2,2-trifluoroethoxy)methyl)-2-thia-4-azabicyclo[4.1.0]hept-3-en-5-yl)-4-fluorophenyl)-5-(2-propyn-1-yloxy)-2-pyrazinecarboxamide;

N-(3-((1S,5S,6S)-3-amino-5-(fluoromethyl)-1-((2,2,2-trifluoroethoxy)methyl)-2-thia-4-azabicyclo[4.1.0]hept-3-en-5-yl)-4-fluorophenyl)-5-chloro-2-pyridinecarboxamide;

N-(3-((1S,5S,6S)-3-amino-5-(fluoromethyl)-1-((1-methylethoxy)methyl)-2-thia-4-azabicyclo[4.1.0]hept-3-en-5-yl)-4-fluorophenyl)-5-(2-propyn-1-yloxy)-2-pyrazinecarboxamide;

N-(3-((1S,5S,6S)-3-amino-5-(fluoromethyl)-1-(1H-1,2,3-triazol-4-yl)-2-thia-4-azabicyclo[4.1.0]hept-3-en-5-yl)-4-fluorophenyl)-5-chloro-2-pyridinecarboxamide;

N-(3-((1S,5S,6S)-3-amino-5-(fluoromethyl)-1-(1H-1,2,3-triazol-4-yl)-2-thia-4-azabicyclo[4.1.0]hept-3-en-5-yl)-4-fluorophenyl)-2-(1,3-oxazol-2-ylmethoxy)pyrido[3,4-b]pyrazin-5-amine;

N-(3-((1S,5S,6S)-3-amino-5-(fluoromethyl)-1-(1-propyn-1-yl)-2-thia-4-azabicyclo[4.1.0]hept-3-en-5-yl)-4-fluorophenyl)-2-(1,3-oxazol-2-ylmethoxy)pyrido[3,4-b]pyrazin-5-amine;

N-(3-((1S,5S,6S)-3-amino-5-(fluoromethyl)-1-(1H-1,2,3-triazol-4-yl)-2-thia-4-azabicyclo[4.1.0]hept-3-en-5-yl)-4-fluorophenyl)-5-(2-propyn-1-yloxy)-2-pyrazinecarboxamide;

N-(3-((1S,5S,6S)-3-amino-5-(fluoromethyl)-1-(1H-1,2,3-triazol-4-yl)-2-thia-4-azabicyclo[4.1.0]hept-3-en-5-yl)-4-fluorophenyl)-2-(2-propyn-1-yloxy)pyrido[3,4-b]pyrazin-5-amine;

4-((3-((1R,5S,6S)-3-amino-7,7-difluoro-1-(hydroxymethyl)-5-methyl-2-thia-4-azabicyclo[4.1.0]hept-3-en-5-yl)-4-fluorophenyl)amino)pyrido[3,2-d]pyrimidine-7-carbonitrile; or N-(3-((4S,4aR,7aS)-2-amino-4-(fluoromethyl)-4a,4b,5,7-tetrahydro-4H-thieno[3',4':2,3]cyclopropa[1,2-e][1,3]thiazin-4-yl)-4-fluorophenyl)-5-chloropicolinamide.

57. The compound of claim 1, or a tautomer or pharmaceutically acceptable salt thereof, selected from (1S,5S,6S)-3-amino-5-(2,3-difluoro-5-(((5-(2,2,3,3-tetrafluoropropoxy)-2-pyrazinyl)carbonyl)amino)phenyl)-N,5-dimethyl-2-thia-4-azabicyclo[4.1.0]hept-3-ene-1-carboxamide;

N-(5-((1S,5S,6S)-3-amino-1-cyano-5-methyl-2-thia-4-azabicyclo[4.1.0]hept-3-en-5-yl)-6-methoxy-3-pyridinyl)-5-(2-propyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(((1S)-1-methyl-2-propyn-1-yl)oxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-5-(((1S)-1-methyl-2-propyn-1-yl)oxy)-2-pyrazinecarboxamide;

(1S,5S,6S)-3-amino-5-(2,3-difluoro-5-(((5-(((1S)-1-methyl-2-propyn-1-yl)oxy)-2-pyrazinyl)carbonyl)amino)phenyl)-N,5-dimethyl-2-thia-4-azabicyclo[4.1.0]hept-3-ene-1-carboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-((1R)-2,2,2-trifluoro-1-methylethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-((1S)-2,2,2-trifluoro-1-methylethoxy)-2-pyrazinecarboxamide;

N-(3-((1S,5S,6S)-3-amino-5-methyl-1-((trideuteriummethyloxy)methyl)-2-thia-4-azabicyclo[4.1.0]hept-3-en-5-yl)-4,5-difluorophenyl)-5-(2-propyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-((1S)-2-methoxy-1-methylethoxy)-2-pyrazinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-5-((1S)-2-methoxy-1-methylethoxy)-2-pyrazinecarboxamide;

(1S,5S,6S)-3-amino-5-(2-fluoro-5-(((5-(2,2,2-trifluoroethoxy)-2-pyrazinyl)carbonyl)amino)phenyl)-5-methyl-N-(2,2,2-trifluoroethyl)-2-thia-4-azabicyclo[4.1.0]hept-3-ene-1-carboxamide;

(1S,5S,6S)-3-amino-5-(2-fluoro-5-(((5-(2,2,2-trifluoroethoxy)-2-pyrazinyl)carbonyl)amino)phenyl)-N,5-dimethyl-2-thia-4-azabicyclo[4.1.0]hept-3-ene-1-carboxamide;

(1S,5S,6S)-3-amino-N-((1S)-1,2-dimethylpropyl)-5-(2-fluoro-5-(((5-(2,2,2-trifluoroethoxy)-2-pyrazinyl)carbonyl)amino)phenyl)-5-methyl-2-thia-4-azabicyclo[4.1.0]hept-3-ene-1-carboxamide;

methyl (1S,5S,6S)-3-amino-5-(2,3-difluoro-5-(((5-(2-propyn-1-yloxy)-2-pyrazinyl)carbonyl)amino)phenyl)-5-methyl-2-thia-4-azabicyclo[4.1.0]hept-3-ene-1-carboxylate;

(1S,5S,6S)-3-amino-5-(2-fluoro-5-(((5-(2,2,2-trifluoroethoxy)-2-pyrazinyl)carbonyl)amino)phenyl)-5-methyl-N-(1-methylethyl)-2-thia-4-azabicyclo[4.1.0]hept-3-ene-1-carboxamide;

(1S,5S,6S)-3-amino-N-ethyl-5-(2-fluoro-5-(((5-(2,2,2-trifluoroethoxy)-2-pyrazinyl)carbonyl)amino)phenyl)-5-methyl-2-thia-4-azabicyclo[4.1.0]hept-3-ene-1-carboxamide;

(1S,5S,6S)-3-amino-5-(2-fluoro-5-(((5-(((1S)-1-methyl-2-propyn-1-yl)oxy)-2-pyrazinyl)carbonyl)amino)phenyl)-N,5-dimethyl-2-thia-4-azabicyclo[4.1.0]hept-3-ene-1-carboxamide;

(1S,5S,6S)-3-amino-5-(2-fluoro-5-((2-(2-propyn-1-yloxy)pyrido[3,4-b]pyrazin-5-yl)amino)phenyl)-N,5-dimethyl-2-thia-4-azabicyclo[4.1.0]hept-3-ene-1-carboxamide;

tert-butyl (((1S,5S,6S)-3-amino-5-(2,3-difluoro-5-(((5-(2-propyn-1-yloxy)-2-pyrazinyl)carbonyl)amino)phenyl)-5-methyl-2-thia-4-azabicyclo[4.1.0]hept-3-en-1-yl)methyl)carbamate;

N-(3-((1S,5S,6S)-3-amino-1-(aminomethyl)-5-methyl-2-thia-4-azabicyclo[4.1.0]hept-3-en-5-yl)-4,5-difluorophenyl)-5-(2-propyn-1-yloxy)-2-pyrazinecarboxamide;

(1S,5S,6S)-3-amino-N-((1R)-2,2-difluorocyclopropyl)-5-(2-fluoro-5-(((5-(2,2,2-trifluoroethoxy)-2-pyrazinyl)carbonyl)amino)phenyl)-5-methyl-2-thia-4-azabicyclo[4.1.0]hept-3-ene-1-carboxamide;

(1S,5S,6S)-3-amino-N-((1S)-2,2-difluorocyclopropyl)-5-(2-fluoro-5-(((5-(2,2,2-trifluoroethoxy)-2-pyrazinyl)carbonyl)amino)phenyl)-5-methyl-2-thia-4-azabicyclo[4.1.0]hept-3-ene-1-carboxamide;

(1S,5S,6S)-3-amino-N-(2-fluoro-1,1-dimethylethyl)-5-(2-fluoro-5-(((5-(2,2,2-trifluoroethoxy)-2-pyrazinyl)carbonyl)amino)phenyl)-5-methyl-2-thia-4-azabicyclo[4.1.0]hept-3-ene-1-carboxamide;

(1S,5S,6S)-3-amino-5-(2-fluoro-5-(((5-(2,2,2-trifluoroethoxy)-2-pyrazinyl)carbonyl)amino)phenyl)-N-methoxy-N,5-dimethyl-2-thia-4-azabicyclo[4.1.0]hept-3-ene-1-carboxamide;

(1S,5S,6S)-3-amino-5-(5-(((5-chloro-2-pyridinyl)carbonyl)amino)-2-fluorophenyl)-N, 5-dimethyl-2-thia-4-azabicyclo[4.1.0]hept-3-ene-1-carboxamide;

(1S,5S,6S)-3-amino-N-tert-butyl-5-(5-(((5-cyano-2-pyridinyl)carbonyl)amino)-2-fluorophenyl)-5-methyl-2-thia-4-azabicyclo[4.1.0]hept-3-ene-1-carboxamide;

(1S,5S,6S)-3-amino-5-(2-fluoro-5-(((5-(2-propyn-1-yloxy)-2-pyrazinyl)carbonyl)amino)phenyl)-N, 5-dimethyl-2-thia-4-azabicyclo[4.1.0]hept-3-ene-1-carboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(((1R)-1-methyl-2-propyn-1-yl)oxy)-2-pyrazinecarboxamide;

N-(5-((1S,5S,6S)-3-amino-1-(difluoromethyl)-5-methyl-2-thia-4-azabicyclo[4.1.0]hept-3-en-5-yl)-6-methoxy-3-pyridinyl)-5-(2-propyn-1-yloxy)-2-pyrazinecarboxamide;

N-(5-((1S,5S,6S)-3-amino-1-(difluoromethyl)-5-methyl-2-thia-4-azabicyclo[4.1.0]hept-3-en-5-yl)-6-methoxy-3-pyridinyl)-5-chloro-2-pyridinecarboxamide;

N-(3-((1S,5S,6S)-3-amino-1-(((3R)-3-fluoro-1-pyrrolidinyl)carbonyl)-5-methyl-2-thia-4-azabicyclo[4.1.0]hept-3-en-5-yl)-4-fluorophenyl)-5-(2,2,2-trifluoroethoxy)-2-pyrazinecarboxamide;

N-(3-((1S,5S,6S)-3-amino-1-(((3 S)-3-fluoro-1-pyrrolidinyl)carbonyl)-5-methyl-2-thia-4-azabicyclo[4.1.0]hept-3-en-5-yl)-4-fluorophenyl)-5-(2,2,2-trifluoroethoxy)-2-pyrazinecarboxamide;

(1S,5S,6S)-3-amino-N-cyclopropyl-5-(2-fluoro-5-(((5-(((1S)-1-methyl-2-propyn-1-yl)oxy)-2-pyrazinyl)carbonyl)amino)phenyl)-5-methyl-2-thia-4-azabicyclo[4.1.0]hept-3-ene-1-carboxamide;

(1S,5S,6S)-3-amino-N-tert-butyl-5-(2-fluoro-5-(((5-(((1S)-1-methyl-2-propyn-1-yl)oxy)-2-pyrazinyl)carbonyl)amino)phenyl)-5-methyl-2-thia-4-azabicyclo[4.1.0]hept-3-ene-1-carboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-((1S)-2,2,2-trifluoro-1-methylethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-((1R)-2,2,2-trifluoro-1-methylethoxy)-2-pyrazinecarboxamide;

(1S,5S,6S)-3-amino-N-((1R)-1,2-dimethylpropyl)-5-(2-fluoro-5-(((5-(2,2,2-trifluoroethoxy)-2-pyrazinyl)carbonyl)amino)phenyl)-5-methyl-2-thia-4-azabicyclo[4.1.0]hept-3-ene-1-carboxamide;

N-(3-((1S,5S,6S)-3-amino-5-methyl-1-(4-morpholinylcarbonyl)-2-thia-4-azabicyclo[4.1.0]hept-3-en-5-yl)-4-fluorophenyl)-5-(2,2,2-trifluoroethoxy)-2-pyrazinecarboxamide;

(1S,5S,6S)-3-amino-N-(2,2-difluoroethyl)-5-(2-fluoro-5-(((5-(2,2,2-trifluoroethoxy)-2-pyrazinyl)carbonyl)amino)phenyl)-5-methyl-2-thia-4-azabicyclo[4.1.0]hept-3-ene-1-carboxamide;

(1S,5S,6S)-3-amino-5-(2-fluoro-5-(((5-(2,2,2-trifluoroethoxy)-2-pyrazinyl)carbonyl)amino)phenyl)-N,N, 5-trimethyl-2-thia-4-azabicyclo[4.1.0]hept-3-ene-1-carboxamide;

(1S,5S,6S)-3-amino-N-cyclopropyl-5-(2-fluoro-5-(((5-(((1S)-2-methoxy-1-methylethoxy)-2-pyrazinyl)carbonyl)amino)phenyl)-5-methyl-2-thia-4-azabicyclo [4.1.0]hept-3-ene-1-carboxamide;

(1S,5S,6S)-3-amino-N-tert-butyl-5-(2-fluoro-5-(((5-(2,2, 2-trifluoroethoxy)-2-pyrazinyl)carbonyl)amino)phenyl)-5-methyl-2-thia-4-azabicyclo[4.1.0]hept-3-ene-1-carboxamide;

(1S,5S,6S)-3-amino-N-tert-butyl-5-(2-fluoro-5-(((5-((1S)-2-methoxy-1-methylethoxy)-2-pyrazinyl)carbonyl)amino)phenyl)-5-methyl-2-thia-4-azabicyclo [4.1.0]hept-3-ene-1-carboxamide;

N-(3-((1S,5S,6S)-3-amino-5-methyl-1-(4-morpholinylcarbonyl)-2-thia-4-azabicyclo[4.1.0]hept-3-en-5-yl)-4, 5-difluorophenyl)-5-(2-propyn-1-yloxy)-2-pyrazinecarboxamide;

N-(3-((1S,5S,6S)-3-amino-5-methyl-1-(4-morpholinylcarbonyl)-2-thia-4-azabicyclo[4.1.0]hept-3-en-5-yl)-4-fluorophenyl)-5-(2-propyn-1-yloxy)-2-pyrazinecarboxamide;

(1S,5S,6S)-3-amino-N-(2-fluoro-1,1-dimethylethyl)-5-(2-fluoro-5-(((5-(2-propyn-1-yloxy)-2-pyrazinyl)carbonyl)amino)phenyl)-5-methyl-2-thia-4-azabicyclo [4.1.0]hept-3-ene-1-carboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-chloro-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-((3-methyl-1,2,4-oxadiazol-5-yl)methoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(((1S)-1-methyl-2-propyn-1-yl)oxy)-2-pyrazinecarboxamide;

N-(3-((1S,5S,6S)-3-amino-1-cyano-5-methyl-2-thia-4-azabicyclo[4.1.0]hept-3-en-5-yl)-4,5-difluorophenyl)-5-((1S)-2-methoxy-1-methylethoxy)-2-pyrazinecarboxamide;

N-(3-((1S,5S,6S)-3-amino-1-cyano-5-methyl-2-thia-4-azabicyclo[4.1.0]hept-3-en-5-yl)-4,5-difluorophenyl)-5-(((1S)-1-methyl-2-propyn-1-yl)oxy)-2-pyrazinecarboxamide;

N-(3-((1S,5S,6S)-3-amino-1-cyano-5-methyl-2-thia-4-azabicyclo[4.1.0]hept-3-en-5-yl)-4,5-difluorophenyl)-5-(2,2,2-trifluoroethoxy)-2-pyridinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-((5-methyl-1,2,4-oxadiazol-3-yl)methoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-((3-methyl-1,2,4-oxadiazol-5-yl)methoxy)-2-pyrazinecarboxamide;

N-(3-((1S,5S,6S)-3-amino-1-cyano-5-methyl-2-thia-4-azabicyclo[4.1.0]hept-3-en-5-yl)-4,5-difluorophenyl)-3-methyl-5-(2,2,2-trifluoroethoxy)-2-pyridinecarboxamide;

N-(3-((1S,5S,6S)-3-amino-1-cyano-5-methyl-2-thia-4-azabicyclo[4.1.0]hept-3-en-5-yl)-4,5-difluorophenyl)-3-methyl-5-(2-propyn-1-yloxy)-2-pyridinecarboxamide;

(1S,5S,6S)-3-amino-N-ethyl-5-(2-fluoro-5-(((5-(2-propyn-1-yloxy)-2-pyrazinyl)carbonyl)amino)phenyl)-5-methyl-2-thia-4-azabicyclo[4.1.0]hept-3-ene-1-carboxamide;

(1S,5S,6S)-3-amino-5-(5-(((5-cyano-2-pyridinyl)carbonyl)amino)-2-fluorophenyl)-N-(2-fluoro-1,1-dimethylethyl)-5-methyl-2-thia-4-azabicyclo[4.1.0]hept-3-ene-1-carboxamide;

(1S,5S,6S)-3-amino-N-(2-fluoro-1,1-dimethyl ethyl)-5-(2-fluoro-5-(((5-(((1S)-1-methyl-2-propyn-1-yl)oxy)-2-pyrazinyl)carbonyl)amino)phenyl)-5-methyl-2-thia-4-azabicyclo[4.1.0]hept-3-ene-1-carboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(cyclobutylmethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(cyclopropylmethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(3-oxetanylmethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(((2R)-2-methoxypropyl)oxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(((2 S)-2-methoxypropyl)oxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-((1S)-2-methoxy-1-methylethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(2,2-difluoroethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-((3,3-difluorocyclobutyl)methoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-oxo-4,5-dihydro-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(2-methylpropoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-((2R)-2-oxetanylmethoxy)-2- pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-((2 S)-2-oxetanylmethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-((2-methyl-2-propen-1-yl)oxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-((3-methyl-5-isoxazolyl)methoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-((5-methyl-3-isoxazolyl)methoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(benzyloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(1,3-thiazol-2-ylmethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(((1R)-2,2-difluorocyclopropyl)methoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(((1S)-2,2-difluorocyclopropyl)methoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(2-propen-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-((5-methyl-1,3,4-oxadiazol-2-yl)methoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-ethoxy-2-pyrazinecarboxamide;

N-(3-((1S,5S,6S)-3-amino-1-(difluoromethyl)-5-methyl-2-thia-4-azabicyclo[4.1.0]hept-3-en-5-yl)-4-fluorophenyl)-5-((3-methyl-1,2,4-oxadiazol-5-yl)methoxy)-2-pyrazinecarboxamide;

(1S,5S,6S)-3-amino-N-(2-fluoroethyl)-5-(2-fluoro-5-(((5-(2,2,2-trifluoroethoxy)-2-pyrazinyl)carbonyl)amino)phenyl)-5-methyl-2-thia-4-azabicyclo[4.1.0]hept-3-ene-1-carboxamide;

(1S,5S,6S)-3-amino-5-(2-fluoro-5-(((5-(2,2,2-trifluoroethoxy)-2-pyrazinyl)carbonyl)amino)phenyl)-5-methyl-N-(1-methylcyclopropyl)-2-thia-4-azabicyclo[4.1.0]hept-3-ene-1-carboxamide;

N-(3-((1S,5S,6S)-1-((acetylamino)methyl)-3-amino-5-methyl-2-thia-4-azabicyclo[4.1.0]hept-3-en-5-yl)-4,5-difluorophenyl)-5-(2-propyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluoro-5-methylphenyl)-5-(2-propyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluoro-5-methylphenyl)-5-((3-methyl-1,2,4-oxadiazol-5-yl)methoxy)-2-pyrazinecarboxamide;

(1S,5S,6S)-3-amino-N-((1R)-2,2-difluoro-1-methylethyl)-5-(2-fluoro-5-(((5-(2,2,2-trifluoroethoxy)-2-pyrazinyl)carbonyl)amino)phenyl)-5-methyl-2-thia-4-azabicyclo[4.1.0]hept-3-ene-1-carboxamide;

(1S,5S,6S)-3-amino-N-((1S)-2,2-difluoro-1-methylethyl)-5-(2-fluoro-5-(((5-(2,2,2-trifluoroethoxy)-2-pyrazinyl)carbonyl)amino)phenyl)-5-methyl-2-thia-4-azabicyclo[4.1.0]hept-3-ene-1-carboxamide;

N-(3-((1S,5S,6S)-3-amino-1-(ethoxymethyl)-5-methyl-2-thia-4-azabicyclo[4.1.0]hept-3-en-5-yl)-4,5-difluorophenyl)-5-(2-propyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(3-pentyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(3-butyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-((1-methylcyclopropyl)methoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(((1R)-1-methyl-2-propen-1-yl)oxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(((1S)-1-methyl-2-propen-1-yl)oxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(2-fluoroethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(cyclopropylmethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(cyclobutylmethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(3-oxetanylmethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(2-methylpropoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(2,2-difluoroethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-((2R)-2-oxetanylmethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-((2 S)-2-oxetanylmethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(3-pentyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(3-butyn-1-yloxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-methylcyclopropyl)methoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(((1R)-1-methyl-2-propen-1-yl)oxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(((1S)-1-methyl-2-propen-1-yl)oxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(2-fluoroethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluoro-5-methylphenyl)-5-(2,2,2-trifluoroethoxy)-2-pyrazinecarboxamide;

N-(3-((1S,5S,6S)-3-amino-1-(methoxymethyl)-5-methyl-2-thia-4-azabicyclo[4.1.0]hept-3-en-5-yl)-4-fluoro-5-methylphenyl)-5-chloro-2-pyridinecarboxamide;

N-(3-((1S,5S,6S)-3-amino-1-(methoxymethyl)-5-methyl-2-thia-4-azabicyclo[4.1.0]hept-3-en-5-yl)-4-fluorophenyl)-5-(oxetan-3-yloxy)pyrazine-2-carboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(oxetan-3-yloxy)pyrazine-2-carboxamide;

N-(3-((1S,5S,6S)-3-amino-1-(methoxymethyl)-5-methyl-2-thia-4-azabicyclo[4.1.0]hept-3-en-5-yl)-4,5-difluorophenyl)-5-(neopentyloxy)pyrazine-2-carboxamide;

N-(3-((1S,5S,6S)-1-acetyl-3-amino-5-methyl-2-thia-4-azabicyclo[4.1.0]hept-3-en-5-yl)-4,5-difluorophenyl)-5-(prop-2-yn-1-yloxy)pyrazine-2-carboxamide;

N-(3-((1S,5S,6S)-3-amino-1-(methoxymethyl)-5-methyl-2-thia-4-azabicyclo[4.1.0]hept-3-en-5-yl)-4-fluoro-5-methylphenyl)-5-(oxazol-2-ylmethoxy)pyrazine-2-carboxamide;

N-(3-((1S,5S,6S)-3-amino-1-(difluoromethyl)-5-methyl-2-thia-4-azabicyclo[4.1.0]hept-3-en-5-yl)-4-fluoro-5-methylphenyl)-5-(prop-2-yn-1-yloxy)pyrazine-2-carboxamide;

N-(3-((1S,5S,6S)-3-amino-1-(difluoromethyl)-5-methyl-2-thia-4-azabicyclo[4.1.0]hept-3-en-5-yl)-4-fluoro-5-methylphenyl)-5-(2,2,2-trifluoroethoxy)pyrazine-2-carboxamide;

N-(3-((1S,5S,6S)-3-amino-5-(fluoromethyl)-2-thia-4-azabicyclo[4.1.0]hept-3-en-5-yl)-4,5-difluorophenyl)-5-chloropicolinamide;

N-(3-((1S,5S,6S)-3-amino-1-(difluoromethyl)-5-methyl-2-thia-4-azabicyclo[4.1.0]hept-3-en-5-yl)-4-fluoro-5-methylphenyl)-5-(oxazol-2-ylmethoxy)pyrazine-2-carboxamide; or N-(3-((1S,5S,6S)-3-amino-1-(difluoromethyl)-5-methyl-2-thia-4-azabicyclo[4.1.0]hept-3-en-5-yl)-4-fluoro-5-methylphenyl)-5-((3-methyl-1,2,4-oxadiazol-5-yl)methoxy)pyrazine-2-carboxamide.

58. The compound of claim 1, or a stereoisomer or pharmaceutically acceptable salt thereof, selected from

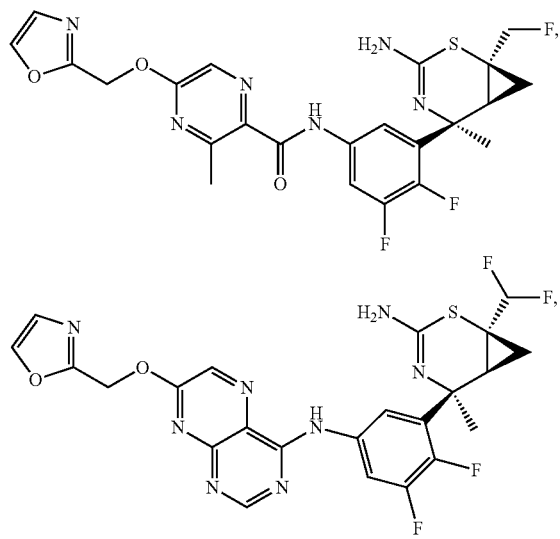

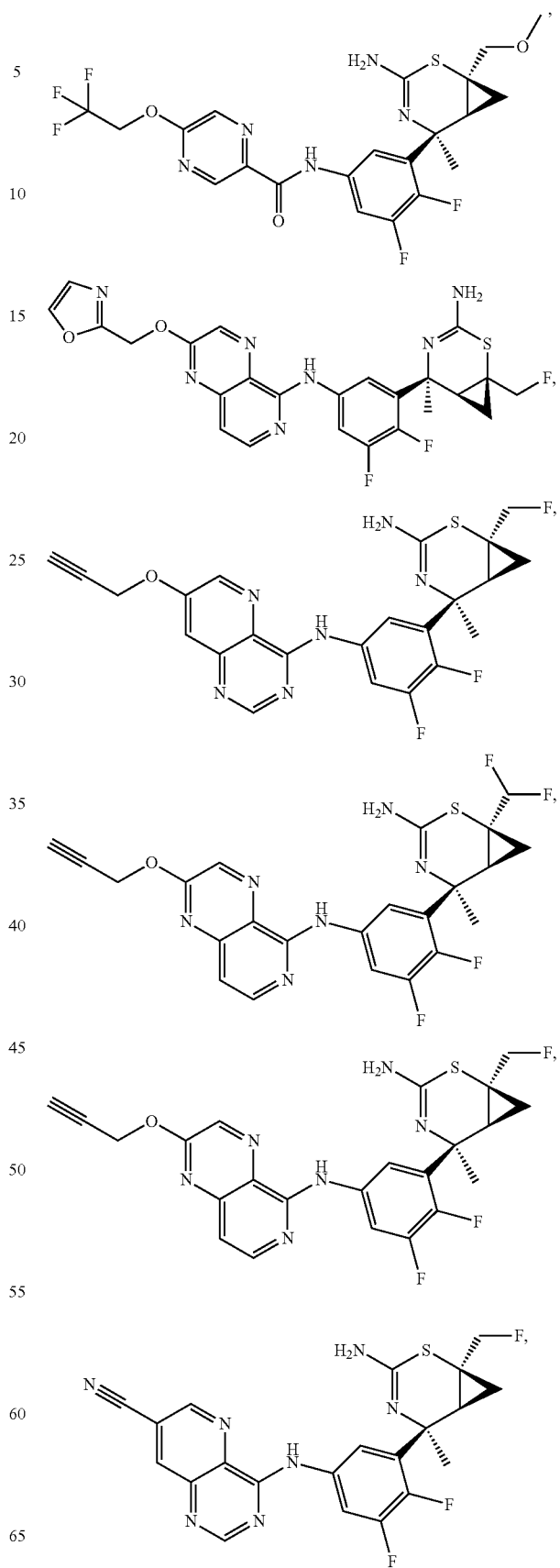

769
-continued
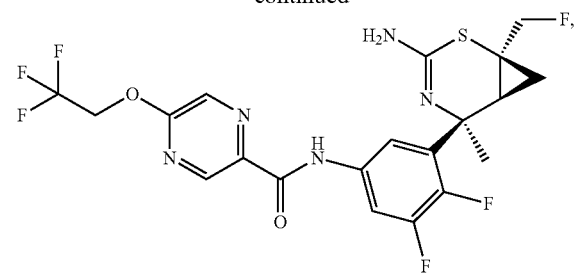
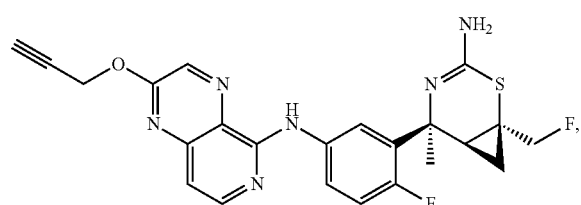
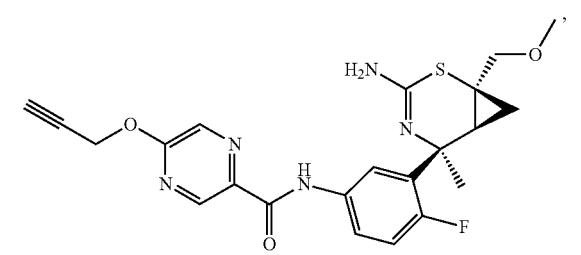
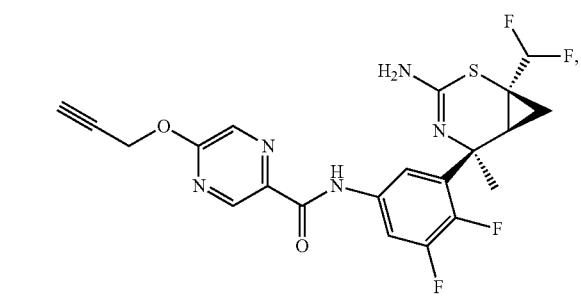
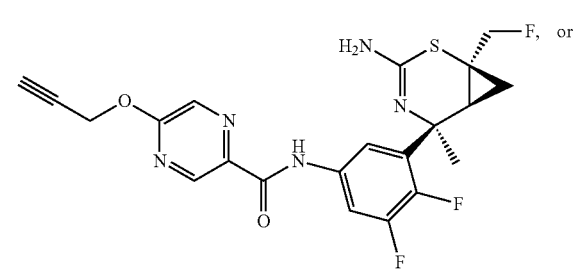
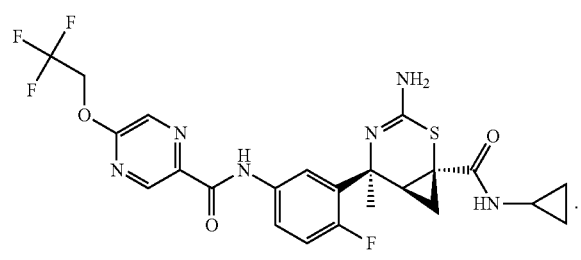
770
59. The compound of claim 1, or a stereoisomer or pharmaceutically acceptable salt thereof, selected from
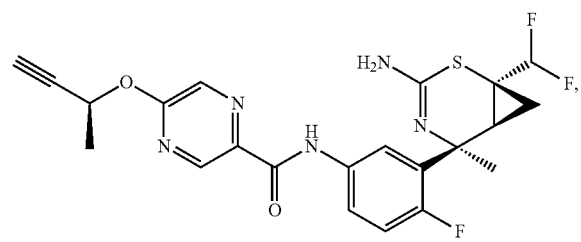
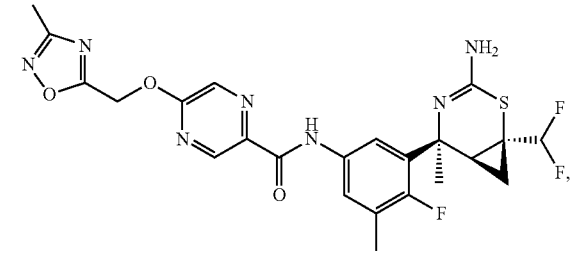
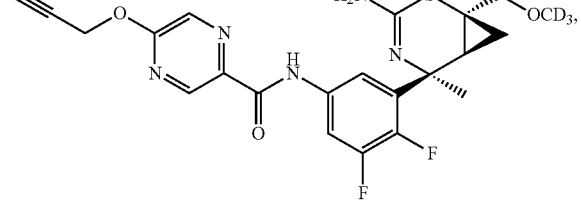
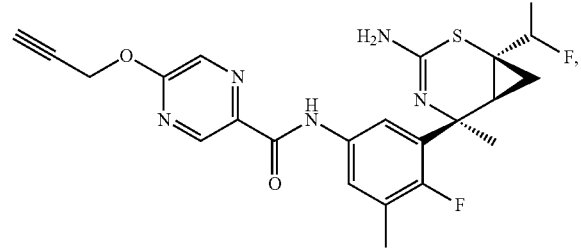
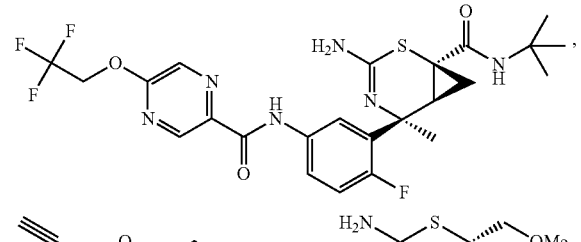
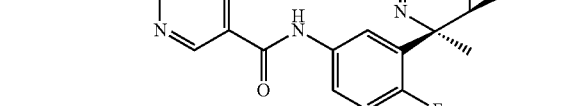
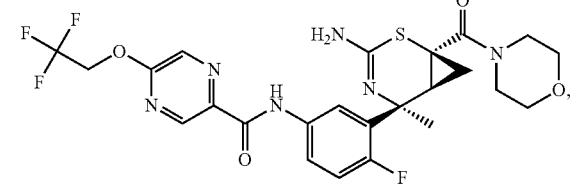

-continued

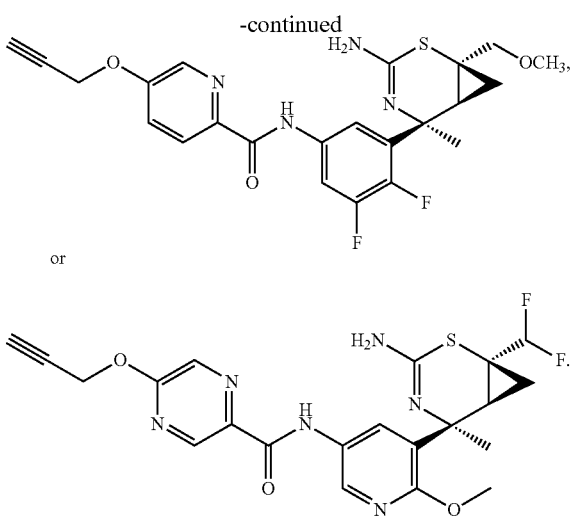

or

60. A pharmaceutical composition comprising the compound according to claim 1 and a pharmaceutically acceptable excipient.

61. A pharmaceutical composition comprising the compound according to claim 49 and a pharmaceutically acceptable excipient.

62. A pharmaceutical composition comprising the compound according to claim 50 and a pharmaceutically acceptable excipient.

63. A pharmaceutical composition comprising the compound according to claim 51 and a pharmaceutically acceptable excipient.

64. A pharmaceutical composition comprising the compound according to claim 52 and a pharmaceutically acceptable excipient.

65. A pharmaceutical composition comprising the compound according to claim 53 and a pharmaceutically acceptable excipient.

66. A pharmaceutical composition comprising the compound according to claim 54 and a pharmaceutically acceptable excipient.

67. A method for reducing beta amyloid peptide levels in the cerebral spinal fluid of a subject, the method comprising administering the compound according to claim 1 to the subject.

68. A method for reducing beta amyloid peptide levels in the cerebral spinal fluid of a subject, the method comprising administering the compound according to claim 49 to the subject.

69. A method for reducing beta amyloid peptide levels in the cerebral spinal fluid of a subject, the method comprising administering the compound according to claim 50 to the subject.

70. A method for reducing beta amyloid peptide levels in the cerebral spinal fluid of a subject, the method comprising administering the compound according to claim 51 to the subject.

71. A method for reducing beta amyloid peptide levels in the cerebral spinal fluid of a subject, the method comprising administering the compound according to claim 52 to the subject.

72. A method for reducing beta amyloid peptide levels in the cerebral spinal fluid of a subject, the method comprising administering the compound according to claim 53 to the subject.

73. A method for reducing beta amyloid peptide levels in the cerebral spinal fluid of a subject, the method comprising administering the compound according to claim 54 to the subject.

74. A method for treating Alzheimer's disease, cognitive impairment or a combination thereof in a subject, the method comprising administering the compound according to claim 1 to the subject.

75. A method for treating Alzheimer's disease, cognitive impairment or a combination thereof in a subject, the method comprising administering the compound according to claim 49 to the subject.

76. A method for treating Alzheimer's disease, cognitive impairment or a combination thereof in a subject, the method comprising administering the compound according to claim 50 to the subject.

77. A method for treating Alzheimer's disease, cognitive impairment or a combination thereof in a subject, the method comprising administering the compound according to claim 51 to the subject.

78. A method for treating Alzheimer's disease, cognitive impairment or a combination thereof in a subject, the method comprising administering the compound according to claim 52 to the subject.

79. A method for treating Alzheimer's disease, cognitive impairment or a combination thereof in a subject, the method comprising administering the compound according to claim 53 to the subject.

80. A method for treating Alzheimer's disease, cognitive impairment or a combination thereof in a subject, the method comprising administering the compound according to claim 54 to the subject.

81. A method for treating a neurological disorder in a subject, the method comprising administering to the subject the compound of claim 1, wherein the neurological disorder is selected from mild cognitive impairment, Down's syndrome, Hereditary cerebral hemorrhage with dutch-type amyloidosis, cerebral amyloid angiopathy, degenerative dementia, dementia associated with Parkinson's disease, dementia associated with supranuclear palsy, dementia associated with cortical basal degeneration, diffuse lewy body type of Alzheimer's disease or a combination thereof.

82. A method for treating a neurological disorder in a subject, the method comprising administering to the subject the compound of claim 49, wherein the neurological disorder is selected from mild cognitive impairment, Down's syndrome, Hereditary cerebral hemorrhage with dutch-type amyloidosis, cerebral amyloid angiopathy, degenerative dementia, dementia associated with Parkinson's disease, dementia associated with supranuclear palsy, dementia associated with cortical basal degeneration, diffuse lewy body type of Alzheimer's disease or a combination thereof.

83. A method for treating a neurological disorder in a subject, the method comprising administering to the subject the compound of claim 50, wherein the neurological disorder is selected from mild cognitive impairment, Down's syndrome, Hereditary cerebral hemorrhage with dutch-type amyloidosis, cerebral amyloid angiopathy, degenerative dementia, dementia associated with Parkinson's disease, dementia associated with supranuclear palsy, dementia associated with cortical basal degeneration, diffuse lewy body type of Alzheimer's disease or a combination thereof.

84. A method for treating a neurological disorder in a subject, the method comprising administering to the subject the compound of claim 51, wherein the neurological disorder is selected from mild cognitive impairment, Down's syndrome, Hereditary cerebral hemorrhage with dutch-type amyloidosis, cerebral amyloid angiopathy, degenerative dementia, dementia associated with Parkinson's disease, dementia associated with supranuclear palsy, dementia associated with cortical basal degeneration, diffuse lewy body type of Alzheimer's disease or a combination thereof.

85. A method for treating a neurological disorder in a subject, the method comprising administering to the subject the compound of claim 52, wherein the neurological disorder is selected from mild cognitive impairment, Down's syndrome, Hereditary cerebral hemorrhage with dutch-type amyloidosis, cerebral amyloid angiopathy, degenerative dementia, dementia associated with Parkinson's disease, dementia associated with supranuclear palsy, dementia associated with cortical basal degeneration, diffuse lewy body type of Alzheimer's disease or a combination thereof.

86. A method for treating a neurological disorder in a subject, the method comprising administering to the subject the compound of claim 53, wherein the neurological disorder is selected from mild cognitive impairment, Down's syndrome, Hereditary cerebral hemorrhage with dutch-type amyloidosis, cerebral amyloid angiopathy, degenerative dementia, dementia associated with Parkinson's disease, dementia associated with supranuclear palsy, dementia associated with cortical basal degeneration, diffuse lewy body type of Alzheimer's disease or a combination thereof.

87. A method for treating a neurological disorder in a subject, the method comprising administering to the subject the compound of claim 54, wherein the neurological disorder is selected from mild cognitive impairment, Down's syndrome, Hereditary cerebral hemorrhage with dutch-type amyloidosis, cerebral amyloid angiopathy, degenerative dementia, dementia associated with Parkinson's disease, dementia associated with supranuclear palsy, dementia associated with cortical basal degeneration, diffuse lewy body type of Alzheimer's disease or a combination thereof.

88. A method for reducing formation of plaque on the brain of a subject, the method comprising administering the compound of claim 1 to the subject.

89. A method for reducing formation of plaque on the brain of a subject, the method comprising administering the compound of claim 49 to the subject.

90. A method for reducing formation of plaque on the brain of a subject, the method comprising administering the compound of claim 50 to the subject.

91. A method for reducing formation of plaque on the brain of a subject, the method comprising administering the compound of claim 51 to the subject.

92. A method for reducing formation of plaque on the brain of a subject, the method comprising administering the compound of claim 52 to the subject.

93. A method for reducing formation of plaque on the brain of a subject, the method comprising administering the compound of claim 53 to the subject.

94. A method for reducing formation of plaque on the brain of a subject, the method comprising administering the compound of claim 54 to the subject.

95. A process for preparing a compound of Formula I

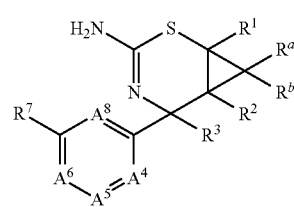

I according to claim 4, the process comprising the step of reacting a protected compound 20

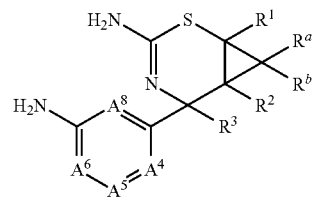

20 wherein each of $R^a$, $R^b$, $R^1$, $R^2$ and $R^3$ and $A^4$, $A^5$, $A^6$ and $A^8$ of compound 20 are as defined in claim 4, with a compound having the structure $R^9$—C(=O)OH in the presence of an anhydride or an acid activating agent, or a structure $R^9$—Cl in the presence of an acid, wherein $R^9$ is as defined in claim 4 to prepare the compound according to claim 4.

\* \* \* \* \*

UNITED STATES PATENT AND TRADEMARK OFFICE
CERTIFICATE OF CORRECTION

PATENT NO. : 9,550,762 B2
APPLICATION NO. : 14/819256
DATED : January 24, 2017
INVENTOR(S) : Jennifer R. Allen et al.

It is certified that error appears in the above-identified patent and that said Letters Patent is hereby corrected as shown below:

In Column 718, Line 54, replace "$R^7$ is NH-$R^9$" with --$R^7$ is –NH-$R^9$--;

In Column 721, Line 4, replace "haloalkoxyl, CN" with --haloalkoxyl, $C_{1-4}$-alkyl, CN--;

In Column 721, Line 18, replace "$C_{1-6}$-alkoxyl" with --$C_{1-6}$-dialkylamino-, $C_{1-6}$-alkoxyl--;

In Column 722, Lines 30-39, replace " 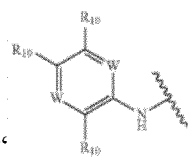 wherein" with -- 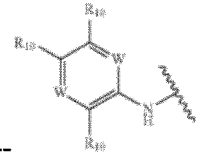 ; wherein--;

In Column 722, Line 54, replace "$C_{1-4}$-alkyl, $CH_2OH$" with --$C_{1-4}$-alkyl, $C_{1-4}$-haloalkyl, $CH_2OH$--;

In Column 723, Lines 20-29, replace " 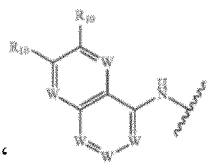 wherein" with -- 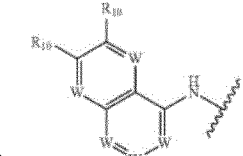 ; wherein--;

In Column 723, Lines 56-65, replace " 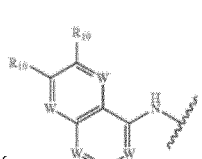 wherein" with -- 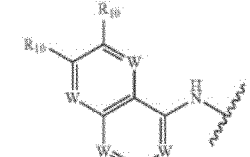 ; wherein--;

In Column 724, Lines 45-46, replace ", $C(O)C_{2-6}$-alkenyl" with --, -$C(O)C_{2-6}$-alkenyl--;

Signed and Sealed this
Twenty-fifth Day of September, 2018

Andrei Iancu
*Director of the United States Patent and Trademark Office*

CERTIFICATE OF CORRECTION (continued)
U.S. Pat. No. 9,550,762 B2

In Column 726, Lines 28-38, replace " 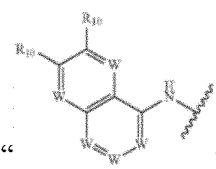 wherein" with -- 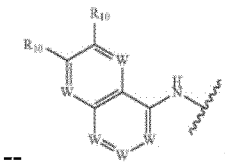 ; wherein--;

In Column 726, Lines 56-66, replace " 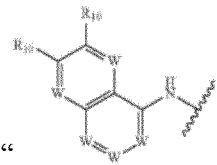 wherein" with -- 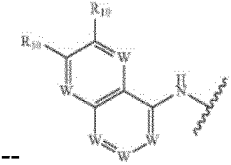 ; wherein--;

In Column 728, Line 13, replace "cyclohexyl, $C_{1-3}$-thioalkoxyl" with --cyclohexyl, $C_{1-3}$-alkylamino-, $C_{1-3}$-dialkylamino-, $C_{1-3}$-thioalkoxyl--;

In Column 728, Line 45, replace "pyrrolidinyl piperazinyl" with --pyrrolidinyl, piperazinyl--;

In Column 729, Line 8, replace "The according" with --The compound according--;

In Column 732, Line 66, replace "$R^{10}$" with --$R^{10}$,--;

In Column 736, Lines 23-30, replace " 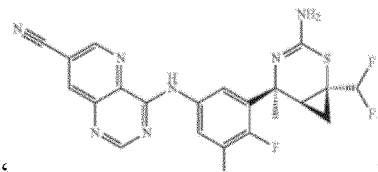 " with -- 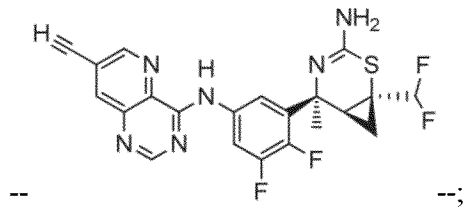 --;

In Column 739, Line 29, replace "N-(5-((1S,5S,6 S)" with --N-(5-((1S,5S,6S)--;

In Column 739, Line 33, replace "N-(5-((1S,5S,6 S)" with --N-(5-((1S,5S,6S)--;

In Column 739, Line 37, replace "N-(5-((1S,5S,6 S)" with --N-(5-((1S,5S,6S)--;

In Column 745, Line 14, replace "N-(3-((1S,5S,6 S)" with --N-(3-((1S,5S,6S)--;

In Column 749, Line 24, replace "5-((2" with --5-(2--;

In Column 749, Line 28, replace "5-((2" with --5-(2--;

In Column 749, Line 32, replace "5-((2" with --5-(2--;

CERTIFICATE OF CORRECTION (continued)
U.S. Pat. No. 9,550,762 B2

In Column 749, Line 53, replace "(2E)-3-((1R,5 S,6 S)" with --(2E)-3-((1R,5S,6S)--;

In Column 749, Line 57, replace "(2E)-3-((1R,5 S,6 S)" with --(2E)-3-((1R,5S,6S)--;

In Column 755, Line 23, replace "2-((3" with --2-(3--;

In Column 762, Line 30, replace "(((3 S)" with --(((3S)--;

In Column 762, Line 67, replace "(((1S)-2-methoxy" with --((1S)-2-methoxy--;

In Column 764, Line 27, replace "(((2 S)" with --(((2S)--;

In Column 764, Line 54, replace "((2 S)" with --((2S)--;

In Column 766, Line 40, replace "((2 S)" with --((2S)--;

In Column 766, Line 52, replace "5-methylcyclopropyl)" with --5-((1-methylcyclopropyl)--;

In Column 767, Lines 55-65, replace " 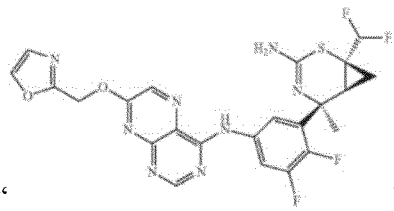 " with -- 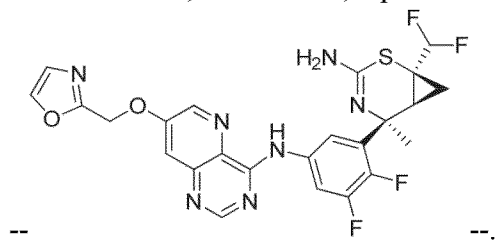 --.